United States Patent
Blair et al.

(10) Patent No.: US 11,510,973 B2
(45) Date of Patent: *Nov. 29, 2022

(54) ALPHAVIRUS ANTIGEN VECTORS

(71) Applicant: Gritstone bio, Inc., Emeryville, CA (US)

(72) Inventors: Wade Blair, Gaithersburg, MD (US); Karin Jooss, Emeryville, CA (US); Amy Rachel Rappaport, Daly City, CA (US); Ciaran Daniel Scallan, San Francisco, CA (US); Leonid Gitlin, Foster City, CA (US)

(73) Assignee: GRITSTONE BIO, INC., Emeryville, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/693,029

(22) Filed: Mar. 11, 2022

(65) Prior Publication Data
US 2022/0226453 A1 Jul. 21, 2022

Related U.S. Application Data

(62) Division of application No. 16/612,352, filed as application No. PCT/US2018/031696 on May 8, 2018.

(60) Provisional application No. 62/590,163, filed on Nov. 22, 2017, provisional application No. 62/523,201, filed on Jun. 21, 2017, provisional application No. 62/503,283, filed on May 8, 2017.

(51) Int. Cl.
| | |
|---|---|
| *A61P 31/12* | (2006.01) |
| *A61K 39/12* | (2006.01) |
| *C12N 15/86* | (2006.01) |
| *A61K 39/00* | (2006.01) |
| *C07K 14/47* | (2006.01) |
| *C07K 14/74* | (2006.01) |

(52) U.S. Cl.
CPC ........... *A61K 39/001191* (2018.08); *A61K 39/001188* (2018.08); *A61K 39/12* (2013.01); *A61P 31/12* (2018.01); *C07K 14/4748* (2013.01); *C07K 14/70539* (2013.01); *C12N 15/86* (2013.01); *A61K 2039/53* (2013.01); *A61K 2039/545* (2013.01); *A61K 2039/585* (2013.01); *A61K 2039/605* (2013.01); *A61K 2039/6037* (2013.01); *A61K 2039/70* (2013.01)

(58) Field of Classification Search
None
See application file for complete search history.

(56) References Cited

U.S. PATENT DOCUMENTS

| | | |
|---|---|---|
| 4,235,871 A | 11/1980 | Papahadjopoulos et al. |
| 4,501,728 A | 2/1985 | Geho et al. |
| 4,656,127 A | 4/1987 | Mundy |
| 4,722,848 A | 2/1988 | Paoletti et al. |
| 4,837,028 A | 6/1989 | Allen |
| 5,019,369 A | 5/1991 | Presant et al. |
| 5,204,253 A | 4/1993 | Sanford et al. |
| 5,217,879 A | 6/1993 | Huang et al. |
| 5,279,833 A | 1/1994 | Rose |
| 5,505,947 A | 4/1996 | Johnston et al. |
| 5,580,859 A | 12/1996 | Felgner et al. |
| 5,589,466 A | 12/1996 | Felgner et al. |
| 5,622,931 A | 4/1997 | Edgington et al. |
| 5,643,576 A | 7/1997 | Johnston et al. |
| 5,662,907 A | 9/1997 | Kubo et al. |
| 5,814,482 A | 9/1998 | Dubensky, Jr. et al. |
| 5,843,723 A | 12/1998 | Dubensky, Jr. et al. |
| 5,849,561 A | 12/1998 | Falck-Pedersen |
| 5,849,589 A | 12/1998 | Tedder et al. |
| 5,851,796 A | 12/1998 | Schatz |
| 6,015,686 A | 1/2000 | Dubensky, Jr. et al. |
| 6,037,135 A | 3/2000 | Kubo et al. |
| 6,083,716 A | 7/2000 | Wilson et al. |
| 6,090,406 A | 7/2000 | Popescu et al. |
| 6,296,854 B1 | 10/2001 | Pushko et al. |
| 6,312,946 B1 | 11/2001 | Yeh et al. |
| 6,365,394 B1 | 4/2002 | Gao et al. |
| 6,376,236 B1 | 4/2002 | Dubensky, Jr. et al. |
| 6,413,935 B1 | 7/2002 | Sette et al. |
| 6,531,135 B1 | 3/2003 | Johnston et al. |
| 6,610,321 B2 | 8/2003 | Huang et al. |
| 6,770,283 B1 | 8/2004 | Garoff et al. |
| 6,783,939 B2 | 8/2004 | Olmsted et al. |
| 7,078,218 B2 | 7/2006 | Smith et al. |
| 7,202,351 B1 | 4/2007 | Sette et al. |
| 7,283,337 B2 | 10/2007 | Sakai et al. |
| 7,285,265 B2 | 10/2007 | Vogels et al. |

(Continued)

FOREIGN PATENT DOCUMENTS

| | | |
|---|---|---|
| CA | 2705787 A1 | 6/2009 |
| CN | 101579528 A | 11/2009 |

(Continued)

OTHER PUBLICATIONS

Ngo et al., "CNTO 859, a humanized anti-tissue factor monoclonal antibody, is a potent inhibitor of breast cancer metastasis and tumor growth in xenograft models," International Journal of Cancer, vol. 120, No. 6, pp. 1261-1267, 2007.

(Continued)

*Primary Examiner* — Stacy B Chen
(74) *Attorney, Agent, or Firm* — Goodwin Procter LLP

(57) ABSTRACT

Disclosed herein are alphavirus vectors that include neoantigen-encoding nucleic acid sequences derived from a tumor of a subject. Also disclosed are nucleotides, cells, and methods associated with the vectors including their use as vaccines.

57 Claims, 75 Drawing Sheets

Specification includes a Sequence Listing.

(56) References Cited

U.S. PATENT DOCUMENTS

| | | |
|---|---|---|
| 7,291,498 B2 | 11/2007 | Roy et al. |
| 7,344,872 B2 | 3/2008 | Gao et al. |
| 7,468,181 B2 | 12/2008 | Vogels et al. |
| 7,531,180 B2 | 5/2009 | Polo et al. |
| 7,541,038 B2 | 6/2009 | Kovacs et al. |
| 7,557,200 B2 | 7/2009 | Wu et al. |
| 7,572,453 B2 | 8/2009 | Polo et al. |
| 7,572,628 B2 | 8/2009 | Dubensky, Jr. et al. |
| 7,605,235 B2 | 10/2009 | Anderson et al. |
| 7,732,129 B1 | 6/2010 | Zhang et al. |
| 7,744,900 B2 | 6/2010 | Dubensky, Jr. et al. |
| 7,771,979 B2 | 8/2010 | Polo et al. |
| 7,820,440 B2 | 10/2010 | Vogels et al. |
| 7,820,441 B2 | 10/2010 | Chamberlain et al. |
| 7,838,277 B2 | 11/2010 | Gao et al. |
| 7,850,977 B2 | 12/2010 | Kamrud et al. |
| 7,888,472 B2 | 2/2011 | Sette et al. |
| 8,052,967 B2 | 11/2011 | Vogels et al. |
| 8,093,021 B2 | 1/2012 | Hurtado et al. |
| 8,119,336 B2 | 2/2012 | Sampath et al. |
| 8,158,418 B2 | 4/2012 | Polo et al. |
| 8,216,834 B2 | 7/2012 | Colloca et al. |
| 8,252,574 B2 | 8/2012 | Mason et al. |
| 8,426,188 B2 | 4/2013 | Weaver et al. |
| 8,460,913 B2 | 6/2013 | Kamrud et al. |
| 8,614,082 B2 | 12/2013 | Frolov et al. |
| 8,617,533 B2 | 12/2013 | Smith et al. |
| 8,637,313 B2 | 1/2014 | Chamberlain et al. |
| 8,647,864 B2 | 2/2014 | Polo et al. |
| 8,673,319 B2 | 3/2014 | Colloca et al. |
| 8,680,258 B2 | 3/2014 | Coffield et al. |
| 8,691,563 B2 | 4/2014 | Pushko et al. |
| 8,722,044 B2 | 5/2014 | Almagro et al. |
| 8,951,525 B2 | 2/2015 | Almagro et al. |
| 8,961,995 B2 | 2/2015 | Frolov et al. |
| 8,999,333 B2 | 4/2015 | Almagro et al. |
| 9,017,696 B2 | 4/2015 | Draper et al. |
| 9,024,001 B2 | 5/2015 | Tang et al. |
| 9,101,572 B2 | 8/2015 | Pushko et al. |
| 9,115,402 B2 | 8/2015 | Hacohen et al. |
| 9,192,661 B2 | 11/2015 | Jain et al. |
| 9,217,159 B2 | 12/2015 | Roy et al. |
| 9,234,181 B2 | 1/2016 | Tang et al. |
| 9,249,191 B2 | 2/2016 | Ueno et al. |
| 9,254,265 B2 | 2/2016 | Geall et al. |
| 9,255,126 B2 | 2/2016 | Polo et al. |
| 9,273,288 B2 | 3/2016 | Mason et al. |
| 9,295,646 B2 | 3/2016 | Brito et al. |
| 9,340,830 B2 | 5/2016 | Lipson et al. |
| 9,353,353 B2 | 5/2016 | Nabel et al. |
| 9,402,888 B2 | 8/2016 | Ertl et al. |
| 9,416,370 B2 | 8/2016 | Smith et al. |
| 9,453,240 B2 | 9/2016 | Chamberlain et al. |
| 9,486,519 B2 | 11/2016 | Sahin et al. |
| 9,487,563 B2 | 11/2016 | Nabel et al. |
| 9,512,190 B2 | 12/2016 | Ueno et al. |
| 9,580,690 B2 | 2/2017 | Weaver et al. |
| 9,714,435 B2 | 7/2017 | Dicks et al. |
| 9,770,463 B2 | 9/2017 | Geall et al. |
| 9,795,668 B2 | 10/2017 | Jain et al. |
| 9,801,897 B2 | 10/2017 | Geall et al. |
| 10,092,636 B2 | 10/2018 | Binder |
| 10,238,733 B2 | 3/2019 | Brito et al. |
| 10,240,128 B2 | 3/2019 | Thirion et al. |
| 10,487,332 B2 | 11/2019 | Geall |
| 10,532,067 B2 | 1/2020 | Geall et al. |
| 2002/0065241 A1 | 5/2002 | Shankara |
| 2002/0119127 A1 | 8/2002 | Sette et al. |
| 2002/0137081 A1 | 9/2002 | Bandman |
| 2003/0044774 A1 | 3/2003 | Valenzuela et al. |
| 2003/0072767 A1 | 4/2003 | Gaiger et al. |
| 2003/0148262 A1 | 8/2003 | Polo et al. |
| 2004/0037843 A1 | 2/2004 | Fikes et al. |
| 2004/0115625 A1 | 6/2004 | Ebner |
| 2004/0248113 A1 | 12/2004 | Sette et al. |
| 2005/0003505 A1 | 1/2005 | Marasco et al. |
| 2005/0123555 A1 | 6/2005 | Olmsted et al. |
| 2005/0196754 A1 | 9/2005 | Drmanac et al. |
| 2005/0271676 A1 | 12/2005 | Sette |
| 2006/0051405 A1 | 3/2006 | MacLachlan et al. |
| 2006/0093623 A1 | 5/2006 | Andrieu et al. |
| 2006/0198854 A1 | 9/2006 | Pushko |
| 2006/0252077 A1 | 11/2006 | Buzby |
| 2006/0292175 A1 | 12/2006 | Polo et al. |
| 2007/0031442 A1 | 2/2007 | Sewell |
| 2007/0055049 A1 | 3/2007 | Grey et al. |
| 2007/0224201 A1 | 9/2007 | Wu et al. |
| 2007/0231347 A1 | 10/2007 | Wilson et al. |
| 2008/0050393 A1 | 2/2008 | Tang et al. |
| 2008/0206837 A1 | 8/2008 | Vogels et al. |
| 2008/0241189 A1 | 10/2008 | Wilson |
| 2009/0075384 A1 | 3/2009 | Kamrud et al. |
| 2009/0081200 A1 | 3/2009 | Wang |
| 2009/0093050 A1 | 4/2009 | Wu et al. |
| 2009/0118181 A1 | 5/2009 | Walker et al. |
| 2009/0253184 A1 | 10/2009 | Clarke et al. |
| 2009/0305344 A1 | 12/2009 | Polo et al. |
| 2010/0041737 A1 | 2/2010 | Naldini et al. |
| 2010/0068218 A1 | 3/2010 | Sette et al. |
| 2010/0120897 A1 | 5/2010 | Hurtado et al. |
| 2010/0183665 A1 | 7/2010 | Kamrud et al. |
| 2010/0286070 A1 | 11/2010 | Verheyden et al. |
| 2010/0330121 A1 | 12/2010 | Dubensky, Jr. et al. |
| 2011/0052634 A1 | 3/2011 | Weaver et al. |
| 2011/0091496 A1 | 4/2011 | Graham et al. |
| 2011/0129498 A1 | 6/2011 | Cortese et al. |
| 2011/0142880 A1 | 6/2011 | Lemiale et al. |
| 2011/0217332 A1 | 9/2011 | Colloca et al. |
| 2011/0293637 A1 | 12/2011 | Hacohen et al. |
| 2012/0027788 A1 | 2/2012 | Colloca et al. |
| 2012/0258126 A1 | 10/2012 | Scholler et al. |
| 2012/0282290 A1 | 11/2012 | Spencer et al. |
| 2012/0328651 A1 | 12/2012 | Colloca et al. |
| 2013/0011426 A1 | 1/2013 | Tureci et al. |
| 2013/0123199 A1 | 5/2013 | Lee |
| 2013/0149375 A1 | 6/2013 | Geall |
| 2013/0171241 A1 | 7/2013 | Geall |
| 2013/0177639 A1 | 7/2013 | Geall et al. |
| 2013/0177640 A1 | 7/2013 | Geall et al. |
| 2013/0189351 A1 | 7/2013 | Geall |
| 2013/0195968 A1 | 8/2013 | Geall et al. |
| 2013/0195969 A1 | 8/2013 | Geall et al. |
| 2013/0202684 A1 | 8/2013 | Geall et al. |
| 2014/0010841 A1 | 1/2014 | Weaver et al. |
| 2014/0141070 A1 | 5/2014 | Geall et al. |
| 2014/0178438 A1 | 6/2014 | Sahin et al. |
| 2014/0227346 A1 | 8/2014 | Geall et al. |
| 2014/0234304 A1 | 8/2014 | Almagro et al. |
| 2014/0242152 A1 | 8/2014 | Geall et al. |
| 2014/0248314 A1 | 9/2014 | Swanson et al. |
| 2014/0255472 A1 | 9/2014 | Geall et al. |
| 2014/0271724 A1 | 9/2014 | Ertl et al. |
| 2014/0271829 A1 | 9/2014 | Lilja et al. |
| 2015/0001108 A1 | 1/2015 | Lee et al. |
| 2015/0110831 A1 | 4/2015 | Gilbert et al. |
| 2015/0125465 A1 | 5/2015 | Binder et al. |
| 2015/0125477 A1 | 5/2015 | Kuttruff-Coqui et al. |
| 2015/0140068 A1 | 5/2015 | Barnett et al. |
| 2015/0167003 A1 | 6/2015 | Naldini et al. |
| 2015/0307897 A1 | 10/2015 | Soden et al. |
| 2016/0008447 A1 | 1/2016 | Hacohen et al. |
| 2016/0074506 A1 | 3/2016 | Jain et al. |
| 2016/0101170 A1 | 4/2016 | Hacohen et al. |
| 2016/0199513 A1 | 7/2016 | Bancel et al. |
| 2016/0289674 A1 | 10/2016 | Bancel et al. |
| 2016/0331822 A1 | 11/2016 | Hacohen et al. |
| 2016/0339090 A1 | 11/2016 | Hacohen et al. |
| 2016/0354409 A1 | 12/2016 | Wang et al. |
| 2017/0028044 A1 | 2/2017 | Soon-Shiong et al. |
| 2017/0212984 A1 | 7/2017 | Yelensky et al. |
| 2017/0340721 A1 | 11/2017 | Volkmann et al. |
| 2018/0000913 A1 | 1/2018 | Hacohen et al. |
| 2018/0050059 A1 | 2/2018 | Geall et al. |
| 2018/0055922 A1 | 3/2018 | Hacohen et al. |

(56) References Cited

U.S. PATENT DOCUMENTS

| | | |
|---|---|---|
| 2018/0153975 A1 | 6/2018 | Fritsch et al. |
| 2018/0363066 A1 | 12/2018 | Chalmers et al. |
| 2019/0025308 A1 | 1/2019 | Cummings et al. |
| 2019/0060432 A1 | 2/2019 | Hacohen et al. |
| 2019/0134184 A1 | 5/2019 | Yu et al. |
| 2019/0256924 A1 | 8/2019 | Vogelstein et al. |
| 2019/0270766 A1 | 9/2019 | Hogrefe et al. |
| 2020/0010849 A1 | 1/2020 | Blair et al. |
| 2021/0213122 A1 | 7/2021 | Blair et al. |
| 2022/0090138 A1 | 3/2022 | Jooss et al. |
| 2022/0125919 A1 | 4/2022 | Jooss et al. |
| 2022/0265797 A1 | 8/2022 | Jooss et al. |

FOREIGN PATENT DOCUMENTS

| | | |
|---|---|---|
| EP | 1585812 A2 | 10/2005 |
| EP | 2044947 A1 | 4/2009 |
| EP | 2370584 A1 | 10/2011 |
| EP | 2590670 B1 | 5/2013 |
| EP | 2590676 B1 | 5/2013 |
| EP | 2917353 A1 | 9/2015 |
| EP | 2947149 A1 | 11/2015 |
| FR | 2650840 A1 | 2/1991 |
| JP | 2007-534295 A | 11/2007 |
| JP | 2011-504724 A | 2/2011 |
| JP | 2014-209917 A | 11/2014 |
| KR | 20060017635 A | 2/2006 |
| RU | 2206329 C2 | 6/2003 |
| WO | 1991/02087 A1 | 2/1991 |
| WO | 1991/06309 A1 | 5/1991 |
| WO | 1992/15712 A1 | 9/1992 |
| WO | 1993/24640 A2 | 12/1993 |
| WO | 1995/07994 A2 | 3/1995 |
| WO | 1995/13392 A1 | 5/1995 |
| WO | 1996/13597 A2 | 5/1996 |
| WO | 1996/18373 A1 | 6/1996 |
| WO | 1997/41241 A1 | 11/1997 |
| WO | 2000/018433 A2 | 4/2000 |
| WO | 2001/055177 A2 | 8/2001 |
| WO | 2001/073027 A2 | 10/2001 |
| WO | 2004/023973 A2 | 3/2004 |
| WO | 2004/055166 A2 | 7/2004 |
| WO | 2005/016961 A1 | 2/2005 |
| WO | 2005/033265 A2 | 4/2005 |
| WO | 2005/071093 A2 | 8/2005 |
| WO | 2006/078294 A2 | 7/2006 |
| WO | 2006/090090 A2 | 8/2006 |
| WO | 2007/024708 A2 | 3/2007 |
| WO | 2007/047749 A1 | 4/2007 |
| WO | 2008/122811 A2 | 10/2008 |
| WO | 2008/145685 A1 | 12/2008 |
| WO | 2009/079185 A2 | 6/2009 |
| WO | 2011/128704 A1 | 10/2011 |
| WO | 2011/143656 A2 | 11/2011 |
| WO | 2012/006359 A1 | 1/2012 |
| WO | 2012/006377 A2 | 1/2012 |
| WO | 2012/006376 A3 | 4/2012 |
| WO | 2012/172058 A1 | 12/2012 |
| WO | 2012/172277 A1 | 12/2012 |
| WO | 2014/072929 A1 | 5/2014 |
| WO | 2014/168874 A2 | 10/2014 |
| WO | 2015/085233 A1 | 6/2015 |
| WO | 2015/095811 A2 | 6/2015 |
| WO | 2016/085904 A1 | 6/2016 |
| WO | 2016/100975 A1 | 6/2016 |
| WO | 2016/100977 A1 | 6/2016 |
| WO | 2016/122414 A1 | 8/2016 |
| WO | 2016/124670 A1 | 8/2016 |
| WO | 2016/154047 A2 | 9/2016 |
| WO | 2016/154246 A1 | 9/2016 |
| WO | 2016/187508 A3 | 1/2017 |
| WO | 2017/106638 A1 | 6/2017 |
| WO | 2017/151940 A2 | 9/2017 |
| WO | 2017/173321 A1 | 10/2017 |
| WO | 2017/184590 A1 | 10/2017 |
| WO | 2017/192924 A1 | 11/2017 |
| WO | 2017/220463 A1 | 12/2017 |
| WO | 2018/028438 A1 | 2/2018 |
| WO | 2018/039131 A1 | 3/2018 |
| WO | 2018/098362 A1 | 5/2018 |
| WO | 2018/102585 A1 | 6/2018 |
| WO | 2018/104911 A1 | 6/2018 |
| WO | 2018/116193 A1 | 6/2018 |
| WO | 2018/119115 A1 | 6/2018 |
| WO | 2018/187356 A2 | 10/2018 |
| WO | 2018/227030 A1 | 12/2018 |
| WO | 2018/232330 A1 | 12/2018 |
| WO | 2019/090156 A1 | 5/2019 |
| WO | 2019/170773 A1 | 9/2019 |
| WO | 2019/226939 A1 | 11/2019 |
| WO | 2019/226941 A1 | 11/2019 |
| WO | 2020/097393 A1 | 5/2020 |
| WO | 2020/243719 A1 | 12/2020 |
| WO | 2021/003348 A1 | 1/2021 |
| WO | 2021/092095 A1 | 5/2021 |
| WO | 2021/119545 A1 | 6/2021 |
| WO | 2021/142437 A1 | 7/2021 |
| WO | 2021216775 A2 | 10/2021 |
| WO | 2022/032196 A2 | 2/2022 |

OTHER PUBLICATIONS

Hong et al, Immuno-PET of Tissue Factor in Pancreatic Cancer, J Nucl Med, vol. 53, No. 11, pp. 1748-1754, 2012.

Trail et al., "Antibody drug conjugates for treatment of breast cancer: Novel targets and diverse approaches in ADC design," Pharmacol. Ther., vol. 181, pp. 126-142, 2018.

De Graaf et al., Beta-Glucuronidase-Mediated Drug Release, Curr Pharm Des., vol. 8, pp. 1391-1403, 2002.

Chari et al., Immunoconjugates Containing Novel Maytansinoids: Promising Anticancer Drugs, Cancer Research, vol. 52, pp. 127-131, 1992.

Kovtun et al., "Antibody-Mytansinoid Conjugates Designed to Bypass Multidrug Resistance," Cancer Research vol. 70, No. 6, pp. 2528-2537, 2010.

Vitetta et al., "Redesigning Nature's Poisons to Create Anti-Tumor Reagents," Science vol. 238, No. 4830, pp. 1098-1104, 1987.

Junutula et al., "Rapid identification of reactive cysteine residues for site-specific labeling of antibody-Fabs," Journal of Immunological Methods 332, No. 1-2 (2008): 41-52.

Junutula et al., "Site-specific conjugation of a cytotoxic drug to an antibody improves the therapeutic index." Nature Biotechnology 26, No. 8 (2008): 925.

Hofer et al., "An engineered selenocysteine defines a unique class of antibody derivatives," Proc. Natl. Acad. Sci. USA, 2008, 105:12451-12456.

Hofer et al., Molecularly defined antibody conjugation through a selenocysteine interface, Biochemistry, vol. 48, No. 50, pp. 12047-12057, 2009.

Hjortoe et al., Tissue factor-factor VIIa-specific up-regulation of IL-8 expression in MDA-MB-231 cells is mediated by PAR-2 and results in increased cell migration, Blood, 2004, vol. 103, No. 8, pp. 3029-3037.

Rowe et al., (eds.) Handbook of Pharmaceutical Excipients, 6th Ed. 2009.

Sakurai et al., "Expression of Tissue Factor in Epithelial Ovarian Carcinoma is Involved in the Development of Venous Thromboembolism," International Journal of Gynecologic Cancer, vol. 27, No. 1, pp. 37-43, 2017.

Cocco et al., "Expression of Tissue factor in Adenocarcinoma and Squamous Cell Carcinoma of the Uterine Cervix: Implications for immunotherapy with hI-con1, a factor VII-IgGFc chimeric protein targeting tissue factor," BMC Cancer, vol. 11 p. 263, 2011.

Christensen et al., Urokinase-type plasminogen activator receptor (uPAR), tissue factor (TF) and epidermal growth factor receptor (EGFR): tumor expression patterns and prognostic value in oral cancer, BMC Cancer, vol. 17, p. 572, 2017.

(56) References Cited

OTHER PUBLICATIONS

Yao et al., Tissue Factor and VEGF Expression in Prostate Carcinoma a Tissue Microarray Study, Cancer Invest., vol. 27, pp. 430-434, 2009.
Abdulkadir et al., "Tissue factor expression and angiogenesisin human prostate carcinoma," Human Pathology 31, No. 4 (2000): 443-447.
Zhang et al., "Pathological expression of tissue factor confers promising antitumor response to a novel therapeutic antibody SC1 in triple negative breast cancer and pancreatic adenocarcinoma," Oncotarget vol. 8, No. 35, pp. 59086-59102, 2017.
Guan et al., "Tissue factor expression and angiogenesis in human glioma." Clinical Biochemistry 35, No. 4 (2002) 321-325.
Carneiro-Lobo et al., Ixolaris, a tissue factor inhibitor, blocks primary tumor growth and angiogenesis in a glioblastoma model, J Thromb Haemost, 2009, 7:1855-1864.
Yeh et al., "Upregulation of Tissue Factor by Activated Stat3 Contributes to Malignant Pleural Effusion Generation via Enhancing Tumor Metastasis and Vascular Permeability in Lung Adenocarcinoma," PLoS One, vol. 8, No. 9, p. e75287, 2013.
Regina et al., "Increased tissue factor expression is associated with reduced survival in non-small cell lung cancer and with mutations of TP53 and PTEN," Clinical Chemistry, vol. 55, No. 10, pp. 1834-1842, 2009.
Lo et al., "Tissue factor expression in the metaplasia-adenoma-carcinoma sequence of gastric cancer in a European population," British Journal of Cancer vol. 107, No. 7, pp. 1125-1130, 2012.
Chen et al., "Immunolocalisation of tissue factor in esophageal cancer is correlated with intratumoral angiogenesis and prognosis of the patient" Acta Histochemica 112, No. 3 (2010): 233-239.
Patry et al., "Tissue factor expression correlates with disease-specific survival in patients with node-negative muscle nvasive bladder cancer," International Journal of Cancer, vol. 122, No. 7, pp. 1592-1597, 2008.
Bromberg et al., Tissue factor promotes melanoma metastasis by a pathway independent of blood coagulation, Proc Natl Acad Sci U S A., 1995, 92:8205-8209.
Silva et al., "Increased Tissue Factor Expression is an Independent Predictor of Mortality in Clear Cell Carcinoma of the Kidney," Int Braz J Urol., 2014, 40:499-506.
Van Den Berg et al., "The relationship between tissue factor and cancer progression: insights from bench and bedside," Blood vol. 119, No. 4, pp. 924-932, 2012.
Tripisciano et al., "Different Potential of Extracellular Vesicles to Support Thrombin Generation: Contributions of Phosphatidylserine, Tissue Factor, and Cellular Origin," Scientific Reports vol. 7, No. 1, pp. 1-11, 2017.
Teplyakov et al., "Crystal structure of tissue factor in complex with antibody 10H10 reveals the signaling epitope," Cellular Signalling vol. 36, pp. 139-144, 2017.
Liepe et al., "A large fraction of HLA class I ligands are proteasome-generated spliced peptides," Science vol. 354, No. 6310, Oct. 21, 2016.
Smith et al., "Comparison of biosequences," Advances in Applied Mathematics vol. 2, No. 4, pp. 482-489, 1981.
Needleman et al., "A General Method Applicable to the Search for Similarities in the Amino Acid Sequence of Two Proteins," Journal of Molecular Biology, vol. 48, No. 3, pp. 443-453, 1970.
Pearson et al., "Improved tools for biological sequence comparison," Proceedings of the National Academy of Sciences, vol. 85, No. 8, pp. 2444-2448, 1988.
Altschul et al., "Basic Local Alignment Search Tool." Journal of Molecular Biology vol. 215, Issue 3 (1990): 403-410.
Kornher et al., "Mutation detection using nucleotide analogs that alter electrophoretic mobility," Nucleic Acids Research vol. 17, No. 19, pp. 7779-7784, 1989.
Sokolov, "Primer extension technique for the detection of single nucleotide in genomic DNA," Nucleic Acids Research, vol. 18, No. 12, p. 3671, 1990.
Syvänen et al., "A Primer-Guided Nucleotide Incorporation Assay in the Genotyping of Apolipoprotein E," Genomics 8, No. 4 (1990): 684-692.
Kuppuswamy et al., "Single nucleotide primer extension to detect genetic diseases: experimental application to hemophilia B (factor IX) and cystic fibrosis genes," Proceedings of the National Academy of Sciences vol. 88, No. 4, pp. 1143-1147, 1991.
Prezant et al., "Trapped-Oligonucleotide Nucleotide Incorporation (TONI) Assay, a Simple Method for Screening Point Mutations," Human Mutation 1, No. 2 (1992): 159-164.
Jgozzoli et al., "Detection of specific alleles by using allele-specific primer extension followed by capture on solid support," Genetic Analysis: Biomolecular Engineering 9, No. 4 (1992): 107-112.
Nyrén et al., "Solid phase DNA minisequencing by an enzymatic luminometric inorganic pyrophosphate detection assay." Analytical Biochemistry 208, No. 1 (1993): 171-175.
Syvänen et al., "Identification of Individuals by Analysis of Biallelic DNA Markers, Using PCR and Solid-Phase Minisequencing," American Journal of Human Genetics vol. 52, No. 1, p. 46 1993.
Merrifield, "Solid phase synthesis." Science 232 (1986): 341-348.
Dupuis et al., "Dendritic cells internalize vaccine adjuvant after intramuscular injection," Cellular Immunology 186, No. 1 (1998), 18-27.
Allison, "The mode of action of immunological adjuvants," Developments in Biological Standardization 92 (1998): 3-11.
Gabrilovich et al., "IL-12 and Mutant P53 Peptide-Pulsed Dendritic Cells for the Specific Immunotherapy of Dancer," Journal of Immunotherapy, vol. 19, No. 6 (1996): 414-418.
Tatsis et al., "Adenoviruses as vaccine vectors," Molecular Therapy vol. 10, No. 4, pp. 616-629, 2004.
Hu et al., "Immunization Delivered by Lentiviral Vectors for Cancer and Infectious Diseases," Immunological Reviews, vol. 239, Issue 1, pp. 45-61, 2011.
Karasaki et al., "Identification of individual cancer-specific somatic mutations for neoantigen-based immunotherapy of lung cancer." Journal of Thoracic Oncology 11, No. 3 (Mar. 2016): 324-333.
Abbas et al., "Structure of human IFIT1 with capped RNA reveals adaptable mRNA binding and mechanisms for sensing N1 and N2 ribose 2?-O methylations." Proceedings of the National Academy of Sciences 114, No. 11 (2017): E2106-E2115.
Nezafat et al., "A novel multi-epitope peptide vaccine against cancer: an in silico approach." Journal of theoretical biology 349 (2014): 121-134.
Mohammed et al., "Phosphorylation-dependent interaction between antigenic peptides and MHC class I: a molecular basis for the presentation of transformed self" Nature immunology 9, No. 11 (2008): 1236-1243.
Toes et al., "Protective anti-tumor immunity induced by vaccination with recombinant adenoviruses encoding multiple tumor-associated cytotoxic T lymphocyte epitopes in a string-of-beads fashion." Proceedings of the National Academy of Sciences 94, No. 26 (1997): 14660-14665.
Wei et al., "Dendritic cells expressing a combined PADRE/MUC4-derived polyepitope DNA vaccine induce multiple cytotoxic T-cell responses." Cancer biotherapy & radiopharmaceuticals 23, No. 1 (2008): 121-128.
Meko'o et al., "Immunopreventive effects against murine H22 hepatocellular carcinoma in vivo by a DNA vaccine targeting a gastrin-releasing peptide." Asian Pacific Journal of Cancer Prevention 15, No. 20 (2014): 9039-9043.
Huang et al., "DNA vaccines for cervical cancer." American journal of translational research 2, No. 1 (2010): 75, 13 pages.
Behrens et al., "Antibody-Drug Conjugates (ADCs) Derived from Interchain Cysteine Cross-Linking Demonstrate Improved Homogeneity and Other Pharmacological Properties over Conventional Heterogeneous ADCs," Molecular Pharmaceutics 12 (11) ( ): 3986-3998, Nov. 2, 2015.
Koizume et al., "Tissue Factor—Factor VII Complex as a Key Regulator of Ovarian Cancer Phenotypes," Biomarkers in Cancer vol. 7, pp. 1-13, Aug. 5, 2015.
Schumacher et al., "Neoantigens in cancer immunotherapy," Science vol. 348, Issue 6230, pp. 69-74, Apr. 3, 2015.

(56) References Cited

OTHER PUBLICATIONS

Rivas et al., "Effect of predicted protein-truncating genetic variants on the human transcriptome," Science vol. 348, No. 6235, pp. 666-669, May 8, 2015.
Sakuma et al., "Lentiviral vectors: basic to translational," Biochemical Journal 443, No. 3 (2012): 603-618.
Cooper et al., "Rescue of splicing-mediated intron loss maximizes expression in lentiviral vectors containing the human ubiquitin C promoter," Nucleic Acids Research vol. 43, No. 1, pp. 682-690, Dec. 17, 2014.
Zufferey et al., "Self-Inactivating Lentivirus Vector for Safe and Efficient In Vivo Gene Delivery," Journal of Virology vol. 72, No. 12, pp. 9873-9880, 1998.
Gros et al., "Prospective identification of neoantigen-specific lymphocytes in the peripheral blood of melanoma patients," Nature Medicine vol. 22, Issue 4, pp. 433-438, Feb. 22, 2016.
Strønen et al., "Targeting of cancer neoantigens with donor-derived T cell receptor repertoires," Science 352, No. 6291 (May 19, 2016): 1337-1341.
Lu et al., "Efficient identification of mutated cancer antigens recognized by T cells associated with durable tumor Yegressions," Clinical Cancer Research vol. 20, No. 13, pp. 3401-3410, 2014.
Stover et al., "New use of BCG for recombinant vaccines," Nature vol. 351, No. 6326, pp. 456-460, 1991.
Boshart et al., "A Very Strong Enhancer is Located Upstream of an Immediate Early Gene of Human Cytomegalovirus," Cell vol. 41, No. 2, 521-530, 1985.
Kost et al.,"The nucleotide sequence of the chick cytoplasmic b-actin gene," Nucleic Acids Research vol. 11, No. 23, pp. 8287-8301, 1983.
Shukla et al., "Comprehensive analysis of cancer-associated somatic mutations in class I HLA genes," Nature Biotechnology vol. 33, No. 11. pp. 1152-1158, Nov. 2015.
McGranahan et al., "Allele-specific HLA loss and immune escape in lung cancer evolution," Cell vol. 171, No. 6, pp. 1259-1271, 2017.
Van Loo et al., "Allele-specific copy number analysis of tumors," Proceedings of the National Academy of Sciences, vol. 107, No. 39, pp. 16910-16915, 2010.
Desrichard et al., "Cancer neoantigens and applications for immunotherapy," Clinical Cancer Research vol. 22, No. 4, pp. 807-812, Feb. 15, 2016.
Gubin et al., "Tumor neoantigens: Building a framework for personalized cancer immunotherapy," The Journal of Clinical Investigation, vol. 125, No. 9, pp. 3413-3421, Sep. 2015.
Rizvi et al., "Mutational landscape determines sensitivity to PD-1 blockade in non-small cell lung cancer," Science vol. 348, No. p. 6230, Apr. 3, 2015.
Snyder et al., "Genetic Basis for Clinical Response to CTLA4 Blockade in Melanoma," New England Journal of Medicine, vol. 371, No. 23, pp. 2189-2199, 2014.
Carreno et al., "A dendritic cell vaccine increases the breadth and diversity of melanoma neoantigen-specific T cells." Science 348, No. 6236 (Apr. 2, 2015): 9 pages.
Tran et al., "Cancer Immunotherapy Based on Mutation-Specific CD4+ T Cells in a Patient with Epithelial Cancer," Science vol. 344, No. 6184, pp. 641-645, 2014.
Lundegaard et al., "State of the art and challenges in sequence based T-cell epitope prediction," Immunome Research vol. 6, No. 2, pp. 1-14, 2010.
Yadav et al., "Predicting immunogenic tumour mutations by combining mass spectrometry and exome sequencing," Nature, vol. 515, No. 7528, pp. 572-576, 2014.
Bassani-Sternberg et al., "Mass Spectrometry of Human Leukocyte Antigen Class I Peptidomes Reveals Strong Effects of Protein Abundance and Turnover on Antigen Presentation," Molecular & Cellular Proteomics Vo. 14, Issue 3, 658-673, Mar. 1, 2015.
Van Allen et al., "Genomic correlates of response to CTLA-4 blockade in metastatic melanoma," Science vol. 350, No. 6257, pp. 207-211, Nov. 11, 2015.
Yoshida et al., "Splicing factor mutations and cancer," Wiley Interdisciplinary Reviews: RNA 5, No. 4 (2014): 445-459.
Cancer Genome Atlas Research Network, "Comprehensive molecular profiling of lung adenocarcinoma," Nature, vol. 511, pp. 543-550, 2014.
Rajasagi et al., "Systematic identification of personal tumor-specific neoantigens in chronic lymphocytic leukemia," Blood, vol. 124, No. 3, pp. 453-462, 2014.
Cieslik et al., "The use of exome capture RNA-seq for highly degraded RNA with application to clinical cancer sequencing," Genome Research vol. 25, No. 9, 1372-1381, Sep. 1, 2015.
Bodini et al., "The hidden genomic landscape of acute myeloid leukemia: subclonal structure revealed by undetected mutations," Blood, The Journal of the American Society of Hematology vol. 125, No. 4 (Jan. 22, 2015): 600-605.
Saunders et al., Strelka: accurate somatic small-variant calling from sequenced tumor-normal sample pairs, Bioinformatics vol. 28, No. 14, pp. 1811-1817, 2012.
Cibulskis et al., "Sensitive detection of somatic point mutations in impure and heterogeneous cancer samples," Nature Biotechnology vol. 31, No. 3, pp. 213-219, 2013.
Wilkerson et al., "Integrated RNA and DNA sequencing improves mutation detection in low purity tumors," Nucleic Acids Research, vol. 42, p. e107, 2014.
Mose et al., "ABRA: improved coding indel detection via assembly-based realignment," Bioinformatics, vol. 30, No. 19, pp. 2813-2815, 2014.
Ye et al., "Pindel: a pattern growth approach to detect break points of large deletions and medium sized insertions from paired-end short reads," Bioinformatics vol. 25, No. 21, pp. 2865-2871, 2009.
Lam et al., "Nucleotide-resolution analysis of structural variants using BreakSeq and a breakpoint library," Nature Biotechnology vol. 28, No. 1, pp. 47-55 2010.
Frampton et al., "Development and validation of a clinical cancer genomic profiling test based on massively parallel DNA sequencing," Nature Biotechnology vol. 31, No. 11, 2013.
Boegel et al., "HLA typing from RNA-Seq sequence reads," Genome Medicine vol. 4, Issue 12, 2013.
Liu et al., "ATHLATES: accurate typing of human leukocyte antigen through exome sequencing," Nucleic Acids Research vol. 41, No. 14, 2013.
Mayor et al., "HLA typing for the next generation," PLoS One vol. 10, No. 5, May 27, 2015.
Roy et al., "Assessing long-distance RNA sequence connectivity via RNA-templated DNA-DNA ligation," Elife vol. 4, p. e03700, Apr. 13, 2015.
Song et al., "CLASS: constrained transcript assembly of RNA-seq reads," BMC Bioinformatics, vol. 14, Supp. 5, S14, BioMed Central, 2013.
Maretty et al. "Bayesian transcriptome assembly," Genome Biology vol. 15, No. 10, Oct. 2014.
Pertea et al., "StringTie enables improved reconstruction of a transcriptome from RNA-seq reads," Nature Biotechnology vol. 33, No. 3, pp. 290-295, Mar. 2015.
Roberts et al., "Identification of novel transcripts in annotated genomes using RNA-Seq," Bioinformatics vol. 27, No. 17, pp. 2325-2329, 2011.
Vitting-Seerup et al., "spliceR: an R package for classification of alternative splicing and prediction of coding potential from RNA-seq data," BMC Bioinformatics, vol. 15, Issue 1, pp. 1-7, 2014.
Skelly et al., "A powerful and flexible statistical framework for testing hypotheses of allele-specific gene expression from RNA-seq data," Genome Research vol. 21, No. 10, pp. 1728-1737, 2011.
Anders et al., "HTSeq—a Python framework to work with high-throughput sequencing data." Bioinformatics vol. 31, No. 2 (Jan. 15, 2015): 166-169.
Furney et al., "SF3B1 Mutations Are Associated with Alternative Splicing in Uveal Melanoma," Cancer Discovery vol. 3, Issue 10, pp. 1122-1129, 2013.
Zhou et al., "A Chemical Genetics Approach for the Functional Assessment of Novel Cancer Genes," Cancer Research vol. 75, No. 10, pp. 1949-1958, May 15, 2015.

(56) References Cited

OTHER PUBLICATIONS

Maguire et al., "SF3B1 mutations constitute a novel therapeutic target in breast cancer," The Journal of Pathology vol. 235, No. 4 pp. 571-580, Mar. 2015.
Carithers et al., "A Novel Approach to High-Quality Postmortem Tissue Procurement: The GTEx Project," Biopreservation and Biobanking, vol. 13, No. 5, 311-319, Oct. 1, 2015.
Xu et al., "RNA CoMPASS: A Dual Approach for Pathogen and Host Transcriptome Analysis of RNA-Seq Datasets," PloS ONE, vol. 9, Issue 2, p. e89445, 2014.
Andreatta et al., "Gapped sequence alignment using artificial neural networks: application to the MHC class I system," Bioinformatics 1 (Feb. 15, 2015): 7 pages.
Jørgensen et al., "NETMHCSTAB-predicting stability of peptide—MHC-I complexes; impacts for cytotoxic T lymphocyte epitope discovery," Immunology vol. 141, No. 1, pp. 18-26, 2014.
Larsen et al., "An integrative approach to CTL epitope prediction: a combined algorithm integrating MHC class I binding, TAP transport efficiency, and proteasomal cleavage predictions," European Journal of Immunology, vol. 35, No. 8, pp. 2295-2303, 2005.
Nielsen et al., "The role of the proteasome in generating cytotoxic T-cell epitopes: insights obtained from improved predictions of proteasomal cleavage," Immunogenetics vol. 57, No. 1-2, pp. 33-41, 2005.
Boisvert et al., "A Quantitative Spatial Proteomics Analysis of Proteome Turnover in Human Cells," Molecular & Cellular Proteomics, vol. 11, Issue. 3, Mar. 1, 2012.
Duan et al., "Genomic and bioinformatic profiling of mutational neoepitopes reveals new rules to predict anticancer immunogenicity," Journal of Experimental Medicine vol. 211, No. 11, Oct. 20, 2014.
Calis et al., "Properties of MHC Class I Presented Peptides That enhance immunogenicity." PLoS Comput Biol. vol. 9, Issue 10 (Oct. 24, 2013): e1003266, 13 pages.
Zhang et al., "Intra-tumor Heterogeneity in Localized Lung Adenocarcinomas Delineated by Multi-region Sequencing," Science vol. 346, No. 6206, pp. 256-259, 2014.
Walter et al., "Clonal Architecture of Secondary Acute Myeloid Leukemia," New England Journal of Medicine, vol. 366, Issue 12, pp. 1090-1098, 2012.
Hunt et al., "Characterization of Peptides Bound to the Class I MHC Molecule HLA-A2.1 by Mass Spectrometry," Science vol. 255, pp. 1261-1263, 1992.
Zarling et al., "Identification of class I MHC-associated phosphopeptides as targets for cancer immunotherapy," Proceedings of the National Academy of Sciences, vol. 103, No. 40, pp. 14889-14894, 2006.
Abelin et al., "Complementary IMAC enrichment methods for HLA-associated phosphopeptide identification by mass spectrometry," Nature Protocols 10(9) (2015): 1308-1318.
Barnstable et al., "Production of Monoclonal Antibodies to Group A Erythrocytes, HLA and Other Human Cell Surface Antigens-New Tools for Genetic Analysis," Cell vol. 14, Sep. 20, 1978.
Goldman et al., "HLA-DA monoclonal antibodies inhibit the proliferation of normal and chronic granulocytic leukaemia myeloid progenitor cell," British Journal of Haematology 52, No. 3 (1982): 411-420.
Eng et al., "Comet: An open-source MS/MS sequence database search tool," Proteomics vol. 13, No. 1, pp. 22-24, 2013.
Eng et al., "A Deeper Look into Comet—Implementation and Features," Journal of the American Society for Mass Spectrometry vol. 26, No. 11, pp. 1865-1874, 2015.
Käll et al., "Semi-supervised learning for peptide identification from shotgun proteomics datasets," Nature Methods vol. 4, No. 11, pp. 923-925, 2007.
Käll et al., "Assigning Significance to Peptides Identified by Tandem Mass Spectrometry Using Decoy Databases," Journal of Proteome Research vol. 7, No. 01, pp. 29-34, 2008.
Käll et al., "Non-parametric estimation of posterior error probabilities associated with peptides identified by tandem mass spectrometry," Bioinformatics vol. 24, No. 16, pp. i42-i48, 2008.
Kinney et al., "Nucleotide sequence of the 26 S mRNA of the virulent Trinidad donkey strain of Venezuelan equine encephalitis virus and deduced sequence of the encoded structural proteins," Virology 152, No. 2 (1986): 400-413.
Slansky et al., "Enhanced Antigen-Specific Antitumor Immunity with Altered Peptide Ligands that Stabilize the MHC-Peptide-TCR Complex," Immunity vol. 13, No. 4, pp. 529-538, 2000.
Huang et al., "The immunodominant major histocompatibility complex class I-restricted antigen of a murine colon tumor derives from an endogenous retroviral gene product," Proceedings of the National Academy of Sciences vol. 93, No. 18, pp. 9730-9735, 1996.
Johnson et al., "Molecular Determinants of Alphavirus Neurovirulence: Nucleotide and Deduced Protein Sequence Changes during Attenuation of Venezuelan Equine Encephalitis Virus," Journal of General Virology vol. 67, Issue 9, pp. 1951-1960, 1986.
Aarnoudse et al., "TCR Reconstitution in Jurkat Reporter Cells Facilitates the Identification of Novel Tumor Antigens by CDNA Expression Cloning," International Journal of Vancer 99, 7013 (2002).
Alexander et al., "Development of High Potency Universal DR-Restricted Helper Epitopes by Modification of High Affinity DR-Blocking Peptides." Immunity vol. 1, Issue 9 (1994): 751-761.
Banu et al., "Building and Optimizing a Virus-specific T Cell Receptor Library for Targeted Immunotherapy in Viral Infections." Scientific Reports vol. 4, pp. 4166, 2014.
Cornet et al., "Optimal organization of a polypeptide-based candidate cancer vaccine composed of cryptic tumor peptides with enhanced immunogenicity," Vaccine vol. 24, No. 12, pp. 2102-2109, 2006.
Depla et al., "Rational Design of a Multiepitope Vaccine Encoding T-Lymphocyte Epitopes for Treatment of Chronic Hepatitis B Virus Infections," Journal of Virology vol. 82, No. 1, pp. 435-450, 2008.
Ishioka et al., "Utilization of MHC Class I Transgenic Mice for Development of Minigene DNA Vaccines Encoding Multiple HLA-Restricted CTL Epitopes," The Journal of Immunology vol. 162, No. 7, pp. 3915-3925, 1999.
Janetzki et al., "Guidelines for the automated evaluation of Elispot assays," Nature Protocols vol. 10, No. 7, pp. 1098-1115, Jul. 2015.
Lyons et al., "Influence of Human CDS on Antigen Recognition by T-Cell Receptor-Transduced Cells," Cancer Research vol. 66, No. 23, p. 11455-11461,2006.
Nagai et al., "Aurora kinase A-specific T-cell receptor gene transfer redirects T lymphocytes to display effective antileukemia reactivity," Blood, The Journal of the American Society of Hematology, vol. 119, No. 2, pp. 368-376, 2012.
Panina-Bordignon et al., "Universally immunogenic T cell epitopes: promiscuous binding to human MHC class II and promiscuous recognition by T cells," European Journal of Immunology 19, No. 12 (1989): 2237-2242.
Vitiello et al., "Analysis of the HLA-restricted Influenza-specific Cytotoxic T Lymphocyte Response in Transgenic Mice Carrying a Chimeric Human-Mouse Class I Major Histocompatibility Complex," The Journal of Experimental Medicine, vol. 173, No. 4, pp. 1007-1015, 1991.
Yachi et al., "Altered Peptide Ligands Induce Delayed CD8-T Cell Receptor Interaction—a Role for CD8 in Distinguishing Antigen Quality," Immunity vol. 25, No. 2, pp. 203-211, 2006.
Pushko et al., "Replicon-Helper Systems from Attenuated Venezuelan Equine Encephalitis Virus: Expression of Heterologous Genes in Vitro and Immunization against Heterologous Pathogens in Vivo," Virology vol. 239, No. 2, pp. 389-401, 1997.
Strauss et al., "The Alphaviruses: Gene Expression, Replication, and Evolution," Microbiological Reviews, vol. 58, No. 3, pp. 491-562, 1994.
Rhëme et al., "Alphaviral cytotoxicity and its implication in vector development," Experimental Physiology vol. 90, No. 1, pp. 45-52, 2005.
Riley et al., "Recent advances in nanomaterials for gene delivery—a review," Nanomaterials, vol. 7, No. 5, p. 94, 2017.
Frolov et al., "Cis-acting RNA elements at the 5' end of Sindbis virus genome RNA regulate minus- and plus-strand RNA synthesis," RNA vol. 7, No. 11, pp. 1638-1651, 2001.

(56) References Cited

OTHER PUBLICATIONS

Jose et al., "A structural and functional perspective of alphavirus replication and assembly," Future Microbiology, vol. 1, No. 7, pp. 837-856, 2009.

Li et al., "RSEM: accurate transcript quantification from RNA-Seq data with or without a reference genome." BMC bioinformatics 12, No. 1 (2011): 323, 16 pages.

Pearson et al., "MHC class I-associated peptides derive from selective regions of the human genome," The Journal of Clinical Investigation, vol. 126, No. 12, pp. 4690-4701, Dec. 1, 2016.

Mommen et al., "Sampling from the Proteome to the Human Leukocyte Antigen-DR (HLA-DR) Ligandome ProceedsVia High Specificity," Molecular & Cellular Proteomics, vol. 15, No. 4, pp. 1412-1423, Apr. 1, 2016.

Kreiter et al., "Mutant MHC class II epitopes drive therapeutic immune responses to cancer," Nature, vol. 520, No. 7549, pp. 692-696, Apr. 2015.

Andreatta et al., "Accurate pan-specific prediction of peptide-MHC class II binding affinity with improved binding core identification." Immunogenetics 67, No. 11-12 (Nov. 2015): 641-650.

Nielsen et al., "NN-align. An artificial neural network-based alignment algorithm for MHC class II peptide binding prediction," BMC Bioinformatics, vol. 10, No. 1, p. 296, 2009.

Nielsen et al., "Prediction of MHC class II binding affinity using SMM-align, a novel stabilization matrix alignment method," BMC Bioinformatics, vol. 8, No. 1, pp. 238, 2007.

Zhang, et al., "Peaks DB: De Novo Sequencing Assisted Database Search for Sensitive and Accurate Peptide Identification," Molecular & Cellular Proteomics vol. 11, No. 4, 2012.

Jensen et al., "Improved methods for predicting peptide binding affinity to MHC class II molecules," Immunology vol. 154, Issue 3, pp. 394-406, 2018.

Carter et al., "Absolute quantification of somatic DNA alterations in human cancer," Nature Biotechnology vol. 30, No. 5, 413-421, 2012.

PCT/US18/31696—International Search Report and Written Opinion, dated Aug. 3, 2018, 12 pages.

Qiu et al., "Reviving virus based cancer vaccines by using cytomegalovirus vectors expressing modified tumor antigens," OncoImmunology vol. 5, No. 1, p. e1056974, Jan. 2, 2016.

Farina et al., "Replication-Defective Vector Based on a Chimpanzee Adenovirus," Journal of Virology vol. 75, No. 23, pp. 11603-11613, 2001.

Ljungberg et al., "Self-replicating alphavirus RNA vaccines," Expert Review of Vaccines vol. 14, No. 2, pp. 177-194, Feb. 1, 2015.

Lundstrom, "Alphavirus-Based Vaccines," Viruses vol. 6, No. 6, pp. 2392-2415, 2014.

Geall et al., "Nonviral delivery of self-amplifying RNA vaccines," Proceedings of the National Academy of Sciences, vol. 109, Issue 36, pp. 14604-14609, 2012.

Rodriguez et al., "DNA Immunization with Minigenes: Low Frequency of Memory Cytotoxic T Lymphocytes and Inefficient Antiviral Protection Are Rectified by Ubiquitination," Journal of Virology vol. 72, No. 6, pp. 5174-5181, 1998.

Velders et al., "Defined Flanking Spacers and Enhanced Proteolysis is Essential for Eradication of Established Tumors by an Epitope String DNA Vaccine," The Journal of Immunology, vol. 166, No. 9, pp. 5366-5373, 2001.

Kreiter et al., "Increased Antigen Presentation Efficiency by Coupling Antigens to MHC Class I Trafficking Signals," The Journal of Immunology, vol. 180, No. 1, pp. 309-318, 2008.

Rodriguez et al., "DNA Immunization: Ubiquitination of a Viral Protein Enhances Cytotoxic T-Lymphocyte Induction and Antiviral Protection but Abrogates Antibody Induction," Journal of Virology vol. 71, No. 11, pp. 8497-8503, 1997.

James et al., "Tetramer-guided epitope mapping reveals broad, individualized repertoires of tetanus toxin-specific CD4+ T cells and suggests HLA-based differences in epitope recognition," International Immunology vol. 19, No. 11, pp. 1291-1301, 2007.

Jayaraman et al., "Maximizing the Potency of siRNA Lipid Nanoparticles for Hepatic Gene Silencing In Vivo," Angewandte Chemie vol. 51, pp. 8529-8533, 2012.

Démoulins et al., "Polyethylenimine-based polyplex delivery of self-replicating RNA vaccines," Nanomedicine: Nanotechnology, Biology and Medicine vol. 12, No. 3, pp. 711-722, Apr. 1, 2016.

Chahal et al., "Dendrimer-RNA nanoparticles generate protective immunity against lethal Ebola, H1N1 influenza, and Toxoplasma gondii challenges with a single dose," Proceedings of the National Academy of Sciences vol. 113, No. 29 E4133-E4142, Jul. 19, 2016.

PCT/US18/31696—International Preliminary Report on Patentabilty, dated Nov. 12, 2019, 9 pages.

Vajdy et al., "Mucosal adjuvants and delivery systems for protein-, DNA- and RNA-based vaccines," Immunology and Cell Biology, vol. 82, No. 6, pp. 617-627, 2004.

Fleeton et al., "Self-Replicative RNA Vaccines Elicit Protection against Influenza A Virus, Respiratory Syncytial Virus, and a Tickborne Encephalitis Virus," The Journal of Infectious Diseases vol. 183, No. 9, pp. 1395-1398, 2001.

Strejan et al., "Suppression of chronic-relapsing experimental allergic encephalomyelitis in strain-13 guinea pigs by administration of liposome-associated myelin basic protein." Journal of Neuroimmunology 7 (1984): 27-41.

Johanning et al., "A Sindbis virus mRNA polynucleotide vector achieves prolonged and high level heterologous gene expression in vivo," Nucleic Aids Research vol. 23, Issue 9, pp. 1495-1501, 1995.

Martinon et al., "Induction of virus-specific cytotoxic T lymphocytes in vivo by liposome-entrapped mRNA," European Journal of Immunology 23, No. 7 (1993): 1719-1722.

Leitner et al., "DNA and RNA-based vaccines: principles, progress and prospects," Vaccine vol. 18, No. 9-10, pp. 765-777, 1999.

Del Val et al., "Efficient Processing of an Antigenic Sequence for Presentation by MHC Class I Molecules Depends an Its Neighboring Residues in the Protein," Cell vol. 66, No. 6, pp. 1145-1153, 1991.

Holzhütter et al., "A Theoretical Approach Towards the Identification of Cleavage-Determining Amino Acid Motifs of the 20S Proteasome," Journal of Molecular Biology, vol. 286, Issue 4, pp. 1251-1265, 1999.

Nussbaum et al., "Cleavage motifs of the yeast 20S proteasome β subunits deduced from digests of enolase 1," Proceedings of the National Academy of Sciences, vol. 95, No. 21, pp. 12504-12509, 1998.

Eggers et al., "The Cleavage Preference of the Proteasome Governs the Yield of Antigenic Peptides," The Journal of Experimental Medicine vol. 182, No. 6, pp. 1865-1870, 1995.

Borthwick et al., "Vaccine-elicited human T cells recognizing conserved protein regions inhibit HIV-1." Molecular therapy 22, No. 2 (2014): 464-475.

Ager et al., "31st Annual Meeting and Associated Programs of the Society for Immunotherapy of Cancer (SITC 2016) part two," in Journal for ImmunoTherapy of Cancer, vol. 4, Supplement 1, p. 73, 2016.

Warimwe et al. "Immunogenicity and efficacy of a chimpanzee adenovirus-vectored Rift Valley fever vaccine in mice," Virology Journal vol. 10, No. 1, pp. 1-9, 2013.

Cappuccini et al. "Immunogenicity and efficacy of the novel cancer vaccine based on simian adenovirus and MVA vectors alone and in combination with PD-1 mAb in a mouse model of prostate cancer," Cancer Immunol. Immunother. Vol. 65, No. 6, pp. 701-713, Apr. 6, 2016.

Aurisicchio et al., "Immunogenicity and Therapeutic Efficacy of a Dual-Component Genetic Cancer Vaccine Cotargeting Carcinoembryonic Antigen and HER2/neu in Preclinical Models," Human Gene Therapy, vol. 25, Issue 2, pp. 121-131, Feb. 2014.

Morris et al. "Simian adenoviruses as vaccine vectors." Future Virology, vol. 11, No. 9 pp. 649-659, Sep. 15, 2016.

Leytourneau et al. "Design and Pre-Clinical Evaluation of a Universal HIV-1 Vaccine," PloS ONE, vol. 2, No. 10, p. e984, 2007.

Colloca et al., "Vaccine Vectors Derived from a Large Collection of Simian Adenoviruses Induce Potent Cellular Immunity Across Multiple Species," Science Translational Medicine, vol. 4, No. 115, 115ra2, 2012.

(56) References Cited

OTHER PUBLICATIONS

Levy et al. "A melanoma multiepitope polypeptide induces specific CD8+ T-cell response," Cellular Immunology, vol. 250, No. 1-2, pp. 24-30, 2007.
Tatsis et al. "Chimpanzee-origin adenovirus vectors as vaccine carriers," Gene Therapy vol. 13, No. 5, pp. 421-429, 2006.
Zappasodi et al., "Alphavirus-based vaccines in melanoma: rationale and potential improvements in immunotherapeutic combinations." Immunotherapy 7, No. 9 (Sep. 2015): 981-997.
Riabov et al., "Anti-tumor effect of the alphavirus-based virus-like particlevector expressing prostate-specific antigen n a HLA-DR transgenic mouse model of prostate cancer." Vaccine 33, No. 41 (Oct. 5, 2015): 5386-5395.
Fang et al., "Stable antibody expression at therapeutic levels using the 2A peptide." Nature biotechnology 23, No. 5 (2005): 584-590.
Wu et al., "Targeting genes: delivery and persistent expression of a foreign gene driven by mammalian regulatory elements in vivo." Journal of Biological Chemistry 264, No. 29 (1989): 16985-16987.
Fisher et al., "The transmembrane domain of diphtheria toxin improves molecular conjugate gene transfer." Biochemical Journal 321, No. 1 (1997): 49-58.
Szoka et al., "Comparative properties and methods of preparation of lipid vesicles (liposomes)." Annual review of biophysics and bioengineering 9, No. 1 (1980): 467-508.
Wolff et al., "Direct gene transfer into mouse muscle in vivo." Science 247, No. 4949 (1990): 1465-1468.
Felgner et al., "Lipofection: a highly efficient, lipid-mediated DNA-transfection procedure." Proceedings of the National Academy of Sciences 84, No. 21 (1987): 7413-7417.
Mannino et al., "Liposome mediated gene transfer." Biotechniques 6, No. 7 (1988): 682-690.
Konarska et al., "Recognition of cap structure in splicing in vitro of mRNA precursors." Cell 38, No. 3 (1984): 731-736.
Huang, "Sindbis virus vectors for expression in animal cells." Current Opinion in Biotechnology 7, No. 5 (1996): 531-535.
Wan et al., "High-sensitivity monitoring of ctDNA by patient-specific sequencing panels and integration of variant reads." bioRxiv (2019): 759399, pp. 1-37.
Wang et al., "Identification of T Cell Receptors Targeting KRAS-Mutated Human Tumors", Cancer Immunology Research 4(3) Mar. 2016, pp. 204-214.
Hacohen et al., "Getting personal with neoantigen-based therapeutic cancer vaccines." Cancer immunology research 1, No. 1 (2013): 11-15.

Lundstrom, Kenneth. "Alphavirus-based vaccines." Current opinion in molecular therapeutics 4, No. 1 (2002): 28-34.
Alexander et al., "Linear Padre T helper epitope and carbohydrate B cell epitope conjugates induce specific high titer IgG antibody responses." The Journal of Immunology 164, No. 3 (Feb. 2000): 1625-1633.
Kim et al., "Neopepsee: accurate genome-level prediction of neoantigens by harnessing sequence and amino acid mmunogenicity information." Annals of Oncology 29, No. 4 (Apr. 2018): 1030-1036.
Ott et al., "An immunogenic personal neoantigen vaccine for patients with melanoma" Nature 547, No. 7662 (Jul. 2017): 217-221.
Gen Bank: AF394196.1—Simian adenovirus 25, complete genome, 15 pages, 2001.
Fluet et al., "Effects of rapid antigen degradation and VEE glycoprotein specificity on immune responses induced by a VEE replicon vaccine." Virology 370, No. 1 (Jan. 2008): 22-32.
Ogawa et al., "An Attempt of Cytokine Gene Therapy Using Adenovirus Vectors," Partial Translation of: Biotherapy, 1998, vol. 12 No 5, p. 785-787.
Nielsen et al., "An in vitro-transcribed-mRNA polyepitope construct encoding 32 distinct HLA class I-restricted epitopes from Cmv, Ebv, and Influenza for use as a functional control in human immune monitoring studies." Journal of mmunological methods 360, No. 1-2 (2010): 149-156.
Bergmann et al., "Differential effects of flanking residues on presentation of epitopes from chimeric peptides." Journal of virology 68, No. 8 (1994): 5306-5310.
Carroll et al., "Alphavirus replicon-based adjuvants enhance the immunogenicity and effectiveness of Fluzone in rhesus macaques." Vaccine 29, No. 5 (2011): 931-940.
Thompson et al.,"The contribution of type I interferon signaling to immunity induced by alphavirus replicon vaccines." Vaccine 26, No. 39 (2008): 4998-5003.
Ljungberg et al.,. "Increased immunogenicity of a DNA-launched Venezuelan equine encephalitis virus-based replicon DNA vaccine." Journal of virology 81, No. 24 (2007): 13412-13423.
Channon et al., "Improved adenoviral vectors: cautious optimism for gene therapy." QJM: monthly journal of the Association of Physicians 90, No. 2 (1997): 105-109.
Gao et al., "Biology of adenovirus vectors with E1 and E4 deletions for liver-directed gene therapy." Journal of virology 70, No. 12 (1996): 8934-8943.
Andrews et al., "Generation and characterization of E1/E2a/E3/E4-deficient adenoviral vectors encoding human factor VIII." Molecular Therapy 3, No. 3 (2001): 329-336.
Farina et al., "Replication-defective vector based on a chimpanzee adenovirus." Journal of virology 75, No. 23 (2001) 11603-11613.

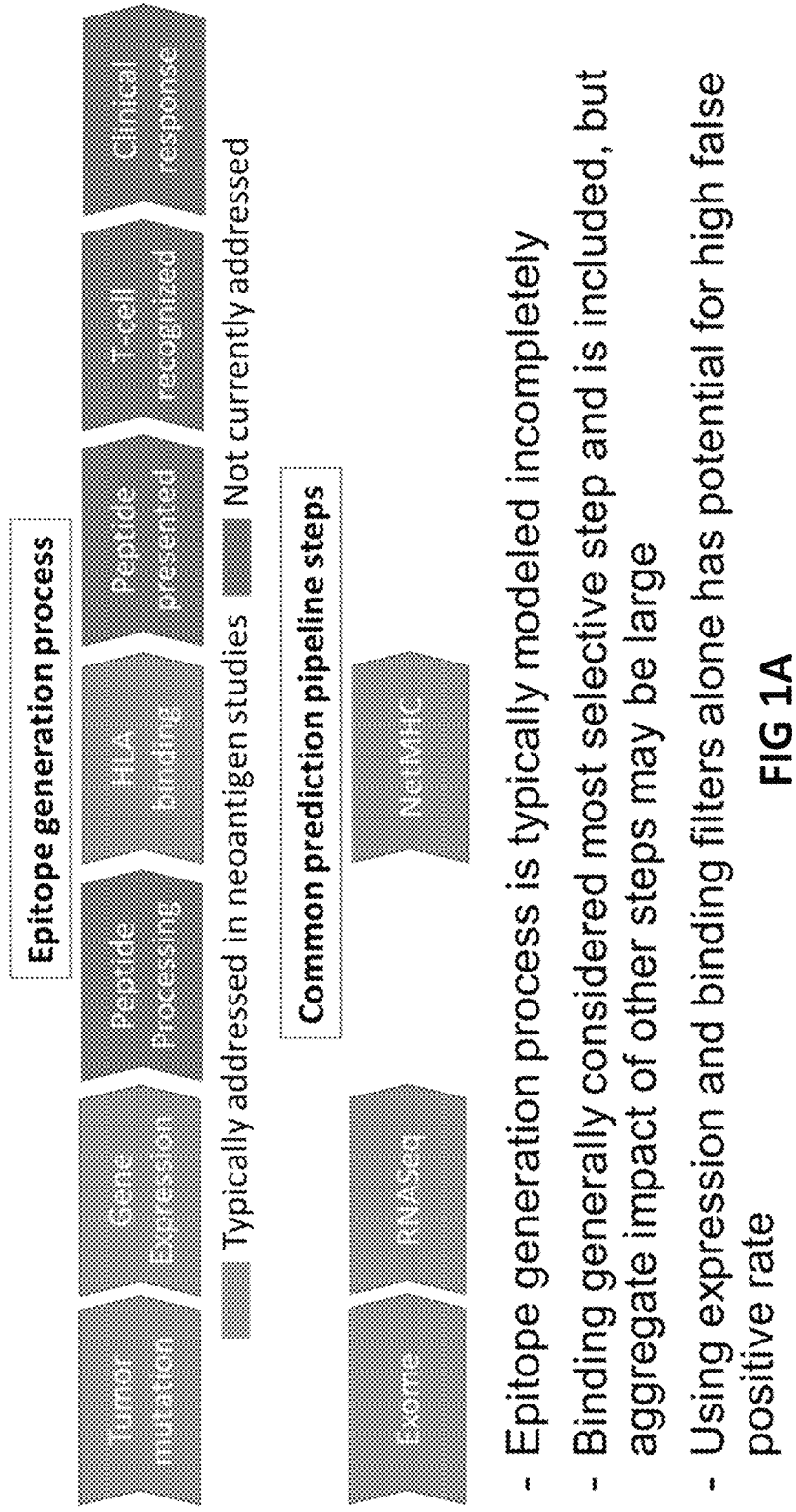

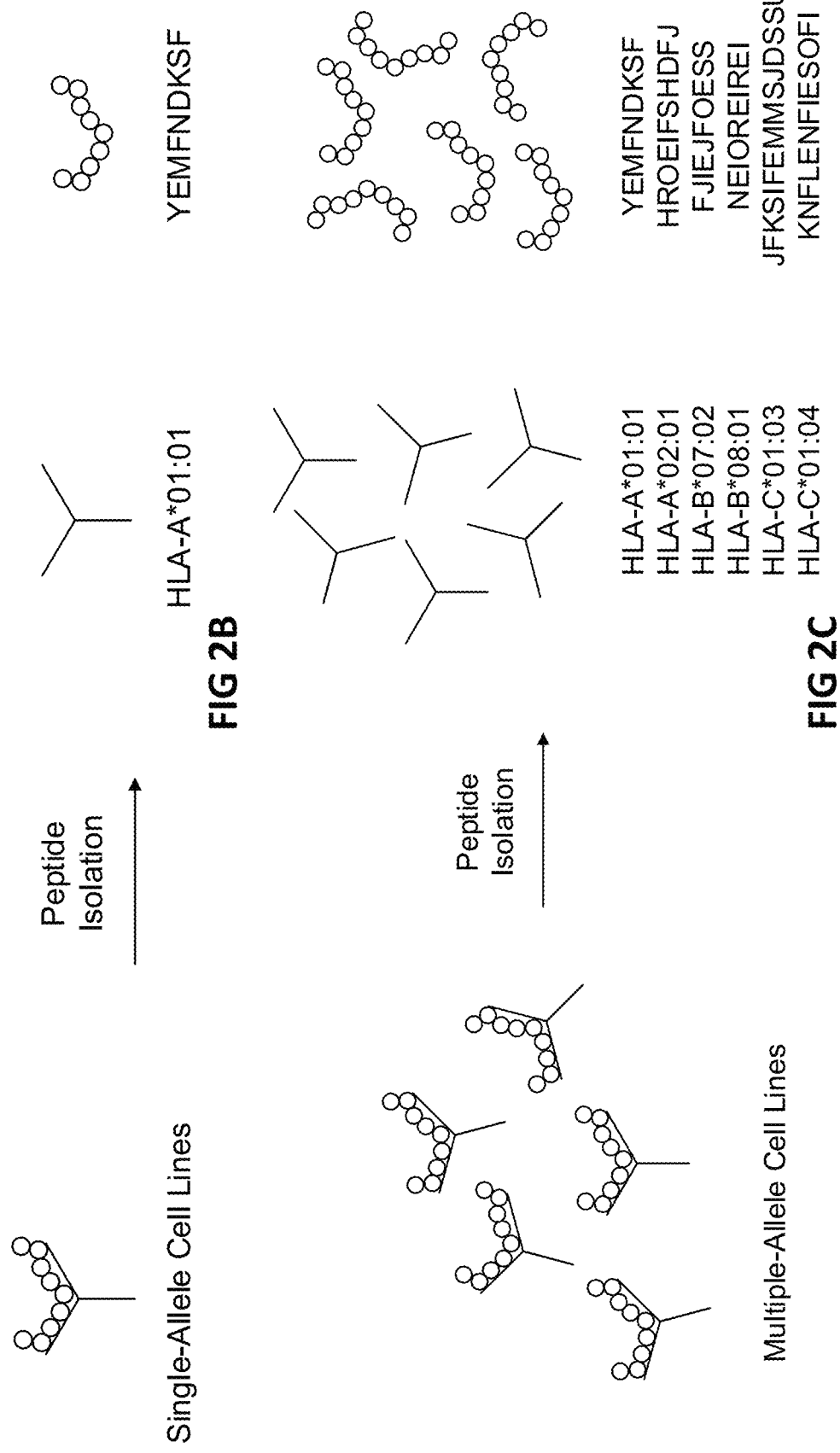

Training Data
170A

| Allele-Dependent ($x^i$) | | | | Allele-Independent ($w^i$) | | Label ($y^i$) |
|---|---|---|---|---|---|---|
| Peptide Sequence ($p^i$) | Affinity ($b^i$-nM) | Stability ($s^i$-h) | Allele ($a^i$) | C-Flanking Sequence ($c^i$) | mRNA Q. ($m^i$-FPKM) | |
| QCEIOWARE | 1000 | 1 | HLA-C*01:03 | FJELFISBOSJFIE | $10^2$ | Not Presented |
| FIEUHFWI | 1500 | 15 | HLA-C*01:03 | FEGRKUOOI | $10^{-3}$ | Presented |
| FEWRHRJTRUJR | 650 | 20 | HLA-C*01:03 | PJFIOEJOIJGEIO | $10^1$ | Presented |
| QIEJOEIJE | 500 | 1 | HLA-B*07:02 | PJFIOEJOIJGEIO | 1 | Presented |
| | 600 | 14 | HLA-C*01:03 | | | |
| | 1200 | 7 | HLA-A*01:01 | | | |

FIG 4A

Training Data
170A

| Peptide Sequence ($p^i$) | Affinity ($b^i$-nM) | Stability ($s^i$-h) | Allele ($a^i$) |
|---|---|---|---|
| QCEIOWAREFLKEIGJ | 1000 | 1 | HLA-DRB3:01:01 |

Allele-Dependent ($x^i$) { Peptide Sequence, Affinity, Stability }

FIG 4B

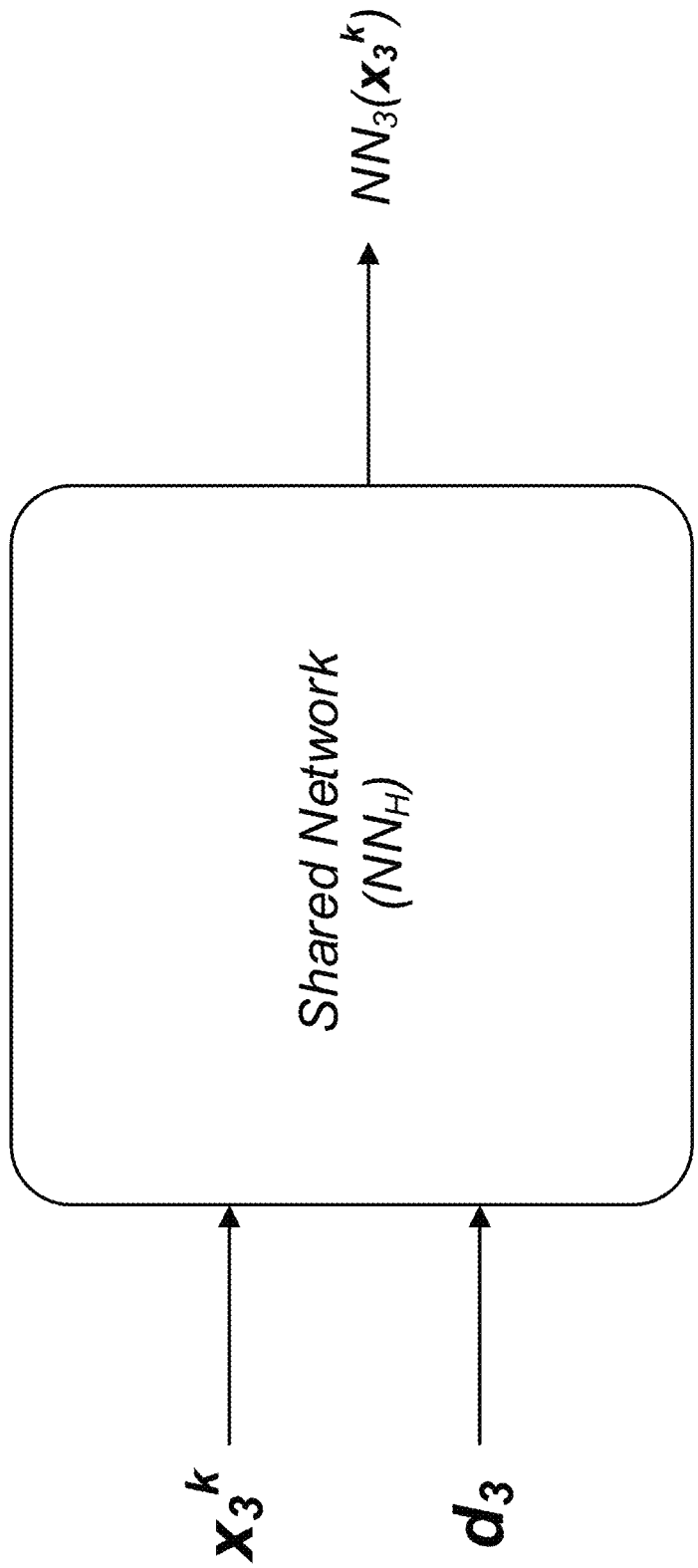

| Model | AUC | Log Loss | PPV at 10% Recall |
|---|---|---|---|
| Sigmoid-of-Sums | 0.9278 | 12.2 · 10⁻⁴ | 0.114 |
| Sum-of-Sigmoids | 0.9723 | 5.78 · 10⁻⁴ | 0.152 |
| Hyperbolic Tangent | 0.9734 | 5.72 · 10⁻⁴ | 0.156 |
| Second Order | 0.9727 | 5.74 · 10⁻⁴ | 0.160 |

FIG 13C

| Model | AUC | Log Loss | PPV at 10% Recall |
|---|---|---|---|
| With A2/B7 Single-Allele Data | 0.9818 | 5.40 · 10⁻⁴ | 0.215 |
| Without A2/B7 Single-Allele Data | 0.9803 | 5.31 · 10⁻⁴ | 0.211 |

FIG 13D

| Allele | P2 | P9 |
|---|---|---|
| A2 | L 80% | V 58% |
|  | M 5% | L 32% |
| B7 | P 98% | L 76% |
|  |  | A 8% |

FIG 13F

| Setup | Correlation |
|---|---|
| A2 model predicting B7 | 0.004 |
| A2 model predicting A2 | 0.294 |
| B7 model predicting B7 | 0.366 |
| B7 model predicting A2 | 0.002 |

FIG 13E

| Model | AUC | Log Loss | PPV at 10% Recall |
|---|---|---|---|
| Allele-interacting | 0.9723 | $5.78 \cdot 10^{-4}$ | 0.152 |
| Allele-noninteracting | 0.9732 | $5.53 \cdot 10^{-4}$ | 0.188 |

FIG 13G

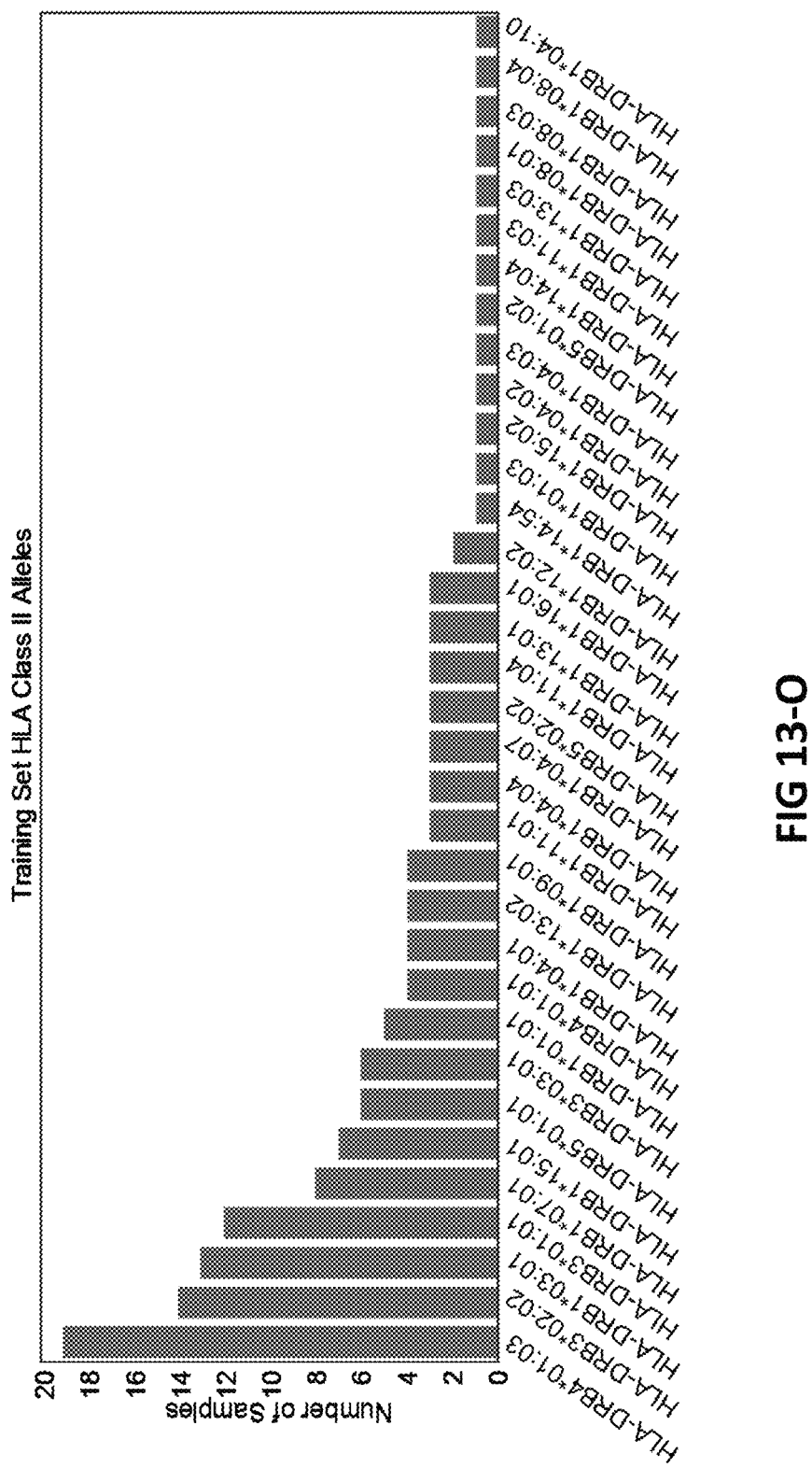
FIG 13-O

| # | HLA | Sequence | Origin |
|---|---|---|---|
| 1 | A*0201 | NLVPMVATV | HCMV pp65 (495–503) |
| 2 | A*0201 | CLGGLLTMV | EBV LMP2A (426-434) |
| 3 | A*0201 | GLCTLVAML | EBV BMLF1 (280–288) |
| 4 | A*0201 | LLFGYPVYV | HTLV-1 Tax (11-19) |
| 5 | A*0201 | GILGFVFTL | Influenza A Matrix 1 (58–66) |
|   | MHC-II | AKFVAAWTLKAAA | PADRE (artificial seq) |
|   | MHC-II | QYIKANSKFIGITE | Tetanus toxoid (830–844) |

| #  | HLA    | Sequence   | Origin                    |
|----|--------|------------|---------------------------|
| 1  | A*02:01 | NLVPMVATV  | HCMV pp65 495-504         |
| 2  | A*02:01 | CLGGLLTMV  | EBV LMP-2 426-434         |
| 3  | A*02:01 | GLCTLVAML  | EBV BMLF-1 259-267        |
| 4  | A*02:01 | LLFGYPVYV  | HTLV1 Tax 11-19           |
| 5  | A*02:01 | GILGFVFTL  | Influenza A MP 58-66      |
| 6  | A*02:01 | DLMGYIPAV  | HCV core 132-140          |
| 7  | A*02:01 | FLPSDFFPSV | HBV core antigen 18-27    |
| 8  | A*02:01 | FLLTRILTI  | HBV envelope 183-191      |
| 9  | A*02:01 | WLSLLVPFV  | HBV surface antigen 172-181 |
| 10 | A*02:01 | FLLSLGIHL  | HBV polymerase 573-581    |
| 11 | A*02:01 | ILKEPVHGV  | HIV-1 RT 476-484          |
| 12 | A*02:01 | YMLDLQPETT | HPV 16 E7 11-20           |
| 13 | A*02:01 | CINGVCWTV  | HCV NS3 1073-1081         |
| 14 | A*02:01 | YLLPRRGPRL | HCV core 35-44            |
| 15 | A*02:01 | FLYALALLL  | EBV LMP-2 356-364         |
| 16 | A*02:01 | AAGIGILTV  | MELAN-A/MART-1 (27-35)    |
| 17 | A*02:01 | SLLMWITQV  | NY-ESO-1(157-165) C9V     |
| 18 | A*03:01 | KLGGALQAK  | CVM-IE1                   |
| 19 | A*03:01 | RLRAEAQVK  | EBV-EBNA-3a               |
| 20 | B*44:05 | EENLLDFVRF | EBV EBNASC (281-290)      |
| 21 | B*44:05 | EEYLQAFTY  | Self ABCD3 protein        |

FIG 19B

NHP Epitopes

| | MHC | Sequence |
|---|---|---|
| 1 | Mamu*01 | CTPYDINQM |
| 4 | Mamu*01 | TTPESANL |
| 7 | Mamu*01 | CAPPGYALL |
| 10 | Mamu*01 | SGPKTNIIV |
| 14 | Mamu*01 | LSPRTLNAW |
| 18 | Mamu*01 | TVPWPNASL |

Murine MHC-I Epitopes

| | MHC | Sequence |
|---|---|---|
| 2 | H-2Kb | SIINFEKL |
| 5 | H-2Ld | SPSYAYHQF |
| 8 | H-2Db | EGPRNQDWL |
| 11 | H-2Kb | DWENVSPEL |
| 13 | H-2Kb | SIIVFNLL |
| 15 | H-2Db | ASMTNMELM |
| 17 | H-2Db | AQLANDVVL |
| 19 | H-2Kb | SVYDFFVWL |
| 20 | H-2Ld | MNKYAYHML |

Human Epitopes

| | HLA | Sequence |
|---|---|---|
| 3 | A*02:01 | GILGFVFTL |
| 6 | A*02:01 | LLFGYPVYV |
| 9 | A*02:01 | GLCTLVAML |
| 12 | A*02:01 | NLVPMVATV |
| 16 | A*02:01 | CLGGLLTMV |

Universal MHC-II Epitopes

| | HLA | Sequence |
|---|---|---|
| 1 | MHC-II | AKFVAAWTLKAAA |
| 2 | MHC-II | QYIKANSKFIGITEL |

FIG 20B

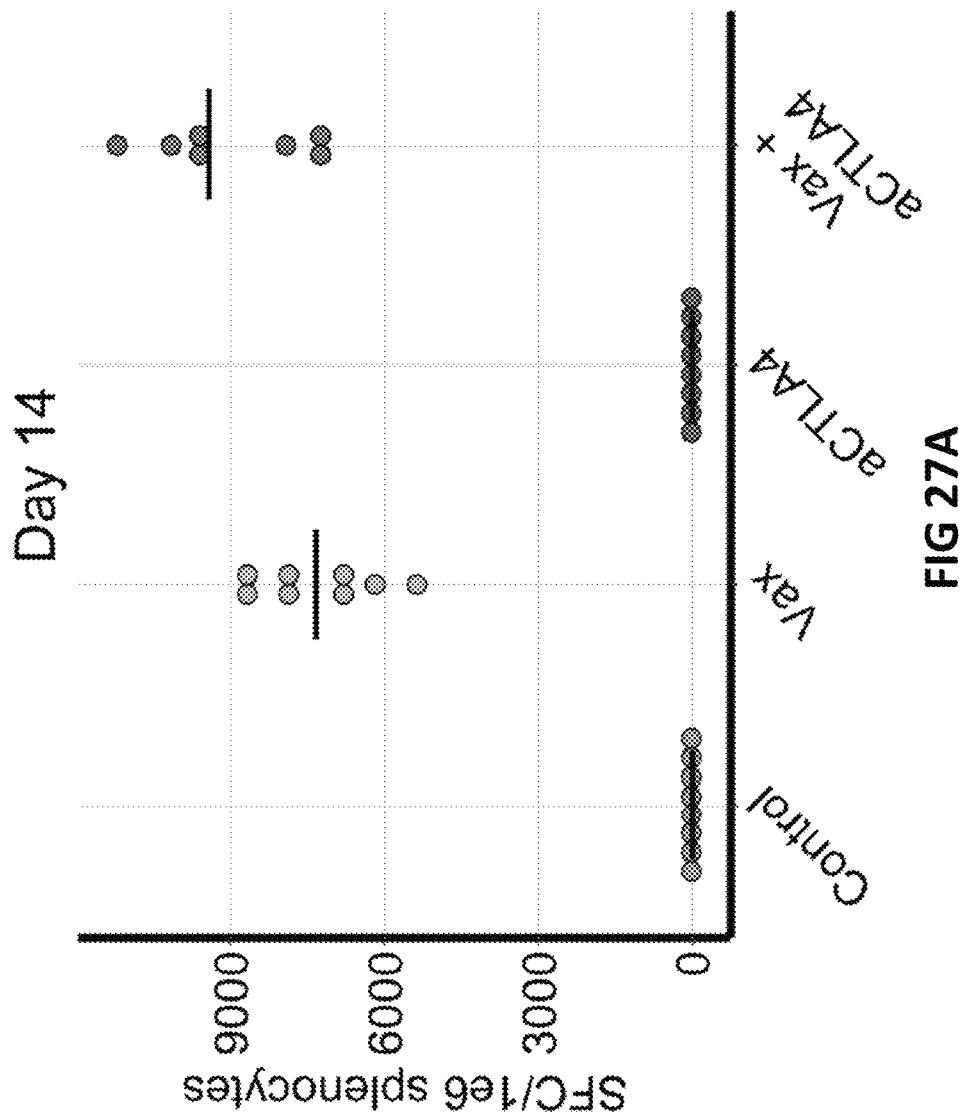

ALPHAVIRUS ANTIGEN VECTORS

PRIORITY CLAIMS AND RELATED APPLICATIONS

This application is a divisional of U.S. application Ser. No. 16/612,352, filed Nov. 8, 2019, which is the National Stage of International Application No. PCT/US2018/031696, filed Aug. 5, 2018, which claims the benefit of U.S. Provisional Application No. 62/590,163, filed Nov. 22, 2017, U.S. Provisional Application No. 62/523,201, filed Jun. 21, 2017, and U.S. Provisional Application No. 62/503,283, filed May 8, 2017, the entire contents of each is incorporated herein by reference for all purposes.

SEQUENCE LISTING

The instant application contains a Sequence Listing which has been submitted via EFS-Web and is hereby incorporated herein by reference in its entirety. Said ASCII copy, created on Aug. 31, 2022, is named GSO-006D1_SL.txt, and is 470,810 bytes in size.

BACKGROUND

Therapeutic vaccines based on tumor-specific neoantigens hold great promise as a next-generation of personalized cancer immunotherapy.[1-3] Cancers with a high mutational burden, such as non-small cell lung cancer (NSCLC) and melanoma, are particularly attractive targets of such therapy given the relatively greater likelihood of neoantigen generation.[4,5] Early evidence shows that neoantigen-based vaccination can elicit T-cell responses[6] and that neoantigen targeted cell-therapy can cause tumor regression under certain circumstances in selected patients.[7]

One question for neoantigen vaccine design is which of the many coding mutations present in subject tumors can generate the "best" therapeutic neoantigens, e.g., antigens that can elicit anti-tumor immunity and cause tumor regression.

Initial methods have been proposed incorporating mutation-based analysis using next-generation sequencing, RNA gene expression, and prediction of MHC binding affinity of candidate neoantigen peptides[8]. However, these proposed methods can fail to model the entirety of the epitope generation process, which contains many steps (e.g., TAP transport, proteasomal cleavage, and/or TCR recognition) in addition to gene expression and MHC binding[9]. Consequently, existing methods are likely to suffer from reduced low positive predictive value (PPV). (FIG. 1A)

Indeed, analyses of peptides presented by tumor cells performed by multiple groups have shown that <5% of peptides that are predicted to be presented using gene expression and MHC binding affinity can be found on the tumor surface MHC[10,11] (FIG. 1B). This low correlation between binding prediction and MHC presentation was further reinforced by recent observations of the lack of predictive accuracy improvement of binding-restricted neoantigens for checkpoint inhibitor response over the number of mutations alone.[12]

This low positive predictive value (PPV) of existing methods for predicting presentation presents a problem for neoantigen-based vaccine design. If vaccines are designed using predictions with a low PPV, most patients are unlikely to receive a therapeutic neoantigen and fewer still are likely to receive more than one (even assuming all presented peptides are immunogenic). Thus, neoantigen vaccination with current methods is unlikely to succeed in a substantial number of subjects having tumors. (FIG. 1C)

Additionally, previous approaches generated candidate neoantigens using only cis-acting mutations, and largely neglected to consider additional sources of neo-ORFs, including mutations in splicing factors, which occur in multiple tumor types and lead to aberrant splicing of many genes[13], and mutations that create or remove protease cleavage sites.

Finally, standard approaches to tumor genome and transcriptome analysis can miss somatic mutations that give rise to candidate neoantigens due to suboptimal conditions in library construction, exome and transcriptome capture, sequencing, or data analysis. Likewise, standard tumor analysis approaches can inadvertently promote sequence artifacts or germline polymorphisms as neoantigens, leading to inefficient use of vaccine capacity or auto-immunity risk, respectively.

In addition to the challenges of current neoantigen prediction methods certain challenges also exist with the available vector systems that can be used for neoantigen delivery in humans, many of which are derived from humans. For example, many humans have pre-existing immunity to human viruses as a result of previous natural exposure, and this immunity can be a major obstacle to the use of recombinant human viruses for neoantigen delivery for cancer treatment.

SUMMARY

Disclosed herein is a composition for delivery of a neoantigen expression system, comprising: the neoantigen expression system, wherein the neoantigen expression system comprises one or more vectors, the one or more vectors comprising: (a) an RNA alphavirus backbone, wherein the RNA alphavirus backbone comprises: (i) at least one promoter nucleotide sequence, and (ii) at least one polyadenylation (poly(A)) sequence; and (b) a neoantigen cassette, wherein the neoantigen cassette comprises: (i) at least one neoantigen-encoding nucleic acid sequence derived from a tumor present within a subject, comprising: (I) at least one tumor-specific and subject-specific MHC class I neoantigen-encoding nucleic acid sequence derived from the tumor, and comprising: (A) a MHC class I epitope encoding nucleic acid sequence with at least one alteration that makes the encoded peptide sequence distinct from the corresponding peptide sequence encoded by a wild-type nucleic acid sequence, and (B) optionally, a 5' linker sequence, and (C) optionally, a 3' linker sequence; (ii) optionally, a second promoter nucleotide sequence operably linked to the neoantigen-encoding nucleic acid sequence; and (iii) optionally, at least one MHC class II antigen-encoding nucleic acid sequence; (iv) optionally, at least one nucleic acid sequence encoding a GPGPG amino acid linker sequence (SEQ ID NO:56); and (v) optionally, at least one second poly(A) sequence, wherein the second poly(A) sequence is a native poly(A) sequence or an exogenous poly(A) sequence to the alphavirus.

Also disclosed herein is a composition for delivery of a neoantigen expression system, comprising: the neoantigen expression system, wherein the neoantigen expression system comprises one or more vectors, the one or more vectors comprising: (a) an RNA alphavirus backbone, wherein the RNA alphavirus backbone comprises the nucleic acid sequence set forth in SEQ ID NO:6, wherein the RNA alphavirus backbone sequence comprises a 26S promoter nucleotide sequence and a poly(A) sequence, wherein the 26S promoter sequence is endogenous to the RNA alphavirus backbone, and wherein the poly(A) sequence is endogenous to the RNA alphavirus backbone; and (b) a neoantigen cassette integrated between the 26S promoter nucleotide sequence and the poly(A) sequence, wherein the neoantigen cassette comprises: (i) at least one neoantigen-encoding nucleic acid sequence derived from a tumor present within a subject, comprising: (I) at least 10 tumor-specific and subject-specific MHC class I neoantigen-encoding nucleic acid sequences linearly linked to each other and each comprising: (A) a MHC class I epitope encoding nucleic acid sequence with at least one alteration that makes the encoded peptide sequence distinct from the corresponding peptide sequence encoded by a wild-type nucleic acid sequence, wherein the MHC I epitope encoding nucleic acid sequence encodes a MHC class I epitope 7-15 amino acids in length, (B) a 5' linker sequence, wherein the 5' linker sequence encodes a native N-terminal amino acid sequence of the MHC I epitope, and wherein the 5' linker sequence encodes a peptide that is at least 3 amino acids in length, (C) a 3' linker sequence, wherein the 3' linker sequence encodes a native N-terminal acid sequence of the MHC I epitope, and wherein the 3' linker sequence encodes a peptide that is at least 3 amino acids in length, and wherein the neoantigen cassette is operably linked to the 26S promoter nucleotide sequence, wherein each of the MHC class I neoantigen-encoding nucleic acid sequences encodes a polypeptide that is between 13 and 25 amino acids in length, and wherein each 3' end of each MHC class I neoantigen-encoding nucleic acid sequence is linked to the 5' end of the following MHC class I neoantigen-encoding nucleic acid sequence with the exception of the final MHC class I neoantigen-encoding nucleic acid sequence in the neoantigen cassette; and (ii) at least two MHC class II antigen-encoding nucleic acid sequences comprising: (I) a PADRE MHC class II sequence (SEQ ID NO:48), (II) a Tetanus toxoid MHC class II sequence (SEQ ID NO:46), (III) a first nucleic acid sequence encoding a GPGPG amino acid linker sequence (SEQ ID NO: 56) linking the PADRE MHC class II sequence and the Tetanus toxoid MHC class II sequence, (IV) a second nucleic acid sequence encoding a GPGPG amino acid linker sequence (SEQ ID NO: 56) linking the 5' end of the at least two MHC class II antigen-encoding nucleic acid sequences to the at least 20 tumor-specific and subject-specific MHC class I neoantigen-encoding nucleic acid sequences, (V) optionally, a third nucleic acid sequence encoding a GPGPG amino acid linker sequence (SEQ ID NO: 56) at the 3' end of the at least two MHC class II antigen-encoding nucleic acid sequences.

In some aspects, an ordered sequence of each element of the neoantigen cassette is described in the formula, from 5' to 3', comprising:

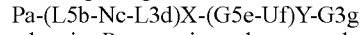

wherein P comprises the second promoter nucleotide sequence, where a=0 or 1, N comprises one of the MHC class I epitope encoding nucleic acid sequences, where c=1, L5 comprises the 5' linker sequence, where b=0 or 1, L3 comprises the 3' linker sequence, where d=0 or 1, G5 comprises one of the at least one nucleic acid sequences encoding a GPGPG amino acid linker (SEQ ID NO: 56), where e=0 or 1, G3 comprises one of the at least one nucleic acid sequences encoding a GPGPG amino acid linker (SEQ ID NO: 56), where g=0 or 1, U comprises one of the at least one MHC class II antigen-encoding nucleic acid sequence, where f=1, X=1 to 400, where for each X the corresponding Nc is a epitope encoding nucleic acid sequence, and Y=0, 1, or 2, where for each Y the corresponding Uf is an antigen-encoding nucleic acid sequence. In some aspects, for each X the corresponding Nc is a distinct MHC class I epitope encoding nucleic acid sequence. In some aspects, for each Y the corresponding Uf is a distinct MHC class II antigen-encoding nucleic acid sequence.

In some aspects, a=0, b=1, d=1, e=1, g=1, h=1, X=20, Y=2, the at least one promoter nucleotide sequence is a single 26S promoter nucleotide sequence provided by the RNA alphavirus backbone, the at least one polyadenylation poly(A) sequence is a poly(A) sequence of at least 100 consecutive A nucleotides provided by the RNA alphavirus backbone, each N encodes a MHC class I epitope 7-15 amino acids in length, L5 is a native 5' linker sequence that encodes a native N-terminal amino acid sequence of the MHC I epitope, and wherein the 5' linker sequence encodes a peptide that is at least 3 amino acids in length, L3 is a native 3' linker sequence that encodes a native nucleic-terminal acid sequence of the MHC I epitope, and wherein the 3' linker sequence encodes a peptide that is at least 3 amino acids in length, U is each of a PADRE class II sequence and a Tetanus toxoid MHC class II sequence, the RNA alphavirus backbone is the sequence set forth in SEQ ID NO:6, and each of the MHC class I neoantigen-encoding nucleic acid sequences encodes a polypeptide that is between 13 and 25 amino acids in length.

In some aspects, any of the above compositions further comprise a nanoparticulate delivery vehicle. The nanoparticulate delivery vehicle, in some aspects, may be a lipid nanoparticle (LNP). In some aspects, the LNP comprises ionizable amino lipids. In some aspects, the ionizable amino lipids comprise MC3-like (dilinoleylmethyl-4-dimethylaminobutyrate) molecules. In some aspects, the nanoparticulate delivery vehicle encapsulates the neoantigen expression system.

In some aspects, any of the above compositions further comprise a plurality of LNPs, wherein the LNPs comprise: the neoantigen expression system; a cationic lipid; a non-cationic lipid; and a conjugated lipid that inhibits aggregation of the LNPs, wherein at least about 95% of the LNPs in the plurality of LNPs either: have a non-lamellar morphology; or are electron-dense.

In some aspects, the non-cationic lipid is a mixture of (1) a phospholipid and (2) cholesterol or a cholesterol derivative.

In some aspects, the conjugated lipid that inhibits aggregation of the LNPs is a polyethyleneglycol (PEG)-lipid conjugate. In some aspects, the PEG-lipid conjugate is selected from the group consisting of: a PEG-diacylglycerol (PEG-DAG) conjugate, a PEG dialkyloxypropyl (PEG-DAA) conjugate, a PEG-phospholipid conjugate, a PEG-ceramide (PEG-Cer) conjugate, and a mixture thereof. In some aspects the PEG-DAA conjugate is a member selected from the group consisting of: a PEG-didecyloxypropyl ($C_{10}$) conjugate, a PEG-dilauryloxypropyl ($C_{12}$) conjugate, a PEG-dimyristyloxypropyl ($C_{14}$) conjugate, a PEG-dipalmityloxypropyl ($C_{16}$) conjugate, a PEG-distearyloxypropyl ($C_{18}$) conjugate, and a mixture thereof.

In some aspects, the neoantigen expression system is fully encapsulated in the LNPs.

In some aspects, the non-lamellar morphology of the LNPs comprises an inverse hexagonal ($H_{II}$) or cubic phase structure.

In some aspects, the cationic lipid comprises from about 10 mol % to about 50 mol % of the total lipid present in the LNPs. In some aspects, the cationic lipid comprises from about 20 mol % to about 50 mol % of the total lipid present in the LNPs. In some aspects, the cationic lipid comprises from about 20 mol % to about 40 mol % of the total lipid present in the LNPs.

In some aspects, the non-cationic lipid comprises from about 10 mol % to about 60 mol % of the total lipid present in the LNPs. In some aspects, the non-cationic lipid comprises from about 20 mol % to about 55 mol % of the total lipid present in the LNPs. In some aspects, the non-cationic lipid comprises from about 25 mol % to about 50 mol % of the total lipid present in the LNPs.

In some aspects, the conjugated lipid comprises from about 0.5 mol % to about 20 mol % of the total lipid present in the LNPs. In some aspects, the conjugated lipid comprises from about 2 mol % to about 20 mol % of the total lipid present in the LNPs. In some aspects, the conjugated lipid comprises from about 1.5 mol % to about 18 mol % of the total lipid present in the LNPs.

In some aspects, greater than 95% of the LNPs have a non-lamellar morphology. In some aspects, greater than 95% of the LNPs are electron dense.

In some aspects, any of the above compositions further comprise a plurality of LNPs, wherein the LNPs comprise: a cationic lipid comprising from 50 mol % to 65 mol % of the total lipid present in the LNPs; a conjugated lipid that inhibits aggregation of LNPs comprising from 0.5 mol % to 2 mol % of the total lipid present in the LNPs; and a non-cationic lipid comprising either: a mixture of a phospholipid and cholesterol or a derivative thereof, wherein the phospholipid comprises from 4 mol % to 10 mol % of the total lipid present in the LNPs and the cholesterol or derivative thereof comprises from 30 mol % to 40 mol % of the total lipid present in the LNPs; a mixture of a phospholipid and cholesterol or a derivative thereof, wherein the phospholipid comprises from 3 mol % to 15 mol % of the total lipid present in the LNPs and the cholesterol or derivative thereof comprises from 30 mol % to 40 mol % of the total lipid present in the LNPs; or up to 49.5 mol % of the total lipid present in the LNPs and comprising a mixture of a phospholipid and cholesterol or a derivative thereof, wherein the cholesterol or derivative thereof comprises from 30 mol % to 40 mol % of the total lipid present in the LNPs.

In some aspects, any of the above compositions further comprise a plurality of LNPs, wherein the LNPs comprise: a cationic lipid comprising from 50 mol % to 85 mol % of the total lipid present in the LNPs; a conjugated lipid that inhibits aggregation of LNPs comprising from 0.5 mol % to 2 mol % of the total lipid present in the LNPs; and a non-cationic lipid comprising from 13 mol % to 49.5 mol % of the total lipid present in the LNPs.

In some aspects, the phospholipid comprises dipalmitoylphosphatidylcholine (DPPC), distearoylphosphatidylcholine (DSPC), or a mixture thereof.

In some aspects, the conjugated lipid comprises a polyethyleneglycol (PEG)-lipid conjugate. In some aspects, the PEG-lipid conjugate comprises a PEG-diacylglycerol (PEG-DAG) conjugate, a PEG-dialkyloxypropyl (PEG-DAA) conjugate, or a mixture thereof. In some aspects, the PEG-DAA conjugate comprises a PEG-dimyristyloxypropyl (PEG-DMA) conjugate, a PEG-distearyloxypropyl (PEG-DSA) conjugate, or a mixture thereof. In some aspects, the PEG portion of the conjugate has an average molecular weight of about 2,000 daltons.

In some aspects, the conjugated lipid comprises from 1 mol % to 2 mol % of the total lipid present in the LNPs.

In some aspects, the LNP comprises a compound having a structure of Formula I:

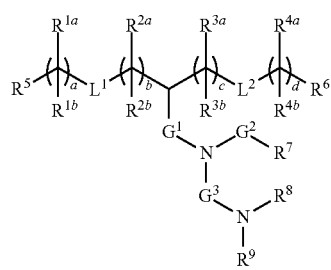

I or a pharmaceutically acceptable salt, tautomer, prodrug or stereoisomer thereof, wherein: $L^1$ and $L^2$ are each independently -O(C=O)-, —(C=O)O-, —C(=O)-, -O-, —S(O)$_x$-, —S—S—, —C(=O)S—, —SC(=O)-, —R$^a$C(=O)-, —C(=O)R$^a$—, —R$^a$C(=O)R$^a$—, —OC(=O)R$^a$—, —R$^a$C(=O)O- or a direct bond; $G^1$ is $C_1$-$C_2$ alkylene, —(C=O)-, -O(C=O)-, —SC(=O)-, —R$^a$C(=O)- or a direct bond: —C(=O)-, —(C=O)O-, —C(=O)S—, —C(=O)R$^a$— or a direct bond; G is $C_1$-$C_6$ alkylene; R$^a$ is H or C1-C12 alkyl; $R^{1a}$ and $R^{1b}$ are, at each occurrence, independently either: (a) H or $C_1$-$C_{12}$ alkyl; or (b) $R^{1a}$ is H or $C_1$-$C_{12}$ alkyl, and $R^{1b}$ together with the carbon atom to which it is bound is taken together with an adjacent $R^{1b}$ and the carbon atom to which it is bound to form a carbon-carbon double bond; $R^{2a}$ and $R^{2b}$ are, at each occurrence, independently either: (a) H or $C_1$-$C_{12}$ alkyl; or (b) $R^2$ is H or $C_1$-$C_{12}$ alkyl, and $R^{2b}$ together with the carbon atom to which it is bound is taken together with an adjacent $R^{2b}$ and the carbon atom to which it is bound to form a carbon-carbon double bond; $R^{3a}$ and $R^{3b}$ are, at each occurrence, independently either (a): H or $C_1$-$C_{12}$ alkyl; or (b) $R^{3a}$ is H or $C_1$-$C_{12}$ alkyl, and $R^{3b}$ together with the carbon atom to which it is bound is taken together with an adjacent R and the carbon atom to which it is bound to form a carbon-carbon double bond; $R^{4a}$ and $R^{4b}$ are, at each occurrence, independently either: (a) H or C1-C12 alkyl; or (b) $R^{4a}$ is H or C1-C12 alkyl, and $R^{4b}$ together with the carbon atom to which it is bound is taken together with an adjacent $R^{4b}$ and the carbon atom to which it is bound to form a carbon-carbon double bond; $R^5$ and $R^6$ are each independently H or methyl; $R^7$ is C4-C20 alkyl; $R^8$ and $R^9$ are each independently C1-C12 alkyl; or $R^8$ and $R^9$, together with the nitrogen atom to which they are attached, form a 5, 6 or 7-membered heterocyclic ring; a, b, c and d are each independently an integer from 1 to 24; and x is 0, 1 or 2.

In some aspects, the LNP comprises a compound having a structure of Formula II:

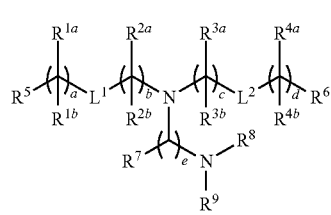

II or a pharmaceutically acceptable salt, tautomer, prodrug or stereoisomer thereof, wherein: $L^1$ and $L^2$ are each independently -O(C=O)-, —(C=O)O- or a carbon-carbon double bond;

$R^{1a}$ and $R^{1b}$ are, at each occurrence, independently either (a) H or $C_1$-$C_{12}$ alkyl, or (b) $R^{1a}$ is H or $C_1$-$C_{12}$ alkyl, and $R^{1b}$ together with the carbon atom to which it is bound is taken together with an adjacent $R^{1b}$ and the carbon atom to which it is bound to form a carbon-carbon double bond; $R^{2a}$ and $R^{2b}$ are, at each occurrence, independently either (a) H or $C_1$-$C_{12}$ alkyl, or (b) $R^{2a}$ is H or $C_1$-$C_{12}$ alkyl, and $R^{2b}$ together with the carbon atom to which it is bound is taken together with an adjacent $R^{2b}$ and the carbon atom to which it is bound to form a carbon-carbon double bond; $R^{3a}$ and $R^{3b}$ are, at each occurrence, independently either (a) H or $C_1$-$C_{12}$ alkyl, or (b) $R^{3a}$ is H or $C_1$-$C_{12}$ alkyl, and $R^{3b}$ together with the carbon atom to which it is bound is taken together with an adjacent $R^{3b}$ and the carbon atom to which it is bound to form a carbon-carbon double bond; $R^{4a}$ and $R^{4b}$ are, at each occurrence, independently either (a) H or $C_1$-$C_{12}$ alkyl, or (b) $R^{4a}$ is H or $C_1$-$C_{12}$ alkyl, and $R^{4b}$ together with the carbon atom to which it is bound is taken together with an adjacent $R^{4b}$ and the carbon atom to which it is bound to form a carbon-carbon double bond; $R^5$ and $R^6$ are each independently methyl or cycloalkyl; $R^7$ is, at each occurrence, independently H or $C_1$-$C_{12}$ alkyl; $R^8$ and $R^9$ are each independently unsubstituted C1-C12 alkyl; or $R^8$ and $R^9$, together with the nitrogen atom to which they are attached, form a 5, 6 or 7-membered heterocyclic ring comprising one nitrogen atom; a and d are each independently an integer from 0 to 24; b and c are each independently an integer from 1 to 24; and e is 1 or 2, provided that: at least one of $R^{1a}$, $R_{2a}$, $R^{3a}$ or $R^{4a}$ is C1-C12 alkyl, or at least one of $L^1$ or $L^2$ is -0(C=0)- or —(C=0)0-; and $R^{1a}$ and $R^{1b}$ are not isopropyl when a is 6 or n-butyl when a is 8.

In some aspects, any of the above compositions further comprise one or more excipients comprising a neutral lipid, a steroid, and a polymer conjugated lipid. In some aspects, the neutral lipid comprises at least one of 1,2-Distearoyl-sn-glycero-3-phosphocholine (DSPC), 1,2-Dipalmitoyl-sn-glycero-3-phosphocholine (DPPC), 1,2-Dimyristoyl-sn-glycero-3-phosphocholine (DMPC), 1-Palmitoyl-2-oleoyl-sn-glycero-3-phosphocholine (POPC), 1,2-dioleoyl-sn-glycero-3-phosphocholine (DOPC), and 1,2-Dioleoyl-sn-glycero-3-phosphoethanolamine (DOPE). In some aspects, the neutral lipid is DSPC.

In some aspects, the molar ratio of the compound to the neutral lipid ranges from about 2:1 to about 8:1.

In some aspects, the steroid is cholesterol. In some aspects, the molar ratio of the compound to cholesterol ranges from about 2:1 to 1:1.

In some aspects, the polymer conjugated lipid is a pegylated lipid. In some aspects, the molar ratio of the compound to the pegylated lipid ranges from about 100:1 to about 25:1. In some aspects, the pegylated lipid is PEG-DAG, a PEG polyethylene (PEG-PE), a PEG-succinoyl-diacylglycerol (PEG-S-DAG), PEG-cer or a PEG dialkyoxypropylcarbamate. In some aspects, the pegylated lipid has the following structure III:

III

\O—(—O—)$_z$—O—C(=O)—N(R$^{11}$)—R$^{10}$ or a pharmaceutically acceptable salt, tautomer or stereoisomer thereof, wherein: $R^{10}$ and $R^{11}$ are each independently a straight or branched, saturated or unsaturated alkyl chain containing from 10 to 30 carbon atoms, wherein the alkyl chain is optionally interrupted by one or more ester bonds; and z has a mean value ranging from 30 to 60. In some aspects, $R^{10}$ and $R^{11}$ are each independently straight, saturated alkyl chains having 12 to 16 carbon atoms. In some aspects, the average z is about 45.

start here

In some aspects, the LNP self-assembles into non-bilayer structures when mixed with polyanionic nucleic acid. In some aspects, the non-bilayer structures have a diameter between 60 nm and 120 nm. In some aspects, the non-bilayer structures have a diameter of about 70 nm, about 80 nm, about 90 nm, or about 100 nm. In some aspects, wherein the nanoparticulate delivery vehicle has a diameter of about 100 nm.

In some aspects, the neoantigen cassette is integrated between the at least one promoter nucleotide sequence and the at least one poly(A) sequence. In some aspects, the at least one promoter nucleotide sequence is operably linked to the neoantigen-encoding nucleic acid sequence.

In some aspects, the one or more vectors comprise one or more +–stranded RNA vectors. In some aspects, the one or more +–stranded RNA vectors comprise a 5' 7-methylguanosine (m7g) cap. In some aspects, the one or more +–stranded RNA vectors are produced by in vitro transcription. In some aspects, the one or more vectors are self-replicating within a mammalian cell.

In some aspects, the RNA alphavirus backbone comprises at least one nucleotide sequence of an Aura virus, a Fort Morgan virus, a Venezuelan equine encephalitis virus, a Ross River virus, a Semliki Forest virus, a Sindbis virus, or a Mayaro virus. In some aspects, the RNA alphavirus backbone comprises at least one nucleotide sequence of a Venezuelan equine encephalitis virus. In some aspects, the RNA alphavirus backbone comprises at least sequences for nonstructural protein-mediated amplification, a 26S promoter sequence, a poly(A) sequence, a nonstructural protein 1 (nsP1) gene, a nsP2 gene, a nsP3 gene, and a nsP4 gene encoded by the nucleotide sequence of the Aura virus, the Fort Morgan virus, the Venezuelan equine encephalitis virus, the Ross River virus, the Semliki Forest virus, the Sindbis virus, or the Mayaro virus. In some aspects, the RNA alphavirus backbone comprises at least sequences for nonstructural protein-mediated amplification, a 26S promoter sequence, and a poly(A) sequence encoded by the nucleotide sequence of the Aura virus, the Fort Morgan virus, the Venezuelan equine encephalitis virus, the Ross River virus, the Semliki Forest virus, the Sindbis virus, or the Mayaro virus. In some aspects, sequences for nonstructural protein-mediated amplification are selected from the group consisting of: an alphavirus 5' UTR, a 51-nt CSE, a 24-nt CSE, a 26S subgenomic promoter sequence, a 19-nt CSE, an alphavirus 3' UTR, or combinations thereof.

In some aspects, the RNA alphavirus backbone does not encode structural virion proteins capsid, E2 and E1. In some aspects, the neoantigen cassette is inserted in place of the structural virion proteins within the nucleotide sequence of the Aura virus, the Fort Morgan virus, the Venezuelan equine encephalitis virus, the Ross River virus, the Semliki Forest virus, the Sindbis virus, or the Mayaro virus.

In some aspects, the Venezuelan equine encephalitis virus (VEE) comprises the strain TC-83. In some aspects, the Venezuelan equine encephalitis virus comprises the sequence set forth in SEQ ID NO:3 or SEQ ID NO:5. In some aspects, the Venezuelan equine encephalitis virus comprises the sequence of SEQ ID NO:3 or SEQ ID NO:5 further comprising a deletion between base pair 7544 and 11175. In some aspects, the RNA alphavirus backbone is the sequence set forth in SEQ ID NO:6 or SEQ ID NO:7. In some aspects, the neoantigen cassette is inserted to replace the deletion between base pair 7544 and 11175 set forth in the sequence of SEQ ID NO:3 or SEQ ID NO:5

In some aspects, the insertion of the neoantigen cassette provides for transcription of a polycistronic RNA comprising the nsP1-4 genes and the at least one of antigen-encoding nucleic acid sequences, wherein the nsP1-4 genes and the at least one of antigen-encoding nucleic acid sequences are in separate open reading frames.

In some aspects, the at least one promoter nucleotide sequence is the native 26S promoter nucleotide sequence encoded by the RNA alphavirus backbone. In some aspects, the at least one promoter nucleotide sequence is an exogenous RNA promoter. In some aspects, the second promoter nucleotide sequence is a 26S promoter nucleotide sequence. In some aspects, the second promoter nucleotide sequence comprises multiple 26S promoter nucleotide sequences, wherein each 26S promoter nucleotide sequence provides for transcription of one or more of the separate open reading frames.

In some aspects, the one or more neoantigen expression vectors are each at least 300nt in size. In some aspects, the one or more neoantigen expression vectors are each at least 1 kb in size. In some aspects, the one or more neoantigen expression vectors are each 2 kb in size. In some aspects, the one or more neoantigen expression vectors are each less than 5 kb in size.

In some aspects, at least one of the at least one neoantigen-encoding nucleic acid sequences encodes a polypeptide sequence or portion thereof that is presented by MHC class I on the tumor cell. In some aspects, each antigen-encoding nucleic acid sequence is linked directly to one another. In some aspects, at least one of the at least one antigen-encoding nucleic acid sequences is linked to a distinct antigen-encoding nucleic acid sequence with a nucleic acid sequence encoding a linker. In some aspects, the linker links two MHC class I sequences or an MHC class I sequence to an MHC class II sequence. In some aspects, the linker is selected from the group consisting of: (1) consecutive glycine residues, at least 2, 3, 4, 5, 6, 7, 8, 9, or 10 residues in length; (2) consecutive alanine residues, at least 2, 3, 4, 5, 6, 7, 8, 9, or 10 residues in length; (3) two arginine residues (RR); (4) alanine, alanine, tyrosine (AAY); (5) a consensus sequence at least 2, 3, 4, 5, 6, 7, 8, 9, or 10 amino acid residues in length that is processed efficiently by a mammalian proteasome; and (6) one or more native sequences flanking the antigen derived from the cognate protein of origin and that is at least 2, 3, 4, 5, 6, 7, 8, 9, 10, 11, 12, 13, 14, 15, 16, 17, 18, 19, 20, or 2-20 amino acid residues in length. In some aspects, the linker links two MHC class II sequences or an MHC class II sequence to an MHC class I sequence. In some aspects, the linker comprises the sequence GPGPG (SEQ ID NO: 56).

In some aspects, at least one sequence of the at least one antigen-encoding nucleic acid sequences is linked, operably or directly, to a separate or contiguous sequence that enhances the expression, stability, cell trafficking, processing and presentation, and/or immunogenicity of the at least one antigen-encoding nucleic acid sequences. In some aspects, the separate or contiguous sequence comprises at least one of: a ubiquitin sequence, a ubiquitin sequence modified to increase proteasome targeting (e.g., the ubiquitin sequence contains a Gly to Ala substitution at position 76), an immunoglobulin signal sequence (e.g., IgK), a major histocompatibility class I sequence, lysosomal-associated membrane protein (LAMP)-1, human dendritic cell lysosomal-associated membrane protein, and a major histocompatibility class II sequence; optionally wherein the ubiquitin sequence modified to increase proteasome targeting is A76.

In some aspects, at least one of the at least one neoantigen-encoding nucleic acid sequences encodes a polypeptide sequence or portion thereof that has increased binding affinity to its corresponding MHC allele relative to the translated, corresponding wild-type, nucleic acid sequence. In some aspects, at least one of the at least one neoantigen-encoding nucleic acid sequences in the plurality encodes a polypeptide sequence or portion thereof that has increased binding stability to its corresponding MHC allele relative to the translated, corresponding wild-type, nucleic acid sequence. In some aspects, at least one of the at least one neoantigen-encoding nucleic acid sequences in the plurality encodes a polypeptide sequence or portion thereof that has an increased likelihood of presentation on its corresponding MHC allele relative to the translated, corresponding wild-type, nucleic acid sequence.

In some aspects, at least one mutation comprises a point mutation, a frameshift mutation, a non-frameshift mutation, a deletion mutation, an insertion mutation, a splice variant, a genomic rearrangement, or a proteasome-generated spliced antigen.

In some aspects, the tumor is selected from the group consisting of: lung cancer, melanoma, breast cancer, ovarian cancer, prostate cancer, kidney cancer, gastric cancer, colon cancer, testicular cancer, head and neck cancer, pancreatic cancer, bladder cancer, brain cancer, B-cell lymphoma, acute myelogenous leukemia, adult acute lymphoblastic leukemia, chronic myelogenous leukemia, chronic lymphocytic leukemia, T cell lymphocytic leukemia, non-small cell lung cancer, and small cell lung cancer.

In some aspects, the at least one neoantigen-encoding nucleic acid sequence comprises at least 2-10, 2, 3, 4, 5, 6, 7, 8, 9, or 10 nucleic acid sequences. In some aspects, the at least one neoantigen-encoding nucleic acid sequence comprises at least 11-20, 15-20, 11-100, 11-200, 11-300, 11-400, 11, 12, 13, 14, 15, 16, 17, 18, 19, 20 or up to 400 nucleic acid sequences.

In some aspects, the at least one neoantigen-encoding nucleic acid sequence comprises at least 2-400 nucleic acid sequences and wherein at least two of the neoantigen-encoding nucleic acid sequences encode polypeptide sequences or portions thereof that are presented by MHC class I on the tumor cell surface. In some aspects, at least two of the neoantigen-encoding nucleic acid sequences encode polypeptide sequences or portions thereof that are presented by MHC class I on the tumor cell surface. In some aspects, when administered to the subject and translated, at least one of the neoantigens encoded by the at least one neoantigen-encoding nucleic acid sequence are presented on antigen presenting cells resulting in an immune response targeting at least one of the neoantigens on the tumor cell surface. In some aspects, the at least one neoantigen-encoding nucleic acid sequences when administered to the subject and translated, at least one of the MHC class I or class II neoantigens are presented on antigen presenting cells resulting in an immune response targeting at least one of the neoantigens on the tumor cell surface, and optionally wherein the expression of each of the at least one neoantigen-encoding nucleic acid sequences is driven by the at least one promoter nucleotide sequence.

In some aspects, each MHC class I neoantigen-encoding nucleic acid sequence encodes a polypeptide sequence between 8 and 35 amino acids in length, optionally 9-17, 9-25, 8, 9, 10, 11, 12, 13, 14, 15, 16, 17, 18, 19, 20, 21, 22, 23, 24, 25, 26, 27, 28, 29, 30, 31, 32, 33, 34 or 35 amino acids in length.

In some aspects, at least one MHC class II antigen-encoding nucleic acid sequence is present. In some aspects, at least one MHC class II antigen-encoding nucleic acid sequence is present and comprises at least one MHC class II neoantigen-encoding nucleic acid sequence that comprises at least one mutation that makes it distinct from the corresponding wild-type, parental nucleic acid sequence. In some aspects, the at least one MHC class II antigen-encoding nucleic acid sequence is 12-20, 12, 13, 14, 15, 16, 17, 18, 19, 20, or 20-40 amino acids in length. In some aspects, the at least one MHC class II antigen-encoding nucleic acid sequence is present and comprises at least one universal MHC class II antigen-encoding nucleic acid sequence, optionally wherein the at least one universal sequence comprises at least one of Tetanus toxoid and PADRE.

In some aspects, the at least one promoter nucleotide sequence or the second promoter nucleotide sequence is inducible. In some aspects, the at least one promoter nucleotide sequence or the second promoter nucleotide sequence is non-inducible.

In some aspects, the at least one poly(A) sequence comprises a poly(A) sequence native to the alphavirus. In some aspects, the at least one poly(A) sequence comprises a poly(A) sequence exogenous to the alphavirus. In some aspects, the at least one poly(A) sequence is operably linked to at least one of the at least one antigen-encoding nucleic acid sequences. In some aspects, the at least one poly(A) sequence is at least 20, at least 30, at least 40, at least 50, at least 60, at least 70, at least 80, or at least 90 consecutive A nucleotides. In some aspects, the at least one poly(A) sequence is at least 100 consecutive A nucleotides.

In some aspects, the neoantigen cassette further comprises at least one of: an intron sequence, a woodchuck hepatitis virus posttranscriptional regulatory element (WPRE) sequence, an internal ribosome entry sequence (IRES) sequence, a nucleotide sequence encoding a 2A self cleaving peptide sequence, a nucleotide sequence encoding a Furin cleavage site, or a sequence in the 5' or 3' non-coding region known to enhance the nuclear export, stability, or translation efficiency of mRNA that is operably linked to at least one of the at least one antigen-encoding nucleic acid sequences.

In some aspects, the neoantigen cassette further comprises a reporter gene, including but not limited to, green fluorescent protein (GFP), a GFP variant, secreted alkaline phosphatase, luciferase, a luciferase variant, or a detectable peptide or epitope. In some aspects, the detectable peptide or epitope is selected from the group consisting of an HA tag, a Flag tag, a His-tag, or a V5 tag.

In some aspects, the one or more vectors further comprise one or more nucleic acid sequences encoding at least one immune modulator. In some aspects, the immune modulator is an anti-CTLA4 antibody or an antigen-binding fragment thereof, an anti-PD-1 antibody or an antigen-binding fragment thereof, an anti-PD-L1 antibody or an antigen-binding fragment thereof, an anti-4-1BB antibody or an antigen-binding fragment thereof, or an anti-OX-40 antibody or an antigen-binding fragment thereof. In some aspects, the antibody or antigen-binding fragment thereof is a Fab fragment, a Fab' fragment, a single chain Fv (scFv), a single domain antibody (sdAb) either as single specific or multiple specificities linked together (e.g., camelid antibody domains), or full-length single-chain antibody (e.g., full-length IgG with heavy and light chains linked by a flexible linker). In some aspects, the heavy and light chain sequences of the antibody are a contiguous sequence separated by either a self-cleaving sequence such as 2A or IRES; or the heavy and light chain sequences of the antibody are linked by a flexible linker such as consecutive glycine residues.

In some aspects, the immune modulator is a cytokine. In some aspects, the cytokine is at least one of IL-2, IL-7, IL-12, IL-15, or IL-21 or variants thereof of each.

Also, disclosed herein is an adenovirus vector comprising a neoantigen cassette, the neoantigen cassette comprising: a plurality of antigen-encoding nucleic acid sequences derived from a tumor present within a subject, the plurality comprising: at least two MHC class I neoantigen-encoding nucleic acid sequences each comprising at least one alteration that makes it distinct from the corresponding wild-type, parental nucleic acid sequence, and optionally, at least one MHC class II antigen-encoding nucleic acid sequence; and at least one promoter sequence operably linked to at least one sequence of the plurality.

In some aspects, the adenovirus vector is a chimpanzee adenovirus (ChAd) vector, optionally a C68 vector. In some aspects, the adenovirus vector comprises the sequence set forth in SEQ ID NO:1. In some aspects, the adenovirus vector comprises the sequence set forth in SEQ ID NO:1, except that the sequence is fully deleted or functionally deleted in at least one gene selected from the group consisting of the chimpanzee adenovirus E1A, E1B, E2A, E2B, E3, E4, L1, L2, L3, L4, and L5 genes of the sequence set forth in SEQ ID NO: 1, optionally wherein the sequence is fully deleted or functionally deleted in: (1) E1A and E1B; (2) E1A, E1B, and E3; or (3) E1A, E1B, E3, and E4 of the sequence set forth in SEQ ID NO: 1. In some aspects, the adenovirus vector comprises a gene or regulatory sequence obtained from the sequence of SEQ ID NO: 1, optionally wherein the gene is selected from the group consisting of the chimpanzee adenovirus inverted terminal repeat (ITR), E1A, E1B, E2A, E2B, E3, E4, L1, L2, L3, L4, and L5 genes of the sequence set forth in SEQ ID NO: 1.

In some aspects, the neoantigen cassette is inserted in the adenovirus vector at the E1 region, E3 region, and/or any deleted AdV region that allows incorporation of the neoantigen cassette.

In some aspects, the at least one promoter sequence of the adenovirus vector is inducible. In some aspects, the at least one promoter sequence of the adenovirus vector is non-inducible. In some aspects, the at least one promoter sequence of the adenovirus vector is a CMV, SV40, EF-1, RSV, PGK, or EBV promoter sequence.

In some aspects, the neoantigen cassette of the adenovirus vector further comprises at least one polyA sequence operably linked to at least one of the sequences in the plurality, optionally wherein the polyA sequence is located 3' of the at least one sequence in the plurality.

In some aspects, the adenovirus vector is generated from one of a first generation, a second generation, or a helper-dependent adenoviral vector.

In some aspects, the adenovirus vector comprises one or more deletions between base pair number 577 and 3407 and optionally wherein the adenovirus vector further comprises one or more deletions between base pair 27,141 and 32,022 or between base pair 27,816 and 31,332 of the sequence set forth in SEQ ID NO:1. In some aspects, the adenovirus vector further comprises one or more deletions between base pair number 3957 and 10346, base pair number 21787 and 23370, and base pair number 33486 and 36193 of the sequence set forth in SEQ ID NO:1.

In some aspects, the at least one MHC class I neoantigen-encoding nucleic acid sequence is selected by performing the steps of: (a) obtaining at least one of exome, transcriptome, or whole genome tumor nucleotide sequencing data from the tumor, wherein the tumor nucleotide sequencing data is used to obtain data representing peptide sequences of each of a set of neoantigens; (b) inputting the peptide sequence of each neoantigen into a presentation model to generate a set of numerical likelihoods that each of the neoantigens is presented by one or more of the MHC alleles on the tumor cell surface of the tumor, the set of numerical likelihoods having been identified at least based on received mass spectrometry data; and (c) selecting a subset of the set of neoantigens based on the set of numerical likelihoods to generate a set of selected neoantigens which are used to generate the at least one MHC class I neoantigen-encoding nucleic acid sequence.

In some aspects, each of the at least one MHC class I neoantigen-encoding nucleic acid sequence is selected by performing the steps of: (a) obtaining at least one of exome, transcriptome, or whole genome tumor nucleotide sequencing data from the tumor, wherein the tumor nucleotide sequencing data is used to obtain data representing peptide sequences of each of a set of neoantigens; (b) inputting the peptide sequence of each neoantigen into a presentation model to generate a set of numerical likelihoods that each of the neoantigens is presented by one or more of the MHC alleles on the tumor cell surface of the tumor, the set of numerical likelihoods having been identified at least based on received mass spectrometry data; and (c) selecting a subset of the set of neoantigens based on the set of numerical likelihoods to generate a set of selected neoantigens which are used to generate the at least one MHC class I neoantigen-encoding nucleic acid sequence.

In some aspects, a number of the set of selected neoantigens is 2-20.

In some aspects, the presentation model represents dependence between: presence of a pair of a particular one of the MHC alleles and a particular amino acid at a particular position of a peptide sequence; and likelihood of presentation on the tumor cell surface, by the particular one of the MHC alleles of the pair, of such a peptide sequence comprising the particular amino acid at the particular position.

In some aspects, selecting the set of selected neoantigens comprises selecting neoantigens that have an increased likelihood of being presented on the tumor cell surface relative to unselected neoantigens based on the presentation model. In some aspects, selecting the set of selected neoantigens comprises selecting neoantigens that have an increased likelihood of being capable of inducing a tumor-specific immune response in the subject relative to unselected neoantigens based on the presentation model. In some aspects, selecting the set of selected neoantigens comprises selecting neoantigens that have an increased likelihood of being capable of being presented to naïve T cells by professional antigen presenting cells (APCs) relative to unselected neoantigens based on the presentation model, optionally wherein the APC is a dendritic cell (DC). In some aspects, selecting the set of selected neoantigens comprises selecting neoantigens that have a decreased likelihood of being subject to inhibition via central or peripheral tolerance relative to unselected neoantigens based on the presentation model. In some aspects, selecting the set of selected neoantigens comprises selecting neoantigens that have a decreased likelihood of being capable of inducing an autoimmune response to normal tissue in the subject relative to unselected neoantigens based on the presentation model. In some aspects, exome or transcriptome nucleotide sequencing data is obtained by performing sequencing on the tumor tissue. In some aspects, the sequencing is next generation sequencing (NGS) or any massively parallel sequencing approach.

In some aspects, the neoantigen cassette comprises junctional epitope sequences formed by adjacent sequences in the neoantigen cassette. In some aspects, at least one or each junctional epitope sequence has an affinity of greater than 500 nM for MHC. In some aspects, each junctional epitope sequence is non-self. In some aspects, the neoantigen cassette does not encode a non-therapeutic MHC class I or class II epitope nucleic acid sequence comprising a translated, wild-type nucleic acid sequence, wherein the non-therapeutic epitope is predicted to be displayed on an MHC allele of the subject. In some aspects, the non-therapeutic predicted MHC class I or class II epitope sequence is a junctional epitope sequence formed by adjacent sequences in the neoantigen cassette. In some aspects, the prediction is based on presentation likelihoods generated by inputting sequences of the non-therapeutic epitopes into a presentation model. In some aspects, an order of the at least one antigen-encoding nucleic acid sequences in the neoantigen cassette is determined by a series of steps comprising: (a) generating a set of candidate neoantigen cassette sequences corresponding to different orders of the at least one antigen-encoding nucleic acid sequences; (b) determining, for each candidate neoantigen cassette sequence, a presentation score based on presentation of non-therapeutic epitopes in the candidate neoantigen cassette sequence; and (c) selecting a candidate cassette sequence associated with a presentation score below a predetermined threshold as the neoantigen cassette sequence for a neoantigen vaccine.

Also disclosed herein is a pharmaceutical composition comprising any of the compositions disclosed herein (such as an alphavirus-based or ChAd-based vector disclosed herein) and a pharmaceutically acceptable carrier. In some aspects, the pharmaceutical composition further comprises an adjuvant. In some aspects, the pharmaceutical composition further comprises an immune modulator. In some aspects, the immune modulator is an anti-CTLA4 antibody or an antigen-binding fragment thereof, an anti-PD-1 antibody or an antigen-binding fragment thereof, an anti-PD-L1 antibody or an antigen-binding fragment thereof, an anti-4-1BB antibody or an antigen-binding fragment thereof, or an anti-OX-40 antibody or an antigen-binding fragment thereof.

Also disclosed herein is an isolated nucleotide sequence or set of isolated nucleotide sequences comprising the neoantigen cassette of any of the above composition claims and one or more elements obtained from the sequence of SEQ ID NO:3 or SEQ ID NO:5, optionally wherein the one or more elements are selected from the group consisting of the sequences necessary for nonstructural protein-mediated amplification, the 26S promoter nucleotide sequence, the poly(A) sequence, and the nsP1-4 genes of the sequence set forth in SEQ ID NO:3 or SEQ ID NO:5, and optionally wherein the nucleotide sequence is cDNA. In some aspects, the sequence or set of isolated nucleotide sequences comprises a neoantigen cassette disclosed herein inserted at position 7544 of the sequence set forth in SEQ ID NO:6 or SEQ ID NO:7. In some aspects, the isolated nucleotide sequence further comprises a T7 or SP6 RNA polymerase promoter nucleotide sequence 5' of the one or more elements obtained from the sequence of SEQ ID NO:3 or SEQ ID NO:5, and optionally one or more restriction sites 3' of the poly(A) sequence. In some aspects, the the neoantigen cassette disclosed herein is inserted at position 7563 of SEQ ID NO:8 or SEQ ID NO:9. In another aspect, the sequences set forth in SEQ ID NO:8 or SEQ ID NO:9 further comprise an additional adenine nucleotide inserted at position 17.

Also disclosed herein is an isolated nucleotide sequence comprising a neoantigen cassette disclosed herein and at least one promoter disclosed herein. In some aspects, the isolated nucleotide sequence further comprises a ChAd-based gene. In some aspects, the ChAd-based gene is obtained from the sequence of SEQ ID NO: 1, optionally wherein the gene is selected from the group consisting of the chimpanzee adenovirus ITR, E1A, E1B, E2A, E2B, E3, E4, L1, L2, L3, L4, and L5 genes of the sequence set forth in SEQ ID NO: 1, and optionally wherein the nucleotide sequence is cDNA.

Also disclosed herein is an isolated cell comprising an isolated nucleotide sequence disclosed herein, optionally wherein the cell is a BHK-21, CHO, HEK293 or variants thereof, 911, HeLa, A549, LP-293, PER.C6, or AE1-2a cell.

Also disclosed herein is a vector comprising an isolated nucleotide sequence disclosed herein.

Also disclosed herein is a kit comprising a vector or a composition disclosed herein and instructions for use.

Also disclosed herein is a method for treating a subject with cancer, the method comprising administering to the subject a vector disclosed herein or a pharmaceutical composition disclosed herein. In some aspects, the at least one MHC class I neoantigen-encoding nucleic acid sequence derived from a tumor are derived from the tumor of the subject with cancer. In some aspects, the at least one MHC class I neoantigen-encoding nucleic acid sequence are not derived from the tumor of the subject with cancer.

Also disclosed herein is a method for inducing an immune response in a subject, the method comprising administering to the subject any of the compositions, vectors, or pharmaceutical compositions described herein.

In some aspects, the vector or composition is administered intramuscularly (IM), intradermally (ID), or subcutaneously (SC), or intravenously (IV).

In some aspects, the methods described herein further comprise administration of one or more immune modulators, optionally wherein the immune modulator is administered before, concurrently with, or after administration of the composition or pharmaceutical composition. In some aspects, the one or more immune modulators are selected from the group consisting of: an anti-CTLA4 antibody or an antigen-binding fragment thereof, an anti-PD-1 antibody or an antigen-binding fragment thereof, an anti-PD-L1 antibody or an antigen-binding fragment thereof, an anti-4-1BB antibody or an antigen-binding fragment thereof, or an anti-OX-40 antibody or an antigen-binding fragment thereof. In some aspects, the immune modulator is administered intravenously (IV), intramuscularly (IM), intradermally (ID), or subcutaneously (SC). In some aspects, the subcutaneous administration is near the site of the composition or pharmaceutical composition administration or in close proximity to one or more vector or composition draining lymph nodes.

In some aspects, the methods described herein further comprise administering to the subject a second vaccine composition. In some aspects, the second vaccine composition is administered prior to the administration of the composition or the pharmaceutical composition described above. In some aspects, the second vaccine composition is administered subsequent to the administration of the composition or the pharmaceutical compositions described above. In some aspects, the second vaccine composition is the same as the composition or the pharmaceutical compositions described above. In some aspects, the second vaccine composition is different from the composition or the pharmaceutical compositions described above. In some aspects, the second vaccine composition comprises a chimpanzee adenovirus vector encoding at least one antigen-encoding nucleic acid sequence. In some aspects, the at least one antigen-encoding nucleic acid sequence encoded by the chimpanzee adenovirus vector is the same as the at least one antigen-encoding nucleic acid sequence of any of the above compositions or vectors.

Also disclosed herein is a method of manufacturing the one or more vectors of any of the above compositions, the method comprising: obtaining a linearized DNA sequence comprising the RNA alphavirus backbone and the neoantigen cassette; in vitro transcribing the linearized DNA sequence by addition of the linearized DNA sequence to a in vitro transcription reaction containing all the necessary components to transcribe the linearized DNA sequence into RNA, optionally further comprising in vitro addition of the m7g cap to the resulting RNA; and isolating the one or more vectors from the in vitro transcription reaction. In some aspects, the linearized DNA sequence is generated by linearizing a DNA plasmid sequence or by amplification using PCR. In some aspects, the DNA plasmid sequence is generated using one of bacterial recombination or full genome DNA synthesis or full genome DNA synthesis with amplification of synthesized DNA in bacterial cells. In some aspects, the isolating the one or more vectors from the in vitro transcription reaction involves one or more of phenol chloroform extraction, silica column based purification, or similar RNA purification methods.

Also disclosed herein is a method of manufacturing any of the compositions disclosed herein, the method comprising: providing components for the nanoparticulate delivery vehicle; providing the neoantigen expression system; and providing conditions sufficient for the nanoparticulate delivery vehicle and the neoantigen expression system to produce the composition for delivery of the neoantigen expression system. In some aspects, the conditions are provided by microfluidic mixing.

Also disclosed herein is a method of manufacturing a adenovirus vector disclosed herein, the method comprising: obtaining a plasmid sequence comprising the at least one promoter sequence and the neoantigen cassette; transfecting the plasmid sequence into one or more host cells; and isolating the adenovirus vector from the one or more host cells.

In some aspects, isolating comprises: lysing the host cell to obtain a cell lysate comprising the adenovirus vector; and purifying the adenovirus vector from the cell lysate.

In some aspects, the plasmid sequence is generated using one of bacterial recombination or full genome DNA synthesis or full genome DNA synthesis with amplification of synthesized DNA in bacterial cells. In some aspects, the one or more host cells are at least one of CHO, HEK293 or variants thereof, 911, HeLa, A549, LP-293, PER.C6, and AE1-2a cells. In some aspects, purifying the adenovirus vector from the cell lysate involves one or more of chromatographic separation, centrifugation, virus precipitation, and filtration.

BRIEF DESCRIPTION OF THE SEVERAL VIEWS OF THE DRAWINGS

These and other features, aspects, and advantages of the present invention will become better understood with regard to the following description, and accompanying drawings, where:

FIG. 1A shows current clinical approaches to neoantigen identification.

FIG. 2B, FIG. 2C, FIG. 2D, and FIG. 2E illustrate a method of obtaining presentation information, in accordance with an embodiment. FIG. 2B discloses SEQ ID NO: 62. FIG. 2C discloses SEQ ID NOS 62-67, respectively, in order of appearance. FIG. 2D discloses SEQ ID NO: 157. FIG. 2E discloses SEQ ID NOS 62-65, 68, and 67, respectively in order of appearance.

FIG. 4A illustrates an example set of training data, according to one embodiment related to MHC class I alleles. FIG. 4A discloses Peptide Sequences as SEQ ID NOS 70-73 and C-Flanking Sequences as SEQ ID NOS 74, 158, 159, and 159, respectively, in order of appearance. FIG. 4B illustrates an example set of training data, according to one embodiment related to an MHC class II allele. FIG. 4B discloses SEQ ID NO: 75.

FIG. 6B illustrates an example network model NN$_H$(•) shared by MHC alleles, according to another embodiment.

FIG. 13C shows performance results for peptide presentation determined by mass-spectrometry for an example function-of-sums model (equation (13)), an example sum-of-functions model (equation (19)), and an example second order model (equation (23)) for predicting peptide presentation. The first column refers to the the area-under-curve (AUC) of the receiver operating characteristic (ROC) when each presentation model was applied to the test set, the second column refers to the value of the negative log likelihood loss, and the third column refers to the the positive predictive value (PPV) at a 10% recall rate.

FIG. 13D shows performance results for peptide presentation determined by mass-spectrometry for two example presentation models that are trained with and without single-allele mass spectrometry data. The first column refers to the the area-under-curve (AUC) of the receiver operating characteristic (ROC) when each presentation model was applied to the test set, the second column refers to the value of the negative log likelihood loss, and the third column refers to the the positive predictive value (PPV) at a 10% recall rate.

FIG. 13E shows performance results for peptide presentation determined by mass-spectrometry for two example presentation models that are trained with and without single-allele mass spectrometry data. "Correlation" refers to the correlation between the actual labels that indicate whether the peptide was presented on the corresponding allele in the test data, and the label for prediction.

FIG. 13F shows the frequency of common anchor residues at positions 2 (P2) and 9 (P9) among nonamers predicted by a presentation model trained without single-allele mass spectrometry data.

FIG. 13G shows performance results for peptide presentation determined by mass-spectrometry for an example presentation model that incorporated C- and N-terminal flanking sequences as allele-interacting variables, and an example presentation model that incorporated C- and N-terminal flanking sequences as allele-noninteracting variables. The first column refers to the the area-under-curve (AUC) of the receiver operating characteristic (ROC) when each presentation model was applied to the test set, the second column refers to the value of the negative log likelihood loss, and the third column refers to the the positive predictive value (PPV) at a 10% recall rate.

FIG. 13-O is a histogram that depicts the quantity of samples in which a particular MHC class II molecule allele was identified.

FIG. 19B illustrates in vivo evaluation of the impact of epitope position in long 21-mer cassettes and shows the sequence information on the T cell epitopes used. Figure discloses SEQ ID NOS 132, 133, 136, 135, 134, 162-164, 137, and 165-176, respectively, in order of appearance.

FIG. 20B illustrates final cassette design for preclinical IND-enabling studies and shows the sequence information for the T cell epitopes used that are presented on class I MHC of non-human primate (SEQ ID NOS 177-182, respectively, in order of appearance), mouse (SEQ ID NOS 57, 58 and 183-189, respectively, in order of appearance) and human origin (SEQ ID NOS 134-136, 132, and 133, respectively, in order of appearance), as well as sequences of 2 universal MHC class II epitopes PADRE and Tetanus toxoid (SEQ ID NOS 160 and 190, respectively, in order of appearance).

FIG. 27A illustrates antigen-specific T-cell responses following heterologous prime/boost in B16-OVA tumor bearing mice. B16-OVA tumor bearing C57BL/6J mice were injected with adenovirus expressing GFP (Ad5-GFP) and boosted with VEE-Luciferase srRNA formulated with MC3 LNP (Control) or Ad5-UbAAY and boosted with VEE-UbAAY srRNA (Vax). Both the Control and Vax groups were also treated with an IgG control mAb. A third group was treated with the Ad5-GFP prime/VEE-Luciferase srRNA boost in combination with anti-CTLA-4 (aCTLA-4), while the fourth group was treated with the Ad5-UbAAY prime/VEE-UbAAY boost in combination with anti-CTLA-4 (Vax+aCTLA-4). In addition, all mice were treated with anti-PD-1 mAb starting at day 21. T-cell responses were measured by IFN-gamma ELISPOT. Mice were sacrificed and spleens and lymph nodes collected at 14 days post immunization with adenovirus.

DETAILED DESCRIPTION

I. Definitions

Figure 1B:
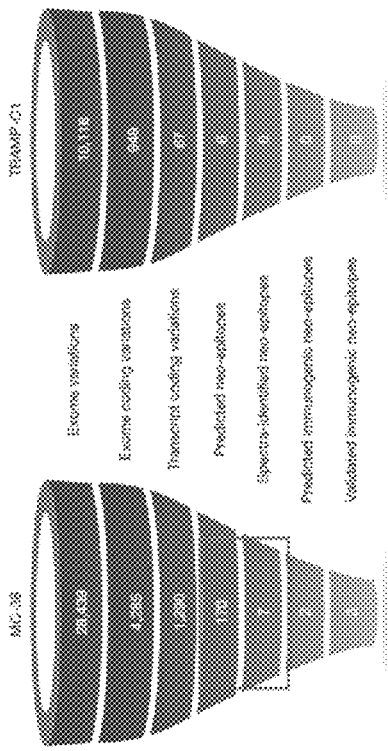
FIG. 1B shows that <5% of predicted bound peptides are presented on tumor cells.

In general, terms used in the claims and the specification are intended to be construed as having the plain meaning understood by a person of ordinary skill in the art. Certain terms are defined below to provide additional clarity. In case of conflict between the plain meaning and the provided definitions, the provided definitions are to be used.

As used herein the term "antigen" is a substance that induces an immune response.

As used herein the term "neoantigen" is an antigen that has at least one alteration that makes it distinct from the corresponding wild-type antigen, e.g., via mutation in a tumor cell or post-translational modification specific to a tumor cell. A neoantigen can include a polypeptide sequence or a nucleotide sequence. A mutation can include a frameshift or nonframeshift indel, missense or nonsense substitution, splice site alteration, genomic rearrangement or gene fusion, or any genomic or expression alteration giving rise to a neoORF. A mutations can also include a splice variant. Post-translational modifications specific to a tumor cell can include aberrant phosphorylation. Post-translational modifications specific to a tumor cell can also include a proteasome-generated spliced antigen. See Liepe et al., A large fraction of HLA class I ligands are proteasome-generated spliced peptides; Science. 2016 Oct. 21; 354(6310):354-358.

As used herein the term "tumor neoantigen" is a neoantigen present in a subject's tumor cell or tissue but not in the subject's corresponding normal cell or tissue.

As used herein the term "neoantigen-based vaccine" is a vaccine construct based on one or more neoantigens, e.g., a plurality of neoantigens.

As used herein the term "candidate neoantigen" is a mutation or other aberration giving rise to a new sequence that may represent a neoantigen.

As used herein the term "coding region" is the portion(s) of a gene that encode protein.

As used herein the term "coding mutation" is a mutation occurring in a coding region.

As used herein the term "ORF" means open reading frame.

As used herein the term "NEO-ORF" is a tumor-specific ORF arising from a mutation or other aberration such as splicing.

As used herein the term "missense mutation" is a mutation causing a substitution from one amino acid to another.

As used herein the term "nonsense mutation" is a mutation causing a substitution from an amino acid to a stop codon or causing removal of a canonical start codon.

As used herein the term "frameshift mutation" is a mutation causing a change in the frame of the protein.

As used herein the term "indel" is an insertion or deletion of one or more nucleic acids.

As used herein, the term percent "identity," in the context of two or more nucleic acid or polypeptide sequences, refer to two or more sequences or subsequences that have a specified percentage of nucleotides or amino acid residues that are the same, when compared and aligned for maximum correspondence, as measured using one of the sequence comparison algorithms described below (e.g., BLASTP and BLASTN or other algorithms available to persons of skill) or by visual inspection. Depending on the application, the percent "identity" can exist over a region of the sequence being compared, e.g., over a functional domain, or, alternatively, exist over the full length of the two sequences to be compared.

For sequence comparison, typically one sequence acts as a reference sequence to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters. Alternatively, sequence similarity or dissimilarity can be established by the combined presence or absence of particular nucleotides, or, for translated sequences, amino acids at selected sequence positions (e.g., sequence motifs).

Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally Ausubel et al., infra).

One example of an algorithm that is suitable for determining percent sequence identity and sequence similarity is the BLAST algorithm, which is described in Altschul et al., J. Mol. Biol. 215:403-410 (1990). Software for performing BLAST analyses is publicly available through the National Center for Biotechnology Information.

As used herein the term "non-stop or read-through" is a mutation causing the removal of the natural stop codon.

As used herein the term "epitope" is the specific portion of an antigen typically bound by an antibody or T cell receptor.

As used herein the term "immunogenic" is the ability to elicit an immune response, e.g., via T cells, B cells, or both.

As used herein the term "HLA binding affinity" "MHC binding affinity" means affinity of binding between a specific antigen and a specific MHC allele.

As used herein the term "bait" is a nucleic acid probe used to enrich a specific sequence of DNA or RNA from a sample.

As used herein the term "variant" is a difference between a subject's nucleic acids and the reference human genome used as a control.

As used herein the term "variant call" is an algorithmic determination of the presence of a variant, typically from sequencing.

As used herein the term "polymorphism" is a germline variant, i.e., a variant found in all DNA-bearing cells of an individual.

As used herein the term "somatic variant" is a variant arising in non-germline cells of an individual.

As used herein the term "allele" is a version of a gene or a version of a genetic sequence or a version of a protein.

As used herein the term "HLA type" is the complement of HLA gene alleles.

As used herein the term "nonsense-mediated decay" or "NMD" is a degradation of an mRNA by a cell due to a premature stop codon.

As used herein the term "truncal mutation" is a mutation originating early in the development of a tumor and present in a substantial portion of the tumor's cells.

As used herein the term "subclonal mutation" is a mutation originating later in the development of a tumor and present in only a subset of the tumor's cells.

As used herein the term "exome" is a subset of the genome that codes for proteins. An exome can be the collective exons of a genome.

As used herein the term "logistic regression" is a regression model for binary data from statistics where the logit of the probability that the dependent variable is equal to one is modeled as a linear function of the dependent variables.

As used herein the term "neural network" is a machine learning model for classification or regression consisting of multiple layers of linear transformations followed by element-wise nonlinearities typically trained via stochastic gradient descent and back-propagation.

As used herein the term "proteome" is the set of all proteins expressed and/or translated by a cell, group of cells, or individual.

As used herein the term "peptidome" is the set of all peptides presented by MHC-I or MHC-II on the cell surface. The peptidome may refer to a property of a cell or a collection of cells (e.g., the tumor peptidome, meaning the union of the peptidomes of all cells that comprise the tumor).

As used herein the term "ELISPOT" means Enzyme-linked immunosorbent spot assay—which is a common method for monitoring immune responses in humans and animals.

As used herein the term "dextramers" is a dextran-based peptide-MHC multimers used for antigen-specific T-cell staining in flow cytometry.

As used herein the term "tolerance or immune tolerance" is a state of immune non-responsiveness to one or more antigens, e.g. self-antigens.

As used herein the term "central tolerance" is a tolerance affected in the thymus, either by deleting self-reactive T-cell clones or by promoting self-reactive T-cell clones to differentiate into immunosuppressive regulatory T-cells (Tregs).

As used herein the term "peripheral tolerance" is a tolerance affected in the periphery by downregulating or anergizing self-reactive T-cells that survive central tolerance or promoting these T cells to differentiate into Tregs.

The term "sample" can include a single cell or multiple cells or fragments of cells or an aliquot of body fluid, taken from a subject, by means including venipuncture, excretion, ejaculation, massage, biopsy, needle aspirate, lavage sample, scraping, surgical incision, or intervention or other means known in the art.

The term "subject" encompasses a cell, tissue, or organism, human or non-human, whether in vivo, ex vivo, or in vitro, male or female. The term subject is inclusive of mammals including humans.

The term "mammal" encompasses both humans and non-humans and includes but is not limited to humans, non-human primates, canines, felines, murines, bovines, equines, and porcines.

The term "clinical factor" refers to a measure of a condition of a subject, e.g., disease activity or severity. "Clinical factor" encompasses all markers of a subject's health status, including non-sample markers, and/or other characteristics of a subject, such as, without limitation, age and gender. A clinical factor can be a score, a value, or a set of values that can be obtained from evaluation of a sample (or population of samples) from a subject or a subject under a determined condition. A clinical factor can also be predicted by markers and/or other parameters such as gene expression surrogates. Clinical factors can include tumor type, tumor sub-type, and smoking history.

The term "antigen-encoding nucleic acid sequences derived from a tumor" refers to nucleic acid sequences directly extracted from the tumor, e.g. via RT-PCR; or sequence data obtained by sequencing the tumor and then synthesizing the nucleic acid sequences using the sequencing data, e.g., via various synthetic or PCR-based methods known in the art.

The term "alphavirus" refers to members of the family Togaviridae, and are positive-sense single-stranded RNA viruses. Alphaviruses are typically classified as either Old World, such as Sindbis, Ross River, Mayaro, Chikungunya, and Semliki Forest viruses, or New World, such as eastern equine encephalitis, Aura, Fort Morgan, or Venezuelan equine encephalitis and its derivative strain TC-83. Alphaviruses are typically self-replicating RNA viruses.

The term "alphavirus backbone" refers to minimal sequence(s) of an alphavirus that allow for self-replication of the viral genome. Minimal sequences can include conserved sequences for nonstructural protein-mediated amplification, a nonstructural protein 1 (nsP1) gene, a nsP2 gene, a nsP3 gene, a nsP4 gene, and a polyA sequence, as well as sequences for expression of subgenomic viral RNA including a 26S promoter element.

The term "sequences for nonstructural protein-mediated amplification" includes alphavirus conserved sequence elements (CSE) well known to those in the art. CSEs include, but are not limited to, an alphavirus 5' UTR, a 51-nt CSE, a 24-nt CSE, or other 26S subgenomic promoter sequence, a 19-nt CSE, and an alphavirus 3' UTR.

The term "RNA polymerase" includes polymerases that catalyze the production of RNA polynucleotides from a DNA template. RNA polymerases include, but are not limited to, bacteriophage derived polymerases including T3, T7, and SP6.

The term "lipid" includes hydrophobic and/or amphiphilic molecules. Lipids can be cationic, anionic, or neutral. Lipids can be synthetic or naturally derived, and in some instances biodegradable. Lipids can include cholesterol, phospholipids, lipid conjugates including, but not limited to, polyethyleneglycol (PEG) conjugates (PEGylated lipids), waxes, oils, glycerides, fats, and fat-soluble vitamins. Lipids can also include dilinoleylmethyl-4-dimethylaminobutyrate (MC3) and MC3-like molecules.

The term "lipid nanoparticle" or "LNP" includes vesicle like structures formed using a lipid containing membrane surrounding an aqueous interior, also referred to as liposomes. Lipid nanoparticles includes lipid-based compositions with a solid lipid core stabilized by a surfactant. The core lipids can be fatty acids, acylglycerols, waxes, and mixtures of these surfactants. Biological membrane lipids such as phospholipids, sphingomyelins, bile salts (sodium taurocholate), and sterols (cholesterol) can be utilized as stabilizers. Lipid nanoparticles can be formed using defined ratios of different lipid molecules, including, but not limited to, defined ratios of one or more cationic, anionic, or neutral lipids. Lipid nanoparticles can encapsulate molecules within an outer-membrane shell and subsequently can be contacted with target cells to deliver the encapsulated molecules to the host cell cytosol. Lipid nanoparticles can be modified or functionalized with non-lipid molecules, including on their surface. Lipid nanoparticles can be single-layered (unilamellar) or multi-layered (multilamellar). Lipid nanoparticles can be complexed with nucleic acid. Unilamellar lipid nanoparticles can be complexed with nucleic acid, wherein the nucleic acid is in the aqueous interior. Multilamellar lipid nanoparticles can be complexed with nucleic acid, wherein the nucleic acid is in the aqueous interior, or to form or sandwiched between Abbreviations: MHC: major histocompatibility complex; HLA: human leukocyte antigen, or the human MHC gene locus; NGS: next-generation sequencing; PPV: positive predictive value; TSNA: tumor-specific neoantigen; FFPE: formalin-fixed, paraffin-embedded; NMD: nonsense-mediated decay; NSCLC: non-small-cell lung cancer; DC: dendritic cell.

It should be noted that, as used in the specification and the appended claims, the singular forms "a," "an," and "the" include plural referents unless the context clearly dictates otherwise.

Unless specifically stated or otherwise apparent from context, as used herein the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein are modified by the term about.

Any terms not directly defined herein shall be understood to have the meanings commonly associated with them as understood within the art of the invention. Certain terms are discussed herein to provide additional guidance to the practitioner in describing the compositions, devices, methods and the like of aspects of the invention, and how to make or use them. It will be appreciated that the same thing may be said in more than one way. Consequently, alternative language and synonyms may be used for any one or more of the terms discussed herein. No significance is to be placed upon whether or not a term is elaborated or discussed herein. Some synonyms or substitutable methods, materials and the like are provided. Recital of one or a few synonyms or equivalents does not exclude use of other synonyms or equivalents, unless it is explicitly stated. Use of examples, including examples of terms, is for illustrative purposes only and does not limit the scope and meaning of the aspects of the invention herein.

All references, issued patents and patent applications cited within the body of the specification are hereby incorporated by reference in their entirety, for all purposes.

II. Methods of Identifying Neoantigens

Disclosed herein are methods for identifying neoantigens from a tumor of a subject that are likely to be presented on the cell surface of the tumor or immune cells, including professional antigen presenting cells such as dendritic cells, and/or are likely to be immunogenic. As an example, one such method may comprise the steps of: obtaining at least one of exome, transcriptome or whole genome tumor nucleotide sequencing data from the tumor cell of the subject, wherein the tumor nucleotide sequencing data is used to obtain data representing peptide sequences of each of a set of neoantigens, and wherein the peptide sequence of each neoantigen comprises at least one alteration that makes it distinct from the corresponding wild-type peptide sequence; inputting the peptide sequence of each neoantigen into one or more presentation models to generate a set of numerical likelihoods that each of the neoantigens is presented by one or more MHC alleles on the tumor cell surface of the tumor cell of the subject or cells present in the tumor, the set of numerical likelihoods having been identified at least based on received mass spectrometry data; and selecting a subset of the set of neoantigens based on the set of numerical likelihoods to generate a set of selected neoantigens.

The presentation model can comprise a statistical regression or a machine learning (e.g., deep learning) model trained on a set of reference data (also referred to as a training data set) comprising a set of corresponding labels, wherein the set of reference data is obtained from each of a plurality of distinct subjects where optionally some subjects can have a tumor, and wherein the set of reference data comprises at least one of: data representing exome nucleotide sequences from tumor tissue, data representing exome nucleotide sequences from normal tissue, data representing transcriptome nucleotide sequences from tumor tissue, data representing proteome sequences from tumor tissue, and data representing MHC peptidome sequences from tumor tissue, and data representing MHC peptidome sequences from normal tissue. The reference data can further comprise mass spectrometry data, sequencing data, RNA sequencing data, and proteomics data for single-allele cell lines engineered to express a predetermined MHC allele that are subsequently exposed to synthetic protein, normal and tumor human cell lines, and fresh and frozen primary samples, and T cell assays (e.g., ELISPOT). In certain aspects, the set of reference data includes each form of reference data.

The presentation model can comprise a set of features derived at least in part from the set of reference data, and wherein the set of features comprises at least one of allele dependent-features and allele-independent features. In certain aspects each feature is included.

Also disclosed herein are methods for generating an output for constructing a personalized cancer vaccine by identifying one or more neoantigens from one or more tumor cells of a subject that are likely to be presented on a surface of the tumor cells. As an example, one such method may comprise the steps of: obtaining at least one of exome, transcriptome, or whole genome nucleotide sequencing data from the tumor cells and normal cells of the subject, wherein the nucleotide sequencing data is used to obtain data representing peptide sequences of each of a set of neoantigens identified by comparing the nucleotide sequencing data from the tumor cells and the nucleotide sequencing data from the normal cells, and wherein the peptide sequence of each neoantigen comprises at least one alteration that makes it distinct from the corresponding wild-type, peptide sequence identified from the normal cells of the subject; encoding the peptide sequences of each of the neoantigens into a corresponding numerical vector, each numerical vector including information regarding a plurality of amino acids that make up the peptide sequence and a set of positions of the amino acids in the peptide sequence; inputting the numerical vectors, using a computer processor, into a deep learning presentation model to generate a set of presentation likelihoods for the set of neoantigens, each presentation likelihood in the set representing the likelihood that a corresponding neoantigen is presented by one or more class II MHC alleles on the surface of the tumor cells of the subject, the deep learning presentation model; selecting a subset of the set of neoantigens based on the set of presentation likelihoods to generate a set of selected neoantigens; and generating the output for constructing the personalized cancer vaccine based on the set of selected neoantigens.

In some embodiments, the presentation model comprises a plurality of parameters identified at least based on a training data set and a function representing a relation between the numerical vector received as an input and the presentation likelihood generated as output based on the numerical vector and the parameters. In certain embodiments, the training data set comprises labels obtained by mass spectrometry measuring presence of peptides bound to at least one class II MHC allele identified as present in at least one of a plurality of samples, training peptide sequences encoded as numerical vectors including information regarding a plurality of amino acids that make up the peptide sequence and a set of positions of the amino acids in the peptide sequence, and at least one HLA allele associated with the training peptide sequences.

Dendritic cell presentation to naïve T cell features can comprise at least one of: A feature described above. The dose and type of antigen in the vaccine. (e.g., peptide, mRNA, virus, etc.): (1) The route by which dendritic cells (DCs) take up the antigen type (e.g., endocytosis, micropinocytosis); and/or (2) The efficacy with which the antigen is taken up by DCs. The dose and type of adjuvant in the vaccine. The length of the vaccine antigen sequence. The number and sites of vaccine administration. Baseline patient immune functioning (e.g., as measured by history of recent infections, blood counts, etc). For RNA vaccines: (1) the turnover rate of the mRNA protein product in the dendritic cell; (2) the rate of translation of the mRNA after uptake by dendritic cells as measured in in vitro or in vivo experiments; and/or (3) the number or rounds of translation of the mRNA after uptake by dendritic cells as measured by in vivo or in vitro experiments. The presence of protease cleavage motifs in the peptide, optionally giving additional weight to proteases typically expressed in dendritic cells (as measured by RNA-seq or mass spectrometry). The level of expression of the proteasome and immunoproteasome in typical activated dendritic cells (which may be measured by RNA-seq, mass spectrometry, immunohistochemistry, or other standard techniques). The expression levels of the particular MHC allele in the individual in question (e.g., as measured by RNA-seq or mass spectrometry), optionally measured specifically in activated dendritic cells or other immune cells. The probability of peptide presentation by the particular MHC allele in other individuals who express the particular MHC allele, optionally measured specifically in activated dendritic cells or other immune cells. The probability of peptide presentation by MHC alleles in the same family of molecules (e.g., HLA-A, HLA-B, HLA-C, HLA-DQ, HLA-DR, HLA-DP) in other individuals, optionally measured specifically in activated dendritic cells or other immune cells.

Immune tolerance escape features can comprise at least one of: Direct measurement of the self-peptidome via protein mass spectrometry performed on one or several cell types. Estimation of the self-peptidome by taking the union of all k-mer (e.g. 5-25) substrings of self-proteins. Estimation of the self-peptidome using a model of presentation similar to the presentation model described above applied to all non-mutation self-proteins, optionally accounting for germline variants.

Ranking can be performed using the plurality of neoantigens provided by at least one model based at least in part on the numerical likelihoods. Following the ranking a selecting can be performed to select a subset of the ranked neoantigens according to a selection criteria. After selecting a subset of the ranked peptides can be provided as an output.

A number of the set of selected neoantigens may be 20.

The presentation model may represent dependence between presence of a pair of a particular one of the MHC alleles and a particular amino acid at a particular position of a peptide sequence; and likelihood of presentation on the tumor cell surface, by the particular one of the MHC alleles of the pair, of such a peptide sequence comprising the particular amino acid at the particular position.

A method disclosed herein can also include applying the one or more presentation models to the peptide sequence of the corresponding neoantigen to generate a dependency score for each of the one or more MHC alleles indicating whether the MHC allele will present the corresponding neoantigen based on at least positions of amino acids of the peptide sequence of the corresponding neoantigen.

A method disclosed herein can also include transforming the dependency scores to generate a corresponding per-allele likelihood for each MHC allele indicating a likelihood that the corresponding MHC allele will present the corresponding neoantigen; and combining the per-allele likelihoods to generate the numerical likelihood.

The step of transforming the dependency scores can model the presentation of the peptide sequence of the corresponding neoantigen as mutually exclusive.

A method disclosed herein can also include transforming a combination of the dependency scores to generate the numerical likelihood.

The step of transforming the combination of the dependency scores can model the presentation of the peptide sequence of the corresponding neoantigen as interfering between MHC alleles.

The set of numerical likelihoods can be further identified by at least an allele noninteracting feature, and a method disclosed herein can also include applying an allele noninteracting one of the one or more presentation models to the allele noninteracting features to generate a dependency score for the allele noninteracting features indicating whether the peptide sequence of the corresponding neoantigen will be presented based on the allele noninteracting features.

A method disclosed herein can also include combining the dependency score for each MHC allele in the one or more MHC alleles with the dependency score for the allele noninteracting feature; transforming the combined dependency scores for each MHC allele to generate a corresponding per-allele likelihood for the MHC allele indicating a likelihood that the corresponding MHC allele will present the corresponding neoantigen; and combining the per-allele likelihoods to generate the numerical likelihood.

A method disclosed herein can also include transforming a combination of the dependency scores for each of the MHC alleles and the dependency score for the allele non-interacting features to generate the numerical likelihood.

A set of numerical parameters for the presentation model can be trained based on a training data set including at least a set of training peptide sequences identified as present in a plurality of samples and one or more MHC alleles associated with each training peptide sequence, wherein the training peptide sequences are identified through mass spectrometry on isolated peptides eluted from MHC alleles derived from the plurality of samples.

The samples can also include cell lines engineered to express a single MHC class I or class II allele.

The samples can also include cell lines engineered to express a plurality of MHC class I or class II alleles.

The samples can also include human cell lines obtained or derived from a plurality of patients.

The samples can also include fresh or frozen tumor samples obtained from a plurality of patients.

The samples can also include fresh or frozen tissue samples obtained from a plurality of patients.

The samples can also include peptides identified using T-cell assays.

The training data set can further include data associated with: peptide abundance of the set of training peptides present in the samples; peptide length of the set of training peptides in the samples.

The training data set may be generated by comparing the set of training peptide sequences via alignment to a database comprising a set of known protein sequences, wherein the set of training protein sequences are longer than and include the training peptide sequences.

The training data set may be generated based on performing or having performed nucleotide sequencing on a cell line to obtain at least one of exome, transcriptome, or whole genome sequencing data from the cell line, the sequencing data including at least one nucleotide sequence including an alteration.

The training data set may be generated based on obtaining at least one of exome, transcriptome, and whole genome normal nucleotide sequencing data from normal tissue samples.

The training data set may further include data associated with proteome sequences associated with the samples.

The training data set may further include data associated with MHC peptidome sequences associated with the samples.

The training data set may further include data associated with peptide-MHC binding affinity measurements for at least one of the isolated peptides.

The training data set may further include data associated with peptide-MHC binding stability measurements for at least one of the isolated peptides.

The training data set may further include data associated with transcriptomes associated with the samples.

The training data set may further include data associated with genomes associated with the samples.

The training peptide sequences may be of lengths within a range of k-mers where k is between 8-15, inclusive for MHC class I or 6-30 inclusive for MHC class II.

A method disclosed herein can also include encoding the peptide sequence using a one-hot encoding scheme.

A method disclosed herein can also include encoding the training peptide sequences using a left-padded one-hot encoding scheme.

A method of treating a subject having a tumor, comprising performing the steps of any of the neoantigen identification methods described herein, and further comprising obtaining a tumor vaccine comprising the set of selected neoantigens, and administering the tumor vaccine to the subject.

A method disclosed herein can also include identifying one or more T cells that are antigen-specific for at least one of the neoantigens in the subset. In some embodiments, the identification comprises co-culturing the one or more T cells with one or more of the neoantigens in the subset under conditions that expand the one or more antigen-specific T cells. In further embodiments, the identification comprises contacting the one or more T cells with a tetramer comprising one or more of the neoantigens in the subset under conditions that allow binding between the T cell and the tetramer. In even further embodiments, the method disclosed herein can also include identifying one or more T cell receptors (TCR) of the one or more identified T cells. In certain embodiments, identifying the one or more T cell receptors comprises sequencing the T cell receptor sequences of the one or more identified T cells. The method disclosed herein can further comprise genetically engineering a plurality of T cells to express at least one of the one or more identified T cell receptors; culturing the plurality of T cells under conditions that expand the plurality of T cells; and infusing the expanded T cells into the subject. In some embodiments, genetically engineering the plurality of T cells to express at least one of the one or more identified T cell receptors comprises cloning the T cell receptor sequences of the one or more identified T cells into an expression vector; and transfecting each of the plurality of T cells with the expression vector. In some embodiments, the method disclosed herein further comprises culturing the one or more identified T cells under conditions that expand the one or more identified T cells; and infusing the expanded T cells into the subject.

Also disclosed herein is an isolated T cell that is antigen-specific for at least one selected neoantigen in the subset.

Also disclosed herein is a methods for manufacturing a tumor vaccine, comprising the steps of: obtaining at least one of exome, transcriptome or whole genome tumor nucleotide sequencing data from the tumor cell of the subject, wherein the tumor nucleotide sequencing data is used to obtain data representing peptide sequences of each of a set of neoantigens, and wherein the peptide sequence of each neoantigen comprises at least one alteration that makes it distinct from the corresponding wild-type peptide sequence; inputting the peptide sequence of each neoantigen into one or more presentation models to generate a set of numerical likelihoods that each of the neoantigens is presented by one or more MHC alleles on the tumor cell surface of the tumor cell of the subject, the set of numerical likelihoods having been identified at least based on received mass spectrometry data; and selecting a subset of the set of neoantigens based on the set of numerical likelihoods to generate a set of selected neoantigens; and producing or having produced a tumor vaccine comprising the set of selected neoantigens.

Also disclosed herein is a tumor vaccine including a set of selected neoantigens selected by performing the method comprising the steps of: obtaining at least one of exome, transcriptome or whole genome tumor nucleotide sequencing data from the tumor cell of the subject, wherein the tumor nucleotide sequencing data is used to obtain data representing peptide sequences of each of a set of neoantigens, and wherein the peptide sequence of each neoantigen comprises at least one alteration that makes it distinct from the corresponding wild-type peptide sequence; inputting the peptide sequence of each neoantigen into one or more presentation models to generate a set of numerical likelihoods that each of the neoantigens is presented by one or more MHC alleles on the tumor cell surface of the tumor cell of the subject, the set of numerical likelihoods having been identified at least based on received mass spectrometry data; and selecting a subset of the set of neoantigens based on the set of numerical likelihoods to generate a set of selected neoantigens; and producing or having produced a tumor vaccine comprising the set of selected neoantigens.

The tumor vaccine may include one or more of a nucleotide sequence, a polypeptide sequence, RNA, DNA, a cell, a plasmid, or a vector.

The tumor vaccine may include one or more neoantigens presented on the tumor cell surface.

The tumor vaccine may include one or more neoantigens that is immunogenic in the subject.

The tumor vaccine may not include one or more neoantigens that induce an autoimmune response against normal tissue in the subject.

The tumor vaccine may include an adjuvant.

The tumor vaccine may include an excipient.

A method disclosed herein may also include selecting neoantigens that have an increased likelihood of being presented on the tumor cell surface relative to unselected neoantigens based on the presentation model.

A method disclosed herein may also include selecting neoantigens that have an increased likelihood of being capable of inducing a tumor-specific immune response in the subject relative to unselected neoantigens based on the presentation model.

A method disclosed herein may also include selecting neoantigens that have an increased likelihood of being capable of being presented to naïve T cells by professional antigen presenting cells (APCs) relative to unselected neoantigens based on the presentation model, optionally wherein the APC is a dendritic cell (DC).

A method disclosed herein may also include selecting neoantigens that have a decreased likelihood of being subject to inhibition via central or peripheral tolerance relative to unselected neoantigens based on the presentation model.

A method disclosed herein may also include selecting neoantigens that have a decreased likelihood of being capable of inducing an autoimmune response to normal tissue in the subject relative to unselected neoantigens based on the presentation model.

The exome or transcriptome nucleotide sequencing data may be obtained by performing sequencing on the tumor tissue.

The sequencing may be next generation sequencing (NGS) or any massively parallel sequencing approach.

The set of numerical likelihoods may be further identified by at least MHC-allele interacting features comprising at least one of: the predicted affinity with which the MHC allele and the neoantigen encoded peptide bind; the predicted stability of the neoantigen encoded peptide-MHC complex; the sequence and length of the neoantigen encoded peptide; the probability of presentation of neoantigen encoded peptides with similar sequence in cells from other individuals expressing the particular MHC allele as assessed by mass-spectrometry proteomics or other means; the expression levels of the particular MHC allele in the subject in question (e.g. as measured by RNA-seq or mass spectrometry); the overall neoantigen encoded peptide-sequence-independent probability of presentation by the particular MHC allele in other distinct subjects who express the particular MHC allele; the overall neoantigen encoded peptide-sequence-independent probability of presentation by MHC alleles in the same family of molecules (e.g., HLA-A, HLA-B, HLA-C, HLA-DQ, HLA-DR, HLA-DP) in other distinct subjects.

The set of numerical likelihoods are further identified by at least MHC-allele noninteracting features comprising at least one of: the C- and N-terminal sequences flanking the neoantigen encoded peptide within its source protein sequence; the presence of protease cleavage motifs in the neoantigen encoded peptide, optionally weighted according to the expression of corresponding proteases in the tumor cells (as measured by RNA-seq or mass spectrometry); the turnover rate of the source protein as measured in the appropriate cell type; the length of the source protein, optionally considering the specific splice variants ("isoforms") most highly expressed in the tumor cells as measured by RNA-seq or proteome mass spectrometry, or as predicted from the annotation of germline or somatic splicing mutations detected in DNA or RNA sequence data; the level of expression of the proteasome, immunoproteasome, thymoproteasome, or other proteases in the tumor cells (which may be measured by RNA-seq, proteome mass spectrometry, or immunohistochemistry); the expression of the source gene of the neoantigen encoded peptide (e.g., as measured by RNA-seq or mass spectrometry); the typical tissue-specific expression of the source gene of the neoantigen encoded peptide during various stages of the cell cycle; a comprehensive catalog of features of the source protein and/or its domains as can be found in e.g. uniProt or PDB http://www.rcsb.org/pdb/home/home.do; features describing the properties of the domain of the source protein containing the peptide, for example: secondary or tertiary structure (e.g., alpha helix vs beta sheet); alternative splicing; the probability of presentation of peptides from the source protein of the neoantigen encoded peptide in question in other distinct subjects; the probability that the peptide will not be detected or over-represented by mass spectrometry due to technical biases; the expression of various gene modules/pathways as measured by RNASeq (which need not contain the source protein of the peptide) that are informative about the state of the tumor cells, stroma, or tumor-infiltrating lymphocytes (TILs); the copy number of the source gene of the neoantigen encoded peptide in the tumor cells; the probability that the peptide binds to the TAP or the measured or predicted binding affinity of the peptide to the TAP; the expression level of TAP in the tumor cells (which may be measured by RNA-seq, proteome mass spectrometry, immunohistochemistry); presence or absence of tumor mutations, including, but not limited to: driver mutations in known cancer driver genes such as EGFR, KRAS, ALK, RET, ROS1, TP53, CDKN2A, CDKN2B, NTRK1, NTRK2, NTRK3, and in genes encoding the proteins involved in the antigen presentation machinery (e.g., B2M, HLA-A, HLA-B, HLA-C, TAP-1, TAP-2, TAPBP, CALR, CNX, ERP57, HLA-DM, HLA-DMA, HLA-DMB, HLA-DO, HLA-DOA, HLA-DOB, HLA-DP, HLA-DPA1, HLA-DPB1, HLA-DQ, HLA-DQA1, HLA-DQA2, HLA-DQB1, HLA-DQB2, HLA-DR, HLA-DRA, HLA-DRB1, HLA-DRB3, HLA-DRB4, HLA-DRB5 or any of the genes coding for components of the proteasome or immunoproteasome). Peptides whose presentation relies on a component of the antigen-presentation machinery that is subject to loss-of-function mutation in the tumor have reduced probability of presentation; presence or absence of functional germline polymorphisms, including, but not limited to: in genes encoding the proteins involved in the antigen presentation machinery (e.g., B2M, HLA-A, HLA-B, HLA-C, TAP-1, TAP-2, TAPBP, CALR, CNX, ERP57, HLA-DM, HLA-DMA, HLA-DMB, HLA-DO, HLA-DOA, HLA-DOB, HLA-DP, HLA-DPA1, HLA-DPB1, HLA-DQ, HLA-DQA1, HLA-DQA2, HLA-DQB1, HLA-DQB2, HLA-DR, HLA-DRA, HLA-DRB1, HLA-DRB3, HLA-DRB4, HLA-DRB5 or any of the genes coding for components of the proteasome or immunoproteasome); tumor type (e.g., NSCLC, melanoma); clinical tumor subtype (e.g., squamous lung cancer vs. non-squamous); smoking history; the typical expression of the source gene of the peptide in the relevant tumor type or clinical subtype, optionally stratified by driver mutation.

The at least one alteration may be a frameshift or non-frameshift indel, missense or nonsense substitution, splice site alteration, genomic rearrangement or gene fusion, or any genomic or expression alteration giving rise to a neoORF.

The tumor cell may be selected from the group consisting of: lung cancer, melanoma, breast cancer, ovarian cancer, prostate cancer, kidney cancer, gastric cancer, colon cancer, testicular cancer, head and neck cancer, pancreatic cancer, brain cancer, B-cell lymphoma, acute myelogenous leukemia, chronic myelogenous leukemia, chronic lymphocytic leukemia, and T cell lymphocytic leukemia, non-small cell lung cancer, and small cell lung cancer.

A method disclosed herein may also include obtaining a tumor vaccine comprising the set of selected neoantigens or a subset thereof, optionally further comprising administering the tumor vaccine to the subject.

At least one of neoantigens in the set of selected neoantigens, when in polypeptide form, may include at least one of: a binding affinity with MHC with an IC50 value of less than 1000 nM, for MHC Class I polypeptides a length of 8-15, 8, 9, 10, 11, 12, 13, 14, or 15 amino acids, for MHC Class II polypeptides a length of 6-30, 6, 7, 8, 9, 10, 11, 12, 13, 14, 15, 16, 17, 18, 19, 20, 21, 22, 23, 24, 25, 26, 27, 28, 29, or 30 amino acids, presence of sequence motifs within or near the polypeptide in the parent protein sequence promoting proteasome cleavage, and presence of sequence motifs promoting TAP transport. For MHC Class II, presence of sequence motifs within or near the peptide promoting cleavage by extracellular or lysosomal proteases (e.g., cathepsins) or HLA-DM catalyzed HLA binding.

Also disclosed herein is a methods for generating a model for identifying one or more neoantigens that are likely to be presented on a tumor cell surface of a tumor cell, comprising the steps of: receiving mass spectrometry data comprising data associated with a plurality of isolated peptides eluted from major histocompatibility complex (MHC) derived from a plurality of samples; obtaining a training data set by at least identifying a set of training peptide sequences present in the samples and one or more MHCs associated with each training peptide sequence; training a set of numerical parameters of a presentation model using the training data set comprising the training peptide sequences, the presentation model providing a plurality of numerical likelihoods that peptide sequences from the tumor cell are presented by one or more MHC alleles on the tumor cell surface.

The presentation model may represent dependence between: presence of a particular amino acid at a particular position of a peptide sequence; and likelihood of presentation, by one of the MHC alleles on the tumor cell, of the peptide sequence containing the particular amino acid at the particular position.

The samples can also include cell lines engineered to express a single MHC class I or class II allele.

The samples can also include cell lines engineered to express a plurality of MHC class I or class II alleles.

The samples can also include human cell lines obtained or derived from a plurality of patients.

The samples can also include fresh or frozen tumor samples obtained from a plurality of patients.

The samples can also include peptides identified using T-cell assays.

The training data set may further include data associated with: peptide abundance of the set of training peptides present in the samples; peptide length of the set of training peptides in the samples.

A method disclosed herein can also include obtaining a set of training protein sequences based on the training peptide sequences by comparing the set of training peptide sequences via alignment to a database comprising a set of known protein sequences, wherein the set of training protein sequences are longer than and include the training peptide sequences.

A method disclosed herein can also include performing or having performed mass spectrometry on a cell line to obtain at least one of exome, transcriptome, or whole genome nucleotide sequencing data from the cell line, the nucleotide sequencing data including at least one protein sequence including a mutation.

A method disclosed herein can also include: encoding the training peptide sequences using a one-hot encoding scheme.

A method disclosed herein can also include obtaining at least one of exome, transcriptome, and whole genome normal nucleotide sequencing data from normal tissue samples; and training the set of parameters of the presentation model using the normal nucleotide sequencing data.

The training data set may further include data associated with proteome sequences associated with the samples.

The training data set may further include data associated with MHC peptidome sequences associated with the samples.

The training data set may further include data associated with peptide-MHC binding affinity measurements for at least one of the isolated peptides.

The training data set may further include data associated with peptide-MHC binding stability measurements for at least one of the isolated peptides.

The training data set may further include data associated with transcriptomes associated with the samples.

The training data set may further include data associated with genomes associated with the samples.

A method disclosed herein may also include logistically regressing the set of parameters.

The training peptide sequences may be lengths within a range of k-mers where k is between 8-15, inclusive for MHC class I or 6-30, inclusive for MHC class II.

A method disclosed herein may also include encoding the training peptide sequences using a left-padded one-hot encoding scheme.

A method disclosed herein may also include determining values for the set of parameters using a deep learning algorithm.

Disclosed herein is are methods for identifying one or more neoantigens that are likely to be presented on a tumor cell surface of a tumor cell, comprising executing the steps of: receiving mass spectrometry data comprising data associated with a plurality of isolated peptides eluted from major histocompatibility complex (MHC) derived from a plurality of fresh or frozen tumor samples; obtaining a training data set by at least identifying a set of training peptide sequences present in the tumor samples and presented on one or more MHC alleles associated with each training peptide sequence; obtaining a set of training protein sequences based on the training peptide sequences; and training a set of numerical parameters of a presentation model using the training protein sequences and the training peptide sequences, the presentation model providing a plurality of numerical likelihoods that peptide sequences from the tumor cell are presented by one or more MHC alleles on the tumor cell surface.

The presentation model may represent dependence between: presence of a pair of a particular one of the MHC alleles and a particular amino acid at a particular position of a peptide sequence; and likelihood of presentation on the tumor cell surface, by the particular one of the MHC alleles of the pair, of such a peptide sequence comprising the particular amino acid at the particular position.

A method disclosed herein can also include selecting a subset of neoantigens, wherein the subset of neoantigens is selected because each has an increased likelihood that it is presented on the cell surface of the tumor relative to one or more distinct tumor neoantigens.

A method disclosed herein can also include selecting a subset of neoantigens, wherein the subset of neoantigens is selected because each has an increased likelihood that it is capable of inducing a tumor-specific immune response in the subject relative to one or more distinct tumor neoantigens.

A method disclosed herein can also include selecting a subset of neoantigens, wherein the subset of neoantigens is selected because each has an increased likelihood that it is capable of being presented to naïve T cells by professional antigen presenting cells (APCs) relative to one or more distinct tumor neoantigens, optionally wherein the APC is a dendritic cell (DC).

A method disclosed herein can also include selecting a subset of neoantigens, wherein the subset of neoantigens is selected because each has a decreased likelihood that it is subject to inhibition via central or peripheral tolerance relative to one or more distinct tumor neoantigens.

A method disclosed herein can also include selecting a subset of neoantigens, wherein the subset of neoantigens is selected because each has a decreased likelihood that it is capable of inducing an autoimmune response to normal tissue in the subject relative to one or more distinct tumor neoantigens.

A method disclosed herein can also include selecting a subset of neoantigens, wherein the subset of neoantigens is selected because each has a decreased likelihood that it will be differentially post-translationally modified in tumor cells versus APCs, optionally wherein the APC is a dendritic cell (DC).

The practice of the methods herein will employ, unless otherwise indicated, conventional methods of protein chemistry, biochemistry, recombinant DNA techniques and pharmacology, within the skill of the art. Such techniques are explained fully in the literature. See, e.g., T. E. Creighton, *Proteins: Structures and Molecular Properties* (W.H. Freeman and Company, 1993); A. L. Lehninger, *Biochemistry* (Worth Publishers, Inc., current addition); Sambrook, et al., *Molecular Cloning: A Laboratory Manual* (2nd Edition, 1989); *Methods In Enzymology* (S. Colowick and N. Kaplan eds., Academic Press, Inc.); *Remington's Pharmaceutical Sciences,* 18th Edition (Easton, Pa.: Mack Publishing Company, 1990); Carey and Sundberg *Advanced Organic Chemistry* $3^{rd}$ Ed. (Plenum Press) Vols A and B(1992).

III. Identification of Tumor Specific Mutations in Neoantigens

Also disclosed herein are methods for the identification of certain mutations (e.g., the variants or alleles that are present in cancer cells). In particular, these mutations can be present in the genome, transcriptome, proteome, or exome of cancer cells of a subject having cancer but not in normal tissue from the subject.

Genetic mutations in tumors can be considered useful for the immunological targeting of tumors if they lead to changes in the amino acid sequence of a protein exclusively in the tumor. Useful mutations include: (1) non-synonymous mutations leading to different amino acids in the protein; (2) read-through mutations in which a stop codon is modified or deleted, leading to translation of a longer protein with a novel tumor-specific sequence at the C-terminus; (3) splice site mutations that lead to the inclusion of an intron in the mature mRNA and thus a unique tumor-specific protein sequence; (4) chromosomal rearrangements that give rise to a chimeric protein with tumor-specific sequences at the junction of 2 proteins (i.e., gene fusion); (5) frameshift mutations or deletions that lead to a new open reading frame with a novel tumor-specific protein sequence. Mutations can also include one or more of nonframeshift indel, missense or nonsense substitution, splice site alteration, genomic rearrangement or gene fusion, or any genomic or expression alteration giving rise to a neoORF.

Peptides with mutations or mutated polypeptides arising from for example, splice-site, frameshift, readthrough, or gene fusion mutations in tumor cells can be identified by sequencing DNA, RNA or protein in tumor versus normal cells.

Also mutations can include previously identified tumor specific mutations. Known tumor mutations can be found at the Catalogue of Somatic Mutations in Cancer (COSMIC) database.

A variety of methods are available for detecting the presence of a particular mutation or allele in an individual's DNA or RNA. Advancements in this field have provided accurate, easy, and inexpensive large-scale SNP genotyping. For example, several techniques have been described including dynamic allele-specific hybridization (DASH), microplate array diagonal gel electrophoresis (MADGE), pyrosequencing, oligonucleotide-specific ligation, the TaqMan system as well as various DNA "chip" technologies such as the Affymetrix SNP chips. These methods utilize amplification of a target genetic region, typically by PCR. Still other methods, based on the generation of small signal molecules by invasive cleavage followed by mass spectrometry or immobilized padlock probes and rolling-circle amplification. Several of the methods known in the art for detecting specific mutations are summarized below.

PCR based detection means can include multiplex amplification of a plurality of markers simultaneously. For example, it is well known in the art to select PCR primers to generate PCR products that do not overlap in size and can be analyzed simultaneously. Alternatively, it is possible to amplify different markers with primers that are differentially labeled and thus can each be differentially detected. Of course, hybridization based detection means allow the differential detection of multiple PCR products in a sample. Other techniques are known in the art to allow multiplex analyses of a plurality of markers.

Several methods have been developed to facilitate analysis of single nucleotide polymorphisms in genomic DNA or cellular RNA. For example, a single base polymorphism can be detected by using a specialized exonuclease-resistant nucleotide, as disclosed, e.g., in Mundy, C. R. (U.S. Pat. No. 4,656,127). According to the method, a primer complementary to the allelic sequence immediately 3' to the polymorphic site is permitted to hybridize to a target molecule obtained from a particular animal or human. If the polymorphic site on the target molecule contains a nucleotide that is complementary to the particular exonuclease-resistant nucleotide derivative present, then that derivative will be incorporated onto the end of the hybridized primer. Such incorporation renders the primer resistant to exonuclease, and thereby permits its detection. Since the identity of the exonuclease-resistant derivative of the sample is known, a finding that the primer has become resistant to exonucleases reveals that the nucleotide(s) present in the polymorphic site of the target molecule is complementary to that of the nucleotide derivative used in the reaction. This method has the advantage that it does not require the determination of large amounts of extraneous sequence data.

A solution-based method can be used for determining the identity of a nucleotide of a polymorphic site. Cohen, D. et al. (French Patent 2,650,840; PCT Appln. No. WO91/02087). As in the Mundy method of U.S. Pat. No. 4,656,127, a primer is employed that is complementary to allelic sequences immediately 3' to a polymorphic site. The method determines the identity of the nucleotide of that site using labeled dideoxynucleotide derivatives, which, if complementary to the nucleotide of the polymorphic site will become incorporated onto the terminus of the primer.

An alternative method, known as Genetic Bit Analysis or GBA is described by Goelet, P. et al. (PCT Appln. No. 92/15712). The method of Goelet, P. et al. uses mixtures of labeled terminators and a primer that is complementary to the sequence 3' to a polymorphic site. The labeled terminator that is incorporated is thus determined by, and complementary to, the nucleotide present in the polymorphic site of the target molecule being evaluated. In contrast to the method of Cohen et al. (French Patent 2,650,840; PCT Appln. No. WO91/02087) the method of Goelet, P. et al. can be a heterogeneous phase assay, in which the primer or the target molecule is immobilized to a solid phase.

Several primer-guided nucleotide incorporation procedures for assaying polymorphic sites in DNA have been described (Komher, J. S. et al., Nucl. Acids. Res. 17:7779-7784 (1989); Sokolov, B. P., Nucl. Acids Res. 18:3671 (1990); Syvanen, A.-C., et al., Genomics 8:684-692 (1990); Kuppuswamy, M. N. et al., Proc. Natl. Acad. Sci. (U.S.A.) 88:1143-1147 (1991); Prezant, T. R. et al., Hum. Mutat. 1:159-164 (1992); Ugozzoli, L. et al., GATA 9:107-112 (1992); Nyren, P. et al., Anal. Biochem. 208:171-175 (1993)). These methods differ from GBA in that they utilize incorporation of labeled deoxynucleotides to discriminate between bases at a polymorphic site. In such a format, since the signal is proportional to the number of deoxynucleotides incorporated, polymorphisms that occur in runs of the same nucleotide can result in signals that are proportional to the length of the run (Syvanen, A.-C., et al., Amer. J. Hum. Genet. 52:46-59 (1993)).

A number of initiatives obtain sequence information directly from millions of individual molecules of DNA or RNA in parallel. Real-time single molecule sequencing-by-synthesis technologies rely on the detection of fluorescent nucleotides as they are incorporated into a nascent strand of DNA that is complementary to the template being sequenced. In one method, oligonucleotides 30-50 bases in length are covalently anchored at the 5' end to glass cover slips. These anchored strands perform two functions. First, they act as capture sites for the target template strands if the templates are configured with capture tails complementary to the surface-bound oligonucleotides. They also act as primers for the template directed primer extension that forms the basis of the sequence reading. The capture primers function as a fixed position site for sequence determination using multiple cycles of synthesis, detection, and chemical cleavage of the dye-linker to remove the dye. Each cycle consists of adding the polymerase/labeled nucleotide mixture, rinsing, imaging and cleavage of dye. In an alternative method, polymerase is modified with a fluorescent donor molecule and immobilized on a glass slide, while each nucleotide is color-coded with an acceptor fluorescent moiety attached to a gamma-phosphate. The system detects the interaction between a fluorescently-tagged polymerase and a fluorescently modified nucleotide as the nucleotide becomes incorporated into the de novo chain. Other sequencing-by-synthesis technologies also exist.

Any suitable sequencing-by-synthesis platform can be used to identify mutations. As described above, four major sequencing-by-synthesis platforms are currently available: the Genome Sequencers from Roche/454 Life Sciences, the 1G Analyzer from Illumina/Solexa, the SOLiD system from Applied BioSystems, and the Heliscope system from Helicos Biosciences. Sequencing-by-synthesis platforms have also been described by Pacific BioSciences and VisiGen Biotechnologies. In some embodiments, a plurality of nucleic acid molecules being sequenced is bound to a support (e.g., solid support). To immobilize the nucleic acid on a support, a capture sequence/universal priming site can be added at the 3' and/or 5' end of the template. The nucleic acids can be bound to the support by hybridizing the capture sequence to a complementary sequence covalently attached to the support. The capture sequence (also referred to as a universal capture sequence) is a nucleic acid sequence complementary to a sequence attached to a support that may dually serve as a universal primer.

As an alternative to a capture sequence, a member of a coupling pair (such as, e.g., antibody/antigen, receptor/ligand, or the avidin-biotin pair as described in, e.g., US Patent Application No. 2006/0252077) can be linked to each fragment to be captured on a surface coated with a respective second member of that coupling pair.

Subsequent to the capture, the sequence can be analyzed, for example, by single molecule detection/sequencing, e.g., as described in the Examples and in U.S. Pat. No. 7,283,337, including template-dependent sequencing-by-synthesis. In sequencing-by-synthesis, the surface-bound molecule is exposed to a plurality of labeled nucleotide triphosphates in the presence of polymerase. The sequence of the template is determined by the order of labeled nucleotides incorporated into the 3' end of the growing chain. This can be done in real time or can be done in a step-and-repeat mode. For real-time analysis, different optical labels to each nucleotide can be incorporated and multiple lasers can be utilized for stimulation of incorporated nucleotides.

Sequencing can also include other massively parallel sequencing or next generation sequencing (NGS) techniques and platforms. Additional examples of massively parallel sequencing techniques and platforms are the Illumina HiSeq or MiSeq, Thermo PGM or Proton, the Pac Bio RS II or Sequel, Qiagen's Gene Reader, and the Oxford Nanopore MinION. Additional similar current massively parallel sequencing technologies can be used, as well as future generations of these technologies.

Any cell type or tissue can be utilized to obtain nucleic acid samples for use in methods described herein. For example, a DNA or RNA sample can be obtained from a tumor or a bodily fluid, e.g., blood, obtained by known techniques (e.g. venipuncture) or saliva. Alternatively, nucleic acid tests can be performed on dry samples (e.g. hair or skin). In addition, a sample can be obtained for sequencing from a tumor and another sample can be obtained from normal tissue for sequencing where the normal tissue is of the same tissue type as the tumor. A sample can be obtained for sequencing from a tumor and another sample can be obtained from normal tissue for sequencing where the normal tissue is of a distinct tissue type relative to the tumor.

Tumors can include one or more of lung cancer, melanoma, breast cancer, ovarian cancer, prostate cancer, kidney cancer, gastric cancer, colon cancer, testicular cancer, head and neck cancer, pancreatic cancer, brain cancer, B-cell lymphoma, acute myelogenous leukemia, chronic myelogenous leukemia, chronic lymphocytic leukemia, and T cell lymphocytic leukemia, non-small cell lung cancer, and small cell lung cancer.

Alternatively, protein mass spectrometry can be used to identify or validate the presence of mutated peptides bound to MHC proteins on tumor cells. Peptides can be acid-eluted from tumor cells or from HLA molecules that are immunoprecipitated from tumor, and then identified using mass spectrometry.

IV. Neoantigens

Neoantigens can include nucleotides or polypeptides. For example, a neoantigen can be an RNA sequence that encodes for a polypeptide sequence. Neoantigens useful in vaccines can therefore include nucleotide sequences or polypeptide sequences.

Disclosed herein are isolated peptides that comprise tumor specific mutations identified by the methods disclosed herein, peptides that comprise known tumor specific mutations, and mutant polypeptides or fragments thereof identified by methods disclosed herein. Neoantigen peptides can be described in the context of their coding sequence where a neoantigen includes the nucleotide sequence (e.g., DNA or RNA) that codes for the related polypeptide sequence.

One or more polypeptides encoded by a neoantigen nucleotide sequence can comprise at least one of: a binding affinity with MHC with an IC50 value of less than 1000 nM, for MHC Class I peptides a length of 8-15, 8, 9, 10, 11, 12, 13, 14, or 15 amino acids, presence of sequence motifs within or near the peptide promoting proteasome cleavage, and presence or sequence motifs promoting TAP transport. For MHC Class II peptides a length 6-30, 6, 7, 8, 9, 10, 11, 12, 13, 14, 15, 16, 17, 18, 19, 20, 21, 22, 23, 24, 25, 26, 27, 28, 29, or 30 amino acids, presence of sequence motifs within or near the peptide promoting cleavage by extracellular or lysosomal proteases (e.g., cathepsins) or HLA-DM catalyzed HLA binding.

One or more neoantigens can be presented on the surface of a tumor.

One or more neoantigens can be is immunogenic in a subject having a tumor, e.g., capable of eliciting a T cell response or a B cell response in the subject.

One or more neoantigens that induce an autoimmune response in a subject can be excluded from consideration in the context of vaccine generation for a subject having a tumor.

The size of at least one neoantigenic peptide molecule can comprise, but is not limited to, about 5, about 6, about 7, about 8, about 9, about 10, about 11, about 12, about 13, about 14, about 15, about 16, about 17, about 18, about 19, about 20, about 21, about 22, about 23, about 24, about 25, about 26, about 27, about 28, about 29, about 30, about 31, about 32, about 33, about 34, about 35, about 36, about 37, about 38, about 39, about 40, about 41, about 42, about 43, about 44, about 45, about 46, about 47, about 48, about 49, about 50, about 60, about 70, about 80, about 90, about 100, about 110, about 120 or greater amino molecule residues, and any range derivable therein. In specific embodiments the neoantigenic peptide molecules are equal to or less than 50 amino acids.

Neoantigenic peptides and polypeptides can be: for MHC Class I 15 residues or less in length and usually consist of between about 8 and about 11 residues, particularly 9 or 10 residues; for MHC Class II, 6-30 residues, inclusive.

If desirable, a longer peptide can be designed in several ways. In one case, when presentation likelihoods of peptides on HLA alleles are predicted or known, a longer peptide could consist of either: (1) individual presented peptides with an extensions of 2-5 amino acids toward the N- and C-terminus of each corresponding gene product; (2) a concatenation of some or all of the presented peptides with extended sequences for each. In another case, when sequencing reveals a long (>10 residues) neoepitope sequence present in the tumor (e.g. due to a frameshift, read-through or intron inclusion that leads to a novel peptide sequence), a longer peptide would consist of: (3) the entire stretch of novel tumor-specific amino acids—thus bypassing the need for computational or in vitro test-based selection of the strongest HLA-presented shorter peptide. In both cases, use of a longer peptide allows endogenous processing by patient cells and may lead to more effective antigen presentation and induction of T cell responses.

Neoantigenic peptides and polypeptides can be presented on an HLA protein. In some aspects neoantigenic peptides and polypeptides are presented on an HLA protein with greater affinity than a wild-type peptide. In some aspects, a neoantigenic peptide or polypeptide can have an IC50 of at least less than 5000 nM, at least less than 1000 nM, at least less than 500 nM, at least less than 250 nM, at least less than 200 nM, at least less than 150 nM, at least less than 100 nM, at least less than 50 nM or less.

In some aspects, neoantigenic peptides and polypeptides do not induce an autoimmune response and/or invoke immunological tolerance when administered to a subject.

Also provided are compositions comprising at least two or more neoantigenic peptides. In some embodiments the composition contains at least two distinct peptides. At least two distinct peptides can be derived from the same polypeptide. By distinct polypeptides is meant that the peptide vary by length, amino acid sequence, or both. The peptides are derived from any polypeptide known to or have been found to contain a tumor specific mutation. Suitable polypeptides from which the neoantigenic peptides can be derived can be found for example in the COSMIC database. COSMIC curates comprehensive information on somatic mutations in human cancer. The peptide contains the tumor specific mutation. In some aspects the tumor specific mutation is a driver mutation for a particular cancer type.

Neoantigenic peptides and polypeptides having a desired activity or property can be modified to provide certain desired attributes, e.g., improved pharmacological characteristics, while increasing or at least retaining substantially all of the biological activity of the unmodified peptide to bind the desired MHC molecule and activate the appropriate T cell. For instance, neoantigenic peptide and polypeptides can be subject to various changes, such as substitutions, either conservative or non-conservative, where such changes might provide for certain advantages in their use, such as improved MHC binding, stability or presentation. By conservative substitutions is meant replacing an amino acid residue with another which is biologically and/or chemically similar, e.g., one hydrophobic residue for another, or one polar residue for another. The substitutions include combinations such as Gly, Ala; Val, Ile, Leu, Met; Asp, Glu; Asn, Gln; Ser, Thr; Lys, Arg; and Phe, Tyr. The effect of single amino acid substitutions may also be probed using D-amino acids. Such modifications can be made using well known peptide synthesis procedures, as described in e.g., Merrifield, Science 232:341-347 (1986), Barany & Merrifield, The Peptides, Gross & Meienhofer, eds. (N.Y., Academic Press), pp. 1-284 (1979); and Stewart & Young, Solid Phase Peptide Synthesis, (Rockford, Ill., Pierce), 2d Ed. (1984).

Modifications of peptides and polypeptides with various amino acid mimetics or unnatural amino acids can be particularly useful in increasing the stability of the peptide and polypeptide in vivo. Stability can be assayed in a number of ways. For instance, peptidases and various biological media, such as human plasma and serum, have been used to test stability. See, e.g., Verhoef et al., Eur. J. Drug Metab Pharmacokin. 11:291-302 (1986). Half-life of the peptides can be conveniently determined using a 25% human serum (v/v) assay. The protocol is generally as follows. Pooled human serum (Type AB, non-heat inactivated) is delipidated by centrifugation before use. The serum is then diluted to 25% with RPMI tissue culture media and used to test peptide stability. At predetermined time intervals a small amount of reaction solution is removed and added to either 6% aqueous trichloracetic acid or ethanol. The cloudy reaction sample is cooled (4 degrees C.) for 15 minutes and then spun to pellet the precipitated serum proteins. The presence of the peptides is then determined by reversed-phase HPLC using stability-specific chromatography conditions.

The peptides and polypeptides can be modified to provide desired attributes other than improved serum half-life. For instance, the ability of the peptides to induce CTL activity can be enhanced by linkage to a sequence which contains at least one epitope that is capable of inducing a T helper cell response. Immunogenic peptides/T helper conjugates can be linked by a spacer molecule. The spacer is typically comprised of relatively small, neutral molecules, such as amino acids or amino acid mimetics, which are substantially uncharged under physiological conditions. The spacers are typically selected from, e.g., Ala, Gly, or other neutral spacers of nonpolar amino acids or neutral polar amino acids. It will be understood that the optionally present spacer need not be comprised of the same residues and thus can be a hetero- or homo-oligomer. When present, the spacer will usually be at least one or two residues, more usually three to six residues. Alternatively, the peptide can be linked to the T helper peptide without a spacer.

A neoantigenic peptide can be linked to the T helper peptide either directly or via a spacer either at the amino or carboxy terminus of the peptide. The amino terminus of either the neoantigenic peptide or the T helper peptide can be acylated. Exemplary T helper peptides include tetanus toxoid 830-843, influenza 307-319, malaria circumsporozoite 382-398 and 378-389.

Proteins or peptides can be made by any technique known to those of skill in the art, including the expression of proteins, polypeptides or peptides through standard molecular biological techniques, the isolation of proteins or peptides from natural sources, or the chemical synthesis of proteins or peptides. The nucleotide and protein, polypeptide and peptide sequences corresponding to various genes have been previously disclosed, and can be found at computerized databases known to those of ordinary skill in the art. One such database is the National Center for Biotechnology Information's Genbank and GenPept databases located at the National Institutes of Health website. The coding regions for known genes can be amplified and/or expressed using the techniques disclosed herein or as would be known to those of ordinary skill in the art. Alternatively, various commercial preparations of proteins, polypeptides and peptides are known to those of skill in the art.

In a further aspect a neoantigen includes a nucleic acid (e.g. polynucleotide) that encodes a neoantigenic peptide or portion thereof. The polynucleotide can be, e.g., DNA, cDNA, PNA, CNA, RNA (e.g., mRNA), either single- and/or double-stranded, or native or stabilized forms of polynucleotides, such as, e.g., polynucleotides with a phosphorothiate backbone, or combinations thereof and it may or may not contain introns. A still further aspect provides an expression vector capable of expressing a polypeptide or portion thereof. Expression vectors for different cell types are well known in the art and can be selected without undue experimentation. Generally, DNA is inserted into an expression vector, such as a plasmid, in proper orientation and correct reading frame for expression. If necessary, DNA can be linked to the appropriate transcriptional and translational regulatory control nucleotide sequences recognized by the desired host, although such controls are generally available in the expression vector. The vector is then introduced into the host through standard techniques. Guidance can be found e.g. in Sambrook et al. (1989) Molecular Cloning, A Laboratory Manual, Cold Spring Harbor Laboratory, Cold Spring Harbor, N.Y.

V. Vaccine Compositions

Also disclosed herein is an immunogenic composition, e.g., a vaccine composition, capable of raising a specific immune response, e.g., a tumor-specific immune response. Vaccine compositions typically comprise a plurality of neoantigens, e.g., selected using a method described herein. Vaccine compositions can also be referred to as vaccines.

A vaccine can contain between 1 and 30 peptides, 2, 3, 4, 5, 6, 7, 8, 9, 10, 11, 12, 13, 14, 15, 16, 17, 18, 19, 20, 21, 22, 23, 24, 25, 26, 27, 28, 29, or 30 different peptides, 6, 7, 8, 9, 10 11, 12, 13, or 14 different peptides, or 12, 13 or 14 different peptides. Peptides can include post-translational modifications. A vaccine can contain between 1 and 100 or more nucleotide sequences, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 or more different nucleotide sequences, 6, 7, 8, 9, 10 11, 12, 13, or 14 different nucleotide sequences, or 12, 13 or 14 different nucleotide sequences. A vaccine can contain between 1 and 30 neoantigen sequences, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 or more different neoantigen sequences, 6, 7, 8, 9, 10 11, 12, 13, or 14 different neoantigen sequences, or 12, 13 or 14 different neoantigen sequences.

In one embodiment, different peptides and/or polypeptides or nucleotide sequences encoding them are selected so that the peptides and/or polypeptides capable of associating with different MHC molecules, such as different MHC class I molecules and/or different MHC class II molecules. In some aspects, one vaccine composition comprises coding sequence for peptides and/or polypeptides capable of associating with the most frequently occurring MHC class I molecules and/or different MHC class II molecules. Hence, vaccine compositions can comprise different fragments capable of associating with at least 2 preferred, at least 3 preferred, or at least 4 preferred MHC class I molecules and/or different MHC class II molecules.

The vaccine composition can be capable of raising a specific cytotoxic T-cells response and/or a specific helper T-cell response.

A vaccine composition can further comprise an adjuvant and/or a carrier. Examples of useful adjuvants and carriers are given herein below. A composition can be associated with a carrier such as e.g. a protein or an antigen-presenting cell such as e.g. a dendritic cell (DC) capable of presenting the peptide to a T-cell.

Adjuvants are any substance whose admixture into a vaccine composition increases or otherwise modifies the immune response to a neoantigen. Carriers can be scaffold structures, for example a polypeptide or a polysaccharide, to which a neoantigen, is capable of being associated. Optionally, adjuvants are conjugated covalently or non-covalently.

The ability of an adjuvant to increase an immune response to an antigen is typically manifested by a significant or substantial increase in an immune-mediated reaction, or reduction in disease symptoms. For example, an increase in humoral immunity is typically manifested by a significant increase in the titer of antibodies raised to the antigen, and an increase in T-cell activity is typically manifested in increased cell proliferation, or cellular cytotoxicity, or cytokine secretion. An adjuvant may also alter an immune response, for example, by changing a primarily humoral or Th response into a primarily cellular, or Th response.

Suitable adjuvants include, but are not limited to 1018 ISS, alum, aluminium salts, Amplivax, AS15, BCG, CP-870, 893, CpG7909, CyaA, dSLIM, GM-CSF, IC30, IC31, Imiquimod, ImuFact IMP321, IS Patch, ISS, ISCOMATRIX, Juvlmmune, LipoVac, MF59, monophosphoryl lipid A, Montanide IMS 1312, Montanide ISA 206, Montanide ISA 50V, Montanide ISA-51, OK-432, OM-174, OM-197-MP-EC, ONTAK, PepTel vector system, PLG microparticles, resiquimod, SRL172, Virosomes and other Virus-like particles, YF-17D, VEGF trap, R848, beta-glucan, Pam3Cys, Aquila's QS21 stimulon (Aquila Biotech, Worcester, Mass., USA) which is derived from saponin, mycobacterial extracts and synthetic bacterial cell wall mimics, and other proprietary adjuvants such as Ribi's Detox. Quil or Superfos. Adjuvants such as incomplete Freund's or GM-CSF are useful. Several immunological adjuvants (e.g., MF59) specific for dendritic cells and their preparation have been described previously (Dupuis M, et al., Cell Immunol. 1998; 186(1):18-27; Allison A C; Dev Biol Stand. 1998; 92:3-11). Also cytokines can be used. Several cytokines have been directly linked to influencing dendritic cell migration to lymphoid tissues (e.g., TNF-alpha), accelerating the maturation of dendritic cells into efficient antigen-presenting cells for T-lymphocytes (e.g., GM-CSF, IL-1 and IL-4) (U.S. Pat. No. 5,849,589, specifically incorporated herein by reference in its entirety) and acting as immunoadjuvants (e.g., IL-12) (Gabrilovich D I, et al., J Immunother Emphasis Tumor Immunol. 1996 (6):414-418).

CpG immunostimulatory oligonucleotides have also been reported to enhance the effects of adjuvants in a vaccine setting. Other TLR binding molecules such as RNA binding TLR 7, TLR 8 and/or TLR 9 may also be used.

Other examples of useful adjuvants include, but are not limited to, chemically modified CpGs (e.g. CpR, Idera), Poly(I:C)(e.g. polyi:C12U), non-CpG bacterial DNA or RNA as well as immunoactive small molecules and antibodies such as cyclophosphamide, sunitinib, bevacizumab, celebrex, NCX-4016, sildenafil, tadalafil, vardenafil, sorafinib, XL-999, CP-547632, pazopanib, ZD2171, AZD2171, ipilimumab, tremelimumab, and SC58175, which may act therapeutically and/or as an adjuvant. The amounts and concentrations of adjuvants and additives can readily be determined by the skilled artisan without undue experimentation. Additional adjuvants include colony-stimulating factors, such as Granulocyte Macrophage Colony Stimulating Factor (GM-CSF, sargramostim).

A vaccine composition can comprise more than one different adjuvant. Furthermore, a therapeutic composition can comprise any adjuvant substance including any of the above or combinations thereof. It is also contemplated that a vaccine and an adjuvant can be administered together or separately in any appropriate sequence.

A carrier (or excipient) can be present independently of an adjuvant. The function of a carrier can for example be to increase the molecular weight of in particular mutant to increase activity or immunogenicity, to confer stability, to increase the biological activity, or to increase serum half-life. Furthermore, a carrier can aid presenting peptides to T-cells. A carrier can be any suitable carrier known to the person skilled in the art, for example a protein or an antigen presenting cell. A carrier protein could be but is not limited to keyhole limpet hemocyanin, serum proteins such as transferrin, bovine serum albumin, human serum albumin, thyroglobulin or ovalbumin, immunoglobulins, or hormones, such as insulin or palmitic acid. For immunization of humans, the carrier is generally a physiologically acceptable carrier acceptable to humans and safe. However, tetanus toxoid and/or diptheria toxoid are suitable carriers. Alternatively, the carrier can be dextrans for example sepharose.

Cytotoxic T-cells (CTLs) recognize an antigen in the form of a peptide bound to an MHC molecule rather than the intact foreign antigen itself. The MHC molecule itself is located at the cell surface of an antigen presenting cell. Thus, an activation of CTLs is possible if a trimeric complex of peptide antigen, MHC molecule, and APC is present. Correspondingly, it may enhance the immune response if not only the peptide is used for activation of CTLs, but if additionally APCs with the respective MHC molecule are added. Therefore, in some embodiments a vaccine composition additionally contains at least one antigen presenting cell.

Neoantigens can also be included in viral vector-based vaccine platforms, such as vaccinia, fowlpox, self-replicating alphavirus, marabavirus, adenovirus (See, e.g., Tatsis et al., Adenoviruses, *Molecular Therapy* (2004) 10, 616-629), or lentivirus, including but not limited to second, third or hybrid second/third generation lentivirus and recombinant lentivirus of any generation designed to target specific cell types or receptors (See, e.g., Hu et al., Immunization Delivered by Lentiviral Vectors for Cancer and Infectious Diseases, *Immunol Rev.* (2011) 239(1): 45-61, Sakuma et al., Lentiviral vectors: basic to translational, *Biochem J.* (2012) 443(3):603-18, Cooper et al., Rescue of splicing-mediated intron loss maximizes expression in lentiviral vectors containing the human ubiquitin C promoter, *Nucl. Acids Res.* (2015) 43 (1): 682-690, Zufferey et al., Self-Inactivating Lentivirus Vector for Safe and Efficient In Vivo Gene Delivery, *J. Virol.* (1998) 72 (12): 9873-9880). Dependent on the packaging capacity of the above mentioned viral vector-based vaccine platforms, this approach can deliver one or more nucleotide sequences that encode one or more neoantigen peptides. The sequences may be flanked by non-mutated sequences, may be separated by linkers or may be preceded with one or more sequences targeting a subcellular compartment (See, e.g., Gros et al., Prospective identification of neoantigen-specific lymphocytes in the peripheral blood of melanoma patients, *Nat Med.* (2016) 22 (4):433-8, Stronen et al., Targeting of cancer neoantigens with donor-derived T cell receptor repertoires, *Science.* (2016) 352 (6291):1337-41, Lu et al., Efficient identification of mutated cancer antigens recognized by T cells associated with durable tumor regressions, *Clin Cancer Res.* (2014) 20(13):3401-10). Upon introduction into a host, infected cells express the neoantigens, and thereby elicit a host immune (e.g., CTL) response against the peptide(s). Vaccinia vectors and methods useful in immunization protocols are described in, e.g., U.S. Pat. No. 4,722,848. Another vector is BCG (Bacille Calmette Guerin). BCG vectors are described in Stover et al. (*Nature* 351:456-460 (1991)). A wide variety of other vaccine vectors useful for therapeutic administration or immunization of neoantigens, e.g., *Salmonella typhi* vectors, and the like will be apparent to those skilled in the art from the description herein.

V.A. Neoantigen Cassette

The methods employed for the selection of one or more neoantigens, the cloning and construction of a "cassette" and its insertion into a viral vector are within the skill in the art given the teachings provided herein. By "neoantigen cassette" is meant the combination of a selected neoantigen or plurality of neoantigens and the other regulatory elements necessary to transcribe the neoantigen(s) and express the transcribed product. A neoantigen or plurality of neoantigens can be operatively linked to regulatory components in a manner which permits transcription. Such components include conventional regulatory elements that can drive expression of the neoantigen(s) in a cell transfected with the viral vector. Thus the neoantigen cassette can also contain a selected promoter which is linked to the neoantigen(s) and located, with other, optional regulatory elements, within the selected viral sequences of the recombinant vector.

Useful promoters can be constitutive promoters or regulated (inducible) promoters, which will enable control of the amount of neoantigen(s) to be expressed. For example, a desirable promoter is that of the cytomegalovirus immediate early promoter/enhancer [see, e.g., Boshart et al, Cell, 41:521-530 (1985)]. Another desirable promoter includes the Rous sarcoma virus LTR promoter/enhancer. Still another promoter/enhancer sequence is the chicken cytoplasmic beta-actin promoter [T. A. Kost et al, Nucl. Acids Res., 11(23):8287 (1983)]. Other suitable or desirable promoters can be selected by one of skill in the art.

The neoantigen cassette can also include nucleic acid sequences heterologous to the viral vector sequences including sequences providing signals for efficient polyadenylation of the transcript (poly(A), poly-A or pA) and introns with functional splice donor and acceptor sites. A common poly-A sequence which is employed in the exemplary vectors of this invention is that derived from the papovavirus SV-40. The poly-A sequence generally can be inserted in the cassette following the neoantigen-based sequences and before the viral vector sequences. A common intron sequence can also be derived from SV-40, and is referred to as the SV-40 T intron sequence. A neoantigen cassette can also contain such an intron, located between the promoter/enhancer sequence and the neoantigen(s). Selection of these and other common vector elements are conventional [see, e.g., Sambrook et al, "Molecular Cloning. A Laboratory Manual.", 2d edit., Cold Spring Harbor Laboratory, New York (1989) and references cited therein] and many such sequences are available from commercial and industrial sources as well as from Genbank.

A neoantigen cassette can have one or more neoantigens. For example, a given cassette can include 1-10, 1-20, 1-30, 10-20, 15-25, 15-20, 1, 2, 3, 4, 5, 6, 7, 8, 9, 10, 11, 12, 13, 14, 15, 16, 17, 18, 19, 20, or more neoantigens. Neoantigens can be linked directly to one another. Neoantigens can also be linked to one another with linkers. Neoantigens can be in any orientation relative to one another including N to C or C to N.

As above stated, the neoantigen cassette can be located in the site of any selected deletion in the viral vector, such as the site of the E1 gene region deletion or E3 gene region deletion, among others which may be selected.

The neoantigen cassette can be described using the following formula to describe the ordered sequence of each element, from 5' to 3':

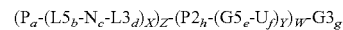

$$(P_a\text{-}(L5_b\text{-}N_c\text{-}L3_d)_X)_Z\text{-}(P2_h\text{-}(G5_e\text{-}U_f)_Y)_W\text{-}G3_g$$

wherein P and P2 comprise promoter nucleotide sequences, N comprises an MHC class I epitope encoding nucleic acid sequence, L5 comprises a 5' linker sequence, L3 comprises a 3' linker sequence, G5 comprises a nucleic acid sequences encoding an amino acid linker, G3 comprises one of the at least one nucleic acid sequences encoding an amino acid linker, U comprises an MHC class II antigen-encoding nucleic acid sequence, where for each X the corresponding Nc is a epitope encoding nucleic acid sequence, where for each Y the corresponding Uf is an antigen-encoding nucleic acid sequence. The composition and ordered sequence can be further defined by selecting the number of elements present, for example where a=0 or 1, where b=0 or 1, where c=1, where d=0 or 1, where e=0 or 1, where f=1, where g=0 or 1, where h=0 or 1, X=1 to 400, Y=0, 1, 2, 3, 4 or 5, Z=1 to 400, and W=0, 1, 2, 3, 4 or 5.

In one example, elements present include where a=0, b=1, d=1, e=1, g=1, h=0, X=10, Y=2, Z=1, and W=1, describing where no additional promoter is present (i.e. only the promoter nucleotide sequence provided by the RNA alphavirus backbone is present), 20 MHC class I epitope are present, a 5' linker is present for each N, a 3' linker is present for each N, 2 MHC class II epitopes are present, a linker is present linking the two MHC class II epitopes, a linker is present linking the 5' end of the two MHC class II epitopes to the 3' linker of the final MHC class I epitope, and a linker is present linking the 3' end of the two MHC class II epitopes to the to the RNA alphavirus backbone. Examples of linking the 3' end of the neoantigen cassette to the RNA alphavirus backbone include linking directly to the 3' UTR elements provided by the RNA alphavirus backbone, such as a 3' 19-nt CSE. Examples of linking the 5' end of the neoantigen cassette to the RNA alphavirus backbone include linking directly to a 26S promoter sequence, an alphavirus 5' UTR, a 51-nt CSE, or a 24-nt CSE.

Other examples include: where a=1 describing where a promoter other than the promoter nucleotide sequence provided by the RNA alphavirus backbone is present; where a=1 and Z is greater than 1 where multiple promoters other than the promoter nucleotide sequence provided by the RNA alphavirus backbone are present each driving expression of 1 or more distinct MHC class I epitope encoding nucleic acid sequences; where h=1 describing where a separate promoter is present to drive expression of the MHC class II antigen-encoding nucleic acid sequences; and where g=0 describing the MHC class II antigen-encoding nucleic acid sequence, if present, is directly linked to the RNA alphavirus backbone.

Other examples include where each MHC class I epitope that is present can have a 5' linker, a 3' linker, neither, or both. In examples where more than one MHC class I epitope is present in the same neoantigen cassette, some MHC class I epitopes may have both a 5' linker and a 3' linker, while other MHC class I epitopes may have either a 5' linker, a 3' linker, or neither. In other examples where more than one MHC class I epitope is present in the same neoantigen cassette, some MHC class I epitopes may have either a 5' linker or a 3' linker, while other MHC class I epitopes may have either a 5' linker, a 3' linker, or neither.

In examples where more than one MHC class II epitope is present in the same neoantigen cassette, some MHC class II epitopes may have both a 5' linker and a 3' linker, while other MHC class II epitopes may have either a 5' linker, a 3' linker, or neither. In other examples where more than one MHC class II epitope is present in the same neoantigen cassette, some MHC class II epitopes may have either a 5' linker or a 3' linker, while other MHC class II epitopes may have either a 5' linker, a 3' linker, or neither.

The promoter nucleotide sequences P and/or P2 can be the same as a promoter nucleotide sequence provided by the RNA alphavirus backbone. For example, the promoter sequence provided by the RNA alphavirus backbone, Pn and P2, can each comprise a 26S subgenomic promoter. The promoter nucleotide sequences P and/or P2 can be different from the promoter nucleotide sequence provided by the RNA alphavirus backbone, as well as can be different from each other.

The 5' linker L5 can be a native sequence or a non-natural sequence. Non-natural sequence include, but are not limited to, AAY, RR, and DPP. The 3' linker L3 can also be a native sequence or a non-natural sequence. Additionally, L5 and L3 can both be native sequences, both be non-natural sequences, or one can be native and the other non-natural. For each X, the amino acid linkers can be 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 or more amino acids in length. For each X, the amino acid linkers can be also be at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, at least 26, at least 27, at least 28, at least 29, or at least 30 amino acids in length.

The amino acid linker G5, for each Y, can be 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 or more amino acids in length. For each Y, the amino acid linkers can be also be at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, at least 26, at least 27, at least 28, at least 29, or at least 30 amino acids in length.

The amino acid linker G3 can be 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 or more amino acids in length. G3 can be also be at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, at least 26, at least 27, at least 28, at least 29, or at least 30 amino acids in length.

For each X, each N can encodes a MHC class I epitope 7-15 amino acids in length. For each X, each N can also encodes a MHC class I epitope 5, 6, 7, 8, 9, 10, 11, 12, 13, 14, 15, 16, 17, 18, 19, 20, 21, 22, 23, 24, 25, 26, 27, 28, 29, or 30 amino acids in length. For each X, each N can also encodes a MHC class I epitope at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, at least 26, at least 27, at least 28, at least 29, or at least 30 amino acids in length.

V.B. Immune Checkpoints

Vectors described herein, such as C68 vectors described herein or alphavirus vectors described herein, can comprise a nucleic acid which encodes at least one neoantigen and the same or a separate vector can comprise a nucleic acid which encodes at least one immune modulator (e.g., an antibody such as an scFv) which binds to and blocks the activity of an immune checkpoint molecule. Vectors can comprise a neoantigen cassette and one or more nucleic acid molecules encoding a checkpoint inhibitor.

Illustrative immune checkpoint molecules that can be targeted for blocking or inhibition include, but are not limited to, CTLA-4, 4-1BB (CD137), 4-1BBL (CD137L), PDL1, PDL2, PD1, B7-H3, B7-H4, BTLA, HVEM, TIM3, GALS, LAG3, TIM3, B7H3, B7H4, VISTA, KIR, 2B4 (belongs to the CD2 family of molecules and is expressed on all NK, γδ, and memory CD8+ (αβ) T cells), CD160 (also referred to as BY55), and CGEN-15049. Immune checkpoint inhibitors include antibodies, or antigen binding fragments thereof, or other binding proteins, that bind to and block or inhibit the activity of one or more of CTLA-4, PDL1, PDL2, PD1, B7-H3, B7-H4, BTLA, HVEM, TIM3, GALS, LAG3, TIM3, B7H3, B7H4, VISTA, KIR, 2B4, CD160, and CGEN-15049. Illustrative immune checkpoint inhibitors include Tremelimumab (CTLA-4 blocking antibody), anti-OX40, PD-L1 monoclonal Antibody (Anti-B7-H1; MEDI4736), ipilimumab, MK-3475 (PD-1 blocker), Nivolumamb (anti-PD1 antibody), CT-011 (anti-PD1 antibody), BY55 monoclonal antibody, AMP224 (anti-PDL1 antibody), BMS-936559 (anti-PDL1 antibody), MPLDL3280A (anti-PDL1 antibody), MSB0010718C (anti-PDL1 antibody) and Yervoy/ipilimumab (anti-CTLA-4 checkpoint inhibitor). Antibody-encoding sequences can be engineered into vectors such as C68 using ordinary skill in the art. An exemplary method is described in Fang et al., Stable antibody expression at therapeutic levels using the 2A peptide. *Nat Biotechnol.* 2005 May; 23(5):584-90. Epub 2005 Apr. 17; herein incorporated by reference for all purposes.

V.C. Additional Considerations for Vaccine Design and Manufacture

V.C.1. Determination of a Set of Peptides that Cover All Tumor Subclones

Truncal peptides, meaning those presented by all or most tumor subclones, can be prioritized for inclusion into the vaccine.[53] Optionally, if there are no truncal peptides predicted to be presented and immunogenic with high probability, or if the number of truncal peptides predicted to be presented and immunogenic with high probability is small enough that additional non-truncal peptides can be included in the vaccine, then further peptides can be prioritized by estimating the number and identity of tumor subclones and choosing peptides so as to maximize the number of tumor subclones covered by the vaccine.[54]

V.C.2. Neoantigen Prioritization

After all of the above above neoantigen filters are applied, more candidate neoantigens may still be available for vaccine inclusion than the vaccine technology can support. Additionally, uncertainty about various aspects of the neoantigen analysis may remain and tradeoffs may exist between different properties of candidate vaccine neoantigens. Thus, in place of predetermined filters at each step of the selection process, an integrated multi-dimensional model can be considered that places candidate neoantigens in a space with at least the following axes and optimizes selection using an integrative approach.

1. Risk of auto-immunity or tolerance (risk of germline) (lower risk of auto-immunity is typically preferred)
2. Probability of sequencing artifact (lower probability of artifact is typically preferred)
3. Probability of immunogenicity (higher probability of immunogenicity is typically preferred)
4. Probability of presentation (higher probability of presentation is typically preferred)
5. Gene expression (higher expression is typically preferred)
6. Coverage of HLA genes (larger number of HLA molecules involved in the presentation of a set of neoantigens may lower the probability that a tumor will escape immune attack via downregulation or mutation of HLA molecules)
7. Coverage of HLA classes (covering both HLA-I and HLA-II may increase the probability of therapeutic response and decrease the probability of tumor escape)

Additionally, optionally, neoantigens can be deprioritized (e.g., excluded) from the vaccination if they are predicted to be presented by HLA alleles lost or inactivated in either all or part of the patient's tumor. HLA allele loss can occur by either somatic mutation, loss of heterozygosity, or homozygous deletion of the locus. Methods for detection of HLA allele somatic mutation are well known in the art, e.g. (Shukla et al., 2015). Methods for detection of somatic LOH and homozygous deletion (including for HLA locus) are likewise well described. (Carter et al., 2012; McGranahan et al., 2017; Van Loo et al., 2010).

V.D. Alphavirus

V.D.1. Alphavirus Biology

Alphaviruses are members of the family Togaviridae, and are positive-sense single stranded RNA viruses. Alphaviruses can also be referred to as self-replicating RNA or srRNA. Members are typically classified as either Old World, such as Sindbis, Ross River, Mayaro, Chikungunya, and Semliki Forest viruses, or New World, such as eastern equine encephalitis, Aura, Fort Morgan, or Venezuelan equine encephalitis virus and its derivative strain TC-83 (Strauss Microbrial Review 1994). A natural alphavirus genome is typically around 12 kb in length, the first two-thirds of which contain genes encoding non-structural proteins (nsPs) that form RNA replication complexes for self-replication of the viral genome, and the last third of which contains a subgenomic expression cassette encoding structural proteins for virion production (Frolov RNA 2001).

A model lifecycle of an alphavirus involves several distinct steps (Strauss Microbrial Review 1994, Jose Future Microbiol 2009). Following virus attachment to a host cell, the virion fuses with membranes within endocytic compartments resulting in the eventual release of genomic RNA into the cytosol. The genomic RNA, which is in a plus-strand orientation and comprises a 5' methylguanylate cap and 3' polyA tail, is translated to produce non-structural proteins nsP1-4 that form the replication complex. Early in infection, the plus-strand is then replicated by the complex into a minus-stand template. In the current model, the replication complex is further processed as infection progresses, with the resulting processed complex switching to transcription of the minus-strand into both full-length positive-strand genomic RNA, as well as the 26S subgenomic positive-strand RNA containing the structural genes. Several conserved sequence elements (CSEs) of alphavirus have been identified to potentially play a role in the various RNA replication steps including; a complement of the 5' UTR in the replication of plus-strand RNAs from a minus-strand template, a 51-nt CSE in the replication of minus-strand synthesis from the genomic template, a 24-nt CSE in the junction region between the nsPs and the 26S RNA in the transcription of the subgenomic RNA from the minus-strand, and a 3' 19-nt CSE in minus-strand synthesis from the plus-strand template.

Following the replication of the various RNA species, virus particles are then typically assembled in the natural lifecycle of the virus. The 26S RNA is translated and the resulting proteins further processed to produce the structural proteins including capsid protein, glycoproteins E1 and E2, and two small polypeptides E3 and 6K (Strauss 1994). Encapsidation of viral RNA occurs, with capsid proteins normally specific for only genomic RNA being packaged, followed by virion assembly and budding at the membrane surface.

V.D.2. Alphavirus as a Delivery Vector

Alphaviruses have previously been engineered for use as expression vector systems (Pushko 1997, Rheme 2004). Alphaviruses offer several advantages, particularly in a vaccine setting where heterologous antigen expression can be desired. Due to its ability to self-replicate in the host cytosol, alphavirus vectors are generally able to produce high copy numbers of the expression cassette within a cell resulting in a high level of heterologous antigen production. Additionally, the vectors are generally transient, resulting in improved biosafety as well as reduced induction of immunological tolerance to the vector. The public, in general, also lacks pre-existing immunity to alphavirus vectors as compared to other standard viral vectors, such as human adenovirus. Alphavirus based vectors also generally result in cytotoxic responses to infected cells. Cytotoxicity, to a certain degree, can be important in a vaccine setting to properly illicit an immune response to the heterologous antigen expressed. However, the degree of desired cytotoxicity can be a balancing act, and thus several attenuated alphaviruses have been developed, including the TC-83 strain of VEE. Thus, an example of a neoantigen expression vector described herein can utilize an alphavirus backbone that allows for a high level of neoantigen expression, elicits a robust immune response to neoantigen, does not elicit an immune response to the vector itself, and can be used in a safe manner. Furthermore, the neoantigen expression cassette can be designed to elicit different levels of an immune response through optimization of which alphavirus sequences the vector uses, including, but not limited to, sequences derived from VEEor its attenuated derivative TC-83.

Several expression vector design strategies have been engineered using alphavirus sequences (Pushko 1997). In one strategy, a alphavirus vector design includes inserting a second copy of the 26S promoter sequence elements downstream of the structural protein genes, followed by a heterologous gene (Frolov 1993). Thus, in addition to the natural non-structural and structural proteins, an additional subgenomic RNA is produced that expresses the heterologous protein. In this system, all the elements for production of infectious virions are present and, therefore, repeated rounds of infection of the expression vector in non-infected cells can occur.

Another expression vector design makes use of helper virus systems (Pushko 1997). In this strategy, the structural proteins are replaced by a heterologous gene. Thus, following self-replication of viral RNA mediated by still intact non-structural genes, the 26S subgenomic RNA provides for expression of the heterologous protein. Traditionally, additional vectors that expresses the structural proteins are then supplied in trans, such as by co-transfection of a cell line, to produce infectious virus. A system is described in detail in U.S. Pat. No. 8,093,021, which is herein incorporated by reference in its entirety, for all purposes. The helper vector system provides the benefit of limiting the possibility of forming infectious particles and, therefore, improves biosafety. In addition, the helper vector system reduces the total vector length, potentially improving the replication and expression efficiency. Thus, an example of a neoantigen expression vector described herein can utilize an alphavirus backbone wherein the structural proteins are replaced by a neoantigen cassette, the resulting vector both reducing biosafety concerns, while at the same time promoting efficient expression due to the reduction in overall expression vector size.

V.D.3. Alphavirus Production In Vitro

Alphavirus delivery vectors are generally positive-sense RNA polynucleotides. A convenient technique well-known in the art for RNA production is in vitro transcription IVT. In this technique, a DNA template of the desired vector is first produced by techniques well-known to those in the art, including standard molecular biology techniques such as cloning, restriction digestion, ligation, gene synthesis, and polymerase chain reaction (PCR). The DNA template contains a RNA polymerase promoter at the 5' end of the sequence desired to be transcribed into RNA. Promoters include, but are not limited to, bacteriophage polymerase promoters such as T3, T7, or SP6. The DNA template is then incubated with the appropriate RNA polymerase enzyme, buffer agents, and nucleotides (NTPs). The resulting RNA polynucleotide can optionally be further modified including, but limited to, addition of a 5' cap structure such as 7-methylguanosine or a related structure, and optionally modifying the 3' end to include a polyadenylate (polyA) tail. The RNA can then be purified using techniques well-known in the field, such as phenol-chloroform extraction.

V.D.4. Delivery Via Lipid Nanoparticle

An important aspect to consider in vaccine vector design is immunity against the vector itself (Riley 2017). This may be in the form of preexisting immunity to the vector itself, such as with certain human adenovirus systems, or in the form of developing immunity to the vector following administration of the vaccine. The latter is an important consideration if multiple administrations of the same vaccine are performed, such as separate priming and boosting doses, or if the same vaccine vector system is to be used to deliver different neoantigen cassettes.

In the case of alphavirus vectors, the standard delivery method is the previously discussed helper virus system that provides capsid, E1, and E2 proteins in trans to produce infectious viral particles. However, it is important to note that the E1 and E2 proteins are often major targets of neutralizing antibodies (Strauss 1994). Thus, the efficacy of using alphavirus vectors to deliver neoantigens of interest to target cells may be reduced if infectious particles are targeted by neutralizing antibodies.

An alternative to viral particle mediated gene delivery is the use of nanomaterials to deliver expression vectors (Riley 2017). Nanomaterial vehicles, importantly, can be made of non-immunogenic materials and generally avoid eliciting immunity to the delivery vector itself. These materials can include, but are not limited to, lipids, inorganic nanomaterials, and other polymeric materials. Lipids can be cationic, anionic, or neutral. The materials can be synthetic or naturally derived, and in some instances biodegradable. Lipids can include fats, cholesterol, phospholipids, lipid conjugates including, but not limited to, polyethyleneglycol (PEG) conjugates (PEGylated lipids), waxes, oils, glycerides, and fat soluable vitamins.

Lipid nanoparticles (LNPs) are an attractive delivery system due to the amphiphilic nature of lipids enabling formation of membranes and vesicle like structures (Riley 2017). In general, these vesicles deliver the expression vector by absorbing into the membrane of target cells and releasing nucleic acid into the cytosol. In addition, LNPs can be further modified or functionalized to facilitate targeting of specific cell types. Another consideration in LNP design is the balance between targeting efficiency and cytotoxicity. Lipid compositions generally include defined mixtures of cationic, neutral, anionic, and amphipathic lipids. In some instances, specific lipids are included to prevent LNP aggregation, prevent lipid oxidation, or provide functional chemical groups that facilitate attachment of additional moieties. Lipid composition can influence overall LNP size and stability. In an example, the lipid composition comprises dilinoleylmethyl-4-dimethylaminobutyrate (MC3) or MC3-like molecules. MC3 and MC3-like lipid compositions can be formulated to include one or more other lipids, such as a PEG or PEG-conjugated lipid, a sterol, or neutral lipids.

Nucleic-acid vectors, such as expression vectors, exposed directly to serum can have several undesirable consequences, including degradation of the nucleic acid by serum nucleases or off-target stimulation of the immune system by the free nucleic acids. Therefore, encapsulation of the alphavirus vector can be used to avoid degradation, while also avoiding potential off-target affects. In certain examples, an alphavirus vector is fully encapsulated within the delivery vehicle, such as within the aqueous interior of an LNP. Encapsulation of the alphavirus vector within an LNP can be carried out by techniques well-known to those skilled in the art, such as microfluidic mixing and droplet generation carried out on a microfluidic droplet generating device. Such devices include, but are not limited to, standard T-junction devices or flow-focusing devices. In an example, the desired lipid formulation, such as MC3 or MC3-like containing compositions, is provided to the droplet generating device in parallel with the alphavirus delivery vector and other desired agents, such that the delivery vector and desired agents are fully encapsulated within the interior of the MC3 or MC3-like based LNP. In an example, the droplet generating device can control the size range and size distribution of the LNPs produced. For example, the LNP can have a size ranging from 1 to 1000 nanometers in diameter, e.g., 1, 10, 50, 100, 500, or 1000 nanometers. Following droplet generation, the delivery vehicles encapsulating the expression vectors can be further treated or modified to prepare them for administration.

V.E. Chimpanzee Adenovirus (ChAd)

V.E.1. Viral Delivery with Chimpanzee Adenovirus

Vaccine compositions for delivery of one or more neoantigens (e.g., via a neoantigen cassette) can be created by providing adenovirus nucleotide sequences of chimpanzee origin, a variety of novel vectors, and cell lines expressing chimpanzee adenovirus genes. A nucleotide sequence of a chimpanzee C68 adenovirus (also referred to herein as ChAdV68) can be used in a vaccine composition for neoantigen delivery (See SEQ ID NO: 1). Use of C68 adenovirus derived vectors is described in further detail in U.S. Pat. No. 6,083,716, which is herein incorporated by reference in its entirety, for all purposes.

In a further aspect, provided herein is a recombinant adenovirus comprising the DNA sequence of a chimpanzee adenovirus such as C68 and a neoantigen cassette operatively linked to regulatory sequences directing its expression. The recombinant virus is capable of infecting a mammalian, preferably a human, cell and capable of expressing the neoantigen cassette product in the cell. In this vector, the native chimpanzee E1 gene, and/or E3 gene, and/or E4 gene can be deleted. A neoantigen cassette can be inserted into any of these sites of gene deletion. The neoantigen cassette can include a neoantigen against which a primed immune response is desired.

In another aspect, provided herein is a mammalian cell infected with a chimpanzee adenovirus such as C68.

In still a further aspect, a novel mammalian cell line is provided which expresses a chimpanzee adenovirus gene (e.g., from C68) or functional fragment thereof.

In still a further aspect, provided herein is a method for delivering a neoantigen cassette into a mammalian cell comprising the step of introducing into the cell an effective amount of a chimpanzee adenovirus, such as C68, that has been engineered to express the neoantigen cassette.

Still another aspect provides a method for eliciting an immune response in a mammalian host to treat cancer. The method can comprise the step of administering to the host an effective amount of a recombinant chimpanzee adenovirus, such as C68, comprising a neoantigen cassette that encodes one or more neoantigens from the tumor against which the immune response is targeted.

Also disclosed is a non-simian mammalian cell that expresses a chimpanzee adenovirus gene obtained from the sequence of SEQ ID NO: 1. The gene can be selected from the group consisting of the adenovirus E1A, E1B, E2A, E2B, E3, E4, L1, L2, L3, L4 and L5 of SEQ ID NO: 1.

Also disclosed is a nucleic acid molecule comprising a chimpanzee adenovirus DNA sequence comprising a gene obtained from the sequence of SEQ ID NO: 1. The gene can be selected from the group consisting of said chimpanzee adenovirus E1A, E1B, E2A, E2B, E3, E4, L1, L2, L3, L4 and L5 genes of SEQ ID NO: 1. In some aspects the nucleic acid molecule comprises SEQ ID NO: 1. In some aspects the nucleic acid molecule comprises the sequence of SEQ ID NO: 1, lacking at least one gene selected from the group consisting of E1A, E1B, E2A, E2B, E3, E4, L1, L2, L3, L4 and L5 genes of SEQ ID NO: 1.

Also disclosed is a vector comprising a chimpanzee adenovirus DNA sequence obtained from SEQ ID NO: 1 and a neoantigen cassette operatively linked to one or more regulatory sequences which direct expression of the cassette in a heterologous host cell, optionally wherein the chimpanzee adenovirus DNA sequence comprises at least the cis-elements necessary for replication and virion encapsidation, the cis-elements flanking the neoantigen cassette and regulatory sequences. In some aspects, the chimpanzee adenovirus DNA sequence comprises a gene selected from the group consisting of E1A, E1B, E2A, E2B, E3, E4, L1, L2, L3, L4 and L5 gene sequences of SEQ ID NO: 1. In some aspects the vector can lack the E1A and/or E1B gene.

Also disclosed herein is a host cell transfected with a vector disclosed herein such as a C68 vector engineered to expression a neoantigen cassette. Also disclosed herein is a human cell that expresses a selected gene introduced therein through introduction of a vector disclosed herein into the cell.

Also disclosed herein is a method for delivering a neoantigen cassette to a mammalian cell comprising introducing into said cell an effective amount of a vector disclosed herein such as a C68 vector engineered to expression the neoantigen cassette.

Also disclosed herein is a method for producing a neoantigen comprising introducing a vector disclosed herein into a mammalian cell, culturing the cell under suitable conditions and producing the neoantigen.

V.E.2. E1-Expressing Complementation Cell Lines

To generate recombinant chimpanzee adenoviruses (Ad) deleted in any of the genes described herein, the function of the deleted gene region, if essential to the replication and infectivity of the virus, can be supplied to the recombinant virus by a helper virus or cell line, i.e., a complementation or packaging cell line. For example, to generate a replication-defective chimpanzee adenovirus vector, a cell line can be used which expresses the E1 gene products of the human or chimpanzee adenovirus; such a cell line can include HEK293 or variants thereof. The protocol for the generation of the cell lines expressing the chimpanzee E1 gene products (Examples 3 and 4 of U.S. Pat. No. 6,083,716) can be followed to generate a cell line which expresses any selected chimpanzee adenovirus gene.

An AAV augmentation assay can be used to identify a chimpanzee adenovirus E1-expressing cell line. This assay is useful to identify E1 function in cell lines made by using the E1 genes of other uncharacterized adenoviruses, e.g., from other species. That assay is described in Example 4B of U.S. Pat. No. 6,083,716.

A selected chimpanzee adenovirus gene, e.g., E1, can be under the transcriptional control of a promoter for expression in a selected parent cell line. Inducible or constitutive promoters can be employed for this purpose. Among inducible promoters are included the sheep metallothionine promoter, inducible by zinc, or the mouse mammary tumor virus (MMTV) promoter, inducible by a glucocorticoid, particularly, dexamethasone. Other inducible promoters, such as those identified in International patent application WO95/13392, incorporated by reference herein can also be used in the production of packaging cell lines. Constitutive promoters in control of the expression of the chimpanzee adenovirus gene can be employed also.

A parent cell can be selected for the generation of a novel cell line expressing any desired C68 gene. Without limitation, such a parent cell line can be HeLa [ATCC Accession No. CCL 2], A549 [ATCC Accession No. CCL 185], KB [CCL 17], Detroit [e.g., Detroit 510, CCL 72] and WI-38

[CCL 75] cells. Other suitable parent cell lines can be obtained from other sources. Parent cell lines can include CHO, HEK293 or variants thereof, 911, HeLa, A549, LP-293, PER.C6, or AE1-2a.

An E1-expressing cell line can be useful in the generation of recombinant chimpanzee adenovirus E1 deleted vectors. Cell lines constructed using essentially the same procedures that express one or more other chimpanzee adenoviral gene products are useful in the generation of recombinant chimpanzee adenovirus vectors deleted in the genes that encode those products. Further, cell lines which express other human Ad E1 gene products are also useful in generating chimpanzee recombinant Ads.

V.E.3. Recombinant Viral Particles as Vectors

The compositions disclosed herein can comprise viral vectors, that deliver at least one neoantigen to cells. Such vectors comprise a chimpanzee adenovirus DNA sequence such as C68 and a neoantigen cassette operatively linked to regulatory sequences which direct expression of the cassette. The C68 vector is capable of expressing the cassette in an infected mammalian cell. The C68 vector can be functionally deleted in one or more viral genes. A neoantigen cassette comprises at least one neoantigen under the control of one or more regulatory sequences such as a promoter. Optional helper viruses and/or packaging cell lines can supply to the chimpanzee viral vector any necessary products of deleted adenoviral genes.

The term "functionally deleted" means that a sufficient amount of the gene region is removed or otherwise altered, e.g., by mutation or modification, so that the gene region is no longer capable of producing one or more functional products of gene expression. Mutations or modifications that can result in functional deletions include, but are not limited to, nonsense mutations such as introduction of premature stop codons and removal of canonical and non-canonical start codons, mutations that alter mRNA splicing or other transcriptional processing, or combinations thereof. If desired, the entire gene region can be removed.

Modifications of the nucleic acid sequences forming the vectors disclosed herein, including sequence deletions, insertions, and other mutations may be generated using standard molecular biological techniques and are within the scope of this invention.

V.E.4. Construction of the Viral Plasmid Vector

The chimpanzee adenovirus C68 vectors useful in this invention include recombinant, defective adenoviruses, that is, chimpanzee adenovirus sequences functionally deleted in the E1a or E1b genes, and optionally bearing other mutations, e.g., temperature-sensitive mutations or deletions in other genes. It is anticipated that these chimpanzee sequences are also useful in forming hybrid vectors from other adenovirus and/or adeno-associated virus sequences. Homologous adenovirus vectors prepared from human adenoviruses are described in the published literature [see, for example, Kozarsky I and II, cited above, and references cited therein, U.S. Pat. No. 5,240,846].

In the construction of useful chimpanzee adenovirus C68 vectors for delivery of a neoantigen cassette to a human (or other mammalian) cell, a range of adenovirus nucleic acid sequences can be employed in the vectors. A vector comprising minimal chimpanzee C68 adenovirus sequences can be used in conjunction with a helper virus to produce an infectious recombinant virus particle. The helper virus provides essential gene products required for viral infectivity and propagation of the minimal chimpanzee adenoviral vector. When only one or more selected deletions of chimpanzee adenovirus genes are made in an otherwise functional viral vector, the deleted gene products can be supplied in the viral vector production process by propagating the virus in a selected packaging cell line that provides the deleted gene functions in trans.

V.E.5. Recombinant Minimal Adenovirus

A minimal chimpanzee Ad C68 virus is a viral particle containing just the adenovirus cis-elements necessary for replication and virion encapsidation. That is, the vector contains the cis-acting 5' and 3' inverted terminal repeat (ITR) sequences of the adenoviruses (which function as origins of replication) and the native 5' packaging/enhancer domains (that contain sequences necessary for packaging linear Ad genomes and enhancer elements for the E1 promoter). See, for example, the techniques described for preparation of a "minimal" human Ad vector in International Patent Application WO96/13597 and incorporated herein by reference.

V.E.6. Other Defective Adenoviruses

Recombinant, replication-deficient adenoviruses can also contain more than the minimal chimpanzee adenovirus sequences. These other Ad vectors can be characterized by deletions of various portions of gene regions of the virus, and infectious virus particles formed by the optional use of helper viruses and/or packaging cell lines.

As one example, suitable vectors may be formed by deleting all or a sufficient portion of the C68 adenoviral immediate early gene E1a and delayed early gene E1b, so as to eliminate their normal biological functions. Replication-defective E1-deleted viruses are capable of replicating and producing infectious virus when grown on a chimpanzee adenovirus-transformed, complementation cell line containing functional adenovirus E1a and E1b genes which provide the corresponding gene products in trans. Based on the homologies to known adenovirus sequences, it is anticipated that, as is true for the human recombinant E1-deleted adenoviruses of the art, the resulting recombinant chimpanzee adenovirus is capable of infecting many cell types and can express neoantigen(s), but cannot replicate in most cells that do not carry the chimpanzee E1 region DNA unless the cell is infected at a very high multiplicity of infection.

As another example, all or a portion of the C68 adenovirus delayed early gene E3 can be eliminated from the chimpanzee adenovirus sequence which forms a part of the recombinant virus.

Chimpanzee adenovirus C68 vectors can also be constructed having a deletion of the E4 gene. Still another vector can contain a deletion in the delayed early gene E2a.

Deletions can also be made in any of the late genes L1 through L5 of the chimpanzee C68 adenovirus genome. Similarly, deletions in the intermediate genes IX and IVa2 can be useful for some purposes. Other deletions may be made in the other structural or non-structural adenovirus genes.

The above discussed deletions can be used individually, i.e., an adenovirus sequence can contain deletions of E1 only. Alternatively, deletions of entire genes or portions thereof effective to destroy or reduce their biological activity can be used in any combination. For example, in one exemplary vector, the adenovirus C68 sequence can have deletions of the E1 genes and the E4 gene, or of the E1, E2a and E3 genes, or of the E1 and E3 genes, or of E1, E2a and E4 genes, with or without deletion of E3, and so on. As discussed above, such deletions can be used in combination with other mutations, such as temperature-sensitive mutations, to achieve a desired result.

The cassette comprising neoantigen(s) be inserted optionally into any deleted region of the chimpanzee C68 Ad virus.

Alternatively, the cassette can be inserted into an existing gene region to disrupt the function of that region, if desired.

V.E.7. Helper Viruses

Depending upon the chimpanzee adenovirus gene content of the viral vectors employed to carry the neoantigen cassette, a helper adenovirus or non-replicating virus fragment can be used to provide sufficient chimpanzee adenovirus gene sequences to produce an infective recombinant viral particle containing the cassette.

Useful helper viruses contain selected adenovirus gene sequences not present in the adenovirus vector construct and/or not expressed by the packaging cell line in which the vector is transfected. A helper virus can be replication-defective and contain a variety of adenovirus genes in addition to the sequences described above. The helper virus can be used in combination with the E1-expressing cell lines described herein.

For C68, the "helper" virus can be a fragment formed by clipping the C terminal end of the C68 genome with SspI, which removes about 1300 bp from the left end of the virus. This clipped virus is then co-transfected into an E1-expressing cell line with the plasmid DNA, thereby forming the recombinant virus by homologous recombination with the C68 sequences in the plasmid.

Helper viruses can also be formed into poly-cation conjugates as described in Wu et al, J. Biol. Chem., 264:16985-16987 (1989); K. J. Fisher and J. M. Wilson, Biochem. J., 299:49 (Apr. 1, 1994). Helper virus can optionally contain a reporter gene. A number of such reporter genes are known to the art. The presence of a reporter gene on the helper virus which is different from the neoantigen cassette on the adenovirus vector allows both the Ad vector and the helper virus to be independently monitored. This second reporter is used to enable separation between the resulting recombinant virus and the helper virus upon purification.

V.E.8. Assembly of Viral Particle and Infection of a Cell Line

Assembly of the selected DNA sequences of the adenovirus, the neoantigen cassette, and other vector elements into various intermediate plasmids and shuttle vectors, and the use of the plasmids and vectors to produce a recombinant viral particle can all be achieved using conventional techniques. Such techniques include conventional cloning techniques of cDNA, in vitro recombination techniques (e.g., Gibson assembly), use of overlapping oligonucleotide sequences of the adenovirus genomes, polymerase chain reaction, and any suitable method which provides the desired nucleotide sequence. Standard transfection and co-transfection techniques are employed, e.g., CaPO4 precipitation techniques or liposome-mediated transfection methods such as lipofectamine. Other conventional methods employed include homologous recombination of the viral genomes, plaquing of viruses in agar overlay, methods of measuring signal generation, and the like.

For example, following the construction and assembly of the desired neoantigen cassette-containing viral vector, the vector can be transfected in vitro in the presence of a helper virus into the packaging cell line. Homologous recombination occurs between the helper and the vector sequences, which permits the adenovirus-neoantigen sequences in the vector to be replicated and packaged into virion capsids, resulting in the recombinant viral vector particles.

The resulting recombinant chimpanzee C68 adenoviruses are useful in transferring a neoantigen cassette to a selected cell. In in vivo experiments with the recombinant virus grown in the packaging cell lines, the E1-deleted recombinant chimpanzee adenovirus demonstrates utility in transferring a cassette to a non-chimpanzee, preferably a human, cell.

V.E.9. Use of the Recombinant Virus Vectors

The resulting recombinant chimpanzee C68 adenovirus containing the neoantigen cassette (produced by cooperation of the adenovirus vector and helper virus or adenoviral vector and packaging cell line, as described above) thus provides an efficient gene transfer vehicle which can deliver neoantigen(s) to a subject in vivo or ex vivo.

The above-described recombinant vectors are administered to humans according to published methods for gene therapy. A chimpanzee viral vector bearing a neoantigen cassette can be administered to a patient, preferably suspended in a biologically compatible solution or pharmaceutically acceptable delivery vehicle. A suitable vehicle includes sterile saline. Other aqueous and non-aqueous isotonic sterile injection solutions and aqueous and non-aqueous sterile suspensions known to be pharmaceutically acceptable carriers and well known to those of skill in the art may be employed for this purpose.

The chimpanzee adenoviral vectors are administered in sufficient amounts to transduce the human cells and to provide sufficient levels of neoantigen transfer and expression to provide a therapeutic benefit without undue adverse or with medically acceptable physiological effects, which can be determined by those skilled in the medical arts. Conventional and pharmaceutically acceptable routes of administration include, but are not limited to, direct delivery to the liver, intranasal, intravenous, intramuscular, subcutaneous, intradermal, oral and other parental routes of administration. Routes of administration may be combined, if desired.

Dosages of the viral vector will depend primarily on factors such as the condition being treated, the age, weight and health of the patient, and may thus vary among patients. The dosage will be adjusted to balance the therapeutic benefit against any side effects and such dosages may vary depending upon the therapeutic application for which the recombinant vector is employed. The levels of expression of neoantigen(s) can be monitored to determine the frequency of dosage administration.

Recombinant, replication defective adenoviruses can be administered in a "pharmaceutically effective amount", that is, an amount of recombinant adenovirus that is effective in a route of administration to transfect the desired cells and provide sufficient levels of expression of the selected gene to provide a vaccinal benefit, i.e., some measurable level of protective immunity. C68 vectors comprising a neoantigen cassette can be co-administered with adjuvant. Adjuvant can be separate from the vector (e.g., alum) or encoded within the vector, in particular if the adjuvant is a protein. Adjuvants are well known in the art.

Conventional and pharmaceutically acceptable routes of administration include, but are not limited to, intranasal, intramuscular, intratracheal, subcutaneous, intradermal, rectal, oral and other parental routes of administration. Routes of administration may be combined, if desired, or adjusted depending upon the immunogen or the disease. For example, in prophylaxis of rabies, the subcutaneous, intratracheal and intranasal routes are preferred. The route of administration primarily will depend on the nature of the disease being treated.

The levels of immunity to neoantigen(s) can be monitored to determine the need, if any, for boosters. Following an assessment of antibody titers in the serum, for example, optional booster immunizations may be desired

VI. Therapeutic and Manufacturing Methods

Also provided is a method of inducing a tumor specific immune response in a subject, vaccinating against a tumor, treating and or alleviating a symptom of cancer in a subject by administering to the subject one or more neoantigens such as a plurality of neoantigens identified using methods disclosed herein.

In some aspects, a subject has been diagnosed with cancer or is at risk of developing cancer. A subject can be a human, dog, cat, horse or any animal in which a tumor specific immune response is desired. A tumor can be any solid tumor such as breast, ovarian, prostate, lung, kidney, gastric, colon, testicular, head and neck, pancreas, brain, melanoma, and other tumors of tissue organs and hematological tumors, such as lymphomas and leukemias, including acute myelogenous leukemia, chronic myelogenous leukemia, chronic lymphocytic leukemia, T cell lymphocytic leukemia, and B cell lymphomas.

A neoantigen can be administered in an amount sufficient to induce a CTL response.

A neoantigen can be administered alone or in combination with other therapeutic agents. The therapeutic agent is for example, a chemotherapeutic agent, radiation, or immunotherapy. Any suitable therapeutic treatment for a particular cancer can be administered.

In addition, a subject can be further administered an anti-immunosuppressive/immunostimulatory agent such as a checkpoint inhibitor. For example, the subject can be further administered an anti-CTLA antibody or anti-PD-1 or anti-PD-L1. Blockade of CTLA-4 or PD-L1 by antibodies can enhance the immune response to cancerous cells in the patient. In particular, CTLA-4 blockade has been shown effective when following a vaccination protocol.

The optimum amount of each neoantigen to be included in a vaccine composition and the optimum dosing regimen can be determined. For example, a neoantigen or its variant can be prepared for intravenous (i.v.) injection, sub-cutaneous (s.c.) injection, intradermal (i.d.) injection, intraperitoneal (i.p.) injection, intramuscular (i.m.) injection. Methods of injection include s.c., i.d., i.p., i.m., and i.v. Methods of DNA or RNA injection include i.d., i.m., s.c., i.p. and i.v. Other methods of administration of the vaccine composition are known to those skilled in the art.

A vaccine can be compiled so that the selection, number and/or amount of neoantigens present in the composition is/are tissue, cancer, and/or patient-specific. For instance, the exact selection of peptides can be guided by expression patterns of the parent proteins in a given tissue. The selection can be dependent on the specific type of cancer, the status of the disease, earlier treatment regimens, the immune status of the patient, and, of course, the HLA-haplotype of the patient. Furthermore, a vaccine can contain individualized components, according to personal needs of the particular patient. Examples include varying the selection of neoantigens according to the expression of the neoantigen in the particular patient or adjustments for secondary treatments following a first round or scheme of treatment.

For a composition to be used as a vaccine for cancer, neoantigens with similar normal self-peptides that are expressed in high amounts in normal tissues can be avoided or be present in low amounts in a composition described herein. On the other hand, if it is known that the tumor of a patient expresses high amounts of a certain neoantigen, the respective pharmaceutical composition for treatment of this cancer can be present in high amounts and/or more than one neoantigen specific for this particularly neoantigen or pathway of this neoantigen can be included.

Compositions comprising a neoantigen can be administered to an individual already suffering from cancer. In therapeutic applications, compositions are administered to a patient in an amount sufficient to elicit an effective CTL response to the tumor antigen and to cure or at least partially arrest symptoms and/or complications. An amount adequate to accomplish this is defined as "therapeutically effective dose." Amounts effective for this use will depend on, e.g., the composition, the manner of administration, the stage and severity of the disease being treated, the weight and general state of health of the patient, and the judgment of the prescribing physician. It should be kept in mind that compositions can generally be employed in serious disease states, that is, life-threatening or potentially life threatening situations, especially when the cancer has metastasized. In such cases, in view of the minimization of extraneous substances and the relative nontoxic nature of a neoantigen, it is possible and can be felt desirable by the treating physician to administer substantial excesses of these compositions.

For therapeutic use, administration can begin at the detection or surgical removal of tumors. This is followed by boosting doses until at least symptoms are substantially abated and for a period thereafter.

The pharmaceutical compositions (e.g., vaccine compositions) for therapeutic treatment are intended for parenteral, topical, nasal, oral or local administration. A pharmaceutical compositions can be administered parenterally, e.g., intravenously, subcutaneously, intradermally, or intramuscularly. The compositions can be administered at the site of surgical exiscion to induce a local immune response to the tumor. Disclosed herein are compositions for parenteral administration which comprise a solution of the neoantigen and vaccine compositions are dissolved or suspended in an acceptable carrier, e.g., an aqueous carrier. A variety of aqueous carriers can be used, e.g., water, buffered water, 0.9% saline, 0.3% glycine, hyaluronic acid and the like. These compositions can be sterilized by conventional, well known sterilization techniques, or can be sterile filtered. The resulting aqueous solutions can be packaged for use as is, or lyophilized, the lyophilized preparation being combined with a sterile solution prior to administration. The compositions may contain pharmaceutically acceptable auxiliary substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, triethanolamine oleate, etc.

Neoantigens can also be administered via liposomes, which target them to a particular cells tissue, such as lymphoid tissue. Liposomes are also useful in increasing half-life. Liposomes include emulsions, foams, micelles, insoluble monolayers, liquid crystals, phospholipid dispersions, lamellar layers and the like. In these preparations the neoantigen to be delivered is incorporated as part of a liposome, alone or in conjunction with a molecule which binds to, e.g., a receptor prevalent among lymphoid cells, such as monoclonal antibodies which bind to the CD45 antigen, or with other therapeutic or immunogenic compositions. Thus, liposomes filled with a desired neoantigen can be directed to the site of lymphoid cells, where the liposomes then deliver the selected therapeutic/immunogenic compositions. Liposomes can be formed from standard vesicle-forming lipids, which generally include neutral and negatively charged phospholipids and a sterol, such as cholesterol. The selection of lipids is generally guided by consideration of, e.g., liposome size, acid lability and stability of the liposomes in the blood stream. A variety of methods are available for preparing liposomes, as described in, e.g., Szoka et al., Ann. Rev. Biophys. Bioeng. 9; 467 (1980), U.S. Pat. Nos. 4,235,871, 4,501,728, 4,501,728, 4,837,028, and 5,019,369.

For targeting to the immune cells, a ligand to be incorporated into the liposome can include, e.g., antibodies or fragments thereof specific for cell surface determinants of the desired immune system cells. A liposome suspension can be administered intravenously, locally, topically, etc. in a dose which varies according to, inter alia, the manner of administration, the peptide being delivered, and the stage of the disease being treated.

For therapeutic or immunization purposes, nucleic acids encoding a peptide and optionally one or more of the peptides described herein can also be administered to the patient. A number of methods are conveniently used to deliver the nucleic acids to the patient. For instance, the nucleic acid can be delivered directly, as "naked DNA". This approach is described, for instance, in Wolff et al., Science 247: 1465-1468 (1990) as well as U.S. Pat. Nos. 5,580,859 and 5,589,466. The nucleic acids can also be administered using ballistic delivery as described, for instance, in U.S. Pat. No. 5,204,253. Particles comprised solely of DNA can be administered. Alternatively, DNA can be adhered to particles, such as gold particles. Approaches for delivering nucleic acid sequences can include viral vectors, mRNA vectors, and DNA vectors with or without electroporation.

The nucleic acids can also be delivered complexed to cationic compounds, such as cationic lipids. Lipid-mediated gene delivery methods are described, for instance, in 9618372WOAWO 96/18372; 9324640WOAWO 93/24640; Mannino & Gould-Fogerite, BioTechniques 6(7): 682-691 (1988); U.S. Pat. No. 5,279,833 Rose U.S. Pat. Nos. 5,279, 833; 9,106,309WOAWO 91/06309; and Felgner et al., Proc. Natl. Acad. Sci. USA 84: 7413-7414 (1987).

Neoantigens can also be included in viral vector-based vaccine platforms, such as vaccinia, fowlpox, self-replicating alphavirus, marabavirus, adenovirus (See, e.g., Tatsis et al., Adenoviruses, *Molecular Therapy* (2004) 10, 616-629), or lentivirus, including but not limited to second, third or hybrid second/third generation lentivirus and recombinant lentivirus of any generation designed to target specific cell types or receptors (See, e.g., Hu et al., Immunization Delivered by Lentiviral Vectors for Cancer and Infectious Diseases, *Immunol Rev*. (2011) 239(1): 45-61, Sakuma et al., Lentiviral vectors: basic to translational, *Biochem J*. (2012) 443(3):603-18, Cooper et al., Rescue of splicing-mediated intron loss maximizes expression in lentiviral vectors containing the human ubiquitin C promoter, *Nucl. Acids Res*. (2015) 43 (1): 682-690, Zufferey et al., Self-Inactivating Lentivirus Vector for Safe and Efficient In Vivo Gene Delivery, *J. Virol*. (1998) 72 (12): 9873-9880). Dependent on the packaging capacity of the above mentioned viral vector-based vaccine platforms, this approach can deliver one or more nucleotide sequences that encode one or more neoantigen peptides. The sequences may be flanked by non-mutated sequences, may be separated by linkers or may be preceded with one or more sequences targeting a subcellular compartment (See, e.g., Gros et al., Prospective identification of neoantigen-specific lymphocytes in the peripheral blood of melanoma patients, *Nat Med*. (2016) 22 (4):433-8, Stronen et al., Targeting of cancer neoantigens with donor-derived T cell receptor repertoires, *Science*. (2016) 352 (6291):1337-41, Lu et al., Efficient identification of mutated cancer antigens recognized by T cells associated with durable tumor regressions, *Clin Cancer Res*. (2014) 20(13):3401-10). Upon introduction into a host, infected cells express the neoantigens, and thereby elicit a host immune (e.g., CTL) response against the peptide(s). Vaccinia vectors and methods useful in immunization protocols are described in, e.g., U.S. Pat. No. 4,722,848. Another vector is BCG (Bacille Calmette Guerin). BCG vectors are described in Stover et al. (Nature 351:456-460 (1991)). A wide variety of other vaccine vectors useful for therapeutic administration or immunization of neoantigens, e.g., *Salmonella typhi* vectors, and the like will be apparent to those skilled in the art from the description herein.

A means of administering nucleic acids uses minigene constructs encoding one or multiple epitopes. To create a DNA sequence encoding the selected CTL epitopes (minigene) for expression in human cells, the amino acid sequences of the epitopes are reverse translated. A human codon usage table is used to guide the codon choice for each amino acid. These epitope-encoding DNA sequences are directly adjoined, creating a continuous polypeptide sequence. To optimize expression and/or immunogenicity, additional elements can be incorporated into the minigene design. Examples of amino acid sequence that could be reverse translated and included in the minigene sequence include: helper T lymphocyte, epitopes, a leader (signal) sequence, and an endoplasmic reticulum retention signal. In addition, MHC presentation of CTL epitopes can be improved by including synthetic (e.g. poly-alanine) or naturally-occurring flanking sequences adjacent to the CTL epitopes. The minigene sequence is converted to DNA by assembling oligonucleotides that encode the plus and minus strands of the minigene. Overlapping oligonucleotides (30-100 bases long) are synthesized, phosphorylated, purified and annealed under appropriate conditions using well known techniques. The ends of the oligonucleotides are joined using T4 DNA ligase. This synthetic minigene, encoding the CTL epitope polypeptide, can then cloned into a desired expression vector.

Purified plasmid DNA can be prepared for injection using a variety of formulations. The simplest of these is reconstitution of lyophilized DNA in sterile phosphate-buffer saline (PBS). A variety of methods have been described, and new techniques can become available. As noted above, nucleic acids are conveniently formulated with cationic lipids. In addition, glycolipids, fusogenic liposomes, peptides and compounds referred to collectively as protective, interactive, non-condensing (PINC) could also be complexed to purified plasmid DNA to influence variables such as stability, intramuscular dispersion, or trafficking to specific organs or cell types.

Also disclosed is a method of manufacturing a tumor vaccine, comprising performing the steps of a method disclosed herein; and producing a tumor vaccine comprising a plurality of neoantigens or a subset of the plurality of neoantigens.

Neoantigens disclosed herein can be manufactured using methods known in the art. For example, a method of producing a neoantigen or a vector (e.g., a vector including at least one sequence encoding one or more neoantigens) disclosed herein can include culturing a host cell under conditions suitable for expressing the neoantigen or vector wherein the host cell comprises at least one polynucleotide encoding the neoantigen or vector, and purifying the neoantigen or vector. Standard purification methods include chromatographic techniques, electrophoretic, immunological, precipitation, dialysis, filtration, concentration, and chromatofocusing techniques.

Host cells can include a Chinese Hamster Ovary (CHO) cell, NSO cell, yeast, or a HEK293 cell. Host cells can be transformed with one or more polynucleotides comprising at least one nucleic acid sequence that encodes a neoantigen or vector disclosed herein, optionally wherein the isolated polynucleotide further comprises a promoter sequence operably linked to the at least one nucleic acid sequence that encodes the neoantigen or vector. In certain embodiments the isolated polynucleotide can be cDNA.

VII. Neoantigen Use and Administration

A vaccination protocol can be used to dose a subject with one or more neoantigens. A priming vaccine and a boosting vaccine can be used to dose the subject. The priming vaccine can be based on C68 (e.g., the sequences shown in SEQ ID NO:1 or 2) or srRNA (e.g., the sequences shown in SEQ ID NO:3 or 4) and the boosting vaccine can be based on C68 (e.g., the sequences shown in SEQ ID NO:1 or 2) or srRNA (e.g., the sequences shown in SEQ ID NO:3 or 4). Each vector typically includes a cassette that includes neoantigens. Cassettes can include about 20 neoantigens, separated by spacers such as the natural sequence that normally surrounds each antigen or other non-natural spacer sequences such as AAY. Cassettes can also include MHCII antigens such a tetanus toxoid antigen and PADRE antigen, which can be considered universal class II antigens. Cassettes can also include a targeting sequence such as a ubiquitin targeting sequence. In addition, each vaccine dose can be administered to the subject in conjunction with (e.g., concurrently, before, or after) a checkpoint inhibitor (CPI). CPI's can include those that inhibit CTLA4, PD1, and/or PDL1 such as antibodies or antigen-binding portions thereof. Such antibodies can include tremelimumab or durvalumab.

A priming vaccine can be injected (e.g., intramuscularly) in a subject. Bilateral injections per dose can be used. For example, one or more injections of ChAdV68 (C68) can be used (e.g., total dose $1\times10^{12}$ viral particles); one or more injections of self-replicating RNA (srRNA) at low vaccine dose selected from the range 0.001 to 1 ug RNA, in particular 0.1 or 1 ug can be used; or one or more injections of srRNA at high vaccine dose selected from the range 1 to 100 ug RNA, in particular 10 or 100 ug can be used.

A vaccine boost (boosting vaccine) can be injected (e.g., intramuscularly) after prime vaccination. A boosting vaccine can be administered about every 1, 2, 3, 4, 5, 6, 7, 8, 9, or 10 weeks, e.g., every 4 weeks and/or 8 weeks after the prime. Bilateral injections per dose can be used. For example, one or more injections of ChAdV68 (C68) can be used (e.g., total dose $1\times10^{12}$ viral particles); one or more injections of self-replicating RNA (srRNA) at low vaccine dose selected from the range 0.001 to 1 ug RNA, in particular 0.1 or 1 ug can be used; or one or more injections of srRNA at high vaccine dose selected from the range 1 to 100 ug RNA, in particular 10 or 100 ug can be used.

Anti-CTLA-4 (e.g., tremelimumab) can also be administered to the subject. For example, anti-CTLA4 can be administered subcutaneously near the site of the intramuscular vaccine injection (ChAdV68 prime or srRNA low doses) to ensure drainage into the same lymph node. Tremelimumab is a selective human IgG2 mAb inhibitor of CTLA-4. Target Anti-CTLA-4 (tremelimumab) subcutaneous dose is typically 70-75 mg (in particular 75 mg) with a dose range of, e.g., 1-100 mg or 5-420 mg.

In certain instances an anti-PD-L1 antibody can be used such as durvalumab (MEDI 4736). Durvalumab is a selective, high affinity human IgG1 mAb that blocks PD-L1 binding to PD-1 and CD80. Durvalumab is generally administered at 20 mg/kg i.v. every 4 weeks.

Immune monitoring can be performed before, during, and/or after vaccine administration. Such monitoring can inform safety and efficacy, among other parameters.

To perform immune monitoring, PBMCs are commonly used. PBMCs can be isolated before prime vaccination, and after prime vaccination (e.g. 4 weeks and 8 weeks). PBMCs can be harvested just prior to boost vaccinations and after each boost vaccination (e.g. 4 weeks and 8 weeks).

T cell responses can be assessed as part of an immune monitoring protocol. T cell responses can be measured using one or more methods known in the art such as ELISpot, intracellular cytokine staining, cytokine secretion and cell surface capture, T cell proliferation, MHC multimer staining, or by cytotoxicity assay. T cell responses to epitopes encoded in vaccines can be monitored from PBMCs by measuring induction of cytokines, such as IFN-gamma, using an ELISpot assay. Specific CD4 or CD8 T cell responses to epitopes encoded in vaccines can be monitored from PBMCs by measuring induction of cytokines captured intracellularly or extracellularly, such as IFN-gamma, using flow cytometry. Specific CD4 or CD8 T cell responses to epitopes encoded in the vaccines can be monitored from PBMCs by measuring T cell populations expressing T cell receptors specific for epitope/MHC class I complexes using MHC multimer staining. Specific CD4 or CD8 T cell responses to epitopes encoded in the vaccines can be monitored from PBMCs by measuring the ex vivo expansion of T cell populations following 3H-thymidine, bromodeoxyuridine and carboxyfluoresceine-diacetate-succinimidylester (CFSE) incorporation. The antigen recognition capacity and lytic activity of PBMC-derived T cells that are specific for epitopes encoded in vaccines can be assessed functionally by chromium release assay or alternative colorimetric cytotoxicity assays.

VIII. Neoantigen Identification

VIII.A. Neoantigen Candidate Identification

Research methods for NGS analysis of tumor and normal exome and transcriptomes have been described and applied in the neoantigen identification space. [6,14,15] The example below considers certain optimizations for greater sensitivity and specificity for neoantigen identification in the clinical setting. These optimizations can be grouped into two areas, those related to laboratory processes and those related to the NGS data analysis.

VIII.A.1. Laboratory Process Optimizations

The process improvements presented here address challenges in high-accuracy neoantigen discovery from clinical specimens with low tumor content and small volumes by extending concepts developed for reliable cancer driver gene assessment in targeted cancer panels[16] to the whole-exome and -transcriptome setting necessary for neoantigen identification. Specifically, these improvements include:

1. Targeting deep (>500×) unique average coverage across the tumor exome to detect mutations present at low mutant allele frequency due to either low tumor content or subclonal state.

2. Targeting uniform coverage across the tumor exome, with <5% of bases covered at <100x, so that the fewest possible neoantigens are missed, by, for instance:
   a. Employing DNA-based capture probes with individual probe QC[17]
   b. Including additional baits for poorly covered regions
3. Targeting uniform coverage across the normal exome, where <5% of bases are covered at <20x so that the fewest neoantigens possible remain unclassified for somatic/germline status (and thus not usable as TSNAs)
4. To minimize the total amount of sequencing required, sequence capture probes will be designed for coding regions of genes only, as non-coding RNA cannot give rise to neoantigens. Additional optimizations include:
   a. supplementary probes for HLA genes, which are GC-rich and poorly captured by standard exome sequencing[18]
   b. exclusion of genes predicted to generate few or no candidate neoantigens, due to factors such as insufficient expression, suboptimal digestion by the proteasome, or unusual sequence features.
5. Tumor RNA will likewise be sequenced at high depth (>100M reads) in order to enable variant detection, quantification of gene and splice-variant ("isoform") expression, and fusion detection. RNA from FFPE samples will be extracted using probe-based enrichment[19], with the same or similar probes used to capture exomes in DNA.

VIII.A.2. NGS Data Analysis Optimizations

Improvements in analysis methods address the suboptimal sensitivity and specificity of common research mutation calling approaches, and specifically consider customizations relevant for neoantigen identification in the clinical setting. These include:

1. Using the HG38 reference human genome or a later version for alignment, as it contains multiple MHC regions assemblies better reflective of population polymorphism, in contrast to previous genome releases.
2. Overcoming the limitations of single variant callers[20] by merging results from different programs[5]
   a. Single-nucleotide variants and indels will be detected from tumor DNA, tumor RNA and normal DNA with a suite of tools including: programs based on comparisons of tumor and normal DNA, such as Strelka[21] and Mutect[22]; and programs that incorporate tumor DNA, tumor RNA and normal DNA, such as UNCeqR, which is particularly advantageous in low-purity samples[23].
   b. Indels will be determined with programs that perform local re-assembly, such as Strelka and ABRA[24].
   c. Structural rearrangements will be determined using dedicated tools such as Pindel[25] or Breakseq[26].
3. In order to detect and prevent sample swaps, variant calls from samples for the same patient will be compared at a chosen number of polymorphic sites.
4. Extensive filtering of artefactual calls will be performed, for instance, by:
   a. Removal of variants found in normal DNA, potentially with relaxed detection parameters in cases of low coverage, and with a permissive proximity criterion in case of indels
   b. Removal of variants due to low mapping quality or low base quality[27].
   c. Removal of variants stemming from recurrent sequencing artifacts, even if not observed in the corresponding normal[27]. Examples include variants primarily detected on one strand.
   d. Removal of variants detected in an unrelated set of controls[27]
5. Accurate HLA calling from normal exome using one of seq2HLA[28], ATHLATES[29] or Optitype and also combining exome and RNA sequencing data[28]. Additional potential optimizations include the adoption of a dedicated assay for HLA typing such as long-read DNA sequencing[30], or the adaptation of a method for joining RNA fragments to retain continuity[31].
6. Robust detection of neo-ORFs arising from tumor-specific splice variants will be performed by assembling transcripts from RNA-seq data using CLASS[32], Bayesembler[33], StringTie[34] or a similar program in its reference-guided mode (i.e., using known transcript structures rather than attempting to recreate transcripts in their entirety from each experiment). While Cufflinks[35] is commonly used for this purpose, it frequently produces implausibly large numbers of splice variants, many of them far shorter than the full-length gene, and can fail to recover simple positive controls. Coding sequences and nonsense-mediated decay potential will be determined with tools such as SpliceR[36] and MAMBA[37], with mutant sequences re-introduced. Gene expression will be determined with a tool such as Cufflinks[35] or Express (Roberts and Pachter, 2013). Wild-type and mutant-specific expression counts and/or relative levels will be determined with tools developed for these purposes, such as ASE[38] or HTSeq[39]. Potential filtering steps include:
   a. Removal of candidate neo-ORFs deemed to be insufficiently expressed.
   b. Removal of candidate neo-ORFs predicted to trigger non-sense mediated decay (NMD).
7. Candidate neoantigens observed only in RNA (e.g., neoORFs) that cannot directly be verified as tumor-specific will be categorized as likely tumor-specific according to additional parameters, for instance by considering:
   a. Presence of supporting tumor DNA-only cis-acting frameshift or splice-site mutations
   b. Presence of corroborating tumor DNA-only trans-acting mutation in a splicing factor. For instance, in three independently published experiments with R625-mutant SF3B1, the genes exhibiting the most differentially splicing were concordant even though one experiment examined uveal melanoma patients[40], the second a uveal melanoma cell line[41], and the third breast cancer patients[42].
   c. For novel splicing isoforms, presence of corroborating "novel" splice-junction reads in the RNASeq data.
   d. For novel re-arrangements, presence of corroborating juxta-exon reads in tumor DNA that are absent from normal DNA
   e. Absence from gene expression compendium such as GTEx[43] (i.e. making germline origin less likely)
8. Complementing the reference genome alignment-based analysis by comparing assembled DNA tumor and normal reads (or k-mers from such reads) directly to avoid alignment and annotation based errors and artifacts. (e.g. for somatic variants arising near germline variants or repeat-context indels)

In samples with poly-adenylated RNA, the presence of viral and microbial RNA in the RNA-seq data will be assessed using RNA CoMPASS[44] or a similar method, toward the identification of additional factors that may predict patient response.

VIII.B. Isolation and Detection of HLA Peptides

Isolation of HLA-peptide molecules was performed using classic immunoprecipitation (IP) methods after lysis and solubilization of the tissue sample (55-58). A clarified lysate was used for HLA specific IP.

Immunoprecipitation was performed using antibodies coupled to beads where the antibody is specific for HLA molecules. For a pan-Class I HLA immunoprecipitation, a pan-Class I CR antibody is used, for Class II HLA-DR, an HLA-DR antibody is used. Antibody is covalently attached to NHS-sepharose beads during overnight incubation. After covalent attachment, the beads were washed and aliquoted for IP. (59, 60) Immunoprecipitations can also be performed with antibodies that are not covalently attached to beads. Typically this is done using sepharose or magnetic beads coated with Protein A and/or Protein G to hold the antibody to the column. Some antibodies that can be used to selectively enrich MHC/peptide complex are listed below.

| Antibody Name | Specificity |
| --- | --- |
| W6/32 | Class I HLA-A, B, C |
| L243 | Class II — HLA-DR |
| Tu36 | Class II — HLA-DR |
| LN3 | Class II — HLA-DR |
| Tu39 | Class II — HLA-DR, DP, DQ |

The clarified tissue lysate is added to the antibody beads for the immunoprecipitation. After immunoprecipitation, the beads are removed from the lysate and the lysate stored for additional experiments, including additional IPs. The IP beads are washed to remove non-specific binding and the HLA/peptide complex is eluted from the beads using standard techniques. The protein components are removed from the peptides using a molecular weight spin column or C18 fractionation. The resultant peptides are taken to dryness by SpeedVac evaporation and in some instances are stored at −20 C prior to MS analysis.

Dried peptides are reconstituted in an HPLC buffer suitable for reverse phase chromatography and loaded onto a C-18 microcapillary HPLC column for gradient elution in a Fusion Lumos mass spectrometer (Thermo). MS1 spectra of peptide mass/charge (m/z) were collected in the Orbitrap detector at high resolution followed by MS2 low resolution scans collected in the ion trap detector after HCD fragmentation of the selected ion. Additionally, MS2 spectra can be obtained using either CID or ETD fragmentation methods or any combination of the three techniques to attain greater amino acid coverage of the peptide. MS2 spectra can also be measured with high resolution mass accuracy in the Orbitrap detector.

MS2 spectra from each analysis are searched against a protein database using Comet (61, 62) and the peptide identification are scored using Percolator (63-65). Additional sequencing is performed using PEAKS studio (Bioinformatics Solutions Inc.) and other search engines or sequencing methods can be used including spectral matching and de novo sequencing (97).

VIII.B.1. MS Limit of Detection Studies in Support of Comprehensive HLA Peptide Sequencing.

Figure 1C:
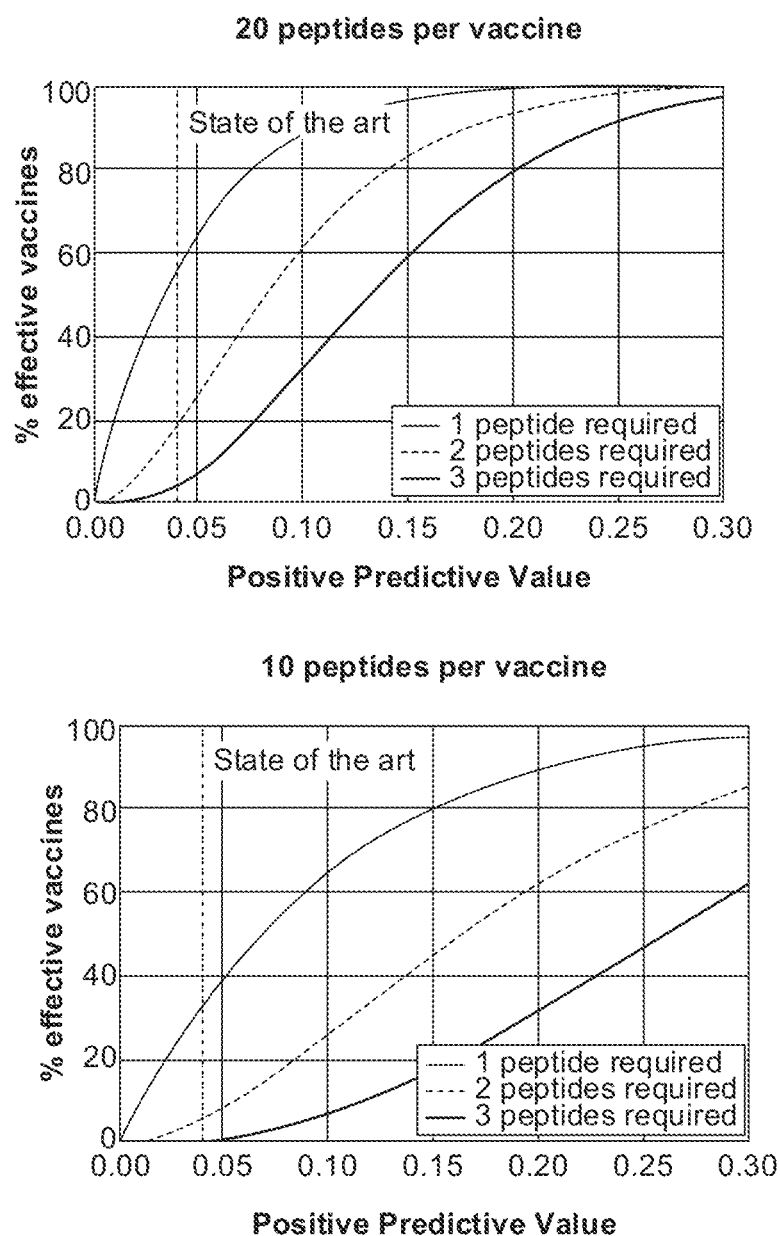
FIG. 1C shows the impact of the neoantigen prediction specificity problem.
Figure 1D:
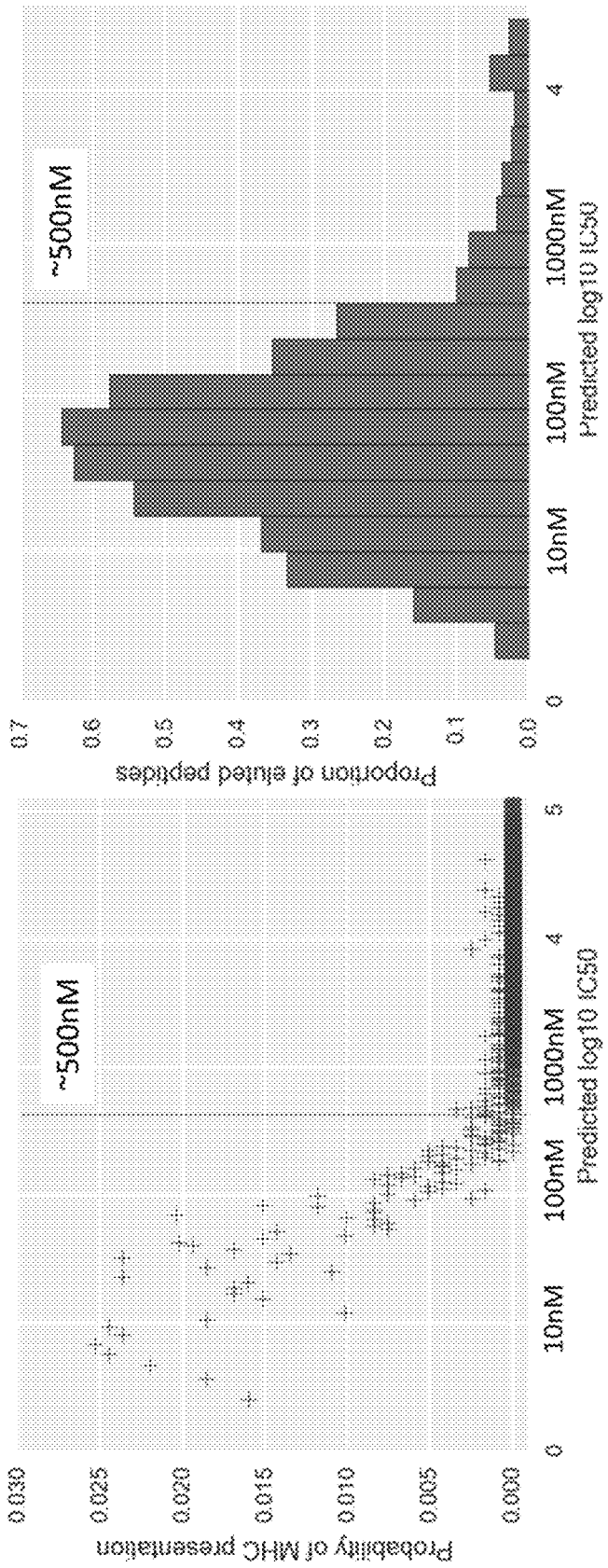
FIG. 1D shows that binding prediction is not sufficient for neoantigen identification.
Figure 1E:
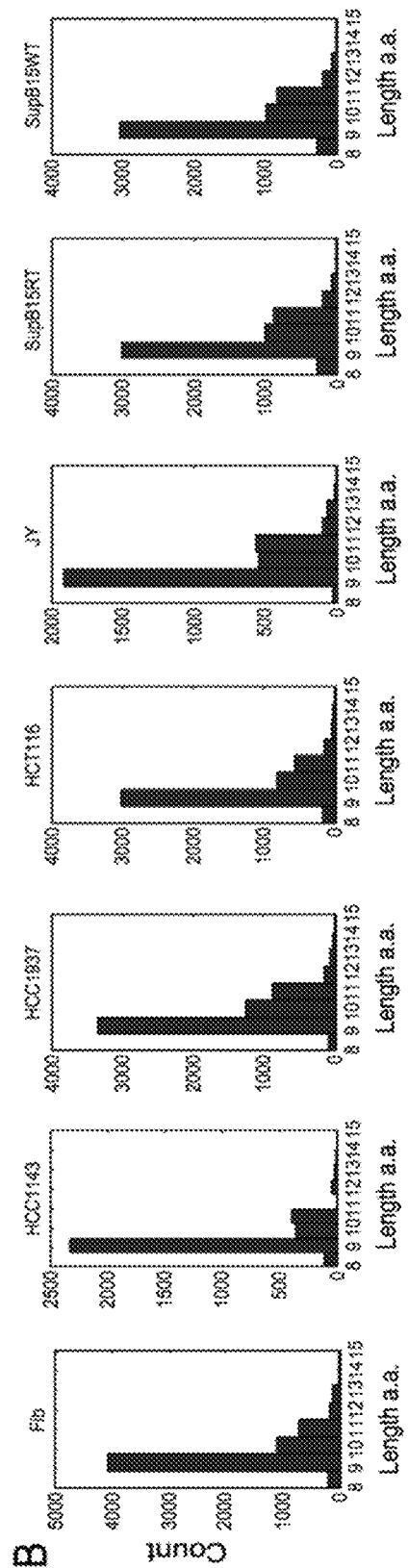
FIG. 1E shows probability of MHC-I presentation as a function of peptide length.
Figure 1F:
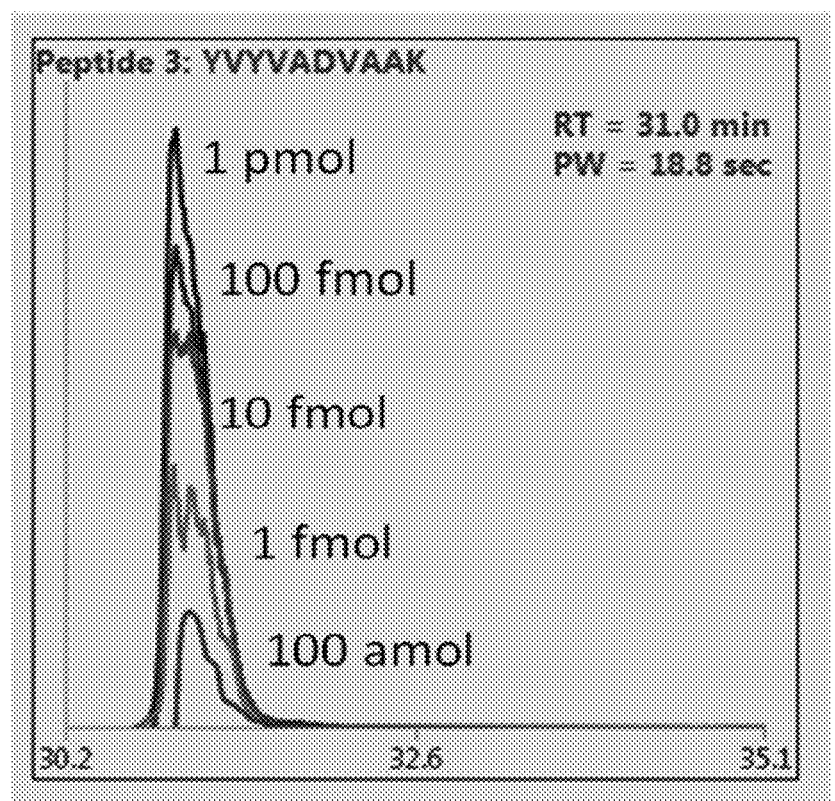
FIG. 1F shows an example peptide spectrum generated from Promega's dynamic range standard. Figure discloses SEQ ID NO: 59.
Figure 1F:
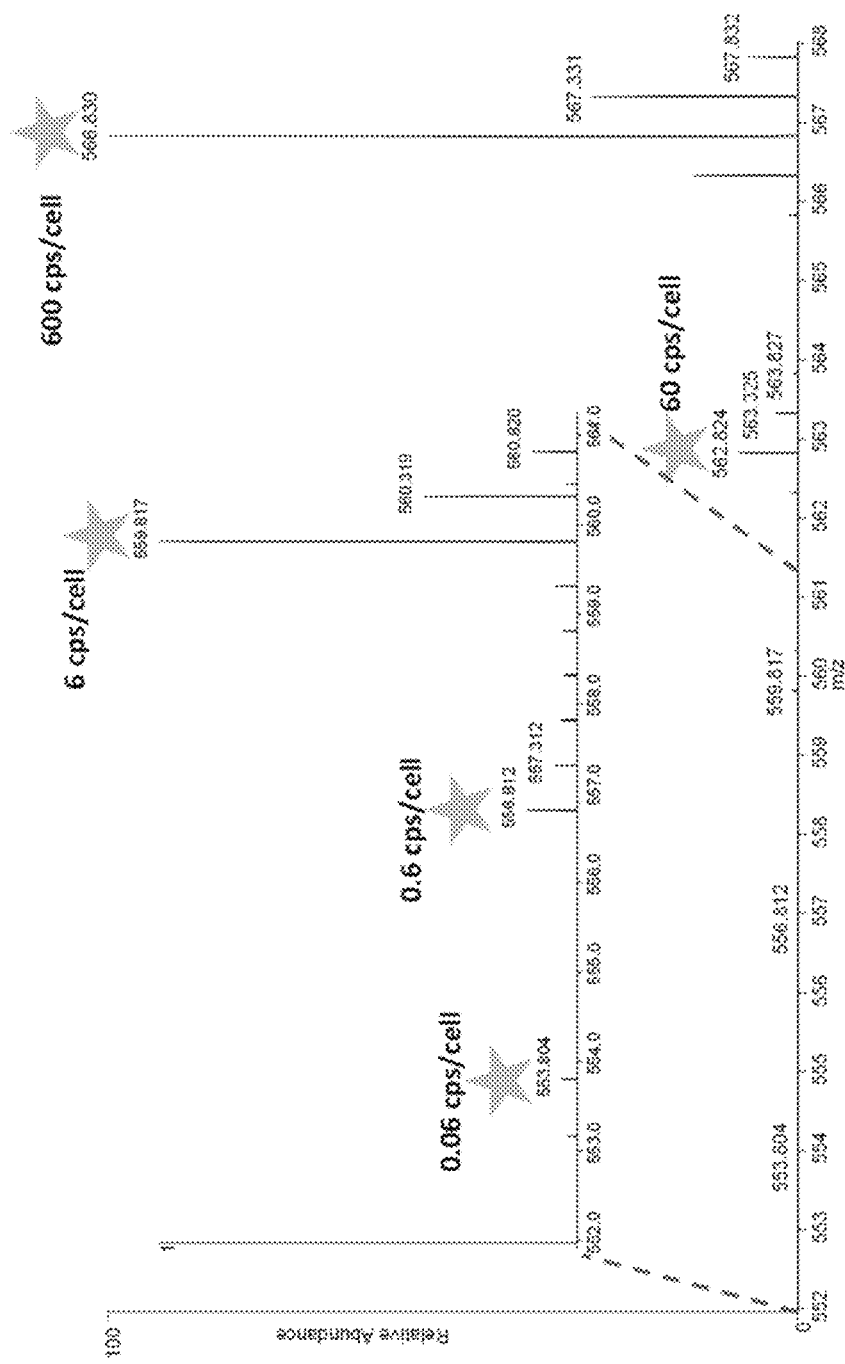
Figure 1G:
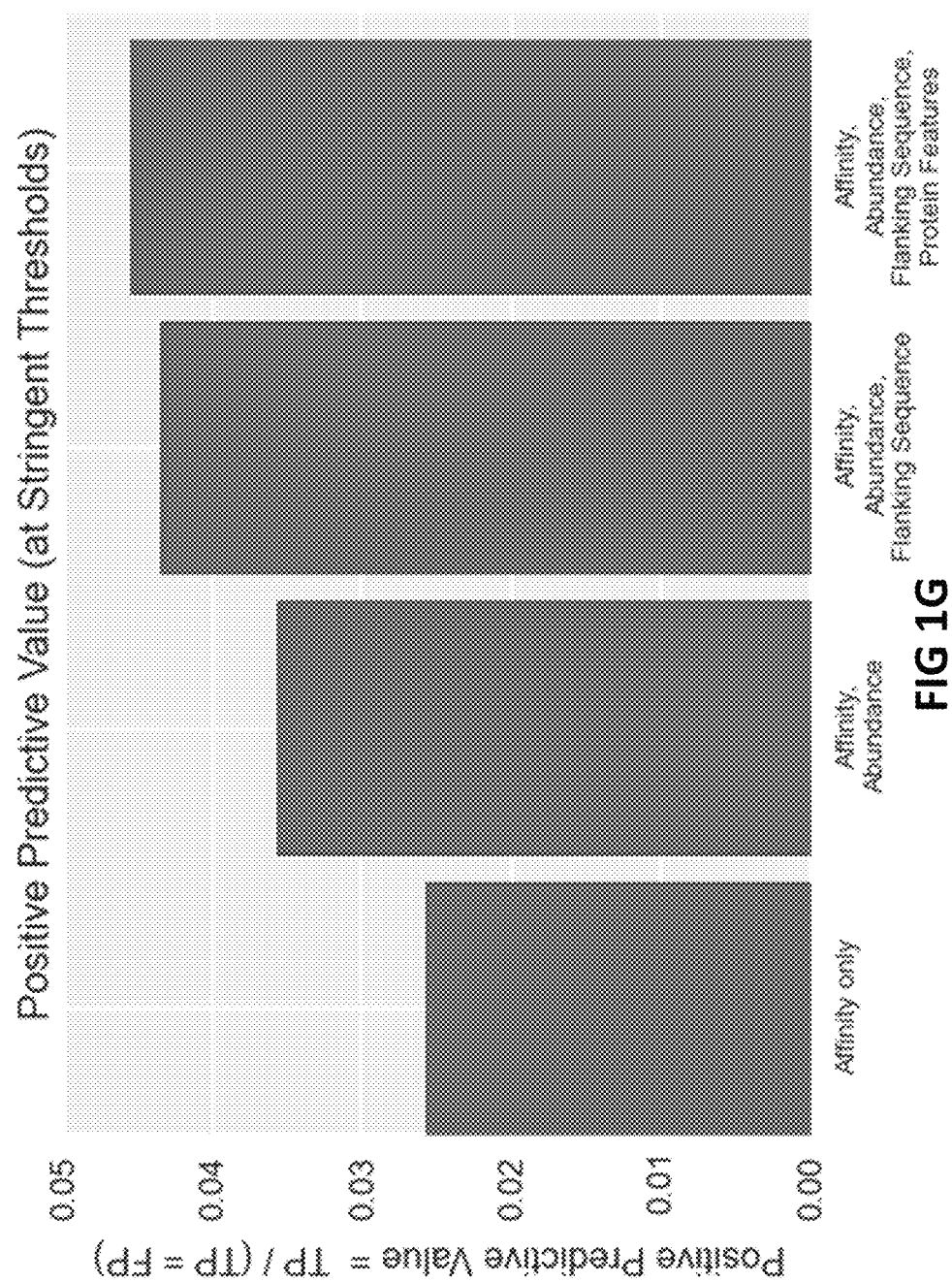
FIG. 1G shows how the addition of features increases the model positive predictive value.

Using the peptide YVYVADVAAK (SEQ ID NO: 59) it was determined what the limits of detection are using different amounts of peptide loaded onto the LC column. The amounts of peptide tested were 1 µmol, 100 fmol, 10 fmol, 1 fmol, and 100 amol. (Table 1) The results are shown in FIG. 1F. These results indicate that the lowest limit of detection (LoD) is in the attomol range ($10^{-18}$), that the dynamic range spans five orders of magnitude, and that the signal to noise appears sufficient for sequencing at low femtomol ranges ($10^{-15}$).

TABLE 1

| Peptide m/z | Loaded on Column | Copies/Cell in 1e9cells |
| --- | --- | --- |
| 566.830 | 1 pmol | 600 |
| 562.823 | 100 fmol | 60 |
| 559.816 | 10 fmol | 6 |
| 556.810 | 1 fmol | 0.6 |
| 553.802 | 100 amol | 0.06 |

IX. Presentation Model

IX.A. System Overview

Figure 2A:
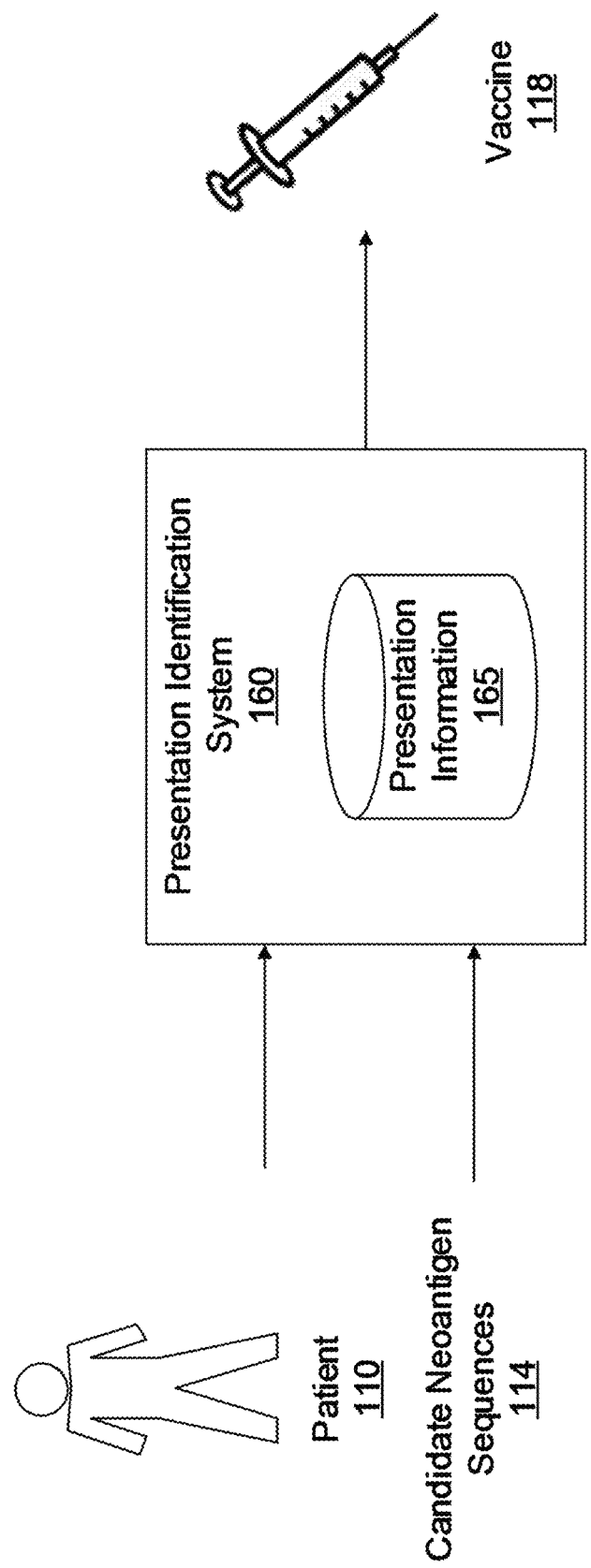
FIG. 2A is an overview of an environment for identifying likelihoods of peptide presentation in patients, in accordance with an embodiment.

FIG. 2A is an overview of an environment 100 for identifying likelihoods of peptide presentation in patients, in accordance with an embodiment. The environment 100 provides context in order to introduce a presentation identification system 160, itself including a presentation information store 165.

The presentation identification system 160 is one or computer models, embodied in a computing system as discussed below with respect to FIG. 14, that receives peptide sequences associated with a set of MHC alleles and determines likelihoods that the peptide sequences will be presented by one or more of the set of associated MHC alleles. The presentation identification system 160 may be applied to both class I and class II MHC alleles. This is useful in a variety of contexts. One specific use case for the presentation identification system 160 is that it is able to receive nucleotide sequences of candidate neoantigens associated with a set of MHC alleles from tumor cells of a patient 110 and determine likelihoods that the candidate neoantigens will be presented by one or more of the associated MHC alleles of the tumor and/or induce immunogenic responses in the immune system of the patient 110. Those candidate neoantigens with high likelihoods as determined by system 160 can be selected for inclusion in a vaccine 118, such an anti-tumor immune response can be elicited from the immune system of the patient 110 providing the tumor cells.

The presentation identification system 160 determines presentation likelihoods through one or more presentation models. Specifically, the presentation models generate likelihoods of whether given peptide sequences will be presented for a set of associated MHC alleles, and are generated based on presentation information stored in store 165. For example, the presentation models may generate likelihoods of whether a peptide sequence "YVYVADVAAK (SEQ ID NO: 59)" will be presented for the set of alleles HLA-A*02:01, HLA-A*03:01, HLA-B*07:02, HLA-B*08:03, HLA-C*01:04, HLA-A*06:03, HLA-B*01:04 on the cell surface of the sample. The presentation information 165 contains information on whether peptides bind to different types of MHC alleles such that those peptides are presented by MHC alleles, which in the models is determined depending on positions of amino acids in the peptide sequences. The presentation model can predict whether an unrecognized peptide sequence will be presented in association with an associated set of MHC alleles based on the presentation information 165. As previously mentioned, the presentation models may be applied to both class I and class II MHC alleles.

IX.B. Presentation Information

Figure 2D:
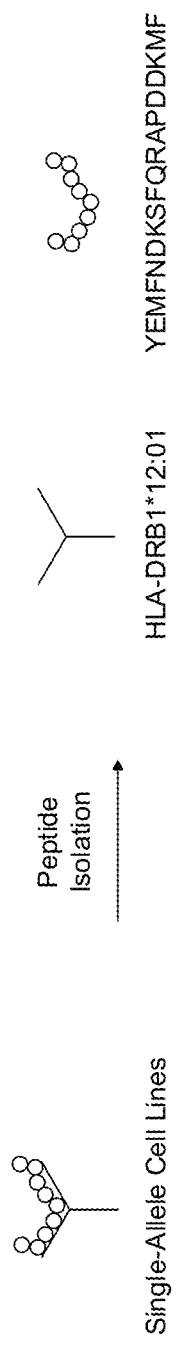
Figure 2E:
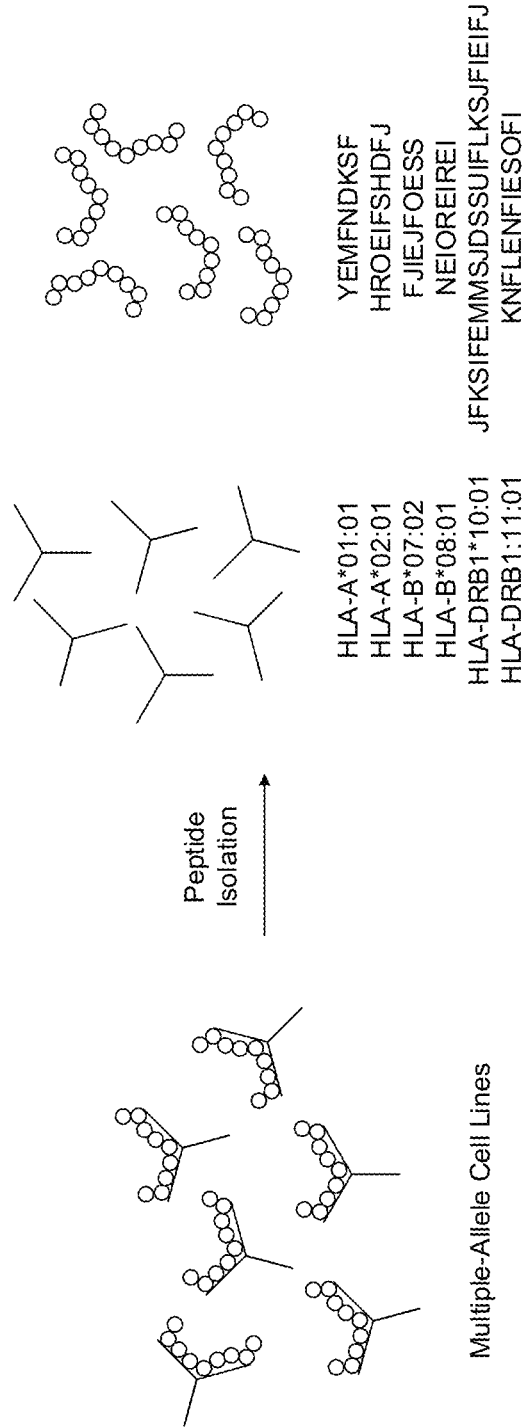

FIG. 2 illustrates a method of obtaining presentation information, in accordance with an embodiment. The presentation information 165 includes two general categories of information: allele-interacting information and allele-noninteracting information. Allele-interacting information includes information that influence presentation of peptide sequences that are dependent on the type of MHC allele. Allele-noninteracting information includes information that influence presentation of peptide sequences that are independent on the type of MHC allele.

IX.B.1. Allele-Interacting Information

Allele-interacting information primarily includes identified peptide sequences that are known to have been presented by one or more identified MHC molecules from humans, mice, etc. Notably, this may or may not include data obtained from tumor samples. The presented peptide sequences may be identified from cells that express a single MHC allele. In this case the presented peptide sequences are generally collected from single-allele cell lines that are engineered to express a predetermined MHC allele and that are subsequently exposed to synthetic protein. Peptides presented on the MHC allele are isolated by techniques such as acid-elution and identified through mass spectrometry. FIG. 2B shows an example of this, where the example peptide YEMFNDKS, presented on the predetermined MHC allele HLA-A*01:01, is isolated and identified through mass spectrometry. FIG. 2D shows another example of this, where the example peptide YEMFNDKSQRAPDDKMF (SEQ ID NO: 61), presented on the predetermined MHC allele HLA-DRB1*12:01, is isolated and identified through mass spectrometry. Since in these situations peptides are identified through cells engineered to express a single predetermined MHC protein, the direct association between a presented peptide and the MHC protein to which it was bound to is definitively known.

The presented peptide sequences may also be collected from cells that express multiple MHC alleles. Typically in humans, 6 different types of MHC-I and up to 12 different types of MHC-II molecules are expressed for a cell. Such presented peptide sequences may be identified from multiple-allele cell lines that are engineered to express multiple predetermined MHC alleles. Such presented peptide sequences may also be identified from tissue samples, either from normal tissue samples or tumor tissue samples. In this case particularly, the MHC molecules can be immunoprecipitated from normal or tumor tissue. Peptides presented on the multiple MHC alleles can similarly be isolated by techniques such as acid-elution and identified through mass spectrometry. FIG. 2C shows an example of this, where the six example peptides, YEMFNDKSF (SEQ ID NO: 62), HROEIFSHDFJ (SEQ ID NO: 63), FJIEJFOESS (SEQ ID NO: 64), NEIOREIREI (SEQ ID NO: 65), JFKSIFEMMSJDSSU (SEQ ID NO: 66), and KNFLENFIESOFI (SEQ ID NO: 67), are presented on identified MHC alleles HLA-A*01:01, HLA-A*02:01, HLA-B*07:02, HLA-B*08:01, HLA-C*01:03, and HLA-C*01:04 and are isolated and identified through mass spectrometry. In another example, FIG. 2C shows where the six example peptides, YEMFNDKSF (SEQ ID NO: 62), HROEIFSHDFJ (SEQ ID NO: 63), FJIEJFOESS (SEQ ID NO: 64), NEIOREIREI (SEQ ID NO: 65), JFKSIFEMMSJDSSUI-FLKSJFIEIFJ (SEQ ID NO: 68), and KNFLENFIESOFI (SEQ ID NO: 67), are presented on identified class I MHC alleles HLA-A*01:01, HLA-A*02:01, HLA-B*07:02, HLA-B*08:01, and class II MHC alleles HLA-DRB1*10:01, HLA-DRB1:11:01 and are isolated and identified through mass spectrometry. In contrast to single-allele cell lines, in these examples the direct association between a presented peptide and the MHC protein to which it was bound to may be unknown since the bound peptides are isolated from the MHC molecules before being identified.

Allele-interacting information can also include mass spectrometry ion current which depends on both the concentration of peptide-MHC molecule complexes, and the ionization efficiency of peptides. The ionization efficiency varies from peptide to peptide in a sequence-dependent manner. Generally, ionization efficiency varies from peptide to peptide over approximately two orders of magnitude, while the concentration of peptide-MHC complexes varies over a larger range than that.

Allele-interacting information can also include measurements or predictions of binding affinity between a given MHC allele and a given peptide (94, 95, 96). One or more affinity models can generate such predictions. For example, going back to the example shown in FIG. 1D, presentation information 165 may include a binding affinity prediction of 1000 nM between the peptide YEMFNDKSF (SEQ ID NO: 62) and the class I allele HLA-A*01:01. Few peptides with IC50>1000 nm are presented by the MHC, and lower IC50 values increase the probability of presentation. Presentation information 165 may include a binding affinity prediction between the peptide KNFLENFIESOFI (SEQ ID NO: 67) and the class II allele HLA-DRB1:11:01.

Allele-interacting information can also include measurements or predictions of stability of the MHC complex. One or more stability models that can generate such predictions. More stable peptide-MHC complexes (i.e., complexes with longer half-lives) are more likely to be presented at high copy number on tumor cells and on antigen-presenting cells that encounter vaccine antigen. For example, going back to the example shown in FIG. 2C, presentation information 165 may include a stability prediction of a half-life of 1 h for the class I molecule HLA-A*01:01. Presentation information 165 may also include a stability prediction of a half-life for the class II molecule HLA-DRB1:11:01.

Allele-interacting information can also include the measured or predicted rate of the formation reaction for the peptide-MHC complex. Complexes that form at a higher rate are more likely to be presented on the cell surface at high concentration.

Figure 5:
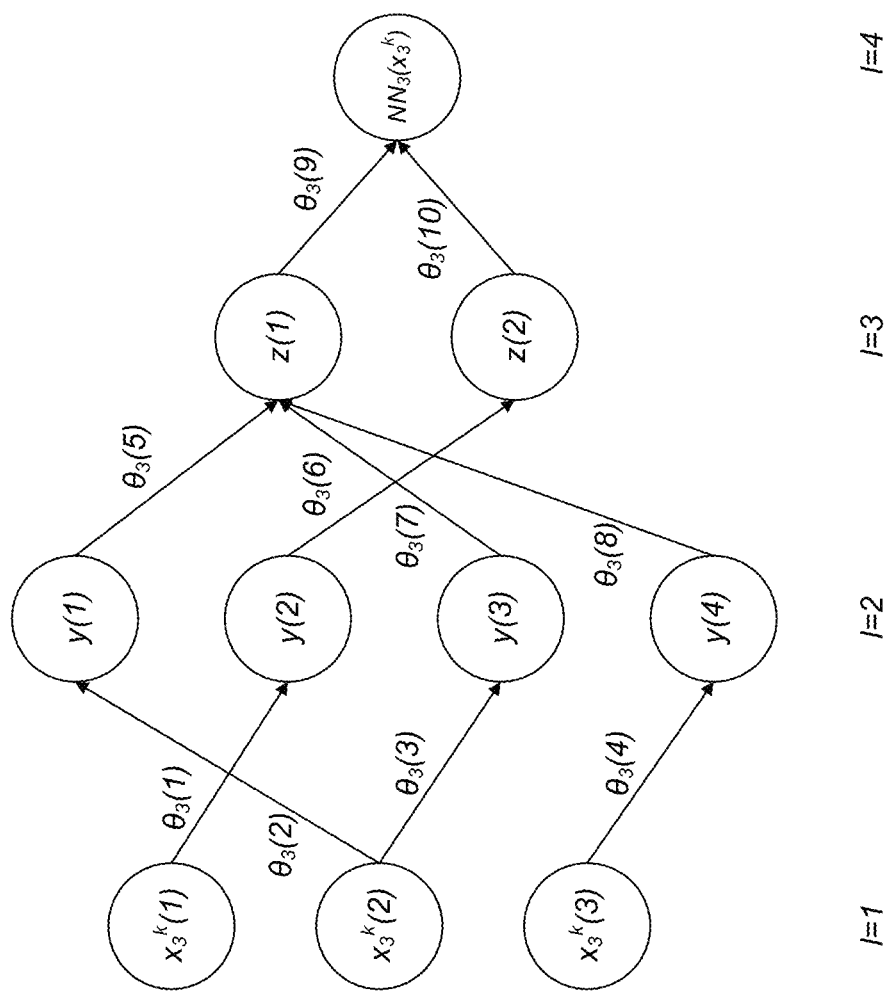
FIG. 5 illustrates an example network model in association with an MHC allele.

Allele-interacting information can also include the sequence and length of the peptide. MHC class I molecules typically prefer to present peptides with lengths between 8 and 15 peptides. 60-80% of presented peptides have length 9. Histograms of presented peptide lengths from several cell lines are shown in FIG. 5. MHC class II molecules typically prefer to present peptides with lengths between 6-30 peptides.

Allele-interacting information can also include the presence of kinase sequence motifs on the neoantigen encoded peptide, and the absence or presence of specific post-translational modifications on the neoantigen encoded peptide. The presence of kinase motifs affects the probability of post-translational modification, which may enhance or interfere with MHC binding.

Allele-interacting information can also include the expression or activity levels of proteins involved in the process of post-translational modification, e.g., kinases (as measured or predicted from RNA seq, mass spectrometry, or other methods).

Allele-interacting information can also include the probability of presentation of peptides with similar sequence in cells from other individuals expressing the particular MHC allele as assessed by mass-spectrometry proteomics or other means.

Allele-interacting information can also include the expression levels of the particular MHC allele in the individual in question (e.g. as measured by RNA-seq or mass spectrometry). Peptides that bind most strongly to an MHC allele that is expressed at high levels are more likely to be presented than peptides that bind most strongly to an MHC allele that is expressed at a low level.

Allele-interacting information can also include the overall neoantigen encoded peptide-sequence-independent probability of presentation by the particular MHC allele in other individuals who express the particular MHC allele.

Allele-interacting information can also include the overall peptide-sequence-independent probability of presentation by MHC alleles in the same family of molecules (e.g., HLA-A, HLA-B, HLA-C, HLA-DQ, HLA-DR, HLA-DP) in other individuals. For example, HLA-C molecules are typically expressed at lower levels than HLA-A or HLA-B molecules, and consequently, presentation of a peptide by HLA-C is a priori less probable than presentation by HLA-A or HLA-B. For another example, HLA-DP is typically expressed at lower levels than HLA-DR or HLA-DQ; consequently, presentation of a peptide by HLA-DP is a prior less probable than presentation by HLA-DR or HLA-DQ.

Allele-interacting information can also include the protein sequence of the particular MHC allele.

Any MHC allele-noninteracting information listed in the below section can also be modeled as an MHC allele-interacting information.

IX.B.2. Allele-noninteracting Information

Allele-noninteracting information can include C-terminal sequences flanking the neoantigen encoded peptide within its source protein sequence. For MHC-I, C-terminal flanking sequences may impact proteasomal processing of peptides. However, the C-terminal flanking sequence is cleaved from the peptide by the proteasome before the peptide is transported to the endoplasmic reticulum and encounters MHC alleles on the surfaces of cells. Consequently, MHC molecules receive no information about the C-terminal flanking sequence, and thus, the effect of the C-terminal flanking sequence cannot vary depending on MHC allele type. For example, going back to the example shown in FIG. 2C, presentation information 165 may include the C-terminal flanking sequence FOEIFNDKSLDKFJI (SEQ ID NO: 69) of the presented peptide FJIEJFOESS (SEQ ID NO: 64) identified from the source protein of the peptide.

Allele-noninteracting information can also include mRNA quantification measurements. For example, mRNA quantification data can be obtained for the same samples that provide the mass spectrometry training data. As later described in reference to FIG. 13H, RNA expression was identified to be a strong predictor of peptide presentation. In one embodiment, the mRNA quantification measurements are identified from software tool RSEM. Detailed implementation of the RSEM software tool can be found at Bo Li and Colin N. Dewey. *RSEM: accurate transcript quantification from RNA-Seq data with or without a reference genome*. BMC Bioinformatics, 12:323, August 2011. In one embodiment, the mRNA quantification is measured in units of fragments per kilobase of transcript per Million mapped reads (FPKM).

Allele-noninteracting information can also include the N-terminal sequences flanking the peptide within its source protein sequence.

Allele-noninteracting information can also include the source gene of the peptide sequence. The source gene may be defined as the Ensembl protein family of the peptide sequence. In other examples, the source gene may be defined as the source DNA or the source RNA of the peptide sequence. The source gene can, for example, be represented as a string of nucleotides that encode for a protein, or alternatively be more categorically represented based on a named set of known DNA or RNA sequences that are known to encode specific proteins. In another example, allele-noninteracting information can also include the source transcript or isoform or set of potential source transcripts or isoforms of the peptide sequence drawn from a database such as Ensembl or RefSeq.

Allele-noninteracting information can also include the presence of protease cleavage motifs in the peptide, optionally weighted according to the expression of corresponding proteases in the tumor cells (as measured by RNA-seq or mass spectrometry). Peptides that contain protease cleavage motifs are less likely to be presented, because they will be more readily degraded by proteases, and will therefore be less stable within the cell.

Allele-noninteracting information can also include the turnover rate of the source protein as measured in the appropriate cell type. Faster turnover rate (i.e., lower half-life) increases the probability of presentation; however, the predictive power of this feature is low if measured in a dissimilar cell type.

Allele-noninteracting information can also include the length of the source protein, optionally considering the specific splice variants ("isoforms") most highly expressed in the tumor cells as measured by RNA-seq or proteome mass spectrometry, or as predicted from the annotation of germline or somatic splicing mutations detected in DNA or RNA sequence data.

Allele-noninteracting information can also include the level of expression of the proteasome, immunoproteasome, thymoproteasome, or other proteases in the tumor cells (which may be measured by RNA-seq, proteome mass spectrometry, or immunohistochemistry). Different proteasomes have different cleavage site preferences. More weight will be given to the cleavage preferences of each type of proteasome in proportion to its expression level.

Allele-noninteracting information can also include the expression of the source gene of the peptide (e.g., as measured by RNA-seq or mass spectrometry). Possible optimizations include adjusting the measured expression to account for the presence of stromal cells and tumor-infiltrating lymphocytes within the tumor sample. Peptides from more highly expressed genes are more likely to be presented. Peptides from genes with undetectable levels of expression can be excluded from consideration.

Allele-noninteracting information can also include the probability that the source mRNA of the neoantigen encoded peptide will be subject to nonsense-mediated decay as predicted by a model of nonsense-mediated decay, for example, the model from Rivas et al, Science 2015.

Allele-noninteracting information can also include the typical tissue-specific expression of the source gene of the peptide during various stages of the cell cycle. Genes that are expressed at a low level overall (as measured by RNA-seq or mass spectrometry proteomics) but that are known to be expressed at a high level during specific stages of the cell cycle are likely to produce more presented peptides than genes that are stably expressed at very low levels.

Allele-noninteracting information can also include a comprehensive catalog of features of the source protein as given in e.g. uniProt or PDB http://www.rcsb.org/pdb/home/home.do. These features may include, among others: the secondary and tertiary structures of the protein, subcellular localization 11, Gene ontology (GO) terms. Specifically, this information may contain annotations that act at the level of the protein, e.g., 5' UTR length, and annotations that act at the level of specific residues, e.g., helix motif between residues 300 and 310. These features can also include turn motifs, sheet motifs, and disordered residues.

Allele-noninteracting information can also include features describing the properties of the domain of the source protein containing the peptide, for example: secondary or tertiary structure (e.g., alpha helix vs beta sheet); Alternative splicing.

Allele-noninteracting information can also include features describing the presence or absence of a presentation hotspot at the position of the peptide in the source protein of the peptide.

Allele-noninteracting information can also include the probability of presentation of peptides from the source protein of the peptide in question in other individuals (after adjusting for the expression level of the source protein in those individuals and the influence of the different HLA types of those individuals).

Allele-noninteracting information can also include the probability that the peptide will not be detected or over-represented by mass spectrometry due to technical biases.

The expression of various gene modules/pathways as measured by a gene expression assay such as RNASeq, microarray(s), targeted panel(s) such as Nanostring, or single/multi-gene representatives of gene modules measured by assays such as RT-PCR (which need not contain the source protein of the peptide) that are informative about the state of the tumor cells, stroma, or tumor-infiltrating lymphocytes (TILs).

Allele-noninteracting information can also include the copy number of the source gene of the peptide in the tumor cells. For example, peptides from genes that are subject to homozygous deletion in tumor cells can be assigned a probability of presentation of zero.

Allele-noninteracting information can also include the probability that the peptide binds to the TAP or the measured or predicted binding affinity of the peptide to the TAP. Peptides that are more likely to bind to the TAP, or peptides that bind the TAP with higher affinity are more likely to be presented by MHC-I.

Allele-noninteracting information can also include the expression level of TAP in the tumor cells (which may be measured by RNA-seq, proteome mass spectrometry, immunohistochemistry). For MHC-I, higher TAP expression levels increase the probability of presentation of all peptides.

Allele-noninteracting information can also include the presence or absence of tumor mutations, including, but not limited to:
 i. Driver mutations in known cancer driver genes such as EGFR, KRAS, ALK, RET, ROS1, TP53, CDKN2A, CDKN2B, NTRK1, NTRK2, NTRK3
 ii. In genes encoding the proteins involved in the antigen presentation machinery (e.g., B2M, HLA-A, HLA-B, HLA-C, TAP-1, TAP-2, TAPBP, CALR, CNX, ERP57, HLA-DM, HLA-DMA, HLA-DMB, HLA-DO, HLA-DOA, HLA-DOB, HLA-DP, HLA-DPA1, HLA-DPB1, HLA-DQ, HLA-DQA1, HLA-DQA2, HLA-DQB1, HLA-DQB2, HLA-DR, HLA-DRA, HLA-DRB1, HLA-DRB3, HLA-DRB4, HLA-DRB5 or any of the genes coding for components of the proteasome or immunoproteasome). Peptides whose presentation relies on a component of the antigen-presentation machinery that is subject to loss-of-function mutation in the tumor have reduced probability of presentation.

Presence or absence of functional germline polymorphisms, including, but not limited to:
 i. In genes encoding the proteins involved in the antigen presentation machinery (e.g., B2M, HLA-A, HLA-B, HLA-C, TAP-1, TAP-2, TAPBP, CALR, CNX, ERP57, HLA-DM, HLA-DMA, HLA-DMB, HLA-DO, HLA-DOA, HLA-DOB, HLA-DP, HLA-DPA1, HLA-DPB1, HLA-DQ, HLA-DQA1, HLA-DQA2, HLA-DQB1, HLA-DQB2, HLA-DR, HLA-DRA, HLA-DRB1, HLA-DRB3, HLA-DRB4, HLA-DRB5 or any of the genes coding for components of the proteasome or immunoproteasome)

Allele-noninteracting information can also include tumor type (e.g., NSCLC, melanoma).

Allele-noninteracting information can also include known functionality of HLA alleles, as reflected by, for instance HLA allele suffixes. For example, the N suffix in the allele name HLA-A*24:09N indicates a null allele that is not expressed and is therefore unlikely to present epitopes; the full HLA allele suffix nomenclature is described at https://www.ebi.ac.uk/ipd/imgt/hla/nomenclature/suffixes.html.

Allele-noninteracting information can also include clinical tumor subtype (e.g., squamous lung cancer vs. non-squamous).

Allele-noninteracting information can also include smoking history.

Allele-noninteracting information can also include history of sunburn, sun exposure, or exposure to other mutagens.

Allele-noninteracting information can also include the typical expression of the source gene of the peptide in the relevant tumor type or clinical subtype, optionally stratified by driver mutation. Genes that are typically expressed at high levels in the relevant tumor type are more likely to be presented.

Allele-noninteracting information can also include the frequency of the mutation in all tumors, or in tumors of the same type, or in tumors from individuals with at least one shared MHC allele, or in tumors of the same type in individuals with at least one shared MHC allele.

In the case of a mutated tumor-specific peptide, the list of features used to predict a probability of presentation may also include the annotation of the mutation (e.g., missense, read-through, frameshift, fusion, etc.) or whether the mutation is predicted to result in nonsense-mediated decay (NMD). For example, peptides from protein segments that are not translated in tumor cells due to homozygous early-stop mutations can be assigned a probability of presentation of zero. NMD results in decreased mRNA translation, which decreases the probability of presentation.

IX.C. Presentation Identification System

Figure 3:
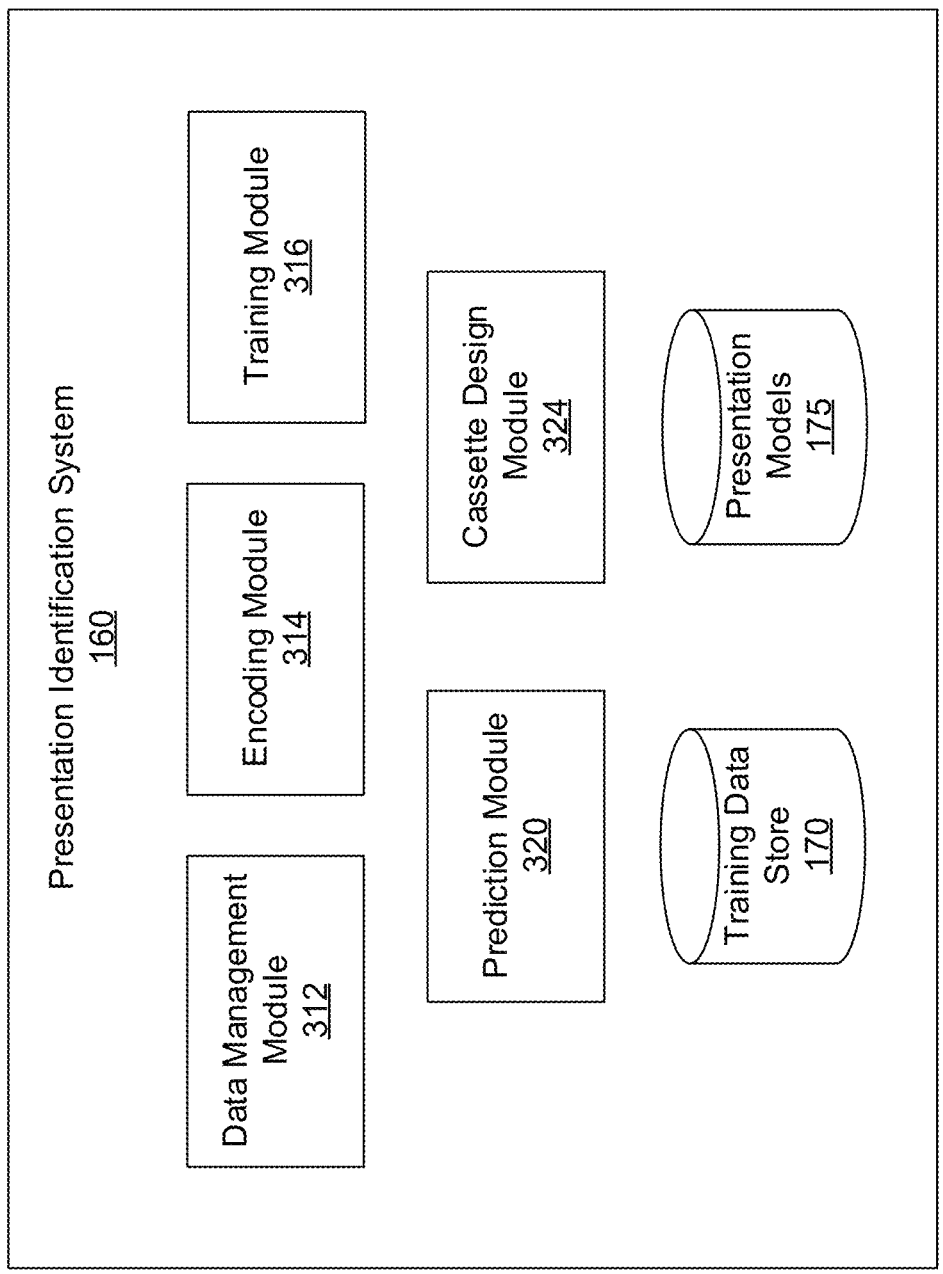
FIG. 3 is a high-level block diagram illustrating the computer logic components of the presentation identification system, according to one embodiment.

FIG. 3 is a high-level block diagram illustrating the computer logic components of the presentation identification system 160, according to one embodiment. In this example embodiment, the presentation identification system 160 includes a data management module 312, an encoding module 314, a training module 316, and a prediction module 320. The presentation identification system 160 is also comprised of a training data store 170 and a presentation models store 175. Some embodiments of the model management system 160 have different modules than those described here. Similarly, the functions can be distributed among the modules in a different manner than is described here.

IX.C.1. Data Management Module

The data management module 312 generates sets of training data 170 from the presentation information 165. Each set of training data contains a plurality of data instances, in which each data instance i contains a set of independent variables $z^i$ that include at least a presented or non-presented peptide sequence $p^i$, one or more associated MHC alleles $a^i$ associated with the peptide sequence $p^i$, and a dependent variable $y^i$ that represents information that the presentation identification system 160 is interested in predicting for new values of independent variables.

In one particular implementation referred throughout the remainder of the specification, the dependent variable $y^i$ is a binary label indicating whether peptide $p^i$ was presented by the one or more associated MHC alleles $a^i$. However, it is appreciated that in other implementations, the dependent variable $y^i$ can represent any other kind of information that the presentation identification system 160 is interested in predicting dependent on the independent variables $z^i$. For example, in another implementation, the dependent variable $y^i$ may also be a numerical value indicating the mass spectrometry ion current identified for the data instance.

The peptide sequence $p^i$ for data instance i is a sequence of $k_i$ amino acids, in which $k_i$ may vary between data instances i within a range. For example, that range may be 8-15 for MHC class I or 6-30 for MHC class II. In one specific implementation of system 160, all peptide sequences $p^i$ in a training data set may have the same length, e.g. 9. The number of amino acids in a peptide sequence may vary depending on the type of MHC alleles (e.g., MHC alleles in humans, etc.). The MHC alleles $a^i$ for data instance i indicate which MHC alleles were present in association with the corresponding peptide sequence $p^i$.

The data management module 312 may also include additional allele-interacting variables, such as binding affinity $b^i$ and stability $s^i$ predictions in conjunction with the peptide sequences $p^i$ and associated MHC alleles $a^i$ contained in the training data 170. For example, the training data 170 may contain binding affinity predictions $b^i$ between a peptide $p^i$ and each of the associated MHC molecules indicated in $a^i$. As another example, the training data 170 may contain stability predictions $s^i$ for each of the MHC alleles indicated in $a^i$.

The data management module 312 may also include allele-noninteracting variables $w^i$, such as C-terminal flanking sequences and mRNA quantification measurements in conjunction with the peptide sequences $p^i$.

The data management module 312 also identifies peptide sequences that are not presented by MHC alleles to generate the training data 170. Generally, this involves identifying the "longer" sequences of source protein that include presented peptide sequences prior to presentation. When the presentation information contains engineered cell lines, the data management module 312 identifies a series of peptide sequences in the synthetic protein to which the cells were exposed to that were not presented on MHC alleles of the cells. When the presentation information contains tissue samples, the data management module 312 identifies source proteins from which presented peptide sequences originated from, and identifies a series of peptide sequences in the source protein that were not presented on MHC alleles of the tissue sample cells.

The data management module 312 may also artificially generate peptides with random sequences of amino acids and identify the generated sequences as peptides not presented on MHC alleles. This can be accomplished by randomly generating peptide sequences allows the data management module 312 to easily generate large amounts of synthetic data for peptides not presented on MHC alleles. Since in reality, a small percentage of peptide sequences are presented by MHC alleles, the synthetically generated peptide sequences are highly likely not to have been presented by MHC alleles even if they were included in proteins processed by cells.

FIG. 4A illustrates an example set of training data 170A, according to one embodiment. Specifically, the first 3 data instances in the training data 170A indicate peptide presentation information from a single-allele cell line involving the allele HLA-C*01:03 and 3 peptide sequences QCEIOWARE (SEQ ID NO: 70), FIEUHFWI (SEQ ID NO: 71), and FEWRHRJTRUJR (SEQ ID NO: 72). The fourth data instance in the training data 170A indicates peptide information from a multiple-allele cell line involving the alleles HLA-B*07:02, HLA-C*01:03, HLA-A*01:01 and a peptide sequence QIEJOEIJE (SEQ ID NO: 73). The first data instance indicates that peptide sequence QCEIOWARE (SEQ ID NO: 70) was not presented by the allele HLA-C*01:03. As discussed in the prior two paragraphs, the peptide sequence may be randomly generated by the data management module 312 or identified from source protein of presented peptides. The training data 170A also includes a binding affinity prediction of 1000 nM and a stability prediction of a half-life of 1 h for the peptide sequence-allele pair. The training data 170A also includes allele-noninteracting variables, such as the C-terminal flanking sequence of the peptide FJELFISBOSJFIE (SEQ ID NO: 74), and a mRNA quantification measurement of $10^2$ TPM. The fourth data instance indicates that peptide sequence QIEJOEIJE (SEQ ID NO: 73) was presented by one of the alleles HLA-B*07:02, HLA-C*01:03, or HLA-A*01:01. The training data 170A also includes binding affinity predictions and stability predictions for each of the alleles, as well as the C-terminal flanking sequence of the peptide and the mRNA quantification measurement for the peptide.

FIG. 4B illustrates another example set of training data 170A, according to one embodiment. Specifically, the first data instances in the training data 170A indicate peptide presentation information from a single-allele cell line involving the class II allele HLA-DRB3:01:01 and the peptide sequence QCEIOWAREFLKEIGJ (SEQ ID NO: 75). The first data instance indicates that peptide sequence QCEIOWAREFLKEIGJ (SEQ ID NO: 75) was not presented by the allele HLA-DRB3:01:01.

IX.C.2. Encoding Module

The encoding module 314 encodes information contained in the training data 170 into a numerical representation that can be used to generate the one or more presentation models. In one implementation, the encoding module 314 one-hot encodes sequences (e.g., peptide sequences or C-terminal flanking sequences) over a predetermined 20-letter amino acid alphabet. Specifically, a peptide sequence $p^i$ with $k_i$ amino acids is represented as a row vector of $20 \cdot k_i$ elements, where a single element among $p^i_{20 \cdot (j-1)+1}$, $p^i_{20 \cdot (j-1)+2}$, ..., $p^i_{20 \cdot j}$ that corresponds to the alphabet of the amino acid at the j-th position of the peptide sequence has a value of 1. Otherwise, the remaining elements have a value of 0. As an example, for a given alphabet {A, C, D, E, F, G, H, I, K, L, M, N, P, Q, R, S, T, V, W, Y}, the peptide sequence EAF of 3 amino acids for data instance i may be represented by the row vector of 60 elements $p^i$=[0 0 0 1 0 0 0 0 0 0 0 0 0 0 0 0 0 0 0 0 1 0 0 0 0 0 0 0 0 0 0 0 0 0 0 0 0 0 0 0 0 0 0 0 0 1 0 0 0 0 0 0 0 0 0 0 0 0 0 0]. The C-terminal flanking sequence $c^i$ can be similarly encoded as described above, as well as the protein sequence $d_h$ for MHC alleles, and other sequence data in the presentation information.

When the training data 170 contains sequences of differing lengths of amino acids, the encoding module 314 may further encode the peptides into equal-length vectors by adding a PAD character to extend the predetermined alphabet. For example, this may be performed by left-padding the peptide sequences with the PAD character until the length of the peptide sequence reaches the peptide sequence with the greatest length in the training data 170. Thus, when the peptide sequence with the greatest length has $k_{max}$ amino acids, the encoding module 314 numerically represents each sequence as a row vector of $(20+1) \cdot k_{max}$ elements. As an example, for the extended alphabet {PAD, A, C, D, E, F, G, H, I, K, L, M, N, P, Q, R, S, T, V, W, Y} and a maximum amino acid length of $k_{max}=5$, the same example peptide sequence EAF of 3 amino acids may be represented by the row vector of 105 elements $p^i$=[0 0 0 0 0 0 0 0 0 0 0 0 0 0 0 0 0 0 0 0 0 1 0 0 0 0 0 0 0 0 0 0 0 0 0 0 0 0 0 0 0 0 0 1 0 0 0 0 0 0 0 0 0 0 0 0 0 0 0 0 0 1 0 0 0 0 0 0 0 0 0 0 0 0 0 0 0 0 0 0 0 0 0 0 0 0 0 1 0 0 0 0 0 0 0 0 0 0 0 0 0 0 0 0 0]. The C-terminal flanking sequence $c^i$ or other sequence data can be similarly encoded as described above. Thus, each independent variable or column in the peptide sequence $p^i$ or $c^j$ represents presence of a particular amino acid at a particular position of the sequence.

Although the above method of encoding sequence data was described in reference to sequences having amino acid sequences, the method can similarly be extended to other types of sequence data, such as DNA or RNA sequence data, and the like.

The encoding module 314 also encodes the one or more MHC alleles $a^i$ for data instance i as a row vector of m elements, in which each element h=1, 2, ..., m corresponds to a unique identified MHC allele. The elements corresponding to the MHC alleles identified for the data instance i have a value of 1. Otherwise, the remaining elements have a value of 0. As an example, the alleles HLA-B*07:02 and HLA-C*01:03 for a data instance i corresponding to a multiple-allele cell line among m=4 unique identified MHC allele types {HLA-A*01:01, HLA-C*01:08, HLA-B*07:02, HLA-C*01:03} may be represented by the row vector of 4 elements $a^i$=[0 0 1 1], in which $a_3^i$=1 and $a_4^i$=1. As another example, the elements corresponding to the MHC alleles identified for the data instance i have a value of 1. Otherwise, the remaining elements have a value of 0. As an example, the alleles HLA-B*07:02 and HLA-DRB1*10:01 for a data instance i corresponding to a multiple-allele cell line among m=4 unique identified MHC allele types {HLA-A*01:01, HLA-C*01:08, HLA-B*07:02, HLA-DRB1*10:01} may be represented by the row vector of 4 elements $a^i$=[0 0 1 1], in which $a_3^i$=1 and $a_4^i$=1. Although the examples described herein with 4 identified MHC allele types, the number of MHC allele types can be hundreds or thousands in practice. As previously discussed, each data instance i typically contains at most 6 different MHC class I allele types in association with the peptide sequence $p_i$, and/or at most 4 different MHC class II DR allele types in association with the peptide sequence $p_i$, and/or at most 12 different MHC class II allele types in association with the peptide sequence $p_i$.

The encoding module 314 also encodes the label $y_i$ for each data instance i as a binary variable having values from the set of {0, 1}, in which a value of 1 indicates that peptide $x^i$ was presented by one of the associated MHC alleles $a^i$, and a value of 0 indicates that peptide $x^i$ was not presented by any of the associated MHC alleles $a^i$. When the dependent variable $y_i$ represents the mass spectrometry ion current, the encoding module 314 may additionally scale the values using various functions, such as the log function having a range of $[-\infty, \infty]$ for ion current values between $[0, \infty]$.

The encoding module 314 may represent a pair of allele-interacting variables $x_h^i$ for peptide $p_i$ and an associated MHC allele h as a row vector in which numerical representations of allele-interacting variables are concatenated one after the other. For example, the encoding module 314 may represent $x_h^i$ as a row vector equal to $[p^i]$, $[p^i\ b_h^i]$, $[p^i\ s_h^i]$, or $[p^i\ b_h^i\ s_h^i]$, where $b_h^i$ is the binding affinity prediction for peptide $p_i$ and associated MHC allele h, and similarly for $s_h^i$ for stability. Alternatively, one or more combination of allele-interacting variables may be stored individually (e.g., as individual vectors or matrices).

In one instance, the encoding module 314 represents binding affinity information by incorporating measured or predicted values for binding affinity in the allele-interacting variables $x_h^i$.

In one instance, the encoding module 314 represents binding stability information by incorporating measured or predicted values for binding stability in the allele-interacting variables $x_h^i$.

In one instance, the encoding module 314 represents binding on-rate information by incorporating measured or predicted values for binding on-rate in the allele-interacting variables $x_h^i$.

In one instance, for peptides presented by class I MHC molecules, the encoding module 314 represents peptide length as a vector $T_k = [\mathbb{1}(L_k=8)\ \mathbb{1}(L_k=9)\ \mathbb{1}(L_k=10)\ \mathbb{1}(L_k=11)\ \mathbb{1}(L_k=12)\ \mathbb{1}(L_k=13)\ \mathbb{1}(L_k=14)\ \mathbb{1}(L_k=15)]$ where $\mathbb{1}$ is the indicator function, and $L_k$ denotes the length of peptide $p_k$. The vector $T_k$ can be included in the allele-interacting variables $x_h^i$. In another instance, for peptides presented by class II MHC molecules, the encoding module 314 represents peptide length as a vector $T_k = [\mathbb{1}(L_k=6)\ \mathbb{1}(L_k=7)\ \mathbb{1}(L_k=8)\ \mathbb{1}(L_k=9)\ \mathbb{1}(L_k=10)\ \mathbb{1}(L_k=11)\ \mathbb{1}(L_k=12)\ \mathbb{1}(L_k=13)\ \mathbb{1}(L_k=14)\ \mathbb{1}(L_k=15)\ \mathbb{1}(L_k=16)\ \mathbb{1}(L_k=17)\ \mathbb{1}(L_k=18)\ \mathbb{1}(L_k=19)\ \mathbb{1}(L_k=20)\ \mathbb{1}(L_k=21)\ \mathbb{1}(L_k=22)\ \mathbb{1}(L_k=23)\ \mathbb{1}(L_k=24)\ \mathbb{1}(L_k=25)\ \mathbb{1}(L_k=26)\ \mathbb{1}(L_k=27)\ \mathbb{1}(L_k=28)\ \mathbb{1}(L_k=29)\ \mathbb{1}(L_k=30)]$ where $\mathbb{1}$ is the indicator function, and $L_k$ denotes the length of peptide $p_k$. The vector $T_k$ can be included in the allele-interacting variables $x_h^i$.

In one instance, the encoding module 314 represents RNA expression information of MHC alleles by incorporating RNA-seq based expression levels of MHC alleles in the allele-interacting variables $x_h^i$.

Similarly, the encoding module 314 may represent the allele-noninteracting variables $w^i$ as a row vector in which numerical representations of allele-noninteracting variables are concatenated one after the other. For example, $w^i$ may be a row vector equal to $[c^i]$ or $[c^i\ m^i\ w^i]$ in which $w^i$ is a row vector representing any other allele-noninteracting variables in addition to the C-terminal flanking sequence of peptide $p^i$ and the mRNA quantification measurement $m^i$ associated with the peptide. Alternatively, one or more combination of allele-noninteracting variables may be stored individually (e.g., as individual vectors or matrices).

In one instance, the encoding module 314 represents turnover rate of source protein for a peptide sequence by incorporating the turnover rate or half-life in the allele-noninteracting variables $w^i$.

In one instance, the encoding module 314 represents length of source protein or isoform by incorporating the protein length in the allele-noninteracting variables $w^i$.

In one instance, the encoding module 314 represents activation of immunoproteasome by incorporating the mean expression of the immunoproteasome-specific proteasome subunits including the $\beta 1_i$, $\beta 2_i$, $\beta 5_i$ subunits in the allele-noninteracting variables $w^i$.

In one instance, the encoding module 314 represents the RNA-seq abundance of the source protein of the peptide or gene or transcript of a peptide (quantified in units of FPKM, TPM by techniques such as RSEM) can be incorporating the abundance of the source protein in the allele-noninteracting variables $w^i$.

In one instance, the encoding module 314 represents the probability that the transcript of origin of a peptide will undergo nonsense-mediated decay (NMD) as estimated by the model in, for example, Rivas et. al. *Science,* 2015 by incorporating this probability in the allele-noninteracting variables $w^i$.

In one instance, the encoding module 314 represents the activation status of a gene module or pathway assessed via RNA-seq by, for example, quantifying expression of the genes in the pathway in units of TPM using e.g., RSEM for each of the genes in the pathway then computing a summary statistics, e.g., the mean, across genes in the pathway. The mean can be incorporated in the allele-noninteracting variables $w^i$.

In one instance, the encoding module 314 represents the copy number of the source gene by incorporating the copy number in the allele-noninteracting variables $w^i$.

In one instance, the encoding module 314 represents the TAP binding affinity by including the measured or predicted TAP binding affinity (e.g., in nanomolar units) in the allele-noninteracting variables $w^i$.

In one instance, the encoding module 314 represents TAP expression levels by including TAP expression levels measured by RNA-seq (and quantified in units of TPM by e.g., RSEM) in the allele-noninteracting variables $w^i$.

In one instance, the encoding module 314 represents tumor mutations as a vector of indicator variables (i.e., $d^k=1$ if peptide $p^k$ comes from a sample with a KRAS G12D mutation and 0 otherwise) in the allele-noninteracting variables $w^i$.

In one instance, the encoding module 314 represents germline polymorphisms in antigen presentation genes as a vector of indicator variables (i.e., $d^k=1$ if peptide $p^k$ comes from a sample with a specific germline polymorphism in the TAP). These indicator variables can be included in the allele-noninteracting variables $w^i$.

In one instance, the encoding module 314 represents tumor type as a length-one one-hot encoded vector over the alphabet of tumor types (e.g., NSCLC, melanoma, colorectal cancer, etc). These one-hot-encoded variables can be included in the allele-noninteracting variables $w^i$.

In one instance, the encoding module 314 represents MHC allele suffixes by treating 4-digit HLA alleles with different suffixes. For example, HLA-A*24:09N is considered a different allele from HLA-A*24:09 for the purpose of the model. Alternatively, the probability of presentation by an N-suffixed MHC allele can be set to zero for all peptides, because HLA alleles ending in the N suffix are not expressed.

In one instance, the encoding module 314 represents tumor subtype as a length-one one-hot encoded vector over the alphabet of tumor subtypes (e.g., lung adenocarcinoma, lung squamous cell carcinoma, etc). These one hot-encoded variables can be included in the allele-noninteracting variables $w^i$.

In one instance, the encoding module 314 represents smoking history as a binary indicator variable ($d^k=1$ if the patient has a smoking history, and 0 otherwise), that can be included in the allele-noninteracting variables $w^i$. Alternatively, smoking history can be encoded as a length-one one-hot-encoded variable over an alphabet of smoking severity. For example, smoking status can be rated on a 1-5 scale, where 1 indicates nonsmokers, and 5 indicates current heavy smokers. Because smoking history is primarily relevant to lung tumors, when training a model on multiple tumor types, this variable can also be defined to be equal to 1 if the patient has a history of smoking and the tumor type is lung tumors and zero otherwise.

In one instance, the encoding module 314 represents sunburn history as a binary indicator variable ($d^k=1$ if the patient has a history of severe sunburn, and 0 otherwise), which can be included in the allele-noninteracting variables $w^i$. Because severe sunburn is primarily relevant to melanomas, when training a model on multiple tumor types, this variable can also be defined to be equal to 1 if the patient has a history of severe sunburn and the tumor type is melanoma and zero otherwise.

In one instance, the encoding module 314 represents distribution of expression levels of a particular gene or transcript for each gene or transcript in the human genome as summary statistics (e,g., mean, median) of distribution of expression levels by using reference databases such as TCGA. Specifically, for a peptide $p^k$ in a sample with tumor type melanoma, we can include not only the measured gene or transcript expression level of the gene or transcript of origin of peptide $p^k$ in the allele-noninteracting variables $w^i$, but also the mean and/or median gene or transcript expression of the gene or transcript of origin of peptide $p^k$ in melanomas as measured by TCGA.

In one instance, the encoding module 314 represents mutation type as a length-one one-hot-encoded variable over the alphabet of mutation types (e.g., missense, frameshift, NMD-inducing, etc). These one hot-encoded variables can be included in the allele-noninteracting variables $w^i$.

In one instance, the encoding module 314 represents protein-level features of protein as the value of the annotation (e.g., 5' UTR length) of the source protein in the allele-noninteracting variables $w^i$. In another instance, the encoding module 314 represents residue-level annotations of the source protein for peptide $p^i$ by including an indicator variable, that is equal to 1 if peptide $p^i$ overlaps with a helix motif and 0 otherwise, or that is equal to 1 if peptide $p^i$ is completely contained with within a helix motif in the allele-noninteracting variables $w^i$. In another instance, a feature representing proportion of residues in peptide $p^i$ that are contained within a helix motif annotation can be included in the allele-noninteracting variables $w^i$.

In one instance, the encoding module 314 represents type of proteins or isoforms in the human proteome as an indicator vector $o^k$ that has a length equal to the number of proteins or isoforms in the human proteome, and the corresponding element $o^k_i$ is 1 if peptide, comes from protein i and 0 otherwise.

In one instance, the encoding module 314 represents the source gene $G=\text{gene}(p^i)$ of peptide $p^i$ as a categorical variable with L possible categories, where L denotes the upper limit of the number of indexed source genes 1, 2, . . . , L.

The encoding module 314 may also represent the overall set of variables $z^i$ for peptide $p^i$ and an associated MHC allele h as a row vector in which numerical representations of the allele-interacting variables $x^i$ and the allele-noninteracting variables $w^i$ are concatenated one after the other. For example, the encoding module 314 may represent $z_h^i$ as a row vector equal to $[x_h^i\ w^i]$ or $[w_i\ x_h^i]$.

X. Training Module

The training module 316 constructs one or more presentation models that generate likelihoods of whether peptide sequences will be presented by MHC alleles associated with the peptide sequences. Specifically, given a peptide sequence $p^k$ and a set of MHC alleles $a^k$ associated with the peptide sequence $p^k$, each presentation model generates an estimate $u_k$ indicating a likelihood that the peptide sequence $p^k$ will be presented by one or more of the associated MHC alleles $a^k$.

X.A. Overview

The training module 316 constructs the one more presentation models based on the training data sets stored in store 170 generated from the presentation information stored in 165. Generally, regardless of the specific type of presentation model, all of the presentation models capture the dependence between independent variables and dependent variables in the training data 170 such that a loss function is minimized. Specifically, the loss function $l(y_{i \in S}, u_{i \in S}, \theta)$ represents discrepancies between values of dependent variables $y_{i \in S}$ for one or more data instances S in the training data 170 and the estimated likelihoods $u_{i \in S}$ for the data instances S generated by the presentation model. In one particular implementation referred throughout the remainder of the specification, the loss function $(y_{i \in S}, u_{i \in S}, \theta)$ is the negative log likelihood function given by equation (1a) as follows:

$$\ell(y_{i \in S}, u_{i \in S}; \theta) = \sum_{i \in S}(y_i \log u_i + (1-y_i)\log(1-u_i)). \quad (1a)$$

However, in practice, another loss function may be used. For example, when predictions are made for the mass spectrometry ion current, the loss function is the mean squared loss given by equation 1b as follows:

$$\ell(y_{i \in S}, u_{i \in S}; \theta) = \sum_{i \in S}(\|y_i - u_i\|_2^2). \quad (1b)$$

The presentation model may be a parametric model in which one or more parameters $\theta$ mathematically specify the dependence between the independent variables and dependent variables. Typically, various parameters of parametric-type presentation models that minimize the loss function $(y_{i \in S}, u_{i \in S}, \theta)$ are determined through gradient-based numerical optimization algorithms, such as batch gradient algorithms, stochastic gradient algorithms, and the like. Alternatively, the presentation model may be a non-parametric model in which the model structure is determined from the training data 170 and is not strictly based on a fixed set of parameters.

X.B. Per-Allele Models

The training module 316 may construct the presentation models to predict presentation likelihoods of peptides on a per-allele basis. In this case, the training module 316 may train the presentation models based on data instances S in the training data 170 generated from cells expressing single MHC alleles.

In one implementation, the training module 316 models the estimated presentation likelihood $u_k$ for peptide, for a specific allele h by:

$$u_k^h = Pr(p^k\ \text{presented; MHC allele}\ h) = f(g_h(x_h^k; \theta_h)), \quad (2)$$

where peptide sequence $x_h^k$ denotes the encoded allele-interacting variables for peptide $p^k$ and corresponding MHC allele h, $f(\cdot)$ is any function, and is herein throughout is referred to as a transformation function for convenience of description. Further, $g_h(\cdot)$ is any function, is herein throughout referred to as a dependency function for convenience of description, and generates dependency scores for the allele-interacting variables $x_h^k$ based on a set of parameters $\theta_h$ determined for MHC allele h. The values for the set of parameters $\theta_h$ for each MHC allele h can be determined by minimizing the loss function with respect to $\theta_h$, where i is each instance in the subset S of training data 170 generated from cells expressing the single MHC allele h.

The output of the dependency function $g_h(x_h^k; \theta_h)$ represents a dependency score for the MHC allele h indicating whether the MHC allele h will present the corresponding neoantigen based on at least the allele interacting features $x_h^k$, and in particular, based on positions of amino acids of the peptide sequence of peptide $p^k$. For example, the dependency score for the MHC allele h may have a high value if the MHC allele h is likely to present the peptide $p^k$, and may have a low value if presentation is not likely. The transformation function $f(\cdot)$ transforms the input, and more specifically, transforms the dependency score generated by $g_h(x_h^k; \theta_h)$ in this case, to an appropriate value to indicate the likelihood that the peptide $p^k$ will be presented by an MHC allele.

In one particular implementation referred throughout the remainder of the specification, $f(\cdot)$ is a function having the range within [0, 1] for an appropriate domain range. In one example, $f(\cdot)$ is the expit function given by:

$$f(z) = \frac{\exp(z)}{1+\exp(z)}. \quad (4)$$

As another example, $f(\cdot)$ can also be the hyperbolic tangent function given by:

$$f(z) = \tanh(z) \quad (5)$$

when the values for the domain z is equal to or greater than 0. Alternatively, when predictions are made for the mass spectrometry ion current that have values outside the range [0, 1], $f(\cdot)$ can be any function such as the identity function, the exponential function, the log function, and the like.

Thus, the per-allele likelihood that a peptide sequence $p^k$ will be presented by a MHC allele h can be generated by applying the dependency function $g_h(\cdot)$ for the MHC allele h to the encoded version of the peptide sequence $p^k$ to generate the corresponding dependency score. The dependency score may be transformed by the transformation function $f(\cdot)$ to generate a per-allele likelihood that the peptide sequence $p^k$ will be presented by the MHC allele h.

X.B.1 Dependency Functions for Allele Interacting Variables

In one particular implementation referred throughout the specification, the dependency function $g_h(\cdot)$ is an affine function given by:

$$g_h(x_h^i; \theta_h) = x_h^i \cdot \theta_h. \quad (6)$$

that linearly combines each allele-interacting variable in $x_h^k$ with a corresponding parameter in the set of parameters $\theta_h$ determined for the associated MHC allele.

In another particular implementation referred throughout the specification, the dependency function $g_h(\cdot)$ is a network function given by:

$$g_h(x_h^i;\theta_h)=NN_h(x_h^i;\theta_h). \qquad (7)$$

represented by a network model $NN_h(\cdot)$ having a series of nodes arranged in one or more layers. A node may be connected to other nodes through connections each having an associated parameter in the set of parameters $\theta_h$. A value at one particular node may be represented as a sum of the values of nodes connected to the particular node weighted by the associated parameter mapped by an activation function associated with the particular node. In contrast to the affine function, network models are advantageous because the presentation model can incorporate non-linearity and process data having different lengths of amino acid sequences. Specifically, through non-linear modeling, network models can capture interaction between amino acids at different positions in a peptide sequence and how this interaction affects peptide presentation.

In general, network models $NN_h(\cdot)$ may be structured as feed-forward networks, such as artificial neural networks (ANN), convolutional neural networks (CNN), deep neural networks (DNN), and/or recurrent networks, such as long short-term memory networks (LSTM), bi-directional recurrent networks, deep bi-directional recurrent networks, and the like.

In one instance referred throughout the remainder of the specification, each MHC allele in h=1, 2, . . . , m is associated with a separate network model, and $NN_h(\cdot)$ denotes the output(s) from a network model associated with MHC allele h.

FIG. 5 illustrates an example network model $NN_3(\cdot)$ in association with an arbitrary MHC allele h=3. As shown in FIG. 5, the network model $NN_3(\cdot)$ for MHC allele h=3 includes three input nodes at layer l=1, four nodes at layer l=2, two nodes at layer l=3, and one output node at layer l=4. The network model $NN_3(\cdot)$ is associated with a set of ten parameters $\theta_3(1), \theta_3(2), \ldots, \theta_3(10)$. The network model $NN_3(\cdot)$ receives input values (individual data instances including encoded polypeptide sequence data and any other training data used) for three allele-interacting variables $x_3^k(1), x_3^k(2),$ and $x_3^k(3)$ for MHC allele h=3 and outputs the value $NN_3(x_3^k)$. The network function may also include one or more network models each taking different allele interacting variables as input.

In another instance, the identified MHC alleles h=1, 2, . . . , m are associated with a single network model $NN_H(\cdot)$, and $NN_h(\cdot)$ denotes one or more outputs of the single network model associated with MHC allele h. In such an instance, the set of parameters $\theta_h$ may correspond to a set of parameters for the single network model, and thus, the set of parameters $\theta_h$ may be shared by all MHC alleles.

Figure 6A:
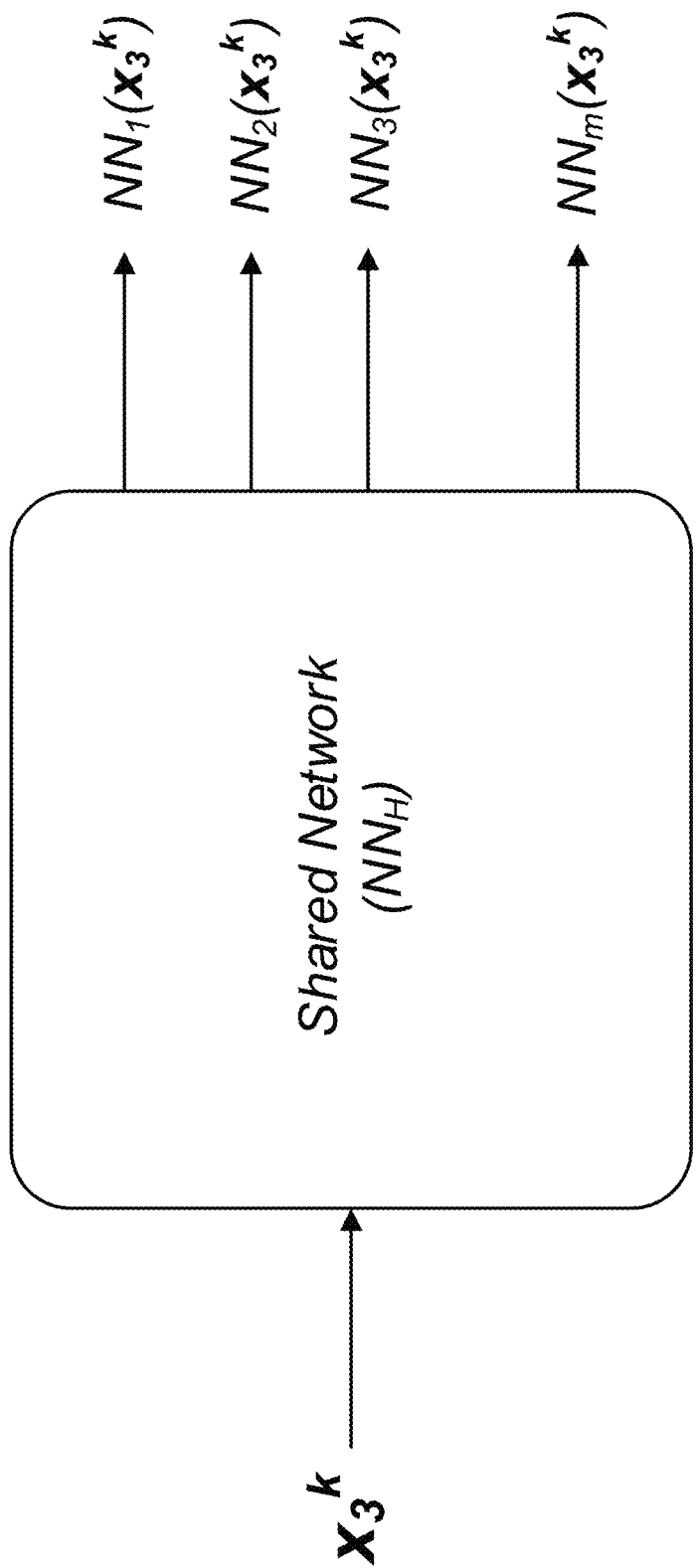
FIG. 6A illustrates an example network model NNH(•) shared by MHC alleles, according to one embodiment.

FIG. 6A illustrates an example network model $NN_H(\cdot)$ shared by MHC alleles h=1, 2, . . . , m. As shown in FIG. 6A, the network model $NN_H(\cdot)$ includes m output nodes each corresponding to an MHC allele. The network model $NN_3(\cdot)$ receives the allele-interacting variables $x_3^k$ for MHC allele h=3 and outputs m values including the value $NN_3(x_3^k)$ corresponding to the MHC allele h=3.

In yet another instance, the single network model $NN_H(\cdot)$ may be a network model that outputs a dependency score given the allele interacting variables $x_h^k$ and the encoded protein sequence $d_h$ of an MHC allele h. In such an instance, the set of parameters $\theta_h$ may again correspond to a set of parameters for the single network model, and thus, the set of parameters $\theta_h$ may be shared by all MHC alleles. Thus, in such an instance, $NN_h(\cdot)$ may denote the output of the single network model $NN_H(\cdot)$ given inputs $[x_h^k d_h]$ to the single network model. Such a network model is advantageous because peptide presentation probabilities for MHC alleles that were unknown in the training data can be predicted just by identification of their protein sequence.

FIG. 6B illustrates an example network model $NN_H(\cdot)$ shared by MHC alleles. As shown in FIG. 6B, the network model $NN_H(\cdot)$ receives the allele interacting variables and protein sequence of MHC allele h=3 as input, and outputs a dependency score $NN_3(x_3^k)$ corresponding to the MHC allele h=3.

In yet another instance, the dependency function $g_h(\cdot)$ can be expressed as:

$$g_h(x_h^k;\theta_h)=g'_h(x_h^k;\theta'_h)+\theta_h^0$$

where $g'_h(x_h^k;\theta'_h)$ is the affine function with a set of parameters $\theta'_h$, the network function, or the like, with a bias parameter $\theta_h^0$ in the set of parameters for allele interacting variables for the MHC allele that represents a baseline probability of presentation for the MHC allele h.

In another implementation, the bias parameter $\theta_h^0$ may be shared according to the gene family of the MHC allele h. That is, the bias parameter $\theta_h^0$ for MHC allele h may be equal to $\theta_{gene(h)}^0$, where gene(h) is the gene family of MHC allele h. For example, class I MHC alleles HLA-A*02:01, HLA-A*02:02, and HLA-A*02:03 may be assigned to the gene family of "HLA-A," and the bias parameter $\theta_h^0$ for each of these MHC alleles may be shared. As another example, class II MHC alleles HLA-DRB1:10:01, HLA-DRB1:11:01, and HLA-DRB3:01:01 may be assigned to the gene family of "HLA-DRB," and the bias parameter $\theta_h^0$ for each of these MHC alleles may be shared.

Returning to equation (2), as an example, the likelihood that peptide $p^k$ will be presented by MHC allele h=3, among m=4 different identified MHC alleles using the affine dependency function $g_h(\cdot)$, can be generated by:

$$u_k^3 = f(x_3^k \cdot \theta_3),$$

where $x_3^k$ are the identified allele-interacting variables for MHC allele h=3, and $\theta_3$ are the set of parameters determined for MHC allele h=3 through loss function minimization.

As another example, the likelihood that peptide $p^k$ will be presented by MHC allele h=3, among m=4 different identified MHC alleles using separate network transformation functions $g_h(\cdot)$ can be generated by:

$$u_k^3 = f(NN_3(x_3^k;\theta_3)),$$

where $x_3^k$ are the identified allele-interacting variables for MHC allele h=3, and $\theta_3$ are the set of parameters determined for the network model $NN_3(\cdot)$ associated with MHC allele h=3.

Figure 7:
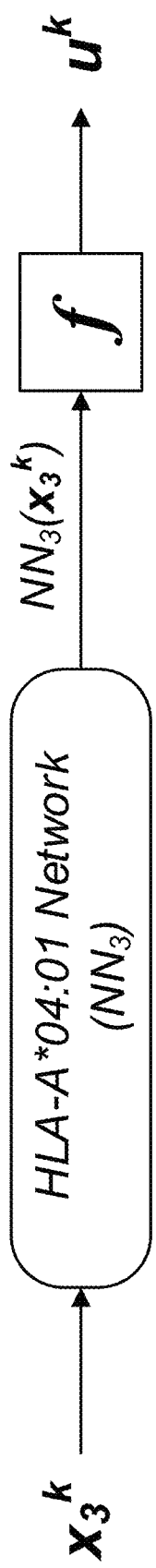
FIG. 7 illustrates generating a presentation likelihood for a peptide in association with an MHC allele using an example network model.

FIG. 7 illustrates generating a presentation likelihood for peptide $p^k$ in association with MHC allele h=3 using an example network model $NN_3(\cdot)$. As shown in FIG. 7, the network model $NN_3(\cdot)$ receives the allele-interacting variables $x_3^k$ for MHC allele h=3 and generates the output $NN_3(x_3^k)$. The output is mapped by function $f(\cdot)$ to generate the estimated presentation likelihood $u_k$.

X.B.2. Per-Allele with Allele-Noninteracting Variables

In one implementation, the training module 316 incorporates allele-noninteracting variables and models the estimated presentation likelihood $u_k$ for peptide $p^k$ by:

$$u_k^h = Pr(p^k \text{ presented}) = f(g_w(w^k;\theta_w) + g_h(x_h^i;\theta_h)), \qquad (8)$$

where $w^k$ denotes the encoded allele-noninteracting variables for peptide $p^k$, $g_w(\cdot)$ is a function for the allele-noninteracting variables $w^k$ based on a set of parameters $\theta_w$ determined for the allele-noninteracting variables. Specifically, the values for the set of parameters $\theta_h$ for each MHC allele h and the set of parameters $\theta_w$ for allele-noninteracting variables can be determined by minimizing the loss function with respect to $\theta_h$ and $\theta_w$, where i is each instance in the subset S of training data 170 generated from cells expressing single MHC alleles.

The output of the dependency function $g_w(w^k;\theta_w)$ represents a dependency score for the allele noninteracting variables indicating whether the peptide $p^k$ will be presented by one or more MHC alleles based on the impact of allele noninteracting variables. For example, the dependency score for the allele noninteracting variables may have a high value if the peptide $p^k$ is associated with a C-terminal flanking sequence that is known to positively impact presentation of the peptide $p^k$, and may have a low value if the peptide $p^k$ is associated with a C-terminal flanking sequence that is known to negatively impact presentation of the peptide $p^k$.

According to equation (8), the per-allele likelihood that a peptide sequence $p^k$ will be presented by a MHC allele h can be generated by applying the function $g_h(\cdot)$ for the MHC allele h to the encoded version of the peptide sequence $p^k$ to generate the corresponding dependency score for allele interacting variables. The function $g_w(\cdot)$ for the allele noninteracting variables are also applied to the encoded version of the allele noninteracting variables to generate the dependency score for the allele noninteracting variables. Both scores are combined, and the combined score is transformed by the transformation function $f(\cdot)$ to generate a per-allele likelihood that the peptide sequence $p^k$ will be presented by the MHC allele h.

Alternatively, the training module 316 may include allele-noninteracting variables $w^k$ in the prediction by adding the allele-noninteracting variables $w^k$ to the allele-interacting variables $x_h^k$ in equation (2). Thus, the presentation likelihood can be given by:

$$u_k^h = Pr(p^k \text{ presented; allele } h) = f(g_h([x_h^k w^k];\theta_h)). \quad (9)$$

X.B.3 Dependency Functions for Allele-Noninteracting Variables

Similarly to the dependency function $g_h(\cdot)$ for allele-interacting variables, the dependency function $g_w(\cdot)$ for allele noninteracting variables may be an affine function or a network function in which a separate network model is associated with allele-noninteracting variables $w^k$.

Specifically, the dependency function $g_w(\cdot)$ is an affine function given by:

$$g_w(w_k;\theta_w) = w^k \cdot \theta_w.$$

that linearly combines the allele-noninteracting variables in $w^k$ with a corresponding parameter in the set of parameters $\theta_w$.

The dependency function $g_w(\cdot)$ may also be a network function given by:

$$g_h(w^k;\theta_w) = NN_w(w^k;\theta_w).$$

represented by a network model $NN_w(\cdot)$ having an associated parameter in the set of parameters $\theta_w$. The network function may also include one or more network models each taking different allele noninteracting variables as input.

In another instance, the dependency function $g_w(\cdot)$ for the allele-noninteracting variables can be given by:

$$g_w(w^k;\theta_w) = g'_w(w^k;\theta'_w) + h(m^k;\theta_w^m), \quad (10)$$

where $g'_w(w^k;\theta'_w)$ is the affine function, the network function with the set of allele noninteracting parameters $\theta'_w$, or the like, $m_k$ is the mRNA quantification measurement for peptide $p^k$, $h(\cdot)$ is a function transforming the quantification measurement, and $\theta_w^m$ is a parameter in the set of parameters for allele noninteracting variables that is combined with the mRNA quantification measurement to generate a dependency score for the mRNA quantification measurement. In one particular embodiment referred throughout the remainder of the specification, $h(\cdot)$ is the log function, however in practice $h(\cdot)$ may be any one of a variety of different functions.

In yet another instance, the dependency function $g_w(\cdot)$ for the allele-noninteracting variables can be given by:

$$g_w(w_k;\theta_w) = g'_w(w_k;\theta'_w) + \theta_w^o \cdot o_k, \quad (11)$$

where $g'_w(w^k;\theta'_w)$ is the affine function, the network function with the set of allele noninteracting parameters $\theta'_w$, or the like, $o^k$ is the indicator vector described above representing proteins and isoforms in the human proteome for peptide $p^k$, and $\theta_w^o$ is a set of parameters in the set of parameters for allele noninteracting variables that is combined with the indicator vector. In one variation, when the dimensionality of $o^k$ and the set of parameters $\theta_w^o$ are significantly high, a parameter regularization term, such as $\lambda \cdot \|\theta_w^o\|$, where $\|\cdot\|$ represents L1 norm, L2 norm, a combination, or the like, can be added to the loss function when determining the value of the parameters. The optimal value of the hyperparameter $\lambda$ can be determined through appropriate methods.

In yet another instance, the dependency function $g_w(\cdot)$ for the allele-noninteracting variables can be given by:

$$g_w(w^k;\theta_w) = g'_w(w^k;\theta'_w) + \sum_{l=1}^{L} \mathbb{1}(gene(p^k = l)) \cdot \theta_w^l, \quad (12)$$

where $g'_w(w^k;\theta'_w)$ is the affine function, the network function with the set of allele noninteracting parameters $\theta'_w$, or the like, $\mathbb{1}(gene(p^k=l))$ is the indicator function that equals to 1 if peptide $p^k$ is from source gene l as described above in reference to allele noninteracting variables, and $\theta_w^l$ is a parameter indicating "antigenicity" of source gene l. In one variation, when L is significantly high, and thus, the number of parameters $\theta_w^{l=1,2,\ldots,L}$ are significantly high, a parameter regularization term, such as $\lambda \cdot \|\theta_w^l\|$, where $\|\cdot\|$ represents L1 norm, L2 norm, a combination, or the like, can be added to the loss function when determining the value of the parameters. The optimal value of the hyperparameter $\lambda$ can be determined through appropriate methods.

In practice, the additional terms of any of equations (10), (11), and (12) may be combined to generate the dependency function $g_w(\cdot)$ for allele noninteracting variables. For example, the term $h(\cdot)$ indicating mRNA quantification measurement in equation (10) and the term indicating source gene antigenicity in equation (12) may be summed together along with any other affine or network function to generate the dependency function for allele noninteracting variables.

Returning to equation (8), as an example, the likelihood that peptide $p^k$ will be presented by MHC allele h=3, among m=4 different identified MHC alleles using the affine transformation functions $g_h(\cdot)$, $g_w(\cdot)$ can be generated by:

$$u_k^3 = f(w^k \cdot \theta_w + x_3^k \cdot \theta_3),$$

where $w^k$ are the identified allele-noninteracting variables for peptide $p^k$, and $\theta_w$ are the set of parameters determined for the allele-noninteracting variables.

As another example, the likelihood that peptide $p^k$ will be presented by MHC allele h=3, among m=4 different identified MHC alleles using the network transformation functions $g_h(\cdot)$, $g_w(\cdot)$, can be generated by:

$$u_k^3 = f(NN_w(w^k; \theta_w) + NN_3(x_3^k; \theta_3))$$

where $w^k$ are the identified allele-interacting variables for peptide $p^k$, and $\theta_w$ are the set of parameters determined for allele-noninteracting variables.

Figure 8:
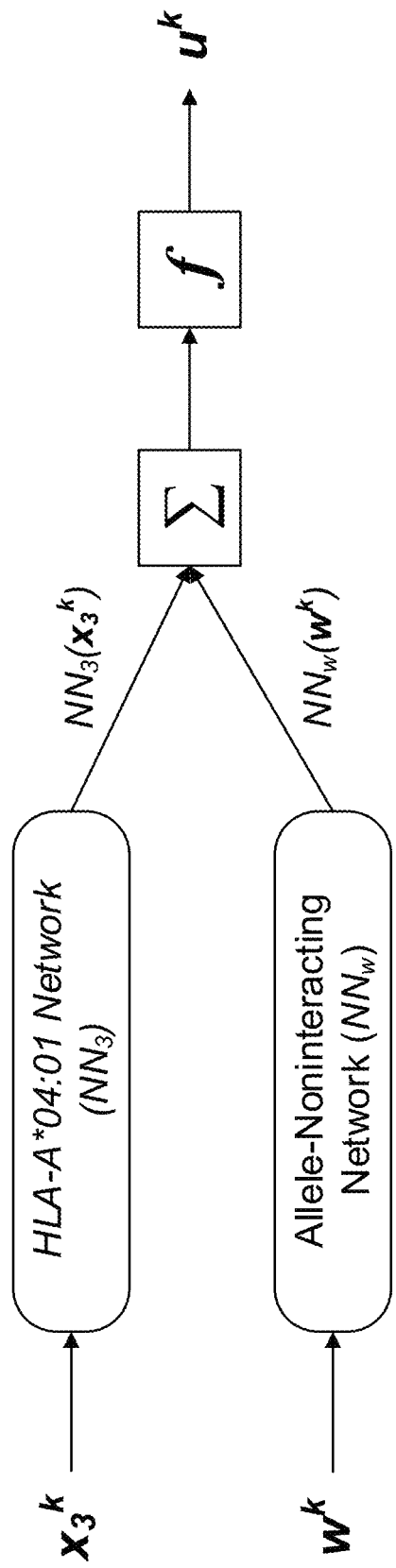
FIG. 8 illustrates generating a presentation likelihood for a peptide in association with a MHC allele using example network models.

FIG. 8 illustrates generating a presentation likelihood for peptide $p^k$ in association with MHC allele h=3 using example network models $NN_3(\cdot)$ and $NN_w(\cdot)$. As shown in FIG. 8, the network model $NN_3(\cdot)$ receives the allele-interacting variables $x_3^k$ for MHC allele h=3 and generates the output $NN_3(x_3^k)$. The network model $NN_w(\cdot)$ receives the allele-noninteracting variables $w^k$ for peptide $p^k$ and generates the output $NN_w(w^k)$. The outputs are combined and mapped by function $f(\cdot)$ to generate the estimated presentation likelihood $u_k$.

X.C. Multiple-Allele Models

The training module 316 may also construct the presentation models to predict presentation likelihoods of peptides in a multiple-allele setting where two or more MHC alleles are present. In this case, the training module 316 may train the presentation models based on data instances Sin the training data 170 generated from cells expressing single MHC alleles, cells expressing multiple MHC alleles, or a combination thereof.

X.C.1. Example 1: Maximum of Per-Allele Models

In one implementation, the training module 316 models the estimated presentation likelihood $u_k$ for peptide $p^k$ in association with a set of multiple MHC alleles H as a function of the presentation likelihoods $u_k^{h \in H}$ determined for each of the MHC alleles h in the set H determined based on cells expressing single-alleles, as described above in conjunction with equations (2)-(11). Specifically, the presentation likelihood $u_k$ can be any function of $u_k^{h \in H}$. In one implementation, as shown in equation (12), the function is the maximum function, and the presentation likelihood $u_k$ can be determined as the maximum of the presentation likelihoods for each MHC allele h in the set H.

$$u_k = Pr(p^k \text{ presented; alleles } H) = \max(u_k^{h \in H}).$$

X.C.2. Example 2.1: Function-of-Sums Models

In one implementation, the training module 316 models the estimated presentation likelihood $u_k$ for peptide $p^k$ by:

$$u_k = Pr(p^k \text{ presented}) = f\left(\sum_{h=1}^{m} a_h^k \cdot g_h(x_h^k; \theta_h)\right), \quad (13)$$

where elements $a_h^k$ are 1 for the multiple MHC alleles H associated with peptide sequence $p^k$ and $x_h^k$ denotes the encoded allele-interacting variables for peptide $p^k$ and the corresponding MHC alleles. The values for the set of parameters $\theta_h$ for each MHC allele h can be determined by minimizing the loss function with respect to $\theta_h$, where i is each instance in the subset S of training data 170 generated from cells expressing single MHC alleles and/or cells expressing multiple MHC alleles. The dependency function $g_h$ may be in the form of any of the dependency functions $g_h$ introduced above in sections X.B.1.

According to equation (13), the presentation likelihood that a peptide sequence $p^k$ will be presented by one or more MHC alleles h can be generated by applying the dependency function $g_h(\cdot)$ to the encoded version of the peptide sequence $p^k$ for each of the MHC alleles H to generate the corresponding score for the allele interacting variables. The scores for each MHC allele h are combined, and transformed by the transformation function $f(\cdot)$ to generate the presentation likelihood that peptide sequence $p^k$ will be presented by the set of MHC alleles H.

The presentation model of equation (13) is different from the per-allele model of equation (2), in that the number of associated alleles for each peptide, can be greater than 1. In other words, more than one element in $a_h^k$ can have values of 1 for the multiple MHC alleles H associated with peptide sequence $p^k$.

As an example, the likelihood that peptide $p^k$ will be presented by MHC alleles h=2, h=3, among m=4 different identified MHC alleles using the affine transformation functions $g_h(\cdot)$, can be generated by:

$$u_k = f(x_2^k \cdot \theta_2 + x_3^k \cdot \theta_3),$$

where $x_2^k$, $x_3^k$ are the identified allele-interacting variables for MHC alleles h=2, h=3, and $\theta_2$, $\theta_3$ are the set of parameters determined for MHC alleles h=2, h=3.

As another example, the likelihood that peptide $p^k$ will be presented by MHC alleles h=2, h=3, among m=4 different identified MHC alleles using the network transformation functions $g_h(\cdot)$, $g_w(\cdot)$, can be generated by:

$$u_k = \theta(NN_2(x_2^k; \theta_2) + NN_3(x_3^k; \theta_3)),$$

where $NN_2(\cdot)$, $NN_3(\cdot)$ are the identified network models for MHC alleles h=2, h=3, and $\theta_2$, $\theta_3$ are the set of parameters determined for MHC alleles h=2, h=3.

Figure 9:
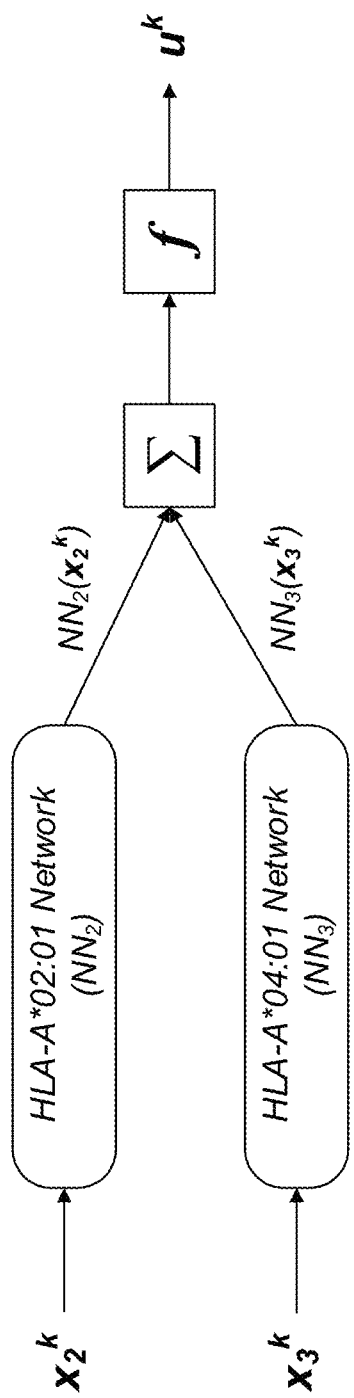
FIG. 9 illustrates generating a presentation likelihood for a peptide in association with MHC alleles using example network models.

FIG. 9 illustrates generating a presentation likelihood for peptide $p^k$ in association with MHC alleles h=2, h=3 using example network models $NN_2(\cdot)$ and $NN_3(\cdot)$. As shown in FIG. 9, the network model $NN_2(\cdot)$ receives the allele-interacting variables $x_2^k$ for MHC allele h=2 and generates the output $NN_2(x_2^k)$ and the network model $NN_3(\cdot)$ receives the allele-interacting variables $x_3^k$ for MHC allele h=3 and generates the output $NN_3(x_3^k)$. The outputs are combined and mapped by function $f(\cdot)$ to generate the estimated presentation likelihood $u_k$.

X.C.3. Example 2.2: Function-of-Sums Models with Allele-Noninteracting Variables In one implementation, the training module 316 incorporates allele-noninteracting variables and models the estimated presentation likelihood $u_k$ for peptide $p^k$ by:

$$u_k = Pr(p^k \text{ presented}) = f\left(g_w(w^k; \theta_w) + \sum_{h=1}^{m} a_h^k \cdot g_h(x_h^k; \theta_h)\right), \quad (14)$$

where $w^k$ denotes the encoded allele-noninteracting variables for peptide $p^k$. Specifically, the values for the set of parameters $\theta_h$ for each MHC allele h and the set of parameters $\theta^w$ for allele-noninteracting variables can be determined by minimizing the loss function with respect to $\theta_h$ and $\theta_w$, where i is each instance in the subset S of training data 170 generated from cells expressing single MHC alleles and/or cells expressing multiple MHC alleles. The dependency function $g_w$ may be in the form of any of the dependency functions $g_w$ introduced above in sections X.B.3.

Thus, according to equation (14), the presentation likelihood that a peptide sequence $p^k$ will be presented by one or more MHC alleles H can be generated by applying the function $g_h(\cdot)$ to the encoded version of the peptide sequence $p^k$ for each of the MHC alleles H to generate the corresponding dependency score for allele interacting variables for each MHC allele h. The function $g_w(\cdot)$ for the allele noninteracting variables is also applied to the encoded version of the allele noninteracting variables to generate the dependency score for the allele noninteracting variables. The scores are combined, and the combined score is transformed by the transformation function $f(\cdot)$ to generate the presentation likelihood that peptide sequence $p^k$ will be presented by the MHC alleles H.

In the presentation model of equation (14), the number of associated alleles for each peptide $p^k$ can be greater than 1. In other words, more than one element in $a_h^k$ can have values of 1 for the multiple MHC alleles H associated with peptide sequence $p^k$.

As an example, the likelihood that peptide $p^k$ will be presented by MHC alleles h=2, h=3, among m=4 different identified MHC alleles using the affine transformation functions $g_h(\cdot)$, $g_w(\cdot)$, can be generated by:

$$u_k = f(w^k \cdot \theta_w + x_2^k \cdot \theta_2 + x_3^k \cdot \theta_3),$$

where $w^k$ are the identified allele-noninteracting variables for peptide $p^k$, and $\theta_w$ are the set of parameters determined for the allele-noninteracting variables.

As another example, the likelihood that peptide $p^k$ will be presented by MHC alleles h=2, h=3, among m=4 different identified MHC alleles using the network transformation functions $g_h(\cdot)$, $g_w(\cdot)$, can be generated by:

$$u_k = f(NN_w(w^k;\theta_w) + NN_2(x_2^k;\theta_2) + NN_3(x_3^k;\theta_3))$$

where $w^k$ are the identified allele-interacting variables for peptide $p^k$, and $\theta_w$ are the set of parameters determined for allele-noninteracting variables.

Figure 10:
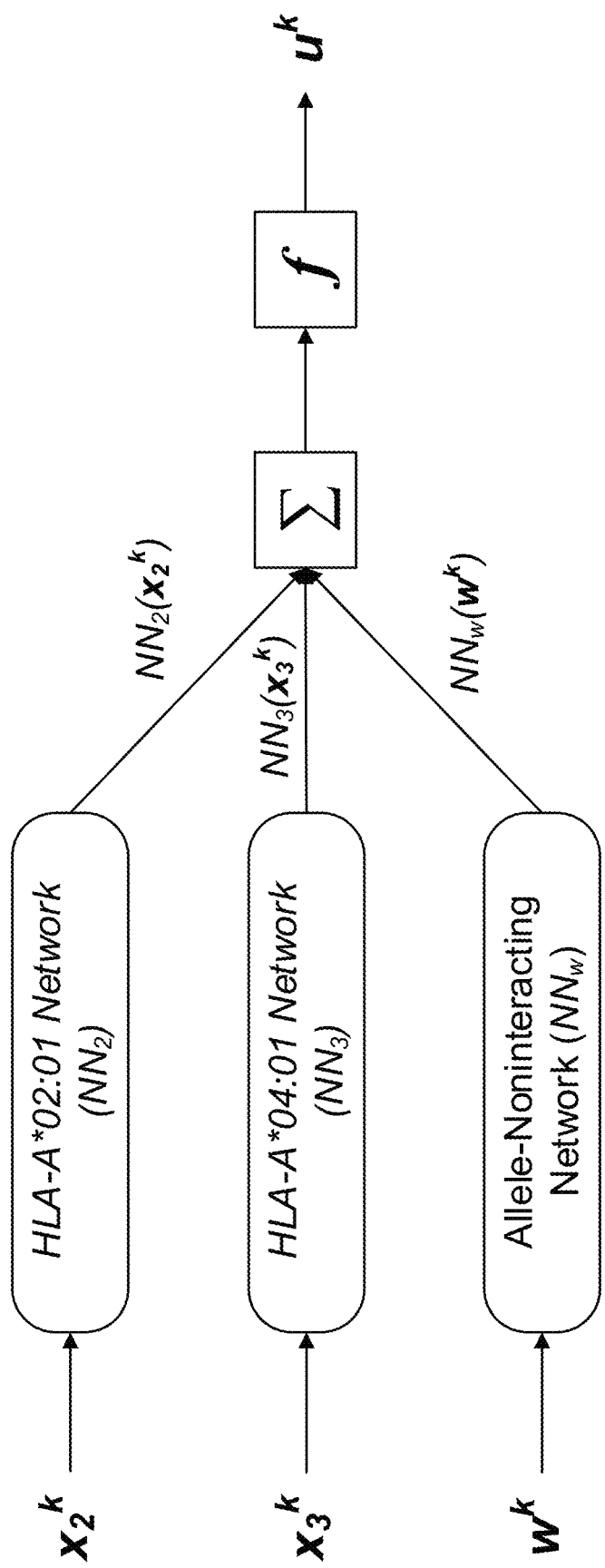
FIG. 10 illustrates generating a presentation likelihood for a peptide in association with MHC alleles using example network models.

FIG. 10 illustrates generating a presentation likelihood for peptide $p^k$ in association with MHC alleles h=2, h=3 using example network models $NN_2(\cdot)$, $NN_3(\cdot)$, and $NN_w(\cdot)$. As shown in FIG. 10, the network model $NN_2(\cdot)$ receives the allele-interacting variables $x_2^k$ for MHC allele h=2 and generates the output $NN_2(x_2^k)$. The network model $NN_3(\cdot)$ receives the allele-interacting variables $x_3^k$ for MHC allele h=3 and generates the output $NN_3(x_3^k)$. The network model $NN_w(\cdot)$ receives the allele-noninteracting variables $w^k$ for peptide $p^k$ and generates the output $NN_w(w^k)$. The outputs are combined and mapped by function $f(\cdot)$ to generate the estimated presentation likelihood $u_k$.

Alternatively, the training module 316 may include allele-noninteracting variables $w^k$ in the prediction by adding the allele-noninteracting variables $w^k$ to the allele-interacting variables $x_h^k$ in equation (15). Thus, the presentation likelihood can be given by:

$$u_k = Pr(p^k \text{ presented}) = f\left(\sum_{h=1}^{m} a_h^k \cdot g_h([x_h^k w^k]; \theta_h)\right). \tag{15}$$

X.C.4. Example 3.1: Models Using Implicit Per-Allele Likelihoods

In another implementation, the training module 316 models the estimated presentation likelihood $u_k$ for peptide $p^k$ by:

$$u_k = Pr(p^k \text{ presented}) = r(s(v=[a_1^k \cdot u'^1_k(\theta) \ldots a_m^k \cdot u'^m_k(\theta)])), \tag{16}$$

where elements $a_h^k$ are 1 for the multiple MHC alleles $h \in H$ associated with peptide sequence $p^k$, $u'^h_k$ is an implicit per-allele presentation likelihood for MHC allele h, vector v is a vector in which element $v_h$ corresponds to $a_h^k \cdot u'^h_k$, $s(\cdot)$ is a function mapping the elements of v, and $r(\cdot)$ is a clipping function that clips the value of the input into a given range. As described below in more detail, $s(\cdot)$ may be the summation function or the second-order function, but it is appreciated that in other embodiments, $s(\cdot)$ can be any function such as the maximum function. The values for the set of parameters $\theta$ for the implicit per-allele likelihoods can be determined by minimizing the loss function with respect to $\theta$, where i is each instance in the subset S of training data 170 generated from cells expressing single MHC alleles and/or cells expressing multiple MHC alleles.

The presentation likelihood in the presentation model of equation (17) is modeled as a function of implicit per-allele presentation likelihoods $u'^h_k$ that each correspond to the likelihood peptide $p^k$ will be presented by an individual MHC allele h. The implicit per-allele likelihood is distinct from the per-allele presentation likelihood of section X.B in that the parameters for implicit per-allele likelihoods can be learned from multiple allele settings, in which direct association between a presented peptide and the corresponding MHC allele is unknown, in addition to single-allele settings. Thus, in a multiple-allele setting, the presentation model can estimate not only whether peptide $p^k$ will be presented by a set of MHC alleles H as a whole, but can also provide individual likelihoods $u'k^{h \in H}$ that indicate which MHC allele h most likely presented peptide $p^k$. An advantage of this is that the presentation model can generate the implicit likelihoods without training data for cells expressing single MHC alleles.

In one particular implementation referred throughout the remainder of the specification, $r(\cdot)$ is a function having the range [0, 1]. For example, $r(\cdot)$ may be the clip function:

$$r(z) = \min(\max(z,0),1),$$

where the minimum value between z and 1 is chosen as the presentation likelihood $u_k$. In another implementation, $r(\cdot)$ is the hyperbolic tangent function given by:

$$r(z) = \tanh(z)$$

when the values for the domain z is equal to or greater than 0.

X.C.5. Example 3.2: Sum-of-Functions Model

In one particular implementation, $s(\cdot)$ is a summation function, and the presentation likelihood is given by summing the implicit per-allele presentation likelihoods:

$$u_k = Pr(p^k \text{ presented}) = r\left(\sum_{h=1}^{m} a_h^k \cdot u'^h_k(\theta)\right). \tag{17}$$

In one implementation, the implicit per-allele presentation likelihood for MHC allele h is generated by:

$$u'^h_k = f(g_h(x_h^k;\theta_h)), \tag{18}$$

such that the presentation likelihood is estimated by:

$$u_k = Pr(p^k \text{ presented}) = r\left(\sum_{h=1}^{m} a_h^k \cdot f(g_h(x_h^k;\theta_h))\right). \tag{19}$$

According to equation (19), the presentation likelihood that a peptide sequence $p^k$ will be presented by one or more MHC alleles H can be generated by applying the function $g_h(\cdot)$ to the encoded version of the peptide sequence $p^k$ for each of the MHC alleles H to generate the corresponding dependency score for allele interacting variables. Each dependency score is first transformed by the function $f(\cdot)$ to generate implicit per-allele presentation likelihoods $u'^h_k$. The per-allele likelihoods $u'^h_k$ are combined, and the clipping function may be applied to the combined likelihoods to clip the values into a range [0, 1] to generate the presentation likelihood that peptide sequence $p^k$ will be presented by the set of MHC alleles H The dependency function $g_h$ may be in the form of any of the dependency functions $g_h$ introduced above in sections X.B.1.

As an example, the likelihood that peptide $p^k$ will be presented by MHC alleles h=2, h=3, among m=4 different identified MHC alleles using the affine transformation functions $g_h(\cdot)$, can be generated by:

$$u_k = r(f(x_2^k \cdot \theta_2) + f(x_3^k \cdot \theta_3)),$$

where $x_2^k$, $x_3^k$ are the identified allele-interacting variables for MHC alleles h=2, h=3, and $\theta_2$, $\theta_3$ are the set of parameters determined for MHC alleles h=2, h=3.

As another example, the likelihood that peptide $p^k$ will be presented by MHC alleles h=2, h=3, among m=4 different identified MHC alleles using the network transformation functions $g_h(\cdot)$, $g_w(\cdot)$, can be generated by:

$$u_k = r(f(NN_2(x_2^k;\theta_2)) + f(NN_3(x_3^k;\theta_3))),$$

where $NN_2(\cdot)$, $NN_3(\cdot)$ are the identified network models for MHC alleles h=2, h=3, and $\theta_2$, $\theta_3$ are the set of parameters determined for MHC alleles h=2, h=3.

Figure 11:
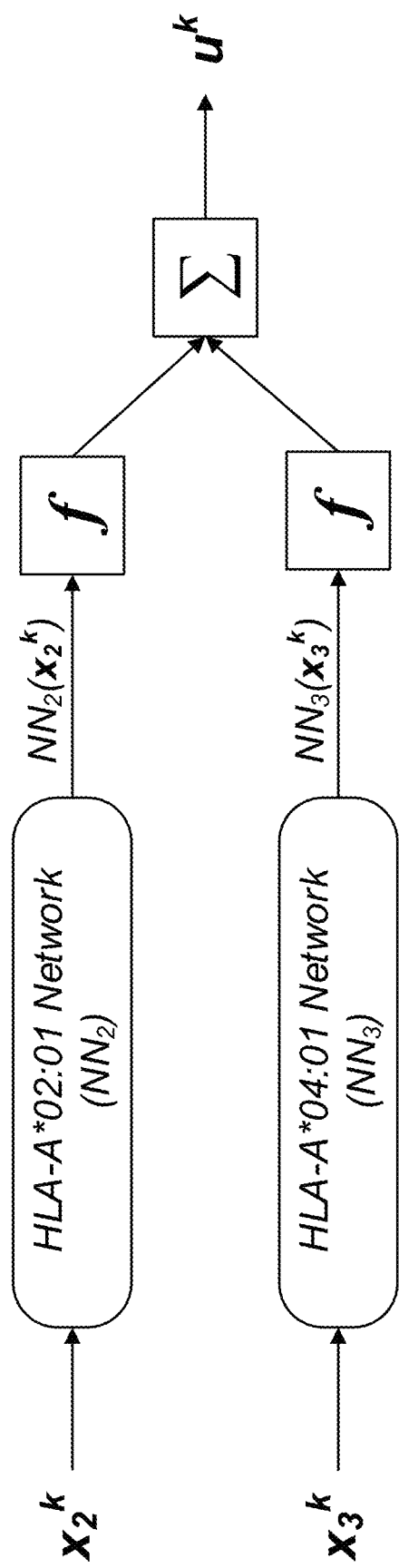
FIG. 11 illustrates generating a presentation likelihood for a peptide in association with MHC alleles using example network models.

FIG. 11 illustrates generating a presentation likelihood for peptide $p^k$ in association with MHC alleles h=2, h=3 using example network models $NN_2(\cdot)$ and $NN_3(\cdot)$. As shown in FIG. 9, the network model $NN_2(\cdot)$ receives the allele-interacting variables $x_2^k$ for MHC allele h=2 and generates the output $NN_2(x_2^k)$ and the network model $NN_3(\cdot)$ receives the allele-interacting variables $x_3^k$ for MHC allele h=3 and generates the output $NN_3(x_3^k)$. Each output is mapped by function $f(\cdot)$ and combined to generate the estimated presentation likelihood $u_k$.

In another implementation, when the predictions are made for the log of mass spectrometry ion currents, $r(\cdot)$ is the log function and $f(\cdot)$ is the exponential function.

X.C.6. Example 3.3: Sum-of-Functions Models with Allele-noninteracting Variables In one implementation, the implicit per-allele presentation likelihood for MHC allele h is generated by:

$$u'^h_k = f(g_h(x_h^k;\theta_h) + g_w(w^k;\theta_w)) \quad (20)$$

such that the presentation likelihood is generated by:

$$u_k = Pr(p^k \text{ presented}) = r\left(\sum_{h=1}^{m} a_h^k \cdot f(g_w(w^k;\theta_w) + g_h(x_h^k;\theta_h))\right), \quad (21)$$

to incorporate the impact of allele noninteracting variables on peptide presentation.

According to equation (21), the presentation likelihood that a peptide sequence $p^k$ will be presented by one or more MHC alleles H can be generated by applying the function $g_h(\cdot)$ to the encoded version of the peptide sequence $p^k$ for each of the MHC alleles H to generate the corresponding dependency score for allele interacting variables for each MHC allele h. The function $g_w(\cdot)$ for the allele noninteracting variables is also applied to the encoded version of the allele noninteracting variables to generate the dependency score for the allele noninteracting variables. The score for the allele noninteracting variables are combined to each of the dependency scores for the allele interacting variables.

Each of the combined scores are transformed by the function $f(\cdot)$ to generate the implicit per-allele presentation likelihoods. The implicit likelihoods are combined, and the clipping function may be applied to the combined outputs to clip the values into a range [0,1] to generate the presentation likelihood that peptide sequence $p^k$ will be presented by the MHC alleles H The dependency function $g_w$ may be in the form of any of the dependency functions $g_w$ introduced above in sections X.B.3.

As an example, the likelihood that peptide $p^k$ will be presented by MHC alleles h=2, h=3, among m=4 different identified MHC alleles using the affine transformation functions $g_h(\cdot)$, $g_w(\cdot)$, can be generated by:

$$u_k = r(f(w^k \cdot \theta_w + x_2^k \cdot \theta_2) + f(w^k \cdot \theta_w + x_3^k \cdot \theta_3)),$$

where $w^k$ are the identified allele-noninteracting variables for peptide $p^k$, and $\theta_w$ are the set of parameters determined for the allele-noninteracting variables.

As another example, the likelihood that peptide $p^k$ will be presented by MHC alleles h=2, h=3, among m=4 different identified MHC alleles using the network transformation functions $g_h(\cdot)$, $g_w(\cdot)$, can be generated by:

$$u_k = r(f(NN_w(w^k;\theta_w) + NN_2(x_2^k;\theta_2)) + f(NN_w(w^k;\theta_w) + NN_3(x_3^k;\theta_3))))$$

where $w^k$ are the identified allele-interacting variables for peptide $p^k$, and $\theta_w$ are the set of parameters determined for allele-noninteracting variables.

Figure 12:
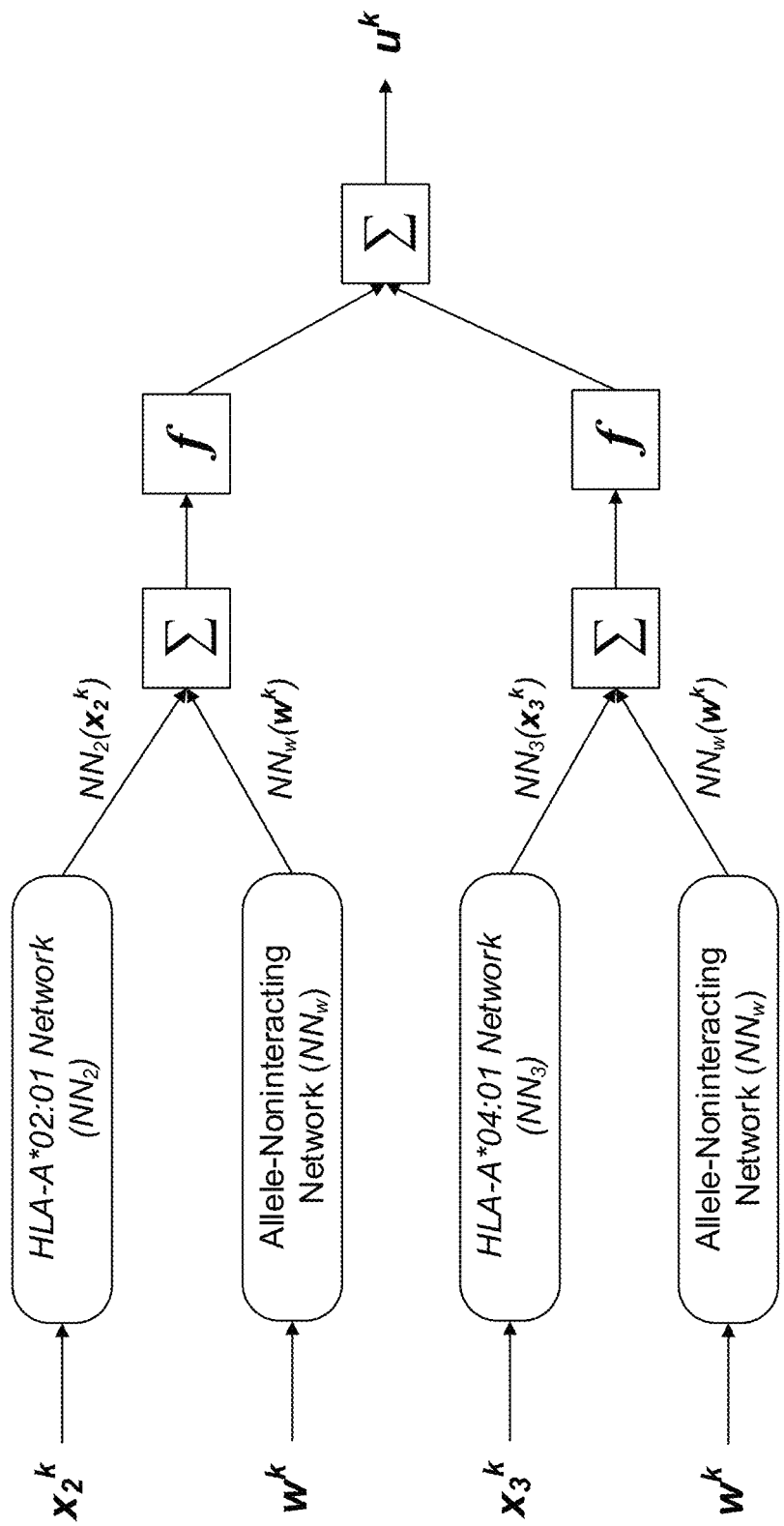
FIG. 12 illustrates generating a presentation likelihood for a peptide in association with MHC alleles using example network models.

FIG. 12 illustrates generating a presentation likelihood for peptide $p^k$ in association with MHC alleles h=2, h=3 using example network models $NN_2(\cdot)$, $NN_3(\cdot)$, and $NN_w(\cdot)$. As shown in FIG. 12, the network model $NN_2(\cdot)$ receives the allele-interacting variables $x_2^k$ for MHC allele h=2 and generates the output $NN_2(x_2^k)$. The network model $NN_w(\cdot)$ receives the allele-noninteracting variables $w^k$ for peptide $p^k$ and generates the output $NN_w(w^k)$. The outputs are combined and mapped by function $f(\cdot)$. The network model $NN_3(\cdot)$ receives the allele-interacting variables $x_3^k$ for MHC allele h=3 and generates the output $NN_3(x_3^k)$, which is again combined with the output $NN_w(w^k)$ of the same network model $NN_w(\cdot)$ and mapped by function $f(\cdot)$. Both outputs are combined to generate the estimated presentation likelihood $u_k$.

In another implementation, the implicit per-allele presentation likelihood for MHC allele h is generated by:

$$u'^h_k = f(g_h([x_h^k w^k];\theta_h)). \quad (22)$$

such that the presentation likelihood is generated by:

$$u_k = Pr(p^k \text{ presented}) = r\left(\sum_{h=1}^{m} a_h^k \cdot f(g_h([x_h^k w^k];\theta_h))\right).$$

X.C.7. Example 4: Second Order Models

In one implementation, $s(\cdot)$ is a second-order function, and the estimated presentation likelihood $u_k$ for peptide $p^k$ is given by:

$$u_k = Pr(p^k \text{ presented}) = \sum_{h=1}^{m} a_h^k \cdot u'^h_k(\theta) - \sum_{h=1}^{m} \sum_{j<h} a_h^k \cdot a_j^k \cdot u'^h_k(\theta) \cdot u'^j_k(\theta) \quad (23)$$

where elements $u'^h_k$ are the implicit per-allele presentation likelihood for MHC allele h. The values for the set of parameters θ for the implicit per-allele likelihoods can be determined by minimizing the loss function with respect to θ, where i is each instance in the subset S of training data 170 generated from cells expressing single MHC alleles and/or cells expressing multiple MHC alleles. The implicit per-allele presentation likelihoods may be in any form shown in equations (18), (20), and (22) described above.

In one aspect, the model of equation (23) may imply that there exists a possibility peptide $p^k$ will be presented by two MHC alleles simultaneously, in which the presentation by two HLA alleles is statistically independent.

According to equation (23), the presentation likelihood that a peptide sequence $p^k$ will be presented by one or more MHC alleles H can be generated by combining the implicit per-allele presentation likelihoods and subtracting the likelihood that each pair of MHC alleles will simultaneously present the peptide $p^k$ from the summation to generate the presentation likelihood that peptide sequence $p^k$ will be presented by the MHC alleles H.

As an example, the likelihood that peptide $p^k$ will be presented by HLA alleles h=2, h=3, among m=4 different identified HLA alleles using the affine transformation functions $g_h(\bullet)$, can be generated by:

$$u_k = f(x_2^k \cdot \theta_2) + f(x_3^k \cdot \theta_3) - f(x_2^k \cdot \theta_2) \cdot f(x_3^k \cdot \theta_3),$$

where $x_2^k$, $x_3^k$ are the identified allele-interacting variables for HLA alleles h=2, h=3, and $\theta_2$, $\theta_3$ are the set of parameters determined for HLA alleles h=2, h=3.

As another example, the likelihood that peptide $p_k$ will be presented by HLA alleles h=2, h=3, among m=4 different identified HLA alleles using the network transformation functions $g_h(\bullet)$, $g_w(\bullet)$, can be generated by:

$$u_k = f(NN_2(x_2^k;\theta_2)) + f(NN_3(x_3^k;\theta_3)) - f(NN_2(x_2^k;\theta_2)) \cdot f(NN_3(x_3^k;\theta_3)),$$

where $NN_2(\bullet)$, $NN_3(\bullet)$ are the identified network models for HLA alleles h=2, h=3, and $\theta_2$, $\theta_3$ are the set of parameters determined for HLA alleles h=2, h=3.

XI.A Example 5: Prediction Module

The prediction module 320 receives sequence data and selects candidate neoantigens in the sequence data using the presentation models. Specifically, the sequence data may be DNA sequences, RNA sequences, and/or protein sequences extracted from tumor tissue cells of patients. The prediction module 320 processes the sequence data into a plurality of peptide sequences $p^k$ having 8-15 amino acids for MHC-I or 6-30 amino acids for MHC-II. For example, the prediction module 320 may process the given sequence "IEFROE-IFJEF (SEQ ID NO: 76) into three peptide sequences having 9 amino acids "IEFROEIFJ (SEQ ID NO: 77)," "EFROE-IFJE (SEQ ID NO: 78)," and "FROEIFJEF (SEQ ID NO: 79)." In one embodiment, the prediction module 320 may identify candidate neoantigens that are mutated peptide sequences by comparing sequence data extracted from normal tissue cells of a patient with the sequence data extracted from tumor tissue cells of the patient to identify portions containing one or more mutations.

The presentation module 320 applies one or more of the presentation models to the processed peptide sequences to estimate presentation likelihoods of the peptide sequences. Specifically, the prediction module 320 may select one or more candidate neoantigen peptide sequences that are likely to be presented on tumor HLA molecules by applying the presentation models to the candidate neoantigens. In one implementation, the presentation module 320 selects candidate neoantigen sequences that have estimated presentation likelihoods above a predetermined threshold. In another implementation, the presentation model selects the N candidate neoantigen sequences that have the highest estimated presentation likelihoods (where N is generally the maximum number of epitopes that can be delivered in a vaccine). A vaccine including the selected candidate neoantigens for a given patient can be injected into the patient to induce immune responses.

XI.B. Example 6: Cassette Design Module

XI.B.1 Overview

The cassette design module 324 generates a vaccine cassette sequence based on the v selected candidate peptides for injection into a patient. Specifically, for a set of selected peptides $p^k$, k=1, 2, . . . , v for inclusion in a vaccine of capacity v, the cassette sequence is given by concatenation of a series of therapeutic epitope sequences $p'^k$, k=1, 2, . . . , v that each include the sequence of a corresponding peptide $p^k$. In one embodiment, the cassette design module 324 may concatenate the epitopes directly adjacent to one another. For example, a vaccine cassette C may be represented as:

$$C = [p'^{t_1} p'^{t_2} \ldots p'^{t_v}] \qquad (24)$$

where $p'^{ti}$ denotes the i-th epitope of the cassette. Thus, $t_i$ corresponds to an index k=1, 2, . . . , v for the selected peptide at the i-th position of the cassette. In another embodiment, the cassette design module 324 may concatenate the epitopes with one or more optional linker sequences in between adjacent epitopes. For example, a vaccine cassette C may be represented as:

$$C = [p'^{t_1} l_{(t_1,t_2)} p'^{t_2} l_{(t_2,t_3)} \ldots l_{(t_{v-1},t_v)} p'^{t_v}] \qquad (25)$$

where $l_{(ti,tj)}$ denotes a linker sequence placed between the i-th epitope $p'^{ti}$ and the j=i+1-th epitope $p'^{j=i+1}$ of the cassette. The cassette design module 324 determines which of the selected epitopes $p'^k$, k=1, 2, . . . , v are arranged at the different positions of the cassette, as well as any linker sequences placed between the epitopes. A cassette sequence C can be loaded as a vaccine based on any of the methods described in the present specification.

In one embodiment, the set of therapeutic epitopes may be generated based on the selected peptides determined by the prediction module 320 associated with presentation likelihoods above a predetermined threshold, where the presentation likelihoods are determined by the presentation models. However it is appreciated that in other embodiments, the set of therapeutic epitopes may be generated based on any one or more of a number of methods (alone or in combination), for example, based on binding affinity or predicted binding affinity to HLA class I or class II alleles of the patient, binding stability or predicted binding stability to HLA class I or class II alleles of the patient, random sampling, and the like.

In one embodiment, the therapeutic epitopes $p'^k$ may correspond to the selected peptides $p^k$ themselves. In another embodiment, the therapeutic epitopes $p'^k$ may also include C- and/or N-terminal flanking sequences in addition to the selected peptides. For example, an epitope $p'^k$ included in the cassette may be represented as a sequence $[n^k\ p^k\ c^k]$ where $c^k$ is a C-terminal flanking sequence attached the C-terminus of the selected peptide $p^k$, and $n^k$ is an N-terminal flanking sequence attached to the N-terminus of the selected peptide $p^k$. In one instance referred throughout the remainder of the specification, the N- and C-terminal flanking sequences are the native N- and C-terminal flanking sequences of the therapeutic vaccine epitope in the context of its source protein. In one instance referred throughout the remainder of the specification, the therapeutic epitope $p'^k$ represents a fixed-length epitope. In another instance, the therapeutic epitope $p'^k$ can represent a variable-length epitope, in which the length of the epitope can be varied depending on, for example, the length of the C- or N-flanking sequence. For example, the C-terminal flanking sequence $c^k$ and the N-terminal flanking sequence $n^k$ can each have varying lengths of 2-5 residues, resulting in 16 possible choices for the epitope $p'^k$.

In one embodiment, the cassette design module 324 generates cassette sequences by taking into account presentation of junction epitopes that span the junction between a pair of therapeutic epitopes in the cassette. Junction epitopes are novel non-self but irrelevant epitope sequences that arise in the cassette due to the process of concatenating therapeutic epitopes and linker sequences in the cassette. The novel sequences of junction epitopes are different from the therapeutic epitopes of the cassette themselves. A junction epitope spanning epitopes $p'^{ti}$ and $p'^{tj}$ may include any epitope sequence that overlaps with both $p'^{ti}$ or $p'^{tj}$ that is different from the sequences of therapeutic epitopes $p'^{ti}$ and $p'^{tj}$ themselves. Specifically, each junction between epitope $p'^{ti}$ and an adjacent epitope $p'^{tj}$ of the cassette with or without an optional linker sequence $l^{(ti,tj)}$ may be associated with $n_{(ti,tj)}$ junction epitopes $e_n^{(ti,tj)}$, n=1, 2, . . . , $n_{(ti,tj)}$. The junction epitopes may be sequences that at least partially overlap with both epitopes $p'^{ti}$ and $p'^{tj}$, or may be sequences that at least partially overlap with linker sequences placed between the epitopes $p'^{ti}$ and $p'^{tj}$. Junction epitopes may be presented by MHC class I, MHC class II, or both.

Figure 38:
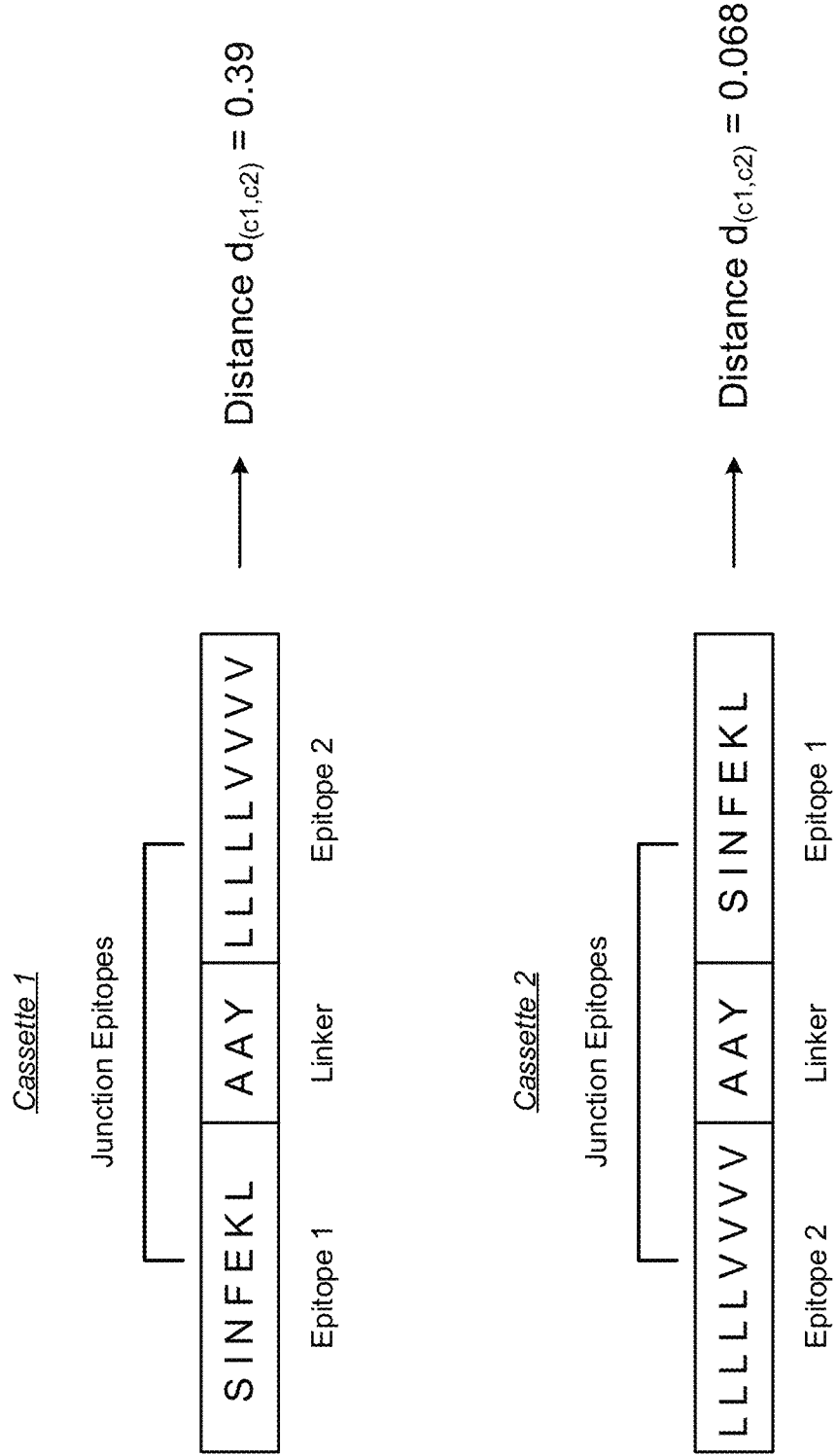
FIG. 38 illustrates determining distance metrics for two example cassette sequences. Figure discloses SEQ ID NOS 191 and 192, respectively, in order of appearance.

FIG. 38 shows two example cassette sequences, cassette 1 ($C_1$) and cassette 2 ($C_2$). Each cassette has a vaccine capacity of v=2, and includes therapeutic epitopes $p'^{t1}=p^1$=SINFEKL (SEQ ID NO: 80) and $p'^{t2}=p^2$=LLLLLVVVV (SEQ ID NO: 81), and a linker sequence $l^{(t1,t2)}$=AAY in between the two epitopes. Specifically, the sequence of cassette $C_1$ is given by [$p^1$ $l^{(t1,t2)}$ $p^2$], while the sequence of cassette $C_2$ is given by [$p^2$ $l^{(t1,t2)}$ $p^1$]. Example junction epitopes $e_n^{(1,2)}$ of cassette $C_1$ may be sequences such as EKLAAYLLL (SEQ ID NO: 82), KLAAYLLLL (SEQ ID NO: 83), and FEKLAAYL (SEQ ID NO: 84) that span across both epitopes $p^{t1}$ and $p^{t2}$ in the cassette, and may be sequences such as AAYLLLLL (SEQ ID NO: 85) and YLLLLLVVV (SEQ ID NO: 86) that span across the linker sequence and a single selected epitope in the cassette. Similarly, example junction epitopes $e_m^{(2,1)}$ of cassette $C_2$ may be sequences such as VVVVAAYSIN (SEQ ID NO: 87), VVVVAAY (SEQ ID NO: 88), and AYSINFEK (SEQ ID NO: 89). Although both cassettes involve the same set of sequences $p^1$, $l^{(c1,c2)}$, and $p^2$, the set of junction epitopes that are identified are different depending on the ordered sequence of the therapeutic epitopes within the cassette.

In one embodiment, the cassette design module 324 generates a cassette sequence that reduces the likelihood that junction epitopes are presented in the patient. Specifically, when the cassette is injected into the patient, junction epitopes have the potential to be presented by HLA class I or HLA class II alleles of the patient, and stimulate a CD8 or CD4 T-cell response, respectively. Such reactions are often times undesirable because T-cells reactive to the junction epitopes have no therapeutic benefit, and may diminish the immune response to the selected therapeutic epitopes in the cassette by antigenic competition.[76]

In one embodiment, the cassette design module 324 iterates through one or more candidate cassettes, and determines a cassette sequence for which a presentation score of junction epitopes associated with that cassette sequence is below a numerical threshold. The junction epitope presentation score is a quantity associated with presentation likelihoods of the junction epitopes in the cassette, and a higher value of the junction epitope presentation score indicates a higher likelihood that junction epitopes of the cassette will be presented by HLA class I or HLA class II or both.

In one embodiment, the cassette design module 324 may determine a cassette sequence associated with the lowest junction epitope presentation score among the candidate cassette sequences. In one instance, the presentation score for a given cassette sequence C is determined based on a set of distance metrics $d(e_n^{(ti,tj)}, n=1, 2, \ldots, n_{(ti,tj)}=d_{(ti,tj)}$ each associated with a junction in the cassette C. Specifically, a distance metric $d_{(ti,tj)}$ specifies a likelihood that one or more of the junction epitopes spanning between the pair of adjacent therapeutic epitopes $p'^{ti}$ and $p'^{tj}$ will be presented. The junction epitope presentation score for cassette C can then be determined by applying a function (e.g., summation, statistical function) to the set of distance metrics for the cassette C. Mathematically, the presentation score is given by:

$$\text{score} = h(d_{(t_1,t_2)}, d_{(t_2,t_3)}, \ldots, d_{(t_{v-1},t_v)}) \quad (26)$$

where $h(\bullet)$ is some function mapping the distance metrics of each junction to a score. In one particular instance referred throughout the remainder of the specification, the function $h(\bullet)$ is the summation across the distance metrics of the cassette.

The cassette design module 324 may iterate through one or more candidate cassette sequences, determine the junction epitope presentation score for the candidate cassettes, and identify an optimal cassette sequence associated with a junction epitope presentation score below the threshold. In one particular embodiment referred throughout the remainder of the specification, the distance metric $d(\bullet)$ for a given junction may be given by the sum of the presentation likelihoods or the expected number presented junction epitopes as determined by the presentation models described in sections VII and VIII of the specification. However, it is appreciated that in other embodiments, the distance metric may be derived from other factors alone or in combination with the models like the one exemplified above, where these other factors may include deriving the distance metric from any one or more of (alone or in combination): HLA binding affinity or stability measurements or predictions for HLA class I or HLA class II, and a presentation or immunogenicity model trained on HLA mass spectrometry or T-cell epitope data, for HLA class I or HLA class II. In one embodiment, the distance metric may combine information about HLA class I and HLA class II presentation. For example, the distance metric could be the number of junction epitopes predicted to bind any of the patient's HLA class I or HLA class II alleles with binding affinity below a threshold. In another example, the distance metric could be the expected number of epitopes predicted to be presented by any of the patient's HLA class I or HLA class II alleles.

The cassette design module 324 may further check the one or more candidate cassette sequences to identify if any of the junction epitopes in the candidate cassette sequences are self-epitopes for a given patient for whom the vaccine is being designed. To accomplish this, the cassette design module 324 checks the junction epitopes against a known database such as BLAST. In one embodiment, the cassette design module may be configured to design cassettes that avoid junction self-epitopes by setting the distance metric $d_{(ti,tj)}$ to a very large value (e.g., 100) for pairs of epitopes $t_i, t_j$ where contatenating epitope $t_i$ to the N-terminus of epitope $t_j$ results in the formation of a junction self-epitope.

Returning to the example in FIG. 38 the cassette design module 324 determines (for example) a distance metric $d_{(t1,t2)}=d_{(1,2)}=0.39$ for the single junction $(t_1,t_2)$ in cassette $C_1$ given by the summation of presentation likelihoods of all possible junction epitopes $e_n^{(t1,t2)}=e_n^{(1,2)}$ having lengths, for example, from 8 to 15 amino acids for MHC class I, or 6-30 amino acids for MHC class II. Since no other junctions are present in cassette $C_1$, the junction epitope presentation score, which is a summation across the distance metrics for cassette $C_1$, is also given by 0.39. The cassette design module 324 also determines a distance metric $d_{(t1,t2)}=d_{(2,1)}=0.068$ for the single junction in cassette $C_2$ given by the summation of presentation likelihoods of all possible junction epitopes $e_n^{(t1,t2)}=e_n^{(2,1)}$ having lengths from 8 to 15 for MHC class I, or 9-30 amino acids for MHC class II. In this example, the junction epitope presentation score for cassette $C_2$ is also given by the distance metric of the single junction 0.068. The cassette design module 324 outputs the cassette sequence of $C_2$ as the optimal cassette since the junction epitope presentation score is lower than the cassette sequence of $C_1$.

In some cases, the cassette design module 324 can perform a brute force approach and iterates through all or most possible candidate cassette sequences to select the sequence with the smallest junction epitope presentation score. However, the number of such candidate cassettes can be prohibitively large as the capacity of the vaccine v increases. For example, for a vaccine capacity of v=20 epitopes, the cassette design module 324 has to iterate through ~$10^{18}$ possible candidate cassettes to determine the cassette with the lowest junction epitope presentation score. This determination may be computationally burdensome (in terms of computational processing resources required), and sometimes intractable, for the cassette design module 324 to complete within a reasonable amount of time to generate the vaccine for the patient. Moreover, accounting for the possible junction epitopes for each candidate cassette can be even more burdensome. Thus, the cassette design module 324 may select a cassette sequence based on ways of iterating through a number of candidate cassette sequences that are significantly smaller than the number of candidate cassette sequences for the brute force approach.

In one embodiment, the cassette design module 324 generates a subset of randomly or at least pseudo-randomly generated candidate cassettes, and selects the candidate cassette associated with a junction epitope presentation score below a predetermined threshold as the cassette sequence. Additionally, the cassette design module 324 may select the candidate cassette from the subset with the lowest junction epitope presentation score as the cassette sequence. For example, the cassette design module 324 may generate a subset of ~1 million candidate cassettes for a set of v=20 selected epitopes, and select the candidate cassette with the smallest junction epitope presentation score. Although generating a subset of random cassette sequences and selecting a cassette sequence with a low junction epitope presentation score out of the subset may be sub-optimal relative to the brute force approach, it requires significantly less computational resources thereby making its implementation technically feasible. Further, performing the brute force method as opposed to this more efficient technique may only result in a minor or even negligible improvement in junction epitope presentation score, thus making it not worthwhile from a resource allocation perspective.

In another embodiment, the cassette design module 324 determines an improved cassette configuration by formulating the epitope sequence for the cassette as an asymmetric traveling salesman problem (TSP). Given a list of nodes and distances between each pair of nodes, the TSP determines a sequence of nodes associated with the shortest total distance to visit each node exactly once and return to the original node. For example, given cities A, B, and C with known distances between each other, the solution of the TSP generates a closed sequence of cities, for which the total distance traveled to visit each city exactly once is the smallest among possible routes. The asymmetric version of the TSP determines the optimal sequence of nodes when the distance between a pair of nodes are asymmetric. For example, the "distance" for traveling from node A to node B may be different from the "distance" for traveling from node B to node A.

The cassette design module 324 determines an improved cassette sequence by solving an asymmetric TSP, in which each node corresponds to a therapeutic epitope $p'^k$. The distance from a node corresponding to epitope $p'^k$ to another node corresponding to epitope $p'^m$ is given by the junction epitope distance metric $d_{(k,m)}$, while the distance from the node corresponding to the epitope $p'^m$ to the node corresponding to epitope $p'^k$ is given by the distance metric $d_{(m,k)}$ that may be different from the distance metric $d_{(k,m)}$. By solving for an improved optimal cassette using an asymmetric TSP, the cassette design module 324 can find a cassette sequence that results in a reduced presentation score across the junctions between epitopes of the cassette. The solution of the asymmetric TSP indicates a sequence of therapeutic epitopes that correspond to the order in which the epitopes should be concatenated in a cassette to minimize the junction epitope presentation score across the junctions of the cassette. Specifically, given the set of therapeutic epitopes k=1, 2, . . . , v, the cassette design module 324 determines the distance metrics $d_{(k,m)}$, k,m=1, 2, . . . , v for each possible ordered pair of therapeutic epitopes in the cassette. In other words, for a given pair k, m of epitopes, both the distance metric $d_{(k,m)}$ for concatenating therapeutic epitope $p'^m$ after epitope $p'^k$ and the distance metric $d_{(m,k)}$ for concatenating therapeutic epitope $p'^k$ after epitope $p'^m$ is determined, since these distance metrics may be different from each other.

In one embodiment, the cassette design module 324 solves the asymmetric TSP through an integer linear programming problem. Specifically, the cassette design module 324 generates a (v+1)×(v+1) path matrix P given by the following:

$$P = \begin{bmatrix} 0 & 0^{1 \times v} \\ 0^{v \times 1} & D \end{bmatrix}. \tag{26}$$

The v×v matrix D is an asymmetric distance matrix, where each element D(k, m), k=1, 2, . . . , v; m=1, 2, . . . , v corresponds to the distance metric for a junction from epitope $p'^k$ to epitope $p'^m$. Rows k=2, . . . , v of P correspond to nodes of the original epitopes, while row 1 and column 1 corresponds to a "ghost node" that is at zero distance from all other nodes. The addition of the "ghost node" to the matrix encodes the notion that the vaccine cassette is linear rather than circular, so there is no junction between the first and last epitopes. In other words, the sequence is not circular, and the first epitope is not assumed to be concatenated after the last epitope in the sequence. Let $x_{km}$ denote a binary variable whose value is 1 if there is a directed path (i.e., an epitope-epitope junction in the cassette) where epitope $p'^k$ is concatenated to the N-terminus of epitope $p'^m$ and 0 otherwise. In addition, let E denote the set of all v therapeutic vaccine epitopes, and let $S \subset E$ denote a subset of epitopes. For any such subset S, let out(S) denote the number of epitope-epitope junctions $x_{km}=1$ where k is an epitope in S and m is an epitope in E\S. Given a known path matrix P, the cassette design module 324 finds a path matrix X that solves the following integer linear programming problem:

$$\min_x \sum_{k=1}^{v+1} \sum_{k \neq m, m=1}^{v+1} P_{km} \cdot x_{km} \quad (27)$$

in which $P_{km}$ denotes element P(k,m) of the path matrix P, subject to the following constraints:

$$\sum_{k=1}^{v+1} x_{km} = 1, \quad m = 1, 2, \ldots, v+1$$

$$\sum_{m=1}^{v+1} x_{km} = 1, \quad k = 1, 2, \ldots, v+1$$

$$x_{kk} = 0, \quad k = 1, 2, \ldots, v+1$$

$$out(S) \geq 1, \quad S \subset E, 2 \leq |S| \leq |V|/2$$

The first two constraints guarantee that each epitope appears exactly once in the cassette. The last constraint ensures that the cassette is connected. In other words, the cassette encoded by x is a connected linear protein sequence.

The solutions for $x_{km}$, k,m=1, 2, . . . , v+1 in the integer linear programming problem of equation (27) indicates the closed sequence of nodes and ghost nodes that can be used to infer one or more sequences of therapeutic epitopes for the cassette that lower the presentation score of junction epitopes. Specifically, a value of $x_{km}=1$ indicates that a "path" exists from node k to node m, or in other words, that therapeutic epitope $p'^m$ should be concatenated after therapeutic epitope $p'^k$ in the improved cassette sequence. A solution of $x_{km}=0$ indicates that no such path exists, or in other words, that therapeutic epitope $p'^m$ should not be concatenated after therapeutic epitope $p'^k$ in the improved cassette sequence. Collectively, the values of $x_{km}$ in the integer programming problem of equation (27) represent a sequence of nodes and the ghost node, in which the path enters and exists each node exactly once. For example, the values of $x_{ghost,1}=1$, $x_{13}=1$, $x_{32}=1$, and $x_{2,ghost}=1$ (0 otherwise) may indicate a sequence ghost→1→3→2→ghost of nodes and ghost nodes.

Once the sequence has been solved for, the ghost nodes are deleted from the sequence to generate a refined sequence with only the original nodes corresponding to therapeutic epitopes in the cassette. The refined sequence indicates the order in which selected epitopes should be concatenated in the cassette to improve the presentation score. For example, continuing from the example in the previous paragraph, the ghost node may be deleted to generate a refined sequence 1→3→2. The refined sequence indicates one possible way to concatenate epitopes in the cassette, namely $p^1 \rightarrow p^3 \rightarrow p^2$.

In one embodiment, when the therapeutic epitopes $p'^k$ are variable-length epitopes, the cassette design module 324 determines candidate distance metrics corresponding to different lengths of the therapeutic epitopes $p'^k$ and $p'^m$, and identifies the distance metric $d_{(k,m)}$ as the smallest candidate distance metric. For example, epitopes $p'^k[n^k\ p^k\ c^k]$ and $p'^m=[n^m\ p^m\ c^m]$ may each include a corresponding N- and C-terminal flanking sequence that can vary from (in one embodiment) 2-5 amino acids. Thus, the junction between epitopes $p'^k$ and $p'^m$ is associated with 16 different sets of junction epitopes based on the 4 possible length values of $n^k$ and the 4 possible length values of $c^m$ that are placed in the junction. The cassette design module 324 may determine candidate distance metrics for each set of junction epitopes, and determine the distance metric $d^{(k,m)}$ as the smallest value. The cassette design module 324 can then construct the path matrix P and solve for the integer linear programming problem in equation (27) to determine the cassette sequence.

Compared to the random sampling approach, solving for the cassette sequence using the integer programming problem requires determination of v×(v−1) distance metrics each corresponding to a pair of therapeutic epitopes in the vaccine. A cassette sequence determined through this approach can result in a sequence with significantly less presentation of junction epitopes while potentially requiring significantly less computational resources than the random sampling approach, especially when the number of generated candidate cassette sequences is large.

XI.B.2. Comparison of Junction Epitope Presentation for Cassette Sequences Generated by Random Sampling vs. Asymmetric TSP Two cassette sequences including v=20 therapeutic epitopes were generated by random sampling 1,000,000 permutations (cassette sequence $C_1$), and by solving the integer linear programming problem in equation (27) (cassette sequence $C_2$). The distance metrics, and thus, the presentation score was determined based on the presentation model described in equation (14), in which f is the sigmoid function, $x_h^i$ is the sequence of peptide $p^i$, $g_h(\bullet)$ is the neural network function, w includes the flanking sequence, the log transcripts per kilobase million (TPM) of peptide $p^i$, the antigenicity of the protein of peptide $p^i$, and the sample ID of origin of peptide $p^i$, and $g_w(\bullet)$ of the flanking sequence and the log TPM are neural network functions, respectively. Each of the neural network functions for $g_h(\bullet)$ included one output node of a one-hidden-layer multilayer perceptron (MLP) with input dimensions 231 (11 residues×21 characters per residue, including pad characters), width 256, rectified linear unit (ReLU) activations in the hidden layer, linear activations in the output layer, and one output node per HLA allele in the training data set. The neural network function for the flanking sequence was a one hidden-layer MLP with input dimension 210 (5 residues of N-terminal flanking sequence+5 residues of C-terminal flanking sequence×21 characters per residue, including the pad characters), width 32, ReLU activations in the hidden layer and linear activation in the output layer. The neural network function for the RNA log TPM was a one hidden layer MLP with input dimension 1, width 16, ReLU activations in the hidden layer and linear activation in the output layer. The presentation models were constructed for HLA alleles HLA-A*02:04, HLA-A*02:07, HLA-B*40:01, HLA-B*40:02, HLA-C*16:02, and HLA-C*16:04. The presentation score indicating the expected number of presented junction epitopes of the two cassette sequences were compared. Results showed that the presentation score for the cassette sequence generated by solving the equation of (27) was associated with a ~4 fold improvement over the presentation score for the cassette sequence generated by random sampling.

Specifically, the v=20 epitopes were given by:

(SEQ ID NO: 90)
p'[1] = YNYSYWISIFAHTMWYNIWHVQWNK (SEQ ID NO: 91)
p'[2] = IEALPYVFLQDQFELRLLKGEQGNN (SEQ ID NO: 92)
p'[3] = DSEETNTNYLHYCHFHWTWAQQTTV (SEQ ID NO: 93)
p'[4] = GMLSQYELKDCSLGFSWNDPAKYLR (SEQ ID NO: 94)
p'[5] = VRIDKFLMYVWYSAPFSAYPLYQDA (SEQ ID NO: 95)
p'[6] = CVHIYNNYPRMLGIPFSVMVSGFAM (SEQ ID NO: 96)
p'[7] = FTFKGNIWIEMAGQFERTWNYPLSL (SEQ ID NO: 97)
p'[8] = ANDDTPDFRKCYIEDHSFRFSQTMN (SEQ ID NO: 98)
p'[9] = AAQYIACMVNRQMTIVYHLTRWGMK (SEQ ID NO: 99)
p'[10] = KYLKEFTQLLTFVDCYMWITFCGPD (SEQ ID NO: 100)
p'[11] = AMHYRTDIHGYWIEYRQVDNQMWNT (SEQ ID NO: 101)
p'[12] = THVNEHQLEAVYRFHQVHCRFPYEN (SEQ ID NO: 102)
p'[13] = QTFSECLFFHCLKVWNNVKYAKSLK (SEQ ID NO: 103)
p'[14] = SFSSWHYKESHIALLMSPKKNHNNT (SEQ ID NO: 104)
p'[15] = ILDGIMSRWEKVCTRQTRYSYCQCA (SEQ ID NO: 105)
p'[16] = YRAAQMSKWPNKYFDFPEFMAYMPI (SEQ ID NO: 106)
p'[17] = PRPGMPCQHHNTHGLNDRQAFDDFV (SEQ ID NO: 107)
p'[18] = HNIISDETEVWEQAPHITWVYMWCR (SEQ ID NO: 108)
p'[19] = AYSWPVVPMKWIPYRALCANHPPGT (SEQ ID NO: 109)
p'[20] = HVMPHVAMNICNWYEFLYRISHIGR.

In the first example, 1,000,000 different candidate cassette sequences were randomly generated with the 20 therapeutic epitopes. The presentation score was generated for each of the candidate cassette sequences. The candidate cassette sequence identified to have the lowest presentation score was:

(SEQ ID NO: 110)
$C_1$ = THVNEHQLEAVYRFHQVHCRFPYENAMHYQMWNTYRAAQMSKWPN

KYFDFPEFMAYMPICVHIYNNYPRMLGIPFSVMVSGFAMAYSWPVVPMKW

IPYRALCANHPPGTANDDTPDFRKCYIEDHSFRFSQTMNIEALPYVFLQD

QFELRLLKGEQGNNDSEETNTNYLHYCHFHWTWAQQTTVILDGIMSRWEK

-continued

VCTRQTRYSYCQCAFTFKGNIWIEMAGQFERTWNYPLSLSFSSWHYKESH

IALLMSPKKNHNNTQTFSECLFFHCLKVWNNVKYAKSLKHVMPHVAMNIC

NWYEFLYRISHIGRHNIISDETEVWEQAPHITWVYMWCRVRIDKFLMYVW

YSAPFSAYPLYQDAKYLKEFTQLLTFVDCYMWITFCGPDAAQYIACMVNR

QMTIVYHLTRWGMKYNYSYWISIFAHTMWYNIWHVQWNKGMLSQYELKDC

SLGFSWNDPAKYLRPRPGMPCQHHNTHGLNDRQAFDDFV with a presentation score of 6.1 expected number of presented junction epitopes. The median presentation score of the 1,000,000 random sequences was 18.3. The experiment shows that the expected number of presented junction epitopes can be significantly reduced by identifying a cassette sequence among randomly sampled cassettes.

In the second example, a cassette sequence $C_2$ was identified by solving the integer linear programming problem in equation (27). Specifically, the distance metric of each potential junction between a pair of therapeutic epitopes was determined. The distance metrics were used to solve for the solution to the integer programming problem. The cassette sequence identified by this approach was:

(SEQ ID NO: 111)
$C_2$ = IEALPYVFLQDQFELRLLKGEQGNNILDGIMSRWEKVCTRQTRYS

YCQCAHVMPHVAMNICNWYEFLYRISHIGRTHVNEHQLEAVYRFHQVHCR

FPYENFTFKGNIWIEMAGQFERTWNYPLSLAMHYQMWNTSFSSWHYKESH

IALLMSPKKNHNNTVRIDKFLMYVWYSAPFSAYPLYQDAQTFSECLFFHC

LKVWNNVKYAKSLKYRAAQMSKWPNKYFDFPEFMAYMPIAYSWPVVPMKW

IPYRALCANHPPGTCVHIYNNYPRMLGIPFSVMVSGFAMHNIISDETEVW

EQAPHITWVYMWCRAAQYIACMVNRQMTIVYHLTRWGMKYNYSYWISIFA

HTMWYNIWHVQWNKGMLSQYELKDCSLGFSWNDPAKYLRKYLKEFTQLLT

FVDCYMWITFCGPDANDDTPDFRKCYIEDHSFRFSQTMNDSEETNTNYLH

YCHFHWTWAQQTTVPRPGMPCQHHNTHGLNDRQAFDDFV with a presentation score of 1.7. The presentation score of cassette sequence $C_2$ showed a ~4 fold improvement over the presentation score of cassette sequence $C_1$, and a ~11 fold improvement over the median presentation score of the 1,000,000 randomly generated candidate cassettes. The runtime for generating cassette $C_1$ was 20 seconds on a single thread of a 2.30 GHz Intel Xeon E5-2650 CPU. The runtime for generating cassette $C_2$ was 1 second on a single thread of the same CPU. Thus in this example, the cassette sequence identified by solving the integer programming problem of equation (27) produces a ~4-fold better solution at 20-fold reduced computational cost.

The results show that the integer programming problem can potentially provide a cassette sequence with a lower number of presented junction epitopes than one identified from random sampling, potentially with less computation resources.

XI.B.3. Comparison of Junction Epitope Presentation for Cassette Sequence Selection Generated by MHCflurry and the Presentation Model In this example, cassette sequences including v=20 therapeutic epitopes were selected based off tumor/normal exome sequencing, tumor transcriptome sequencing and HLA typing of a lung cancer sample were generated by random sampling 1,000,000 permutations, and by solving the integer linear programming problem in equation (27). The distance metrics, and thus, the presentation score were determined based on the number of junction epitopes predicted by MHCflurry, an HLA-peptide binding affinity predictor, to bind the patient's HLAs with affinity below a variety of thresholds (e.g., 50-1000 nM, or higher, or lower). In this example, the 20 nonsynoymous somatic mutations chosen as therapeutic epitopes were selected from among the 98 somatic mutations identified in the tumor sample by ranking the mutations according to the presentation model in Section XI.B above. However, it is appreciated that in other embodiments, the therapeutic epitopes may be selected based on other criteria; such as those based stability, or combinations of criteria such as presentation score, affinity, and so on. In addition, it is appreciated that the criteria used for prioritizing therapeutic epitopes for inclusion in the vaccine need not be the same as the criteria used for determining the distance metric D(k, m) used in the cassette design module 324.

The patient's HLA class I alleles were HLA-A*01:01, HLA-A*03:01, HLA-B*07:0 2, HLA-B*35:03, HLA-C*07: 02, HLA-C*14:02.

Specifically in this example, the v=20 therapeutic epitopes were

SSTPYLYYGTSSVSYQFPMVPGGDR (SEQ ID NO: 112)

EMAGKIDLLRDSYIFQLFWREAAEP (SEQ ID NO: 113)

ALKQRTWQALAHKYNSQPSVSLRDF (SEQ ID NO: 114)

VSSHSSQATKDSAVGLKYSASTPVR (SEQ ID NO: 115)

KEAIDAWAPYLPEYIDHVISPGVTS (SEQ ID NO: 116)

SPVITAPPSSPVFDTSDIRKEPMNI (SEQ ID NO: 117)

PAEVAEQYSEKLVYMPHTFFIGDHA (SEQ ID NO: 118)

MADLDKLNIHSIIQRLLEVRGS (SEQ ID NO: 119)

AAAYNEKSGRITLLSLLFQKVFAQI (SEQ ID NO: 120)

KIEEVRDAMENEIRTQLRRQAAAHT (SEQ ID NO: 121)

DRGHYVLCDFGSTTNKFQNPQTEGV (SEQ ID NO: 122)

QVDNRKAEAEEAIKRLSYISQKVSD (SEQ ID NO: 123)

CLSDAGVRKMTAAVRVMKRGLENLT (SEQ ID NO: 124)

LPPRSLPSDPFSQVPASPQSQSSSQ (SEQ ID NO: 125)

ELVLEDLQDGDVKMGGSFRGAFSNS (SEQ ID NO: 126)

VTMDGVREEDLASFSLRKRWESEPH (SEQ ID NO: 127)

IVGVMFFERAFDEGADAIYDHINEG (SEQ ID NO: 128)

TVTPTPTPTGTQSPTPTPITTTTTV (SEQ ID NO: 129)

QEEMPPRPCGGHTSSSLPKSHLEPS (SEQ ID NO: 130)

PNIQAVLLPKKTDSHHKAKGK (SEQ ID NO: 131)

Results from this example in the table below compare the number of junction epitopes predicted by MHCflurry to bind the patient's HLAs with affinity below the value in the threshold column (where nM stands for nanoMolar) as found via three example methods. For the first method, the optimal cassette found via the traveling salesman problem (ATSP) formulation described above with is run-time. For the second method, the optimal cassette as determined by taking the best cassette found after 1 million random samples. For the third method, the median number of junction epitopes was found in the 1 million random samples.

| Threshold (nM) | ATSP # Binding Junction Epitopes | Random Sampling # Binding Junction Epitopes | Median # Binding Junction Epitopes |
|---|---|---|---|
| 50 | 0 | 0 | 3 |
| 100 | 0 | 0 | 7 |
| 150 | 0 | 1 | 12 |
| 500 | 15 | 26 | 55 |
| 1000 | 68 | 91 | 131 |

The results of this example illustrate that any one of a number of criteria may be used to identify whether or not a given cassette design meets design requirements. Specifically, as demonstrated by prior examples, the selected cassette sequence out of many candidates may be specified by the cassette sequence having a lowest junction epitope presentation score, or at least such a score below an identified threshold. This example represents that another criteria, such as binding affinity, may be used to specify whether or not a given cassette design meets design requirements. For this criteria, a threshold binding affinity (e.g., 50-1000, or greater or lower) may be set specifying that the cassette design sequence should have fewer than some threshold number of junction epitopes above the threshold (e.g., 0), and any one of a number of methods may be used (e.g., methods one through three illustrated in the table) can be used to identify if a given candidate cassette sequence meets those requirements. These example methods further illustrate that depending on the method used, the thresholds may need to be set differently. Other criteria may be envisioned, such as those based stability, or combinations of criteria such as presentation score, affinity, and so on.

In another example, the same cassettes were generated using the same HLA type and 20 therapeutic epitopes from earlier in this section (XI.C), but instead of using distance metrics based off binding affinity prediction, the distance metric for epitopes m, k was the number of peptides spanning them to k junction predicted to be presented by the patient's HLA class I alleles with probability of presentation above a series of thresholds (between probability of 0.005 and 0.5, or higher, or lower), where the probabilities of presentation were determined by the presentation model in Section XI.B above. This example further illustrates the breadth of criteria that may be considered in identifying whether a given candidate cassette sequence meets design requirements for use in the vaccine.

| Threshold (probability) | ATSP # Junction Epitopes | Random Sampling # Junction Epitopes | Median # Junction Epitopes |
|---|---|---|---|
| 0.005 | 58 | 79 | 118 |
| 0.01 | 39 | 59 | 93 |
| 0.05 | 7 | 33 | 47 |
| 0.1 | 5 | 14 | 35 |
| 0.2 | 1 | 8 | 25 |
| 0.5 | 0 | 2 | 14 |

The examples above have identified that the criteria for determining whether a candidate cassette sequence may vary by implementation. Each of these examples has illustrated that the count of the number of junction epitopes falling above or below the criteria may be a count used in determining whether the candidate cassette sequence meets that criteria. For example, if the criteria is number of epitopes meeting or exceeding a threshold binding affinity for HLA, whether the candidate cassette sequence has greater or fewer than that number may determine whether the candidate cassette sequence meets the criteria for use as the selected cassette for the vaccine. Similarly if the criteria is the number of junction epitopes exceeding a threshold presentation likelihood.

However, in other embodiments, calculations other than counting can be performed to determine whether a candidate cassette sequence meets the design criteria. For example, rather than the count of epitopes exceeding/falling below some threshold, it may instead be determined what proportion of junction epitopes exceed or fall below the threshold, for example whether the top X % of junction epitopes have a presentation likelihood above some threshold Y, or whether X % percent of junction epitopes have an HLA binding affinity less than or greater than Z nM. These are merely examples, generally the criteria may be based on any attribute of either individual junction epitopes, or statistics derived from aggregations of some or all of the junction epitopes. Here, X can generally be any number between 0 and 100% (e.g., 75% or less) and Y can be any value between 0 and 1, and Z can be any number suitable to the criteria in question. These values may be determined empirically, and depend on the models and criteria used, as well as the quality of the training data used.

As such, in certain aspects, junction epitopes with high probabilities of presentation can be removed; junction epitopes with low probabilities of presentation can be retained; junction epitopes that bind tightly, i.e., junction epitopes with binding affinity below 1000 nM or 500 nM or some other threshold can be removed; and/or junction epitopes that bind weakly, i.e., junction epitopes with binding affinity above 1000 nM or 500 nM or some other threshold can be retained.

Although the examples above have identified candidate sequences using an implementation of the presentation model described above, these principles apply equally to an implementation where the epitopes for arrangement in the cassette sequences are identified based on other types of models as well, such as those based on affinity, stability, and so on.

XII. Example 7: Experimentation Results Showing Example Presentation Model Performance The validity of the various presentation models described above were tested on test data T that were subsets of training data 170 that were not used to train the presentation models or a separate dataset from the training data 170 that have similar variables and data structures as the training data 170.

A relevant metric indicative of the performance of a presentation models is:

$$\text{Positive Predictive Value } (PPV) = P(y_{i \in T} = 1 \mid u_{i \in T} \geq t) = \frac{\sum_{i \in T} \mathbb{1}(y_i = 1, u_i \geq t)}{\sum_{i \in T} \mathbb{1}(u_i \geq t)}$$

that indicates the ratio of the number of peptide instances that were correctly predicted to be presented on associated HLA alleles to the number of peptide instances that were predicted to be presented on the HLA alleles. In one implementation, a peptide $p^i$ in the test data T was predicted to be presented on one or more associated HLA alleles if the corresponding likelihood estimate $u_i$ is greater or equal to a given threshold value t. Another relevant metric indicative of the performance of presentation models is:

$$\text{Recall} = P(u_{i \in T} \geq t \mid y_{i \in T} = 1) = \frac{\sum_{i \in T} \mathbb{1}(y_i = 1, u_i \geq t)}{\sum_{i \in T} \mathbb{1}(y_i = 1)}$$

that indicates the ratio of the number of peptide instances that were correctly predicted to be presented on associated HLA alleles to the number of peptide instances that were known to be presented on the HLA alleles. Another relevant metric indicative of the performance of presentation models is the area-under-curve (AUC) of the receiver operating characteristic (ROC). The ROC plots the recall against the false positive rate (FPR), which is given by:

$$FPR = P(u_{i \in T} \geq t \mid y_{i \in T} = 0) = \frac{\sum_{i \in T} \mathbb{1}(y_i = 0, u_i \geq t)}{\sum_{i \in T} \mathbb{1}(y_i = 0)}.$$

Figure 13A:
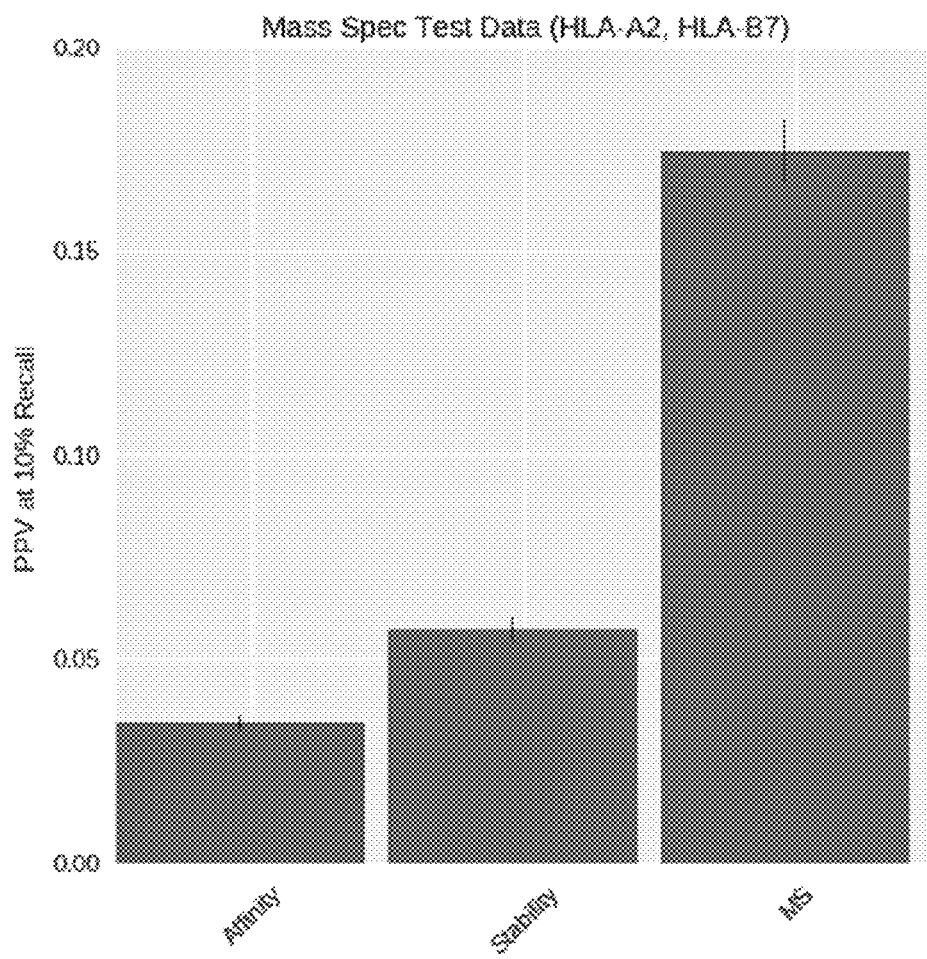
FIG. 13A shows performance results for peptide presentation determined by mass-spectrometry comparing various peptide presentation models. Shown are result for the maximum of per-alleles presentation model shown in equation (12) using the affine dependency function $g_h(•)$ and the expit function $f(•)$ and trained on a subset of mass spectrometry data for HLA-A*02:01 and HLA-B*07:02 ("MS"). Also shown are state-of-the-art models based on affinity predictions NETMHCpan "Affinity" and based on stability predictions NETMHCstab "Stability." The data shows the positive predictive value (PPV) at a 10% recall rate, and error bars (as indicated in solid lines) show 95% confidence intervals.

XII.A. Comparison of Presentation Model Performance on Mass Spectrometry Data Against State-of-the-Art Model FIG. 13A compares performance results of an example presentation model, as presented herein, and state-of-the-art models for predicting peptide presentation on multiple-allele mass spectrometry data. Results showed that the example presentation model performed significantly better at predicting peptide presentation than state-of-the-art models based on affinity and stability predictions.

Specifically, the example presentation model shown in FIG. 13A as "MS" was the maximum of per-alleles presentation model shown in equation (12), using the affine dependency function $g_h(\cdot)$ and the expit function $f(\cdot)$. The example presentation model was trained based on a subset of the single-allele HLA-A*02:01 mass spectrometry data from the IEDB data set (data set "D1") (data can be found at http://www.iedb.org/doc/mhc_ligand_full.zip) and a subset of the single-allele HLA-B*07:02 mass spectrometry from the IEDB data set (data set "D2") (data can be found at http://www.iedb.org/doc/mhc_ligand_full.zip). All peptides from source protein that contain presented peptides in the test set were eliminated from the training data such that the example presentation model could not simply memorize the sequences of presented antigens.

The model shown in FIG. 13A as "Affinity" was a model similar to the current state-of-the-art model that predicts peptide presentation based on affinity predictions NETMHCpan. Implementation of NETMHCpan is provided in detail at http://www.cbs.dtu.dk/services/NetMHCpan/. The model shown in FIG. 13A as "Stability" was a model similar to the current state-of-the-art model that predicts peptide presentation based on stability predictions NETMHCstab. Implementation of NETMHCstab is provided in detail at http://www.cbs.dtu.dk/services/NetMHCstab-1.0/. The test data that is a subset of the multiple-allele JY cell line HLA-A*02:01 and HLA-B*07:02 mass spectrometry data from the Bassani-Sternberg data set (data set "D3") (data can be found at www.ebi.ac.uk/pride/archive/projects/PXD000394). The error bars (as indicated in solid lines) show 95% confidence intervals.

As shown in the results of FIG. 13A, the example presentation model trained on mass spectrometry data had a significantly higher PPV value at 10% recall rate relative to the state-of-the-art models that predict peptide presentation based on MHC binding affinity predictions or MHC binding stability predictions. Specifically, the example presentation model had approximately 14% higher PPV than the model based on affinity predictions, and had approximately 12% higher PPV than the model based on stability predictions.

These results demonstrate that the example presentation model had significantly better performance than the state-of-the-art models that predict peptide presentation based on MHC binding affinity or MHC binding stability predictions even though the example presentation model was not trained based on protein sequences that contained presented peptides.

Figure 13B:
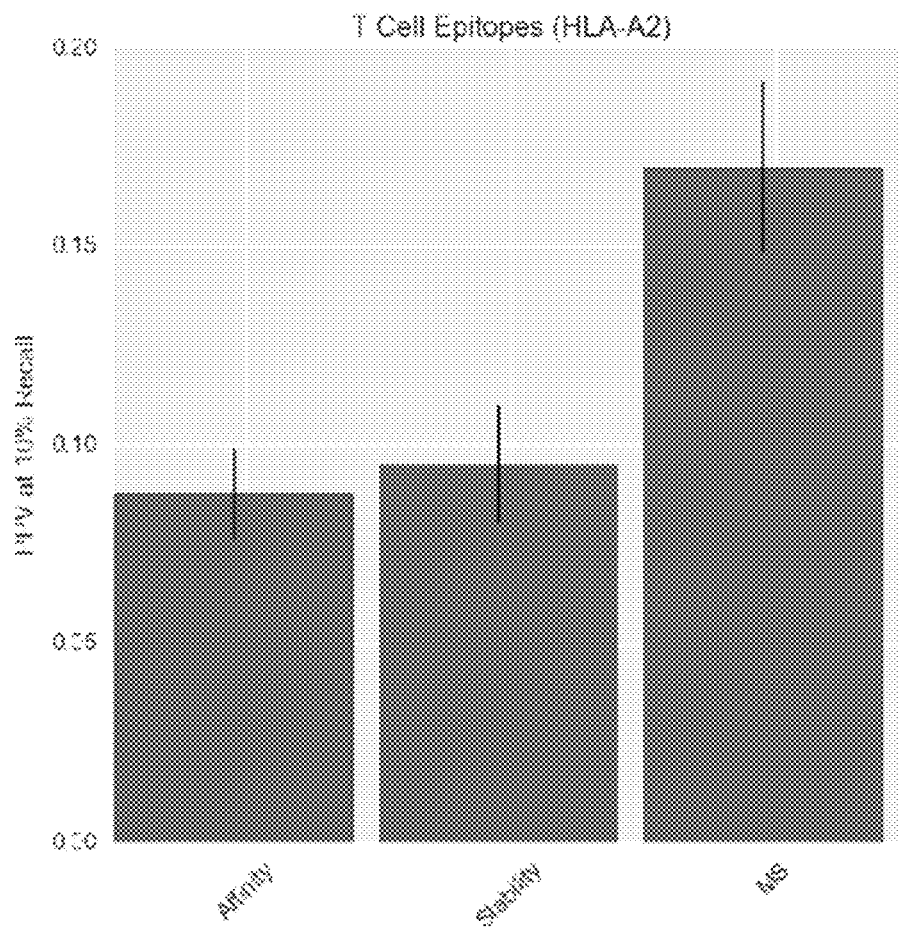
FIG. 13B shows performance results for peptide presentation determined by T-cell epitopes comparing various peptide presentation models. Shown are results for the maximum of per-alleles presentation model shown in equation (12) using the affine dependency function $g_h(•)$ and the expit function $f(•)$ and trained on a subset of mass spectrometry data for HLA-A*02:01. Also shown are state-of-the-art models based on affinity predictions NETMHCpan "Affinity" and based on stability predictions NETMHCstab "Stability." The data shows the positive predictive value (PPV) at a 10% recall rate, and error bars (as indicated in solid lines) show 95% confidence intervals.

XII.B. Comparison of Presentation Model Performance on T-Cell Epitope Data Against State-of-the-Art Models FIG. 13B compares performance results of another example presentation model, as presented herein, and state-of-the-art models for predicting peptide presentation on T-cell epitope data. T-cell epitope data contains peptide sequences that were presented by MHC alleles on the cell surface, and recognized by T-cells. Results showed that even though the example presentation model is trained based on mass spectrometry data, the example presentation model performed significantly better at predicting T-cell epitopes than state-of-the-art models based on affinity and stability predictions. In other words, the results of FIG. 13B indicated that not only did the example presentation model perform better than state-of-the-art models at predicting peptide presentation on mass spectrometry test data, but the example presentation model also performed significantly better than state-of-the-art models at predicting epitopes that were actually recognized by T-cells. This is an indication that the variety of presentation models as presented herein can provide improved identification of antigens that are likely to induce immunogenic responses in the immune system.

Specifically, the example presentation model shown in FIG. 13B as "MS" was the per-allele presentation model shown in equation (2), using the affine transformation function $g_h(\bullet)$ and the expit function $f(\bullet)$ that was trained based on a subset of data set D1. All peptides from source protein that contain presented peptides in the test set were eliminated from the training data such that the presentation model could not simply memorize the sequences of presented antigens.

Each of the models were applied to the test data that is a subset of mass spectrometry data on HLA-A*02:01 T-cell epitope data (data set "D4") (data can be found at www.iedb.org/doc/tcell full v3.zip). The model shown in FIG. 13B as "Affinity" was a model similar to the current state-of-the-art model that predicts peptide presentation based on affinity predictions NETMHCpan, and the model shown in FIG. 13B as "Stability" was a model similar to the current state-of-the-art model that predicts peptide presentation based on stability predictions NETMHCstab. The error bars (as indicated in solid lines) show 95% confidence intervals.

As shown in the results of FIG. 13A, the per-allele presentation model trained on mass spectrometry data had a significantly higher PPV value at 10% recall rate than the state-of-the-art models that predict peptide presentation based on MHC binding affinity or MHC binding stability predictions even though the presentation model was not trained based on protein sequences that contained presented peptides. Specifically, the per-allele presentation model had approximately 9% higher PPV than the model based on affinity predictions, and had approximately 8% higher PPV than the model based on stability predictions.

These results demonstrated that the example presentation model trained on mass spectrometry data performed significantly better than state-of-the-art models on predicting epitopes that were recognized by T-cells.

XII.C. Comparison of Different Presentation Model Performances on Mass Spectrometry Data FIG. 13C compares performance results for an example function-of-sums model (equation (13)), an example sum-of-functions model (equation (19)), and an example second order model (equation (23)) for predicting peptide presentation on multiple-allele mass spectrometry data. Results showed that the sum-of-functions model and second order model performed better than the function-of-sums model. This is because the function-of-sums model implies that alleles in a multiple-allele setting can interfere with each other for peptide presentation, when in reality, the presentation of peptides are effectively independent.

Specifically, the example presentation model labeled as "sigmoid-of-sums" in FIG. 13C was the function-of-sums model using a network dependency function $g_h(\bullet)$ the identity function $f(\bullet)$, and the expit function $r(\bullet)$. The example model labeled as "sum-of-sigmoids" was the sum-of-functions model in equation (19) with a network dependency function $g_h(\bullet)$, the expit function $f(\bullet)$, and the identity function $r(\bullet)$. The example model labeled as "hyperbolic tangent" was the sum-of-functions model in equation (19) with a network dependency function $g_h(\bullet)$, the expit function $f(\bullet)$, and the hyperbolic tangent function $r(\bullet)$. The example model labeled as "second order" was the second order model in equation (23) using an implicit per-allele presentation likelihood form shown in equation (18) with a network dependency function $g_h(\bullet)$ and the expit function $f(\bullet)$. Each model was trained based on a subset of data set D1, D2, and D3. The example presentation models were applied to a test data that is a random subset of data set D3 that did not overlap with the training data.

As shown in FIG. 13C, the first column refers to the AUC of the ROC when each presentation model was applied to the test set, the second column refers to the value of the negative log likelihood loss, and the third column refers to the PPV at 10% recall rate. As shown in FIG. 13C, the performance of presentation models "sum-of-sigmoids," "hyperbolic tangent," and "second order" were approximately tied at approximately 15-16% PPV at 10% recall, while the performance of the model "sigmoid-of-sums" was slightly lower at approximately 11%.

As discussed previously in section X.C.4., the results showed that the presentation models "sum-of-sigmoids," "hyperbolic tangent," and "second order" have high values of PPV compared to the "sigmoid-of-sums" model because the models correctly account for how peptides are presented independently by each MHC allele in a multiple-allele setting.

XII.D. Comparison of Presentation Model Performance with and without Training on Single-Allele Mass Spectrometry Data FIG. 13D compares performance results for two example presentation models that are trained with and without single-allele mass spectrometry data on predicting peptide presentation for multiple-allele mass spectrometry data. The results indicated that example presentation models that are trained without single-allele data achieve comparable performance to that of example presentation models trained with single-allele data.

The example model "with A2/B7 single-allele data" was the "sum-of-sigmoids" presentation model in equation (19) with a network dependency function $g_h(\cdot)$ the expit function $f(\cdot)$, and the identity function $r(\cdot)$. The model was trained based on a subset of data set D3 and single-allele mass spectrometry data for a variety of MHC alleles from the IEDB database (data can be found at: http://www.iedb.org/doc/mhc_ligand_full.zip). The example model "without A2/B7 single-allele data" was the same model, but trained based on a subset of the multiple-allele D3 data set without single-allele mass spectrometry data for alleles HLA-A*02:01 and HLA-B*07:02, but with single-allele mass spectrometry data for other alleles. Within the multiple-allele training data, cell line HCC1937 expressed HLA-B*07:02 but not HLA-A*02:01, and cell line HCT116 expressed HLA-A*02:01 but not HLA-B*07:02. The example presentation models were applied to a test data that was a random subset of data set D3 and did not overlap with the training data.

As shown in FIG. 13D, the predictions based on the implicit per-allele presentation likelihoods for MHC allele HLA-A*02:01 performed significantly better on single-allele test data for MHC allele HLA-A*02:01 rather than for MHC allele HLA-B*07:02. Similar results are shown for MHC allele HLA-B*07:02.

These results indicate that the implicit per-allele presentation likelihoods of the presentation model can correctly predict and distinguish binding motifs to individual MHC alleles, even though direct association between the peptides and each individual MHC allele was not known in the training data.

XII.E. Comparison of Per-Allele Prediction Performance without Training on Single-Allele Mass Spectrometry Data FIG. 13E shows performance for the "without A2/B7 single-allele data" and "with A2/B7 single-allele data" example models shown in FIG. 13D on single-allele mass spectrometry data for alleles HLA-A*02:01 and HLA-B*07:02 that were held out in the analysis shown in FIG. 13D. Results indicate that even through the example presentation model is trained without single-allele mass spectrometry data for these two alleles, the model is able to learn binding motifs for each MHC allele.

The column "Correlation" refers to the correlation between the actual labels that indicate whether the peptide was presented on the corresponding allele in the test data, and the label for prediction. As shown in FIG. 13E, "A2 model predicting B7" indicates the performance of the model when peptide presentation is predicted for single-allele HLA-B*07:02 data based on the implicit per-allele presentation likelihood estimate for MHC allele HLA-A*02:01. Similarly, "A2 model predicting A2" indicates the performance of the model when peptide presentation is predicted for single-allele HLA-A*02:01 based on the implicit per-allele presentation likelihood estimate for MHC allele HLA-A*02:01. "B7 model predicting B7" indicates the performance of the model when peptide presentation is predicted for single-allele HLA-B*07:02 data based on the implicit per-allele presentation likelihood estimate for MHC allele HLA-B*07:02. "B7 model predicting A2" indicates the performance of the model when peptide presentation is predicted for single-allele HLA-A*02:01 based on the implicit per-allele presentation likelihood estimate for MHC allele HLA-B*07:02.

As shown in FIG. 13E, the predictive capacity of implicit per-allele likelihoods for an HLA allele is significantly higher for the intended allele, and significantly lower for the other HLA allele. Similarly to the results shown in FIG. 13D, the example presentation models correctly learned to differentiate peptide presentation of individual alleles HLA-A*02:01 and HLA-B*07:02, even though direct association between peptide presentation and these alleles were not present in the multiple-allele training data.

XII.F. Frequently Ocurring Anchor Residues in Per-Allele Predictions Match Known Canonical Anchor Motifs FIG. 13F shows the common anchor residues at positions 2 and 9 among nonamers predicted by the "without A2/B7 single-allele data" example model shown in FIG. 13D. The peptides were predicted to be presented if the estimated likelihood was above 5%. Results show that most common anchor residues in the peptides identified for presentation on the MHC alleles HLA-A*02:01 and HLA-B*07:02 matched previously known anchor motifs for these MHC alleles. This indicates that the example presentation models correctly learned peptide binding based on particular positions of amino acids of the peptide sequences, as expected.

As shown in FIG. 13F, amino acids L/M at position 2 and amino acids V/L at position 9 were known to be canonical anchor residue motifs (as shown in Table 4 of https://link.springer.com/article/10.1186/1745-7580-4-2) for HLA-A*02:01, and amino acid P at position 2 and amino acids L/V at position 9 were known to be canonical anchor residue motifs for HLA-B*07:02. The most common anchor residue motifs at positions 2 and 9 for peptides identified the model matched the known canonical anchor residue motifs for both HLA alleles.

XII.G. Comparison of Presentation Model Performances with and without Allele Noninteracting Variables FIG. 13G compares performance results between an example presentation model that incorporated C- and N-terminal flanking sequences as allele-interacting variables, and an example presentation model that incorporated C- and N-terminal flanking sequences as allele-noninteracting variables. Results showed that incorporating C- and N-terminal flanking sequences as allele noninteracting variables significantly improved model performance. More specifically, it is valuable to identify appropriate features for peptide presentation that are common across different MHC alleles, and model them such that statistical strength for these allele-noninteracting variables are shared across MHC alleles to improve presentation model performance.

The example "allele-interacting" model was the sum-of-functions model using the form of implicit per-allele presentation likelihoods in equation (22) that incorporated C- and N-terminal flanking sequences as allele-interacting variables, with a network dependency function $g_h(\cdot)$ and the expit function $f(\cdot)$. The example "allele-noninteracting" model was the sum-of-functions model shown in equation (21) that incorporated C- and N-terminal flanking sequences as allele-noninteracting variables, with a network dependency function $g_h(\cdot)$ and the expit function $f(\cdot)$. The allele-noninteracting variables were modeled through a separate network dependency function $g_w(\cdot)$. Both models were trained on a subset of data set D3 and single-allele mass spectrometry data for a variety of MHC alleles from the IEDB database (data can be found at: http://www.iedb.org/doc/mhc_ligand_full.zip). Each of the presentation models was applied to a test data set that is a random subset of data set D3 that did not overlap with the training data.

As shown in FIG. 13G, incorporating C- and N-terminal flanking sequences in the example presentation model as allele-noninteracting variables achieved an approximately 3% improvement in PPV value relative to modeling them as allele-interacting variables. This is because, in general, the "allele-noninteracting" example presentation model was able to share statistical strength of allele-noninteracting variables across MHC alleles by modeling the effect with a separate network dependency function with very little addition in computing power.

XII.H. Dependency Between Presented Peptides and mRNA Quantification

Figure 13H:
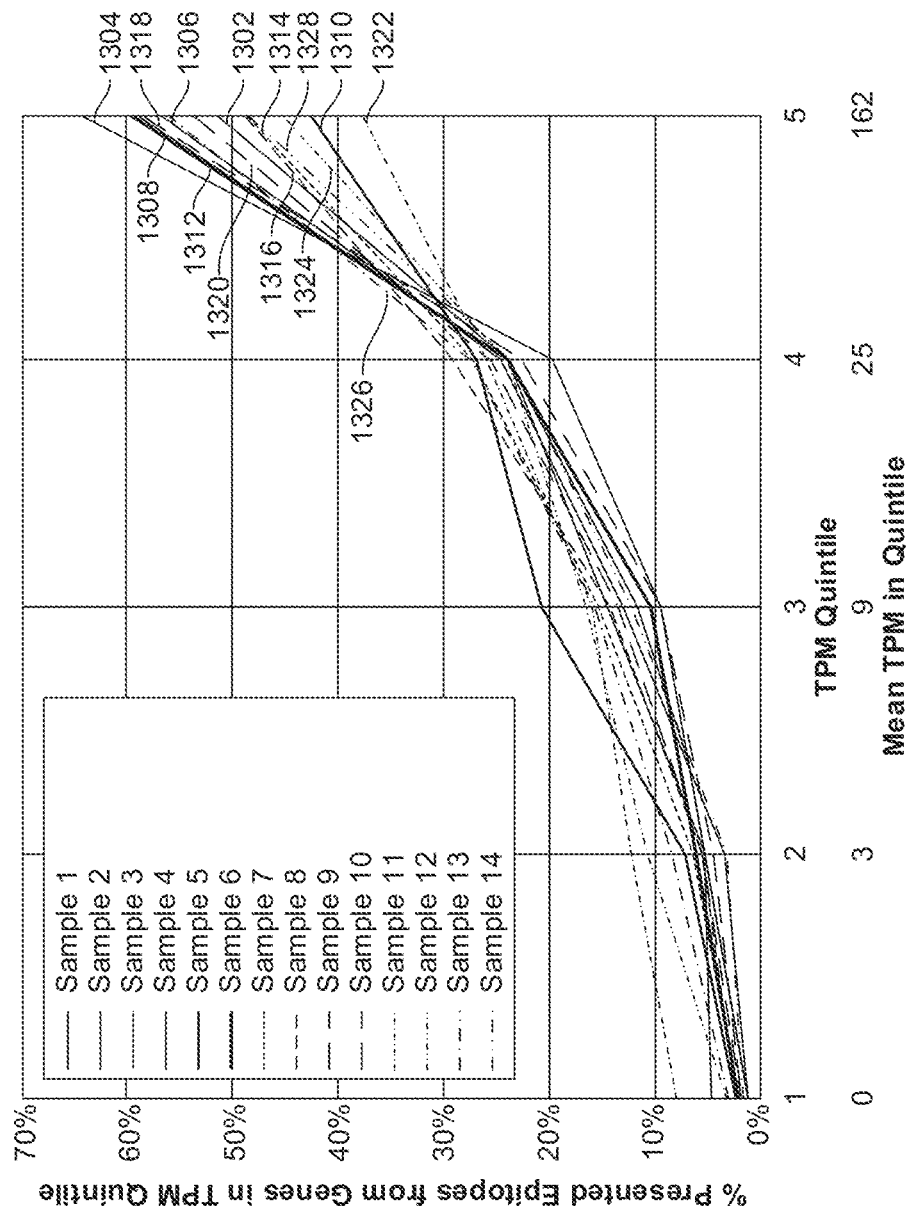
FIG. 13H shows the dependency between mRNA abundance and the frequency of peptides presented on a tumor cell as determined by mass-spectrometry. The horizontal axis indicates mRNA expression in terms of transcripts per million (TPM) quartiles. The vertical axis indicates fraction of presented epitopes from genes in corresponding mRNA expression quartiles. Each solid line is a plot relating the two measurements from a tumor sample that is associated with corresponding mass spectrometry data and mRNA expression measurements.

FIG. 13H shows the dependency between mRNA abundance and the frequency of peptides presented on a tumor cell as determined by mass-spectrometry. Results show that there is a strong dependency between mRNA expression and peptide presentation.

Specifically, the horizontal axis in FIG. 13H indicates mRNA expression in terms of transcripts per million (TPM) quartiles. The vertical axis in FIG. 13H indicates fraction of presented epitopes from genes in corresponding mRNA expression quartiles. Each solid line is a plot relating the two measurements from a tumor sample that is associated with corresponding mass spectrometry data and mRNA expression measurements. As shown in FIG. 13H, there is a strong positive correlation between mRNA expression, and the fraction of peptides in the corresponding gene. Specifically, peptides from genes in the top quartile of RNA expression are more than 20 times likely to be presented than the bottom quartile. Moreover, essentially 0 peptides are presented from genes that are not detected through RNA.

The results indicate that the performance of the presentation model can be greatly improved by incorporating mRNA quantification measurements, as these measurements are strongly predictive of peptide presentation.

Figure 13I:
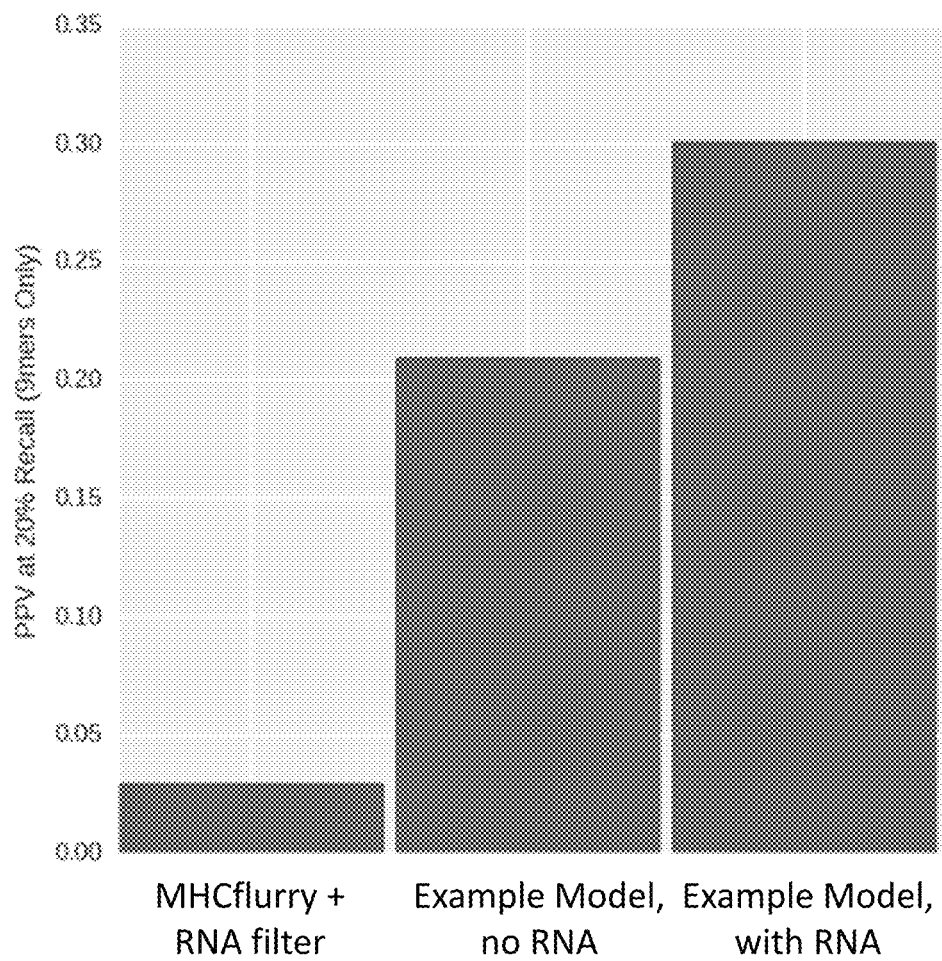
FIG. 13I shows performance performance results for peptide presentation determined by mass-spectrometry for example presentation models"MHCflurry+RNA filter" is a model similar to the current state-of-the-art model that predicts peptide presentation based on affinity predictions with a standard gene expression filter that removed all peptides from proteins with mRNA quantification measurements that were less than 3.2 FPKM. The "Example Model, no RNA" model is the "sum-of-sigmoids" example presentation model shown in equation (21). The "Example Model, with RNA" model is the "sum-of-sigmoids" presentation model shown in equation (19) incorporating mRNA quantification data through a log function. The data shows the positive predictive value (PPV) at a 20% recall rate.

XII.I. Comparison of Presentation Model Performance with Incorporation of RNA Quantification Data FIG. 13I shows performance of two example presentation models, one of which is trained based on mass spectrometry tumor cell data, another of which incorporates mRNA quantification data and mass spectrometry tumor cell data. As expected from FIG. 13H, results indicated that there is a significant improvement in performance by incorporating mRNA quantification measurements in the example presentation model, since the mRNA expression is a strong indicator of peptide presentation.

"MHCflurry+RNA filter" was a model similar to the current state-of-the-art model that predicts peptide presentation based on affinity predictions. It was implemented using MHCflurry along with a standard gene expression filter that removed all peptides from proteins with mRNA quantification measurements that were less than 3.2 FPKM. Implementation of MHCflurry is provided in detail at https://github.com/hammerlab/mhcflurry/, and at http://biorxiv.org/content/early/2016/05/22/054775. The "Example Model, no RNA" model was the "sum-of-sigmoids" example presentation model shown in equation (21) with the network dependency function $g_h(\cdot)$ the network dependency function $g_w(\cdot)$, and the expit function $f(\cdot)$. The "Example Model, no RNA" model incorporated C-terminal flanking sequences as allele-noninteracting variables through a network dependency function $g_w(\cdot)$.

The "Example Model, with RNA" model was the "sum-of-sigmoids" presentation model shown in equation (19) with network dependency function $g_h(\cdot)$ the network dependency function $g_w(\cdot)$ in equation (10) incorporating mRNA quantification data through a log function, and the expit function $f(\cdot)$. The "Example Model, with RNA" model incorporated C-terminal flanking sequences as allele-noninteracting variables through the network dependency functions $g_w(\cdot)$ and incorporated mRNA quantification measurements through the log function.

Each model was trained on a combination of the single-allele mass spectrometry data from the IEDB data set, 7 cell lines from the multiple-allele mass spectrometry data from the Bassani-Sternberg data set, and 20 mass spectrometry tumor samples. Each model was applied to a test set including 5,000 held-out proteins from 7 tumor samples that constituted 9,830 presented peptides from a total of 52,156,840 peptides.

As shown in the first two bar graphs of FIG. 13I, the "Example Model, no RNA" model has a PPV value at 20% Recall of 21%, while that of the state-of-the-art model is approximately 3%, This indicates an initial performance improvement of 18% in PPV value, even without the incorporation of mRNA quantification measurements. As shown in the third bar graph of FIG. 13I, the "Example Model, with RNA" model that incorporates mRNA quantification data into the presentation model shows a PPV value of approximately 30%, which is almost a 10% increase in performance compared to the example presentation model without mRNA quantification measurements.

Thus, results indicate that as expected from the findings in FIG. 13H, mRNA expression is indeed a strong predictor of peptide prediction, that allows significant improvement in the performance of a presentation model with very little addition of computational complexity.

XII.J. Example of Parameters Determined for MHC Allele HLA-C*16:04

Figure 13J:
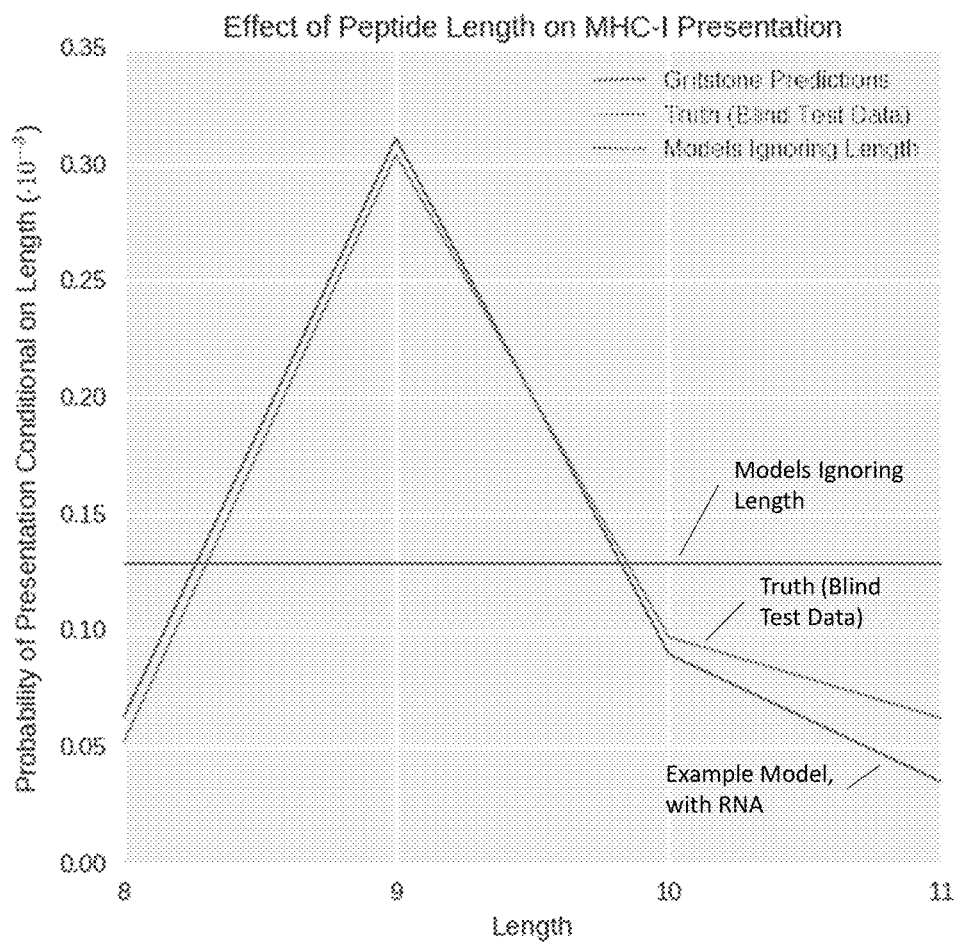
FIG. 13J shows the probability of peptide presentation for different peptide lengths for presentation models that take peptide length into account and state-of-the-art models that do not account for peptide length when predicting peptide presentation. The plot "Truth (Blind Test Data)" showed the proportion of presented peptides according to the length of the peptide in a sample test data set. The plot "Models Ignoring Length" indicated predicted measurements if state-of-the-art models that ignore peptide length applied to the same test data set for presentation prediction. The "Example Model, with RNA" model is the "sum-of-sigmoids" presentation model shown in equation (19) incorporating mRNA quantification data through a log function.

FIG. 13J compares probability of peptide presentation for different peptide lengths between results generated by the "Example Model, with RNA" presentation model described in reference to FIG. 13I, and predicted results by state-of-the-art models that do not account for peptide length when predicting peptide presentation. Results indicated that the "Example Model, with RNA" example presentation model from FIG. 13I captured variation in likelihoods across peptides of differing lengths.

The horizontal axis denoted samples of peptides with lengths 8, 9, 10, and 11. The vertical axis denoted the probability of peptide presentation conditioned on the lengths of the peptide. The plot "Truth (Blind Test Data)" showed the proportion of presented peptides according to the length of the peptide in a sample test data set. The presentation likelihood varied with the length of the peptide. For example, as shown in FIG. 13J, a 10mer peptide with canonical HLA-A2 L/V anchor motifs was approximately 3 times less likely to be presented than a 9mer with the same anchor residues. The plot "Models Ignoring Length" indicated predicted measurements if state-of-the-art models that ignore peptide length were to be applied to the same test data set for presentation prediction. These models may be NetMHC versions before version 4.0, NetMHCpan versions before version 3.0, and MHCflurry, that do not take into account variation in peptide presentation according to peptide length. As shown in FIG. 13J, the proportion of presented peptides would be constant across different values of peptide length, indicating that these models would fail to capture variation in peptide presentation according to length. The plot "Example Model, with RNA" indicated measurements generated from the "Example Model, with RNA" presentation model. As shown in FIG. 13J, the measurements generated by the "Example Model, with RNA" model closely followed those shown in "Truth (Blind Test Data)" and correctly accounted for different degrees of peptide presentation for lengths 8, 9, 10, and 11.

Thus, the results showed that the example presentation models as presented herein generated improved predictions not only for 9mer peptides, but also for peptides of other lengths between 8-15, which account for up to 40% of the presented peptides in HLA class I alleles.

XII.K. Example of Parameters Determined for MHC Allele HLA-C*16:04

The following shows a set of parameters determined for a variation of the per-allele presentation model (equation (2)) for MHC allele HLA-C*16:04 denoted by h:

$$u_k = \mathrm{expit}(\mathrm{relu}(x_h^k \cdot W_h^1 + b_h^1) \cdot W_h^2 + b_h^2),$$

where relu(•) is the rectified linear unit (RELU) function, and $W_h^1$, $b_h^1$, $W_h^2$, and $b_h^2$ are the set of parameters θ determined for the model. The allele interacting variables $x_h^k$ consist of peptide sequences. The dimensions of $W_h^1$ are (231×256), the dimensions of $b_h^1$ (1×256), the dimensions of $W_h^2$ are (256×1), and $b_h^2$ is a scalar. For demonstration purposes, values for $b_h^1$, $b_h^2$, $W_h^1$, and $W_h^2$ are described in detail in PCT publication WO2017106638, herein incorporated by reference for all that it teaches.

XII.L. MHC II Example 1

Methods for determining MHC class II neoantigens are described in more detail in international application PCT/US2018/028438, herein incorporated by reference for all that it teaches.

Figure 13K:
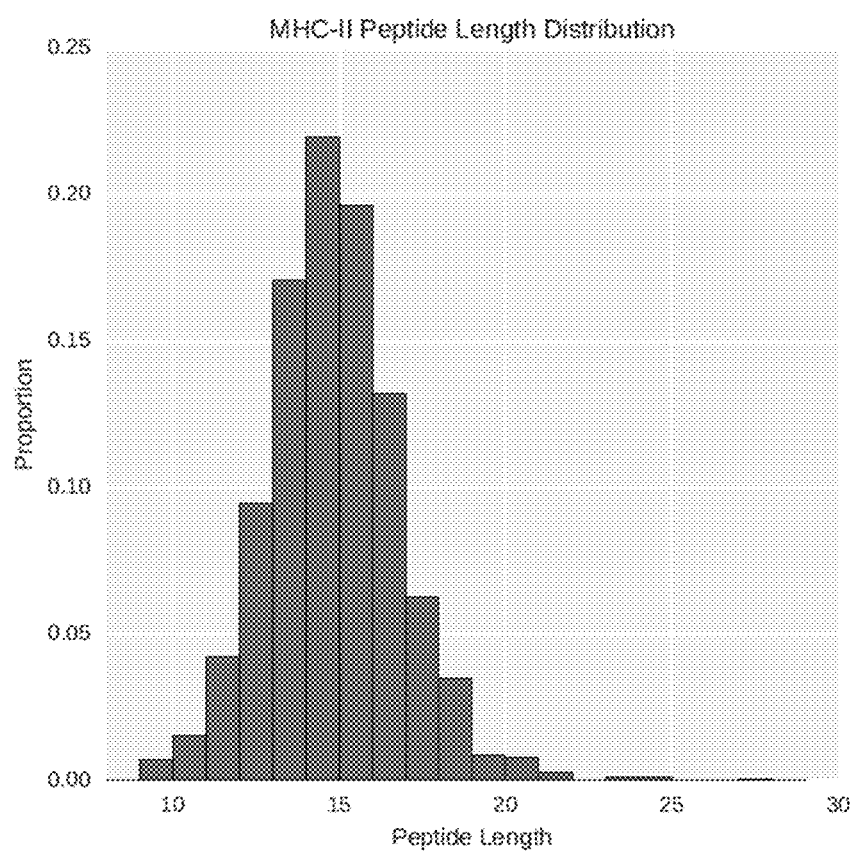
FIG. 13K is a histogram of lengths of peptides eluted from class II MHC alleles on human tumor cells and tumor infiltrating lymphocytes (TIL) using mass spectrometry.

FIG. 13K is a histogram of lengths of peptides eluted from class II MHC alleles on human tumor cells and tumor infiltrating lymphocytes (TIL) using mass spectrometry. Specifically, mass spectrometry peptidomics was performed on HLA-DRB1*12:01 homozygote alleles ("Dataset 1") and HLA-DRB1*12:01, HLA-DRB1*10:01 multi-allele samples ("Dataset 2"). Results show that lengths of peptides eluted from class II MHC alleles range from 6-30 amino acids. The frequency distribution shown in FIG. 13K is similar to that of lengths of peptides eluted from class II MHC alleles using state-of-the-art mass spectrometry techniques, as shown in FIG. 1C of reference 91.

Figure 13L:
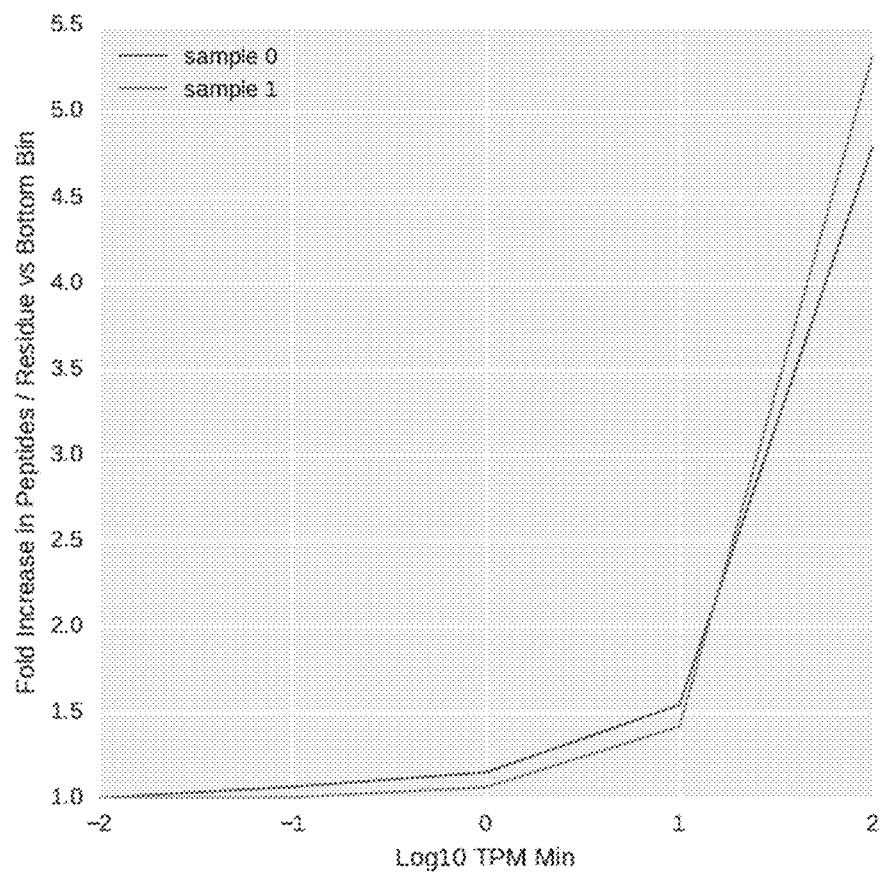
FIG. 13L illustrates the dependency between mRNA quantification and presented peptides per residue for two example datasets.

FIG. 13L illustrates the dependency between mRNA quantification and presented peptides per residue for Dataset 1 and Dataset 2. Results show that there is a strong dependency between mRNA expression and peptide presentation for class II MHC alleles.

Specifically, the horizontal axis in FIG. 13B indicates mRNA expression in terms of $\log_{10}$ transcripts per million (TPM) bins. The vertical axis in FIG. 13L indicates peptide presentation per residue as a multiple of that of the lowest bin corresponding to mRNA expression between $10^{-2} < \log_{10} \mathrm{TPM} < 10^{-1}$. One solid line is a plot relating mRNA quantification and peptide presentation for Dataset 1, and another is for Dataset 2. As shown in FIG. 13L, there is a strong positive correlation between mRNA expression, and peptide presentation per residue in the corresponding gene. Specifically, peptides from genes in the range of $10^1 < \log_{10} \mathrm{TPM} < 10^2$ of RNA expression are more than 5 times likely to be presented than the bottom bin.

The results indicate that the performance of the presentation model can be greatly improved by incorporating mRNA quantification measurements, as these measurements are strongly predictive of peptide presentation.

Figure 13M:
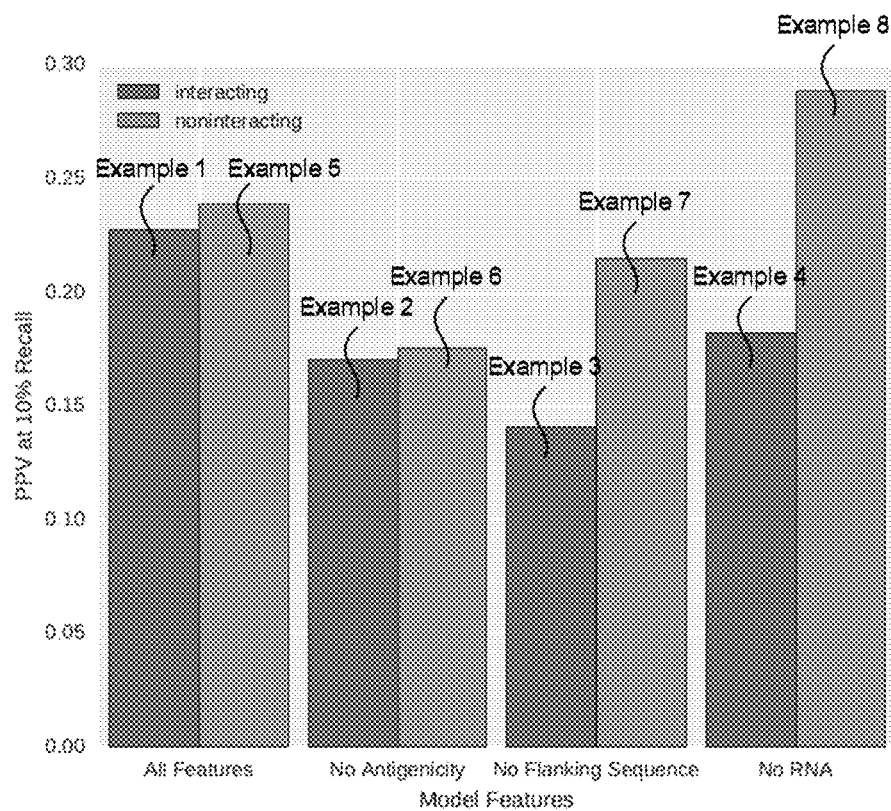
FIG. 13M compares performance results for example presentation models trained and tested using two example datasets.

FIG. 13M compares performance results for example presentation models trained and tested using Dataset 1 and Dataset 2. For each set of model features of the example presentation models, FIG. 13M depicts a PPV value at 10% recall when the features in the set of model features are classified as allele interacting features, and alternatively when the features in the set of model features are classified as allele non-interacting features variables. As seen in FIG. 13M, for each set of model features of the example presentation models, a PPV value at 10% recall that was identified when the features in the set of model features were classified as allele interacting features is shown on the left side, and a PPV value at 10% recall that was identified when the features in the set of model features were classified as allele non-interacting features is shown on the right side. Note that the feature of peptide sequence was always classified as an allele interacting feature for the purposes of FIG. 13M. Results showed that the presentation models achieved a PPV value at 10% recall varying from 14% up to 29%, which are significantly (approximately 500-fold) higher than PPV for a random prediction.

Peptide sequences of lengths 9-20 were considered for this experiment. The data was split into training, validation, and testing sets. Blocks of peptides of 50 residue blocks from both Dataset 1 and Dataset 2 were assigned to training and testing sets. Peptides that were duplicated anywhere in the proteome were removed, ensuring that no peptide sequence appeared both in the training and testing set. The prevalence of peptide presentation in the training and testing set was increased by 50 times by removing non-presented peptides. This is because Dataset 1 and Dataset 2 are from human tumor samples in which only a fraction of the cells are class II HLA alleles, resulting in peptide yields that were roughly 10 times lower than in pure samples of class II HLA alleles, which is still an underestimate due to imperfect mass spectrometry sensitivity. The training set contained 1,064 presented and 3,810,070 non-presented peptides. The test set contained 314 presented and 807,400 non-presented peptides.

Example model 1 was the sum-of-functions model in equation (22) using a network dependency function $g_h(\bullet)$, the expit function $f(\bullet)$ and the identity function $r(\bullet)$. The network dependency function $g_h(\bullet)$ was structured as a multi-layer perceptron (MLP) with 256 hidden nodes and rectified linear unit (ReLU) activations. In addition to the peptide sequence, the allele interacting variables w contained the one-hot encoded C-terminal and N-terminal flanking sequence, a categorical variable indicating index of source gene $G = \mathrm{gene}(p^i)$ of peptide $p^i$, and a variable indicating mRNA quantification measurement. Example model 2 was identical to example model 1, except that the C-terminal and N-terminal flanking sequence was omitted from the allele interacting variables. Example model 3 was identical to example model 1, except that the index of source gene was omitted from the allele interacting variables. Example model 4 was identical to example model 1, except that the mRNA quantification measurement was omitted from the allele interacting variables.

Example model 5 was the sum-of-functions model in equation (20) with a network dependency function $g_h(\bullet)$, the expit function $f(\bullet)$, the identity function $r(\bullet)$, and the dependency function $g_w(\bullet)$ of equation (12). The dependency function $g_w(\bullet)$ also included a network model taking mRNA quantification measurement as input, structured as a MLP with 16 hidden nodes and ReLU activations, and a network model taking C-flanking sequence as input, structured as a MLP with 32 hidden nodes and ReLU activations. The network dependency function $g_h(\bullet)$ was structured as a multi-layer perceptron with 256 hidden nodes and rectified linear unit (ReLU) activations. Example model 6 was identical to example model 5, except that the network model for C-terminal and N-terminal flanking sequence was omitted. Example model 7 was identical to example model 5, except that the index of source gene was omitted from the allele noninteracting variables. Example model 8 was identical to example model 5, except that the network model for mRNA quantification measurement was omitted.

The prevalence of presented peptides in the test set was approximately 1/2400, and therefore, the PPV of a random prediction would also be approximately 1/2400=0.00042. As shown in FIG. 13M, the best-performing presentation model achieved a PPV value of approximately 29%, which is roughly 500 times better than the PPV value of a random prediction.

XII.M. MHC II Example 2

Figure 13N:
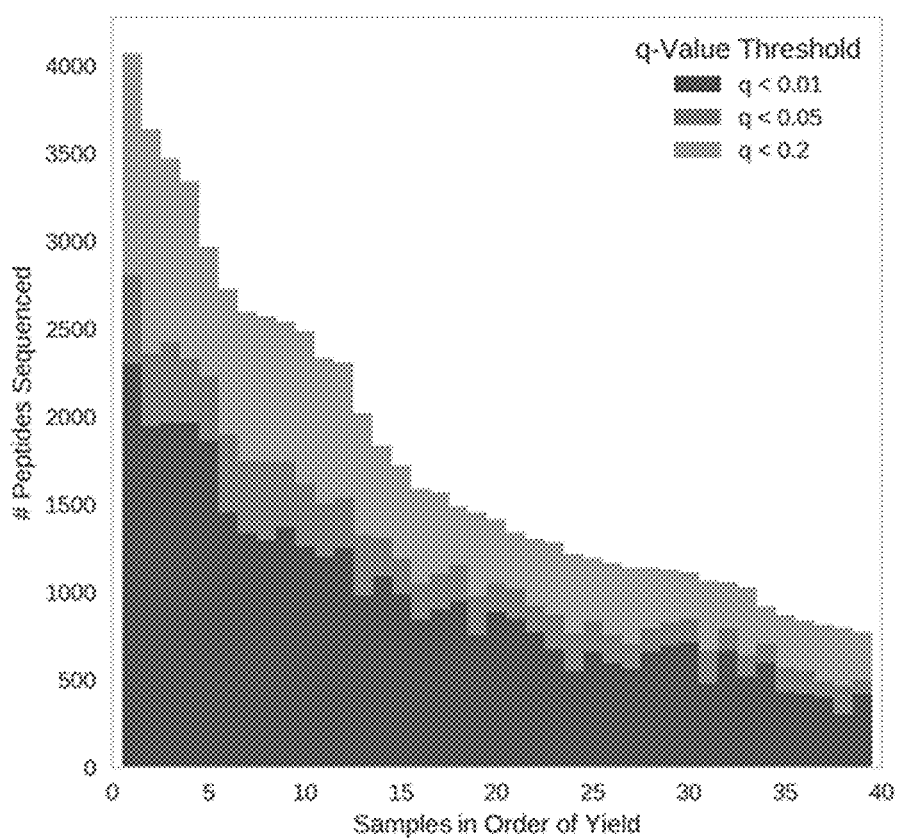
FIG. 13N is a histogram that depicts the quantity of peptides sequenced using mass spectrometry for each sample of a total of 39 samples comprising HLA class II molecules.

FIG. 13N is a histogram that depicts the quantity of peptides sequenced using mass spectrometry for each sample of a total of 39 samples comprising HLA class II molecules. Furthermore, for each sample of the plurality of samples, the histogram shown in FIG. 13N depicts the quantity of peptides sequenced using mass spectrometry at different q-value thresholds. Specifically, for each sample of the plurality of samples, FIG. 13N depicts the quantity of peptides sequenced using mass spectrometry with a q-value of less than 0.01, with a q-value of less than 0.05, and with a q-value of less than 0.2.

As noted above, each sample of the 39 samples of FIG. 13N comprised HLA class II molecules. More specifically, each sample of the 39 samples of FIG. 13N comprised HLA-DR molecules. The HLA-DR molecule is one type of HLA class II molecule. Even more specifically, each sample of the 39 samples of FIG. 13N comprised HLA-DRB1 molecules, HLA-DRB3 molecules, HLA-DRB4 molecules, and/or HLA-DRB5 molecules. The HLA-DRB1 molecule, the HLA-DRB3 molecule, the HLA-DRB4 molecule, and the HLA-DRB5 molecule are types of the HLA-DR molecule.

While this particular experiment was performed using samples comprising HLA-DR molecules, and particularly HLA-DRB1 molecules, HLA-DRB3 molecules, HLA-DRB4 molecules, and HLA-DRB5 molecules, in alternative embodiments, this experiment can be performed using samples comprising one or more of any type(s) of HLA class II molecules.

For example, in alterative embodiments, identical experiments can be performed using samples comprising HLA-DP and/or HLA-DQ molecules. This ability to model any type (s) of MHC class II molecules using the same techniques, and still achieve reliable results, is well known by those skilled in the art. For instance, Jensen, Kamilla Kjaergaard, et al.[76] is one example of a recent scientific paper that uses identical methods for modeling binding affinity for HLA-DR molecules as well as for HLA-DQ and HLA-DP molecules. Therefore, one skilled in the art would understand that the experiments and models described herein can be used to separately or simultaneously model not only HLA-DR molecules, but any other MHC class II molecule, while still producing reliable results.

To sequence the peptides of each sample of the 39 total samples, mass spectrometry was performed for each sample. The resulting mass spectrum for the sample was then searched with Comet and scored with Percolator to sequence the peptides. Then, the quantity of peptides sequenced in the sample was identified for a plurality of different Percolator q-value thresholds. Specifically, for the sample, the quantity of peptides sequenced with a Percolator q-value of less than 0.01, with a Percolator q-value of less than 0.05, and with a Percolator q-value of less than 0.2 were determined.

For each sample of the 39 samples, the quantity of peptides sequenced at each of the different Percolator q-value thresholds is depicted in FIG. 13N. For example, as seen in FIG. 13N, for the first sample, approximately 4000 peptides with a q-value of less than 0.2 were sequenced using mass spectrometry, approximately 2800 peptides with a q-value of less than 0.05 were sequenced using mass spectrometry, and approximately 2300 peptides with a q-value of less than 0.01 were sequenced using mass spectrometry.

Overall, FIG. 13N demonstrates the ability to use mass spectrometry to sequence a large quantity of peptides from samples containing MHC class II molecules, at low q-values. In other words, the data depicted in FIG. 13N demonstrate the ability to reliably sequence peptides that may be presented by MHC class II molecules, using mass spectrometry.

FIG. 13O is a histogram that depicts the quantity of samples in which a particular MHC class II molecule allele was identified. More specifically, for the 39 total samples comprising HLA class II molecules, FIG. 13O depicts the quantity of samples in which certain MHC class II molecule alleles were identified.

As discussed above with regard to FIG. 13N, each sample of the 39 samples of FIG. 13N comprised HLA-DRB1 molecules, HLA-DRB3 molecules, HLA-DRB4 molecules, and/or HLA-DRB5 molecules. Therefore, FIG. 13O depicts the quantity of samples in which certain alleles for HLA-DRB1, HLA-DRB3, HLA-DRB4, and HLA-DRB5 molecules were identified. To identify the HLA alleles present in a sample, HLA class II DR typing is performed for the sample. Then, to identify the quantity of samples in which a particular HLA allele was identified, the number of samples in which the HLA allele was identified using HLA class II DR typing is simply summed. For example, as depicted in FIG. 13O, 19 samples of the 39 total samples contained the HLA class II molecule allele HLA-DRB4*01: 03. In other words, 19 samples of the 39 total samples contained the allele HLA-DRB4*01:03 for the HLA-DRB4 molecule. Overall, FIG. 13O depicts the ability to identify a wide range of HLA class II molecule alleles from the 39 samples comprising HLA class II molecules.

Figure 13P:
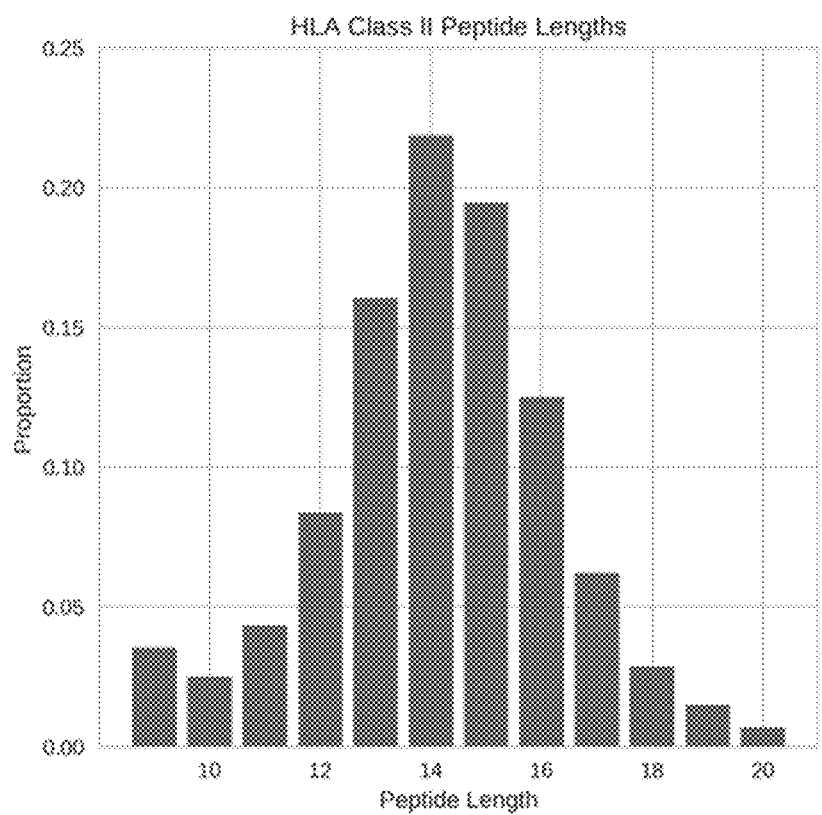
FIG. 13P is a histogram that depicts the proportion of peptides presented by the MHC class II molecules in the 39 total samples, for each peptide length of a range of peptide lengths.

FIG. 13P is a histogram that depicts the proportion of peptides presented by the MHC class II molecules in the 39 total samples, for each peptide length of a range of peptide lengths. To determine the length of each peptide in each sample of the 39 total samples, each peptide was sequenced using mass spectrometry as discussed above with regard to FIG. 13N, and then the number of residues in the sequenced peptide was simply quantified.

As noted above, MHC class II molecules typically present peptides with lengths of between 9-20 amino acids. Accordingly, FIG. 13P depicts the proportion of peptides presented by the MHC class II molecules in the 39 samples for each peptide length between 9-20 amino acids, inclusive. For example, as shown in FIG. 13P, approximately 22% of the peptides presented by the MHC class II molecules in the 39 samples comprise a length of 14 amino acids.

Based on the data depicted in FIG. 13P, modal lengths for the peptides presented by the MHC class II molecules in the 39 samples were identified to be 14 and 15 amino acids in length. These modal lengths identified for the peptides presented by the MHC class II molecules in the 39 samples are consistent with previous reports of modal lengths for peptides presented by MHC class II molecules. Additionally, as also consistent with previous reports, the data of FIG. 13P indicates that more than 60% of the peptides presented by the MHC class II molecules from the 39 samples comprise lengths other than 14 and 15 amino acids. In other words, FIG. 13P indicates that while peptides presented by MHC class II molecules are most frequently 14 or 15 amino acids in length, a large proportion of peptides presented by MHC class II molecules are not 14 or 15 amino acids in length. Accordingly, it is a poor assumption to assume that peptides of all lengths have equal probabilities of being presented by MHC class II molecules, or that only peptides that comprise a length of 14 or 15 amino acids are presented by MHC class II molecules. As discussed in detail below with regard to FIG. 13T, these faulty assumptions are currently used in many state-of-the-art models for predicting peptide presentation by MHC class II molecules, and therefore, the presentation likelihoods predicted by these models are often unreliable.

Figure 13Q:
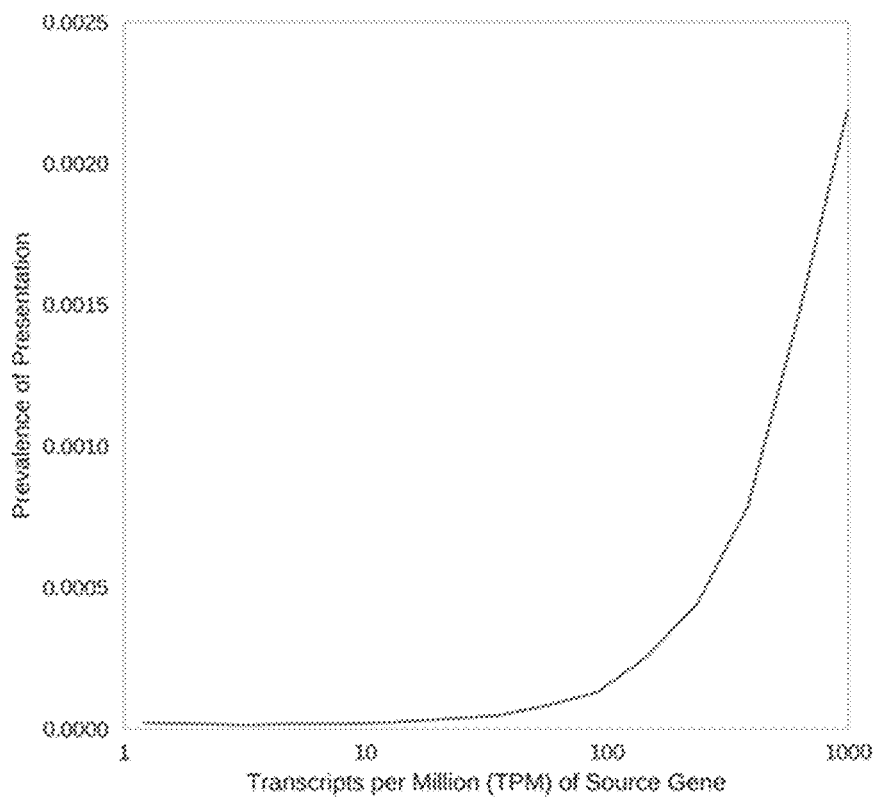
FIG. 13Q is a line graph that depicts the relationship between gene expression and prevalence of presentation of the gene expression product by a MHC class II molecule, for genes present in the 39 samples.

FIG. 13Q is a line graph that depicts the relationship between gene expression and prevalence of presentation of the gene expression product by a MHC class II molecule, for genes present in the 39 samples. More specifically, FIG. 13Q depicts the relationship between gene expression and the proportion of residues resulting from the gene expression that form the N-terminus of a peptide presented by a MHC class II molecule. To quantify gene expression in each sample of the 39 total samples, RNA sequencing is performed on the RNA included in each sample. In FIG. 13Q, gene expression is measured by RNA sequencing in units of transcripts per million (TPM). To identify prevalence of presentation of gene expression products for each sample of the 39 samples, identification of HLA class II DR peptidomic data was performed for each sample.

As depicted in FIG. 13Q, for the 39 samples, there is a strong correlation between gene expression level and presentation of residues of the expressed gene product by a MHC class II molecule. Specifically, as shown in FIG. 13Q, peptides resulting from expression of the least-expressed genes are more than 100-fold less likely to be presented by a MHC class II molecule, than peptides resulting from expression of the most-expressed genes. In simpler terms, the products of more highly expressed genes are more frequently presented by MHC class II molecules.

FIGS. 13H-J are line graphs that compare the performance of various presentation models at predicting the likelihood that peptides in a testing dataset of peptides will be presented by at least one of the MHC class II molecules present in the testing dataset. As shown in FIGS. 13H-J, the performance of a model at predicting the likelihood that a peptide will be presented by at least one of the MHC class II molecules present in the testing dataset is determined by identifying a ratio of a true positive rate to a false positive rate for each prediction made by the model. These ratios identified for a given model can be visualized as a ROC (receiver operator characteristic) curve, in a line graph with an x-axis quantifying false positive rate and a y-axis quantifying true positive rate. An area under the curve (AUC) is used to quantify the performance of the model. Specifically, a model with a greater AUC has a higher performance (i.e., greater accuracy) relative to a model with a lesser AUC. In FIGS. 13H-J, the blacked dashed line with a slope of 1 (i.e., a ratio of true positive rate to false positive rate of 1) depicts the expected curve for randomly guessing likelihoods of peptide presentation. The AUC for the dashed line is 0.5. ROC curves and the AUC metric are discussed in detail with regard to the top portion of Section XII. above.

Figure 13R:
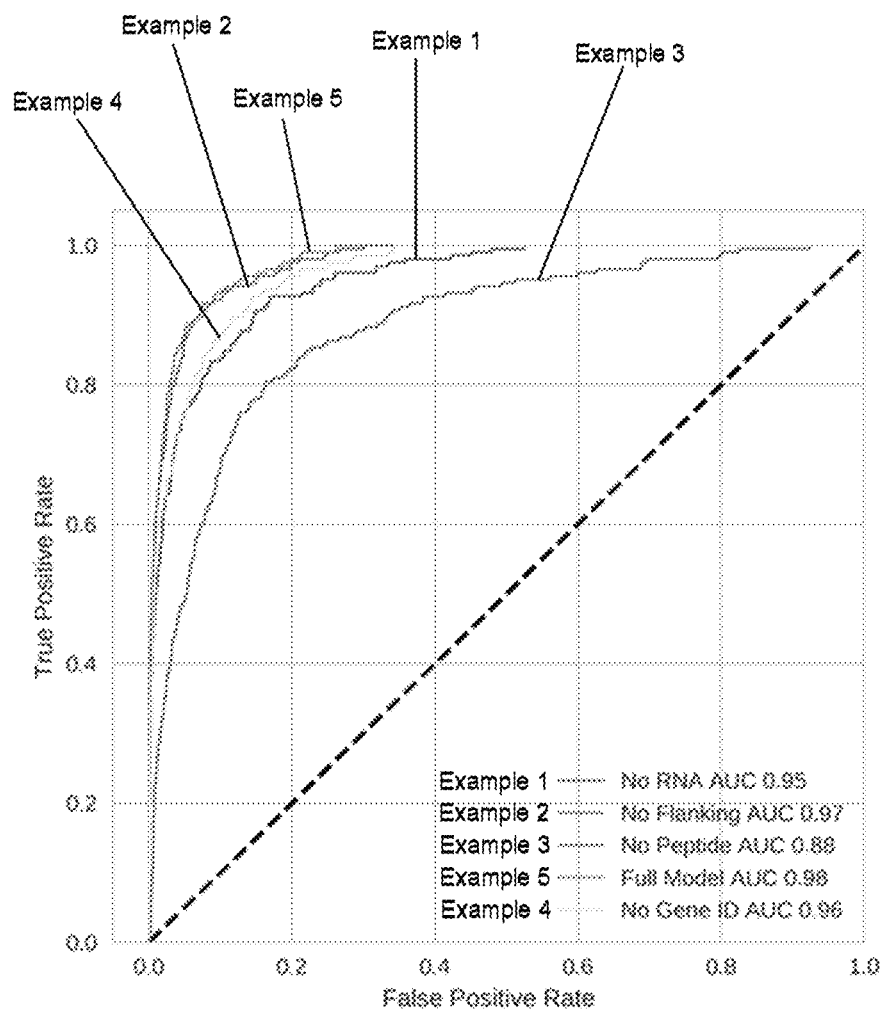
FIG. 13R is a line graph that compares the performance of identical models with varying inputs, at predicting the likelihood that peptides in a testing dataset of peptides will be presented by a MHC class II molecule.

FIG. 13R is a line graph that compares the performance of five example presentation models at predicting the likelihood that peptides in a testing dataset of peptides will be presented by a MHC class II molecule, given different sets of allele interacting and allele non-interacting variables. In other words, FIG. 13R quantifies the relative importance of various allele interacting and allele non-interacting variables for predicting the likelihood that a peptide will be presented by a MHC class II molecule.

The model architecture of each example presentation model of the five example presentations models used to generate the ROC curves of the line graph of FIG. 13R, comprised an ensemble of five sum-of-sigmoids models. Each sum-of-sigmoids model in the ensemble was configured to model peptide presentation for up to four unique HLA-DR alleles per sample. Furthermore, each sum-of-sigmoids model in the ensemble was configured to make predictions of peptide presentation likelihood based on the following allele interacting and allele non-interacting variables: peptide sequence, flanking sequence, RNA expression in units of TPM, gene identifier, and sample identifier. The allele interacting component of each sum-of-sigmoids model in the ensemble was a one-hidden-layer MLP with ReLu activations as 256 hidden units.

Prior to using the example models to predict the likelihood that the peptides in a testing dataset of peptides will be presented by a MHC class II molecule, the example models were trained and validated. To train, validate, and finally test the example models, the data described above for the 39 samples was split into training, validation, and testing datasets.

To ensure that no peptides appeared in more than one of the training, validation, and testing datasets, the following procedure was performed. First all peptides from the 39 total samples that appeared in more than one location in the proteome were removed. Then, the peptides from the 39 total samples were partitioned into blocks of 10 adjacent peptides. Each block of the peptides from the 39 total samples was assigned uniquely to the training dataset, the validation dataset, or the testing dataset. In this way, no peptide appeared in more than one dataset of the training, validation, and testing datasets.

Out of the 28,081,944 peptides in the 39 total samples, the training dataset comprised 21,077 peptides presented by MHC class II molecules from 38 of the 39 total samples. The 21,077 peptides included in the training dataset were between lengths of 9 and 20 amino acids, inclusive. The example models used to generate the ROC curves in FIG. 13R were trained on the training dataset using the ADAM optimizer and early stopping.

The validation dataset consisted of 2,346 peptides presented by MHC class II molecules from the same 38 samples used in the training dataset. The validation set was used only for early stopping.

The testing dataset comprised peptides presented by MHC class II molecules that were identified from a tumor sample using mass spectrometry. Specifically, the testing dataset comprised 203 peptides presented by MHC class II molecules—specifically HLA-DRB1*07:01, HLA-DRB1*15:01, HLA-DRB4*01:03, and HLA-DRB5*01:01 molecules—that were identified from the tumor sample. The peptides included in the testing dataset were held out of the training dataset described above.

As noted above, FIG. 13R quantifies the relative importance of various allele interacting variables and allele non-interacting variables for predicting the likelihood that a peptide will be presented by a MHC class II molecule. As also noted above, the example models used to generate the ROC curves of the line graph of FIG. 13R were configured to make predictions of peptide presentation likelihood based on the following allele interacting and allele non-interacting variables: peptide sequence, flanking sequence, RNA expression in units of TPM, gene identifier, and sample identifier. To quantify the relative importance of four of these five variables (peptide sequence, flanking sequence, RNA expression, and gene identifier) for predicting the likelihood that a peptide will be presented by a MHC class II molecule, each example model of the five the example models described above was tested using data from the testing dataset, with a different combination of the four variables. Specifically, for each peptide of the testing dataset, an example model 1 generated predictions of peptide presentation likelihood based on a peptide sequence, a flanking sequence, a gene identifier, and a sample identifier, but not on RNA expression. Similarly, for each peptide of the testing dataset, an example model 2 generated predictions of peptide presentation likelihood based on a peptide sequence, RNA expression, a gene identifier, and a sample identifier, but not on a flanking sequence. Similarly, for each peptide of the testing dataset, an example model 3 generated predictions of peptide presentation likelihood based on a flanking sequence, RNA expression, a gene identifier, and a sample identifier, but not on a peptide sequence. Similarly, for each peptide of the testing dataset, an example model 4 generated predictions of peptide presentation likelihood based on a flanking sequence, RNA expression, a peptide sequence, and a sample identifier, but not on a gene identifier. Finally, for each peptide of the testing dataset, an example model 5 generated predictions of peptide presentation likelihood based on all five variables of flanking sequence, RNA expression, peptide sequence, sample identifier, and gene identifier.

The performance of each of these five example models is depicted in the line graph of FIG. 13R. Specifically, each of the five example models is associated with a ROC curve that depicts a ratio of a true positive rate to a false positive rate for each prediction made by the model. For instance, FIG. 13R depicts a curve for the example model 1 that generated predictions of peptide presentation likelihood based on a peptide sequence, a flanking sequence, a gene identifier, and a sample identifier, but not on RNA expression. FIG. 13R depicts a curve for the example model 2 that generated predictions of peptide presentation likelihood based on a peptide sequence, RNA expression, a gene identifier, and a sample identifier, but not on a flanking sequence. FIG. 13R also depicts a curve for the example model 3 that generated predictions of peptide presentation likelihood based on a flanking sequence, RNA expression, a gene identifier, and a sample identifier, but not on a peptide sequence. FIG. 13R also depicts a curve for the example model 4 that generated predictions of peptide presentation likelihood based on a flanking sequence, RNA expression, a peptide sequence, and a sample identifier, but not on a gene identifier. And finally FIG. 13R depicts a curve for the example model 5 that generated predictions of peptide presentation likelihood based on all five variables of flanking sequence, RNA expression, peptide sequence, sample identifier, and gene identifier.

As noted above, the performance of a model at predicting the likelihood that a peptide will be presented by a MHC class II molecule is quantified by identifying an AUC for a ROC curve that depicts a ratio of a true positive rate to a false positive rate for each prediction made by the model. A model with a greater AUC has a higher performance (i.e., greater accuracy) relative to a model with a lesser AUC. As shown in FIG. 13R, the curve for the example model 5 that generated predictions of peptide presentation likelihood based on all five variables of flanking sequence, RNA expression, peptide sequence, sample identifier, and gene identifier, achieved the highest AUC of 0.98. Therefore the example model 5 that used all five variables to generate predictions of peptide presentation achieved the best performance. The curve for the example model 2 that generated predictions of peptide presentation likelihood based on a peptide sequence, RNA expression, a gene identifier, and a sample identifier, but not on a flanking sequence, achieved the second highest AUC of 0.97. Therefore, the flanking sequence can be identified as the least important variable for predicting the likelihood that a peptide will be presented by a MHC class II molecule. The curve for the example model 4 generated predictions of peptide presentation likelihood based on a flanking sequence, RNA expression, a peptide sequence, and a sample identifier, but not on a gene identifier, achieved the third highest AUC of 0.96. Therefore, the gene identifier can be identified as the second least important variable for predicting the likelihood that a peptide will be presented by a MHC class II molecule. The curve for the example model 3 that generated predictions of peptide presentation likelihood based on a flanking sequence, RNA expression, a gene identifier, and a sample identifier, but not on a peptide sequence, achieved the lowest AUC of 0.88. Therefore, the peptide sequence can be identified as the most important variable for predicting the likelihood that a peptide will be presented by a MHC class II molecule. The curve for the example model 1 that generated predictions of peptide presentation likelihood based on a peptide sequence, a flanking sequence, a gene identifier, and a sample identifier, but not on RNA expression, achieved the second lowest AUC of 0.95. Therefore, RNA expression can be identified as the second most important variable for predicting the likelihood that a peptide will be presented by a MHC class II molecule.

Figure 13S:
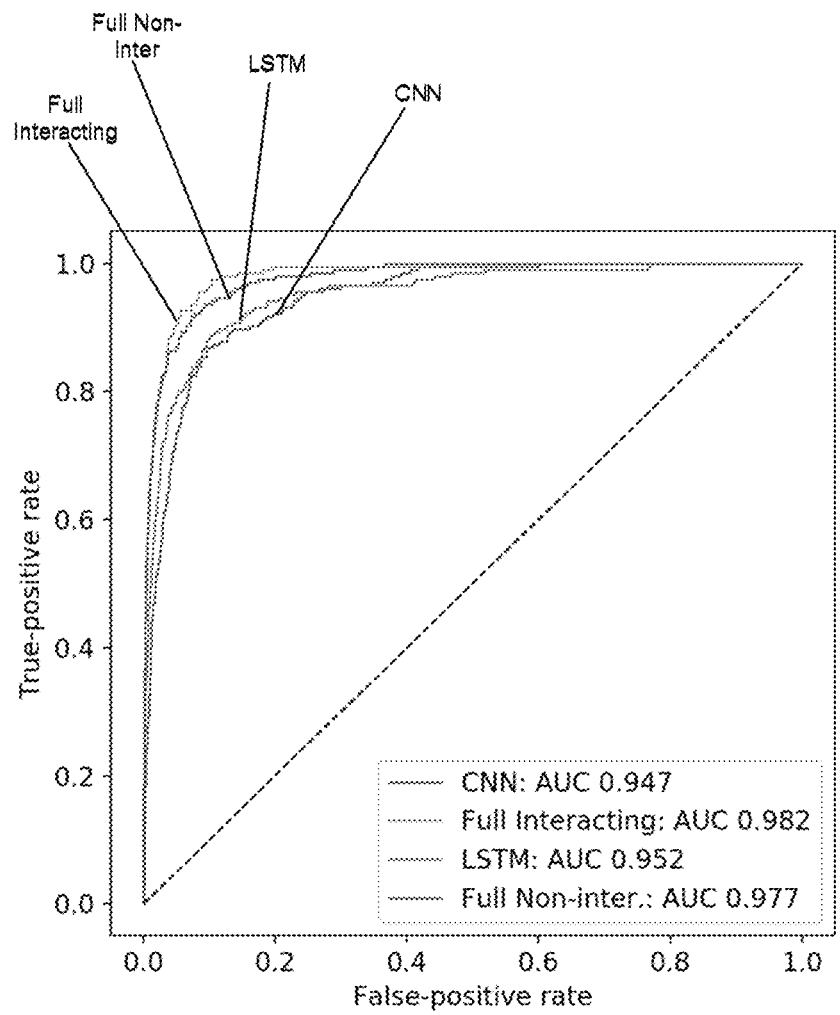
FIG. 13S is a line graph that compares the performance of four different models at predicting the likelihood that peptides in a testing dataset of peptides will be presented by a MHC class II molecule.

FIG. 13S is a line graph that compares the performance of four different presentation models at predicting the likelihood that peptides in a testing dataset of peptides will be presented by a MHC class II molecule.

The first model tested in FIG. 13S is referred to herein as a "full non-interacting model." The full non-interacting model is one embodiment of the presentation models described above in which allele-noninteracting variables $w^k$ and allele-interacting variables $x_h^k$ are input into separate dependency functions such as, for example, a neural network, and then the outputs of these separate dependency functions are added. Specifically, the full non-interacting model is one embodiment of the presentation models described above in which allele-noninteracting variables $w^k$ are input into a dependency function $g_w$, allele-interacting variables $x_h^k$ are input into separate dependency function $g_h$, and the outputs of the dependency function $g_w$ and the dependency function $g_h$ are added together. Therefore, in some embodiments, the full non-interacting model determines the likelihood of peptide presentation using equation 8 as shown above. Furthermore, embodiments of the full non-interacting model in which allele-noninteracting variables $w^k$ are input into a dependency function $g_w$, allele-interacting variables $x_h^k$ are input into separate dependency function $g_h$, and the outputs of the dependency function $g_w$ and the dependency function $g_h$ are added, are discussed in detail above with regard to the top portion of Section X.B.2., the bottom portion of Section X.B.3., the top portion of Section X.C.3., and the top portion of Section X.C.6.

The second model tested in FIG. 13S is referred to herein as a "full interacting model." The full interacting model is one embodiment of the presentation models described above in which allele-noninteracting variables $w^k$ are concatenated directly to allele-interacting variables $x_h^k$ before being input into a dependency function such as, for example, a neural network. Therefore, in some embodiments, the full interacting model determines the likelihood of peptide presentation using equation 9 as shown above. Furthermore, embodiments of the full interacting model in which allele-noninteracting variables $w^k$ are concatenated with allele-interacting variables $x_h^k$ before the variables are input into a dependency function are discussed in detail above with regard to the bottom portion of Section X.B.2., the bottom portion of Section X.C.2., and the bottom portion of Section X.C.5.

The third model tested in FIG. 13S is referred to herein as a "CNN model." The CNN model comprises a convolutional neural network, and is similar to the full non-interacting model described above. However, the layers of the convolutional neural network of the CNN model differ from the layers of the neural network of the full non-interacting model. Specifically, the input layer of the convolutional neural network of the CNN model accepts a 20-mer peptide string and subsequently embeds the 20-mer peptide string as a (n, 20, 21) tensor. The next layers of the convolutional neural network of the CNN model comprise a 1-D convolutional kernel layer of size 5 with a stride of 1, a global max pooling layer, a dropout layer with p=0.2, and finally a dense 34-node layer with a ReLu activation.

The fourth and final model tested in FIG. 13S is referred to herein as a "LSTM model." The LSTM model comprises a long short-term memory neural network. The input layer of the long short-term memory neural network of the LSTM model accepts a 20-mer peptide string and subsequently embeds the 20-mer peptide string as a (n, 20, 21) tensor. The next layers of the long short-term memory neural network of the LSTM model comprise a long short-term memory layer with 128 nodes, a dropout layer with p=0.2, and finally a dense 34-node layer with a ReLu activation.

Prior to using each of the four models of FIG. 13S to predict the likelihood that the peptides in the testing dataset of peptides will be presented by a MHC class II molecule, the models were trained using the 38-sample training dataset described above and validated using the validation dataset described above. Following this training and validation of the models, each of the four models was tested using the held-out $39^{th}$ sample testing dataset described above. Specifically, for each of the four models, each peptide of the testing dataset was input into the model, and the model subsequently output a presentation likelihood for the peptide.

The performance of each of the four models is depicted in the line graph in FIG. 13S. Specifically, each of the four models is associated with a ROC curve that depicts a ratio of a true positive rate to a false positive rate for each prediction made by the model. For instance, FIG. 13S depicts a ROC curve for the CNN model, a ROC curve for the full interacting model, a ROC curve for the LSTM model, and a ROC curve for the full non-interacting model.

As noted above, the performance of a model at predicting the likelihood that a peptide will be presented by a MHC class II molecule is quantified by identifying an AUC for a ROC curve that depicts a ratio of a true positive rate to a false positive rate for each prediction made by the model. A model with a greater AUC has a higher performance (i.e., greater accuracy) relative to a model with a lesser AUC. As shown in FIG. 13S, the curve for the full interacting model achieved the highest AUC of 0.982. Therefore the full interacting model achieved the best performance. The curve for the full non-interacting model achieved the second highest AUC of 0.977. Therefore, the full non-interacting model achieved the second best performance. The curve for the CNN model achieved the lowest AUC of 0.947. Therefore the CNN model achieved the worst performance. The curve for the LSTM model achieved the second lowest AUC of 0.952. Therefore, the LSTM model achieved the second worst performance. However, note that all models tested in FIG. 13S have an AUC that is greater than 0.9. Accordingly, despite the architectural variance between them, all models tested in FIG. 13S are capable of achieving relatively accurate predictions of peptide presentation.

Figure 13T:
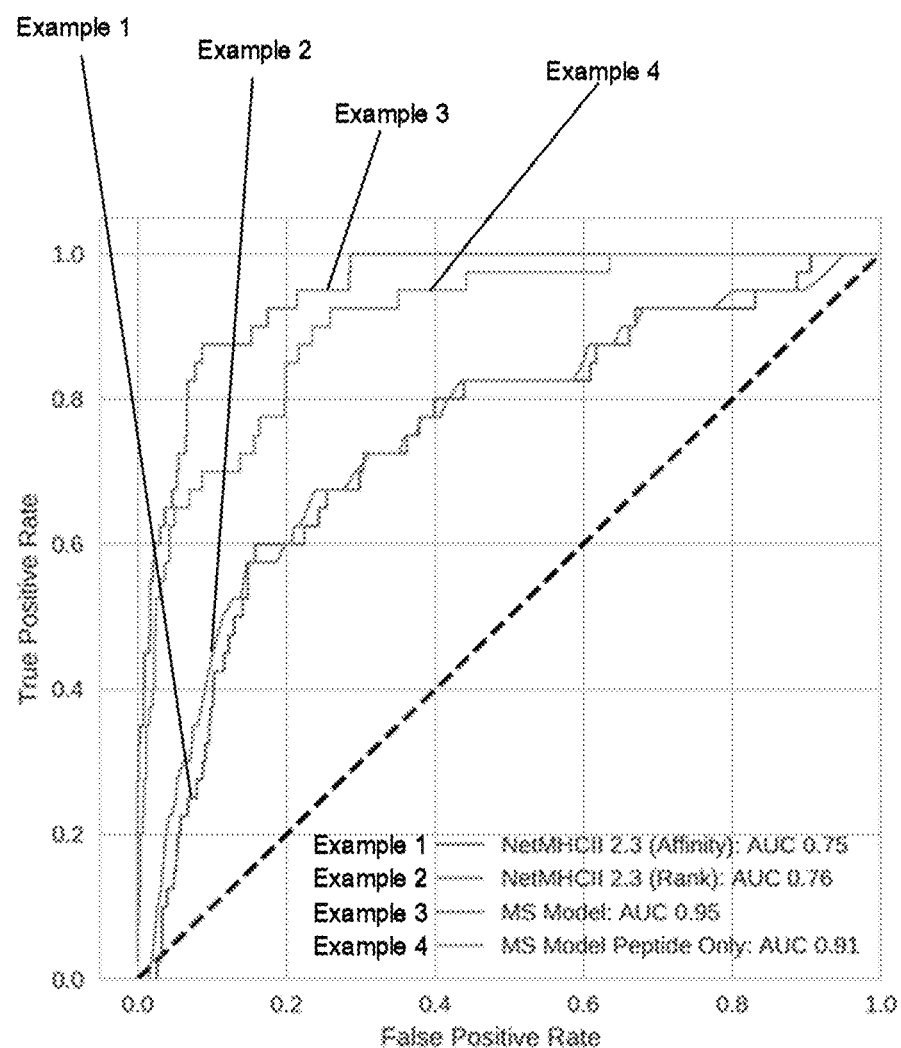
FIG. 13T is a line graph that compares the performance of a best-in-class prior art model using two different criteria and the presentation model disclosed herein with two different inputs, at predicting the likelihood that peptides in a testing dataset of peptides will be presented by a MHC class II molecule.

FIG. 13T is a line graph that compares the performance of two example best-in-class prior art models given two different criteria, and two example presentation models given two different sets of allele interacting and allele non-interacting variables, at predicting the likelihood that peptides in a testing dataset of peptides will be presented by a MHC class II molecule. Specifically, FIG. 13T is a line graph that compares the performance of an example best-in-class prior art model that utilizes minimum NetMHCII 2.3 predicted binding affinity as a criterion to generate predictions (example model 1), an example best-in-class prior art model that utilizes minimum NetMHCII 2.3 predicted binding rank as a criterion to generate predictions (example model 2), an example presentation model that generates predictions of peptide presentation likelihood based on MHC class II molecule type and peptide sequence (example model 4), and an example presentation model that generates predictions of peptide presentation likelihood based on MHC class II molecule type, peptide sequence, RNA expression, gene identifier, and flanking sequence (example model 3).

The best-in-class prior art model used as example model 1 and example model 2 in FIG. 13T is the NetMHCII 2.3 model. The NetMHCII 2.3 model generates predictions of peptide presentation likelihood based on MHC class II molecule type and peptide sequence. The NetMHCII 2.3 model was tested using the NetMHCII 2.3 website (www.cbs.dtu.dk/services/NetMHCII/, PMID 29315598)[76].

As noted above, the NetMHCII 2.3 model was tested according to two different criteria. Specifically, example model 1 model generated predictions of peptide presentation likelihood according to minimum NetMHCII 2.3 predicted binding affinity, and example model 2 generated predictions of peptide presentation likelihood according to minimum NetMHCII 2.3 predicted binding rank.

The presentation model used as example model 3 and example model 4 is an embodiment of the presentation model disclosed herein that is trained using data obtained via mass spectrometry. As noted above, the presentation model generated predictions of peptide presentation likelihood based on two different sets of allele interacting and allele non-interacting variables. Specifically, example model 4 generated predictions of peptide presentation likelihood based on MHC class II molecule type and peptide sequence (the same variable used by the NetMHCII 2.3 model), and example model 3 generated predictions of peptide presentation likelihood based on MHC class II molecule type, peptide sequence, RNA expression, gene identifier, and flanking sequence.

Prior using the example models of FIG. 13T to predict the likelihood that the peptides in the testing dataset of peptides will be presented by a MHC class II molecule, the models were trained and validated. The NetMHCII 2.3 model (example model 1 and example model 2) was trained and validated using its own training and validation datasets based on HLA-peptide binding affinity assays deposited in the immune epitope database (IEDB, www.iedb.org). The training dataset used to train the NetMHCII 2.3 model is known to comprise almost exclusively 15-mer peptides. On the other hand, example models 3 and 4 were trained using the training dataset described above with regard to FIG. 13R and validated and using the validation dataset described above with regard to FIG. 13R.

Following the training and validation of the models, each of the models was tested using a testing dataset. As noted above, the NetMHCII 2.3 model is trained on a dataset comprising almost exclusively 15-mer peptides, meaning that NetMHCII 3.2 does not have the ability to give different priority to peptides of different weights, thereby reducing the predictive performance for NetMHCII 3.2 on HLA class II presentation mass spectrometry data containing peptides of all lengths. Therefore, to provide a fair comparison between the models not affected by variable peptide length, the testing dataset included exclusively 15-mer peptides. Specifically, the testing dataset comprised 933 15-mer peptides. 40 of the 933 peptides in the testing dataset were presented by MHC class II molecules—specifically by HLA-DRB1*07:01, HLA-DRB1*15:01, HLA-DRB4*01:03, and HLA-DRB5*01:01 molecules. The peptides included in the testing dataset were held out of the training datasets described above.

To test the example models using the testing dataset, for each of the example models, for each peptide of the 933 peptides in the testing dataset, the model generated a prediction of presentation likelihood for the peptide. Specifically, for each peptide in the testing dataset, the example 1 model generated a presentation score for the peptide by the MHC class II molecules using MHC class II molecule types and peptide sequence, by ranking the peptide by the minimum NetMHCII 2.3 predicted binding affinity across the four HLA class II DR alleles in the testing dataset. Similarly, for each peptide in the testing dataset, the example 2 model generated a presentation score for the peptide by the MHC class II molecules using MHC class II molecule types and peptide sequence, by ranking the peptide by the minimum NetMHCII 2.3 predicted binding rank (i.e., quantile normalized binding affinity) across the four HLA class II DR alleles in the testing dataset. For each peptide in the testing dataset, the example 4 model generated a presentation likelihood for the peptide by the MHC class II molecules based on MHC class II molecule type and peptide sequence. Similarly, for each peptide in the testing dataset, the example model 3 generated a presentation likelihood for the peptide by the MHC class II molecules based on MHC class II molecule types, peptide sequence, RNA expression, gene identifier, and flanking sequence.

The performance of each of the four example models is depicted in the line graph in FIG. 13T. Specifically, each of the four example models is associated with a ROC curve that depicts a ratio of a true positive rate to a false positive rate for each prediction made by the model. For instance, FIG. 13T depicts a ROC curve for the example 1 model that utilized minimum NetMHCII 2.3 predicted binding affinity to generate predictions, a ROC curve for the example 2 model that utilized minimum NetMHCII 2.3 predicted binding rank to generate predictions, a ROC curve for the example 4 model that generated peptide presentation likelihoods based on MHC class II molecule type and peptide sequence, and a ROC curve for the example 3 model that generated peptide presentation likelihoods based on MHC class II molecule type, peptide sequence, RNA expression, gene identifier, and flanking sequence.

As noted above, the performance of a model at predicting the likelihood that a peptide will be presented by a MHC class II molecule is quantified by identifying an AUC for a ROC curve that depicts a ratio of a true positive rate to a false positive rate for each prediction made by the model. A model with a greater AUC has a higher performance (i.e., greater accuracy) relative to a model with a lesser AUC. As shown in FIG. 13T, the curve for the example 3 model that generated peptide presentation likelihoods based on MHC class II molecule type, peptide sequence, RNA expression, gene identifier, and flanking sequence, achieved the highest AUC of 0.95. Therefore the example 3 model that generated peptide presentation likelihoods based on MHC class II molecule type, peptide sequence, RNA expression, gene identifier, and flanking sequence achieved the best performance. The curve for the example 4 model that generated peptide presentation likelihoods based on MHC class II molecule type and peptide sequence achieved the second highest AUC of 0.91. Therefore, the example 4 model that generated peptide presentation likelihoods based on MHC class II molecule type and peptide sequence achieved the second best performance. The curve for the example 1 model that utilized minimum NetMHCII 2.3 predicted binding affinity to generate predictions achieved the lowest AUC of 0.75. Therefore the example 1 model that utilized minimum NetMHCII 2.3 predicted binding affinity to generate predictions achieved the worst performance. The curve for the example 2 model that utilized minimum NetMHCII 2.3 predicted binding rank to generate predictions achieved the second lowest AUC of 0.76. Therefore, the example 2 model that utilized minimum NetMHCII 2.3 predicted binding rank to generate predictions achieved the second worst performance.

As shown in FIG. 13T, the discrepancy in performance between the example models 1 and 2 and the example models 3 and 4 is large. Specifically, the performance of the NetMHCII 2.3 model (that utilizes either criterion of minimum NetMHCII 2.3 predicted binding affinity or minimum NetMHCII 2.3 predicted binding rank) is almost 25% lower than the performance of the presentation model disclosed herein (that generates peptide presentation likelihoods based on either MHC class II molecule type and peptide sequence, or on MHC class II molecule type, peptide sequence, RNA expression, gene identifier, and flanking sequence). Therefore, FIG. 13T demonstrates that the presentation models disclosed herein are capable of achieving significantly more accurate presentation predictions than the current best-in-class prior art model, the NetMHCII 2.3 model.

Even further, as discussed above, the NetMHCII 2.3 model is trained on a training dataset that comprises almost exclusively 15-mer peptides. As a result, the NetMHCII 2.3 model is not trained to learn which peptides lengths are more likely to be presented by MHC class II molecules. Therefore, the NetMHCII 2.3 model does not weight its predictions of likelihood of peptide presentation by MHC class II molecules according to the length of the peptide. In other words, the NetMHCII 2.3 model does not modify its predictions of likelihood of peptide presentation by MHC class II molecules for peptides that have lengths outside of the modal peptide length of 15 amino acids. As a result, the NetMHCII 2.3 model overpredicts the likelihood of presentation of peptides with lengths greater or less than 15 amino acids.

On the other hand, the presentation models disclosed herein are trained using peptide data obtained via mass spectrometry, and therefore can be trained on training dataset that comprise peptides of all different lengths. As a result, the presentation models disclosed herein are able to learn which peptides lengths are more likely to be presented by MHC class II molecules. Therefore, the presentation models disclosed herein can weight predictions of likelihood of peptide presentation by MHC class II molecules according to the length of the peptide. In other words, the presentation models disclosed herein are able to modify their predictions of likelihood of peptide presentation by MHC class II molecules for peptides that have lengths outside of the modal peptide length of 15 amino acids. As a result, the presentation models disclosed herein are capable of achieving significantly more accurate presentation predictions for peptides of lengths greater than or less than 15 amino acids, than the current best-in-class prior art model, the NetMHCII 2.3 model. This is one advantage of using the presentation models disclosed herein to predict likelihood of peptide presentation by MHC class II molecules.

XII.N. Example of Parameters Determined for MHC II Alleles

The following shows a set of parameters determined for a variation of the multi-allele presentation model (equation (16)) generating implicit per-allele presentation likelihoods for class II MHC alleles HLA-DRB1*12:01 and HLA-DRB1*10:01:

$$u = \text{expit}(\text{relu}(X \cdot W^1 + b^1) \cdot W^2 + b^2),$$

where relu(•) is the rectified linear unit (RELU) function, $W^1$, $b^1$, $W^2$, and $b^2$ are the set of parameters $\theta$ determined for the model. The allele-interacting variables X are contained in a 1×399) matrix consisting of 1 row of one-hot encoded and middle-padded peptide sequences per input peptide. The dimensions of $W^1$ are (399×256), the dimensions of $b^1$ (1×256), the dimensions of $W^2$ are (256×2), and $b^2$ are (1×2). The first column of the output indicates the implicit per-allele probability of presentation for the peptide sequence by the allele HLA-DRB1*12:01, and the second column of the output indicates the implicit per-allele for the peptide sequence by the allele HLA-DRB1*10:01. For demonstration purposes, values for $W^1$, $b^1$, $W^2$, and $b^2$ are described in detail in international application PCT/US2018/028438, herein incorporated by reference for all that it teaches.

XIII. Example Computer

Figure 14:
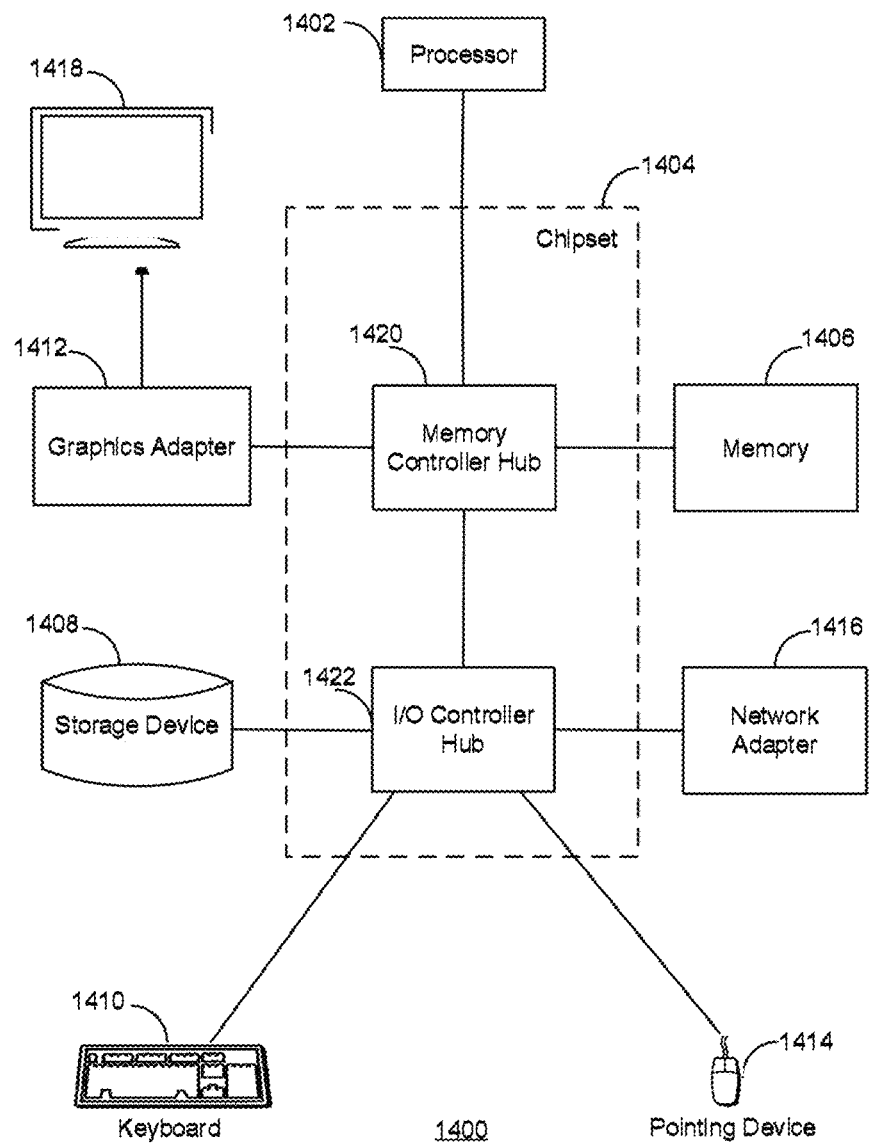
FIG. 14 illustrates an example computer for implementing the entities shown in FIGS. 1 and 3.

FIG. 14 illustrates an example computer 1400 for implementing the entities shown in FIGS. 1 and 3. The computer 1400 includes at least one processor 1402 coupled to a chipset 1404. The chipset 1404 includes a memory controller hub 1420 and an input/output (I/O) controller hub 1422. A memory 1406 and a graphics adapter 1412 are coupled to the memory controller hub 1420, and a display 1418 is coupled to the graphics adapter 1412. A storage device 1408, an input device 1414, and network adapter 1416 are coupled to the I/O controller hub 1422. Other embodiments of the computer 1400 have different architectures.

The storage device 1408 is a non-transitory computer-readable storage medium such as a hard drive, compact disk read-only memory (CD-ROM), DVD, or a solid-state memory device. The memory 1406 holds instructions and data used by the processor 1402. The input interface 1414 is a touch-screen interface, a mouse, track ball, or other type of pointing device, a keyboard, or some combination thereof, and is used to input data into the computer 1400. In some embodiments, the computer 1400 may be configured to receive input (e.g., commands) from the input interface 1414 via gestures from the user. The graphics adapter 1412 displays images and other information on the display 1418. The network adapter 1416 couples the computer 1400 to one or more computer networks.

The computer 1400 is adapted to execute computer program modules for providing functionality described herein. As used herein, the term "module" refers to computer program logic used to provide the specified functionality. Thus, a module can be implemented in hardware, firmware, and/or software. In one embodiment, program modules are stored on the storage device 1408, loaded into the memory 1406, and executed by the processor 1402.

The types of computers 1400 used by the entities of FIG. 1 can vary depending upon the embodiment and the processing power required by the entity. For example, the presentation identification system 160 can run in a single computer 1400 or multiple computers 1400 communicating with each other through a network such as in a server farm. The computers 1400 can lack some of the components described above, such as graphics adapters 1412, and displays 1418.

XIV. Neoantigen Delivery Vector Example

Below are examples of specific embodiments for carrying out the present invention. The examples are offered for illustrative purposes only, and are not intended to limit the scope of the present invention in any way. Efforts have been made to ensure accuracy with respect to numbers used (e.g., amounts, temperatures, etc.), but some experimental error and deviation should, of course, be allowed for.

The practice of the present invention will employ, unless otherwise indicated, conventional methods of protein chemistry, biochemistry, recombinant DNA techniques and pharmacology, within the skill of the art. Such techniques are explained fully in the literature. See, e.g., T. E. Creighton, *Proteins: Structures and Molecular Properties* (W.H. Freeman and Company, 1993); A. L. Lehninger, *Biochemistry* (Worth Publishers, Inc., current addition); Sambrook, et al., *Molecular Cloning: A Laboratory Manual* (2nd Edition, 1989); *Methods In Enzymology* (S. Colowick and N. Kaplan eds., Academic Press, Inc.); *Remington's Pharmaceutical Sciences*, 18th Edition (Easton, Pa.: Mack Publishing Company, 1990); Carey and Sundberg *Advanced Organic Chemistry* $3^{rd}$ Ed. (Plenum Press) Vols A and B(1992).

XIV.A. Neoantigen Cassette Design

Through vaccination, multiple class I MHC restricted tumor-specific neoantigens (TSNAs) that stimulate the corresponding cellular immune response(s) can be delivered. In one example, a vaccine cassette was engineered to encode multiple epitopes as a single gene product where the epitopes were either embedded within their natural, surrounding peptide sequence or spaced by non-natural linker sequences. Several design parameters were identified that could potentially impact antigen processing and presentation and therefore the magnitude and breadth of the TSNA specific CD8 T cell responses. In the present example, several model cassettes were designed and constructed to evaluate: (1) whether robust T cell responses could be generated to multiple epitopes incorporated in a single expression cassette; (2) what makes an optimal linker placed between the TSNAs within the expression cassette—that leads to optimal processing and presentation of all epitopes; (3) if the relative position of the epitopes within the cassette impact T cell responses; (4) whether the number of epitopes within a cassette influences the magnitude or quality of the T cell responses to individual epitopes; (5) if the addition of cellular targeting sequences improves T cell responses.

Two readouts were developed to evaluate antigen presentation and T cell responses specific for marker epitopes within the model cassettes: (1) an in vitro cell-based screen which allowed assessment of antigen presentation as gauged by the activation of specially engineered reporter T cells (Aarnoudse et al., 2002; Nagai et al., 2012); and (2) an in vivo assay that used HLA-A2 transgenic mice (Vitiello et al., 1991) to assess post-vaccination immunogenicity of cassette-derived epitopes of human origin by their corresponding epitope-specific T cell responses (Cornet et al., 2006; Depla et al., 2008; Ishioka et al., 1999).

XIV.B. Neoantigen Cassette Design Evaluation

XIV.B.1. Methods and Materials

TCR and Cassette Design and Cloning

The selected TCRs recognize peptides NLVPMVATV (SEQ ID NO: 132) (PDB #5D2N), CLGGLLTMV (SEQ ID NO: 133) (PDB #3REV), GILGFVFTL (SEQ ID NO: 134) (PDB #1OGA) LLFGYPVYV (SEQ ID NO: 135) (PDB #1AO7) when presented by A*0201. Transfer vectors were constructed that contain 2A peptide-linked TCR subunits (beta followed by alpha), the EMCV IRES, and 2A-linked CD8 subunits (beta followed by alpha and by the puromycin resistance gene). Open reading frame sequences were codon-optimized and synthesized by GeneArt.

Cell Line Generation for In Vitro Epitope Processing and Presentation Studies

Peptides were purchased from ProImmune or Genscript diluted to 10 mg/mL with 10 mM tris(2-carboxyethyl) phosphine (TCEP) in water/DMSO (2:8, v/v). Cell culture medium and supplements, unless otherwise noted, were from Gibco. Heat inactivated fetal bovine serum (FBShi) was from Seradigm. QUANTI-Luc Substrate, Zeocin, and Puromycin were from InvivoGen. Jurkat-Lucia NFAT Cells (InvivoGen) were maintained in RPMI 1640 supplemented with 10% FBShi, Sodium Pyruvate, and 100 µg/mL Zeocin. Once transduced, these cells additionally received 0.3 µg/mL Puromycin. T2 cells (ATCC CRL-1992) were cultured in Iscove's Medium (IMDM) plus 20% FBShi. U-87 MG (ATCC HTB-14) cells were maintained in MEM Eagles Medium supplemented with 10% FBShi.

Jurkat-Lucia NFAT cells contain an NFAT-inducible Lucia reporter construct. The Lucia gene, when activated by the engagement of the T cell receptor (TCR), causes secretion of a coelenterazine-utilizing luciferase into the culture medium. This luciferase can be measured using the QUANTI-Luc luciferase detection reagent. Jurkat-Lucia cells were transduced with lentivirus to express antigen-specific TCRs. The HIV-derived lentivirus transfer vector was obtained from GeneCopoeia, and lentivirus support plasmids expressing VSV-G (pCMV-VsvG), Rev (pRSV-Rev) and Gag-pol (pCgpV) were obtained from Cell Design Labs.

Lentivirus was prepared by transfection of 50-80% confluent T75 flasks of HEK293 cells with Lipofectamine 2000 (Thermo Fisher), using 40 µl of lipofectamine and 20 µg of the DNA mixture (4:2:1:1 by weight of the transfer plasmid: pCgpV:pRSV-Rev:pCMV-VsvG). 8-10 mL of the virus-containing media were concentrated using the Lenti-X system (Clontech), and the virus resuspended in 100-200 µl of fresh medium. This volume was used to overlay an equal volume of Jurkat-Lucia cells (5×10E4-1×10E6 cells were used in different experiments).

Following culture in 0.3 µg/ml puromycin-containing medium, cells were sorted to obtain clonality. These Jurkat-Lucia TCR clones were tested for activity and selectivity using peptide loaded T2 cells.

In Vitro Epitope Processing and Presentation Assay

T2 cells are routinely used to examine antigen recognition by TCRs. T2 cells lack a peptide transporter for antigen processing (TAP deficient) and cannot load endogenous peptides in the endoplasmic reticulum for presentation on the MHC. However, the T2 cells can easily be loaded with exogenous peptides. The five marker peptides (NLVPMVATV (SEQ ID NO: 132), CLGGLLTMV (SEQ ID NO: 133), GLCTLVAML (SEQ ID NO: 136), LLFGYPVYV (SEQ ID NO: 135), GILGFVFTL (SEQ ID NO: 134)) and two irrelevant peptides (WLSLLVPFV (SEQ ID NO: 137), FLLTRICT (SEQ ID NO: 138)) were loaded onto T2 cells. Briefly, T2 cells were counted and diluted to 1×106 cells/mL with IMDM plus 1% FBShi. Peptides were added to result in 10 µg peptide/1×106 cells. Cells were then incubated at 37° C. for 90 minutes. Cells were washed twice with IMDM plus 20% FBShi, diluted to 5×10E5 cells/mL and 100 µL plated into a 96-well Costar tissue culture plate. Jurkat-Lucia TCR clones were counted and diluted to 5×10E5 cells/mL in RPMI 1640 plus 10% FBShi and 100 µL added to the T2 cells. Plates were incubated overnight at 37° C., 5% CO2. Plates were then centrifuged at 400 g for 3 minutes and 20 µL supernatant removed to a white flat bottom Greiner plate. QUANTI-Luc substrate was prepared according to instructions and 50 µL/well added. Luciferase expression was read on a Molecular Devices SpectraMax iE3x.

To test marker epitope presentation by the adenoviral cassettes, U-87 MG cells were used as surrogate antigen presenting cells (APCs) and were transduced with the adenoviral vectors. U-87 MG cells were harvested and plated in culture media as 5×10E5 cells/100 µl in a 96-well Costar tissue culture plate. Plates were incubated for approximately 2 hours at 37° C. Adenoviral cassettes were diluted with MEM plus 10% FBShi to an MOI of 100, 50, 10, 5, 1 and 0 and added to the U-87 MG cells as 5 µl/well. Plates were again incubated for approximately 2 hours at 37° C. Jurkat-Lucia TCR clones were counted and diluted to 5×10E5 cells/mL in RPMI plus 10% FBShi and added to the U-87 MG cells as 100 µL/well. Plates were then incubated for approximately 24 hours at 37° C., 5% CO2. Plates were centrifuged at 400 g for 3 minutes and 20 µL supernatant removed to a white flat bottom Greiner plate. QUANTI-Luc substrate was prepared according to instructions and 50 µL/well added. Luciferase expression was read on a Molecular Devices SpectraMax iE3x.

Mouse Strains for Immunogenicity Studies

Transgenic HLA-A2.1 (HLA-A2 Tg) mice were obtained from Taconic Labs, Inc. These mice carry a transgene consisting of a chimeric class I molecule comprised of the human HLA-A2.1 leader, α1, and α2 domains and the murine H2-Kb α3, transmembrane, and cytoplasmic domains (Vitiello et al., 1991). Mice used for these studies were the first generation offspring (F1) of wild type BALB/cAnNTac females and homozygous HLA-A2.1 Tg males on the C57Bl/6 background.

Adenovirus Vector (Ad5v) Immunizations

HLA-A2 Tg mice were immunized with $1\times10^{10}$ to $1\times10^{6}$ viral particles of adenoviral vectors via bilateral intramuscular injection into the tibialis anterior. Immune responses were measured at 12 days post-immunization.

Lymphocyte Isolation

Lymphocytes were isolated from freshly harvested spleens and lymph nodes of immunized mice. Tissues were dissociated in RPMI containing 10% fetal bovine serum with penicillin and streptomycin (complete RPMI) using the GentleMACS tissue dissociator according to the manufacturer's instructions.

Ex Vivo Enzyme-Linked Immunospot (ELISPOT) Analysis

ELISPOT analysis was performed according to ELISPOT harmonization guidelines (Janetzki et al., 2015) with the mouse IFNg ELISpotPLUS kit (MABTECH). $1\times10^{5}$ splenocytes were incubated with 10 uM of the indicated peptides for 16 hours in 96-well IFNg antibody coated plates. Spots were developed using alkaline phosphatase. The reaction was timed for 10 minutes and was quenched by running the plate under tap water. Spots were counted using an AID vSpot Reader Spectrum. For ELISPOT analysis, wells with saturation >50% were recorded as "too numerous to count". Samples with deviation of replicate wells >10% were excluded from analysis. Spot counts were then corrected for well confluency using the formula: spot count+2×(spot count×% confluence/[100%−% confluence]). Negative background was corrected by subtraction of spot counts in the negative peptide stimulation wells from the antigen stimulated wells. Finally, wells labeled too numerous to count were set to the highest observed corrected value, rounded up to the nearest hundred.

Ex Vivo Intracellular Cytokine Staining (ICS) and Flow Cytometry Analysis

Freshly isolated lymphocytes at a density of $2-5\times10^{6}$ cells/mL were incubated with 10 uM of the indicated peptides for 2 hours. After two hours, brefeldin A was added to a concentration of 5 ug/ml and cells were incubated with stimulant for an additional 4 hours. Following stimulation, viable cells were labeled with fixable viability dye eFluor780 according to manufacturer's protocol and stained with anti-CD8 APC (clone 53-6.7, BioLegend) at 1:400 dilution. Anti-IFNg PE (clone XMG1.2, BioLegend) was used at 1:100 for intracellular staining. Samples were collected on an Attune NxT Flow Cytometer (Thermo Scientific). Flow cytometry data was plotted and analyzed using FlowJo. To assess degree of antigen-specific response, both the percent IFNg+ of CD8+ cells and the total IFNg+ cell number/$1\times10^{6}$ live cells were calculated in response to each peptide stimulant.

XIV.B.2. In Vitro Evaluation of Neoantigen Cassette Designs

Figure 15:
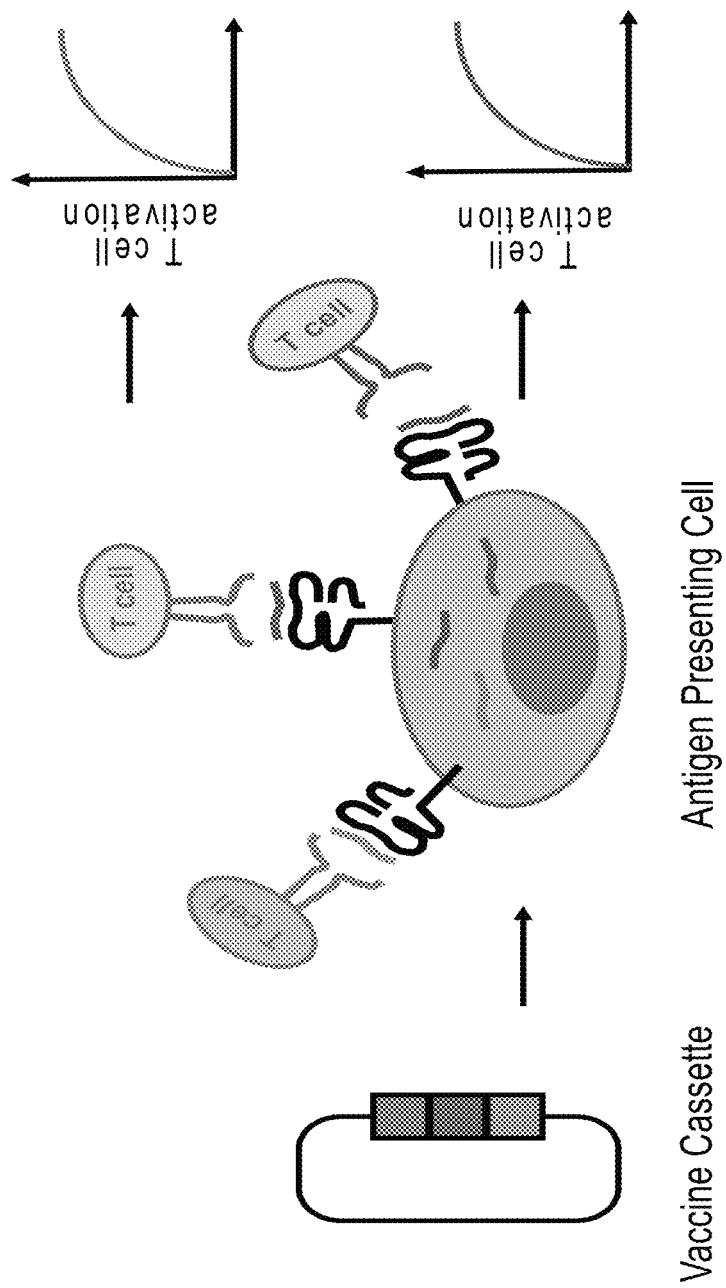
FIG. 15 illustrates development of an in vitro T cell activation assay. Schematic of the assay in which the delivery of a vaccine cassette to antigen presenting cells, leads to expression, processing and MHC-restricted presentation of distinct peptide antigens. Reporter T cells engineered with T cell receptors that match the specific peptide-MHC combination become activated resulting in luciferase expression.

As an example of neoantigen cassette design evaluation, an in vitro cell-based assay was developed to assess whether selected human epitopes within model vaccine cassettes were being expressed, processed, and presented by antigen-presenting cells (FIG. 15). Upon recognition, Jurkat-Lucia reporter T cells that were engineered to express one of five TCRs specific for well-characterized peptide-HLA combinations become activated and translocate the nuclear factor of activated T cells (NFAT) into the nucleus which leads to transcriptional activation of a luciferase reporter gene. Antigenic stimulation of the individual reporter CD8 T cell lines was quantified by bioluminescence.

Individual Jurkat-Lucia reporter lines were modified by lentiviral transduction with an expression construct that includes an antigen-specific TCR beta and TCR alpha chain separated by a P2A ribosomal skip sequence to ensure equimolar amounts of translated product (Banu et al., 2014). The addition of a second CD8 beta-P2A-CD8 alpha element to the lentiviral construct provided expression of the CD8 co-receptor, which the parent reporter cell line lacks, as CD8 on the cell surface is crucial for the binding affinity to target pMHC molecules and enhances signaling through engagement of its cytoplasmic tail (Lyons et al., 2006; Yachi et al., 2006).

After lentiviral transduction, the Jurkat-Lucia reporters were expanded under puromycin selection, subjected to single cell fluorescence assisted cell sorting (FACS), and the monoclonal populations tested for luciferase expression. This yielded stably transduced reporter cell lines for specific peptide antigens 1, 2, 4, and 5 with functional cell responses. (Table 2).

TABLE 2

Development of an in vitro T cell activation assay.
Peptide-specific T cell recognition as measured by
induction of luciferase indicates effective processing
and presentation of the vaccine cassette antigens.

| Epitope | Short Cassette Design AAY |
|---|---|
| 1 | 24.5 ± 0.5 |
| 2 | 11.3 ± 0.4 |
| 3* | n/a |
| 4 | 26.1 ± 3.1 |
| 5 | 46.3 ± 1.9 |

*Reporter T cell for epitope 3 not yet generated

In another example, a series of short cassettes, all marker epitopes were incorporated in the same position (FIG. 16A) and only the linkers separating the HLA-A*0201 restricted epitopes (FIG. 16B) were varied. Reporter T cells were individually mixed with U-87 antigen-presenting cells (APCs) that were infected with adenoviral constructs expressing these short cassettes, and luciferase expression was measured relative to uninfected controls. All four antigens in the model cassettes were recognized by matching reporter T cells, demonstrating efficient processing and presentation of multiple antigens. The magnitude of T cell responses follow largely similar trends for the natural and AAY-linkers. The antigens released from the RR-linker based cassette show lower luciferase inductions (Table 3). The DPP-linker, designed to disrupt antigen processing, produced a vaccine cassette that led to low epitope presentation (Table 3).

TABLE 3

Evaluation of linker sequences in short cassettes. Luciferase induction in the in vitro T cell activation assay indicated that, apart from the DPP-based cassette, all linkers facilitated efficient release of the cassette antigens. T cell epitope only (no linker) = 9AA, natural linker one side = 17AA, natural linker both sides = 25 AA, non-natural linkers = AAY, RR, DPP

| | Short Cassette Designs | | | | | |
|---|---|---|---|---|---|---|
| Epitope | 9AA | 17AA | 25AA | AAY | RR | DPP |
| 1 | 33.6 ± 0.9 | 42.8 ± 2.1 | 42.3 ± 2.3 | 24.5 ± 0.5 | 21.7 ± 0.9 | 0.9 ± 0.1 |
| 2 | 12.0 ± 0.9 | 10.3 ± 0.6 | 14.6 ± 04 | 11.3 ± 0.4 | 8.5 ± 0.3 | 1.1 ± 0.2 |
| 3* | n/a | n/a | n/a | n/a | n/a | n/a |
| 4 | 26.6 ± 2.5 | 16.1 ± 0.6 | 16.6 ± 0.8 | 26.1 ± 3.1 | 12.5 ± 0.8 | 1.3 ± 0.2 |
| 5 | 29.7 ± 0.6 | 21.2 ± 0.7 | 24.3 ± 1.4 | 46.3 ± 1.9 | 19.7 ± 0.4 | 1.3 ± 0.1 |

*Reporter T cell for epitope 3 not yet generated

Figure 17:
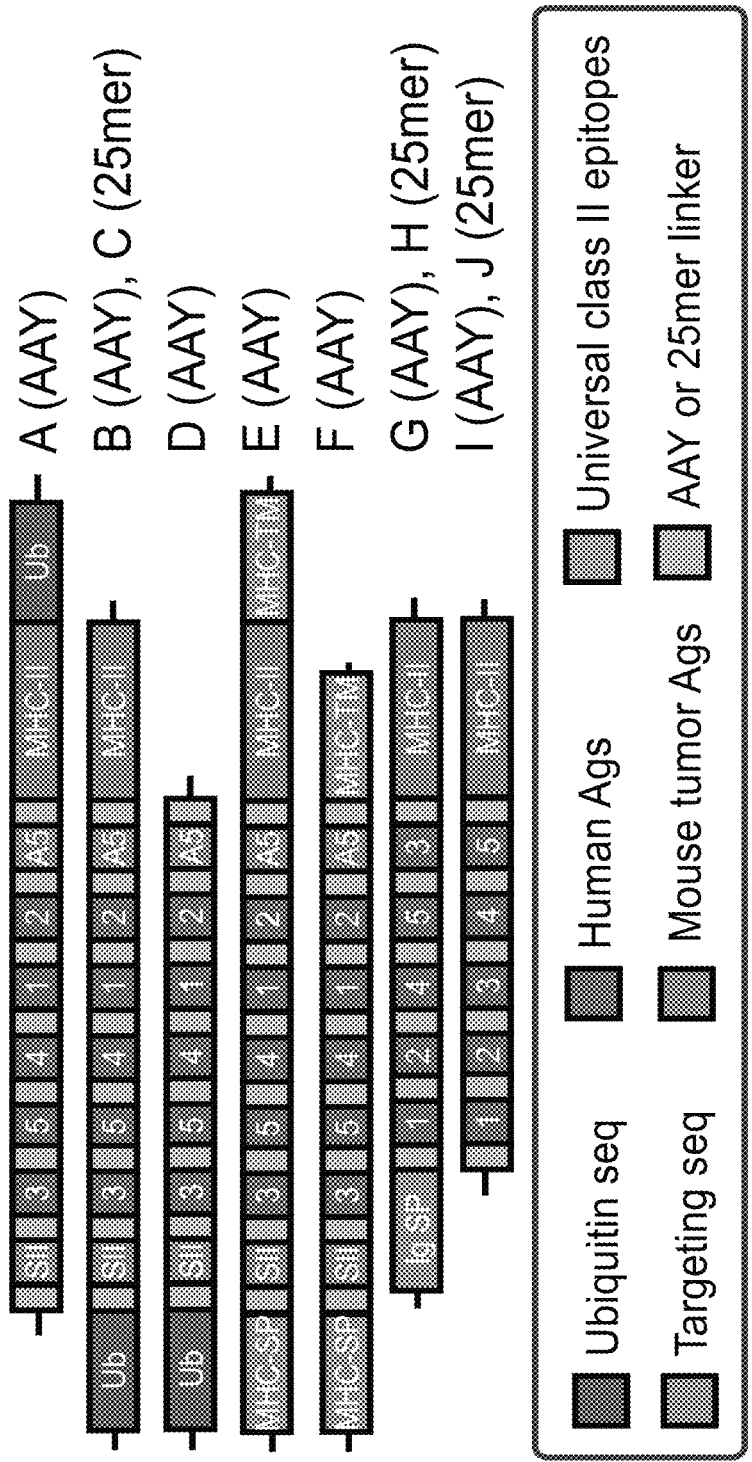
FIG. 17 illustrates evaluation of cellular targeting sequences added to model vaccine cassettes. The targeting cassettes extend the short cassette designs with ubiquitin (Ub), signal peptides (SP) and/or transmembrane (TM) domains, feature next to the five marker human T cell epitopes (epitopes 1 through 5) also two mouse T cell epitopes SIINFEKL (SII) (SEQ ID NO: 57) and SPSYAYHQF (A5) (SEQ ID NO: 58), and use either the non natural linker AAY- or natural linkers flanking the T cell epitopes on both sides (25mer).

In another example, an additional series of short cassettes were constructed that, besides human and mouse epitopes, contained targeting sequences such as ubiquitin (Ub), MHC and Ig-kappa signal peptides (SP), and/or MHC transmembrane (TM) motifs positioned on either the N- or C-terminus of the cassette. (FIG. 17). When delivered to U-87 APCs by adenoviral vector, the reporter T cells again demonstrated efficient processing and presentation of multiple cassette-derived antigens. However, the magnitude of T cell responses were not substantially impacted by the various targeting features (Table 4).

model carries a transgene consisting partly of human HLA-A*0201 and mouse H2-Kb thus encoding a chimeric class I MHC molecule consisting of the human HLA-A2.1 leader, α1 and α2 domains ligated to the murine a3, transmembrane and cytoplasmic H2-Kb domain (Vitiello et al., 1991). The chimeric molecule allows HLA-A*02:01-restricted antigen presentation whilst maintaining the species-matched interaction of the CD8 co-receptor with the α3 domain on the MHC.

For the short cassettes, all marker epitopes generated a T cell response, as determined by IFN-gamma ELISPOT, that

TABLE 4

Evaluation of cellular targeting sequences added to model vaccine cassettes. Employing the in vitro T cell activation assay demonstrated that the four HLA-A*0201 restricted marker epitopes are liberated efficiently from the model cassettes and targeting sequences did not substantially improve T cell recognition and activation.

| | Short Cassette Designs | | | | | | | | | |
|---|---|---|---|---|---|---|---|---|---|---|
| Epitope | A | B | C | D | E | F | G | H | I | J |
| 1 | 32.5 ± 1.5 | 31.8 ± 0.8 | 29.1 ± 1.2 | 29.1 ± 1.1 | 28.4 ± 0.7 | 20.4 ± 0.5 | 35.0 ± 1.3 | 30.3 ± 2.0 | 22.5 ± 0.9 | 38.1 ± 1.6 |
| 2 | 6.1 ± 0.2 | 6.3 ± 0.2 | 7.6 ± 0.4 | 7.0 ± 0.5 | 5.9 ± 0.2 | 3.7 ± 0.2 | 7.6 ± 0.4 | 5.4 ± 0.3 | 6.2 ± 0.4 | 6.4 ± 0.3 |
| 3* | n/a | n/a | n/a | n/a | n/a | n/a | n/a | n/a | n/a | n/a |
| 4 | 12.3 ± 1.1 | 14.1 ± 0.7 | 12.2 ± 0.8 | 13.7 ± 1.0 | 11.7 ± 0.8 | 10.6 ± 0.4 | 11.0 ± 0.6 | 7.6 ± 0.6 | 16.1 ± 0.5 | 8.7 ± 0.5 |
| 5 | 44.4 ± 2.8 | 53.6 ± 1.6 | 49.9 ± 3.3 | 50.5 ± 2.8 | 41.7 ± 2.8 | 36.1 ± 1.1 | 46.5 ± 2.1 | 31.4 ± 0.6 | 75.4 ± 1.6 | 35.7 ± 2.2 |

*Reporter T cell for epitope 3 not yet generated

XIV.B.3. In Vivo Evaluation of Neoantigen Cassette Designs

Figures 16A, 16B:
FIG. 16A illustrates evaluation of linker sequences in short cassettes and shows five class I MHC restricted epitopes (epitopes 1 through 5) concatenated in the same position relative to each other followed by two universal class II MHC epitopes (MHC-II). Various iterations were generated using different linkers. In some cases the T cell epitopes are directly linked to each other. In others, the T cell epitopes are flanked on one or both sides by its natural sequence. In other iterations, the T cell epitopes are linked by the non-natural sequences AAY, RR, and DPP.
FIG. 16B illustrates evaluation of linker sequences in short cassettes and shows sequence information on the T cell epitopes embedded in the short cassettes. Figure discloses SEQ ID NOS 132, 133, 136, 135, 134, 160, and 161, respectively, in order of appearance.
Figure 18:
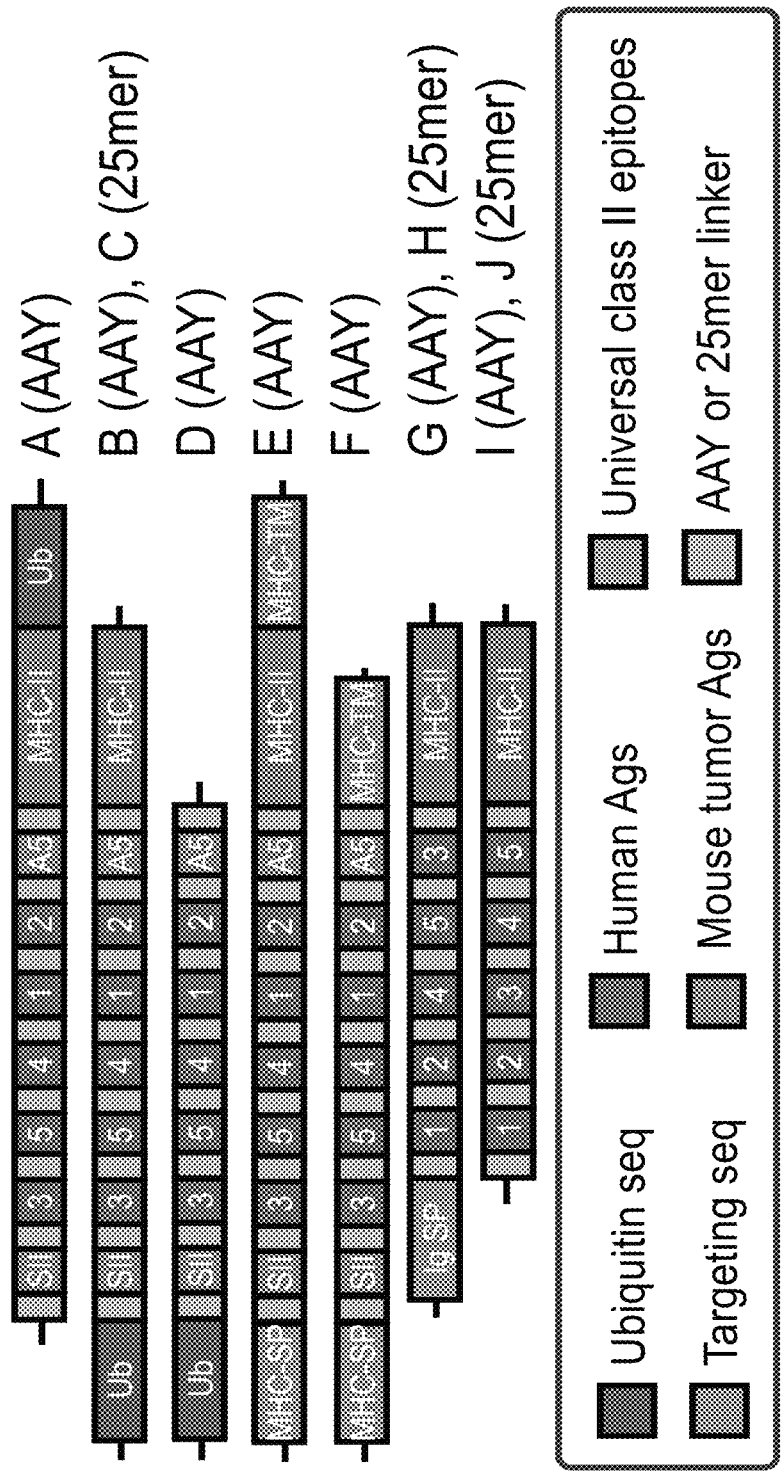
FIG. 18 illustrates in vivo evaluation of linker sequences in short cassettes. A) Experimental design of the in vivo evaluation of vaccine cassettes using HLA-A2 transgenic mice.
Figure 19A:
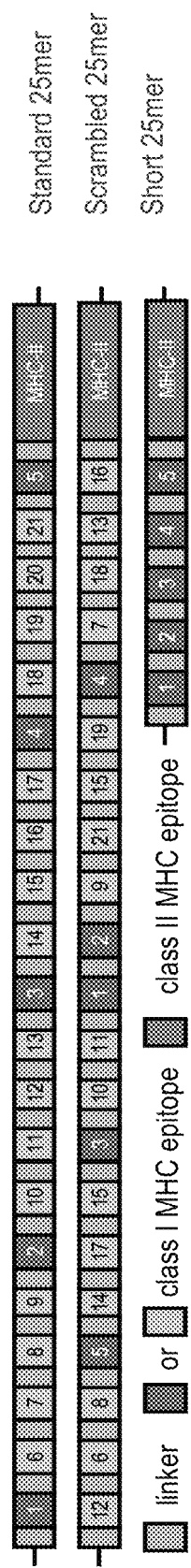
FIG. 19A illustrates in vivo evaluation of the impact of epitope position in long 21-mer cassettes and shows the design of long cassettes entails five marker class I epitopes (epitopes 1 through 5) contained in their 25-mer natural sequence (linker=natural flanking sequences), spaced with additional well-known T cell class I epitopes (epitopes 6 through 21) contained in their 25-mer natural sequence, and two universal class II epitopes (MHC-II0, with only the relative position of the class I epitopes varied.

As another example of neoantigen cassette design evaluation, vaccine cassettes were designed to contain 5 well-characterized human class I MHC epitopes known to stimulate CD8 T cells in an HLA-A*02:01 restricted fashion (FIG. 16A, 17, 19A). For the evaluation of their in vivo immunogenicity, vaccine cassettes containing these marker epitopes were incorporated in adenoviral vectors and used to infect HLA-A2 transgenic mice (FIG. 18). This mouse was approximately 10-50× stronger of what has been commonly reported (Cornet et al., 2006; Depla et al., 2008; Ishioka et al., 1999). Of all the linkers evaluated, the concatamer of 25mer sequences, each containing a minimal epitope flanked by their natural amino acids sequences, generated the largest and broadest T cell response (Table 5). Intracellular cytokine staining (ICS) and flow cytometry analysis revealed that the antigen-specific T cell responses are derived from CD8 T cells.

TABLE 5

In vivo evaluation of linker sequences in short cassettes. ELISPOT data indicated that HLA-A2 transgenic mice, 17 days post-infection with 1e11 adenovirus viral particles, generated a T cell response to all class I MHC restricted epitopes in the cassette.

| | Short Cassette Designs | | | | | |
|---|---|---|---|---|---|---|
| Epitope | 9AA | 17AA | 25AA | AAY | RR | DPP |
| 1 | 2020 +/− 583 | 2505 +/− 1281 | 6844 +/− 956 | 1489 +/− 762 | 1675 +/− 690 | 1781 +/− 774 |
| 2 | 4472 +/− 755 | 3792 +/− 1319 | 7629 +/− 996 | 3851 +/− 1748 | 4726 +/− 1715 | 5868 +/− 1427 |
| 3 | 5830 +/− 315 | 3629 +/− 862 | 7253 +/− 491 | 4813 +/− 1761 | 6779 +/− 1033 | 7328 +/− 1700 |

TABLE 5-continued

In vivo evaluation of linker sequences in short cassettes. ELISPOT data indicated that HLA-A2 transgenic mice, 17 days post-infection with 1e11 adenovirus viral particles, generated a T cell response to all class I MHC restricted epitopes in the cassette.

| | Short Cassette Designs | | | | | |
|---|---|---|---|---|---|---|
| Epitope | 9AA | 17AA | 25AA | AAY | RR | DPP |
| 4 | 5536 +/− 375 | 2446 +/− 955 | 2961 +/− 1487 | 4230 +/− 1759 | 6518 +/− 909 | 7222 +/− 1824 |
| 5 | 8800 +/− 0 | 7943 +/− 821 | 8423 +/− 442 | 8312 +/− 696 | 8800 +/− 0 | 1836 +/− 328 |

In another example, a series of long vaccine cassettes was constructed and incorporated in adenoviral vectors that, next to the original 5 marker epitopes, contained an additional 16 HLA-A*02:01, A*03:01 and B*44:05 epitopes with known CD8 T cell reactivity (FIG. 19A, B). The size of these long cassettes closely mimicked the final clinical cassette design, and only the position of the epitopes relative to each other was varied. The CD8 T cell responses were comparable in magnitude and breadth for both long and short vaccine cassettes, demonstrating that (a) the addition of more epitopes did not substantially impact the magnitude of immune response to the original set of epitopes, and (b) the position of an epitope in a cassette did not substantially influence the ensuing T cell response to it (Table 6).

TABLE 6

In vivo evaluation of the impact of epitope position in long cassettes. ELISPOT data indicated that HLA-A2 transgenic mice, 17 days post-infection with 5e10 adenovirus viral particles, generated a T cell response comparable in magnitude for both long and short vaccine cassettes.

| | Long Cassette Designs | | |
|---|---|---|---|
| Epitope | Standard | Scrambled | Short |
| 1 | 863 +/− 1080 | 804 +/− 1113 | 1871 +/− 2859 |
| 2 | 6425 +/− 1594 | 28 +/− 62 | 5390 +/− 1357 |
| 3* | 23 +/− 30 | 36 +/− 18 | 0 +/− 48 |
| 4 | 2224 +/− 1074 | 2727 +/− 644 | 2637 +/− 1673 |
| 5 | 7952 +/− 297 | 8100 +/− 0 | 8100 +/− 0 |

*Suspected technical error caused an absence of a T cell response.

XIV.B.4. Neoantigen Cassette Design for Immunogenicity and Toxicology Studies

In summary, the findings of the model cassette evaluations (FIG. 16-19, Tables 2-6) demonstrated that, for model vaccine cassettes, robustimmunogenicity was achieved when a "string of beads" approach was employed that encodes around 20 epitopes in the context of an adenovirus-based vector. The epitopes were assembled by concatenating 25mer sequences, each embedding a minimal CD8 T cell epitope (e.g. 9 amino acid residues) that were flanked on both sides by its natural, surrounding peptide sequence (e.g. 8 amino acid residues on each side). As used herein, a "natural" or "native" flanking sequence refers to the N- and/or C-terminal flanking sequence of a given epitope in the naturally occurring context of that epitope within its source protein. For example, the HCMV pp65 MHC I epitope NLVPMVATV (SEQ ID NO: 132) is flanked on its 5' end by the native 5' sequence WQAGILAR (SEQ ID NO: 139) and on its 3' end by the native 3' sequence QGQNLKYQ (SEQ ID NO: 140), thus generating the WQAGILARNLVPMVATVQGQNLKYQ (SEQ ID NO: 141) 25mer peptide found within the HCMV pp65 source protein. The natural or native sequence can also refer to a nucleotide sequence that encodes an epitope flanked by native flanking sequence(s). Each 25mer sequence is directly connected to the following 25mer sequence. In instances where the minimal CD8 T cell epitope is greater than or less than 9 amino acids, the flanking peptide length can be adjusted such that the total length is still a 25mer peptide sequence. For example, a 10 amino acid CD8 T cell epitope can be flanked by an 8 amino acid sequence and a 7 amino acid. The concatamer was followed by two universal class II MHC epitopes that were included to stimulate CD4 T helper cells and improve overall in vivo immunogenicity of the vaccine cassette antigens. (Alexander et al., 1994; Panina-Bordignon et al., 1989) The class II epitopes were linked to the final class I epitope by a GPGPG amino acid linker (SEQ ID NO:56). The two class II epitopes were also linked to each other by a GPGPG amino acid linker (SEQ ID NO: 56), as a well as flanked on the C-terminus by a GPGPG amino acid linker (SEQ ID NO: 56). Neither the position nor the number of epitopes appeared to substantially impact T cell recognition or response. Targeting sequences also did not appear to substantially impact the immunogenicity of cassette-derived antigens.

Figure 20A:
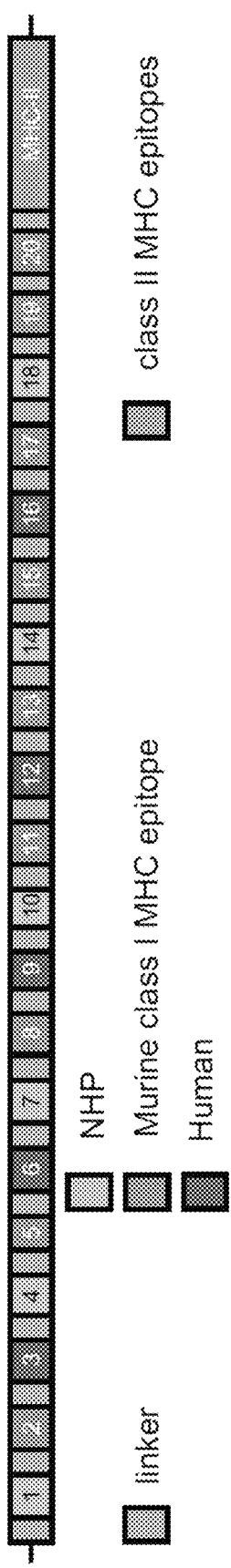
FIG. 20A illustrates final cassette design for preclinical IND-enabling studies and shows the design of the final cassettes comprises 20 MHC I epitopes contained in their 25-mer natural sequence (linker=natural flanking sequences), composed of 6 non-human primate (NHP) epitopes, 5 human epitopes, 9 murine epitopes, as well as 2 universal MHC class II epitopes.

As a further example, based on the in vitro and in vivo data obtained with model cassettes (FIG. 16-19, Tables 2-6), a cassette design was generated that alternates well-characterized T cell epitopes known to be immunogenic in non-human primates (NHPs), mice and humans. The 20 epitopes, all embedded in their natural 25mer sequences, are followed by the two universal class II MHC epitopes that were present in all model cassettes evaluated (FIG. 20). This cassette design was used to study immunogenicity as well as pharmacology and toxicology studies in multiple species.

XV. ChAd Neoantigen Cassette Delivery Vector

XV.A. ChAd Neoantigen Cassette Delivery Vector Construction

In one example, Chimpanzee adenovirus (ChAd) was engineered to be a delivery vector for neoantigen cassettes. In a further example, a full-length ChAdV68 vector was synthesized based on AC_000011.1 (sequence 2 from U.S. Pat. No. 6,083,716) with E1 (nt 457 to 3014) and E3 (nt 27,816-31,332) sequences deleted. Reporter genes under the control of the CMV promoter/enhancer were inserted in place of the deleted E1 sequences. Transfection of this clone into HEK293 cells did not yield infectious virus. To confirm the sequence of the wild-type C68 virus, isolate VR-594 was obtained from the ATCC, passaged, and then independently sequenced (SEQ ID NO:10). When comparing the AC_000011.1 sequence to the ATCC VR-594 sequence (SEQ ID NO:10) of wild-type ChAdV68 virus, 6 nucleotide differences were identified. In one example, a modified ChAdV68 vector was generated based on AC_000011.1, with the corresponding ATCC VR-594 nucleotides substituted at five positions (ChAdV68.5WTnt SEQ ID NO:1).

In another example, a modified ChAdV68 vector was generated based on AC_000011.1 with E1 (nt 577 to 3403) and E3 (nt 27,816-31,332) sequences deleted and the corresponding ATCC VR-594 nucleotides substituted at four positions. A GFP reporter (ChAdV68.4WTnt.GFP; SEQ ID NO:11) or model neoantigen cassette (ChAdV68.4WTnt.MAG25mer; SEQ ID NO:12) under the control of the CMV promoter/enhancer was inserted in place of deleted E1 sequences.

In another example, a modified ChAdV68 vector was generated based on AC_000011.1 with E1 (nt 577 to 3403) and E3 (nt 27,125-31,825) sequences deleted and the corresponding ATCC VR-594 nucleotides substituted at five positions. A GFP reporter (ChAdV68.5WTnt.GFP; SEQ ID NO:13) or model neoantigen cassette (ChAdV68.5WTnt.MAG25mer; SEQ ID NO:2) under the control of the CMV promoter/enhancer was inserted in place of deleted E1 sequences.

Full-Length ChAdVC68 sequence "ChAdV68.5WTnt"; AC_000011.1 sequence with corresponding ATCC VR-594 nucleotides substituted at five positions.

(SEQ ID NO: 1)

CCATCTTCAATAATATACCTCAAACTTTTTGTGCGCGTTAATATGCAAATGAGGCGTTTGAATTTGGGGAGGAA

GGGCGGTGATTGGTCGAGGGATGAGCGACCGTTAGGGGCGGGGCGAGTGACGTTTTGATGACGTGGTTGCGAGG

AGGAGCCAGTTTGCAAGTTCTCGTGGGAAAAGTGACGTCAAACGAGGTGTGGTTTGAACACGGAAATACTCAAT

TTTCCCGCGCTCTCTGACAGGAAATGAGGTGTTTCTGGGCGGATGCAAGTGAAAACGGGCCATTTTCGCGCGAA

AACTGAATGAGGAAGTGAAAATCTGAGTAATTTCGCGTTTATGGCAGGGAGGAGTATTTGCCGAGGGCCGAGTA

GACTTTGACCGATTACGTGGGGGTTTCGATTACCGTGTTTTTCACCTAAATTTCCGCGTACGGTGTCAAAGTCC

GGTGTTTTTACGTAGGTGTCAGCTGATCGCCAGGGTATTTAAACCTGCGCTCTCCAGTCAAGAGGCCACTCTTG

AGTGCCAGCGAGAAGAGTTTTCTCCTCCGCGCCGCGAGTCAGATCTACACTTTGAAAGATGAGGCACCTGAGAG

ACCTGCCCGATGAGAAAATCATCATCGCTTCCGGGAACGAGATTCTGGAACTGGTGGTAAATGCCATGATGGGC

GACGACCCTCCGGAGCCCCCCACCCCATTTGAGACACCTTCGCTGCACGATTTGTATGATCTGGAGGTGGATGT

GCCCGAGGACGATCCCAATGAGGAGGCGGTAAATGATTTTTTTAGCGATGCCGCGCTGCTAGCTGCCGAGGAGG

CTTCGAGCTCTAGCTCAGACAGCGACTCTTCACTGCATACCCCTAGACCCGGCAGAGGTGAGAAAAAGATCCCC

GAGCTTAAAGGGGAAGAGATGGACTTGCGCTGCTATGAGGAATGCTTGCCCCCGAGCGATGATGAGGACGAGCA

GGCGATCCAGAACGCAGCGAGCCAGGGAGTGCAAGCCGCCAGCGAGAGCTTTGCGCTGGACTGCCCGCCTCTGC

CCGGACACGGCTGTAAGTCTTGTGAATTTCATCGCATGAATACTGGAGATAAAGCTGTGTTGTGTGCACTTTGC

TATATGAGAGCTTACAACCATTGTGTTTACAGTAAGTGTGATTAAGTTGAACTTTAGAGGGAGGCAGAGAGCAG

GGTGACTGGGCGATGACTGGTTTATTTATGTATATATGTTCTTTATATAGGTCCCGTCTCTGACGCAGATGATG

AGACCCCCACTACAAAGTCCACTTCGTCACCCCCAGAAATTGGCACATCTCCACCTGAGAATATTGTTAGACCA

GTTCCTGTTAGAGCCACTGGGAGGAGAGCAGCTGTGGAATGTTTGGATGACTTGCTACAGGGTGGGGTTGAACC

TTTGGACTTGTGTACCCGGAAACGCCCCAGGCACTAAGTGCCACACATGTGTGTTTACTTGAGGTGATGTCAGT

ATTTATAGGGTGTGGAGTGCAATAAAAAATGTGTTGACTTTAAGTGCGTGGTTTATGACTCAGGGGTGGGGACT

GTGAGTATATAAGCAGGTGCAGACCTGTGTGGTTAGCTCAGAGCGGCATGGAGATTTGGACGGTCTTGGAAGAC

TTTCACAAGACTAGACAGCTGCTAGAGAACGCCTCGAACGGAGTCTCTTACCTGTGGAGATTCTGCTTCGGTGG

CGACCTAGCTAGGCTAGTCTACAGGGCCAAACAGGATTATAGTGAACAATTTGAGGTTATTTTGAGAGAGTGTT

CTGGTCTTTTTGACGCTCTTAACTTGGGCCATCAGTCTCACTTTAACCAGAGGATTTCGAGAGCCCTTGATTTT

ACTACTCCTGGCAGAACCACTGCAGCAGTAGCCTTTTTTGCTTTTATTCTTGACAAATGGAGTCAAGAAACCCA

TTTCAGCAGGGATTACCAGCTGGATTTCTTAGCAGTAGCTTTGTGGAGAACATGGAAGTGCCAGCGCCTGAATG

CAATCTCCGGCTACTTGCCGGTACAGCCGCTAGACACTCTGAGGATCCTGAATCTCCAGGAGAGTCCCAGGGCA

CGCCAACGTCGCCAGCAGCAGCAGCAGGAGGAGGATCAAGAAGAGAACCCGAGAGCCGGCCTGGACCCTCCGGC

GGAGGAGGAGGAGTAGCTGACCTGTTTCCTGAACTGCGCCGGGTGCTGACTAGGTCTTCGAGTGGTCGGGAGAG

GGGGATTAAGCGGGAGAGGCATGATGAGACTAATCACAGAACTGAACTGACTGTGGGTCTGATGAGTCGCAAGC

GCCCAGAAACAGTGTGGTGGCATGAGGTGCAGTCGACTGGCACAGATGAGGTGTCGGTGATGCATGAGAGGTTT

TCTCTAGAACAAGTCAAGACTTGTTGGTTAGAGCCTGAGGATGATTGGGAGGTAGCCATCAGGAATTATGCCAA

-continued

```
GCTGGCTCTGAGGCCAGACAAGAAGTACAAGATTACTAAGCTGATAAATATCAGAAATGCCTGCTACATCTCAG

GGAATGGGGCTGAAGTGGAGATCTGTCTCCAGGAAAGGGTGGCTTTCAGATGCTGCATGATGAATATGTACCCG

GGAGTGGTGGGCATGGATGGGGTTACCTTTATGAACATGAGGTTCAGGGGAGATGGGTATAATGGCACGGTCTT

TATGGCCAATACCAAGCTGACAGTCCATGGCTGCTCCTTCTTTGGGTTTAATAACACCTGCATCGAGGCCTGGG

GTCAGGTCGGTGTGAGGGGCTGCAGTTTTTCAGCCAACTGGATGGGGTCGTGGGCAGGACCAAGAGTATGCTG

TCCGTGAAGAAATGCTTGTTTGAGAGGTGCCACCTGGGGGTGATGAGCGAGGGCGAAGCCAGAATCCGCCACTG

CGCCTCTACCGAGACGGGCTGCTTTGTGCTGTGCAAGGGCAATGCTAAGATCAAGCATAATATGATCTGTGGAG

CCTCGGACGAGCGCGGCTACCAGATGCTGACCTGCGCCGGCGGGAACAGCCATATGCTGGCCACCGTACATGTG

GCTTCCCATGCTCGCAAGCCCTGGCCCGAGTTCGAGCACAATGTCATGACCAGGTGCAATATGCATCTGGGGTC

CCGCCGAGGCATGTTCATGCCCTACCAGTGCAACCTGAATTATGTGAAGGTGCTGCTGGAGCCCGATGCCATGT

CCAGAGTGAGCCTGACGGGGGTGTTTGACATGAATGTGGAGGTGTGGAAGATTCTGAGATATGATGAATCCAAG

ACCAGGTGCCGAGCCTGCGAGTGCGGAGGGAAGCATGCCAGGTTCCAGCCCGTGTGTGTGGATGTGACGGAGGA

CCTGCGACCCGATCATTTGGTGTTGCCCTGCACCGGGACGGAGTTCGGTTCCAGCGGGAAGAATCTGACTAGA

GTGAGTAGTGTTCTGGGGCGGGGAGGACCTGCATGAGGGCCAGAATAACTGAAATCTGTGCTTTTCTGTGTGT

TGCAGCAGCATGAGCGGAAGCGGCTCCTTTGAGGGAGGGTATTCAGCCCTTATCTGACGGGCGTCTCCCCTC

CTGGGCGGGAGTGCGTCAGAATGTGATGGGATCCACGGTGGACGGCCGGCCCGTGCAGCCCGCGAACTCTTCAA

CCCTGACCTATGCAACCCTGAGCTCTTCGTCGTTGGACGCAGCTGCCGCCGCAGCTGCTGCATCTGCCGCCAGC

GCCGTGCGCGGAATGGCCATGGGCGCCGGCTACTACGGCACTCTGGTGGCCAACTCGAGTTCCACCAATAATCC

CGCCAGCCTGAACGAGGAGAAGCTGTTGCTGCTGATGGCCCAGCTCGAGGCCTTGACCCAGCGCCTGGGCGAGC

TGACCCAGCAGGTGGCTCAGCTGCAGGAGCAGACGCGGGCCGCGGTTGCCACGGTGAAATCCAAATAAAAAATG

AATCAATAAATAAACGGAGACGGTTGTTGATTTTAACACAGAGTCTGAATCTTTATTTGATTTTTCGCGCGCGG

TAGGCCCTGGACCACCGGTCTCGATCATTGAGCACCCGGTGGATCTTTTCCAGGACCCGGTAGAGGTGGGCTTG

GATGTTGAGGTACATGGGCATGAGCCCGTCCCGGGGGTGGAGGTAGCTCCATTGCAGGGCCTCGTGCTCGGGGG

TGGTGTTGTAAATCACCCAGTCATAGCAGGGGCGCAGGGCATGGTGTTGCACAATATCTTTGAGGAGGAGACTG

ATGGCCACGGGCAGCCCTTTGGTGTAGGTGTTTACAAATCTGTTGAGCTGGGAGGGATGCATGCGGGGGGAGAT

GAGGTGCATCTTGGCCTGGATCTTGAGATTGGCGATGTTACCGCCCAGATCCCGCCTGGGGTTCATGTTGTGCA

GGACCACCAGCACGGTGTATCCGGTGCACTTGGGGAATTTATCATGCAACTTGGAAGGGAAGGCGTGAAAGAAT

TTGGCGACGCCTTTGTGCCCGCCCAGGTTTTCCATGCACTCATCCATGATGATGGCGATGGGCCCGTGGGCGGC

GGCCTGGGCAAAGACGTTTCGGGGTCGGACACATCATAGTTGTGGTCCTGGGTGAGGTCATCATAGGCCATTT

TAATGAATTTGGGGCGGAGGGTGCCGGACTGGGGACAAAGGTACCCTCGATCCCGGGGGCGTAGTTCCCCTCA

CAGATCTGCATCTCCCAGGCTTTGAGCTCGGAGGGGGGATCATGTCCACCTGCGGGGCGATAAAGAACACGGT

TTCCGGGGCGGGGAGATGAGCTGGGCCGAAAGCAAGTTCCGGAGCAGCTGGGACTTGCCGCAGCCGGTGGGGC

CGTAGATGACCCCGATGACCGGCTGCAGGTGGTAGTTGAGGGAGAGACAGCTGCCGTCCTCCCGGAGGAGGGGG

GCCACCTCGTTCATCATCTCGCGCACGTGCATGTTCTCGCGCACCAGTTCCGCCAGGAGGCGCTCTCCCCCCAG

GGATAGGAGCTCCTGGAGCGAGGCGAAGTTTTTCAGCGGCTTGAGTCCGTCGGCCATGGGCATTTTGGAGAGGG

TTTGTTGCAAGAGTTCCAGGCGGTCCCAGAGCTCGGTGATGTGCTCTACGGCATCTCGATCCAGCAGACCTCCT

CGTTTCGCGGGTTGGGACGGCTGCGGGAGTAGGGCACCAGACGATGGGCGTCCAGCGCAGCCAGGGTCCGGTCC

TTCCAGGGTCGCAGCGTCCGCGTCAGGGTGGTCTCCGTCACGGTGAAGGGGTGCGCGCCGGGCTGGGCGCTTGC

GAGGGTGCGCTTCAGGCTCATCCGGCTGGTCGAAAACCGCTCCCGATCGGCGCCCTGCGCGTCGGCCAGGTAGC

AATTGACCATGAGTTCGTAGTTGAGCGCCTCGGCCGCGTGGCCTTTGGCGCGGAGCTTACCTTTGGAAGTCTGC
```

-continued

```
CCGCAGGCGGGACAGAGGAGGGACTTGAGGGCGTAGAGCTTGGGGGCGAGGAAGACGGACTCGGGGCGTAGGC
GTCCGCGCCGCAGTGGGCGCAGACGGTCTCGCACTCCACGAGCCAGGTGAGGTCGGGCTGGTCGGGGTCAAAAA
CCAGTTTCCCGCCGTTCTTTTTGATGCGTTTCTTACCTTTGGTCTCCATGAGCTCGTGTCCCCGCTGGGTGACA
AAGAGGCTGTCCGTGTCCCCGTAGACCGACTTTATGGGCCGGTCCTCGAGCGGTGTGCCGCGGTCCTCCTCGTA
GAGGAACCCCGCCCACTCCGAGACGAAAGCCCGGGTCCAGGCCAGCACGAAGGAGGCCACGTGGGACGGGTAGC
GGTCGTTGTCCACCAGCGGGTCCACCTTTTCCAGGGTATGCAAACACATGTCCCCCTCGTCCACATCCAGGAAG
GTGATTGGCTTGTAAGTGTAGGCCACGTGACCGGGGGTCCCGGCCGGGGGGGTATAAAAGGGTGCGGGTCCCTG
CTCGTCCTCACTGTCTTCCGGATCGCTGTCCAGGAGCGCCAGCTGTTGGGGTAGGTATTCCCTCTCGAAGGCGG
GCATGACCTCGGCACTCAGGTTGTCAGTTTCTAGAAACGAGGAGGATTTGATATTGACGGTGCCGGCGGAGATG
CCTTTCAAGAGCCCCTCGTCCATCTGGTCAGAAAAGACGATCTTTTTGTTGTCGAGCTTGGTGGCGAAGGAGCC
GTAGAGGGCGTTGGAGAGGAGCTTGGCGATGGAGCGCATGGTCTGGTTTTTTTCCTTGTCGGCGCGCTCCTTGG
CGGCGATGTTGAGCTGCACGTACTCGCGCGCCACGCACTTCCATTCGGGGAAGACGGTGGTCAGCTCGTCGGGC
ACGATTCTGACCTGCCAGCCCCGATTATGCAGGGTGATGAGGTCCACACTGGTGGCCACCTCGCCGCGCAGGGG
CTCATTAGTCCAGCAGAGGCGTCCGCCCTTGCGCGAGCAGAAGGGGGGCAGGGGGTCCAGCATGACCTCGTCGG
GGGGGTCGGCATCGATGGTGAAGATGCCGGGCAGGAGGTCGGGGTCAAAGTAGCTGATGAAGTGGCCAGATCG
TCCAGGGCAGCTTGCCATTCGCGCACGGCCAGCGCGCGCTCGTAGGGACTGAGGGGCGTGCCCCAGGGCATGGG
ATGGGTAAGCGCGGAGGCGTACATGCCGCAGATGTCGTAGACGTAGAGGGGCTCCTCGAGGATGCCGATGTAGG
TGGGGTAGCAGCGCCCCCCGCGGATGCTGGCGCGCACGTAGTCATACAGCTCGTGCGAGGGGGCGAGGAGCCCC
GGGCCCAGGTTGGTGCGACTGGGCTTTTCGGCGCGGTAGACGATCTGGCGGAAAATGGCATGCGAGTTGGAGGA
GATGGTGGGCCTTTGGAAGATGTTGAAGTGGGCGTGGGGCAGTCCGACCGAGTCGCGGATGAAGTGGGCGTAGG
AGTCTTGCAGCTTGGCGACGAGCTCGGCGGTGACTAGGACGTCCAGAGCGCAGTAGTCGAGGGTCTCCTGGATG
ATGTCATACTTGAGCTGTCCCTTTTGTTTCCACAGCTCGCGGTTGAGAAGGAACTCTTCGCGGTCCTTCCAGTA
CTCTTCGAGGGGGAACCCGTCCTGATCTGCACGGTAAGAGCCTAGCATGTAGAACTGGTTGACGGCCTTGTAGG
CGCAGCAGCCCTTCTCCACGGGGAGGGCGTAGGCCTGGGCGGCCTTGCGCAGGGAGGTGTGCGTGAGGGCGAAA
GTGTCCCTGACCATGACCTTGAGGAACTGGTGCTTGAAGTCGATATCGTCGCAGCCCCCCTGCTCCCAGAGCTG
GAAGTCCGTGCGCTTCTTGTAGGCGGGGTTGGGCAAAGCGAAAGTAACATCGTTGAAGAGGATCTTGCCCGCGC
GGGGCATAAAGTTGCGAGTGATGCGGAAAGGTTGGGGCACCTCGGCCCGGTTGTTGATGACCTGGGCGGCGAGC
ACGATCTCGTCGAAGCCGTTGATGTTGTGGCCCACGATGTAGAGTTCCACGAATCGCGGACGGCCCTTGACGTG
GGGCAGTTTCTTGAGCTCCTCGTAGGTGAGCTCGTCGGGGTCGCTGAGCCCGTGCTGCTCGAGCGCCCAGTCGG
CGAGATGGGGGTTGGCGCGGAGGAAGGAAGTCCAGAGATCCACGGCCAGGGCGGTTTGCAGACGGTCCCGGTAC
TGACGGAACTGCTGCCCGACGGCCATTTTTTCGGGGGTGACGCAGTAGAAGGTGCGGGGGTCCCCGTGCCAGCG
ATCCCATTTGAGCTGGAGGGCGAGATCGAGGGCGAGCTCGACGAGCCGGTCGTCCCCGGAGAGTTTCATGACCA
GCATGAAGGGGACGAGCTGCTTGCCGAAGGACCCCATCCAGGTGTAGGTTTCCACATCGTAGGTGAGGAAGAGC
CTTTCGGTGCGAGGATGCGAGCCGATGGGGAAGAACTGGATCTCCTGCCACCAATTGGAGGAATGGCTGTTGAT
GTGATGGAAGTAGAAATGCCGACGGCGCGCCGAACACTCGTGCTTGTGTTTATACAAGCGGCCACAGTGCTCGC
AACGCTGCACGGGATGCACGTGCTGCACGAGCTGTACCTGAGTTCCTTTGACGAGGAATTTCAGTGGGAAGTGG
AGTCGTGGCGCCTGCATCTCGTGCTGTACTACGTCGTGGTGGTCGGCCTGGCCCTCTTCTGCCTCGATGGTGGT
CATGCTGACGAGCCCGCGCGGGAGGCAGGTCCAGACCTCGGCGCGAGCGGGTCGGAGAGCGAGGACGAGGGCGC
GCAGGCCGGAGCTGTCCAGGGTCCTGAGACGCTGCGGAGTCAGGTCAGTGGGCAGCGGCGGCGCGCGGTTGACT
TGCAGGAGTTTTTCCAGGGCGCGCGGGAGGTCCAGATGGTACTTGATCTCCACCGCGCCATTGGTGGCGACGTC
GATGGCTTGCAGGGTCCCGTGCCCCTGGGGTGTGACCACCGTCCCCCGTTTCTTCTTGGGCGGCTGGGGCGACG
```

-continued

```
GGGGCGGTGCCTCTTCCATGGTTAGAAGCGGCGGCGAGGACGCGCGCCGGGCGGCAGGGGCGGCTCGGGCCCG
GAGGCAGGGGCGGCAGGGGCACGTCGGCGCCGCGCGCGGGTAGGTTCTGGTACTGCGCCCGGAGAAGACTGGCG
TGAGCGACGACGCGACGGTTGACGTCCTGGATCTGACGCCTCTGGGTGAAGGCCACGGGACCCGTGAGTTTGAA
CCTGAAAGAGAGTTCGACAGAATCAATCTCGGTATCGTTGACGGCGGCCTGCCGCAGGATCTCTTGCACGTCGC
CCGAGTTGTCCTGGTAGGCGATCTCGGTCATGAACTGCTCGATCTCCTCCTCTTGAAGGTCTCCGCGGCCGGCG
CGCTCCACGGTGGCCGCGAGGTCGTTGGAGATGCGGCCCATGAGCTGCGAGAAGGCGTTCATGCCCGCCTCGTT
CCAGACGCGGCTGTAGACCACGACGCCCTCGGGATCGCgGGCGCGCATGACCACCTGGGCGAGGTTGAGCTCCA
CGTGGCGCGTGAAGACCGCGTAGTTGCAGAGGCGCTGGTAGAGGTAGTTGAGCGTGGTGGCGATGTGCTCGGTG
ACGAAGAAATACATGATCCAGCGGCGGAGCGGCATCTCGCTGACGTCGCCCAGCGCCTCCAAACGTTCCATGGC
CTCGTAAAAGTCCACGGCGAAGTTGAAAAACTGGGAGTTGCGCGCCGAGACGGTCAACTCCTCCTCCAGAAGAC
GGATGAGCTCGGCGATGGTGGCGCGCACCTCGCGCTCGAAGGCCCCCGGGAGTTCCTCCACTTCCTCTTCTTCC
TCCTCCACTAACATCTCTTCTACTTCCTCCTCAGGCGGCAGTGGTGGCGGGGAGGGGGCCTGCGTCGCCGGCG
GCGCACGGGCAGACGGTCGATGAAGCGCTCGATGGTCTCGCCGCGCCGGCGTCGCATGGTCTCGGTGACGGCGC
GCCCGTCCTCGCGGGGCCGCAGCGTGAAGACGCCGCCGCGCATCTCCAGGTGGCCGGGGGGGTCCCCGTTGGGC
AGGGAGAGGGCGCTGACGATGCATCTTATCAATTGCCCCGTAGGGACTCCGCGCAAGGACCTGAGCGTCTCGAG
ATCCACGGGATCTGAAAACCGCTGAACGAAGGCTTCGAGCCAGTCGCAGTCGCAAGGTAGGCTGAGCACGGTTT
CTTCTGGCGGGTCATGTTGGTTGGGAGCGGGGCGGGCGATGCTGCTGGTGATGAAGTTGAAATAGGCGGTTCTG
AGACGGCGGATGGTGGCGAGGAGCACCAGGTCTTTGGGCCCGGCTTGCTGGATGCGCAGACGGTCGGCCATGCC
CCAGGCGTGGTCCTGACACCTGGCCAGGTCCTTGTAGTAGTCCTGCATGAGCCGCTCCACGGGCACCTCCTCCT
CGCCCGCGCGGCCGTGCATGCGCGTGAGCCCGAAGCCGCGCTGGGGCTGGACGAGCGCCAGGTCGGCGACGACG
CGCTCGGCGAGGATGGCTTGCTGGATCTGGGTGAGGGTGGTCTGGAAGTCATCAAAGTCGACGAAGCGGTGGTA
GGCTCCGGTGTTGATGGTGTAGGAGCAGTTGGCCATGACGGACCAGTTGACGGTCTGGTGGCCCGGACGCACGA
GCTCGTGGTACTTGAGGCGCGAGTAGGCGCGCGTGTCGAAGATGTAGTCGTTGCAGGTGCGCACCAGGTACTGG
TAGCCGATGAGGAAGTGCGGCGGCGGCTGGCGGTAGAGCGGCCATCGCTCGGTGGCGGGGGCGCCGGGCGCGAG
GTCCTCGAGCATGGTGCGGTGGTAGCCGTAGATGTACCTGGACATCCAGGTGATGCCGGCGGCGGTGGTGGAGG
CGCGCGGGAACTCGCGGACGCGGTTCCAGATGTTGCGCAGCGGCAGGAAGTAGTTCATGGTGGGCACGGTCTGG
CCCGTGAGGCGCGCGCAGTCGTGGATGCTCTATACGGGCAAAAACGAAAGCGGTCAGCGGCTCGACTCCGTGGC
CTGGAGGCTAAGCGAACGGGTTGGGCTGCGCGTGTACCCCGGTTCGAATCTCGAATCAGGCTGGAGCCGCAGCT
AACGTGGTATTGGCACTCCCGTCTCGACCCAAGCCTGCACCAACCCTCCAGGATACGGAGGCGGGTCGTTTTGC
AACTTTTTTTTGGAGGCCGGATGAGACTAGTAAGCGCGGAAAGCGGCCGACCGCGATGGCTCGCTGCCGTAGTC
TGGAGAAGAATCGCCAGGGTTGCGTTGCGGTGTGCCCCGGTTCGAGGCCGGCCGGATTCCGCGGCTAACGAGGG
CGTGGCTGCCCCGTCGTTTCCAAGACCCCATAGCCAGCCGACTTCTCCAGTTACGGAGCGAGCCCCTCTTTTGT
TTTGTTTGTTTTTGCCAGATGCATCCCGTACTGCGGCAGATGCGCCCCACCACCCTCCACCGCAACAACAGCC
CCCTCCACAGCCGGCGCTTCTGCCCCCGCCCCAGCAGCAACTTCCAGCCACGACCGCCGCGGCCGCCGTGAGCG
GGGCTGGACAGAGTTATGATCACCAGCTGGCCTTGGAAGAGGGCGAGGGGCTGGCGCGCCTGGGGCGTCGTCG
CCCGGAGCGGCACCCGCGCGTGCAGATGAAAAGGGACGCTCGCGAGGCCTACGTGCCCAAGCAGAACCTGTTCAG
AGACAGGAGCGGCGAGGAGCCCGAGGAGATGCGCGCGGCCCGGTTCCACGCGGGGCGGGAGCTGCGGCGCGGCC
TGGACCGAAAGAGGGTGCTGAGGGACGAGGATTTCGAGGCGGACGAGCTGACGGGGATCAGCCCCGCGCGCGCG
CACGTGGCCGCGGCCAACCTGGTCACGGCGTACGAGCAGACCGTGAAGGAGGAGAGCAACTTCCAAAAATCCTT
CAACAACCACGTGCGCACCCTGATCGCGCGCGAGGAGGTGACCCTGGGCCTGATGCACCTGTGGGACCTGCTGG
```

-continued
```
AGGCCATCGTGCAGAACCCCACCAGCAAGCCGCTGACGGCGCAGCTGTTCCTGGTGGTGCAGCATAGTCGGGAC

AACGAAGCGTTCAGGGAGGCGCTGCTGAATATCACCGAGCCCGAGGGCCGCTGGCTCCTGGACCTGGTGAACAT

TCTGCAGAGCATCGTGGTGCAGGAGCGCGGGCTGCCGCTGTCCGAGAAGCTGGCGGCCATCAACTTCTCGGTGC

TGAGTTTGGGCAAGTACTACGCTAGGAAGATCTACAAGACCCCGTACGTGCCCATAGACAAGGAGGTGAAGATC

GACGGGTTTTACATGCGCATGACCCTGAAAGTGCTGACCCTGAGCGACGATCTGGGGGTGTACCGCAACGACAG

GATGCACCGTGCGGTGAGCGCCAGCAGGCGGCGCGAGCTGAGCGACCAGGAGCTGATGCATAGTCTGCAGCGGG

CCCTGACCGGGGCCGGGACCGAGGGGGAGAGCTACTTTGACATGGGCGCGGACCTGCACTGGCAGCCCAGCCGC

CGGGCCTTGGAGGCGGCGGCAGGACCCTACGTAGAAGAGGTGGACGATGAGGTGGACGAGGAGGGCGAGTACCT

GGAAGACTGATGGCGCGACCGTATTTTTGCTAGATGCAACAACAACAGCCACCTCCTGATCCCGCGATGCGGGC

GGCGCTGCAGAGCCAGCCGTCCGGCATTAACTCCTCGGACGATTGGACCCAGGCCATGCAACGCATCATGGCGC

TGACGACCCGCAACCCCGAAGCCTTTAGACAGCAGCCCCAGGCCAACCGGCTCTCGGCCATCCTGGAGGCCGTG

GTGCCCTCGCGCTCCAACCCCACGCACGAGAAGGTCCTGGCCATCGTGAACGCGCTGGTGGAGAACAAGGCCAT

CCGCGGCGACGAGGCCGGCCTGGTGTACAACGCGCTGCTGGAGCGCGTGCCCGCTACAACAGCACCAACGTGC

AGACCAACCTGGACCGCATGGTGACCGACGTGCGCGAGGCCGTGGCCCAGCGCGAGCGGTTCCACCGCGAGTCC

AACCTGGGATCCATGGTGGCGCTGAACGCCTTCCTCAGCACCCAGCCCGCCAACGTGCCCCGGGGCCAGGAGGA

CTACACCAACTTCATCAGCGCCCTGCGCCTGATGGTGACCGAGGTGCCCCAGAGCGAGGTGTACCAGTCCGGGC

CGGACTACTTCTTCCAGACCAGTCGCCAGGGCTTGCAGACCGTGAACCTGAGCCAGGCTTTCAAGAACTTGCAG

GGCCTGTGGGCGTGCAGGCCCCGGTCGGGACCGCGCGACGGTGTCGAGCCTGCTGACGCCGAACTCGCGCCT

GCTGCTGCTGCTGGTGGCCCCCTTCACGGACAGCGGCAGCATCAACCGCAACTCGTACCTGGGCTACCTGATTA

ACCTGTACCGCGAGGCCATCGGCCAGGCGCACGTGGACGAGCAGACCTACCAGGAGATCACCCACGTGAGCCGC

GCCCTGGGCCAGGACGACCCGGGCAACCTGGAAGCCACCCTGAACTTTTTGCTGACCAACCGGTCGCAGAAGAT

CCCGCCCCAGTACGCGCTCAGCACCGAGGAGGAGCGCATCCTGCGTTACGTGCAGCAGAGCGTGGGCCTGTTCC

TGATGCAGGAGGGGCCACCCCCAGCGCCGCGCTCGACATGACCGCGCGCAACATGGAGCCCAGCATGTACGCC

AGCAACCGCCCGTTCATCAATAAACTGATGGACTACTTGCATCGGGCGGCCGCCATGAACTCTGACTATTTCAC

CAACGCCATCCTGAATCCCCACTGGCTCCCGCCGCCGGGGTTCTACACGGGCGAGTACGACATGCCCGACCCCA

ATGACGGGTTCCTGTGGGACGATGTGGACAGCAGCGTGTTCTCCCCCCGACCGGGTGCTAACGAGCGCCCCTTG

TGGAAGAAGGAAGGCAGCGACCGACGCCCGTCCTCGGCGCTGTCCGGCCGCGAGGGTGCTGCCGCGGCGGTGCC

CGAGGCCGCCAGTCCTTTCCCGAGCTTGCCCTTCTCGCTGAACAGTATCCGCAGCAGCGAGCTGGGCAGGATCA

CGCGCCCGCGCTTGCTGGGCGAAGAGGAGTACTTGAATGACTCGCTGTTGAGACCCGAGCGGGAGAAGAACTTC

CCCAATAACGGGATAGAAAGCCTGGTGGACAAGATGAGCCGCTGGAAGACGTATGCGCAGGAGCACAGGGACGA

TCCCCGGGCGTCGCAGGGGGCCACGAGCCGGGGCAGCGCCGCCCGTAAACGCCGGTGGCACGACAGGCAGCGGG

GACAGATGTGGGACGATGAGGACTCCGCCGACGACAGCAGCGTGTTGGACTTGGGTGGGAGTGGTAACCCGTTC

GCTCACCTGCGCCCCCGTATCGGGCGCATGATGTAAGAGAAACCGAAAATAAATGATACTCACCAAGGCCATGG

CGACCAGCGTGCGTTCGTTTCTTCTCTGTTGTTGTTGTATCTAGTATGATGAGGCGTGCGTACCCGGAGGGTCC

TCCTCCCTCGTACGAGAGCGTGATGCAGCAGGCGATGGCGGCGGCGGCGATGCAGCCCCCGCTGGAGGCTCCTT

ACGTGCCCCCGCGGTACCTGGCGCCTACGGAGGGGCGGAACAGCATTCGTTACTCGGAGCTGGCACCCTTGTAC

GATACCACCCGGTTGTACCTGGTGGACAACAAGTCGGCGGACATCGCCTCGCTGAACTACCAGAACGACCACAG

CAACTTCCTGACCACCGTGGTGCAGAACAATGACTTCACCCCCACGGAGGCCAGCACCCAGACCATCAACTTTG

ACGAGCGCTCGCGGTGGGCGGCCAGCTGAAAACCATCATGCACACCAACATGCCCAACGTGAACGAGTTCATG

TACAGCAACAAGTTCAAGGCGCGGGTGATGGTCTCCCGCAAGACCCCCAATGGGGTGACAGTGACAGAGGATTA

TGATGGTAGTCAGGATGAGCTGAAGTATGAATGGGTGGAATTTGAGCTGCCCGAAGGCAACTTCTCGGTGACCA
```

-continued

```
TGACCATCGACCTGATGAACAACGCCATCATCGACAATTACTTGGCGGTGGGGCGGCAGAACGGGGTGCTGGAG
AGCGACATCGGCGTGAAGTTCGACACTAGGAACTTCAGGCTGGGCTGGGACCCCGTGACCGAGCTGGTCATGCC
CGGGGTGTACACCAACGAGGCTTTCCATCCCGATATTGTCTTGCTGCCCGGCTGCGGGGTGGACTTCACCGAGA
GCCGCCTCAGCAACCTGCTGGGCATTCGCAAGAGGCAGCCCTTCCAGGAAGGCTTCCAGATCATGTACGAGGAT
CTGGAGGGGGCAACATCCCCGCGCTCCTGGATGTCGACGCCTATGAGAAAAGCAAGGAGGATGCAGCAGCTGA
AGCAACTGCAGCCGTAGCTACCGCCTCTACCGAGGTCAGGGGCGATAATTTTGCAAGCGCCGCAGCAGTGGCAG
CGGCCGAGGCGGCTGAAACCGAAAGTAAGATAGTCATTCAGCCGGTGGAGAAGGATAGCAAGAACAGGAGCTAC
AACGTACTACCGGACAAGATAAACACCGCCTACCGCAGCTGGTACCTAGCCTACAACTATGGCGACCCCGAGAA
GGGCGTGCGCTCCTGGACGCTGCTCACCACCTCGGACGTCACCTGCGGCGTGGAGCAAGTCTACTGGTCGCTGC
CCGACATGATGCAAGACCCGGTCACCTTCCGCTCCACGCGTCAAGTTAGCAACTACCCGGTGGTGGGCGCCGAG
CTCCTGCCCGTCTACTCCAAGAGCTTCTTCAACGAGCAGGCCGTCTACTCGCAGCAGCTGCGCGCCTTCACCTC
GCTTACGCACGTCTTCAACCGCTTCCCCGAGAACCAGATCCTCGTCCGCCCGCCCGCGCCCACCATTACCACCG
TCAGTGAAAACGTTCCTGCTCTCACAGATCACGGGACCCTGCCGCTGCGCAGCAGTATCCGGGGAGTCCAGCGC
GTGACCGTTACTGACGCCAGACGCCGCCACCTGCCCCTACGTCTACAAGGCCCTGGGCATAGTCGCGCCGCGCGT
CCTCTCGAGCCGCACCTTCTAAATGTCCATTCTCATCTCGCCCAGTAATAACACCGGTTGGGGCCTGCGCGCGC
CCAGCAAGATGTACGGAGGCGCTCGCCAACGCTCCACGCAACACCCCGTGCGCGTGCGCGGGCACTTCCGCGCT
CCCTGGGGCGCCCTCAAGGGCCGCGTGCGGTCGCGCACCACCGTCGACGACGTGATCGACCAGGTGGTGGCCGA
CGCGCGCAACTACACCCCCGCCGCCGCGCCCGTCTCCACCGTGGACGCCGTCATCGACAGCGTGGTGGCcGACG
CGCGCCGGTACGCCCGCGCCAAGAGCCGGCGGCGGCGCATCGCCCGGCGGCACCGGAGCACCCCCGCCATGCGC
GCGGCGCGAGCCTTGCTGCGCAGGGCCAGGCGCACGGGACGCAGGGCCATGCTCAGGGCGGCCAGACGCGCGGC
TTCAGGCGCCAGCGCCGGCAGGACCCGGAGACGCGCGGCCACGGCGGCGGCAGCGGCCATCGCCAGCATGTCCC
GCCCGCGGCGAGGGAACGTGTACTGGGTGCGCGACGCCGCCACCGGTGTGCGCGTGCCCGTGCGCACCCGCCCC
CCTCGCACTTGAAGATGTTCACTTCGCGATGTTGATGTGTCCCAGCGGCGAGGAGGATGTCCAAGCGCAAATTC
AAGGAAGAGATGCTCCAGGTCATCGCGCCTGAGATCTACGGCCCTGCGGTGGTGAAGGAGGAAAGAAAGCCCCG
CAAAATCAAGCGGGTCAAAAAGGACAAAAAGGAAGAAGAAAGTGATGTGGACGGATTGGTGGAGTTTGTGCGCG
AGTTCGCCCCCCGGCGGCGCGTGCAGTGGCGCGGGCGGAAGGTGCAACCGGTGCTGAGACCCGGCACCACCGTG
GTCTTCACGCCCGGCGAGCGCTCCGGCACCGCTTCCAAGCGCTCCTACGACGAGGTGTACGGGGATGATGATAT
TCTGGAGCAGGCGGCCGAGCGCCTGGGCGAGTTTGCTTACGGCAAGCGCAGCCGTTCCGCACCGAAGGAAGAGG
CGGTGTCCATCCCGCTGGACCACGGCAACCCCACGCCGAGCCTCAAGCCCGTGACCTTGCAGCAGGTGCTGCCG
ACCGCGGCGCCGCGCCGGGGGTTCAAGCGCGAGGGCGAGGATCTGTACCCCACCATGCAGCTGATGGTGCCCAA
GCGCCAGAAGCTGGAAGACGTGCTGGAGACCATGAAGGTGGACCCGGACGTGCAGCCCGAGGTCAAGGTGCGGC
CCATCAAGCAGGTGGCCCCGGGCCTGGGCGTGCAGACCGTGGACATCAAGATTCCCACGGAGCCCATGGAAACG
CAGACCGAGCCCATGATCAAGCCCAGCACCAGCACCATGGAGGTGCAGACGGATCCCTGGATGCCATCGGCTCC
TAGTCGAAGACCCCGGCGCAAGTACGGCGCGGCCAGCCTGCTGATGCCCAACTACGCGCTGCATCCTTCCATCA
TCCCCACGCCGGGCTACCGCGGCACGCGCTTCTACCGCGGTCATACCAGCAGCCGCCGCCGCAAGACCACCACT
CGCCGCCGCCGTCGCCGCACCGCCGCTGCAACCACCCCTGCCGCCCTGGTGCGGAGAGTGTACCGCCGCGGCCG
CGCACCTCTGACCCTGCCGCGCGCGCTACCACCCGAGCATCGCCATTTAAACTTTCGCCtGCTTTGCAGATC
AATGGCCCTCACATGCCGCCTTCGCGTTCCCATTACGGGCTACCGAGGAAGAAAACCGCGCCGTAGAAGGCTGG
CGGGGAACGGGATGCGTCGCCACCACCACCGGCGGCGGCGCGCCATCAGCAAGCGGTTGGGGGGAGGCTTCCTG
CCCGCGCTGATCCCCATCATCGCCGCGGCGATCGGGGCGATCCCCGGCATTGCTTCCGTGGCGGTGCAGGCCTC
```

-continued

TCAGCGCCACTGAGACACACTTGGAAACATCTTGTAATAAACCaATGGACTCTGACGCTCCTGGTCCTGTGATG

TGTTTTCGTAGACAGATGGAAGACATCAATTTTTCGTCCCTGGCTCCGCGACACGGCACGCGGCCGTTCATGGG

CACCTGGAGCGACATCGGCACCAGCCAACTGAACGGGGGCGCCTTCAATTGGAGCAGTCTCTGGAGCGGGCTTA

AGAATTTCGGGTCCACGCTTAAAACCTATGGCAGCAAGGCGTGGAACAGCACCACAGGGCAGGCGCTGAGGGAT

AAGCTGAAAGAGCAGAACTTCCAGCAGAAGGTGGTCGATGGGCTCGCCTCGGGCATCAACGGGGTGGTGGACCT

GGCCAACCAGGCCGTGCAGCGGCAGATCAACAGCCGCCTGGACCCGGTGCCGCCCGCCGGCTCCGTGGAGATGC

CGCAGGTGGAGGAGGAGCTGCCTCCCCTGGACAAGCGGGGCGAGAAGCGACCCCGCCCCGATGCGGAGGAGACG

CTGCTGACGCACACGGACGAGCCGCCCCCGTACGAGGAGGCGGTGAAACTGGGTCTGCCCACCACGCGGCCCAT

CGCGCCCCTGGCCACCGGGGTGCTGAAACCCGAAAAGCCCGCGACCCTGGACTTGCCTCCTCCCCAGCCTTCCC

GCCCCTCTACAGTGGCTAAGCCCCTGCCGCCGGTGGCCGTGGCCCGCGCGCGACCCGGGGGCACCGCCCGCCCT

CATGCGAACTGGCAGAGCACTCTGAACAGCATCGTGGGTCTGGGAGTGCAGAGTGTGAAGCGCCGCCGCTGCTA

TTAAACCTACCGTAGCGCTTAACTTGCTTGTCTGTGTGTATGTATTATGTCGCCGCCGCCGCTGTCCACCAG

AAGGAGGAGTGAAGAGGCGCGTCGCCGAGTTGCAAGATGGCCACCCCATCGATGCTGCCCCAGTGGGCGTACAT

GCACATCGCCGGACAGGACGCTTCGGAGTACCTGAGTCCGGGTCTGGTGCAGTTTGCCCGCGCCACAGACACCT

ACTTCAGTCTGGGGAACAAGTTTAGGAACCCCACGGTGGCGCCCACGCACGATGTGACCACCGACCGCAGCCAG

CGGCTGACGCTGCGCTTCGTGCCCGTGGACCGCGAGGACAACACCTACTCGTACAAAGTGCGCTACACGCTGGC

CGTGGGCGACAACCGCGTGCTGGACATGGCCAGCACCTACTTTGACATCCGCGGCGTGCTGGATCGGGGCCCTA

GCTTCAAACCCTACTCCGGCACCGCCTACAACAGTCTGGCCCCCAAGGGAGCACCCAACACTTGTCAGTGGACA

TATAAAGCCGATGGTGAAACTGCCACAGAAAAAACCTATACATATGGAAATGCACCCGTGCAGGGCATTAACAT

CACAAAAGATGGTATTCAACTTGGAACTGACACCGATGATCAGCCAATCTACGCAGATAAAACCTATCAGCCTG

AACCTCAAGTGGGTGATGCTGAATGGCATGACATCACTGGTACTGATGAAAAGTATGGAGGCAGAGCTCTTAAG

CCTGATACCAAAATGAAGCCTTGTTATGGTTCTTTTGCCAAGCCTACTAATAAAGAAGGAGGTCAGGCAAATGT

GAAAACAGGAACAGGCACTACTAAAGAATATGACATAGACATGGCTTTCTTTGACAACAGAAGTGCGGCTGCTG

CTGGCCTAGCTCCAGAAATTGTTTTGTATACTGAAAATGTGGATTTGGAAACTCCAGATACCCATATTGTATAC

AAAGCAGGCACAGATGACAGCAGCTCTTCTATTAATTTGGGTCAGCAAGCCATGCCCAACAGACCTAACTACAT

TGGTTTCAGAGACAACTTTATCGGGCTCATGTACTACAACAGCACTGGCAATATGGGGGTGCTGGCCGGTCAGG

CTTCTCAGCTGAATGCTGTGGTTGACTTGCAAGACAGAAACACCGAGCTGTCCTACCAGCTCTTGCTTGACTCT

CTGGGTGACAGAACCCGGTATTTCAGTATGTGGAATCAGGCGGTGGACAGCTATGATCCTGATGTGCGCATTAT

TGAAAATCATGGTGTGGAGGATGAACTTCCCAACTATTGTTTCCCTCTGGATGCTGTTGGCAGAACAGATACTT

ATCAGGGAATTAAGGCTAATGGAACTGATCAAACCACATGGACCAAAGATGACAGTGTCAATGATGCTAATGAG

ATAGGCAAGGGTAATCCATTCGCCATGGAAATCAACATCCAAGCCAACCTGTGGAGGAACTTCCTCTACGCCAA

CGTGGCCCTGTACCTGCCCGACTCTTACAAGTACACGCCGGCCAATGTTACCCTGCCCACCAACACCAACACCT

ACGATTACATGAACGGCCGGGTGGTGGCGCCCTCGCTGGTGGACTCCTACATCAACATCGGGGCGCGCTGGTCG

CTGGATCCCATGGACAACGTGAACCCCTTCAACCACCACCGCAATGCGGGGCTGCGCTACCGCTCCATGCTCCT

GGGCAACGGGCGCTACGTGCCCTTCCACATCCAGGTGCCCCAGAAATTTTTCGCCATCAAGAGCCTCCTGCTCC

TGCCCGGGTCCTACACCTACGAGTGGAACTTCCGCAAGGACGTCAACATGATCCTGCAGAGCTCCCTCGGCAAC

GACCTGCGCACGGACGGGGCCTCCATCTCCTTCACCAGCATCAACCTCTACGCCACCTTCTTCCCCATGGCGCA

CAACACGGCCTCCACGCTCGAGGCCATGCTGCGCAACGACACCAACGACCAGTCCTTCAACGACTACCTCTCGG

CGGCCAACATGCTCTACCCCATCCCGGCCAACGCCACCAACGTGCCCATCTCCATCCCTCGCGCAACTGGGCC

GCCTTCCGCGGCTGGTCCTTCACGCGTCTCAAGACCAAGGAGACGCCCTCGCTGGGCTCCGGGTTCGACCCCTA

CTTCGTCTACTCGGGCTCCATCCCCTACCTCGACGGCACCTTCTACCTCAACCACACCTTCAAGAAGGTCTCCA

-continued

```
TCACCTTCGACTCCTCCGTCAGCTGGCCCGGCAACGACCGGCTCCTGACGCCCAACGAGTTCGAAATCAAGCGC

ACCGTCGACGGCGAGGGCTACAACGTGGCCCAGTGCAACATGACCAAGGACTGGTTCCTGGTCCAGATGCTGGC

CCACTACAACATCGGCTACCAGGGCTTCTACGTGCCCGAGGGCTACAAGGACCGCATGTACTCCTTCTTCCGCA

ACTTCCAGCCCATGAGCCGCCAGGTGGTGGACGAGGTCAACTACAAGGACTACCAGGCCGTCACCCTGGCCTAC

CAGCACAACAACTCGGGCTTCGTCGGCTACCTCGCGCCCACCATGCGCCAGGGCCAGCCCTACCCCGCCAACTA

CCCCTACCCGCTCATCGGCAAGAGCGCCGTCACCAGCGTCACCCAGAAAAAGTTCCTCTGCGACAGGGTCATGT

GGCGCATCCCCTTCTCCAGCAACTTCATGTCCATGGGCGCGCTCACCGACCTCGGCCAGAACATGCTCTATGCC

AACTCCGCCCACGCGCTAGACATGAATTTCGAAGTCGACCCCATGGATGAGTCCACCCTTCTCTATGTTGTCTT

CGAAGTCTTCGACGTCGTCCGAGTGCACCAGCCCCACCGCGGCGTCATCGAGGCCGTCTACCTGCGCACCCCCT

TCTCGGCCGGTAACGCCACCACCTAAGCTCTTGCTTCTTGCAAGCCATGGCCGCGGGCTCCGGCGAGCAGGAGC

TCAGGGCCATCATCCGCGACCTGGGCTGCGGGCCCTACTTCCTGGGCACCTTCGATAAGCGCTTCCCGGGATTC

ATGGCCCCGCACAAGCTGGCCTGCGCCATCGTCAACACGGCCGGCCGCGAGACCGGGGGCGAGCACTGGCTGGC

CTTCGCCTGGAACCCGCGCTCGAACACCTGCTACCTCTTCGACCCCTTCGGGTTCTCGGACGAGCGCCTCAAGC

AGATCTACCAGTTCGAGTACGAGGGCCTGCTGCGCCGCAGCGCCCTGGCCACCGAGGACCGCTGCGTCACCCTG

GAAAAGTCCACCCAGACCGTGCAGGGTCCGCGCTCGGCCGCCTGCGGGCTCTTCTGCTGCATGTTCCTGCACGC

CTTCGTGCACTGGCCCGACCGCCCCATGGACAAGAACCCCACCATGAACTTGCTGACGGGGGTGCCCAACGGCA

TGCTCCAGTCGCCCCAGGTGGAACCCACCCTGCGCCGCAACCAGGAGGCGCTCTACCGCTTCCTCAACTCCCAC

TCCGCCTACTTTCGCTCCCACCGCGCGCGCATCGAGAAGGCCACCGCCTTCGACCGCATGAATCAAGACATGTA

AACCGTGTGTGTATGTTAAATGTCTTTAATAAACAGCACTTTCATGTTACACATGCATCTGAGATGATTTATTT

AGAAATCGAAAGGGTTCTGCCGGGTCTCGGCATGGCCCGCGGGCAGGGACACGTTGCGGAACTGGTACTTGGCC

AGCCACTTGAACTCGGGGATCAGCAGTTTGGGCAGCGGGGTGTCGGGGAAGGAGTCGGTCCACAGCTTCCGCGT

CAGTTGCAGGGCGCCCAGCAGGTCGGGCGCGGAGATCTTGAAATCGCAGTTGGGACCCGCGTTCTGCGCGCGGG

AGTTGCGGTACACGGGGTTGCAGCACTGGAACACCATCAGGGCCGGGTGCTTCACGCTCGCCAGCACCGTCGCG

TCGGTGATGCTCTCCACGTCGAGGTCCTCGGCGTTGGCCATCCCGAAGGGGGTCATCTTGCAGGTCTGCCTTCC

CATGGTGGGCACGCACCCGGGCTTGTGGTTGCAATCGCAGTGCAGGGGGATCAGCATCATCTGGGCCTGGTCGG

CGTTCATCCCCGGGTACATGGCCTTCATGAAAGCCTCCAATTGCCTGAACGCCTGCTGGGCCTTGGCTCCCTCG

GTGAAGAAGACCCCGCAGGACTTGCTAGAGAACTGGTTGGTGGCGCACCCGGCGTCGTGCACGCAGCAGCGCGC

GTCGTTGTTGGCCAGCTGCACCACGCTGCGCCCCAGCGGTTCTGGGTGATCTTGGCCCGGTCGGGGTTCTCCT

TCAGCGCGCGCTGCCCGTTCTCGCTCGCCACATCCATCTCGATCATGTGCTCCTTCTGGATCATGGTGGTCCCG

TGCAGGCACCGCAGCTTGCCCTCGGCCTCGGTGCACCCGTGCAGCCACAGCGCGCACCCGGTGCACTCCCAGTT

CTTGTGGGCGATCTGGGAATGCGCGTGACGAAGCCCTGCAGGAAGCGGCCCATCATGGTGGTCAGGGTCTTGT

TGCTAGTGAAGGTCAGCGGAATGCCGCGGTGCTCCTCGTTGATGTACAGGTGGCAGATGCGGCGGTACACCTCG

CCCTGCTCGGGCATCAGCTGGAAGTTGGCTTTCAGGTCGGTCTCCACGCGGTAGCGGTCCATCAGCATAGTCAT

GATTTCCATACCCTTCTCCCAGGCCGAGACGATGGGCAGGCTCATAGGGTTCTTCACCATCATCTTAGCGCTAG

CAGCCGCGGCCAGGGGTCGCTCTCGTCCAGGGTCTCAAAGCTCCGCTTGCCGTCCTTCTCGGTGATCCGCACC

GGGGGGTAGCTGAAGCCCACGGCCGCCAGCTCCTCCTCGGCCTGTCTTTCGTCCTCGCTGTCCTGGCTGACGTC

CTGCAGGACCACATGCTTGGTCTTGCGGGGTTTCTTCTTGGGCGGCAGCGGCGGCGGAGATGTTGGAGATGGCG

AGGGGGAGCGCGAGTTCTCGCTCACCACTACTATCTCTTCCTCTTCTTGGTCCGAGGCCACGCGGCGGTAGGTA

TGTCTCTTCGGGGGCAGAGGCGGAGGCGACGGGCTCTCGCCGCCGCGACTTGGCGGATGGCTGGCAGAGCCCCT

TCCGCGTTCGGGGGTGCGCTCCCGGCGGCGCTCTGACTGACTTCCTCCGCGGCCGGCCATTGTGTTCTCCTAGG
```

-continued

GAGGAACAACAAGCATGGAGACTCAGCCATCGCCAACCTCGCCATCTGCCCCCACCGCCGACGAGAAGCAGCAG

CAGCAGAATGAAAGCTTAACCGCCCCGCCGCCCAGCCCCGCCACCTCCGACGCGGCCGTCCCAGACATGCAAGA

GATGGAGGAATCCATCGAGATTGACCTGGGCTATGTGACGCCCGCGGAGCACGAGGAGGAGCTGGCAGTGCGCT

TTTCACAAGAAGAGATACACCAAGAACAGCCAGAGCAGGAAGCAGAGAATGAGCAGAGTCAGGCTGGGCTCGAG

CATGACGGCGACTACCTCCACCTGAGCGGGGGGAGGACGCGCTCATCAAGCATCTGGCCCGGCAGGCCACCAT

CGTCAAGGATGCGCTGCTCGACCGCACCGAGGTGCCCCTCAGCGTGGAGGAGCTCAGCCGCGCCTACGAGTTGA

ACCTCTTCTCGCCGCGCGTGCCCCCCAAGCGCCAGCCCAATGGCACCTGCGAGCCCAACCCGCGCCTCAACTTC

TACCCGGTCTTCGCGGTGCCCGAGGCCCTGGCCACCTACCACATCTTTTTCAAGAACCAAAAGATCCCCGTCTC

CTGCCGCGCCAACCGCACCCGCGCCGACGCCCTTTTCAACCTGGGTCCCGGCGCCCGCCTACCTGATATCGCCT

CCTTGGAAGAGGTTCCCAAGATCTTCGAGGGTCTGGGCAGCGACGAGACTCGGGCCGCGAACGCTCTGCAAGGA

GAAGGAGGAGAGCATGAGCACCACAGCGCCCTGGTCGAGTTGGAAGGCGACAACGCGCGGCTGGCGGTGCTCAA

ACGCACGGTCGAGCTGACCCATTTCGCCTACCCGGCTCTGAACCTGCCCCCCAAAGTCATGAGCGCGGTCATGG

ACCAGGTGCTCATCAAGCGCGCGTCGCCCATCTCCGAGGACGAGGGCATGCAAGACTCCGAGGAGGGCAAGCCC

GTGGTCAGCGACGAGCAGCTGGCCCGGTGGCTGGGTCCTAATGCTAGTCCCCAGAGTTTGGAAGAGCGGCGCAA

ACTCATGATGGCCGTGGTCCTGGTGACCGTGGAGCTGGAGTGCCTGCGCCGCTTCTTCGCCGACGCGGAGACCC

TGCGCAAGGTCGAGGAGAACCTGCACTACCTCTTCAGGCACGGGTTCGTGCGCCAGGCCTGCAAGATCTCCAAC

GTGGAGCTGACCAACCTGGTCTCCTACATGGGCATCTTGCACGAGAACCGCCTGGGGCAGAACGTGCTGCACAC

CACCCTGCGCGGGGAGGCCCGGCGCGACTACATCCGCGACTGCGTCTACCTCTACCTCTGCCACACCTGGCAGA

CGGGCATGGGCGTGTGGCAGCAGTGTCTGGAGGAGCAGAACCTGAAAGAGCTCTGCAAGCTCCTGCAGAAGAAC

CTCAAGGGTCTGTGGACCGGGTTCGACGAGCGCACCACCGCCTCGGACCTGGCCGACCTCATTTTCCCCGAGCG

CCTCAGGCTGACGCTGCGCAACGGCCTGCCCGACTTTATGAGCCAAAGCATGTTGCAAAACTTTCGCTCTTTCA

TCCTCGAACGCTCCGGAATCCTGCCCCGCCACCTGCTCCGCGCTGCCCTCGGACTTCGTGCCGCTGACCTTCCGC

GAGTGCCCCCCGCCGCTGTGGAGCCACTGCTACCTGCTGCGCCTGGCCAACTACCTGGCCTACCACTCGGACGT

GATCGAGGACGTCAGCGGCGAGGGCCTGCTCGAGTGCCACTGCCGCTGCAACCTCTGCACGCCGCACCGCTCCC

TGGCCTGCAACCCCCAGCTGCTGAGCGAGACCCAGATCATCGGCACCTTCGAGTTGCAAGGGCCCAGCGAAGGC

GAGGGTTCAGCCGCCAAGGGGGGTCTGAAACTCACCCCGGGGCTGTGGACCTCGGCCTACTTGCGCAAGTTCGT

GCCCGAGGACTACCATCCCTTCGAGATCAGGTTCTACGAGGACCAATCCCATCCGCCCAAGGCCGAGCTGTCGG

CCTGCGTCATCACCCAGGGGGCGATCCTGGCCCAATTGCAAGCCATCCAGAAATCCCGCCAAGAATTCTTGCTG

AAAAAGGGCCGCGGGGTCTACCTCGACCCCCAGACCGGTGAGGAGCTCAACCCCGGCTTCCCCCAGGATGCCCC

GAGGAAACAAGAAGCTGAAAGTGGAGCTGCCGCCCGTGGAGGATTTGGAGGAAGACTGGGAGAACAGCAGTCAG

GCAGAGGAGGAGGAGATGGAGGAAGACTGGGACAGCACTCAGGCAGAGGAGGACAGCCTGCAAGACAGTCTGGA

GGAAGACGAGGAGGAGGCAGAGGAGGAGGTGGAAGAAGCAGCCGCCGCCAGACCGTCGTCCTCGGCGGGGAGA

AAGCAAGCAGCACGGATACCATCTCCGCTCCGGGTCGGGGTCCCGCTCGACCACACAGTAGATGGGACGAGACC

GGACGATTCCCGAACCCCACCACCCAGACCGGTAAGAAGGAGCGGCAGGGATACAAGTCCTGGCGGGGGCACAA

AAACGCCATCGTCTCCTGCTTGCAGGCCTGCGGGGGCAACATCTCCTTCACCCGGCGCTACCTGCTCTTCCACC

GCGGGGTGAACTTTCCCCGCAACATCTTGCATTACTACCGTCACCTCCACAGCCCCTACTACTTCCAAGAAGAG

GCAGCAGCAGCAGAAAAAGACCAGCAGAAAACCAGCAGCTAGAAAATCCACAGCGGCGGCAGCAGGTGGACTGA

GGATCGCGGCGAACGAGCCGGCGCAAACCCGGGAGCTGAGGAACCGGATCTTTCCCACCCTCTATGCCATCTTC

CAGCAGAGTCGGGGGCAGGAGCAGGAACTGAAAGTCAAGAACCGTTCTCTGCGCTCGCTCACCCGCAGTTGTCT

GTATCACAAGAGCGAAGACCAACTTCAGCGCACTCTCGAGGACGCCGAGGCTCTCTTCAACAAGTACTGCGCGC

TCACTCTTAAAGAGTAGCCCGCGCCCGCCCAGTCGCAGAAAAAGGCGGGAATTACGTCACCTGTGCCCTTCGCC

-continued

```
CTAGCCGCCTCCACCCATCATCATGAGCAAAGAGATTCCCACGCCTTACATGTGGAGCTACCAGCCCCAGATGG
GCCTGGCCGCCGGTGCCGCCCAGGACTACTCCACCCGCATGAATTGGCTCAGCGCCGGGCCCGCGATGATCTCA
CGGGTGAATGACATCCGCGCCCACCGAAACCAGATACTCCTAGAACAGTCAGCGCTCACCGCCACGCCCCGCAA
TCACCTCAATCCGCGTAATTGGCCCGCCGCCCTGGTGTACCAGGAAATTCCCCAGCCCACGACCGTACTACTTC
CGCGAGACGCCCAGGCCGAAGTCCAGCTGACTAACTCAGGTGTCCAGCTGGCGGGCGGCGCCACCCTGTGTCGT
CACCGCCCCGCTCAGGGTATAAAGCGGCTGGTGATCCGGGGCAGAGGCACACAGCTCAACGACGAGGTGGTGAG
CTCTTCGCTGGGTCTGCGACCTGACGGAGTCTTCCAACTCGCCGGATCGGGGAGATCTTCCTTCACGCCTCGTC
AGGCCGTCCTGACTTTGGAGAGTTCGTCCTCGCAGCCCCGCTCGGGTGGCATCGGCACTCTCCAGTTCGTGGAG
GAGTTCACTCCCTCGGTCTACTTCAACCCCTTCTCCGGCTCCCCGGCCACTACCCGGACGAGTTCATCCCGAA
CTTCGACGCCATCAGCGAGTCGGTGGACGGCTACGATTGAATGTCCCATGGTGGCGCAGCTGACCTAGCTCGGC
TTCGACACCTGGACCACTGCCGCCGCTTCCGCTGCTTCGCTCGGGATCTCGCCGAGTTTGCCTACTTTGAGCTG
CCCGAGGAGCACCCTCAGGGCCCGGCCCACGGAGTGCGGATCGTCGTCGAAGGGGGCCTCGACTCCCACCTGCT
TCGGATCTTCAGCCAGCGTCCGATCCTGGTCGAGCGCGAGCAAGGACAGACCCTTCTGACTCTGTACTGCATCT
GCAACCACCCCGGCCTGCATGAAAGTCTTTGTTGTCTGCTGTGTACTGAGTATAATAAAAGCTGAGATCAGCGA
CTACTCCGGACTTCCGTGTGTTCCTGAATCCATCAACCAGTCTTTGTTCTTCACCGGGAACGAGACCGAGCTCC
AGCTCCAGTGTAAGCCCCACAAGAAGTACCTCACCTGGCTGTTCCAGGGCTCCCCGATCGCCGTTGTCAACCAC
TGCGACAACGACGGAGTCCTGCTGAGCGGCCCTGCCAACCTTACTTTTTCCACCCGCAGAAGCAAGCTCCAGCT
CTTCCAACCCTTCCTCCCCGGGACCTATCAGTGCGTCTCGGGACCCTGCCATCACACCTTCCACCTGATCCCGA
ATACCACAGCGTCGCTCCCCGCTACTAACAACCAAACTAACCTCCACCAACGCCACCGTCGCGACCTTTCTGAA
TCTAATACTACCACCCACACCGGAGGTGAGCTCCGAGGTCAACCAACCTCTGGGATTTACTACGGCCCCTGGGA
GGTGGTTGGGTTAATAGCGCTAGGCCTAGTTGCGGGTGGGCTTTTGGTTCTCTGCTACCTATACCTCCCTTGCT
GTTCGTACTTAGTGGTGCTGTGTTGCTGGTTTAAGAAATGGGGAAGATCACCCTAGTGAGCTGCGGTGCGCTGG
TGGCGGTGTTGCTTTCGATTGTGGGACTGGGCGGTGCGGCTGTAGTGAAGGAGAAGGCCGATCCCTGCTTGCAT
TTCAATCCCAACAAATGCCAGCTGAGTTTTCAGCCCGATGGCAATCGGTGCGCGGTACTGATCAAGTGCGGATG
GGAATGCGAGAACGTGAGAATCGAGTACAATAACAAGACTCGGAACAATACTCTCGCGTCCGTGTGGCAGCCCG
GGGACCCCGAGTGGTACACCGTCTCTGTCCCCGGTGCTGACGGCTCCCCGCGCACCGTGAATAATACTTTCATT
TTTGCGCACATGTGCGACACGGTCATGTGGATGAGCAAGCAGTACGATATGTGGCCCCCCACGAAGGAGAACAT
CGTGGTCTTCTCCATCGCTTACAGCCTGTGCACGGCGCTAATCACCGCTATCGTGTGCCTGAGCATTCACATGC
TCATCGCTATTCGCCCCAGAAATAATGCCGAAAAAGAAAAACAGCCATAACGTTTTTTTCACACCTTTTTCAG
ACCATGGCCTCTGTTAAATTTTTGCTTTTATTTGCCAGTCTCATTGCCGTCATTCATGGAATGAGTAATGAGAA
AATTACTATTTACACTGGCACTAATCACACATTGAAAGGTCCAGAAAAAGCCACAGAAGTTTCATGGTATTGTT
ATTTTAATGAATCAGATGTATCTACTGAACTCTGTGGAAACAATAACAAAAAAAATGAGAGCATTACTCTCATC
AAGTTTCAATGTGGATCTGACTTAACCCTAATTAACATCACTAGAGACTATGTAGGTATGTATTATGGAACTAC
AGCAGGCATTTCGGACATGGAATTTTATCAAGTTTCTGTGTCTGAACCCACCACGCCTAGAATGACCACAACCA
CAAAAACTACACCTGTTACCACTATGCAGCTCACTACCAATAACATTTTTGCCATGCGTCAAATGGTCAACAAT
AGCACTCAACCCACCCCACCCAGTGAGGAAATTCCCAAATCCATGATTGGCATTATTGTTGCTGTAGTGGTGTG
CATGTTGATCATCGCCTTGTGCATGGTGTACTATGCCTTCTGCTACAGAAAGCACAGACTGAACGACAAGCTGG
AACACTTACTAAGTGTTGAATTTAATTTTTTAGAACCATGAAGATCCTAGGCCTTTTAATTTTTTCTATCATT
ACCTCTGCTCTATGCAATTCTGACAATGAGGACGTTACTGTCGTTGTCGGATCAAATTATACACTGAAAGGTCC
AGCGAAGGGTATGCTTTCGTGGTATTGCTATTTTGGATCTGACACTACAGAAACTGAATTATGCAATCTTAAGA
```

-continued

```
ATGGCAAAATTCAAAATTCTAAAATTAACAATTATATATGCAATGGTACTGATCTGATACTCCTCAATATCACG
AAATCATATGCTGGCAGTTACACCTGCCCTGGAGATGATGCTGACAGTATGATTTTTTACAAAGTAACTGTTGT
TGATCCCACTACTCCACCTCCACCCACCACAACTACTCACACCACACACACAGATCAAACCGCAGCAGAGGAGG
CAGCAAAGTTAGCCTTGCAGGTCCAAGACAGTTCATTTGTTGGCATTACCCCTACACCTGATCAGCGGTGTCCG
GGGCTGCTAGTCAGCGGCATTGTCGGTGTGCTTTCGGGATTAGCAGTCATAATCATCTGCATGTTCATTTTTGC
TTGCTGCTATAGAAGGCTTTACCGACAAAAATCAGACCCACTGCTGAACCTCTATGTTTAATTTTTTCCAGAGT
CATGAAGGCAGTTAGCGCTCTAGTTTTTTGTTCTTTGATTGGCATTGTTTTTGCAATCCTATTCCTAAAGTTA
GCTTTATTAAAGATGTGAATGTTACTGAGGGGGGCAATGTGACACTGGTAGGTGTAGAGGGTGCTGAAAACACC
ACCTGGACAAAATACCACCTCAATGGGTGGAAAGATATTTGCAATTGGAGTGTATTAGTTTATACATGTGAGGG
AGTTAATCTTACCATTGTCAATGCCACCTCAGCTCAAAATGGTAGAATTCAAGGACAAAGTGTCAGTGTATCTA
ATGGGTATTTTACCCAACATACTTTTATCTATGACGTTAAAGTCATACCACTGCCTACGCCTAGCCCACCTAGC
ACTACCACACAGACAACCCACACTACACAGACAACCACATACAGTACATTAAATCAGCCTACCACCACTACAGC
AGCAGAGGTTGCCAGCTCGTCTGGGGTCCGAGTGGCATTTTTGATGTGGGCCCCATCTAGCAGTCCCACTGCTA
GTACCAATGAGCAGACTACTGAATTTTTGTCCACTGTCGAGAGCCACACCACAGCTACCTCCAGTGCCTTCTCT
AGCACCGCCAATCTCTCCTCGCTTTCCTCTACACCAATCAGTCCCGCTACTACTCCTAGCCCCGCTCCTCTTCC
CACTCCCCTGAAGCAAACAGACGGCGGCATGCAATGGCAGATCACCCTGCTCATTGTGATCGGGTTGGTCATCC
TGGCCGTGTTGCTCTACTACATCTTCTGCCGCCGCATTCCCAACGCGCACCGCAAGCCGGTCTACAAGCCCATC
ATTGTCGGGCAGCCGGAGCCGCTTCAGGTGGAAGGGGGTCTAAGGAATCTTCTCTTCTCTTTTACAGTATGGTG
ATTGAACTATGATTCCTAGACAATTCTTGATCACTATTCTTATCTGCCTCCTCCAAGTCTGTGCCACCCTCGCT
CTGGTGGCCAACGCCAGTCCAGACTGTATTGGGCCCTTCGCCTCCTACGTGCTCTTTGCCTTCACCACCTGCAT
CTGCTGCTGTAGCATAGTCTGCCTGCTTATCACCTTCTTCCAGTTCATTGACTGGATCTTTGTGCGCATCGCCT
ACCTGCGCCACCACCCCCAGTACCGCGACCAGCGAGTGGCGCGGCTGCTCAGGCTCCTCTGATAAGCATGCGGG
CTCTGCTACTTCTCGCGCTTCTGCTGTTAGTGCTCCCCCGTCCCGTCGACCCCCGGTCCCCCACCCAGTCCCCC
GAGGAGGTCCGCAAATGCAAATTCCAAGAACCCTGGAAATTCCTCAAATGCTACCGCCAAAAATCAGACATGCA
TCCCAGCTGGATCATGATCATTGGGATCGTGAACATTCTGGCCTGCACCCTCATCTCCTTTGTGATTTACCCCT
GCTTTGACTTTGGTTGGAACTCGCCAGAGGCGCTCTATCTCCCGCCTGAACCTGACACACCACCACAGCAACCT
CAGGCACACGCACTACCACCACTACAGCCTAGGCCACAATACATGCCCATATTAGACTATGAGGCCGAGCCACA
GCGACCCATGCTCCCCGCTATTAGTTACTTCAATCTAACCGGCGGAGATGACTGACCCACTGGCCAACAACAAC
GTCAACGACCTTCTCCTGGACATGGACGGCCGCGCCTCGGAGCAGCGACTCGCCCAACTTCGCATTCGCCAGCA
GCAGGAGAGAGCCGTCAAGGAGCTGCAGGATGCGGTGGCCATCCACCAGTGCAAGAGAGGCATCTTCTGCCTGG
TGAAACAGGCCAAGATCTCCTACGAGGTCACTCCAAACGACCATCGCCTCTCCTACGAGCTCCTGCAGCAGCGC
CAGAAGTTCACCTGCCTGGTCGGAGTCAACCCCATCGTCATCACCCAGCAGTCTGGCGATACCAAGGGGTGCAT
CCACTGCTCCTGCGACTCCCCCGACTGCGTCCACACTCTGATCAAGACCCTCTGCGGCCTCCGCGACCTCCTCC
CCATGAACTAATCACCCCCTTATCCAGTGAAATAAAGATCATATTGATGATGATTTTACAGAAATAAAAAATAA
TCATTTGATTTGAAATAAAGATACAATCATATTGATGATTTGAGTTTAACAAAAAAATAAAGAATCACTTACTT
GAAATCTGATACCAGGTCTCTGTCCATGTTTTCTGCCAACACCACTTCACTCCCCTCTTCCCAGCTCTGGTACT
GCAGGCCCCGGCGGGCTGCAAACTTCCTCCACACGCTGAAGGGGATGTCAAATTCCTCCTGTCCCTCAATCTTC
ATTTTATCTTCTATCAGATGTCCAAAAAGCGCGTCCGGGTGGATGATGACTTCGACCCCGTCTACCCCTACGAT
GCAGACAACGCACCGACCGTGCCCTTCATCAACCCCCCCTTCGTCTCTTCAGATGGATTCCAAGAGAAGCCCCT
GGGGGTGTTGTCCCTGCGACTGGCCGACCCCGTCACCACCAAGAACGGGGAAATCACCCTCAAGCTGGGAGAGG
GGGTGGACCTCGATTCCTCGGGAAAACTCATCTCCAACACGGCCACCAAGGCCGCCGCCCCTCTCAGTTTTTCC
```

-continued

AACAACACCATTTCCCTTAACATGGATCACCCCTTTTACACTAAAGATGGAAAATTATCCTTACAAGTTTCTCC

ACCATTAAATATACTGAGAACAAGCATTCTAAACACACTAGCTTTAGGTTTTGGATCAGGTTTAGGACTCCGTG

GCTCTGCCTTGGCAGTACAGTTAGTCTCTCCACTTACATTTGATACTGATGGAAACATAAAGCTTACCTTAGAC

AGAGGTTTGCATGTTACAACAGGAGATGCAATTGAAAGCAACATAAGCTGGGCTAAAGGTTTAAAATTTGAAGA

TGGAGCCATAGCAACCAACATTGGAAATGGGTTAGAGTTTGGAAGCAGTAGTACAGAAACAGGTGTTGATGATG

CTTACCCAATCCAAGTTAAACTTGGATCTGGCCTTAGCTTTGACAGTACAGGAGCCATAATGGCTGGTAACAAA

GAAGACGATAAACTCACTTTGTGGACAACACCTGATCCATCACCAAACTGTCAAATACTCGCAGAAAATGATGC

AAAACTAACACTTTGCTTGACTAAATGTGGTAGTCAAATACTGGCCACTGTGTCAGTCTTAGTTGTAGGAAGTG

GAAACCTAAACCCCATTACTGGCACCGTAAGCAGTGCTCAGGTGTTTCTACGTTTTGATGCAAACGGTGTTCTT

TTAACAGAACATTCTACACTAAAAAAATACTGGGGGTATAGGCAGGGAGATAGCATAGATGGCACTCCATATAC

CAATGCTGTAGGATTCATGCCCAATTTAAAAGCTTATCCAAAGTCACAAAGTTCTACTACTAAAAATAATATAG

TAGGGCAAGTATACATGAATGGAGATGTTTCAAAACCTATGCTTCTCACTATAACCCTCAATGGTACTGATGAC

AGCAACAGTACATATTCAATGTCATTTTCATACACCTGGACTAATGGAAGCTATGTTGGAGCAACATTTGGGC

TAACTCTTATACCTTCTCATACATCGCCCAAGAATGAACACTGTATCCCACCCTGCATGCCAACCCTTCCCACC

CCACTCTGTGGAACAAACTCTGAAACACAAAATAAAATAAAGTTCAAGTGTTTTATTGATTCAACAGTTTTACA

GGATTCGAGCAGTTATTTTTCCTCCACCCTCCCAGGACATGGAATACACCACCCTCTCCCCCCGCACAGCCTTG

AACATCTGAATGCCATTGGTGATGGACATGCTTTTGGTCTCCACGTTCCACACAGTTTCAGAGCGAGCCAGTCT

CGGGTCGGTCAGGGAGATGAAACCCTCCGGGCACTCCCGCATCTGCACCTCACAGCTCAACAGCTGAGGATTGT

CCTCGGTGGTCGGGATCACGGTTATCTGGAAGAAGCAGAAGAGCGGCGGTGGGAATCATAGTCCGCGAACGGGA

TCGGCCGGTGGTGTCGCATCAGGCCCCGCAGCAGTCGCTGCCGCCGCCGCTCCGTCAAGCTGCTGCTCAGGGGG

TCCGGGTCCAGGGACTCCCTCAGCATGATGCCCACGGCCCTCAGCATCAGTCGTCTGGTGCGGCGGGCGCAGCA

GCGCATGCGGATCTCGCTCAGGTCGCTGCAGTACGTGCAACACAGAACCACCAGGTTGTTCAACAGTCCATAGT

TCAACACGCTCCAGCCGAAACTCATCGCGGGAAGGATGCTACCCACGTGGCCGTCGTACCAGATCCTCAGGTAA

ATCAAGTGGTGCCCCCTCCAGAACACGCTGCCCACGTACATGATCTCCTTGGGCATGTGGCGGTTCACCACCTC

CCGGTACCACATCACCCTCTGGTTGAACATGCAGCCCCGGATGATCCTGCGGAACCACAGGGCCAGCACCGCCC

CGCCCGCCATGCAGCGAAGAGACCCCGGGTCCCGGCAATGGCAATGGAGGACCCACCGCTCGTACCCGTGGATC

ATCTGGGAGCTGAACAAGTCTATGTTGGCACAGCACAGGCATATGCTCATGCATCTCTTCAGCACTCTCAACTC

CTCGGGGGTCAAAACCATATCCCAGGGCACGGGGAACTCTTGCAGGACAGCGAACCCCGCAGAACAGGGCAATC

CTCGCACAGAACTTACATTGTGCATGGACAGGGTATCGCAATCAGGCAGCACCGGGTGATCCTCCACCAGAGAA

GCGCGGGTCTCGGTCTCCTCACAGCGTGGTAAGGGGGCCGGCCGATACGGGTGATGGCGGGACGCGGCTGATCG

TGTTCGCGACCGTGTCATGATGCAGTTGCTTTCGGACATTTTCGTACTTGCTGTAGCAGAACCTGGTCCGGGCG

CTGCACACCGATCGCCGGCGGCGGTCTCGGCGCTTGGAACGCTCGGTGTTGAAATTGTAAAACAGCCACTCTCT

CAGACCGTGCAGCAGATCTAGGGCCTCAGGAGTGATGAAGATCCCATCATGCCTGATGGCTCTGATCACATCGA

CCACCGTGGAATGGGCCAGACCCAGCCAGATGATGCAATTTTGTTGGGTTTCGGTGACGGCGGGGAGGGAAGA

ACAGGAAGAACCATGATTAACTTTTAATCCAAACGGTCTCGGAGTACTTCAAAATGAAGATCGCGGAGATGGCA

CCTCTCGCCCCCGCTGTGTTGGTGGAAAATAACAGCCAGGTCAAAGGTGATACGGTTCTCGAGATGTTCCACGG

TGGCTTCCAGCAAAGCCTCCACGCGCACATCCAGAAACAAGACAATAGCGAAAGCGGGAGGGTTCTCTAATTCC

TCAATCATCATGTTACACTCCTGCACCATCCCCAGATAATTTTCATTTTTCCAGCCTTGAATGATTCGAACTAG

TTCcTGAGGTAAATCCAAGCCAGCCATGATAAAGAGCTCGCGCAGAGCGCCCTCCACCGGCATTCTTAAGCACA

CCCTCATAATTCCAAGATATTCTGCTCCTGGTTCACCTGCAGCAGATTGACAAGCGGAATATCAAAATCTCTGC

-continued

```
CGCGATCCCTGAGCTCCTCCCTCAGCAATAACTGTAAGTACTCTTTCATATCCTCTCCGAAATTTTTAGCCATA

GGACCACCAGGAATAAGATTAGGGCAAGCCACAGTACAGATAAACCGAAGTCCTCCCCAGTGAGCATTGCCAAA

TGCAAGACTGCTATAAGCATGCTGGCTAGACCCGGTGATATCTTCCAGATAACTGGACAGAAAATCGCCCAGGC

AATTTTTAAGAAAATCAACAAAAGAAAAATCCTCCAGGTGGACGTTTAGAGCCTCGGGAACAACGATGAAGTAA

ATGCAAGCGGTGCGTTCCAGCATGGTTAGTTAGCTGATCTGTAGAAAAAACAAAAATGAACATTAAACCATGCT

AGCCTGGCGAACAGGTGGGTAAATCGTTCTCTCCAGCACCAGGCAGGCCACGGGGTCTCCGGCGCGACCCTCGT

AAAAATTGTCGCTATGATTGAAAACCATCACAGAGAGACGTTCCCGGTGGCCGGCGTGAATGATTCGACAAGAT

GAATACACCCCCGGAACATTGGCGTCCGCGAGTGAAAAAAAGCGCCCGAGGAAGCAATAAGGCACTACAATGCT

CAGTCTCAAGTCCAGCAAAGCGATGCCATGCGGATGAAGCACAAAATTCTCAGGTGCGTACAAAATGTAATTAC

TCCCCTCCTGCACAGGCAGCAAAGCCCCCGATCCCTCCAGGTACACATACAAAGCCTCAGCGTCCATAGCTTAC

CGAGCAGCAGCACACAACAGGCGCAAGAGTCAGAGAAAGGCTGAGCTCTAACCTGTCCACCCGCTCTCTGCTCA

ATATATAGCCCAGATCTACACTGACGTAAAGGCCAAAGTCTAAAAATACCCGCCAAATAATCACACACGCCCAG

CACACGCCCAGAAACCGGTGACACACTCAAAAAAATACGCGCACTTCCTCAAACGCCCAAAACTGCCGTCATTT

CCGGGTTCCCACGCTACGTCATCAAAACACGACTTTCAAATTCCGTCGACCGTTAAAAACGTCACCCGCCCCGC

CCCTAACGGTCGCCCGTCTCTCAGCCAATCAGCGCCCCGCATCCCCAAATTCAAACACCTCATTTGCATATTAA

CGCGCACAAAAAGTTTGAGGTATATTATTGATGATGG
```

ATCC VR-594 C68; Independently sequenced; Full Length C68

(SEQ ID NO: 10)

```
CCATCTTCAATAATATACCTCAAACTTTTTGTGCGCGTTAATATGCAAATGAGGCGTTTGAATTTGGGGAGGAA

GGGCGGTGATTGGTCGAGGGATGAGCGACCGTTAGGGGCGGGGCGAGTGACGTTTTGATGACGTGGTTGCGAGG

AGGAGCCAGTTTGCAAGTTCTCGTGGGAAAAGTGACGTCAAACGAGGTGTGGTTTGAACACGGAAATACTCAAT

TTTCCCGCGCTCTCTGACAGGAAATGAGGTGTTTCTGGGCGGATGCAAGTGAAAACGGGCCATTTTCGCGCGAA

AACTGAATGAGGAAGTGAAAATCTGAGTAATTTCGCGTTTATGGCAGGGAGGAGTATTTGCCGAGGGCCGAGTA

GACTTTGACCGATTACGTGGGGGTTTCGATTACCGTGTTTTTCACCTAAATTTCCGCGTACGGTGTCAAAGTCC

GGTGTTTTTACGTAGGTGTCAGCTGATCGCCAGGGTATTTAAACCTGCGCTCTCCAGTCAAGAGGCCACTCTTG

AGTGCCAGCGAGAAGAGTTTTCTCCTCCGCGCCGCGAGTCAGATCTACACTTTGAAAGATGAGGCACCTGAGAG

ACCTGCCCGATGAGAAAATCATCATCGCTTCCGGGAACGAGATTCTGGAACTGGTGGTAAATGCCATGATGGGC

GACGACCCTCCGGAGCCCCCCACCCCATTTGAGACACCTTCGCTGCACGATTTGTATGATCTGGAGGTGGATGT

GCCCGAGGACGATCCCAATGAGGAGGCGGTAAATGATTTTTTTAGCGATGCCGCGCTGCTAGCTGCCGAGGAGG

CTTCGAGCTCTAGCTCAGACAGCGACTCTTCACTGCATACCCCTAGACCCGGCAGAGGTGAGAAAAAGATCCCC

GAGCTTAAAGGGGAAGAGATGGACTTGCGCTGCTATGAGGAATGCTTGCCCCCGAGCGATGATGAGGACGAGCA

GGCGATCCAGAACGCAGCGAGCCAGGGAGTGCAAGCCGCCAGCGAGAGCTTTGCGCTGGACTGCCCGCCTCTGC

CCGGACACGGCTGTAAGTCTTGTGAATTTCATCGCATGAATACTGGAGATAAAGCTGTGTTGTGTGCACTTTGC

TATATGAGAGCTTACAACCATTGTGTTTACAGTAAGTGTGATTAAGTTGAACTTTAGAGGGAGGCAGAGAGCAG

GGTGACTGGGCGATGACTGGTTTATTTATGTATATATGTTCTTTATATAGGTCCCGTCTCTGACGCAGATGATG

AGACCCCCACTACAAAGTCCACTTCGTCACCCCCAGAAATTGGCACATCTCCACCTGAGAATATTGTTAGACCA

GTTCCTGTTAGAGCCACTGGGAGGAGAGCAGCTGTGGAATGTTTGGATGACTTGCTACAGGGTGGGGTTGAACC

TTTGGACTTGTGTACCCGGAAACGCCCCAGGCACTAAGTGCCACACATGTGTGTTTACTTGAGGTGATGTCAGT

ATTTATAGGGTGTGGAGTGCAATAAAAAATGTGTTGACTTTAAGTGCGTGGTTTATGACTCAGGGGTGGGGACT

GTGAGTATATAAGCAGGTGCAGACCTGTGTGGTTAGCTCAGAGCGGCATGGAGATTTGGACGGTCTTGGAAGAC

TTTCACAAGACTAGACAGCTGCTAGAGAACGCCTCGAACGGAGTCTCTTACCTGTGGAGATTCTGCTTCGGTGG

CGACCTAGCTAGGCTAGTCTACAGGGCCAAACAGGATTATAGTGAACAATTTGAGGTTATTTTGAGAGAGTGTT
```

-continued

CTGGTCTTTTTGACGCTCTTAACTTGGGCCATCAGTCTCACTTTAACCAGAGGATTTCGAGAGCCCTTGATTTT
ACTACTCCTGGCAGAACCACTGCAGCAGTAGCCTTTTTTGCTTTTATTCTTGACAAATGGAGTCAAGAAACCCA
TTTCAGCAGGGATTACCAGCTGGATTTCTTAGCAGTAGCTTTGTGGAGAACATGGAAGTGCCAGCGCCTGAATG
CAATCTCCGGCTACTTGCCGGTACAGCCGCTAGACACTCTGAGGATCCTGAATCTCCAGGAGAGTCCCAGGGCA
CGCCAACGTCGCCAGCAGCAGCAGGAGGAGGATCAAGAAGAGAACCCGAGAGCCGGCCTGGACCCTCCGGC
GGAGGAGGAGGAGTAGCTGACCTGTTTCCTGAACTGCGCCGGGTGCTGACTAGGTCTTCGAGTGGTCGGAGAG
GGGGATTAAGCGGGAGAGGCATGATGAGACTAATCACAGAACTGAACTGACTGTGGGTCTGATGAGTCGCAAGC
GCCCAGAAACAGTGTGGTGGCATGAGGTGCAGTCGACTGGCACAGATGAGGTGTCGGTGATGCATGAGAGGTTT
TCTCTAGAACAAGTCAAGACTTGTTGGTTAGAGCCTGAGGATGATTGGGAGGTAGCCATCAGGAATTATGCCAA
GCTGGCTCTGAGGCCAGACAAGAAGTACAAGATTACTAAGCTGATAAATATCAGAAATGCCTGCTACATCTCAG
GGAATGGGGCTGAAGTGGAGATCTGTCTCCAGGAAAGGGTGGCTTTCAGATGCTGCATGATGAATATGTACCCG
GGAGTGGTGGGCATGGATGGGGTTACCTTTATGAACATGAGGTTCAGGGGAGATGGGTATAATGGCACGGTCTT
TATGGCCAATACCAAGCTGACAGTCCATGGCTGCTCCTTCTTTGGGTTTAATAACACCTGCATCGAGGCCTGGG
GTCAGGTCGGTGTGAGGGGCTGCAGTTTTTCAGCCAACTGGATGGGGGTCGTGGGCAGGACCAAGAGTATGCTG
TCCGTGAAGAAATGCTTGTTTGAGAGGTGCCACCTGGGGGTGATGAGCGAGGGCGAAGCCAGAATCCGCCACTG
CGCCTCTACCGAGACGGGCTGCTTTGTGCTGTGCAAGGGCAATGCTAAGATCAAGCATAATATGATCTGTGGAG
CCTCGGACGAGCGCGGCTACCAGATGCTGACCTGCGCCGGCGGGAACAGCCATATGCTGGCCACCGTACATGTG
GCTTCCCATGCTCGCAAGCCCTGGCCCGAGTTCGAGCACAATGTCATGACCAGGTGCAATATGCATCTGGGGTC
CCGCCGAGGCATGTTCATGCCCTACCAGTGCAACCTGAATTATGTGAAGGTGCTGCTGGAGCCCGATGCCATGT
CCAGAGTGAGCCTGACGGGGGTGTTTGACATGAATGTGGAGGTGTGGAAGATTCTGAGATATGATGAATCCAAG
ACCAGGTGCCGAGCCTGCGAGTGCGGAGGGAAGCATGCCAGGTTCCAGCCCGTGTGTGTGGATGTGACGGAGGA
CCTGCGACCCGATCATTTGGTGTTGCCCTGCACCGGGACGGAGTTCGGTTCCAGCGGGGAAGAATCTGACTAGA
GTGAGTAGTGTTCTGGGGCGGGGAGGACCTGCATGAGGGCCAGAATAACTGAAATCTGTGCTTTTCTGTGTGT
TGCAGCAGCATGAGCGGAAGCGGCTCCTTTGAGGGAGGGGTATTCAGCCCTTATCTGACGGGGCGTCTCCCCTC
CTGGGCGGGAGTGCGTCAGAATGTGATGGGATCCACGGTGGACGGCCGGCCCGTGCAGCCCGCGAACTCTTCAA
CCCTGACCTATGCAACCCTGAGCTCTTCGTCGTTGGACGCAGCTGCCGCCGCAGCTGCTGCATCTGCCGCCAGC
GCCGTGCGCGGAATGGCCATGGGCGCCGGCTACTACGGCACTCTGGTGGCCAACTCGAGTTCCACCAATAATCC
CGCCAGCCTGAACGAGGAGAAGCTGTTGCTGCTGATGGCCCAGCTCGAGGCCTTGACCCAGCGCCTGGGCGAGC
TGACCCAGCAGGTGGCTCAGCTGCAGGAGCAGACGCGGGCCGCGGTTGCCACGGTGAAATCCAAATAAAAAATG
AATCAATAAATAAACGGAGACGGTTGTTGATTTTAACACAGAGTCTGAATCTTTATTTGATTTTTCGCGCGCGG
TAGGCCCTGGACCACCGGTCTCGATCATTGAGCACCCGGTGGATCTTTTCCAGGACCCGGTAGAGGTGGGCTTG
GATGTTGAGGTACATGGGCATGAGCCCGTCCCGGGGGTGGAGGTAGCTCCATTGCAGGGCCTCGTGCTCGGGGG
TGGTGTTGTAAATCACCCAGTCATAGCAGGGGCGCAGGGCATGGTGTTGCACAATATCTTTGAGGAGGAGACTG
ATGGCCACGGGCAGCCCTTTGGTGTAGGTGTTTACAAATCTGTTGAGCTGGGAGGGATGCATGCGGGGGAGAT
GAGGTGCATCTTGGCCTGGATCTTGAGATTGGCGATGTTACCGCCCAGATCCCGCCTGGGGTTCATGTTGTGCA
GGACCACCAGCACGGTGTATCCGGTGCACTTGGGGAATTTATCATGCAACTTGGAAGGGAAGGCGTGAAAGAAT
TTGGCGACGCCTTTGTGCCCGCCCAGGTTTTCCATGCACTCATCCATGATGATGGCGATGGGCCCGTGGCGGC
GGCCTGGGCAAAGACGTTTCGGGGGTCGGACACATCATAGTTGTGGTCCTGGGTGAGGTCATCATAGGCCATTT
TAATGAATTTGGGGCGGAGGGTGCCGACTGGGGGACAAAGGTACCCTCGATCCCGGGGCGTAGTTCCCCTCA
CAGATCTGCATCTCCCAGGCTTTGAGCTCGGAGGGGGGGATCATGTCCACCTGCGGGGCGATAAAGAACACGGT

-continued

```
TTCCGGGGCGGGGGAGATGAGCTGGGCCGAAAGCAAGTTCCGGAGCAGCTGGGACTTGCCGCAGCCGGTGGGGC
CGTAGATGACCCCGATGACCGGCTGCAGGTGGTAGTTGAGGGAGAGACAGCTGCCGTCCTCCCGGAGGAGGGGG
GCCACCTCGTTCATCATCTCGCGCACGTGCATGTTCTCGCGCACCAGTTCCGCCAGGAGGCGCTCTCCCCCCAG
GGATAGGAGCTCCTGGAGCGAGGCGAAGTTTTTCAGCGGCTTGAGTCCGTCGGCCATGGGCATTTTGGAGAGGG
TTTGTTGCAAGAGTTCCAGGCGGTCCCAGAGCTCGGTGATGTGCTCTACGGCATCTCGATCCAGCAGACCTCCT
CGTTTCGCGGGTTGGGACGGCTGCGGGAGTAGGGCACCAGACGATGGGCGTCCAGCGCAGCCAGGGTCCGGTCC
TTCCAGGGTCGCAGCGTCCGCGTCAGGGTGGTCTCCGTCACGGTGAAGGGGTGCGCGCCGGGCTGGGCGCTTGC
GAGGGTGCGCTTCAGGCTCATCCGGCTGGTCGAAAACCGCTCCCGATCGGCGCCCTGCGCGTCGGCCAGGTAGC
AATTGACCATGAGTTCGTAGTTGAGCGCCTCGGCCGCGTGGCCTTTGGCGCGGAGCTTACCTTTGGAAGTCTGC
CCGCAGGCGGGACAGAGGAGGGACTTGAGGGCGTAGAGCTTGGGGGCGAGGAAGACGGACTCGGGGGCGTAGGC
GTCCGCGCCGCAGTGGGCGCAGACGGTCTCGCACTCCACGAGCCAGGTGAGGTCGGGCTGGTCGGGGTCAAAAA
CCAGTTTCCCGCCGTTCTTTTTGATGCGTTTCTTACCTTTGGTCTCCATGAGCTCGTGTCCCCGCTGGGTGACA
AAGAGGCTGTCCGTGTCCCCGTAGACCGACTTTATGGGCCGGTCCTCGAGCGGTGTGCCGCGGTCCTCCTCGTA
GAGGAACCCCGCCCACTCCGAGACGAAAGCCCGGGTCCAGGCCAGCACGAAGGAGGCCACGTGGGACGGGTAGC
GGTCGTTGTCCACCAGCGGGTCCACCTTTTCCAGGGTATGCAAACACATGTCCCCCTCGTCCACATCCAGGAAG
GTGATTGGCTTGTAAGTGTAGGCCACGTGACCGGGGGTCCCGGCCGGGGGGGTATAAAAGGGTGCGGGTCCCTG
CTCGTCCTCACTGTCTTCCGGATCGCTGTCCAGGAGCGCCAGCTGTTGGGGTAGGTATTCCCTCTCGAAGGCGG
GCATGACCTCGGCACTCAGGTTGTCAGTTTCTAGAAACGAGGAGGATTTGATATTGACGGTGCCGGCGGAGATG
CCTTTCAAGAGCCCCTCGTCCATCTGGTCAGAAAAGACGATCTTTTTGTTGTCGAGCTTGGTGGCGAAGGAGCC
GTAGAGGGCGTTGGAGAGGAGCTTGGCGATGGAGCGCATGGTCTGGTTTTTTTCCTTGTCGGCGCGCTCCTTGG
CGGCGATGTTGAGCTGCACGTACTCGCGCGCCACGCACTTCCATTCGGGGAAGACGGTGGTCAGCTCGTCGGGC
ACGATTCTGACCTGCCAGCCCCGATTATGCAGGGTGATGAGGTCCACACTGGTGGCCACCTCGCCGCGCAGGGG
CTCATTAGTCCAGCAGAGGCGTCCGCCCTTGCGCGAGCAGAAGGGGGCAGGGGTCCAGCATGACCTCGTCGG
GGGGGTCGGCATCGATGGTGAAGATGCCGGGCAGGAGGTCGGGGTCAAAGTAGCTGATGGAAGTGGCCAGATCG
TCCAGGGCAGCTTGCCATTCGCGCACGGCCAGCGCGCGCTCGTAGGGACTGAGGGGCGTGCCCCAGGGCATGGG
ATGGGTAAGCGCGGAGGCGTACATGCCGCAGATGTCGTAGACGTAGAGGGGCTCCTCGAGGATGCCGATGTAGG
TGGGGTAGCAGCGCCCCCCGCGGATGCTGGCGCGCACGTAGTCATACAGCTCGTGCGAGGGGCGAGGAGCCCC
GGGCCCAGGTTGGTGCGACTGGGCTTTTCGGCGCGGTAGACGATCTGGCGGAAAATGGCATGCGAGTTGGAGGA
GATGGTGGGCCTTTGGAAGATGTTGAAGTGGGCGTGGGGCAGTCCGACCGAGTCGCGGATGAAGTGGGCGTAGG
AGTCTTGCAGCTTGGCGACGAGCTCGGCGGTGACTAGGACGTCCAGAGCGCAGTAGTCGAGGGTCTCCTGGATG
ATGTCATACTTGAGCTGTCCCTTTTGTTTCCACAGCTCGCGGTTGAGAAGGAACTCTTCGCGGTCCTTCCAGTA
CTCTTCGAGGGGAACCCGTCCTGATCTGCACGGTAAGAGCCTAGCATGTAGAACTGGTTGACGGCCTTGTAGG
CGCAGCAGCCCTTCTCCACGGGGAGGGCGTAGGCCTGGGCGGCCTTGCGCAGGGAGGTGTGCGTGAGGGCGAAA
GTGTCCCTGACCATGACCTTGAGGAACTGGTGCTTGAAGTCGATATCGTCGCAGCCCCCTGCTCCCAGAGCTG
GAAGTCCGTGCGCTTCTTGTAGGCGGGGTTGGGCAAAGCGAAAGTAACATCGTTGAAGAGGATCTTGCCCGCGC
GGGGCATAAAGTTGCGAGTGATGCGGAAAGGTTGGGGCACCTCGGCCCGGTTGTTGATGACCTGGGCGGCGAGC
ACGATCTCGTCGAAGCCGTTGATGTTGTGGCCCACGATGTAGAGTTCCACGAATCGCGGACGGCCCTTGACGTG
GGGCAGTTTCTTGAGCTCCTCGTAGGTGAGCTCGTCGGGGTCGCTGAGCCCGTGCTGCTCGAGCGCCCAGTCGG
CGAGATGGGGGTTGGCGCGGAGGAAGGAAGTCCAGAGATCCACGGCCAGGGCGGTTTGCAGACGGTCCCGGTAC
TGACGGAACTGCTGCCCGACGCCATTTTTTCGGGGGTGACGCAGTAGAAGGTGCGGGGGTCCCCGTGCCAGCG
ATCCCATTTGAGCTGGAGGGCGAGATCGAGGGCGAGCTCGACGAGCCGGTCGTCCCCGGAGAGTTTCATGACCA
```

```
GCATGAAGGGGACGAGCTGCTTGCCGAAGGACCCCATCCAGGTGTAGGTTTCCACATCGTAGGTGAGGAAGAGC
CTTTCGGTGCGAGGATGCGAGCCGATGGGAAGAACTGGATCTCCTGCCACCAATTGGAGGAATGGCTGTTGAT
GTGATGGAAGTAGAAATGCCGACGGCGCGCCGAACACTCGTGCTTGTGTTTATACAAGCGGCCACAGTGCTCGC
AACGCTGCACGGGATGCACGTGCTGCACGAGCTGTACCTGAGTTCCTTTGACGAGGAATTTCAGTGGGAAGTGG
AGTCGTGGCGCCTGCATCTCGTGCTGTACTACGTCGTGGTGGTCGGCCTGGCCCTCTTCTGCCTCGATGGTGGT
CATGCTGACGAGCCCGCGGGAGGCAGGTCCAGACCTCGGCGCGAGCGGGTCGGAGAGCGAGGACGAGGGCGC
GCAGGCCGGAGCTGTCCAGGGTCCTGAGACGCTGCGGAGTCAGGTCAGTGGGCAGCGGCGGCGCGCGGTTGACT
TGCAGGAGTTTTTCCAGGGCGCGCGGGAGGTCCAGATGGTACTTGATCTCCACCGCGCCATTGGTGGCGACGTC
GATGGCTTGCAGGGTCCCGTGCCCCTGGGGTGTGACCACCGTCCCCCGTTTCTTCTTGGGCGGCTGGGGCGACG
GGGGCGGTGCCTCTTCCATGGTTAGAAGCGGCGGCGAGGACGCGCGCCGGGCGGCAGGGCGGCTCGGGGCCCG
GAGGCAGGGCGGCAGGGGCACGTCGGCGCCGCGCGCGGGTAGGTTCTGGTACTGCGCCCGGAGAAGACTGGCG
TGAGCGACGACGCGACGGTTGACGTCCTGGATCTGACGCCTCTGGGTGAAGGCCACGGGACCCGTGAGTTTGAA
CCTGAAAGAGAGTTCGACAGAATCAATCTCGGTATCGTTGACGGCGGCCTGCCGCAGGATCTCTTGCACGTCGC
CCGAGTTGTCCTGGTAGGCGATCTCGGTCATGAACTGCTCGATCTCCTCCTCTTGAAGGTCTCCGCGGCCGGCG
CGCTCCACGGTGGCCGCGAGGTCGTTGGAGATGCGGCCCATGAGCTGCGAGAAGGCGTTCATGCCCGCCTCGTT
CCAGACGCGGCTGTAGACCACGACGCCCTCGGGATCGCgGGCGCGCATGACCACCTGGGCGAGGTTGAGCTCCA
CGTGGCGCGTGAAGACCGCGTAGTTGCAGAGGCGCTGGTAGAGGTAGTTGAGCGTGGTGGCGATGTGCTCGGTG
ACGAAGAAATACATGATCCAGCGGCGGAGCGGCATCTCGCTGACGTCGCCCAGCGCCTCCAAACGTTCCATGGC
CTCGTAAAAGTCCACGGCGAAGTTGAAAAACTGGGAGTTGCGCGCCGAGACGGTCAACTCCTCCTCCAGAAGAC
GGATGAGCTCGGCGATGGTGGCGCGCACCTCGCGCTCGAAGGCCCCCGGGAGTTCCTCCACTTCCTCTTCTTCC
TCCTCCACTAACATCTCTTCTACTTCCTCCTCAGGCGGCAGTGGTGGCGGGGAGGGGCCTGCGTCGCCGGCG
GCGCACGGGCAGACGGTCGATGAAGCGCTCGATGGTCTCGCCGCGCCGGCGTCGCATGGTCTCGGTGACGGCGC
GCCCGTCCTCGCGGGCCGCAGCGTGAAGACGCCGCCGCGCATCTCCAGGTGGCCGGGGGGGTCCCCGTTGGGC
AGGGAGAGGGCGCTGACGATGCATCTTATCAATTGCCCCGTAGGGACTCCGCGCAAGGACCTGAGCGTCTCGAG
ATCCACGGGATCTGAAAACCGCTGAACGAAGGCTTCGAGCCAGTCGCAGTCGCAAGGTAGGCTGAGCACGGTTT
CTTCTGGCGGGTCATGTTGGTTGGGAGCGGGGCGGGCGATGCTGCTGGTGATGAAGTTGAAATAGGCGGTTCTG
AGACGGCGGATGGTGGCGAGGAGCACCAGGTCTTTGGGCCCGGCTTGCTGGATGCGCAGACGGTCGGCCATGCC
CCAGGCGTGGTCCTGACACCTGGCCAGGTCCTTGTAGTAGTCCTGCATGAGCCGCTCCACGGGCACCTCCTCCT
CGCCCGCGCGGCCGTGCATGCGCGTGAGCCCGAAGCCGCGCTGGGCTGGACGAGCGCCAGGTCGGCGACGACG
CGCTCGGCGAGGATGGCTTGCTGGATCTGGGTGAGGGTGGTCTGGAAGTCATCAAAGTCGACGAAGCGGTGGTA
GGCTCCGGTGTTGATGGTGTAGGAGCAGTTGGCCATGACGGACCAGTTGACGGTCTGGTGGCCCGGACGCACGA
GCTCGTGGTACTTGAGGCGCGAGTAGGCGCGCGTGTCGAAGATGTAGTCGTTGCAGGTGCGCACCAGGTACTGG
TAGCCGATGAGGAAGTGCGGCGGCGGCTGGCGGTAGAGCGGCCATCGCTCGGTGGCGGGGCGCCGGGCGCGAG
GTCCTCGAGCATGGTGCGGTGGTAGCCGTAGATGTACCTGGACATCCAGGTGATGCCGGCGGCGGTGGTGGAGG
CGCGCGGGAACTCGCGGACGCGGTTCCAGATGTTGCGCAGCGGCAGGAAGTAGTTCATGGTGGGCACGGTCTGG
CCCGTGAGGCGCGCGCAGTCGTGGATGCTCTATACGGGCAAAAACGAAAGCGGTCAGCGGCTCGACTCCGTGGC
CTGGAGGCTAAGCGAACGGGTTGGGCTGCGCGTGTACCCCGGTTCGAATCTGAATCAGGCTGGAGCCGCAGCT
AACGTGGTATTGGCACTCCCGTCTCGACCCAAGCCTGCACCAACCCTCCAGGATACGGAGGCGGGTCGTTTTGC
AACTTTTTTTTGGAGGCCGGATGAGACTAGTAAGCGCGGAAAGCGGCCGACCGCGATGGCTCGCTGCCGTAGTC
TGGAGAAGAATCGCCAGGGTTGCGTTGCGGTGTGCCCCGGTTCGAGGCCGGCCGGATTCCGCGGCTAACGAGGG
```

-continued

```
CGTGGCTGCCCCGTCGTTTCCAAGACCCCATAGCCAGCCGACTTCTCCAGTTACGGAGCGAGCCCCTCTTTGT

TTTGTTTGTTTTTGCCAGATGCATCCCGTACTGCGGCAGATGCGCCCCCACCACCCTCCACCGCAACAACAGCC

CCCTCCACAGCCGGCGCTTCTGCCCCCGCCCCAGCAGCAACTTCCAGCCACGACCGCCGCGGCCGCCGTGAGCG

GGGCTGGACAGAGTTATGATCACCAGCTGGCCTTGGAAGAGGGCGAGGGGCTGGCGCGCCTGGGGGCGTCGTCG

CCGGAGCGGCACCCGCGCGTGCAGATGAAAAGGGACGCTCGCGAGGCCTACGTGCCCAAGCAGAACCTGTTCAG

AGACAGGAGCGGCGAGGAGCCCGAGGAGATGCGCGCGGCCCGGTTCCACGCGGGGCGGGAGCTGCGGCGCGGCC

TGGACCGAAAGAGGGTGCTGAGGGACGAGGATTTCGAGGCGGACGAGCTGACGGGGATCAGCCCCGCGCGCGCG

CACGTGGCCGCGGCCAACCTGGTCACGGCGTACGAGCAGACCGTGAAGGAGGAGAGCAACTTCCAAAAATCCTT

CAACAACCACGTGCGCACCCTGATCGCGCGCGAGGAGGTGACCCTGGGCCTGATGCACCTGTGGGACCTGCTGG

AGGCCATCGTGCAGAACCCCACCAGCAAGCCGCTGACGGCGCAGCTGTTCCTGGTGGTGCAGCATAGTCGGGAC

AACGAAGCGTTCAGGGAGGCGCTGCTGAATATCACCGAGCCCGAGGGCCGCTGGCTCCTGGACCTGGTGAACAT

TCTGCAGAGCATCGTGGTGCAGGAGCGCGGGCTGCCGCTGTCCGAGAAGCTGGCGGCCATCAACTTCTCGGTGC

TGAGTTTGGGCAAGTACTACGCTAGGAAGATCTACAAGACCCCGTACGTGCCCATAGACAAGGAGGTGAAGATC

GACGGGTTTTACATGCGCATGACCCTGAAAGTGCTGACCCTGAGCGACGATCTGGGGGTGTACCGCAACGACAG

GATGCACCGTGCGGTGAGCGCCAGCAGGCGGCGCGAGCTGAGCGACCAGGAGCTGATGCATAGTCTGCAGCGGG

CCCTGACCGGGGCCGGGACCGAGGGGGAGAGCTACTTTGACATGGGCGCGGACCTGCACTGGCAGCCCAGCCGC

CGGGCCTTGGAGGCGGCGGCAGGACCCTACGTAGAAGAGGTGGACGATGAGGTGGACGAGGAGGGCGAGTACCT

GGAAGACTGATGGCGCGACCGTATTTTTGCTAGATGCAACAACAACAGCCACCTCCTGATCCCGCGATGCGGGC

GGCGCTGCAGAGCCAGCCGTCCGGCATTAACTCCTCGGACGATTGGACCCAGGCCATGCAACGCATCATGGCGC

TGACGACCCGCAACCCCGAAGCCTTTAGACAGCAGCCCCAGGCCAACCGGCTCTCGGCCATCCTGGAGGCCGTG

GTGCCCTCGCGCTCCAACCCCACGCACGAGAAGGTCCTGGCCATCGTGAACGCGCTGGTGGAGAACAAGGCCAT

CCGCGGCGACGAGGCCGGCCTGGTGTACAACGCGCTGCTGGAGCGCGTGGCCCGCTACAACAGCACCAACGTGC

AGACCAACCTGGACCGCATGGTGACCGACGTGCGCGAGGCCGTGGCCCAGCGCGAGCGGTTCCACCGCGAGTCC

AACCTGGGATCCATGGTGGCGCTGAACGCCTTCCTCAGCACCCAGCCCGCCAACGTGCCCCGGGGCCAGGAGGA

CTACACCAACTTCATCAGCGCCCTGCCCCTGATGGTGACCGAGGTGCCCCAGAGCGAGGTGTACCAGTCCGGGC

CGGACTACTTCTTCCAGACCAGTCGCCAGGGCTTGCAGACCGTGAACCTGAGCCAGGCTTTCAAGAACTTGCAG

GGCCTGTGGGGCGTGCAGGCCCCGGTCGGGACCGCGCGACGGTGTCGAGCCTGCTGACGCCGAACTCGCGCCT

GCTGCTGCTGCTGGTGGCCCCCCTTCACGGACAGCGGCAGCATCAACCGCAACTCGTACCTGGGCTACCTGATTA

ACCTGTACCGCGAGGCCATCGGCCAGGCGCACGTGGACGAGCAGACCTACCAGGAGATCACCCACGTGAGCCGC

GCCCTGGGCCAGGACGACCCGGGCAACCTGGAAGCCACCCTGAACTTTTTGCTGACCAACCGGTCGCAGAAGAT

CCCGCCCCAGTACGCGCTCAGCACCGAGGAGGAGCGCATCCTGCGTTACGTGCAGCAGAGCGTGGGCCTGTTCC

TGATGCAGGAGGGGCCACCCCCAGCGCCGCGCTCGACATGACCGCGCGCAACATGGAGCCCAGCATGTACGCC

AGCAACCGCCCGTTCATCAATAAACTGATGGACTACTTGCATCGGGCGGCCGCCATGAACTCTGACTATTTCAC

CAACGCCATCCTGAATCCCCACTGGCTCCCGCCGCCGGGGTTCTACACGGGCGAGTACGACATGCCCGACCCCA

ATGACGGGTTCCTGTGGGACGATGTGGACAGCAGCGTGTTCTCCCCCCGACCGGGTGCTAACGAGCGCCCCTTG

TGGAAGAAGGAAGGCAGCGACCGACGCCCGTCCTCGGCGCTGTCCGGCCGCGAGGGTGCTGCCGCGGCGGTGCC

CGAGGCCGCCAGTCCTTTCCCGAGCTTGCCCTTCTCGCTGAACAGTATCCGCAGCAGCGAGCTGGGCAGGATCA

CGCGCCCGCGCTTGCTGGGCGAAGAGGAGTACTTGAATGACTCGCTGTTGAGACCCGAGCGGGAGAAGAACTTC

CCCAATAACGGGATAGAAAGCCTGGTGGACAAGATGAGCCGCTGGAAGACGTATGCGCAGGAGCACAGGGACGA

TCCCCGGGCGTCGCAGGGGGCCACGAGCCGGGCAGCGCCGCCCGTAAAGCCGGTGGCACGACAGGCAGCGGG

GACAGATGTGGGACGATGAGGACTCCGCCGACGACAGCAGCGTGTTGGACTTGGGTGGGAGTGGTAACCCGTTC
```

-continued

```
GCTCACCTGCGCCCCCGTATCGGGCGCATGATGTAAGAGAAACCGAAAATAAATGATACTCACCAAGGCCATGG

CGACCAGCGTGCGTTCGTTTCTTCTCTGTTGTTGTTGTATCTAGTATGATGAGGCGTGCGTACCCGGAGGGTCC

TCCTCCCTCGTACGAGAGCGTGATGCAGCAGGCGATGGCGGCGGCGGCGATGCAGCCCCCGCTGGAGGCTCCTT

ACGTGCCCCGCGGTACCTGGCGCCTACGGAGGGGCGGAACAGCATTCGTTACTCGGAGCTGGCACCCTTGTAC

GATACCACCCGGTTGTACCTGGTGGACAACAAGTCGGCGGACATCGCCTCGCTGAACTACCAGAACGACCACAG

CAACTTCCTGACCACCGTGGTGCAGAACAATGACTTCACCCCCACGGAGGCCAGCACCCAGACCATCAACTTTG

ACGAGCGCTCGCGGTGGGGCGGCCAGCTGAAAACCATCATGCACACCAACATGCCCAACGTGAACGAGTTCATG

TACAGCAACAAGTTCAAGGCGCGGGTGATGGTCTCCCGCAAGACCCCCAATGGGGTGACAGTGACAGAGGATTA

TGATGGTAGTCAGGATGAGCTGAAGTATGAATGGGTGGAATTTGAGCTGCCCGAAGGCAACTTCTCGGTGACCA

TGACCATCGACCTGATGAACAACGCCATCATCGACAATTACTTGGCGGTGGGGCGGCAGAACGGGGTGCTGGAG

AGCGACATCGGCGTGAAGTTCGACACTAGGAACTTCAGGCTGGGCTGGGACCCCGTGACCGAGCTGGTCATGCC

CGGGGTGTACACCAACGAGGCTTTCCATCCCGATATTGTCTTGCTGCCCGGCTGCGGGGTGGACTTCACCGAGA

GCCGCCTCAGCAACCTGCTGGGCATTCGCAAGAGGCAGCCCTTCCAGGAAGGCTTCCAGATCATGTACGAGGAT

CTGGAGGGGGGCAACATCCCCGCGCTCCTGGATGTCGACGCCTATGAGAAAAGCAAGGAGGATGCAGCAGCTGA

AGCAACTGCAGCCGTAGCTACCGCCTCTACCGAGGTCAGGGGCGATAATTTTGCAAGCGCCGCAGCAGTGGCAG

CGGCCGAGGCGGCTGAAACCGAAAGTAAGATAGTCATTCAGCCGGTGGAGAAGGATAGCAAGAACAGGAGCTAC

AACGTACTACCGGACAAGATAAACACCGCCTACCGCAGCTGGTACCTAGCCTACAACTATGGCGACCCCGAGAA

GGGCGTGCGCTCCTGGACGCTGCTCACCACCTCGGACGTCACCTGCGGCGTGGAGCAAGTCTACTGGTCGCTGC

CCGACATGATGCAAGACCCGGTCACCTTCCGCTCCACGCGTCAAGTTAGCAACTACCCGGTGGTGGGCGCCGAG

CTCCTGCCCGTCTACTCCAAGAGCTTCTTCAACGAGCAGGCCGTCTACTCGCAGCAGCTGCGCGCCTTCACCTC

GCTTACGCACGTCTTCAACCGCTTCCCCGAGAACCAGATCCTCGTCCGCCCGCCCGCGCCCACCATTACCACCG

TCAGTGAAAACGTTCCTGCTCTCACAGATCACGGACCCTGCCGCTGCGCAGCAGTATCCGGGGAGTCCAGCGC

GTGACCGTTACTGACGCCAGACGCCGCACCTGCCCCTACGTCTACAAGGCCCTGGGCATAGTCGCGCCGCGCGT

CCTCTCGAGCCGCACCTTCTAAATGTCCATTCTCATCTCGCCCAGTAATAACACCGGTTGGGGCCTGCGCGCGC

CCAGCAAGATGTACGGAGGCGCTCGCCAACGCTCCACGCAACACCCCGTGCGCGTGCGCGGGCACTTCCGCGCT

CCCTGGGGCGCCCTCAAGGGCCGCGTGCGGTCGCGCACCACCGTCGACGACGTGATCGACCAGGTGGTGGCCGA

CGCGCGCAACTACACCCCCGCCGCCGCGCCCGTCTCCACCGTGGACGCCGTCATCGACAGCGTGGTGGCcGACG

CGCGCCGGTACGCCCGCGCCAAGAGCCGGCGGCGGCGCATCGCCCGGCGGCACCGGAGCACCCCCGCCATGCGC

GCGGCGCGAGCCTTGCTGCGCAGGGCCAGGCGCACGGGACGCAGGGCCATGCTCAGGGCGGCCAGACGCGCGGC

TTCAGGCGCCAGCGCCGGCAGGACCCGGAGACGCGCGGCCACGGCGGCGGCAGCGGCCATCGCCAGCATGTCCC

GCCCGCGGCGAGGGAACGTGTACTGGGTGCGCGACGCCGCCACCGGTGTGCGCGTGCCCGTGCGCACCCGCCCC

CCTCGCACTTGAAGATGTTCACTTCGCGATGTTGATGTGTCCCAGCGGCGAGGAGGATGTCCAAGCGCAAATTC

AAGGAAGAGATGCTCCAGGTCATCGCGCCTGAGATCTACGGCCCTGCGGTGGTGAAGGAGGAAAGAAAGCCCCG

CAAAATCAAGCGGGTCAAAAAGGACAAAAAGGAAGAAGAAAGTGATGTGGACGGATTGGTGGAGTTTGTGCGCG

AGTTCGCCCCCCGGCGGCGCGTGCAGTGGCGCGGGCGGAAGGTGCAACCGGTGCTGAGACCCGGCACCACCGTG

GTCTTCACGCCCGGCGAGCGCTCCGGCACCGCTTCCAAGCGCTCCTACGACGAGGTGTACGGGGATGATGATAT

TCTGGAGCAGGCGGCCGAGCGCCTGGGCGAGTTTGCTTACGGCAAGCGCAGCCGTTCCGCACCGAAGGAAGAGG

CGGTGTCCATCCCGCTGGACCACGGCAACCCCACGCCGAGCCTCAAGCCCGTGACCTTGCAGCAGGTGCTGCCG

ACCGCGGCGCCGCGCCGGGGGTTCAAGCGCGAGGGCGAGGATCTGTACCCCACCATGCAGCTGATGGTGCCCAA

GCGCCAGAAGCTGGAAGACGTGCTGGAGACCATGAAGGTGGACCCGGACGTGCAGCCCGAGGTCAAGGTGCGGC
```

-continued

CCATCAAGCAGGTGGCCCCGGGCCTGGGCGTGCAGACCGTGGACATCAAGATTCCCACGGAGCCCATGGAAACG

CAGACCGAGCCCATGATCAAGCCCAGCACCAGCACCATGGAGGTGCAGACGGATCCCTGGATGCCATCGGCTCC

TAGTCGAAGACCCCGGCGCAAGTACGGCGCGGCCAGCCTGCTGATGCCCAACTACGCGCTGCATCCTTCCATCA

TCCCCACGCCGGGCTACCGCGGCACGCGCTTCTACCGCGGTCATACCAGCAGCCGCCGCCGCAAGACCACCACT

CGCCGCCGCCGTCGCCGCACCGCCGCTGCAACCACCCCTGCCGCCCTGGTGCGGAGAGTGTACCGCCGCGGCCG

CGCACCTCTGACCCTGCCGCGCGCGCTACCACCCGAGCATCGCCCATTTAAACTTTCGCCtGCTTTGCAGATC

AATGGCCCTCACATGCCGCCTTCGCGTTCCCATTACGGGCTACCGAGGAAGAAAACCGCGCCGTAGAAGGCTGG

CGGGGAACGGGATGCGTCGCCACCACCACCGGCGGCGGCGCGCCATCAGCAAGCGGTTGGGGGGAGGCTTCCTG

CCCGCGCTGATCCCCATCATCGCCGCGGCGATCGGGGCGATCCCCGGCATTGCTTCCGTGGCGGTGCAGGCCTC

TCAGCGCCACTGAGACACACTTGGAAACATCTTGTAATAAACCaATGGACTCTGACGCTCCTGGTCCTGTGATG

TGTTTTCGTAGACAGATGGAAGACATCAATTTTTCGTCCCTGGCTCCGCGACACGGCACGCGGCCGTTCATGGG

CACCTGGAGCGACATCGGCACCAGCCAACTGAACGGGGGCGCCTTCAATTGGAGCAGTCTCTGGAGCGGGCTTA

AGAATTTCGGGTCCACGCTTAAAACCTATGGCAGCAAGGCGTGGAACAGCACCACAGGGCAGGCGCTGAGGGAT

AAGCTGAAAGAGCAGAACTTCCAGCAGAAGGTGGTCGATGGGCTCGCCTCGGGCATCAACGGGGTGGTGGACCT

GGCCAACCAGGCCGTGCAGCGGCAGATCAACAGCCGCCTGGACCCGGTGCCGCCCGCCGGCTCCGTGGAGATGC

CGCAGGTGGAGGAGGAGCTGCCTCCCCTGGACAAGCGGGGCGAGAAGCGACCCCGCCCCGATGCGGAGGAGACG

CTGCTGACGCACACGGACGAGCCGCCCCCGTACGAGGAGGCGGTGAAACTGGGTCTGCCCACCACGCGGCCCAT

CGCGCCCCTGGCCACCGGGGTGCTGAAACCCGAAAAGCCCGCGACCCTGGACTTGCCTCCTCCCCAGCCTTCCC

GCCCCTCTACAGTGGCTAAGCCCTGCCGCCGGTGGCCGTGGCCCGCGCGCGACCCGGGGGCACCGCCCGCCCT

CATGCGAACTGGCAGAGCACTCTGAACAGCATCGTGGGTCTGGGAGTGCAGAGTGTGAAGCGCCGCCGCTGCTA

TTAAACCTACCGTAGCGCTTAACTTGCTTGTCTGTGTGTATGTATTATGTCGCCGCCGCCGCTGTCCACCAG

AAGGAGGAGTGAAGAGGCGCGTCGCCGAGTTGCAAGATGGCCACCCCATCGATGCTGCCCCAGTGGGCGTACAT

GCACATCGCCGACAGGACGCTTCGGAGTACCTGAGTCCGGGTCTGGTGCAGTTTGCCCGCGCCACAGACACCT

ACTTCAGTCTGGGGAACAAGTTTAGGAACCCCACGGTGGCGCCCACGCACGATGTGACCACCGACCGCAGCCAG

CGGCTGACGCTGCGCTTCGTGCCCGTGGACCGCGAGGACAACACCTACTCGTACAAAGTGCGCTACACGCTGGC

CGTGGGCGACAACCGCGTGCTGGACATGGCCAGCACCTACTTTGACATCCGCGGCGTGCTGGATCGGGGCCCTA

GCTTCAAACCCTACTCCGGCACCGCCTACAACAGTCTGGCCCCCAAGGGAGCACCCAACACTTGTCAGTGGACA

TATAAAGCCGATGGTGAAACTGCCACAGAAAAAACCTATACATATGGAAATGCACCCGTGCAGGGCATTAACAT

CACAAAAGATGGTATTCAACTTGGAACTGACACCGATGATCAGCCAATCTACGCAGATAAAACCTATCAGCCTG

AACCTCAAGTGGGTGATGCTGAATGGCATGACATCACTGGTACTGATGAAAAGTATGGAGGCAGAGCTCTTAAG

CCTGATACCAAAATGAAGCCTTGTTATGGTTCTTTTGCCAAGCCTACTAATAAAGAAGGAGGTCAGGCAAATGT

GAAAACAGGAACAGGCACTACTAAAGAATATGACATAGACATGGCTTTCTTTGACAACAGAAGTGCGGCTGCTG

CTGGCCTAGCTCCAGAAATTGTTTTGTATACTGAAAATGTGGATTTGGAAACTCCAGATACCCATATTGTATAC

AAAGCAGGCACAGATGACAGCAGCTCTTCTATTAATTTGGGTCAGCAAGCCATGCCCAACAGACCTAACTACAT

TGGTTTCAGAGACAACTTTATCGGGCTCATGTACTACAACAGCACTGGCAATATGGGGGTGCTGGCCGGTCAGG

CTTCTCAGCTGAATGCTGTGGTTGACTTGCAAGACAGAAACACCGAGCTGTCCTACCAGCTCTTGCTTGACTCT

CTGGGTGACAGAACCCGGTATTTCAGTATGTGGAATCAGGCGGTGGACAGCTATGATCCTGATGTGCGCATTAT

TGAAAATCATGGTGTGGAGGATGAACTTCCCAACTATTGTTTCCCTCTGGATGCTGTTGGCAGAACAGATACTT

ATCAGGGAATTAAGGCTAATGGAACTGATCAAACCACATGGACCAAAGATGACAGTGTCAATGATGCTAATGAG

ATAGGCAAGGGTAATCCATTCGCCATGGAAATCAACATCCAAGCCAACCTGTGGAGGAACTTCCTCTACGCCAA

CGTGGCCCTGTACCTGCCCGACTCTTACAAGTACACGCCGGCCAATGTTACCCTGCCCACCAACACCAACACCT

-continued

```
ACGATTACATGAACGGCCGGGTGGTGGCGCCCTCGCTGGTGGACTCCTACATCAACATCGGGGCGCGCTGGTCG
CTGGATCCCATGGACAACGTGAACCCCTTCAACCACCACCGCAATGCGGGGCTGCGCTACCGCTCCATGCTCCT
GGGCAACGGGCGCTACGTGCCCTTCCACATCCAGGTGCCCCAGAAATTTTTCGCCATCAAGAGCCTCCTGCTCC
TGCCCGGGTCCTACACCTACGAGTGGAACTTCCGCAAGGACGTCAACATGATCCTGCAGAGCTCCCTCGGCAAC
GACCTGCGCACGGACGGGGCCTCCATCTCCTTCACCAGCATCAACCTCTACGCCACCTTCTTCCCCATGGCGCA
CAACACGGCCTCCACGCTCGAGGCCATGCTGCGCAACGACACCAACGACCAGTCCTTCAACGACTACCTCTCGG
CGGCCAACATGCTCTACCCCATCCCGGCCAACGCCACCAACGTGCCCATCTCCATCCCTCGCGCAACTGGGCC
GCCTTCCGCGGCTGGTCCTTCACGCGTCTCAAGACCAAGGAGACGCCCTCGCTGGGCTCCGGGTTCGACCCCTA
CTTCGTCTACTCGGGCTCCATCCCCTACCTCGACGGCACCTTCTACCTCAACCACACCTTCAAGAAGGTCTCCA
TCACCTTCGACTCCTCCGTCAGCTGGCCCGGCAACGACCGGCTCCTGACGCCCAACGAGTTCGAAATCAAGCGC
ACCGTCGACGGCGAGGGCTACAACGTGGCCCAGTGCAACATGACCAAGGACTGGTTCCTGGTCCAGATGCTGGC
CCACTACAACATCGGCTACCAGGGCTTCTACGTGCCCGAGGGCTACAAGGACCGCATGTACTCCTTCTTCCGCA
ACTTCCAGCCCATGAGCCGCCAGGTGGTGGACGAGGTCAACTACAAGGACTACCAGGCCGTCACCCTGGCCTAC
CAGCACAACAACTCGGGCTTCGTCGGCTACCTCGCGCCCACCATGCGCCAGGGCCAGCCCTACCCCGCCAACTA
CCCCTACCCGCTCATCGGCAAGAGCGCCGTCACCAGCGTCACCCAGAAAAAGTTCCTCTGCGACAGGGTCATGT
GGCGCATCCCCTTCTCCAGCAACTTCATGTCCATGGGCGCGCTCACCGACCTCGGCCAGAACATGCTCTATGCC
AACTCCGCCCACGCGCTAGACATGAATTTCGAAGTCGACCCCATGGATGAGTCCACCCTTCTCTATGTTGTCTT
CGAAGTCTTCGACGTCGTCCGAGTGCACCAGCCCCACCGCGCGTCATCGAGGCCGTCTACCTGCGCACCCCCT
TCTCGGCCGGTAACGCCACCACCTAAGCTCTTGCTTCTTGCAAGCCATGGCCGCGGGCTCCGGCGAGCAGGAGC
TCAGGGCCATCATCCGCGACCTGGGCTGCGGGCCCTACTTCCTGGGCACCTTCGATAAGCGCTTCCCGGGATTC
ATGGCCCCGCACAAGCTGGCCTGCGCCATCGTCAACACGGCCGGCCGCGAGACCGGGGGCGAGCACTGGCTGGC
CTTCGCCTGGAACCCGCGCTCGAACACCTGCTACCTCTTCGACCCCTTCGGGTTCTCGGACGAGCGCCTCAAGC
AGATCTACCAGTTCGAGTACGAGGGCCTGCTGCGCCGCAGCGCCCTGGCCACCGAGGACCGCTGCGTCACCCTG
GAAAAGTCCACCCAGACCGTGCAGGGTCCGCGCTCGGCCGCCTGCGGGCTCTTCTGCTGCATGTTCCTGCACGC
CTTCGTGCACTGGCCCGACCGCCCCATGGACAAGAACCCCACCATGAACTTGCTGACGGGGGTGCCCAACGGCA
TGCTCCAGTCGCCCCAGGTGGAACCCACCCTGCGCCGCAACCAGGAGGCGCTCTACCGCTTCCTCAACTCCCAC
TCCGCCTACTTTCGCTCCCACCGCGCGCGCATCGAGAAGGCCACCGCCTTCGACCGCATGAATCAAGACATGTA
AACCGTGTGTGTATGTTAAATGTCTTTAATAAACAGCACTTTCATGTTACACATGCATCTGAGATGATTTATTT
AGAAATCGAAAGGGTTCTGCCGGGTCTCGGCATGGCCCGCGGGCAGGGACACGTTGCGGAACTGGTACTTGGCC
AGCCACTTGAACTCGGGGATCAGCAGTTTGGGCAGCGGGGTGTCGGGGAAGGAGTCGGTCCACAGCTTCCGCGT
CAGTTGCAGGGCGCCCAGCAGGTCGGGCGCGGAGATCTTGAAATCGCAGTTGGGACCCGCGTTCTGCGCGCGGG
AGTTGCGGTACACGGGGTTGCAGCACTGGAACACCATCAGGGCCGGGTGCTTCACGCTCGCCAGCACCGTCGCG
TCGGTGATGCTCTCCACGTCGAGGTCCTCGGCGTTGGCCATCCCGAAGGGGGTCATCTTGCAGGTCTGCCTTCC
CATGGTGGGCACGCACCCGGGCTTGTGGTTGCAATCGCAGTGCAGGGGGATCAGCATCATCTGGGCCTGGTCGG
CGTTCATCCCCGGGTACATGGCCTTCATGAAAGCCTCCAATTGCCTGAACGCCTGCTGGGCCTTGGCTCCCTCG
GTGAAGAAGACCCCGCAGGACTTGCTAGAGAACTGGTTGGTGGCGCACCCGGCGTCGTGCACGCAGCAGCGCGC
GTCGTTGTTGGCCAGCTGCACCACGCTGCGCCCCAGCGGTTCTGGGTGATCTTGGCCCGGTCGGGGTTCTCCT
TCAGCGCGCGCTGCCCGTTCTCGCTCGCCACATCCATCTCGATCATGTGCTCCTTCTGGATCATGGTGGTCCCG
TGCAGGCACCGCAGCTTGCCCTCGGCCTCGGTGCACCCGTGCAGCCACAGCGCGCACCCGGTGCACTCCCAGTT
CTTGTGGGCGATCTGGGAATGCGCGTGCACGAAGCCCTGCAGGAAGCGGCCCATCATGGTGGTCAGGGTCTTGT
```

-continued

```
TGCTAGTGAAGGTCAGCGGAATGCCGCGGTGCTCCTCGTTGATGTACAGGTGGCAGATGCGGCGGTACACCTCG
CCCTGCTCGGGCATCAGCTGGAAGTTGGCTTTCAGGTCGGTCTCCACGCGGTAGCGGTCCATCAGCATAGTCAT
GATTTCCATACCCTTCTCCCAGGCCGAGACGATGGGCAGGCTCATAGGGTTCTTCACCATCATCTTAGCGCTAG
CAGCCGCGGCCAGGGGGTCGCTCTCGTCCAGGGTCTCAAAGCTCCGCTTGCCGTCCTTCTCGGTGATCCGCACC
GGGGGGTAGCTGAAGCCCACGGCCGCCAGCTCCTCCTCGGCCTGTCTTTCGTCCTCGCTGTCCTGGCTGACGTC
CTGCAGGACCACATGCTTGGTCTTGCGGGGTTTCTTCTTGGGCGGCAGCGGCGGCGGAGATGTTGGAGATGGCG
AGGGGGAGCGCGAGTTCTCGCTCACCACTACTATCTCTTCCTCTTCTTGGTCCGAGGCCACGCGGCGGTAGGTA
TGTCTCTTCGGGGGCAGAGGCGGAGGCGACGGGCTCTCGCCGCCGCGACTTGGCGGATGGCTGGCAGAGCCCCT
TCCGCGTTCGGGGGTGCGCTCCCGGCGGCGCTCTGACTGACTTCCTCCGCGGCCGGCCATTGTGTTCTCCTAGG
GAGGAACAACAAGCATGGAGACTCAGCCATCGCCAACCTCGCCATCTGCCCCCACCGCCGACGAGAAGCAGCAG
CAGCAGAATGAAAGCTTAACCGCCCCGCCGCCCAGCCCCGCCACCTCCGACGCGCCGTCCCAGACATGCAAGA
GATGGAGGAATCCATCGAGATTGACCTGGGCTATGTGACGCCCGCGGAGCACGAGGAGGAGCTGGCAGTGCGCT
TTTCACAAGAAGAGATACACCAAGAACAGCCAGAGCAGGAAGCAGAGAATGAGCAGAGTCAGGCTGGGCTCGAG
CATGACGGCGACTACCTCCACCTGAGCGGGGGGGAGGACGCGCTCATCAAGCATCTGGCCCGGCAGGCCACCAT
CGTCAAGGATGCGCTGCTCGACCGCACCGAGGTGCCCCTCAGCGTGGAGGAGCTCAGCCGCGCCTACGAGTTGA
ACCTCTTCTCGCCGCGCGTGCCCCCCAAGCGCCAGCCCAATGGCACCTGCGAGCCCAACCCGCGCCTCAACTTC
TACCCGGTCTTCGCGGTGCCCGAGGCCCTGGCCACCTACCACATCTTTTTCAAGAACCAAAAGATCCCCGTCTC
CTGCCGCGCCAACCGCACCCGCGCCGACGCCCTTTTCAACCTGGGTCCCGGCGCCCGCCTACCTGATATCGCCT
CCTTGGAAGAGGTTCCCAAGATCTTCGAGGGTCTGGGCAGCGACGAGACTCGGGCCGCGAACGCTCTGCAAGGA
GAAGGAGGAGAGCATGAGCACCACAGCGCCCTGGTCGAGTTGGAAGGCGACAACGCGCGGCTGGCGGTGCTCAA
ACGCACGGTCGAGCTGACCCATTTCGCCTACCCGGCTCTGAACCTGCCCCCCAAAGTCATGAGCGCGGTCATGG
ACCAGGTGCTCATCAAGCGCGCGTCGCCCATCTCCGAGGACGAGGGCATGCAAGACTCCGAGGAGGGCAAGCCC
GTGGTCAGCGACGAGCAGCTGGCCCGGTGGCTGGGTCCTAATGCTAGTCCCCAGAGTTTGGAAGAGCGGCGCAA
ACTCATGATGGCCGTGGTCCTGGTGACCGTGGAGCTGGAGTGCCTGCGCCGCTTCTTCGCCGACGCGGAGACCC
TGCGCAAGGTCGAGGAGAACCTGCACTACCTCTTCAGGCACGGGTTCGTGCGCCAGGCCTGCAAGATCTCCAAC
GTGGAGCTGACCAACCTGGTCTCCTACATGGGCATCTTGCACGAGAACCGCCTGGGGCAGAACGTGCTGCACAC
CACCCTGCGCGGGGAGGCCCGGCGCGACTACATCCGCGACTGCGTCTACCTCTACCTCTGCCACACCTGGCAGA
CGGGCATGGGCGTGTGGCAGCAGTGTCTGGAGGAGCAGAACCTGAAAGAGCTCTGCAAGCTCCTGCAGAAGAAC
CTCAAGGGTCTGTGGACCGGGTTCGACGAGCGCACCACCGCCTCGGACCTGGCCGACCTCATTTTCCCCGAGCG
CCTCAGGCTGACGCTGCGCAACGGCCTGCCCGACTTTATGAGCCAAAGCATGTTGCAAAACTTTCGCTCTTTCA
TCCTCGAACGCTCCGGAATCCTGCCCGCCACCTGCTCCGCGCTGCCCTCGGACTTCGTGCCGCTGACCTTCCGC
GAGTGCCCCCCGCCGCTGTGGAGCCACTGCTACCTGCTGCGCCTGGCCAACTACCTGGCCTACCACTCGGACGT
GATCGAGGACGTCAGCGGCGAGGGCCTGCTCGAGTGCCACTGCCGCTGCAACCTCTGCACGCCGCACCGCTCCC
TGGCCTGCAACCCCCAGCTGCTGAGCGAGACCCAGATCATCGGCACCTTCGAGTTGCAAGGGCCCAGCGAAGGC
GAGGGTTCAGCCGCCAAGGGGGGTCTGAAACTCACCCCGGGGCTGTGGACCTCGGCCTACTTGCGCAAGTTCGT
GCCCGAGGACTACCATCCCTTCGAGATCAGGTTCTACGAGGACCAATCCCATCCGCCCAAGGCCGAGCTGTCGG
CCTGCGTCATCACCCAGGGGGCGATCCTGGCCCAATTGCAAGCCATCCAGAAATCCCGCCAAGAATTCTTGCTG
AAAAAGGGCCGCGGGGTCTACCTCGACCCCCAGACCGGTGAGGAGCTCAACCCCGGCTTCCCCCAGGATGCCCC
GAGGAAACAAGAAGCTGAAAGTGGAGCTGCCGCCCGTGGAGGATTTGGAGGAAGACTGGGAGAACAGCAGTCAG
GCAGAGGAGGAGGAGATGGAGGAAGACTGGGACAGCACTCAGGCAGAGGAGGACAGCCTGCAAGACAGTCTGGA
GGAAGACGAGGAGGAGGCAGAGGAGGAGGTGGAAGAAGCAGCCGCCGCCAGACCGTCGTCCTCGGCGGGGGAGA
```

-continued

```
AAGCAAGCAGCACGGATACCATCTCCGCTCCGGGTCGGGGTCCCGCTCGACCACACAGTAGATGGGACGAGACC
GGACGATTCCCGAACCCCACCACCCAGACCGGTAAGAAGGAGCGGCAGGGATACAAGTCCTGGCGGGGGCACAA
AAACGCCATCGTCTCCTGCTTGCAGGCCTGCGGGGGCAACATCTCCTTCACCCGGCGCTACCTGCTCTTCCACC
GCGGGGTGAACTTTCCCCGCAACATCTTGCATTACTACCGTCACCTCCACAGCCCCTACTACTTCCAAGAAGAG
GCAGCAGCAGCAGAAAAAGACCAGCAGAAAACCAGCAGCTAGAAAATCCACAGCGGCGGCAGCAGGTGGACTGA
GGATCGCGGCGAACGAGCCGGCGCAAACCCGGGAGCTGAGGAACCGGATCTTTCCCACCCTCTATGCCATCTTC
CAGCAGAGTCGGGGGCAGGAGCAGGAACTGAAAGTCAAGAACCGTTCTCTGCGCTCGCTCACCCGCAGTTGTCT
GTATCACAAGAGCGAAGACCAACTTCAGCGCACTCTCGAGGACGCCGAGGCTCTCTTCAACAAGTACTGCGCGC
TCACTCTTAAAGAGTAGCCCGCGCCCGCCCAGTCGCAGAAAAAGGCGGGAATTACGTCACCTGTGCCCTTCGCC
CTAGCCGCCTCCACCCATCATCATGAGCAAAGAGATTCCCACGCCTTACATGTGGAGCTACCAGCCCCAGATGG
GCCTGGCCGCCGGTGCCGCCCAGGACTACTCCACCCGCATGAATTGGCTCAGCGCCGGGCCCGCGATGATCTCA
CGGGTGAATGACATCCGCGCCCACCGAAACCAGATACTCCTAGAACAGTCAGCGCTCACCGCCACGCCCCGCAA
TCACCTCAATCCGCGTAATTGGCCCGCCGCCCTGGTGTACCAGGAAATTCCCCAGCCCACGACCGTACTACTTC
CGCGAGACGCCCAGGCCGAAGTCCAGCTGACTAACTCAGGTGTCCAGCTGGCGGCGGCGCCACCCTGTGTCGT
CACCGCCCCGCTCAGGGTATAAAGCGGCTGGTGATCCGGGGCAGAGGCACACAGCTCAACGACGAGGTGGTGAG
CTCTTCGCTGGGTCTGCGACCTGACGGAGTCTTCCAACTCGCCGGATCGGGGAGATCTTCCTTCACGCCTCGTC
AGGCCGTCCTGACTTTGGAGAGTTCGTCCTCGCAGCCCCGCTCGGGTGGCATCGGCACTCTCCAGTTCGTGGAG
GAGTTCACTCCCTCGGTCTACTTCAACCCCTTCTCCGGCTCCCCCGGCCACTACCCGGACGAGTTCATCCCGAA
CTTCGACGCCATCAGCGAGTCGGTGGACGGCTACGATTGAATGTCCCATGGTGGCGCAGCTGACCTAGCTCGGC
TTCGACACCTGGACCACTGCCGCCGCTTCCGCTGCTTCGCTCGGGATCTCGCCGAGTTTGCCTACTTTGAGCTG
CCCGAGGAGCACCCTCAGGGCCCGGCCCACGGAGTGCGGATCGTCGTCGAAGGGGCCTCGACTCCCACCTGCT
TCGGATCTTCAGCCAGCGTCCGATCCTGGTCGAGCGCGAGCAAGGACAGACCCTTCTGACTCTGTACTGCATCT
GCAACCACCCCGGCCTGCATGAAAGTCTTTGTTGTCTGCTGTGTACTGAGTATAATAAAAGCTGAGATCAGCGA
CTACTCCGGACTTCCGTGTGTTCCTGAATCCATCAACCAGTCTTTGTTCTTCACCGGGAACGAGACCGAGCTCC
AGCTCCAGTGTAAGCCCCACAAGAAGTACCTCACCTGGCTGTTCCAGGGCTCCCCGATCGCCGTTGTCAACCAC
TGCGACAACGACGGAGTCCTGCTGAGCGGCCCTGCCAACCTTACTTTTTCCACCCGCAGAAGCAAGCTCCAGCT
CTTCCAACCCTTCCTCCCCGGGACCTATCAGTGCGTCTCGGGACCCTGCCATCACACCTTCCACCTGATCCCGA
ATACCACAGCGTCGCTCCCCGCTACTAACAACCAAACTAACCTCCACCAACGCCACCGTCGCGACCTTTCTGAA
TCTAATACTACCACCCACACCGGAGGTGAGCTCCGAGGTCAACCAACCTCTGGGATTTACTACGGCCCCTGGGA
GGTGGTTGGGTTAATAGCGCTAGGCCTAGTTGCGGGTGGGCTTTTGGTTCTCTGCTACCTATACCTCCCTTGCT
GTTCGTACTTAGTGGTGCTGTGTTGCTGGTTTAAGAAATGGGGAAGATCACCCTAGTGAGCTGCGGTGCGCTGG
TGGCGGTGTTGCTTTCGATTGTGGGACTGGGCGGTGCGGCTGTAGTGAAGGAGAAGGCCGATCCCTGCTTGCAT
TTCAATCCCAACAAATGCCAGCTGAGTTTTCAGCCCGATGGCAATCGGTGCGCGGTACTGATCAAGTGCGGATG
GGAATGCGAGAACGTGAGAATCGAGTACAATAACAAGACTCGGAACAATACTCTCGCGTCCGTGTGGCAGCCCG
GGGACCCCGAGTGGTACACCGTCTCTGTCCCCGGTGCTGACGGCTCCCCGCACCGTGAATAATACTTTCATT
TTTGCGCACATGTGCGACACGGTCATGTGGATGAGCAAGCAGTACGATATGTGGCCCCCCACGAAGGAGAACAT
CGTGGTCTTCTCCATCGCTTACAGCCTGTGCACGGCGCTAATCACCGCTATCGTGTGCCTGAGCATTCACATGC
TCATCGCTATTCGCCCCAGAAATAATGCCGAAAAAGAAAAACAGCCATAACGTTTTTTTTCACACCTTTTTCAG
ACCATGGCCTCTGTTAAATTTTTGCTTTTATTTGCCAGTCTCATTGCCGTCATTCATGGAATGAGTAATGAGAA
AATTACTATTTACACTGGCACTAATCACACATTGAAAGGTCCAGAAAAAGCCACAGAAGTTTCATGGTATTGTT
```

-continued

```
ATTTTAATGAATCAGATGTATCTACTGAACTCTGTGGAAACAATAACAAAAAAAATGAGAGCATTACTCTCATC
AAGTTTCAATGTGGATCTGACTTAACCCTAATTAACATCACTAGAGACTATGTAGGTATGTATTATGGAACTAC
AGCAGGCATTTCGGACATGGAATTTTATCAAGTTTCTGTGTCTGAACCCACCACGCCTAGAATGACCACAACCA
CAAAAACTACACCTGTTACCACTATGCAGCTCACTACCAATAACATTTTTGCCATGCGTCAAATGGTCAACAAT
AGCACTCAACCCACCCCACCCAGTGAGGAAATTCCCAAATCCATGATTGGCATTATTGTTGCTGTAGTGGTGTG
CATGTTGATCATCGCCTTGTGCATGGTGTACTATGCCTTCTGCTACAGAAAGCACAGACTGAACGACAAGCTGG
AACACTTACTAAGTGTTGAATTTTAATTTTTTAGAACCATGAAGATCCTAGGCCTTTTAATTTTTTCTATCATT
ACCTCTGCTCTATGCAATTCTGACAATGAGGACGTTACTGTCGTTGTCGGATCAAATTATACACTGAAAGGTCC
AGCGAAGGGTATGCTTTCGTGGTATTGCTATTTTGGATCTGACACTACAGAAACTGAATTATGCAATCTTAAGA
ATGGCAAAATTCAAAATTCTAAAATTAACAATTATATATGCAATGGTACTGATCTGATACTCCTCAATATCACG
AAATCATATGCTGGCAGTTACACCTGCCCTGGAGATGATGCTGACAGTATGATTTTTTACAAAGTAACTGTTGT
TGATCCCACTACTCCACCTCCACCCACCACAACTACTCACACCACACACACAGATCAAACCGCAGCAGAGGAGG
CAGCAAAGTTAGCCTTGCAGGTCCAAGACAGTTCATTTGTTGGCATTACCCCTACACCTGATCAGCGGTGTCCG
GGGCTGCTAGTCAGCGGCATTGTCGGTGTGCTTTCGGGATTAGCAGTCATAATCATCTGCATGTTCATTTTTGC
TTGCTGCTATAGAAGGCTTTACCGACAAAAATCAGACCCACTGCTGAACCTCTATGTTTAATTTTTTCCAGAGT
CATGAAGGCAGTTAGCGCTCTAGTTTTTTGTTCTTTGATTGGCATTGTTTTTTGCAATCCTATTCCTAAAGTTA
GCTTTATTAAAGATGTGAATGTTACTGAGGGGGGCAATGTGACACTGGTAGGTGTAGAGGGTGCTGAAAACACC
ACCTGGACAAAATACCACCTCAATGGGTGGAAAGATATTTGCAATTGGAGTGTATTAGTTTATACATGTGAGGG
AGTTAATCTTACCATTGTCAATGCCACCTCAGCTCAAAATGGTAGAATTCAAGGACAAAGTGTCAGTGTATCTA
ATGGGTATTTTACCCAACATACTTTTATCTATGACGTTAAAGTCATACCACTGCCTACGCCTAGCCCACCTAGC
ACTACCACACAGACAACCCACACTACACAGACAACCACATACAGTACATTAAATCAGCCTACCACCACTACAGC
AGCAGAGGTTGCCAGCTCGTCTGGGGTCCGAGTGGCATTTTTGATGTtGGCCCCATCTAGCAGTCCCACTGCTA
GTACCAATGAGCAGACTACTGAATTTTTGTCCACTGTCGAGAGCCACACCACAGCTACCTCCAGTGCCTTCTCT
AGCACCGCCAATCTCTCCTCGCTTTCCTCTACACCAATCAGTCCCGCTACTACTCCTAGCCCCGCTCCTCTTCC
CACTCCCCTGAAGCAAACAGACGGCGGCATGCAATGGCAGATCACCCTGCTCATTGTGATCGGGTTGGTCATCC
TGGCCGTGTTGCTCTACTACATCTTCTGCCGCCGCATTCCCAACGCGCACCGCAAGCCGGTCTACAAGCCCATC
ATTGTCGGGCAGCCGGAGCCGCTTCAGGTGGAAGGGGGTCTAAGGAATCTTCTCTTCTCTTTTACAGTATGGTG
ATTGAACTATGATTCCTAGACAATTCTTGATCACTATTCTTATCTGCCTCCTCCAAGTCTGTGCCACCCTCGCT
CTGGTGGCCAACGCCAGTCCAGACTGTATTGGGCCCTTCGCCTCCTACGTGCTCTTTGCCTTCACCACCTGCAT
CTGCTGCTGTAGCATAGTCTGCCTGCTTATCACCTTCTTCCAGTTCATTGACTGGATCTTTGTGCGCATCGCCT
ACCTGCGCCACCACCCCAGTACCGCGACCAGCGAGTGGCGCGGCTGCTCAGGCTCCTCTGATAAGCATGCGGG
CTCTGCTACTTCTCGCGCTTCTGCTGTTAGTGCTCCCCCGTCCCGTCGACCCCCGGTCCCCACCCAGTCCCCC
GAGGAGGTCCGCAAATGCAAATTCCAAGAACCCTGGAAATTCCTCAAATGCTACCGCCAAAAATCAGACATGCA
TCCCAGCTGGATCATGATCATTGGGATCGTGAACATTCTGGCCTGCACCCTCATCTCCTTTGTGATTTACCCCT
GCTTTGACTTTGGTTGGAACTCGCCAGAGGCGCTCTATCTCCCGCCTGAACCTGACACACCACCACAGCAACCT
CAGGCACACGCACTACCACCACTACAGCCTAGGCCACAATACATGCCCATATTAGACTATGAGGCCGAGCCACA
GCGACCCATGCTCCCCGCTATTAGTTACTTCAATCTAACCGGCGGAGATGACTGACCCACTGGCCAACAACAAC
GTCAACGACCTTCTCCTGGACATGGACGGCCGCGCCTCGGAGCAGCGACTCGCCCAACTTCGCATTCGCCAGCA
GCAGGAGAGAGCCGTCAAGGAGCTGCAGGATGCGGTGGCCATCCACCAGTGCAAGAGAGGCATCTTCTGCCTGG
TGAAACAGGCCAAGATCTCCTACGAGGTCACTCCAAACGACCATCGCCTCTCCTACGAGCTCCTGCAGCAGCGC
CAGAAGTTCACCTGCCTGGTCGGAGTCAACCCCATCGTCATCACCCAGCAGTCTGGCGATACCAAGGGGTGCAT
```

-continued

```
CCACTGCTCCTGCGACTCCCCCGACTGCGTCCACACTCTGATCAAGACCCTCTGCGGCCTCCGCGACCTCCTCC

CCATGAACTAATCACCCCCTTATCCAGTGAAATAAAGATCATATTGATGATGATTTTACAGAAATAAAAAATAA

TCATTTGATTTGAAATAAAGATACAATCATATTGATGATTTGAGTTTAACAAAAAAATAAAGAATCACTTACTT

GAAATCTGATACCAGGTCTCTGTCCATGTTTTCTGCCAACACCACTTCACTCCCCTCTTCCCAGCTCTGGTACT

GCAGGCCCCGGCGGGCTGCAAACTTCCTCCACACGCTGAAGGGGATGTCAAATTCCTCCTGTCCCTCAATCTTC

ATTTTATCTTCTATCAGATGTCCAAAAAGCGCGTCCGGGTGGATGATGACTTCGACCCCGTCTACCCCTACGAT

GCAGACAACGCACCGACCGTGCCCTTCATCAACCCCCCCTTCGTCTCTTCAGATGGATTCCAAGAGAAGCCCCT

GGGGGTGTTGTCCCTGCGACTGGCCGACCCCGTCACCACCAAGAACGGGGAAATCACCCTCAAGCTGGGAGAGG

GGGTGGACCTCGATTCCTCGGGAAAACTCATCTCCAACACGGCCACCAAGGCCGCCGCCCCTCTCAGTTTTTCC

AACAACACCATTTCCCTTAACATGGATCACCCCTTTTACACTAAAGATGGAAAATTATCCTTACAAGTTTCTCC

ACCATTAAATATACTGAGAACAAGCATTCTAAACACACTAGCTTTAGGTTTTGGATCAGGTTTAGGACTCCGTG

GCTCTGCCTTGGCAGTACAGTTAGTCTCTCCACTTACATTTGATACTGATGGAAACATAAAGCTTACCTTAGAC

AGAGGTTTGCATGTTACAACAGGAGATGCAATTGAAAGCAACATAAGCTGGGCTAAAGGTTTAAAATTTGAAGA

TGGAGCCATAGCAACCAACATTGGAAATGGGTTAGAGTTTGGAAGCAGTAGTACAGAAACAGGTGTTGATGATG

CTTACCCAATCCAAGTTAAACTTGGATCTGGCCTTAGCTTTGACAGTACAGGAGCCATAATGGCTGGTAACAAA

GAAGACGATAAACTCACTTTGTGGACAACACCTGATCCATCACCAAACTGTCAAATACTCGCAGAAAATGATGC

AAAACTAACACTTTGCTTGACTAAATGTGGTAGTCAAATACTGGCCACTGTGTCAGTCTTAGTTGTAGGAAGTG

GAAACCTAAACCCCATTACTGGCACCGTAAGCAGTGCTCAGGTGTTTCTACGTTTTGATGCAAACGGTGTTCTT

TTAACAGAACATTCTACACTAAAAAAATACTGGGGGTATAGGCAGGGAGATAGCATAGATGGCACTCCATATAC

CAATGCTGTAGGATTCATGCCCAATTTAAAAGCTTATCCAAAGTCACAAAGTTCTACTACTAAAAATAATATAG

TAGGGCAAGTATACATGAATGGAGATGTTTCAAAACCTATGCTTCTCACTATAACCCTCAATGGTACTGATGAC

AGCAACAGTACATATTCAATGTCATTTTCATACACCTGGACTAATGGAAGCTATGTTGGAGCAACATTTGGGGC

TAACTCTTATACCTTCTCATACATCGCCCAAGAATGAACACTGTATCCCACCCTGCATGCCAACCCTTCCCACC

CCACTCTGTGGAACAAACTCTGAAACACAAAATAAAATAAAGTTCAAGTGTTTTATTGATTCAACAGTTTTACA

GGATTCGAGCAGTTATTTTTCCTCCACCCTCCCAGGACATGGAATACACCACCCTCTCCCCCCGCACAGCCTTG

AACATCTGAATGCCATTGGTGATGGACATGCTTTTGGTCTCCACGTTCCACACAGTTTCAGAGCGAGCCAGTCT

CGGGTCGGTCAGGGAGATGAAACCCTCCGGGCACTCCCGCATCTGCACCTCACAGCTCAACAGCTGAGGATTGT

CCTCGGTGGTCGGGATCACGGTTATCTGGAAGAAGCAGAAGAGCGGCGGTGGGAATCATAGTCCGCGAACGGGA

TCGGCCGGTGGTGTCGCATCAGGCCCCGCAGCAGTCGCTGCCGCCGCCGCTCCGTCAAGCTGCTGCTCAGGGGG

TCCGGGTCCAGGGACTCCCTCAGCATGATGCCCACGGCCCTCAGCATCAGTCGTCTGGTGCGGCGGGCGCAGCA

GCGCATGCGGATCTCGCTCAGGTCGCTGCAGTACGTGCAACACAGAACCACCAGGTTGTTCAACAGTCCATAGT

TCAACACGCTCCAGCCGAAACTCATCGCGGGAAGGATGCTACCCACGTGGCCGTCGTACCAGATCCTCAGGTAA

ATCAAGTGGTGCCCCCTCCAGAACACGCTGCCCACGTACATGATCTCCTTGGGCATGTGGCGGTTCACCACCTC

CCGGTACCACATCACCCTCTGGTTGAACATGCAGCCCCGGATGATCCTGCGGAACCACAGGGCCAGCACCGCCC

CGCCCGCCATGCAGCGAAGAGACCCCGGGTCCCGGCAATGGCAATGGAGGACCCACCGCTCGTACCCGTGGATC

ATCTGGGAGCTGAACAAGTCTATGTTGGCACAGCACAGGCATATGCTCATGCATCTCTTCAGCACTCTCAACTC

CTCGGGGGTCAAAACCATATCCCAGGGCACGGGGAACTCTTGCAGGACAGCGAACCCCGCAGAACAGGGCAATC

CTCGCACAGAACTTACATTGTGCATGGACAGGGTATCGCAATCAGGCAGCACCGGGTGATCCTCCACCAGAGAA

GCGCGGGTCTCGGTCTCCTCACAGCGTGGTAAGGGGGCCGGCCGATACGGGTGATGGCGGGACGCGGCTGATCG

TGTTCGCGACCGTGTCATGATGCAGTTGCTTTCGGACATTTTCGTACTTGCTGTAGCAGAACCTGGTCCGGGCG
```

-continued

```
CTGCACACCGATCGCCGGCGGCGGTCTCGGCGCTTGGAACGCTCGGTGTTGAAATTGTAAAACAGCCACTCTCT

CAGACCGTGCAGCAGATCTAGGGCCTCAGGAGTGATGAAGATCCCATCATGCCTGATGGCTCTGATCACATCGA

CCACCGTGGAATGGGCCAGACCCAGCCAGATGATGCAATTTTGTTGGGTTTCGGTGACGGCGGGGGAGGGAAGA

ACAGGAAGAACCATGATTAACTTTTAATCCAAACGGTCTCGGAGTACTTCAAAATGAAGATCGCGGAGATGGCA

CCTCTCGCCCCCGCTGTGTTGGTGGAAAATAACAGCCAGGTCAAAGGTGATACGGTTCTCGAGATGTTCCACGG

TGGCTTCCAGCAAAGCCTCCACGCGCACATCCAGAAACAAGACAATAGCGAAAGCGGGAGGGTTCTCTAATTCC

TCAATCATCATGTTACACTCCTGCACCATCCCCAGATAATTTTCATTTTTCCAGCCTTGAATGATTCGAACTAG

TTCcTGAGGTAAATCCAAGCCAGCCATGATAAAGAGCTCGCGCAGAGCGCCCTCCACCGGCATTCTTAAGCACA

CCCTCATAATTCCAAGATATTCTGCTCCTGGTTCACCTGCAGCAGATTGACAAGCGGAATATCAAATCTCTGC

CGCGATCCCTGAGCTCCTCCCTCAGCAATAACTGTAAGTACTCTTTCATATCCTCTCCGAAATTTTTAGCCATA

GGACCACCAGGAATAAGATTAGGGCAAGCCACAGTACAGATAAACCGAAGTCCTCCCCAGTGAGCATTGCCAAA

TGCAAGACTGCTATAAGCATGCTGGCTAGACCCGGTGATATCTTCCAGATAACTGGACAGAAAATCGCCCAGGC

AATTTTTAAGAAAATCAACAAAAGAAAAATCCTCCAGGTGGACGTTTAGAGCCTCGGGAACAACGATGAAGTAA

ATGCAAGCGGTGCGTTCCAGCATGGTTAGTTAGCTGATCTGTAGAAAAAACAAAAATGAACATTAAACCATGCT

AGCCTGGCGAACAGGTGGGTAAATCGTTCTCTCCAGCACCAGGCAGGCCACGGGGTCTCCGGCGCGACCCTCGT

AAAAATTGTCGCTATGATTGAAAACCATCACAGAGAGACGTTCCCGGTGGCCGGCGTGAATGATTCGACAAGAT

GAATACACCCCCGGAACATTGGCGTCCGCGAGTGAAAAAAAGCGCCCGAGGAAGCAATAAGGCACTACAATGCT

CAGTCTCAAGTCCAGCAAAGCGATGCCATGCGGATGAAGCACAAAATTCTCAGGTGCGTACAAAATGTAATTAC

TCCCCTCCTGCACAGGCAGCAAAGCCCCCGATCCCTCCAGGTACACATACAAAGCCTCAGCGTCCATAGCTTAC

CGAGCAGCAGCACACAACAGGCGCAAGAGTCAGAGAAAGGCTGAGCTCTAACCTGTCCACCCGCTCTCTGCTCA

ATATATAGCCCAGATCTACACTGACGTAAAGGCCAAAGTCTAAAAATACCCGCCAAATAATCACACACGCCCAG

CACACGCCCAGAAACCGGTGACACACTCAAAAAAATACGCGCACTTCCTO\AACGCCCAAAACTGCCGTCATTT

CCGGGTTCCCACGCTACGTCATCAAAACGACTTTCAAATTCCGTCGACCGTTAAAAACGTCACCCGCCCCGC

CCCTAACGGTCGCCCGTCTCTCAGCCAATCAGCGCCCCGCATCCCCAAATTCAAACACCTCATTTGCATATTAA

CGCGCACAAAAAGTTTGAGGTATATTATTGATGATGG
```

ChAdV68.4WTnt.GFP; AC_000011.1 with E1 (nt 577 to 3403) and
E3 (nt 27,816-31,332) sequences deleted; corresponding ATCC VR-594
nucleotides substituted at four positions; GFP reporter under the control
of the CMV promoter/enhancer inserted in place of deleted E1

(SEQ ID NO: 11)

```
CCATCTTCAATAATATACCTCAAACTTTTTCTGCGCGTTAATATGCAAATGAGGCGTTTGAATTTGGGGAGGAA

GGGCGGTGATTGGTCGAGGGATGAGCGACCGTTAGGGGGGGGGCGACTGACGTTTTGATGACGTGGTTGCGAGG

AGGAGCCAGTTTGCAAGTTCTCGTGGGAAAAGTGACGTCAAACGAGGTGTGGTTTGAACACGGAAATACTCAAT

TTTCCCGCGCTCTCTGACAGGAAATGAGGTCTTTCTGGGCGGATGCAAGTGAAAACGGGCCATTTTCGCGCGAA

AACTGAATGAGGAAGTGAAAATCTGAGTAATTTCGCGTTTATGGCAGGGAGGAGTATTTGCCGAGGGCCGAGTA

GACTTTGACCGATTACGTGGGGGTTTCGATTACCGTGTTTTTCACCTAAATTTCCGCGTACGGTGTCAAAGTCC

GGTGTTTTTACGTAGGTGTCAGCTGATCGCCAGGGTATTTAAACCTGCGCTCTCCAGTCAAGAGGCCACTCTTG

AGTGCCAGCGAGAAGAGTTTTCTCCTCCGCGCCGCGAGTCAGATCTACACTTTGAAAGTAGGGATAACAGGGTA

ATgacattgattattgactagttGttaaTAGTAATCAATTACGGGGTCATTAGTTCATAGCCCATATATGGAGT

TCCGCGTTACATAACTTACGGTAAATGGCCCGCCTGGCTGACCGCCCAACGACCCCCGCCCATTGACGTCAATA

ATGACGTATGTTCCCATAGTAACGCCAATAGGGACTTTCCATTGACGTCAATGGGTGGAGTATTTACGGTAAAC

TGCCCACTTGGCAGTACATCAAGTGTATCATATGCCAAGTCCGCCCCCTATTGACGTCAATGACGGTAAATGGC

CCGCCTGGCATTATGCCCAGTACATGACCTTACGGGACTTTCCTACTTGGCAGTACATCTACGTATTAGTCATC
```

-continued

```
GCTATTACCATGgTGATGCGGTTTTGGCAGTACACCAATGGGCGTGGATAGCGGTTTGACTCACGGGGATTTCC
AAGTCTCCACCCCATTGACGTCAATGGGAGTTTGTTTTGGCACCAAAATCAACGGGACTTTCCAAAATGTCGTA
ATAACCCCGCCCCGTTGACGCAAATGGGCGGTAGGCGTGTACGGTGGGAGGTCTATATAAGCAGAgcTCGTTTA
GTGAACCGTCAGATCGCCTGGAACGCCATCCACGCTGTTTTGACCTCCATAGAAGACAGCGATCGCGccaccAT
GGTGAGCAAGGGCGAGGAGCTGTTCACCGGGGTGGTGCCCATCCTGGTCGAGCTGGACGGCGACGTAAACGGCC
ACAAGTTCAGCGTGTCCGGCGAGGGCGAGGGCGATGCCACCTACGGCAAGCTGACCCTGAAGTTCATCTGCACC
ACCGGCAAGCTGCCCGTGCCCTGGCCCACCCTCGTGACCACCCTGACCTACGGCGTGCAGTGCTTCAGCCGCTA
CCCCGACCACATGAAGCAGCACGACTTCTTCAAGTCCGCCATGCCCGAAGGCTACGTCCAGGAGCGCACCATCT
TCTTCAAGGACGACGGCAACTACAAGACCCGCGCCGAGGTGAAGTTCGAGGGCGACACCCTGGTGAACCGCATC
GAGCTGAAGGGCATCGACTTCAAGGAGGACGGCAACATCCTGGGGCACAAGCTGGAGTACAACTACAACAGCCA
CAACGTCTATATCATGGCCGACAAGCAGAAGAACGGCATCAAGGTGAACTTCAAGATCCGCCACAACATCGAGG
ACGGCAGCGTGCAGCTCGCCGACCACTACCAGCAGAACACCCCCATCGGCGACGGCCCCGTGCTGCTGCCCGAC
AACCACTACCTGAGCACCCAGTCCGCCCTGAGCAAAGACCCCAACGAGAAGCGCGATCACATGGTCCTGCTGGA
GTTCGTGACCGCCGCCGGGATCACTCTCGGCATGGACGAGCTtTACAAGTAGtgaGTTTAAACTCCCATTTAAA
TGTGAGGGTTAATGCTTCGAGCAGACATGATAAGATACATTGATGAGTTTGGACAAACCACAACTAGAATGCAG
TGAAAAAAATGCTTTATTTGTGAAATTTGTGATGCTATTGCTTTATTTGTAACCATTATAAGCTGCAATAAACA
AGTTAACAACAACAATTGCATTCATTTTATGTTTCAGGTTCAGGGGAGATGTGGGAGGTTTTTTAAAGCAAGT
AAAACCTCTACAAATGTGGTAAAATAACTATAACGGTCCTAAGGTAGCGAGTGAGTAGTGTTCTGGGGCGGGGG
AGGACCTGCATGAGGGCCAGAATAACTGAAATCTGTGCTTTTCTGTGTGTTGCAGCAGCATGAGCGGAAGCGGC
TCCTTTGAGGGAGGGGTATTCAGCCCTTATCTGACGGGGCGTCTCCCCTCCTGGGCGGGAGTGCGTCAGAATGT
GATGGGATCCACGGTGGACGGCCGGCCCGTGCAGCCGCGAACTCTTCAACCCTGACCTATGCAACCCTGAAGCT
CTTCGTCGTTGGACGCAGCTGCCGCCGCAGCTGCTGCATCTGCCGCCAGCGCCGTGCGCGGAATGGCCATGGGC
GCCGGCTACTACGGCACTCTGGTGGCCAACTCGAGTTCCACCAATAATCCCGCCAGCCTGAACGAGGAGAAGCT
GTTGCTGCTGATGGCCCAGCTCGAGGCCTTGACCCAGCGCCTGGGCGAGCTGACCCAGCAGGTGGCTCAGCTGC
AGGAGCAGACGCGGGCCGCGGTTGCCACGGTGAAATCCAAATAAAAAATGAATCAATAAATAAACGGAGACGGT
TGTTGATTTTAACACAGAGTCTGAATCTTTATTTGATTTTTCGCGCGCGGTAGGCCCTGGACCACCGGTCTCGA
TCATTGAGCACCCGGTGGATCTTTTCCAGGACCCGGTAGAGGTGGGCTTGGATGTTGAGGTACATGGGCATGAG
CCCGTCCCGGGGGTGGAGGTAGCTCCATTGCAGGGCCTCGTGCTCGGGGTGGTGTTGTAAATCACCCAGTCAT
AGCAGGGGCGCAGGGCATGGTGTTGCACAATATCTTTGAGGAGGAGACTGATGGCCACGGGCAGCCCTTTGGTG
TAGGTGTTTACAAATCTGTTGAGCTGGGAGGGATGCATGCGGGGGAGATGAGGTGCATCTTGGCCTGGATCTT
GAGATTGGCGATGTTACCGCCCAGATCCCGCCTGGGGTTCATGTTGTGCAGGACCACCAGCACGGTGTATCCGG
TGCACTTGGGGAATTTATCATGCAACTTGGAAGGGAAGGCGTGAAAGAATTTGGCGACGCCTTTGTGCCCGCCC
AGGTTTTCCATGCACTCATCCATGATGATGGCGATGGGCCCGTGGGCGGCGGCCTGGGCAAAGACGTTTCGGGG
GTCGGACACATCATAGTTGTGGTCCTGGGTGAGGTCATCATAGGCCATTTTAATGAATTTGGGGCGGAGGGTGC
CGGACTGGGGGACAAAGGTACCCTCGATCCCGGGGGCGTAGTTCCCCTCACAGATCTGCATCTCCCAGGCTTTG
AGCTCGGAGGGGGGATCATGTCCACCTGCGGGGCGATAAAGAACACGGTTTCCGGGGCGGGGAGATGAGCTG
GGCCGAAAGCAAGTTCCGGAGCAGCTGGGACTTGCCGCAGCCGGTGGGGCCGTAGATGACCCCGATGACCGGCT
GCAGGTGGTAGTTGAGGGAGAGACAGCTGCCGTCCTCCCGGAGGAGGGGGCCACCTCGTTCATCATCTCGCGC
ACGTGCATGTTCTCGCGCACCAGTTCCGCCAGGAGGCGCTCTCCCCCAGGGATAGGAGCTCCTGGAGCGAGGC
GAAGTTTTTCAGCGGCTTGAGTCCGTCGGCCATGGGCATTTTGGAGAGGGTTTGTTGCAAGAGTTCCAGGCGGT
CCCAGAGCTCGGTGATGTGCTCTACGGCATCTCGATCCAGCAGACCTCCTCGTTTCGCGGGTTGGGACGGCTGC
```

-continued

```
GGGAGTAGGGCACCAGACGATGGGCGTCCAGCGCAGCCAGGGTCCGGTCCTTCCAGGGTCGCAGCGTCCGCGTC

AGGGTGGTCTCCGTCACGGTGAAGGGGTGCGCGCCGGGCTGGGCGCTTGCGAGGGTGCGCTTCAGGCTCATCCG

GCTGGTCGAAAACCGCTCCCGATCGGCGCCCTGCGCGTCGGCCAGGTAGCAATTGACCATGAGTTCGTAGTTGA

GCGCCTCGGCCGCGTGGCCTTTGGCGCGGAGCTTACCTTTGGAAGTCTGCCCGCAGGCGGGACAGAGGAGGGAC

TTGAGGGCGTAGAGCTTGGGGGCGAGGAAGACGGACTCGGGGGCGTAGGCGTCCGCGCCGCAGTGGGCGCAGAC

GGTCTCGCACTCCACGAGCCAGGTGAGGTCGGGCTGGTCGGGGTCAAAAACCAGTTTCCCGCCGTTCTTTTTGA

TGCGTTTCTTACCTTTGGTCTCCATGAGCTCGTGTCCCCGCTGGGTGACAAAGAGGCTGTCCGTGTCCCCGTAG

ACCGACTTTATGGGCCGGTCCTCGAGCGGTGTGCCGCGGTCCTCCTCGTAGAGGAACCCCGCCCACTCCGAGAC

GAAAGCCCGGGTCCAGGCCAGCACGAAGGAGGCCACGTGGGACGGGTAGCGGTCGTTGTCCACCAGCGGGTCCA

CCTTTTCCAGGGTATGCAAACACATGTCCCCCTCGTCCACATCCAGGAAGGTGATTGGCTTGTAAGTGTAGGCC

ACGTGACCGGGGGTCCCGGCCGGGGGGGTATAAAAGGGTGCGGGTCCCTGCTCGTCCTCACTGTCTTCCGGATC

GCTGTCCAGGAGCGCCAGCTGTTGGGGTAGGTATTCCCTCTCGAAGGCGGGCATGACCTCGGCACTCAGGTTGT

CAGTTTCTAGAAACGAGGAGGATTTGATATTGACGGTGCCGGCGGAGATGCCTTTCAAGAGCCCCTCGTCCATC

TGGTCAGAAAAGACGATCTTTTTGTTGTCGAGCTTGGTGGCGAAGGAGCCGTAGAGGGCGTTGGAGAGGAGCTT

GGCGATGGAGCGCATGGTCTGGTTTTTTTCCTTGTCGGCGCGCTCCTTGGCGGCGATGTTGAGCTGCACGTACT

CGCGCGCCACGCACTTCCATTCGGGGAAGACGGTGGTCAGCTCGTCGGGCACGATTCTGACCTGCCAGCCCCGA

TTATGCAGGGTGATGAGGTCCACACTGGTGGCCACCTCGCCGCGCAGGGGCTCATTAGTCCAGCAGAGGCGTCC

GCCCTTGCGCGAGCAGAAGGGGGCAGGGGGTCCAGCATGACCTCGTCGGGGGGGTCGGCATCGATGGTGAAGA

TGCCGGGCAGGAGGTCGGGGTCAAAGTAGCTGATGGAAGTGGCCAGATCGTCCAGGGCAGCTTGCCATTCGCGC

ACGGCCAGCGCGCtCTCGTAGGGACTGAGGGGCGTGCCCCAGGGCATGGGATGGGTAAGCGCGGAGGCGTACAT

GCCGCAGATGTCGTAGACGTAGAGGGGCTCCTCGAGGATGCCGATGTAGGTGGGGTAGCAGCGCCCCCCGCGGA

TGCTGGCGCGCACGTAGTCATACAGCTCGTGCGAGGGGGCGAGGAGCCCCGGGCCCAGGTTGGTGCGACTGGGC

TTTTCGGCGCGGTAGACGATCTGGCGGAAAATGGCATGCGAGTTGGAGGAGATGGTGGGCCTTTGGAAGATGTT

GAAGTGGGCGTGGGGCAGTCCGACCGAGTCGCGGATGAAGTGGGCGTAGGAGTCTTGCAGCTTGGCGACGAGCT

CGGCGGTGACTAGGACGTCCAGAGCGCAGTAGTCGAGGGTCTCCTGGATGATGTCATACTTGAGCTGTCCCTTT

TGTTTCCACAGCTCGCGGTTGAGAAGGAACTCTTCGCGGTCCTTCCAGTACTCTTCGAGGGGGAACCCGTCCTG

ATCTGCACGGTAAGAGCCTAGCATGTAGAACTGGTTGACGGCCTTGTAGGCGCAGCAGCCCTTCTCCACGGGGA

GGGCGTAGGCCTGGGCGGCCTTGCGCAGGGAGGTGTGCGTGAGGGCGAAAGTGTCCCTGACCATGACCTTGAGG

AACTGGTGCTTGAAGTCGATATCGTCGCAGCCCCCTGCTCCCAGAGCTGGAAGTCCGTGCGCTTCTTGTAGGC

GGGGTTGGGCAAAGCGAAAGTAACATCGTTGAAGAGGATCTTGCCCGCGCGGGGCATAAAGTTGCGAGTGATGC

GGAAAGGTTGGGGCACCTCGGCCCGGTTGTTGATGACCTGGGCGGCGAGCACGATCTCGTCGAAGCCGTTGATG

TTGTGGCCCACGATGTAGAGTTCCACGAATCGCGGACGGCCCTTGACGTGGGGCAGTTTCTTGAGCTCCTCGTA

GGTGAGCTCGTCGGGGTCGCTGAGCCCGTGCTGCTCGAGCGCCCAGTCGGCGAGATGGGGGTTGGCGCGGAGGA

AGGAAGTCCAGAGATCCACGGCCAGGGCGGTTTGCAGACGGTCCCGGTACTGACGGAACTGCTGCCCGACGGCC

ATTTTTTCGGGGGTGACGCAGTAGAAGGTGCGGGGGTCCCCGTGCCAGCGATCCCATTTGAGCTGGAGGGCGAG

ATCGAGGGCGAGCTCGACGAGCCGGTCGTCCCCGGAGAGTTTCATGACCAGCATGAAGGGGACGAGCTGCTTGC

CGAAGGACCCCATCCAGGTGTAGGTTTCCACATCGTAGGTGAGGAAGAGCCTTTCGGTGCGAGGATGCGAGCCG

ATGGGGAAGAACTGGATCTCCTGCCACCAATTGGAGGAATGGCTGTTGATGTGATGGAAGTAGAAATGCCGACG

GCGCGCCGAACACTCGTGCTTGTGTTTATACAAGCGGCCACAGTGCTCGCAACGCTGCACGGGATGCACGTGCT

GCACGAGCTGTACCTGAGTTCCTTTGACGAGGAATTTCAGTGGGAAGTGGAGTCGTGGCGCCTGCATCTCGTGC
```

-continued

```
TGTACTACGTCGTGGTGGTCGGCCTGGCCCTCTTCTGCCTCGATGGTGGTCATGCTGACGAGCCCGCGCGGGAG
GCAGGTCCAGACCTCGGCGCGAGCGGGTCGGAGAGCGAGGACGAGGGCGCGCAGGCCGGAGCTGTCCAGGGTCC
TGAGACGCTGCGGAGTCAGGTCAGTGGGCAGCGGCGGCGCGCGGTTGACTTGCAGGAGTTTTTCCAGGGCGCGC
GGGAGGTCCAGATGGTACTTGATCTCCACCGCGCCATTGGTGGCGACGTCGATGGCTTGCAGGGTCCCGTGCCC
CTGGGGTGTGACCACCGTCCCCCGTTTCTTCTTGGGCGGCTGGGGCGACGGGGCGGTGCCTCTTCCATGGTTA
GAAGCGGCGGCGAGGACGCGCGCCGGGCGGCAGGGGCGGCTCGGGGCCCGGAGGCAGGGGCGGCAGGGGCACGT
CGGCGCCGCGCGCGGGTAGGTTCTGGTACTGCGCCCGGAGAAGACTGGCGTGAGCGACGACGCGACGGTTGACG
TCCTGGATCTGACGCCTCTGGGTGAAGGCCACGGGACCCGTGAGTTTGAACCTGAAAGAGAGTTCGACAGAATC
AATCTCGGTATCGTTGACGGCGGCCTGCCGCAGGATCTCTTGCACGTCGCCCGAGTTGTCCTGGTAGGCGATCT
CGGTCATGAACTGCTCGATCTCCTCCTCTTGAAGGTCTCCGCGGCCGGCGCGCTCCACGGTGGCCGCGAGGTCG
TTGGAGATGCGGCCCATGAGCTGCGAGAAGGCGTTCATGCCCGCCTCGTTCCAGACGCGGCTGTAGACCACGAC
GCCCTCGGGATCGCgGGCGCGCATGACCACCTGGGCGAGGTTGAGCTCCACGTGGCGCGTGAAGACCGCGTAGT
TGCAGAGGCGCTGGTAGAGGTAGTTGAGCGTGGTGGCGATGTGCTCGGTGACGAAGAAATACATGATCCAGCGG
CGGAGCGGCATCTCGCTGACGTCGCCCAGCGCCTCCAAACGTTCCATGGCCTCGTAAAAGTCCACGGCGAAGTT
GAAAAACTGGGAGTTGCGCGCCGAGACGGTCAACTCCTCCTCCAGAAGACGGATGAGCTCGGCGATGGTGGCGC
GCACCTCGCGCTCGAAGGCCCCCGGGAGTTCCTCCACTTCCTCTTCTTCCTCCTCCACTAACATCTCTTCTACT
TCCTCCTCAGGCGGCAGTGGTGGCGGGGGAGGGGCCTGCGTCGCCGGCGGCGCACGGGCAGACGGTCGATGAA
GCGCTCGATGGTCTCGCCGCGCCGGCGTCGCATGGTCTCGGTGACGGCGCGCCCGTCCTCGCGGGGCCGCAGCG
TGAAGACGCCGCCGCGCATCTCCAGGTGGCCGGGGGGGTCCCCGTTGGGCAGGGAGAGGGCGCTGACGATGCAT
CTTATCAATTGCCCCGTAGGGACTCCGCGCAAGGACCTGAGCGTCTCGAGATCCACGGGATCTGAAAACCGCTG
AACGAAGGCTTCGAGCCAGTCGCAGTCGCAAGGTAGGCTGAGCACGGTTTCTTCTGGCGGGTCATGTTGGTTGG
GAGCGGGGCGGGCGATGCTGCTGGTGATGAAGTTGAAATAGGCGGTTCTGAGACGGCGGATGGTGGCGAGGAGC
ACCAGGTCTTTGGGCCCGGCTTGCTGGATGCGCAGACGGTCGGCCATGCCCCAGGCGTGGTCCTGACACCTGGC
CAGGTCCTTGTAGTAGTCCTGCATGAGCCGCTCCACGGGCACCTCCTCCTCGCCCGCGCGGCCGTGCATGCGCG
TGAGCCCGAAGCCGCGCTGGGGCTGGACGAGCGCCAGGTCGGCGACGACGCGCTCGGCGAGGATGGCTTGCTGG
ATCTGGGTGAGGGTGGTCTGGAAGTCATCAAAGTCGACGAAGCGGTGGTAGGCTCCGGTGTTGATGGTGTAGGA
GCAGTTGGCCATGACGGACCAGTTGACGGTCTGGTGGCCCGGACGCACGAGCTCGTGGTACTTGAGGCGCGAGT
AGGCGCGCGTGTCGAAGATGTAGTCGTTGCAGGTGCGCACCAGGTACTGGTAGCCGATGAGGAAGTGCGGCGGC
GGCTGGCGGTAGAGCGGCCATCGCTCGGTGGCGGGGGCGCCGGGCGCGAGGTCCTCGAGCATGGTGCGGTGGTA
GCCGTAGATGTACCTGGACATCCAGGTGATGCCGGCGGCGGTGGTGGAGGCGCGCGGGAACTCGCGGACGCGGT
TCCAGATGTTGCGCAGCGGCAGGAAGTAGTTCATGGTGGGCACGGTCTGGCCCGTGAGGCGCGCGCAGTCGTGG
ATGCTCTATACGGGCAAAAACGAAAGCGGTCAGCGGCTCGACTCCGTGGCCTGGAGGCTAAGCGAACGGGTTGG
GCTGCGCGTGTACCCCGGTTCGAATCTCGAATCAGGCTGGAGCCGCAGCTAACGTGGTATTGGCACTCCCGTCT
CGACCCAAGCCTGCACCAACCCTCCAGGATACGGAGGCGGGTCGTTTTGCAACTTTTTTTTGGAGGCCGGATGA
GACTAGTAAGCGCGGAAAGCGGCCGACCGCGATGGCTCGCTGCCGTAGTCTGGAGAAGAATCGCCAGGGTTGCG
TTGCGGTGTGCCCCGGTTCGAGGCCGGCCGGATTCCGCGGCTAACGAGGGCGTGGCTGCCCCGTCGTTTCCAAG
ACCCCATAGCCAGCCGACTTCTCCAGTTACGGAGCGAGCCCCTCTTTTGTTTTGTTTGTTTTTGCCAGATGCAT
CCCGTACTGCGGCAGATGCGCCCCCACCACCCTCCACCGCAACAACAGCCCCCTCCACAGCCGGCGCTTCTGCC
CCCGCCCCAGCAGCAACTTCCAGCCACGACCGCCGCGGCCGCCGTGAGCGGGCTGGACAGAGTTATGATCACC
AGCTGGCCTTGAAGAGGGCGAGGGGCTGGCGCGCCTGGGGCGTCGTCGCCGGAGCGGCACCCGCGCGTGCAG
ATGAAAAGGGACGCTCGCGAGGCCTACGTGCCCAAGCAGAACCTGTTCAGAGACAGGAGCGGCGAGGAGCCCGA
```

-continued

```
GGAGATGCGCGCGGCCCGGTTCCACGCGGGGCGGGAGCTGCGGCGCGGCCTGGACCGAAAGAGGGTGCTGAGGG
ACGAGGATTTCGAGGCGGACGAGCTGACGGGGATCAGCCCCGCGCGCGCACGTGGCCGCGGCCAACCTGGTC
ACGGCGTACGAGCAGACCGTGAAGGAGGAGAGCAACTTCCAAAAATCCTTCAACAACCACGTGCGCACCCTGAT
CGCGCGCGAGGAGGTGACCCTGGGCCTGATGCACCTGTGGGACCTGCTGGAGGCCATCGTGCAGAACCCCACCA
GCAAGCCGCTGACGGCGCAGCTGTTCCTGGTGGTGCAGCATAGTCGGGACAACGAAGCGTTCAGGGAGGCGCTG
CTGAATATCACCGAGCCCGAGGGCCGCTGGCTCCTGGACCTGGTGAACATTCTGCAGAGCATCGTGGTGCAGGA
GCGCGGGCTGCCGCTGTCCGAGAAGCTGGCGGCCATCAACTTCTCGGTGCTGAGTTTGGGCAAGTACTACGCTA
GGAAGATCTACAAGACCCCGTACGTGCCCATAGACAAGGAGGTGAAGATCGACGGGTTTTACATGCGCATGACC
CTGAAAGTGCTGACCCTGAGCGACGATCTGGGGGTGTACCGCAACGACAGGATGCACCGTGCGGTGAGCGCCAG
CAGGCGGCGCGAGCTGAGCGACCAGGAGCTGATGCATAGTCTGCAGCGGGCCCTGACCGGGGCCGGGACCGAGG
GGGAGAGCTACTTTGACATGGGCGCGGACCTGCACTGGCAGCCCAGCCGCCGGGCCTTGGAGGCGGCGGCAGGA
CCCTACGTAGAAGAGGTGGACGATGAGGTGGACGAGGAGGGCGAGTACCTGGAAGACTGATGGCGCGACCGTAT
TTTTGCTAGATGCAACAACAACAGCCACCTCCTGATCCCGCGATGCGGGCGGCGCTGCAGAGCCAGCCGTCCGG
CATTAACTCCTCGGACGATTGGACCCAGGCCATGCAACGCATCATGGCGCTGACGACCCGCAACCCCGAAGCCT
TTAGACAGCAGCCCCAGGCCAACCGGCTCTCGGCCATCCTGGAGGCCGTGGTGCCCTCGCGCTCCAACCCCACG
CACGAGAAGGTCCTGGCCATCGTGAACGCGCTGGTGGAGAACAAGGCCATCCGCGGCGACGAGGCCGGCCTGGT
GTACAACGCGCTGCTGGAGCGCGTGGCCCGCTACAACAGCACCAACGTGCAGACCAACCTGGACCGCATGGTGA
CCGACGTGCGCGAGGCCGTGGCCCAGCGCGAGCGGTTCCACCGCGAGTCCAACCTGGGATCCATGGTGGCGCTG
AACGCCTTCCTCAGCACCCAGCCCGCCAACGTGCCCCGGGGCCAGGAGGACTACACCAACTTCATCAGCGCCCT
GCGCCTGATGGTGACCGAGGTGCCCCAGAGCGAGGTGTACCAGTCCGGGCCGGACTACTTCTTCCAGACCAGTC
GCCAGGGCTTGCAGACCGTGAACCTGAGCCAGGCTTTCAAGAACTTGCAGGGCCTGTGGGCGTGCAGGCCCCG
GTCGGGGACCGCGCGACGGTGTCGAGCCTGCTGACGCCGAACTCGCGCCTGCTGCTGCTGCTGGTGGCCCCCTT
CACGGACAGCGGCAGCATCAACCGCAACTCGTACCTGGGCTACCTGATTAACCTGTACCGCGAGGCCATCGGCC
AGGCGCACGTGGACGAGCAGACCTACCAGGAGATCACCCACGTGAGCCGCGCCCTGGGCCAGGACGACCCGGGC
AACCTGGAAGCCACCCTGAACTTTTTGCTGACCAACCGGTCGCAGAAGATCCCGCCCCAGTACGCGCTCAGCAC
CGAGGAGGAGCGCATCCTGCGTTACGTGCAGCAGAGCGTGGGCCTGTTCCTGATGCAGGAGGGGGCCACCCCCA
GCGCCGCGCTCGACATGACCGCGCGCAACATGGAGCCCAGCATGTACGCCAGCAACCGCCCGTTCATCAATAAA
CTGATGGACTACTTGCATCGGGCGGCCGCCATGAACTCTGACTATTTCACCAACGCCATCCTGAATCCCCACTG
GCTCCCGCCGCCGGGGTTCTACACGGGCGAGTACGACATGCCCGACCCCAATGACGGGTTCCTGTGGGACGATG
TGGACAGCAGCGTGTTCTCCCCCCGACCGGGTGCTAACGAGCGCCCCTTGTGGAAGAAGGAAGGCAGCGACCGA
CGCCCGTCCTCGGCGCTGTCCGGCCGCGAGGGTGCTGCCGCGGCGGTGCCCGAGGCCGCCAGTCCTTTCCCGAG
CTTGCCCTTCTCGCTGAACAGTATCCGCAGCAGCGAGCTGGGCAGGATCACGCGCCCGCGCTTGCTGGGCGAAG
AGGAGTACTTGAATGACTCGCTGTTGAGACCCGAGCGGGAGAAGAACTTCCCCAATAACGGGATAGAAAGCCTG
GTGGACAAGATGAGCCGCTGGAAGACGTATGCGCAGGAGCACAGGGACGATCCCCGGGCGTCGCAGGGGCCAC
GAGCCGGGGCAGCGCCGCCCGTAAACGCCGGTGGCACGACAGGCAGCGGGACAGATGTGGGACGATGAGGACT
CCGCCGACGACAGCAGCGTGTTGGACTTGGGTGGGAGTGGTAACCCGTTCGCTCACCTGCGCCCCCGTATCGGG
CGCATGATGTAAGAGAAACCGAAAATAAATGATACTCACCAAGGCCATGGCGACCAGCGTGCGTTCGTTTCTTC
TCTGTTGTTGTTGTATCTAGTATGATGAGGCGTGCGTACCCGGAGGGTCCTCCTCCCTCGTACGAGAGCGTGAT
GCAGCAGGCGATGGCGGCGGCGGCGATGCAGCCCCCGCTGGAGGCTCCTTACGTGCCCCCGCGGTACCTGGCGC
CTACGGAGGGGCGGAACAGCATTCGTTACTCGGAGCTGGCACCCTTGTACGATACCACCCGGTTGTACCTGGTG
```

-continued

```
GACAACAAGTCGGCGGACATCGCCTCGCTGAACTACCAGAACGACCACAGCAACTTCCTGACCACCGTGGTGCA

GAACAATGACTTCACCCCCACGGAGGCCAGCACCCAGACCATCAACTTTGACGAGCGCTCGCGGTGGGGCGGCC

AGCTGAAAACCATCATGCACACCAACATGCCCAACGTGAACGAGTTCATGTACAGCAACAAGTTCAAGGCGCGG

GTGATGGTCTCCCGCAAGACCCCCAATGGGGTGACAGTGACAGAGGATTATGATGGTAGTCAGGATGAGCTGAA

GTATGAATGGGTGGAATTTGAGCTGCCCGAAGGCAACTTCTCGGTGACCATGACCATCGACCTGATGAACAACG

CCATCATCGACAATTACTTGGCGGTGGGGCGGCAGAACGGGGTGCTGGAGAGCGACATCGGCGTGAAGTTCGAC

ACTAGGAACTTCAGGCTGGGCTGGGACCCCGTGACCGAGCTGGTCATGCCCGGGGTGTACACCAACGAGGCTTT

CCATCCCGATATTGTCTTGCTGCCCGGCTGCGGGGTGGACTTCACCGAGAGCCGCCTCAGCAACCTGCTGGGCA

TTCGCAAGAGGCAGCCCTTCCAGGAAGGCTTCCAGATCATGTACGAGGATCTGGAGGGGGGCAACATCCCCGCG

CTCCTGGATGTCGACGCCTATGAGAAAAGCAAGGAGGATGCAGCAGCTGAAGCAACTGCAGCCGTAGCTACCGC

CTCTACCGAGGTCAGGGGCGATAATTTTGCAAGCGCCGCAGCAGTGGCAGCGGCCGAGGCGGCTGAAACCGAAA

GTAAGATAGTCATTCAGCCGGTGGAGAAGGATAGCAAGAACAGGAGCTACAACGTACTACCGGACAAGATAAAC

ACCGCCTACCGCAGCTGGTACCTAGCCTACAACTATGGCGACCCCGAGAAGGGCGTGCGCTCCTGGACGCTGCT

CACCACCTCGGACGTCACCTGCGCGTGGAGCAAGTCTACTGGTCGCTGCCCGACATGATGCAAGACCCGGTCA

CCTTCCGCTCCACGCGTCAAGTTAGCAACTACCCGGTGGTGGGCGCCGAGCTCCTGCCCGTCTACTCCAAGAGC

TTCTTCAACGAGCAGGCCGTCTACTCGCAGCAGCTGCGCGCCTTCACCTCGCTTACGCACGTCTTCAACCGCTT

CCCCGAGAACCAGATCCTCGTCCGCCCGCCCGCGCCCACCATTACCACCGTCAGTGAAAACGTTCCTGCTCTCA

CAGATCACGGGACCCTGCCGCTGCGCAGCAGTATCCGGGGAGTCCAGCGCGTGACCGTTACTGACGCCAGACGC

CGCACCTGCCCCTACGTCTACAAGGCCCTGGGCATAGTCGCGCCGCGCGTCCTCTCGAGCCGCACCTTCTAAAT

GTCCATTCTCATCTCGCCCAGTAATAACACCGGTTGGGGCCTGCGCGCGCCCAGCAAGATGTACGGAGGCGCTC

GCCAACGCTCCACGCAACACCCCGTGCGCGTGCGCGGGCACTTCCGCGCTCCCTGGGGCGCCCTCAAGGGCCGC

GTGCGGTCGCGCACCACCGTCGACGACGTGATCGACCAGGTGGTGGCCGACGCGCGCAACTACACCCCCGCCGC

CGCGCCCGTCTCCACCGTGGACGCCGTCATCGACAGCGTGGTGGCcGACGCGCGCCGGTACGCCCGCGCCAAGA

GCCGGCGGCGGCGCATCGCCCGGCGGCACCGGAGCACCCCCGCCATGCGCGCGGCGCGAGCCTTGCTGCGCAGG

GCCAGGCGCACGGGACGCAGGGCCATGCTCAGGGCGGCCAGACGCGCGGCTTCAGGCGCCAGCGCCGGCAGGAC

CCGGAGACGCGCGGCCACGGCGGCGGCAGCGGCCATCGCCAGCATGTCCCGCCCGCGGCGAGGGAACGTGTACT

GGGTGCGCGACGCCGCCACCGGTGTGCGCGTGCCCGTGCGCACCCGCCCCCCTCGCACTTGAAGATGTTCACTT

CGCGATGTTGATGTGTCCCAGCGGCGAGGAGGATGTCCAAGCGCAAATTCAAGGAAGAGATGCTCCAGGTCATC

GCGCCTGAGATCTACGCCCTGCGGTGGTGAAGGAGGAAAGAAAGCCCCGCAAAATCAAGCGGGTCAAAAAGGA

CAAAAAGGAAGAAGAAAGTGATGTGGACGGATTGGTGGAGTTTGTGCGCGAGTTCGCCCCCCGGCGGCGCGTGC

AGTGGCGCGGGCGGAAGGTGCAACCGGTGCTGAGACCCGGCACCACCGTGGTCTTCACGCCCGGCGAGCGCTCC

GGCACCGCTTCCAAGCGCTCCTACGACGAGGTGTACGGGATGATGATATTCTGGAGCAGGCGGCCGAGCGCCT

GGGCGAGTTTGCTTACGGCAAGCGCAGCCGTTCCGCACCGAAGGAAGAGGCGGTGTCCATCCCGCTGGACCACG

GCAACCCCACGCCGAGCCTCAAGCCCGTGACCTTGCAGCAGGTGCTGCCGACCGCGGCGCCGCGCCGGGGGTTC

AAGCGCGAGGGCGAGGATCTGTACCCCACCATGCAGCTGATGGTGCCCAAGCGCCAGAAGCTGGAAGACGTGCT

GGAGACCATGAAGGTGGACCCGGACGTGCAGCCCGAGGTCAAGGTGCGGCCCATCAAGCAGGTGGCCCCGGGCC

TGGGCGTGCAGACCGTGGACATCAAGATTCCCACGGAGCCCATGGAAACGCAGACCGAGCCCATGATCAAGCCC

AGCACCAGCACCATGGAGGTGCAGACGGATCCCTGGATGCCATCGCCTCCTAGTCGAAGACCCCGGCGCAAGTA

CGGCGCGGCCAGCCTGCTGATGCCCAACTACGCGCTGCATCCTTCCATCATCCCCACGCCGGGCTACCGCGGCA

CGCGCTTCTACCGCGGTCATACCAGCAGCCGCCGCCGCAAGACCACCACTCGCCGCCGCCGTCGCCGCACCGCC

GCTGCAACCACCCCTGCCGCCCTGGTGCGGAGAGTGTACCGCCGCGGCCGCGCACCTCTGACCCTGCCGCGCGC
```

-continued

```
GCGCTACCACCCGAGCATCGCCATTTAAACTTTCGCCtGCTTTGCAGATCAATGGCCCTCACATGCCGCCTTCG
CGTTCCCATTACGGGCTACCGAGGAAGAAAACCGCGCCGTAGAAGGCTGGCGGGGAACGGGATGCGTCGCCACC
ACCACCGGCGGCGGCGCGCCATCAGCAAGCGGTTGGGGGGAGGCTTCCTGCCCGCGCTGATCCCCATCATCGCC
GCGGCGATCGGGGCGATCCCCGGCATTGCTTCCGTGGCGGTGCAGGCCTCTCAGCGCCACTGAGACACACTTGG
AAACATCTTGTAATAAACCaATGGACTCTGACGCTCCTGGTCCTGTGATGTGTTTTCGTAGACAGATGGAAGAC
ATCAATTTTTCGTCCCTGGCTCCGCGACACGGCACGCGGCCGTTCATGGGCACCTGGAGCGACATCGGCACCAG
CCAACTGAACGGGGGCGCCTTCAATTGGAGCAGTCTCTGGAGCGGGCTTAAGAATTTCGGGTCCACGCTTAAAA
CCTATGGCAGCAAGGCGTGGAACAGCACCACAGGGCAGGCGCTGAGGGATAAGCTGAAAGAGCAGAACTTCCAG
CAGAAGGTGGTCGATGGGCTCGCCTCGGGCATCAACGGGGTGGTGGACCTGGCCAACCAGGCCGTGCAGCGGCA
GATCAACAGCCGCCTGGACCCGGTGCCGCCCGCCGGCTCCGTGGAGATGCCGCAGGTGGAGGAGGAGCTGCCTC
CCCTGGACAAGCGGGGCGAGAAGCGACCCCGCCCCGATGCGGAGGAGACGCTGCTGACGCACACGGACGAGCCG
CCCCCGTACGAGGAGGCGGTGAAACTGGGTCTGCCCACCACGCGGCCCATCGCGCCCCTGGCCACCGGGGTGCT
GAAACCCGAAAAGCCCGCGACCCTGGACTTGCCTCCTCCCCAGCCTTCCCGCCCCTCTACAGTGGCTAAGCCCC
TGCCGCCGGTGGCCGTGGCCCGCGCGCGACCCGGGGGCACCGCCCGCCCTCATGCGAACTGGCAGAGCACTCTG
AACAGCATCGTGGGTCTGGGAGTGCAGAGTGTGAAGCGCCGCCGCTGCTATTAAACCTACCGTAGCGCTTAACT
TGCTTGTCTGTGTGTGTATGTATTATGTCGCCGCCGCCGCTGTCCACCAGAAGGAGGAGTGAAGAGGCGCGTCG
CCGAGTTGCAAGATGGCCACCCCATCGATGCTGCCCCAGTGGGCGTACATGCACATCGCCGGACAGGACGCTTC
GGAGTACCTGAGTCCGGGTCTGGTGCAGTTTGCCCGCGCCACAGACACCTACTTCAGTCTGGGGAACAAGTTTA
GGAACCCCACGGTGGCGCCCACGCACGATGTGACCACCGACCGCAGCCAGCGGCTGACGCTGCGCTTCGTGCCC
GTGGACCGCGAGGACAACACCTACTCGTACAAAGTGCGCTACACGCTGGCCGTGGGCGACAACCGCGTGCTGGA
CATGGCCAGCACCTACTTTGACATCCGCGGCGTGCTGGATCGGGGCCCTAGCTTCAAACCCTACTCCGGCACCG
CCTACAACAGTCTGGCCCCCAAGGGAGCACCCAACACTTGTCAGTGGACATATAAAGCCGATGGTGAAACTGCC
ACAGAAAAAACCTATACATATGGAAATGCACCCGTGCAGGGCATTAACATCACAAAAGATGGTATTCAACTTGG
AACTGACACCGATGATCAGCCAATCTACGCAGATAAAACCTATCAGCCTGAACCTCAAGTGGGTGATGCTGAAT
GGCATGACATCACTGGTACTGATGAAAAGTATGGAGGCAGAGCTCTTAAGCCTGATACCAAAATGAAGCCTTGT
TATGGTTCTTTTGCCAAGCCTACTAATAAAGAAGGAGGTCAGGCAAATGTGAAAACAGGAACAGGCACTACTAA
AGAATATGACATAGACATGGCTTTCTTTGACAACAGAAGTGCGGCTGCTGCTGGCCTAGCTCCAGAAATTGTTT
TGTATACTGAAAATGTGGATTTGGAAACTCCAGATACCCATATTGTATACAAAGCAGGCACAGATGACAGCAGC
TCTTCTATTAATTTGGGTCAGCAAGCCATGCCCAACAGACCTAACTACATTGGTTTCAGAGACAACTTTATCGG
GCTCATGTACTACAACAGCACTGGCAATATGGGGGTGCTGGCCGGTCAGGCTTCTCAGCTGAATGCTGTGGTTG
ACTTGCAAGACAGAAACACCGAGCTGTCCTACCAGCTCTTGCTTGACTCTCTGGGTGACAGAACCCGGTATTTC
AGTATGTGGAATCAGGCGGTGGACAGCTATGATCCTGATGTGCGCATTATTGAAAATCATGGTGTGGAGGATGA
ACTTCCCAACTATTGTTTCCCTCTGGATGCTGTTGGCAGAACAGATACTTATCAGGGAATTAAGGCTAATGAA
CTGATCAAACCACATGGACCAAAGATGACAGTGTCAATGATGCTAATGAGATAGGCAAGGGTAATCCATTCGCC
ATGGAAATCAACATCCAAGCCAACCTGTGGAGGAACTTCCTCTACGCCAACGTGGCCCTGTACCTGCCCGACTC
TTACAAGTACACGCCGGCCAATGTTACCCTGCCCACCAACACCAACACCTACGATTACATGAACGGCCGGGTGG
TGGCGCCCTCGCTGGTGGACTCCTACATCAACATCGGGGCGCGCTGGTCGCTGGATCCCATGGACAACGTGAAC
CCCTTCAACCACCACCGCAATGCGGGGCTGCGCTACCGCTCCATGCTCCTGGGCAACGGGCGCTACGTGCCCTT
CCACATCCAGGTGCCCCAGAAATTTTTCGCCATCAAGAGCCTCCTGCTCCTGCCCGGTCCTACACCTACGAGT
GGAACTTCCGCAAGGACGTCAACATGATCCTGCAGAGCTCCCTCGGCAACGACCTGCGCACGGACGGGGCCTCC
```

```
ATCTCCTTCACCAGCATCAACCTCTACGCCACCTTCTTCCCCATGGCGCACAACACGGCCTCCACGCTCGAGGC
CATGCTGCGCAACGACACCAACGACCAGTCCTTCAACGACTACCTCTCGGCGGCCAACATGCTCTACCCCATCC
CGGCCAACGCCACCAACGTGCCCATCTCCATCCCCTCGCGCAACTGGGCCGCCTTCCGCGGCTGGTCCTTCACG
CGTCTCAAGACCAAGGAGACGCCCTCGCTGGGCTCCGGGTTCGACCCCTACTTCGTCTACTCGGGCTCCATCCC
CTACCTCGACGGCACCTTCTACCTCAACCACACCTTCAAGAAGGTCTCCATCACCTTCGACTCCTCCGTCAGCT
GGCCCGGCAACGACCGGCTCCTGACGCCCAACGAGTTCGAAATCAAGCGCACCGTCGACGGCGAGGGCTACAAC
GTGGCCCAGTGCAACATGACCAAGGACTGGTTCCTGGTCCAGATGCTGGCCCACTACAACATCGGCTACCAGGG
CTTCTACGTGCCCGAGGGCTACAAGGACCGCATGTACTCCTTCTTCCGCAACTTCCAGCCCATGAGCCGCCAGG
TGGTGGACGAGGTCAACTACAAGGACTACCAGGCCGTCACCCTGGCCTACCAGCACAACAACTCGGGCTTCGTC
GGCTACCTCGCGCCCACCATGCGCCAGGGCCAGCCCTACCCCGCCAACTACCCCTACCCGCTCATCGGCAAGAG
CGCCGTCACCAGCGTCACCCAGAAAAAGTTCCTCTGCGACAGGGTCATGTGGCGCATCCCCTTCTCCAGCAACT
TCATGTCCATGGGCGCGCTCACCGACCTCGGCCAGAACATGCTCTATGCCAACTCCGCCCACGCGCTAGACATG
AATTTCGAAGTCGACCCCATGGATGAGTCCACCCTTCTCTATGTTGTCTTCGAAGTCTTCGACGTCGTCCGAGT
GCACCAGCCCCACCGCGGCGTCATCGAGGCCGTCTACCTGCGCACCCCCTTCTCGGCCGGTAACGCCACCACCT
AAGCTCTTGCTTCTTGCAAGCCATGGCCGCGGGCTCCGGCGAGCAGGAGCTCAGGGCCATCATCCGCGACCTGG
GCTGCGGGCCCTACTTCCTGGGCACCTTCGATAAGCGCTTCCCGGGATTCATGGCCCCGCACAAGCTGGCCTGC
GCCATCGTCAACACGGCCGGCCGCGAGACCGGGGGCGAGCACTGGCTGGCCTTCGCCTGGAACCCGCGCTCGAA
CACCTGCTACCTCTTCGACCCCTTCGGGTTCTCGGACGAGCGCCTCAAGCAGATCTACCAGTTCGAGTACGAGG
GCCTGCTGCCGCAGCGCCCTGGCCACCGAGGACCGCTGCGTCACCCTGGAAAAGTCCACCCAGACCGTGCAG
GGTCCGCGCTCGGCCGCCTGCGGGCTCTTCTGCTGCATGTTCCTGCACGCCTTCGTGCACTGGCCCGACCGCCC
CATGGACAAGAACCCCACCATGAACTTGCTGACGGGGGTGCCCAACGGCATGCTCCAGTCGCCCCAGGTGGAAC
CCACCCTGCGCCGCAACCAGGAGGCGCTCTACCGCTTCCTCAACTCCCACTCCGCCTACTTTCGCTCCCACCGC
GCGCGCATCGAGAAGGCCACCGCCTTCGACCGCATGAATCAAGACATGTAAACCGTGTGTGTATGTTAAATGTC
TTTAATAAACAGCACTTTCATGTTACACATGCATCTGAGATGATTTATTTAGAAATCGAAAGGGTTCTGCCGGG
TCTCGGCATGGCCCGCGGGCAGGGACACGTTGCGGAACTGGTACTTGGCCAGCCACTTGAACTCGGGGATCAGC
AGTTTGGGCAGCGGGGTGTCGGGGAAGGAGTCGGTCCACAGCTTCCGCGTCAGTTGCAGGGCGCCCAGCAGGTC
GGGCGCGGAGATCTTGAAATCGCAGTTGGGACCCGCGTTCTGCGCGCGGGAGTTGCGGTACACGGGGTTGCAGC
ACTGGAACACCATCAGGGCCGGGTGCTTCACGCTCGCCAGCACCGTCGCGTCGGTGATGCTCTCCACGTCGAGG
TCCTCGGCGTTGGCCATCCCGAAGGGGGTCATCTTGCAGGTCTGCCTTCCCATGGTGGGCACGCACCCGGGCTT
GTGGTTGCAATCGCAGTGCAGGGGATCAGCATCATCTGGGCCTGGTCGGCGTTCATCCCCGGGTACATGGCCT
TCATGAAAGCCTCCAATTGCCTGAACGCCTGCTGGGCCTTGGCTCCCTCGGTGAAGAAGACCCCGCAGGACTTG
CTAGAGAACTGGTTGGTGGCGCACCCGGCGTCGTGCACGCAGCAGCGCGTCGTTGTTGGCCAGCTGCACCAC
GCTGCGCCCCAGCGGTTCTGGGTGATCTTGGCCCGGTCGGGGTTCTCCTTCAGCGCGCGCTGCCCGTTCTCGC
TCGCCACATCCATCTCGATCATGTGCTCCTTCTGGATCATGGTGGTCCCGTGCAGGCACCGCAGCTTGCCCTCG
GCCTCGGTGCACCCGTGCAGCCACAGCGCGCACCCGGTGCACTCCCAGTTCTTGTGGGCGATCTGGGAATGCGC
GTGCACGAAGCCCTGCAGGAAGCGGCCCATCATGGTGGTCAGGGTCTTGTTGCTAGTGAAGGTCAGCGGAATGC
CGCGGTGCTCCTCGTTGATGTACAGGTGGCAGATGCGGCGGTACACCTCGCCCTGCTCGGGCATCAGCTGGAAG
TTGGCTTTCAGGTCGGTCTCCACGCGGTAGCGGTCCATCAGCATAGTCATGATTTCCATACCCTTCTCCCAGGC
CGAGACGATGGGCAGGCTCATAGGGTTCTTCACCATCATCTTAGCGCTAGCAGCCGCGGCCAGGGGGTCGCTCT
CGTCCAGGGTCTCAAAGCTCCGCTTGCCGTCCTTCTCGGTGATCCGCACCGGGGGGTAGCTGAAGCCCACGGCC
GCCAGCTCCTCCTCGGCCTGTCTTTCGTCCTCGCTGTCCTGGCTGACGTCCTGCAGGACCACATGCTTGGTCTT
```

-continued

```
GCGGGGTTTCTTCTTGGGCGGCAGCGGCGGCGGAGATGTTGGAGATGGCGAGGGGGAGCGCGAGTTCTCGCTCA
CCACTACTATCTCTTCCTCTTCTTGGTCCGAGGCCACGCGGCGGTAGGTATGTCTCTTCGGGGGCAGAGGCGGA
GGCGACGGGCTCTCGCCGCCGCGACTTGGCGGATGGCTGGCAGAGCCCCTTCCGCGTTCGGGGGTGCGCTCCCG
GCGGCGCTCTGACTGACTTCCTCCGCGGCCGGCCATTGTGTTCTCCTAGGGAGGAACAACAAGCATGGAGACTC
AGCCATCGCCAACCTCGCCATCTGCCCCACCGCCGACGAGAAGCAGCAGCAGCAGAATGAAAGCTTAACCGCC
CCGCCGCCCAGCCCCGCCACCTCCGACGCGGCCGTCCCAGACATGCAAGAGATGGAGGAATCCATCGAGATTGA
CCTGGGCTATGTGACGCCCGCGGAGCACGAGGAGGAGCTGGCAGTGCGCTTTTCACAAGAAGAGATACACCAAG
AACAGCCAGAGCAGGAAGCAGAGAATGAGCAGAGTCAGGCTGGGCTCGAGCATGACGGCGACTACCTCCACCTG
AGCGGGGGGAGGACGCGCTCATCAAGCATCTGGCCCGGCAGGCCACCATCGTCAAGGATGCGCTGCTCGACCG
CACCGAGGTGCCCCTCAGCGTGGAGGAGCTCAGCCGCGCCTACGAGTTGAACCTCTTCTCGCCGCGCGTGCCCC
CCAAGCGCCAGCCCAATGGCACCTGCGAGCCCAACCCGCGCCTCAACTTCTACCCGGTCTTCGCGGTGCCCGAG
GCCCTGGCCACCTACCACATCTTTTTCAAGAACCAAAAGATCCCCGTCTCCTGCCGCGCCAACCGCACCCGCGC
CGACGCCCTTTTCAACCTGGGTCCCGGCGCCCGCCTACCTGATATCGCCTCCTTGGAAGAGGTTCCCAAGATCT
TCGAGGGTCTGGGCAGCGACGAGACTCGGCCGCGAACGCTCTGCAAGGAGAAGGAGGAGAGCATGAGCACCAC
AGCGCCCTGGTCGAGTTGGAAGGCGACAACGCGCGGCTGGCGGTGCTCAAACGCACGGTCGAGCTGACCCATTT
CGCCTACCCGGCTCTGAACCTGCCCCCCAAAGTCATGAGCGCGGTCATGGACCAGGTGCTCATCAAGCGCGCGT
CGCCCATCTCCGAGGACGAGGGCATGCAAGACTCCGAGGAGGGCAAGCCCGTGGTCAGCGACGAGCAGCTGGCC
CGGTGGCTGGGTCCTAATGCTAGTCCCCAGAGTTTGGAAGAGCGGCGCAAACTCATGATGGCCGTGGTCCTGGT
GACCGTGGAGCTGGAGTGCCTGCGCCGCTTCTTCGCCGACGCGGAGACCCTGCGCAAGGTCGAGGAGAACCTGC
ACTACCTCTTCAGGCACGGGTTCGTGCGCCAGGCCTGCAAGATCTCCAACGTGGAGCTGACCAACCTGGTCTCC
TACATGGGCATCTTGCACGAGAACCGCCTGGGGCAGAACGTGCTGCACACCACCCTGCGCGGGGAGGCCCGGCG
CGACTACATCCGCGACTGCGTCTACCTCTACCTCTGCCACACCTGGCAGACGGGCATGGGCGTGTGGCAGCAGT
GTCTGGAGGAGCAGAACCTGAAAGAGCTCTGCAAGCTCCTGCAGAAGAACCTCAAGGGTCTGTGGACCGGGTTC
GACGAGCGCACCACCGCCTCGGACCTGGCCGACCTCATTTTCCCCGAGCGCCTCAGGCTGACGCTGCGCAACGG
CCTGCCCGACTTTATGAGCCAAAGCATGTTGCAAAACTTTCGCTCTTTCATCCTCGAACGCTCCGGAATCCTGC
CCGCCACCTGCTCCGCGCTGCCCTCGGACTTCGTGCCGCTGACCTTCCGCGAGTGCCCCCCGCCGCTGTGGAGC
CACTGCTACCTGCTGCGCCTGGCCAACTACCTGGCCTACCACTCGGACGTGATCGAGGACGTCAGCGGCGAGGG
CCTGCTCGAGTGCCACTGCCGCTGCAACCTCTGCACGCCGCACCGCTCCCTGGCCTGCAACCCCCAGCTGCTGA
GCGAGACCCAGATCATCGGCACCTTCGAGTTGCAAGGGCCCAGCGAAGGCGAGGGTTCAGCCGCCAAGGGGGT
CTGAAACTCACCCCGGGGCTGTGGACCTCGGCCTACTTGCGCAAGTTCGTGCCCGAGGACTACCATCCCTTCGA
GATCAGGTTCTACGAGGACCAATCCCATCCGCCCAAGGCCGAGCTGTCGGCCTGCGTCATCACCCAGGGGGCGA
TCCTGGCCCAATTGCAAGCCATCCAGAAATCCCGCCAAGAATTCTTGCTGAAAAAGGGCCGCGGGGTCTACCTC
GACCCCCAGACCGGTGAGGAGCTCAACCCCGGCTTCCCCCAGGATGCCCCGAGGAAACAAGAAGCTGAAAGTGG
AGCTGCCGCCCGTGGAGGATTTGGAGGAAGACTGGGAGAACAGCAGTCAGGCAGAGGAGGAGGAGATGGAGGAA
GACTGGGACAGCACTCAGGCAGAGGAGGACAGCCTGCAAGACAGTCTGGAGGAAGACGAGGAGGAGGCAGAGGA
GGAGGTGGAAGAAGCAGCCGCCGCCAGACCGTCGTCCTCGGCGGGGAGAAAGCAAGCAGCACGGATACCATCT
CCGCTCCGGGTCGGGTCCCGCTCGACCACACAGTAGATGGGACGAGACCGGACGATTCCCGAACCCCACCACC
CAGACCGGTAAGAAGGAGCGGCAGGGATACAAGTCCTGGCGGGGGCACAAAAACGCCATCGTCTCCTGCTTGCA
GGCCTGCGGGGCAACATCTCCTTCACCCGGCGCTACCTGCTCTTCCACCGCGGGGTGAACTTTCCCCGCAACA
TCTTGCATTACTACCGTCACCTCCACAGCCCCTACTACTTCCAAGAAGAGGCAGCAGCAGCAGAAAAAGACCAG
```

-continued

```
CAGAAAACCAGCAGCTAGAAAATCCACAGCGGCGGCAGCAGGTGGACTGAGGATCGCGGCGAACGAGCCGGCGC
AAACCCGGGAGCTGAGGAACCGGATCTTTCCCACCCTCTATGCCATCTTCCAGCAGAGTCGGGGCAGGAGCAG
GAACTGAAAGTCAAGAACCGTTCTCTGCGCTCGCTCACCCGCAGTTGTCTGTATCACAAGAGCGAAGACCAACT
TCAGCGCACTCTCGAGGACGCCGAGGCTCTCTTCAACAAGTACTGCGCGCTCACTCTTAAAGAGTAGCCCGCGC
CCGCCCAGTCGCAGAAAAAGGCGGGAATTACGTCACCTGTGCCCTTCGCCCTAGCCGCCTCCACCCATCATCAT
GAGCAAAGAGATTCCCACGCCTTACATGTGGAGCTACCAGCCCCAGATGGGCCTGGCCGCCGGTGCCGCCCAGG
ACTACTCCACCCGCATGAATTGGCTCAGCGCCGGGCCCGCGATGATCTCACGGGTGAATGACATCCGCGCCCAC
CGAAACCAGATACTCCTAGAACAGTCAGCGCTCACCGCCACGCCCCGCAATCACCTCAATCGCGTAATTGGCC
CGCCGCCCTGGTGTACCAGGAAATTCCCCAGCCCACGACCGTACTACTTCCGCGAGACGCCCAGGCCGAAGTCC
AGCTGACTAACTCAGGTGTCCAGCTGGCGGGCGGCGCCACCCTGTGTCGTCACCGCCCCGCTCAGGGTATAAAG
CGGCTGGTGATCCGGGGCAGAGGCACACAGCTCAACGACGAGGTGGTGAGCTCTTCGCTGGGTCTGCGACCTGA
CGGAGTCTTCCAACTCGCCGGATCGGGGAGATCTTCCTTCACGCCTCGTCAGGCCGTCCTGACTTTGGAGAGTT
CGTCCTCGCAGCCCCGCTCGGGTGGCATCGGCACTCTCCAGTTCGTGGAGGAGTTCACTCCCTCGGTCTACTTC
AACCCCTTCTCCGGCTCCCCCGGCCACTACCCGGACGAGTTCATCCCGAACTTCGACGCCATCAGCGAGTCGGT
GGACGGCTACGATTGAATGTCCCATGGTGGCGCAGCTGACCTAGCTCGGCTTCGACACCTGGACCACTGCCGCC
GCTTCCGCTGCTTCGCTCGGGATCTCGCCGAGTTTGCCTACTTTGAGCTGCCCGAGGAGCACCCTCAGGGCCCG
GCCCACGGAGTGCGGATCGTCGTCGAAGGGGGCCTCGACTCCCACCTGCTTCGGATCTTCAGCCAGCGTCCGAT
CCTGGTCGAGCGCGAGCAAGGACAGACCCTTCTGACTCTGTACTGCATCTGCAACCACCCCGGCCTGCATGAAA
GTCTTTGTTGTCTGCTGTGTACTGAGTATAATAAAAGCTGAGATCAGCGACTACTCCGGACTTCCGTGTGTTCC
TGAATCCATCAACCAGTCTTTGTTCTTCACCGGGAACGAGACCGAGCTCCAGCTCCAGTGTAAGCCCCACAAGA
AGTACCTCACCTGGCTGTTCCAGGGCTCCCCGATCGCCGTTGTCAACCACTGCGACAACGACGGAGTCCTGCTG
AGCGGCCCTGCCAACCTTACTTTTTCCACCCGCAGAAGCAAGCTCCAGCTCTTCAACCCTTCCTCCCCGGGAC
CTATCAGTGCGTCTCGGGACCCTGCCATCACACCTTCCACCTGATCCCGAATACCACAGCGTCGCTCCCCGCTA
CTAACAACCAAACTAACCTCCACCAACGCCACCGTCGCGACGGCCACAATACATGCCCATATTAGACTATGAGG
CCGAGCCACAGCGACCCATGCTCCCCGCTATTAGTTACTTCAATCTAACCGGCGGAGATGACTGACCCACTGGC
CAACAACAACGTCAACGACCTTCTCCTGGACATGGACGGCCGCGCCTCGGAGCAGCGACTCGCCCAACTTCGCA
TTCGCCAGCAGCAGGAGAGAGCCGTCAAGGAGCTGCAGGATGCGGTGGCCATCCACCAGTGCAAGAGAGGCATC
TTCTGCCTGGTGAAACAGGCCAAGATCTCCTACGAGGTCACTCCAAACGACCATCGCCTCTCCTACGAGCTCCT
GCAGCAGCGCCAGAAGTTCACCTGCCTGGTCGGAGTCAACCCCATCGTCATCACCCAGCAGTCTGGCGATACCA
AGGGGTGCATCCACTGCTCCTGCGACTCCCCCGACTGCGTCCACACTCTGATCAAGACCCTCTGCGGCCTCCGC
GACCTCCTCCCCATGAACTAATCACCCCCTTATCCAGTGAAATAAAGATCATATTGATGATGATTTTACAGAAA
TAAAAAATAATCATTTGATTTGAAATAAAGATACAATCATATTGATGATTTGAGTTTAACAAAAAAATAAAGAA
TCACTTACTTGAAATCTGATACCAGGTCTCTGTCCATGTTTTCTGCCAACACCACTTCACTCCCCTCTTCCCAG
CTCTGGTACTGCAGGCCCCGGCGGGCTGCAAACTTCCTCCACACGCTGAAGGGGATGTCAAATTCCTCCTGTCC
CTCAATCTTCATTTTATCTTCTATCAGATGTCCAAAAAGCGCGTCCGGTGGATGATGACTTCGACCCCGTCTA
CCCCTACGATGCAGACAACGCACCGACCGTGCCCTTCATCAACCCCCCCTTCGTCTCTTCAGATGGATTCCAAG
AGAAGCCCCTGGGGGTGTTGTCCCTGCGACTGGCCGACCCCGTCACCACCAAGAACGGGGAAATCACCCTCAAG
CTGGGAGAGGGGTGGACCTCGATTCCTCGGGAAAACTCATCTCCAACACGGCCACCAAGGCCGCCGCCCCTCT
CAGTTTTTCCAACAACACCATTTCCCTTAACATGGATCACCCCTTTTACACTAAAGATGGAAAATTATCCTTAC
AAGTTTCTCCACCATTAAATATACTGAGAACAAGCATTCTAAACACACTAGCTTTAGGTTTTGGATCAGGTTTA
GGACTCCGTGGCTCTGCCTTGGCAGTACAGTTAGTCTCTCCACTTACATTTGATACTGATGGAAACATAAAGCT
```

-continued

```
TACCTTAGACAGAGGTTTGCATGTTACAACAGGAGATGCAATTGAAAGCAACATAAGCTGGGCTAAAGGTTTAA

AATTTGAAGATGGAGCCATAGCAACCAACATTGGAAATGGGTTAGAGTTTGGAAGCAGTAGTACAGAAACAGGT

GTTGATGATGCTTACCCAATCCAAGTTAAACTTGGATCTGGCCTTAGCTTTGACAGTACAGGAGCCATAATGGC

TGGTAACAAAGAAGACGATAAACTCACTTTGTGGACAACACCTGATCCATCACCAAACTGTCAAATACTCGCAG

AAAATGATGCAAAACTAACACTTTGCTTGACTAAATGTGGTAGTCAAATACTGGCCACTGTGTCAGTCTTAGTT

GTAGGAAGTGGAAACCTAAACCCCATTACTGGCACCGTAAGCAGTGCTCAGGTGTTTCTACGTTTTGATGCAAA

CGGTGTTCTTTTAACAGAACATTCTACACTAAAAAAATACTGGGGGTATAGGCAGGGAGATAGCATAGATGGCA

CTCCATATACCAATGCTGTAGGATTCATGCCCAATTTAAAAGCTTATCCAAAGTCACAAAGTTCTACTACTAAA

AATAATATAGTAGGGCAAGTATACATGAATGGAGATGTTTCAAAACCTATGCTTCTCACTATAACCCTCAATGG

TACTGATGACAGCAACAGTACATATTCAATGTCATTTTCATACACCTGGACTAATGGAAGCTATGTTGGAGCAA

CATTTGGGCTAACTCTTATACCTTCTCATACATCGCCCAAGAATGAACACTGTATCCCACCCTGCATGCCAAC

CCTTCCCACCCCACTCTGTGGAACAAACTCTGAAACACAAAATAAAATAAAGTTCAAGTGTTTTATTGATTCAA

CAGTTTTACAGGATTCGAGCAGTTATTTTTCCTCCACCCTCCCAGGACATGGAATACACCACCCTCTCCCCCCG

CACAGCCTTGAACATCTGAATGCCATTGGTGATGGACATGCTTTTGGTCTCCACGTTCCACACAGTTTCAGAGC

GAGCCAGTCTCGGGTCGGTCAGGGAGATGAAACCCTCCGGGCACTCCCGCATCTGCACCTCACAGCTCAACAGC

TGAGGATTGTCCTCGGTGGTCGGGATCACGGTTATCTGGAAGAAGCAGAAGAGCGGCGGTGGGAATCATAGTCC

GCGAACGGGATCGGCCGGTGGTGTCGCATCAGGCCCCGCAGCAGTCGCTGCCGCCGCCGCTCCGTCAAGCTGCT

GCTCAGGGGGTCCGGGTCCAGGGACTCCCTCAGCATGATGCCCACGCCCTCAGCATCAGTCGTCTGGTGCGGC

GGGCGCAGCAGCGCATGCGGATCTCGCTCAGGTCGCTGCAGTACGTGCAACACAGAACCACCAGGTTGTTCAAC

AGTCCATAGTTCAACACGCTCCAGCCGAAACTCATCGCGGGAAGGATGCTACCCACGTGGCCGTCGTACCAGAT

CCTCAGGTAAATCAAGTGGTGCCCCCTCCAGAACACGCTGCCCACGTACATGATCTCCTTGGGCATGTGGCGGT

TCACCACCTCCCGGTACCACATCACCCTCTGGTTGAACATGCAGCCCCGGATGATCCTGCGGAACCACAGGGCC

AGCACCGCCCCGCCCGCCATGCAGCGAAGAGACCCCGGGTCCCGGCAATGGCAATGGAGGACCCACCGCTCGTA

CCCGTGGATCATCTGGGAGCTGAACAAGTCTATGTTGGCACAGCACAGGCATATGCTCATGCATCTCTTCAGCA

CTCTCAACTCCTCGGGGGTCAAAACCATATCCCAGGGCACGGGGAACTCTTGCAGGACAGCGAACCCCGCAGAA

CAGGGCAATCCTCGCACAGAACTTACATTGTGCATGGACAGGGTATCGCAATCAGGCAGCACCGGGTGATCCTC

CACCAGAGAAGCGCGGGTCTCGGTCTCCTCACAGCGTGGTAAGGGGGCCGGCCGATACGGGTGATGGCGGGACG

CGGCTGATCGTGTTCGCGACCGTGTCATGATGCAGTTGCTTTCGGACATTTTCGTACTTGCTGTAGCAGAACCT

GGTCCGGGCGCTGCACACCGATCGCCGGCGGCGGTCTCGGCGCTTGGAACGCTCGGTGTTGAAATTGTAAAACA

GCCACTCTCTCAGACCGTGCAGCAGATCTAGGGCCTCAGGAGTGATGAAGATCCCATCATGCCTGATGGCTCTG

ATCACATCGACCACCGTGGAATGGCCAGACCCAGCCAGATGATGCAATTTTGTTGGGTTTCGGTGACGGCGGG

GGAGGGAAGAACAGGAAGAACCATGATTAACTTTTAATCCAAACGGTCTCGGAGTACTTCAAAATGAAGATCGC

GGGAGATGGCACCTCTCGCCCCCGCTGTGTTGGTGGAAAATAACAGCCAGGTCAAAGGTGATACGGTTCTCGAGA

TGTTCCACGGTGGCTTCCAGCAAAGCCTCCACGCGCACATCCAGAAACAAGACAATAGCGAAAGCGGGAGGGTT

CTCTAATTCCTCAATCATCATGTTACACTCCTGCACCATCCCCAGATAATTTTCATTTTTCCAGCCTTGAATGA

TTCGAACTAGTTCGTGAGGTAAATCCAAGCCAGCCATGATAAAGAGCTCGCGCAGAGCGCCCTCCACCGGCATT

CTTAAGCACACCCTCATAATTCCAAGATATTCTGCTCCTGGTTCACCTGCAGCAGATTGACAAGCGGAATATCA

AAATCTCTGCCGCGATCCCTGAGCTCCTCCCTCAGCAATAACTGTAAGTACTCTTTCATATCCTCTCCGAAATT

TTTAGCCATAGGACCACCAGGAATAAGATTAGGGCAAGCCACAGTACAGATAAACCGAAGTCCTCCCCAGTGAG

CATTGCCAAATGCAAGACTGCTATAAGCATGCTGGCTAGACCCGGTGATATCTTCCAGATAACTGGACAGAAAA
```

-continued

TCGCCCAGGCAATTTTTAAGAAAATCAACAAAAGAAAAATCCTCCAGGTGGACGTTTAGAGCCTCGGGAACAAC

GATGAAGTAAATGCAAGCGGTGCGTTCCAGCATGGTTAGTTAGCTGATCTGTAGAAAAAACAAAAATGAACATT

AAACCATGCTAGCCTGGCGAACAGGTGGGTAAATCGTTCTCTCCAGCACCAGGCAGGCCACGGGGTCTCCGGCG

CGACCCTCGTAAAAATTGTCGCTATGATTGAAAACCATCACAGAGAGACGTTCCCGGTGGCCGGCGTGAATGAT

TCGACAAGATGAATACACCCCCGGAACATTGGCGTCCGCGAGTGAAAAAAAGCGCCCGAGGAAGCAATAAGGCA

CTACAATGCTCAGTCTCAAGTCCAGCAAAGCGATGCCATGCGGATGAAGCACAAAATTCTCAGGTGCGTACAAA

ATGTAATTACTCCCCTCCTGCACAGGCAGCAAAGCCCCCGATCCCTCCAGGTACACATACAAAGCCTCAGCGTC

CATAGCTTACCGAGCAGCAGCACACAACAGGCGCAAGAGTCAGAGAAAGGCTGAGCTCTAACCTGTCCACCCGC

TCTCTGCTCAATATATAGCCCAGATCTACACTGACGTAAAGGCCAAAGTCTAAAAATACCCGCCAAATAATCAC

ACACGCCCAGCACACGCCCAGAAACCGGTGACACACTCAAAAAAATACGCGCACTTCCTCAAACGCCCAAAACT

GCCGTCATTTCCGGGTTCCCACGCTACGTCATCAAAACACGACTTTCAAATTCCGTCGACCGTTAAAAACGTCA

CCCGCCCCGCCCCTAACGGTCGCCCGTCTCTCAGCCAATCAGCGCCCCGCATCCCCAAATTCAAACACCTCATT

TGCATATTAACGCGCACAAAAAGTTTGAGGTATATTATTGATGATGG

ChAdV68.4WTnt.MAG25mer; AC_000011.1 with E1 (nt 577 to 3403) and E3
(nt 27,816-31,332) sequences deleted; corresponding ATCC VR-594
nucleotides substituted at four positions; model neoantigen cassette
under the control of the CMV promoter/enhancer inserted in place of
deleted E1

(SEQ ID NO: 12)

CCATCTTCAATAATATACCTCAAACTTTTTGTGCGCGTTAATATGCAAATGAGGCGTTTGAATTTGGGGAGGAA

GGGCGGTGATTGGTCGAGGGATGAGCGACCGTTAGGGGCGGGGCGAGTGACGTTTTGATGACGTGGTTGCGAGG

AGGAGCCAGTTTGCAAGTTCTCGTGGGAAAAGTGACGTCAAACGAGGTGTGGTTTGAACACGGAAATACTCAAT

TTTCCCGCGCTCTCTGACAGGAAATGAGGTGTTTCTGGGCGGATGCAAGTGAAAACGGGCCATTTTCGCGCGAA

AACTGAATGAGGAAGTGAAAATCTGAGTAATTTCGCGTTTATGGCAGGGAGGAGTATTTGCCGAGGGCCGAGTA

GACTTTGACCGATTACGTGGGGGTTTCGATTACCGTGTTTTTCACCTAAATTTCCGCGTACGGTGTCAAAGTCC

GGTGTTTTTACGTAGGTGTCAGCTGATCGCCAGGGTATTTAAACCTGCGCTCTCCAGTCAAGAGGCCACTCTTG

AGTGCCAGCGAGAAGAGTTTTCTCCTCCGCGCCGCGAGTCAGATCTACACTTTGAAAGTAGGGATAACAGGGTA

ATgacattgattattgactagttGttaaTAGTAATCAATTACGGGGTCATTAGTTCATAGCCCATATATGGAGT

TCCGCGTTACATAACTTACGGTAAATGGCCCGCCTGGCTGACCGCCCAACGACCCCCGCCCATTGACGTCAATA

ATGACGTATGTTCCCATAGTAACGCCAATAGGGACTTTCCATTGACGTCAATGGGTGGAGTATTTACGGTAAAC

TGCCCACTTGGCAGTACATCAAGTGTATCATATGCCAAGTCCGCCCCCTATTGACGTCAATGACGGTAAATGGC

CCGCCTGGCATTATGCCCAGTACATGACCTTACGGGACTTTCCTACTTGGCAGTACATCTACGTATTAGTCATC

GCTATTACCATGgTGATGCGGTTTTGGCAGTACACCAATGGGCGTGGATAGCGGTTTGACTCACGGGGATTTCC

AAGTCTCCACCCCATTGACGTCAATGGGAGTTTGTTTTGGCACCAAAATCAACGGGACTTTCCAAAATGTCGTA

ATAACCCCGCCCCGTTGACGCAAATGGGCGGTAGGCGTGTACGGTGGGAGGTCTATATAAGCAGAgcTCGTTTA

GTGAACCGTCAGATCGCCTGGAACGCCATCCACGCTGTTTTGACCTCCATAGAAGACAGCGATCGCGccaccAT

GGCCGGGATGTTCCAGGCACTGTCCGAAGGCTGCACACCCTATGATATTAACCAGATGCTGAATGTCCTGGGAG

ACCACCAGGTCTCTGGCCTGGAGCAGCTGGAGAGCATCATCAACTTCGAGAAGCTGACCGAGTGGACAAGCTCC

AATGTGATGCCTATCCTGTCCCCACTGACCAAGGGCATCCTGGGCTTCGTGTTTACCCTGACAGTGCCTTCTGA

GCGGGGCCTGTCTTGCATCAGCGAGGCAGACGCAACCACACCAGAGTCCGCCAATCTGGGCGAGGAGATCCTGT

CTCAGCTGTACCTGTGGCCCCGGGTGACATATCACTCCCCTTCTTACGCCTATCACCAGTTCGAGCGGAGAGCC

AAGTACAAGAGACACTTCCCAGGCTTTGGCCAGTCTCTGCTGTTCGGCTACCCCGTGTACGTGTTCGGCGATTG

CGTGCAGGGCGACTGGGATGCCATCCGGTTTAGATACTGCGCACCACCTGGATATGCACTGCTGAGGTGTAACG

ACACCAATTATTCCGCCCTGCTGGCAGTGGGCGCCCTGGAGGGCCCTCGCAATCAGGATTGGCTGGGCGTGCCA

-continued

AGGCAGCTGGTGACACGCATGCAGGCCATCCAGAACGCAGGCCTGTGCACCCTGGTGGCAATGCTGGAGGAGAC

AATCTTCTGGCTGCAGGCCTTTCTGATGGCCCTGACCGACAGCGGCCCCAAGACAAACATCATCGTGGATTCCC

AGTACGTGATGGGCATCTCCAAGCCTTCTTTCCAGGAGTTTGTGGACTGGGAGAACGTGAGCCCAGAGCTGAAT

TCCACCGATCAGCCATTCTGGCAGGCAGGAATCCTGGCAAGGAACCTGGTGCCTATGGTGGCCACAGTGCAGGG

CCAGAATCTGAAGTACCAGGGCCAGAGCCTGGTCATCAGCGCCTCCATCATCGTGTTTAACCTGCTGGAGCTGG

AGGGCGACTATCGGGACGATGGCAACGTGTGGGTGCACACCCCACTGAGCCCCAGAACACTGAACGCCTGGGTG

AAGGCCGTGGAGGAGAAGAAGGGCATCCCAGTGCACCTGGAGCTGGCCTCCATGACCAATATGGAGCTGATGTC

TAGCATCGTGCACCAGCAGGTGAGGACATACGGACCCGTGTTCATGTGCCTGGGAGGCCTGCTGACCATGGTGG

CAGGAGCCGTGTGGCTGACAGTGCGGGTGCTGGAGCTGTTCAGAGCCGCCCAGCTGGCCAACGATGTGGTGCTG

CAGATCATGGAGCTGTGCGGAGCAGCCTTTCGCCAGGTGTGCCACACCACAGTGCCATGGCCCAATGCCTCCCT

GACCCCCAAGTGGAACAATGAGACAACACAGCCTCAGATCGCCAACTGTAGCGTGTACGACTTCTTCGTGTGGC

TGCACTACTATAGCGTGAGGGATACCCTGTGCCCCGCGTGACATACCACATGAATAAGTACGCCTATCACATG

CTGGAGAGGCGCGCCAAGTATAAGAGAGGCCCTGGCCCAGGCGCAAAGTTTGTGGCAGCATGGACCCTGAAGGC

CGCCGCCGGCCCCGGCCCCGGCCAGTATATCAAGGCTAACAGTAAGTTCATTGGAATCACAGAGCTGGGACCCG

GACCTGGATAATGAGTTTAAACTCCCATTTAAATGTGAGGGTTAATGCTTCGAGCAGACATGATAAGATACATT

GATGAGTTTGGACAAACCACAACTAGAATGCAGTGAAAAAAATGCTTTATTTGTGAAATTTGTGATGCTATTGC

TTTATTTGTAACCATTATAAGCTGCAATAAACAAGTTAACAACAACAATTGCATTCATTTTATGTTTCAGGTTC

AGGGGGAGATGTGGGAGGTTTTTTAAAGCAAGTAAAACCTCTACAAATGTGGTAAAATAACTATAACGGTCCTA

AGGTAGCGAGTGAGTAGTGTTCTGGGGCGGGGGAGGACCTGCATGAGGGCCAGAATAACTGAAATCTGTGCTTT

TCTGTGTGTTGCAGCAGCATGAGCGGAAGCGGCTCCTTTGAGGGAGGGGTATTCAGCCCTTATCTGACGGGGCG

TCTCCCCTCCTGGGCGGGAGTGCGTCAGAATGTGATGGGATCCACGGTGGACGGCCGGCCCGTGCAGCCCGCGA

ACTCTTCAACCCTGACCTATGCAACCCTGAGCTCTTCGTCGTTGGACGCAGCTGCCGCCGCAGCTGCTGCATCT

GCCGCCAGCGCCGTGCGCGGAATGGCCATGGGCGCCGGCTACTACGGCACTCTGGTGGCCAACTCGAGTTCCAC

CAATAATCCCGCCAGCCTGAACGAGGAGAAGCTGTTGCTGCTGATGGCCCAGCTCGAGGCCTTGACCCAGCGCC

TGGGCGAGCTGACCCAGCAGGTGGCTCAGCTGCAGGAGCAGACGCGGGCCGCGGTTGCCACGGTGAAATCCAAA

TAAAAAATGAATCAATAAATAAACGGAGACGGTTGTTGATTTTAACACAGAGTCTGAATCTTTATTTGATTTTT

CGCGCGCGGTAGGCCCTGGACCACCGGTCTCGATCATTGAGCACCCGGTGGATCTTTTCCAGGACCCGGTAGAG

GTGGGCTTGGATGTTGAGGTACATGGGCATGAGCCCGTCCCGGGGGTGGAGGTAGCTCCATTGCAGGGCCTCGT

GCTCGGGGGTGGTGTTGTAAATCACCCAGTCATAGCAGGGGCGCAGGGCATGGTGTTGCACAATATCTTTGAGG

AGGAGACTGATGGCCACGGGCAGCCCTTTGGTGTAGGTGTTTACAAATCTGTTGAGCTGGGAGGGATGCATGCG

GGGGGAGATGAGGTGCATCTTGGCCTGGATCTTGAGATTGGCGATGTTACCGCCCAGATCCCGCCTGGGGTTCA

TGTTGTGCAGGACCACCAGCACGGTGTATCCGGTGCACTTGGGGAATTTATCATGCAACTTGGAAGGGAAGGCG

TGAAAGAATTTGGCGACGCCTTTGTGCCCGCCCAGGTTTTCCATGCACTCATCCATGATGATGGCGATGGGCCC

GTGGGCGGCGGCCTGGGCAAAGACGTTTCGGGGGTCGGACACATCATAGTTGTGGTCCTGGGTGAGGTCATCAT

AGGCCATTTTAATGAATTTGGGGCGGAGGGTGCCGGACTGGGGGACAAAGGTACCCTCGATCCCGGGGCGTAG

TTCCCCTCACAGATCTGCATCTCCCAGGCTTTGAGCTCGGAGGGGGGATCATGTCCACCTGCGGGCGATAAA

GAACACGGTTTCCGGGGCGGGGAGATGAGCTGGCCGAAAGCAAGTTCCGGAGCAGCTGGGACTTGCCGCAGC

CGGTGGGGCCGTAGATGACCCCGATGACCGGCTGCAGGTGGTAGTTGAGGGAGAGACAGCTGCCGTCCTCCCGG

AGGAGGGGGCCACCTCGTTCATCATCTCGCGCACGTGCATGTTCTCGCGCACCAGTTCCGCCAGGAGGCGCTC

TCCCCCCAGGGATAGGAGCTCCTGGAGCGAGGCGAAGTTTTTCAGCGGCTTGAGTCCGTCGGCCATGGGCATTT

-continued

```
TGGAGAGGGTTTGTTGCAAGAGTTCCAGGCGGTCCCAGAGCTCGGTGATGTGCTCTACGGCATCTCGATCCAGC

AGACCTCCTCGTTTCGCGGGTTGGGACGGCTGCGGGAGTAGGGCACCAGACGATGGGCGTCCAGCGCAGCCAGG

GTCCGGTCCTTCCAGGGTCGCAGCGTCCGCGTCAGGGTGGTCTCCGTCACGGTGAAGGGGTGCGCGCCGGGCTG

GGCGCTTGCGAGGGTGCGCTTCAGGCTCATCCGGCTGGTCGAAAACCGCTCCCGATCGGCGCCCTGCGCGTCGG

CCAGGTAGCAATTGACCATGAGTTCGTAGTTGAGCGCCTCGGCCGCGTGGCCTTTGGCGCGGAGCTTACCTTTG

GAAGTCTGCCCGCAGGCGGGACAGAGGAGGGACTTGAGGGCGTAGAGCTTGGGGGCGAGGAAGACGGACTCGGG

GGCGTAGGCGTCCGCGCCGCAGTGGGCGCAGACGGTCTCGCACTCCACGAGCCAGGTGAGGTCGGGCTGGTCGG

GGTCAAAAACCAGTTTCCCGCCGTTCTTTTTGATGCGTTTCTTACCTTTGGTCTCCATGAGCTCGTGTCCCCGC

TGGGTGACAAAGAGGCTGTCCGTGTCCCCGTAGACCGACTTTATGGGCCGGTCCTCGAGCGGTGTGCCGCGGTC

CTCCTCGTAGAGGAACCCCGCCCACTCCGAGACGAAAGCCCGGGTCCAGGCCAGCACGAAGGAGGCCACGTGGG

ACGGGTAGCGGTCGTTGTCCACCAGCGGGTCCACCTTTTCCAGGGTATGCAAACACATGTCCCCCTCGTCCACA

TCCAGGAAGGTGATTGGCTTGTAAGTGTAGGCCACGTGACCGGGGGTCCCGGCCGGGGGGGTATAAAAGGGTGC

GGGTCCCTGCTCGTCCTCACTGTCTTCCGGATCGCTGTCCAGGAGCGCCAGCTGTTGGGGTAGGTATTCCCTCT

CGAAGGCGGGCATGACCTCGGCACTCAGGTTGTCAGTTTCTAGAAACGAGGAGGATTTGATATTGACGGTGCCG

GCGGAGATGCCTTTCAAGAGCCCCTCGTCCATCTGGTCAGAAAAGACGATCTTTTTGTTGTCGAGCTTGGTGGC

GAAGGAGCCGTAGAGGGCGTTGGAGAGGAGCTTGGCGATGGAGCGCATGGTCTGGTTTTTTTCCTTGTCGGCGC

GCTCCTTGGCGGCGATGTTGAGCTGCACGTACTCGCGCGCCACGCACTTCCATTCGGGGAAGACGGTGGTCAGC

TCGTCGGGCACGATTCTGACCTGCCAGCCCCGATTATGCAGGGTGATGAGGTCCACACTGGTGGCCACCTCGCC

GCGCAGGGGCTCATTAGTCCAGCAGAGGCGTCCGCCCTTGCGCGAGCAGAAGGGGGGCAGGGGGTCCAGCATGA

CCTCGTCGGGGGGTCGGCATCGATGGTGAAGATGCCGGGCAGGAGGTCGGGGTCAAAGTAGCTGATGGAAGTG

GCCAGATCGTCCAGGGCAGCTTGCCATTCGCGCACGGCCAGCGCGCtCTCGTAGGGACTGAGGGGCGTGCCCCA

GGGCATGGGATGGGTAAGCGCGGAGGCGTACATGCCGCAGATGTCGTAGACGTAGAGGGGCTCCTCGAGGATGC

CGATGTAGGTGGGGTAGCAGCGCCCCCCGCGGATGCTGGCGCGCACGTAGTCATACAGCTCGTGCGAGGGGCG

AGGAGCCCCGGGCCCAGGTTGGTGCGACTGGGCTTTTCGGCGCGGTAGACGATCTGGCGGAAAATGGCATGCGA

GTTGGAGGAGATGGTGGGCCTTTGGAAGATGTTGAAGTGGGCGTGGGGCAGTCCGACCGAGTCGCGGATGAAGT

GGGCGTAGGAGTCTTGCAGCTTGGCGACGAGCTCGGCGGTGACTAGGACGTCCAGAGCGCAGTAGTCGAGGGTC

TCCTGGATGATGTCATACTTGAGCTGTCCCTTTTGTTTCCACAGCTCGCGGTTGAGAAGGAACTCTTCGCGGTC

CTTCCAGTACTCTTCGAGGGGGAACCCGTCCTGATCTGCACGGTAAGAGCCTAGCATGTAGAACTGGTTGACGG

CCTTGTAGGCGCAGCAGCCCTTCTCCACGGGGAGGGCGTAGGCCTGGGCGGCCTTGCGCAGGGAGGTGTGCGTG

AGGGCGAAAGTGTCCCTGACCATGACCTTGAGGAACTGGTGCTTGAAGTCGATATCGTCGCAGCCCCCTGCTC

CCAGAGCTGGAAGTCCGTGCGCTTCTTGTAGGCGGGGTTGGGCAAAGCGAAAGTAACATCGTTGAAGAGGATCT

TGCCCGCGCGGGGCATAAAGTTGCGAGTGATGCGGAAAGGTTGGGGCACCTCGGCCCGGTTGTTGATGACCTGG

GCGGCGAGCACGATCTCGTCGAAGCCGTTGATGTTGTGGCCCACGATGTAGAGTTCCACGAATCGCGGACGGCC

CTTGACGTGGGCAGTTTCTTGAGCTCCTCGTAGGTGAGCTCGTCGGGGTCGCTGAGCCCGTGCTGCTCGAGCG

CCCAGTCGGCGAGATGGGGGTTGGCGCGGAGGAAGGAAGTCCAGAGATCCACGCCAGGGCGGTTTGCAGACGG

TCCCGGTACTGACGGAACTGCTGCCCGACGGCCATTTTTTCGGGGGTGACGCAGTAGAAGGTGCGGGGGTCCCC

GTGCCAGCGATCCCATTTGAGCTGGAGGGCGAGATCGAGGGCGAGCTCGACGAGCCGGTCGTCCCCGGAGAGTT

TCATGACCAGCATGAAGGGGACGAGCTGCTTGCCGAAGGACCCCATCCAGGTGTAGGTTTCCACATCGTAGGTG

AGGAAGAGCCTTTCGGTGCGAGGATGCGAGCCGATGGGAAGAACTGGATCTCCTGCCACCAATTGGAGGAATG

GCTGTTGATGTGATGGAAGTAGAAATGCCGACGGCGCGCCGAACACTCGTGCTTGTGTTTATACAAGCGGCCAC

AGTGCTCGCAACGCTGCACGGGATGCACGTGCTGCACGAGCTCTACCTGAGTTCCTTTGACGAGGAATTTCAGT
```

-continued

```
GGGAAGTGGAGTCGTGGCGCCTGCATCTCGTGCTGTACTACGTCGTGGTGGTCGGCCTGGCCCTCTTCTGCCTC
GATGGTGGTCATGCTGACGAGCCCGCGCGGGAGGCAGGTCCAGACCTCGGCGCGAGCGGGTCGGAGAGCGAGGA
CGAGGGCGCGCAGGCCGGAGCTGTCCAGGGTCCTGAGACGCTGCGGAGTCAGGTCAGTGGGCAGCGGCGGCGCG
CGGTTGACTTGCAGGAGTTTTTCCAGGGCGCGCGGGAGGTCCAGATGGTACTTGATCTCCACCGCGCCATTGGT
GGCGACGTCGATGGCTTGCAGGGTCCCGTGCCCCTGGGGTGTGACCACCGTCCCCCGTTTCTTCTTGGGCGGCT
GGGGCGACGGGGCGGTGCCTCTTCCATGGTTAGAAGCGGCGGCGAGGACGCGCGCCGGGCGGCAGGGGCGGCT
CGGGGCCCGGAGGCAGGGGCGGCAGGGGCACGTCGGCGCCGCGCGCGGGTAGGTTCTGGTACTGCGCCCGGAGA
AGACTGGCGTGAGCGACGACGCGACGGTTGACGTCCTGGATCTGACGCCTCTGGGTGAAGGCCACGGGACCCGT
GAGTTTGAACCTGAAAGAGAGTTCGACAGAATCAATCTCGGTATCGTTGACGGCGGCCTGCCGCAGGATCTCTT
GCACGTCGCCCGAGTTGTCCTGGTAGGCGATCTCGGTCATGAACTGCTCGATCTCCTCCTCTTGAAGGTCTCCG
CGGCCGGCGCGCTCCACGGTGGCCGCGAGGTCGTTGGAGATGCGGCCCATGAGCTGCGAGAAGGCGTTCATGCC
CGCCTCGTTCCAGACGCGGCTGTAGACCACGACGCCCTCGGGATCGCgGGCGCGCATGACCACCTGGGCGAGGT
TGAGCTCCACGTGGCGCGTGAAGACCGCGTAGTTGCAGAGGCGCTGGTAGAGGTAGTTGAGCGTGGTGGCGATG
TGCTCGGTGACGAAGAAATACATGATCCAGCGGCGGAGCGGCATCTCGCTGACGTCGCCCAGCGCCTCCAAACG
TTCCATGGCCTCGTAAAAGTCCACGGCGAAGTTGAAAAACTGGGAGTTGCGCGCCGAGACGGTCAACTCCTCCT
CCAGAAGACGGATGAGCTCGGCGATGGTGGCGCGCACCTCGCGCTCGAAGGCCCCCGGGAGTTCCTCCACTTCC
TCTTCTTCCTCCTCCACTAACATCTCTTCTACTTCCTCCTCAGGCGGCAGTGGTGGCGGGGGAGGGGCCTGCG
TCGCCGGCGGCGCACGGGCAGACGGTCGATGAAGCGCTCGATGGTCTCGCCGCGCCGGCGTCGCATGGTCTCGG
TGACGGCGCGCCCGTCCTCGCGGGGCCGCAGCGTGAAGACGCCGCCGCGCATCTCCAGGTGGCCGGGGGGGTCC
CCGTTGGGCAGGGAGAGGGCGCTGACGATGCATCTTATCAATTGCCCCGTAGGGACTCCGCGCAAGGACCTGAG
CGTCTCGAGATCCACGGGATCTGAAAACCGCTGAACGAAGGCTTCGAGCCAGTCGCAGTCGCAAGGTAGGCTGA
GCACGGTTTCTTCTGGCGGGTCATGTTGGTTGGGAGCGGGCGGGCGATGCTGCTGGTGATGAAGTTGAAATAG
GCGGTTCTGAGACGGCGGATGGTGGCGAGGAGCACCAGGTCTTTGGGCCCGGCTTGCTGGATGCGCAGACGGTC
GGCCATGCCCCAGGCGTGGTCCTGACACCTGGCCAGGTCCTTGTAGTAGTCCTGCATGAGCCGCTCCACGGGCA
CCTCCTCCTCGCCCGCGCGCCGTGCATGCGCGTGAGCCCGAAGCCGCGCTGGGGCTGGACGAGCGCCAGGTCG
GCGACGACGCGCTCGGCGAGGATGGCTTGCTGGATCTGGGTGAGGGTGGTCTGGAAGTCATCAAAGTCGACGAA
GCGGTGGTAGGCTCCGGTGTTGATGGTGTAGGAGCAGTTGGCCATGACGGACCAGTTGACGGTCTGGTGGCCCG
GACGCACGAGCTCGTGGTACTTGAGGCGCGAGTAGGCGCGCGTGTCGAAGATGTAGTCGTTGCAGGTGCGCACC
AGGTACTGGTAGCCGATGAGGAAGTGCGGCGGCGGCTGGCGGTAGAGCGGCCATCGCTCGGTGGCGGGGGCGCC
GGGCGCGAGGTCCTCGAGCATGGTGCGGTGGTAGCCGTAGATGTACCTGGACATCCAGGTGATGCCGGCGGCGG
TGGTGGAGGCGCGCGGGAACTCGCGGACGCGGTTCCAGATGTTGCGCAGCGGCAGGAAGTAGTTCATGGTGGGC
ACGGTCTGGCCCGTGAGGCGCGCGCAGTCGTGGATGCTCTATACGGGCAAAAACGAAAGCGGTCAGCGGCTCGA
CTCCGTGGCCTGGAGGCTAAGCGAACGGGTTGGGCTGCGCGTGTACCCCGGTTCGAATCTCGAATCAGGCTGGA
GCCGCAGCTAACGTGGTATTGGCACTCCCGTCTCGACCCAAGCCTGCACCAACCCTCCAGGATACGGAGGCGGG
TCGTTTTGCAACTTTTTTTTGGAGGCCGGATGAGACTAGTAAGCGCGGAAAGCGGCCGACCGCGATGGCTCGCT
GCCGTAGTCTGGAGAAGAATCGCCAGGGTTGCGTTGCGGTGTGCCCCGGTTCGAGGCCGGCCGGATTCCGCGGC
TAACGAGGGCGTGGCTGCCCCGTCGTTTCCAAGACCCCATAGCCAGCCGACTTCTCCAGTTACGGAGCGAGCCC
CTCTTTTGTTTTGTTTGTTTTTGCCAGATGCATCCCGTACTGCGGCAGATGCGCCCCCACCACCCTCCACCGCA
ACAACAGCCCCCTCCACAGCCGGCGCTTCTGCCCCCGCCCCAGCAGCAACTTCCAGCCACGACCGCCGCGGCCG
CCGTGAGCGGGGCTGGACAGAGTTATGATCACCAGCTGGCCTTGGAAGAGGGCGAGGGGCTGGCGCGCCTGGGG
```

-continued

```
GCGTCGTCGCCGGAGCGGCACCCGCGCGTGCAGATGAAAAGGGACGCTCGCGAGGCCTACGTGCCCAAGCAGAA
CCTGTTCAGAGACAGGAGCGGCGAGGAGCCCGAGGAGATGCGCGCGCCCGGTTCCACGCGGGGCGGGAGCTGC
GGCGCGGCCTGGACCGAAAGAGGGTGCTGAGGGACGAGGATTTCGAGGCGGACGAGCTGACGGGGATCAGCCCC
GCGCGCGCGCACGTGGCCGCGGCCAACCTGGTCACGGCGTACGAGCAGACCGTGAAGGAGGAGAGCAACTTCCA
AAAATCCTTCAACAACCACGTGCGCACCCTGATCGCGCGCGAGGAGGTGACCCTGGGCCTGATGCACCTGTGGG
ACCTGCTGGAGGCCATCGTGCAGAACCCCACCAGCAAGCCGCTGACGGCGCAGCTGTTCCTGGTGGTGCAGCAT
AGTCGGGACAACGAAGCGTTCAGGGAGGCGCTGCTGAATATCACCGAGCCCGAGGGCCGCTGGCTCCTGGACCT
GGTGAACATTCTGCAGAGCATCGTGGTGCAGGAGCGCGGGCTGCCGCTGTCCGAGAAGCTGGCGGCCATCAACT
TCTCGGTGCTGAGTTTGGGCAAGTACTACGCTAGGAAGATCTACAAGACCCCGTACGTGCCCATAGACAAGGAG
GTGAAGATCGACGGGTTTTACATGCGCATGACCCTGAAAGTGCTGACCCTGAGCGACGATCTGGGGGTGTACCG
CAACGACAGGATGCACCGTGCGGTGAGCGCCAGCAGGCGGCGCGAGCTGAGCGACCAGGAGCTGATGCATAGTC
TGCAGCGGGCCCTGACCGGGGCCGGGACCGAGGGGGAGAGCTACTTTGACATGGGCGCGGACCTGCACTGGCAG
CCCAGCCGCCGGGCCTTGGAGGCGGCGGCAGGACCCTACGTAGAAGAGGTGGACGATGAGGTGGACGAGGAGGG
CGAGTACCTGGAAGACTGATGGCGCGACCGTATTTTTGCTAGATGCAACAACAACAGCCACCTCCTGATCCCGC
GATGCGGGCGGCGCTGCAGAGCCAGCCGTCCGGCATTAACTCCTCGGACGATTGGACCCAGGCCATGCAACGCA
TCATGGCGCTGACGACCCGCAACCCCGAAGCCTTTAGACAGCAGCCCCAGGCCAACCGGCTCTCGGCCATCCTG
GAGGCCGTGGTGCCCTCGCGCTCCAACCCCACGCACGAGAAGGTCCTGGCCATCGTGAACGCGCTGGTGGAGAA
CAAGGCCATCCGCGGCGACGAGGCCGGCCTGGTGTACAACGCGCTGCTGGAGCGCGTGGCCCGCTACAACAGCA
CCAACGTGCAGACCAACCTGGACCGCATGGTGACCGACGTGCGCGAGGCCGTGGCCCAGCGCGAGCGGTTCCAC
CGCGAGTCCAACCTGGGATCCATGGTGGCGCTGAACGCCTTCCTCAGCACCCAGCCCGCCAACGTGCCCCGGGG
CCAGGAGGACTACACCAACTTCATCAGCGCCCTGCGCCTGATGGTGACCGAGGTGCCCCAGAGCGAGGTGTACC
AGTCCGGGCCGGACTACTTCTTCCAGACCAGTCGCCAGGGCTTGCAGACCGTGAACCTGAGCCAGGCTTTCAAG
AACTTGCAGGGCCTGTGGGCGTGCAGGCCCCGGTCGGGGACCGCGCGACGTGTCGAGCCTGCTGACGCCGAA
CTCGCGCCTGCTGCTGCTGCTGGTGGCCCCCTTCACGGACAGCGGCAGCATCAACCGCAACTCGTACCTGGGCT
ACCTGATTAACCTGTACCGCGAGGCCATCGGCCAGGCGCACGTGGACGAGCAGACCTACCAGGAGATCACCCAC
GTGAGCCGCGCCCTGGGCCAGGACGACCCGGGCAACCTGGAAGCCACCCTGAACTTTTTGCTGACCAACCGGTC
GCAGAAGATCCCGCCCCAGTACGCGCTCAGCACCGAGGAGGAGCGCATCCTGCGTTACGTGCAGCAGAGCGTGG
GCCTGTTCCTGATGCAGGAGGGGCCACCCCCAGCGCCGCGCTCGACATGACCGCGCGCAACATGGAGCCCAGC
ATGTACGCCAGCAACCGCCCGTTCATCAATAAACTGATGGACTACTTGCATCGGGCGGCCGCCATGAACTCTGA
CTATTTCACCAACGCCATCCTGAATCCCCACTGGCTCCCGCCGCCGGGGTTCTACACGGGCGAGTACGACATGC
CCGACCCCAATGACGGGTTCCTGTGGGACGATGTGGACAGCAGCGTGTTCTCCCCCCGACCGGGTGCTAACGAG
CGCCCCTTGTGGAAGAAGGAAGGCAGCGACCGACGCCCGTCCTCGGCGCTGTCCGGCCGCGAGGGTGCTGCCGC
GGCGGTGCCCGAGGCCGCCAGTCCTTTCCCGAGCTTGCCCTTCTCGCTGAACAGTATCCGCAGCAGCGAGCTGG
GCAGGATCACGCGCCCGCGCTTGCTGGGCGAAGAGGAGTACTTGAATGACTCGCTGTTGAGACCCGAGCGGGAG
AAGAACTTCCCCAATAACGGGATAGAAAGCCTGGTGGACAAGATGAGCCGCTGGAAGACGTATGCGCAGGAGCA
CAGGGACGATCCCCGGGCGTCGCAGGGGGCCACGAGCCGGGCAGCGCCGCCCGTAAACGCCGGTGGCACGACA
GGCAGCGGGGACAGATGTGGGACGATGAGGACTCCGCCGACGACAGCAGCGTGTTGGACTTGGGTGGGAGTGGT
AACCCGTTCGCTCACCTGCGCCCCCGTATCGGGCGCATGATGTAAGAGAAACCGAAAATAAATGATACTCACCA
AGGCCATGGCGACCAGCGTGCGTTCGTTTCTTCTCTGTTGTTGTTGTATCTAGTATGATGAGGCGTGCGTACCC
GGAGGGTCCTCCTCCCTCGTACGAGAGCGTGATGCAGCAGGCGATGCGGCGGCGGCGATGCAGCCCCCGCTGG
AGGCTCCTTACGTGCCCCCGCGGTACCTGGCGCCTACGGAGGGGCGGAACAGCATTCGTTACTCGGAGCTGGCA
```

-continued

```
CCCTTGTACGATACCACCCGGTTGTACCTGGTGGACAACAAGTCGGCGGACATCGCCTCGCTGAACTACCAGAA
CGACCACAGCAACTTCCTGACCACCGTGGTGCAGAACAATGACTTCACCCCCACGGAGGCCAGCACCCAGACCA
TCAACTTTGACGAGCGCTCGCGGTGGGGCGGCCAGCTGAAAACCATCATGCACACCAACATGCCCAACGTGAAC
GAGTTCATGTACAGCAACAAGTTCAAGGCGCGGGTGATGGTCTCCCGCAAGACCCCCAATGGGGTGACAGTGAC
AGAGGATTATGATGGTAGTCAGGATGAGCTGAAGTATGAATGGGTGGAATTTGAGCTGCCCGAAGGCAACTTCT
CGGTGACCATGACCATCGACCTGATGAACAACGCCATCATCGACAATTACTTGGCGGTGGGGCGGCAGAACGGG
GTGCTGGAGAGCGACATCGGCGTGAAGTTCGACACTAGGAACTTCAGGCTGGGCTGGGACCCCGTGACCGAGCT
GGTCATGCCCGGGGTGTACACCAACGAGGCTTTCCATCCCGATATTGTCTTGCTGCCCGGCTGCGGGGTGGACT
TCACCGAGAGCCGCCTCAGCAACCTGCTGGGCATTCGCAAGAGGCAGCCCTTCCAGGAAGGCTTCCAGATCATG
TACGAGGATCTGGAGGGGGCAACATCCCCGCGCTCCTGGATGTCGACGCCTATGAGAAAAGCAAGGAGGATGC
AGCAGCTGAAGCAACTGCAGCCGTAGCTACCGCCTCTACCGAGGTCAGGGGCGATAATTTTGCAAGCGCCGCAG
CAGTGGCAGCGGCCGAGGCGGCTGAAACCGAAAGTAAGATAGTCATTCAGCCGGTGGAGAAGGATAGCAAGAAC
AGGAGCTACAACGTACTACCGGACAAGATAAACACCGCCTACCGCAGCTGGTACCTAGCCTACAACTATGGCGA
CCCCGAGAAGGGCGTGCGCTCCTGGACGCTGCTCACCACCTCGGACGTCACCTGCGCGTGGAGCAAGTCTACT
GGTCGCTGCCCGACATGATGCAAGACCCGGTCACCTTCCGCTCCACGCGTCAAGTTAGCAACTACCCGGTGGTG
GGCGCCGAGCTCCTGCCCGTCTACTCCAAGAGCTTCTTCAACGAGCAGGCCGTCTACTCGCAGCAGCTGCGCGC
CTTCACCTCGCTTACGCACGTCTTCAACCGCTTCCCCGAGAACCAGATCCTCGTCCGCCCGCCCGCGCCCACCA
TTACCACCGTCAGTGAAAACGTTCCTGCTCTCACAGATCACGGGACCCTGCCGCTGCGCAGCAGTATCCGGGGA
GTCCAGCGCGTGACCGTTACTGACGCCAGACGCCGCACCTGCCCCTACGTCTACAAGGCCCTGGGCATAGTCGC
GCCGCGCGTCCTCTCGAGCCGCACCTTCTAAATGTCCATTCTCATCTCGCCCAGTAATAACACCGGTTGGGGCC
TGCGCGCGCCCAGCAAGATGTACGGAGGCGCTCGCCAACGCTCCACGCAACACCCCGTGCGCGTGCGCGGGCAC
TTCCGCGCTCCCTGGGGCGCCCTCAAGGGCCGCGTGCGGTCGCGCACCACCGTCGACGACGTGATCGACCAGGT
GGTGGCCGACGCGCGCAACTACACCCCCGCCGCCGCGCCCGTCTCCACCGTGGACGCCGTCATCGACAGCGTGG
TGGCcGACGCGCGCCGGTACGCCCGCGCCAAGAGCCGGCGGCGGCGCATCGCCCGGCGGCACCGGAGCACCCCC
GCCATGCGCGCGGCGCGAGCCTTGCTGCGCAGGGCCAGGCGCACGGGACGCAGGGCCATGCTCAGGGCGGCCAG
ACGCGCGGCTTCAGGCGCCAGCGCCGGCAGGACCCGGAGACGCGCGGCCACGGCGGCGGCAGCGGCCATCGCCA
GCATGTCCGCCCGCGGCGAGGGAACGTGTACTGGGTGCGCGACGCCGCCACCGGTGTGCGCGTGCCCGTGCGC
ACCCGCCCCCCTCGCACTTGAAGATGTTCACTTCGCGATGTTGATGTGTCCCAGCGGCGAGGAGGATGTCCAAG
CGCAAATTCAAGGAAGAGATGCTCCAGGTCATCGCGCCTGAGATCTACGGCCCTGCGGTGGTGAAGGAGGAAAG
AAAGCCCCGCAAAATCAAGCGGGTCAAAAAGGACAAAAAGGAAGAAGAAAGTGATGTGGACGGATTGGTGGAGT
TTGTGCGCGAGTTCGCCCCCCGGCGGCGCGTGCAGTGGCGCGGGCGGAAGGTGCAACCGGTGCTGAGACCCGGC
ACCACCGTGGTCTTCACGCCCGGCGAGCGCTCCGGCACCGCTTCCAAGCGCTCCTACGACGAGGTGTACGGGGA
TGATGATATTCTGGAGCAGGCGGCCGAGCGCCTGGGCGAGTTTGCTTACGGCAAGCGCAGCCGTTCCGCACCGA
AGGAAGAGGCGGTGTCCATCCCGCTGGACCACGGCAACCCCACGCCGAGCCTCAAGCCCGTGACCTTGCAGCAG
GTGCTGCCGACCGCGGCGCCGCGCGGGGTTCAAGCGCGAGGGCGAGGATCTGTACCCCACCATGCAGCTGAT
GGTGCCCAAGCGCCAGAAGCTGGAAGACGTGCTGGAGACCATGAAGGTGGACCCGGACGTGCAGCCCGAGGTCA
AGGTGCGGCCCATCAAGCAGGTGGCCCCGGGCCTGGGCGTGCAGACCGTGGACATCAAGATTCCCACGGAGCCC
ATGGAAACGCAGACCGAGCCCATGATCAAGCCCAGCACCAGCACCATGGAGGTGCAGACGGATCCCTGGATGCC
ATCGGCTCCTAGTCGAAGACCCCGGCGCAAGTACGGCGCGGCCAGCCTGCTGATGCCCAACTACGCGCTGCATC
CTTCCATCATCCCCACGCCGGGCTACCGCGGCACGCGCTTCTACCGCGGTCATACCAGCAGCCGCCGCCGCAAG
```

-continued

```
ACCACCACTCGCCGCCGCCGTCGCCGCACCGCCGCTGCAACCACCCCTGCCGCCCTGGTGCGGAGAGTGTACCG
CCGCGGCCGCGCACCTCTGACCCTGCCGCGCGCGCGCTACCACCCGAGCATCGCCATTTAAACTTTCGCCtGCT
TTGCAGATCAATGGCCCTCACATGCCGCCTTCGCGTTCCCATTACGGGCTACCGAGGAAGAAAACCGCGCCGTA
GAAGGCTGGCGGGGAACGGGATGCGTCGCCACCACCACCGGCGGCGGCGCGCCATCAGCAAGCGGTTGGGGGGA
GGCTTCCTGCCCGCGCTGATCCCCATCATCGCCGCGGCGATCGGGGCGATCCCCGGCATTGCTTCCGTGGCGGT
GCAGGCCTCTCAGCGCCACTGAGACACACTTGGAAACATCTTGTAATAAACCaATGGACTCTGACGCTCCTGGT
CCTGTGATGTGTTTTCGTAGACAGATGGAAGACATCAATTTTTCGTCCCTGGCTCCGCGACACGGCACGCGGCC
GTTCATGGGCACCTGGAGCGACATCGGCACCAGCCAACTGAACGGGGGCGCCTTCAATTGGAGCAGTCTCTGGA
GCGGGCTTAAGAATTTCGGGTCCACGCTTAAAACCTATGGCAGCAAGGCGTGGAACAGCACCACAGGGCAGGCG
CTGAGGGATAAGCTGAAAGAGCAGAACTTCCAGCAGAAGGTGGTCGATGGGCTCGCCTCGGGCATCAACGGGGT
GGTGGACCTGGCCAACCAGGCCGTGCAGCGGCAGATCAACAGCCGCCTGGACCCGGTGCCGCCCGCCGGCTCCG
TGGAGATGCCGCAGGTGGAGGAGGAGCTGCCTCCCCTGGACAAGCGGGGCGAGAAGCGACCCCGCCCCGATGCG
GAGGAGACGCTGCTGACGCACACGGACGAGCCGCCCCCGTACGAGGAGGCGGTGAAACTGGGTCTGCCCACCAC
GCGGCCCATCGCGCCCCTGGCCACCGGGGTGCTGAAACCCGAAAAGCCCGCGACCCTGGACTTGCCTCCTCCCC
AGCCTTCCCGCCCCTCTACAGTGGCTAAGCCCCTGCCGCCGGTGGCCGTGGCCCGCGCGCGACCCGGGGCACC
GCCCGCCCTCATGCGAACTGGCAGAGCACTCTGAACAGCATCGTGGGTCTGGGAGTGCAGAGTGTGAAGCGCCG
CCGCTGCTATTAAACCTACCGTAGCGCTTAACTTGCTTGTCTGTGTGTATGTATTATGTCGCCGCCGCCGCT
GTCCACCAGAAGGAGGAGTGAAGAGGCGCGTCGCCGAGTTGCAAGATGGCCACCCCATCGATGCTGCCCCAGTG
GGCGTACATGCACATCGCCGGACAGGACGCTTCGGAGTACCTGAGTCCGGGTCTGGTGCAGTTTGCCCGCGCCA
CAGACACCTACTTCAGTCTGGGGAACAAGTTTAGGAACCCCACGGTGGCGCCCACGCACGATGTGACCACCGAC
CGCAGCCAGCGGCTGACGCTGCGCTTCGTGCCCGTGGACCGCGAGGACAACACCTACTCGTACAAAGTGCGCTA
CACGCTGGCCGTGGGCGACAACCGCGTGCTGGACATGGCCAGCACCTACTTTGACATCCGCGGCGTGCTGGATC
GGGGCCCTAGCTTCAAACCCTACTCCGGCACCGCCTACAACAGTCTGGCCCCCAAGGGAGCACCCAACACTTGT
CAGTGGACATATAAAGCCGATGGTGAAACTGCCACAGAAAAAACCTATACATATGGAAATGCACCCGTGCAGGG
CATTAACATCACAAAAGATGGTATTCAACTTGGAACTGACACCGATGATCAGCCAATCTACGCAGATAAAACCT
ATCAGCCTGAACCTCAAGTGGGTGATGCTGAATGGCATGACATCACTGGTACTGATGAAAAGTATGGAGGCAGA
GCTCTTAAGCCTGATACCAAAATGAAGCCTTGTTATGGTTCTTTTGCCAAGCCTACTAATAAAGAAGGAGGTCA
GGCAAATGTGAAAACAGGAACAGGCACTACTAAAGAATATGACATAGACATGGCTTTCTTTGACAACAGAAGTG
CGGCTGCTGCTGGCCTAGCTCCAGAAATTGTTTTGTATACTGAAAATGTGGATTTGGAAACTCCAGATACCCAT
ATTGTATACAAAGCAGGCACAGATGACAGCAGCTCTTCTATTAATTTGGGTCAGCAAGCCATGCCCAACAGACC
TAACTACATTGGTTTCAGAGACAACTTTATCGGGCTCATGTACTACAACAGCACTGGCAATATGGGGGTGCTGG
CCGGTCAGGCTTCTCAGCTGAATGCTGTGGTTGACTTGCAAGACAGAAACACCGAGCTGTCCTACCAGCTCTTG
CTTGACTCTCTGGGTGACAGAACCCGGTATTTCAGTATGTGGAATCAGGCGGTGGACAGCTATGATCCTGATGT
GCGCATTATTGAAAATCATGGTGTGGAGGATGAACTTCCCAACTATTGTTTCCCTCTGGATGCTGTTGGCAGAA
CAGATACTTATCAGGGAATTAAGGCTAATGGAACTGATCAAACCACATGGACCAAAGATGACAGTGTCAATGAT
GCTAATGAGATAGGCAAGGGTAATCCATTCGCCATGGAAATCAACATCCAAGCCAACCTGTGGAGGAACTTCCT
CTACGCCAACGTGGCCCTGTACCTGCCCGACTCTTACAAGTACACGCCGGCCAATGTTACCCTGCCCACCAACA
CCAACACCTACGATTACATGAACGGCCGGGTGGTGGCGCCCTCGCTGGTGGACTCCTACATCAACATCGGGGCG
CGCTGGTCGCTGGATCCCATGGACAACGTGAACCCCTTCAACCACCACCGCAATGCGGGGCTGCGCTACCGCTC
CATGCTCCTGGGCAACGGGCGCTACGTGCCCTTCCACATCCAGGTGCCCCAGAAATTTTTCGCCATCAAGAGCC
TCCTGCTCCTGCCCGGGTCCTACACCTACGAGTGGAACTTCCGCAAGGACGTCAACATGATCCTGCAGAGCTCC
```

-continued

```
CTCGGCAACGACCTGCGCACGGACGGGGCCTCCATCTCCTTCACCAGCATCAACCTCTACGCCACCTTCTTCCC
CATGGCGCACAACACGGCCTCCACGCTCGAGGCCATGCTGCGCAACGACACCAACGACCAGTCCTTCAACGACT
ACCTCTCGGCGGCCAACATGCTCTACCCCATCCCGGCCAACGCCACCAACGTGCCCATCTCCATCCCCTCGCGC
AACTGGGCCGCCTTCCGCGGCTGGTCCTTCACGCGTCTCAAGACCAAGGAGACGCCCTCGCTGGGCTCCGGGTT
CGACCCCTACTTCGTCTACTCGGGCTCCATCCCCTACCTCGACGGCACCTTCTACCTCAACCACACCTTCAAGA
AGGTCTCCATCACCTTCGACTCCTCCGTCAGCTGGCCCGGCAACGACCGGCTCCTGACGCCCAACGAGTTCGAA
ATCAAGCGCACCGTCGACGGCGAGGGCTACAACGTGGCCCAGTGCAACATGACCAAGGACTGGTTCCTGGTCCA
GATGCTGGCCCACTACAACATCGGCTACCAGGGCTTCTACGTGCCCGAGGGCTACAAGGACCGCATGTACTCCT
TCTTCCGCAACTTCCAGCCCATGAGCCGCCAGGTGGTGGACGAGGTCAACTACAAGGACTACCAGGCCGTCACC
CTGGCCTACCAGCACAACAACTCGGGCTTCGTCGGCTACCTCGCGCCCACCATGCGCCAGGGCCAGCCCTACCC
CGCCAACTACCCCTACCCGCTCATCGGCAAGAGCGCCGTCACCAGCGTCACCCAGAAAAAGTTCCTCTGCGACA
GGGTCATGTGGCGCATCCCCTTCTCCAGCAACTTCATGTCCATGGGCGCGCTCACCGACCTCGGCCAGAACATG
CTCTATGCCAACTCCGCCCACGCGCTAGACATGAATTTCGAAGTCGACCCCATGGATGAGTCCACCCTTCTCTA
TGTTGTCTTCGAAGTCTTCGACGTCGTCCGAGTGCACCAGCCCCACCGCGGCGTCATCGAGGCCGTCTACCTGC
GCACCCCCTTCTCGGCCGGTAACGCCACCACCTAAGCTCTTGCTTCTTGCAAGCCATGGCCGCGGGCTCCGGCG
AGCAGGAGCTCAGGGCCATCATCCGCGACCTGGGCTGCGGGCCCTACTTCCTGGGCACCTTCGATAAGCGCTTC
CCGGGATTCATGGCCCCGCACAAGCTGGCCTGCGCCATCGTCAACACGGCCGGCCGCGAGACCGGGGGCGAGCA
CTGGCTGGCCTTCGCCTGGAACCCGCGCTCGAACACCTGCTACCTCTTCGACCCCTTCGGGTTCTCGGACGAGC
GCCTCAAGCAGATCTACCAGTTCGAGTACGAGGGCCTGCTGCGCCGCAGCGCCCTGGCCACCGAGGACCGCTGC
GTCACCCTGGAAAAGTCCACCCAGACCGTGCAGGGTCCGCGCTCGGCCGCCTGCGGGCTCTTCTGCTGCATGTT
CCTGCACGCCTTCGTGCACTGGCCCGACCGCCCCATGGACAAGAACCCCACCATGAACTTGCTGACGGGGGTGC
CCAACGGCATGCTCCAGTCGCCCCAGGTGGAACCCACCCTGCGCCGCAACCAGGAGGCGCTCTACCGCTTCCTC
AACTCCCACTCCGCCTACTTTCGCTCCCACCGCGCGCGCATCGAGAAGGCCACCGCCTTCGACCGCATGAATCA
AGACATGTAAACCGTGTGTGTATGTTAAATGTCTTTAATAAACAGCACTTTCATGTTACACATGCATCTGAGAT
GATTTATTTAGAAATCGAAAGGGTTCTGCCGGGTCTCGGCATGGCCCGCGGGCAGGGACACGTTGCGGAACTGG
TACTTGGCCAGCCACTTGAACTCGGGGATCAGCAGTTTGGGCAGCGGGGTGTCGGGGAAGGAGTCGGTCCACAG
CTTCCGCGTCAGTTGCAGGGCGCCCAGCAGGTCGGGCGCGGAGATCTTGAAATCGCAGTTGGGACCCGCGTTCT
GCGCGCGGGAGTTGCGGTACACGGGGTTGCAGCACTGGAACACCATCAGGGCCGGGTGCTTCACGCTCGCCAGC
ACCGTCGCGTCGGTGATGCTCTCCACGTCGAGGTCCTCGGCGTTGGCCATCCCGAAGGGGGTCATCTTGCAGGT
CTGCCTTCCCATGGTGGGCACGCACCCGGGCTTGTGGTTGCAATCGCAGTGCAGGGGATCAGCATCATCTGGG
CCTGGTCGGCGTTCATCCCCGGGTACATGGCCTTCATGAAAGCCTCCAATTGCCTGAACGCCTGCTGGGCCTTG
GCTCCCTCGGTGAAGAAGACCCCGCAGGACTTGCTAGAGAACTGGTTGGTGGCGCACCCGGCGTCGTGCACGCA
GCAGCGCGCGTCGTTGTTGGCCAGCTGCACCACGCTGCGCCCCAGCGGTTCTGGGTGATCTTGGCCCGGTCGG
GGTTCTCCTTCAGCGCGCGCTGCCCGTTCTCGCTCGCCACATCCATCTCGATCATGTGCTCCTTCTGGATCATG
GTGGTCCCGTGCAGGCACCGCAGCTTGCCCTCGGCCTCGGTGCACCCGTGCAGCCACAGCGCGCACCCGGTGCA
CTCCCAGTTCTTGTGGGCGATCTGGGAATGCGCGTGCACGAAGCCCTGCAGGAAGCGGCCCATCATGGTGGTCA
GGGTCTTGTTGCTAGTGAAGGTCAGCGGAATGCCGCGGTGCTCCTCGTTGATGTACAGGTGGCAGATGCGGCGG
TACACCTCGCCCTGCTCGGGCATCAGCTGGAAGTTGGCTTTCAGGTCGGTCTCCACGCGGTAGCGGTCCATCAG
CATAGTCATGATTTCCATACCCTTCTCCCAGGCCGAGACGATGGGCAGGCTCATAGGGTTCTTCACCATCATCT
TAGCGCTAGCAGCCGCGGCCAGGGGGTCGCTCTCGTCCAGGGTCTCAAAGCTCCGCTTGCCGTCCTTCTCGGTG
```

-continued

```
ATCCGCACCGGGGGGTAGCTGAAGCCCACGGCCGCCAGCTCCTCCTCGGCCTGTCTTCGTCCTCGCTGTCCTG
GCTGACGTCCTGCAGGACCACATGCTTGGTCTTGCGGGGTTTCTTCTTGGGCGGCAGCGGCGGCGGAGATGTTG
GAGATGGCGAGGGGGAGCGCGAGTTCTCGCTCACCACTACTATCTCTTCCTCTTCTTGGTCCGAGGCCACGCGG
CGGTAGGTATGTCTCTTCGGGGGCAGAGGCGGAGGCGACGGGCTCTCGCCGCCGCGACTTGGCGGATGGCTGGC
AGAGCCCCTTCCGCGTTCGGGGGTGCGCTCCCGGCGGCGCTCTGACTGACTTCCTCCGCGGCCGGCCATTGTGT
TCTCCTAGGGAGGAACAACAAGCATGGAGACTCAGCCATCGCCAACCTCGCCATCTGCCCCCACCGCCGACGAG
AAGCAGCAGCAGCAGAATGAAAGCTTAACCGCCCCGCCGCCCAGCCCCGCCACCTCCGACGCGGCCGTCCCAGA
CATGCAAGAGATGGAGGAATCCATCGAGATTGACCTGGGCTATGTGACGCCCGCGGAGCACGAGGAGGAGCTGG
CAGTGCGCTTTTCACAAGAAGAGATACACCAAGAACAGCCAGAGCAGGAAGCAGAGAATGAGCAGAGTCAGGCT
GGGCTCGAGCATGACGGCGACTACCTCCACCTGAGCGGGGGGAGGACGCGCTCATCAAGCATCTGGCCCGGCA
GGCCACCATCGTCAAGGATGCGCTGCTCGACCGCACCGAGGTGCCCCTCAGCGTGGAGGAGCTCAGCCGCGCCT
ACGAGTTGAACCTCTTCTCGCCGCGCGTGCCCCCCAAGCGCCAGCCCAATGGCACCTGCGAGCCCAACCCGCGC
CTCAACTTCTACCCGGTCTTCGCGGTGCCCGAGGCCCTGGCCACCTACCACATCTTTTTCAAGAACCAAAAGAT
CCCCGTCTCCTGCCGCGCCAACCGCACCCGCGCCGACGCCCTTTTCAACCTGGGTCCCGGCGCCCGCCTACCTG
ATATCGCCTCCTTGGAAGAGGTTCCCAAGATCTTCGAGGGTCTGGGCAGCGACGAGACTCGGGCCGCGAACGCT
CTGCAAGGAGAAGGAGGAGAGCATGAGCACCACAGCGCCCTGGTCGAGTTGGAAGGCGACAACGCGCGGCTGGC
GGTGCTCAAACGCACGGTCGAGCTGACCCATTTCGCCTACCCGGCTCTGAACCTGCCCCCCAAAGTCATGAGCG
CGGTCATGGACCAGGTGCTCATCAAGCGCGCGTCGCCCATCTCCGAGGACGAGGGCATGCAAGACTCCGAGGAG
GGCAAGCCCGTGGTCAGCGACGAGCAGCTGGCCCGGTGGCTGGGTCCTAATGCTAGTCCCCAGAGTTTGGAAGA
GCGGCGCAAACTCATGATGGCCGTGGTCCTGGTGACCGTGGAGCTGGAGTGCCTGCGCCGCTTCTTCGCCGACG
CGGAGACCCTGCGCAAGGTCGAGGAGAACCTGCACTACCTCTTCAGGCACGGGTTCGTGCGCCAGGCCTGCAAG
ATCTCCAACGTGGAGCTGACCAACCTGGTCTCCTACATGGGCATCTTGCACGAGAACCGCCTGGGGCAGAACGT
GCTGCACACCCCCTGCGCGGGGAGGCCCGGCGCGACTACATCCGCGACTGCGTCTACCTCTACCTCTGCCACA
CCTGGCAGACGGGCATGGGCGTGTGGCAGCAGTGTCTGGAGGAGCAGAACCTGAAAGAGCTCTGCAAGCTCCTG
CAGAAGAACCTCAAGGGTCTGTGGACCGGGTTCGACGAGCGCACCACCGCCTCGGACCTGGCCGACCTCATTTT
CCCCGAGCGCCTCAGGCTGACGCTGCGCAACGGCCTGCCCGACTTTATGAGCCAAAGCATGTTGCAAAACTTTC
GCTCTTTCATCCTCGAACGCTCCGGAATCCTGCCCCGCCACCTGCTCCGCGCTGCCCTCGGACTTCGTGCCGCTG
ACCTTCCGCGAGTGCCCCCCGCCGCTGTGGAGCCACTGCTACCTGCTGCGCCTGGCCAACTACCTGGCCTACCA
CTCGGACGTGATCGAGGACGTCAGCGGCGAGGGCCTGCTCGAGTGCCACTGCCGCTGCAACCTCTGCACGCCGC
ACCGCTCCCTGGCCTGCAACCCCCAGCTGCTGAGCGAGACCCAGATCATCGGCACCTTCGAGTTGCAAGGGCCC
AGCGAAGGCGAGGGTTCAGCCGCCAAGGGGGGTCTGAAACTCACCCCGGGGCTGTGGACCTCGGCCTACTTGCG
CAAGTTCGTGCCCGAGGACTACCATCCCTTCGAGATCAGGTTCTACGAGGACCAATCCCATCCGCCCAAGGCCG
AGCTGTCGGCCTGCGTCATCACCCAGGGGGCGATCCTGGCCCAATTGCAAGCCATCCAGAAATCCCGCCAAGAA
TTCTTGCTGAAAAAGGGCCGCGGGGTCTACCTCGACCCCCAGACCGGTGAGGAGCTCAACCCCGGCTTCCCCCA
GGATGCCCCGAGGAAACAAGAAGCTGAAAGTGGAGCTGCCGCCCGTGGAGGATTTGGAGGAAGACTGGGAGAAC
AGCAGTCAGGCAGAGGAGGAGGAGATGGAGGAAGACTGGACAGCACTCAGGCAGAGGAGGACAGCCTGCAAGA
CAGTCTGGAGGAAGACGAGGAGGAGGCAGAGGAGGAGGTGGAAGAAGCAGCCGCCGCCAGACCGTCGTCCTCGG
CGGGGGAGAAAGCAAGCAGCACGGATACCATCTCCGCTCCGGGTCGGGGTCCCGCTCGACCACACAGTAGATGG
GACGAGACCGGACGATTCCCGAACCCCACCACCCAGACCGGTAAGAAGGAGCGGCAGGGATACAAGTCCTGGCG
GGGGCACAAAAACGCCATCGTCTCCTGCTTGCAGGCCTGCGGGGCAACATCTCCTTCACCCGGCGCTACCTGC
TCTTCCACCGCGGGGTGAACTTTCCCCGCAACATCTTGCATTACTACCGTCACCTCCACAGCCCCTACTACTTC
```

-continued

```
CAAGAAGAGGCAGCAGCAGCAGAAAAAGACCAGCAGAAAACCAGCAGCTAGAAAATCCACAGCGGCGGCAGCAG
GTGGACTGAGGATCGCGGCGAACGAGCCGGCGCAAACCCGGGAGCTGAGGAACCGGATCTTTCCCACCCTCTAT
GCCATCTTCCAGCAGAGTCGGGGGCAGGAGCAGGAACTGAAAGTCAAGAACCGTTCTCTGCGCTCGCTCACCCG
CAGTTGTCTGTATCACAAGAGCGAAGACCAACTTCAGCGCACTCTCGAGGACGCCGAGGCTCTCTTCAACAAGT
ACTGCGCGCTCACTCTTAAAGAGTAGCCCGCGCCCGCCCAGTCGCAGAAAAAGGCGGGAATTACGTCACCTGTG
CCCTTCGCCCTAGCCGCCTCCACCCATCATCATGAGCAAAGAGATTCCCACGCCTTACATGTGGAGCTACCAGC
CCCAGATGGGCCTGGCCGCCGGTGCCGCCCAGGACTACTCCACCCGCATGAATTGGCTCAGCGCCGGGCCCGCG
ATGATCTCACGGGTGAATGACATCCGCGCCCACCGAAACCAGATACTCCTAGAACAGTCAGCGCTCACCGCCAC
GCCCCGCAATCACCTCAATCCGCGTAATTGGCCCGCCGCCCTGGTGTACCAGGAAATTCCCCAGCCCACGACCG
TACTACTTCCGCGAGACGCCCAGGCCGAAGTCCAGCTGACTAACTCAGGTGTCCAGCTGGCGGGCGGCGCCACC
CTGTGTCGTCACCGCCCCGCTCAGGGTATAAAGCGGCTGGTGATCCGGGGCAGAGGCACACAGCTCAACGACGA
GGTGGTGAGCTCTTCGCTGGGTCTGCGACCTGACGGAGTCTTCCAACTCGCCGGATCGGGGAGATCTTCCTTCA
CGCCTCGTCAGGCCGTCCTGACTTTGGAGAGTTCGTCCTCGCAGCCCCGCTCGGGTGGCATCGGCACTCTCCAG
TTCGTGGAGGAGTTCACTCCCTCGGTCTACTTCAACCCCTTCTCCGGCTCCCCCGGCCACTACCCGGACGAGTT
CATCCCGAACTTCGACGCCATCAGCGAGTCGGTGGACGGCTACGATTGAATGTCCCATGGTGGCGCAGCTGACC
TAGCTCGGCTTCGACACCTGGACCACTGCCGCGCTTCCGCTGCTTCGCTCGGGATCTCGCCGAGTTTGCCTAC
TTTGAGCTGCCCGAGGAGCACCCTCAGGGCCCGGCCCACGGAGTGCGGATCGTCGTCGAAGGGGGCCTCGACTC
CCACCTGCTTCGGATCTTCAGCCAGCGTCCGATCCTGGTCGAGCGCGAGCAAGGACAGACCCTTCTGACTCTGT
ACTGCATCTGCAACCACCCCGGCCTGCATGAAAGTCTTTGTTGTCTGCTGTGTACTGAGTATAATAAAAGCTGA
GATCAGCGACTACTCCGGACTTCCGTGTGTTCCTGAATCCATCAACCAGTCTTTGTTCTTCACCGGGAACGAGA
CCGAGCTCCAGCTCCAGTGTAAGCCCCACAAGAAGTACCTCACCTGGCTGTTCCAGGGCTCCCCGATCGCCGTT
GTCAACCACTGCGACAACGACGGAGTCCTGCTGAGCGGCCCTGCCAACCTTACTTTTTCCACCCGCAGAAGCAA
GCTCCAGCTCTTCCAACCCTTCCTCCCCGGGACCTATCAGTGCGTCTCGGGACCCTGCCATCACACCTTCCACC
TGATCCCGAATACCACAGCGTCGCTCCCCGCTACTAACAACCAAACTAACCTCCACCAACGCCACCGTCGCGAC
GGCCACAATACATGCCCATATTAGACTATGAGGCCGAGCCACAGCGACCCATGCTCCCCGCTATTAGTTACTTC
AATCTAACCGGCGGAGATGACTGACCCACTGGCCAACAACAACGTCAACGACCTTCTCCTGGACATGGACGGCC
GCGCCTCGGAGCAGCGACTCGCCCAACTTCGCATTCGCCAGCAGCAGGAGAGAGCCGTCAAGGAGCTGCAGGAT
GCGGTGGCCATCCACCAGTGCAAGAGAGGCATCTTCTGCCTGGTGAAACAGGCCAAGATCTCCTACGAGGTCAC
TCCAAACGACCATCGCCTCTCCTACGAGCTCCTGCAGCAGCGCCAGAAGTTCACCTGCCTGGTCGGAGTCAACC
CCATCGTCATCACCCAGCAGTCTGGCGATACCAAGGGGTGCATCCACTGCTCCTGCGACTCCCCGACTGCGTC
CACACTCTGATCAAGACCCTCTGCGGCCTCCGCGACCTCCTCCCCATGAACTAATCACCCCCTTATCCAGTGAA
ATAAAGATCATATTGATGATGATTTTACAGAAATAAAAAATAATCATTTGATTTGAAATAAAGATACAATCATA
TTGATGATTTGAGTTTAACAAAAAAATAAAGAATCACTTACTTGAAATCTGATACCAGGTCTCTGTCCATGTTT
TCTGCCAACACCACTTCACTCCCCTCTTCCCAGCTCTGGTACTGCAGGCCCCGGCGGGCTGCAAACTTCCTCCA
CACGCTGAAGGGGATGTCAAATTCCTCCTGTCCCTCAATCTTCATTTTATCTTCTATCGATGTCCAAAAAGCG
CGTCCGGGTGGATGATGACTTCGACCCCGTCTACCCCTACGATGCAGACAACGCACCGACCGTGCCCTTCATCA
ACCCCCCCTTCGTCTCTTCAGATGGATTCCAAGAGAAGCCCCTGGGGGTGTTGTCCCTGCGACTGGCCGACCCC
GTCACCACCAAGAACGGGGAAATCACCCTCAAGCTGGGAGAGGGGGTGGACCTCGATTCCTCGGGAAAACTCAT
CTCCAACACGGCCACCAAGGCCGCCGCCCCTCTCAGTTTTTCCAACAACACCATTTCCCTTAACATGGATCACC
CCTTTTACACTAAAGATGGAAAATTATCCTTACAAGTTTCTCCACCATTAAATATACTGAGAACAAGCATTCTA
```

-continued
AACACACTAGCTTTAGGTTTTGGATCAGGTTTAGGACTCCGTGGCTCTGCCTTGGCAGTACAGTTAGTCTCTCC
ACTTACATTTGATACTGATGGAAACATAAAGCTTACCTTAGACAGAGGTTTGCATGTTACAACAGGAGATGCAA
TTGAAAGCAACATAAGCTGGGCTAAAGGTTTAAAATTTGAAGATGGAGCCATAGCAACCAACATTGGAAATGGG
TTAGAGTTTGGAAGCAGTAGTACAGAAACAGGTGTTGATGATGCTTACCCAATCCAAGTTAAACTTGGATCTGG
CCTTAGCTTTGACAGTACAGGAGCCATAATGGCTGGTAACAAAGAAGACGATAAACTCACTTTGTGGACAACAC
CTGATCCATCACCAAACTGTCAAATACTCGCAGAAAATGATGCAAAACTAACACTTTGCTTGACTAAATGTGGT
AGTCAAATACTGGCCACTGTGTCAGTCTTAGTTGTAGGAAGTGGAAACCTAAACCCCATTACTGGCACCGTAAG
CAGTGCTCAGGTGTTTCTACGTTTTGATGCAAACGGTGTTCTTTTAACAGAACATTCTACACTAAAAAAATACT
GGGGGTATAGGCAGGGAGATAGCATAGATGGCACTCCATATACCAATGCTGTAGGATTCATGCCCAATTTAAAA
GCTTATCCAAAGTCACAAAGTTCTACTACTAAAAATAATATAGTAGGGCAAGTATACATGAATGGAGATGTTTC
AAAACCTATGCTTCTCACTATAACCCTCAATGGTACTGATGACAGCAACAGTACATATTCAATGTCATTTTCAT
ACACCTGGACTAATGGAAGCTATGTTGGAGCAACATTTGGGGCTAACTCTTATACCTTCTCATACATCGCCCAA
GAATGAACACTGTATCCCACCCTGCATGCCAACCCTTCCCACCCCACTCTGTGGAACAAACTCTGAAACACAAA
ATAAAATAAAGTTCAAGTGTTTTATTGATTCAACAGTTTTACAGGATTCGAGCAGTTATTTTTCCTCCACCCTC
CCAGGACATGGAATACACCACCCTCTCCCCCCGCACAGCCTTGAACATCTGAATGCCATTGGTGATGGACATGC
TTTTGGTCTCCACGTTCCACACAGTTTCAGAGCGAGCCAGTCTCGGGTCGGTCAGGGAGATGAAACCCTCCGGG
CACTCCCGCATCTGCACCTCACAGCTCAACAGCTGAGGATTGTCCTCGGTGGTCGGGATCACGGTTATCTGGAA
GAAGCAGAAGAGCGGCGGTGGGAATCATAGTCCGCGAACGGGATCGGCCGGTGGTGTCGCATCAGGCCCCGCAG
CAGTCGCTGCCGCCGCCGCTCCGTCAAGCTGCTGCTCAGGGGGTCCGGGTCCAGGGACTCCCTCAGCATGATGC
CCACGGCCCTCAGCATCAGTCGTCTGGTGCGGCGGGCGCAGCAGCGCATGCGGATCTCGCTCAGGTCGCTGCAG
TACGTGCAACACAGAACCACCAGGTTGTTCAACAGTCCATAGTTCAACACGCTCCAGCCGAAACTCATCGCGGG
AAGGATGCTACCCACGTGGCCGTCGTACCAGATCCTCAGGTAAATCAAGTGGTGCCCCTCCAGAACACGCTGC
CCACGTACATGATCTCCTTGGGCATGTGGCGGTTCACCACCTCCCGGTACCACATCACCCTCTGGTTGAACATG
CAGCCCCGGATGATCCTGCGGAACCACAGGGCCAGCACCGCCCCGCCCGCCATGCAGCGAAGAGACCCCGGGTC
CCGGCAATGGCAATGGAGGACCCACCGCTCGTACCCGTGGATCATCTGGGAGCTGAACAAGTCTATGTTGGCAC
AGCACAGGCATATGCTCATGCATCTCTTCAGCACTCTCAACTCCTCGGGGGTCAAAACCATATCCCAGGGCACG
GGGAACTCTTGCAGGACAGCGAACCCCGCAGAACAGGGCAATCCTCGCACAGAACTTACATTGTGCATGGACAG
GGTATCGCAATCAGGCAGCACCGGGTGATCCTCCACCAGAGAAGCGCGGGTCTCGGTCTCCTCACAGCGTGGTA
AGGGGGCCGGCCGATACGGGTGATGGCGGGACGCGGCTGATCGTGTTCGCGACCGTGTCATGATGCAGTTGCTT
TCGGACATTTTCGTACTTGCTGTAGCAGAACCTGGTCCGGGCGCTGCACACCGATCGCCGGCGGCGGTCTCGGC
GCTTGGAACGCTCGGTGTTGAAATTGTAAAACAGCCACTCTCTCAGACCGTGCAGCAGATCTAGGGCCTCAGGA
GTGATGAAGATCCCATCATGCCTGATGGCTCTGATCACATCGACCACCGTGGAATGGGCCAGACCCAGCCAGAT
GATGCAATTTTGTTGGGTTTCGGTGACGGCGGGGGAGGGAAGAACAGGAAGAACCATGATTAACTTTTAATCCA
AACGGTCTCGGAGTACTTCAAAATGAAGATCGCGGAGATGGCACCTCTCGCCCCCGCTGTGTTGGTGGAAAATA
ACAGCCAGGTCAAAGGTGATACGGTTCTCGAGATGTTCCACGGTGGCTTCCAGCAAAGCCTCCACGCGCACATC
CAGAAACAAGACAATAGCGAAAGCGGGAGGGTTCTCTAATTCCTCAATCATCATGTTACACTCCTGCACCATCC
CCAGATAATTTTCATTTTTCCAGCCTTGAATGATTCGAACTAGTTCGTGAGGTAAATCCAAGCCAGCCATGATA
AAGAGCTCGCGCAGAGCGCCCTCCACCGGCATTCTTAAGCACACCCTCATAATTCCAAGATATTCTGCTCCTGG
TTCACCTGCAGCAGATTGACAAGCGGAATATCAAAATCTCTGCCGCGATCCCTGAGCTCCTCCCTCAGCAATAA
CTGTAAGTACTCTTTCATATCCTCTCCGAATTTTTAGCCATAGGACCACCAGGAATAAGATTAGGGCAAGCCA
CAGTACAGATAAACCGAAGTCCTCCCCAGTGAGCATTGCCAAATGCAAGACTGCTATAAGCATGCTGGCTAGAC -continued

CCGGTGATATCTTCCAGATAACTGGACAGAAAATCGCCCAGGCAATTTTTAAGAAAATCAACAAAAGAAAAATC

CTCCAGGTGGACGTTTAGAGCCTCGGGAACAACGATGAAGTAAATGCAAGCGGTGCGTTCCAGCATGGTTAGTT

AGCTGATCTGTAGAAAAAACAAAAATGAACATTAAACCATGCTAGCCTGGCGAACAGGTGGGTAAATCGTTCTC

TCCAGCACCAGGCAGGCCACGGGGTCTCCGGCGCGACCCTCGTAAAAATTGTCGCTATGATTGAAAACCATCAC

AGAGAGACGTTCCCGGTGGCCGGCGTGAATGATTCGACAAGATGAATACACCCCCGGAACATTGGCGTCCGCGA

GTGAAAAAAAGCGCCCGAGGAAGCAATAAGGCACTACAATGCTCAGTCTCAAGTCCAGCAAAGCGATGCCATGC

GGATGAAGCACAAAATTCTCAGGTGCGTACAAAATGTAATTACTCCCCTCCTGCACAGGCAGCAAAGCCCCCGA

TCCCTCCAGGTACACATACAAAGCCTCAGCGTCCATAGCTTACCGAGCAGCAGCACACAACAGGCGCAAGAGTC

AGAGAAAGGCTGAGCTCTAACCTGTCCACCCGCTCTCTGCTCAATATATAGCCCAGATCTACACTGACGTAAAG

GCCAAAGTCTAAAAATACCCGCCAAATAATCACACACGCCCAGCACACGCCCAGAAACCGGTGACACACTCAAA

AAAATACGCGCACTTCCTCAAACGCCCAAAACTGCCGTCATTTCCGGGTTCCCACGCTACGTCATCAAAACACG

ACTTTCAAATTCCGTCGACCGTTAAAAACGTCACCCGCCCCGCCCCTAACGGTCGCCCGTCTCTCAGCCAATCA

GCGCCCCGCATCCCCAAATTCAAACACCTCATTTGCATATTAACGCGCACAAAAAGTTTGAGGTATATTATTGA

TGATGG

ChAdV68.5WTnt.GFP; AC_000011.1 with E1 (nt 577 to 3403) and E3 (nt 27,125-
31,825) sequences deleted; corresponding ATCC VR-594 nucleotides
substituted at five positions; GFP reporter under the control of the CMV
promoter/enhancer inserted in place of deleted E1

(SEQ ID NO: 13)

CCATCTTCAATAATATACCTCAAACTTTTTGTGCGCGTTAATATGCAAATGAGGCGTTTGAATTTGGGGAGGAA

GGGCGGTGATTGGTCGAGGGATGAGCGACCGTTAGGGGCGGGGCGAGTGACGTTTTGATGACGTGGTTGCGAGG

AGGAGCCAGTTTGCAAGTTCTCGTGGGAAAAGTGACGTCAAACGAGGTGTGGTTTGAACACGGAAATACTCAAT

TTTCCCGCGCTCTCTGACAGGAAATGAGGTGTTTCTGGGCGGATGCAAGTGAAAACGGGCCATTTTCGCGCGAA

AACTGAATGAGGAAGTGAAAATCTGAGTAATTTCGCGTTTATGGCAGGGAGGAGTATTTGCCGAGGGCCGAGTA

GACTTTGACCGATTACGTGGGGGTTTCGATTACCGTGTTTTTCACCTAAATTTCCGCGTACGGTGTCAAAGTCC

GGTGTTTTTACGTAGGTGTCAGCTGATCGCCAGGGTATTTAAACCTGCGCTCTCCAGTCAAGAGGCCACTCTTG

AGTGCCAGCGAGAAGAGTTTTCTCCTCCGCGCCGCGAGTCAGATCTACACTTTGAAAGTAGGGATAACAGGGTA

ATgacattgattattgactagttGttaaTAGTAATCAATTACGGGGTCATTAGTTCATAGCCCATATATGGAGT

TCCGCGTTACATAACTTACGGTAAATGGCCCGCCTGGCTGACCGCCCAACGACCCCGCCCCATTGACGTCAATA

ATGACGTATGTTCCCATAGTAACGCCAATAGGGACTTTCCATTGACGTCAATGGGTGGAGTATTTACGGTAAAC

TGCCCACTTGGCAGTACATCAAGTGTATCATATGCCAAGTCCGCCCCCTATTGACGTCAATGACGGTAAATGGC

CCGCCTGGCATTATGCCCAGTACATGACCTTACGGGACTTTCCTACTTGGCAGTACATCTACGTATTAGTCATC

GCTATTACCATGgTGATGCGGTTTTGGCAGTACACCAATGGGCGTGGATAGCGGTTTGACTCACGGGGATTTCC

AAGTCTCCACCCCATTGACGTCAATGGGAGTTTGTTTTGGCACCAAAATCAACGGGACTTTCCAAAATGTCGTA

ATAACCCCGCCCCGTTGACGCAAATGGGCGGTAGGCGTGTACGGTGGGAGGTCTATATAAGCAGAgcTCGTTTA

GTGAACCGTCAGATCGCCTGGAACGCCATCCACGCTGTTTTGACCTCCATAGAAGACAGCGATCGCGccaccAT

GGTGAGCAAGGGCGAGGAGCTGTTCACCGGGGTGGTGCCCATCCTGGTCGAGCTGGACGGCGACGTAAACGGCC

ACAAGTTCAGCGTGTCCGGCGAGGGCGAGGGCGATGCCACCTACGGCAAGCTGACCCTGAAGTTCATCTGCACC

ACCGGCAAGCTGCCCGTGCCCTGGCCCACCCTCGTGACCACCCTGACCTACGGCGTGCAGTGCTTCAGCCGCTA

CCCCGACCACATGAAGCAGCACGACTTCTTCAAGTCCGCCATGCCCGAAGGCTACGTCCAGGAGCGCACCATCT

TCTTCAAGGACGACGGCAACTACAAGACCCGCGCCGAGGTGAAGTTCGAGGGCGACACCCTGGTGAACCGCATC

GAGCTGAAGGGCATCGACTTCAAGGAGGACGGCAACATCCTGGGGCACAAGCTGGAGTACAACTACAACAGCCA

CAACGTCTATATCATGGCCGACAAGCAGAAGAACGGCATCAAGGTGAACTTCAAGATCCGCCACAACATCGAGG

-continued

```
ACGGCAGCGTGCAGCTCGCCGACCACTACCAGCAGAACACCCCCATCGGCGACGGCCCCGTGCTGCTGCCCGAC

AACCACTACCTGAGCACCCAGTCCGCCCTGAGCAAAGACCCCAACGAGAAGCGCGATCACATGGTCCTGCTGGA

GTTCGTGACCGCCGCCGGGATCACTCTCGGCATGGACGAGCTtTACAAGTAGtgaGTTTAAACTCCCATTTAAA

TGTGAGGGTTAATGCTTCGAGCAGACATGATAAGATACATTGATGAGTTTGGACAAACCACAACTAGAATGCAG

TGAAAAAAATGCTTTATTTGTGAAATTTGTGATGCTATTGCTTTATTTGTAACCATTATAAGCTGCAATAAACA

AGTTAACAACAACAATTGCATTCATTTTATGTTTCAGGTTCAGGGGGAGATGTGGGAGGTTTTTTAAAGCAAGT

AAAACCTCTACAAATGTGGTAAAATAACTATAACGGTCCTAAGGTAGCGAGTGAGTAGTGTTCTGGGGCGGGGG

AGGACCTGCATGAGGGCCAGAATAACTGAAATCTGTGCTTTTCTGTGTGTTGCAGCAGCATGAGCGGAAGCGGC

TCCTTTGAGGGAGGGGTATTCAGCCCTTATCTGACGGGGCGTCTCCCCTCCTGGGCGGGAGTGCGTCAGAATGT

GATGGGATCCACGTGGACGGCCGGCCCGTGCAGCCCGCGAACTCTTCAACCCTGACCTATGCAACCCTGAGCT

CTTCGTCGTTGGACGCAGCTGCCGCCGCAGCTGCTGCATCTGCCGCCAGCGCCGTGCGCGGAATGGCCATGGGC

GCCGGCTACTACGGCACTCTGGTGGCCAACTCGAGTTCCACCAATAATCCCGCCAGCCTGAACGAGGAGAAGCT

GTTGCTGCTGATGGCCCAGCTCGAGGCCTTGACCCAGCGCCTGGGCGAGCTGACCCAGCAGGTGGCTCAGCTGC

AGGAGCAGACGCGGGCCGCGGTTGCCACGGTGAAATCCAAATAAAAAATGAATCAATAAATAAACGGAGACGGT

TGTTGATTTTAACACAGAGTCTGAATCTTTATTTGATTTTTCGCGCGCGGTAGGCCCTGGACCACCGGTCTCGA

TCATTGAGCACCCGGTGGATCTTTTCCAGGACCCGGTAGAGGTGGGCTTGGATGTTGAGGTACATGGGCATGAG

CCCGTCCCGGGGGTGGAGGTAGCTCCATTGCAGGGCCTCGTGCTCGGGGGTGGTGTTGTAAATCACCCAGTCAT

AGCAGGGGCGCAGGGCATGGTGTTGCACAATATCTTTGAGGAGGAGACTGATGGCCACGGGCAGCCCTTTGGTG

TAGGTGTTTACAAATCTGTTGAGCTGGGAGGGATGCATGCGGGGGGAGATGAGGTGCATCTTGGCCTGGATCTT

GAGATTGGCGATGTTACCGCCCAGATCCCGCCTGGGGTTCATGTTGTGCAGGACCACCAGCACGGTGTATCCGG

TGCACTTGGGGAATTTATCATGCAACTTGGAAGGGAAGGCGTGAAAGAATTTGGCGACGCCTTTGTGCCCGCCC

AGGTTTTCCATGCACTCATCCATGATGATGGCGATGGGCCCGTGGGCGGCGGCCTGGGCAAAGACGTTTCGGGG

GTCGGACACATCATAGTTGTGGTCCTGGGTGAGGTCATCATAGGCCATTTTAATGAATTTGGGGCGGAGGGTGC

CGGACTGGGGGACAAAGGTACCCTCGATCCCGGGGGCGTAGTTCCCCTCACAGATCTGCATCTCCCAGGCTTTG

AGCTCGGAGGGGGGGATCATGTCCACCTGCGGGGCGATAAAGAACACGGTTTCCGGGGCGGGGGAGATGAGCTG

GGCCGAAAGCAAGTTCCGGAGCAGCTGGGACTTGCCGCAGCCGGTGGGGCCGTAGATGACCCCGATGACCGGCT

GCAGGTGGTAGTTGAGGGAGAGACAGCTGCCGTCCTCCCGGAGGAGGGGGCCACCTCGTTCATCATCTCGCGC

ACGTGCATGTTCTCGCGCACCAGTTCCGCCAGGAGGCGCTCTCCCCCCAGGGATAGGAGCTCCTGGAGCGAGGC

GAAGTTTTTCAGCGGCTTGAGTCCGTCGGCCATGGGCATTTTGGAGAGGGTTTGTTGCAAGAGTTCCAGGCGGT

CCCAGAGCTCGGTGATGTGCTCTACGGCATCTCGATCCAGCAGACCTCCTCGTTTCGCGGGTTGGGACGGCTGC

GGGAGTAGGGCACCAGACGATGGGCGTCCAGCGCAGCCAGGGTCCGGTCCTTCCAGGGTCGCAGCGTCCGCGTC

AGGGTGGTCTCCGTCACGGTGAAGGGGTGCGCGCCGGGCTGGGCGCTTGCGAGGGTGCGCTTCAGGCTCATCCG

GCTGGTCGAAAACCGCTCCCGATCGGCGCCCTGCGCGTCGGCCAGGTAGCAATTGACCATGAGTTCGTAGTTGA

GCGCCTCGGCCGCGTGGCCTTTGGCGCGGAGCTTACCTTTGGAAGTCTGCCCGCAGGCGGGACAGAGGAGGGAC

TTGAGGGCGTAGAGCTTGGGGCGAGGAAGACGGACTCGGGGCGTAGGCGTCCGCGCCGCAGTGGGCGCAGAC

GGTCTCGCACTCCACGAGCCAGGTGAGGTCGGGCTGGTCGGGGTCAAAAACCAGTTTCCCGCCGTTCTTTTGA

TGCGTTTCTTACCTTTGGTCTCCATGAGCTCGTGTCCCCGCTGGGTGACAAAGAGGCTGTCCGTGTCCCCGTAG

ACCGACTTTATGGGCCGGTCCTCGAGCGGTGTGCCGCGGTCCTCCTCGTAGAGGAACCCCGCCCACTCCGAGAC

GAAAGCCCGGGTCCAGGCCAGCACGAAGGAGGCCACGTGGGACGGGTAGCGGTCGTTGTCCACCAGCGGGTCCA

CCTTTTCCAGGGTATGCAAACACATGTCCCCCTCGTCCACATCCAGGAAGGTGATTGGCTTGTAAGTGTAGGCC
```

-continued
ACGTGACCGGGGGTCCCGGCCGGGGGGGTATAAAAGGGTGCGGGTCCCTGCTCGTCCTCACTGTCTTCCGGATC
GCTGTCCAGGAGCGCCAGCTGTTGGGGTAGGTATTCCCTCTCGAAGGCGGGCATGACCTCGGCACTCAGGTTGT
CAGTTTCTAGAAACGAGGAGGATTTGATATTGACGGTGCCGGCGGAGATGCCTTTCAAGAGCCCCTCGTCCATC
TGGTCAGAAAAGACGATCTTTTTGTTGTCGAGCTTGGTGGCGAAGGAGCCGTAGAGGGCGTTGGAGAGGAGCTT
GGCGATGGAGCGCATGGTCTGGTTTTTTTCCTTGTCGGCGCGCTCCTTGGCGGCGATGTTGAGCTGCACGTACT
CGCGCGCCACGCACTTCCATTCGGGGAAGACGGTGGTCAGCTCGTCGGGCACGATTCTGACCTGCCAGCCCCGA
TTATGCAGGGTGATGAGGTCCACACTGGTGGCCACCTCGCCGCGCAGGGGCTCATTAGTCCAGCAGAGGCGTCC
GCCCTTGCGCGAGCAGAAGGGGGGCAGGGGGTCCAGCATGACCTCGTCGGGGGGGTCGGCATCGATGGTGAAGA
TGCCGGGCAGGAGGTCGGGGTCAAAGTAGCTGATGGAAGTGGCCAGATCGTCCAGGGCAGCTTGCCATTCGCGC
ACGGCCAGCGCGCGCTCGTAGGGACTGAGGGGCGTGCCCCAGGGCATGGGATGGGTAAGCGCGGAGGCGTACAT
GCCGCAGATGTCGTAGACGTAGAGGGGCTCCTCGAGGATGCCGATGTAGGTGGGGTAGCAGCGCCCCCCGCGGA
TGCTGGCGCGCACGTAGTCATACAGCTCGTGCGAGGGGGCGAGGAGCCCCGGGCCCAGGTTGGTGCGACTGGGC
TTTTCGGCGCGGTAGACGATCTGGCGGAAAATGGCATGCGAGTTGGAGGAGATGGTGGGCCTTTGGAAGATGTT
GAAGTGGGCGTGGGGCAGTCCGACCGAGTCGCGGATGAAGTGGGCGTAGGAGTCTTGCAGCTTGGCGACGAGCT
CGGCGGTGACTAGGACGTCCAGAGCGCAGTAGTCGAGGGTCTCCTGGATGATGTCATACTTGAGCTGTCCCTTT
TGTTTCCACAGCTCGCGGTTGAGAAGGAACTCTTCGCGGTCCTTCCAGTACTCTTCGAGGGGGAACCCGTCCTG
ATCTGCACGGTAAGAGCCTAGCATGTAGAACTGGTTGACGGCCTTGTAGGCGCAGCAGCCCTTCTCCACGGGGA
GGGCGTAGGCCTGGGCGGCCTTGCGCAGGGAGGTGTGCGTGAGGGCGAAAGTGTCCCTGACCATGACCTTGAGG
AACTGGTGCTTGAAGTCGATATCGTCGCAGCCCCCTGCTCCCAGAGCTGGAAGTCCGTGCGCTTCTTGTAGGC
GGGGTTGGGCAAAGCGAAAGTAACATCGTTGAAGAGGATCTTGCCCGCGCGGGGCATAAAGTTGCGAGTGATGC
GGAAAGGTTGGGGCACCTCGGCCCGGTTGTTGATGACCTGGGCGGCGAGCACGATCTCGTCGAAGCCGTTGATG
TTGTGGCCCACGATGTAGAGTTCCACGAATCGCGGACGGCCCTTGACGTGGGGCAGTTTCTTGAGCTCCTCGTA
GGTGAGCTCGTCGGGGTCGCTGAGCCCGTGCTGCTCGAGCGCCCAGTCGGCGAGATGGGGGTTGGCGCGGAGGA
AGGAAGTCCAGAGATCCACGGCCAGGGCGGTTTGCAGACGGTCCCGGTACTGACGGAACTGCTGCCCGACGGCC
ATTTTTTCGGGGGTGACGCAGTAGAAGGTGCGGGGGTCCCCGTGCCAGCGATCCCATTTGAGCTGGAGGGCGAG
ATCGAGGGCGAGCTCGACGAGCCGGTCGTCCCCGGAGAGTTTCATGACCAGCATGAAGGGGACGAGCTGCTTGC
CGAAGGACCCCATCCAGGTGTAGGTTTCCACATCGTAGGTGAGGAAGAGCCTTTCGGTGCGAGGATGCGAGCCG
ATGGGGAAGAACTGGATCTCCTGCCACCAATTGGAGGAATGGCTGTTGATGTGATGGAAGTAGAAATGCCGACG
GCGCGCCGAACACTCGTGCTTGTGTTTATACAAGCGGCCACAGTGCTCGCAACGCTGCACGGGATGCACGTGCT
GCACGAGCTGTACCTGAGTTCCTTTGACGAGGAATTTCAGTGGGAAGTGGAGTCGTGGCGCCTGCATCTCGTGC
TGTACTACGTCGTGGTGGTCGGCCTGGCCCTCTTCTGCCTCGATGGTGGTCATGCTGACGAGCCCGCGCGGGAG
GCAGGTCCAGACCTCGGCGCGAGCGGGTCGGAGAGCGAGGACGAGGGCGCGCAGGCCGGAGCTGTCCAGGGTCC
TGAGACGCTGCGGAGTCAGGTCAGTGGGCAGCGGCGGCGCGCGGTTGACTTGCAGGAGTTTTTCCAGGGCGCGC
GGGAGGTCCAGATGGTACTTGATCTCCACCGCGCCATTGGTGGCGACGTCGATGGCTTGCAGGGTCCCGTGCCC
CTGGGGTGTGACCACCGTCCCCCGTTTCTTCTTGGGCGGCTGGGGCGACGGGGGCGGTGCCTCTTCCATGGTTA
GAAGCGGCGGCGAGGACGCGCGCCGGGCGGCAGGGCGGCTCGGGGCCCGGAGGCAGGGGCGGCAGGGGCACGT
CGGCGCCGCGCGCGGGTAGGTTCTGGTACTGCGCCCGGAGAAGACTGGCGTGAGCGACGACGCGACGGTTGACG
TCCTGGATCTGACGCCTCTGGGTGAAGGCCACGGGACCCGTGAGTTTGAACCTGAAAGAGAGTTCGACAGAATC
AATCTCGGTATCGTTGACGGCGGCCTGCCGCAGGATCTCTTGCACGTCGCCCGAGTTGTCCTGGTAGGCGATCT
CGGTCATGAACTGCTCGATCTCCTCCTCTTGAAGGTCTCCGCGGCCGGCGCGCTCCACGGTGGCCGCGAGGTCG
TTGGAGATGCGGCCCATGAGCTGCGAGAAGGCGTTCATGCCCGCCTCGTTCCAGACGCGGCTGTAGACCACGAC -continued

```
GCCCTCGGGATCGCgGGCGCGCATGACCACCTGGGCGAGGTTGAGCTCCACGTGGCGCGTGAAGACCGCGTAGT
TGCAGAGGCGCTGGTAGAGGTAGTTGAGCGTGGTGGCGATGTGCTCGGTGACGAAGAAATACATGATCCAGCGG
CGGAGCGGCATCTCGCTGACGTCGCCCAGCGCCTCCAAACGTTCCATGGCCTCGTAAAAGTCCACGGCGAAGTT
GAAAAACTGGGAGTTGCGCGCCGAGACGGTCAACTCCTCCTCCAGAAGACGGATGAGCTCGGCGATGGTGGCGC
GCACCTCGCGCTCGAAGGCCCCCGGGAGTTCCTCCACTTCCTCTTCTTCCTCCTCCACTAACATCTCTTCTACT
TCCTCCTCAGGCGGCAGTGGTGGCGGGGGAGGGGGCCTGCGTCGCCGGCGGCGCACGGGCAGACGGTCGATGAA
GCGCTCGATGGTCTCGCCGCGCCGGCGTCGCATGGTCTCGGTGACGGCGCGCCCGTCCTCGCGGGGCCGCAGCG
TGAAGACGCCGCCGCGCATCTCCAGGTGGCCGGGGGGGTCCCCGTTGGGCAGGGAGAGGGCGCTGACGATGCAT
CTTATCAATTGCCCCGTAGGGACTCCGCGCAAGGACCTGAGCGTCTCGAGATCCACGGGATCTGAAAACCGCTG
AACGAAGGCTTCGAGCCAGTCGCAGTCGCAAGGTAGGCTGAGCACGGTTTCTTCTGGCGGGTCATGTTGGTTGG
GAGCGGGGCGGGCGATGCTGCTGGTGATGAAGTTGAAATAGGCGGTTCTGAGACGGCGGATGGTGGCGAGGAGC
ACCAGGTCTTTGGGCCCGGCTTGCTGGATGCGCAGACGGTCGGCCATGCCCCAGGCGTGGTCCTGACACCTGGC
CAGGTCCTTGTAGTAGTCCTGCATGAGCCGCTCCACGGGCACCTCCTCCTCGCCCGCGCGGCCGTGCATGCGCG
TGAGCCCGAAGCCGCGCTGGGGCTGGACGAGCGCCAGGTCGGCGACGACGCGCTCGGCGAGGATGGCTTGCTGG
ATCTGGGTGAGGGTGGTCTGGAAGTCATCAAAGTCGACGAAGCGGTGGTAGGCTCCGGTGTTGATGGTGTAGGA
GCAGTTGGCCATGACGACCAGTTGACGGTCTGGTGGCCCGGACGCACGAGCTCGTGGTACTTGAGGCGCGAGT
AGGCGCGCGTGTCGAAGATGTAGTCGTTGCAGGTGCGCACCAGGTACTGGTAGCCGATGAGGAAGTGCGGCGGC
GGCTGGCGGTAGAGCGGCCATCGCTCGGTGGCGGGGGCGCCGGGCGCGAGGTCCTCGAGCATGGTGCGGTGGTA
GCCGTAGATGTACCTGGACATCCAGGTGATGCCGGCGGCGGTGGTGGAGGCGCGCGGGAACTCGCGGACGCGGT
TCCAGATGTTGCGCAGCGGCAGGAAGTAGTTCATGGTGGGCACGGTCTGGCCCGTGAGGCGCGCGCAGTCGTGG
ATGCTCTATACGGGCAAAAACGAAAGCGGTCAGCGGCTCGACTCCGTGGCCTGGAGGCTAAGCGAACGGGTTGG
GCTGCGCGTGTACCCCGGTTCGAATCTCGAATCAGGCTGGAGCCGCAGCTAACGTGGTATTGGCACTCCCGTCT
CGACCCAAGCCTGCACCAACCCTCCAGGATACGGAGGCGGGTCGTTTTGCAACTTTTTTTTGGAGGCCGGATGA
GACTAGTAAGCGCGGAAAGCGGCCGACCGCGATGGCTCGCTGCCGTAGTCTGGAGAAGAATCGCCAGGGTTGCG
TTGCGGTGTGCCCCGGTTCGAGGCCGGCCGGATTCCGCGGCTAACGAGGGCGTGGCTGCCCCGTCGTTTCCAAG
ACCCCATAGCCAGCCGACTTCTCCAGTTACGGAGCGAGCCCCTCTTTTGTTTTGTTTGTTTTTGCCAGATGCAT
CCCGTACTGCGGCAGATGCGCCCCCACCACCCTCCACCGCAACAACAGCCCCCTCCACAGCCGGCGCTTCTGCC
CCCGCCCCAGCAGCAACTTCCAGCCACGACCGCCGCGGCCGCCGTGAGCGGGGCTGGACAGAGTTATGATCACC
AGCTGGCCTTGGAAGAGGGCGAGGGGCTGGCGCGCCTGGGGCGTCGTCGCCGGAGCGGCACCCGCGCGTGCAG
ATGAAAAGGGACGCTCGCGAGGCCTACGTGCCCAAGCAGAACCTGTTCAGAGACAGGAGCGGCGAGGAGCCCGA
GGAGATGCGCGCGGCCCGGTTCCACGCGGGGCGGGAGCTGCGGCGCGGCCTGGACCGAAAGAGGGTGCTGAGGG
ACGAGGATTTCGAGGCGGACGAGCTGACGGGGATCAGCCCCGCGCGCGCACGTGGCCGCGGCCAACCTGGTC
ACGGCGTACGAGCAGACCGTGAAGGAGGAGAGCAACTTCCAAAAATCCTTCAACAACCACGTGCGCACCCTGAT
CGCGCGCGAGGAGGTGACCCTGGGCCTGATGCACCTGTGGGACCTGCTGGAGGCCATCGTGCAGAACCCCACCA
GCAAGCCGCTGACGGCGCAGCTGTTCCTGGTGGTGCAGCATAGTCGGGACAACGAAGCGTTCAGGGAGGCGCTG
CTGAATATCACCGAGCCCGAGGGCCGCTGGCTCCTGGACCTGGTGAACATTCTGCAGAGCATCGTGGTGCAGGA
GCGCGGGCTGCCGCTGTCCGAGAAGCTGGCGGCCATCAACTTCTCGGTGCTGAGTTTGGGCAAGTACTACGCTA
GGAAGATCTACAAGACCCCGTACGTGCCCATAGACAAGGAGGTGAAGATCGACGGGTTTTACATGCGCATGACC
CTGAAAGTGCTGACCCTGAGCGACGATCTGGGGGTGTACCGCAACGACAGGATGCACCGTGCGGTGAGCGCCAG
CAGGCGGCGCGAGCTGAGCGACCAGGAGCTGATGCATAGTCTGCAGCGGGCCCTGACCGGGGCCGGGACCGAGG
```

-continued

```
GGGAGAGCTACTTTGACATGGGCGCGGACCTGCACTGGCAGCCCAGCCGCCGGGCCTTGGAGGCGGCGGCAGGA
CCCTACGTAGAAGAGGTGGACGATGAGGTGGACGAGGAGGGCGAGTACCTGGAAGACTGATGGCGCGACCGTAT
TTTTGCTAGATGCAACAACAACAGCCACCTCCTGATCCCGCGATGCGGGCGGCGCTGCAGAGCCAGCCGTCCGG
CATTAACTCCTCGGACGATTGGACCCAGGCCATGCAACGCATCATGGCGCTGACGACCCGCAACCCCGAAGCCT
TTAGACAGCAGCCCCAGGCCAACCGGCTCTCGGCCATCCTGGAGGCCGTGGTGCCCTCGCGCTCCAACCCCACG
CACGAGAAGGTCCTGGCCATCGTGAACGCGCTGGTGGAGAACAAGGCCATCCGCGGCGACGAGGCCGGCCTGGT
GTACAACGCGCTGCTGGAGCGCGTGGCCCGCTACAACAGCACCAACGTGCAGACCAACCTGGACCGCATGGTGA
CCGACGTGCGCGAGGCCGTGGCCCAGCGCGAGCGGTTCCACCGCGAGTCCAACCTGGGATCCATGGTGGCGCTG
AACGCCTTCCTCAGCACCCAGCCCGCCAACGTGCCCCGGGGCCAGGAGGACTACACCAACTTCATCAGCGCCCT
GCGCCTGATGGTGACCGAGGTGCCCCAGAGCGAGGTGTACCAGTCCGGGCCGGACTACTTCTTCCAGACCAGTC
GCCAGGGCTTGCAGACCGTGAACCTGAGCCAGGCTTTCAAGAACTTGCAGGGCCTGTGGGCGTGCAGGCCCCG
GTCGGGGACCGCGCGACGGTGTCGAGCCTGCTGACGCCGAACTCGCGCCTGCTGCTGCTGCTGGTGGCCCCCTT
CACGGACAGCGGCAGCATCAACCGCAACTCGTACCTGGGCTACCTGATTAACCTGTACCGCGAGGCCATCGGCC
AGGCGCACGTGGACGAGCAGACCTACCAGGAGATCACCCACGTGAGCCGCGCCCTGGGCCAGGACGACCCGGGC
AACCTGGAAGCCACCCTGAACTTTTTGCTGACCAACCGGTCGCAGAAGATCCCGCCCCAGTACGCGCTCAGCAC
CGAGGAGGAGCGCATCCTGCGTTACGTGCAGCAGAGCGTGGGCCTGTTCCTGATGCAGGAGGGGGCCACCCCCA
GCGCCGCGCTCGACATGACCGCGCGCAACATGGAGCCCAGCATGTACGCCAGCAACCGCCCGTTCATCAATAAA
CTGATGGACTACTTGCATCGGGCGGCCGCCATGAACTCTGACTATTTCACCAACGCCATCCTGAATCCCCACTG
GCTCCCGCCGCCGGGGTTCTACACGGGCGAGTACGACATGCCCGACCCCAATGACGGGTTCCTGTGGGACGATG
TGGACAGCAGCGTGTTCTCCCCCCGACCGGGTGCTAACGAGCGCCCCTTGTGGAAGAAGGAAGGCAGCGACCGA
CGCCCGTCCTCGGCGCTGTCCGGCCGCGAGGGTGCTGCCGCGGCGGTGCCCGAGGCCGCCAGTCCTTTCCCGAG
CTTGCCCTTCTCGCTGAACAGTATCCGCAGCAGCGAGCTGGGCAGGATCACGCGCCCGCGCTTGCTGGGCGAAG
AGGAGTACTTGAATGACTCGCTGTTGAGACCCGAGCGGGAGAAGAACTTCCCCAATAACGGGATAGAAAGCCTG
GTGGACAAGATGAGCCGCTGGAAGACGTATGCGCAGGAGCACAGGGACGATCCCCGGGCGTCGCAGGGGGCCAC
GAGCCGGGGCAGCGCCGCCCGTAAACGCCGGTGGCACGACAGGCAGCGGGGACAGATGTGGGACGATGAGGACT
CCGCCGACGACAGCAGCGTGTTGGACTTGGGTGGGAGTGGTAACCCGTTCGCTCACCTGCGCCCCCGTATCGGG
CGCATGATGTAAGAGAAACCGAAAATAAATGATACTCACCAAGGCCATGGCGACCAGCGTGCGTTCGTTTCTTC
TCTGTTGTTGTTGTATCTAGTATGATGAGGCGTGCGTACCCGGAGGGTCCTCCTCCCTCGTACGAGAGCGTGAT
GCAGCAGGCGATGCGGCGGCGGCGATGCAGCCCCCGCTGGAGGCTCCTTACGTGCCCCCGCGGTACCTGGCGC
CTACGGAGGGGCGGAACAGCATTCGTTACTCGGAGCTGGCACCCTTGTACGATACCACCCGGTTGTACCTGGTG
GACAACAAGTCGGCGGACATCGCCTCGCTGAACTACCAGAACGACCACAGCAACTTCCTGACCACCGTGGTGCA
GAACAATGACTTCACCCCCACGGAGGCCAGCACCCAGACCATCAACTTTGACGAGCGCTCGCGGTGGGGCGGCC
AGCTGAAAACCATCATGCACACCAACATGCCCAACGTGAACGAGTTCATGTACAGCAACAAGTTCAAGGCGCGG
GTGATGGTCTCCCGCAAGACCCCCAATGGGGTGACAGTGACAGAGGATTATGATGGTAGTCAGGATGAGCTGAA
GTATGAATGGGTGGAATTTGAGCTGCCCGAAGGCAACTTCTCGGTGACCATGACCATCGACCTGATGAACAACG
CCATCATCGACAATTACTTGGCGGTGGGGCGGCAGAACGGGGTGCTGGAGAGCGACATCGGCGTGAAGTTCGAC
ACTAGGAACTTCAGGCTGGGCTGGGACCCCGTGACCGAGCTGGTCATGCCCGGGGTGTACACCAACGAGGCTTT
CCATCCCGATATTGTCTTGCTGCCCGGCTGCGGGGTGGACTTCACCGAGAGCCGCCTCAGCAACCTGCTGGGCA
TTCGCAAGAGGCAGCCCTTCCAGGAAGGCTTCCAGATCATGTACGAGGATCTGGAGGGGGCAACATCCCCGCG
CTCCTGGATGTCGACGCCTATGAGAAAAGCAAGGAGGATGCAGCAGCTGAAGCAACTGCAGCCGTAGCTACCGC
CTCTACCGAGGTCAGGGGCGATAATTTTGCAAGCGCCGCAGCAGTGGCAGCGGCCGAGGCGGCTGAAACCGAAA
```

-continued

```
GTAAGATAGTCATTCAGCCGGTGGAGAAGGATAGCAAGAACAGGAGCTACAACGTACTACCGGACAAGATAAAC

ACCGCCTACCGCAGCTGGTACCTAGCCTACAACTATGGCGACCCCGAGAAGGGCGTGCGCTCCTGGACGCTGCT

CACCACCTCGGACGTCACCTGCGGCGTGGAGCAAGTCTACTGGTCGCTGCCCGACATGATGCAAGACCCGGTCA

CCTTCCGCTCCACGCGTCAAGTTAGCAACTACCCGGTGGTGGGCGCCGAGCTCCTGCCCGTCTACTCCAAGAGC

TTCTTCAACGAGCAGGCCGTCTACTCGCAGCAGCTGCGCGCCTTCACCTCGCTTACGCACGTCTTCAACCGCTT

CCCCGAGAACCAGATCCTCGTCCGCCCGCCCGCGCCCACCATTACCACCGTCAGTGAAAACGTTCCTGCTCTCA

CAGATCACGGGACCCTGCCGCTGCGCAGCAGTATCCGGGGAGTCCAGCGCGTGACCGTTACTGACGCCAGACGC

CGCACCTGCCCCTACGTCTACAAGGCCCTGGGCATAGTCGCGCCGCGCGTCCTCTCGAGCCGCACCTTCTAAAT

GTCCATTCTCATCTCGCCCAGTAATAACACCGGTTGGGGCCTGCGCGCGCCCAGCAAGATGTACGGAGGCGCTC

GCCAACGCTCCACGCAACACCCCGTGCGCGTGCGCGGGCACTTCCGCGCTCCCTGGGGCGCCCTCAAGGGCCGC

GTGCGGTCGCGCACCACCGTCGACGACGTGATCGACCAGGTGGTGGCCGACGCGCGCAACTACACCCCCGCCGC

CGCGCCCGTCTCCACCGTGGACGCCGTCATCGACAGCGTGGTGGCcGACGCGCGCCGGTACGCCCGCGCCAAGA

GCCGGCGGCGGCGCATCGCCCGGCGGCACCGGAGCACCCCCGCCATGCGCGCGGCGCGAGCCTTGCTGCGCAGG

GCCAGGCGCACGGGACGCAGGGCCATGCTCAGGGCGGCCAGACGCGCGGCTTCAGGCGCCAGCGCCGGCAGGAC

CCGGAGACGCGCGGCCACGGCGGCGGCAGCGGCCATCGCCAGCATGTCCCGCCCGCGGCGAGGGAACGTGTACT

GGGTGCGCGACGCCGCCACCGGTGTGCGCGTGCCCGTGCGCACCCGCCCCCCTCGCACTTGAAGATGTTCACTT

CGCGATGTTGATGTGTCCCAGCGGCGAGGAGGATGTCCAAGCGCAAATTCAAGGAAGAGATGCTCCAGGTCATC

GCGCCTGAGATCTACGCCCTGCGGTGGTGAAGGAGGAAAGAAAGCCCCGCAAAATCAAGCGGGTCAAAAAGGA

CAAAAAGGAAGAAGAAAGTGATGTGGACGGATTGGTGGAGTTTGTGCGCGAGTTCGCCCCCCGGCGGCGCGTGC

AGTGGCGCGGGCGGAAGGTGCAACCGGTGCTGAGACCCGGCACCACCGTGGTCTTCACGCCCGGCGAGCGCTCC

GGCACCGCTTCCAAGCGCTCCTACGACGAGGTGTACGGGATGATGATATTCTGGAGCAGGCGGCCGAGCGCCT

GGGCGAGTTTGCTTACGGCAAGCGCAGCCGTTCCGCACCGAAGGAAGAGGCGGTGTCCATCCCGCTGGACCACG

GCAACCCCACGCCGAGCCTCAAGCCCGTGACCTTGCAGCAGGTGCTGCCGACCGCGGCGCCGCGCCGGGGGTTC

AAGCGCGAGGGCGAGGATCTGTACCCCACCATGCAGCTGATGGTGCCCAAGCGCCAGAAGCTGGAAGACGTGCT

GGAGACCATGAAGGTGGACCCGGACGTGCAGCCCGAGGTCAAGGTGCGGCCCATCAAGCAGGTGGCCCCGGGCC

TGGGCGTGCAGACCGTGGACATCAAGATTCCCACGGAGCCCATGGAAACGCAGACCGAGCCCATGATCAAGCCC

AGCACCAGCACCATGGAGGTGCAGACGGATCCCTGGATGCCATCGGCTCCTAGTCGAAGACCCCGGCGCAAGTA

CGGCGCGGCCAGCCTGCTGATGCCCAACTACGCGCTGCATCCTTCCATCATCCCCACGCCGGGCTACCGCGGCA

CGCGCTTCTACCGCGGTCATACCAGCAGCCGCCGCCGCAAGACCACCACTCGCCGCCGCCGTCGCCGCACCGCC

GCTGCAACCACCCCTGCCGCCCTGGTGCGGAGAGTGTACCGCCGCGGCCGCGCACCTCTGACCCTGCCGCGCGC

GCGCTACCACCCGAGCATCGCCATTTAAACTTTCGCCtGCTTTGCAGATCAATGGCCCTCACATGCCGCCTTCG

CGTTCCCATTACGGGCTACCGAGGAAGAAAACCGCGCCGTAGAAGGCTGGCGGGAACGGGATGCGTCGCCACC

ACCACCGGCGGCGGCGCGCCATCAGCAAGCGGTTGGGGGAGGCTTCCTGCCCGCGCTGATCCCCATCATCGCC

GCGGCGATCGGGGCGATCCCCGGCATTGCTTCCGTGGCGGTGCAGGCCTCTCAGCGCCACTGAGACACACTTGG

AAACATCTTGTAATAAACCaATGGACTCTGACGCTCCTGGTCCTGTGATGTGTTTTCGTAGACAGATGGAAGAC

ATCAATTTTTCGTCCCTGGCTCCGCGACACGGCACGCGGCCGTTCATGGGCACCTGGAGCGACATCGGCACCAG

CCAACTGAACGGGGGCGCCTTCAATTGGAGCAGTCTCTGGAGCGGGCTTAAGAATTTCGGGTCCACGCTTAAAA

CCTATGGCAGCAAGGCGTGGAACAGCACCACAGGGCAGGCGCTGAGGGATAAGCTGAAAGAGCAGAACTTCCAG

CAGAAGGTGGTCGATGGGCTCGCCTCGGGCATCAACGGGGTGGTGGACCTGGCCAACCAGGCCGTGCAGCGGCA

GATCAACAGCCGCCTGGACCCGGTGCCGCCCGCCGGCTCCGTGGAGATGCCGCAGGTGGAGGAGGAGCTGCCTC
```

-continued

```
CCCTGGACAAGCGGGGCGAGAAGCGACCCCGCCCCGATGCGGAGGAGACGCTGCTGACGCACACGGACGAGCCG
CCCCCGTACGAGGAGGCGGTGAAACTGGGTCTGCCCACCACGCGGCCCATCGCGCCCCTGGCCACCGGGGTGCT
GAAACCCGAAAAGCCCGCGACCCTGGACTTGCCTCCTCCCCAGCCTTCCCGCCCCTCTACAGTGGCTAAGCCCC
TGCCGCCGGTGGCCGTGGCCCGCGCGCGACCCGGGGGCACCGCCCGCCCTCATGCGAACTGGCAGAGCACTCTG
AACAGCATCGTGGGTCTGGGAGTGCAGAGTGTGAAGCGCCGCCGCTGCTATTAAACCTACCGTAGCGCTTAACT
TGCTTGTCTGTGTGTGTATGTATTATGTCGCCGCCGCCGCTGTCCACCAGAAGGAGGAGTGAAGAGGCGCGTCG
CCGAGTTGCAAGATGGCCACCCCATCGATGCTGCCCCAGTGGGCGTACATGCACATCGCCGGACAGGACGCTTC
GGAGTACCTGAGTCCGGGTCTGGTGCAGTTTGCCCGCGCCACAGACACCTACTTCAGTCTGGGGAACAAGTTTA
GGAACCCCACGGTGGCGCCCACGCACGATGTGACCACCGACCGCAGCCAGCGGCTGACGCTGCGCTTCGTGCCC
GTGGACCGCGAGGACAACACCTACTCGTACAAAGTGCGCTACACGCTGGCCGTGGGCGACAACCGCGTGCTGGA
CATGGCCAGCACCTACTTTGACATCCGCGGCGTGCTGGATCGGGGCCCTAGCTTCAAACCCTACTCCGGCACCG
CCTACAACAGTCTGGCCCCCAAGGGAGCACCCAACACTTGTCAGTGGACATATAAAGCCGATGGTGAAACTGCC
ACAGAAAAAACCTATACATATGGAAATGCACCCGTGCAGGGCATTAACATCACAAAAGATGGTATTCAACTTGG
AACTGACACCGATGATCAGCCAATCTACGCAGATAAAACCTATCAGCCTGAACCTCAAGTGGGTGATGCTGAAT
GGCATGACATCACTGGTACTGATGAAAAGTATGGAGGCAGAGCTCTTAAGCCTGATACCAAAATGAAGCCTTGT
TATGGTTCTTTTGCCAAGCCTACTAATAAAGAAGGAGGTCAGGCAAATGTGAAAACAGGAACAGGCACTACTAA
AGAATATGACATAGACATGGCTTTCTTTGACAACAGAAGTGCGGCTGCTGCTGGCCTAGCTCCAGAAATTGTTT
TGTATACTGAAAATGTGGATTTGGAAACTCCAGATACCCATATTGTATACAAAGCAGGCACAGATGACAGCAGC
TCTTCTATTAATTTGGGTCAGCAAGCCATGCCCAACAGACCTAACTACATTGGTTTCAGAGACAACTTTATCGG
GCTCATGTACTACAACAGCACTGGCAATATGGGGGTGCTGGCCGGTCAGGCTTCTCAGCTGAATGCTGTGGTTG
ACTTGCAAGACAGAAACACCGAGCTGTCCTACCAGCTCTTGCTTGACTCTCTGGGTGACAGAACCCGGTATTTC
AGTATGTGGAATCAGGCGGTGGACAGCTATGATCCTGATGTGCGCATTATTGAAAATCATGGTGTGGAGGATGA
ACTTCCCAACTATTGTTTCCCTCTGGATGCTGTTGGCAGAACAGATACTTATCAGGGAATTAAGGCTAATGGAA
CTGATCAAACCACATGGACCAAAGATGACAGTGTCAATGATGCTAATGAGATAGGCAAGGGTAATCCATTCGCC
ATGGAAATCAACATCCAAGCCAACCTGTGGAGGAACTTCCTCTACGCCAACGTGGCCCTGTACCTGCCCGACTC
TTACAAGTACACGCCGGCCAATGTTACCCTGCCCACCAACACCAACACCTACGATTACATGAACGGCCGGGTGG
TGGCGCCCTCGCTGGTGGACTCCTACATCAACATCGGGGCGCGCTGGTCGCTGGATCCCATGGACAACGTGAAC
CCCTTCAACCACCACCGCAATGCGGGGCTGCGCTACCGCTCCATGCTCCTGGGCAACGGGCGCTACGTGCCCTT
CCACATCCAGGTGCCCCAGAAATTTTTCGCCATCAAGAGCCTCCTGCTCCTGCCCGGGTCCTACACCTACGAGT
GGAACTTCCGCAAGGACGTCAACATGATCCTGCAGAGCTCCCTCGGCAACGACCTGCGCACGGACGGGGCCTCC
ATCTCCTTCACCAGCATCAACCTCTACGCCACCTTCTTCCCCATGGCGCACAACACGGCCTCCACGCTCGAGGC
CATGCTGCGCAACGACACCAACGACCAGTCCTTCAACGACTACCTCTCGGCGGCCAACATGCTCTACCCCATCC
CGGCCAACGCCACCAACGTGCCCATCTCCATCCCCTCGCGCAACTGGGCCGCCTTCCGCGGCTGGTCCTTCACG
CGTCTCAAGACCAAGGAGACGCCCTCGCTGGGCTCCGGGTTCGACCCCTACTTCGTCTACTCGGGCTCCATCCC
CTACCTCGACGGCACCTTCTACCTCAACCACACCTTCAAGAAGGTCTCCATCACCTTCGACTCCTCCGTCAGCT
GGCCCGGCAACGACCGGCTCCTGACGCCCAACGAGTTCGAAATCAAGCGCACCGTCGACGGCGAGGGCTACAAC
GTGGCCCAGTGCAACATGACCAAGGACTGGTTCCTGGTCCAGATGCTGGCCCACTACAACATCGGCTACCAGGG
CTTCTACGTGCCCGAGGGCTACAAGGACCGCATGTACTCCTTCTTCCGCAACTTCCAGCCCATGAGCCGCCAGG
TGGTGGACGAGGTCAACTACAAGGACTACCAGGCCGTCACCCTGGCCTACCAGCACAACAACTCGGGCTTCGTC
GGCTACCTCGCGCCCACCATGCGCCAGGGCCAGCCCTACCCCGCCAACTACCCCTACCCGCTCATCGGCAAGAG
CGCCGTCACCAGCGTCACCCAGAAAAAGTTCCTCTGCGACAGGGTCATGTGGCGCATCCCCTTCTCCAGCAACT
```

-continued

```
TCATGTCCATGGGCGCGCTCACCGACCTCGGCCAGAACATGCTCTATGCCAACTCCGCCCACGCGCTAGACATG

AATTTCGAAGTCGACCCCATGGATGAGTCCACCCTTCTCTATGTTGTCTTCGAAGTCTTCGACGTCGTCCGAGT

GCACCAGCCCCACCGCGGCGTCATCGAGGCCGTCTACCTGCGCACCCCCTTCTCGGCCGGTAACGCCACCACCT

AAGCTCTTGCTTCTTGCAAGCCATGGCCGCGGGCTCCGGCGAGCAGGAGCTCAGGGCCATCATCCGCGACCTGG

GCTGCGGGCCCTACTTCCTGGGCACCTTCGATAAGCGCTTCCCGGGATTCATGGCCCCGCACAAGCTGGCCTGC

GCCATCGTCAACACGGCCGGCCGCGAGACCGGGGGCGAGCACTGGCTGGCCTTCGCCTGGAACCCGCGCTCGAA

CACCTGCTACCTCTTCGACCCCTTCGGGTTCTCGGACGAGCGCCTCAAGCAGATCTACCAGTTCGAGTACGAGG

GCCTGCTGCGCCGCAGCGCCCTGGCCACCGAGGACCGCTGCGTCACCCTGGAAAAGTCCACCCAGACCGTGCAG

GGTCCGCGCTCGGCCGCCTGCGGGCTCTTCTGCTGCATGTTCCTGCACGCCTTCGTGCACTGGCCCGACCGCCC

CATGGACAAGAACCCCACCATGAACTTGCTGACGGGGGTGCCCAACGGCATGCTCCAGTCGCCCAGGTGGAAC

CCACCCTGCGCCGCAACCAGGAGGCGCTCTACCGCTTCCTCAACTCCCACTCCGCCTACTTTCGCTCCCACCGC

GCGCGCATCGAGAAGGCCACCGCCTTCGACCGCATGAATCAAGACATGTAAACCGTGTGTGTATGTTAAATGTC

TTTAATAAACAGCACTTTCATGTTACACATGCATCTGAGATGATTTATTTAGAAATCGAAAGGGTTCTGCCGGG

TCTCGGCATGGCCCGCGGGCAGGGACACGTTGCGGAACTGGTACTTGGCCAGCCACTTGAACTCGGGGATCAGC

AGTTTGGGCAGCGGGGTGTCGGGGAAGGAGTCGGTCCACAGCTTCCGCGTCAGTTGCAGGGCGCCCAGCAGGTC

GGGCGCGGAGATCTTGAAATCGCAGTTGGGACCCGCGTTCTGCGCGGGAGTTGCGGTACACGGGGTTGCAGC

ACTGGAACACCATCAGGGCCGGGTGCTTCACGCTCGCCAGCACCGTCGCGTCGGTGATGCTCTCCACGTCGAGG

TCCTCGGCGTTGGCCATCCCGAAGGGGGTCATCTTGCAGGTCTGCCTTCCCATGGTGGGCACGCACCCGGGCTT

GTGGTTGCAATCGCAGTGCAGGGGATCAGCATCATCTGGGCCTGGTCGGCGTTCATCCCCGGGTACATGGCCT

TCATGAAAGCCTCCAATTGCCTGAACGCCTGCTGGGCCTTGGCTCCCTCGGTGAAGAAGACCCCGCAGGACTTG

CTAGAGAACTGGTTGGTGGCGCACCCGGCGTCGTGCACGCAGCAGCGCGTCGTTGTTGGCCAGCTGCACCAC

GCTGCGCCCCAGCGGTTCTGGGTGATCTTGGCCCGGTCGGGGTTCTCCTTCAGCGCGCGCTGCCCGTTCTCGC

TCGCCACATCCATCTCGATCATGTGCTCCTTCTGGATCATGGTGGTCCCGTGCAGGCACCGCAGCTTGCCCTCG

GCCTCGGTGCACCCGTGCAGCCACAGCGCGCACCCGGTGCACTCCCAGTTCTTGTGGGCGATCTGGGAATGCGC

GTGCACGAAGCCCTGCAGGAAGCGGCCCATCATGGTGGTCAGGGTCTTGTTGCTAGTGAAGGTCAGCGGAATGC

CGCGGTGCTCCTCGTTGATGTACAGGTGGCAGATGCGGCGGTACACCTCGCCCTGCTCGGGCATCAGCTGGAAG

TTGGCTTTCAGGTCGGTCTCCACGCGGTAGCGGTCCATCAGCATAGTCATGATTTCCATACCCTTCTCCCAGGC

CGAGACGATGGGCAGGCTCATAGGGTTCTTCACCATCATCTTAGCGCTAGCAGCCGCGGCCAGGGGTCGCTCT

CGTCCAGGGTCTCAAAGCTCCGCTTGCCGTCCTTCTCGGTGATCCGCACCGGGGGGTAGCTGAAGCCCACGCC

GCCAGCTCCTCCTCGGCCTGTCTTTCGTCCTCGCTGTCCTGGCTGACGTCCTGCAGGACCACATGCTTGGTCTT

GCGGGGTTTCTTCTTGGGCGGCAGCGGCGGCGGAGATGTTGGAGATGGCGAGGGGGAGCGCGAGTTCTCGCTCA

CCACTACTATCTCTTCCTCTTCTTGGTCCGAGGCCACGCGGCGGTAGGTATGTCTCTTCGGGGGCAGAGGCGGA

GGCGACGGGCTCTCGCCGCCGCGACTTGGCGGATGGCTGGCAGAGCCCCTTCCGCGTTCGGGGGTGCGCTCCCG

GCGGCGCTCTGACTGACTTCCTCCGCGGCCGGCCATTGTGTTCTCCTAGGGAGGAACAACAAGCATGGAGACTC

AGCCATCGCCAACCTCGCCATCTGCCCCCACCGCCGACGAGAAGCAGCAGCAGCAGAATGAAAGCTTAACCGCC

CCGCCGCCCAGCCCCGCCACCTCCGACGCGGCCGTCCCAGACATGCAAGAGATGGAGGAATCCATCGAGATTGA

CCTGGGCTATGTGACGCCCGCGGAGCACGAGGAGGAGCTGGCAGTGCGCTTTTCACAAGAAGAGATACACCAAG

AACAGCCAGAGCAGGAAGCAGAGAATGAGCAGAGTCAGGCTGGGCTCGAGCATGACGGCGACTACCTCCACCTG

AGCGGGGGGAGGACGCGCTCATCAAGCATCTGGCCCGGCAGGCCACCATCGTCAAGGATGCGCTGCTCGACCG

CACCGAGGTGCCCCTCAGCGTGGAGGAGCTCAGCCGCGCCTACGAGTTGAACCTCTTCTCGCCGCGCGTGCCCC
```

-continued

```
CCAAGCGCCAGCCCAATGGCACCTGCGAGCCCAACCCGCGCCTCAACTTCTACCCGGTCTTCGCGGTGCCCGAG
GCCCTGGCCACCTACCACATCTTTTTCAAGAACCAAAAGATCCCCGTCTCCTGCCGCGCCAACCGCACCCGCGC
CGACGCCCTTTTCAACCTGGGTCCCGGCGCCCGCCTACCTGATATCGCCTCCTTGGAAGAGGTTCCCAAGATCT
TCGAGGGTCTGGGCAGCGACGAGACTCGGGCCGCGAACGCTCTGCAAGGAGAAGGAGGAGAGCATGAGCACCAC
AGCGCCCTGGTCGAGTTGGAAGGCGACAACGCGCGGCTGGCGGTGCTCAAACGCACGGTCGAGCTGACCCATTT
CGCCTACCCGGCTCTGAACCTGCCCCCCAAAGTCATGAGCGCGGTCATGGACCAGGTGCTCATCAAGCGCGCGT
CGCCCATCTCCGAGGACGAGGGCATGCAAGACTCCGAGGAGGGCAAGCCCGTGGTCAGCGACGAGCAGCTGGCC
CGGTGGCTGGGTCCTAATGCTAGTCCCCAGAGTTTGGAAGAGCGGCGCAAACTCATGATGGCCGTGGTCCTGGT
GACCGTGGAGCTGGAGTGCCTGCGCCGCTTCTTCGCCGACGCGGAGACCCTGCGCAAGGTCGAGGAGAACCTGC
ACTACCTCTTCAGGCACGGGTTCGTGCGCCAGGCCTGCAAGATCTCCAACGTGGAGCTGACCAACCTGGTCTCC
TACATGGGCATCTTGCACGAGAACCGCCTGGGGCAGAACGTGCTGCACACCACCCTGCGCGGGGAGGCCCGGCG
CGACTACATCCGCGACTGCGTCTACCTCTACCTCTGCCACACCTGGCAGACGGGCATGGGCGTGTGGCAGCAGT
GTCTGGAGGAGCAGAACCTGAAAGAGCTCTGCAAGCTCCTGCAGAAGAACCTCAAGGGTCTGTGGACCGGGTTC
GACGAGCGCACCACCGCCTCGGACCTGGCCGACCTCATTTTCCCCGAGCGCCTCAGGCTGACGCTGCGCAACGG
CCTGCCCGACTTTATGAGCCAAAGCATGTTGCAAAACTTTCGCTCTTTCATCCTCGAACGCTCCGGAATCCTGC
CCGCCACCTGCTCCGCGCTGCCCTCGGACTTCGTGCCGCTGACCTTCCGCGAGTGCCCCCCGCCGCTGTGGAGC
CACTGCTACCTGCTGCGCCTGGCCAACTACCTGGCCTACCACTCGGACGTGATCGAGGACGTCAGCGGCGAGGG
CCTGCTCGAGTGCCACTGCCGCTGCAACCTCTGCACGCCGCACCGCTCCCTGGCCTGCAACCCCCAGCTGCTGA
GCGAGACCCAGATCATCGGCACCTTCGAGTTGCAAGGGCCCAGCGAAGGCGAGGGTTCAGCCGCCAAGGGGGGT
CTGAAACTCACCCCGGGGCTGTGGACCTCGGCCTACTTGCGCAAGTTCGTGCCCGAGGACTACCATCCCTTCGA
GATCAGGTTCTACGAGGACCAATCCCATCCGCCCAAGGCCGAGCTGTCGGCCTGCGTCATCACCCAGGGGGCGA
TCCTGGCCCAATTGCAAGCCATCCAGAAATCCCGCCAAGAATTCTTGCTGAAAAAGGGCCGCGGGGTCTACCTC
GACCCCCAGACCGGTGAGGAGCTCAACCCCGGCTTCCCCCAGGATGCCCCGAGGAAACAAGAAGCTGAAAGTGG
AGCTGCCGCCCGTGGAGGATTTGGAGGAAGACTGGGAGAACAGCAGTCAGGCAGAGGAGGAGGAGATGGAGGAA
GACTGGGACAGCACTCAGGCAGAGGAGGACAGCCTGCAAGACAGTCTGGAGGAAGACGAGGAGGAGGCAGAGGA
GGAGGTGGAAGAAGCAGCCGCCGCCAGACCGTCGTCCTCGGCGGGGAGAAAGCAAGCAGCACGGATACCATCT
CCGCTCCGGGTCGGGGTCCCGCTCGACCACACAGTAGATGGGACGAGACCGGACGATTCCCGAACCCCACCACC
CAGACCGGTAAGAAGGAGCGGCAGGGATACAAGTCCTGGCGGGGGCACAAAAACGCCATCGTCTCCTGCTTGCA
GGCCTGCGGGGGCAACATCTCCTTCACCCGGCGCTACCTGCTCTTCCACCGCGGGGTGAACTTTCCCCGCAACA
TCTTGCATTACTACCGTCACCTCCACAGCCCCTACTACTTCCAAGAAGAGGCAGCAGCAGCAGAAAAAGACCAG
CAGAAAACCAGCAGCTAGAAAATCCACAGCGGCGGCAGCAGGTGGACTGAGGATCGCGGCGAACGAGCCGGCGC
AAACCCGGGAGCTGAGGAACCGGATCTTTCCCACCCTCTATGCCATCTTCCAGCAGAGTCGGGGGCAGGAGCAG
GAACTGAAAGTCAAGAACCGTTCTCTGCGCTCGCTCACCCGCAGTTGTCTGTATCACAAGAGCGAAGACCAACT
TCAGCGCACTCTCGAGGACGCCGAGGCTCTCTTCAACAAGTACTGCGCGCTCACTCTTAAAGAGTAGCCCGCGC
CCGCCCAGTCGCAGAAAAAGGCGGGAATTACGTCACCTGTGCCCTTCGCCCTAGCCGCCTCCACCCATCATCAT
GAGCAAAGAGATTCCCACGCCTTACATGTGGAGCTACCAGCCCCAGATGGGCCTGGCCGCCGGTGCCGCCCAGG
ACTACTCCACCCGCATGAATTGGCTCAGCGCCGGGCCGCGATGATCTCACGGGTGAATGACATCCGCGCCCAC
CGAAACCAGATACTCCTAGAACAGTCAGCGCTCACCGCCACGCCCCGCAATCACCTCAATCCGCGTAATTGGCC
CGCCGCCCTGGTGTACCAGGAAATTCCCCAGCCCACGACCGTACTACTTCCGCGAGACGCCCAGGCCGAAGTCC
AGCTGACTAACTCAGGTGTCCAGCTGGCGGGCGGCGCCACCCTGTGTCGTCACCGCCCCGCTCAGGGTATAAAG
CGGCTGGTGATCCGGGGCAGAGGCACACAGCTCAACGACGAGGTGGTGAGCTCTTCGCTGGGTCTGCGACCTGA
```

```
CGGAGTCTTCCAACTCGCCGGATCGGGGAGATCTTCCTTCACGCCTCGTCAGGCCGTCCTGACTTTGGAGAGTT
CGTCCTCGCAGCCCCGCTCGGGTGGCATCGGCACTCTCCAGTTCGTGGAGGAGTTCACTCCCTCGGTCTACTTC
AACCCCTTCTCCGGCTCCCCCGGCCACTACCCGGACGAGTTCATCCCGAACTTCGACGCCATCAGCGAGTCGGT
GGACGGCTACGATTGAAACTAATCACCCCCTTATCCAGTGAAATAAAGATCATATTGATGATGATTTTACAGAA
ATAAAAAATAATCATTTGATTTGAAATAAAGATACAATCATATTGATGATTTGAGTTTAACAAAAAAATAAAGA
ATCACTTACTTGAAATCTGATACCAGGTCTCTGTCCATGTTTTCTGCCAACACCACTTCACTCCCCTCTTCCCA
GCTCTGGTACTGCAGGCCCCGGCGGGCTGCAAACTTCCTCCACACGCTGAAGGGGATGTCAAATTCCTCCTGTC
CCTCAATCTTCATTTTATCTTCTATCAGATGTCCAAAAAGCGCGTCCGGGTGGATGATGACTTCGACCCCGTCT
ACCCCTACGATGCAGACAACGCACCGACCGTGCCCTTCATCAACCCCCCCTTCGTCTCTTCAGATGGATTCCAA
GAGAAGCCCCTGGGGGTGTTGTCCCTGCGACTGGCCGACCCCGTCACCACCAAGAACGGGGAAATCACCCTCAA
GCTGGGAGAGGGGGTGGACCTCGATTCCTCGGGAAAACTCATCTCCAACACGGCCACCAAGGCCGCCGCCCCTC
TCAGTTTTTCCAACAACACCATTTCCCTTAACATGGATCACCCCTTTTACACTAAAGATGGAAAATTATCCTTA
CAAGTTTCTCCACCATTAAATATACTGAGAACAAGCATTCTAAACACACTAGCTTTAGGTTTTGGATCAGGTTT
AGGACTCCGTGGCTCTGCCTTGGCAGTACAGTTAGTCTCTCCACTTACATTTGATACTGATGGAAACATAAAGC
TTACCTTAGACAGAGGTTTGCATGTTACAACAGGAGATGCAATTGAAAGCAACATAAGCTGGGCTAAAGGTTTA
AAATTTGAAGATGGAGCCATAGCAACCAACATTGGAAATGGGTTAGAGTTTGGAAGCAGTAGTACAGAAACAGG
TGTTGATGATGCTTACCCAATCCAAGTTAAACTTGGATCTGGCCTTAGCTTTGACAGTACAGGAGCCATAATGG
CTGGTAACAAAGAAGACGATAAACTCACTTTGTGGACAACACCTGATCCATCACCAAACTGTCAAATACTCGCA
GAAAATGATGCAAAACTAACACTTTGCTTGACTAAATGTGGTAGTCAAATACTGGCCACTGTGTCAGTCTTAGT
TGTAGGAAGTGGAAACCTAAACCCCATTACTGGCACCGTAAGCAGTGCTCAGGTGTTTCTACGTTTTGATGCAA
ACGGTGTTCTTTTAACAGAACATTCTACACTAAAAAAATACTGGGGGTATAGGCAGGGAGATAGCATAGATGGC
ACTCCATATACCAATGCTGTAGGATTCATGCCCAATTTAAAAGCTTATCCAAAGTCACAAAGTTCTACTACTAA
AAATAATATAGTAGGGCAAGTATACATGAATGGAGATGTTTCAAAACCTATGCTTCTCACTATAACCCTCAATG
GTACTGATGACAGCAACAGTACATATTCAATGTCATTTTCATACACCTGGACTAATGGAAGCTATGTTGGAGCA
ACATTTGGGCTAACTCTTATACCTTCTCATACATCGCCCAAGAATGAACACTGTATCCCACCCTGCATGCCAA
CCCTTCCCACCCCACTCTGTGGAACAAACTCTGAAACACAAAATAAAATAAAGTTCAAGTGTTTTATTGATTCA
ACAGTTTTACAGGATTCGAGCAGTTATTTTTCCTCCACCCTCCCAGGACATGGAATACACCACCCTCTCCCCCC
GCACAGCCTTGAACATCTGAATGCCATTGGTGATGGACATGCTTTTGGTCTCCACGTTCCACACAGTTTCAGAG
CGAGCCAGTCTCGGGTCGGTCAGGGAGATGAAACCCTCCGGGCACTCCCGCATCTGCACCTCACAGCTCAACAG
CTGAGGATTGTCCTCGGTGGTCGGGATCACGGTTATCTGGAAGAAGCAGAAGAGCGGCGGTGGGAATCATAGTC
CGCGAACGGGATCGGCCGTGGTGTCGCATCAGGCCCCGCAGCAGTCGCTGCCGCCGCCGCTCCGTCAAGCTGC
TGCTCAGGGGGTCCGGGTCCAGGGACTCCCTCAGCATGATGCCCACGGCCCTCAGCATCAGTCGTCTGGTGCGG
CGGGCGCAGCAGCGCATGCGGATCTCGCTCAGGTCGCTGCAGTACGTGCAACACAGAACCACCAGGTTGTTCAA
CAGTCCATAGTTCAACACGCTCCAGCCGAAACTCATCGCGGGAAGGATGCTACCCACGTGGCCGTCGTACCAGA
TCCTCAGGTAAATCAAGTGGTGCCCCCTCCAGAACACGCTGCCCACGTACATGATCTCCTTGGGCATGTGGCGG
TTCACCACCTCCCGGTACCACATCACCCTCTGGTTGAACATGCAGCCCCGGATGATCCTGCGGAACCACAGGGC
CAGCACCGCCCCGCCCGCCATGCAGCGAAGAGACCCCGGGTCCCGGCAATGGCAATGGAGGACCCACCGCTCGT
ACCCGTGGATCATCTGGGAGCTGAACAAGTCTATGTTGGCACAGCACAGGCATATGCTCATGCATCTCTTCAGC
ACTCTCAACTCCTCGGGGGTCAAAACCATATCCCAGGGCACGGGGAACTCTTGCAGGACAGCGAACCCCGCAGA
ACAGGGCAATCCTCGCACAGAACTTACATTGTGCATGGACAGGGTATCGCAATCAGGCAGCACCGGGTGATCCT
```

-continued

```
CCACCAGAGAAGCGCGGGTCTCGGTCTCCTCACAGCGTGGTAAGGGGGCCGGCCGATACGGGTGATGGCGGGAC

GCGGCTGATCGTGTTCGCGACCGTGTCATGATGCAGTTGCTTTCGGACATTTTCGTACTTGCTGTAGCAGAACC

TGGTCCGGGCGCTGCACACCGATCGCCGGCGGCGGTCTCGGCGCTTGGAACGCTCGGTGTTGAAATTGTAAAAC

AGCCACTCTCTCAGACCGTGCAGCAGATCTAGGGCCTCAGGAGTGATGAAGATCCCATCATGCCTGATGGCTCT

GATCACATCGACCACCGTGGAATGGGCCAGACCCAGCCAGATGATGCAATTTTGTTGGGTTTCGGTGACGGCGG

GGGAGGGAAGAACAGGAAGAACCATGATTAACTTTTAATCCAAACGGTCTCGGAGTACTTCAAAATGAAGATCG

CGGAGATGGCACCTCTCGCCCCCGCTGTGTTGGTGGAAAATAACAGCCAGGTCAAAGGTGATACGGTTCTCGAG

ATGTTCCACGGTGGCTTCCAGCAAAGCCTCCACGCGCACATCCAGAAACAAGACAATAGCGAAAGCGGGAGGGT

TCTCTAATTCCTCAATCATCATGTTACACTCCTGCACCATCCCCAGATAATTTTCATTTTTCCAGCCTTGAATG

ATTCGAACTAGTTCcTGAGGTAAATCCAAGCCAGCCATGATAAAGAGCTCGCGCAGAGCGCCCTCCACCGGCAT

TCTTAAGCACACCCTCATAATTCCAAGATATTCTGCTCCTGGTTCACCTGCAGCAGATTGACAAGCGGAATATC

AAAATCTCTGCCGCGATCCCTGAGCTCCTCCCTCAGCAATAACTGTAAGTACTCTTTCATATCCTCTCCGAAAT

TTTTAGCCATAGGACCACCAGGAATAAGATTAGGGCAAGCCACAGTACAGATAAACCGAAGTCCTCCCCAGTGA

GCATTGCCAAATGCAAGACTGCTATAAGCATGCTGGCTAGACCCGGTGATATCTTCCAGATAACTGGACAGAAA

ATCGCCCAGGCAATTTTTAAGAAAATCAACAAAAGAAAAATCCTCCAGGTGGACGTTTAGAGCCTCGGGAACAA

CGATGAAGTAAATGCAAGCGGTGCGTTCCAGCATGGTTAGTTAGCTGATCTGTAGAAAAAACAAAAATGAACAT

TAAACCATGCTAGCCTGGCGAACAGGTGGGTAAATCGTTCTCTCCAGCACCAGGCAGGCCACGGGGTCTCCGGC

GCGACCCTCGTAAAAATTGTCGCTATGATTGAAAACCATCACAGAGAGACGTTCCCGGTGGCCGGCGTGAATGA

TTCGACAAGATGAATACACCCCCGGAACATTGGCGTCCGCGAGTGAAAAAAAGCGCCCGAGGAAGCAATAAGGC

ACTACAATGCTCAGTCTCAAGTCCAGCAAAGCGATGCCATGCGGATGAAGCACAAAATTCTCAGGTGCGTACAA

AATGTAATTACTCCCCTCCTGCACAGGCAGCAAAGCCCCCGATCCCTCCAGGTACACATACAAAGCCTCAGCGT

CCATAGCTTACCGAGCAGCAGCACACAACAGGCGCAAGAGTCAGAGAAAGGCTGAGCTCTAACCTGTCCACCCG

CTCTCTGCTCAATATATAGCCCAGATCTACACTGACGTAAAGGCCAAAGTCTAAAAATACCCGCCAAATAATCA

CACACGCCCAGCACACGCCCAGAAACCGGTGACACACTCAAAAAAATACGCGCACTTCCTCAAACGCCCAAAAC

TGCCGTCATTTCCGGGTTCCCACGCTACGTCATCAAAACACGACTTTCAAATTCCGTCGACCGTTAAAAACGTC

ACCCGCCCCGCCCCTAACGGTCGCCCGTCTCTCAGCCAATCAGCGCCCCGCATCCCCAAATTCAAACACCTCAT

TTGCATATTAACGCGCACAAAAAGTTTGAGGTATATTATTGATGATGG
```

XV.B. ChAd Neoantigen Cassette Delivery Vector Testing

XV.B.1. ChAd Vector Evaluation Methods and Materials
Transfection of HEK293A Cells Using Lipofectamine DNA for the ChAdV68 constructs (ChAdV68.4WTnt.GFP, ChAdV68.5WTnt.GFP, ChAdV68.4WTnt.MAG25mer and ChAdV68.5WTnt.MAG25mer) was prepared and transfected into HEK293A cells using the following protocol.

10 ug of plasmid DNA was digested with Pact to liberate the viral genome. DNA was then purified using GeneJet DNA cleanup Micro columns (Thermo Fisher) according to manufacturer's instructions for long DNA fragments, and eluted in 20 ul of pre-heated water; columns were left at 37 degrees for 0.5-1 hours before the elution step.

HEK293A cells were introduced into 6-well plates at a cell density of $10^6$ cells/well 14-18 hours prior to transfection. Cells were overlaid with 1 ml of fresh medium (DMEM-10% hiFBS with pen/strep and glutamate) per well. 1-2 ug of purified DNA was used per well in a transfection with twice the ul volume (2-4 ul) of Lipofectamine2000, according to the manufacturer's protocol. 0.5 ml of OPTI-MEM medium containing the transfection mix was added to the 1 ml of normal growth medium in each well, and left on cells overnight.

Transfected cell cultures were incubated at 37° C. for at least 5-7 days. If viral plaques were not visible by day 7 post-transfection, cells were split 1:4 or 1:6, and incubated at 37° C. to monitor for plaque development. Alternatively, transfected cells were harvested and subjected to 3 cycles of freezing and thawing and the cell lysates were used to infect HEK293A cells and the cells were incubated until virus plaques were observed.

Transfection of ChAdV68 Vectors into HEK293A Cells Using Calcium Phosphate and Generation of the Tertiary Viral Stock DNA for the ChAdV68 constructs (ChAdV68.4WTnt.GFP, ChAdV68.5WTnt.GFP, ChAdV68.4WTnt.MAG25mer, ChAdV68.5WTnt.MAG25mer) was prepared and transfected into HEK293A cells using the following protocol.

HEK293A cells were seeded one day prior to the transfection at $10^6$ cells/well of a 6 well plate in 5% BS/DMEM/ 1×P/S, 1×Glutamax. Two wells are needed per transfection.

Two to four hours prior to transfection the media was changed to fresh media. The ChAdV68.4WTnt.GFP plasmid was linearized with PacI. The linearized DNA was then phenol chloroform extracted and precipitated using one tenth volume of 3M Sodium acetate pH 5.3 and two volumes of 100% ethanol. The precipitated DNA was pelleted by centrifugation at 12,000×g for 5 min before washing 1× with 70% ethanol. The pellet was air dried and re-suspended in 50 μL of sterile water. The DNA concentration was determined using a NanoDrop (ThermoFisher) and the volume adjusted to 5 μg of DNA/50 μL.

169 μL of sterile water was added to a microfuge tube. 5 μL of 2M $CaCl_2$ was then added to the water and mixed gently by pipetting. 50 μL of DNA was added dropwise to the $CaCl_2$ water solution. Twenty six μL of 2M $CaCl_2$ was then added and mixed gently by pipetting twice with a micro-pipetor. This final solution should consist of 5 μg of DNA in 250 μL of 0.25M $CaCl_2$. A second tube was then prepared containing 250 μL of 2×HBS (Hepes buffered solution). Using a 2 mL sterile pipette attached to a Pipet-Aid air was slowly bubbled through the 2×HBS solution. At the same time the DNA solution in the 0.25M $CaCl_2$ solution was added in a dropwise fashion. Bubbling was continued for approximately 5 seconds after addition of the final DNA droplet. The solution was then incubated at room temperature for up to 20 minutes before adding to 293A cells. 250 μL of the DNA/Calcium phosphate solution was added dropwise to a monolayer of 293A cells that had been seeded one day prior at $10^6$ cells per well of a 6 well plate. The cells were returned to the incubator and incubated overnight. The media was changed 24 h later. After 72 h the cells were split 1:6 into a 6 well plate. The monolayers were monitored daily by light microscopy for evidence of cytopathic effect (CPE). 7-10 days post transfection viral plaques were observed and the monolayer harvested by pipetting the media in the wells to lift the cells. The harvested cells and media were transferred to a 50 mL centrifuge tube followed by three rounds of freeze thawing (at $-80°$ C. and $37°$ C.). The subsequent lysate, called the primary virus stock was clarified by centrifugation at full speed on a bench top centrifuge (4300× g) and a proportion of the lysate 10-50%) used to infect 293A cells in a T25 flask. The infected cells were incubated for 48 h before harvesting cells and media at complete CPE. The cells were once again harvested, freeze thawed and clarified before using this secondary viral stock to infect a T150 flask seeded at $1.5×10^7$ cells per flask. Once complete CPE was achieved at 72 h the media and cells were harvested and treated as with earlier viral stocks to generate a tertiary stock.

Production in 293F Cells

ChAdV68 virus production was performed in 293F cells grown in 293 FreeStyle™ (ThermoFisher) media in an incubator at 8% $CO_2$. On the day of infection cells were diluted to $10^6$ cells per mL, with 98% viability and 400 mL were used per production run in 1 L Shake flasks (Corning). 4 mL of the tertiary viral stock with a target MOI of >3.3 was used per infection. The cells were incubated for 48-72 h until the viability was <70% as measured by Trypan blue. The infected cells were then harvested by centrifugation, full speed bench top centrifuge and washed in 1×PBS, re-centrifuged and then re-suspended in 20 mL of 10 mM Tris pH7.4. The cell pellet was lysed by freeze thawing 3× and clarified by centrifugation at 4,300×g for 5 minutes.

Purification by CsCl Centrifugation

Viral DNA was purified by CsCl centrifugation. Two discontinuous gradient runs were performed. The first to purify virus from cellular components and the second to further refine separation from cellular components and separate defective from infectious particles.

10 mL of 1.2 (26.8 g CsCl dissolved in 92 mL of 10 mM Tris pH 8.0) CsCl was added to polyallomer tubes. Then 8 mL of 1.4 CsCl (53 g CsCl dissolved in 87 mL of 10 mM Tris pH 8.0) was carefully added using a pipette delivering to the bottom of the tube. The clarified virus was carefully layered on top of the 1.2 layer. If needed more 10 mM Tris was added to balance the tubes. The tubes were then placed in a SW-32Ti rotor and centrifuged for 2 h 30 min at $10°$ C. The tube was then removed to a laminar flow cabinet and the virus band pulled using an 18 gauge needle and a 10 mL syringe. Care was taken not to remove contaminating host cell DNA and protein. The band was then diluted at least 2× with 10 mM Tris pH 8.0 and layered as before on a discontinuous gradient as described above. The run was performed as described before except that this time the run was performed overnight. The next day the band was pulled with care to avoid pulling any of the defective particle band. The virus was then dialyzed using a Slide-a-Lyzer™ Cassette (Pierce) against ARM buffer (20 mM Tris pH 8.0, 25 mM NaCl, 2.5% Glycerol). This was performed 3×, 1 h per buffer exchange. The virus was then aliquoted for storage at $-80'$C.

Viral Assays

VP concentration was performed by using an OD 260 assay based on the extinction coefficient of $1.1×10^{12}$ viral particles (VP) is equivalent to an Absorbance value of 1 at OD260 nm. Two dilutions (1:5 and 1:10) of adenovirus were made in a viral lysis buffer (0.1% SDS, 10 mM Tris pH 7.4, 1 mM EDTA). OD was measured in duplicate at both dilutions and the VP concentration/mL was measured by multiplying the OD260 value X dilution factor X $1.1×10^{12}$VP.

An infectious unit (IU) titer was calculated by a limiting dilution assay of the viral stock. The virus was initially diluted 100× in DMEM/5% NS/1× PS and then subsequently diluted using 10-fold dilutions down to $1×10^{-7}$. 100 μL of these dilutions were then added to 293A cells that were seeded at least an hour before at 3e5 cells/well of a 24 well plate. This was performed in duplicate. Plates were incubated for 48 h in a CO2 (5%) incubator at $37°$ C. The cells were then washed with 1×PBS and were then fixed with 100% cold methanol ($-20°$ C.). The plates were then incubated at $-20°$ C. for a minimum of 20 minutes. The wells were washed with 1×PBS then blocked in 1×PBS/0.1% BSA for 1 h at room temperature. A rabbit anti-Ad antibody (Abcam, Cambridge, Mass.) was added at 1:8,000 dilution in blocking buffer (0.25 ml per well) and incubated for 1 h at room temperature. The wells were washed 4× with 0.5 mL PBS per well. A HRP conjugated Goat anti-Rabbit antibody (Bethyl Labs, Montgomery Tex.) diluted 1000× was added per well and incubated for 1 h prior to a final round of washing. 5 PBS washes were performed and the plates were developed using DAB (Diaminobenzidine tetrahydrochloride) substrate in Tris buffered saline (0.67 mg/mL DAB in 50 mM Tris pH 7.5, 150 mM NaCl) with 0.01% $H_2O_2$. Wells were developed for 5 min prior to counting. Cells were counted under a 10× objective using a dilution that gave between 4-40 stained cells per field of view. The field of view that was used was a 0.32 $mm^2$ grid of which there are equivalent to 625 per field of view on a 24 well plate. The number of infectious viruses/mL can be determined by the number of stained cells per grid multiplied by the number of grids per field of view multiplied by a dilution factor 10. Similarly, when working with GFP expressing cells florescent can be used rather than capsid staining to determine the number of GFP expressing virions per mL.

Immunizations

C57BL/6J female mice and Balb/c female mice were injected with 1×10$^8$ viral particles (VP) of ChAdV68.5WTnt.MAG25mer in 100 uL volume, bilateral intramuscular injection (50 uL per leg).

Splenocyte Dissociation

Spleen and lymph nodes for each mouse were pooled in 3 mL of complete RPMI (RPMI, 10% FBS, penicillin/streptomycin). Mechanical dissociation was performed using the gentleMACS Dissociator (Miltenyi Biotec), following manufacturer's protocol. Dissociated cells were filtered through a 40 micron filter and red blood cells were lysed with ACK lysis buffer (150 mM NH$_4$Cl, 10 mM KHCO$_3$, 0.1 mM Na2EDTA). Cells were filtered again through a 30 micron filter and then resuspended in complete RPMI. Cells were counted on the Attune NxT flow cytometer (Thermo Fisher) using propidium iodide staining to exclude dead and apoptotic cells. Cell were then adjusted to the appropriate concentration of live cells for subsequent analysis.

Ex Vivo Enzyme-Linked Immunospot (ELISPOT) Analysis

ELISPOT analysis was performed according to ELISPOT harmonization guidelines {DOI: 10.1038/nprot.2015.068} with the mouse IFNg ELISpotPLUS kit (MABTECH). 5×10$^4$ splenocytes were incubated with 10 uM of the indicated peptides for 16 hours in 96-well IFNg antibody coated plates. Spots were developed using alkaline phosphatase. The reaction was timed for 10 minutes and was terminated by running plate under tap water. Spots were counted using an AID vSpot Reader Spectrum. For ELISPOT analysis, wells with saturation >50% were recorded as "too numerous to count". Samples with deviation of replicate wells >10% were excluded from analysis. Spot counts were then corrected for well confluency using the formula: spot count+2×(spot count×% confluence/[100%−% confluence]). Negative background was corrected by subtraction of spot counts in the negative peptide stimulation wells from the antigen stimulated wells. Finally, wells labeled too numerous to count were set to the highest observed corrected value, rounded up to the nearest hundred.

XV.B.2. Production of ChAdV68 Viral Delivery Particles after DNA Transfection

Figure 21A:
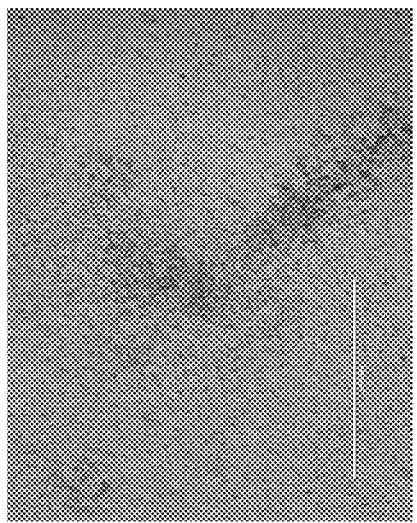
FIG. 21A illustrates ChAdV68.4WTnt.GFP virus production after transfection. HEK293A cells were transfected with ChAdV68.4WTnt.GFP DNA using the calcium phosphate protocol. Viral replication was observed 10 days after transfection and ChAdV68.4WTnt.GFP viral plaques were visualized using light microscopy (40× magnification).
Figure 21B:
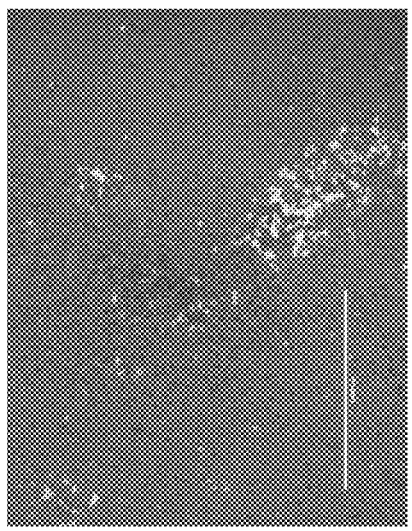
FIG. 21B illustrates ChAdV68.4WTnt.GFP virus production after transfection. HEK293A cells were transfected with ChAdV68.4WTnt.GFP DNA using the calcium phosphate protocol. Viral replication was observed 10 days after transfection and ChAdV68.4WTnt.GFP viral plaques were visualized using fluorescent microscopy at 40× magnification.
Figure 21C:
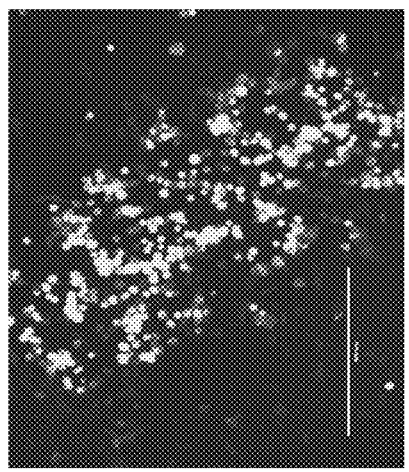
FIG. 21C illustrates ChAdV68.4WTnt.GFP virus production after transfection. HEK293A cells were transfected with ChAdV68.4WTnt.GFP DNA using the calcium phosphate protocol. Viral replication was observed 10 days after transfection and ChAdV68.4WTnt.GFP viral plaques were visualized using fluorescent microscopy at 100× magnification.
Figure 22A:
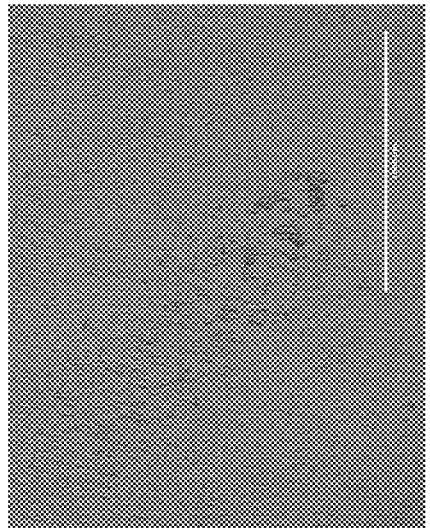
FIG. 22A illustrates ChAdV68.5WTnt.GFP virus production after transfection. HEK293A cells were transfected with ChAdV68.5WTnt.GFP DNA using the lipofectamine protocol. Viral replication (plaques) was observed 10 days after transfection. A lysate was made and used to reinfect a T25 flask of 293A cells. ChAdV68.5WTnt.GFP viral plaques were visualized and photographed 3 days later using light microscopy (40× magnification)
Figure 22B:
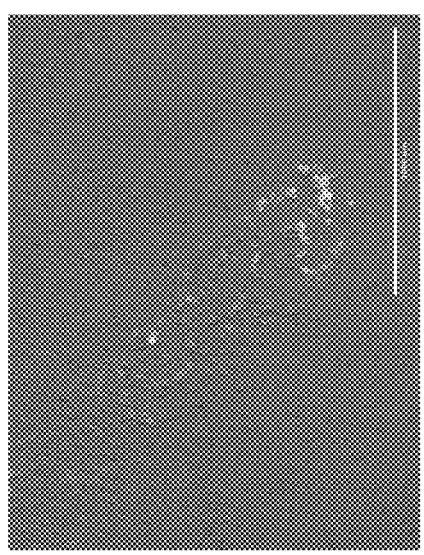
FIG. 22B illustrates ChAdV68.5WTnt.GFP virus production after transfection. HEK293A cells were transfected with ChAdV68.5WTnt.GFP DNA using the lipofectamine protocol. Viral replication (plaques) was observed 10 days after transfection. A lysate was made and used to reinfect a T25 flask of 293A cells. ChAdV68.5WTnt.GFP viral plaques were visualized and photographed 3 days later using fluorescent microscopy at 40× magnification.
Figure 22C:
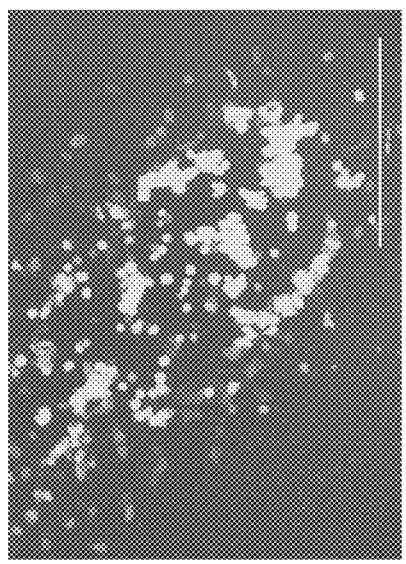
FIG. 22C illustrates ChAdV68.5WTnt.GFP virus production after transfection. HEK293A cells were transfected with ChAdV68.5WTnt.GFP DNA using the lipofectamine protocol. Viral replication (plaques) was observed 10 days after transfection. A lysate was made and used to reinfect a T25 flask of 293A cells. ChAdV68.5WTnt.GFP viral plaques were visualized and photographed 3 days later using fluorescent microscopy at 100× magnification.

In one example, ChAdV68.4WTnt.GFP (FIG. 21) and ChAdV68.5WTnt.GFP (FIG. 22) DNA was transfected into HEK293A cells and virus replication (viral plaques) was observed 7-10 days after transfection. ChAdV68 viral plaques were visualized using light (FIGS. 21 A and 22A) and fluorescent microscopy (FIG. 21 B-C and FIG. 22 B-C). GFP denotes productive ChAdV68 viral delivery particle production.

XV.B.3. ChAdV68 Viral Delivery Particles Expansion

Figure 23:
FIG. 23 illustrates the viral particle production scheme.

In one example, ChAdV68.4WTnt.GFP, ChAdV68.5WTnt.GFP, and ChAdV68.5WTnt.MAG25mer viruses were expanded in HEK293F cells and a purified virus stock produced 18 days after transfection (FIG. 23). Viral particles were quantified in the purified ChAdV68 virus stocks and compared to adenovirus type 5 (Ad5) and ChAdVY25 (a closely related ChAdV; Dicks, 2012, PloS ONE 7, e40385) viral stocks produced using the same protocol. ChAdV68 viral titers were comparable to Ad5 and ChAdVY25 (Table 7).

TABLE 7

Adenoviral vector production in 293F suspension cells

| Construct | Average VP/cell +/− SD |
|---|---|
| Ad5-Vectors (Multiple vectors) | 2.96e4 +/− 2.26e4 |
| Ad5-GFP | 3.89e4 |
| chAdY25-GFP | 1.75e3 +/− 6.03e1 |
| ChAdV68.4WTnt.GFP | 1.2e4 +/− 6.5e3 |
| ChAdV68.5WTnt.GFP | 1.8e3 |
| ChAdV68.5WTnt.MAG25mer | 1.39e3 +/− 1.1e3 |

*SD is only reported where multiple Production runs have been performed

XV.B.4. Evaluation of Immunogenicity in Tumor Models

Figure 29:
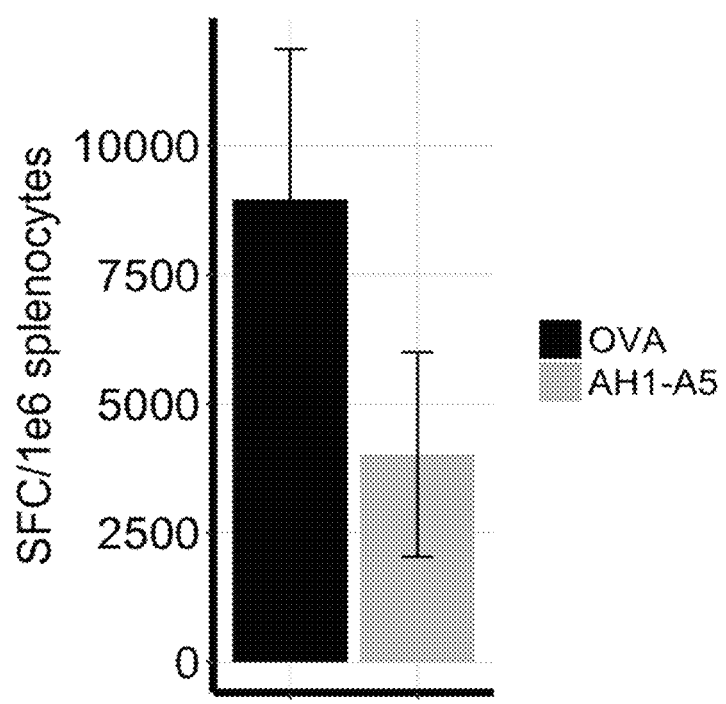
FIG. 29 illustrates ChAdV68 eliciting T-Cell responses to mouse tumor antigens in mice. Mice were immunized with ChAdV68.5WTnt.MAG25mer, and T-cell responses to the MHC class I epitope SIINFEKL (OVA) (SEQ ID NO: 57) were measured in C57BL/6J female mice and the MHC class I epitope AH1-A5 measured in Balb/c mice. Mean spot forming cells (SFCs) per $10^6$ splenocytes measured in ELISpot assays presented. Error bars represent standard deviation.

C68 vector expressing mouse tumor antigens were evaluated in mouse immunogenicity studies to demonstrate the C68 vector elicits T-cell responses. T-cell responses to the MHC class I epitope SIINFEKL (SEQ ID NO: 57) were measured in C57BL/6J female mice and the MHC class I epitope AH1-A5 (Slansky et al., 2000, Immunity 13:529-538) measured in Balb/c mice. As shown in FIG. 29, strong T-cell responses relative to control were measured after immunization of mice with ChAdV68.5WTnt.MAG25mer. Mean cellular immune responses of 8957 or 4019 spot forming cells (SFCs) per 10$^6$ splenocytes were observed in ELISpot assays when C57BL/6J or Balb/c mice were immunized with ChAdV68.5WTnt.MAG25mer, respectively, 10 days after immunization.

XVI. Alphavirus Neoantigen Cassette Delivery Vector

XVI.A. Alphavirus Delivery Vector Evaluation Materials and Methods

In Vitro Transcription to Generate RNA

For in vitro testing: plasmid DNA was linearized by restriction digest with PmeI, column purified following manufacturer's protocol (GeneJet DNA cleanup kit, Thermo) and used as template. In vitro transcription was performed using the RiboMAX Large Scale RNA production System (Promega) with the m$^7$G cap analog (Promega) according to manufacturer's protocol. mRNA was purified using the RNeasy kit (Qiagen) according to manufacturer's protocol.

For in vivo studies: RNA was generated and purified by TriLInk Biotechnologies and capped with Enzymatic Capt.

Transfection of RNA

HEK293A cells were seeded at 6e4 cells/well for 96 wells and 2e5 cells/well for 24 wells, ~16 hours prior to transfection. Cells were transfected with mRNA using MessengerMAX lipofectamine (Invitrogen) and following manufacturer's protocol. For 96-wells, 0.15 uL of lipofectamine and 10 ng of mRNA was used per well, and for 24-wells, 0.75 uL of lipofectamine and 150 ng of mRNA was used per well. A GFP expressing mRNA (TriLink Biotechnologies) was used as a transfection control.

Luciferase Assay

Luciferase reporter assay was performed in white-walled 96-well plates with each condition in triplicate using the ONE-Glo luciferase assay (Promega) following manufacturer's protocol. Luminescence was measured using the SpectraMax.

qRT-PCR

Transfected cells were rinsed and replaced with fresh media 2 hours post transfection to remove any untransfected mRNA. Cells were then harvested at various timepoints in RLT plus lysis buffer (Qiagen), homogenized using a QiaShredder (Qiagen) and RNA was extracted using the RNeasy kit (Qiagen), all according to manufacturer's protocol. Total RNA was quantified using a Nanodrop (Thermo Scientific). qRT-PCR was performed using the Quantitect Probe One-Step RT-PCR kit (Qiagen) on the qTower[3] (Analytik Jena) according to manufacturer's protocol, using 20 ng of total RNA per reaction. Each sample was run in triplicate for each probe. Actin or GusB were used as reference genes. Custom primer/probes were generated by IDT (Table 8).

TABLE 8 qPCR primers/probes

| Target | | | SEQ ID NO: |
|---|---|---|---|
| Luci | Primer1 | GTGGTGTGCAGCGAGAATAG | 142 |
| | Primer2 | CGCTCGTTGTAGATGTCGTTAG | 143 |
| | Probe | /56-FAM/TTGCAGTTC/ZEN/TTCATGCCCGTGTTG/3IABkFQ/ | 144 |
| GusB | Primer1 | GTTTTTGATCCAGACCCAGATG | 145 |
| | Primer2 | GCCCATTATTCAGAGCGAGTA | 146 |
| | Probe | /56-FAM/TGCAGGGTT/ZEN/TCACCAGGATCCAC/3IABkFQ/ | 147 |
| ActB | Primer1 | CCTTGCACATGCCGGAG | 148 |
| | Primer2 | ACAGAGCCTCGCCTTTG | 149 |
| | Probe | /56-FAM/TCATCCATG/ZEN/GTGAGCTGGCGG/3IABkFQ/ | 150 |
| MAG-25mer Set1 | Primer1 | CTGAAAGCTCGGTTTGCTAATG | 151 |
| | Primer2 | CCATGCTGGAAGAGACAATCT | 152 |
| | Probe | /56-FAM/CGTTTCTGA/ZEN/TGGCGCTGACCGATA/3IABkFQ/ | 153 |
| MAG-25mer Set2 | Primer1 | TATGCCTATCCTGTCTCCTCTG | 154 |
| | Primer2 | GCTAATGCAGCTAAGTCCTCTC | 155 |
| | Probe | /56-FAM/TGTTTACCC/ZEN/TGACCGTGCCTTCTG/3IABkFQ/ | 156 |

B16-OVA Tumor Model

C57BL/6J mice were injected in the lower left abdominal flank with $10^5$ B16-OVA cells/animal. Tumors were allowed to grow for 3 days prior to immunization.

CT26 Tumor Model

Balb/c mice were injected in the lower left abdominal flank with $10^6$ CT26 cells/animal. Tumors were allowed to grow for 7 days prior to immunization.

Immunizations

For srRNA vaccine, mice were injected with 10 ug of RNA in 100 uL volume, bilateral intramuscular injection (50 uL per leg). For Ad5 vaccine, mice were injected with $5\times10^{10}$ viral particles (VP) in 100 uL volume, bilateral intramuscular injection (50 uL per leg). Animals were injected with anti-CTLA-4 (clone 9D9, BioXcell), anti-PD-1 (clone RMP1-14, BioXcell) or anti-IgG (clone MPC-11, BioXcell), 250 ug dose, 2 times per week, via intraperitoneal injection.

In Vivo Bioluminescent Imaging

At each timepoint mice were injected with 150 mg/kg luciferin substrate via intraperitoneal injection and bioluminescence was measured using the IVIS In vivo imaging system (PerkinElmer) 10-15 minutes after injection.

Splenocyte Dissociation

Spleen and lymph nodes for each mouse were pooled in 3 mL of complete RPMI (RPMI, 10% FBS, penicillin/streptomycin). Mechanical dissociation was performed using the gentleMACS Dissociator (Miltenyi Biotec), following manufacturer's protocol. Dissociated cells were filtered through a 40 micron filter and red blood cells were lysed with ACK lysis buffer (150 mM $NH_4Cl$, 10 mM $KHCO_3$, 0.1 mM $Na_2EDTA$). Cells were filtered again through a 30 micron filter and then resuspended in complete RPMI. Cells were counted on the Attune NxT flow cytometer (Thermo Fisher) using propidium iodide staining to exclude dead and apoptotic cells. Cell were then adjusted to the appropriate concentration of live cells for subsequent analysis.

Ex Vivo Enzyme-Linked Immunospot (ELISPOT) Analysis

ELISPOT analysis was performed according to ELISPOT harmonization guidelines {DOI: 10.1038/nprot.2015.068} with the mouse IFNg ELISpotPLUS kit (MABTECH). $5\times10^4$ splenocytes were incubated with 10 uM of the indicated peptides for 16 hours in 96-well IFNg antibody coated plates. Spots were developed using alkaline phosphatase. The reaction was timed for 10 minutes and was terminated by running plate under tap water. Spots were counted using an AID vSpot Reader Spectrum. For ELISPOT analysis, wells with saturation >50% were recorded as "too numerous to count". Samples with deviation of replicate wells >10% were excluded from analysis. Spot counts were then corrected for well confluency using the formula: spot count+ 2×(spot count×% confluence/[100%−% confluence]). Negative background was corrected by subtraction of spot counts in the negative peptide stimulation wells from the antigen stimulated wells. Finally, wells labeled too numerous to count were set to the highest observed corrected value, rounded up to the nearest hundred.

XVI.B. Alphavirus Vector

XVI.B.1. Alphavirus Vector In Vitro Evaluation

Figure 24:
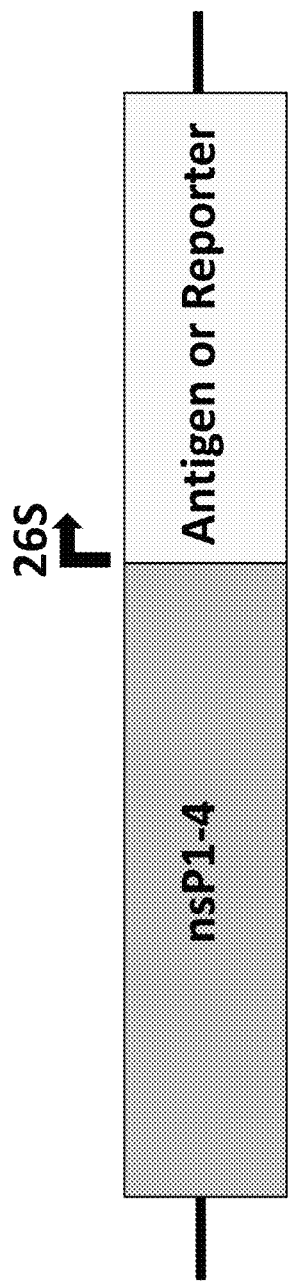
FIG. 24 illustrates the alphavirus derived VEE self-replicating RNA (srRNA) vector.

In one implementation of the present invention, a RNA alphavirus backbone for the neoantigen expression system was generated from a Venezuelan Equine Encephalitis (VEE) (Kinney, 1986, Virology 152: 400-413) based self-replicating RNA (srRNA) vector. In one example, the sequences encoding the structural proteins of VEE located 3' of the 26S sub-genomic promoter were deleted (VEE sequences 7544 to 11,175 deleted; numbering based on Kinney et al 1986; SEQ ID NO:6) and replaced by antigen sequences (SEQ ID NO:14 and SEQ ID NO:4) or a luciferase reporter (e.g., VEE-Luciferase, SEQ ID NO:15) (FIG. 24). RNA was transcribed from the srRNA DNA vector in vitro, transfected into HEK293A cells and luciferase reporter expression was measured. In addition, an (non-replicating) mRNA encoding luciferase was transfected for comparison. An 30,000-fold increase in srRNA reporter signal was observed for VEE-Luciferase srRNA when comparing the 23 hour measurement vs the 2 hour measurement (Table 9). In contrast, the mRNA reporter exhibited a less than 10-fold increase in signal over the same time period (Table 9).

TABLE 9

Expression of luciferase from VEE self-replicating vector increases over time. HEK293A cells transfected with 10 ng of VEE-Luciferase srRNA or 10 ng of non-replicating luciferase mRNA (TriLink L-6307) per well in 96 wells. Luminescence was measured at various times post transfection. Luciferase expression is reported as relative luminescence units (RLU). Each data point is the mean +/− SD of 3 transfected wells.

| Construct | Timepoint (hr) | Mean RLU | Standard Dev (triplicate wells) |
|---|---|---|---|
| mRNA | 2 | 878.6666667 | 120.27904522 |
| mRNA | 5 | 1847.333333 | 978.515372 |
| mRNA | 9 | 4847 | 868.3271273 |
| mRNA | 23 | 8639.333333 | 751.6816702 |
| SRRNA | 2 | 27 | 15 |
| SRRNA | 5 | 4884.333333 | 2955.158935 |
| SRRNA | 9 | 182065.5 | 16030.81784 |
| SRRNA | 23 | 783658.3333 | 68985.05538 |

In another example, replication of the srRNA was confirmed directly by measuring RNA levels after transfection of either the luciferase encoding srRNA (VEE-Luciferase) or an srRNA encoding a multi-epitope cassette (VEE-MAG25mer) using quantitative reverse transcription polymerase chain reaction (qRT-PCR). An ~150-fold increase in RNA was observed for the VEE-luciferase srRNA (Table 10), while a 30-50-fold increase in RNA was observed for the VEE-MAG25mer srRNA (Table 11). These data confirm that the VEE srRNA vectors replicate when transfected into cells.

TABLE 10

Direct measurement of RNA replication in VEE-Luciferase srRNA transfected cells. HEK293A cells transfected with VEE-Luciferase srRNA (150 ng per well, 24-well) and RNA levels quantified by qRT-PCR at various times after transfection. Each measurement was normalized based on the Actin reference gene and fold-change relative to the 2 hour timepoint is presented.

| Timepoint (hr) | Luciferase Ct | Actin Ct | dCt | Ref dCt | ddCt | Relative Fold change |
|---|---|---|---|---|---|---|
| 2 | 20.51 | 18.14 | 2.38 | 2.38 | 0.00 | 1.00 |
| 4 | 20.09 | 18.39 | 1.70 | 2.38 | −0.67 | 1.59 |
| 6 | 15.50 | 18.19 | −2.69 | 2.38 | −5.07 | 33.51 |
| 8 | 13.51 | 18.36 | −4.85 | 2.38 | −7.22 | 149.43 |

TABLE 11

Direct measurement of RNA replication in VEE-MAG25mer srRNA transfected cells. HEK293 cells transfected with VEE-MAG25mer srRNA (150 ng per well, 24-well) and RNA levels quantified by qRT-PCR at various times after transfection. Each measurement was normalized based on the GusB reference gene and fold-change relative to the 2 hour timepoint is presented. Different lines on the graph represent 2 different qPCR primer/probe sets, both of which detect the epitope cassette region of the srRNA.

| Primer/probe | Timepoint (hr) | GusB Ct | Ct | dCt | Ref dCt | ddCt | Relative Fold-Change |
|---|---|---|---|---|---|---|---|
| Set1 | 2 | 18.96 | 22.41 | −3.45 | −3.45 | 0.00 | 1.00 |
| Set1 | 4 | 17.46 | 22.27 | −4.81 | −3.45 | −1.37 | 2.58 |
| Set1 | 6 | 14.87 | 22.04 | −7.17 | −3.45 | −3.72 | 13.21 |

TABLE 11-continued

Direct measurement of RNA replication in VEE-MAG25mer srRNA transfected cells. HEK293 cells transfected with VEE-MAG25mer srRNA (150 ng per well, 24-well) and RNA levels quantified by qRT-PCR at various times after transfection. Each measurement was normalized based on the GusB reference gene and fold-change relative to the 2 hour timepoint is presented. Different lines on the graph represent 2 different qPCR primer/probe sets, both of which detect the epitope cassette region of the srRNA.

| Primer/probe | Timepoint (hr) | GusB Ct | Ct | dCt | Ref dCt | ddCt | Relative Fold-Change |
|---|---|---|---|---|---|---|---|
| Set1 | 8 | 14.16 | 22.19 | −8.02 | −3.45 | −4.58 | 23.86 |
| Set1 | 24 | 13.16 | 22.01 | −8.86 | −3.45 | −5.41 | 42.52 |
| Set1 | 36 | 13.53 | 22.63 | −9.10 | −3.45 | −5.66 | 50.45 |
| Set2 | 2 | 17.75 | 22.41 | −4.66 | −4.66 | 0.00 | 1.00 |
| Set2 | 4 | 16.66 | 22.27 | −5.61 | −4.66 | −0.94 | 1.92 |
| Set2 | 6 | 14.22 | 22.04 | −7.82 | −4.66 | −3.15 | 8.90 |
| Set2 | 8 | 13.18 | 22.19 | −9.01 | −4.66 | −4.35 | 20.35 |
| Set2 | 24 | 12.22 | 22.01 | −9.80 | −4.66 | −5.13 | 35.10 |
| Set2 | 36 | 13.08 | 22.63 | −9.55 | −4.66 | −4.89 | 29.58 |

XVI.B.2. Alphavirus Vector in vivo Evaluation

Figure 25:
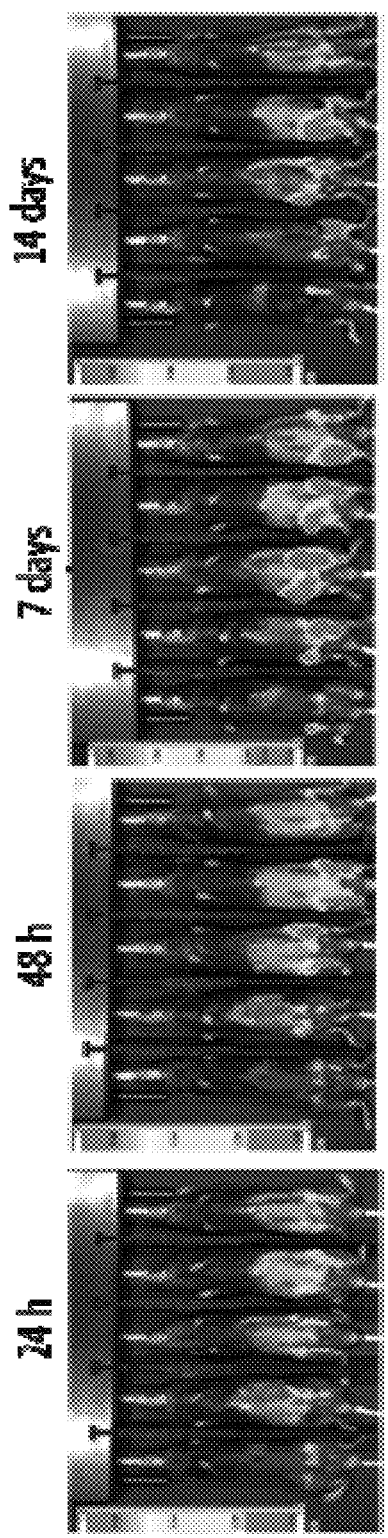
FIG. 25 illustrates in vivo reporter expression after inoculation of C57BL/6J mice with VEE-Luciferase srRNA. Shown are representative images of luciferase signal following immunization of C57BL/6J mice with VEE-Luciferase srRNA (10 ug per mouse, bilateral intramuscular injection, MC3 encapsulated) at various timepoints.

In another example, VEE-Luciferase reporter expression was evaluated in vivo. Mice were injected with 10 ug of VEE-Luciferase srRNA encapsulated in lipid nanoparticle (MC3) and imaged at 24 and 48 hours, and 7 and 14 days post injection to determine bioluminescent signal. Luciferase signal was detected at 24 hours post injection and increased over time and appeared to peak at 7 days after srRNA injection (FIG. 25).

XVI.B.3. Alphavirus Vector Tumor Model Evaluation

In one implementation, to determine if the VEE srRNA vector directs antigen-specific immune responses in vivo, a VEE srRNA vector was generated (VEE-UbAAY, SEQ ID NO:14) that expresses 2 different MHC class I mouse tumor epitopes, SIINFEKL (SEQ ID NO: 57) and AH1-A5 (Slansky et al., 2000, Immunity 13:529-538). The SFL (SIINFEKL (SEQ ID NO: 57)) epitope is expressed by the B16-OVA melanoma cell line, and the AH1-A5 (SPSYAYHQF (SEQ ID NO: 58); Slansky et al., 2000, Immunity) epitope induces T cells targeting a related epitope (AH1/SPSYVYHQF (SEQ ID NO: 193); Huang et al., 1996, Proc Natl Acad Sci USA 93:9730-9735) that is expressed by the CT26 colon carcinoma cell line. In one example, for in vivo studies, VEE-UbAAY srRNA was generated by in vitro transcription using T7 polymerase (TriLink Biotechnologies) and encapsulated in a lipid nanoparticle (MC3).

Figure 26A:
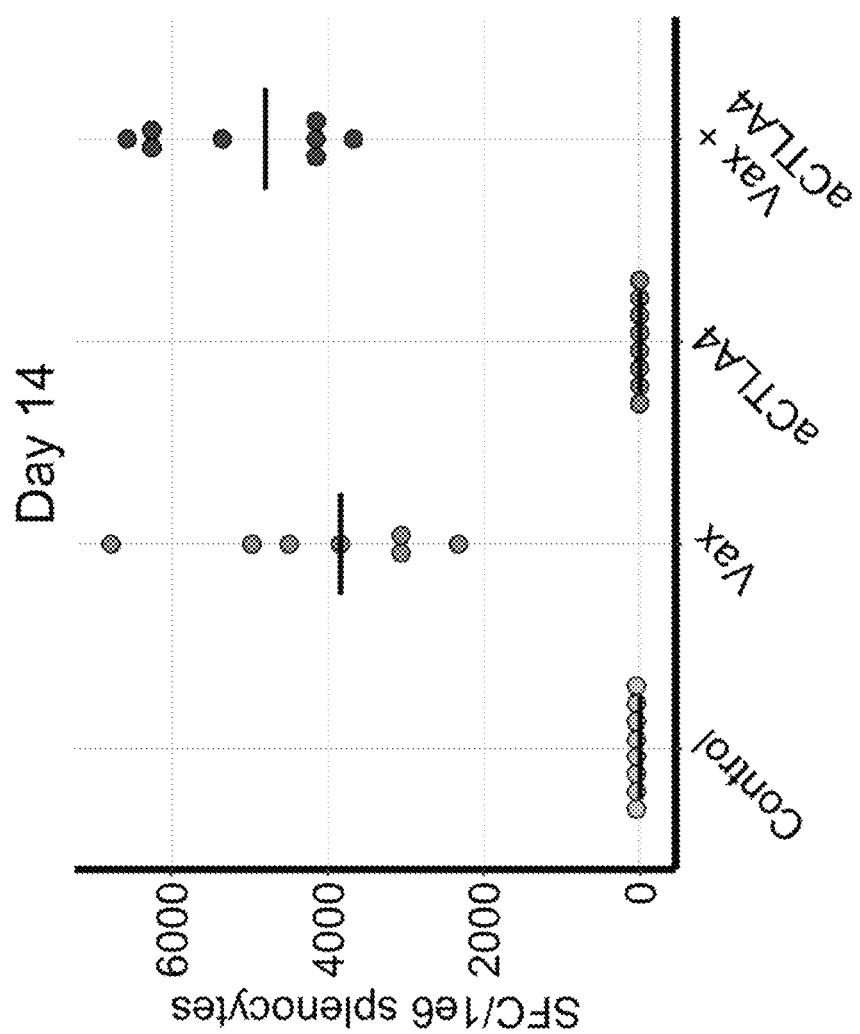
FIG. 26A illustrates T-cell responses measured 14 days after immunization with VEE srRNA formulated with MC3 LNP in B16-OVA tumor bearing mice. B16-OVA tumor bearing C57BL/6J mice were injected with 10 ug of VEE-Luciferase srRNA (control), VEE-UbAAY srRNA (Vax), VEE-Luciferase srRNA and anti-CTLA-4 (aCTLA-4) or VEE-UbAAY srRNA and anti-CTLA-4 (Vax+aCTLA-4). In addition, all mice were treated with anti-PD1 mAb starting at day 7. Each group consisted of 8 mice. Mice were sacrificed and spleens and lymph nodes were collected 14 days after immunization. SIINFEKL-specific T-cell responses ("SIINFEKL" disclosed as SEQ ID NO: 57) were assessed by IFN-gamma ELISPOT and are reported as spot-forming cells (SFC) per 106 splenocytes. Lines represent medians.
Figure 26B:
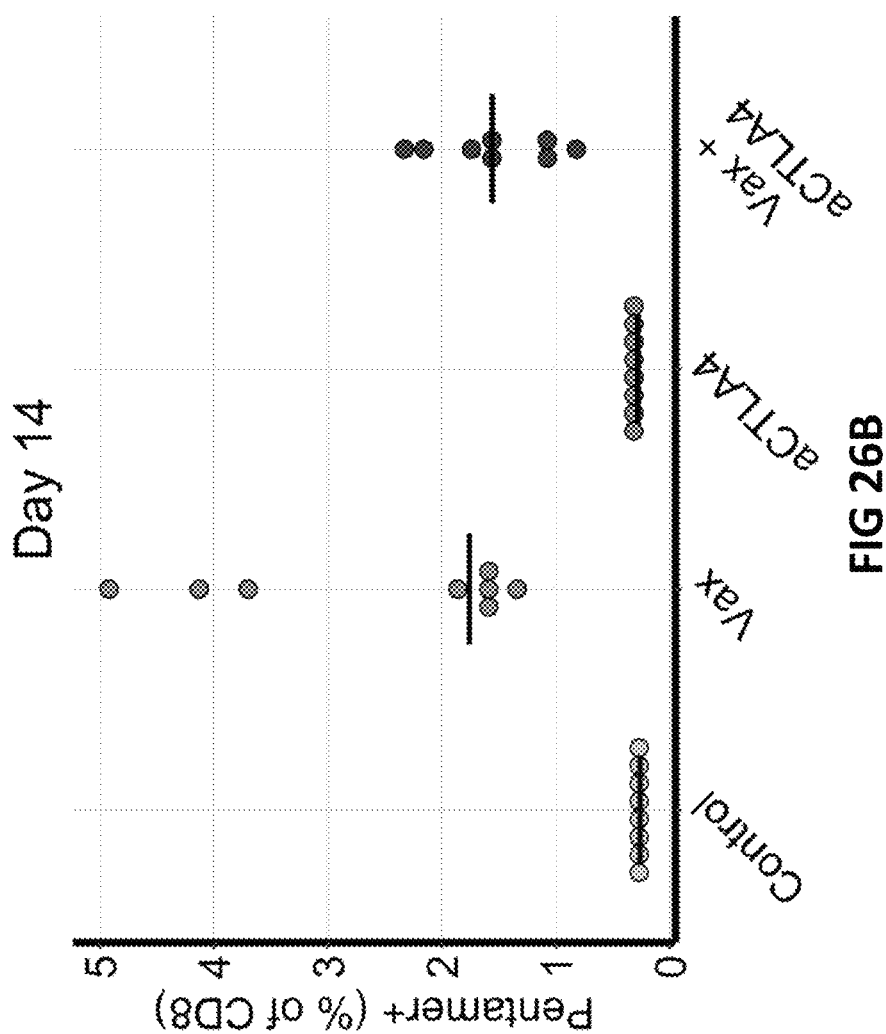
FIG. 26B illustrates T-cell responses measured 14 days after immunization with VEE srRNA formulated with MC3 LNP in B16-OVA tumor bearing mice. B16-OVA tumor bearing C57BL/6J mice were injected with 10 ug of VEE-Luciferase srRNA (control), VEE-UbAAY srRNA (Vax), VEE-Luciferase srRNA and anti-CTLA-4 (aCTLA-4) or VEE-UbAAY srRNA and anti-CTLA-4 (Vax+aCTLA-4). In addition, all mice were treated with anti-PD1 mAb starting at day 7. Each group consisted of 8 mice. Mice were sacrificed and spleens and lymph nodes were collected 14 days after immunization. SIINFEKL-specific T-cell responses ("SIINFEKL" disclosed as SEQ ID NO: 57) were assessed by MHCI-pentamer staining, reported as pentamer positive cells as a percent of CD8 positive cells. Lines represent medians.

A strong antigen-specific T-cell response targeting SFL, relative to control, was observed two weeks after immunization of B16-OVA tumor bearing mice with MC3 formulated VEE-UbAAY srRNA. In one example, a median of 3835 spot forming cells (SFC) per $10^6$ splenocytes was measured after stimulation with the SFL peptide in ELISpot assays (FIG. 26A, Table 12) and 1.8% (median) of CD8 T-cells were SFL antigen-specific as measured by pentamer staining (FIG. 26B, Table 12). In another example, co-administration of an anti-CTLA-4 monoclonal antibody (mAb) with the VEE srRNA vaccine resulted in a moderate increase in overall T-cell responses with a median of 4794.5 SFCs per $10^6$ splenocytes measured in the ELISpot assay (FIG. 26A, Table 12).

TABLE 12

Results of ELISPOT and MHCI-pentamer staining assays 14 days post VEE srRN/immunization in B16-OVA tumor bearing C57BL/6J mice.

| Group | Mouse | SFC/1e6 splenocytes | Pentamer positive (% of CD8) | Group | Mouse | SFC/1e6 splenocytes | Pentamer positive (% of CD8) |
|---|---|---|---|---|---|---|---|
| Control | 1 | 47 | 0.22 | Vax | 1 | 6774 | 4.92 |
|  | 2 | 80 | 0.32 |  | 2 | 2323 | 1.34 |
|  | 3 | 0 | 0.27 |  | 3 | 2997 | 1.52 |
|  | 4 | 0 | 0.29 |  | 4 | 4492 | 1.86 |
|  | 5 | 0 | 0.27 |  | 5 | 4970 | 3.7 |
|  | 6 | 0 | 0.25 |  | 6 |  | 4.13 |
|  | 7 | 0 | 0.23 |  | 7 | 3835 | 1.66 |
|  | 8 | 87 | 0.25 |  | 8 | 3119 | 1.64 |
| aCTLA4 | 1 | 0 | 0.24 | Vax + | 1 | 6232 | 2.16 |
|  | 2 | 0 | 0.26 | aCTLA4 | 2 | 4242 | 0.82 |
|  | 3 | 0 | 0.39 |  | 3 | 5347 | 1.57 |
|  | 4 | 0 | 0.28 |  | 4 | 6568 | 2.33 |
|  | 5 | 0 | 0.28 |  | 5 | 6269 | 1.55 |
|  | 6 | 0 | 0.28 |  | 6 | 4056 | 1.74 |
|  | 7 | 0 | 0.31 |  | 7 | 4163 | 1.14 |
|  | 8 | 6 | 0.26 |  | 8 | 3667 | 1.01 |

* Note that results from mouse #6 in the Vax group were excluded from analysis due to high variability between triplicate wells.

Figure 27B:
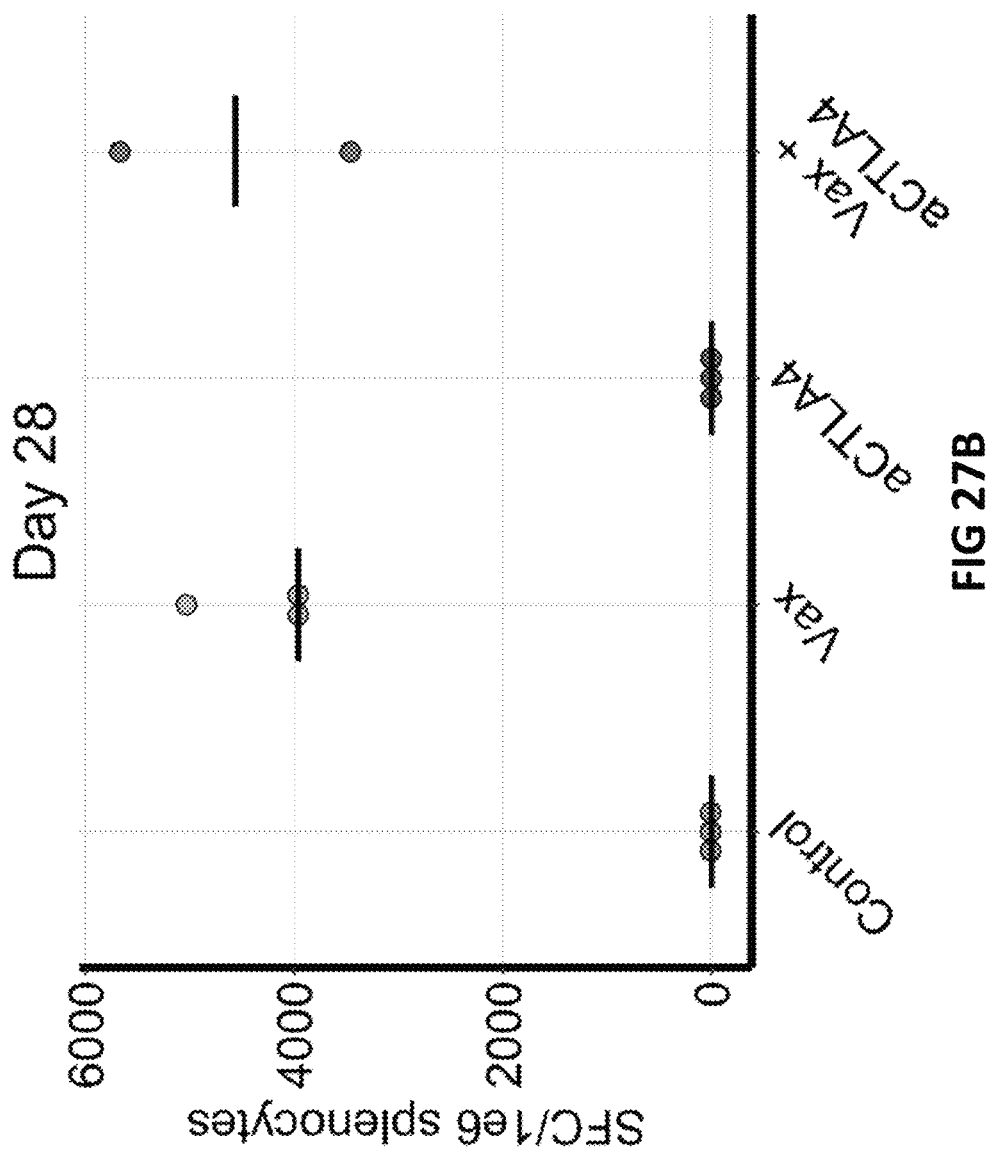
FIG. 27B illustrates antigen-specific T-cell responses following heterologous prime/boost in B16-OVA tumor bearing mice. B16-OVA tumor bearing C57BL/6J mice were injected with adenovirus expressing GFP (Ad5-GFP) and boosted with VEE-Luciferase srRNA formulated with MC3 LNP (Control) or Ad5-UbAAY and boosted with VEE-UbAAY srRNA (Vax). Both the Control and Vax groups were also treated with an IgG control mAb. A third group was treated with the Ad5-GFP prime/VEE-Luciferase srRNA boost in combination with anti-CTLA-4 (aCTLA-4), while the fourth group was treated with the Ad5-UbAAY prime/VEE-UbAAY boost in combination with anti-CTLA-4 (Vax+aCTLA-4). In addition, all mice were treated with anti-PD-1 mAb starting at day 21. T-cell responses were measured by IFN-gamma ELISPOT. Mice were sacrificed and spleens and lymph nodes collected at 14 days post immunization with adenovirus and 14 days post boost with srRNA (day 28 after prime).
Figure 27C:
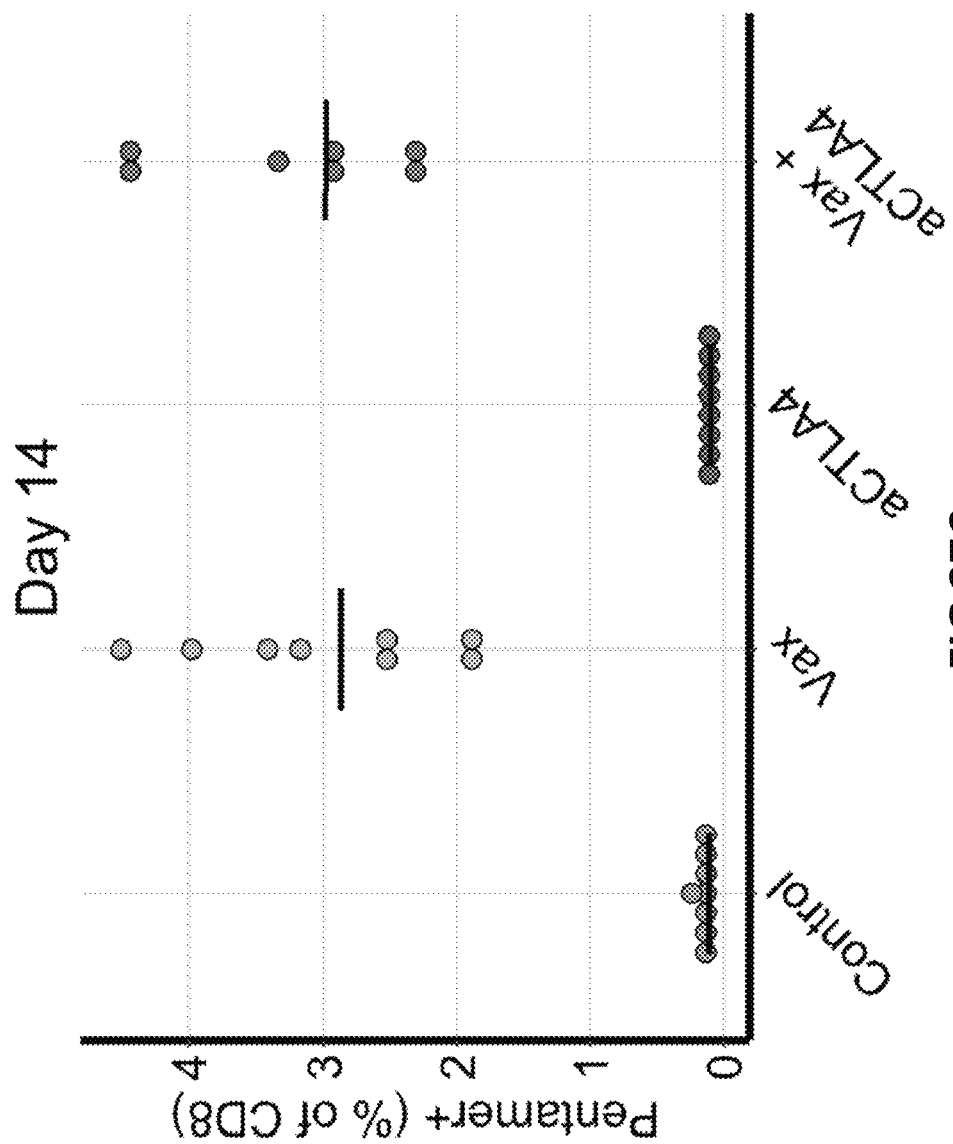
FIG. 27C illustrates antigen-specific T-cell responses following heterologous prime/boost in B16-OVA tumor bearing mice. B16-OVA tumor bearing C57BL/6J mice were injected with adenovirus expressing GFP (Ad5-GFP) and boosted with VEE-Luciferase srRNA formulated with MC3 LNP (Control) or Ad5-UbAAY and boosted with VEE-UbAAY srRNA (Vax). Both the Control and Vax groups were also treated with an IgG control mAb. A third group was treated with the Ad5-GFP prime/VEE-Luciferase srRNA boost in combination with anti-CTLA-4 (aCTLA-4), while the fourth group was treated with the Ad5-UbAAY prime/VEE-UbAAY boost in combination with anti- CTLA-4 (Vax+aCTLA-4). In addition, all mice were treated with anti-PD-1 mAb starting at day 21. T-cell responses were measured by MHC class I pentamer staining. Mice were sacrificed and spleens and lymph nodes collected at 14 days post immunization with adenovirus.
Figure 27D:
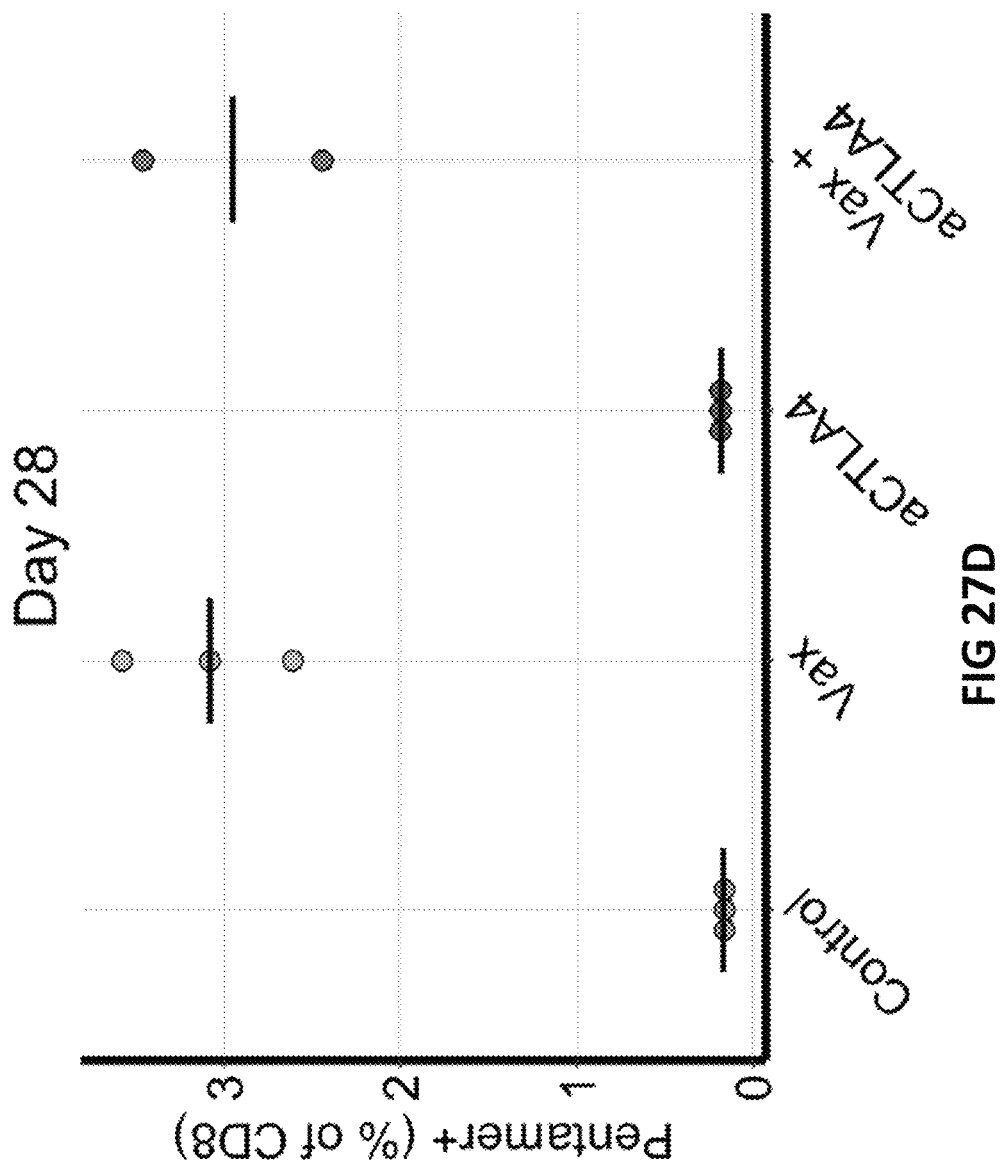
FIG. 27D illustrates antigen-specific T-cell responses following heterologous prime/boost in B16-OVA tumor bearing mice. B16-OVA tumor bearing C57BL/6J mice were injected with adenovirus expressing GFP (Ad5-GFP) and boosted with VEE-Luciferase srRNA formulated with MC3 LNP (Control) or Ad5-UbAAY and boosted with VEE-UbAAY srRNA (Vax). Both the Control and Vax groups were also treated with an IgG control mAb. A third group was treated with the Ad5-GFP prime/VEE-Luciferase srRNA boost in combination with anti-CTLA-4 (aCTLA-4), while the fourth group was treated with the Ad5-UbAAY prime/VEE-UbAAY boost in combination with anti-CTLA-4 (Vax+aCTLA-4). In addition, all mice were treated with anti-PD-1 mAb starting at day 21. T-cell responses were measured by MHC class I pentamer staining. Mice were sacrificed and spleens and lymph nodes collected at 14 days post immunization with adenovirus and 14 days post boost with srRNA (day 28 after prime).

In another implementation, to mirror a clinical approach, a heterologous prime/boost in the B16-OVA and CT26 mouse tumor models was performed, where tumor bearing mice were immunized first with adenoviral vector expressing the same antigen cassette (Ad5-UbAAY), followed by a boost immunization with the VEE-UbAAY srRNA vaccine 14 days after the Ad5-UbAAY prime. In one example, an antigen-specific immune response was induced by the Ad5-UbAAY vaccine resulting in 7330 (median) SFCs per $10^6$ splenocytes measured in the ELISpot assay (FIG. 27A, Table 13) and 2.9% (median) of CD8 T-cells targeting the SFL antigen as measured by pentamer staining (FIG. 27C, Table 13). In another example, the T-cell response was maintained 2 weeks after the VEE-UbAAY srRNA boost in the B16-OVA model with 3960 (median) SFL-specific SFCs per $10^6$ splenocytes measured in the ELISpot assay (FIG. 27B, Table 13) and 3.1% (median) of CD8 T-cells targeting the SFL antigen as measured by pentamer staining (FIG. 27D, Table 13).

TABLE 13

Immune monitoring of B16-OVA mice following heterologous prime/boost with Ad5 vaccine prime and srRNA boost.

| Group | Mouse | SFC/1e6 splenocytes | Pentamer positive (% of CD8) | Group | Mouse | SFC/1e6 splenocytes | Pentamer positive (% of CD8) |
|---|---|---|---|---|---|---|---|
| Day 14 ||||||||
| Control | 1 | 0 | 0.10 | Vax | 1 | 8514 | 1.87 |
|  | 2 | 0 | 0.09 |  | 2 | 7779 | 1.91 |
|  | 3 | 0 | 0.11 |  | 3 | 6177 | 3.17 |
|  | 4 | 46 | 0.18 |  | 4 | 7945 | 3.41 |
|  | 5 | 0 | 0.11 |  | 5 | 8821 | 4.51 |
|  | 6 | 16 | 0.11 |  | 6 | 6881 | 2.48 |
|  | 7 | 0 | 0.24 |  | 7 | 5365 | 2.57 |
|  | 8 | 37 | 0.10 |  | 8 | 6705 | 3.98 |
| aCTLA4 | 1 | 0 | 0.08 | Vax + | 1 | 9416 | 2.35 |
|  | 2 | 29 | 0.10 | aCTLA4 | 2 | 7918 | 3.33 |
|  | 3 | 0 | 0.09 |  | 3 | 10153 | 4.50 |
|  | 4 | 29 | 0.09 |  | 4 | 7212 | 2.98 |
|  | 5 | 0 | 0.10 |  | 5 | 11203 | 4.38 |
|  | 6 | 49 | 0.10 |  | 6 | 9784 | 2.27 |
|  | 7 | 0 | 0.10 |  | 8 | 7267 | 2.87 |
|  | 8 | 31 | 0.14 |  |  |  |  |
| Day 28 ||||||||
| Control | 2 | 0 | 0.17 | Vax | 1 | 5033 | 2.61 |
|  | 4 | 0 | 0.15 |  | 2 | 3958 | 3.08 |
|  | 6 | 20 | 0.17 |  | 4 | 3960 | 3.58 |
| aCTLA4 | 1 | 7 | 0.23 | Vax + | 4 | 3460 | 2.44 |
|  | 2 | 0 | 0.18 | aCTLA4 | 5 | 5670 | 3.46 |
|  | 3 | 0 | 0.14 |  |  |  |  |

Figure 28A:
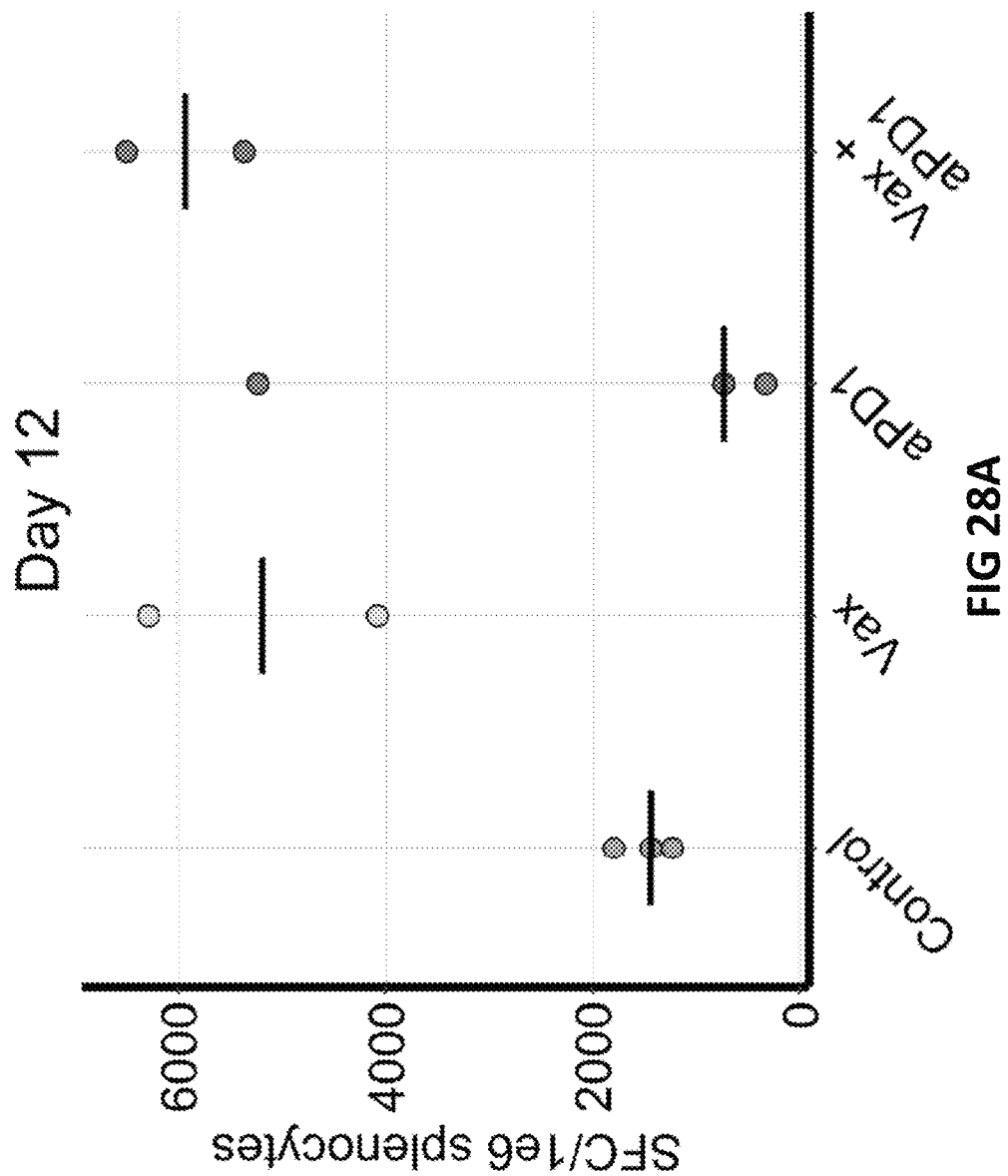
FIG. 28A illustrates antigen-specific T-cell responses following heterologous prime/boost in CT26 (Balb/c) tumor bearing mice. Mice were immunized with Ad5-GFP and boosted 15 days after the adenovirus prime with VEE-Luciferase srRNA formulated with MC3 LNP (Control) or primed with Ad5-UbAAY and boosted with VEE-UbAAY srRNA (Vax). Both the Control and Vax groups were also treated with an IgG control mAb. A separate group was administered the Ad5-GFP/VEE-Luciferase srRNA prime/boost in combination with anti-PD-1 (aPD1), while a fourth group received the Ad5-UbAAY/VEE-UbAAY srRNA prime/boost in combination with an anti-PD-1 mAb (Vax+aPD1). T-cell responses to the AH1 peptide were measured using IFN-gamma ELISPOT. Mice were sacrificed and spleens and lymph nodes collected at 12 days post immunization with adenovirus.
Figure 28B:
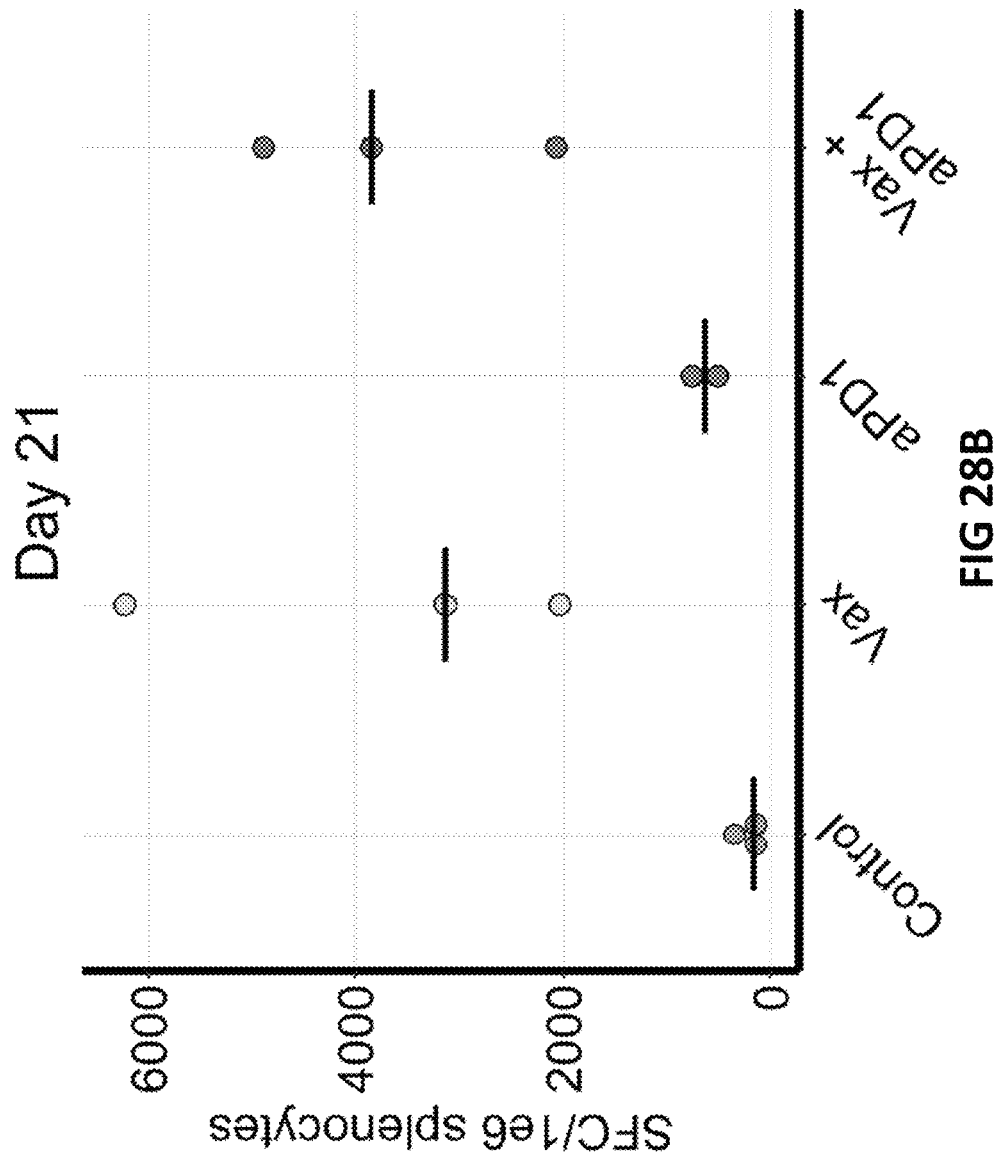
FIG. 28B illustrates antigen-specific T-cell responses following heterologous prime/boost in CT26 (Balb/c) tumor bearing mice. Mice were immunized with Ad5-GFP and boosted 15 days after the adenovirus prime with VEE-Luciferase srRNA formulated with MC3 LNP (Control) or primed with Ad5-UbAAY and boosted with VEE-UbAAY srRNA (Vax). Both the Control and Vax groups were also treated with an IgG control mAb. A separate group was administered the Ad5-GFP/VEE-Luciferase srRNA prime/boost in combination with anti-PD-1 (aPD1), while a fourth group received the Ad5-UbAAY/VEE-UbAAY srRNA prime/boost in combination with an anti-PD-1 mAb (Vax+aPD1). T-cell responses to the AH1 peptide were measured using IFN-gamma ELISPOT. Mice were sacrificed and spleens and lymph nodes collected at 12 days post immunization with adenovirus and 6 days post boost with srRNA (day 21 after prime).

In another implementation, similar results were observed after an Ad5-UbAAY prime and VEE-UbAAY srRNA boost in the CT26 mouse model. In one example, an AH1 antigen-specific response was observed after the Ad5-UbAAY prime (day 14) with a mean of 5187 SFCs per $10^6$ splenocytes measured in the ELISpot assay (FIG. 28A, Table 14) and 3799 SFCs per $10^6$ splenocytes measured in the ELISpot assay after the VEE-UbAAY srRNA boost (day 28) (FIG. 28B, Table 14).

TABLE 14

Immune monitoring after heterologous prime/boost in CT26 tumor mouse model.

| Day 12 | | | Day 21 | | |
|---|---|---|---|---|---|
| Group | Mouse | SFC/1e6 splenocytes | Group | Mouse | SFC/1e6 splenocytes |
| Control | 1 | 1799 | Control | 9 | 167 |
|  | 2 | 1442 |  | 10 | 115 |
|  | 3 | 1235 |  | 11 | 347 |
| aPD1 | 1 | 737 | aPD1 | 8 | 511 |
|  | 2 | 5230 |  | 11 | 758 |
|  | 3 | 332 | Vax | 9 | 3133 |
| Vax | 1 | 6287 |  | 10 | 2036 |
|  | 2 | 4086 |  | 11 | 6227 |
| Vax + | 1 | 5363 | Vax + | 8 | 3844 |
| aPD1 | 2 | 6500 | aPD1 | 9 | 2071 |
|  |  |  |  | 11 | 4888 |

XVII. ChAdV/srRNA Combination Tumor Model Evaluation

Various dosing protocols using ChAdV68 and self-replicating RNA (srRNA) were evaluated in murine CT26 tumor models.

XVII.A ChAdV/srRNA Combination Tumor Model Evaluation

Methods and Materials

Tumor Injection

Balb/c mice were injected with the CT26 tumor cell line. 7 days after tumor cell injection, mice were randomized to the different study arms (28-40 mice per group) and treatment initiated. Balb/c mice were injected in the lower left abdominal flank with $10^6$ CT26 cells/animal. Tumors were allowed to grow for 7 days prior to immunization. The study arms are described in detail in Table 15.

Immunizations

For srRNA vaccine, mice were injected with 10 ug of VEE-MAG25mer srRNA in 100 uL volume, bilateral intramuscular injection (50 uL per leg). For C68 vaccine, mice were injected with $1 \times 10^{11}$ viral particles (VP) of ChAdV68.5WTnt.MAG25mer in 100 uL volume, bilateral intramuscular injection (50 uL per leg). Animals were injected with anti-PD-1 (clone RMP1-14, BioXcell) or anti-IgG (clone MPC-11, BioXcell), 250 ug dose, 2 times per week, via intraperitoneal injection.

Splenocyte Dissociation

Spleen and lymph nodes for each mouse were pooled in 3 mL of complete RPMI (RPMI, 10% FBS, penicillin/streptomycin). Mechanical dissociation was performed using the gentleMACS Dissociator (Miltenyi Biotec), following manufacturer's protocol. Dissociated cells were filtered through a 40 micron filter and red blood cells were lysed with ACK lysis buffer (150 mM $NH_4Cl$, 10 mM $KHCO_3$, 0.1 mM Na2EDTA). Cells were filtered again through a 30 micron filter and then resuspended in complete RPMI. Cells were counted on the Attune NxT flow cytometer (Thermo Fisher) using propidium iodide staining to exclude dead and apoptotic cells. Cell were then adjusted to the appropriate concentration of live cells for subsequent analysis.

Ex Vivo Enzyme-Linked Immunospot (ELISPOT) Analysis

ELISPOT analysis was performed according to ELISPOT harmonization guidelines {DOI: 10.1038/nprot.2015.068} with the mouse IFNg ELISpotPLUS kit (MABTECH). $5 \times 10^4$ splenocytes were incubated with 10 uM of the indicated peptides for 16 hours in 96-well IFNg antibody coated plates. Spots were developed using alkaline phosphatase. The reaction was timed for 10 minutes and was terminated by running plate under tap water. Spots were counted using an AID vSpot Reader Spectrum. For ELISPOT analysis, wells with saturation >50% were recorded as "too numerous to count". Samples with deviation of replicate wells >10% were excluded from analysis. Spot counts were then corrected for well confluency using the formula: spot count+ 2×(spot count×% confluence/[100%−% confluence]). Negative background was corrected by subtraction of spot counts

TABLE 15

ChAdV/srRNA Combination Tumor Model Evaluation Study Arms

| Group | N | Treatment | Dose | Volume | Schedule | Route |
|---|---|---|---|---|---|---|
| 1 | 40 | chAd68 control | 1e11 vp | 2x 50 uL | day 0 | IM |
|  |  | srRNA control | 10 ug | 50 uL | day 14, 28, 42 | IM |
|  |  | Anti-PD1 | 250 ug | 100 uL | 2x/week (start day 0) | IP |
| 2 | 40 | chAd68 control | 1e11 vp | 2x 50 uL | day 0 | IM |
|  |  | srRNA control | 10 ug | 50 uL | day 14, 28, 42 | IM |
|  |  | Anti-IgG | 250 ug | 100 uL | 2x/week (start day 0) | IP |
| 3 | 28 | chAd68 vaccine | 1e11 vp | 2x 50 uL | day 0 | IM |
|  |  | srRNA vaccine | 10 ug | 50 uL | day 14, 28, 42 | IM |
|  |  | Anti-PD1 | 250 ug | 100 uL | 2x/week (start day 0) | IP |
| 4 | 28 | chAd68 vaccine | 1e11 vp | 2x 50 uL | day 0 | IM |
|  |  | srRNA vaccine | 10 ug | 50 uL | day 14, 28, 42 | IM |
|  |  | Anti-IgG | 250 ug | 100 uL | 2x/week (start day 0) | IP |
| 5 | 28 | srRNA vaccine | 10 ug | 50 uL | day 0, 28, 42 | IM |
|  |  | chAd68 vaccine | 1e11 vp | 2x 50 uL | day 14 | IM |
|  |  | Anti-PD1 | 250 ug | 100 uL | 2x/week (start day 0) | IP |
| 6 | 28 | srRNA vaccine | 10 ug | 50 uL | day 0, 28, 42 | IM |
|  |  | chAd68 vaccine | 1e11 vp | 2x 50 uL | day 14 | IM |
|  |  | Anti-IgG | 250 ug | 100 uL | 2x/week (start day 0) | IP |
| 7 | 40 | srRNA vaccine | 10 ug | 50 uL | day 0, 14, 28, 42 | IM |
|  |  | Anti-PD1 | 250 ug | 100 uL | 2x/week (start day 0) | IP |
| 8 | 40 | srRNA vaccine | 10 ug | 50 uL | day 0, 14, 28, 42 | IM |
|  |  | Anti-IgG | 250 ug | 100 uL | 2x/week (start day 0) | IP | in the negative peptide stimulation wells from the antigen stimulated wells. Finally, wells labeled too numerous to count were set to the highest observed corrected value, rounded up to the nearest hundred.

XVII.B ChAdV/srRNA Combination Evaluation in a CT26 Tumor Model

The immunogenicity and efficacy of the ChAdV68.5WTnt.MAG25mer/VEE-MAG25mer srRNA heterologous prime/boost or VEE-MAG25mer srRNA homologous prime/boost vaccines were evaluated in the CT26 mouse tumor model. Balb/c mice were injected with the CT26 tumor cell line. 7 days after tumor cell injection, mice were randomized to the different study arms and treatment initiated. The study arms are described in detail in Table 15 and more generally in Table 16.

TABLE 16

Prime/Boost Study Arms

| Group | Prime | Boost |
|---|---|---|
| 1 | Control | Control |
| 2 | Control + anti-PD-1 | Control +anti-PD-1 |
| 3 | ChAdV68.5WTnt.MAG25mer | VEE-MAG25mer srRNA |
| 4 | ChAdV68.5WTnt.MAG25mer + anti-PD-1 | VEE-MAG25mer srRNA + anti-PD-1 |
| 5 | VEE-MAG25mer srRNA | ChAdV68.5WTnt.MAG25mer |
| 6 | VEE-MAG25mer srRNA + anti-PD-1 | ChAdV68.5WTnt.MAG25mer + anti-PD-1 |
| 7 | VEE-MAG25mer srRNA | VEE-MAG25mer srRNA |
| 8 | VEE-MAG25mer srRNA + anti-PD-1 | VEE-MAG25mer srRNA + anti-PD-1 |

Spleens were harvested 14 days after the prime vaccination for immune monitoring. Tumor and body weight measurements were taken twice a week and survival was monitored. Strong immune responses relative to control were observed in all active vaccine groups.

Figure 30:
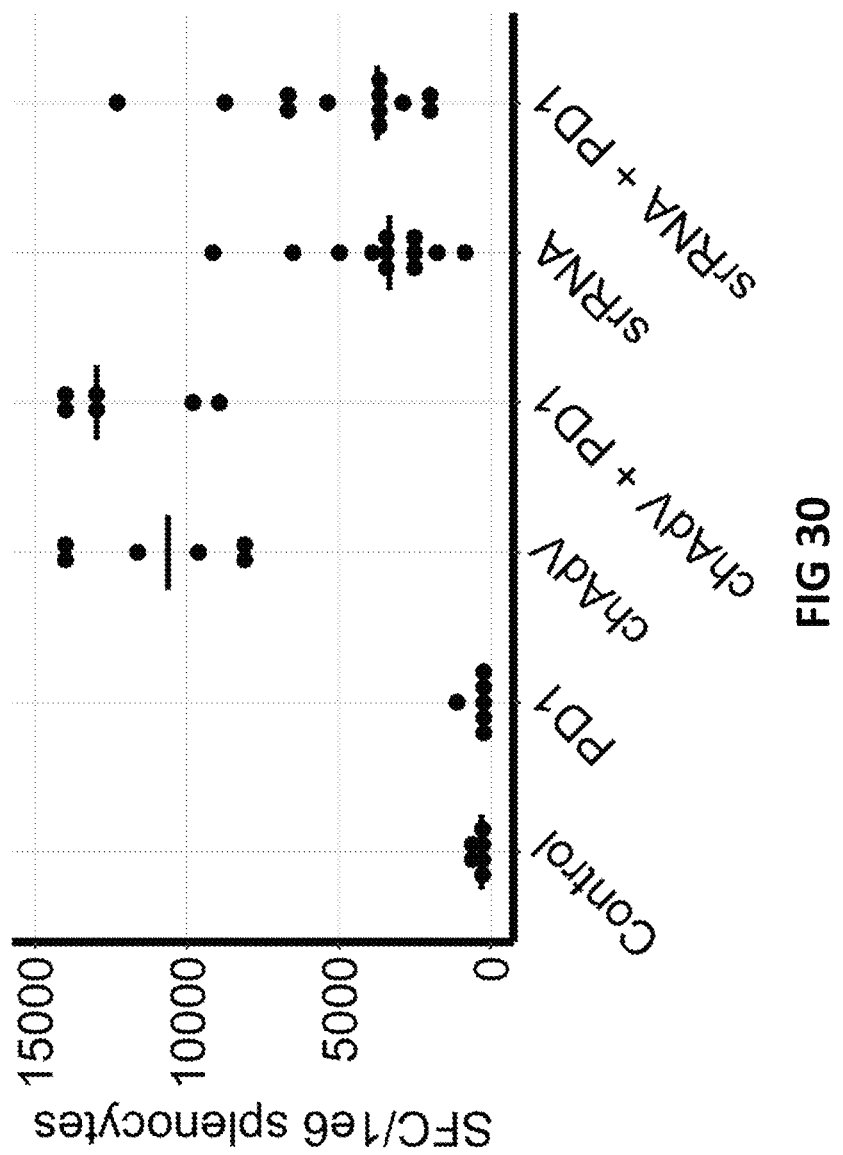
FIG. 30 illustrates cellular immune responses in a CT26 tumor model following a single immunization with either ChAdV6, ChAdV+anti-PD-1, srRNA, srRNA+anti-PD-1, or anti-PD-1 alone. Antigen-specific IFN-gamma production was measured in splenocytes for 6 mice from each group using ELISpot. Results are presented as spot forming cells (SFC) per $10^6$ splenocytes. Median for each group indicated by horizontal line. P values determined using the Dunnett's multiple comparison test; *P<0.0001, P<0.001, *P<0.05. ChAdV=ChAdV68.5WTnt.MAG25mer; srRNA=VEE-MAG25mer srRNA.

Median cellular immune responses of 10,630, 12,976, 3319, or 3745 spot forming cells (SFCs) per $10^6$ splenocytes were observed in ELISpot assays in mice immunized with ChAdV68.5WTnt.MAG25mer (ChAdV/group 3), ChAdV68.5WTnt.MAG25mer+anti-PD-1 (ChAdV+PD-1/group 4), VEE-MAG25mer srRNA (srRNA/median for groups 5 & 7 combined), or VEE-MAG25mer srRNA+anti-PD-1 (srRNA+PD-1/median for groups 6 & 8 combined), respectively, 14 days after the first immunization (FIG. 30 and Table 17). In contrast, the vaccine control (group 1) or vaccine control with anti-PD-1 (group 2) exhibited median cellular immune responses of 296 or 285 SFC per $10^6$ splenocytes, respectively.

TABLE 17

Cellular immune responses in a CT26 tumor model

| Treatment | Median SFC/$10^6$ Splenocytes |
|---|---|
| Control | 296 |
| PD1 | 285 |
| ChAdV68.5WTnt.MAG25mer (ChAdV) | 10630 |
| ChAdV68.5WTnt.MAG25mer + PD1 (ChAdV + PD-1) | 12976 |

TABLE 17-continued

Cellular immune responses in a CT26 tumor model

| Treatment | Median SFC/$10^6$ Splenocytes |
|---|---|
| VEE-MAG25mer srRNA (srRNA) | 3319 |
| VEE-MAG25mer srRNA + PD-1 (srRNA + PD1) | 3745 |

Figure 31:
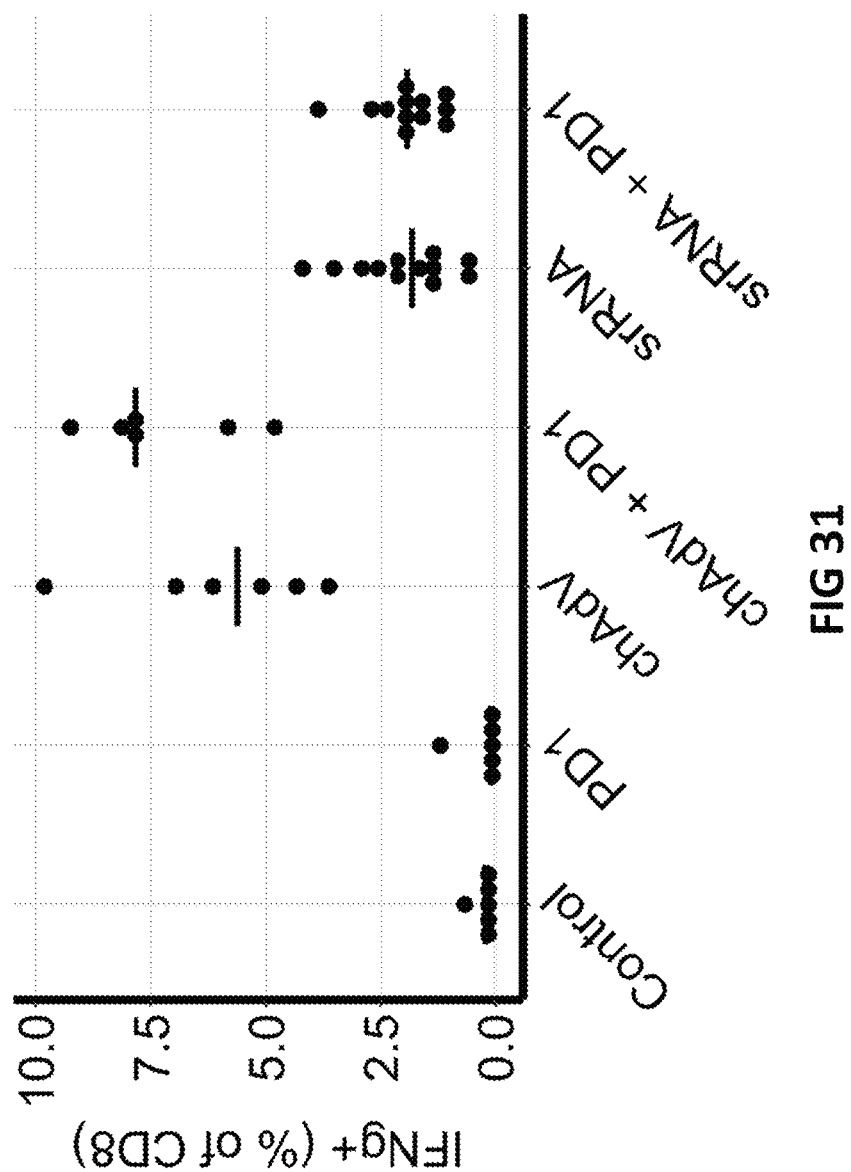
FIG. 31 illustrates CD8 T-Cell responses in a CT26 tumor model following a single immunization with either ChAdV6, ChAdV+anti-PD-1, srRNA, srRNA+anti-PD-1, or anti-PD-1 alone. Antigen-specific IFN-gamma production in CD8 T cells measured using ICS and results presented as antigen-specific CD8 T cells as a percentage of total CD8 T cells. Median for each group indicated by horizontal line. P values determined using the Dunnett's multiple comparison test; *P<0.0001, P<0.001, *P<0.05. ChAdV=ChAdV68.5WTnt.MAG25mer; srRNA=VEE-MAG25mer srRNA.

Consistent with the ELISpot data, 5.6, 7.8, 1.8 or 1.9% of CD8 T cells (median) exhibited antigen-specific responses in intracellular cytokine staining (ICS) analyses for mice immunized with ChAdV68.5WTnt.MAG25mer (ChAdV/group 3), ChAdV68.5WTnt.MAG25mer+anti-PD-1 (ChAdV+PD-1/group 4), VEE-MAG25mer srRNA (srRNA/median for groups 5 & 7 combined), or VEE-MAG25mer srRNA+anti-PD-1 (srRNA+PD-1/median for groups 6 & 8 combined), respectively, 14 days after the first immunization (FIG. 31 and Table 18). Mice immunized with the vaccine control or vaccine control combined with anti-PD-1 showed antigen-specific CD8 responses of 0.2 and 0.1%, respectively.

TABLE 18

CD8 T-Cell responses in a CT26 tumor model

| Treatment | Median % CD8 IFN-gamma Positive |
|---|---|
| Control | 0.21 |
| PD1 | 0.1 |
| ChAdV68.5WTnt.MAG25mer (ChAdV) | 5.6 |
| ChAdV68.5WTnt.MAG25mer + PD1 (ChAdV + PD-1) | 7.8 |
| VEE-MAG25mer srRNA (srRNA) | 1.8 |
| VEE-MAG25mer srRNA + PD-1 (srRNA +PD1) | 1.9 |

Figure 32:
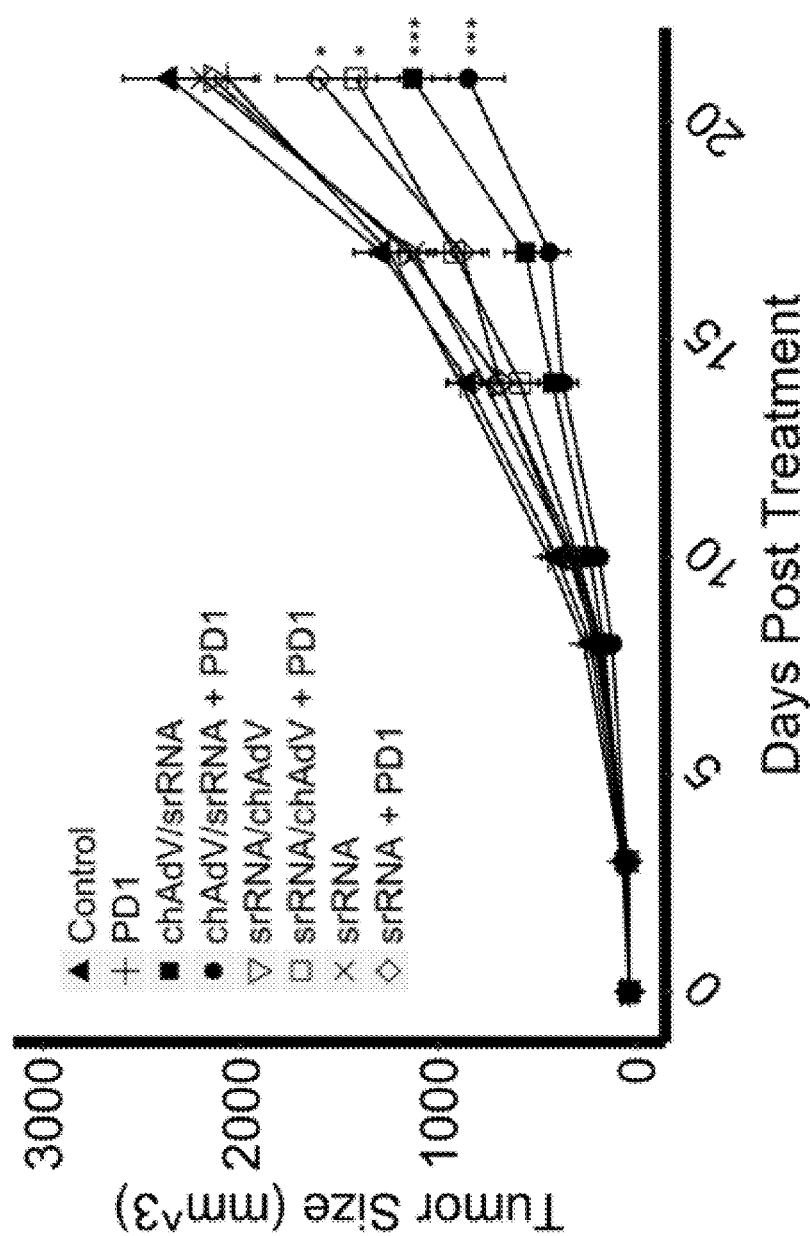
FIG. 32 illustrates tumor growth in a CT26 tumor model following immunization with a ChAdV/srRNA heterologous prime/boost, a srRNA/ChAdV heterologous prime/boost, or a srRNA/srRNA homologous primer/boost. Also illustrated in a comparison of the prime/boost immunizations with or without administration of anti-PD1 during prime and boost. Tumor volumes measured twice per week and mean tumor volumes presented for the first 21 days of the study. 22-28 mice per group at study initiation. Error bars represent standard error of the mean (SEM). P values determined using the Dunnett's test; *P<0.0001, P<0.001, *P<0.05. ChAdV=ChAdV68.5WTnt.MAG25mer; srRNA=VEE-MAG25mer srRNA.

Tumor growth was measured in the CT26 colon tumor model for all groups, and tumor growth up to 21 days after treatment initiation (28 days after injection of CT-26 tumor cells) is presented. Mice were sacrificed 21 days after treatment initiation based on large tumor sizes (>2500 mm$^3$); therefore, only the first 21 days are presented to avoid analytical bias. Mean tumor volumes at 21 days were 1129, 848, 2142, 1418, 2198 and 1606 mm$^3$ for ChAdV68.5WTnt.MAG25mer prime/VEE-MAG25mer srRNA boost (group 3), ChAdV68.5WTnt.MAG25mer prime/VEE-MAG25mer srRNA boost+anti-PD-1 (group 4), VEE-MAG25mer srRNA prime/ChAdV68.5WTnt.MAG25mer boost (group 5), VEE-MAG25mer srRNA prime/ChAdV68.5WTnt.MAG25mer boost+anti-PD-1 (group 6), VEE-MAG25mer srRNA prime/VEE-MAG25mer srRNA boost (group 7) and VEE-MAG25mer srRNA prime/VEE-MAG25mer srRNA boost+anti-PD-1 (group 8), respectively (FIG. 32 and Table 19). The mean tumor volumes in the vaccine control or vaccine control combined with anti-PD-1 were 2361 or 2067 mm³, respectively. Based on these data, vaccine treatment with ChAdV68.5WTnt.MAG25mer/VEE-MAG25mer srRNA (group 3), ChAdV68.5WTnt.MAG25mer/VEE-MAG25mer srRNA+anti-PD-1 (group 4), VEE-MAG25mer srRNA/ChAdV68.5WTnt.MAG25mer+anti-PD-1 (group 6) and VEE-MAG25mer srRNA/VEE-MAG25mer srRNA+anti-PD-1 (group 8) resulted in a reduction of tumor growth at 21 days that was significantly different from the control (group 1).

TABLE 19

Tumor size at day 21 measured in the CT26 model

| Treatment | Tumor Size (mm³) | SEM |
| --- | --- | --- |
| Control | 2361 | 235 |
| PD1 | 2067 | 137 |
| chAdV/srRNA | 1129 | 181 |
| chAdV/srRNA + PD1 | 848 | 182 |
| srRNA/chAdV | 2142 | 233 |
| srRNA/chAdV + PD1 | 1418 | 220 |
| srRNA | 2198 | 134 |
| srRNA +PD1 | 1606 | 210 |

Figure 33:
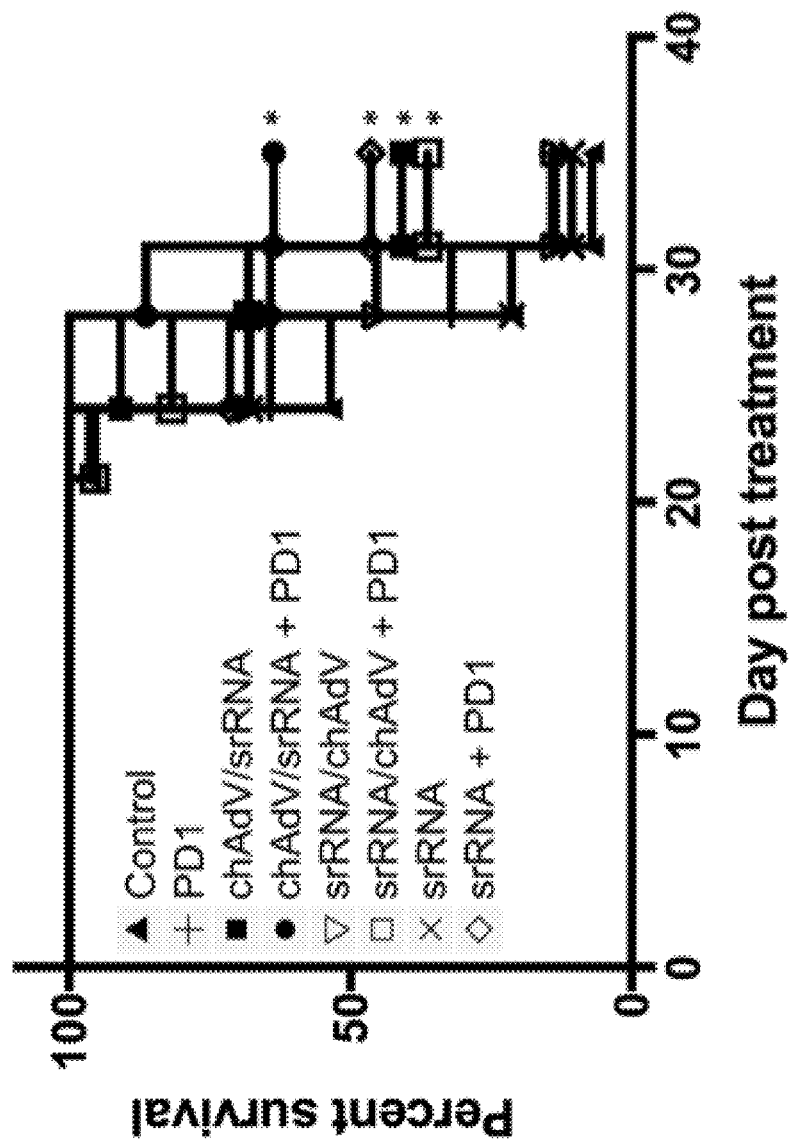
FIG. 33 illustrates survival in a CT26 tumor model following immunization with a ChAdV/srRNA heterologous prime/boost, a srRNA/ChAdV heterologous prime/boost, or a srRNA/srRNA homologous primer/boost. Also illustrated in a comparison of the prime/boost immunizations with or without administration of anti-PD1 during prime and boost. P values determined using the log-rank test; *P<0.0001, P<0.001, *P<0.01. ChAdV=ChAdV68.5WTnt.MAG25mer; srRNA=VEE-MAG25mer srRNA.

Survival was monitored for 35 days after treatment initiation in the CT-26 tumor model (42 days after injection of CT-26 tumor cells). Improved survival was observed after vaccination of mice with 4 of the combinations tested. After vaccination, 64%, 46%, 41% and 36% of mice survived with ChAdV68.5WTnt.MAG25mer prime/VEE-MAG25mer srRNA boost in combination with anti-PD-1 (group 4; P<0.0001 relative to control group 1), VEE-MAG25mer srRNA prime/VEE-MAG25mer srRNA boost in combination with anti-PD-1 (group 8; P=0.0006 relative to control group 1), ChAdV68.5WTnt.MAG25mer prime/VEE-MAG25mer srRNA boost (group 3; P=0.0003 relative to control group 1) and VEE-MAG25mer srRNA prime/ChAdV68.5WTnt.MAG25mer boost in combination with anti-PD-1 (group 6; P=0.0016 relative to control group 1), respectively (FIG. 33 and Table 20). Survival was not significantly different from the control group 1 (<14%) for the remaining treatment groups [VEE-MAG25mer srRNA-prime/ChAdV68.5WTnt.MAG25mer boost (group 5), VEE-MAG25mer srRNA prime/VEE-MAG25mer srRNA boost (group 7) and anti-PD-1 alone (group 2)].

TABLE 20

Survival in the CT26 model

| Timepoint | Control | PD1 | chAdV/ srRNA | chAdV/ srRNA + PD1 | srRNA/ chAdV | srRNA/ chAdV + PD1 | srRNA | srRNA + PD1 |
| --- | --- | --- | --- | --- | --- | --- | --- | --- |
| 0 | 100 | 100 | 100 | 100.00 | 100.00 | 100 | 100 | 100 |
| 21 | 96 | 100 | 100 | 100 | 100 | 95 | 100 | 100 |
| 24 | 54 | 64 | 91 | 100 | 68 | 82 | 68 | 71 |
| 28 | 21 | 32 | 68 | 86 | 45 | 68 | 21 | 64 |
| 31 | 7 | 14 | 41 | 64 | 14 | 36 | 11 | 46 |
| 35 | 7 | 14 | 41 | 64 | 14 | 36 | 11 | 46 |

In conclusion, ChAdV68.5WTnt.MAG25mer and VEE-MAG25mer srRNA elicited strong T-cell responses to mouse tumor antigens encoded by the vaccines, relative to control. Administration of a ChAdV68.5WTnt.MAG25mer prime and VEE-MAG25mer srRNA boost with or without co-administration of anti-PD-1, VEE-MAG25mer srRNA prime and ChAdV68.5WTnt.MAG25mer boost in combination with anti-PD-1 or administration of VEE-MAG25mer srRNA as a homologous prime boost immunization in combination with anti-PD-1 to tumor bearing mice resulted in improved survival.

XVIII. Non-Human Primate Studies

Various dosing protocols using ChAdV68 and self-replicating RNA (srRNA) were evaluated in non-human primates (NHP).

Materials and Methods

A priming vaccine was injected intramuscularly (IM) in each NHP to initiate the study (vaccine prime). One or more boosting vaccines (vaccine boost) were also injected intramuscularly in each NHP. Bilateral injections per dose were administered according to groups outlined in tables and summarized below.

Immunizations

Mamu-A*01 Indian rhesus macaques were immunized bilaterally with $1 \times 10^{12}$ viral particles ($5 \times 10^{11}$ viral particles per injection) of ChAdV68.5WTnt.MAG25mer, 30 ug of VEE-MAG25MER srRNA, 100 ug of VEE-MAG25mer srRNA or 300 ug of VEE-MAG25mer srRNA formulated in LNP-1 or LNP-2. Vaccine boosts of 30 ug, 100 ug or 300 ug VEE-MAG25mer srRNA were administered intramuscularly at the indicated time after prime vaccination.

Immune Monitoring

PBMCs were isolated at indicated times after prime vaccination using Lymphocyte Separation Medium (LSM, MP Biomedicals) and LeucoSep separation tubes (Greiner Bio-One) and resuspended in RPMI containing 10% FBS and penicillin/streptomycin. Cells were counted on the Attune NxT flow cytometer (Thermo Fisher) using propidium iodide staining to exclude dead and apoptotic cells. Cell were then adjusted to the appropriate concentration of live cells for subsequent analysis. For each monkey in the studies, T cell responses were measured using ELISpot or flow cytometry methods. T cell responses to 6 different rhesus macaque Mamu-A*01 class I epitopes encoded in the vaccines were monitored from PBMCs by measuring induction of cytokines, such as IFN-gamma, using ex vivo enzyme-linked immunospot (ELISpot) analysis. ELISpot analysis was performed according to ELISPOT harmonization guidelines {DOI: 10.1038/nprot.2015.068} with the monkey IFNg ELISpotPLUS kit (MABTECH). 200,000 PBMCs were incubated with 10 uM of the indicated peptides for 16 hours in 96-well IFNg antibody coated plates. Spots were developed using alkaline phosphatase. The reaction was timed for 10 minutes and was terminated by running plate under tap water. Spots were counted using an AID vSpot Reader Spectrum. For ELISPOT analysis, wells with saturation >50% were recorded as "too numerous to count". Samples with deviation of replicate wells >10% were excluded from analysis. Spot counts were then corrected for well confluency using the formula: spot count+ 2×(spot count×% confluence/[100%−% confluence]). Negative background was corrected by subtraction of spot counts in the negative peptide stimulation wells from the antigen stimulated wells. Finally, wells labeled too numerous to count were set to the highest observed corrected value, rounded up to the nearest hundred.

Specific CD4 and CD8 T cell responses to 6 different rhesus macaque Mamu-A*01 class I epitopes encoded in the vaccines were monitored from PBMCs by measuring induction of intracellular cytokines, such as IFN-gamma, using flow cytometry. The results from both methods indicate that cytokines were induced in an antigen-specific manner to epitopes.

Immunogenicity in Rhesus Macaques

This study was designed to (a) evaluate the immunogenicity and preliminary safety of VEE-MAG25mer srRNA 30 µg and 100 µg doses as a homologous prime/boost or heterologous prime/boost in combination with ChAdV68.5WTnt.MAG25mer; (b) compare the immune responses of VEE-MAG25mer srRNA in lipid nanoparticles using LNP1 versus LNP2; (c) evaluate the kinetics of T-cell responses to VEE-MAG25mer srRNA and ChAdV68.5WTnt.MAG25mer immunizations.

The study arm was conducted in Mamu-A*01 Indian rhesus macaques to demonstrate immunogenicity. Select antigens used in this study are only recognized in Rhesus macaques, specifically those with a Mamu-A*01 MHC class I haplotype. Mamu-A*01 Indian rhesus macaques were randomized to the different study arms (6 macaques per group) and administered an IM injection bilaterally with either ChAdV68.5WTnt.MAG25mer or VEE-MAG25mer srRNA vector encoding model antigens that includes multiple Mamu-A*01 restricted epitopes. The study arms were as described below.

TABLE 21

Non-GLP immunogenicity study in Indian Rhesus Macaques

| Group | Prime | Boost 1 | Boost 2 |
|---|---|---|---|
| 1 | VEE-MAG25mer srRNA-LNP1 (30 µg) | VEE-MAG25mer srRNA-LNP1 (30 µg) | VEE-MAG25mer srRNA-LNP1 (30 µg) |
| 2 | VEE-MAG25mer srRNA-LNP1 (100 µg) | VEE-MAG25mer srRNA-LNP1 (100 µg) | VEE-MAG25mer srRNA-LNP1 (100 µg) |
| 3 | VEE-MAG25mer srRNA-LNP2 (100 µg) | VEE-MAG25mer srRNA-LNP2 (100 µg) | VEE-MAG25mer srRNA-LNP2 (100 µg) |
| 4 | ChAdV68.5WTnt. MAG25mer | VEE-MAG25mer srRNA-LNP1 (100 µg) | VEE-MAG25mer srRNA-LNP1 (100 µg) |

PBMCs were collected prior to immunization and on weeks 1, 2, 3, 4, 5, 6, 8, 9, and 10 after the initial immunization for immune monitoring.

Results

Antigen-specific cellular immune responses in peripheral blood mononuclear cells (PBMCs) were measured to six different Mamu-A*01 restricted epitopes prior to immunization and 1, 2, 3, 4, 5, 6, 8, 9, and 10 weeks after the initial immunization. Animals received a boost immunization with VEE-MAG25mer srRNA on weeks 4 and 8 with either 30 µg or 100 µg doses, and either formulated with LNP1 or LNP2, as described in Table 21. Combined immune responses to all six epitopes were plotted for each immune monitoring timepoint (FIG. 34A-D and Tables 22-25).

Figure 34A:
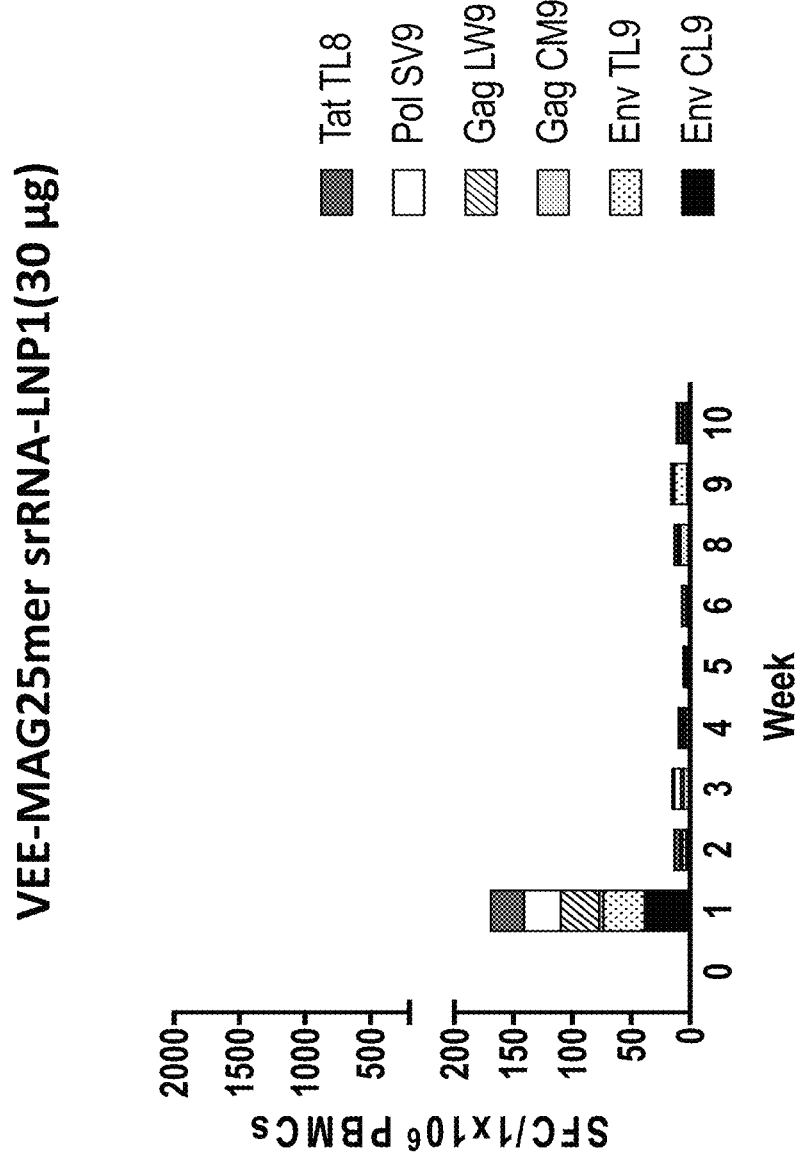
FIG. 34A, FIG. 34B, FIG. 34C, and FIG. 34D illustrate antigen-specific cellular immune responses measured using ELISpot. Antigen-specific IFN-gamma production to six different mamu A01 restricted epitopes was measured in PBMCs for the VEE-MAG25mer srRNA-LNP1(30 µg) (FIG. 34A), VEE-MAG25mer srRNA-LNP1(100 µg) (FIG. 34B), or VEE-MAG25mer srRNA-LNP2(100 µg) (FIG. 34C) homologous prime/boost or the ChAdV68.5WTnt.MAG25mer/VEE-MAG25mer srRNA heterologous prime/boost group (FIG. 34D) using ELISpot 1, 2, 3, 4, 5, 6, 8, 9, or 10 weeks after the first boost immunization (6 rhesus macaques per group). Results are presented as mean spot forming cells (SFC) per $10^6$ PBMCs for each epitope in a stacked bar graph format. Values for each animal were normalized to the levels at pre-bleed (week 0).
Figure 34B:
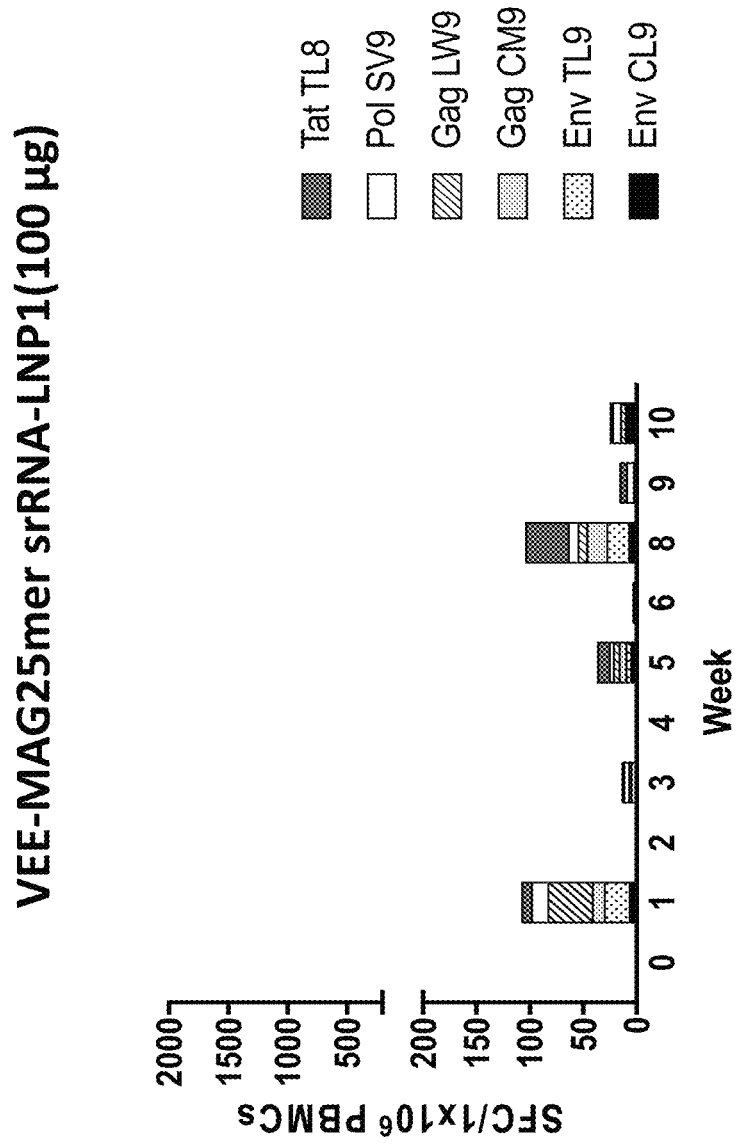
Figure 34C:
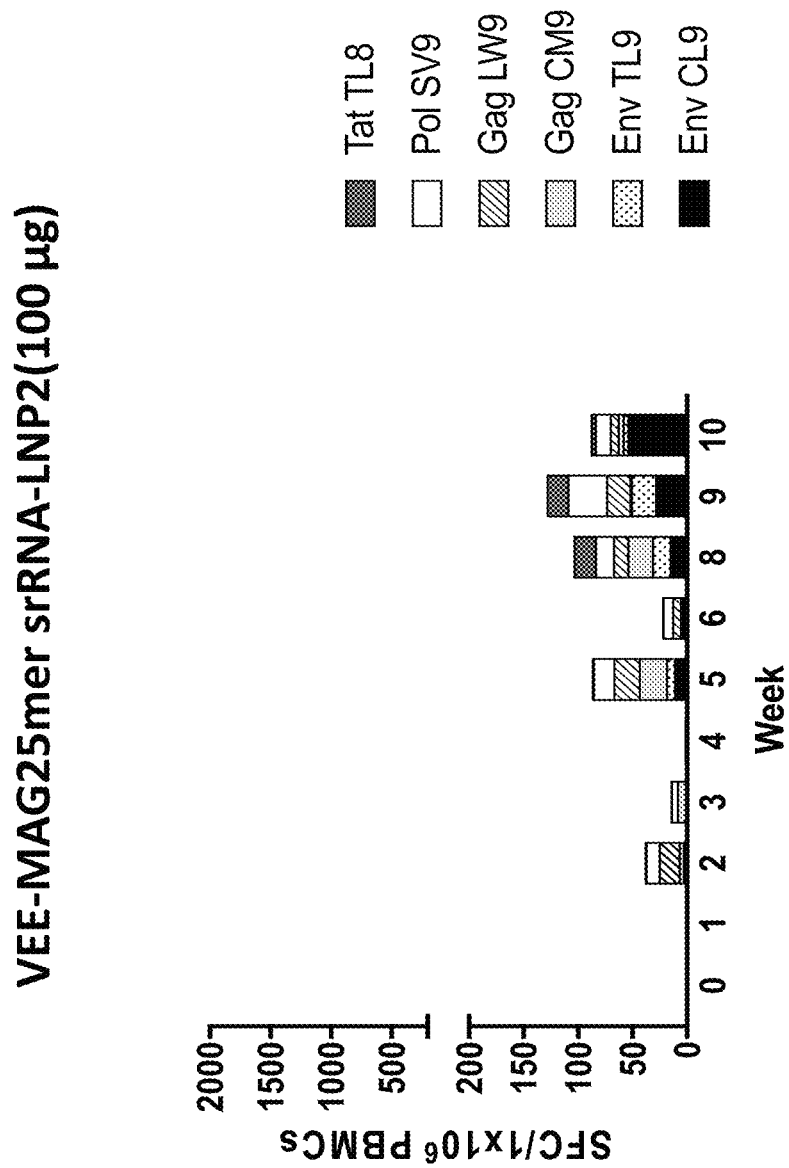

Combined antigen-specific immune responses were observed at all measurements with 170, 14, 15, 11, 7, 8, 14, 17, 12 SFCs per $10^6$ PBMCs (six epitopes combined) 1, 2, 3, 4, 5, 6, 8, 9, or 10 weeks after an initial VEE-MAG25mer srRNA-LNP1(30 µg) prime immunization, respectively (FIG. 34A). Combined antigen-specific immune responses were observed at all measurements with 108, −3, 14, 1, 37, 4, 105, 17, 25 SFCs per $10^6$ PBMCs (six epitopes combined) 1, 2, 3, 4, 5, 6, 8, 9, or 10 weeks after an initial VEE-MAG25mer srRNA-LNP1(100 µg) prime immunization, respectively (FIG. 34B). Combined antigen-specific immune responses were observed at all measurements with −17, 38, 14, −2, 87, 21, 104, 129, 89 SFCs per $10^6$ PBMCs (six epitopes combined) 1, 2, 3, 4, 5, 6, 8, 9, or 10 weeks after an initial VEE-MAG25mer srRNA-LNP2(100 µg) prime immunization, respectively (FIG. 34C). Negative values are a result of normalization to pre-bleed values for each epitope/animal.

Figure 34D:
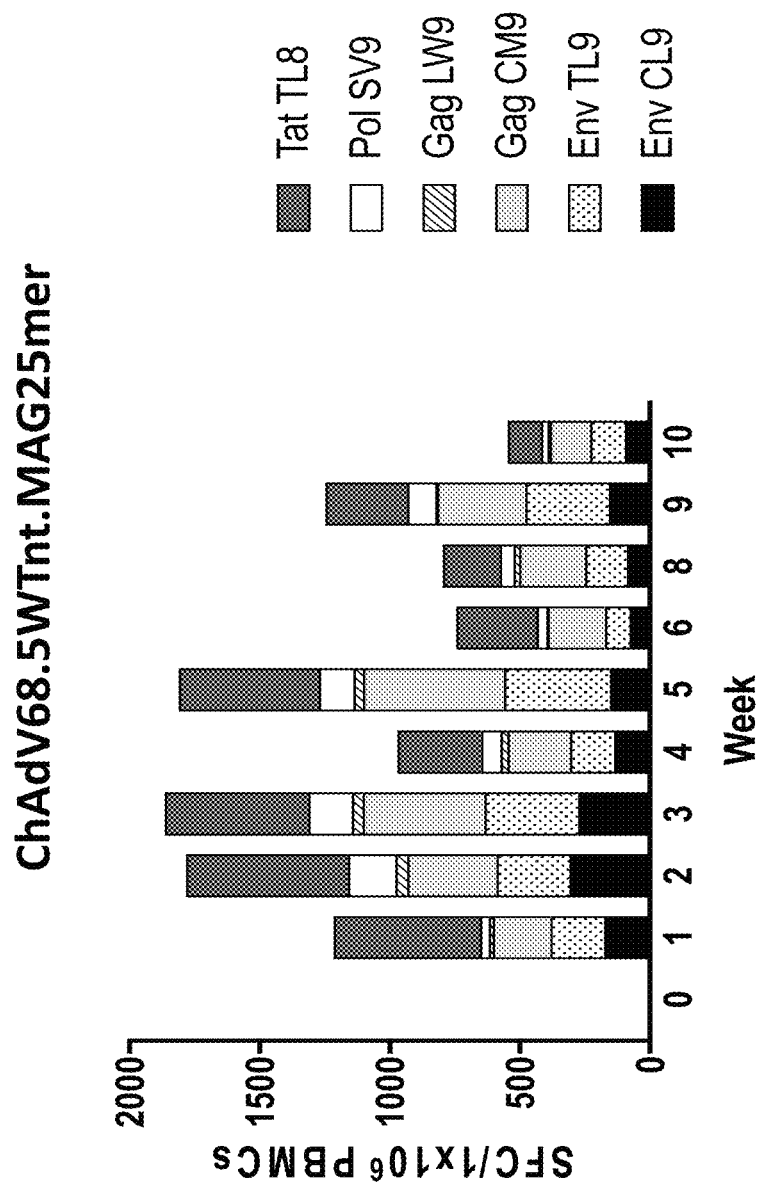

Combined antigen-specific immune responses were observed at all measurements with 1218, 1784, 1866, 973, 1813, 747, 797, 1249, and 547 SFCs per $10^6$ PBMCs (six epitopes combined) 1, 2, 3, 4, 5, 6, 8, 9, and 10 weeks after an initial ChAdV68.5WTnt.MAG25mer prime immunization, respectively (FIG. 34D). The immune response showed the expected profile with peak immune responses measured ~2-3 weeks after the prime immunization followed by a contraction in the immune response after 4 weeks. Combined antigen-specific cellular immune responses of 1813 SFCs per $10^6$ PBMCs (six epitopes combined) were measured 5 weeks after the initial immunization with ChAdV68.5WTnt.MAG25mer (i.e., 1 week after the first boost with VEE-MAG25mer srRNA). The immune response measured 1 week after the first boost with VEE-MAG25mer srRNA (week 5) was comparable to the peak immune response measured for the ChAdV68.5WTnt.MAG25mer prime immunization (week 3) (FIG. 34D). Combined antigen-specific cellular immune responses of 1249 SFCs per $10^6$ PBMCs (six epitopes combined) was measured 9 weeks after the initial immunization with ChAdV68.5WTnt.MAG25mer, respectively (i.e., 1 week after the second boost with VEE-MAG25mer srRNA). The immune responses measured 1 week after the second boost with VEE-MAG25mer srRNA (week 9) was ~2-fold higher than that measured just before the boost immunization (FIG. 34D).

TABLE 22

Mean spot forming cells (SFC) per $10^6$ PBMCs for each epitope ± SEM for VEE-MAG25mer srRNA-LNP1(30 µg) (Group 1)

| | Antigen | | | | | |
|---|---|---|---|---|---|---|
| Wk | Env CL9 | Env TL9 | Gag CM9 | Gag LW9 | Pol SV9 | Tat TL8 |
| 1 | 0 ± 0 | 0 ± 0 | 0 ± 0 | 0 ± 0 | 0 ± 0 | 0 ± 0 |
| 2 | 39.7 ± 22.7 | 35.4 ± 25.1 | 3.2 ± 3.6 | 33 ± 28.1 | 30.9 ± 20.3 | 28.3 ± 17.5 |
| 3 | 2 ± 2.4 | 0.2 ± 1.8 | 1.8 ± 2.4 | 3.7 ± 1.9 | 1.7 ± 2.8 | 4.9 ± 2.3 |
| 4 | 1 ± 1.8 | 0.3 ± 1.2 | 5.5 ± 3.6 | 2.3 ± 2.2 | 5.7 ± 2.7 | 0.8 ± 0.8 |
| 5 | 0.5 ± 0.9 | 1.4 ± 3.8 | 3.1 ± 1.6 | 2.3 ± 2.7 | 1.9 ± 2 | 1.4 ± 1.2 |
| 6 | 1.9 ± 1.8 | −0.3 ± 3 | 1.7 ± 1.2 | 1.4 ± 1.4 | 0.8 ± 1.1 | 1.1 ± 1 |
| 8 | −0.4 ± 0.8 | −0.9 ± 2.9 | 0.5 ± 1.3 | 3 ± 1.1 | 2.2 ± 2.1 | 3.7 ± 2 |
| 9 | 1 ± 1.7 | 1.2 ± 4.2 | 7.2 ± 3.9 | 0.5 ± 0.7 | 1.6 ± 3 | 3 ± 1 |
| 10 | 3.8 ± 1.8 | 11 ± 5 | −1.1 ± 1.1 | 1.9 ± 0.9 | 1.3 ± 1.6 | 0.2 ± 0.5 |

TABLE 23

Mean spot forming cells (SFC) per $10^6$ PBMCs for each epitope ± SEM for VEE-MAG25mer srRNA-LNP1(100 µg) (Group 2)

| | Antigen | | | | | |
|---|---|---|---|---|---|---|
| Wk | Env CL9 | Env TL9 | Gag CM9 | Gag LW9 | Pol SV9 | Tat TL8 |
| 1 | 0 ± 0 | 0 ± 0 | 0 ± 0 | 0 ± 0 | 0 ± 0 | 0 ± 0 |
| 2 | 7.9 ± 17.2 | 23.2 ± 17.4 | 11.4 ± 4.9 | 41.7 ± 16.5 | 15 ± 13.5 | 8.9 ± 6.2 |
| 3 | −3.1 ± 4.6 | −7.2 ± 6.5 | 2.3 ± 2.3 | −0.3 ± 2.7 | 2.7 ± 5.1 | 2.2 ± 1.4 |
| 4 | 1.9 ± 3.8 | −6.2 ± 7.6 | 10.5 ± 4.1 | 1.2 ± 2.9 | 5.6 ± 4.9 | 1.1 ± 0.8 |
| 5 | −2.6 ± 7 | −8 ± 5.9 | 1.5 ± 1.7 | 6.4 ± 2.3 | 0.7 ± 4.3 | 3.3 ± 1.3 |
| 6 | 6.3 ± 6.3 | 4.4 ± 8.3 | 6.6 ± 4.4 | 5.2 ± 5.2 | 3.9 ± 5 | 10.8 ± 6.9 |
| 8 | −3.6 ± 7.2 | −6.8 ± 7.3 | −0.8 ± 1.2 | 3.4 ± 4.2 | 6.4 ± 7.5 | 5.7 ± 2.7 |
| 9 | 8.1 ± 2.4 | 20.6 ± 23.4 | 18.9 ± 5.7 | 8.1 ± 8.9 | 9 ± 11.2 | 40 ± 17.6 |
| 10 | 3.1 ± 8 | −3.9 ± 8.5 | 3.3 ± 1.8 | 0.6 ± 2.9 | 7.4 ± 6.4 | 6.1 ± 2.5 |

TABLE 24

Mean spot forming cells (SFC) per $10^6$ PBMCs for each epitope ± SEM for VEE-MAG25mer srRNA-LNP2(100 µg) (Group 3)

| | Antigen | | | | | |
|---|---|---|---|---|---|---|
| Wk | Env CL9 | Env TL9 | Gag CM9 | Gag LW9 | Pol SV9 | Tat TL8 |
| 1 | 0 ± 0 | 0 ± 0 | 0 ± 0 | 0 ± 0 | 0 ± 0 | 0 ± 0 |
| 2 | −5.9 ± 3.8 | −0.3 ± 0.5 | −0.5 ± 1.5 | −5.7 ± 6.1 | −1 ± 1.3 | −3.2 ± 5.5 |
| 3 | 0.7 ± 5.2 | 3.4 ± 2.4 | 4.2 ± 4.6 | 18.3 ± 15.5 | 11.9 ± 5.1 | −0.4 ± 8.2 |
| 4 | −3.8 ± 5.5 | 2.3 ± 1.8 | 11.3 ± 6.1 | −3.1 ± 5.6 | 8.5 ± 4 | −1.5 ± 6.1 |
| 5 | −3.7 ± 5.7 | −0.1 ± 0.7 | −0.2 ± 1.6 | 3.4 ± 8.5 | 3 ± 3.1 | −4.6 ± 5 |
| 6 | 12.3 ± 15 | 7.8 ± 4.9 | 24.7 ± 19.8 | 23.2 ± 22.5 | 18.7 ± 15.8 | 0.5 ± 6.2 |
| 8 | 5.9 ± 12.3 | −0.1 ± 0.7 | −0.5 ± 1.3 | 8.8 ± 14.4 | 8.7 ± 8 | −1.3 ± 4 |
| 9 | 16.1 ± 13.4 | 16.5 ± 4 | 22.9 ± 4.2 | 13 ± 13.2 | 16.4 ± 7.8 | 19.6 ± 9.2 |
| 10 | 29.9 ± 21.8 | 22 ± 19.5 | 0.5 ± 2.6 | 22.2 ± 22.6 | 35.3 ± 15.8 | 19.4 ± 17.3 |

TABLE 25

Mean spot forming cells (SFC) per $10^6$ PBMCs for each epitope ± SEM for ChAdV68.5WTntMAG25mer prime

| | Antigen | | | | | |
|---|---|---|---|---|---|---|
| Wk | Env CL9 | Env TL9 | Gag CM9 | Gag LW9 | Pol SV9 | Tat TL8 |
| 1 | 178 ± 68.7 | 206.5 ± 94.8 | 221.2 ± 120 | 15.4 ± 16.7 | 33.3 ± 25.9 | 563.5 ± 174.4 |
| 2 | 311.2 ± 165.5 | 278.8 ± 100.9 | 344.6 ± 110.8 | 46.3 ± 13.5 | 181.6 ± 76.8 | 621.4 ± 220.9 |
| 3 | 277.3 ± 101.1 | 359.6 ± 90.5 | 468.2 ± 106.6 | 41.7 ± 11.1 | 169.8 ± 57.8 | 549.4 ± 115.7 |

TABLE 25-continued

Mean spot forming cells (SFC) per $10^6$ PBMCs for each epitope ± SEM for ChAdV68.5WTntMAG25mer prime

| | Antigen | | | | | |
|---|---|---|---|---|---|---|
| Wk | Env CL9 | Env TL9 | Gag CM9 | Gag LW9 | Pol SV9 | Tat TL8 |
| 4 | 140 ± 46.5 | 169.6 ± 46.8 | 239.4 ± 37 | 26.5 ± 11.4 | 75 ± 31.6 | 322.2 ± 50.7 |
| 5 | 155.6 ± 62.1 | 406.7 ± 96.4 | 542.7 ± 143.3 | 35.1 ± 16.6 | 134.2 ± 53.7 | 538.5 ± 91.9 |
| 6 | 78.9 ± 42.5 | 95.5 ± 29.4 | 220.9 ± 75.3 | −1.4 ± 5.3 | 43.4 ± 19.6 | 308.1 ± 42.6 |
| 8 | 88.4 ± 30.4 | 162.1 ± 30.3 | 253.4 ± 78.6 | 21.4 ± 11.2 | 53.7 ± 22.3 | 217.8 ± 45.2 |
| 9 | 158.5 ± 69 | 322.3 ± 87.2 | 338.2 ± 137.1 | 5.6 ± 12.4 | 109.2 ± 17.9 | 314.8 ± 43.4 |
| 10 | 97.3 ± 32.5 | 133.2 ± 27 | 154.9 ± 59.2 | 10 ± 6 | 26 ± 16.7 | 125.5 ± 27.7 |

Non-GLP RNA Dose Ranging Study (Higher Doses) in Indian Rhesus Macaques

This study was designed to (a) evaluate the immunogenicity of VEE-MAG25mer srRNA at a dose of 300 µg as a homologous prime/boost or heterologous prime/boost in combination with ChAdV68.5WTnt.MAG25mer; (b) compare the immune responses of VEE-MAG25mer srRNA in lipid nanoparticles using LNP1 versus LNP2 at the 300 µg dose; and (c) evaluate the kinetics of T-cell responses to VEE-MAG25mer srRNA and ChAdV68.5WTnt.MAG25mer immunizations.

The study arm was conducted in Mamu-A*01 Indian rhesus macaques to demonstrate immunogenicity. Vaccine immunogenicity in nonhuman primate species, such as Rhesus, is the best predictor of vaccine potency in humans. Furthermore, select antigens used in this study are only recognized in Rhesus macaques, specifically those with a Mamu-A*01 MHC class I haplotype. Mamu-A*01 Indian rhesus macaques were randomized to the different study arms (6 macaques per group) and administered an IM injection bilaterally with either ChAdV68.5-WTnt.MAG25mer or VEE-MAG25mer srRNA encoding model antigens that includes multiple Mamu-A*01 restricted antigens. The study arms were as described below.

PBMCs were collected prior to immunization and 4, 5, 6, 7, 8, 10, 11, 12, 13, 14, 15, 16, 17, 18, 19, 20, 21, 22, 23 or 24 weeks after the initial immunization for immune monitoring for group 1 (heterologous prime/boost). PBMCs were collected prior to immunization and 4, 5, 7, 8, 10, 11, 12, 13, 14, or 15 weeks after the initial immunization for immune monitoring for groups 2 and 3 (homologous prime/boost).

Results

Figure 35:
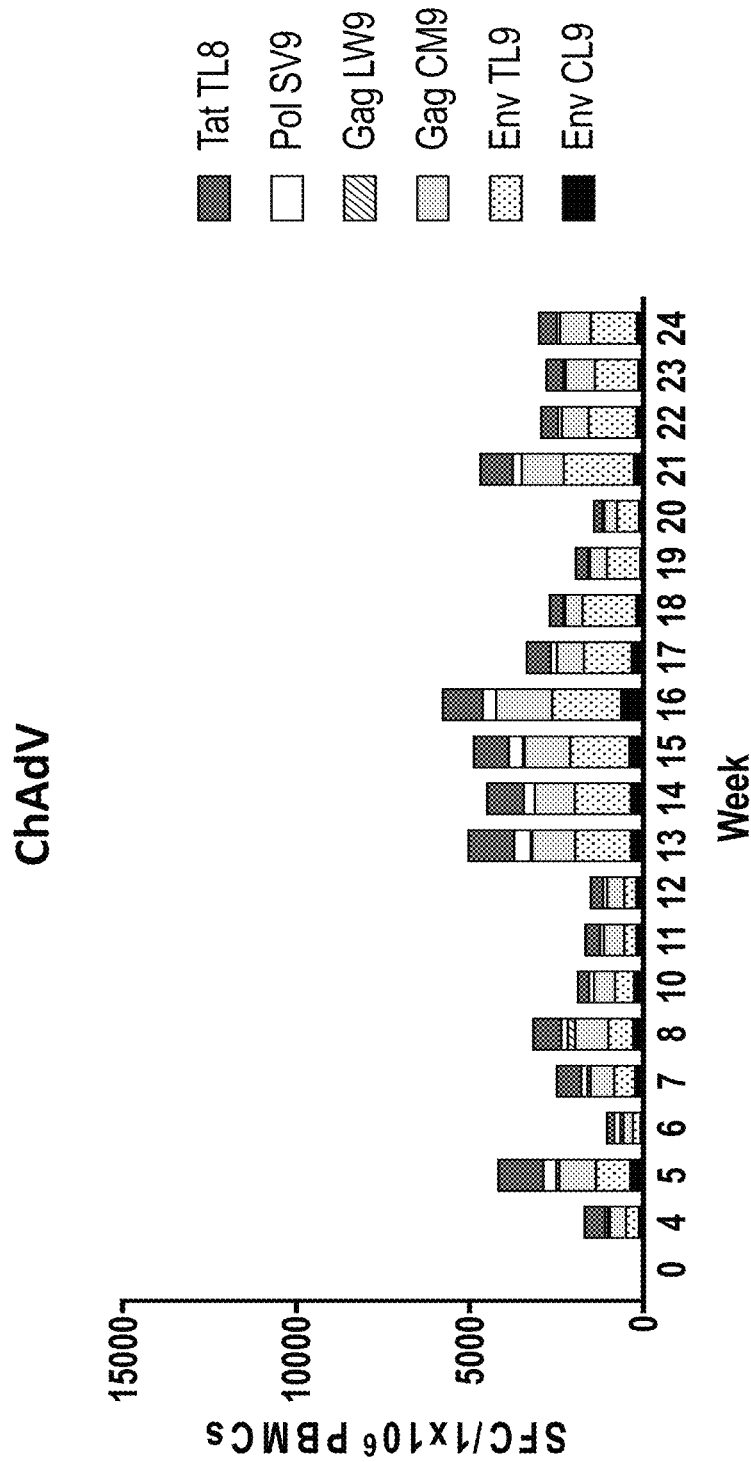
FIG. 35 shows antigen-specific cellular immune response measured using ELISpot. Antigen-specific IFN-gamma production to six different mamu A01 restricted epitopes was measured in PBMCs after immunization with the ChAdV68.5WTnt.MAG25mer/VEE-MAG25mer srRNA heterologous prime/boost regimen using ELISpot prior to immunization and 4, 5, 6, 7, 8, 10, 11, 12, 13, 14, 15, 16, 17, 18, 19, 20, 21, 22, 23 or 24 weeks after the initial immunization. Results are presented as mean spot forming cells (SFC) per $10^6$ PBMCs for each epitope (6 rhesus macaques per group) in a stacked bar graph format.

Mamu-A*01 Indian rhesus macaques were immunized with ChAdV68.5-WTnt.MAG25mer. Antigen-specific cellular immune responses in peripheral blood mononuclear cells (PBMCs) were measured to six different Mamu-A*01 restricted epitopes prior to immunization and 4, 5, 6, 7, 8, 10, 11, 12, 13, 14, 15, 16, 17, 18, 19, 20, 21, 22, 23 or 24 weeks after the initial immunization (FIG. 35 and Table 27). Animals received boost immunizations with VEE-MAG25mer srRNA using the LNP2 formulation on weeks 4, 12, and 20. Combined antigen-specific immune responses of 1750, 4225, 1100, 2529, 3218, 1915, 1708, 1561, 5077, 4543, 4920, 5820, 3395, 2728, 1996, 1465, 4730, 2984, 2828, or 3043 SFCs per $10^6$ PBMCs (six epitopes combined) were measured 4, 5, 6, 7, 8, 10, 11, 12, 13, 14, 15, 16, 17, 18, 19, 20, 21, 22, 23 or 24 weeks after the initial immunization with ChAdV68.5WTnt.MAG25mer (FIG. 35). Immune responses measured 1 week after the second boost immunization (week 13) with VEE-MAG25mer srRNA were ~3-fold higher than that measured just before the boost immunization (week 12). Immune responses measured 1 week after the third boost immunization (week 21) with VEE-MAG25mer srRNA, were ~3-fold higher than that measured just before the boost immunization (week 20), similar to the response observed for the second boost.

Figure 36:
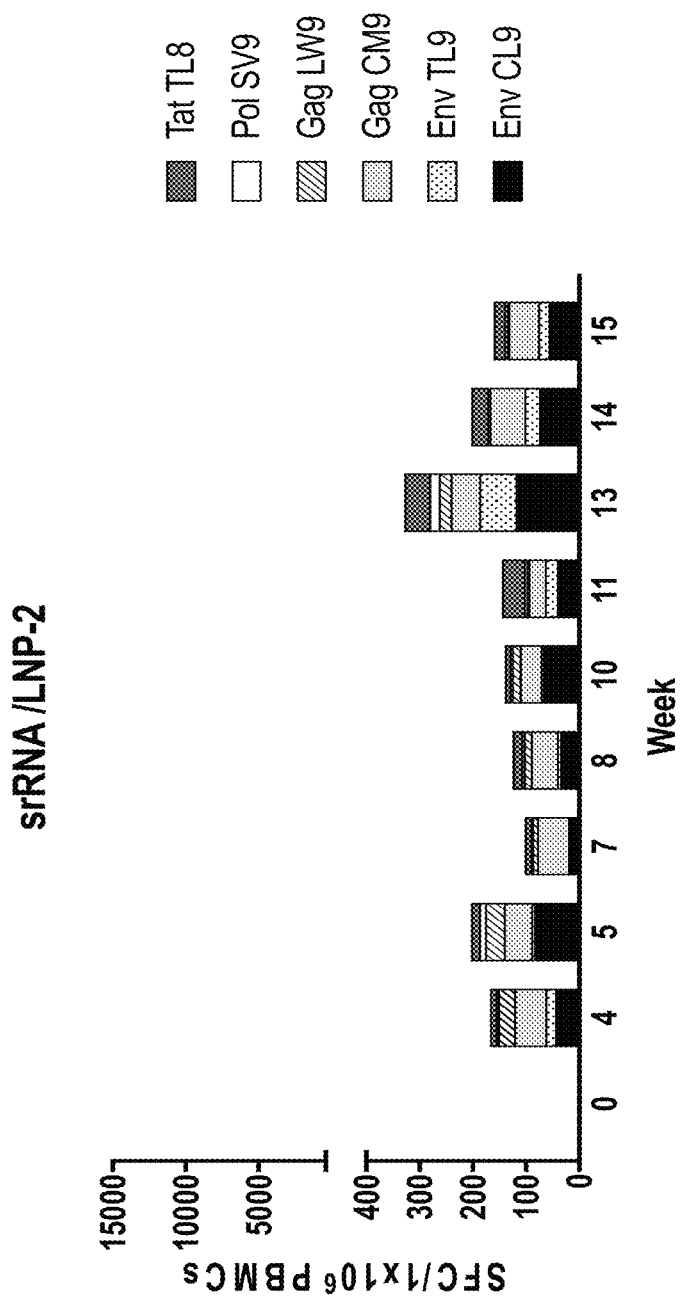
FIG. 36 shows antigen-specific cellular immune response measured using ELISpot. Antigen-specific IFN-gamma production to six different mamu A01 restricted epitopes was measured in PBMCs after immunization with the VEE-MAG25mer srRNA LNP2 homologous prime/boost regimen using ELISpot prior to immunization and 4, 5, 6, 7, 8, 10, 11, 12, 13, 14, or 15 weeks after the initial immunization. Results are presented as mean spot forming cells (SFC) per $10^6$ PBMCs for each epitope (6 rhesus macaques per group) in a stacked bar graph format.
Figure 37:
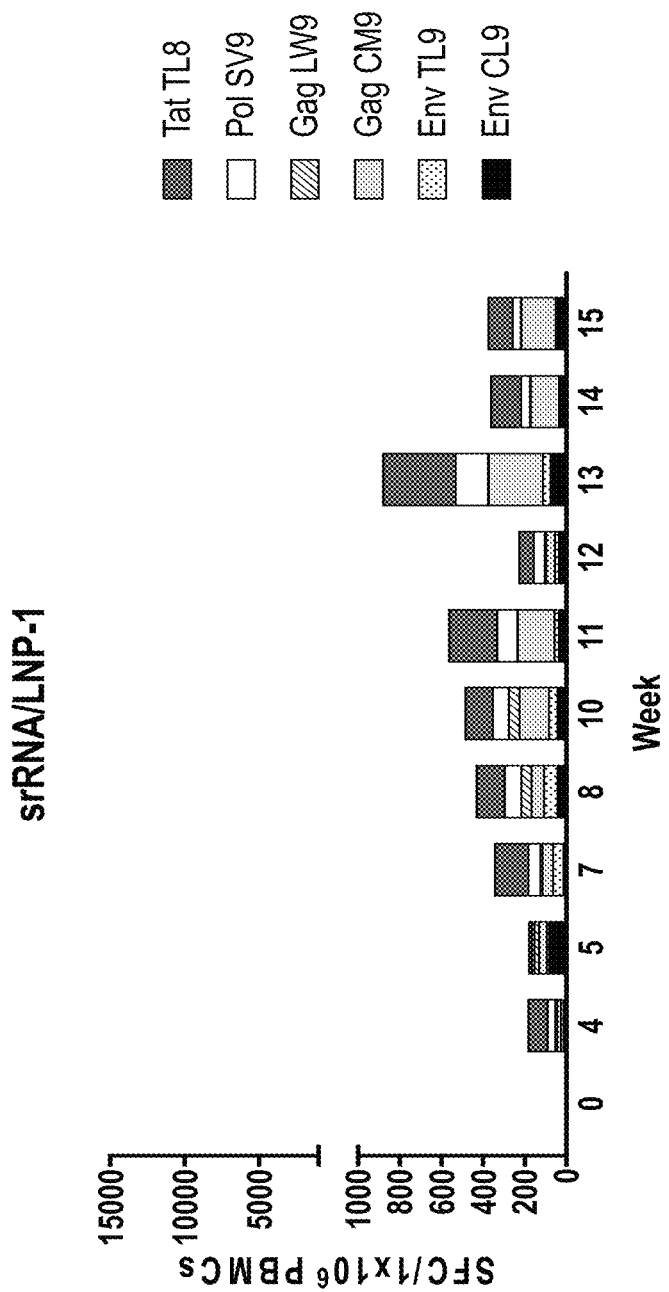
FIG. 37 shows antigen-specific cellular immune response measured using ELISpot. Antigen-specific IFN-gamma production to six different mamu A01 restricted epitopes was measured in PBMCs after immunization with the VEE-MAG25mer srRNA LNP1 homologous prime/boost regimen using ELISpot prior to immunization and 4, 5, 6, 7, 8, 10, 11, 12, 13, 14, or 15 weeks after the initial immunization. Results are presented as mean spot forming cells (SFC) per $10^6$ PBMCs for each epitope (6 rhesus macaques per group) in a stacked bar graph format.

Mamu-A*01 Indian rhesus macaques were also immunized with VEE-MAG25mer srRNA using two different LNP formulations (LNP1 and LNP2). Antigen-specific cellular immune responses in peripheral blood mononuclear cells (PBMCs) were measured to six different Mamu-A*01 restricted epitopes prior to immunization and 4, 5, 6, 7, 8, 10, 11, 12, 13, 14, or 15 weeks after the initial immunization (FIGS. 36 and 37, Tables 28 and 29). Animals received boost immunizations with VEE-MAG25mer srRNA using the respective LNP1 or LNP2 formulation on weeks 4 and 12. Combined antigen-specific immune responses of 168, 204, 103, 126, 140, 145, 330, 203, and 162 SFCs per 106 PBMCs (six epitopes combined) were measured 4, 5, 7, 8, 10, 11, 13, 14, 15 weeks after the immunization with VEE-MAG25mer srRNA-LNP2 (FIG. 36). Combined antigen-specific immune responses of 189, 185, 349, 437, 492, 570, 233, 886, 369, and 381 SFCs per $10^6$ PBMCs (six epitopes combined) were measured 4, 5, 7, 8, 10, 11, 12, 13, 14, 15 weeks after the immunization with VEE-MAG25mer srRNA-LNP1 (FIG. 37).

TABLE 26

Non-GLP immunogenicity study in Indian Rhesus Macaques

| Group | Prime | Boost 1 | Boost 2 | Boost 3 |
|---|---|---|---|---|
| 1 | ChAdV68.5WTnt.MAG25mer | VEE-MAG25mer srRNA-LNP2 (300 µg) | VEE-MAG25mer srRNA-LNP2 (300 µg) | VEE-MAG25mer srRNA-LNP2 (300 µg) |
| 2 | VEE-MAG25mer srRNA-LNP2 (300 µg) | VEE-MAG25mer srRNA-LNP2 (300 µg) | VEE-MAG25mer srRNA-LNP2 (300 µg) | |
| 3 | VEE-MAG25mer srRNA-LNP1 (300 µg) | VEE-MAG25mer srRNA-LNP1 (300 µg) | VEE-MAG25mer srRNA-LNP1 (300 µg) | |

TABLE 27

Mean spot forming cells (SFC) per $10^6$ PBMCs for each epitope ± SEM for priming vaccination with ChAdV68.5WTntMAG25mer (Group 1)

| | Antigen | | | | | |
|---|---|---|---|---|---|---|
| Wk | Env CL9 | Env TL9 | Gag CM9 | Gag LW9 | Pol SV9 | Tat TL8 |
| 4 | 173 ± 41.6 | 373.5 ± 87.3 | 461.4 ± 74.2 | 38.4 ± 26.1 | 94.5 ± 26 | 609.2 ± 121.9 |
| 5 | 412.7 ± 138.4 | 987.8 ± 283.3 | 1064.4 ± 266.9 | 85.6 ± 31.2 | 367.2 ± 135.2 | 1306.8 ± 332.8 |
| 6 | 116.2 ± 41.2 | 231.1 ± 46.3 | 268.3 ± 90.7 | 86.1 ± 42 | 174.3 ± 61 | 223.9 ± 38.1 |
| 7 | 287.4 ± 148.7 | 588.9 ± 173.9 | 693.2 ± 224.8 | 92.1 ± 33.5 | 172.9 ± 55.6 | 694.6 ± 194.8 |
| 8 | 325.4 ± 126.6 | 735.8 ± 212 | 948.9 ± 274.5 | 211.3 ± 62.7 | 179.1 ± 50 | 817.3 ± 185.2 |
| 10 | 312 ± 129.7 | 543.2 ± 188.4 | 618.6 ± 221.7 | −5.7 ± 4.1 | 136.5 ± 51.3 | 309.9 ± 85.6 |
| 11 | 248.5 ± 81.1 | 348.7 ± 129.8 | 581.1 ± 205.5 | −3.1 ± 4.4 | 119 ± 51.2 | 413.7 ± 144.8 |
| 12 | 261.9 ± 68.2 | 329.9 ± 83 | 486.5 ± 118.6 | −1.2 ± 5.1 | 132.8 ± 31.8 | 350.9 ± 69.3 |
| 13 | 389.3 ± 167.7 | 1615.8 ± 418.3 | 1244.3 ± 403.6 | 1.3 ± 8.1 | 522.5 ± 155 | 1303.3 ± 385.6 |
| 14 | 406.3 ± 121.6 | 1616 ± 491.7 | 1142.3 ± 247.2 | 6.6 ± 11.1 | 322.7 ± 94.1 | 1048.6 ± 215.6 |
| 15 | 446.8 ± 138.7 | 1700.8 ± 469.1 | 1306.3 ± 294.4 | 43 ± 24.5 | 421.2 ± 87.9 | 1001.5 ± 236.4 |
| 16 | 686.8 ± 268.8 | 1979.5 ± 541.7 | 1616.8 ± 411.8 | 2.4 ± 7.8 | 381.9 ± 116.4 | 1152.8 ± 352.7 |
| 17 | 375.8 ± 109.3 | 1378.6 ± 561.2 | 773.1 ± 210.3 | −1.4 ± 4.3 | 177.6 ± 93.7 | 691.7 ± 245 |
| 18 | 255.9 ± 99.7 | 1538.4 ± 498.1 | 498.7 ± 152.3 | −5.3 ± 3.3 | 26.2 ± 13.4 | 413.9 ± 164.8 |
| 19 | 133 ± 62.6 | 955.9 ± 456.8 | 491.1 ± 121.8 | −5.7 ± 4.1 | 50.3 ± 25.4 | 371.2 ± 123.7 |
| 20 | 163.7 ± 55.8 | 641.7 ± 313.5 | 357.9 ± 91.1 | 2.6 ± 7.5 | 41.4 ± 24.2 | 257.8 ± 68.9 |
| 21 | 319.9 ± 160.5 | 2017.1 ± 419.9 | 1204.8 ± 335.2 | −3.7 ± 5.1 | 268.1 ± 109.6 | 924.1 ± 301 |
| 22 | 244.7 ± 105.6 | 1370.9 ± 563.5 | 780.3 ± 390 | −3.6 ± 5.1 | 118.2 ± 68.1 | 473.3 ± 249.3 |
| 23 | 176.7 ± 81.8 | 1263.7 ± 527.3 | 838.6 ± 367.9 | −5.7 ± 4.1 | 73.6 ± 49 | 480.9 ± 163.9 |
| 24 | 236.5 ± 92 | 1324.7 ± 589.3 | 879.7 ± 321 | −0.4 ± 5.7 | 104 ± 53.1 | 498 ± 135.8 |

TABLE 28

Mean spot forming cells (SFC) per $10^6$ PBMCs for each epitope ± SEM for priming vaccination with VEE-MAG25mer srRNA-LNP2 (300 µg) (Group 2)

| | Antigen | | | | | |
|---|---|---|---|---|---|---|
| Wk | Env CL9 | Env TL9 | Gag CM9 | Gag LW9 | Pol SV9 | Tat TL8 |
| 4 | 46 ± 27.1 | 18.4 ± 6.8 | 58.3 ± 45.8 | 29.9 ± 20.8 | 4.9 ± 2.3 | 10.7 ± 4 |
| 5 | 85.4 ± 54 | 5.2 ± 5.8 | 52.4 ± 51.2 | 34.5 ± 35 | 11.8 ± 12.2 | 14.4 ± 7.9 |
| 7 | 18.6 ± 32.5 | 1.9 ± 1.7 | 59.4 ± 55.7 | 9.3 ± 10.7 | 3.3 ± 3 | 10.7 ± 6.1 |
| 8 | 36.6 ± 39.4 | 6.3 ± 3.9 | 48.7 ± 39.9 | 13.5 ± 8.8 | 3.8 ± 3.6 | 17.2 ± 9.7 |
| 10 | 69.1 ± 59.1 | 4.4 ± 1.9 | 39.3 ± 38 | 14.7 ± 10.8 | 4.4 ± 5.3 | 8.5 ± 5.3 |
| 11 | 43 ± 38.8 | 22.6 ± 21.1 | 30.2 ± 26.2 | 3.3 ± 2.2 | 5.8 ± 3.5 | 40.3 ± 25.5 |
| 13 | 120.4 ± 78.3 | 68.2 ± 43.9 | 54.2 ± 36.8 | 21.8 ± 7.4 | 17.7 ± 6.1 | 47.4 ± 27.3 |
| 14 | 76 ± 44.8 | 28 ± 19.5 | 65.9 ± 64.3 | −0.3 ± 1.3 | 2.5 ± 2 | 31.1 ± 26.5 |
| 15 | 58.9 ± 41.4 | 19.5 ± 15.1 | 55.4 ± 51 | 2.5 ± 2 | 5.5 ± 3.6 | 20.1 ± 15.7 |

TABLE 29

Mean spot forming cells (SFC) per $10^6$ PBMCs for each epitope ± SEM for priming vaccination with VEE-MAG25mer srRNA-LNP1 (300 µg) (Group 3)

| | Antigen | | | | | |
|---|---|---|---|---|---|---|
| Wk | Env CL9 | Env TL9 | Gag CM9 | Gag LW9 | Pol SV9 | Tat TL8 |
| 4 | 19.5 ± 8.7 | 13.3 ± 13.1 | 16.5 ± 15.3 | 10.5 ± 7.3 | 35.9 ± 24.8 | 92.9 ± 91.6 |
| 5 | 87.9 ± 43.9 | 12.7 ± 11.7 | 37.2 ± 31.9 | 21.1 ± 23.8 | 13.2 ± 13.7 | 12.6 ± 13.7 |
| 7 | 21.1 ± 13.3 | 48.8 ± 48.4 | 51.7 ± 39.5 | 9.1 ± 10.5 | 58.6 ± 55.8 | 159.4 ± 159 |
| 8 | 47.7 ± 21.7 | 66.4 ± 52.2 | 59.8 ± 57.4 | 49.4 ± 28 | 79.4 ± 63 | 133.8 ± 132.1 |
| 10 | 49 ± 30.2 | 42.2 ± 41.1 | 139.3 ± 139.3 | 51.6 ± 51.2 | 78.2 ± 75.8 | 131.7 ± 131.6 |
| 11 | 42 ± 26.8 | 20.9 ± 21.4 | 177.1 ± 162 | −6.3 ± 4.3 | 104.3 ± 104.1 | 231.5 ± 230.1 |
| 12 | 40.2 ± 19 | 20.3 ± 11.9 | 42.2 ± 46.7 | 3.7 ± 6.7 | 57 ± 44.7 | 70 ± 69.2 |
| 13 | 81.2 ± 48.9 | 38.2 ± 37.6 | 259.4 ± 222.2 | −4 ± 4.1 | 164.1 ± 159.3 | 347.5 ± 343.5 |
| 14 | 34.5 ± 31.8 | 5.3 ± 11.6 | 138.6 ± 137.3 | −4.7 ± 5.2 | 52.3 ± 52.9 | 142.6 ± 142.6 |
| 15 | 49 ± 24 | 6.7 ± 9.8 | 167.1 ± 163.8 | −6.4 ± 4.2 | 47.8 ± 42.3 | 116.6 ± 114.5 | srRNA Dose Ranging Study

In one implementation of the present invention, an srRNA dose ranging study can be conducted in mamu A01 Indian rhesus macaques to identify which srRNA dose to progress to NHP immunogenicity studies. In one example, Mamu A01 Indian rhesus macaques can be administered with an srRNA vector encoding model antigens that includes multiple mamu A01 restricted epitopes by IM injection. In another example, an anti-CTLA-4 monoclonal antibody can be administered SC proximal to the site of IM vaccine injection to target the vaccine draining lymph node in one group of animals. PBMCs can be collected every 2 weeks after the initial vaccination for immune monitoring. The study arms are described in below (Table 30).

TABLE 30

Non-GLP RNA dose ranging study in Indian Rhesus Macaques

| Group | Prime | Boost 1 | Boost 2 |
|---|---|---|---|
| 1 | srRNA-LNP (Low Dose) | srRNA-LNP (Low Dose) | srRNA-LNP (Low Dose) |
| 2 | srRNA-LNP (Mid Dose) | srRNA-LNP (Mid Dose) | srRNA-LNP (Mid Dose) |
| 3 | srRNA-LNP (High Dose) | srRNA-LNP (High Dose) | srRNA-LNP (High Dose) |
| 4 | srRNA-LNP (High Dose) + anti-CTLA-4 | srRNA-LNP (High Dose) + anti-CTLA-4 | srRNA-LNP (High Dose) + anti-CTLA-4 |

* Dose range of srRNA to be determined with the high dose ≤300 µg.

Immunogenicity Study in Indian Rhesus Macaques

In one implementation of the present invention, vaccine studies can be conducted in mamu A01 Indian rhesus macaques to demonstrate immunogenicity. In one example, Mamu A01 Indian rhesus macaques can be administered an IM injection with a ChAdV and/or srRNA vector encoding model antigens that includes multiple mamu A01 restricted antigens. In another example, an anti-CTLA-4 monoclonal antibody will be administered SC proximal to the site of IM vaccine injection to some of the groups. PBMCs can be collected every 2 weeks after the initial vaccination for immune monitoring. The study arms are described in below (Table 31).

TABLE 31

Non-GLP immunogenicity study in Indian Rhesus Macaques

| Group | Prime | Boost 1 | Boost 2 |
|---|---|---|---|
| 1 | ChAdV | srRNA-LNP* | srRNA-LNP |
| 2 | srRNA-LNP | ChAdV | srRNA-LNP |
| 3 | srRNA-LNP | srRNA-LNP | ChAdV |
| 4 | srRNA-LNP + anti-CTLA-4 | srRNA-LNP + anti-CTLA-4 | srRNA-LNP + anti-CTLA-4 |
| 5 | ChAdV + anti-CTLA-4 | srRNA-LNP + anti-CTLA-4 | srRNA-LNP + anti-CTLA-4 |
| 6 | srRNA-LNP + anti-CTLA-4 | ChAdV + anti-CTLA-4 | srRNA-LNP + anti-CTLA-4 |

*srRNA dose to be determined based on srRNA dose range study.

XIX. Identification of MHC/Peptide Target-Reactive T Cells and TCRs

T cells can be isolated from blood, lymph nodes, or tumors of patients. T cells can be enriched for antigen-specific T cells, e.g., by sorting antigen-MHC tetramer binding cells or by sorting activated cells stimulated in an in vitro co-culture of T cells and antigen-pulsed antigen presenting cells. Various reagents are known in the art for antigen-specific T cell identification including antigen-loaded tetramers and other MHC-based reagents.

Antigen-relevant alpha-beta (or gamma-delta) TCR dimers can be identified by single cell sequencing of TCRs of antigen-specific T cells. Alternatively, bulk TCR sequencing of antigen-specific T cells can be performed and alpha-beta pairs with a high probability of matching can be determined using a TCR pairing method known in the art.

Alternatively or in addition, antigen-specific T cells can be obtained through in vitro priming of naïve T cells from healthy donors. T cells obtained from PBMCs, lymph nodes, or cord blood can be repeatedly stimulated by antigen-pulsed antigen presenting cells to prime differentiation of antigen-experienced T cells. TCRs can then be identified similarly as described above for antigen-specific T cells from patients.

Certain Sequences

Sequences for vectors, cassettes, and antibodies are shown below.

```
Tremelimumab VL (SEQ ID NO: 16)
PSSLSASVGDRVTITCRSQSINSYLDWYQQKPGKAPKLLIYAASSLQSGVPSRFSGSGSGTDFTLTISSLQ
PEDFATYYCQQYYSTPFTFGPGTKVEIKRTVAAPSVFIFPPSDEQLKSGTASVVCLLNNFYPREAKV Tremelimumab VH (SEQ ID NO: 17)
GVVQPGRSLRLSCAASGFTFSSYGMHWVRQAPGKGLEWVAVIWYDGSNKYYADSVKGRFTISRDNSK
NTLYLQMNSLRAEDTAVYYCARDPRGATLYYYYGMDVWGQGTTVTVSSASTKGPSVFPLAPCSRSTS
ESTAALGCLVKDYFPEPVTVSWNSGALTSGVH Tremelimumab VH CDR1 (SEQ ID NO: 18)
GFTFSSYGMH
```

Tremelimumab VH CDR2 (SEQ ID NO: 19)
VIWYDGSNKYYADSV

Tremelimumab VH CDR3 (SEQ ID NO: 20)
DPRGATLYYYYGMDV

Tremelimumab VL CDR1 (SEQ ID NO: 21)
RASQSINSYLD

Tremelimumab VL CDR2 (SEQ ID NO: 22)
AASSLQS

Tremelimumab VL CDR3 (SEQ ID NO: 23)
QQYYSTPFT

Durvalumab (MEDI4736) VL (SEQ ID NO: 24)
EIVLTQSPGTLSLSPGERATLSCRASQRVSSSYLAWYQQKPGQAPRLLIYDASSRATGIPDRFSGSGSGTD
FTLTISRLEPEDFAVYYCQQYGSLPWTFGQGTKVEIK MEDI4736 VH (SEQ ID NO: 25)
EVQLVESGGGLVQPGGSLRLSCAASGFTFSRYWMSWVRQAPGKGLEWVANIKQDGSEKYYVDSVKGR
FTISRDNAKNSLYLQMNSLRAEDTAVYYCAREGGWFGELAFDYWGQGTLVTVSS

MEDI4736 VH CDR1 (SEQ ID NO: 26)
RYWMS

MEDI4736 VH CDR2 (SEQ ID NO: 27)
NIKQDGSEKYYVDSVKG

MEDI4736 VH CDR3 (SEQ ID NO: 28)
EGGWFGELAFDY

MEDI4736 VL CDR1 (SEQ ID NO: 29)
RASQRVSSSYLA

MEDI4736 VL CDR2 (SEQ ID NO: 30)
DASSRAT

MEDI4736 VL CDR3 (SEQ ID NO: 31)
QQYGSLPWT

UbA76-25merPDTT nucleotide (SEQ ID NO: 32)
GCCCGGGCATTTAAATGCGATCGCATCGATtacgactotagaatagtotagtccgcaggccaccatgC
AGATCTTCGTGAAGACCCTGACCGGCAAGACCATCACCCTAGAGGTGGAGCCCAGTGACACCATCGAGAACGTG
AAGGCCAAGATCCAGGATAAAGAGGGCATCCCCCCTGACCAGCAGAGGCTGATCTTTGCCGGCAAGCAGCTGGA
AGATGGCCGACACCCTCTCTGATTACAACATCCAGAAGGAGTCAACCCTGCACCTGGTCCTTCGCCTGAGAGGTG
cCatgtttcaggcgctgagcgaaggctgcaccccgtatgatattaaccagatgctgaacgtgctgggcgatcat
caggtctcaggccttgagcagcttgagagtataatcaactttgaaaaactgactgaatggaccagttctaatgt
tatgCCTATCCTGTCTCCTCTGACAAAGGGCATCCTGGGCTTCGTGTTTACCCTGACCGTGCCTTCTGAGAGAG
GACTTagctgcattagcgaagcggatgcgaccaccccggaaagcgcgaacctgggcgaagaaattctgagccag
ctgtatctttggccaagggtgacctaccattcccctagttatgcttaccaccaatttgaaagacgagccaaata
taaaagaCACTTCCCCGGCTTTGGCCAGAGCCTGCTGTTTGGCTACCCTGTGTACGTGTTCGGCGATTGCGTGC
AGGGCGATtgggatgcgattcgcttcgctattgcgcgccgccgggctatgcgctgctgcgctgcaacgataac
aactatagcgctctgctggctgtggggggccctagaaggacccaggaatcaggactggcttggtgtcccaagaca
acttgtaactCGGATGCAGGCTATTCAGAATGCCGGCCTGTGTACCCTGGTGGCCATGCTGGAAGAGACAATCT
TCTGGCTGCAAgcgtttctgatggcgctgaccgatagcggccccgaaaaccaacattattgtgataGcagtat
gtgatgggcattagcaaaccgagctttcaggaatttgtggattgggaaaacgtgagcccggaactgaacagcac
cgatcagccgtttTGGCAAGCCGGAATCCTGGCCAGAAATCTGGTGCCTATGGTGGCCACAGTGCAGGGCCAGA
ACCTGAAGTACCAGggtcagtcactagtcatctctgcttctatcattgtcttcaacctgCtggaactggaaggt
gattatcgagatgatggcaacgtgtgggtgcataccccgctgagcccgcgcaccctgaacgcgtgggtgaaagc
ggtgaagaaaaaaaaggtattccagttcacctagagctggccagtatgaccaacaTggagctcatgagcagta
ttgtgcatcagcaggtcAGAACATACGGCCCCGTGTTCATGTGTCTCGGCGGACTGCTTACAATGGTGGCTGGT
GCTGTGTGGCTGACAGTGcgagtgctcgagctgttccgggccgcgcagctggccaacgacgtggtcctccagat
catggagctttgtggtgcagcgtttcgccaggtgtgccataccaccgtgccgtgccgaacgcgagcctgaccc
cgaaatggaacaacgaaaccacccagcccagatcgccaactgcagcgtgtatgactttttttgtgtggctccat
tattattctgttcgagacacactttggccaagggtgacctaccatatgaacaaatatgcgtatcatatgctgga
aagacgagccaaatataaaagaGGACCAGGACCTGGCGCTAAATTTGTGGCCGCCTGGACACTGAAAGCCGCTG
CTGGTCCTGGACCTGGCCAGTACATCAAGGCCAACAGCAAGTTCATCGGCATCACCGAACTCGGACCCGGACCA
GGCTGATGATTTCGAAATTTAAATAAGCTTGCGGCCGCTAGGGATAACAGGGTAATtatcacgcccaaacattt
acagccgcggtgtcaaaaaccgcgtgg UbA76-25merPDTT polypeptide (SEQ ID NO: 33)
MQIFVKTLTGKTITLEVEPSDTIENVKAKIQDKEGIPPDQQRLIFAGKQLEDGRTLSDYNIQKESTLH
LVLRLRGAMFQALSEGCTPYDINQMLNVLGDHQVSGLEQLESIINFEKLTEWTSSNVMPILSPLTKGILGFVFT
LTVPSERGLSCISEADATTPESANLGEEILSQLYLWPRVTYHSPSYAYHQFERRAKYKRHFPGFGQSLLEGYPV
YVFGDCVQGDWDAIRFRYCAPPGYALLRCNDTNYSALLAVGALEGPRNQDWLGVPRQLVTRMQAIQNAGLCTLV
AMLEETIFWLQAFLMALTDSGPKTNIIVDSQYVMGISKPSFQEFVDWENVSPELNSTDQPFWQAGILARNLVPM
VATVQGQNLKYQGQSLVISASIIVFNLLELEGDYRDDGNVWVETPLSPRTLNAWVKAVEEKKGIPVHLELASMT
NMELMSSIVHQQVRTYGPVFMCLGGLLTMVAGAVWLTVRVLELFRAAQLANDVVLQIMELCGAAFRQVCHTTVP WPNASLTPKWNNETTQPQIANCSVYDFFVWLHYYSVRDTLWPRVTYHMNKYAYHMLERRAKYKRGPGPGAKEVA
AWTLKAAAGPGPGQYIKANSKFIGITELGPGPG MAG-25merPDTT nucleotide (SEQ TD NO: 34)
ATGGCCGGGATGTTCCAGGCACTGTCCGAAGGCTGCACACCCTATGATATTAACCAGATGCTGAATGTCCTGGG
AGACCACCAGGTCTCTGGCCTGGAGCAGCTGGAGAGCATCATCAACTTGAGAAGCTGACCGAGTGGACAAGCT
CCAATGTGATGCCTATCCTGTCCCCACTGACCAAGGGCATCCTGGGCTTCGTGTTTACCCTGACACTGCCTTCT
GAGCGGGGCCTGTCTTGCATCAGCGAGGCAGACGCAACCACACCAGAGTCCGCCAATCTGGGCGAGGAGATCCT
GTCTCAGCTGTACCTGTGGCCCCGGGTGACATATCACTTCCCCTTCTTACGCCTATCACCAGTTCGAGCGGAGAG
CCAAGTACAAGAGACACTTCCCAGGCTTTGGCCAGTCTCTGCTGTTCGGCTACCCCGTGTACGTGTTCGGCGAT
TGCGTGCAGGGCGACTGGGATGCCATCCGGTTTAGATACTGCGCACCACCTGGATATGCACTGCTGAGGTGTAA
CGACACCAATTATTCCGCCCTGCTGGCAGTGGGCGCCCTGGAGGGCCCTCGCAATCAGGATTGGCTGGGCGTGC
CAAGGCAGCTGGTGACACGCATGCAGGCCATCCAGAACGCAGGCCTGTGCACCCTGGTGGCAATGCTGGAGGAG
ACAATCTTCTGGCTGCAGGCCTTTCTGATGGCCCTGACCGACAGCGGCCCCAAGACAAACATCATCGTGGATTC
CCAGTACGTGATGGGCATCTCCAAGCCTTCTTTCCAGGAGTTTGTGGACTGGGAGAACGTGAGCCCAGAGCTGA
ATTCCACCGATCAGCCATTCTGGCAGGCAGGAATCCTGGCAAGGAACCTGGTGCCTATGGTGGCCACAGTGCAG
GGCCAGAATCTGAAGTACCAGGGCCAGAGCCTGGTCATCAGCGCCTCCATCATCGTGTTTAACCTGCTGGAGCT
GGAGGGCGACTATCGGGACGATGGCAACGTGTGGGTGCACACCCCACTGAGCCCCAGAACACTGAACGCCTGGG
TGAAGGCCGTGGAGGAGAAGAAGGGCATCCCAGTGCACCTGGAGCTGGCCTCCATGACCAATATGGAGCTGATG
TCTAGCATCGTGCACCAGCAGGTGAGGACATACGGACCCGTGTTCATGTGCCTGGGAGGCCTGCTGACCATGGT
GGCAGGAGCCGTGTGGCTGACAGTGCGGGTGCTGGAGCTGTTCAGAGCCGCCCAGCTGGCCAACGATGTGGTGC
TGCAGATCATGGAGCTGTGCGGAGCAGCCTTTCGCCAGGTGTGCCACACCACAGTGCCATGGCCCAATGCCTCC
CTGACCCCCAAGTGGAACAATCAGACAACACAGCCTCAGATCGCCAACTGTAGCGTGTACGACTTCTTCGTGTG
GCTGCACTACTATAGCGTGAGGGATACCCTGTGGCCCCGCGTGACATACCACATGAATAAGTACGCCTATCACA
TGCTGGAGAGGCGCGCCAAGTATAAGAGAGGCCCTGGCCCAGGCGCAAAGTTTGTGGCAGCATGGACCCTGAAG
GCCGCCGCCGGCCCCGGCCCCGGCCAGTATATCAAGGCTAACAGTAAGTTCATTGGAATCACAGAGCTGGGACC
CGGACCTGGA MAG-25merPDTT polypeptide (SEQ ID NO: 35)
MAGMFQALSEGCTPYDINQMLNVLGDHQVSGLEQLESIINFEKLTEWTSSNVMPILSPLTKGILGFVF
TLTVPSERGLSCISEADATTPESANLGEEILSQLYLWPRVTYHSPSYAYHQFERRAKYKRHFPGFGQSLLFGYP
VYVFGDCVQGDWDAIRFRYCAPPGYALLRCNDTNYSALLAVGALEGPRNQDWLGVPRQLVTRMQAIQNAGLCTL
VAMLEETIFWLQAFLMALTDSGPKTNIIVDSQYVMGISKPSFQEFVDWENVSPELNSTDQPFWQAGILARNLVP
MVATVQGQNLKYQGQSLVISASIIVFNLLELEGDYRDDGNVWVHTPLSPRTLNAWVKAVEEKKGIPVHLELASM
TNMELMSSIVHQQVRTYGPVFMCLGGLLTMVAGAVWLTVRVLELFRAAQLANDVVLQIMELCGAAFRQVCHTTV
PWPNASLTPKWNNETTQPQIANCSVYDFFVWLHYYSVRDTLWPRVTYHMNKYAYHMLERRAKYKRGPGPGAKEV
AAWTLKAAAGPGPGQYIKANSKFIGITELGPGPG Ub7625merPDTT NoSFL nucleotide (SEQ ID NO: 36)
GCCCGGGCATTTAAATGCGATCGCATCGATtacgactctagaatagtctagtccgcaggccaccatgC
AGATCTTCGTGAAGACCCTGACCGGCAAGACCATCACCCTAGAGGTGGAGCCCAGTGACACCATCGAGAACGTG
AAGGCCAAGATCCAGGATAAAGAGGGCATCCCCCCTGACCAGCAGAGGCTGATCTTTGCCGGCAAGCAGCTGGA
AGATGGCCGCACCCTCTCTGATTACAACATCCAGAAGGAGTCAACCCTGCACCTGGTCCTTCGCTCGAGAGGTG
cCatgtttcaggcgctgagcgaaggctgcacccccgtatgatattaaccagatgctgaacgtgctgggcgatcat
cagtttaagcacatcaaagcctttgaccggacatttgctaacaacccaggtcccatggttgtgtttgccacacc
tgggCCTATCCTGTCTCCTCTGACAAAGGGCATCCTGGGCTTCGTGTTTACCCTGACCGTGCCTTCTGAGAGAG
GACTTagctgcattagcgaagcggatgcgaccaccccggaaagccgaacctggtaccctgtggccaatgctgcag
ctgtatctttggccaagggtgacctaccattccctagttatgcttaccaccaatttgaaagacgagccaaata
taaaagaCACTTCCCCGGCTTTGGCCAGAGCCTGCTGTTTGGCTACCCTGTGTACGTGTTCGGCGATTGCGTGC
AGGGCGATtgggatgcgattcgctttcgctattgcgcgccgccgggctatgcgctgctgcgctgcaacgatacc
aactatagcgctctgctggctgtggggggccctagaaggacccaggaatcaggccttgggtttggtgtcccaagaca
acttgtaactCGGATGCAGGCTATTCAGAATGCCGGCCTGTGTACCCTGGTGGCCATGCTGGAAGAGACAATCT
TCTGGCTGCAAgcgtttctgatggcgctgaccgatagcggccccgaaaaccaacattattgtggatagccagtat
gtgatgggcattagcaaaccgagctttcaggaatttgtggattgggaaaacgtgagcccggaactgaacagcac
cgatcagccgtttTGGCAAGCCGGAATCCTGGCCAGAAATCTGGTGCCTATGGTGGCCACAGTGCAGGGCCAGA
ACCTGAAGTACCAGggtcagtcactagtcatcctgcttctatcattgtcttcaacctgCtggaactggaaggt
gattatcgagatgatggcaacgtgtgggtgcataccccgctgagcccgcgcaccctgaacgcgtgggtgaaagc
ggtggaagaaaaaaagggtattccagttcacctagagctggccagtatgaccaacaTggagctcatgagcagta
ttgtgcatcagcaggtcAGAACATACGGCCCCGTGTTCATGTGCCTGGGCCGGACTGCTTACAATGGTGGCTGGT
GCTGTGTGGCTGACAGTGCgagtgctcgagctgttccggccgcgcagctggccaacgacgtggtcctccagat
catggagctttgtggtgcagcgtttcgccaggtgtgccataccaccgtgccgtggccgaacgcgagcctgaccc
cgaaatggaacaacgaaaccacccagcccagatcgccaactgcagcgtgtatgacttttttgtgtggctccat
tattattctgttcgagacacactttggccaagggtgacctaccatatgaacaaatatgcgtatcatatgctgga
aagacgagccaaatataaaagaGGACCAGGACCTGGCGTAAATTTGTGGCCGCCTGGACACTGAAAGCCGCTG
CTGGTCCTGGACCTGGCCAGTACATCAAGGCCAACAGCAAGTTCATCGGCATCACCGAACTCGGACCCGGACCA
GGCTGATGATTTCGAAATTTAAATAAGCTTGCGGCCGCTAGGGATAACAGGGTAATtatcacgcccaaacatttt
acagccgcggtgtcaaaaaccgcgtgg Ub7625merPDTT NoSFL polypeptide (SEQ ID NO: 37)
MQIFVKTLTGKTITLEVEPSDTIENVKAKIQDKEGIPPDQQRLIFAGKQLEDGRTLSDYNIQKESTLH
LVLRLRGAMFQALSEGCTPYDINQMLNVLGDHQFKHIKAFDRTFANNPGPMVVFATPGPILSPLTKGILGFVFT
LTVPSERGLSCISEADATTPESANLGEEILSQLYLWPRVTYHSPSYAYHQFERRAKYKRHFPGFGQSLLEGYPV
YVFGDCVQGDWDAIRFRYCAPPGYALLRCNDTNYSALLAVGALEGPRNQDWLGVPRQLVTRMQAIQNAGLCTLV
AMLEETIFWLQAFLMALTDSGPKTNIIVDSQYVMGISKPSFQEFVDWENVSPELNSTDPFWQAGILARNLVPM
VATVQGQNLKYQGQSLVISASIIVFNLLELEGDYRDDGNVWVHTPLSPRTLNAWVKAVEEKKGIPVHLELASMT
NMELMSSIVHQQVRTYGPVFMCLGGLLTMVAGAVWLTVRVLELFRAAQLANDVVLQIMELCGAAFRQVCHTTVP
WPNASLTPKWNNETTQPQIANCSVYDFFVWLHYYSVRDTLWPRVTYHMNKYAYHMLERRAKYKRGPGPGAKEVA
AWTLKAAAGPGPGQYIKANSKFIGITELGPGPG ChAdV68.5WTnt.MAG25mer (SEQ ID NO: 2); AC_000011.1 with E1 (nt 577 to
3403) and E3 (nt 27,125-31,825) sequences deleted; corresponding ATCC VR-
594 nucleotides substituted at five positions; model neoantigen cassette
under the control of the CMV promoter/enhancer inserted in place of
deleted E1; SV40 polyA 3' of cassette

```
CCATCTTCAATAATATACCTCAAACTTTTTGTGCGCGTTAATATGCAAATGAGGCGTTTGAATTTGGG
GAGGAAGGGCGGTGATTGGTCGAGGGATGAGCGACCGTTAGGGGCGGGGCGAGTGACGTTTTGATGACGTGGTT
GCGAGGAGGAGCCAGTTTGCAAGTTCTCGTGGGAAAAGTGACGTCAAACGAGGTGTGGTTTGAACACGGAAATA
CTCAATTTTCCCGCGCTCTCTGACAGGAAATGAGGTGTTTCTGGGCGGATGCAAGTGAAAACGGGCCATTTTCG
CGCGAAAACTGAATGAGGAAGTGAAAATCTGAGTAATTTCGCGTTTATGGCAGGGAGGAGTATTTGCCGAGGGC
CGAGTAGACTTTGACCGATTACGTGGGGGTTTCGATTACCGTGTTTTTCACCTAAATTTCCGCGTACGGTGTCA
AAGTCCGGTGTTTTTACGTAGGTGTCAGCTGATCGCCAGGGTATTTAAACCTGCGCTCTCCAGTCAAGAGGCCA
CTCTTGAGTGCCAGCGAGAAGAGTTTTCTCCTCCGCGCCGCGAGTCAGATCTACACTTTGAAAGTAGGGATAAC
AGGGTAATgacattgattattgactagttGttaaTAGTAATCAATTACGGGGTCATTAGTTCATAGCCCATATA
TGGAGTTCCGCGTTACATAACTTACGGTAAATGGCCCGCCTGGCTGACCGCCCAACGACCCCCGCCCATTGACG
TCAATAATGACGTATGTTCCCATAGTAACGCCAATAGGGACTTTCCATTGACGTCAATGGGTGGAGTATTTACG
GTAAACTGCCCACTTGGCAGTACATCAAGTGTATCATATGCCAAGTCCGCCCCCTATTGACGTCAATGACGGTA
AATGGCCCGCCTGGCATTATGCCCAGTACATGACCTTACGGGACTTTCCTACTTGGCAGTACATCTACGTATTA
GTCATCGCTATTACCATGgTGATGCGGTTTTGGCAGTACACCAATGGGCGTGGATAGCGGTTTGACTCACGGGG
ATTTCCAAGTCTCCACCCCATTGACGTCAATGGGAGTTTGTTTTGGCACCAAAATCAACGGGACTTTCCAAAAT
GTCGTAATAACCCCGCCCCGTTGACGCAAATGGGCGGTAGGCGTGTACGGTGGGAGGTCTATATAAGCAGAgcT
CGTTTAGTGAACCGTCAGATCGCCTGGAACGCCATCCACGCTGTTTTGACCTCCATAGAAGACAGCGATCGCGc
caccATGGCCGGGATGTTCCAGGCACTGTCCGAAGGCTGCACACCCTATGATATTAACCAGATGCTGAATGTCC
TGGGAGACCACCAGGTCTCTGGCCTGGAGCAGCTGGAGAGCATCATCAACTTCGAGAAGCTGACCGAGTGGACA
AGCTCCAATGTGATGCCTATCCTGTCCCCACTGACCAAGGGCATCCTGGGCTTCGTGTTTACCCTGACAGTGCC
TTCTGAGCGGGGCCTGTCTTGCATCAGCGAGGCAGACGCAACCACACCAGAGTCCGCCAATCTGGGCGAGGAGA
TCCTGTCTCAGCTGTACCTGTGGCCCGGGTGACATATCACTCCCCTTCTTACGCCTATCACCAGTTCGAGCGG
AGAGCCAAGTACAAGAGACACTTCCCAGGCTTTGGCCAGTCTCTGCTGTTCGGCTACCCCGTGTACGTGTTCGG
CGATTGCGTGCAGGGCGACTGGGATGCCATCCGGTTTAGATACTGCGCACCACCTGGATATGCACTGCTGAGGT
GTAACGACACCAATTATTCCGCCCTGCTGGCAGTGGGCGCCCTGGAGGGCCCTCGCAATCAGGATTGGCTGGGC
GTGCCAAGGCAGCTGGTGACACGCATGCAGGCCATCCAGAACGCAGGCCTGTGCACCCTGGTGGCAATGCTGGA
GGAGACAATCTTCTGGCTGCAGGCCTTTGTGATGGCCCTGACCGACAGCGGCCCGAAGACAAACATCATCGTGG
ATTCCCAGTACGTGATGGGCATCTCCAAGCCTTCTTTCCAGGAGTTTGTGGACTGGGAGAACGTGAGCCCAGAG
CTGAATTCCACCGATCAGCCATTCTGGCAGGCAGGAATCCTGGCAAGGAACCTGGTGCCTATGGTGGCCACAGT
GCAGGGCCAGAATCTGAAGTACCAGGGCCAGAGCCTGGTCATCAGCGCCTCCATCATCGTGTTTAACCTGCTGG
AGCTGGAGGGCGACTATCGGGACGATGGCAACGTGTGGGTGCAGACCCGACTGAGCCGGAGAACACTGAACGCC
TGGGTGAAGGCCGTGGAGGAGAAGAAGGGCATCCCAGTGCACCTGGAGCTGGCCTCCATGACCAATATGGAGCT
GATGTCTAGCATCGTGCACCAGCAGGTGAGGACATACGGACCCGTGTTCATGTGCCTGGGAGGCCTGCTGACCA
TGGTGGCAGGAGCCGTGTGGCTGACAGTGCGGGTGCTGGAGCTGTTCAGAGCCGCCCAGCTGGCCAACGATGTG
GTGCTGCAGATCATGGAGCTGTGCGGAGCAGCCTTTCGCCAGGTGTGCCACACCACAGTGCCATGGCCCAATGC
CTCCCTGACCCCCAAGTGGAACAATGAGACAACACAGCCTCAGATCGCCAACTGTAGCGTGTACGACTTCTTCG
TGTGGCTGCACTACTATAGCGTGAGGGATACCCTGTGGCCCCGCGTGACATACCACATGAATAAGTACGCCTAT
CACATGCTGGAGAGGCGCGCCAAGTATAAGAGAGCCCTGGCCCAGGCGCAAAGTTTGTGGCAGCATGGACCCT
GAAGGCCGCCGCCGGCCCCGGCCCCGGCCAGTATATCAAGGCTAACAGTAAGTTCATTGGAATCACAGAGCTGG
GACCCGGACCTGGATAATGAGTTTAAACTCCCATTTAAATGTGAGGGTTAATGCTTCGAGCAGACATGATAAGA
TACATTGATGAGTTTGGACAAACCACAACTAGAATGCAGTGAAAAAAATGCTTTATTTGTGAAATTTGTGATGC
TATTGCTTTATTTGTAACCATTATAAGCTGCAATAAACAAGTTAACAACAACAATTGCATTCATTTTATGTTTC
AGGTTCAGGGGGAGATGTGGGAGGTTTTTTAAAGCAAGTAAAAGCTCTACAAATGTGGTAAAATAACTATAACG
GTCCTAAGGTAGCGAGTGAGTAGTGTTCTGGGCGGGGAGGACCTGCATGAGGGCCAGAATAACTGAAATCTG
TGCTTTTCTGTGTGTTGCAGCAGCATGAGCGGAAGCGGCTCCTTTGAGGGAGGGGTATTCAGCCCTTATCTGAC
GGGCGTCTCCCCTCCTGGGCGGGAGTGCGTCAGAATGTGATGGGATCCACGGTGGACGGCCGGCCCGGCCGTGCAGC
CCGCGAACTCTTCAACCCTGACCTATGCAACCCTGAGCTCTTCGTCGTTGGACGCAGCTGCCGCCGCAGCTGCT
GCATCTGCCGCCAGCGCCGTGCGCGGAATGGCCATGGGCGCCGGCTACTACGGCACTCTGGTGGCCAACTCGAG
TTCCACCAATAATCCCGCCAGGCTGAACGAGGAGAAGCTGTTGCTGCTGATGGCCCAGTCGAGGCCTTGACCC
AGCGCCTGGGCGAGCTGACCCAGCAGGTGGCTCAGCTGCAGGAACAGACGCAGGCGGCTTGCCACGGTGAAA
TCCAAATAAAAAATGAATCAATAAATAAACGGAGACGGTTGTTGATTTTAACACAGAGTCTGAATCTTTATTTG
ATTTTTCGCGCGCGGTAGGCCCTGGACCACCGGTCTCGATCATTGAGCACCCGGTGGATCTTTTCCAGGACCCG
GTAGAGGTGGGCTTGGATGTTGAGGTACATGGGCATGAGCCCGTCCCGGGGTGGAGGTAGCTCCATTGCAGGG
CCTCGTGCTCGGGGGCTGGTGTTGTAAATCACCCAGTCATAGCAGGGGCGCAGGGCATGGTGTTGCACAATATCT
TTGAGGAGGAGACTGATGGCCACGGGCAGCCCTTTGGTGTAGGTGTTTACAAATCTGTTGAGCTGGGAGGGATG
CATGCGGGGGAGATGAGGTGCATCTTGGCCTGGATCTTGAGATTGGCGATGTTACCGCCCAGATCCCGCCTGG
GGTTCATGTTGTGCAGGACCACCAGCACGGTGTATCCGGTGCACTTGGGGAATTTATCATGCAACTTGGAAGGG
AAGGCGTGAAAGAATTTGGCGACGCCTTTGTGCCCGCCCAGGTTTTCCATGCACTCATCATGATGATGGCGAT
GGGCCCGTGGGCGGCGGCCTGGGAAAGACGTTTCGGGGGTCGGACACATCATAGTTGTGGTCTCGGTGAGGT
CATCATAGGCCATTTTAATGAATTTGGGGCGGAGGGTGCCGGACTGGGGACAAAGGTACCCTCGATCCCGGG
GCGTAGTTCCCCTCACAGATCTGCATCTCCCAGGCTTTGAGCTCGGAGGGGGGATCATGTCCACCTGCGGGGC
GATAAAGAACACGGTTTCCGGGGCGGGGAGATGAGCTGGGCCGAAAGCAAGTTCCGGAGCAGCTGGGACTTGC
CGCAGCCGGTGGGGCCGTAGATGACCCCGATGACCGGCTGCAGGTGGTAGTTGAGGGAGAAGACAGCTGCCGTCC
TCCCGGAGGAGGGGGCCACCTCGTTCATCATCTCGCGCACGTGCATGTTCTCGCGCACCAGTTCCGCCAGGAG
GCGCTCTCCCCCCAGGGATAGGAGCTCCTGGAGCAGGCGAAGTTTTTCAGCGGCTTGAGTCCGTCGGCCATGG
GCATTTTGGAGAGGGTTGTTGCAAGAGTTCCAGGCGGTCCCAGAGCTCGGTGATGCTCTACGGCATCTCGA
TCCAGCAGACCTCCTCGTTTCGCGGGTTGGGACGGCTGCGGGAGTAGGGCACCAGACGATGGGCGTCCAGCGCA
GCCAGGGTCCGGTCCTTCCAGGGTCGCAGCGTCCGCGTCAGGGTGGTCTCCGTCAGGGTGAGCGTGCGCGCC
GGGCTGGGCGCTTGCGAGGGTGCGCTTCAGGCTCATCCGGCTGGTCGAAAACCGCTCCCGATCGGCGCCCTGCG
CGTCGGCCAGGTAGCAATTGACCATGAGTTCGTAGTTGAGCGCCTCGGCCGCGTGGCCTTTGGCGCGGAGCTTA
CCTTTGGAAGTCTGCCCGCAGGCGGGACAGAGGAGGGACTGAGGGCGTAGAGCTTGGGGGCGAGGAAGACGGA
CTCGGGGGCGTAGGCGTCCGCGCCGCAGTGGGCGCAGACGGTCTCGCACTCCACGAGCCAGGTGAGGTCGGGCT
GGTCGGGGTCAAAAACCAGTTTCCCGCCGTTCTTTTTGATGCGTTTCTTACCTTTGGTCTCCATGAGCTCGTGT
CCCCGCTGGGTGACAAAGAGGCTGTCCGTGTCCCCGTAGACCGACTTTATGGGCCGGTCCTCGAGCGGTGTGCC
```

```
GCGGTCCTCCTCGTAGAGGAACCCCGCCCACTCCGAGACGAAAGCCCGGGTCCAGGCCAGCACGAAGGAGGCCA
CGTGGGACGGGTAGCGGTCGTTGTCCACCAGCGGGTCCACCTTTTCCAGGGTATGCAAACACATGTCCCCCTCG
TCCACATCCAGGAAGGTGATTGGCTTGTAAGTGTAGGCCACGTGACCGGGGGTCCCGGCCGGGGGGGTATAAAA
GGGTGCGGGTCCCTGCTCGTCCTCACTGTCTTCCGGATCGCTGTCCAGGAGCGCCAGCTGTTGGGGTAGGTATT
CCCTCTCGAAGGCGGGCATGACCTCGGCACTCAGGTTGTCAGTTTCTAGAAACGAGGAGGATTTGATATTGACG
GTGCCGGCGGAGATGCCTTTCAAGAGCCCCTCGTCCATCTGGTCAGAAAAGACGATCTTTTTGTTGTCGAGCTT
GGTGGCGAAGGAGCCGTAGAGGGCGTTGGAGAGGAGCTTGGCGATGGAGCGCATGGTCTGGTTTTTTTCCTTGT
CGGCGCGCTCCTTGGCGGCGATGTTGAGCTGCACGTACTCGCGCGCCACGCACTTCCATTCGGGGAAGACGGTG
GTCAGCTCGTCGGGCACGATTCTGACCTGCCAGCCCCGATTATGCAGGGTGATGAGGTCCACACTGGTGGCCAC
CTCGCCGCGCAGGGGCTCATTAGTCCAGCAGAGGCGTCCGCCCTTGCGCGAGCAGAAGGGGGGCAGGGGGTCCA
GCATGACCTCGTCGGGGGGTCGGCATCGATGGTGAAGATGCCGGGCAGGAGGTCGGGTCAAAGTAGCTGATG
GAAGTGGCCAGATCGTCCAGGGCAGCTTGCCATTCGCGCACGGCCAGCGCGCGCTCGTAGGGACTGAGGGGCGT
GCCCCAGGGCATGGGATGGGTAAGCGCGGAGGCGTACATGCCGCAGATGTCGTAGACGTAGAGGGGCTCCTCGA
GGATGCCGATGTAGGTGGGGTAGCAGCGCCCCCCGCGGATGCTGGCGCGCACGTAGTCATACAGCTCGTGCGAG
GGGGCGAGGAGCCCCGGGCCCAGGTTGGTGCGACTGGGCTTTTCGGCGCGGTAGACGATCTGGCGGAAAATGGC
ATGCGAGTTGGAGGAGATGGTGGGCCTTTGGAAGATGTTGAAGTGGGCGTGGGGCAGTCCGACCGAGTCGCGGA
TGAAGTGGGCGTAGGAGTCTTGCAGCTTGGCGACGAGCTCGGCGGTGACTAGGACGTCCAGAGCGCAGTAGTCG
AGGGTCTCCTGGATGATGTCATACTTGAGCTGTCCCTTTTGTTTCCACAGCTCGCGGTTGAGAAGGAACTCTTC
GCGGTCCTTCCAGTACTCTTCGAGGGGGAACCCGTCCTGATCTGCACGGTAAGAGCCTAGCATGTAGAACTGGT
TGACGGCCTTGTAGGCGCAGCAGCCCTTCTCCACGGGGAGGGGTAGGCCTGGGCGGCCTTGCGCAGGGAGGTG
TGCGTGAGGGCGAAAGTGTCCCTGACCATGACCTTGAGGAACTGGTGCTTGAAGTCGATATCGTCGCAGCCCCC
CTGCTCCCAGAAGCTGGAAGTCCGTGCGCTTCTTGTAGGCGGGGTTGGGCAAAGCGAAAGTAACATCGTTGAAGA
GGATCTTGCCCGCGCGGGGCATAAAGTTGCGAGTGATGCGGAAAGGTTGGGGCACCTCGGCCCGGTTGTTGATG
ACCTGGGCGGCGAGCACGATCTCGTCGAAGCCGTTGATGTTGTGGCCCACGATGTAGAGTTCCACGAATCGCGG
ACGGCCCTTGACGTGGGGCAGTTTCTTGAGCTCCTCGTAGGTGAGCTCGTCGGGGTCGCTGAGCCCGTGCTGCT
CGAGCGCCCAGTCGGCGAGATGGGGGTTGGCGCGGAGGAAGGAAGTCCAGAGATCCACGGCCAGGCGGTTTGC
AGACGGTCCCGGTACTGACGGAACTGCTGCCCGACGGCCATTTTTTCGGGGGTGACGCAGTAGAAGGTGCGGGG
GTCCCCGTGCCAGCGATCCCATTTGAGCTGGAGGGCGAGATCGAGGGCGAGCTCGACGAGCCGGTCGTCCCCGG
AGAGTTTGATGACCAGCATGAAGGGGACGAGCTGCTTGCCGAAGGACCCCATCCAGGTGTAGGTTTCCACATCG
TAGGTGAGGAAGAGCCTTTCGGTGCGAGGATGCGAGCCGATGGGAAGAACTGGATCTCCTGCCACCAATTGGA
GGAATGGCTGTTGATGTGATGGAAGTAGAAATGCCGACGGCGCGCCGAACACTCGTGCTTGTGTTTATACAAGC
GGCCACAGTGCTCGCAACGCTGCACGGGATGCACGTGCTGCACGAGCTGTACCTGAGTTCCTTTGACGAGGAAT
TTCAGTGGGAAGTGGAGTCGTGGCGCCTGCATCTCGTGCTGTACTACGTCGTGGTGGTCGGCCTGGCCCTCTTC
TGCCTCGATGGTGGTCATGCTGACGAGGCCGCGCGGGAGGCAGGTCCAGACCTCGGCGCGAGCGGGTCGGAGAG
CGAGGACGAGGGCGCGCAGGCCGGAGCTGTCCAGGGTCCTGAGACGCTGCGAGTCAGGTCAGTGGGCAGCGGC
GGCGCGCGGTTGACTTGCAGGAGTTTTTCCAGGGCGCGGGGGAGGTCGAGATGGTACTTGATCTCCACCGCGGC
ATTGGTGGCGACGTCGATGGCTTGCAGGGTCCCGTGCCCCTGGGGTGTGACCACCGTCCCCCGTTTCTTCTTGG
GCGGCTGGGGCGACGGGGCGGTGCCTCTTCCATGGTTAGAAGGGGCGGCGAGGACGCGCGCGGGCGGCAGGG
GCGGCTCGGGGCCCGGAGGCAGGGCGGCAGGGGCACGTCGGCGCCGCGCGCGGGTAGGTTCTGGTACTGCGCC
CGGAGAAGACTGGCGTGAGCGACGACGCGACGGTTGACGTCCTGGATCTGACGCCTCTGGGTGAAGGCCACGGG
ACCCGTGAGTTTGAACCTGAAAGAGAGTTCGACAGAATCAATCTCGGTATCGTTGACGGCGGCCTGCCGCAGGA
TCTCTTGCACGTCGCCCGAGTTGTCCTGGTAGGCGATCTCGGTCATGAACTGCTCGATCTCCTCCTCTTGAAGG
TCTCCGCGGCCGGCGCGCTCCACGGTGGCCGCGAGGTCGTTGGAGATGCGGCCCATGAGCTGCGAGAAGGCGTT
CATGCCCGCCTCGTTCCAGACGCGGCTGTAGACCACGACGCCCTCGGGATCGCgGGCGCGCATGACCACCTGGG
CGAGGTTGAGCTCCACGTGGCGCGTGAAGACCGCGTAGTTGCAGAGGCGCTGGTAGAGGTAGTTGAGCGTGGTG
GCGATGTGCTCGGTGACGAAGAAATACATGATCCAGCGGCGGAGCGGCATCTCGCTGACGTCGCCCAGCGCCTC
CAAACGTTCCATGGCCTCGTAAAAGTCCACGGCGAAGTTGAAAACTGGGAGTTGCGCGCCGAGACGGTCAACT
CCTCCTCCAGAAGACGGATGAGCTCGGCGATGGTGGCGCGACACCTCGCGCTCGAAGGCCCCCGGGAGTTCCTCC
ACTTCCTCTTCTTCCTCCTCCACTAACATCTCTTCTACTTCCTCCTCAGGCGGCAGTGGTGGCGGGGAGGGGG
CCTGCGTCGCCGGCGGCGCACGGGCAGACGGTCGATGAAGCGCTCGATGGTCTCGCCGCGCCGGCGTCGCATGG
TCTCGGTGACGGCGCGCCCGTCCTCGCGGGGCCGCAGCGTGAAGACGCCGCGCGCATCTCCAGGTGGCCAGGG
GGGTCCCCGTTGGGCAGGGAGAGGGCGCTGACGATGCATCTTATCAATTGCCCCGTAGGGACTCCGCGCAAGGA
CCTGAGCGTCTCGAGATCCACGGGATCTGAAAACCGCTGAACGAAGGCTTCGAGCCAGTCGCAGTCGCAAGGTA
GGCTGAGCACGGTTTCTTCGGCGGGTCATGTTGGTTGGGAGCGGGCGGGCGATGCTGCTGGTGATGAAGTTG
AAATAGGCGGTTCTGAGACGGCGGATGGTGCGAGGAGCACCAGGTCTTTGGGCCCGGCTTGCTGGATGCGCAG
ACGGTCGGCCATGCCCCAGGCGTGGTCCTGAGACCTGGCCAGGTCCTTGTAGTAGTCCTGCATGAGCCGCTCCA
CGGGCACCTCCTCCTCGCCCGCGCGGCCGTGCATGCGCGTGAGCCCGAAGCCGCGCTGGGGCTGGACGAGCGCC
AGGTCGGCGACGACGCGCTCGGCGAGGATGGCTTGCTGGATCTGGGTGAGGGTGGTCTGGAAGTCATCAAAGTC
GACGAAGCGGTGGTAGGCTCCGGTGTTGATGGTGTAGGAGCAGTTGGCCATGACGGACCAGTTGACGGTCTGGT
GGCCCGGACGCACGAGCTCGTGGTACTTGAGGCGCGAGTAGGCGCGCGTGTCGAAGATGTAGTCGTTGCAGGTG
CGCACCAGGTACTGGTAGCCGATGAGGAAGTGCGGCGGCGGCTGGCGGTAGAGGGGCCATCGCTCGGTGGCGGG
GGCGCCGGGCGCGAGGTCCTCGAGCATGGTGCGGTGGTAGCCGTAGATGTACCTGGACATCCAGGTGATGCCGG
CGGCGGTGGTGGAGGCGCGCGGGAACTCGCGGACGCGGTTCCAGATGTTGCGCAGCGGCAGGAAGTAGTTCATG
GTGGGCACGGTCTGGCCCGTGAGGCGCGCAGTCGTGGATGCTCTATACGGGCAAAAACGAAAGCGGTCAGCG
GCTCGACTCCGTGGCCTGGAGGCTAAGCGAACGGGTTGGGCTGCGCGTACCCCGGTTCGAATCTGAATCAG
GCTGGAGCCGCAGCTAACGTGGTATTGGCACTCCCGTCTCGACCCAAGCCTGCACGAACCCTCCAGGATACGGA
GGCGGGTCGTTTTGCAACTTTTTTTGGAGGCCGGATGAGACTAGTAAGCGCGGAAAGCGGCCGACCGCGATGG
CTCGCTGCCGTAGTCTGGAGAAGAATCGCCAGGGTTGCGTTGCGGTTGCCCGGTTCGAGGCCGGCCGGATTC
CGCGGCTAACGAGGGCGTGGCTGCCCCGTCGTTTCCAAGACCCCATAGCCAGCCGACTTCTCCAGTTACGGAGC
GAGCCCCTCTTTTGTTTTGTTTGTTTTTGCCAGATGCATCCCGTACTGCGGCAGATGCGCCCCCACCACCCTCC
ACCGCAACAACAGCCCCTCCACAGCCGGCGCTTCTGCCCCCGCCCAGCAGCAACTTCCAGCCACGACCGCCG
CGGCCGCCGTGAGCGGGCTGGACAGAGTTATGATCACCAGCTGGCCTTGGAAGAGGGCGAGGGCTGGCGCGC
CTGGGGGCGTCGTCGCCGGAGCGGCACCCGCGCGTGCAGATGAAAAGGGAGCGCTCGCGAGGCCTACGTGCCAA
GCAGAACCTGTTCAGAGACAGGAGCGGCGAGGAGCCGAGGAGATGCGCGCGCCCGGTTCCACGCGGGCGGG
AGCTGCGGCGCGGCCTGGACCGAAAGAGGGTGCTGAGGGACGAGGATTTCGAGGCGGACGAGCTGACGGGGATC
AGCCCCGCGCGCGCACGTGGCCGCGGCCAACCTGGTCACGGCGTACGAGCAGACCGTGAAGGAGGAGAGCAA
CTTCCAAAAATCCTTCAACAACCACGTGCGCACCCTGATCGCGCGCGAGGAGGTGACCCTGGGCCTGATGCACC
TGTGGGACCTGCTGGAGGCCATCGTGGAGAACCCCACCAGCAAGCGCTGACGGCGCAGCTGTTCCTGGTGTG
CAGCATAGTCGGGACAACGAAGCGTTCAGGGAGGCGCTGCTGAATATCACCGAGCCCGAGGGCCGCTGGCTCCT
```

```
GGACCTGGTGAACATTCTGCAGAGCATCGTGGTGCAGGAGCGCGGGCTGCCGCTGTCCGAGAAGCTGGCGGCCA
TCAACTTCTCGGTGCTGAGTTTGGGCAAGTACTACGCTAGGAAGATCTACAAGACCCCGTACGTGCCCATAGAC
AAGGAGGTGAAGATCGACGGGTTTTACATGCGCATGACCCTGAAAGTGCTGACCCTGAGCGACGATCTGGGGGT
GTACCGCAACGACAGGATGCACCGTGCGGTGAGCGCCAGCAGGCGGCGCGAGCTGAGCGACCAGGAGCTGATGC
ATAGTCTGCAGCGGGCCCTGACCGGGGCCGGGACCGAGGGGGAGAGCTACTTTGACATGGGCGCGGACCTGCAC
TGGCAGCCCAGCCGCCGGGCGTTGGAGGCGGCGGCAGGACCCTACGTAGAAGAGGTGGACGATGAGGTGGACGA
GGAGGGCGAGTACCTGGAAGACTGATGGCGCGACCGTATTTTTGCTAGATGCAACAACAACAGCCACCTCCTGA
TCCCGCGATGCGGGCGGCGCTGCAGAGCCAGCCGTCCGGCATTAACTCCTCGGACGATTGGACCCAGGCCATGC
AACGCATCATGGCGCTGACGACCCGCAACCCCGAAGCCTTTAGACAGCAGCCCCAGGCCAACCGGCTCTCGGCC
ATCCTGGAGGCCGTGGTGCCCTCGCGCTCCAACCCCACGCACGAGAAGGTCCTGGCCATCGTGAACGCGCTGGT
GGAGAACAAGGCCATCCGCGGCGACGAGGCCGGCCTGGTGTACAACGCGCTGCTGGAGCGCGTGGCCCGCTACA
ACAGCACCAACGTGCAGACCAACCTGGACCGCATGGTGACCGACGTGCGCGAGGCCGTGGCCCAGCGCGAGCGG
TTCCACCGCGAGTCCAACCTGGGATCCATGGTGGCGCTGAACGCCTTCCTCAGCACCCCAGCCGCCAACGTGCC
CCGGGGCCAGGAGGACTACACCAACTTCATCAGCGCCCTGCGCCTGATGGTGACCGAGGTGCCCCAGAGCGAGG
TGTACCAGTCCGGGCCGGACTACTTCTTCCAGACCAGTCGCCAGGGCTTGCAGACCGTGAACCTGAGCCAGGCT
TTCAAGAACTTGCAGGGCCTGTGGGCGTGCAGGCCCCGGTCGGGACCGCGCGACGGTGTCGAGCCTGCTGAC
GCCGAACTCGCGCCTGCTGCTGCTGCTGGTGGCCCCCTTCACGGACAGCGGCAGCATCAACCGCAACTCGTACC
TGGGCTACCTGATTAACTCGTACCGCGAGGCCATCGGGGAGGCGCACGTGGACGAGCAGCATCTACCAGGAGATC
ACCCACGTGAGCCGCGCCCTGGGCAGGACGACCCGGGCAACCTGGAAGCCACCCTGAACTTTTTGCTGACCAA
CCGGTCGCAGAAGATCCCGCCCCAGTACGCGCTGAGCACCGAGGAGGAGCGGATCCTGCGTTACGTGCAGCAGA
GCGTGGGCCTGTTCCTGATGCAGGAGGGGGCCACCCCCAGCGCCGCGCTCGACATGACCGCGCGCAACATGGAG
CCCAGCATGTACGCCAGCAACCGCCCGTTCATCAATAAACTGATGGACTACTTGCATCGGGCGGCCGCCATGAA
CTCTGACTATTTCACCAACGCCATCCTGAATCCCCACTGGCTCCCGCGCCGGGGTTCTACACGGGCGAGTACG
ACATGCCCGACCCCAATGACGGGTTCCTGTGGGACGATGTGGACAGCAGCGTGTTCTCCCCCGACCGGGTGCT
AACGAGCGCCCCTTGTGGAAGAAGGAAGGCAGCGACGGACGCCCGTCCTCGGCGCTGTCCGGCCGCGAGGGTGC
TGCCGCGGCGGTGCCCGAGGCCGCCAGTCCTTTCCCGAGCTTGCCCTTCTCGCTGAACAGTATCCGCAGCAGGG
AGCTGGGCAGGATCACGCGCCCGCGCTTGCTGGGCGAAGAGGAGTACTTGAATGACTCGCTGTTGAGACCCGAG
CGGGAGAAGAACTTCCCCAATAACGGGATAGAAAGCTGGTGGACAAGATGAGCCGCTGGAAGACGTATGCGCA
GGAGCACAGGGACGATCCCCGGGCGTCGCAGGGGGCCACGAGCCGGGCAGCGCCGCCCGTAAACGCCGGTGGC
ACGACAGGCAGCGGGGACAGATGTGGGACGATGAGGACTCCGCCGACGACAGCGCGTGTTGGACTTGGGTGGG
AGTGGTAACCCGTTCGCTCACCTGCGCCCCCGTATCGGGCGCATGATGTAAGAGAAACCGAAAATAAATGATAC
TCACCAAGGCCATGGCGACCAGCGTGCGTTCGTTTCTTCTGTTGTTGTTGTATCTAGTATGATGAGGCGTGC
GTACCCGGAGGGTCCTCCTCCCTCGTACGAGAGCGTGATGCAGCAGGCGATGGCGGCGGCGGCGATGCAGCCCC
CGCTGGAGGCTCCTTACGTGCCCCCGCGGTACCTGGCGCCTACGGAGGGGCGGAACAGCATTCGTTACTCGGAG
CTGGCACCCTTGTACGATACCACCCGGTTGTACCTGGTGGACAACAAGTCGGCGGACATCGCCTCGCTGAACTA
CCAGAACGACCACAGCAACTTCCTGACCACCGTGGTGCAGAACAATGACTTCACCCCCACGGAGGCCAGCACCC
AGACCATCAACTTTGACGAGCGCTCGCGGTGGGGCGGCCAGCTGAAAACCATCATGCACACCAACATGCCCAAC
GTGAACGAGTTCATGTACGACAGCAACAAGTTCAAGGCGCGGGTGATGGTCTCCCGCAAGACCCCCAATGGGGTGAC
AGTGACAGAGGATTATGATGGTAGTCAGGATGAGCTGAAGTATGAATGGGTGGAATTTGAGCTGCCCGAAGGCA
ACTTCTCGGTGACCATGACCATCGACCTGATGAACAACGCCATGATCGACAATTACTTGGCGGTGGGGCGGCAG
AACGGGGTGCTGGAGAGCGACATCGGCGTGAAGTTCGACACTAGGAACTTCAGGCTGGGCTGGGACCCCGTGAC
CGAGCTGGTCATGCCCGGGGTGTACACCAACGAGGCTTTCCATCCCGATATTGTCTTGCTGCCCGGCTGCGGGG
TGGACTTCACCGAGAGCCGCCTCAGCAACCTGCTGGGCATTCGCAAGAGGCAGCCCTTCCAGGAAGGCTTCCAG
ATCATGTACGAGGATCTGGAGGGGGCAACATCCCCGCGCTCCTGGATGTCGACGCCTATGAGAAAAGCAAGGA
GGATGCAGCAGCTGAAGCAACTGCAGCCGTAGCTACCGCCTCTACCGAGGTCAGGGGCGATAATTTTGCAAGCG
CCGCAGCAGTGGCAGCGGCCGAGGCGGCTGAAACCGAAAGTAAGATAGTCATTCAGCCGGTGGAGAAGGATAGC
AAGAACAGGAGCTACAACGTACTACCGGACAAGATAAACACCCGCTACCGCAGCTGGTACCTAGCCTACAACTA
TGGCGACCCCGAGAAGGGCGTGCGCTCCTGGACGCTGCTCACCACCTCGGACGTCACCTGCGGCGTGGAGCAAG
TCTACTGGTCGCTGCCCGACATGATGCAAGACCCGGTCACCTTCCGCTCCACGCGTCAAGTTAGCAACTACCCG
GTGGTGGGCGCCGAGCTCCTGCCCGTCTACTCCAAGAGCTTCTTCAACGAGCAGGCCGTCTACTCGCAGCAGCT
GCGCGCCTTCACCTCGCTTACGCACGTCTTCAACCGCTTCCCCGAGAACCAGATCCTCGTCCGCCCGCCGCC
CCACCATTACCACCGTCAGTGAAAACGTTCCTGCTCTCACAGATCACGGACCCTGCCGCTGCGCAGCAGTATC
CGGGGAGTCCAGCGCGTGACCGTTACTGACGCCAGACGCCGCACCTGCCCCTACGTCTACAAGGCCCTGGGCAT
AGTCGCGCCGCGCGTCCTCTCGAGCCGCACCTTCTAAATGTCCATTCTCATGTCGCCCAGTAATAACACCGGTT
GGGGCCTGCGCGGCGCCCAGCAAGATGTACGGAGGCGCTCGCCAACGCTCCACGCAACACCCCGTGCGCGTGCGC
GGGCACTTCCGCGCTCCCTGGGGCGCCCTCAAGGGCCGCGTGCGGTCGCGCACCACCGTCGACGACGTGATCGA
CCAGGTGGTGGCCGACGCGCGCAACTACACCCCCGCCGCCGCCCGTCTCCACCGTGGACGCGGTCATCGACA
GCGTGGTGGCcGACGCGCGCCGGTACGCCCGCGCCAAGAGCCGGCGGCGGCGCATCGCCCGGCGGCACCGGAGC
ACCCCCGCCATGCGCGCGGCCGGAGCCTTGCTGCGCAGGGCCAGGCCACGGGACGCAGGGCCATGCTCAGGCC
GGCCAGACGCGCGGCTTCAGGCGCCAGCGCCGGCAGGACCCGGAGACGCGGCCACGGCGGCGCAGCAGGCCA
TCGCCAGCATGTCCCGCCCGCGGCGAGGGAACGTGTACTGGGTGCGCGACGCCGCCACCGGTGTGCGCGTGCCC
GTGCGCACCCGCCCCCCTCGCACTTGAAGATGTTCACTTCGCGATGTTGATGTGTCCCAGCGGCGAGGAGGATG
TCCAAGCGCAAATTCAAGGAAGAGATGTCCAGGTCATCGCGCTGAGATCTACGGCCCTGCGGTGGTGAAGGA
GGAAAGAAAGCCCCGCAAAATCAAGCGGGTCAAAAAGGACAAAAAGGAAGAAGAAAGTGATGTGGACGGATTGG
TGGAGTTTGTGCGCGAGTTCGCCCCCCGGCGGCGCGTGCAGTGGCGCGGGCGGAAGGTGCAACCGGTGCTGAGA
CCCGGCACCACCGTGGTCTTCACGCCCGGCGAGCGCTCCGGCACCGCTTCCAAGCGCTCCTACGACGAGGTGTA
CGGGGATGATGATATTCTGGAGCAGGCGGCCGAGCGCCTGGGCGAGTTTGCTTACGCAAGCGCAGCCGTTCCG
CACCGAAGGAAGAGGCGGTGTCCATCCGCTGGACCACGGCAACCCCACGCCGAGCCTCAAGCCCGTGACCTTG
CAGCAGGTGCTGCCGACCGCGGCGCCGCGCGGGGTTCAAGCGCGAGGGCGAGGATCTGTACCCCACCATGCA
GCTGATGGTGCCCAAGCGCCAGAAGCTGGAAGACGTGCTGGAGACCATGAAGGTGGACCCGGACGTGCAGCCCG
AGGTCAAGGTGCGGCCCATCAAGCAGGTGGCCCCGGGCCTGGGCGTGCAGACCGTGGACATCAAGATTCCCACG
GAGCCCATGGAAACGCAGACCGAGCCCATGATCAAGCCCAGCACCAGCACCATGGAGGTGCAGACGGATCCCTG
GATGCCATCGGCTCCTAGTCGAAGACCCCGGCGCAAGTACGGCGCGGCCAGCTGCTGATGCCCAACTACGCGC
TGCATCCTTCCATCATCCCCACGCCGGGCTACCGGCACGCGCTTCTACCGCGGTCATACCAGCAGCCGCCGC
CGCAAGACCACCACTCGCCGCCGCCGTCGCCGCACCGCCGCTGCAACGACCCCTGCCGCCCTGGTGCGGAGAGT
GTACCGCCGCGGCCGCGCACCTCTGACCCTGCCGCGCGCGCGCTACCACCCGAGCATCGCCATTTAAACTTTCG
CCtGCTTTGCAGATCAATGGCCCTCACATGCCGCCTTCGCGTTCCGATTACGGGCTACCGAGGAAGAAAACCGC
GCCGTAGAAGGCTGGCGGGGAACGGGATGCGTCGCCACCACCACCGGCGGCGGCGCGCCATCAGCAAGCGGTTG
GGGGAGGCTTCCTGCCCGCGCTGATCCCCATCATCGGGGCGGCGATGGGGGCGATCCCCGGCATTGCTTCCGT
```

-continued

```
GGCGGTGCAGGCCTCTCAGCGCCACTGAGACACACTTGGAAACATCTTGTAATAAACCAATGGACTCTGACGCT
CCTGGTCCTGTGATGTGTTTTCGTAGACAGATGGAAGACATGAATTTTTCGTCCCTGGCTCCGCGACACGGCAC
GCGGCCGTTCATGGGCACCTGGAGCGACATCGGCACCAGCCAACTGAACGGGGGCGCCTTCAATTGGAGCAGTC
TCTGGAGCGGGCTTAAGAATTTCGGGTCCACGCTTAAAACCTATGGCAGCAAGGCGTGGAACAGCACCACAGGG
CAGGCGCTGAGGGATAAGCTGAAAGAGGAGAACTTCCAGCAGAAGGTGGTCGATGGGCTCGCCTCGGGCATCAA
CGGGGTGGTGGACCTGGCCAACCAGGCCGTGCAGCGGCAGATCAACAGCCGCCTGGACCCGGTGCCGCCCGCCG
GCTCCGTGGAGATGCCGCAGGTGGAGGAGGAGCTGCCTCCCCTGGACAAGCGGGGCGAGAAGCGACCCCGCCCC
GATGCGGAGGAGACGCTGCTGACGCACACGGACGAGCCGCCCCCGTACGAGGAGGCGGTGAAACTGGGTCTGCC
CACCACGCGGCCCCATCGCGCCCCTGGCCACCGGGGTGCTGAAACCCGAAAAGCCCGCGACCCTGGACTTGCCTC
CTCCCCAGCCTTCCCGCCCCTCTACAGTGGCTAAGCCCCTGCCGCCGGTGGCCGTGGCCCGCGCGCGACCCGGG
GGCACCGCCCGCCCTCATGCGAACTGGCAGAGCACTCTGAACAGCATCGTGGGTCTGGGAGTGCAGAGTGTGAA
GCGCCGCCGCTGCTATTAAACCTACCGTAGCGCTTAACTTGCTTGTCTGTGTGTATGTATTATGTCGCCGCC
GCCGCTGTCCACCAGAAGGAGGAGTGAAGAGGCGCGTCGCCGAGTTGCAAGATGGCCACCCCATCGATGCTGCC
CCAGTGGGCGTACATGCAGATCGCCGACAGGACGCTCGGAGTACCTGAGTCCGGGTCTGGTGCAGTTTGCCC
GCGCCACAGACACCTACTTCAGTCTGGGGAACAAGTTTAGGAACCCGACGGTGGCGCCCACGCACGATGTGACC
ACCGACCGCAGCCAGCGGCTGACGCTGCGCTTCGTGCCCGTGGACCGCGAGGACAACACCTACTCGTACAAAGT
GCGCTACACGCTGGCCGTGGGCGACAACCGCGTGCTGGACATGGCCAGCACCTACTTTGACATCCGCGGCGTGC
TGGATCGGGGCCCTAGCTTCAAACCCTACTCCGGCACCGCCTACAACAGTCTGGCCCCCAAGGGAGCACCCAAC
ACTTGTCAGTGGACATATAAAGCCGATGGTGAAACTGCCACAGAAAAAACCTATACATATGGAAATGCACCCGT
GCAGGGCATTAACATCACAAAAGATGGTATTCAACTTGGAACTGACACCGATGATCAGCGAATCTACGCAGATA
AAACCTATCAGCCTGAACCTCAAGTGGGTGATGCTGAATGGCATGACATCACTGGTACTGATGAAAAGTATGGA
GGCAGAGCTCTTAAGCCTGATACCAAAATGAAGCCTTGTTATGGTTCTTTTGCCAAGCCTACTAATAAAGAAGG
AGGTCAGGCAAATGTGAAAACAGGAACAGGCACTACTAAAGAATATGACATAGACATGGGTTTCTTTGACAACA
GAAGTGCGGCTGCTGCTGGCCTAGCTCCAGAAATTGTTTTGTATACTGAAATGTGGATTTGGAAACTCCAGAT
ACCCATATTGTATACAAAGCAGGCACAGATGACAGCAGCTCTTCTATTAATTTGGGTCAGCAAGCCATGCCCAA
CAGACCTAACTACATTGGTTTCAGAGACAACCTTTATCGGGCTCATGTACTCAACAGCACTGGCAATATGGGGG
TGCTGGCCGGTCAGGCTTCTCAGCTGAATGCTGTGGTTGACTTGCAAGACAGAAACACCGAGCTGTCCTACCAG
CTCTTGCTTGACTCTCTGGGTGACAGAACCCGGTATTTCAGTATGTGGAATCAGGCGGTGGACAGCTATGATCC
TGATGTGCGCATTATTGAAAATCATGGTGTGGAGGATGAACTTCCCAACTATTGTTTCCCTCTGGATGCTGTTG
GCAGAACAGATACTTATCAGGGAATTAAGGCTAATGGAACTGATCAAACCACATGGACCAAAGATGACAGTGTC
AATGATGCTAATGAGATAGGCAAGGGTAATCCATTCGCCATGGAAATCAACATCCAAGCCAACCTGTGGAGGAA
CTTCCTCTACGCCAACGTGGCCCTGTACCTGCCCGACTCTTACAAGTACACGCCGGCCAATGTTACCCTGCCCA
CCAACACCAACACCTACGATTACATGAACGGCCGGGTGGTGGCGCCCTCGCTGGTGGACTCCTACATCAACATC
GGGGCGCGTGGTCGCTGGATCCCATGGACAACGTGAACCCCTTCAACCACCACCGCAATGCGGGGCTGCGCTA
CCGCTCCATGCTCCTGGGCAACGGGCGCTACGTGCCCTTCCACATCCAGGTGCCCCAGAAATTTTTCGCCATCA
AGAGCCTCCTGCTCCTGCGCGGGTCCTACACCTACGAGTGGAACTTCCGCAAGGACGTCAACATGATCCTGCAG
AGCTCCCTCGGCAACGACCTGCGCACGCACGGGGCCTCCATCTCCTTCACCAGCATCAACCTCTACGCCACCTT
CTTCCCCATGGCGCACAACACGGCCTCCACGCTCGAGGCCATGCTGCGCAACGACAACGACCAGTCCTTCA
ACGACTACCTCTCGGCGGCCAACATGCTCTACCCCATCCCGGCCAACGCCACCAAGGTGCCCATCTCCATCCCC
TCGCGGAACTGGGGCGCCTTCCGCGGCTGGTCCTTCACGCGTCTCAAGACCAAGGAGACGCCCTCGCTGGGCTC
CGGGTTCGACCCCTACTTCGTCTACTCGGGCTCCATCCCCTACCTCGACGGCACCTTCTACCTCAACCACACCT
TCAAGAAGGTCTCCATCACCTTCGACTCCTCCGTCAGCTGGCCCGGCAACGACGGCTCCTGACGCCCAACGAG
TTCGAAATCAAGCGCACCGTCGACGGCGAGGGCTACAACGTGGCCCAGTGCAACATGACCAAGGACTGGTTCCT
GGTCCAGATGCTGGCCCACTACAACATCGGCTACCAGGGCTTCTACGTGCCCGAGGGCTACAAGGACCGCATGT
ACTCCTTCTTCCGCAACTTCCAGCCCATGAGCCGCCAGGTGGTGGACGAGGTCAACTACAAGGACTACCAGGCC
GTCACCCTGGCCTACCAGCACAACAACTCGGGCTTCGTCGGCTACCTCGCGCCCACCATGCGCCAGGGCCAGCC
CTACCCCGCCAACTACCCCTACCCGCTCATCGGCAAGAGCGCCGTCACCAGCGTCACCCAGAAAAAGTTCCTCT
GCGACAGGGTCATGTGGCGCATCCCCTTCTCCAGCAACTTCATGTCCATGGGCGCGCTCACCGACCTCGGCCAG
AACATGCTCTATGCCAACTCCGCCCACGCGCTAGACATGAATTTCGAAGTCGACCCCATGGATGAGTCCACCCT
TCTCTATGTTGTCTTCGAAGTCTTCGACGTCGTCCGAGTGCACCAGCCCCACCGGGCGTCATCGAGGCCGTCT
ACCTGCGCACCCCTTCTCGGCCGGTAACGCCACCACCTAAGCTCTTGCTTCTTGCAAGCCATGGCCGCGGGCT
CCGGCGAGCAGGAGCTCAGGGCCATCATCCGCGACCTGGGCTGCGGGCCCTACTTCCTGGGCACCTTCGATAAG
CGCTTCCCGGGATTCATGGCCCCGCACAAGCTGGCCTGCGCCATCGTCAACACGGCCGGCCGCGAGACCGGGG
CGAGCACTGGCTGGCCTTCGCCTGGAACCCGCGCTCGAACACCTGCTACCTCTTCGACCCCTTCGGGTTCTCGG
ACGAGCGCCTCAAGCAGATCTACCAGTTCGAGTACGAGGGCCTGCTGCGCCGCAGCCTGGCCACCGAGGAC
CGCTGCGTCACCCTGGAAAAGTCCACCCAGACCGTGCAGGGTCCGCGCTCGGCCGCCTGCGGGCTCTTCTGCTG
CATGTTCCTGCACGCCTTCGTGCACTGGCCCGACCGCCCCATGGACAAGAACCCCACCATGAACTTGCTGACGG
GGGTGCCCAACGGCATGCTCCAGTCGCCCCAGGTGGAACCCACCCTGCGCCGCAACCAGGAGGCGCTCTACCGC
TTCCTCAACTCCCACTCGGCCTACTTTCGCTCCCACCGCGCGCATCGGAGAAGGGCACCGCCTTCGACCGCAT
GAATCAAGACATGTAAACCGTGTGTGTATGTTAAATGTCTTTAATAAACAGCACTTTCATGTTACACATGCATC
TGAGATGATTTATTTAGAAATCGAAAGGGTTCTGCCGGGTCTCGGCATGGCCCGCGGGCAGGACACGTTGCGG
AACTGGTACTTGGCCAGCCACTTGAACTCGGGGATCAGCAGTTTGGGCAGCGGGGTGTCGGGGAAGGAGTCGGT
CCACAGCTTCCGCGTCAGTTGCAGGGCGCCCAGCAGGTCGGGCGCGGAGATCTTGAAATCGCAGTTGGGACCCG
CGTTCTGCGCGCGGGAGTTGCGGTACACGGGGTTGCAGCACTGGAACACCATCAGGGCCGGGTGCTTCACGCTC
GCCAGCACCGTCGCGTCGGTGATGCTCTCCACGTCGAGGTCCTCGGCGTTGGCCATCCCGAAGGGGGTCATCTT
GCAGGTCTGCCTTCCCATGGTGGGCACGCACCCGGGCTTGTGGTTGCAATCGCAGTGCAGGGGGATCAGCATCA
TCTGGGCCTGGTCGGCGTTCATCCCCGGGTACATGGCCTTCATGAAAGCCTCCAATTGCCTGAACGCCTGCTGG
GCCTTGGCTCCGTCGGTGAAGAAGACCCGGCAGGACTTGCTAGAGACATGGTTGCGCCACCCGGCGTCGTG
CACGCAGCAGCGCGCGTCGTTGTTGGCCAGCTGCACCACGCTGCGCCCCAGCGGTTCTGGGTGATCTTGGCC
GGTCGGGGTTCTCCTTCAGCGCGCGCTGCCCGTTCTCGCTCGCCACATCCATCTCGATCATGTGCTCCTTCTGG
ATCATGGTGGTCCCGTGCAGGCACCGCAGCTTGCCCTCGGCCTCGGTGCACCCGTGCAGCCACAGCGCGCACCC
GGTGCACTCCCAGTTCTTGTGGGCGATCTGGGAATGCGCGTGCACGAAGCCCTGCAGGAAGCGGCCCATCATGG
TGGTCAGGGTCTTGTTGCTAGTGAAGGTCAGCGGAATGCCGCGGTGCTCCTCGTTGATGATACAGGTGGCAGATG
CGGCGGTACACCTCGCCCTGCTCGGGCATCAGCTGGAAGTTGGCTTTCAGGTCGGTCTCCACGCGGTAGCGGTC
CATCAGCATAGTCATGATTTCCATACCCTTCTCCCAGGCCGAGACGATGGGCAGGCTCATAGGGTTCTTCACCA
TCATCTTAGCGCTAGCAGCCGCGGCCAGGGGTCGCTCTCGTCCAGGGTCTCAAAGCTCCGCTTGCCGTCCTTC
TCGGTGATCCGCACCGGGGGGTAGCTGAAGCCCACGCCGCCAGCTCCTCCTCGGCCTGTCTTTCGTCCTCGCT
GTCCTGGCTGACGTCCTGCAGGACCACATGCTTGGTGTTGCGGGGTTCTTCTTGGGCGGCAGCGGCGGCGAG
ATGTTGGAGATGGCGAGGGGGAGCGCGAGTTCTCGCTCACCACTACTATCTCTTCCTCTTCTTGGTCCGAGGCC
```

```
ACGCGGCGGTAGGTATGTCTCTTCGGGGGCAGAGGCGGAGGCGACGGGCTCTCGCCGCCGCGACTTGGCGGATG
GCTGGCAGAGCCCCTTCCGCGTTCGGGGGTGCGCTCCCGGCGGCGCTCTGACTGACTTCCTCCGCGGCCGGCCA
TTGTGTTCTCCTAGGGAGGAACAACAAGCATGGAGACTCAGCGATCGCCAACCTCGCCATCTGCCCCCACCGCC
GACGAGAAGCAGCAGCAGCAGAATGAAAGCTTAACCGCCCGGCCGCCCAGCCCCGCCACCTCCGACGCGGCCGT
CCCAGACATGCAAGAGATGGAGGAATCCATCGAGATTGACCTGGGCTTATGTGACGCCCGCGGAGCACGAGGAGG
AGCTGGCAGTGCGCTTTTCACAAGAAGAGATACACCAAGAACAGCCAGAGCAGGAAGCAGAGAATGAGCAGAGT
CAGGCTGGGCTCGAGCATGACGGCGACTACCTCCACCTGAGCGGGGGGGAGGACGCGCTCATCAAGCATCTGGC
CCGGCAGGCCACCATCGTCAAGGATGCGCTGCTCGACCGCACCGAGGTGCCCCTCAGCGTGGAGGAGCTCAGCC
GCGCCTACGAGTTGAACCTCTTCTCGCCGCGCGTGCCCCCCAAGCGCCAGCCCAATGGCACCTGCGAGCCCAAC
CCGCGCCTCAACTTCTACCCGGTCTTCGCGGTGCCCGAGGCCCTGGCCACCTACCACATCTTTTTCAAGAACCA
AAAGATCCCCGTCTCCTGCCGCGCCAACCGCACCCGCGCCGACGCCCTTTTCAACCTGGGTCCCGGCGCCCGCC
TACCTGATATCGCCTCCTTGGAAGAGGTTCCCAAGATCTTCGAGGGTCTGGGCAGCGACGAGACTCGGGCCGCG
AACGCTCTGCAAGGAGAAGGAGGAGAGCATGAGCACCACAGCGCCCTGGTCGAGTTGGAAGGCGACAACGCGCG
GCTGGCGGTGCTCAAACGGACGGTCGAGCTGACCCATTTCGCCTACCCGGCTCTGAACCTGCCCCCGAAAGTCA
TGAGCGCGGTCATGGACCAGGTGCTCATCAAGCGCGCGTCGCCCATCTCCGAGGACGAGGGCATGCAAGACTCC
GAGGGAGGGCAAGCCCGTGGTCAGCGACGAGCAGCTGGCCCGGTGGCTGGGTCCTAATGCTAGTCCCCAGAGTTT
GGAAGAGCGGCGCAAACTCATGATGGCCGTGGTCCTGGTGACCGTGGAGCTGGAGTTGCCTGCGCCGCTTCTTCG
CCGACGCGGAGACCCTGCGCAAGGTCGAGGAGAACCTGCACTACCTCTTCAGGCACGGGTTCGTGCGCCAGGCC
TGCAAGATCTCCAACGTGGAGCTGACCAACCTGGTCTCCTACATGGGCATCTTGCACGGAGAACCGCCTGGGCA
GAACGTGCTGCACACCACCCTGCGCGGGGAGGCCCGGCGCGACTACATCCGCGACTGCGTCTACCTCTACCTGT
GCCACACCTGGCAGACGGGCATGGGCGTGTGGCAGCAGTGTCTGGAGGAGCAGAACCTGAAAGAGCTCTGCAAG
CTCCTGCAGAAGAACCTCAAGGGTCTGTGGACCGGGTTCGACGAGCGCCACCACCGCCTCGGACCTGGCGACCT
CATTTTCCCCGAGCGCCTCAGGCTGACGCTGCGCAACGGCCTGCCCGACTTTATGAGCCAAAGCATGTTGCAAA
ACTTTCGCTCTTTCATCCTCGAACGCTCCGGAATCCTGCCCGCCACCTGCTCCGCGCTGCCCTCGGACTTCGTG
CCGCTGACCTTCCGCGAGTGCCCCCCGCCGCTGTGGAGCCACTGCTACCTGCTGCGCCTGGCCAACTACCTGGC
CTACCACTCGGACGTGATCGAGGACGTCAGCGGCGAGGGCCTGCTCGAGTGCCCACTGCCGCTGCAACCTCTGCA
CGCCGCACCGCTCCCTGGCCTGCAACCCCCAGCTGCTGAGCGAGACCCAGATCATCGGCACCTTCGAGTTGCAA
GGGCCCAGCGAAGGCGAGGGTTCAGCCGCCAAGGGGGGTCTGAAACTGACCCCGGGGCTGTGGACCTCGGCCTA
CTTGCGCAAGTTCGTGCCCGAGGACTACCATCCCTTCGAGATCAGGTTCTACGAGGACCAATCCCATCCGCCCA
AGGCCGAGCTGTCGGCCTGCGTCATCACCCAGGGGGCGATCCTGGCCCAATTGGAAGCCATCCAGAAATCCCGC
CAAGAATTCTTGCTGAAAAAGGGCCGCGGGGTCTACCTCGACCCCCAGACCGGTGAGGAGCTCAACCCCGGCTT
CCCCCAGGATGCCCGAGGAAACAAGAAGCTGAAAGTGGAGCTGCCGCCCGTGGAGGATTGGAGGAAGACTGG
GAGAACAGCAGTCAGGCAGAGGAGGAGGAGATGGAGGAAGACTGGGACAGCACTCAGGCAGAGGAGGACAGCCT
GCAAGACAGTCTGGAGGAAGACGAGGAGGAGGCAGAGGAGGAGGTGGAAGAAGCAGCCGCCGCCGCCAGACCGTCGT
CCTCGGCGGGGGAGAAAGCAAGCAGCACGGATACCATCTCCGCTCCGGGTCGGGGTCCCGCTCGACCACACAGT
AGATGGGACGAGACCGGACGATTCCCGAACCCCACCACCCAGACCGGTAAGAAGGAGCGGCAGGGATACAAGTC
CTGGCGGGGGCACAAAAACGCCATCGTCTCCTGCTTGCAGGCCTGCGGGGGCAACATCTCCTTCACCCGGCGCT
ACCTGCTCTTCCACCGCGGGGTGAACTTTCCCCGCAACATCTTGCATTACTACCGTCACCTCCACACGCCCCTAC
TACTTCCAAGAAGAGGCAGCAGGAGCAGAAAAAGACCAGCAGAAAACCAGCAGCTAGAAAATCCACAGCGGCGG
CAGCAGGTGGACTGAGGATCGCGGCGAACGAGCCGGCGCAAACCCGGGAGCTGAGGAACCGGATCTTTCCCACC
CTCTATGCCATCTTCCAGCAGAGTCGGGGCAGGAGCAGGAACTGAAAGTCAAGAACCGTTCTCTGCGCTCGCT
CACCCGCAGTTGTCTGTATCACAAGAGCGAAGACCAACTTCAGCGCACTCTCGAGGACGCCGCGAGGCTCTCTTCA
ACAAGTACTGCGCGCTCACTCTTAAAGAGTAGCCCGCGCCCGCCCAGTCGCAGAAAAAGGCGGGAATTACGTCA
CCTGTGCCCTTCGCCCTAGCCGCCTCCACCCATCATCATGAGCAAAGAGATTCCCACGCCTTACATGTGGAGCT
ACCAGCCCCAGATGGGCCTGGCCGCCGGTGCCGCCCAGGACTACTCCACCCGCATGAATTGGCTCAGCGCCGGG
CCCGCGATGATCTCACGGGTGAATGACATCCGCGCCCACCGAAACCAGATACTCCTAGAACAGTCAGCGCTCAC
CGCCACGCCCCGCAATCACCTCAATCCGCGTAATTGGCCCGCGCCCTGGTGTACCAGGAAATTCCCCAGCCCA
CGACCGTACTACTTCCGCGAGACGCCCAGGCCGAAGTCCAGCTGACTAACTCAGGTGTCCAGCTGGCGGCGGC
GCCACCCTGTGTCGTCACCGCCCCGCTCAGGGTATAAAGCGGCTGGTGATCGGGGCAGAGGCACACAGCTGAA
CGACGAGGTGGTGAGCTCTTCGCTGGGTCTGCGACCTGACGGAGTCTTCCAACTCGCCGGATCGGGGAGATCTT
CCTTCAGCCTCGTCAGGCCGTCCTGACTTTGGAGAGTTCGTCCTCGCAGCCCGCTCGGGTGGCATCGGCACT
CTCCAGTTCGTGGAGGAGTTCACTCCCTCGGTCTACTTCAACCCCTTCTCCGGCTCCCCCGGCCACTACCCGGA
CGAGTTCATCCCGAACTTCGACGCCATCAGCGAGTCGGTGGACGGCTACGATTGAAACTAATCACCCCCTTATC
CAGTGAAATAAAGATCATATTGATGATGATTTTACAGAAATAAAAATAATCATTTGATTTGAAATAAAGATAC
AATCATATTGATGATTTGAGTTTAAGAAAAAAATAAAGAATCACTTACTTGAAATCTGAATCACAGGTCTCTGTC
CATGTTTTCTGCCAACACCACTTCACTCCCCTCTTCCCAGCTCTGGTACTGCAGGCCCCGGCGGCTGCAAACT
TCCTCCACACGCTGAAGGGGATGTCAAATTCCTCCTGTCCCTCAATCTTCATTTTATCTTCTATCAGATGTCCA
AAAAGCGCGTCCGGGTGGATGATGACTTCGACCCCGTCTACCCCTACGATGCAGACAACGCACCGACCGTGCCC
TTCATCAACCCCCCCTTCGTCTCTTCAGATGGATTCCAAGAGAAGCCCTGGGGGTGTTGTCCTGCGACTGGC
CGACCCCGTCACCACCAAGAACGGGGAAATCACCCTCAAGCTGGGAGAGGGGGTGGACCTCGATTCCTCGGGAA
AACTGATCTCCAACACGGCCACCAAGGCCGCCGCCCCTCTCAGTTTTTCCAACAACACCATTTCCCTTAACATG
GATCACCCCTTTTACACTAAAGATGGAAAATTATCCTTACAAGTTTCTCCACCATTAAATATACTGAGAACAAG
CATTCTAAAGACACTAGCTTTAGGTTTTGGATCAGGTTTAGGACTCCGTGGCTCTGCCTTGGCAGTACAGTTAG
TCTCTCCACTTACATTTGATACTGATGGAAACATAAAGCTTACCTTAGACAGAGGTTTGCATGTTACAACAGGA
GATGCAATTGAAAGCAACATAAGCTGGGCTAAAGGTTTAAAATTTGAAGATGGAGCCATAGCAACCAACATTGG
AAATGGGTTAGAGTTTGGAAGCAGTAGTACAGAAACAGGTGTTGATGATGCTTACCAATCCAAGTTAAACTTG
GATCTGGCCTTAGCTTTGACAGTACAGGAGCCATAATGGCTGGTAACAAAGAAGACGATAAACTCACTTTGTGG
AGAACACCTGATCCATCACCAAACTGTCAAATACTCGCAGAAAATGATGCAAAACTAACACTTTGCTTGACTAA
ATGTGGTAGTCAAATACTGGCCACTGTGTCAGTCTTAGTTGTAGGAAGTGGAAACCTAAACCCCATTACTGGCA
CCGTAAGCAGTGCTCAGGTGTTTCTACGTTTTGATGCAAACGGTGTTCTTTTAACAGAACATTCTACACTAAAA
AAATACTGGGGGTATAGGCAGGGAGATAGCATAGATGGCACTCCATATACCAATGCTGTAGGATTCATGCCCAA
TTTAAAAGCTTATCCAAAGTCACAAAGTTCTACTACTAAAAATAATATAGTAGGGCAAGTATACATGAATGGAG
ATGTTTCAAAACCTATGCTTCTCACTATAACCCTCAATGCTACTGATCCTACAGCAACAGTACATATTCAATGCTCA
TTTTCATACACCTGGACTAATGGAAGCTATGTTGGAGCAACATTTGGGGCTAACTCTTATACCTTCTCATACAT
CGCCCAAGAATGAACACTGTATCCCACCCTGCATGCCAACCCTTCCCACCCCACTCTGTGGAACAAACTCTGAA
ACACAAAATAAAATAAAGTTCAAGTGTTTATTGATTCAACAGTTTTAGAGGATTCGAGCAGTTATTTTCCTC
CACCCTCCCAGGACATGGAATACACCACCCTCTCGCCCCGCACAGCCTTGAACATCTGAATGCCATTGGTGATG
GACATGCTTTTGGTCTCGACGTTCCAGACAGTTTGAGAGCGAGGCAGTCTCGGGTCGGTCAGGGAGATGAAACC
CTCCGGGCACTCCCGCATCTGCACCTCACAGCTCAACAGCTGAGGATTGTCCTCGGTGGTCGGGATCACGGTTA
```

-continued

```
TCTGGAAGAAGCAGAAGAGCGGCGGTGGGAATCATAGTCCGCGAACGGGATCGGCCGGTGGTGTCGCATCAGGC
CCCGCAGCAGTCGCTGCCGCCGCCGCTCCGTCAAGCTGCTGCTCAGGGGGTCCGGGTCCAGGGACTCCCTCAGC
ATGATGCCCACGGCCCTCAGCATCAGTCGTCGGTGCGGCGGGCGCAGCAGCGCATGCGGATCTCGCTCAGGTC
GCTGCAGTACGTGCAACACAGAACCACCAGGTTGTTCAACAGTCCATAGTTCAACACGCTCCAGCCGAAACTCA
TCGCGGGAAGGATGCTACCCACGTGGCCGTCGTACCAGATCCTCAGGTAAATCAAGTGGTGCCCCCTCCAGAAC
ACGCTGCCCACGTACATGATCTCCTTGGGCATGTGGCGGTTCACCACCTCCCGGTACCACATCACCCTCTGGTT
GAACATGCAGCCCCGGATGATCCTGCGGAACGAGAGGGCCAGCACCGCCCCGCCCGCCATGCAGCGAAGAGACC
CCGGGTCCCGGCAATGGCAATGGAGGACCCACCGCTCGTACCCGTGGATCATCTGGGAGCTGAACAAGTCTATG
TTGGCACAGCACAGGCATATGCTCATGCATCTCTTCAGCACTCTCAACTCCTCGGGGGTCAAAACCATATCCCA
GGGCACGGGGAACTCTTGCAGGACAGGGAACCCCGCAGAACAGGGCAATCCTCGCACAGAACTTACATTGTGCA
TGGACAGGGTATCGCAATCAGGCAGCACCGGGTGATCCTCCACCAGAGAAGCGCGGGTCTCGGTCTCCTCACAG
CGTGGTAAGGGGGCCGGCCGATACGGGTGATGGCGGGACGCGGGTGATCGTGTTCGCGACCGTGTCATGATGCA
GTTGCTTTCGGACATTTTCGTACTTGCTGTAGCAGAACCTGGTCCGGGCGCTGCACACCGATCGCCGGCGGCGG
TCTCGGCGCTTGGAACGCTCGGTGTTGAAATTGTAAAACAGCCACTCTCTCAGACCGTGCAGCAGATCTAGGGC
CTCAGGAGTGATGAAGATCCCATCATGCCTGATGGCTCTGATCACATCGACCACCGTGGAATGGGCCAGACCCA
GCCAGATGATGCAATTTTGTTGGGTTTCGGTGACGGCGGGGGAGGGAAGAACAGGAAGAACCATGATTAACTTT
TAATCCAAACGGTCTCGGAGTACTTCAAAATGAAGATCGCGGAGATGCCACCTCTCGCCCCCGCTGTGTTGGTG
GAAAATAACAGCCAGGTCAAAGGTGATACGGTTCTCGACATGTTCCACGGTGGCTTCCAGCAAAGCCTCCACGC
GCACATCCAGAAACAAGACAATAGCGAAAGCGGGAGGGTTCTCTAATTCCTCAATCATCATGTTACACTCCTGC
ACCATCCCCAGATAATTTTCATTTTTCCAGCCTTGAATGATTCGAACTAGTTCcTGAGGTAAATCCAAGCCAGC
CATGATAAAGAGCTCGCGCAGAGCGCCCTCCACCGGCATTCTTAAGCACACCCTCATAATTCCAAGATATTCTG
CTCCTGGTTCACCTGCAGCAGATTGACAAGCGGAATATCAAAATCTTCGCCGCGATCCCTGAGCTCCTCCCTCA
GCAATAACTGTAAGTACTCTTTCATATCCTCTCCGAAATTTTTAGCCATAGGACCACCAGGAATAAGATTAGGG
CAAGCCACAGTACAGATAAACCGAAGTCCTCCCCAGTGAGCATTGCCAAATGCAAGACTGCTATAAGCATGCTG
GCTAGACCCGGTGATATCTTCCAGATAACTGGACAGAAAATCGCCCAGGCAATTTTTAAGAAAATCAACAAAAG
AAAAATCCTCCAGGTGGACGTTTAGAGCCTCGGGAACAACGATGAAGTAAATGCAAGCGGTGCGTTCCAGCATG
GTTAGTTAGCTGATCTGTAGAAAAAACAAAAATGAACATTAAACCATGCTAGCCTGGCGAACAGGTGGGTAAAT
CGTTCTCTCCAGCACCAGGCAGGCCACGGGGTCTCCGGCGCGACCCTCGTAAAAATTGTCGCTATGATTGAAAA
CCATCACAGAGAGACGTTCCCGGTGGCCGGCGTGAATGATTCGACAAGATGAATACACCCCCGGAACATTGGCG
TCCGCGAGTGAAAAAAAGCGCCCGAGGAAGCAATAAGGCACTACAATGCTCAGTCTCAAGTCCAGCAAAGCGAT
GCCATGCGGATGAAGCACAAAATTCTCAGGTGCGTACAAAATGTAATTACTCCCCTCCTGCACAGGCAGCAAAG
CCCGCGATCCCTCCAGGTACACATACAAAGCCTCAGCGTCCATAGCTTACCGAGCAGCAGCACACAACAGGCGC
AAGAGTCAGAGAAAGGCTGAGCTCTAACCTGTCCACCCGCTCTCTGCTCAATATATAGCCCAGATCTACACTGA
CGTAAAGGCCAAAGTCTAAAAATACCCGCCAAATAATCACACACGCCCAGCACACGCCCAGAAACCGGTGACAC
ACTCAAAAAAATACGCGCACTTCCTCAAACGCCCAAAACTGCCGTCATTTCCGGGTTCCCACGCTACGTCATCA
AAACACGACTTTCAAATTCCGTCGACGGTTAAAAACGTGACCCGCCCCGCCCCTAACGGTCGCCCGTCTCTCAG
CCAATCAGCGCCCCGCATCCCCAAATTCAAACACCTCATTTGCATATTAACGCGCACAAAAAGTTTGAGG

Venezuelan equine encephalitis virus [VEE] (SEQ ID NO: 3) GenBank: L01442.2
atgggcggcg catgagagaa gcccagacca attacctacc caaaatggag aaagttcacg
ttgacatcga ggaagacagc ccattcctca gagctttgca gcggagcttc ccgcagtttg
aggtagaagc caagcaggtc actgataatg accatgctaa tgccagagcg ttttcgcatc
tggctttcaa actgatcgaa acggaggtgg acccatccga cacgatcctt gacattggaa
gtgcgcccgc ccgcagaatg tattctaagc acaagtatca ttgtatctgt ccgatgagat
gtgcggaaga tccggacaga ttgtataagt atgcaactaa gctgaagaaa aactgtaagg
aaataactga taaggaattg gacaagaaaa tgaaggagct cgccgccgtc atgagcgacc
ctgacctgga aactgagact atgtgcctcc acgacgacga gtcgtgtcgc tacgaaggcc
aagtcgctgt ttaccaggat gtatacgcgg ttgacggacc gacaagtctc tatcaccaag
ccaataaggg agttagagtc gcctactgga taggctttga caccaccccct tttatgttta
agaacttggc tggagcatat ccatcatact ctaccaactg ggccgacgaa accgtgttaa
cggctcgtaa cataggccta tgcagctctg acgttatgga gcggtcacgt agagggatgt
ccattcttag aaagaagtat ttgaaaccat ccaacaatgt tctattctct gttggctcga
ccatctacca cgagaagagg gacttactga ggagctggca cctgccgtct gtatttcact
tacgtggcaa gcaaaattac acatgtcggt gtgagactat agttagttgc gacgggtacg
tcgttaaaag aatagctatc agtccaggcc tgtatgggaa gccttcaggc tatgctgcta
cgatgcaccg cgagggattc tgtgctgcaa aagtgacaga cacattgaac ggggagaggg
tctcttttcc cgtgtgcacg tatgtgccag ctacattgtg tgaccaaatg actggcatac
tggcaacaga tgtcagtgcg gacgacgcgc aaaaactgct ggttgggctc aaccagcgta
tagtcgtcaa cggtcgcacc cagagaaaca ccaataccat gaaaaattac cttttgcccg
tagtggccca ggcatttgct aggtgggcaa aggaatataa ggaagatcaa gaagatgaaa
ggccactagg actacgagat agacagttag tcatggggtg ttgttgggct tttagaaggc
acaagataac atctatttat aagcgcccgg atacccaaac catcatcaaa gtgaacagcg
atttccactc attcgtgctg cccaggatag gcagtaacac attggagatc gggctgagaa
caagaatcag gaaaatgtta gaggagcaca aggagccgtc acctctcatt accgccgagg
acgtacaaga agctaagtgc gcagccgatg aggctaagga ggtgcgtgaa gccgaggagt
tgcgcgcagc tctaccacct ttggcagctg atgttgagga gcccactctg gaagccgatg
tcgacttgat gttacaagag gctggggccg gctcagtgga gacacctgtg gcttgataa
aggttaccag ctacgctggc gaggacaaga tcggctctta cgctgtgctt tctccgcagg
ctgtactcaa gagtgaaaaa ttatcttgca tccaccctct cgaacaa gtcatagtga
taacacactc tggccgaaaa gggcgttatg ccgtggaacc ataccatggt aaagtagtgg
tgccagaggg acatgcaata cccgtccagg actttcaagc tctgagtgaa agtgccacca
ttgtgtacaa cgaacgtgag ttcgtaaaca ggtacctgca ccatattgcc acacatggag
gagcgctgaa cactgatgaa gaatattaca aaactgtcaa gcccagcgag cacgacggcg
aatacctgta cgacatcgac aggaaacagt gcgtcaagaa agaactagtc actgggctag
ggctcacagg cgagctggtg gatcctccct tccatgaatt cgcctacgag agtctgagaa
cacgaccagc cgctccttac caagtaccaa ccataggggt gtatggcgtg ccaggatcag
gcaagtctgg catcattaaa agcgcagtca ccaaaaaaga tctagtggtg agcgccaaga
aagaaaactg tgcagaaatt ataagggacg tcaagaaaat gaagggctg acgtcaatg
ccagaactgt ggactcagtg ctcttgaatg gatgcaaaca ccccgtagag accctgtata
```

```
ttgacgaagc ttttgcttgt catgcaggta ctctcagagc gctcatagcc attataagac
ctaaaaaggc agtgctctgc ggggatccca aacagtgcgg ttttttttaac atgatgtgcc
tgaaagtgca ttttaaccac gagatttgca cacaagtctt ccacaaaagc atctctcgcc
gttgcactaa atctgtgact tcggtcgtct caaccttgtt ttacgacaaa aaaatgagaa
cgacgaatcc gaaagagact aagattgtga ttgcacactac cggcagtacc aaacctaagc
aggacgatct cattctcact tgtttcagag ggtgggtgaa gcagttgcaa atagattaca
aaggcaacga aataatgacg gcagctgcct ctcaagggct gacccgtaaa ggtgtgtatg
ccgttcggta caaggtgaat gaaaatcctc tgtacgcacc cacctcagaa catgtgaacg
tcctactgac ccgcacggag gaccgcatcg tgtggaaaac actagccggc gacccatgga
taaaaacact gactgccaag taccctggga atttcactgc cacgatagag gagtggcaag
cagagcatga tgccatcatg aggcacatct tggagagacc ggaccctacc gacgtcttcc
agaataaggc aaacgtgtgt tgggccaagg ctttagtgcc ggtgctgaag accgctggca
tagacatgac cactgaacaa tggaacactg tggattattt tgaaacggac aaagctcact
cagcagagat agtattgaac caactatgcg tgaggttctt tggactcgat ctggactccg
gtctattttc tgcacccact gttccgttat ccattaggaa taatcactgg gataactccc
cgtcgcctaa catgtacggg ctgaataaag aagtggtccg tcagctctct cgcaggtacc
cacaactgcc tcgggcagtt gccactggaa gagtctatga catgaacact ggtacactgc
gcaattatga tccgcgcata aacctagtac ctgtaaacag aagactgcct catgctttag
tcctccacca taatgaacac ccacagagtg acttttcttc attcgtcagc aaattgaagg
gcagaactgt cctggtggtc ggggaaaagt tgtccgtccc aggcaaaatg gttgactggt
tgtcagaccg gcctgaggct accttcagag ctcggctgga tttaggcatc ccaggtgatg
tgcccaaata tgacataata tttgttaatg tgaggaccc atataaatac catcactatc
agcagtgtga agaccatgcc attaagctta gcatgttgac caagaaagct tgtctgcatc
tgaatcccgg cggaacctgt gtcagcatag gttatggtta cgctgacagg gccagcgaaa
gcatcattgg tgctatagcg cggcagttca agttttcccg ggtatgcaaa ccgaaatcct
cacttgaaga gacggaagtt ctgtttgtat tcattgggta cgatcgcagc gcccgtacgc
acaatcctta caagctttca tcaaccttga ccaacattta tacaggttcc agactccacg
aagccggatg tgcaccctca tatcatgtgg tgcgagggga tattgccacg gccaccgaag
gagtgattat aaatgctgct aacagcaaag acaacctggc ggaggggtg tgcggagcgc
tgtataagaa attcccggaa agcttcgatt tacagccgat cgaagtagga aaagcgcgac
tggtcaaagg tgcagctaaa catatcattc atgccgtagg accaaacttc aacaaagttt
cggaggttga aggtgacaaa cagttggcag aggcttatga gtccatcgct aagattgtca
acgataacaa ttacaagtca gtagcgattc cactgttgtc caccggcatc ttttccggga
acaaagatcg actaacccaa tcattgaacc atttgctgac agctttagac accactgatg
cagatgtagc catatactgc agggacaaga aatgggaaat gactctcaag gaagcagtgg
ctaggagaga agcagtggag gagatatgca tatccgacga ctcttcagtg acagaacctg
atgcagagct ggtgagggtg catccgaaga gttctttggc tggaaggaag ggctacagca
caagcgatgg caaaactttc tcatatttgg aagggaccaa gtttcaccag gcggccaagg
atatagcaga aattaatgcc atgtggcccg ttgcaacgga ggcaatgag caggtatgca
tgtatatcct cggagaaagc atgagcagta ttaggtcgaa atgccccgtc gaagagtcgg
aagcctccac accaccctagc acgctgcctt gcttgtgcat ccatgccatg actccagaaa
gagtacagcg cctaaaagcc tcacgtcag aacaaattac tgtgtgctca tccttttccat
tgccgaagta tagaatcact ggtgtgcaga agatccaatg ctcccagcct atattgttct
caccgaaagt gcctgcgtat attcatccaa ggaagtatct cgtggaaaca ccaccggtag
acgagactcc ggagccatcg gcagagaacc aatccacaga ggggcacacct gaacaaccac
cacttataac cgaggatgag accaggacta gaacgcctga gccgatcatc atcgaagagg
aagaagagga tagcataagt ttgctgtcag atgccccgac ccaccaggtg ctgcaagtcg
aggcagacat tcacgggccg ccctctgtat ctagctcatc ctggtccatt cctcatgcat
ccgactttga tgtggacagt ttatccatac ttgacaccct ggaggagct agcgtgacca
gcggggcaac gtcagccgag actaactctt acttcgcaaa gagtatggag tttctggcgc
gaccggtgcc tgcgcctcga acagtattca ggaaccctcc acatcccgct ccgcgcacaa
gaacaccgtc acttgcaccc agcagggcct gctcgagaac cagcctagtt tccacccccgc
caggcgtgaa tagggtgatc actagagagg agctcgaggc gcttacccccg tcacgcactc
ctagcaggtc ggtctcgaga accagcctgg tctccaaccc gccaggcgta aatagggtga
ttacaagaga ggagtttgag gcgttcgtag cacaacaaca atgacggttt gatgcgggtg
catacatctt ttcctccgac accggtcaag ggcatttaca acaaaaatca gtaaggcaaa
cggtgctatc cgaagtggtg ttggagagga ccgaattgga gatttcgtat gccccgcgcc
tcgaccaaga aaaagaagaa ttactacgca agaaattaca gttaaatccc acacctgcta
acagaagcag ataccagtcc aggaaggtgg agaacatgaa agccataaca gctagacgta
ttctgcaagg cctagggcat tattttgaagg cagaaggaaa agtggagtgc taccgaaccc
tgcatcctgt tcctttgtat tcatctagtg tgaaccgtgc cttttcaagc cccaaggtcg
cagtggaagc ctgtaacgcc atgttgaaag agaactttcc gactgtggct tcttactgta
ttattccaga gtacgatgcc tatttggaca tggttgacgg agcttcatgc tgcttagaca
ctgccagttt ttgccctgca aagctgcgca gctttccaaa gaaacactcc tatttggaac
ccacaatacg atcggcagtg ccttcagcga tccagaacac gctccagaac gtcctggcag
ctgccacaaa aagaaattgc aatgtcacgc aaatgagaga attgcccgta ttggattcgg
cggcctttaa tgtggaatgc ttcaagaaat atgcgtgtaa taatgaatat tgggaaacgt
ttaaagaaaa ccccatcagg cttactgaag aaaacgtggt aaattacatt accaaattaa
aaggaccaaa agctgctgct cttttttgcga agacacataa tttgaatatg ttgcaggaca
taccaatgga caggtttgta atggacttaa agagagacgt gaaagtgact ccaggaacaa
aacatactga agaacggccc aaggtacagg tgatccaggc tgccgatccg ctagcaacag
cgtatctgtg cggaatccac cgagagctgg ttaggagatt aaatgcggtc ctgcttccga
acattcatac actgtttgat atgtcggctg aagactttga cgctattata gccgagcact
tccagctgg ggattgtgtt ctggaaactg acatcgcgtc gtttgataaa agtgaggacg
acgccatggc tctgaccgcg ttaatgattc tggaagactt aggtgtggac gcagagctgt
tgacgctgat tgaggcggct ttcggcgaaa tttcatcaat acatttgccc actaaaacta
aatttaaatt cggagccatg atgaaatctg gaatgttcct cacactgttt gtgaacacag
tcattaacat tgtaatcgca agcagagtgt tgagagaacg gctaaccgga tcaccatgtg
cagcattcat tggagatgac aatatcgtga aaggagtcaa atcggacaaa ttaatggcag
```

-continued

```
acaggtgcgc cacctggttg aatatggaag tcaagattat agatgctgtg gtgggcgaga
aagcgcctta tttctgtgga gggtttattt tgtgtgactc cgtgaccggc acagcgtgcc
gtgtggcaga ccccctaaaa aggctgttta agcttggcaa acctctggca gcagacgatg
aacatgatga tgcaggagaa agggcattgc atgaagagtc aacacgctgg aaccgagtgg
gtattctttc agagctgtgc aaggcagtag aatcaaggta tgaaaccgta ggaacttcca
tcatagttat ggccatgact actctagcta gcagtgttaa atcattcagc tacctgagag
gggccctat aactctctac ggctaacctg aatggactac gacatagtct agtccgccaa
gatgttcccg ttccagccaa tgtatccgat gcagccaatg ccctatcgca acccgttcgc
ggccccgcgc aggccctggt tccccagaac cgacccttt ctggcgatgc aggtgcagga
attaacccgc tcgatggcta acctgacgtt caagcaacgc cgggacgcgc cacctgaggg
gccatccgct aagaaaccga agaaggaggc ctcgcaaaaa cagaaagggg gaggccaagg
gaagaagaag aagaaccaag ggaagaagaa ggctaagaca gggccgccta atccgaaggc
acagaatgga aacaagaaga agaccaacaa gaaaccaggc aagagacagc gcatggtcat
gaaattggaa tctgacaaga cgttcccaat catgttggaa gggaagataa acggctacgc
ttgtgtggtc ggagggaagt tattcaggcc gatgcatgtg gaaggcaaga tcgacaacga
cgttctggcc gcgcttaaga cgaagaaagc atccaaatac gatcttgagt atgcagatgt
gccacagaac atgcgggccg atacattcaa atacacccat gagaaacccc aaggctatta
cagctggcat catggagcag tccaaatatga aaatggtgc ttcacggtgc cgaaaggagt
tggggccaag ggagacagcg gacgacccat tctggataac cagggacggg tggtcgctat
tgtgctggga ggtgtgaatg aaggatctag gacagccctt tcagtcgtca tgtgaaacga
gaagggagtt accgtgaagt atactccgga gaactgcgag caatggtcac tagtgaccac
catgtgtctg ctcgccaatg tgacgttccc atgtgctcaa ccaccaattt gctacgacag
aaaaccagca gagactttgg ccatgctcag cgttaacgtt gacaacccgg gctacgatga
gctgctggaa gcagctgtta agtgccccgg aaggaaaagg agatccaccg aggagctgtt
taaggagtat aagctaacgc gcccttacat ggccagatgc atcagatgtg cagttgggag
ctgccatagt ccaatagcaa tcgaggcagt aaagagcgac gggcacgacg gttatgttag
acttcagact tcctcgcagt atggcctgga ttcctccggc aacttaaagg gcaggaccat
gcggtatgac atgcacggga ccattaaaga gataccacta catcaagtgt cactccatac
atctcgcccg tgtcacattg tggatgggca cggttatttc ctgcttgcca ggtgcccggc
aggggactcc atcaccatgg aatttaagaa agattccgtc acacactcct gctcggtgcc
gtatgaagtg aaatttaatc ctgtaggcag agaactctat actcatcccc cagaacacgg
agtagagcaa gcgtgccaag tctacgcaca tgatgcacag aacagaggag cttatgtcga
gatgcacctc ccgggctcag aagtggacag cagtttggtt tccttgagcg gcagttcagt
caccgtgaca cctcctgttg ggactagcgc cctggtggaa tgcgagtgtg gcggcacaaa
gatctccgag accatcaaca agacaaaaca gttcagccag tgcacaaaga aggagcagtg
cagagcatat cggctgcaga acgataagtg ggtgtataat tctgacaaac tgcccaaagc
agcgggagcc accttaaaag gaaaactgca tgtcccattc ttgctggcag acggcaaatg
caccgtgcct ctagcaccag aacctatgat aacctttggt ttcagatcag tgtcactgaa
actgcaccct aagaatccca catatctaac cacccgccaa cttgctgatg agcctcacta
cacgcacgag ctcatatctg aaccagctgt taggaatttt accgtcaccg aaaaagggtg
ggagtttgta tggggaaacc acccgccgaa aaggttttgg gcacaggaaa cagcacccgg
aaatccacat gggctaccgc acgaggtgat aactcattat taccacagat accctatgtc
caccatcctg ggtttgtcaa tttgtgccgc cattgcaacc gtttccgttg cagcgtctac
ctggctgttt tgcagatcta gagttgcgtg cctaactcct taccggctaa cacctaacgc
taggatacca ttttgtctgg ctgtgctttg ctgcgcccgc actgcccggg ccgagaccac
ctgggagtcc ttgatcacc tatggaacaa taaccaacag atgttctgga ttcaattgct
gatccctctg gccgccttga tcgtagtgac tcgcctgctc agtgcgtgt gctgtgtcgt
gccttttta gtcatggccg gcgccgcagg cgcggcgcc tacgagcacg cgaccacgat
gccgagccaa gcgggaatct cgtataacac tatagtcaac agagcaggct acgcaccact
ccctatcagc ataacaccaa caagatcaa gctgatacct acagtgaact tggagtacgt
cacctgccac tacaaaacag gaatggattc accagccatc aaatgctgcg gatctcagga
atgcactcca acttacaggc ctgatgaaca gtgcaaagtc ttcacagggg tttacccgtt
catgtggggt ggtgcatatt gcttttgcga cactgagaac acccaagtca gcaaggccta
cgtaatgaaa tctgacgact gccttgcgga tcatgctgaa gcatataaag cgcacacagc
ctcagtgcag gcgttcctca acatcacagt gggagaacac tctattgtga ctaccgtgta
tgtgaatgga gaaactcctg tgaatttcaa tgggggtcaaa ttaactgcag gtccgctttc
cacagcttgg acacccttg atcgcaaaat cgtgcagtat gccggggaga tctataatta
tgatttcct gagtatgggg caggacaacc aggagcattt ggagatatac aatccagaac
agtctcaagc tcagatctgt atgccaatac caacctagtc ctgcagagac ccaaagcagg
agcgatccac gtgccataca ctcaggcacc ttcgggtttt gagcaatgga agaaagataa
agctccatca ttgaaattta ccgccccttt cggatgcgaa atatatacaa accccattcg
cgccgaaaac tgtgctgtag gtcaattcc attagccttt gacattcccg acgccttgtt
caccagggtg tcagaaacac cgacactttc agcgccgaa tgcactctta acgagtgcgt
gtattcttcc gactttggtg ggatcgccac ggtcaagtac tcggccagca agtcaggcaa
gtgcgcagtc catgtgccat cagggactgc taccctaaaa gaagcagcag tcgagctaac
cgagcaaggc tcggcgacta tccatttctc gaccgcaaat atccaccgg agttcaggct
ccaaatatgc acatcatatg ttacgtgcaa aggtgattgt caccccccga agaccatat
tgtgacacac cctcagtatc acgcccaaac atttacagcc gcggtgtcaa aaaccgcgtg
gacgtggtta acatcctgc tgggaggatc agccgtaatt attataattg gcttggtgct
ggctactatt gtggccatgt acgtgctgac caaccagaaa cataattgaa tacagcagca
attggcaagc tgcttacata gaactcgcgg cgattggcat gccgccttaa aatttttatt
ttattttttc ttttctttc cgaatcggat tttgtttta atatttc
```

VEE-MAG25mer (SEQ ID NO: 4); contains MAG-25merPDTT nucleotide (bases 30-1755)
atgggcggcgcatgagagaagc

```
aactgataaggaattggacaagaaaatgaaggagctcgccgccgtcatgagcgaccctgacctggaaactgaga
ctatgtgcctccacgacgacgagtcgtgtcgctacgaagggcaagtcgctgtttaccaggatgtatacgcggtt
gacggaccgacaagtctctatcaccaagccaataagggagttagagtcgcctactggataggctttgacaccac
ccctttttatgtttaagaacttggctggagcatatccatcatactctaccaactgggccgacgaaaccgtgttaa
cggctcgtaacataggcctatgcagctctgacgttatggagcggtcacgtaggaggatgtccattcttagaaag
aagtatttgaaaccatccaacaatgttctattctctgttggctcgaccatctaccacgagaagagggacttact
gaggagctggcacctgccgtctgtatttcacttacgtggcaagcaaaattacacatgtcggtgtgagactatag
ttagttgcgacgggtacgtcgttaaaagaatagctatcagtccaggcctgtatgggaagcttcaggctatgct
gctacgatgcaccgcgagggattcttgtgctgcaaagtgacagacacattgaacggggagagggtctcttttcc
cgtgtgcacgtatgtgccagctacattgtgtgaccaaatgactggcatactggcaacagatgtcagtgcggacg
acgcgcaaaaactgctggttgggctcaaccagcgtatagtcgtcaacggtcgcacccagagaaacaccaatacc
atgaaaaattacctttgcccgtagtggcccaggcatttgctaggtgggcaaagaatataaggaagatcaaga
agatgaaaggccactaggactacgagatagacagttagtcatgggtgttgtgggcttttagaaggcacaaga
taacatctatttataagcgcccggatacccaaaccatcatcaaagtgaacagcgattcactcattcgtgctg
cccaggataggcagtaacacattggagatcgggctgagaacaagaatcaggaaaatgttagaggagcacaagga
gccgtcacctctcattaccgccgaggacgtacaagaagctaagtgcgcagccgatgaggctaaggaggtgcgtg
aagccgaggagttgcgcgcagctctaccacctttggcagctgatgttgaggagcccactctggaagccgatgtc
gacttgatgttacaagaggctggggccggctcagtggagacacctcgtggcttgataaaggttaccagctacgc
tggcgaggacaagatcggctcttacgctgtgcttctccgcaggctgtactcaagagtgaaaaattatcttgca
tccaccctctcgctgaacaagtcatagtgataacacactctggccgaaaagggcgttatgccgtggaaccatac
catggtaaagtagtggtgccagagggacatgcaataccgtccaggactttcaagctctgagtgaaagtgccac
cattgtgtacaacgaacgtgagttcgtaaacaggtacctgcaccatattgccacacatggaggagcgctgaaca
ctgatgaagaatattacaaaactgtcaagcccagcgagcacgacggcgaatacctgtacgacatcgacaggaaa
cagtgcgtcaagaaagaactagtcactgggctagggctcacaggcgagctggtggatcctccttccatgaatt
cgcctacgagagtctgagaacacgaccagccgctccttaccaagtaccaaccatagggggtgtatggcgtgccag
gatcaggcaagtctggcatcattaaaagcgcagtcaccaaaagactctagtggtgagcgccaagaaagaaaac
tgtgcagaaattataagggacgtcaagaaaatgaaagggctggacgtcaatgccagaactgtggactcagtgct
cttgaatggatgcaaacaccccgtagagaccctgtatattgacgaagcttttgcttgtcatgcaggtactctca
gagcgctcatagccattataagacctaaaaaggcagtgctctgcggggatcccaaacagtgcggttttttttaac
atgatgtgcctgaaagtgcattttaaccacgagatttgcacacaagtcttccacaaaagcatctctcgccgttg
cactaaatctgtgacttcggtcgtctcaaccttgttttacgacaaaaaaatgagaacgacgaatccgaaagaga
ctaagattgtgattgacactaccggcagtaccaaacctaagcaggacgatctcattctcacttgtttcagaggg
tgggtgaagcagttgcaaatagattacaaaggcaacgaaataatgacggcagctgcctctcaagggctgacccg
taaaggtgtgtatgccgttcggtacaaggtgaatgaaaatcctctgtacgcacccacctcagaacatgtgaacg
tcctactgaccgcacggaggaccgcatcgtgtggaaaacactagccgcgacccatggataaaaacactgact
gccaagtaccctgggaatttcactgccacgatagaggagtggcaagcagagcatgatgccatcatgaggcacat
cttggagagaccggaccctaccgacgtcttccagaataaggcaaacgtgtgtttgggccaaggctttagtgccgg
tgctgaagaccgctggcatagacatgaccactgaacaatggaacactgtggattattttgaaacggacaaagct
cactcagcagagatagtattgaaccaactatgcgtgaggttctttgactcgatctggactccggtctattttc
tgcacccactgttccgttatccattaggaataatcactgggataactccccgtcgcctaacatgtacgggctga
ataaagaagtggtccgtcagctctcgcaggtacccacaactgcctcgggcagttgccactggaagagtctat
gacatgaacactggtacactgcgcaattatgatccgcgcataaacctagtacctgtaaacagaagactgcctca
tgctttagtcctccaccataatgaacacccacagagtgactttctcattcgtcagcaaattgaaggggcagaa
ctgtcctggtggtcggggaaaagttgtccgtcccaggcaaaatggttgactggttgtcagaccggcctgaggct
accttcagagctcggctggatttaggcatcccaggtgatgtgcccaaatatgacataatattttgttaatgtgag
gaccccatataatccatcactatcagcagtgtgaagaccatgccattaagcttagcatgttgaccaagaaag
cttgtctgcatctgaatcccggcgaaccctgtgtcagcatggtatgctcacgctgacaggggccagcgaaagc
atcattggtgctatagcgcggcagttcaagtttccgggtatgcaaaccgaaatcctcacttgaagagacgga
agttctgtttgtattcattgggtacgatcgcaaggcccgtacgcacaatcctacaagctttcatcaaccttga
ccaacatttatacaggttccagactccacgaagccggatgtgcaccctcatatcatgtggtgcgaggggatatt
gccacggccaccgaaggagtgattataaatgctgctaacagcaaaggacaactggcggagggggtgtgcggagc
gctgtataagaaattcccggaaagcttcgatttacgccgatcgaagtaggaaaagcgcgactggtcaaaggtg
cagctaaacatatcattcatgccgtaggaccaaacttcaacaaagtttcggaggttgaaggtgacaaacagttg
gcagaggcttatgagtccatcgctaagattgtcaacgataacaattacaagtcagtagcgattccactgttgtc
caccggcatcttttccgggaacaaagatcgactaacccaatcattgaaccatttgctgacagcttagacacca
ctgatgcagatgtagccatatactgcagggacaagaaatgggaaatgactctcaaggaagcagtggctaggaga
gaagcagtggaggagatatgcatatccgacgacttcagtgacagaacctgatgcagagctggtgagggtgca
tccgaagagttctttggctggaaggaagggctacagcacaagcgatggcaaaactttctcatatttggaaggga
ccaagtttcaccaggcggcccaaggatatagcagaaattaatgccatgtggccgttgcaacggaggccaatgag
caggtatgcatgtatatcctcggagaaagcatgagcagtattaggtcgaaatgccccgtcgaagagtcggaagc
ctccacaccacctagcacgctgccttgcttgtgcatccatgccatgactccagaaagagtacagcgcctaaaag
cctcacgtccagaacaaattactgtgtgctcatcctttccattgccgaagtataaatcactggtgtgcagaag
atccaatgctcccagcctatattgttctcaccgaaagtgcctgcgtatattcatccaaggaagtatctcgtgga
aacaccaccggtagacgagactccggagccatcggcagagaacaatccacagaggggcaacctgaacaaccac
cacttataaccgaggatgagaccaggactagaacgcctgagccgatcatcatcgaagaggaagaagaggatagc
ataagtttgctgtcagatggcccgacccaccaggtgctgcaagtcgaggcagacattcacgggccgccctctgt
atctagctcatcctggtccattcctcatgcatccgactttgatgtggacagtttatccatacttgacaccctgg
agggagctagcgtgaccagcggggcaacgtcagccgagactaactcttacttcgcaaagagtatggagttctg
gcgcgaccggtgcctgcgcctcgaacagtattcaggaaccctccacatcccgctccgcgcacaagaacaccgtc
acttgcacccagcagggcctgctcgagaaccagcctagttccaccccgccaggcgtgaataggggtgatcacta
gagaggagctcgaggcgcttaccccgtcacgcactcctagcaggtcggtctcgagaaccagcctggtctccaac
ccgccaggcgtaaatagggtgattacaagagaggagtttgaggcgttcgtagcacaacaacaatgacggtttga
tgcgggtgcatacatctttttcctccgacaccggtcaagggcatttacaacaaaaatcagtaaggcaaacggtgc
tatccgaagtggtgttggagaggaccgaattggagatttcgtatgccccggcctcgaccaagaaaaagaagaa
ttactacgcaagaaattacagttaaatcccacacctgctaacagaagcagataccagtccaggaaggtggagaa
catgaaagccataacagctagacgtattctgcaaggcctagggcattatttgaaggcagaaggaaaagtggagt
gctaccgaaccctgcatcctgttcctttgtattcatctagtgtgaaccgtgcctttcaagcccaaggtcgca
gtggaagcctgtaacgccatgttgaaagagaactttccgactgtggcttcttactgtattattccagagtacga
tgcctatttggacatggttgacggagcttcatgctgccttagacactgccagttttgccctgcaaagctgcgca
```

```
gctttccaaagaaacactcctatttggaacccacaatacgatcggcagtgccttcagcgatccagaacacgctc
cagaacgtcctggcagctgccacaaaaagaaattgcaatgtcacgcaaatgagagaattgcccgtattggattc
ggcggcctttaatgtggaatgcttcaagaaatatgcgtgtaataatgaatatgggaaacgtttaaagaaaacc
ccatcaggcttactgaagaaaacgtggtaaattacattaccaaattaaaaggaccaaaagctgctgctctttt
gcgaagacacataatttgaatatgttgcaggacataccaatggacagggttttgtaatggacttaaagagagc gt
gaaagtgactccaggaacaaaacatactgaagaacggcccaaggtacaggtgatccaggctgccgatccgctag
caacagcgtatctgtgcggaatccaccgagagctggttaggagattaaatgcggtcctgcttccgaacattcat
acactgtttgatatgtcggctgaagactttgacgctattatagccgagcacttccagcctggggattgtgttct
ggaaactgacatcgcgtcgtttgataaaagtgaggacgacgccatggctctgaccgcgttaatgattctggaag
acttaggtgtggacgcagagctgttgacgctgattgaggcggcttttcggcgaaatttcatcaatacatttgccc
actaaaactaaatttaaattcggagccatgatgaaatctggaatgttcctcacactgtttgtgaacacagtcat
taacattgtaatcgcaagcagagtgttgagagaacggctaaccggatcaccatgtgcagcattcattggagatg
acaatatcgtgaaaggagtcaaatcggacaaattaatggcagacaggtgcgccacctggttgaatatggaagtc
aagattatagatgctgtggtgggcgagaaagcgccttatttctgtggagggtttattttgtgtgactccgtgac
cggcacagcgtgccgtgtggcagacccctaaaaaggctgtttaagcttggcaaacctctggcagcagacgatg
aacatgatgatgacaggagaagggcattgcatgaagagtcaacacgctggaaccgagtgggtattctttcagag
ctgtgcaaggcagtagaatcaaggtatgaaccgtaggaacttccatcatagttatggccatgactactctagc
tagcagtgttaaatcattcagctacctgagagggggcccctataactctctacggctaacctgaatggactacga
ctctagaatagtctttaatTAAGCCACCATGGCAGGCATGTTTCAGGCGCTGAGCGAAGGCTGCACCCCGTATG
ATATTAACCAGATGCTGAACGTGCTGGGCGATCATCAGGTCTCAGGCCTTGAGCAGCTTGAGAGTATAATCAAC
TTTGAAAAACTGACTGAATGGACCAGTTCTAATGTTATGCCTATCCTGTCTCCTCTGACAAAGGGCATCCTGGG
CTTCGTGTTTACCCTGACCGTGCCTTCTGAGAGAGGACTTAGCTGCATTAGCGAAGCGGATGCGACCACCCCGG
AAAGCGCGAACCTGGGCGAAGAAATTCTGAGCCAGCTGTATCTTTGGCCAAGGGTGACCTACCATTCCCCTAGT
TATGCTTACCACCAATTTGAAAGACGAGCCAAATATAAAAGACACTTCCCCGGCTTTGGCCAGAGCTGCTGTT
TGGCTACCCTGTGTACGTGTTCGGCGATTGCGTGCAGGGCGATTGGGATGCGATTCGCTTTCGCTATTGCGCGC
CGCCGGGCTATGCGCTGCTGCGCTGCAACGATACCAACTATAGCGCTCTGCTGGCTGTGGGGGCCCTAGAAGGA
CCCAGGAATCAGGACTGGCTTGGTGTCCCAAGACAACTTGTAACTCGGATGCAGGCTATTCAGAATGCCGGCCT
GTGTACCCTGGTGGCCATGCTGGAAGAGACAATCTTCTGGCTGCAAGCGTTTCTGATGGCGCTGACCGATAGCG
GCCCGAAAACCAACATTATTGTGGATAGCCAGTATGTGATGGGCATTAGCAAACCGAGCTTTCAGGAATTTGTG
GATTGGGAAAACGTGAGCCCGGAACTGAACAGCACCGATCAGCCCGTTTTGGCAAGCCGGAATCCTGGCCAGAAA
TCTGGTGCCTATGGTGGCCACAGTGCAGGGCCAGAACCTGAAGTACCAGGGTCAGTCACTAGTCATCTCTGCTT
CTATCATTGTCTTCAACCTGCTGGAACTGGAAGGTGATTATCGAGATGATGGCAACGTGTGGGTGCATACCCCG
CTGAGCCCGCGCACCCTGAACGCGTGGGTGAAAGCGGTGGAAGAAAAAAAAGGTATTCCAGTTCACCTAGAGCT
GGCCAGTATGACCAACATGGAGCTCATGAGCAGTATTGTGCATCAGGCTCAGAACATACGGCCCCGTGTTCA
TGTGTCTCGGCGGACTGCTTACAATGGTGGCTGGTGCTGTGTGGCTGACAGTGCGAGTGCTCGAGCTGTTCGG
GCCGCGCAGCTGGCCAACGACGTGGTCCTCCAGATCATGGAGCTTTGTGGTGCAGCGTTTCGCCAGGTGTGCCA
TACCACCGTGCCGTGGCCGAACGCGAGCCTGACCCCGAAATGGAACAACGAAACCACCCAGCCCCAGATCGCCA
ACTGCAGCGTGTATGACTTTTTTGTGTGGCTCCATTATTATTCTGTTCGAGACACACTTTGGCCAAGGGTGACC
TACCATATGAACAAATATGCGTATCATATGCTGGAAAGACGAGCCAAATATAAAAGAGGACCAGGACCTGGCGC
TAAATTTGTGGCCGCCTGGACACTGAAAGCGCTGCTGGTCCTGGACCTGGCCAGTACATCAAGGCCAACAGCA
AGTTCATCGGCATCACCGAACTCGGACCCGGACCAGGCTGATGATTcgaacggccgtatcacgcccaaacattt
acagccgcggtgtcaaaaaccgcgtggacgtggttaacatccctgctgggaggatcagccgtaattattataat
tggcttggtgctggctactattgtggccatgtacgtgctgaccaaccagaaacataattgaatacagcagcaat
tggcaagctgcttacatagaactcgcggcgattggcatgccgccttaaaattttttattttattttttcttttct
tttccgaatcggatttttgttttttaatatttcaaaaaaaaaaaaaaaaaaaaaaaaaaaaaaaaaaaaaaaa
aaaaaaaaaaaaaaaaaaaaaaaaaaaaaaaaaaaa Venezuelan equine encephalitis virus strain TC-83 [TC-83] (SEQ ID NO: 5)
GenBank: L01443.1
ATAGGCGGCGCATGAGAGAAGCCCAGACCAATTACCTACCCAAAATGGAGAAAGTTCACG
TTGACATCGAGGAAGACAGCCCATTCCTCAGAGCTTTGCAGCGGAGCTTCCCGCAGTTTG
AGGTAGAAGCCAAGCAGGTCACTGATAATGACCATGCTAATGCCAGAGCGTTTTCGCATC
TGGCTTCAAAACTGATCGAAACGGAGGTGGACCCATCCGACACGATCCTTGACATTGGAA
GTGCGCCCGCCCGCAGAATGTATTCTAAGCACAAGTATCATTGTATCGTCCGATGAGAT
GTGCGGAAGATCCGGACAGATTGTATAAGTATGCAACTAAGCTGAAGAAAAACTGTAAGG
AAATAACTGATAAGGAATTGGACAAGAAAATGAAGGAGCTCGCCGCCGTCATGAGCGACC
CTGACCTGGAAACTGAGACTATGTGCCTCCACGACGACGAGTCGTGTCGCTACGAAGGGC
AAGTCGCTGTTTACCAGGATGTATACGCGGTTGACGGACCGACAAGTCTCTATCACCAAG
CCAATAAGGGAGTTAGAGTCGCCTACTGGATAGGCTTTGACACCACCCCCTTTATGTTTA
AGAACTTGGCTGGAGCATATCCATCATACTCTACCAACTGGGCCGACGAAACCGTGTTAA
CGGCTCGTAACATAGGCCTATGCAGCTCTGACGTTATGGAGCGGTCACGTAGAGGGATGT
CCATTCTTAGAAAGAAGTATTTGAAACCATCCAACAATGTTCTATTCTCTGTTGGCTCGA
CCATCTACCACGAGAAGAGGGACTTACTGAGGAGCTGGCACCTGCCGTCTGTATTTCACT
TACGTGGCAAGCAAAATTACACATGTCGGTGTGAGACTATAGTTAGTTGCGACGGGTACG
TCGTTAAAAGAATAGCTATCAGTCCAGGCCTGTATGGGAAGCCTTCAGGCTATGCTGCTA
CGATGCACCGCGAGGGATTCTTGTGCTGCAAAGTGACAGACACATTGAACGGGGAGAGGG
TCTCTTTTCCCGTGTGCACGTATGTGCCAGCTACATTGTGTGACCAAATGACTGGCATAC
TGGCAACAGATGTCAGTGCGGACGACGCGCAAAACTGCTGGTTGGGTCAACCAGCGTA
TAGTCGTCAACGGTCGCACCCAGAGAAACACCAATACCATGAAAAATTACCTTTTGCCCG
TAGTGGCCCAGGCATTTGCTAGGTGGGCAAAGGAATATAAGGAAGATCAAGAAGATGAAA
GGCCACTAGGACTACGAGATAGACAGTTAGTCATGGGTGTTGTTGGGCTTTTAGAAGGC
ACAAGATAACATCTATTTATAAGCGCCGGATACCCAAACCATCATCAAAGTGAACAGCG
ATTTCCACTCATTCGTGCTGCCCAGGATAGGCAGTAACACATTGGAGATCGGGCTGAGAA
CAAGAATCAGGAAATGTTAGAGGAGCACAAGGAGCCGTCACCTCTCATTACCGCCGAGG
ACGTACAAGAAGCTAAGTGCGCAGCCGATGAGGCTAAGGAGGTGCGTGAAGCCGAGGAGT
TGCGCGCAGCTCTACCACCTTTGGCAGCTGATGTTGAGGAGCCCACTCTGGAAGCCGATG
TCGACTTGATGTTACAAGAGGCTGGGGCCGGCTCAGTGGAGACACCTCGTGGCTTGATAA
AGGTTACCAGCTACGCTGGCGAGGACAAGATCGGCTCTTACGCTGTGCTTTCTCCGCAGG
CTGTACTCAAGAGTGAAAAATTATCTTGCATCCACCCTCTCGCTGAACAAGTCATAGTGA
```

```
TAACACACTCTGGCCGAAAAGGGCGTTATGCCGTGGAACCATACCATGGTAAAGTAGTGG
TGCCAGAGGGACATGCAATACCCGTCCAGGACTTTTCAAGCTCTGAGTGAAAGTGCCACCA
TTGTGTACAACGAACGTGAGTTCGTAAACAGGTACCTGCACCATATTGCCACACATGGAG
GAGCGCTGAACACTGATGAAGAATATTACAAAACTGTCAAGCCCAGCGAGCACGACGGCG
AATACCTGTACGACATCGACAGGAAACAGTGCGTCAAGAAAGAACTAGTCACTGGGCTAG
GGCTCACAGGCGAGCTGGTGGATCCTCCCTTCCATGAATTCGCCTACGAGAGTCTGAGAA
CACGACCAGCCGCTCCTTACCAAGTACCAACCATAGGGGTGTATGGCGTGCCAGGATCAG
GCAAGTCTGGCATCATTAAAGCGCAGTCACCAAAAAAGATCTAGTGGTGAGCGCCAAGA
AAGAAAACTGTGCAGAAATTATAAGGGACGTCAAGAAAATGAAAGGGCTGGACGTCAATG
CCAGAACTGTGGACTCAGTGCTCTTGAATGGATGCAAACACCCCGTAGAGACCCTGTATA
TTGACGAAGCTTTTGCTTGTCATGCAGGTACTCTCAGAGCGCTCATAGCCATTATAAGAC
CTAAAAAGGCAGTGCTCTGCGGGGATCCCAAACAGTGCGGTTTTTTTAACATGATGTGCC
TGAAAGTGCATTTTAACCACGAGATTTGCACACAAGTCTTCCACAAAAGCATCTCTCGCC
GTTGCACTAAATCTGTGACTTCGGTCGTCTCAACCTTGTTTTACGACAAAAAAATGAGAA
CGACGAATCCGAAAGAGACTAAGATTGTGATTGACACTACCGGCAGTACCAAACCTAAGC
AGGACGATCTCATTCTCACTTGTTTCAGAGGGTGGGTGAAGCAGTTGCAAATAGATTACA
AAGGCAACGAAATAATGACGGCAGCTGCCTCTCAAGGGCTGACCCGTAAAGGTGTGTATG
CCGTTCGGTACAAGGTGAATGAAAATCCTCTGTACGCACCCACCTCAGAACATGTGAACG
TCCTACTGACCCGCACGGAGGACCGCATCGTGTGGAAAACACTAGCCGGCGACCCATGGA
TAAAAACACTGACTGCCAAGTACCCTGGGAATTTCACTGCCACGATAGAGGAGTGGCAAG
CAGAGCATGATGCCATCATGAGGCACATCTTGGAGAGACCGGACCCTACCGACGTCTTCC
AGAATAAGGCAAACGTGTGTTGGGCCAAGGCTTTAGTGCCGGTGCTGAAGACCGCTGGCA
TAGACATGACCACTGAACAATGGAACACTGTGGATTATTTTGAAACGGACAAAGCTCACT
CAGCAGAGATAGTATTGAACCAACTATGCGTGAGGTTCTTTGGACTCGATCTGGACTCCG
GTCTATTTTCTGCACCCACTGTTCCGTTATCCATTAGGAATAATCACTGGGATAACTCCC
CGTCGCCTAACATGTACGGGCTGAATAAAGAAGTGGTCCGTCAGCTCTCTCGCAGGTACC
CACAACTGCCTCGGGCAGTTGCCACTGGAAGAGTCTATGACATGAACACTGGTACACTGC
GCAATTATGATCCGCGCATAAACCTAGTACCTGTAAACAGAAGACTGCCTCATGCTTTAG
TCCTCCACCATAATGAACACCCACAGAGTGACTTTTCTTCATTCGTCAGCAAATTGAAGG
GCAGAACTGTCCTGGTGGTCGGGGAAAAGTTGTCCGTCCCAGGCAAATGGTTGACTGGT
TGTCAGACCGGCCTGAGGCTACCTTCAGAGCTCGGCTGGATTTAGGCATCCCAGGTGATG
TGCCCAAATATGACATAATATTTGTTAATGTGAGGACCCCATATAAATACCATCACTATC
AGCAGTGTGAAGACCATGCCATTAAGCTTAGCATGTTGACCAAGAAAGCTTGTCTGCATC
TGAATCCCGGCGGAACCTGTGTCAGCATAGGTTATGGTTACGCTGACAGGGCCAGCGAAA
GCATCATTGGTGCTATAGCGCGGCAGTTCAAGTTTTCCCGGGTATGCAAACCGAAATCCT
CACTTGAAGAGACGGAAGTTCTGTTTGTATTCATTGGGTACGATCGCAAGGCCCGTACGC
ACAATCCTTACAAGCTTTCATCAACCTTGACCAACATTTATACAGGTTCCAGACTCCACG
AAGCCGGATGTGCACCCTCATATCATGTGGTGCGAGGGGATATTGCCACGGCCACCGAAG
GAGTGATTATAAATGCTGCTAACAGCAAAGGACAACCTGGCGGAGGGGTGTGCGGAGCGC
TGTATAAGAAATTCCCGGAAAGCTTCGATTTACAGCCGATCGAAGTAGGAAAAGCGCGAC
TGGTCAAAGGTGCAGCTAAACATATCATTCATGCCGTAGGACCAAACTTCAACAAAGTTT
CGGAGGTTGAAGGTGACAAACAGTTGGCAGAGGCTTATGAGTCCATCGCTAAGATTGTCA
ACGATAACAATTACAAGTCAGTAGCGATTCCACTGTTGTCCACCGGCATCTTTTCCGGGA
ACAAAGATCGACTAACCCAATCATTGAACCATTTGCTGACAGCTTTAGACACCACTGATG
CAGATGTAGCCATATACTGCAGGGACAAGAAATGGGAAATGACTCTCAAGGAAGCAGTGG
CTAGGAGAGAAGCAGTGGAGGAGATATGCATATCCGACGACTCTTCAGTGACAGAACCTG
ATGCAGAGCTGGTGAGGGTGCATCCGAAGAGTTCTTTGGCTGGAAGGAAGGGCTACAGCA
CAAGCGATGGCAAAACTTTCTCATATTTGGAAGGGACCAAGTTTCACCAGGCGGCCAAGG
ATATAGCAGAAATTAATGCCATGTGGCCCGTTGCAACGGAGGCCAATGAGCAGGTATGCA
TGTATATCCTCGGAGAAAGCATGAGCAGTATTAGGTCGAAATGCCCCGTCGAAGAGTCGG
AAGCCTCCACACCACCTAGCACGCTGCCTTGCTTGTGCATCCATGCCATGACTCCAGAAA
GAGTACAGCGCCTAAAAGCCTCACGTCCAGAACAAATTACTGTGTGCTCATCCTTTCCAT
TGCCGAAGTATAGAATCACTGGTGTGCAGAAGATCCAATGCTCCCAGCCTATATTGTTCT
CACCGAAAGTGCCTGCGTATATTCATCCAAGGAAGTATCTCGTGAAACACCACCGGTAG
ACGAGACTCCGGAGCCATCGGCAGAGAACCAATCCACAGAGGGGACACCTGAACAACCAC
CACTTATAACCGAGGATGAGACCAGGACTAGAACGCCTGAGCCGATCATCATCGAAGAGG
AAGAAGAGGATAGCATAAGTTTGCTGTCAGATGGCCCGACCCACCAGGTGCTGCAAGTCG
AGGCAGACATTCACGGGCCGCCCTCTGTATCTAGCTCATCCTGGTCCATTCCTCATGCAT
CCGACTTTGATGTGGACAGTTTATCCATACTTGACACCCTGGAGGGAGCTAGCGTGACCA
GCGGGGCAACGTCAGCCGAGACTAACTCTTACTTCGCAAAGAGTATGGAGTTTCTGGCGC
GACCGGTGCCTGCGCCTCGAACAGTATTCAGGAACCCTCCACATCCCGCTCCGCGCACAA
GAACACCGTCACTTGCACCCAGCAGGGCCTGCTCGAGAACCAGCCTAGTTTCCACCCCGC
CAGGCGTGAATAGGGTGATCACTAGAGAGGAGCTCGAGGCGCTTACCCCGTCACGCACTC
CTAGCAGGTCGGTCTCGAGAACCAGCCTGGTCTCCAACCCGCCAGGCGTAAATAGGGTGA
TTACAAGAGAGGAGTTTGAGGCGTTCGTAGCACAACAACAATGACGGTTTGATGCGGGTG
CATACATCTTTTCCTCCGACACCGGTCAAGGGCATTTACAACAAAAATCAGTAAGGCAAA
CGGTGCTATCCGAAGTGGTGTTGGAGAGGACCGAATTGGAGATTTCGTATGCCCCGCGCC
TCGACCAAGAAAAGAAGAATTACTACGCAAGAAATTACAGTTAAATCCCACACCTGCTA
ACAGAAGCAGATACCAGTCCAGGAAGGTGGAGAACATGAAAGCCATAACAGCTAGACGTA
TTCTGCAAGGCCTAGGGCATTATTTGAAGGCAGAAGGAAAGTGGAGTGCTACCGAACCC
TGCATCCTGTTCCTTTGTATTCATCTAGTGTGAACCGTGCCTTTTCAAGCCCCAAGGTCG
CAGTGGAAGCCTGTAACGCCATGTTGAAAGAGAACTTTCCGACTGTGGCTTCTTACTGTA
TTATTCCAGAGTACGATGCCTATTTGGACATGGTTGACGGAGCTTCATGCTGCTTAGACA
CTGCCAGTTTTTGCCCTGCAAAGCTGCGCAGCTTTCCAAAGAAACACTCCTATTTGGAAC
CCACAATACGATCGGCAGTGCCTTCAGCGATCCAGAACACGCTCCAGAACGTCCTGGCAG
CTGCCACAAAAAGAAATTGCAATGTCACGCAAATGAGAGAATTGCCCGTATTGGATTCGG
CGGCCTTTAATGTGGAATGCTTCAAGAAATATGCGTGTAATAATGAATATTGGGAAACGT
TTAAAGAAAACCCCATCAGGCTTACTGAAGAAAACGTGGTAAATTACATTACCAAATTAA
AAGGACCAAAAGCTGCTGCTCTTTTTGCGAAGACACATAATTTGAATATGTTGCAGGACA
```

-continued

```
TACCAATGGACAGGTTTGTAATGGACTTAAAGAGAGACGTGAAAGTGACTCCAGGAACAA
AACATACTGAAGAACGGCCCAAGGTACAGGTGATCCAGGCTGCCGATCCGCTAGCAACAG
CGTATCTGTGCGGAATCCACCGAGAGCTGGTTAGGAGATTAAATGCGGTCCTGCTTCCGA
ACATTCATACACTGTTTGATATGTCGGCTGAAGACTTTGACGCTATTATAGCCGAGCACT
TCCAGCCTGGGGATTGTGTTCTGGAAACTGACATCGCGTCGTTTGATAAAAGTGAGGACG
ACGCCATGGCTCTGACCGCGTTAATGATTCTGGAAGACTTAGGTGTGGACGCAGAGCTGT
TGACGCTGATTGAGGCGGCTTTCGGCGAAATTTCATCAATACATTTGCCCACTAAAACTA
AATTTAAATTCGGAGCCATGATGAAATCTGGAATGTTCCTCACACTGTTTGTGAACACAG
TCATTAACATTGTAATCGCAAGCAGAGTGTTGAGAGAACGGCTAACCGGATCACCATGTG
CAGCATTCATTGGAGATGACAATATCGTGAAAGGAGTCAAATCGGACAAATTAATGGCAG
ACAGGTGCGCCACCTGGTTGAATATGGAAGTCAAGATTATAGATGCTGTGGTGGGCGAGA
AAGCGCCTTATTTCTGTGGAGGGTTTATTTTGTGTGACTCCGTGACCGGCACAGCGTGCC
GTGTGGCAGACCCCCTAAAAAGGCTGTTTAAGCTTGGCAAACCTCTGGCAGCAGACGATG
AACATGATGATGACAGGAGAAGGGCATTGCATGAAGAGTCAACACGCTGGAACCGAGTGG
GTATTCTTTCAGAGCTGTGCAAGGCAGTAGAATCAAGGTATGAAACCGTAGGAACTTCCA
TCATAGTTATGGCCATGACTACTCTAGCTAGCAGTGTTAAATCATTCAGCTACCTGAGAG
GGGCCCCTATAACTCTCTACGGCTAACCTGAATGGACTACGACATAGTCTAGTCCGCCAA
GATGTTCCCGTTCCAGCCAATGTATCCGATGCAGCCAATGCCCTATCGCAACCCGTTCGC
GGCCCCGCGCAGGCCCTGGTTCCCCAGAACCGACCCTTTTCTGGCGATGCAGGTGCAGGA
ATTAACCCGCTCGATGGCTAACCTGACGTTCAAGCAACGCCGGGACGCGCCACCTGAGGG
GCCATCCGCTAAGAAACCGAAGAAGGAGGCCTCGCAAAAACAGAAAGGGGGAGGCCAAGG
GAAGAAGAAGAAGAACCAAGGGAAGAAGAAGGCTAAGACAGGGCCGCCTAATCCGAAGGC
ACAGAATGGAAACAAGAAGAAGACCAACAAGAAACCAGGCAAGAGACAGCGCATGGTCAT
GAAATTGGAATCTGACAAGACGTTCCCAATCATGTTGGAAGGGAAGATAAACGGCTACGC
TTGTGTGGTCGGAGGGAAGTTATTCAGGCCGATGCATGTGGAAGGCAAGATCGACAACGA
CGTTCTGGCCGCGCTTAAGACGAAGAAAGCATCCAAATACGATCTTGAGTATGCAGATGT
GCCACAGAACATGCGGGCCGATACATTCAAATACACCCATGAGAAACCCCAAGGCTATTA
CAGCTGGCATCATGGAGCAGTCCAATATGAAAATGGGCGTTTCACGGTGCCGAAAGGAGT
TGGGGCAAGGGAGACAGCGGACGACCCATTCTGGATAACCAGGGACGGGTGGTCGCTAT
TGTGCTGGGAGGTGTGAATGAAGGATCTAGGACAGCCCTTTCAGTCGTCATGTGGAACGA
GAAGGGAGTTACCGTGAAGTATACTCCGGAGAACTGCGAGCAATGGTCACTAGTGACCAC
CATGTGTCTGCTCGCCAATGTGACGTTCCCATGTGCTCAACCACCAATTTGCTACGACAG
AAAACCAGCAGAGACTTTGGCCATGCTCAGCGTTAACGTTGACAACCCGGGCTACGATGA
GCTGCTGGAAGCAGCTGTTAAGTGCCCCGGAAGGAAAAGGAGATCCAACGGAGGAGCTGTT
TAAGGAGTATAAGCTAACGCGCCCTTACATGGCCAGATGCATCAGATGTGCAGTTGGGAG
CTGCCATAGTCCAATAGCAATCGAGGCAGTAAAGAGCGACGGGCACGACGGTTATGTTAG
ACTTCAGACTTCCTCGCAGTATGGCCTGGATTCCTCCGGCAACTTAAAGGGCAGGACCAT
GCGGTATGACATGCACGGGACCATTAAAGAGATACCACTACATCAAGTGTCACTCCATAC
ATCTCGCCCGTGTCACATTGTGGATGGGCACGGTTATTTCCTGCTTGCCAGGTGCCCGGC
AGGGGACTCCATCACCATGGAATTTAAGAAAGATTCCGTCACACACTCCTGCTCGGTGCC
GTATGAAGTGAAATTTAATCCTGTAGGCAGAGAACTCTATACTCATCCCCCAGAACACGG
AGTAGAGCAAGCGTGCCAAGTCTACGCACATGATGCACAGAACAGAGGAGCTTATGTCGA
GATGCACCTCCCGGGCTCAGAAGTGGACAGCAGTTTGGTTTCCTTGAGCGGCAGTTCAGT
CACCGTGACACCTCCTGTTGGGACTAGCGCCCTGGTGGAATGCGAGTGTGGCGGCACAAA
GATCTCCGAGACCATCAACAAGACAAAACAGTTCAGCCAGTGCACAAAGAAGGAGCAGTG
CAGAGCATATCGGCTGCAGAACGATAAGTGGGTGTATAATTCTGACAAACTGCCCAAAGC
AGCGGGAGCCACCTTAAAAGGAAAACTGCATGTCCCATTCTTGCTGGCAGACGGCAAATG
CACCGTGCCTCTAGCACCAGAACCTATGATAACCCTTTGGTTTCAGATCAGTGTCACTGAA
ACTGCACCCTAAGAATCCCACATATCTAACCACCCGCCAACTTGCTGATGAGCCTCACTA
CACGCACGAGCTCATATCTGAACCAGCTGTTAGGAATTTTACCGTCACCGAAAAGGGTG
GGAGTTTGTATGGGAAACCACCCGCCGAAAAGGTTTTGGGCACAGGAAACAGCACCCGG
AAATCCACATGGGCTACCGCACGAGGTGATAACTCATTATTACCACAGATACCCTATGTC
CACCATCCTGGGTTTGTCAATTTGTGCCGCCATTGCAACCGTTTCCGTTGCAGCGTCTAC
CTGGCTGTTTTGCAGATCTAGAGTTGCGTGCCTAACTCCTTACCGGCTAACACCTAACGC
TAGGATACCATTTTGTCTGGCTGTGCTTTGCTGCGCCCGCACTGCCCGGGCCGAGACCAC
CTGGGAGTCCTTGGATCACCTATGGAACAATAACCAACAGATGTTCTGGATTCAATTGCT
GATCCCTCTGGCCGCCTTGATCGTAGTGACTCGCCTGCTCAGGTGCGTGTGCTGTGTCGT
GCCTTTTTTAGTCATGGCCGGCGCCGCAGGCGCCGGCGCCTACGAGCACGCGACCACGAT
GCCGAGCCAAGCGGGAATCTCGTATAACACTATAGTCAACAGAGCAGGCTACGCACCACT
CCCTATCAGCATAACACCAACAAAGATCAAGCTGATACCTACAGTGAACTTGGAGTACGT
CACCTGCCACTACAAAACAGGAATGGATTCACCAGCCATCAAATGCTGCGGATCTCAGGA
ATGCACTCCAACTTACAGGCCTGATGAACAGTGCAAAGTCTTCACAGGGGTTTACCCGTT
CATGTGGGGTGGTGCATATTGCTTTTGCGACACTGAGAACACCCAAGTCAGCAAGGCCTA
CGTAATGAAATCTGACGACTGCCTTGCGGATCATGCTGAAGCATATAAAGCGCACACAGC
CTCAGTGCAGGCGTTCCTCAACATCACAGTGGGAGAACACTCTATTGTGACTACCGTGTA
TGTGAATGGAGAAACTCCTGTGAATTTCAATGGGGTCAAATTAACTGCAGGTCCGCTTTC
CACAGCTTGGACACCCTTTGATCGCAAAATCGTGCAGTATGCCGGGGAGATCTATAATTA
TGATTTTCCTGAGTATGGGCAGGACAACCAGGAGCATTTGGAGATATACAATCCAGAAC
AGTCTCAAGCTCAGATCGTATGCCAATACCAACCTAGTGCTGCAGAGACCCAAAGCAGG
AGCGATCCACGTGCCATACACTCAGGCACCTTCGGGTTTTGAGCAATGGAAGAAAGATAA
AGCTCCATCATTGAAATTTACCGCCCCTTTCGGATGCGAAATATATACAAACCCCATTCG
CGCCGAAAACTGTGCTGTAGGGTCAATTCCATTAGCCTTTGACATTCCCGACGCCTTGTT
CACCAGGGTGTCAGAAACACCGACACTTTCAGCGGCCGAATGCACTCTTAACGAGTGCGT
GTATTCTTCCGACTTTGGTGGGATCGCCACGGTCAAGTACTCGGCCAGCAAGTCAGGCAA
GTGCGCAGTCCATGTGCCATCAGGGACTGCTACCCTAAAAGAAGCAGCAGTCGAGCTAAC
CGAGCAAGGGTCGGCGACTATCCATTTCTCGACCGCAAATATCCACCCGGAGTTCAGGCT
CCAAATATGCACATCATATGTTACGTGCAAAGGTGATTGTCACCCCCGAAAGACCCATAT
TGTGACACACCCTCAGTATCACGCCCAAACATTTACAGCCGCGGTGTCAAAAACCGCGTG
GACGTGGTTAACATCCCTGCTGGGAGGATCAGCCGTAATTATTATAATTGGCTTGGTGCT
```

-continued

```
GGCTACTATTGTGGCCATGTACGTGCTGACCAACCAGAAACATAATTGAATACAGCAGCA
ATTGGCAAGCTGCTTACATAGAACTCGCGGCGATTGGCATGCCGCCTTAAAATTTTTATT
TTATTTTTTCTTTTCTTTTCCGAATCGGATTTTGTTTTTAATATTTC
```

VEE Delivery Vector (SEQ ID NO: 6); VEE genome with nucleotides 7544-11175
deleted [alphavirus structural proteins removed]

```
ATGggcggcgcatgagagaagcccagaccaattacctacccaaaATGGagaaagttcacgttgacatcgaggaa
gacagcccattcctcagagctttgcagcggagcttcccgcagtttgaggtagaagccaagcaggtcactgataa
tgaccatgctaatgccagagcgttttcgcatctggcttcaaaactgatcgaaacggaggtggacccatccgaca
cgatccttgacattggaagtgcgcccgcccgcagaatgtattctaagcacaagtatcattgtatctgtccgatg
agatgtgcggaagatccggacagattgtataagtatgcaactaagctgaagaaaaactgtaaggaaataactga
taaggaattggacaagaaaatgaaggagctcgccgccgtcatgagcgaccctgacctggaaactgagactatgt
gcctccacgacgacgagtcgtgtcgctacgaagggcaagtcgctgtttaccaggatgtatacgcggttgacgga
ccgacaagtctctatcaccaagccaataagggagttagagtcgcctactggataggctttgacaccaccccttt
tatgtttaagaacttggctggagcatatccatcatactctaccaactgggccgacgaaaccgtgttaacggctc
gtaacataggcctatgcagctctgacgttatggagcggtcacgtagagggatgtccattcttagaaagaagtat
ttgaaaccatccaacaatgttctattctctgttggctcgaccatctaccacgagaaggggacttactgaggag
ctggcacctgccgtctgtatttcacttacgtggcaagcaaaattacacatgtcggtgtgagactatagttagtt
gcgacgggtacgtcgttaaaagaatagctatcagtccaggcctgtatggaagccttcaggctatgctgctacg
atgcaccgcgagggattcttgtgctgcaaagtgacagacacattgaacggggagagggtctcttttcccgtgtg
cacgtatgtgccagctacattgtgtgaccaaatgactggcatactggcaacagatgtcagtgcggacgacgcgc
aaaaactgctggttgggctcaaccagcgtatagtcgtcaaccgtcgcacccagagaaacaccaataccatgaa
aattaccttttgcccgtagtggcccaggcatttgctaggtgggcaaaggaatataaggaagatcaagaagatga
aaggccactaggactacgagatagacagttagtcatgggggtgttgttgggcttttagaaggcacaagataacat
ctatttataagcgcccggataccaaaccatcatcaaagtgaacagcgatttccactcattcgtgctgcccagg
ataggcagtaacacattggagatcgggctgagaacaagaatcaggaaaatgttagaggagcacaaggagccgtc
acctctcattaccgccgaggacgtacaagaagctaagtcgcgcagccgatgaggctaaggaggtgcgtgaagccg
aggagttgcgcgcagctctaccaccttggcagctgatgttgaggagcccactctggaagccgatgtcgacttg
atgttacaagaggctggggccggctcagtggagacacctcgtggcttgataaaggttaccagctacgctggcga
ggacaagatcggctcttacgctgtgctttctccgcaggctgtactcaagagtgaaaattatcttgcatccacc
ctctcgctgaacaagtcatagtgataacacactctggccgaaaagggcgttatgccgtggaaccataccatggt
aaagtagtggtgccagagggacatgcaatacccgtccaggactttcaagctctgagtgaaagtgccaccattgt
gtacaacgaacgtgagttcgtaaacaggtacctgcaccatattgccacacatggaggagcgctgaacactgatg
aagaatattacaaaactgtcaagcccagcgagcacgacggcgaatacctgtacgactgtgacaggaaacagtgc
gtcaagaaagaactagtcactgggctagggctcacaggcgagctggtcgatcctcccttccatgaattcgccta
cgagagtctgagaacacgaccagccgctccttaccaagtaccaaccatagggtgtatggcgtgccaggatcag
gcaagtctggcatcattaaaagcgcagtcaccaaaaaagatctagtggtgagcgccaagaaagaaactgtgca
gaaattataagggacgtcaagaaaatgaaagggctggacgtcaatgccagaactgtggactcagtgctcttgaa
tggatgcaaacaccccgtagagaccctgtatattgacgaagcttttgcttgtcatgcaggtactctcagagcgc
tcatagccattataagacctaaaaaggcagtgctctgcggggatcccaaacagtgcggtttttttaacatgatg
tgcctgaaagtgcatttttaaccacgagatttgcacacaagtcttccacaaaagcatctctcgccgttgcactaa
atctgtgacttcggtcgtctcaaccttgttttacgacaaaaaatgagaacgacgaatccgaaagagactaaga
ttgtgattgacactaccggcagtaccaaacctaagcaggacgatctcattctcacttgtttcagagggtgaataaag
aagcagttgcaaatagattacaaaggcaacgaaataatgacggcagctgcctctcaagggctgaccgtaaagg
tgtgtatgccgttcggtacaaggtgaatgaaaatcctctgtacgcacccacctcagaacatgtgaacgtcctac
tgacccgcacggaggaccgcatcgtgtggaaaacactagccggcgacccatggataaaaacactgactgccaag
taccctgggaatttcactgccacgatagaggatggcaagcagagcagatgatgccatcatgagggcacatcttgga
gagaccggaccctaccgacgtcttccagaataaggcaaacgtgtgttgggcaaggctttagtgccggtgctga
agaccgctggcatagacatgaccactgaacaatgaacactgtggattattttgaaacggacaaagctcactca
gcagagatagtattgaaccaactatgcgtgaggttctttggactcgatctggactccggtctattttctgcacc
cactgttccgttatccattaggaataatcactgggataactccccgtgccgtcggtgccggggctgaataaag
aagtggtccgtcagctctctcgcaggtacccacaactgcctcgggcagttgccactggaagagtctatgacatg
aacactggtacactgcgcaattatgatccgcgcataaaacctagtacctgtaaacagaagactgcctcatgcttt
agtcctccaccataatgaacacccacagagtgacttttcttcattcgtcagcaaattgaagggcagaactgtcc
tggtggtcggggaaaagttgtccgtcccaggcaaaatggttgactggttgtcagaccggcctgaggctaccttc
agagctcggctggatttaggcatcccaggtgatgtgcccaaatatgacataatattgttaatgtgaggaccccc
atataaataccatcactatcagcagtgtgaagaccatgccattaagcttagcatgttgaccaagaaagcttgtc
tgcatctgaatcccggcggaacctgtgtcagcataggttatggttacgctgacagggccagcgaaagcatcatt
ggtgctatagccgcggcagttcaagttttcccgggtatgcaaaccgaaatcctcacttgaagagacggaagttct
gtttgtattcattgggtacgatcgcaaggcccgtacgcacaatccttacaagctttcatcaacctttgaccaaca
tttatacaggttccagactccacgaagccggatgtgcaccctcatatcatgtggtcgcagggggatattgccacg
gccaccgaaggagtgattataaatgctgctaacagcaaaggacaacctggcggaggggtgtgcggagcgctgta
taagaaatttcccggaaagcttcgatttacagccgatcgaagtaggaaaagcgcgactggtcaaaggtgcagcta
aacatatcattcatgccgtaggaccaaacttcaacaaagtttcgaaggttgaaggtgacaaacagttggcagag
gcttatgagtccatcgctaagattgtcaacgataacaattacaagtcagtacgcgattccactgttgtccaccgg
catcttttccgggaacaaagatcgactaacccaatcattgaaccatttgctgacagctttagacaccactgatg
cagatgtagccatatactgcagggacaagaaatgggaaatgactctcaaggaagcagtggctaggagagaagca
gtggaggagatgcatatccgacgactcttcagtgacagaacctgatgcagagctggtgagggtgcatccgaa
gagttctttggctggaaggaagggctacagcaaagcgatcgcaaaatttctcatatttgaaggaccaagt
ttcaccaggcggccaaggatatagcagaaattaatgccatgtggcccgttgcaacgaggccaatgagcaggta
tgcatgtatatcctcggagaaagcatgagcagtattaggtcgaaatgccccgtcgaaagtcggaagcctccac
accacctagcacgctgccttgcttgtgcatccatgccatgactccagaaagagtacagcgcctaaaagcctcac
gtccagaacaaattactgtgtgctcatcctttccattgccgaagtataganatcactggtgtgcagaagatccaa
tgctcccagcctatattgttctcaccgaaagtgcctgcgtatattcatcaaggaagtatctcgtggaaacacc
accggtagacgagactccggagccatcggcagaacccaatccacagaggggacacctgaacaaccaccactta
taaccgaggatgagaccaggactagaacgcctgagccgatcatcatcgaagaggaagaaggaataagcataagt
ttgctgtcagatggcccgacccaccaggtgctgcaagtcgaggcagacattcacgggccgccctctgtatctag
ctcatcctggtccattcctcatgcatccgactttgatgtggacagttatccatacttgacaccctggagggag
ctagcgtgaccagcggggcaacgtcagccgagactaactcttacttcgcaaagagtatggagtttctggcgcga
```

-continued ccggtgcctgcgcctcgaacagtattcaggaaccctccacatcccgctccgcgcacaagaacaccgtcacttgc
acccagcagggcctgctcgagaaccagcctagtttccaccccgccaggcgtgaatagggtgatcactagagagg
agctcgaggcgcttaccccgtcacgcactcctagcaggtcggtctcgagaaccagcctggtctccaacccgcca
ggcgtaaatagggtgattacaagagaggagtttgaggcgttcgtagcacaacaacaatgacggtttgatgcggg
tgcatacatcttttcctccgacaccggtcaagggcatttacaacaaaaatcagtaaggcaaacggtgctatccg
aagtggtgttggagaggaccgaattggagatttcgtatgccccgcgcctcgaccaagaaaaagaagaattacta
cgcaagaaattacagttaaatcccacacctgctaacagaagcagataccagtccaggaaggtggagaacatgaa
agccataacagctagacgtattctgcaaggcctagggcattatttgaaggcagaaggaaaagtggagtgctacc
gaaccctgcatcctgttcctttgtattcatctagtgtgaaccgtgccttttcaagccccaaggtcgcagtggaa
gcctgtaacgccatgttgaaagagaactttccgactgtggcttcttactgtattattccagagtacgatgccta
tttggacatggttgacggagcttcatgctgcttagacactgccagtttttgccctgcaaagctgcgcagctttc
caaagaaacactcctatttggaacccacaatacgatcggcagtgccttcagcgatccagaacacgctccagaac
gtcctggcagctgccacaaaaagaaattgcaatgtcacgcaaatgagagaattgcccgtattggattcggcggc
ctttaatgtggaatgcttcaagaaatatgcgtgtaataatgaatattgggaaacgtttaaagaaaccccatca
ggcttactgaagaaaacgtggtaaattacattaccaaattaaaaggaccaaaagctgctgctctttttgcgaag
acacataatttgaatatgttgcaggacataccaatggacaggtttgtaatggacttaaagagagacgtgaaagt
gactccaggaacaaaacatactgaagaacggcccaaggtacaggtgatccaggctgccgatccgctagcaacag
cgtatctgtgcggaatccaccgagagctggttaggagattaaatgcggtcctgcttccgaacattcatacactg
tttgatatgtcggctgaagactttgacgctattatagccgagcacttccagcctggggattgtgttctggaaac
tgacatcgcgtcgtttgataaaagtgaggacgacgccatggctctgaccgcgttaatgattctggaagacttag
gtgtggacgcagagctgttgacgctgattgaggcggctttcggcgaaatttcatcaatacatttgcccactaaa
actaaatttaaattcggagccatgatgaaatctggaatgttcctcacactgtttgtgaacacagtcattaacat
tgtaatcgcaagcagagtgttgagagaacggctaaccggatcaccatgtgcagcattcattggagatgacaata
tcgtgaaaggagtcaaatcggacaaattaatggcagacaggtgcgccacctggttgaatatggaagtcaagatt
atagatgctgtggtgggcgagaaagcgccttatttctgtggagggtttattttgtgtgactccgtgaccggcac
agcgtgccgtgtggcagaccccctaaaaaggctgtttaagcttggcaaacctctggcagcagacgatgaacatg
atgatgacaggagaagggcattgcatgaagagtcaacacgctggaaccgagtgggtattctttcagagctgtgc
aaggcagtagaatcaaggtatgaaaccgtaggaacttccatcatagttatggccatgactactctagctagcag
tgttaaatcattcagctacctgagaggggcccctataactctctacggcTAAcctgaatggactacgactatca
cgcccaaacatttacagccgcggtgtcaaaaaccgcgtggacgtggttaacatccctgctgggaggatcagccg
taattattataattggcttggtgctggctactattgtggccatgtacgtgctgaccaaccagaaacataattga
atacagcagcaattggcaagctgcttacatagaactcgcggcgattggcatgccgccttaaaattttatttta
tttttcttttcttttccgaatcggattttgtttttaatatttcAAAAAAAAAAAAAAAAAAAAAAAAAAAAAA
AAAAAAAAAAAAAAAAAAAAAAAAAAAAAAAAAAAAAAAAAAAAAAAAAA TC-83 Delivery Vector (SEQ ID NO: 7); TC-83 genome with nucleotides 7544-11175 deleted [alphavirus structural proteins removed]
ATAGGCGGCGCATGAGAGAAGCCCAGACCAATTACCTACCCAAAATGGAGAAAGTTCACGTTGACATCGAGGAA
GACAGCCCATTCCTCAGAGCTTTGCAGCGGAGCTTCCCGCAGTTTGAGGTAGAAGCCAAGCAGGTCACTGATAA
TGACCATGCTAATGCCAGAGCGTTTTCGCATCTGGCTTCAAAACTGATCGAAACGGAGGTGGACCCATCCGACA
CGATCCTTGACATTGGAAGTGCGCCCGCCCGCAGAATGTATTCTAAGCACAAGTATCATTGTATCTGTCCGATG
AGATGTGCGGAAGATCCGGACAGATTGTATAAGTATGCAACTAAGCTGAAGAAAAACTGTAAGGAAATAACTGA
TAAGGAATTGGACAAGAAAATGAAGGAGCTCGCCGCCGTCATGAGCGACCCTGACCTGGAAACTGAGACTATGT
GCCTCCACGACGACGAGTCGTGTCGCTACGAAGGGCAAGTCGCTGTTTACCAGGATGTATACGCGGTTGACGGA
CCGACAAGTCTCTATCACCAAGCCAATAAGGGAGTTAGAGTCGCCTACTGGATAGGCTTTGACACCACCCCTTT
TATGTTTAAGAACTTGGCTGGAGCATATCCATCATACTCTACCAACTGGGCCGACGAAACCGTGTTAACGGCTC
GTAACATAGGCCTATGCAGCTCTGACGTTATGGAGCGGTCACGTAGAGGGATGTCCATTCTTAGAAAGAAGTAT
TTGAAACCATCCAACAATGTTCTATTCTCTGTTGGCTCGACCATCTACCACGAGAAGAGGGACTTACTGAGGAG
CTGGCACCTGCCGTCTGTATTTCACTTACGTGGCAAGCAAAATTACACATGTCGGTGTGAGACTATAGTTAGTT
GCGACGGGTACGTCGTTAAAAGAATAGCTATCAGTCCAGGCCTGTATGGGAAGCCTTCAGGCTATGCTGCTACG
ATGCACCGCGAGGGATTCTTGTGCTGCAAAGTGACAGACACATTGAACGGGGAGAGGGTCTCTTTTCCCGTGTG
CACGTATGTGCCAGCTACATTGTGTGACCAAATGACTGGCATACTGGCAACAGATGTCAGTGCGGACGACGCGC
AAAAACTGCTGGTTGGGCTCAACCAGCGTATAGTCGTCAACGGTCGCACCCAGAGAAACACCAATACCATGAAA
AATTACCTTTTGCCCGTAGTGGCCCAGGCATTTGCTAGGTGGGCAAAGGAATATAAGGAAGATCAAGAAGATGA
AAGGCCACTAGGACTACGAGATAGACAGTTAGTCATGGGGTGTTGTTGGGCTTTTAGAAGGCACAAGATAACAT
CTATTTATAAGCGCCCGGATACCCAAACCATCATCAAAGTGAACAGCGATTTCCACTCATTCGTGCTGCCCAGG
ATAGGCAGTAACACATTGGAGATCGGGCTGAGAACAAGAATCAGGAAAATGTTAGAGGAGCACAAGGAGCCGTC
ACCTCTCATTACCGCCGAGGACGTACAAGAAGCTAAGTGCGCAGCCGATGAGGCTAAGGAGGTGCGTGAAGCCG
AGGAGTTGCGCGCAGCTCTACCACCTTTGGCAGCTGATGTTGAGGAGCCCACTCTGGAAGCCGATGTCGACTTG
ATGTTACAAGAGGCTGGGGCCGGCTCAGTGGAGACACCTCGTGGCTTGATAAAGGTTACCAGCTACGATGGCGA
GGACAAGATCGGCTCTTACGCTGTGCTTTCTCCGCAGGCTGTACTCAAGAGTGAAAAATTATCTTGCATCCACC
CTCTCGCTGAACAAGTCATAGTGATAACACACTCTGGCCGAAAAGGGCGTTATGCCGTGGAACCATACCATGGT
AAAGTAGTGGTGCCAGAGGGACATGCAATACCCGTCCAGGACTTTCAAGCTCTGAGTGAAAGTGCCACCATTGT
GTACAACGAACGTGAGTTCGTAAACAGGTACCTGCACCATATTGCCACACATGGAGGAGCGCTGAACACTGATG
AAGAATATTACAAAACTGTCAAGCCCAGCGAGCACGACGGCGAATACCTGTACGACATCGACAGGAAACAGTGC
GTCAAGAAAGAACTAGTCACTGGGCTAGGGCTCACAGGCGAGCTGGTGGATCCTCCCTTCCATGAATTCGCCTA
CGAGAGTCTGAGAACACGACCAGCCGCTCCTTACCAAGTACCAACCATAGGGGTGTATGGCGTGCCAGGATCAG
GCAAGTCTGGCATCATTAAAAGCGCAGTCACCAAAAAAGATCTAGTGGTGAGCGCCAAGAAAGAAAACTGTGCA
GAAATTATAAGGGACGTCAAGAAAATGAAAGGGCTGGACGTCAATGCCAGAACTGTGGACTCAGTGCTCTTGAA
TGGATGCAAACACCCCGTAGAGACCCTGTATATTGACGAAGCTTTTGCTTGTCATGCAGGTACTCTCAGAGCGC
TCATAGCCATTATAAGACCTAAAAAGGCAGTGCTCTGCGGGGATCCCAAACAGTGCGGTTTTTTTAACATGATG
TGCCTGAAAGTGCATTTTAACCACGAGATTTGCACACAAGTCTTCCACAAAAGCATCTCTCGCCGTTGCACTAA
ATCTGTGACTTCGGTCGTCTCAACCTTGTTTTACGACAAAAAAATGAGAACGACGAATCCGAAAGAGACTAAGA
TTGTGATTGACACTACCGGCAGTACCAAACCTAAGCAGGACGATCTCATTCTCACTTGTTTCAGAGGGTGGGTG
AAGCAGTTGCAAATAGATTACAAAGGCAACGAAATAATGACGGCAGCTGCCTCTCAAGGGCTGACCCGTAAAGG
TGTGTATGCCGTTCGGTACAAGGTGAATGAAAATCCTCTGTACGCACCCACCTCAGAACATGTGAACGTCCTAC
TGACCCGCACGGAGGACCGCATCGTGTGGAAAACACTAGCCGGCGACCCATGGATAAAAACACTGACTGCCAAG
TACCCTGGGAATTTCACTGCCACGATAGAGGAGTGGCAAGCAGAGCATGATGCCATCATGAGGCACATCTTGGA
GAGACCGGACCCTACCGACGTCTTCCAGAATAAGGCAAACGTGTGTTGGGCCAAGGCTTTAGTGCCGGTGCTGA -continued AGACCGCTGGCATAGACATGACCACTGAACAATGGAACACTGTGGATTATTTTGAAACGGACAAAGCTCACTCA
GCAGAGATAGTATTGAACCAACTATGCGTGAGGTTCTTTGGACTCGATCTGGACTCCGGTCTATTTTCTGCACC
CACTGTTCCGTTATCCATTAGGAATAATCACTGGGATAACTCCCCGTCGCCTAACATGTACGGGCTGAATAAAG
AAGTGGTCCGTCAGCTCTCTCGCAGGTACCCACAACTGCCTCGGGCAGTTGCCACTGGAAGAGTCTATGACATG
AACACTGGTACACTGCGCAATTATGATCCGCGCATAAACCTAGTACCTGTAAACAGAAGACTGCCTCATGCTTT
AGTCCTCCACCATAATGAACACCCACAGAGTGACTTTTCTTCATTCGTCAGCAAATTGAAGGGCAGAACTGTCC
TGGTGGTCGGGGAAAAGTTGTCCGTCCCAGGCAAAATGGTTGACTGGTTGTCAGACCGGCCTGAGGCTACCTTC
AGAGCTCGGCTGGATTTAGGCATCCCAGGTGATGTGCCCAAATATGACATAATATTTGTTAATGTGAGGACCCC
ATATAAATACCATCACTATCAGCAGTGTGAAGACCATGCCATTAAGCTTAGCATGTTGACCAAGAAAGCTTGTC
TGCATCTGAATCCCGGCGGAACCTGTGTCAGCATAGGTTATGGTTACGCTGACAGGGCCAGCGAAAGCATCATT
GGTGCTATAGCGCGGCAGTTCAAGTTTTCCCGGGTATGCAAACCGAAATCCTCACTTGAAGAGACGGAAGTTCT
GTTTGTATTCATTGGGTACGATCGCAAGGCCCGTACGCACAATCCTTACAAGCTTTCATCAACCTTGACCAACA
TTTATACAGGTTCCAGACTCCACGAAGCCGGATGTGCACCCTCATATCATGTGGTGCGAGGGGATATTGCCACG
GCCACCGAAGGAGTGATTATAAATGCTGCTAACAGCAAAGGACAACCTGGCGGAGGGGTGTGCGGAGCGCTGTA
TAAGAAATTCCCGGAAAGCTTCGATTTACAGCCGATCGAAGTAGGAAAAGCGCGACTGGTCAAAGGTGCAGCTA
AACATATCATTCATGCCGTAGGACCAAACTTCAACAAAGTTTCGGAGGTTGAAGGTGACAAACAGTTGGCAGAG
GCTTATGAGTCCATCGCTAAGATTGTCAACGATAACAATTACAAGTCAGTAGCGATTCCACTGTTGTCCACCGG
CATCTTTTCCGGGAACAAAGATCGACTAACCCAATCATTGAACCATTTGCTGACAGCTTTAGACACCACTGATG
CAGATGTAGCCATATACTGCAGGGACAAGAAATGGGAAATGACTCTCAAGGAAGCAGTGGCTAGGAGAGAAGCA
GTGGAGGAGATATGCATATCCGACGACTCTTCAGTGACAGAACCTGATGCAGAGCTGGTGAGGGTGCATCCGAA
GAGTTCTTTGGCTGGAAGGAAGGGCTACAGCACAAGCGATGGCAAAACTTTCTCATATTTGGAAGGGACCAAGT
TTCACCAGGCGGCCAAGGATATAGCAGAAATTAATGCCATGTGGCCCGTTGCAACGGAGGCCAATGAGCAGGTA
TGCATGTATATCCTCGGAGAAAGCATGAGCAGTATTAGGTCGAAATGCCCCGTCGAAGAGTCGGAAGCCTCCAC
ACCACCTAGCACGCTGCCTTGCTTGTGCATCCATGCCATGACTCCAGAAAGAGTACAGCGCCTAAAAGCCTCAC
GTCCAGAACAAATTACTGTGTGCTCATCCTTTCCATTGCCGAAGTATAGAATCACTGGTGTGCAGAAGATCCAA
TGCTCCCAGCCTATATTGTTCTCACCGAAAGTGCCTGCGTATATTCATCCAAGGAAGTATCTCGTGGAAACACC
ACCGGTAGACGAGACTCCGGAGCCATCGGCAGAGAACCAATCCACAGAGGGGACACCTGAACAACCACCACTTA
TAACCGAGGATGAGACCAGGACTAGAACGCCTGAGCCGATCATCATCGAAGAGGAAGAAGAGGATAGCATAAGT
TTGCTGTCAGATGGCCCGACCCACCAGGTGCTGCAAGTCGAGGCAGACATTCACGGGCCGCCCTCTGTATCTAG
CTCATCCTGGTCCATTCCTCATGCATCCGACTTTGATGTGGACAGTTTATCCATACTTGACACCCTGGAGGGAG
CTAGCGTGACCAGCGGGGCAACGTCAGCCGAGACTAACTCTTACTTCGCAAAGAGTATGGAGTTTCTGGCGCGA
CCGGTGCCTGCGCCTCGAACAGTATTCAGGAACCCTCCACATCCCGCTCCGCGCACAAGAACACCGTCACTTGC
ACCCAGCAGGGCCTGCTCGAGAACCAGCCTAGTTTCCACCCCGCCAGGCGTGAATAGGGTGATCACTAGAGAGG
AGCTCGAGGCGCTTACCCCGTCACGCACTCCTAGCAGGTCGGTCTCGAGAACCAGCCTGGTCTCCAACCCGCCA
GGCGTAAATAGGGTGATTACAAGAGAGGAGTTTGAGGCGTTCGTAGCACAACAACAATGACGGTTTGATGCGGG
TGCATACATCTTTTCCTCCGACACCGGTCAAGGGCATTTACAACAAAAATCAGTAAGGCAAACGGTGCTATCCG
AAGTGGTGTTGGAGAGGACCGAATTGGAGATTTCGTATGCCCCGCGCCTCGACCAAGAAAAAGAAGAATTACTA
CGCAAGAAATTACAGTTAAATCCCACACCTGCTAACAGAAGCAGATACCAGTCCAGGAAGGTGGAGAACATGAA
AGCCATAACAGCTAGACGTATTCTGCAAGGCCTAGGGCATTATTTGAAGGCAGAAGGAAAAGTGGAGTGCTACC
GAACCCTGCATCCTGTTCCTTTGTATTCATCTAGTGTGAACCGTGCCTTTTCAAGCCCCAAGGTCGCAGTGGAA
GCCTGTAACGCCATGTTGAAAGAGAACTTTCCGACTGTGGCTTCTTACTGTATTATTCCAGAGTACGATGCCTA
TTTGGACATGGTTGACGGAGCTTCATGCTGCTTAGACACTGCCAGTTTTTGCCCTGCAAAGCTGCGCAGCTTTC
CAAAGAAACACTCCTATTTGGAACCCACAATACGATCGGCAGTGCCTTCAGCGATCCAGAACACGCTCCAGAAC
GTCCTGGCAGCTGCCACAAAAAGAAATTGCAATGTCACGCAAATGAGAGAATTGCCCGTATTGGATTCGGCGGC
CTTTAATGTGGAATGCTTCAAGAAATATGCGTGTAATAATGAATATTGGGAAACGTTTAAAGAAAACCCCATCA
GGCTTACTGAAGAAAACGTGGTAAATTACATTACCAAATTAAAAGGACCAAAAGCTGCTGCTCTTTTTGCGAAG
ACACATAATTTGAATATGTTGCAGGACATACCAATGGACAGGTTTGTAATGGACTTAAAGAGAGACGTGAAAGT
GACTCCAGGAACAAAACATACTGAAGAACGGCCCAAGGTACAGGTGATCCAGGCTGCCGATCCGCTAGCAACAG
CGTATCTGTGCGGAATCCACCGAGAGCTGGTTAGGAGATTAAATGCGGTCCTGCTTCCGAACATTCATACACTG
TTTGATATGTCGGCTGAAGACTTTGACGCTATTATAGCCGAGCACTTCCAGCCTGGGGATTGTGTTCTGGAAAC
TGACATCGCGTCGTTTGATAAAAGTGAGGACGACGCCATGGCTCTGACCGCGTTAATGATTCTGGAAGACTTAG
GTGTGGACGCAGAGCTGTTGACGCTGATTGAGGCGGCTTTCGGCGAAATTTCATCAATACATTTGCCCACTAAA
ACTAAATTTAAATTCGGAGCCATGATGAAATCTGGAATGTTCCTCACACTGTTTGTGAACACAGTCATTAACAT
TGTAATCGCAAGCAGAGTGTTGAGAGAACGGCTAACCGGATCACCATGTGCAGCATTCATTGGAGATGACAATA
TCGTGAAAGGAGTCAAATCGGACAAATTAATGGCAGACAGGTGCGCCACCTGGTTGAATATGGAAGTCAAGATT
ATAGATGCTGTGGTGGGCGAGAAAGCGCCTTATTTCTGTGGAGGGTTTATTTTGTGTGACTCCGTGACCGGCAC
AGCGTGCCGTGTGGCAGACCCCCTAAAAAGGCTGTTTAAGCTTGGCAAACCTCTGGCAGCAGACGATGAACATG
ATGATGACAGGAGAAGGGCATTGCATGAAGAGTCAACACGCTGGAACCGAGTGGGTATTCTTTCAGAGCTGTGC
AAGGCAGTAGAATCAAGGTATGAAACCGTAGGAACTTCCATCATAGTTATGGCCATGACTACTCTAGCTAGCAG
TGTTAAATCATTCAGCTACCTGAGAGGGGCCCCTATAACTCTCTACGGCTAACCTGAATGGACTACGACTATCA
CGCCCAAACATTTACAGCCGCGGTGTCAAAAACCGCGTGGACGTGGTTAACATCCCTGCTGGGAGGATCAGCCG
TAATTATTATAATTGGCTTGGTGCTGGCTACTATTGTGGCCATGTACGTGCTGACCAACCAGAAACATAATTGA
ATACAGCAGCAATTGGCAAGCTGCTTACATAGAACTCGCGGCGATTGGCATGCCGCCTTAAAATTTTTATTTTA
TTTTTCTTTTCTTTTCCGAATCGGATTTTGTTTTTAATATTTCAAAAAAAAAAAAAAAAAAAAAAAAAAA
AAAAAAAAAAAAAAAAAAAAAAAAAAAAAAAAAAAAAAAAAAAAAA VEE Production Vector (SEQ ID NO: 8); VEE genome with nucleotides 7544-11175 deleted, plus 5' T7-promoter, plus 3' restriction sites TAATACGACTCACTATAGGATGggcggcgcatgagagaagcccagaccaattacctacccaaaATGGagaaagt
tcacgttgacatcgaggaagacagcccattcctcagagctttgcagcggagcttcccgcagtttgaggtagaag
ccaagcaggtcactgataatgaccatgctaatgccagagcgttttcgcatctggcttcaaaactgatcgaaacg
gaggtggacccatccgacacgatccttgacattggaagtgcgcccgcccgcagaatgtattctaagcacaagta
tcattgtatctgtccgatgagatgtgcggaagatccggacagattgtataagtatgcaactaagctgaagaaaa
actgtaaggaaataactgataaggaattggacaagaaaatgaaggagctcgccgccgtcatgagcgaccctgac
ctggaaactgagactatgtgcctccacgacgacgagtcgtgtcgctacgaagggcaagtcgctgtttaccagga
tgtatacgcggttgacggaccgacaagtctctatcaccaagccaataagggagttagagtcgcctactggatag
gctttgacaccacccctttttatgtttaagaacttggctggagcatatccatcatactctaccaactgggccgac
gaaaccgtgttaacggctcgtaacataggcctatgcagctctgacgttatggagcggtcacgtagagggatgtc
cattcttagaaagaagtatttgaaaccatccaacaatgttctattctctgttggctcgaccatctaccacgaga -continued

```
agagggacttactgaggagctggcacctgccgtctgtatttcacttacgtggcaagcaaaattacacatgtcgg
tgtgagactatagttagttgcgacgggtacgtcgttaaaagaatagctatcagtccaggcctgtatgggaagcc
ttcaggctatgctgctacgatgcaccgcgagggattcttgtgctgcaaagtgacagacacattgaacgggaga
gggtctcttttcccgtgtgcacgtatgtgccagctacattgtgtgaccaaatgactggcatactggcaacagat
gtcagtgcggacgacgcgcaaaaactgctggttgggctcaaccagccgtatagtcgtcaacggtcgcacccagag
aaacaccaataccatgaaaaattaccttttgcccgtagtggcccaggcatttgctaggtgggcaaaggaatata
aggaagatcaagaagatgaaaggccactaggactacgagatagacagttagtcatggggtgttgttgggctttt
agaaggcacaagataacatctatttataagcgcccggatacccaaaccatcatcaaagtgaacagcgatttcca
ctcattcgtgctgcccaggataggcagtaacacattggagatcgggctgagaacaagaatcaggaaaatgttag
aggagcacaaggagccgtcacctctcattaccgccgaggacgtacaagaagctaagtgcgcagccgatgaggct
aaggaggtgcgtgaagccgaggagttgcgcgcagctctaccaccttggcagctgatgttgaggagcccactct
ggaagccgatgtcgacttgatgttacaagaggctggggccggctcagtggagacacctcgtggcttgataaagg
ttaccagctacgctggcgaggacaagatcggctcttacgctgtgctttctccgcaggctgtactcaagagtgaa
aaattatcttgcatccaccctctcgctgaacaagtcatagtgataacacactctggccgaaaagggcgttatgc
cgtggaaccataccatggtaaagtagtggtgccagagggacatgcaatacccgtccaggactttcaagctctga
gtgaaagtgccaccattgtgtacaacgaacgtgagttcgtaaacaggtacctgcaccatattgccacacatgga
ggagcgctgaacactgatgaagaatattacaaaactgtcaagcccagcgagcacgacggcgaatacctgtacga
catcgacaggaaacagtgcgtcaagaaagaactagtcactgggctagggctcacaggcgagctggtggatcctc
ccttccatgaattcgcctacgagagtctgagaacacgaccagccgctccttaccaagtaccaaccataggggtg
tatggcgtgccaggatcaggcaagtctggcatcattaaaagcgcagtcaccaaaaaagatctagtggtgagcgc
caagaaagaaaactgtgcagaaattataagggacgtcaagaaaatgaaagggctggacgtcaatgccagaactg
tggactcagtgctcttgaatggatgcaaacacccgtagagaccctgtatattgacgaagcttttgcttgtcat
gcaggtactctcagagcgctcatagccattataagacctaaaaaggcagtgctctgcggggatcccaaacagtg
cggtttttttaacatgatgtgcctgaaagtgcattttaaccacgagatttgcacacaagtcttccacaaaagca
tctctcgccgttgcactaaatctgtgacttcggtcgtctcaaccttgttttacgacaaaaaaatgagaacgacg
aatccgaaagagactaagattgtgattgacactaccggcagtaccaaacctaagcaggacgatctcattctcac
ttgtttcagagggtgggtgaagcagttgcaaatagattacaaaggcaacgaaataatgacggcagctgcctctc
aagggctgacccgtaaaggtgtgtatgccgttcggtacaaggtgaatgaaaatcctctgtacgcacccacctca
gaacatgtgaacgtcctactgacccgcacggaggaccgcatcgtgtggaaaacactagccggcgacccatggat
aaaaacactgactgccaagtaccctgggaatttcactgccacgatagaggagtggcaagcaggagcatgatgcca
tcatgaggcacatcttggagagaccggaccctaccgacgtcttccagaataaggcaaacgtgtgttgggccaag
gctttagtgccggtgctgaagaccgctggcatagacatgaccactgaacaatggaacactgtggattatttga
aacggacaaagctcactcagcagagatagtattgaaccaactatgcgtgaggttctttggactcgatctggact
ccggtctattttctgcaccactgttccgttatccattaggaataactactgggataactccccgtcgcctaac
atgtacgggctgaataaagaagtggtccgtcagctctctcgcaggtacccacaactgcctcgggcagttgccac
tggaagagtctatgacatgaacactggtacactgcgcaattatgatccgcgcataaacctagtacctgtaaaca
gaagactgcctcatgctttagtcctccaccataatgaacacccacagagtgacttttcttcattcgtcagcaaa
ttgaagggcagaactgtcctggtggtcggggaaaagttgtccgtcccaggcaaaatggttgactggttgtcaga
ccggcctgaggctaccttcagagctcggctggatttaggcatcccaggtgatgtgcccaaatatgacataatat
ttgttaatgtgaggaccccatataaataccatcactatcagcagtgtgaagaccatgccattaagcttagcatg
ttgaccaagaaagcttgtctgcatctgaatcccggcggaacctgtgtcagcataggttatggttacgctgacag
ggccagcgaaagcatcattggtgctatagcgcggcagttcaagttttcccgggtatgcaaaccgaaatcctcac
ttgaagagacggaagttctgtttgtattcattgggtacgatcgcaaggcccgtacgcacaatccttacaagctt
tcatcaaccttgaccaacatttatacaggttccagactccacgaagccggatgtgcaccctcatatcatgtggt
gcgagggatattgccacggccaccgaaggagtgattataaatgctgctaacagcaaaggacaacctggcggag
gggtgtgcggagcgctgtataagaaattcccggaaagcttcgatttacagccgatcgaagtaggaaaagcgcga
ctggtcaaaggtgcagctaaacatatcattcatgccgtaggaccaaagctcttcagtgacagaacctgatgcagagc
tggtgagggtgcatccgaagagttctttggctggaaggaagggctcacgcacaagcgatggcaaaactttctca
tatttggaagggaccaagtttcaccaggcggccaaggatatagcagaaattaatgccatgtggcccgttgcaac
ggaggccaatgagcaggtatgcatgtatatcctcggagaaagcatgagcagtattaggtcgaaatgcccgtcg
aagagtcggaagcctccacaccacctagcacgctgccttgcttgtgacgctcttcgtgacagaacctgatgcagagac
cagcgcctaaaagcctcacgtccagaacaaattactgtgtgctcatcctttccattgccgaagtatagaatcac
tggtgtgcagaagatccaatgctcccagcctatattgttctcaccgaaagtgcctgcgtatattcatccaagga
agtatctcgtggaaacaccaccggtagacgagactccggagccatcggcagagaaccaatccacagaggggaca
cctgaacaaccaccacttataaccgaggatgagaccaggactagaacgcctgagccgatcatcatcgaagagga
agaagaggatagcataagtttgctgtcagatggcccgacccaccaggtgctgcaagtcgaggcagacattcacg
ggccgccctctgtatctagctcatcctggtccattcctcatgcatccgactttgatgtggacagtttatccata
cttgacaccctggagggagctagcgtgaccagcggggcaacgtcagccgagactaactcttacttcgcaaagag
tatggagtttctggcgcgaccggtgcctgcgcctcgaacagtattcaggaaccctccacatcccgctccgcgca
caagaacaccgtcacttgcacccagcagggcctgctcgagaaccgactcagtttccaccccgccaggcgtgaat
agggtgatcactagagaggagctcgaggcgcttacccccgtcacgcactcctagcaggtcggtctcgagaaccag
cctggtctccaacccgccaggcgtaaataggtgattacaagagaggagtttgaggcgttcgtagcacaacaac
aatgacggtttgatgcgggtgcatacatcttttcctccgacaccggtcaagggcatttacaacaaaaatcagta
aggcaaacggtgctatccgaagtggtgttggagaggaccgaattggagatttcgtatgccccgcgcctcgacca
agaaaaagaagaattactacgcaagaaattacagttaaatcccacacctgctaacagaagcagataccagtcca
ggaaggtggagaacatgaaagccataacagctagacgtattctgcaaggcctagggcattatttgaaggcagaa
ggaaaagtggagtgctaccgaaccctgcatcctgttcctttgtattcatctagtgtgaaccgtgccttttcaag
ccccaaggtcgcagtggaagcctgtaacgccatgttgaaagagaactttccgactgtggcttcttactgtatta
ttccagagtacgatgcctatttggacatggttgacggagcttcatgctgcttagacactgccagttttttgccct
gcaaagctgcgcagctttccaaagaaacactcctatttggaacccacaatacgatcggcagtgccttcagcgat
ccagaacacgctccagaacgtcctggcagctgccacaaaaagaaattgcaatgtcacgcaaatgagagaattgc
ccgtattggattcggcggccttttaatgtggaatgcttcaagaaatatgcgtgtaataatgaatatttgggaaacg
tttaaagaaacccccatcaggcttactgaagaaaacgtggtaaattacattaccaaattaaaaggaccaaaagc
tgctgctcttttttgcgaagacacataatttgaatatgttgcaggacataccaatggacaggtttgtaatggact
taaagagagacgtgaaagtgactccaggaacaaaacatactgaagaacggcccaaggtacaggtgatccaggct
```

-continued

```
gccgatccgctagcaacagcgtatctgtgcggaatccaccgagagctggttaggagattaaatgcggtcctgct
tccgaacattcatacactgtttgatatgtcggctgaagactttgacgctattatagccgagcacttccagcctg
gggattgtgttctggaaactgacatcgcgtcgtttgataaaagtgaggacgacgccatggctctgaccgcgtta
atgattctggaagacttaggtgtggacgcagagctgttgacgctgattgaggcggctttcggcgaaatttcatc
aatacatttgcccactaaaactaaatttaaattcggagccatgatgaaatctggaatgttcctcacactgtttg
tgaacacagtcattaacattgtaatcgcaagcagagtgttgagagaacggctaaccggatcaccatgtgcagca
ttcattggagatgacaatatcgtgaaaggagtcaaatcggacaaattaatggcagacaggtgcgccacctggtt
gaatatggaagtcaagattatagatgctgtggtgggcgagaaagcgccttatttctgtggagggttttattttgt
gtgactccgtgaccggcacagcgtgccgtgtggcagaccccctaaaaaggctgtttaagcttggcaaacctctg
gcagcagacgatgaacatgatgatgacaggagaagggcattgcatgaagagtcaacacgctggaaccgagtggg
tattctttcagagctgtgcaaggcagtagaatcaaggtatgaaaccgtaggaacttccatcatagttatggcca
tgactactctagctagcagtgttaaatcattcagctacctgagaggggcccctataactctctacggcTAAcct
gaatggactacgactatcacgcccaaacatttacagccgcggtgtcaaaaaccgcgtggacgtggttaacatcc
ctgctgggaggatcagccgtaattattataattggcttggtgctggctgactattgtggccatgtacgtgctgac
caaccagaaacataattgaatacagcagcaattggcaagctgcttacatagaactcgccggcgattggcatgccg
ccttaaaattttttattttatttttttctttctttttccgaatcggattttgtttttaatatttcAAAAAAAAAAA
AAAAAAAAAAAAAAAAAAAAAAAAAAAAAAAAAAAAAAAAAAAAAAAAAAAAAAAAAAAAAAAAA
tacgtagtttaaac
```

TC-83 Production Vector (SEQ ID NO: 9

```
TGACAAACAGTTGGCAGAGGCTTATGAGTCCATCGCTAAGATTGTCAACGATAACAATTACAAGTCAGTAGCGA
TTCCACTGTTGTCCACCGGCATCTTTTCCGGGAACAAAGATCGACTAACCCAATCATTGAACCATTTGCTGACA
GCTTTAGACACCACTGATGCAGATGTAGCCATATACTGCAGGGACAAGAAATGGGAAATGACTCTCAAGGAAGC
AGTGGCTAGGAGAGAAGCAGTGGAGGAGATATGCATATCCGACGACTCTTCAGTGACAGAACCTGATGCAGAGC
TGGTGAGGGTGCATCCGAAGAGTTCTTTGGCTGGAAGGAAGGGCTACAGCACAAGCGATGGCAAAACTTTCTCA
TATTTGGAAGGGACCAAGTTTCACCAGGCGGCCAAGGATATAGCAGAAATTAATGCCATGTGGCCCGTTGCAAC
GGAGGCAATGAGCAGGTATGCATGTATATCCTCGGAGAAAGCATGAGCAGTATTAGGTCGAAATGCCCCGTCG
AAGAGTCGGAAGCCTCCACACCACCTAGCACGCTGCCTTGCTTGTGCATCCATGCCATGACTCCAGAAAGAGTA
CAGCGCCTAAAAGCCTCACGTCCAGAACAAATTACTGTGTGCTCATCCTTTCCATTGCCGAAGTATAGAATCAC
TGGTGTGCAGAAGATCCAATGCTCCCAGCCTATATTGTTCTCACCGAAAGTGCCTGCGTATATTCATCCAAGGA
AGTATCTCGTGGAAACACCACCGGTAGACGAGACTCCGGAGCCATCGGCAGAGAACCAATCCACAGAGGGGACA
CCTGAACAACCACCACTTATAACCGAGGATGAGACCAGGACTAGAACGCCTGAGCCGATCATCATCGAAGAGGA
AGAAGAGGATAGCATAAGTTTGCTGTCAGATGGCCCGACCCACCAGGTGCTGCAAGTCGAGGCAGACATTCACG
GGCCGCCCTCTGTATCTAGCTCATCCTGGTCCATTCCTCATGCATCCGACTTTGATGTGGACAGTTTATCCATA
CTTGACACCCTGGAGGGAGCTAGCGTGACCAGCGGGGCAACGTCAGCCGAGACTAACTCTTACTTCGCAAAGAG
TATGGAGTTTCTGGCGCGACCGGTGCCTGCGCCTCGAACAGTATTCAGGAACCCTCCACATCCCGCTCCGCGCA
CAAGACACCGTCACTTGCACCCAGCAGGGCCTGCTCGAGAACCAGCCTAGTTTCCACCCCGCCAGGCGTGAAT
AGGGTGATCACTAGAGAGGAGCTCGAGGCGCTTACCCCGTCACGCACTCCTAGCAGGTCGGTCTCGAGAACCAG
CCTGGTCTCCAACCCGCCAGGCGTAAATAGGGTGATTACAAGAGAGGAGTTTGAGGCGTTCGTAGCACAACAAC
AATGACGGTTTGATGCGGGTGCATACATCTTTTCCTCCGACACCGGTCAAGGGCATTTACAACAAAAATCAGTA
AGGCAAACGGTGCTATCCGAAGTGGTGTTGGAGAGGACCGAATTGGAGATTTCGTATGCCCCGCGCCTCGACCA
AGAAAAAGAAGAATTACTACGCAAGAAATTACAGTTAAATCCCACACCGCTAACAGAAGCAGATACCAGTCCA
GGAAGGTGGAGAACATGAAAGCCATAACAGCTAGACGTATTCTGCAAGGCCTAGGGCATTATTTGAAGGCAGAA
GGAAAAGTGGAGTGCTACCGAACCCTGCATCCTGTTCCTTTGTATTCATCTAGTGTGAACCGTGCCTTTTCAAG
CCCCAAGGTCGCAGTGGAAGCCTGTAACGCCATGTTGAAAGAGAACTTTCCGACTGTGGCTTCTTACTGTATTA
TTCCAGAGTACGATGCCTATTTGGACATGGTTGACGGAGCTTCGTTAGCACTGCCAGTTTTTTGCCCT
GCAAAGCTGCGCAGCTTTCCAAAGAAACACTCCTATTTGGAACCCACAATACGATCGGCAGTGCCTTCAGCGAT
CCAGAACACGCTCCAGAACGTCCTGGCAGCTGCCACAAAAAGAAATTGCAATGTCACGCAAATGAGAGAATTGC
CCGTATTGGATTCGGCGGCCTTTAATGTGGAATGCTTCAAGAAATATGCGTGTAATAATGAATATTGGGAAACG
TTTAAAGAAAACCCCATCAGGCTTACTGAAGAAAACGTGGTAAATTACATTACCAATTAAAAGGACCAAAAGC
TGCTGCTCTTTTTGCGAAGACACATAATTTGAATATGTTGCAGGACATACCAATGGACAGGTTTGTAATGGACT
TAAAGAGAGACGTGAAAGTGACTCCAGGAACAAAACATACTGAAGAACGGCCCAAGGTACAGGTGATCCAGGCT
GCCGATCCGCTAGCAACAGCGTATCTGTGCGGAATCCACCGAGAGCTGGTTAGGAGATTAAATGCGGTCCTGCT
TCCGAACATTCATACACTGTTTGATATGTCGGCTGAAGACTTTGACGCTATTATAGCCGAGCACTTCCAGCCTG
GGGATTGTGTTCTGGAAACTGACATCGCGTCGTTTGATAAAAGTGAGGACGACGCCATGGCTCTGACCGCGTTA
ATGATTCTGGAAGACTTAGGTGTGGACGCAGAGCTGTTGACGCTGATTGAGGCGGCTTTCGGCGAAATTTCATC
AATACATTTGCCCACTAAAACTAAATTTAAATTCGGAGCCATGATGAAATCTGGAATGTTCCTCACACTGTTTG
TGAACACAGTCATTAACATTGTAATCGCAAGCAGAGTGTTGAGAGAACGCTAACCGGATCACCATGTGCAGCA
TTCATTGGAGATGACAATATCGTGAAAGGAGTCAAATCGGACAAATTAATGGCAGACAGGTGCGCCACCTGGTT
GAATATGGAAGTCAAGATTATAGATGCGTGGTGGGCGAGAAAGCGCCTTATTTCTGTGGAGGGTTTATTTTGT
GTGACTCCGTGACCGGCACAGCGTGCCGTGTGGCAGACCCCCTAAAAAGGCTGTTTAAGCTTGGCAAACCTCTG
GCAGCAGACGATGAACATGATGACAGGAGAAGGGCATTGCATGAAGAGTCAACACGCTGGAACCGAGTGGG
TATTCTTTCAGAGCTGTGCAAGGCAGTAGAATCAAGGTATGAAACCGTAGGAACTTCCATCATAGTTATGGCCA
TGACTACTCTAGCTAGCAGTGTTAAATCATTCAGCTACCTGAGAGGGGCCCCTATAACTCTCTACGGCTAACCT
GAATGGACTACGACTATCACGCCCAAACATTTACAGCCGCGGTGTCAAAAACCGCGTGGACGTGGTTAACATCC
CTGCTGGGAGGATCAGCCGTAATTATTATAATTGGCTTGGTGCTGGCTACTATTGTGGCCATGTACGTGCTGAC
CAACCAGAAATAATTGAATACAGCAGCAATTGGCAAGCTGCTTACATAGAACTCGCGGCGATTGGCATGCCG
CCTTAAAATTTTTATTTTATTTTTCTTTTCTTTTCCGAATCGGATTTTGTTTTTAATATTTCAAAAAAAAAAA
AAAAAAAAAAAAAAAAAAAAAAAAAAAAAAAAAAAAAAAAAAAAAAAAAAAAAAAAAAAAAAAAAtacgta
gtttaaac VEE-UbAAY (SEQ ID NO: 14); VEE delivery vector with MHC class I mouse tumor
epitopes SIINFEKL and

```
cattgtgtacaacgaacgtgagttcgtaaacaggtacctgcaccatattgccacacatggaggagcgctgaaca
ctgatgaagaatattacaaaactgtcaagcccagcgagcacgacggcgaatacctgtacgacatcgacaggaaa
cagtgcgtcaagaaagaactagtcactgggctagggctcacaggcgagctggtggatcctccttccatgaatt
cgcctacgagagtctgagaacacgaccagccgctccttaccaagtaccaaccatagggtgtatggcgtgccag
gatcaggcaagtctggcatcattaaaagcgcagtcaccaaaaagatctagtggtgagcgccaagaaagaaaac
tgtgcagaaattataagggacgtcaagaaaatgaaagggctggacgtcaatgccagaactgtggactcagtgct
cttgaatggatgcaaacaccccgtagagaccctgtatattgacgaagcttttgcttgtcatgcaggtactctca
gagcgctcatagccattataagacctaaaaaggcagtgctctgcggggatcccaaacagtgcggttttttttaac
atgatgtgcctgaaagtgcatttaaccacgagatttgcacacaagtcttccacaaaagcatctctcgccgttg
cactaaatctgtgacttcggtcgtctcaaccttgttttacgacaaaaaaatgagaacgacgaatccgaaagaga
ctaagattgtgattgacactaccggcagtaccaaacctaagcaggacgatctcattctcacttgtttcagaggg
tgggtgaagcagttgcaaatagattacaaaggcaacgaaataatgacggcagctgcctctcaagggctgacccg
taaaggtgtgtatgccgttcggtacaaggtgaatgaaaatcctctgtacgcaccacctcagaacatgtgaacg
tcctactgacccgcacggaggaccgcatcgtgtggaaaacactagccggcgacccatggatataaaaacactgact
gccaagtaccctgggaatttcactgccacgatagaggagtggcaagcagagcatgatgccatcatgaggcacat
cttggagagaccggaccctaccgacgtcttccagaataaggcaaacgtgtgttgggccaaggctttagtgccgg
tgctgaagaccgctggcatagacatgaccactgaacaatggaacactgtggattattttgaaacggacaaagct
cactcagcagagatagtattgaaccaactatgcgtgaggttctttggactcgatctggactccggtctattttc
tgcacccactgttccgttatccattaggaataatcactgggataactccccgtcgcctaacatgtacggctga
ataaagaagtggtccgtcagctctctcgcaggtacccacaactgcctcgggcagttgccactggaagagtctat
gacatgaacactggtacactgcgcaattatgatccgcgcataaacctagtacctgtaaacagaagactgcctca
tgctttagtcctccaccataatgaacacccacagagtgacttttcttcattcgtcgcaaattgaagggcagaa
ctgtcctggtggtcggggaaaagttgtccgtcccaggcaaaatggttgactggttgtcagaccggcctgaggct
accttcagagctcggctggatttaggcatcccaggtgatgtgcccaaatatgacataatatttgttaatgtgag
gacccccataaataccatcactatcagcagtgtgaagaccatgccattaagcttagcatgttgaccaagaaag
cttgtctgcatctgaatcccggcgaacctgtgtcagcataggttatggttacgctgacagggccagcgaaagc
atcattggtgctatagcgcggcagttcaagttttccccgggtatgcaaaccgaaatcctcacttgaagagacga
agttctgtttgtattcattgggtacgatcgcaaggcccgtacgcacaatccttacaagctttcatcaaccttga
ccaacatttatacaggttccagactccacgaagccggatgtgcaccctcatatcatgtggtgcgaggggatatt
gccacggccaccgaaggagtgattataaatgctgctaacagcaaaggacaacctggcggagggggtgtgcggagc
gctgtataagaaatcccggaaagcttcgatttacagccgatcgaagtaggaaaagcgcgactggtcaaggtg
cagctaaacatatcattcatgccgtaggaccaaacttcaacaaagtttcggaggttgaaggtgacaaacagttg
gcagaggcttatgagtccatcgctaagattgtcaacgataacaattacaagtcagtagcgattccactgttgtc
caccggcatccttttccgggaacaaagatcgactaacccaatcattgaaccatttgctgacagctttagacacca
ctgatgcagatgtagccatatactgcagggacaagaaatgggaaatgactcctcaaggaagcagtggctaggaga
gaagcagtggaggagatatgcatatccgacgactcttcagtgacagaacctgatgcagagctggtgagggtgca
tccgaagagttcttttggctggaaggaagggctacagcacaagcgatggcaaaacttttctcatatttggaaggga
ccaagtttcaccaggcggccaaggatatagcagaaattaatgccatgtggcccgttgcaacggaggccaatgag
caggtatgcatgtatatcctcggagaaagcatgagcagtattaggtcgaaatgccccgtcgaagagtcggaagc
ctccacaccacctagcacgctgccttgcttgtgcatccatgccatgactccagaaagagtacagcgcctaaaag
cctcacgtccagaacaaattactgtgtgctcatccttccattgccgaagtataagaatcactggtgtgcagaag
atccaatgctcccagcctatattgttctcaccgaaagtgcctgcgtatattcatccaaggaagtatctcgtgga
aacaccaaccggtagacgagactccggagccatcggcagagaacactccacagagggggacacctgaacaaccac
cacttataaccgaggatgagaccaggactagaacgcctgagccgatcatcatcgaagaggaagaagaggatagc
ataagtttgctgtcagatggcccgacccaccaggtgctgcaagtcgaggcagacattcacgggccgccctctgt
atctagctcatcctggtccattcctcatgcatccgactttgatgtggacagtttatccatacttgacaccctgg
agggagctagcgtgaccagcggggcaacgtcagccgagactaactcttacttcgcaaagatatggagtttctg
gcgcgaccggtgcctgcgcctcgaacagtattcaggaaccctccacatcccgctccgcgcacaagaacaccgtc
acttgcacccagcagggcctgctcgagaaccagcctagtttccaccccgccaggcgtgaataggtgatcacta
gagaggagctcgaggcgcttaccccgtcacgcactcctagcaggtcggtctcgagaaccagcctggtctccaac
ccgccaggcgtaaataggtgattacaagagaggagtttgaggcgttcgtagcacaacaacaatgacggttgga
tgcgggtgcatacatcttttcctccgacaccggtcaagggcatttacaacaaaaatcagtcaaggcaaacggtgc
tatccgaagtggtgttggagaggaccgaattggagatttcgtatgccccgcgcctcgaccaagaaaaagaagaa
ttactacgcaagaaattacagttaaatcccacacctgctaacagaagcagataccagtccaggaaggtggagaa
catgaaagccataacagctagacgtattctgcaaggcctagggcattatttgaaggcagaaggaaaagtggagt
gctaccgaaccctgcatcctgttccttgtattcatctagtgtgaaccgtgccttttcaagcccaagtcgca
gtggaagcctgtaacgccatgttgaaagagaactttccgactgtggcttcttactgtattattccagagtacga
tgcctatttggacatggttgacggagcttcatgctgcttagcactgccagttttgccctgcaaagctgcgca
gctttccaaagaaacactcctatttggaacccacaatacgatcggcagtgccttcagcgatccagaacacgctc
cagaacgtcctggcagctgccacaaaagaaattgcaatgtcacgcaaatgagagaattgcccgtattggattc
ggcggcctttaatgtggaatgcttcaagaaatatgcgtgaataatgaatattgggaaacgtttaaagaaaacc
ccatcaggcttactgaagaaaacgtggtaaattacattaccaaattaaaaggaccaaaagctgctgctcttttt
gcgaagacacataatttgaatatgttgcaggacataccaatggacaggtttgtaatggacttaaagagagacgt
gaaagtgactccaggaacaaaacatactgaagaacggcccaaagctacagtgatccaggctgccgatcgcgctag
caacagcgtatctgtgcggaatccaccgagagctggttaggagattaaatgcggtcctgcttccgaacattcat
acactgtttgatatgtcggctgaagactttgacgctattatagccgagcactccagcctggggattgtgttct
ggaaactgacatcgcgtcgtttgataaaagtgaggacgacgccatggctctgaccgcgttaatgattctggaag
acttaggtgtggacgcagagctgttgacgctgattgaggcggcttcggcgaaatttcatcaatacatttgccc
actaaaactaaatttaaattcggagccatgatgaaatctgaagttcctcacactgtttgtgaacacagtcat
taacattgtaatcgcaagcagagtgttgagaacggctaaccggatcaccatgtgcagcattcattggagatg
acaatatcgtgaaaggagtcaaatcggacaaattaatggcagacaggtgcgccacctggttgaatatggaagtc
aagattatgatgctgtggtgggcgagaaagcgccttatttctgtggaggggtttattttgtgtgactccgtgac
cggcacagcgtgccgtgtggcagacccctaaaaaggctgtttaagcttggcaaacctctggcagcagacgatg
aacatgatgatgacaggagaaaggcattgcatgaagagtcaacacgctgagtgggtattctttcagag
ctgtgcaaggcagtagaatcaaggtatgaaaccgtaggaacttccatcatagttatggccatgactactctagc
tagcagtgttaaatcattcagctacctgagaggggcccctataactctctacggctaacctgaatggactacga
ctctagaatagtctttaattaaagtccgccatatgaggccaccatgCAGATCTTCGTGAAGACCCTGACCGGCA
AGACCATCACCCTAGAGGTGGAGCCCAGTGACACCATCGAGAACGTGAAGGCCAAGATCCAGGATAAAGAGGGC
ATCCCCCCTGACCAGCAGAGGCTGATCTTTGCCGGCAAGCAGCTGGAAGATGGCCGCACCCTCTCTGATTACAA
```

-continued

```
CATCCAGAAGGAGTCAACCCTGCACCTGGTCCTTCGCCTGAGAGGTGGCGCTGCTTACAGTATAATCAACTTTG
AAAAACTGGCTGCTTACGGCATCCTGGGCTTTGTGTTTACACTGGCTGCCTACCTGCTGTTTGGCTATCCTGTG
TACGTGCCCGCTTATGGACTGTGTACCCTGGTGGCCATGCTGGCTGCTTACAATCTGGTGCCTATGGTGGCCAC
AGTGGCCGCCTATTGTCTTGGCGGACTGCTGACAATGGTGGCAGCCTACAgcccgagctatgcgtatcatcagt
tgGCAGCCTACGGCCCAGGACCAGGCgCTAAATTTGTGGCTGCCTGGACACTGAAAGCCGCCGCTGGACCAGGT
CCTGGACAGTACATCAAGGCCAACAGCAAGTTCATCGGCATCACCGAACTCGGCCCAGGACCAGGCTATCCCTA
CGATGTGCCTGATTACGCCTGATagTGATGATTCGAACGGCCGtatcacgcccaaacatttacagccgcggtgt
caaaaaccgcgtggacgtggttaacatccctgctggaggatcagccgtaattattataattggcttggtgctg
gctactattgtggccatgtacgtgctgaccaaccagaaacataattgaatacagcagcaattggcaagctgctt
acatagaactcgcggcgattggcatgccgccttaaaattttttattttatttttctttttcttttccgaatcgga
ttttgttttaatattcAAAAAAAAAAAAAAAAAAAAAAAAAAAAAAAAAAAAAAAAAAAAAAAAAAAAAAAAAAA
AAAAAAAAAAAAAAAAAAAAAAA VEE-Luciferase (SEQ ID NO: 15); VEE delivery vector with luciferase gene
inserted at 7545
ATGggcggcgcatgagagaagcccagaccaattacctacccaaaATGGagaaagttcacgttgacatcgaggaa
gacagcccattcctcagagctttgcagcggagcttcccgcagtttgaggtagaagccaagcaggtcactgataa
tgaccatgctaatgccagagcgttttcgcatctggcttcaaaactgatcgaaacgGaggtggacccatccgaca
cgatccttgacattggaagtgcgcccgcccgcagaatgtattctaagcacaagtatcattgtatctgtccgatg
agatgtgcggaagatccggacagattgtataagtatgcaactaagctgaagaaaactgtaaggaaataactga
taaggaattggacaagaaatgaaggagctcgccgccgtcatgagcgaccctgacctggaaactgagactatgt
gcctccacgacgacgagtcgtgtcgctacgaagggcaagtcgctgtttaccaggatgtatacgcggttgacgga
ccgacaagtctctatcaccaagccaataagggagttagagtcgcctactggataggctttgacaccaccccttt
tatgtttaagaacttggctggagcatatccatcatactctaccaactgggccgacgaaaccgtgttaacggctc
gtaacataggcctatgcagctctgacgttatggagcggtcacgtagagggatgtccattcttagaaagaagtat
ttgaaaccatccaacaatgttctattctctgttggctcgaccatctaccacgagaagagggacttactgaggag
ctggcacctgccgtctgtatttcacttacgtggcaagcaaaattacacatgtcggtgtgagactatagttagtt
gcgacgggtacgtcgttaaaagaatagctatcagtccaggcctgtatgggaagcttcaggctatgctgctacg
atgcaccgcgagggattcttgtgctgcaaagtgacagacacattgaacggggagagggtctcttttcccgtgtg
cacgtatgtgccagctacattgtgtgaccaaatgactggcatactggcaacagatgtcagtgcggacgacgcgc
aaaaactgctggttgggctcaaccagcgtatagtcgtcaacggtcgcacccagagaaacaccaataccatgaaa
aattaccttttgcccgtagtggcccaggcatttgctaggtgggcaaaggaatataaggaagatcaagaagatga
aaggccactaggactacgagatagacagttagtcatggggtgttgtgggcttttagaaggcacaagataacat
ctatttataagcgcccggataccccaaaccatcatcaaagtgaacagcgatttccactcattcgtgctgcccagg
ataggcagtaacacattggagatcgggctgagaacaagaatcaggaaaatgttagaggagcacaaggagccgtc
acctctcattaccgccgaggacgtacaagaagctaagtgcgcagccgatgaggctaaggaggtgcgtgaagccg
aggagttgcgcgcagctctaccacctttggcagctgatgttgaggagcccactctggaagccgatgtcgacttg
atgttacaagaggctggggccggctcagtggagacacctcgtggcttgataaaggttaccagctacgctggcga
ggacaagatcggctcttacgctgtgctttctccgcaggctgtactcaagagtgaaaaattatcttgcatccacc
ctctcgctgaacaagtcatagtgataacacactctggccgaaaagggcgttatgccgtggaaccataccatggt
aaagtagtggtgccagagggacatgcaatacccgtccaggacttcaagctctgagtgaaagtgccaccattgt
gtacaacgaacgtgagttcgtaaacaggtacctgcaccatattgccacacatggaggagcgctgaacactgatg
aagaatattacaaaactgtcaagcccagcgagcacgacggcgaaatacctgtacgacatcgacaggaaacagtgc
gtcaagaaagaactagtcactgggctagggctcacaggcgagctggtggatcctcccttccatgaattcgccta
cgagagtctgagaacacgaccagccgctccttaccaagtaccaaccatagggtgtatggcgtgccaggatcag
gcaagtctggcatcattaaaagcgcagtcaccaaaaaagatctagtggtgagcgccaagaaagaaaactgtgca
gaaattataagggacgtcaagaaaatgaaagggctggacgtcaattgccagaactgtgactcagtgctcttgaa
tggatgcaaacaccccgtagagaccctgtatattgacgaagcttttgcttgtcatgcaggtactctcagagcgc
tcatagccattataagacctaaaaaggcagtgctctgcgggatcccaaacagtgcggttttttaacatgatg
tgcctgaaagtgcattttaaccacgagatttgcacacaagtcttccacaaaagcatctctcgccgttgcactaa
atctgtgacttcggtcgtctcaacctttgttttacgacaaaaaaatgcaaggacgcaatgatgaggaaactaaga
ttgtgattgacactaccggcagtaccaaacctaagcaggacgatctcattctcacttgtttcagagggtgggtg
aagcagttgcaaatagattacaaaggcaacgaaataatgacggcagctgcctctcaagggctgacccgtaaagg
tgtgtatgccgttcggtacaaggtgaatgaaaatcctctgtacgcacccacctcagaacatgtgaacgtcctac
tgaccgccacggaggaccgcatcgtgtgggaaaacactagccggcgacccatggataaaaacactgactgccaag
taccctgggaatttcactgccacgatagaggagtggcaagcagacatgatgccatcatgaggcacatcttgga
gagaccggaccctaccgacgtcttccagaataaggcaaacgtgtgttgggccaaggctttagtgccggtgctga
agaccgctggcatagacatgaccactgaacaatggaacactgtgattattttgaaacggacaaagctcactca
gcagagatagtattgaaccaactatgcgtgaggttctttggactcgatctggactccggtctatttttctgcacc
cactgttccgttatccattaggaataatcactgggataactccccgtcctaacatgtacgggctgaataaag
aagtggtccgtcagctctctcgcaggtacccacaactgcctcgggcagttgccactggaagagtctatgacatg
aacactggtacactgcgcaattatgatccgcgcataaacctagtacctgtaaacagaagactgcctcatgcttt
agtcctccaccataatgaacacccacagagtgactttctcttcattcgtcagcaaattgaagggcagaactgtcc
tggtggtcgggaaaagttgtccgtcccaggcaaaatggttgactggttgtcagaccggcctgaggctaccttc
agagctcggctggatttaggcatcccaggtgatgtgcccaaatatgacaataatttgttaatgtgaggacccc
atataaataccatcactatcagcagtgtgaagaccatgccattaagcttagcatgttgaccaagaaagcttgtc
tgcatctgaatcccggcggaacctgtgtcagcataggttatggttacgctgacaggGccagcgaaagcatcatt
ggtgctatagcgcggcagttcaagttttcccgggtatgcaaaccgaaatcctcacttgaagagacggaagttct
gtttgtattcattgggtacgatcgcaaggcccgtacgcacaatcttacaagctttcatcaaccttgaccaaca
tttatacaggttccagactccacgaagccggatgtgcaccctcatatcatgtggtcgcgagggggatattgccacg
gccaccgaaggagtgattataaatgctgctaacagcaaaggacaacctggcggaggggtgtgcgagcgctgta
taagaaattcccggaaagcttcgatttacagccgatcgaagtaggaaaagcgcgactggtcaaaggtgcagcta
aacatatcattcatgccgtaggaccaaacttcaacaaagtttcggaggttgaaggtgacaaacagttggcagag
gcttatgagtccatcgctaagattgtcaacgataacaattacaagtcagtgcattccactggttccaccggg
catcttttccgggaacaaagatcgactaacccaatcattgaaccatttgctgacagctttagacaccactgatg
cagatgtagccatatactgcagggacaagaaatgggaatgactctcaaggaagcagtggctaggagagaagca
gtggaggagatatgcatatccgacgactcttcagtgacagaacctgatgcagagctggtgagggtgcatccgaa
gagttctttggctgaaggaagggctacagcacaagcgatggcaaaactttctcatatttggaagggaccaagt
ttcaccaggcggccaaggatatagcagaaattaatgccatgtggcccgttgcaacggaggccaatgagcaggta
```

-continued

```
tgcatgtatatcctcggagaaagcatgagcagtattaggtcgaaatgccccgtcgaagagtcggaagcctccac
accacctagcacgctgccttgcttgtgcatccatgccatgactccagaaagagtacagcgcctaaaagcctcac
gtccagaacaaattactgtgtgctcatcctttccattgccgaagtatagaatcactggtgtgcagaagatccaa
tgctcccagcctatattgttctcaccgaaagtgcctgcgtatattcatccaaggaagtatctcgtggaaacacc
accggtagacgagactccggagccatcggcagagaaccaatccacagaggggacacctgaacaaccaccactta
taaccgaggatgagaccaggactagaacgcctgagccgatcatcatcgaagaggaagaagaggatagcataagt
ttgctgtcagatggcccgacccaccaggtgctgcaagtcgaggcagacattcacgggcgccctctgtatctag
ctcatcctggtccattcctcatgcatccgactttgatgtggacagtttatccatacttgacaccctggaggag
ctagcgtgaccagcggggcaacgtcagccgagactaactcttacttcgcaaagagtatggagtttctggcgcga
ccggtgcctgcgcctcgaacagtattcaggaaccctccacatcccgctccgcgcacaagaacaccgtcacttgc
acccagcagggcctgctcgagaaccagcctagtttccaccccgccaggcgtgaataggtgatcactagagagg
agctcgaggcgcttacccgtcacgcactcctagcaggtcggtctcgagaaccagcctggtctccaacccgcca
ggcgtaaataggtgattacaagagaggagtttgaggcgttcgtagcacaacaacaatgacggtttgatgcggg
tgcatacatctttcctccgacaccggtcaagggcatttacaacaaaaatcagtaaggcaaacggtgctatccg
aagtggtgttggagaggaccgaattggagatttcgtatgccccgcgcctcgaccaagaaaaagaagaattacta
cgcaagaaattacagttaaatcccacacctgctaacagaagcagataccagtccaggaaggtggagaacatgaa
agccataacagctagacgtattctgcaaggcctagggcattattgaaggcagaaggaaaagtggagtgctacc
gaaccctgcatcctgttcctttgtattcatctagtgtgaaccgtgccttttcaagccccaaggtcgcagtggaa
gcctgtaacgccatgttgaaagagaactttccgactgtggcttcttactgtattattccagagtacgatgccta
tttgacatggttgacggagcttcatgctgcttagacactgccagtttttgcctgcaaagctgcgcagctttc
caaagaaacactcctatttggaacccacaatacgatcggcagtgccttcagcgatccagaacacgctccagaac
gtcctggcagctgccacaaaaagaaattgcaatgtcacgcaaatgacagtttgcccgtattggattcggcggc
ctttaatgtggaatgcttcaagaaatatgcgtgtaataatgaatattgggaaacgtttaaagaaaacccccatca
ggcttactgaagaaaacgtggtaaattacattaccaaattaaaaggaccaaaagctgctgctcttttttgcgaag
acacataatttgaatatgttgcaggacataccaatggacaggtttgtaatgacttaaagagagacgtgaaagt
gactccaggaacaaaacatactgaagaacggcccaaggtacaggtgatccaggctgccgatccgctagcaacag
cgtatctgtgcggaatccaccgagagctggttaggagattaaatgcggtcctgcttccgaacattcatcactg
tttgatatgtcggctgaagactttgacgctattatagccgagcttccagcctggggattgtgttctggaaac
tgacatcgcgtcgtttgataaaagtgaggacgacgccatggctctgaccgcgttaatgattctggaagacttag
gtgtggacgcagagctgttgacgctgattgaggcggctttcggcgaaatttcatcaatacatttgcccactaaa
actaaatttaaattcggagccatgatgaaatctgaatgttcctcacactgtttgtgaacacagtcattaacat
tgtaatcgcaagcagagtgttgagagaacggctaaccggatcaccatgtgcagcattcattggagatgacaata
tcgtgaaaggagtcaaatcggacaaattaatggcagacaggtgcgccacctggttgaatatgaagtcaagatt
atagatgctgtggtgggcgagaaagcgccttatttctgtggagggtttattttgtgtgactccgtgaccggcac
agcgtgccgtgtggcagacccctaaaaaggctgtttaagcttggcaaacctctggcagcagacgatgaacatg
atgatgacaggagaagggcattgcatgaagagtcaacacgctggaaccgagtgggtattcttcagagctgtgc
aaggcagtagaatcaaggtatgaaaccgtaggaacttccatcatagttatggccatgactactctagctagcag
tgttaaatcattcagctacctgagagggccccctataactctctaccggcTAAcctgaatggactacgactctag
aatagtctttaattaaagtccgccatatgagatggaagatgccaaaaacattaagaagggcccagcgccattct
accccactcgaagacgggaccgccggcgagcagctgcacaaagccatgaagcgctacgccctggtgcccggcacc
atcgcctttaccgacgcacatatcgaggtggacattacctacgccgagtacttcgagatgagcgttcggctggc
agaagctatgaagcgctatgggctgaatacaaaccatcggatcgtggtgtgcagcgagaatagcttgcagttct
tcatgcccgtgtttgggtgccctgttcatcggtgtggctgtggccccagctaacgacatctacaacgagcgcgag
ctgctgaacagcatgggcatcagccagcccaccgtcgtattcgtgagcaagaaagggctgcaaaagatcctcaa
cgtgcaaaagaagctaccgatcatacaaaagatcatcatcatggatagcaagaccgactaccagggcttccaaa
gcatgtacaccttcgtgacttcccatttgccaccggcttcaacgagtacgacttcgtgcccgagagcttcgac
cgggacaaaaccatcgccctgatcatgaacagtagtggcagtaccggattgcccaagggcgtagccctaccgca
ccgcaccgcttgtgtccgattcagtcatgcccgcgacccccatcttcggcaaccagatcatccccgacaccgcta
tcctcagcgtggtgccattcaccacggcttcggcatgttcaccacgctgggctacttgatctgcggctttcgg
gtcgtgctcatgtaccgcttcgaggaggagctattcttgcgcagcttgcaagactataagattcaatctgccct
gctggtgcccacactatttagcttcttcgctaagagcactctcatcgacaagtacgacctaagcaacttgcacg
agatcgccagcggcggggcgccgctcagcaaggaggtaggtgaggccgcaaacgcttccacctaccaggc
atccgccaggggctacggcctgacagaaacaaccagcgccattctgatcaccccccgaaggggacgacaagcctgg
cgcagtaggcaaggtggtgcccttcttcgaggctaaggtggtggacttggacaccggtaagacactgggtgtga
accagcgcggcgagctgtgcgtccgtggcccatgatcatgagcggctacgttaacaaccccgaggctacaaac
gctctcatcgacaaggacggctggctgcacagcggcgacatcgcctactgggacgaggacgagcacttcttcat
cgtggaccggctgaagagcctgatcaaatacaaggctaccaggtagccccagccgaactggagagcatcctgc
tgcaacaccccaacatcttcgacgccggggtcgccggcctgcccgacgacgatgccggcgagctgcccgccgca
gtcgtcgtgctggaacacggtaaaaccatgaccgagaaggagatcgtggactatgtggccagccaggttacaac
cgccaagaagctcgcgcggtggtgttgtcgtggacgaggtgcctaaaggactgaccggcaagttggacgccc
gcaagatccgcgagattctcattaaggccaagaagggcggcaagatcgccgtgtaaTTCGAACGGCCGtatcac
gcccaaacatttacagccgcggtgtcaaaaaccgcgtggacgtggttaacatccctgctgggaggatcagccgt
aattattataattggcttggtgctggctactattgtggccatgtacgtgctgaccaaccagaaacataattgaa
tacagcagcaattggcaagctgcttacatagaactcgcggcgattggcatgccgccttaaaattttatttttat
tttttcttttcttttccgaatcggattttgttttaatatttcAAAAAAAAAAAAAAAAAAAAAAAAAAAAAAA
AAAAAAAAAAAAAAAAAAAAAAAAAAAAAAAAAAAAAAAAAAAAAAAAA
``` ubiquitin (SEQ ID NO: 38)
>UbG76 0-228
```
ATGCAGATCTTCGTGAAGACCCTGACCGGCAAGACCATCACCCTAGAGGTGGAGCCCAGTGACACCATCG
AGAACGTGAAGGCCAAGATCCAGGATAAAGAGGGCATCCCCCCTGACCAGCAGAGGCTGATCTTTGCCGGCAAGCA
GCTGGAAGATGGCCGCACCCTCTCTGATTACAACATCCAGAAGGAGTCAACCCTGCACCTGGTCCTTCGCCTGAGA
GGTGGC
```

Ubiquitin A76 (SEQ ID NO: 39)
>UbA76 0-228
ATGCAGATCTTCGTGAAGACCCTGACCGGCAAGACCATCACCCTAGAGGTGGAGCCCAGTGACACCATCG
AGAACGTGAAGGCCAAGATCCAGGATAAAGAGGGCATCCCCCCTGACCAGCAGAGGCTGATCTTTGCCGGCAAGCA
GCTGGAAGATGGCCGCACCCTCTCTGATTACAACATCCAGAAGGAGTCAACCCTGCACCTGGTCCTTCGCCTGAGA
GGTGCC HLA-A2 (MHC class I) signal peptide (SEQ ID NO: 40)
>MHC SignalPep 0-78
atggccgtcatggcgccccgaaccctcgtcctgctactctcgggggctctggccctgacccagacctggg
cgggctct HLA-A2 (MHC class I) Trans Membrane domain (SEQ ID NO: 41)
>HLA A2 TM Domain 0-201
CCGtcttcccagcccaccatccCCATCGTGGGCAtcattgctggcctggttctcttttggagctgtgatca
ctggagctgtggtcgctgctgtgatgtggaggaggaagagctcagatagaaaaggagggagctactctcaggctgc
aagcagtgacagtgcccagggctctgatgtgtctctcacagcttgtaaagtgtga IgK Leader Seq (SEQ ID NO: 42)
>IgK Leader Seq 0-60
atggagaccgatacactgctgctgtgggtgctgctcctgtgggtgccaggaagcacaggc Human DC-Lamp (SEQ ID NO: 43)
>HumanDCLAMP 0-3178
ggcaccgattcggggcctgcccggacttcgccgcacgctgcagaacctcgcccagcgcccaccatgccc
ggcagctcagcgcggcggccgcgctcttcgcgtccctggccgtaattttgcacgatggcagtcaaatgagagcaaa
agcatttccagaaaccagagattattctcaacctactgcagcagcaacagtacaggacataaaaaaacctgtccag
caaccagctaagcaagcacctcaccaaactttagcagcaagattcatggatggtcatatcacctttcaaacagcgg
ccacagtaaaaattccaacaactaccccagcaactacaaaaaaacctgcaaccaccagcccaattacctacaccct
ggtcacaacccaggccacacccaacaactcacacacagctcctccagttactgaagttacagtcggccctagctta
gccccttattcactgccaccaccatcaccccaccagctcatacagctggaaccagttcatcaaccgtcagccaca
caactgggaacaccactcaacccagtaaccagaccaccccttccagcaactttatcgatagcactgcacaaaagcac
aaccggtcagaagcctgatcaacccacccatgccccaggaacaacggcagctgcccacaataccacccgacagct
gcacctgcctccacggttcctgggcccaccctttgcacctcagccatcgtcagtcaagactggaatttatcaggttc
taaacgaagcagactctgtataaaagcagagatggggatacagctgattgttcaagacaaggagtcggtttttc
acctcggagatacttcaacatcgaccccaacgcaacgcaagcctctgggaactgtggcacccgaaaatccaacctt
ctgttgaattttcagggcggatttgtgaatctcacatttaccaaggatgaagaatcatattatatcagtgaagtgg
gagcctatttgaccgtctcagatccagagacagtttaccaaggaatcaaacatgcggtggtgatgttccagacagc
agtcgggcattccttcaagtgcgtgagtgaacagagcctccagttgtcagcccacctgcaggtgaaaacaaccgat
gtccaacttcaagcctttgattttgaagatgaccactttggaaatgtggatgagtgctcgtctgactacacaattg
tgcttcctgtgattgggcatcgtggttggtctctgccttatgggatgggtgtctataaaatccgcctaaggtg
tcaatcatctggataccagagaatctaattgttgcccgggggaatgaaaataatggaatttagagaactctttca
tcccttccaggatggatgttgggaaattccctcagagtgtgggtccttcaaacaatgtaaaccaccatcttctatt
caaatgaagtgagtcatgtgtgatttaagttcaggcagcacatcaatttctaaatactttttgtttattttatgaa
agatatagtgagctgtttatttttctagtttccttttagaatattttagccactcaaagtcaacatttgagatatgtt
gaattaacataatatatgtaaagtagaataagcctttcaaattataaaccaaggatgcaattgtaactaatactactg
tgtgtgcattgaagattttattttaccccttgatcttaacaaagccttttgctttgttatcaaatggacttcagtgc
tttactatctgtgttttatggtttcatgtaacatacatattcctggtgtagcacttaactccttttccactttaa
atttgttttttgtttttgagacggagtttcactcttgtcacccaggctggagtacagtggcacgatctcggcttat
ggcaacctccgcctcccgggttcaagtgattctcctgcttcagcttcccgagtagctgggattacaggcacacagt
accacgcctggctaattttttgtattttttattatagacgggtttcaccatgttggccagactggtcttgaactcttg
acctcaggtgatccacccacctcagcctcccaaagtgctgggattacaggcatgagccattgcgcccggccttaaa
tgttttttttaatcatcaaaagaacaacatatctcaggttgtctaagtgttttatgtaaaaccaacaaaaagaa
caaatcagcttatattttttatcttgatgactcctgctccagaatgctagactaagaattaggtggctacagatg
gtagaactaaacaataagcaagagacaataataatgcccttaattattaacaaagtgccagagtctaggctaagc
actttatctatatctcattcattctcacaacttataagtgaatgagtaaactgagacttaagggaactgaatcac
ttaaatgtcacctggctaactgatggcagagccagagcttgaattcatgttggtctgacatcaaggtctttggtct
tctccctacaccaagttacctacaagaacaatgacaccacactctgcctgaaggctcacacctcataccagcatac
gctcaccttacagggaaatgggtttatccaggatcatgagacattaggggtagatgaaaggagagctttgcagataa
caaaatagcctatccttaataaatcctccactctctggaaggagactgagggggctttgtaaaacattagtcagttg
ctcatttttatgggattgcttagctgggctgtaaagatgaaggcatcaaataaactcaaagtattttttaaattttt
ttgataatagagaaacttcgctaaccaactgttctttcttgagtgtatagcccccatcttgtggtaacttgctgctt
ctgcacttcatatccatattttcctattgttcactttattctgtagcagccctgccaagaatttattttctgcgt
ttttttttgctgctaaagaaaggaactaagtcaggatgttaacagaaaagtccacataaccctagaattcttagtca
aggaataattcaagtcagcctagagaccatgttgactttcctcatgtgtttccttatgactcagtaagttggcaag
gtcctgactttagtcttaataaaacattgaattgtagtaaaggttttttgcaataaaaacttactttgg Mouse LAMP1 (SEQ ID NO: 44)
>MouseLamp1 0-1858
attccggaggtgaaaaacaatggcacaacgtgtataatggccagcttctctgcctcctttctgaccacct
acgagactgcgaatggttctcagatcgtgaacatttccctgccagcctctgcagaagtactgaaaatggcagttc
ttgtggtaaagaaaatgtttctgaccccagcctcacaattacttttggaagaggatatttactgacactcaacttc
acaaaaaatacaacacgttacagtgtccagcatatgtattttacatataacttgtcagatacagaacattttccca
atgccatcagcaaagagatctacaccatggattccaactgacatcaaggcagacatcaacaaagcataccggtg
tgtcagtgatatccgggtctacatgaagaatgtgaccgttgtgctccgggatgccactatccaggcctacctgtcg
agtggcaacttcagcaaggaagagacacactgcacacaggatggaccttccccaaccactgggcacccagcccct
caccaccacttgtgcccacaaaccccactgtatccaagtacaatgttactggtaacaacggaacctgcctgctggc
ctctatggcactgcaactgaatatcacctacctgaaaaaggacaacaagacggtgaccagagcgttcaacatcagc

```
ccaaatgacacatctagtgggagttgcggtatcaacttggtgaccctgaaagtggagaacaagaacagagccctgg
aattgcagtttgggatgaatgccagctctagcctgttttcttgcaaggagtgcgcttgaatatgactcttcctga
tgccctagtgcccacattcagcatctccaaccattcactgaaagctcttcaggccactgtgggaaactcatacaag
tgcaacactgaggaacacatctttgtcagcaagatgctctccctcaatgtcttcagtgtgcaggtccaggctttca
aggtggacagtgacaggtttgggtctgtggaagagtgtgttcaggatggtaacaacatgttgatccccattgctgt
gggcggtgccctggcagggctgatcctcatcgtcctcattgcctacctcattggcaggaagaggagtcacgccggc
tatcagaccatctagcctggtgggcaggtgcaccagagatgcacaggggcctgttctcacatccccaagcttagat
aggtgtggaagggaggcacactttctggcaaactgttttaaaatctgctttatcaaatgtgaagttcatcttgcaa
catttactatgcacaaaggaataactattgaaatgacggtgttaattttgctaactgggttaaatattgatgagaa
ggctccactgatttgacttttaagacttggtgtttggttcttcattcttttactcagatttaagcctatcaaaggg
atactctggtccagaccttggcctggcaagggtggctgatggttaggctgcacacacttaagaagcaacgggagca
gggaaggcttgcacacaggcacgcacagggtcaacctctggacacttggcttgggctacctggccttgggggggct
gaactctggcatctggctgggtacacacccccccaatttctgtgctctgccaccgtgagctgccactttcctaaa
tagaaaatggcattattttattttttttttgtaaagtgattttccagtcttgtgttggcgttcagggtggccctg
tctctgcactgtgtacaataatagattcacctgctgacgtgtcttgcagcgtaggtgggttgtacactgggcatc
agctcacgtaatgcattgcctgtaacgatgctaataaaaa Human Lamp1 cDNA (SEQ ID NO: 45)
>Human Lamp1 0-2339
ggcccaaccgccgcccgcgcccccgctctccgcaccgtaccccggccgcctcgcgccatggcggcccccgg
cagcgcccggcgaccccctgctgctgctactgctgttgctgctgctcggcctcatgcattgtgcgtcagcagcaatg
tttatggtgaaaaatggcaacgggaccgcgtgcataatggcgactgcctctctgcgccttctcagtgaactacgaca
ccaagagtggccctaagaacatgacctttgacctgccatcagatgccacagtggtgctcaaccgcagctcctgtgg
aaaagagaacacttctgacccccagtctcgtgattgctttggaagagggacatacactcactctcaatttcacgaga
aatgcaacacgttacagcgtccagctcatgagttttgtttataacttgtcagacacacacctttcccaatgcga
gctccaaagaaatcaagactgtggaatctataactgacatcagggcagatatagataaaaaatacagatgtgttag
tggcacccaggtccacatgaacaacgtgaccgtaacgctccatgatgccaccatccaggcgtacctttccaacagc
agcttcagcaggggagagacacgctgtgaacaagacaggccttcccaaccacagcgccccctgcgccacccagcc
cctcgccctcacccgtgcccaagagccctctgtggacaagtacaacgtgagcggcaccaacgggacctgcctgct
ggcagcatgggctgcagctgaacctcacctatgagaggaaggacaacacggtggtcaaggcttctcaacatc
aaccccaacaagacctcggccagcggagctgcggcgcccacctggtgactctggagctgcacagcgagggcacca
ccgtcctgctcttccagttcgggatgaatgcaagttctagccggttttcctacaaggaatccagttgaatacaat
tcttcctgacgccagagaccctgcctttaaagctgccaacggctccctgcgagcgctgcaggccacagtcggcaat
tcctacaagtgcaacgcggaggagcacgtccgtgtcacgaaggcgttttcagtcaatatattcaaagtgtgggtcc
aggctttcaaggtggaaggtggccagtttggctctgtggaggagtgtctgctggacgagaacagcatgctgatccc
catcgctgtgggtggtgccctggcgggggctggtcctcatcgtcctcatcgcctacctcgtcggcaggaagaggagt
cacgcaggctaccagactatctagcctggtgcacgcaggcacagcagctgcaggggcctctgttcctttctctggg
cttagggtcctgtcgaaggggaggcacactttctggcaaactgtttctcaaatctgcttcatccaatgtgaagttca
tcttgcagcatttactatgcacaacagagtaactatcgaaatgacggtgttaattttgctaactgggttaaatatt
ttgctaactggttaaacattaatatttaccaaagtaggattttgagggtgggggtgctctctctgaggggtgggg
gtgccgctgtctctgaggggtgggggtgccgctgtctctgaggggtgggggtgccgctctctctgaggggtgggg
gtgccgctttctctgaggggtgggggtgccgctctctctgaggggtgggggtgctgctctctccgaggggtgga
atgccgctgtctctgaggggtgggggtgccgctctaaattggctccatatcatttgagtttagggttctggtgttt
ggtttcttcattctttactgcactcagatttaagcctacaaagggaaagcctctggccgtcacacgtaggacgca
tgaaggtcactcgtggtgaggctgacatgctcacacattacaacagtagagagggaaaatcctaagacagaggaac
tccagagatgagtgtctggagcgcttcagttcagctttaaaggccaggacgggccacacgtggctggcggcctcgt
tccagtggcggcacgtccttgggcgtctctaatgtctgcagctcaaggggctggcactttttttaaatataaaatgg
gtgttatttttattttttttgtaaagtgattttggtcttctgttgacattcggggtgatcctgttctgcgctgt
gtacaatgtgagatcggtgcgttctcctgatgttttgccgtggcttgggattgtacacgggaccagctcacgtaa
tgcattgcctgtaacaatgtaataaaaagcctctttctttaaaaaaaaaaaaaaaaaaaaaa Tetanus toxoid nulceic acid sequence (SEQ ID NO: 46)
CAGTACATCAAGGCCAACAGCAAGTTCATCGGCATCACCGAACTC Tetanus toxoid amino acid sequence (SEQ ID NO: 47)
QYIKANSKFIGITEL PADRE nulceotide sequence (SEQ ID NO: 48)
GCTAAATTTGTGGCTGCCTGGACACTGAAAGCCGCCGCT PADRE amino acid sequence (SEQ ID NO: 49)
AKFVAAWTLKAAA WPRE (SEQ ID NO: 50)
>WPRE 0-593
aatcaacctctggattacaaaatttgtgaaagattgactggtattcttaactatgttgctccttttacgc
tatgtggatacgctgctttaatgcctttgtatcatgctattgcttcccgtatggctttcattttctcctccttgta
taaatcctggttgctgtctctttatgaggagttgtggcccgttgtcaggcaacgtggcgtggtgtgcactgtgttt
gctgacgcaacccccactggttggggcattgccaccacctgtcagctccttccgggacttcgctttccccctcc
ctattgccacggcggaactcatcgccgcctgccttgcccgctgctggacaggggctcggctgttgggcactgacaa
ttccgtggtgttgtcggggaagctgacgtcctttccatggctgctcgcctgtgttgccacctggattctgcgcggg
acgtccttctgctacgtcccttcggccctcaatccagcggaccttccttcccgcggcctgctgccggctctgcggc
ctcttccgcgtcttcgccttcgccctcagacgagtcggatctccctttgggccgcctccccgcctgt TRES (SEQ ID NO: 51)
>eGFP_TRES_SEAP_Insert 1746-2335
tctcccccccccccctctccctccccccccctaacgttactggccgaagccgcttggaataaggccggt
gtgcgtttgtctatatgttatttccaccatattgccgtcttttggcaatgtgagggcccggaaacctggccctgt
cttcttgacgagcattcctaggggtctttcccctctcgccaaaggaatgcaaggtctgttgaatgtcgtgaaggaa
```

-continued

```
gcagttcctctggaagcttcttgaagacaaacaacgtctgtagcgacccttt gcaggcagcggaaccccccacctg
gcgacaggtgcctctgcggccaaaagccacgtgtataagatacacctgcaaaggcggcacaacccca gtgccacgt
tgtgagttggatagttgtggaaagagtcaaatggctctcctcaagcgtattcaacaaggggctgaaggatgcccag
aaggtacccca ttgtatgggatctgatctggggcctcggtgcacatgctttacatgtgtttagtcgaggttaaaaa
aacgtctaggccccccgaaccacggggacgtggttttcctttgaaaaacacgatgataatatg GFP (SEQ ID NO: 52)
atggtgagcaagggcgaggagctgttcaccggggtggtgcccatcctggtcgagctggacggcgacgtaa
acggccacaagttcagcgtgtccggcgagggcgagggcgatgccacctacggcaagctgaccctgaagttcatctg
caccaccggcaagctgcccgtgccctggcccaccctcgtgaccaccctgacctacggcgtgcagtgcttcagccgc
taccccgaccacatgaagcagcacgacttcttcaagtccgccatgcccgaaggctacgtccaggagcgcaccatct
tcttcaaggacgacggcaactacaagacccgcgccgaggtgaagttcgagggcgacaccctggtgaaccgcatcga
gctgaagggcatcgacttcaaggaggacggcaacatcctggggcacaagctggagtacaactacaacagccacaac
gtctatatcatggccgacaagcagaagaacggcatcaaggtgaacttcaagatccgccacaacatcgaggacggca
gcgtgcagctcgccgaccactaccagcagaacacccccatcggcgacggccccgtgctgctgcccgacaaccacta
cctgagcacccagtccgccctgagcaaagaccccaacgagaagcgcgatcacatggtcctgctggagttcgtgacc
gccgccgggatcactctcggcatggacgagctgtacaagtag SEAP (SEQ ID NO: 53)
atgctgctgctgctgctgctgctgggcctgaggctacagctctccctgggcatcatcccagttgaggagg
agaacccggacttctggaaccgcgaggcagccgaggccctgggtgccgccaagaagctgcagcctgcacagacagc
cgccaagaacctcatcatcttcctgggcgatggggatggggtgtctacggtgacagctgccaggatcctaaaaggg
cagaagaaggacaaactggggcctgagataccccctggccatggaccgcttcccatatgtggctctgtccaagacat
acaatgtagacaaacatgtgccagacagtggagcacacagccacggcctacctgtgcgggtcaagggcaacttcca
gaccattggcttgagtgcagccgcccgctttaaccagtgcaacacgacacgcggcaacgaggtcatctccgtgatg
aatcgggccaagaaagcagggaagtcagtgggagtggtaaccaccacagagtgcagcacgcctcgccagccggca
cctacgcccacacggtgaaccgcaactggtactcggacgccgacgtgcctgcctcggcccgccaggagggtgcca
ggacatcgctacgcagctcatctccaacatggacattgacgtgatcctaggtggaggccgaaagtacatgtttcgc
atgggaaccccagaccctgagtacccagatgactacagccaaggtgggaccaggctggacgggaagaatctggtgc
aggaatggctggcgaagcgccagggtgcccggtatgtgtggaacgcactgagctcatgcaggcttcctggaccc
gtctgtgacccatctcatgggtctctttgagcctggagacatgaaatacgagatccaccgagactccacactggac
ccctccctgatggagatgacagaggctgccctgcgcctgctgagcaggaaccccgcggcttcttcctcttcgtgg
agggtggtcgcatcgaccatggtcatcatgaaagcagggcttaccgggcactgactgagacgatcatgttcgacga
cgccattgagagggcgggccagctcaccagcgaggaggacacgctgagcctcgtcactgccgaccactcccacgtc
ttctccttcggaggctaccccctgcgagggagctccatcttcgggctggcccctggcaaggcccgggacaggaagg
cctacacggtcctcctatacgaaacggtccaggctatgtgctcaaggacggcgcccggccggatgttaccgagag
cgagagcgggagccccgagtatcggcagcagtcagcagtgcccctggacgaagagacccacgcaggcgaggacgtg
gcggtgttcgcgcgcggcccgcaggcgcacctggttcacggcgtgcaggagcagaccttcatagcgcacgtcatgg
ccttcgccgcctgcctggagccctacaccgcctgcgacctggcgcccccgccggcaccaccgacgccgcgcaccc
gggttactctagagtcggggcggccggccgcttcgagcagacatgataa Firefly Luciferase (SEQ ID NO: 54)
atggaagatgccaaaaacattaagaagggcccagcgccattctacccactcgaagacgggaccgccggcg
agcagctgcacaaagccatgaagcgctacgccctggtgcccggcaccatcgcctttaccgacgcacatatcgaggt
ggacattacctacgccgagtacttcgagatgagcgttcggctggcagaagctatgaagcgctatgggctgaataca
aaccatcggatcgtggtgtgcagcgagaatagcttgcagttcttcatgcccgtgttgggtgccctgttcatcggtg
tggctgtggcccagctaacgacatctacaacgagcgcgagctgctgaacagcatgggcatcagccagcccaccgt
cgtattcgtgagcaagaaagggctgcaaaagatcctcaacgtgcaaaagaagtaccgatcatacaaaagatcatc
atcatggatagcaagaccgactaccagggcttccaaagcatgtacaccttcgtgacttcccatttgccaccccggct
tcaacgagtacgacttcgtgcccgagagcttcgaccgggacaaaaccatcgccctgatcatgaacagtagtggcag
taccggattgcccaagggcgtagccctaccgcaccgcaccgcttgtgtccgattcagtcatgcccgcgaccccatc
ttcggcaaccagatcatccccgacaccgctatcctcagcgtggtgccatttcaccacggcttcggcatgttcacca
cgctgggctacttgatctgcggctttcgggtcgtgctcatgtaccgcttcgaggaggagctattcttgcgcagctt
gcaagactataagattcaatctgccctgctggtgcccacactatttagcttcttcgctaagagcactctcatcgac
aagtacgacctaagcaacttgcacgagatcgccagcggcggggcgcgctcagcaaggaggtaggtgaggccgtgg
ccaaacgcttccacctaccaggcatccgccagggctacgccctgacagaaacaaccagcgccattctgatcaccc c
cgaaggggacgacaagcctggcgcagtaggcaaggtggtgcccttcttcgaggctaaggtggtggacttggacacc
ggtaagacactgggtgtgaaccagcgcggcgagctgtgcgtccgtggccccatgatcatgagcggctacgttaaca
accccgaggctacaaacgctctcatcgacaaggacggctggctgcacagcggcgacatcgcctactgggacgagga
cgagcacttcttcatcgtggaccggctgaagagcctgatcaaatacaaggctaccaggtagccccagccgaactg
gagagcatcctgctgcaacaccccaacatcttcgacgccggggtcgccggcctgcccgacgacgatgccggcgagc
tgcccgccgcagtcgtcgtgctggaacacggtaaaaccatgaccgagaaggagatcgtggactatgtggccagcca
ggttacaaccgccaagaagctgcgcggtggtgttgttcgtggacgaggtgcctaaaggactgaccggcaagttg
gacgcccgcaagatccgcgagattctcattaaggccaagaagggcggcaagatcgccgtgtaa FMDV 2A (SEQ ID NO: 55)
GTAAAGCAAACACTGAACTTTGACCTTCTCAAGTTGGCTGGAGACGTTGAGTCCAATCCTGGGCCC
```

REFERENCES

1. Desrichard, A., Snyder, A. & Chan, T. A. Cancer Neoantigens and Applications for Immunotherapy. *Clin. Cancer Res. Off. J. Am. Assoc. Cancer Res.* (2015). doi: 10.1158/1078-0432.CCR-14-3175
2. Schumacher, T. N. & Schreiber, R. D. Neoantigens in cancer immunotherapy. *Science* 348, 69-74 (2015).
3. Gubin, M. M., Artyomov, M. N., Mardis, E. R. & Schreiber, R. D. Tumor neoantigens: building a framework for personalized cancer immunotherapy. *J. Clin. Invest.* 125, 3413-3421 (2015).
4. Rizvi, N. A. et al. Cancer immunology. Mutational landscape determines sensitivity to PD-1 blockade in non-small cell lung cancer. *Science* 348, 124-128 (2015).

5. Snyder, A. et al. Genetic basis for clinical response to CTLA-4 blockade in melanoma. *N. Engl. J. Med.* 371, 2189-2199 (2014).
6. Carreno, B. M. et al. Cancer immunotherapy. A dendritic cell vaccine increases the breadth and diversity of melanoma neoantigen-specific T cells. *Science* 348, 803-808 (2015).
7. Tran, E. et al. Cancer immunotherapy based on mutation-specific CD4+ T cells in a patient with epithelial cancer. *Science* 344, 641-645 (2014).
8. Hacohen, N. & Wu, C. J.-Y. U.S. Patent Application: 0110293637—COMPOSITIONS AND METHODS OF IDENTIFYING TUMOR SPECIFIC NEOANTIGENS. (A1). at <http://appft1.uspto.gov/netacgi/nph-Parser?Sect1=PTO1&Sect2=HITOFF&d=PG01&p=1&u=/netahtml/PTO/srchnum.html&r=1&f=G&l=50&s1=20110293637.PGNR.>
9. Lundegaard, C., Hoof, I., Lund, O. & Nielsen, M. State of the art and challenges in sequence based T-cell epitope prediction. *Immunome Res.* 6 Suppl 2, S3 (2010).
10. Yadav, M. et al. Predicting immunogenic tumour mutations by combining mass spectrometry and exome sequencing. *Nature* 515, 572-576 (2014).
11. Bassani-Sternberg, M., Pletscher-Frankild, S., Jensen, L. J. & Mann, M. Mass spectrometry of human leukocyte antigen class I peptidomes reveals strong effects of protein abundance and turnover on antigen presentation. *Mol. Cell. Proteomics MCP* 14, 658-673 (2015).
12. Van Allen, E. M. et al. Genomic correlates of response to CTLA-4 blockade in metastatic melanoma. *Science* 350, 207-211 (2015).
13. Yoshida, K. & Ogawa, S. Splicing factor mutations and cancer. *Wiley Interdiscip. Rev. RNA* 5, 445-459 (2014).
14. Cancer Genome Atlas Research Network. Comprehensive molecular profiling of lung adenocarcinoma. *Nature* 511, 543-550 (2014).
15. Rajasagi, M. et al. Systematic identification of personal tumor-specific neoantigens in chronic lymphocytic leukemia. *Blood* 124, 453-462 (2014).
16. Downing, S. R. et al. U.S. Patent Application: 0120208706—OPTIMIZATION OF MULTIGENE ANALYSIS OF TUMOR SAMPLES. (A1). at <http://appft1.uspto.gov/netacgi/nph-Parser?Sect1=PTO1&Sect2=HITOFF&d=PG01&p=1&u=/netahtml/PTO/srchnum.html&r=1&f=G&l=50&s1=20120208706.PGNR.>
17. Target Capture for NextGen Sequencing—IDT. at <http://www.idtdna.com/pages/products/nextgen/target-capture>
18. Shukla, S. A. et al. Comprehensive analysis of cancer-associated somatic mutations in class I HLA genes. *Nat. Biotechnol.* 33, 1152-1158 (2015).
19. Cieslik, M. et al. The use of exome capture RNA-seq for highly degraded RNA with application to clinical cancer sequencing. *Genome Res.* 25, 1372-1381 (2015).
20. Bodini, M. et al. The hidden genomic landscape of acute myeloid leukemia: subclonal structure revealed by undetected mutations. *Blood* 125, 600-605 (2015).
21. Saunders, C. T. et al. Strelka: accurate somatic small-variant calling from sequenced tumor-normal sample pairs. *Bioinforma. Oxf. Engl.* 28, 1811-1817 (2012).
22. Cibulskis, K. et al. Sensitive detection of somatic point mutations in impure and heterogeneous cancer samples. *Nat. Biotechnol.* 31, 213-219 (2013).
23. Wilkerson, M. D. et al. Integrated RNA and DNA sequencing improves mutation detection in low purity tumors. *Nucleic Acids Res.* 42, e107 (2014).
24. Mose, L. E., Wilkerson, M. D., Hayes, D. N., Perou, C. M. & Parker, J. S. ABRA: improved coding indel detection via assembly-based realignment. *Bioinforma. Oxf. Engl.* 30, 2813-2815 (2014).
25. Ye, K., Schulz, M. H., Long, Q., Apweiler, R. & Ning, Z. Pindel: a pattern growth approach to detect break points of large deletions and medium sized insertions from paired-end short reads. *Bioinforma. Oxf. Engl.* 25, 2865-2871 (2009).
26. Lam, H. Y. K. et al. Nucleotide-resolution analysis of structural variants using BreakSeq and a breakpoint library. *Nat. Biotechnol.* 28, 47-55 (2010).
27. Frampton, G. M. et al. Development and validation of a clinical cancer genomic profiling test based on massively parallel DNA sequencing. *Nat. Biotechnol.* 31, 1023-1031 (2013).
28. Boegel, S. et al. HLA typing from RNA-Seq sequence reads. *Genome Med.* 4, 102 (2012).
29. Liu, C. et al. ATHLATES: accurate typing of human leukocyte antigen through exome sequencing. *Nucleic Acids Res.* 41, e142 (2013).
30. Mayor, N. P. et al. HLA Typing for the Next Generation. *PloS One* 10, e0127153 (2015).
31. Roy, C. K., Olson, S., Graveley, B. R., Zamore, P. D. & Moore, M. J. Assessing long-distance RNA sequence connectivity via RNA-templated DNA-DNA ligation. *eLife* 4, (2015).
32. Song, L. & Florea, L. CLASS: constrained transcript assembly of RNA-seq reads. *BMC Bioinformatics* 14 Suppl 5, S14 (2013).
33. Maretty, L., Sibbesen, J. A. & Krogh, A. Bayesian transcriptome assembly. *Genome Biol.* 15, 501 (2014).
34. Pertea, M. et al. StringTie enables improved reconstruction of a transcriptome from RNA-seq reads. *Nat. Biotechnol.* 33, 290-295 (2015).
35. Roberts, A., Pimentel, H., Trapnell, C. & Pachter, L. Identification of novel transcripts in annotated genomes using RNA-Seq. *Bioinforma. Oxf. Engl.* (2011). doi:10.1093/bioinformatics/btr355
36. Vitting-Seerup, K., Porse, B. T., Sandelin, A. & Waage, J. spliceR: an R package for classification of alternative splicing and prediction of coding potential from RNA-seq data. *BMC Bioinformatics* 15, 81 (2014).
37. Rivas, M. A. et al. Human genomics. Effect of predicted protein-truncating genetic variants on the human transcriptome. *Science* 348, 666-669 (2015).
38. Skelly, D. A., Johansson, M., Madeoy, J., Wakefield, J. & Akey, J. M. A powerful and flexible statistical framework for testing hypotheses of allele-specific gene expression from RNA-seq data. *Genome Res.* 21, 1728-1737 (2011).
39. Anders, S., Pyl, P. T. & Huber, W. HTSeq—a Python framework to work with high-throughput sequencing data. *Bioinforma. Oxf. Engl.* 31, 166-169 (2015).
40. Furney, S. J. et al. SF3B1 mutations are associated with alternative splicing in uveal melanoma. *Cancer Discov.* (2013). doi:10.1158/2159-8290.CD-13-0330
41. Zhou, Q. et al. A chemical genetics approach for the functional assessment of novel cancer genes. *Cancer Res.* (2015). doi:10.1158/0008-5472.CAN-14-2930
42. Maguire, S. L. et al. SF3B1 mutations constitute a novel therapeutic target in breast cancer. *J. Pathol.* 235, 571-580 (2015).
43. Carithers, L. J. et al. A Novel Approach to High-Quality Postmortem Tissue Procurement: The GTEx Project. *Biopreservation Biobanking* 13, 311-319 (2015).

44. Xu, G. et al. RNA CoMPASS: a dual approach for pathogen and host transcriptome analysis of RNA-seq datasets. *PloS One* 9, e89445 (2014).
45. Andreatta, M. & Nielsen, M. Gapped sequence alignment using artificial neural networks: application to the MHC class I system. *Bioinforma. Oxf. Engl.* (2015). doi:10.1093/bioinformatics/btv639
46. Jorgensen, K. W., Rasmussen, M., Buus, S. & Nielsen, M. NetMHCstab-predicting stability of peptide-MHC-I complexes; impacts for cytotoxic T lymphocyte epitope discovery. *Immunology* 141, 18-26 (2014).
47. Larsen, M. V. et al. An integrative approach to CTL epitope prediction: a combined algorithm integrating MHC class I binding, TAP transport efficiency, and proteasomal cleavage predictions. *Eur. J. Immunol.* 35, 2295-2303 (2005).
48. Nielsen, M., Lundegaard, C., Lund, O. & Keşmir, C. The role of the proteasome in generating cytotoxic T-cell epitopes: insights obtained from improved predictions of proteasomal cleavage. Immunogenetics 57, 33-41 (2005).
49. Boisvert, F.-M. et al. A Quantitative Spatial Proteomics Analysis of Proteome Turnover in Human Cells. *Mol. Cell. Proteomics* 11, M111.011429-M111.011429 (2012).
50. Duan, F. et al. Genomic and bioinformatic profiling of mutational neoepitopes reveals new rules to predict anticancer immunogenicity. *J. Exp. Med.* 211, 2231-2248 (2014).
51. Janeway's Immunobiology: 9780815345312: Medicine & Health Science Books @ Amazon.com. at <http://www.amazon.com/Janeways-Immunobiology-Kenneth-Murphy/dp/0815345313>
52. Calis, J. J. A. et al. Properties of MHC Class I Presented Peptides That Enhance Immunogenicity. *PLoS Comput. Biol.* 9, e1003266 (2013).
53. Zhang, J. et al. Intratumor heterogeneity in localized lung adenocarcinomas delineated by multiregion sequencing. *Science* 346, 256-259 (2014)
54. Walter, M. J. et al. Clonal architecture of secondary acute myeloid leukemia. *N Engl. J. Med.* 366, 1090-1098 (2012).
55. Hunt D F, Henderson R A, Shabanowitz J, Sakaguchi K, Michel H, Sevilir N, Cox A L, Appella E, Engelhard V H. Characterization of peptides bound to the class I MHC molecule HLA-A2.1 by mass spectrometry. Science 1992. 255: 1261-1263.
56. Zarling A L, Polefrone J M, Evans A M, Mikesh L M, Shabanowitz J, Lewis S T, Engelhard V H, Hunt D F. Identification of class I MHC-associated phosphopeptides as targets for cancer immunotherapy. Proc Natl Acad Sci USA. 2006 Oct. 3; 103(40):14889-94.
57. Bassani-Sternberg M, Pletscher-Frankild S, Jensen L J, Mann M. Mass spectrometry of human leukocyte antigen class I peptidomes reveals strong effects of protein abundance and turnover on antigen presentation. Mol Cell Proteomics. 2015 March; 14(3):658-73. doi: 10.1074/mcp.M114.042812.
58. Abelin J G, Trantham P D, Penny S A, Patterson A M, Ward S T, Hildebrand W H, Cobbold M, Bai D L, Shabanowitz J, Hunt D F. Complementary IMAC enrichment methods for HLA-associated phosphopeptide identification by mass spectrometry. Nat Protoc. 2015 September; 10(9):1308-18. doi: 10.1038/nprot.2015.086. Epub 2015 Aug. 6
59. Barnstable C J, Bodmer W F, Brown G, Galfre G, Milstein C, Williams A F, Ziegler A. Production of monoclonal antibodies to group A erythrocytes, HLA and other human cell surface antigens-new tools for genetic analysis. Cell. 1978 May; 14(1):9-20.
60. Goldman J M, Hibbin J, Kearney L, Orchard K, Th'ng K H. HLA-DR monoclonal antibodies inhibit the proliferation of normal and chronic granulocytic leukaemia myeloid progenitor cells. Br J Haematol. 1982 November; 52(3):411-20.
61. Eng J K, Jahan T A, Hoopmann M R. Comet: an open-source M S/M S sequence database search tool. Proteomics. 2013 January; 13(1):22-4. doi: 10.1002/pmic.201200439. Epub 2012 Dec. 4.
62. Eng J K, Hoopmann M R, Jahan T A, Egertson J D, Noble W S, MacCoss M J. A deeper look into Comet—implementation and features. J Am Soc Mass Spectrom. 2015 November; 26(11):1865-74. doi: 10.1007/s13361-015-1179-x. Epub 2015 Jun. 27.
63. Lukas Käll, Jesse Canterbury, Jason Weston, William Stafford Noble and Michael J. MacCoss. Semi-supervised learning for peptide identification from shotgun proteomics datasets. Nature Methods 4:923-925, November 2007
64. Lukas Käll, John D. Storey, Michael J. MacCoss and William Stafford Noble. Assigning confidence measures to peptides identified by tandem mass spectrometry. Journal of Proteome Research, 7(1):29-34, January 2008
65. Lukas Käll, John D. Storey and William Stafford Noble. Nonparametric estimation of posterior error probabilities associated with peptides identified by tandem mass spectrometry. Bioinformatics, 24(16):i42-i48, August 2008
66. Kinney R M, B J Johnson, V L Brown, D W Trent. Nucleotide Sequence of the 26 S mRNA of the Virulent Trinidad Donkey Strain of Venezuelan Equine Encephalitis Virus and Deduced Sequence of the Encoded Structural Proteins. Virology 152 (2), 400-413. 1986 Jul. 30.
67. Jill E Slansky, Frédérique M Rattis, Lisa F Boyd, Tarek Fahmy, Elizabeth M Jaffee, Jonathan P Schneck, David H Margulies, Drew M Pardoll. Enhanced Antigen-Specific Antitumor Immunity with Altered Peptide Ligands that Stabilize the MHC-Peptide-TCR Complex. Immunity, Volume 13, Issue 4, 1 Oct. 2000, Pages 529-538.
68. A Y Huang, P H Gulden, A S Woods, M C Thomas, C D Tong, W Wang, V H Engelhard, G Pasternack, R Cotter, D Hunt, D M Pardoll, and E M Jaffee. The immunodominant major histocompatibility complex class I-restricted antigen of a murine colon tumor derives from an endogenous retroviral gene product. Proc Natl Acad Sci USA.; 93(18): 9730-9735, 1996 Sep. 3.
69. JOHNSON, BARBARA J. B., RICHARD M. KINNEY, CRYSTLE L. KOST AND DENNIS W. TRENT. Molecular Determinants of Alphavirus Neurovirulence: Nucleotide and Deduced Protein Sequence Changes during Attenuation of Venezuelan Equine Encephalitis Virus. J Gen Virol 67:1951-1960, 1986.
70. Aarnoudse, C. A., Kruse, M., Konopitzky, R., Brouwenstijn, N., and Schrier, P. I. (2002). TCR reconstitution in Jurkat reporter cells facilitates the identification of novel tumor antigens by cDNA expression cloning. Int J Cancer 99, 7-13.
71. Alexander, J., Sidney, J., Southwood, S., Ruppert, J., Oseroff, C., Maewal, A., Snoke, K., Serra, H. M., Kubo, R. T., and Sette, A. (1994). Development of high potency universal DR-restricted helper epitopes by modification of high affinity DR-blocking peptides. Immunity 1, 751-761.
72. Banu, N., Chia, A., Ho, Z. Z., Garcia, A. T., Paravasivam, K., Grotenbreg, G. M., Bertoletti, A., and Gehring, A. J. (2014). Building and optimizing a virus-specific T cell receptor library for targeted immunotherapy in viral infections. Scientific Reports 4, 4166.
73. Cornet, S., Miconnet, I., Menez, J., Lemonnier, F., and Kosmatopoulos, K. (2006). Optimal organization of a polypeptide-based candidate cancer vaccine composed of cryptic tumor peptides with enhanced immunogenicity. Vaccine 24, 2102-2109.
74. Depla, E., van der Aa, A., Livingston, B. D., Crimi, C., Allosery, K., de Brabandere, V., Krakover, J., Murthy, S., Huang, M., Power, S., et al. (2008). Rational design of a multiepitope vaccine encoding T-lymphocyte epitopes for treatment of chronic hepatitis B virus infections. Journal of Virology 82, 435-450.
75. Ishioka, G. Y., Fikes, J., Hermanson, G., Livingston, B., Crimi, C., Qin, M., del Guercio, M. F., Oseroff, C., Dahlberg, C., Alexander, J., et al. (1999). Utilization of MHC class I transgenic mice for development of minigene DNA vaccines encoding multiple HLA-restricted CTL epitopes. J Immunol 162, 3915-3925.
76. Janetzki, S., Price, L., Schroeder, H., Britten, C. M., Welters, M. J. P., and Hoos, A. (2015). Guidelines for the automated evaluation of Elispot assays. Nat Protoc 10, 1098-1115.
77. Lyons, G. E., Moore, T., Brasic, N., Li, M., Roszkowski, J. J., and Nishimura, M. I. (2006). Influence of human CD8 on antigen recognition by T-cell receptor-transduced cells. Cancer Res 66, 11455-11461.
78. Nagai, K., Ochi, T., Fujiwara, H., An, J., Shirakata, T., Mineno, J., Kuzushima, K., Shiku, H., Melenhorst, J. J., Gostick, E., et al. (2012). Aurora kinase A-specific T-cell receptor gene transfer redirects T lymphocytes to display effective antileukemia reactivity. Blood 119, 368-376.
79. Panina-Bordignon, P., Tan, A., Termijtelen, A., Demotz, S., Corradin, G., and Lanzavecchia, A. (1989). Universally immunogenic T cell epitopes: promiscuous binding to human MHC class II and promiscuous recognition by T cells. Eur J Immunol 19, 2237-2242.
80. Vitiello, A., Marchesini, D., Furze, J., Sherman, L. A., and Chesnut, R. W. (1991). Analysis of the HLA-restricted influenza-specific cytotoxic T lymphocyte response in transgenic mice carrying a chimeric human-mouse class I major histocompatibility complex. J Exp Med 173, 1007-1015.
81. Yachi, P. P., Ampudia, J., Zal, T., and Gascoigne, N. R. J. (2006). Altered peptide ligands induce delayed CD8-T cell receptor interaction—a role for CD8 in distinguishing antigen quality. Immunity 25, 203-211.
82. Pushko P, Parker M, Ludwig G V, Davis N L, Johnston R E, Smith J F. Replicon-helper systems from attenuated Venezuelan equine encephalitis virus: expression of heterologous genes in vitro and immunization against heterologous pathogens in vivo. Virology. 1997 Dec. 22; 239(2):389-401.
83. Strauss, J H and E G Strauss. The alphaviruses: gene expression, replication, and evolution. Microbiol Rev. 1994 September; 58(3): 491-562.
84. Rheme C, Ehrengruber M U, Grandgirard D. Alphaviral cytotoxicity and its implication in vector development. Exp Physiol. 2005 January; 90(1):45-52. Epub 2004 Nov. 12.
85. Riley, Michael K. II, and Wilfred Vermerris. Recent Advances in Nanomaterials for Gene Delivery—A Review. Nanomaterials 2017, 7(5), 94.
86. Frolov I, Hardy R, Rice C M. Cis-acting RNA elements at the 5' end of Sindbis virus genome RNA regulate minus- and plus-strand RNA synthesis. RNA. 2001 November; 7(11):1638-51.
87. Jose J, Snyder J E, Kuhn R J. A structural and functional perspective of alphavirus replication and assembly. Future Microbiol. 2009 September; 4(7):837-56.
88. Bo Li and C. olin N. Dewey. RSEM: accurate transcript quantification from RNA-Seq data with or without a referenfe genome. BMC Bioinformatics, 12:323, August 2011
89. Hillary Pearson, Tariq Daouda, Diana Paola Granados, Chantal Durette, Eric Bonneil, Mathieu Courcelles, Anja Rodenbrock, Jean-Philippe Laverdure, Caroline Cote, Sylvie Mader, Sébastien Lemieux, Pierre Thibault, and Claude Perreault. MHC class I-associated peptides derive from selective regions of the human genome. The Journal of Clinical Investigation, 2016,
90. Juliane Liepe, Fabio Marino, John Sidney, Anita Jeko, Daniel E. Bunting, Alessandro Sette, Peter M. Kloetzel, Michael P. H. Stumpf, Albert J. R. Heck, Michele Mishto. A large fraction of HLA class I ligands are proteasome-generated spliced peptides. Science, 21, October 2016.
91. Mommen G P., Marino, F., Meiring H D., Poelen, M C., van Gaans-van den Brink, J A., Mohammed S., Heck A J., and van Els C A. Sampling From the Proteome to the Human Leukocyte Antigen-DR (HLA-DR) Ligandome Proceeds Via High Specificity. Mol Cell Proteomics 15(4): 1412-1423, April 2016.
92. Sebastian Kreiter, Mathias Vormehr, Niels van de Roemer, Mustafa Diken, Martin Löwer, Jan Diekmann, Sebastian Boegel, Barbara Schrörs, Fulvia Vascotto, John C. Castle, Arbel D. Tadmor, Stephen P. Schoenberger, Christoph Huber, Özlem Türeci, and Ugur Sahin. Mutant MHC class II epitopes drive therapeutic immune responses to caner. Nature 520, 692-696, April 2015.
93. Tran E., Turcotte S., Gros A., Robbins P. F., Lu Y. C., Dudley M. E., Wunderlich J. R., Somerville R. P., Hogan K., Hinrichs C. S., Parkhurst M. R., Yang J. C., Rosenberg S. A. Cancer immunotherapy based on mutation-specific CD4+ T cells in a patient with epithelial cancer. Science 344(6184) 641-645, May 2014.
94. Andreatta M., Karosiene E., Rasmussen M., Stryhn A., Buus S., Nielsen M.
Accurate pan-specific prediction of peptide-MHC class II binding affinity with improved binding core identification. Immunogenetics 67(11-12) 641-650, November 2015.
95. Nielsen, M., Lund, O. NN-align. An artificial neural network-based alignment algorithm for MHC class II peptide binding prediction. BMC Bioinformatics 10:296, September 2009.
96. Nielsen, M., Lundegaard, C., Lund, O. Prediction of MHC class II binding affinity using SMM-align, a novel stabilization matrix alignment method. BMC Bioinformatics 8:238, July 2007.
97. Zhang, J., et al. PEAKS D B: de novo sequencing assisted database search for sensitive and accurate peptide identification. Molecular & Cellular Proteomics. 11(4):1-8. Jan. 2, 2012.
98. Jensen, Kamilla Kjaergaard, et al. "Improved Methods for Prediting Peptide Binding Affinity to MHC Class II Molecules." Immunology, 2018, doi:10.1111/imm.12889.
99. Carter, S. L., Cibulskis, K., Helman, E., McKenna, A., Shen, H., Zack, T., Laird, P. W., Onofrio, R. C., Winckler, W., Weir, B. A., et al. (2012). Absolute quantification of somatic DNA alterations in human cancer. Nat. Biotechnol. 30, 413-421
100. McGranahan, N., Rosenthal, R., Hiley, C. T., Rowan, A. J., Watkins, T. B. K., Wilson, G. A., Birkbak, N. J., Veeriah, S., Van Loo, P., Herrero, J., et al. (2017). Allele- Specific HLA Loss and Immune Escape in Lung Cancer Evolution. Cell 171, 1259-1271.e11.
101. Shukla, S. A., Rooney, M. S., Rajasagi, M., Tiao, G., Dixon, P. M., Lawrence, M. S., Stevens, J., Lane, W. J., Dellagatta, J. L., Steelman, S., et al. (2015). Comprehensive analysis of cancer-associated somatic mutations in class I HLA genes. Nat. Biotechnol. 33, 1152-1158.
102. Van Loo, P., Nordgard, S. H., Lingjærde, O. C., Russnes, H. G., Rye, I. H., Sun, W., Weigman, V. J., Marynen, P., Zetterberg, A., Naume, B., et al. (2010). Allele-specific copy number analysis of tumors. Proc. Natl. Acad. Sci. U.S.A 107, 16910-16915.
103. Van Loo, P., Nordgard, S. H., Lingjærde, O. C., Russnes, H. G., Rye, I. H., Sun, W., Weigman, V. J., Marynen, P., Zetterberg, A., Naume, B., et al. (2010). Allele-specific copy number analysis of tumors. Proc. Natl. Acad. Sci. U.S.A 107, 16910-16915.

VARIOUS EMBODIMENTS

1. Disclosed herein is a viral vector comprising a neoantigen or plurality of neoantigens. In certain embodiments, a neoantigen is identified using a method disclosed herein, e.g., below. In certain embodiments, a neoantigen has at least one characteristic or property as disclosed herein, e.g., below.
2. Disclosed herein is a method for identifying one or more neoantigens from a tumor cell of a subject that are likely to be presented on the tumor cell surface, comprising the steps of:
   obtaining at least one of exome, transcriptome or whole genome tumor nucleotide sequencing data from the tumor cell of the subject, wherein the tumor nucleotide sequencing data is used to obtain data representing peptide sequences of each of a set of neoantigens, and wherein the peptide sequence of each neoantigen comprises at least one alteration that makes it distinct from the corresponding wild-type, parental peptide sequence;
   inputting the peptide sequence of each neoantigen into one or more presentation models to generate a set of numerical likelihoods that each of the neoantigens is presented by one or more MHC alleles on the tumor cell surface of the tumor cell of the subject, the set of numerical likelihoods having been identified at least based on received mass spectrometry data; and selecting a subset of the set of neoantigens based on the set of numerical likelihoods to generate a set of selected neoantigens.
3. In certain embodiments, a number of the set of selected neoantigens is 20.
4. In certain embodiments, the presentation model represents dependence between:
   presence of a pair of a particular one of the MHC alleles and a particular amino acid at a particular position of a peptide sequence; and
   likelihood of presentation on the tumor cell surface, by the particular one of the MHC alleles of the pair, of such a peptide sequence comprising the particular amino acid at the particular position.
5. In certain embodiments, inputting the peptide sequence comprises:
   applying the one or more presentation models to the peptide sequence of the corresponding neoantigen to generate a dependency score for each of the one or more MHC alleles indicating whether the MHC allele will present the corresponding neoantigen based on at least positions of amino acids of the peptide sequence of the corresponding neoantigen.
6. In certain embodiments, the method further comprises:
   transforming the dependency scores to generate a corresponding per-allele likelihood for each MHC allele indicating a likelihood that the corresponding MHC allele will present the corresponding neoantigen; and
   combining the per-allele likelihoods to generate the numerical likelihood.
7. In certain embodiments, the transforming the dependency scores model the presentation of the peptide sequence of the corresponding neoantigen as mutually exclusive.
8. In certain embodiments, the method further comprises:
   transforming a combination of the dependency scores to generate the numerical likelihood.
9. In certain embodiments, the transforming the combination of the dependency scores models the presentation of the peptide sequence of the corresponding neoantigen as interfering between MHC alleles.
10. In certain embodiments, the set of numerical likelihoods are further identified by at least an allele noninteracting feature, and further comprising:
    applying an allele noninteracting one of the one or more presentation models to the allele noninteracting features to generate a dependency score for the allele noninteracting features indicating whether the peptide sequence of the corresponding neoantigen will be presented based on the allele noninteracting features.
11. In certain embodiments, the method further comprises:
    combining the dependency score for each MHC allele in the one or more MHC alleles with the dependency score for the allele noninteracting feature;
    transforming the combined dependency scores for each MHC allele to generate a corresponding per-allele likelihood for the MHC allele indicating a likelihood that the corresponding MHC allele will present the corresponding neoantigen; and
    combining the per-allele likelihoods to generate the numerical likelihood.
12. In certain embodiments, the method further comprises:
    transforming a combination of the dependency scores for each of the MHC alleles and the dependency score for the allele noninteracting features to generate the numerical likelihood.
13. In certain embodiments, a set of numerical parameters for the presentation model is trained based on a training data set including at least a set of training peptide sequences identified as present in a plurality of samples and one or more MHC alleles associated with each training peptide sequence, wherein the training peptide sequences are identified through mass spectrometry on isolated peptides eluted from MHC alleles derived from the plurality of samples.
14. In certain embodiments, the training data set further includes data on mRNA expression levels of the tumor cell.
15. In certain embodiments, the samples comprise cell lines engineered to express a single MHC class I or class II allele.
16. In certain embodiments, the samples comprise cell lines engineered to express a plurality of MHC class I or class II alleles.
17. In certain embodiments, the samples comprise human cell lines obtained or derived from a plurality of patients.
18. In certain embodiments, the samples comprise fresh or frozen tumor samples obtained from a plurality of patients.

19. In certain embodiments, the samples comprise fresh or frozen tissue samples obtained from a plurality of patients.
20. In certain embodiments, the samples comprise peptides identified using T-cell assays.
21. In certain embodiments, the training data set further comprises data associated with:
    peptide abundance of the set of training peptides present in the samples;
    peptide length of the set of training peptides in the samples.
22. In certain embodiments, the training data set is generated by comparing the set of training peptide sequences via alignment to a database comprising a set of known protein sequences, wherein the set of training protein sequences are longer than and include the training peptide sequences.
23. In certain embodiments, the training data set is generated based on performing or having performed mass spectrometry on a cell line to obtain at least one of exome, transcriptome, or whole genome peptide sequencing data from the cell line, the peptide sequencing data including at least one protein sequence including an alteration.
24. In certain embodiments, the training data set is generated based on obtaining at least one of exome, transcriptome, and whole genome normal nucleotide sequencing data from normal tissue samples.
25. In certain embodiments, the training data set further comprises data associated with proteome sequences associated with the samples.
26. In certain embodiments, the training data set further comprises data associated with MHC peptidome sequences associated with the samples.
27. In certain embodiments, the training data set further comprises data associated with peptide-MHC binding affinity measurements for at least one of the isolated peptides.
28. In certain embodiments, the training data set further comprises data associated with peptide-MHC binding stability measurements for at least one of the isolated peptides.
29. In certain embodiments, the training data set further comprises data associated with transcriptomes associated with the samples.
30. In certain embodiments, the training data set further comprises data associated with genomes associated with the samples.
31. In certain embodiments, the training peptide sequences are of lengths within a range of k-mers where k is between 8-15, inclusive.
32. In certain embodiments, the method further comprises encoding the peptide sequence using a one-hot encoding scheme.
33. In certain embodiments, the method further comprises encoding the training peptide sequences using a left-padded one-hot encoding scheme.
34. Also disclosed herein is a method of treating a subject having a tumor, comprising performing any of the steps of the methods disclosed herein, and further comprising obtaining a tumor vaccine comprising the set of selected neoantigens, and administering the tumor vaccine to the subject.
35. Also disclosed herein is a method of manufacturing a tumor vaccine, comprising performing any of the steps a method disclosed herein, and further comprising producing or having produced a tumor vaccine comprising the set of selected neoantigens.
36. Also disclosed herein is a tumor vaccine comprising a set of selected neoantigens, selected by performing a method disclosed herein.
37. In certain embodiments, the tumor vaccine comprises one or more of a nucleotide sequence, a polypeptide sequence, RNA, DNA, a cell, a plasmid, or a vector.
38. In certain embodiments, the tumor vaccine comprises one or more neoantigens presented on the tumor cell surface.
39. In certain embodiments, the tumor vaccine comprises one or more neoantigens that is immunogenic in the subject.
40. In certain embodiments, the tumor vaccine does not comprise one or more neoantigens that induce an autoimmune response against normal tissue in the subject.
41. In certain embodiments, the tumor vaccine further comprises an adjuvant.
42. In certain embodiments, the tumor vaccine further comprises an excipient.
43. In certain embodiments, selecting the set of selected neoantigens comprises selecting neoantigens that have an increased likelihood of being presented on the tumor cell surface relative to unselected neoantigens based on the presentation model.
44. In certain embodiments, selecting the set of selected neoantigens comprises selecting neoantigens that have an increased likelihood of being capable of inducing a tumor-specific immune response in the subject relative to unselected neoantigens based on the presentation model.
45. In certain embodiments, selecting the set of selected neoantigens comprises selecting neoantigens that have an increased likelihood of being capable of being presented to naïve T cells by professional antigen presenting cells (APCs) relative to unselected neoantigens based on the presentation model, optionally wherein the APC is a dendritic cell (DC).
46. In certain embodiments, selecting the set of selected neoantigens comprises selecting neoantigens that have a decreased likelihood of being subject to inhibition via central or peripheral tolerance relative to unselected neoantigens based on the presentation model.
47. In certain embodiments, selecting the set of selected neoantigens comprises selecting neoantigens that have a decreased likelihood of being capable of inducing an autoimmune response to normal tissue in the subject relative to unselected neoantigens based on the presentation model.
48. In certain embodiments, exome or transcriptome nucleotide sequencing data is obtained by performing sequencing on the tumor tissue.
49. In certain embodiments, sequencing is next generation sequencing (NGS) or any massively parallel sequencing approach.
50. In certain embodiments, the set of numerical likelihoods are further identified by at least MHC-allele interacting features comprising at least one of:
    a. The predicted affinity with which the MHC allele and the neoantigen encoded peptide bind.
    b. The predicted stability of the neoantigen encoded peptide-MHC complex.
    c. The sequence and length of the neoantigen encoded peptide.
    d. The probability of presentation of neoantigen encoded peptides with similar sequence in cells from other individuals expressing the particular MHC allele as assessed by mass-spectrometry proteomics or other means.

e. The expression levels of the particular MHC allele in the subject in question (e.g. as measured by RNA-seq or mass spectrometry).
f. The overall neoantigen encoded peptide-sequence-independent probability of presentation by the particular MHC allele in other distinct subjects who express the particular MHC allele.
g. The overall neoantigen encoded peptide-sequence-independent probability of presentation by MHC alleles in the same family of molecules (e.g., HLA-A, HLA-B, HLA-C, HLA-DQ, HLA-DR, HLA-DP) in other distinct subjects.

51. In certain embodiments, the set of numerical likelihoods are further identified by at least MHC-allele noninteracting features comprising at least one of:
   a. The C- and N-terminal sequences flanking the neoantigen encoded peptide within its source protein sequence.
   b. The presence of protease cleavage motifs in the neoantigen encoded peptide, optionally weighted according to the expression of corresponding proteases in the tumor cells (as measured by RNA-seq or mass spectrometry).
   c. The turnover rate of the source protein as measured in the appropriate cell type.
   d. The length of the source protein, optionally considering the specific splice variants ("isoforms") most highly expressed in the tumor cells as measured by RNA-seq or proteome mass spectrometry, or as predicted from the annotation of germline or somatic splicing mutations detected in DNA or RNA sequence data.
   e. The level of expression of the proteasome, immunoproteasome, thymoproteasome, or other proteases in the tumor cells (which may be measured by RNA-seq, proteome mass spectrometry, or immunohistochemistry).
   f. The expression of the source gene of the neoantigen encoded peptide (e.g., as measured by RNA-seq or mass spectrometry).
   g. The typical tissue-specific expression of the source gene of the neoantigen encoded peptide during various stages of the cell cycle.
   h. A comprehensive catalog of features of the source protein and/or its domains as can be found in e.g. uniProt or PDB http://www.rcsb.org/pdb/home/home.do.
   i. Features describing the properties of the domain of the source protein containing the peptide, for example: secondary or tertiary structure (e.g., alpha helix vs beta sheet); Alternative splicing.
   j. The probability of presentation of peptides from the source protein of the neoantigen encoded peptide in question in other distinct subjects.
   k. The probability that the peptide will not be detected or over-represented by mass spectrometry due to technical biases.
   l. The expression of various gene modules/pathways as measured by RNASeq (which need not contain the source protein of the peptide) that are informative about the state of the tumor cells, stroma, or tumor-infiltrating lymphocytes (TILs).
   m. The copy number of the source gene of the neoantigen encoded peptide in the tumor cells.
   n. The probability that the peptide binds to the TAP or the measured or predicted binding affinity of the peptide to the TAP.
   o. The expression level of TAP in the tumor cells (which may be measured by RNA-seq, proteome mass spectrometry, immunohistochemistry).
   p. Presence or absence of tumor mutations, including, but not limited to:
      i. Driver mutations in known cancer driver genes such as EGFR, KRAS, ALK, RET, ROS1, TP53, CDKN2A, CDKN2B, NTRK1, NTRK2, NTRK3
      ii. In genes encoding the proteins involved in the antigen presentation machinery (e.g., B2M, HLA-A, HLA-B, HLA-C, TAP-1, TAP-2, TAPBP, CALR, CNX, ERP57, HLA-DM, HLA-DMA, HLA-DMB, HLA-DO, HLA-DOA, HLA-DOB, HLA-DP, HLA-DPA1, HLA-DPB1, HLA-DQ, HLA-DQA1, HLA-DQA2, HLA-DQB1, HLA-DQB2, HLA-DR, HLA-DRA, HLA-DRB1, HLA-DRB3, HLA-DRB4, HLA-DRB5 or any of the genes coding for components of the proteasome or immunoproteasome). Peptides whose presentation relies on a component of the antigen-presentation machinery that is subject to loss-of-function mutation in the tumor have reduced probability of presentation.
   q. Presence or absence of functional germline polymorphisms, including, but not limited to:
      i. In genes encoding the proteins involved in the antigen presentation machinery (e.g., B2M, HLA-A, HLA-B, HLA-C, TAP-1, TAP-2, TAPBP, CALR, CNX, ERP57, HLA-DM, HLA-DMA, HLA-DMB, HLA-DO, HLA-DOA, HLA-DOB, HLA-DP, HLA-DPA1, HLA-DPB1, HLA-DQ, HLA-DQA1, HLA-DQA2, HLA-DQB1, HLA-DQB2, HLA-DR, HLA-DRA, HLA-DRB1, HLA-DRB3, HLA-DRB4, HLA-DRB5 or any of the genes coding for components of the proteasome or immunoproteasome)
   r. Tumor type (e.g., NSCLC, melanoma).
   s. Clinical tumor subtype (e.g., squamous lung cancer vs. non-squamous).
   t. Smoking history.
   u. The typical expression of the source gene of the peptide in the relevant tumor type or clinical subtype, optionally stratified by driver mutation.

52. In certain embodiments, the at least one mutation is a frameshift or nonframeshift indel, missense or nonsense substitution, splice site alteration, genomic rearrangement or gene fusion, or any genomic or expression alteration giving rise to a neoORF.

53. In certain embodiments, the tumor cell is selected from the group consisting of: lung cancer, melanoma, breast cancer, ovarian cancer, prostate cancer, kidney cancer, gastric cancer, colon cancer, testicular cancer, head and neck cancer, pancreatic cancer, brain cancer, B-cell lymphoma, acute myelogenous leukemia, chronic myelogenous leukemia, chronic lymphocytic leukemia, and T cell lymphocytic leukemia, non-small cell lung cancer, and small cell lung cancer.

54. In certain embodiments, the method further comprises obtaining a tumor vaccine comprising the set of selected neoantigens or a subset thereof, optionally further comprising administering the tumor vaccine to the subject.

55. In certain embodiments, at least one of neoantigens in the set of selected neoantigens, when in polypeptide form, comprises at least one of: a binding affinity with MHC with an IC50 value of less than 1000 nM, for MHC Class 1 polypeptides a length of 8-15, 8, 9, 10, 11, 12, 13, 14, or 15 amino acids, presence of sequence motifs within or near the polypeptide in the parent protein sequence promoting proteasome cleavage, and presence of sequence motifs promoting TAP transport.

56. Also disclosed herein is a method for generating a model for identifying one or more neoantigens that are likely to be presented on a tumor cell surface of a tumor cell, comprising executing the steps of:
receiving mass spectrometry data comprising data associated with a plurality of isolated peptides eluted from major histocompatibility complex (MHC) derived from a plurality of samples;
obtaining a training data set by at least identifying a set of training peptide sequences present in the samples and one or more MHCs associated with each training peptide sequence;
training a set of numerical parameters of a presentation model using the training data set comprising the training peptide sequences, the presentation model providing a plurality of numerical likelihoods that peptide sequences from the tumor cell are presented by one or more MHC alleles on the tumor cell surface.

57. In certain embodiments, the presentation model represents dependence between:
presence of a particular amino acid at a particular position of a peptide sequence; and
likelihood of presentation, by one of the MHC alleles on the tumor cell, of the peptide sequence containing the particular amino acid at the particular position.

58. In certain embodiments, the samples comprise cell lines engineered to express a single MHC class I or class II allele.

59. In certain embodiments, the samples comprise cell lines engineered to express a plurality of MHC class I or class II alleles.

60. In certain embodiments, the samples comprise human cell lines obtained or derived from a plurality of patients.

61. In certain embodiments, the samples comprise fresh or frozen tumor samples obtained from a plurality of patients.

62. In certain embodiments, the samples comprise peptides identified using T-cell assays.

63. In certain embodiments, the training data set further comprises data associated with:
peptide abundance of the set of training peptides present in the samples;
peptide length of the set of training peptides in the samples.

64. In certain embodiments, obtaining the training data set comprises:
obtaining a set of training protein sequences based on the training peptide sequences by comparing the set of training peptide sequences via alignment to a database comprising a set of known protein sequences, wherein the set of training protein sequences are longer than and include the training peptide sequences.

65. In certain embodiments, obtaining the training data set comprises:
performing or having performed mass spectrometry on a cell line to obtain at least one of exome, transcriptome, or whole genome nucleotide sequencing data from the cell line, the nucleotide sequencing data including at least one protein sequence including a mutation.

66. In certain embodiments, training the set of parameters of the presentation model comprises:
encoding the training peptide sequences using a one-hot encoding scheme.

67. In certain embodiments, the method further comprises:
obtaining at least one of exome, transcriptome, and whole genome normal nucleotide sequencing data from normal tissue samples; and
training the set of parameters of the presentation model using the normal nucleotide sequencing data.

68. In certain embodiments, the training data set further comprises data associated with proteome sequences associated with the samples.

69. In certain embodiments, the training data set further comprises data associated with MHC peptidome sequences associated with the samples.

70. In certain embodiments, the training data set further comprises data associated with peptide-MHC binding affinity measurements for at least one of the isolated peptides.

71. In certain embodiments, the training data set further comprises data associated with peptide-MHC binding stability measurements for at least one of the isolated peptides.

72. In certain embodiments, the training data set further comprises data associated with transcriptomes associated with the samples.

73. In certain embodiments, the training data set further comprises data associated with genomes associated with the samples.

74. In certain embodiments, training the set of numerical parameters further comprises:
logistically regressing the set of parameters.

75. In certain embodiments, the training peptide sequences are of lengths within a range of k-mers where k is between 8-15, inclusive.

76. In certain embodiments, training the set of numerical parameters of the presentation model comprises:
encoding the training peptide sequences using a left-padded one-hot encoding scheme.

77. In certain embodiments, training the set of numerical parameters further comprises:
determining values for the set of parameters using a deep learning algorithm.

78. Also disclosed herein is a method for generating a model for identifying one or more neoantigens that are likely to be presented on a tumor cell surface of a tumor cell, comprising executing the steps of:
receiving mass spectrometry data comprising data associated with a plurality of isolated peptides eluted from major histocompatibility complex (MHC) derived from a plurality of fresh or frozen tumor samples;
obtaining a training data set by at least identifying a set of training peptide sequences present in the tumor samples and presented on one or more MHC alleles associated with each training peptide sequence;
obtaining a set of training protein sequences based on the training peptide sequences; and
training a set of numerical parameters of a presentation model using the training protein sequences and the training peptide sequences, the presentation model providing a plurality of numerical likelihoods that peptide sequences from the tumor cell are presented by one or more MHC alleles on the tumor cell surface.

79. In certain embodiments, the presentation model represents dependence between:
presence of a pair of a particular one of the MHC alleles and a particular amino acid at a particular position of a peptide sequence; and
likelihood of presentation on the tumor cell surface, by the particular one of the MHC alleles of the pair, of such a peptide sequence comprising the particular amino acid at the particular position.

SEQUENCE LISTING

<160> NUMBER OF SEQ ID NOS: 193

<210> SEQ ID NO 1
<211> LENGTH: 36519
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 1

| | | | | | |
|---|---|---|---|---|---|
| ccatcttcaa | taatatacct | caaacttttt | gtgcgcgtta | atatgcaaat | gaggcgtttg | 60 |
| aatttgggga | ggaagggcgg | tgattggtcg | agggatgagc | gaccgttagg | ggcggggcga | 120 |
| gtgacgtttt | gatgacgtgg | ttgcgaggag | gagccagttt | gcaagttctc | gtgggaaaag | 180 |
| tgacgtcaaa | cgaggtgtgg | tttgaacacg | gaaatactca | attttcccgc | gctctctgac | 240 |
| aggaaatgag | gtgtttctgg | gcggatgcaa | gtgaaaacgg | gccattttcg | cgcgaaaact | 300 |
| gaatgaggaa | gtgaaaatct | gagtaatttc | gcgtttatgg | cagggaggag | tatttgccga | 360 |
| gggccgagta | gactttgacc | gattacgtgg | gggtttcgat | taccgtgttt | ttcacctaaa | 420 |
| tttccgcgta | cggtgtcaaa | gtccggtgtt | tttacgtagg | tgtcagctga | tcgccagggt | 480 |
| atttaaacct | gcgctctcca | gtcaagaggc | cactcttgag | tgccagcgag | aagagttttc | 540 |
| tcctccgcgc | cgcgagtcag | atctacactt | tgaaagatga | ggcacctgag | agacctgccc | 600 |
| gatgagaaaa | tcatcatcgc | ttccgggaac | gagattctgg | aactggtggt | aaatgccatg | 660 |
| atgggcgacg | accctccgga | gccccccacc | ccatttgaga | caccttcgct | gcacgatttg | 720 |
| tatgatctgg | aggtggatgt | gcccgaggac | gatcccaatg | aggaggcggt | aaatgatttt | 780 |
| tttagcgatg | ccgcgctgct | agctgccgag | gaggcttcga | gctctagctc | agacagcgac | 840 |
| tcttcactgc | ataccctag | acccggcaga | ggtgagaaaa | agatcccga | gcttaaaggg | 900 |
| gaagagatgg | acttgcgctg | ctatgaggaa | tgcttgcccc | cgagcgatga | tgaggacgag | 960 |
| caggcgatcc | agaacgcagc | gagccaggga | gtgcaagccg | ccagcgagag | ctttgcgctg | 1020 |
| gactgcccgc | ctctgcccgg | acacggctgt | aagtcttgtg | aatttcatcg | catgaatact | 1080 |
| ggagataaag | ctgtgttgtg | tgcactttgc | tatatgagag | cttacaacca | ttgtgtttac | 1140 |
| agtaagtgtg | attaagttga | actttagagg | gaggcagaga | gcagggtgac | tgggcgatga | 1200 |
| ctggtttatt | tatgtatata | tgttctttat | ataggtcccg | tctctgacgc | agatgatgag | 1260 |
| acccccacta | caaagtccac | ttcgtcaccc | ccagaaattg | gcacatctcc | acctgagaat | 1320 |
| attgttagac | cagttcctgt | tagagccact | gggaggagag | cagctgtgga | atgtttggat | 1380 |
| gacttgctac | agggtgggt | tgaacctttg | gacttgtgta | cccggaaacg | ccccaggcac | 1440 |
| taagtgccac | acatgtgtgt | ttacttgagg | tgatgtcagt | atttataggg | tgtggagtgc | 1500 |
| aataaaaaat | gtgttgactt | taagtgcgtg | gtttatgact | caggggtggg | gactgtgagt | 1560 |
| atataagcag | gtgcagacct | gtgtggttag | ctcagagcgg | catggagatt | tggacggtct | 1620 |
| tggaagactt | tcacaagact | agacagctgc | tagagaacgc | ctcgaacgga | gtctcttacc | 1680 |
| tgtggagatt | ctgcttcggt | ggcgacctag | ctaggctagt | ctacagggcc | aaacaggatt | 1740 |
| atagtgaaca | atttgaggtt | attttgagag | agtgttctgg | tctttttgac | gctcttaact | 1800 |
| tgggccatca | gtctcacttt | aaccagagga | tttcgagagc | ccttgatttt | actactcctg | 1860 |
| gcagaaccac | tgcagcagta | gcctttttg | cttttattct | tgacaaatgg | agtcaagaaa | 1920 |
| cccatttcag | cagggattac | cagctggatt | tcttagcagt | agctttgtgg | agaacatgga | 1980 |

-continued

```
agtgccagcg cctgaatgca atctccggct acttgccggt acagccgcta gacactctga    2040
ggatcctgaa tctccaggag agtcccaggg cacgccaacg tcgccagcag cagcagcagg    2100
aggaggatca agaagagaac ccgagagccg gcctggaccc tccggcggag gaggaggagt    2160
agctgacctg tttcctgaac tgcgccgggt gctgactagg tcttcgagtg gtcgggagag    2220
ggggattaag cgggagaggc atgatgagac taatcacaga actgaactga ctgtgggtct    2280
gatgagtcgc aagcgcccag aaacagtgtg gtggcatgag gtgcagtcga ctggcacaga    2340
tgaggtgtcg gtgatgcatg agaggttttc tctagaacaa gtcaagactt gttggttaga    2400
gcctgaggat gattgggagg tagccatcag gaattatgcc aagctggctc tgaggccaga    2460
caagaagtac aagattacta agctgataaa tatcagaaat gcctgctaca tctcagggaa    2520
tggggctgaa gtggagatct gtctccagga aagggtggct ttcagatgct gcatgatgaa    2580
tatgtacccg ggagtggtgg gcatggatgg ggttaccttt atgaacatga ggttcagggg    2640
agatgggtat aatggcacgg tctttatggc caataccaag ctgacagtcc atggctgctc    2700
cttctttggg tttaataaca cctgcatcga ggcctggggt caggtcggtg tgaggggctg    2760 cagttttttca gccaactgga tggggtcgt gggcaggacc aagagtatgc tgtccgtgaa    2820
gaaatgcttg tttgagaggt gccacctggg ggtgatgagc gagggcgaag ccagaatccg    2880
ccactgcgcc tctaccgaga cgggctgctt tgtgctgtgc aagggcaatg ctaagatcaa    2940
gcataatatg atctgtggag cctcggacga gcgcggctac cagatgctga cctgcgccgg    3000
cgggaacagc catatgctgg ccaccgtaca tgtggcttcc catgctcgca agccctggcc    3060
cgagttcgag cacaatgtca tgaccaggtg caatatgcat ctgggtccc gccgaggcat    3120 gttcatgccc taccagtgca acctgaatta tgtgaaggtg ctgctggagc ccgatgccat    3180
gtccagagtg agcctgacgg gggtgtttga catgaatgtg gaggtgtgga agattctgag    3240
atatgatgaa tccaagacca ggtgccgagc ctgcgagtgc ggaggaagc atgccaggtt    3300 ccagcccgtg tgtgtggatg tgacggagga cctgcgaccc gatcatttgg tgttgccctg    3360
caccgggacg gagttcggtt ccagcgggga agaatctgac tagagtgagt agtgttctgg    3420 ggcggggag gacctgcatg agggccagaa taactgaaat ctgtgctttt ctgtgtgttg    3480
cagcagcatg agcggaagcg gctcctttga gggagggta ttcagcccctt atctgacggg    3540 gcgtctcccc tcctgggcgg gagtgcgtca aatgtgatg ggatccacgg tggacggccg    3600
gcccgtgcag cccgcgaact cttcaaccct gacctatgca accctgagct cttcgtcgtt    3660
ggacgcagct gccgccgcag ctgctgcatc tgccgccagc gccgtgcgcg gaatggccat    3720
gggcgccggc tactacggca ctctggtggc caactcgagt tccaccaata atcccgccag    3780
cctgaacgag gagaagctgt tgctgctgat ggcccagctc gaggccttga cccagcgcct    3840
gggcgagctg acccagcagg tggctcagct gcaggagcag acgcgggccg cggttgccac    3900
ggtgaaatcc aaataaaaaa tgaatcaata aataaacgga gacggttgtt gattttaaca    3960
cagagtctga atctttattt gattttttcgc gcgcggtagg ccctgaccaa ccggtctcga    4020
tcattgagca cccggtggat ctttttccagg accgggtaga ggtgggcttg gatgttgagg    4080
tacatggcca tgagcccgtc ccggggtgg aggtagctcc attgcaggc ctcgtgctcg    4140 ggggtggtgt tgtaaatcac ccagtcatag caggggcgca gggcatggtg ttgcacaata    4200
tctttgagga ggagactgat ggccacgggc agccctttgg tgtaggtgtt tacaaatctg    4260
ttgagctggg agggatgcat gcgggggggag atgaggtgca tcttggcctg gatcttgaga    4320
ttggcgatgt taccgcccag atcccgcctg gggttcatgt tgtgcaggac caccagcacg    4380
```

```
gtgtatccgg tgcacttggg gaatttatca tgcaacttgg aagggaaggc gtgaaagaat   4440
ttggcgacgc ctttgtgccc gcccaggttt tccatgcact catccatgat gatggcgatg   4500
ggcccgtggg cggcggcctg ggcaaagacg tttcgggggt cggacacatc atagttgtgg   4560
tcctgggtga ggtcatcata ggccatttta atgaatttgg ggcggagggt gccggactgg   4620
gggacaaagg taccctcgat cccgggggcg tagttcccct cacagatctg catctcccag   4680
gctttgagct cggaggggg gatcatgtcc acctgcgggg cgataaagaa cacgtttcc   4740
ggggcggggg agatgagctg ggccgaaagc aagttccgga gcagctggga cttgccgcag   4800
ccggtggggc cgtagatgac cccgatgacc ggctgcaggt ggtagttgag ggagagacag   4860
ctgccgtcct cccggaggag gggggccacc tcgttcatca tctcgcgcac gtgcatgttc   4920
tcgcgcacca gttccgccag gaggcgctct ccccccaggg ataggagctc ctggagcgag   4980
gcgaagtttt tcagcggctt gagtccgtcg gccatgggca ttttggagag ggtttgttgc   5040
aagagttcca ggcggtccca gagctcgtg atgtgctcta cggcatctcg atccagcaga   5100
cctcctcgtt tcgcgggttg ggacggctgc gggagtaggg caccagacga tgggcgtcca   5160
gcgcagccag ggtccggtcc ttccagggtc gcagcgtccg cgtcagggtg gtctccgtca   5220
cggtgaaggg gtgcgcgccg ggctgggcgc ttgcgagggt gcgcttcagg ctcatccggc   5280
tggtcgaaaa ccgctcccga tcggcgccct gcgcgtcggc caggtagcaa ttgaccatga   5340
gttcgtagtt gagcgcctcg gccgcgtggc ctttggcgcg gagcttacct ttggaagtct   5400
gcccgcaggc gggacagagg agggacttga gggcgtagag cttgggggcg aggaagacgg   5460
actcggggggc gtaggcgtcc gcgccgcagt gggcgcagac ggtctcgcac tccacgagcc   5520
aggtgaggtc gggctggtcg gggtcaaaaa ccagtttccc gccgttcttt ttgatgcgtt   5580
tcttaccttt ggtctccatg agctcgtgtc cccgctgggt gacaaagagg ctgtccgtgt   5640
ccccgtagac cgactttatg ggccggtcct cgagcggtgt gccgcggtcc tcctcgtaga   5700
ggaaccccgc ccactccgag acgaaagccc gggtccaggc cagcacgaag gaggccacgt   5760
gggacgggta gcggtcgttg tccaccagcg ggtccacctt ttccagggta tgcaaacaca   5820
tgtcccccctc gtccacatcc aggaaggtga ttggcttgta agtgtaggcc acgtgaccgg   5880
gggtcccggc cgggggggta taaaagggtg cgggtccctg ctcgtcctca ctgtcttccg   5940
gatcgctgtc caggagcgcc agctgttggg gtaggtattc cctctcgaag gcgggcatga   6000
cctcggcact caggttgtca gtttctagaa acgaggagga tttgatattg acggtgccgg   6060
cggagatgcc tttcaagagc ccctcgtcca tctggtcaga aaagacgatc tttttgttgt   6120
cgagcttggt ggcgaaggag ccgtagaggg cgttggagag gagcttggcg atggagcgca   6180
tggtctggtt tttttccttg tcggcgcgct ccttggcggc gatgttgagc tgcacgtact   6240
cgcgcgccac gcacttccat tcggggaaga cggtggtcag ctcgtcgggc acgattctga   6300
cctgccagcc ccgattatgc agggtgatga ggtccacact ggtggccacc tcgccgcgca   6360
ggggctcatt agtccagcag aggcgtccgc ccttgcgcga gcagaagggg gcaggggggt   6420
ccagcatgac ctcgtcgggg gggtcggcat cgatggtgaa gatgccgggc aggaggtcgg   6480
ggtcaaagta gctgatggaa gtggccagat cgtccagggc agcttgccat cgcgcacgg   6540
ccagcgcgcg ctcgtaggga ctgaggggcg tgccccaggg catgggatgg gtaagcgcgg   6600
aggcgtacat gccgcagatg tcgtagacgt agagggctc ctcgaggatg ccgatgtagg   6660
tggggtagca gcgcccccg cggatgctgg cgcgcacgta gtcatacagc tcgtgcgagg   6720
```

-continued

```
gggcgaggag ccccgggccc aggttggtgc gactgggctt ttcggcgcgg tagacgatct    6780
ggcggaaaat ggcatgcgag ttggaggaga tggtgggcct ttggaagatg ttgaagtggg    6840
cgtggggcag tccgaccgag tcgcggatga agtgggcgta ggagtcttgc agcttggcga    6900
cgagctcggc ggtgactagg acgtccagag cgcagtagtc gagggtctcc tggatgatgt    6960
catacttgag ctgtcccttt tgtttccaca gctcgcggtt gagaaggaac tcttcgcggt    7020
ccttccagta ctcttcgagg gggaacccgt cctgatctgc acggtaagag cctagcatgt    7080
agaactggtt gacggccttg taggcgcagc agcccttctc cacggggagg gcgtaggcct    7140
gggcggcctt gcgcagggag gtgtgcgtga gggcgaaagt gtccctgacc atgaccttga    7200
ggaactggtg cttgaagtcg atatcgtcgc agccccctg ctcccagagc tggaagtccg    7260
tgcgcttctt gtaggcgggg ttgggcaaag cgaaagtaac atcgttgaag aggatcttgc    7320
ccgcgcgggg cataaagttg cgagtgatgc ggaaaggttg gggcacctcg gcccggttgt    7380
tgatgacctg ggcggcgagc acgatctcgt cgaagccgtt gatgttgtgg cccacgatgt    7440
agagttccac gaatcgcgga cggcccttga cgtggggcag tttcttgagc tcctcgtagg    7500
tgagctcgtc ggggtcgctg agcccgtgct gctcgagcgc ccagtcggcg agatgggggt    7560
tggcgcggag gaaggaagtc cagagatcca cggccagggc ggtttgcaga cggtcccggt    7620
actgacggaa ctgctgcccg acggccattt tttcgggggt gacgcagtag aaggtgcggg    7680
ggtccccgtg ccagcgatcc catttgagct ggagggcgag atcgagggcg agctcgacga    7740
gccggtcgtc cccggagagt ttcatgacca gcatgaaggg gacgagctgc ttgccgaagg    7800
accccatcca ggtgtaggtt ccacatcgt aggtgaggaa gagcctttcg gtgcgaggat    7860
gcgagccgat ggggaagaac tggatctcct gccaccaatt ggaggaatgg ctgttgatgt    7920
gatgaagta gaaatgccga cggcgcgccg aacactcgtg cttgtgttta tacaagcggc    7980
cacagtgctc gcaacgctgc acgggatgca cgtgctgcac gagctgtacc tgagttcctt    8040
tgacgaggaa tttcagtggg aagtggagtc gtggcgcctg catctcgtgc tgtactacgt    8100
cgtggtggtc ggcctggccc tcttctgcct cgatggtggt catgctgacg agcccgcgcg    8160
ggaggcaggt ccagacctcg gcgcgagcgg gtcggagagc gaggacgagg gcgcgcaggc    8220
cggagctgtc cagggtcctg agacgctgcg gagtcaggtc agtgggcagc ggcggcgcgc    8280
ggttgacttg caggagtttt tccagggcgc gcgggaggtc cagatggtac ttgatctcca    8340
ccgcgccatt ggtggcgacg tcgatggctt gcagggtccc gtgcccctgg ggtgtgacca    8400
ccgtcccccg tttcttcttg ggcggctggg gcgacggggg cggtgcctct tccatggtta    8460
gaagcggcgg cgaggacgcg cgccgggcgg caggggcggc tcggggcccg gaggcagggg    8520
cggcaggggc acgtcggcgc cgcgcgcggg taggttctgg tactgcgccc ggagaagact    8580
ggcgtgagcg acgacgcgac ggttgacgtc ctggatctga cgcctctggg tgaaggccac    8640
gggacccgtg agtttgaacc tgaaagagag ttcgacagaa tcaatctcgg tatcgttgac    8700
ggcggcctgc cgcaggatct cttgcacgtc gcccgagttg tcctggtagg cgatctcggt    8760
catgaactgc tcgatctcct cctcttgaag gtctccgcgg ccggcgcgct ccacggtggc    8820
cgcgaggtcg ttggagatgc ggcccatgag ctgcagaaag cgttcatgc ccgcctcgtt    8880
ccagacgcgg ctgtagacca cgacgccctc gggatcgcgg gcgcgcatga ccacctgggc    8940
gaggttgagc tccacgtggc gcgtgaagac cgcgtagttg cagaggcgct ggtagaggta    9000
gttgagcgtg gtggcgatgt gctcggtgac gaagaaatac atgatccagc ggcggagcgg    9060
catctcgctg acgtcgccca gcgcctccaa acgttccatg gcctcgtaaa agtccacggc    9120
```

```
gaagttgaaa aactgggagt tgcgcgccga gacggtcaac tcctcctcca gaagacggat    9180
gagctcggcg atggtggcgc gcacctcgcg ctcgaaggcc cccggagtt  cctccacttc    9240 ctcttcttcc tcctccacta acatctcttc tacttcctcc tcaggcggca gtggtggcgg    9300 gggaggggc  ctgcgtcgcc ggcggcgcac gggcagacgg tcgatgaagc gctcgatggt    9360
ctcgccgcgc cggcgtcgca tggtctcggt gacggcgcgc cgtcctcgc  ggggccgcag    9420 cgtgaagacg ccgccgcgca tctccaggtg gccgggggg  tccccgttgg gcagggagag    9480
ggcgctgacg atgcatctta tcaattgccc cgtagggact ccgcgcaagg acctgagcgt    9540
ctcgagatcc acgggatctg aaaaccgctg aacgaaggct tcgagccagt cgcagtcgca    9600
aggtaggctg agcacggttt cttctggcgg gtcatgttgg ttgggagcgg ggcgggcgat    9660
gctgctggtg atgaagttga ataggcggt  tctgagacgg cggatggtgg cgaggagcac    9720
caggtctttg ggcccggctt gctggatgcg cagacggtcg gccatgcccc aggcgtggtc    9780
ctgacacctg gccaggtcct tgtagtagtc ctgcatgagc cgctccacgg gcacctcctc    9840
ctcgcccgcg cggccgtgca tgcgcgtgag cccgaagccg cgctggggct ggacgagcgc    9900
caggtcggcg acgacgcgct cggcgaggat ggcttgctgg atctgggtga gggtggtctg    9960
gaagtcatca aagtcgacga agcggtggta ggctccggtg ttgatggtgt aggagcagtt   10020
ggccatgacg gaccagttga cggtctggtg gcccggacgc acgagctcgt ggtacttgag   10080
gcgcgagtag gcgcgcgtgt cgaagatgta gtcgttgcag gtgcgcacca ggtactggta   10140
gccgatgagg aagtgcggcg gcggctggcg gtagagcggc catcgctcgg tggcggggc    10200 gccgggcgcg aggtcctcga gcatggtgcg gtggtagccg tagatgtacc tggacatcca   10260
ggtgatgccg gcggcggtgg tggaggcgcg cgggaactcg cggacgcggt tccagatgtt   10320
gcgcagcggc aggaagtagt tcatggtggg cacggtctgg cccgtgaggc gcgcgcagtc   10380
gtggatgctc tatacgggca aaaacgaaag cggtcagcgg ctcgactccg tggcctggag   10440
gctaagcgaa cgggttgggc tgcgcgtgta ccccggttcg aatctcgaat caggctggag   10500
ccgcagctaa cgtggtattg gcactcccgt ctcgacccaa gcctgcacca accctccagg   10560
atacggaggc gggtcgtttt gcaacttttt tttggaggcc ggatgagact agtaagcgcg   10620
gaaagcggcc gaccgcgatg gctcgctgcc gtagtctgga gaagaatcgc cagggttgcg   10680
ttgcggtgtg ccccggttcg aggccggccg gattccgcgg ctaacgaggg cgtggctgcc   10740
ccgtcgtttc caagacccca tagccagccg acttctccag ttacggagcg agccctctt    10800 ttgtttgtt  tgttttttgcc agatgcatcc cgtactgcgg cagatgcgcc cccaccaccc   10860
tccaccgcaa caacagcccc ctccacagcc ggcgcttctg ccccgcccc  agcagcaact   10920 tccagccacg accgccgcgg ccgccgtgag cggggctgga cagagttatg atcaccagct   10980
ggccttggaa gagggcgagg ggctggcgcg cctggggcg  tcgtcgccgg agcggcaccc   11040
gcgcgtgcag atgaaaaggg acgctcgcga ggcctacgtg cccaagcaga acctgttcag   11100
agacaggagc ggcgaggagc ccgaggagat gcgcgcggcc cggttccacg cggggcggga   11160
gctgcggcgc ggcctggacc gaaagagggt gctgagggac gaggatttcg aggcggacga   11220
gctgacgggg atcagccccg cgcgcgcgca cgtggccgcg ccaacctgg  tcacggcgta   11280 cgagcagacc gtgaaggagg agagcaactt ccaaaaatcc ttcaacaacc acgtgcgcac   11340
cctgatcgcg cgcgaggagg tgaccctggg cctgatgcac ctgtgggacc tgctggagcc   11400
catcgtgcag aaccccacca gcaagccgct gacggcgcag ctgttcctgg tggtgcagca   11460
```

```
tagtcgggac aacgaagcgt tcagggaggc gctgctgaat atcaccgagc ccgagggccg   11520
ctggctcctg gacctggtga acattctgca gagcatcgtg gtgcaggagc gcgggctgcc   11580
gctgtccgag aagctggcgg ccatcaactt ctcggtgctg agtttgggca agtactacgc   11640
taggaagatc tacaagaccc cgtacgtgcc catagacaag gaggtgaaga tcgacgggtt   11700
ttacatgcgc atgaccctga aagtgctgac cctgagcgac gatctggggg tgtaccgcaa   11760
cgacaggatg caccgtgcgg tgagcgccag caggcggcgc gagctgagcg accaggagct   11820
gatgcatagt ctgcagcggg ccctgaccgg ggccgggacc gaggggggaga gctactttga   11880 catgggcgcg gacctgcact ggcagcccag ccgccgggcc ttggaggcgg cggcaggacc   11940
ctacgtagaa gaggtggacg atgaggtgga cgaggagggc gagtacctgg aagactgatg   12000
gcgcgaccgt attttgcta gatgcaacaa caacagccac ctcctgatcc cgcgatgcgg   12060
gcggcgctgc agagccagcc gtccggcatt aactcctcgg acgattggac ccaggccatg   12120
caacgcatca tggcgctgac gacccgcaac cccgaagcct ttagacagca gcccaggcc   12180 aaccggctct cggccatcct ggaggccgtg gtgccctcgc gctccaaccc cacgcacgag   12240
aaggtcctgg ccatcgtgaa cgcgctggtg gagaacaagg ccatccgcgg cgacgaggcc   12300
ggcctggtgt acaacgcgct gctggagcgc gtggcccgct acaacagcac caacgtgcag   12360
accaacctgg accgcatggt gaccgacgtg cgcgaggccg tgcccagcg cgagcggttc   12420 caccgcgagt ccaacctggg atccatggtg gcgctgaacg ccttcctcag cacccagccc   12480
gccaacgtgc cccggggcca ggaggactac accaacttca tcagcgccct gcgcctgatg   12540
gtgaccgagg tgccccagag cgaggtgtac cagtccgggc cggactactt cttccagacc   12600
agtcgccagg gcttgcagac cgtgaacctg agccaggctt tcaagaactt gcagggcctg   12660
tggggcgtgc aggcccgggt cggggaccgc gcgacggtgt cgagcctgct gacgccgaac   12720
tcgcgcctgc tgctgctgct ggtggccccc ttcacggaca gcggcagcat caaccgcaac   12780
tcgtacctgg gctacctgat taacctgtac cgcgaggcca tcggccaggc gcacgtggac   12840
gagcagacct accaggagat cacccacgtg agccgcgccc tgggccagga cgacccgggc   12900
aacctggaag ccaccctgaa cttttttgctg accaaccggt cgcagaagat cccgccccag   12960
tacgcgctca gcaccgagga ggagcgcatc ctgcgttacg tgcagcagag cgtgggcctg   13020
ttcctgatgc aggaggggc cacccccagc gccgcgctcg acatgaccgc gcgcaacatg   13080
gagcccagca tgtacgccag caaccgcccg ttcatcaata aactgatgga ctacttgcat   13140
cgggcggccg ccatgaactc tgactatttc accaacgcca tcctgaatcc ccactggctc   13200
ccgccgccgg ggttctacac gggcgagtac gacatgcccg accccaatga cgggttcctg   13260
tgggacgatg tggacagcag cgtgttctcc ccccgaccgg gtgctaacga cgcccccttg   13320
tggaagaagg aaggcagcga ccgacgcccg tcctcggcgc tgtccggccg cgagggtgct   13380
gccgcggcgg tgcccgaggc cgccagtcct ttcccgagct gccccttctc gctgaacagt   13440
atccgcagca gcgagctggg caggatcacg cgcccgcgct tgctgggcga agaggagtac   13500
ttgaatgact cgctgttgag acccgagcgg gagaagaact tccccaataa cgggatagaa   13560
agcctggtgg acaagatgag ccgctggaag acgtatgcgc aggagcacag ggacgatccc   13620
cgggcgtcgc aggggggccac gagccggggc agcgccgccc gtaaacgccg gtggcacgac   13680
aggcagcggg gacagatgtg ggacgatgag gactccgccg acgacagcag cgtgttggac   13740
ttgggtggga gtggtaaccc gttcgctcac ctgcgccccc gtatcgggcg catgatgtaa   13800
gagaaaccga aaataaatga tactcaccaa ggccatggcg accagcgtgc gttcgtttct   13860
```

```
tctctgttgt tgttgtatct agtatgatga ggcgtgcgta cccggagggt cctcctccct   13920
cgtacgagag cgtgatgcag caggcgatgg cggcggcggc gatgcagccc ccgctggagg   13980
ctccttacgt gcccccgcgg tacctggcgc ctacggaggg gcggaacagc attcgttact   14040
cggagctggc acccttgtac gataccaccc ggttgtacct ggtggacaac aagtcggcgg   14100
acatcgcctc gctgaactac cagaacgacc acagcaactt cctgaccacc gtggtgcaga   14160
acaatgactt cacccccacg gaggccagca cccagaccat caactttgac gagcgctcgc   14220
ggtggggcgg ccagctgaaa accatcatgc acaccaacat gcccaacgtg aacgagttca   14280
tgtacagcaa caagttcaag gcgcgggtga tggtctcccg caagaccccc aatggggtga   14340
cagtgacaga ggattatgat ggtagtcagg atgagctgaa gtatgaatgg gtggaatttg   14400
agctgcccga aggcaacttc tcggtgacca tgaccatcga cctgatgaac aacgccatca   14460
tcgacaatta cttggcggtg gggcggcaga acggggtgct ggagagcgac atcggcgtga   14520
agttcgacac taggaacttc aggctgggct gggaccccgt gaccgagctg gtcatgcccg   14580
gggtgtacac caacgaggct ttccatcccg atattgtctt gctgcccggc tgcggggtgg   14640
acttcaccga gagccgcctc agcaacctgc tgggcattcg caagaggcag cccttccagg   14700
aaggcttcca gatcatgtac gaggatctgg aggggggcaa catccccgcg ctcctggatg   14760
tcgacgccta tgagaaaagc aaggaggatg cagcagctga agcaactgca gccgtagcta   14820
ccgcctctac cgaggtcagg ggcgataatt ttgcaagcgc cgcagcagtg gcagcggccg   14880
aggcggctga aaccgaaagt aagatagtca ttcagccggt ggagaaggat agcaagaaca   14940
ggagctacaa cgtactaccg gacaagataa acaccgccta ccgcagctgg tacctagcct   15000
acaactatgg cgaccccgag aagggcgtgc gctcctggac gctgctcacc acctcggacg   15060
tcacctgcgg cgtggagcaa gtctactggt cgctgcccga catgatgcaa gacccggtca   15120
ccttccgctc cacgcgtcaa gttagcaact acccggtggt gggcgccgag ctcctgcccg   15180
tctactccaa gagcttcttc aacgagcagg ccgtctactc gcagcagctg cgcgccttca   15240
cctcgcttac gcacgtcttc aaccgcttcc ccgagaacca gatcctcgtc cgcccgcccg   15300
cgcccaccat taccaccgtc agtgaaaacg ttcctgctct cacagatcac gggaccctgc   15360
cgctgcgcag cagtatccgg ggagtccagc gcgtgaccgt tactgacgcc agacgccgca   15420
cctgccccta cgtctacaag gccctgggca tagtcgcgcc gcgcgtcctc tcgagccgca   15480
ccttctaaat gtccattctc atctcgccca gtaataacac cggttggggc ctgcgcgcgc   15540
ccagcaagat gtacggaggc gctcgccaac gctccacgca acaccccgtg cgcgtgcgcg   15600
ggcacttccg cgctccctgg ggcgccctca agggccgcgt gcggtcgcgc accaccgtcg   15660
acgacgtgat cgaccaggtg gtggccgacg cgcgcaacta caccccgcc gccgcgcccg   15720 tctccaccgt ggacgccgtc atcgacagcg tggtggccga cgcgcgccgg tacgcccgcg   15780
ccaagagccg gcgcggcgc atcgcccggc ggcaccggag caccccgcc atgcgcgcgg   15840 cgcgagcctt gctgcgcagg gccaggcgca cgggacgcag ggccatgctc agggcggcca   15900
gacgcgcggc ttcaggcgcc agcgccggca ggacccggag acgcgcggcc acggcggcgg   15960
cagcggccat cgccagcatg tcccgcccgc ggcgagggaa cgtgtactgg gtgcgcgacg   16020
ccgccaccgg tgtgcgcgtg cccgtgcgca cccgcccccc tcgcacttga agatgttcac   16080
ttcgcgatgt tgatgtgtcc cagcggcgag gaggatgtcc aagcgcaaat tcaaggaaga   16140
gatgctccag gtcatcgcgc ctgagatcta cggccctgcg gtggtgaagg aggaaagaaa   16200
```

```
gccccgcaaa atcaagcggg tcaaaaagga caaaaaggaa gaagaaagtg atgtggacgg    16260
attggtggag tttgtgcgcg agttcgcccc ccggcggcgc gtgcagtggc gcgggcggaa    16320
ggtgcaaccg gtgctgagac ccggcaccac cgtggtcttc acgcccggcg agcgctccgg    16380
caccgcttcc aagcgctcct acgacgaggt gtacggggat gatgatattc tggagcaggc    16440
ggccgagcgc ctgggcgagt tgcttacgg caagcgcagc cgttccgcac cgaaggaaga    16500
ggcggtgtcc atcccgctgg accacggcaa ccccacgccg agcctcaagc ccgtgacctt    16560
gcagcaggtg ctgccgaccg cggcgccgcg ccgggggttc aagcgcgagg gcgaggatct    16620
gtacccacc atgcagctga tggtgccaa gcgccagaag ctggaagacg tgctggagac    16680
catgaaggtg gacccggacg tgcagcccga ggtcaaggtg cggcccatca agcaggtggc    16740
cccgggcctg ggcgtgcaga ccgtggacat caagattccc acggagccca tggaaacgca    16800
gaccgagccc atgatcaagc ccagcaccag caccatggag gtgcagacgg atccctggat    16860
gccatcggct cctagtcgaa gaccccggcg caagtacggc gcggccagcc tgctgatgcc    16920
caactacgcg ctgcatcctt ccatcatccc cacgccgggc taccgcggca cgcgcttcta    16980
ccgcggtcat accagcagcc gccgccgcaa gaccaccact cgccgccgcc gtcgccgcac    17040
cgccgctgca accaccctg ccgccctggt gcggagagtg taccgccgcg gccgcgcacc    17100
tctgaccctg ccgcgcgcgc gctaccaccc gagcatcgcc atttaaactt tcgcctgctt    17160
tgcagatcaa tggccctcac atgccgcctt cgcgttccca ttacgggcta ccgaggaaga    17220
aaaccgcgcc gtagaaggct ggcggggaac gggatgcgtc gccaccacca ccggcggcgg    17280
cgcgccatca gcaagcggtt gggggggaggc ttcctgcccg cgctgatccc catcatcgcc    17340
gcggcgatcg gggcgatccc cggcattgct tccgtggcgg tgcaggcctc tcagcgccac    17400
tgagacacac ttggaaacat cttgtaataa accaatggac tctgacgctc ctggtcctgt    17460
gatgtgtttt cgtagacaga tggaagacat caattttttcg tccctggctc cgcgacacgg    17520
cacgcggccg ttcatgggca cctggagcga catcggcacc agccaactga acggggcgc    17580
cttcaattgg agcagtctct ggagcgggct taagaatttc gggtccacgc ttaaaaccta    17640
tggcagcaag cgctggaaca gcaccacagg gcaggcgctg agggataagc tgaaagagca    17700
gaacttccag cagaaggtgg tcgatgggct cgcctcgggc atcaacgggg tggtggacct    17760
ggccaaccag gccgtgcagc ggcagatcaa cagccgcctg acccggtgc cgcccgccgg    17820
ctccgtggag atgccgcagg tggaggagga gctgcctccc ctggacaagc ggggcgagaa    17880
gcgaccccgc cccgatgcgg aggagacgct gctgacgcac acggacgagc cgccccgta    17940
cgaggaggcg gtgaaactgg gtctgcccac cacgcggccc atcgcgcccc tggccaccgg    18000
ggtgctgaaa cccgaaaagc ccgcgaccct ggacttgcct cctccccagc cttcccgccc    18060
ctctacagtg gctaagcccc tgccgccggt ggccgtggcc cgcgcgcgac ccgggggcac    18120
cgcccgccct catgcgaact ggcagagcac tctgaacagc atcgtgggtc tgggagtgca    18180
gagtgtgaag cgccgccgct gctattaaac ctaccgtagc gcttaacttg cttgtctgtg    18240
tgtgtatgta ttatgtcgcc gccgccgctg tccaccagaa ggaggagtga agaggcgcgt    18300
cgccgagttg caagatggcc acccccatcga tgctgcccca gtgggcgtac atgcacatcg    18360
ccggacagga cgcttcggag tacctgagtc cgggtctggt gcagtttgcc cgcgccacag    18420
acacctactt cagtctgggg aacaagtttta ggaaccccac ggtggcgccc acgcacgatg    18480
tgaccaccga ccgcagccag cggctgacgc tgcgcttcgt gcccgtggac cgcgaggaca    18540
acacctactc gtacaaagtg cgctacacgc tggccgtggg cgacaaccgc gtgctggaca    18600
```

```
tggccagcac ctactttgac atccgcggcg tgctggatcg gggccctagc ttcaaaccct   18660
actccggcac cgcctacaac agtctggccc ccaagggagc acccaacact tgtcagtgga   18720
catataaagc cgatggtgaa actgccacag aaaaaaccta tacatatgga aatgcacccg   18780
tgcagggcat taacatcaca aaagatggta ttcaacttgg aactgacacc gatgatcagc   18840
caatctacgc agataaaacc tatcagcctg aacctcaagt gggtgatgct gaatggcatg   18900
acatcactgg tactgatgaa aagtatggag gcagagctct taagcctgat accaaaatga   18960
agccttgtta tggttctttt gccaagccta ctaataaaga aggaggtcag gcaaatgtga   19020
aaacaggaac aggcactact aaagaatatg acatagacat ggctttcttt gacaacagaa   19080
gtgcggctgc tgctggccta gctccagaaa ttgttttgta tactgaaaat gtggatttgg   19140
aaactccaga tacccatatt gtatacaaag caggcacaga tgacagcagc tcttctatta   19200
atttgggtca gcaagccatg cccaacagac ctaactacat tggtttcaga gacaacttta   19260
tcgggctcat gtactacaac agcactggca atatgggggt gctggccggt caggcttctc   19320
agctgaatgc tgtggttgac ttgcaagaca gaaacaccga gctgtcctac cagctcttgc   19380
ttgactctct gggtgacaga acccggtatt tcagtatgtg gaatcaggcg gtggacagct   19440
atgatcctga tgtgcgcatt attgaaaatc atggtgtgga ggatgaactt cccaactatt   19500
gtttccctct ggatgctgtt ggcagaacag atacttatca gggaattaag gctaatggaa   19560
ctgatcaaac cacatggacc aaagatgaca gtgtcaatga tgctaatgag ataggcaagg   19620
gtaatccatt cgccatggaa atcaacatcc aagccaacct gtggaggaac ttcctctacg   19680
ccaacgtggc cctgtacctg cccgactctt acaagtacac gccggccaat gttaccctgc   19740
ccaccaacac caacacctac gattacatga acggccgggt ggtggcgccc tcgctggtgg   19800
actcctacat caacatcggg gcgcgctggt cgctggatcc catggacaac gtgaacccct   19860
tcaaccacca ccgcaatgcg gggctgcgct accgctccat gctcctgggc aacgggcgct   19920
acgtgccctt ccacatccag gtgccccaga aatttttcgc catcaagagc ctcctgctcc   19980
tgcccgggtc ctacacctac gagtggaact tccgcaagga cgtcaacatg atcctgcaga   20040
gctccctcgg caacgacctg cgcacggacg gggcctccat ctccttcacc agcatcaacc   20100
tctacgccac cttcttcccc atggcgcaca cacggcctc acgctcgag gccatgctgc   20160 gcaacgacac caacgaccag tccttcaacg actacctctc ggcggccaac atgctctacc   20220
ccatcccggc caacgccacc aacgtgccca tctccatccc ctcgcgcaac tgggccgcct   20280
tccgcggctg gtccttcacg cgtctcaaga ccaaggagac gccctcgctg ggctcccggt   20340
tcgaccccta cttcgtctac tcgggctcca tcccctacct cgacggcacc ttctacctca   20400
accacacctt caagaaggtc tccatcacct tcgactcctc cgtcagctgg cccggcaacg   20460
accggctcct gacgcccaac gagttcgaaa tcaagcgcac cgtcgacggc gagggctaca   20520
acgtggccca gtgcaacatg accaaggact ggttcctggt ccagatgctg cccactaca   20580 acatcggcta ccagggcttc tacgtgcccg agggctacaa ggaccgcatg tactccttct   20640
tccgcaactt ccagcccatg agccgccagg tggtggacga ggtcaactac aaggactacc   20700
aggccgtcac cctggcctac cagcacaaca actcgggctt cgtcggctac ctcgcgccca   20760
ccatgcgcca gggccagccc taccccgcca actacccta cccgctcatc ggcaagagcg   20820 ccgtcacccag cgtcacccag aaaaagttcc tctgcgacag ggtcatgtgg cgcatcccct   20880
tctccagcaa cttcatgtcc atgggcgcgc tcaccgacct cggccagaac atgctctatg   20940
```

```
ccaactccgc ccacgcgcta gacatgaatt tcgaagtcga ccccatggat gagtccaccc  21000
ttctctatgt tgtcttcgaa gtcttcgacg tcgtccgagt gcaccagccc caccgcggcg  21060
tcatcgaggc cgtctacctg cgcacccccct tctcggccgg taacgccacc acctaagctc  21120
ttgcttcttg caagccatgg ccgcgggctc cggcgagcag gagctcaggg ccatcatccg  21180
cgacctgggc tgcgggccct acttcctggg caccttcgat aagcgcttcc cgggattcat  21240
ggccccgcac aagctggcct gcgccatcgt caacacggcc ggccgcgaga ccgggggcga  21300
gcactggctg gccttcgcct ggaacccgcg ctcgaacacc tgctacctct tcgacccctt  21360
cgggttctcg gacgagcgcc tcaagcagat ctaccagttc gagtacgagg gcctgctgcg  21420
ccgcagcgcc ctggccaccg aggaccgctg cgtcaccctg gaaaagtcca cccagaccgt  21480
gcagggtccg cgctcggccg cctgcgggct cttctgctgc atgttcctgc acgccttcgt  21540
gcactggccc gaccgcccca tggacaagaa ccccaccatg aacttgctga cggggggtgcc  21600
caacggcatg ctccagtcgc cccaggtgga acccaccctg cgccgcaacc aggaggcgct  21660
ctaccgcttc ctcaactccc actccgccta ctttcgctcc caccgcgcgc gcatcgagaa  21720
ggccaccgcc ttcgaccgca tgaatcaaga catgtaaacc gtgtgtgtat gttaaatgtc  21780
tttaataaac agcactttca tgttacacat gcatctgaga tgatttattt agaaatcgaa  21840
agggttctgc cgggtctcgg catggcccgc gggcagggac acgttgcgga actggtactt  21900
ggccagccac ttgaactcgg ggatcagcag tttgggcagc ggggtgtcgg ggaaggagtc  21960
ggtccacagc ttccgcgtca gttgcagggc gcccagcagg tcgggcgcgg agatcttgaa  22020
atcgcagttg gaccccgcgt tctgcgcgcg ggagttgcgg tacacggggt tgcagcactg  22080
gaacaccatc agggccgggt gcttcacgct cgccagcacc gtcgcgtcgg tgatgctctc  22140
cacgtcgagg tcctcggcgt tggccatccc gaaggggggtc atcttgcagg tctgccttcc  22200
catggtgggc acgcacccgg gcttgtggtt gcaatcgcag tgcaggggga tcagcatcat  22260
ctgggcctgg tcgcgttca tccccgggta catggccttc atgaaagcct ccaattgcct  22320
gaacgcctgc tgggccttgg ctccctcggt gaagaagacc ccgcaggact gctagagaa  22380
ctggttggtg gcgcacccgg cgtcgtgcac gcagcagcgc gcgtcgttgt tggccagctg  22440
caccacgctg cgccccagc ggttctgggt gatcttggcc cggtcggggt tctccttcag  22500
cgcgcgctgc ccgttctcgc tcgccacatc catctcgatc atgtgctcct tctgatcat  22560
ggtggtcccg tgcaggcacc gcagcttgcc ctcggcctcg gtgcacccgt gcagccacag  22620
cgcgcacccg gtgcactccc agttcttgtg ggcgatctgg gaatgcgcgt gcacgaagcc  22680
ctgcaggaag cggcccatca tggtggtcag ggtcttgttg ctagtgaagg tcagcggaat  22740
gccgcggtgc tcctcgttga tgtacaggtg gcagatgcgg cggtacacct cgccctgctc  22800
gggcatcagc tggaagttgg ctttcaggtc ggtctccacg cggtagcggt ccatcagcat  22860
agtcatgatt tccatacccct ctcccaggc cgagacgatg gcaggctca tagggttctt  22920
caccatcatc ttagcgctag cagccgcggc caggggggtcg ctctcgtcca gggtctcaaa  22980
gctccgcttg ccgtccttct cggtgatccg caccgggggg tagctgaagc ccacggccgc  23040
cagctcctcc tcggcctgtc tttcgtcctc gctgtcctgg ctgacgtcct gcaggaccac  23100
atgcttggtc ttgcggggtt tcttcttggg cggcagcggc ggcggagatg ttggagatgg  23160
cgagggggag cgcgagttct cgctcaccac tactatctct tcctcttctt ggtccgaggc  23220
cacgcggcgg taggtatgtc tcttcggggg cagaggcgga ggcgacgggc tctcgccgcc  23280
gcgacttggc ggatggctgg cagagcccct tccgcgttcg ggggtgcgct cccggcggcg  23340
```

-continued

```
ctctgactga cttcctccgc ggccggccat tgtgttctcc tagggaggaa caacaagcat    23400
ggagactcag ccatcgccaa cctcgccatc tgccccacc gccgacgaga agcagcagca     23460
gcagaatgaa agcttaaccg ccccgccgcc cagccccgcc acctccgacg cggccgtccc    23520
agacatgcaa gagatggagg aatccatcga gattgacctg gctatgtga cgcccgcgga     23580
gcacgaggag gagctggcag tgcgcttttc acaagaagag atacaccaag aacagccaga    23640
gcaggaagca gagaatgagc agagtcaggc tgggctcgag catgacggcg actacctcca    23700
cctgagcggg ggggaggacg cgctcatcaa gcatctggcc cggcaggcca ccatcgtcaa    23760
ggatgcgctg ctcgaccgca ccgaggtgcc cctcagcgtg gaggagctca gccgcgccta    23820
cgagttgaac ctcttctcgc cgcgcgtgcc ccccaagcgc cagcccaatg cacctgcga    23880
gcccaacccg cgcctcaact tctacccggt cttcgcggtg cccgaggccc tggccaccta    23940
ccacatcttt ttcaagaacc aaaagatccc cgtctcctgc cgcgccaacc gcacccgcgc    24000
cgacgccctt ttcaacctgg gtcccggcgc ccgcctacct gatatcgcct ccttggaaga    24060
ggttcccaag atcttcgagg gtctgggcag cgacgagact cgggccgcga acgctctgca    24120
aggagaagga ggagcatg agcaccacag cgccctggtc gagttggaag gcgacaacgc      24180
gcggctggcg gtgctcaaac gcacggtcga gctgacccat ttcgcctacc ggctctgaa    24240
cctgccccc aaagtcatga gcgcggtcat ggaccaggtg ctcatcaagc gcgcgtcgcc    24300
catctccgag gacgagggca tgcaagactc cgaggagggc aagcccgtgg tcagcgacga    24360
gcagctggcc cggtggctgg gtcctaatgc tagtccccag agtttggaag agcggcgcaa    24420
actcatgatg gccgtggtcc tggtgaccgt ggagctggag tgcctgcgcc gcttcttcgc    24480
cgacgcggag accctgcgca aggtcgagga gaacctgcac tacctcttca ggcacgggtt    24540
cgtgcgccag gcctgcaaga tctccaacgt ggagctgacc aacctggtct cctacatggg    24600
catcttgcac gagaaccgcc tggggcagaa cgtgctgcac accacccctgc gcggggaggc    24660
ccggcgcgac tacatccgcg actgcgtcta cctctacctc tgccacacct ggcagacggg    24720
catgggcgtg tggcagcagt gtctggagga gcagaacctg aaagagctct gcaagctcct    24780
gcagaagaac ctcaagggtc tgtggaccgg gttcgacgag cgcaccaccg cctcggacct    24840
ggccgacctc attttcccg agcgcctcag gctgacgctg cgcaacggcc tgcccgactt    24900
tatgagccaa agcatgttgc aaaactttcg ctctttcatc ctcgaacgct ccggaatcct    24960
gcccgccacc tgctccgcgc tgccctcgga cttcgtgccg ctgaccttcc gcgagtgccc    25020
cccgccgctg tggagccact gctacctgct gcgcctggcc aactacctgg cctaccactc    25080
ggacgtgatc gaggacgtca gcggcgaggg cctgctcgag tgccactgcc gctgcaacct    25140
ctgcacgccg caccgctccc tggcctgcaa ccccccagctg ctgagcgaga cccagatcat    25200
cggcaccttc gagttgcaag ggcccagcga aggcgagggt tcagccgcca agggggtct     25260
gaaactcacc ccggggctgt ggacctcggc ctacttgcgc aagttcgtgc ccgaggacta    25320
ccatcccttc gagatcaggt tctacgagga ccaatcccat ccgcccaagg ccgagctgtc    25380
ggcctgcgtc atcacccagg gggcgatcct ggcccaattg caagccatcc agaaatcccg    25440
ccaagaattc ttgctgaaaa agggccgcgg ggtctacctc gaccccgaga ccggtgagga    25500
gctcaaccc ggcttccccc aggatgcccc gaggaaacaa gaagctgaaa gtggagctgc     25560
cgcccgtgga ggatttggag gaagactggg agaacagcag tcaggcagag gaggaggaga    25620
tggaggaaga ctgggacagc actcaggcag aggaggacag cctgcaagac agtctggagg    25680
```

-continued

```
aagacgagga ggaggcagag gaggaggtgg aagaagcagc cgccgccaga ccgtcgtcct    25740
cggcggggga gaaagcaagc agcacggata ccatctccgc tccgggtcgg ggtcccgctc    25800
gaccacacag tagatgggac gagaccggac gattcccgaa ccccaccacc cagaccggta    25860
agaaggagcg gcagggatac aagtcctggc gggggcacaa aaacgccatc gtctcctgct    25920
tgcaggcctg cgggggcaac atctccttca cccggcgcta cctgctcttc caccgcgggg    25980
tgaactttcc ccgcaacatc ttgcattact accgtcacct ccacagcccc tactacttcc    26040
aagaagaggc agcagcagca gaaaaagacc agcagaaaac cagcagctag aaaatccaca    26100
gcggcggcag caggtggact gaggatcgcg gcgaacgagc cggcgcaaac ccgggagctg    26160
aggaaccgga tctttcccac cctctatgcc atcttccagc agagtcgggg gcaggagcag    26220
gaactgaaag tcaagaaccg ttctctgcgc tcgctcaccc gcagttgtct gtatcacaag    26280
agcgaagacc aacttcagcg cactctcgag gacgccgagg ctctcttcaa caagtactgc    26340
gcgctcactc ttaaagagta gcccgcgccc gcccagtcgc agaaaaaggc gggaattacg    26400
tcacctgtgc ccttcgccct agccgcctcc acccatcatc atgagcaaag agattcccac    26460
gccttacatg tggagctacc agccccagat gggcctggcc gccggtgccg cccaggacta    26520
ctccacccgc atgaattggc tcagcgccgg gcccgcgatg atctcacggg tgaatgacat    26580
ccgcgcccac cgaaaccaga tactcctaga acagtcagcg ctcaccgcca cgccccgcaa    26640
tcacctcaat ccgcgtaatt ggcccgccgc cctggtgtac caggaaattc cccagcccac    26700
gaccgtacta cttccgcgag acgcccaggc cgaagtccag ctgactaact caggtgtcca    26760
gctggcgggg ggcgccaccc tgtgtcgtca ccgccccgct cagggtataa agcggctggt    26820
gatccggggc agaggcacac agctcaacga cgaggtggtg agctcttcgc tgggtctgcg    26880
acctgacgga gtcttccaac tcgccggatc ggggagatct tccttcacgc ctcgtcaggc    26940
cgtcctgact ttggagagtt cgtcctcgca gccccgctcg ggtggcatcg gcactctcca    27000
gttcgtggag gagttcactc cctcggtcta cttcaacccc ttctccggct cccccggcca    27060
ctacccggac gagttcatcc cgaacttcga cgccatcagc gagtcggtgg acggctacga    27120
ttgaatgtcc catggtggcg cagctgacct agctcggctt cgacacctgg accactgccg    27180
ccgcttccgc tgcttcgctc gggatctcgc cgagtttgcc tactttgagc tgcccgagga    27240
gcaccctcag ggcccggccc acggagtgcg gatcgtcgtc gaaggggcc tcgactccca    27300
cctgcttcgg atcttcagcc agcgtccgat cctggtcgag cgcgagcaag gacagaccct    27360
tctgactctg tactgcatct gcaaccaccc cggcctgcat gaaagtcttt gttgtctgct    27420
gtgtactgag tataataaaa gctgagatca gcgactactc cggacttccg tgtgttcctg    27480
aatccatcaa ccagtctttg ttcttcaccg ggaacgagac cgagctccag ctccagtgta    27540
agccccacaa gaagtacctc acctggctgt tccagggctc cccgatcgcc gttgtcaacc    27600
actgcgacaa cgacggagtc ctgctgagcg gccctgccaa ccttactttt tccacccgca    27660
gaagcaagct ccagctcttc caacccttcc tcccgggac ctatcagtgc gtctcggac    27720
cctgccatca caccttccac ctgatcccga ataccacagc gtcgctcccc gctactaaca    27780
accaaactaa cctccaccaa cgccaccgtc gcgacctttc tgaatctaat actaccaccc    27840
acaccggagg tgagctccga ggtcaaccaa cctctgggat ttactacggc ccctgggagg    27900
tggttgggtt aatagcgcta ggcctagttg cgggtgggct tttggttctc tgctaccat    27960
acctcccttg ctgttcgtac ttagtggtgc tgtgttgctg gtttaagaaa tggggaagat    28020
caccctagtg agctgcggtg cgctggtggc ggtgttgctt tcgattgtgg gactgggcgg    28080
```

```
tgcggctgta gtgaaggaga aggccgatcc ctgcttgcat ttcaatccca acaaatgcca   28140
gctgagtttt cagcccgatg gcaatcggtg cgcggtactg atcaagtgcg gatgggaatg   28200
cgagaacgtg agaatcgagt acaataacaa gactcggaac aatactctcg cgtccgtgtg   28260
gcagcccggg gaccccgagt ggtacaccgt ctctgtcccc ggtgctgacg gctcccgcg    28320 caccgtgaat aatactttca tttttgcgca catgtgcgac acggtcatgt ggatgagcaa   28380
gcagtacgat atgtggcccc ccacgaagga gaacatcgtg gtcttctcca tcgcttacag   28440
cctgtgcacg gcgctaatca ccgctatcgt gtgcctgagc attcacatgc tcatcgctat   28500
tcgccccaga aataatgccg aaaaagaaaa acagccataa cgttttttttt cacacctttt   28560 tcagaccatg gcctctgtta aattttttgct tttatttgcc agtctcattg ccgtcattca   28620
tggaatgagt aatgagaaaa ttactattta cactggcact aatcacacat tgaaaggtcc   28680
agaaaaagcc acagaagttt catggtattg ttattttaat gaatcagatg tatctactga   28740
actctgtgga aacaataaca aaaaaatga gagcattact ctcatcaagt ttcaatgtgg   28800
atctgactta accctaatta acatcactag agactatgta ggtatgtatt atggaactac   28860
agcaggcatt tcggacatgg aattttatca agtttctgtg tctgaaccca ccacgcctag   28920
aatgaccaca accacaaaaa ctacacctgt taccactatg cagctcacta ccaataacat   28980
ttttgccatg cgtcaaatgg tcaacaatag cactcaaccc accccaccca gtgaggaaat   29040
tcccaaatcc atgattggca ttattgttgc tgtagtggtg tgcatgttga tcatcgcctt   29100
gtgcatggtg tactatgcct tctgctacag aaagcacaga ctgaacgaca agctggaaca   29160
cttactaagt gttgaatttt aatttttttag aaccatgaag atcctaggcc ttttaattttt  29220 ttctatcatt acctctgctc tatgcaattc tgacaatgag gacgttactg tcgttgtcgg   29280
atcaaattat acactgaaag gtccagcgaa gggtatgctt tcgtggtatt gctattttgg   29340
atctgacact acagaaactg aattatgcaa tcttaagaat ggcaaaattc aaaattctaa   29400
aattaacaat tatatatgca atggtactga tctgatactc ctcaatatca cgaaatcata   29460
tgctggcagt tacacctgcc ctggagatga tgctgacagt atgattttttt acaaagtaac   29520 tgttgttgat cccactactc cacctccacc caccacaact actcacacca cacacacaga   29580
tcaaaccgca gcagaggagg cagcaaagtt agccttgcag gtccaagaca gttcatttgt   29640
tggcattacc cctacacctg atcagcggtg tccggggctg ctagtcagcg gcattgtcgg   29700
tgtgctttcg ggattagcag tcataatcat ctgcatgttc attttttgctt gctgctatag   29760 aaggctttac cgacaaaaat cagacccact gctgaacctc tatgtttaat tttttccaga   29820
gtcatgaagg cagttagcgc tctagttttt tgttctttga ttggcattgt tttttgcaat   29880
cctattccta aagttagctt tattaaagat gtgaatgtta ctgaggggg caatgtgaca   29940 ctggtaggtg tagagggtgc tgaaaacacc acctggacaa ataccacct caatgggtgg   30000 aaagatattt gcaattggag tgtattagtt tatacatgtg agggagttaa tcttaccatt   30060
gtcaatgcca cctcagctca aaatggtaga attcaaggac aaagtgtcag tgtatctaat   30120
gggtatttta cccaacatac tttttatctat gacgttaaag tcataccact gcctacgcct   30180
agcccaccta gcactaccac acagacaacc cacactacac agacaaccac atacagtaca   30240
ttaaatcagc ctaccaccac tacagcagca gaggttgcca gctcgtctgg ggtccgagtg   30300 gcattttttga tgtgggcccc atctagcagt cccactgcta gtaccaatga gcagactact   30360 gaattttttgt ccactgtcga gagccacacc acagctacct ccagtgcctt ctctagcacc   30420
```

```
gccaatctct cctcgctttc ctctacacca atcagtcccg ctactactcc tagccccgct    30480
cctcttccca ctcccctgaa gcaaacagac ggcggcatgc aatggcagat cacccctgctc   30540 attgtgatcg ggttggtcat cctggccgtg ttgctctact acatcttctg ccgccgcatt    30600
cccaacgcgc accgcaagcc ggtctacaag cccatcattg tcgggcagcc ggagccgctt    30660
caggtggaag ggggtctaag gaatcttctc ttctctttta cagtatggtg attgaactat    30720
gattcctaga caattcttga tcactattct tatctgcctc ctccaagtct gtgccaccct    30780
cgctctggtg gccaacgcca gtccagactg tattgggccc ttcgcctcct acgtgctctt    30840
tgccttcacc acctgcatct gctgctgtag catagtctgc ctgcttatca ccttcttcca    30900
gttcattgac tggatctttg tgcgcatcgc ctacctgcgc caccacccc agtaccgcga     30960 ccagcgagtg gcgcggctgc tcaggctcct ctgataagca tgcgggctct gctacttctc    31020
gcgcttctgc tgttagtgct cccccgtccc gtcgaccccc ggtcccccac ccagtccccc    31080
gaggaggtcc gcaaatgcaa attccaagaa ccctggaaat tcctcaaatg ctaccgccaa    31140
aaatcagaca tgcatcccag ctggatcatg atcattggga tcgtgaacat tctgcctgc    31200 accctcatct cctttgtgat ttaccctgc tttgactttg gttggaactc gccagaggcg     31260
ctctatctcc cgcctgaacc tgacacacca ccacagcaac ctcaggcaca cgcactacca    31320
ccactacagc ctaggccaca atacatgcc atattagact atgaggccga gccacagcga     31380
cccatgctcc ccgctattag ttacttcaat ctaaccggcg gagatgactg acccactggc    31440
caacaacaac gtcaacgacc ttctcctgga catggacggc cgcgcctcgg agcagcgact    31500
cgcccaactt cgcattcgcc agcagcagga gagagccgtc aaggagctgc aggatgcggt    31560
ggccatccac cagtgcaaga gaggcatctt ctgcctggtg aaacaggcca agatctccta    31620
cgaggtcact ccaaacgacc atcgcctctc ctacgagctc ctgcagcagc gccagaagtt    31680
cacctgcctg gtcggagtca accccatcgt catcacccag cagtctggcg ataccaaggg    31740
gtgcatccac tgctcctgcg actccccga ctgcgtccac actctgatca agaccctctg      31800
cggcctccgc gacctcctcc ccatgaacta atcaccccct tatccagtga aataaagatc    31860
atattgatga tgatttaca gaaataaaa ataatcattt gatttgaaat aaagatacaa       31920
tcatattgat gatttgagtt taacaaaaaa ataaagaatc acttacttga aatctgatac    31980
caggtctctg tccatgtttt ctgccaacac cacttcactc ccctcttccc agctctggta    32040
ctgcaggccc cggcgggctg caaacttcct ccacacgctg aagggatgt caaattcctc     32100 ctgtccctca atcttcattt tatcttctat cagatgtcca aaaagcgcgt ccgggtggat    32160
gatgacttcg accccgtcta cccctacgat gcagacaacg caccgaccgt gcccttcatc    32220
aaccccccct tcgtctcttc agatggattc caagagaagc cctgggggt gttgtccctg      32280 cgactggccg accccgtcac caccaagaac ggggaaatca cctcaagct gggagagggg    32340 gtggacctcg attcctcggg aaaactcatc tccaacacgg ccaccaaggc cgccgccct    32400 ctcagttttt ccaacaacac catttccctt aacatggatc acccctttta cactaaagat    32460
ggaaaattat ccttacaagt ttctccacca ttaaatatac tgagaacaag cattctaaac    32520
acactagctt taggttttgg atcaggttta ggactccgtg gctctgcctt ggcagtacag    32580
ttagtctctc cacttacatt tgatactgat ggaaacataa agcttacctt agacagaggt    32640
ttgcatgtta caacaggaga tgcaattgaa agcaacataa gctgggctaa aggtttaaaa    32700
tttgaagatg gagccatagc aaccaacatt ggaaatgggt tagagtttgg aagcagtagt    32760
acagaaacag gtgttgatga tgcttaccca atccaagtta aacttggatc tggccttagc    32820
```

```
tttgacagta caggagccat aatggctggt aacaaagaag acgataaact cactttgtgg    32880
acaacacctg atccatcacc aaactgtcaa atactcgcag aaaatgatgc aaaactaaca    32940
ctttgcttga ctaaatgtgg tagtcaaata ctggccactg tgtcagtctt agttgtagga    33000
agtggaaacc taaaccccat tactggcacc gtaagcagtg ctcaggtgtt tctacgtttt    33060
gatgcaaacg gtgttctttt aacagaacat tctacactaa aaaaatactg ggggtatagg    33120
cagggagata gcatagatgg cactccatat accaatgctg taggattcat gcccaattta    33180
aaagcttatc caaagtcaca aagttctact actaaaaata atatagtagg gcaagtatac    33240
atgaatggag atgttttcaaa acctatgctt ctcactataa ccctcaatgg tactgatgac    33300
agcaacagta catattcaat gtcattttca tacacctgga ctaatggaag ctatgttgga    33360
gcaacatttg gggctaactc ttataccttc tcatacatcg cccaagaatg aacactgtat    33420
cccaccctgc atgccaaccc ttcccacccc actctgtgga acaaactctg aaacacaaaa    33480
taaaataaag ttcaagtgtt ttattgattc aacagtttta caggattcga gcagttattt    33540
ttcctccacc ctcccaggac atggaataca ccaccctctc cccccgcaca gccttgaaca    33600
tctgaatgcc attggtgatg acatgctttt tggtctccac gttccacaca gtttcagagc    33660
gagccagtct cgggtcggtc agggagatga aaccctccgg gcactcccgc atctgcacct    33720
cacagctcaa cagctgagga ttgtcctcgg tggtcgggat cacggttatc tggaagaagc    33780
agaagagcgg cggtgggaat catagtccgc gaacgggatc ggccggtggt gtcgcatcag    33840
gccccgcagc agtcgctgcc gccgccgctc cgtcaagctg ctgctcaggg ggtccgggtc    33900
cagggactcc ctcagcatga tgcccacggc cctcagcatc agtcgtctgg tgcggcgggc    33960
gcagcagcgc atgcggatct cgctcaggtc gctgcagtac gtgcaacaca gaaccaccag    34020
gttgttcaac agtccatagt tcaacacgct ccagccgaaa ctcatcgcgg gaaggatgct    34080
acccacgtgg ccgtcgtacc agatcctcag gtaaatcaag tggtgccccc tccagaacac    34140
gctgcccacg tacatgatct ccttgggcat gtggcggttc accacctccc ggtaccacat    34200
caccctctgg ttgaacatgc agccccggat gatcctgcgg aaccacaggg ccagcaccgc    34260
cccgcccgcc atgcagcgaa gagacccccgg gtccggcaa tggcaatgga ggacccaccg    34320
ctcgtacccg tggatcatct gggagctgaa caagtctatg ttggcacagc acaggcatat    34380
gctcatgcat ctcttcagca ctctcaactc ctcggggggtc aaaaccatat cccagggcac    34440
ggggaactct tgcaggacag cgaaccccgc agaacagggc aatcctcgca cagaacttac    34500
attgtgcatg gacagggtat cgcaatcagg cagcaccggg tgatcctcca ccagagaagc    34560
gcgggtctcg gtctcctcac agcgtggtaa ggggggccggc cgatacgggt gatggcggga    34620
cgcggctgat cgtgttcgcg accgtgtcat gatgcagttg ctttcggaca ttttcgtact    34680
tgctgtagca gaacctggtc cgggcgctgc acaccgatcg ccggcggcgg tctcggcgct    34740
tggaacgctc ggtgttgaaa ttgtaaaaca gccactctct cagaccgtgc agcagatcta    34800
gggcctcagg agtgatgaag atcccatcat gcctgatggc tctgatcaca tcgaccaccg    34860
tggaatgggc cagacccagc cagatgatgc aattttgttg ggtttcggtg acggcggggg    34920
agggaagaac aggaagaacc atgattaact tttaatccaa acggtctcgg agtacttcaa    34980
aatgaagatc gcggagatgg cacctctcgc ccccgctgtg ttggtggaaa ataacagcca    35040
ggtcaaaggt gatacggttc tcgagatgtt ccacggtggc ttccagcaaa gcctccacgc    35100
gcacatccag aaacaagaca atagcgaaag cgggagggtt ctctaattcc tcaatcatca    35160
```

```
tgttacactc ctgcaccatc cccagataat tttcattttt ccagccttga atgattcgaa    35220
ctagttcctg aggtaaatcc aagccagcca tgataaagag ctcgcgcaga gcgccctcca    35280
ccggcattct taagcacacc ctcataattc caagatattc tgctcctggt tcacctgcag    35340
cagattgaca agcggaatat caaaatctct gccgcgatcc ctgagctcct ccctcagcaa    35400
taactgtaag tactctttca tatcctctcc gaaattttta gccataggac caccaggaat    35460
aagattaggg caagccacag tacagataaa ccgaagtcct ccccagtgag cattgccaaa    35520
tgcaagactg ctataagcat gctggctaga cccggtgata tcttccagat aactggacag    35580
aaaatcgccc aggcaatttt taagaaaatc aacaaaagaa aaatcctcca ggtggacgtt    35640
tagagcctcg ggaacaacga tgaagtaaat gcaagcggtg cgttccagca tggttagtta    35700
gctgatctgt agaaaaaaca aaaatgaaca ttaaaccatg ctagcctggc gaacaggtgg    35760
gtaaatcgtt ctctccagca ccaggcaggc cacggggtct ccggcgcgac cctcgtaaaa    35820
attgtcgcta tgattgaaaa ccatcacaga gagacgttcc cggtggccgg cgtgaatgat    35880
tcgacaagat gaatacaccc ccggaacatt ggcgtccgcg agtgaaaaaa agcgcccgag    35940
gaagcaataa ggcactacaa tgctcagtct caagtccagc aaagcgatgc catgcggatg    36000
aagcacaaaa ttctcaggtg cgtacaaaat gtaattactc ccctcctgca caggcagcaa    36060
agcccccgat ccctccaggt acacatacaa agcctcagcg tccatagctt accgagcagc    36120
agcacacaac aggcgcaaga gtcagagaaa ggctgagctc taacctgtcc acccgctctc    36180
tgctcaatat atagcccaga tctacactga cgtaaaggcc aaagtctaaa aatacccgcc    36240
aaataatcac acacgcccag cacacgccca gaaaccggtg acacactcaa aaaaatacgc    36300
gcacttcctc aaacgcccaa aactgccgtc atttccgggt tcccacgcta cgtcatcaaa    36360
acacgacttt caaattccgt cgaccgttaa aaacgtcacc cgccccgccc ctaacggtcg    36420
cccgtctctc agccaatcag cgccccgcat ccccaaattc aaacacctca tttgcatatt    36480
aacgcgcaca aaaagtttga ggtatattat tgatgatgg                          36519
```

<210> SEQ ID NO 2
<211> LENGTH: 31588
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 2

```
ccatcttcaa taatatacct caaacttttt gtgcgcgtta atatgcaaat gaggcgtttg     60
aatttgggga ggaagggcgg tgattggtcg agggatgagc gaccgttagg ggcggggcga    120
gtgacgtttt tgatgacgtgg ttgcgaggag gagccagttt gcaagttctc gtgggaaaag    180
tgacgtcaaa cgaggtgtgg tttgaacacg gaaatactca attttcccgc gctctctgac    240
aggaaatgag gtgtttctgg gcggatgcaa gtgaaaacgg gccattttcg cgcgaaaact    300
gaatgaggaa gtgaaaatct gagtaatttc gcgtttatgg cagggaggag tatttgccga    360
gggccgagta gactttgacc gattacgtgg gggtttcgat taccgtgttt ttcacctaaa    420
tttccgcgta cggtgtcaaa gtccggtgtt tttacgtagg tgtcagctga tcgccagggt    480
atttaaacct gcgctctcca gtcaagaggc cactcttgag tgccagcgag aagagttttc    540
tcctccgcgc cgcgagtcag atctacactt tgaaagtagg gataacaggg taatgacatt    600
gattattgac tagttgttaa tagtaatcaa ttacggggtc attagttcat agcccatata    660
```

```
tggagttccg cgttacataa cttacggtaa atggcccgcc tggctgaccg cccaacgacc    720
cccgcccatt gacgtcaata atgacgtatg ttcccatagt aacgccaata gggactttcc    780
attgacgtca atgggtggag tatttacggt aaactgccca cttggcagta catcaagtgt    840
atcatatgcc aagtccgccc cctattgacg tcaatgacgg taaatggccc gcctggcatt    900
atgcccagta catgacctta cgggactttc ctacttggca gtacatctac gtattagtca    960
tcgctattac catggtgatg cggttttggc agtacaccaa tgggcgtgga tagcggtttg   1020
actcacgggg atttccaagt ctccacccca ttgacgtcaa tgggagtttg ttttggcacc   1080
aaaatcaacg ggactttcca aaatgtcgta taaccccgc cccgttgacg caaatgggcg    1140
gtaggcgtgt acggtgggag gtctatataa gcagagctcg tttagtgaac cgtcagatcg   1200
cctggaacgc catccacgct gttttgacct ccatagaaga cagcgatcgc gccaccatgg   1260
ccgggatgtt ccaggcactg tccgaaggct gcacacccta tgatattaac cagatgctga   1320
atgtcctggg agaccaccag gtctctggcc tggagcagct ggagagcatc atcaacttcg   1380
agaagctgac cgagtggaca agctccaatg tgatgcctat cctgtcccca ctgaccaagg   1440
gcatcctggg cttcgtgttt accctgacag tgccttctga gcggggcctg tcttgcatca   1500
gcgaggcaga cgcaaccaca ccagagtccg ccaatctggg cgaggagatc ctgtctcagc   1560
tgtacctgtg gcccgggtg acatatcact ccccttctta cgcctatcac cagttcgagc   1620
ggagagccaa gtacaagaga cacttcccag gctttggcca gtctctgctg ttcggctacc   1680
ccgtgtacgt gttcggcgat gcgtgcagg gcgactggga tgccatccgg tttagatact   1740
gcgcaccacc tggatatgca ctgctgaggt gtaacgacac caattattcc gccctgctgg   1800
cagtgggcgc cctggagggc cctcgcaatc aggattggct gggcgtgcca aggcagctgg   1860
tgacacgcat gcaggccatc cagaacgcag gcctgtgcac cctggtggca atgctggagg   1920
agacaatctt ctggctgcag gccttctga tggccctgac cgacagcggc cccaagacaa   1980
acatcatcgt ggattcccag tacgtgatgg gcatctccaa gccttctttc caggagtttg   2040
tggactggga gaacgtgagc ccagagctga attccaccga tcagccattc tggcaggcag   2100
gaatcctggc aaggaacctg gtgcctatgg tggccacagt gcagggccag aatctgaagt   2160
accagggcca gagcctggtc atcagcgcct ccatcatcgt gtttaacctg ctggagctgg   2220
agggcgacta tcgggacgat ggcaacgtgt gggtgcacac cccactgagc cccagaacac   2280
tgaacgcctg ggtgaaggcc gtggaggaga agaagggcat cccagtgcac ctggagctgg   2340
cctccatgac caatatggag ctgatgtcta gcatcgtgca ccagcaggtg aggacatacg   2400
gacccgtgtt catgtgcctg ggaggcctgc tgaccatggt ggcaggagcc gtgtggctga   2460
cagtgcgggt gctggagctg ttcagagccg cccagctggc caacgatgtg gtgctgcaga   2520
tcatggagct gtgcggagca gccttctcgcc aggtgtgcca caccacagtg ccatggccca   2580
atgcctccct gacccccaag tggaacaatg agacaacaca gcctcagatc gccaactgta   2640
gcgtgtacga cttcttcgtg tggctgcact actatagcgt gagggatacc ctgtggcccc   2700
gcgtgacata ccacatgaat aagtacgcct atcacatgct ggagaggcgc gccaagtata   2760
agagaggccc tggcccaggc gcaaagtttg tggcagcatg gacctgaag gccgccgccg   2820 gccccggccc cggccagtat atcaaggcta acagtaagtt cattggaatc acagagctgg   2880 gacccgacc tggataatga gtttaaactc ccatttaaat gtgagggtta atgcttcgag   2940
cagacatgat aagatacatt gatgagtttg gacaaaccac aactagaatg cagtgaaaaa   3000
aatgctttat ttgtgaaatt tgtgatgcta ttgctttatt tgtaaccatt ataagctgca   3060
```

```
ataaacaagt taacaacaac aattgcattc attttatgtt tcaggttcag ggggagatgt    3120
gggaggtttt ttaaagcaag taaaacctct acaaatgtgg taaaataact ataacggtcc    3180
taaggtagcg agtgagtagt gttctggggc gggggaggac ctgcatgagg gccagaataa    3240
ctgaaatctg tgcttttctg tgtgttgcag cagcatgagc ggaagcggct cctttgaggg    3300
aggggtattc agcccttatc tgacggggcg tctcccctcc tgggcgggag tgcgtcagaa    3360
tgtgatggga tccacggtgg acggccggcc cgtgcagccc gcgaactctt caaccctgac    3420
ctatgcaacc ctgagctctt cgtcgttgga cgcagctgcc gccgcagctg ctgcatctgc    3480
cgccagcgcc gtgcgcggaa tggccatggg cgccggctac tacggcactc tggtggccaa    3540
ctcgagttcc accaataatc ccgccagcct gaacgaggag aagctgttgc tgctgatggc    3600
ccagctcgag gccttgaccc agcgcctggg cgagctgacc cagcaggtgg ctcagctgca    3660
ggagcagacg cgggccgcgg ttgccacggt gaaatccaaa taaaaaatga atcaataaat    3720
aaacggagac ggttgttgat tttaacacag agtctgaatc tttatttgat ttttcgcgcg    3780
cggtaggccc tggaccaccg gtctcgatca ttgagcaccc ggtggatctt ttccaggacc    3840
cggtagaggt gggcttggat gttgaggtac atgggcatga gccgtcccg ggggtggagg    3900 tagctccatt gcagggcctc gtgctcgggg gtggtgttgt aaatcaccca gtcatagcag    3960
gggcgcaggg catggtgttg cacaatatct ttgaggagga gactgatggc cacgggcagc    4020
cctttggtgt aggtgtttac aaatctgttg agctgggagg gatgcatgcg ggggagatg    4080 aggtgcatct tggcctggat cttgagattg gcgatgttac cgcccagatc ccgcctgggg    4140
ttcatgttgt gcaggaccac cagcacggtg tatccggtgc acttgggaa tttatcatgc    4200 aacttggaag ggaaggcgtg aaagaatttg gcgacgcctt tgtgcccgcc caggtttttcc    4260 atgcactcat ccatgatgat ggcgatgggc ccgtgggcgg cggcctgggc aaagacgttt    4320 cggggtcgg acacatcata gttgtggtcc tgggtgaggt catcataggc cattttaatg    4380
aatttggggc ggagggtgcc ggactggggg acaaaggtac cctcgatccc gggggcgtag    4440
ttcccctcac agatctgcat ctcccaggct ttgagctcgg aggggggat catgtccacc    4500 tgcggggcga taaagaacac ggtttccggg gcggggagag tgagctgggc cgaaagcaag    4560
ttccggagca gctgggactt gccgcagccg gtggggccgt agatgacccc gatgaccggc    4620
tgcaggtggt agttgaggga gagacagctg ccgtcctccc ggaggagggg gccacctcg    4680 ttcatcatct cgcgcacgtg catgttctcg cgcaccagtt ccgccaggag gcgctctccc    4740
cccagggata ggagctcctg gagcgaggcg aagttttca gcggcttgag tccgtcggcc    4800
atgggcattt tggagagggt ttgttgcaag agttccaggc ggtcccagag ctcggtgatg    4860
tgctctacgc catctcgatc cagcagacct cctcgtttcg cggttggga cggctgcggg    4920 agtagggcac cagacgatgg gcgtccagcg cagccagggt ccggtccttc cagggtcgca    4980
gcgtccgcgt cagggtggtc tccgtcacgg tgaaggggtg cgcgccgggc tgggcgcttg    5040
cgagggtgcg cttcaggctc atccggctgg tcgaaaaccg ctcccgatcg gcgccctgcg    5100
cgtcggccag gtagcaattg accatgagtt cgtagttgag cgcctcggcc gcgtggcctt    5160
tggcgcggag cttacctttg gaagtctgcc cgcaggcggg acagaggagg gacttgaggg    5220
cgtagagctt gggggcgagg aagacggact cggggggcgta ggcgtccgcg ccgcagtggg    5280
cgcagacggg ctcgcactcc acgagccagg tgaggtcggg ctggtcgggg tcaaaaacca    5340
gtttcccgcc gttcttttg atgcgtttct taccttttggt ctccatgagc tcgtgtcccc    5400
```

```
gctgggtgac aaagaggctg tccgtgtccc cgtagaccga ctttatgggc cggtcctcga    5460
gcggtgtgcc gcggtcctcc tcgtagagga accccgccca ctccgagacg aaagcccggg    5520
tccaggccag cacgaaggag gccacgtggg acgggtagcg gtcgttgtcc accagcgggt    5580
ccaccttttc cagggtatgc aaacacatgt ccccctcgtc cacatccagg aaggtgattg    5640
gcttgtaagt gtaggccacg tgaccggggg tcccggccgg gggggtataa aagggtgcgg    5700
gtccctgctc gtcctcactg tcttccggat cgctgtccag gagcgccagc tgttggggta    5760
ggtattccct ctcgaaggcg ggcatgacct cggcactcag gttgtcagtt tctagaaacg    5820
aggaggattt gatattgacg gtgccggcgg agatgccttt caagagcccc tcgtccatct    5880
ggtcagaaaa gacgatcttt ttgttgtcga gcttggtggc gaaggagccg tagagggcgt    5940
tggagaggag cttggcgatg gagcgcatgg tctggttttt ttccttgtcg gcgcgctcct    6000
tggcggcgat gttgagctgc acgtactcgc gcgccacgca cttccattcg gggaagacgg    6060
tggtcagctc gtcgggcacg attctgacct gccagccccg attatgcagg gtgatgaggt    6120
ccacactggt ggccacctcg ccgcgcaggg gctcattagt ccagcagagg cgtccgccct    6180
tgcgcgagca aaggggggc aggggtcca gcatgacctc gtcgggggg tcggcatcga    6240
tggtgaagat gccgggcagg aggtcggggt caaagtagct gatggaagtg gccagatcgt    6300
ccagggcagc ttgccattcg cgcacggcca gcgcgcgctc gtagggactg aggggcgtgc    6360
cccagggcat gggatgggta agcgcggagg cgtacatgcc gcagatgtcg tagacgtaga    6420
ggggctcctc gaggatgccg atgtaggtgg ggtagcagcg ccccccgcgg atgctggcgc    6480
gcacgtagtc atacagctcg tgcgaggggg cgaggagccc cgggcccagg ttggtgcgac    6540
tgggcttttc ggcgcggtag acgatctggc ggaaaatggc atgcgagttg gaggagatgg    6600
tgggcctttg gaagatgttg aagtgggcgt ggggcagtcc gaccgagtcg cggatgaagt    6660
gggcgtagga gtcttgcagc ttggcgacga gctcggcggt gactaggacg tccagagcgc    6720
agtagtcgag ggtctcctgg atgatgtcat acttgagctg tcccttttgt ttccacagct    6780
cgcggttgag aaggaactct cgcggtcct tccagtactc ttcgagggg aacccgtcct    6840
gatctgcacg gtaagagcct agcatgtaga actggttgac ggccttgtag gcgcagcagc    6900
ccttctccac ggggagggcg taggcctggg cggccttgcg cagggaggtg tgcgtgaggg    6960
cgaaagtgtc cctgaccatg accttgagga actggtgctt gaagtcgata tcgtcgcagc    7020
cccctgctc ccagagctgg aagtccgtgc gcttcttgta ggcggggttg ggcaaagcga    7080
aagtaacatc gttgaagagg atcttgcccg cgcggggcat aaagttgcga gtgatgcgga    7140
aaggttgggg cacctcggcc cggttgttga tgacctgggc ggcgagcacg atctcgtcga    7200
agccgttgat gttgtggccc acgatgtaga gttccacgaa tcgcggacgg cccttgacgt    7260
ggggcagttt cttgagctcc tcgtaggtga gctcgtcggg gtcgctgagc ccgtgctgct    7320
cgagcgccca gtcggcgaga tgggggttgg cgcggaggaa ggaagtccag agatccacgg    7380
ccagggcggt ttgcagacgg tcccggtact gacggaactg ctgcccgacg gccattttt    7440
cgggggtgac gcagtagaag gtgcgggggt ccccgtgcca gcgatcccat ttgagctgga    7500
gggcgagatc gagggcgagc tcgacgagcc ggtcgtcccc ggagagtttc atgaccagca    7560
tgaagggac gagctgcttg ccgaaggacc ccatccaggt gtaggtttcc acatcgtagg    7620
tgaggaagag cctttcggtg cgaggatgcg agccgatggg gaagaactgg atctcctgcc    7680
accaattgga ggaatggctg ttgatgtgat ggaagtagaa atgccgacgg cgcgccgaac    7740
actcgtgctt gtgtttatac aagcggccac agtgctcgca acgctgcacg ggatgcacgt    7800
```

-continued

```
gctgcacgag ctgtacctga gttcctttga cgaggaattt cagtgggaag tggagtcgtg    7860
gcgcctgcat ctcgtgctgt actacgtcgt ggtggtcggc ctggccctct tctgcctcga    7920
tggtggtcat gctgacgagc ccgcgcggga ggcaggtcca gacctcggcg cgagcgggtc    7980
ggagagcgag gacgagggcg cgcaggccgg agctgtccag ggtcctgaga cgctgcggag    8040
tcaggtcagt gggcagcggc ggcgcgcggt tgacttgcag gagttttcc agggcgcgcg     8100 ggaggtccag atggtacttg atctccaccg cgccattggt ggcgacgtcg atggcttgca    8160
gggtcccgtg ccctggggt gtgaccaccg tcccccgttt cttcttgggc ggctggggcg     8220 acggggcgg tgcctcttcc atggttagaa gcggcggcga ggacgcgcgc cgggcggcag     8280
gggcggctcg ggcccggag gcaggggcgg caggggcacg tcggcgccgc gcgcgggtag     8340
gttctggtac tgcgcccgga gaagactggc gtgagcgacg acgcgacggt tgacgtcctg    8400
gatctgacgc ctctgggtga aggccacggg acccgtgagt ttgaacctga aagagagttc    8460
gacagaatca atctcggtat cgttgacggc ggcctgccgc aggatctctt gcacgtcgcc    8520
cgagttgtcc tggtaggcga tctcggtcat gaactgctcg atctcctcct cttgaaggtc    8580
tccgcggccg cgcgctcca cggtggccgc gaggtcgttg gagatgcggc ccatgagctg     8640
cgagaaggcg ttcatgcccg cctcgttcca gacgcggctg tagaccacga cgccctcggg    8700
atcgcgggcg cgcatgacca cctgggcgag gttgagctcc acgtggcgcg tgaagaccgc    8760
gtagttgcag aggcgctggt agaggtagtt gagcgtggtg gcgatgtgct cggtgacgaa    8820
gaaatacatg atccagcggc ggagcggcat ctcgctgacg tcgcccagcg cctccaaacg    8880
ttccatggcc tcgtaaaagt ccacggcgaa gttgaaaaac tgggagttgc gcgccgagac    8940
ggtcaactcc tcctccagaa gacggatgag ctcggcgatg gtggcgcgca cctcgcgctc    9000
gaaggccccc gggagttcct ccacttcctc ttcttcctcc tccactaaca tctcttctac    9060
ttcctcctca ggcggcagtg gtggcggggg aggggcctg cgtcgccggc ggcgcacggg     9120
cagacggtcg atgaagcgct cgatggtctc gccgcgccgg cgtcgcatgg tctcggtgac    9180
ggcgcgcccg tcctcgcggg gccgcagcgt gaagacgccg ccgcgcatct ccaggtggcc    9240
gggggggtcc ccgttgggca gggagagggc gctgacgatg catcttatca attgccccgt    9300
agggactccg cgcaaggacc tgagcgtctc gagatccacg ggatctgaaa accgctgaac    9360
gaaggcttcg agccagtcgc agtcgcaagg taggctgagc acggtttctt ctggcgggtc    9420
atgttggttg ggagcggggc gggcgatgct gctggtgatg aagttgaaat aggcggttct    9480
gagacgcgcg atggtggcga ggagcaccag gtctttgggc ccggcttgct ggatgcgcag    9540
acggtcggcc atgccccagg cgtggtcctg acacctggcc aggtccttgt agtagtcctg    9600
catgagccgc tccacgggca cctcctcctc gcccgcgcgg ccgtgcatgc gcgtgagccc    9660
gaagccgcgc tggggctgga cgagcgccag gtcggcgacg acgcgctcgg cgaggatggc    9720
ttgctggatc tgggtgaggg tggtctggaa gtcatcaaag tcgacgaagc ggtggtaggc    9780
tccggtgttg atggtgtagg agcagttggc catgacggac cagttgacgg tctggtggcc    9840
cggacgcacg agctcgtggt acttgaggcg cgagtaggcg cgcgtgtcga agatgtagtc    9900
gttgcaggtg cgcaccaggt actggtagcc gatgaggaag tgcggcggcg gctggcgta    9960 gagcggccat cgctcggtgg cgggggcgcc gggcgcgagg tcctcgagca tggtgcggtg   10020
gtagccgtag atgtacctgg acatccaggt gatgccggcg gcggtggtgg aggcgcgcgg   10080
gaactcgcgg acgcggttcc agatgttgcg cagcggcagg aagtagttca tggtgggcac   10140
```

```
ggtctggccc gtgaggcgcg cgcagtcgtg gatgctctat acgggcaaaa acgaaagcgg   10200
tcagcggctc gactccgtgg cctggaggct aagcgaacgg gttgggctgc gcgtgtaccc   10260
cggttcgaat ctcgaatcag gctggagccg cagctaacgt ggtattggca ctcccgtctc   10320
gacccaagcc tgcaccaacc ctccaggata cggaggcggg tcgttttgca acttttttt    10380 ggaggccgga tgagactagt aagcgcggaa agcggccgac cgcgatggct cgctgccgta   10440
gtctggagaa gaatcgccag ggttgcgttg cggtgtgccc cggttcgagg ccggccggat   10500
tccgcggcta acgagggcgt ggctgccccg tcgtttccaa gaccccatag ccagccgact   10560
tctccagtta cggagcgagc ccctcttttg ttttgtttgt ttttgccaga tgcatcccgt   10620
actgcggcag atgcgccccc accaccctcc accgcaacaa cagcccccctc cacagccggc   10680 gcttctgccc ccgccccagc agcaacttcc agccacgacc gccgcggccg ccgtgagcgg   10740
ggctggacag agttatgatc accagctggc cttggaagag ggcgaggggc tggcgcgcct   10800
gggggcgtcg tcgccggagc ggcacccgcg cgtgcagatg aaaagggacg ctcgcgaggc   10860
ctacgtgccc aagcagaacc tgttcagaga caggagcggc gaggagcccg aggagatgcg   10920
cgcggcccgg ttccacgcgg ggcgggagct gcggcgcggc ctggaccgaa agagggtgct   10980
gagggacgag gatttcgagg cggacgagct gacggggatc agccccgcgc gcgcgcacgt   11040
ggccgcggcc aacctggtca cggcgtacga gcagaccgtg aaggaggaga gcaacttcca   11100
aaaatccttc aacaaccacg tgcgcaccct gatcgcgcgc gaggaggtga ccctgggcct   11160
gatgcacctg tgggacctgc tggaggccat cgtgcagaac cccaccagca agccgctgac   11220
ggcgcagctg ttcctggtgg tgcagcatag tcggacaaac gaagcgttca gggaggcgct   11280
gctgaatatc accgagcccg agggccgctg gctcctggac ctggtgaaca ttctgcagag   11340
catcgtggtg caggagcgcg ggctgccgct gtccagaag ctggcggcca tcaacttctc   11400
ggtgctgagt ttgggcaagt actacgctag gaagatctac aagacccgt acgtgcccat   11460 agacaaggag gtgaagatcg acgggttta catgcgcatg accctgaaag tgctgaccct   11520
gagcgacgat ctgggggtgt accgcaacga caggatgcac cgtgcggtga cgccagcag   11580 gcggcgcgag ctgagcgacc aggagctgat gcatagtctg cagcgggccc tgaccgggc    11640 cgggaccgag ggggagagct actttgacat gggcgcggac ctgcactggc agcccagccg   11700
ccgggccttg gagcgcggcg gcaggaccct acgtagaagag gtggacgatg aggtggacga   11760
ggagggcgag tacctggaag actgatggcg cgaccgtatt tttgctagat gcaacaacaa   11820
cagccacctc ctgatcccgc gatgcgggcg gcgctgcaga gccagccgtc cggcattaac   11880
tcctcggacg attggaccca ggccatgcaa cgcatcatgg cgctgacgac ccgcaacccc   11940
gaagccttta gacagcagcc ccaggccaac cggctctcgg ccatcctgga ggccgtggtg   12000
ccctcgcgct ccaaccccac gcacgagaag gtcctggcca tcgtgaacgc gctggtggag   12060
aacaaggcca tccgcggcga cgaggccggc ctggtgtaca acgcgctgct ggagcgcgtg   12120
gcccgctaca acagcaccaa cgtgcagacc aacctggacc gcatggtgac cgacgtgcgc   12180
gaggccgtgg cccagcgcga gcggttccac cgcgagtcca acctgggatc catggtggcg   12240
ctgaacgcct tcctcagcac ccagcccgcc aacgtgcccc ggggcagga ggactacacc    12300 aacttcatca gcgccctgcg cctgatggtg accgaggtgc cccagagcga ggtgtaccag   12360
tccgggccgg actacttctt ccagaccagt cgccagggct tgcagaccgt gaacctgagc   12420
caggctttca agaacttgca gggcctgtgg ggcgtgcagg ccccggtcgg ggaccgcgcg   12480
acggtgtcga gcctgctgac gccgaactcg cgcctgctgc tgctgctggt ggccccttc    12540
```

-continued

```
acggacagcg gcagcatcaa ccgcaactcg tacctgggct acctgattaa cctgtaccgc   12600
gaggccatcg gccaggcgca cgtggacgag cagacctacc aggagatcac ccacgtgagc   12660
cgcgccctgg gccaggacga cccgggcaac ctggaagcca ccctgaactt tttgctgacc   12720
aaccggtcgc agaagatccc gccccagtac gcgctcagca ccgaggagga gcgcatcctg   12780
cgttacgtgc agcagagcgt gggcctgttc ctgatgcagg aggggccac ccccagcgcc    12840 gcgctcgaca tgaccgcgcg caacatggag cccagcatgt acgccagcaa ccgcccgttc   12900
atcaataaac tgatggacta cttgcatcgg gcggccgcca tgaactctga ctatttcacc   12960
aacgccatcc tgaatcccca ctggctcccg ccgccggggt tctacacggg cgagtacgac   13020
atgcccgacc ccaatgacgg gttcctgtgg gacgatgtgg acagcagcgt gttctccccc   13080
cgaccgggtg ctaacgagcg ccccttgtgg aagaaggaag gcagcgaccg acgcccgtcc   13140
tcggcgctgt ccggccgcga gggtgctgcc gcggcggtgc ccgaggccgc cagtcctttc   13200
ccgagcttgc ccttctcgct gaacagtatc cgcagcagcg agctgggcag gatcacgcgc   13260
ccgcgcttgc tgggcgaaga ggagtacttg aatgactcgc tgttgagacc cgagcgggag   13320
aagaacttcc ccaataacgg gatagaaagc ctggtggaca agatgagccg ctggaagacg   13380
tatgcgcagg agcacaggga cgatccccgg gcgtcgcagg gggccacgag ccggggcagc   13440
gccgcccgta aacgccggtg gcacgacagg cagcggggac agatgtggga cgatgaggac   13500
tccgccgacg acagcagcgt gttggacttg ggtgggagtg gtaacccgtt cgctcacctg   13560
cgcccccgta tcgggcgcat gatgtaagag aaaccgaaaa taaatgatac tcaccaaggc   13620
catggcgacc agcgtgcgtt cgtttcttct ctgttgttgt tgtatctagt atgatgaggc   13680
gtgcgtaccc ggagggtcct cctccctcgt acgagagcgt gatgcagcag gcgatggcgg   13740
cggcggcgat gcagcccccg ctggaggctc cttacgtgcc cccgcggtac ctggcgccta   13800
cggaggggcg gaacagcatt cgttactcgg agctggcacc cttgtacgat accaccggt    13860 tgtacctggt ggacaacaag tcggcggaca tcgcctcgct gaactaccag aacgaccaca   13920
gcaacttcct gaccaccgtg gtgcagaaca atgacttcac ccccacgag gccagcaccc     13980 agaccatcaa ctttgacgag cgctcgcggt ggggcggcca gctgaaaacc atcatgcaca   14040
ccaacatgcc caacgtgaac gagttcatgt acagcaacaa gttcaaggcg cgggtgatgg   14100
tctcccgcaa gaccccccaat ggggtgacag tgacagagga ttatgatggt agtcaggatg  14160
agctgaagta tgaatgggtg gaatttgagc tgccccgaagg caacttctcg gtgaccatga   14220
ccatcgacct gatgaacaac gccatcatcg acaattactt ggcggtgggg cggcagaacg   14280
gggtgctgga gagcgacatc ggcgtgaagt tcgacactag gaacttcagg ctgggctggg   14340
accccgtgac cgagctggtc atgccccggg tgtacaccaa cgaggctttc catcccgata   14400
ttgtcttgct gcccggctgc ggggtggact tcaccgagag ccgcctcagc aacctgctgg   14460
gcattcgcaa gaggcagccc ttccaggaag gcttccagat catgtacgag gatctggagg   14520
ggggcaacat ccccgcgctc ctggatgtcg acgcctatga gaaaagcaag gaggatgcag   14580
cagctgaagc aactgcagcc gtagctaccc cctctaccga ggtcagggc gataattttg     14640 caagcgccgc agcagtggca gcggccgagg cggctgaaac cgaaagtaag atagtcattc    14700
agccggtgga gaaggatagc aagaacagga gctacaacgt actaccggac aagataaaca   14760
ccgcctaccg cagctggtac ctagcctaca actatgcga ccccgagaag ggcgtgcgct     14820
cctggacgct gctcaccacc tcggacgtca cctgcggcgt ggagcaagtc tactggtcgc   14880
```

-continued

```
tgcccgacat gatgcaagac ccggtcacct tccgctccac gcgtcaagtt agcaactacc    14940
cggtggtggg cgccgagctc ctgcccgtct actccaagag cttcttcaac gagcaggccg    15000
tctactcgca gcagctgcgc gccttcacct cgcttacgca cgtcttcaac cgcttccccg    15060
agaaccagat cctcgtccgc ccgcccgcgc ccaccattac caccgtcagt gaaaacgttc    15120
ctgctctcac agatcacggg accctgccgc tgcgcagcag tatccgggga gtccagcgcg    15180
tgaccgttac tgacgccaga cgccgcacct gcccctacgt ctacaaggcc ctgggcatag    15240
tcgcgccgcg cgtcctctcg agccgcacct tctaaatgtc cattctcatc tcgcccagta    15300
ataacaccgg ttggggcctg cgcgcgccca gcaagatgta cggaggcgct cgccaacgct    15360
ccacgcaaca ccccgtgcgc gtgcgcgggc acttccgcgc tccctggggc gccctcaagg    15420
gccgcgtgcg gtcgcgcacc accgtcgacg acgtgatcga ccaggtggtg gccgacgcgc    15480
gcaactacac ccccgccgcc gcgcccgtct ccaccgtgga cgccgtcatc gacagcgtgg    15540
tggccgacgc gcgccggtac gcccgcgcca agagccggcg gcggcgcatc gcccggcggc    15600
accggagcac ccccgccatg cgcgcggcgc gagccttgct gcgcagggcc aggcgcacgg    15660
gacgcagggc catgctcagg gcggccagac gcgcggcttc aggcgccagc gccggcagga    15720
cccggagacg cgcggccacg gcggcggcag cggccatcgc cagcatgtcc cgcccgcggc    15780
gagggaacgt gtactgggtg cgcgacgccg ccaccggtgt gcgcgtgccc gtgcgcaccc    15840
gccccctcg cacttgaaga tgttcacttc gcgatgttga tgtgtcccag cggcgaggag    15900
gatgtccaag cgcaaattca aggaagagat gctccaggtc atcgcgcctg agatctacgg    15960
ccctgcggtg gtgaaggagg aaagaaagcc ccgcaaaatc aagcgggtca aaaaggacaa    16020
aaaggaagaa gaaagtgatg tggacggatt ggtggagttt gtgcgcgagt tcgcccccg    16080
gcggcgcgtg cagtggcgcg gcggaaggt gcaaccggtg ctgagacccg gcaccaccgt    16140
ggtcttcacg cccggcgagc gctccggcac cgcttccaag cgctcctacg acgaggtgta    16200
cggggatgat gatattctgg agcaggcggc cgagcgcctg ggcgagtttg cttacggcaa    16260
gcgcagccgt tccgcaccga aggaagaggc ggtgtccatc ccgctggacc acggcaaccc    16320
cacgccgagc ctcaagcccg tgaccttgca gcaggtgctg ccgaccgcgg cgccgcgccg    16380
ggggttcaag cgcgagggcg aggatctgta ccccaccatg cagctgatgg tgcccaagcg    16440
ccagaagctg gaagacgtgc tggagaccat gaaggtggac ccggacgtgc agcccgaggt    16500
caaggtgcgg cccatcaagc aggtggcccc gggcctgggc gtgcagaccg tggacatcaa    16560
gattcccacg gagcccatgg aaacgcagac cgagcccatg atcaagccca gcaccagcac    16620
catggaggtg cagacggatc cctggatgcc atcggctcct agtcgaagac cccggcgcaa    16680
gtacggcgcg gccagcctgc tgatgcccaa ctacgcgctg catccttcca tcatccccac    16740
gccgggctac cgcggcacgc gcttctaccg cggtcatacc agcagccgcc gccgcaagac    16800
caccactcgc cgccgccgtc gccgcaccgc cgctgcaacc accctgccg ccctggtgcg    16860
gagagtgtac cgccgcggcc gcgcacctct gaccctgccg cgcgcgcgct accacccgag    16920
catcgccatt taaactttcg cctgctttgc agatcaatgg ccctcacatg ccgccttcgc    16980
gttcccatta cgggctaccg aggaagaaaa ccgcgccgta gaaggctggc ggggaacggg    17040
atgcgtcgcc accaccaccg gcggcggcgc gccatcagca agcggttggg gggaggcttc    17100
ctgcccgcgc tgatccccat catcgccgcg gcgatcgggg cgatcccgg cattgcttcc    17160
gtggcggtgc aggcctctca gcgccactga gacacacttg gaaacatctt gtaataaacc    17220
aatggactct gacgctcctg gtcctgtgat gtgttttcgt agacagatgg aagacatcaa    17280
```

```
tttttcgtcc ctggctccgc gacacggcac gcggccgttc atgggcacct ggagcgacat   17340
cggcaccagc caactgaacg ggggcgcctt caattggagc agtctctgga gcgggcttaa   17400
gaatttcggg tccacgctta aaacctatgg cagcaaggcg tggaacagca ccacagggca   17460
ggcgctgagg ataagctga aagagcagaa cttccagcag aaggtggtcg atgggctcgc   17520
ctcgggcatc aacggggtgg tggacctggc caaccaggcc gtgcagcggc agatcaacag   17580
ccgcctggac ccggtgccgc ccgccggctc cgtggagatg ccgcaggtgg aggaggagct   17640
gcctcccctg gacaagcggg gcgagaagcg accccgcccc gatgcggagg agacgctgct   17700
gacgcacacg gacgagccgc ccccgtacga ggaggcggtg aaactgggtc tgcccaccac   17760
gcggcccatc gcgcccctgg ccaccggggt gctgaaaccc gaaaagcccg cgaccctgga   17820
cttgcctcct ccccagcctt cccgcccctc tacagtggct aagccctgc cgccggtggc   17880
cgtggcccgc gcgcgacccg ggggcaccgc ccgccctcat gcgaactggc agagcactct   17940
gaacagcatc gtgggtctgg gagtgcagag tgtgaagcgc cgccgctgct attaaaccta   18000
ccgtagcgct taacttgctt gtctgtgtgt gtatgtatta tgtcgccgcc gccgctgtcc   18060
accagaagga gggagtgaaga ggcgcgtcgc cgagttgcaa gatggccacc ccatcgatgc   18120
tgccccagtg ggcgtacatg cacatcgccg gacaggacgc ttcggagtac ctgagtccgg   18180
gtctggtgca gtttgccgc gccacagaca cctacttcag tctggggaac aagtttagga   18240
accccacggt ggcgcccacg cacgatgtga ccaccgaccg cagccagcgg ctgacgctgc   18300
gcttcgtgcc cgtggaccgc gaggacaaca cctactcgta caaagtgcgc tacacgctgg   18360
ccgtgggcga caaccgcgtg ctggacatgg ccagcaccta ctttgacatc cgcggcgtgc   18420
tggatcgggg ccctagcttc aaaccctact ccggcaccgc ctacaacagt ctggccccca   18480
agggagcacc caacacttgt cagtggacat ataaagccga tggtgaaact gccacagaaa   18540
aaacctatac atatggaaat gcacccgtgc agggcattaa catcacaaaa gatggtattc   18600
aacttggaac tgacaccgat gatcagccaa tctacgcaga taaaacctat cagcctgaac   18660
ctcaagtggg tgatgctgaa tggcatgaca tcactggtac tgatgaaaag tatggaggca   18720
gagctcttaa gcctgatacc aaaatgaagc cttgttatgg ttcttttgcc aagcctacta   18780
ataaagaagg aggtcaggca aatgtgaaaa caggaacagg cactactaaa gaatatgaca   18840
tagacatggc tttctttgac aacagaagtg cggctgctgc tggcctagct ccagaaattg   18900
ttttgtatac tgaaaatgtg gatttggaaa ctccagatac ccatattgta tacaaagcag   18960
gcacagatga cagcagctct tctattaatt gggtcagca agccatgccc aacagaccta   19020
actacattgg tttcagagac aactttatcg ggctcatgta ctacaacagc actggcaata   19080
tgggggtgct ggccggtcag gcttctcagc tgaatgctgt ggttgacttg caagacgaaa   19140
acaccgagct gtcctaccag ctcttgcttg actctctggg tgacagaacc cggtatttca   19200
gtatgtggaa tcaggcggtg gacagctatg atcctgatgt gcgcattatt gaaaatcatg   19260
gtgtggagga tgaacttccc aactattgtt tccctctgga tgctgttggc agaacagata   19320
cttatcaggg aattaaggct aatgaactg atcaaaccac atggaccaaa gatgacagtg   19380
tcaatgatgc taatgagata ggcaagggta atccattcgc catggaaatc aacatccaag   19440
ccaacctgtg gaggaacttc ctctacgcca acgtggccct gtacctgccc gactcttaca   19500
agtacacgcc ggccaatgtt accctgccca ccaacaccaa cacctacgat tacatgaacg   19560
gccgggtggt ggcgcccctc gctggtggact cctacatcaa catcggggcg cgctggtcgc   19620
```

-continued

```
tggatcccat ggacaacgtg aaccccttca accaccaccg caatgcgggg ctgcgctacc    19680
gctccatgct cctgggcaac gggcgctacg tgcccttcca catccaggtg ccccagaaat    19740
ttttcgccat caagagcctc ctgctcctgc ccgggtccta cacctacgag tggaacttcc    19800
gcaaggacgt caacatgatc ctgcagagct ccctcggcaa cgacctgcgc acggacgggg    19860
cctccatctc cttcaccagc atcaacctct acgccacctt cttccccatg gcgcacaaca    19920
cggcctccac gctcgaggcc atgctgcgca acgacaccaa cgaccagtcc ttcaacgact    19980
acctctcggc ggccaacatg ctctacccca tcccggccaa cgccaccaac gtgcccatct    20040
ccatcccctc gcgcaactgg gccgccttcc gcggctggtc cttcacgcgt ctcaagacca    20100
aggagacgcc ctcgctgggc tccgggttcg accnctactt cgtctactcg ggctccatcc    20160
cctacctcga cggcaccttc tacctcaacc acaccttcaa gaaggtctcc atcaccttcg    20220
actcctccgt cagctggccc ggcaacgacc ggctcctgac gcccaacgag ttcgaaatca    20280
agcgcaccgt cgacggcgag ggctacaacg tgcccagtg caacatgacc aaggactggt    20340
tcctggtcca gatgctggcc cactacaaca tcggctacca gggcttctac gtgcccgagg    20400
gctacaagga ccgcatgtac tccttcttcc gcaacttcca gcccatgagc gccaggtgg    20460
tggacgaggt caactacaag gactaccagg ccgtcaccct ggcctaccag cacaacaact    20520
cgggcttcgt cggctacctc gcgcccacca tgcgccaggg ccagccctac cccgccaact    20580
accctacc gctcatcggc aagagcgccg tcaccagcgt cacccagaaa aagttcctct    20640
gcgacagggt catgtggcgc atccccttct ccagcaactt catgtccatg ggcgcgctca    20700
ccgacctcgg ccagaacatg ctctatgcca actccgccca cgcgctagac atgaatttcg    20760
aagtcgaccc catggatgag tccacccttc tctatgttgt cttcgaagtc ttcgacgtcg    20820
tccgagtgca ccagccccac cgcggcgtca tcgaggccgt ctacctgcgc accccttct    20880
cggccggtaa cgccaccacc taagctcttg cttcttgcaa gccatggccg cgggctccgg    20940
cgagcaggag ctcagggcca tcatccgcga cctgggctgc gggccctact cctgggcac    21000
cttcgataag cgcttcccgg gattcatggc cccgcacaag ctggcctgcg ccatcgtcaa    21060
cacggccggc cgcgagaccg ggggcgagca ctggctggcc ttcgcctgga cccgcgctc    21120
gaacacctgc tacctcttcg acccncttcgg gttctcggac gagcgcctca gcagatcta    21180
ccagttcgag tacgagggcc tgctgcgcgc cagcgccctg gccaccgagg accgctgcgt    21240
caccctggaa aagtccaccc agaccgtgca gggtccgcgc tcggccgcct gcgggctctt    21300
ctgctgcatg ttcctgcacg ccttcgtgca ctggcccgac cgcccatgg acaagaaccc    21360
caccatgaac ttgctgacgg gggtgcccaa cggcatgctc cagtcgcccc aggtggaacc    21420
caccctgcgc cgcaaccagg aggcgctcta ccgcttcctc aactcccact ccgcctactt    21480
tcgctcccac cgcgcgcgca tcgagaaggc caccgccttc gaccgcatga atcaagacat    21540
gtaaaccgtg tgtgtatgtt aaatgtcttt aataaacagc actttcatgt tacacatgca    21600
tctgagatga tttatttaga aatcgaaagg gttctgccgg gtctcggcat ggcccgcggg    21660
cagggacacg ttgcggaact ggtacttggc cagccacttg aactcgggga tcagcagttt    21720
gggcagcggg gtgtcgggga aggagtcggt ccacagcttc cgcgtcagtt gcagggcgcc    21780
cagcaggtcg ggcgcggaga tcttgaaatc gcagttggga cccgcgttct gcgcgcggga    21840
gttgcggtac acggggttgc agcactggaa caccatcagg gccgggtgct tcacgctcgc    21900
cagcaccgtc gcgtcggtga tgctctccac gtcgaggtcc tcggcgttgg ccatcccgaa    21960
gggggtcatc ttgcaggtct gccttcccat ggtgggcacg cacccgggct tgtggttgca    22020
```

```
atcgcagtgc aggggatca gcatcatctg ggcctggtcg gcgttcatcc ccgggtacat   22080
ggccttcatg aaagcctcca attgcctgaa cgcctgctgg gccttggctc cctcggtgaa   22140
gaagaccccg caggacttgc tagagaactg gttggtggcg cacccggcgt cgtgcacgca   22200
gcagcgcgcg tcgttgttgg ccagctgcac cacgctgcgc ccccagcggt ctgggtgat   22260 cttggcccgg tcggggttct ccttcagcgc gcgctgcccg ttctcgctcg ccacatccat   22320
ctcgatcatg tgctccttct ggatcatggt ggtcccgtgc aggcaccgca gcttgccctc   22380
ggcctcggtg cacccgtgca gccacagcgc gcacccggtg cactcccagt tcttgtgggc   22440
gatctgggaa tgcgcgtgca cgaagccctg caggaagcgg cccatcatgg tggtcagggt   22500
cttgttgcta gtgaaggtca gcggaatgcc gcggtgctcc tcgttgatgt acaggtggca   22560
gatgcggcgt acacctcgc cctgctcggg catcagctgg aagttggctt tcaggtcggt   22620
ctccacgcgg tagcggtcca tcagcatagt catgatttcc ataccttct cccaggccga   22680 gacgatgggc aggctcatag ggttcttcac catcatctta gcgctagcag ccgcggccag   22740
ggggtcgctc tcgtccaggg tctcaaagct ccgcttgccg tccttctcgg tgatccgcac   22800 cgggggtag ctgaagccca cggccgccag ctcctcctcg gcctgtcttt cgtcctcgct   22860
gtcctggctg acgtcctgca ggaccacatg cttggtcttg cggggtttct tcttgggcgg   22920
cagcggcggc ggagatgttg gagatggcga ggggagcgc gagttctcgc tcaccactac   22980
tatctcttcc tcttcttggt ccgaggccac gcggcggtag gtatgtctct tcgggggcag   23040
aggcggaggc gacgggctct cgccgccgcg acttggcgga tggctggcag agcccccttcc   23100 gcgttcgggg gtgcgctccc ggcggcgctc tgactgactt cctccgcggc cggccattgt   23160
gttctcctag ggaggaacaa caagcatgga gactcagcca tcgccaacct cgccatctgc   23220
ccccaccgcc gacgagaagc agcagcagca gaatgaaagc ttaaccgccc cgccgcccag   23280
ccccgccacc tccgacgcgg ccgtcccaga catgcaagag atggaggaat ccatcgagat   23340
tgacctgggc tatgtgacgc ccgcggagca cgaggaggag ctggcagtgc gcttttcaca   23400
agaagagata caccaagaac agccagagca ggaagcagag aatgagcaga gtcaggctgg   23460
gctcgagcat gacggcgact acctccacct gagcggggg gaggacgcgc tcatcaagca   23520
tctggcccgg caggccacca tcgtcaagga tgcgctgctc gaccgcaccg aggtgcccct   23580
cagcgtggag gagctcagcc gcgcctacga gttgaacctc ttctcgccgc gcgtgccccc   23640
caagcgccag cccaatggca cctgcgagcc caacccgcgc ctcaacttct acccggtctt   23700
cgcggtgccc gaggccctgg ccacctacca catcttttc aagaaccaaa agatccccgt   23760
ctcctgccgc gccaaccgca cccgcgccga cgcccttttc aacctgggtc ccggcgcccg   23820
cctacctgat atcgcctcct ggaagaggt tcccaagatc ttcgagggtc tgggcagcga   23880
cgagactcgg gccgcgaacg ctctgcaagg agaaggagga gagcatgagc accacagcgc   23940
cctggtcgag ttggaaggcg acaacgcgcg gctggcggtg ctcaaacgca cggtcgagct   24000
gacccatttc gcctacccgg ctctgaacct gcccccaaa gtcatgagcg cggtcatgga   24060
ccaggtgctc atcaagcgcg cgtcgcccat ctccgaggac gagggcatgc aagactccga   24120
ggagggcaag cccgtggtca gcgacgagca gctggcccgg tggctgggtc ctaatgctag   24180
tccccagagt ttggaagagc ggcgcaaact catgatggcc gtggtcctgg tgaccgtgga   24240
gctggagtgc ctgcgccgct tcttcgccga cgcggagacc ctgcgcaagg tcgaggagaa   24300
cctgcactac ctcttcaggc acgggttcgt gcgccaggcc tgcaagatct ccaacgtgga   24360
```

```
gctgaccaac ctggtctcct acatgggcat cttgcacgag aaccgcctgg ggcagaacgt   24420
gctgcacacc accctgcgcg gggaggcccg gcgcgactac atccgcgact gcgtctacct   24480
ctacctctgc cacacctggc agacgggcat gggcgtgtgg cagcagtgtc tggaggagca   24540
gaacctgaaa gagctctgca agctcctgca gaagaacctc aagggtctgt ggaccgggtt   24600
cgacgagcgc accaccgcct cggacctggc cgacctcatt ttccccgagc gcctcaggct   24660
gacgctgcgc aacggcctgc ccgactttat gagccaaagc atgttgcaaa actttcgctc   24720
tttcatcctc gaacgctccg gaatcctgcc cgccacctgc tccgcgctgc cctcggactt   24780
cgtgccgctg accttccgcg agtgcccccc gccgctgtgg agccactgct acctgctgcg   24840
cctggccaac tacctggcct accactcgga cgtgatcgag gacgtcagcg gcgagggcct   24900
gctcgagtgc cactgccgct gcaacctctg cacgccgcac cgctccctgg cctgcaaccc   24960
ccagctgctg agcgagaccc agatcatcgg caccttcgag ttgcaagggc ccagcgaagg   25020
cgagggttca gccgccaagg ggggtctgaa actcaccccg gggctgtgga cctcggccta   25080
cttgcgcaag ttcgtgcccg aggactacca tcccttcgag atcaggttct acgaggacca   25140
atcccatccg cccaaggccg agctgtcggc ctgcgtcatc acccaggggg cgatcctggc   25200
ccaattgcaa gccatccaga aatcccgcca agaattcttg ctgaaaaagg gccgcggggt   25260
ctacctcgac ccccagaccg gtgaggagct caaccccggc ttcccccagg atgccccgag   25320
gaaacaagaa gctgaaagtg gagctgccgc ccgtggagga tttggaggaa gactgggaga   25380
acagcagtca ggcagaggag gaggagatgg aggaagactg gacagcact caggcagagg   25440 aggacagcct gcaagacagt ctggaggaag acgaggagga ggcagaggag gaggtggaag   25500
aagcagccgc cgccagaccg tcgtcctcgg cggggagaa agcaagcagc acggatacca   25560
tctccgctcc gggtcggggt cccgctcgac cacacagtag atgggacgag accggacgat   25620
tcccgaaccc caccacccag accggtaaga aggagcggca gggatacaag tcctggcggg   25680
ggcacaaaaa cgccatcgtc tcctgcttgc aggcctgcgg gggcaacatc tccttcaccc   25740
ggcgctacct gctcttccac cgcggggtga actttccccg caacatcttg cattactacc   25800
gtcacctcca cagcccctac tacttccaag aagaggcagc agcagcagaa aaagaccagc   25860
agaaaaccag cagctagaaa atccacagcg gcggcagcag gtggactgag gatcgcggcg   25920
aacgagccgc cgcaaacccg ggagctgagg aaccggatct ttcccacccct ctatgccatc   25980 ttccagcaga gtcgggggca ggagcaggaa ctgaaagtca agaaccgttc tctgcgctcg   26040
ctcacccgca gttgtctgta tcacaagagc gaagaccaac ttcagcgcac tctcgaggac   26100
gccgaggctc tcttcaacaa gtactgcgcg ctcactctta aagagtagcc cgcgcccgcc   26160
cagtcgcaga aaaaggcggg aattacgtca cctgtgccct tcgccctagc cgcctccacc   26220
catcatcatg agcaaagaga ttcccacgcc ttacatgtgg agctaccagc cccagatggg   26280
cctggccgcc ggtgccgccc aggactactc cacccgcatg aattggctca gcgccgggcc   26340
cgcgatgatc tcacgggtga atgacatccg cgcccaccga aaccagatac tcctagaaca   26400
gtcagcgctc accgccacgc cccgcaatca cctcaatccg cgtaattggc ccgccgccct   26460
ggtgtaccag gaaattcccc agcccacgac cgtactactt ccgcgagacg cccaggccga   26520
agtccagctg actaactcag gtgtccagct ggcgggcggc gccaccctgt gtcgtcaccg   26580
ccccgctcag ggtataaagc ggctggtgat ccggggcaga ggcacacagc tcaacgacga   26640
ggtggtgagc tcttcgctgg gtctgcgacc tgacggagtc ttccaactcg ccggatcggg   26700
gagatcttcc ttcacgcctc gtcaggccgt cctgactttg gagagttcgt cctcgcagcc   26760
```

```
ccgctcgggt ggcatcggca ctctccagtt cgtggaggag ttcactccct cggtctactt   26820
caaccccttc tccggctccc ccggccacta cccggacgag ttcatcccga acttcgacgc   26880
catcagcgag tcgtggacg gctacgattg aaactaatca ccccctttatc cagtgaaata   26940 aagatcatat tgatgatgat tttacagaaa taaaaaataa tcatttgatt tgaaataaag   27000
atacaatcat attgatgatt tgagtttaac aaaaaaataa agaatcactt acttgaaatc   27060
tgataccagg tctctgtcca tgttttctgc caacaccact tcactcccct cttcccagct   27120
ctggtactgc aggccccggc gggctgcaaa cttcctccac acgctgaagg ggatgtcaaa   27180
ttcctcctgt ccctcaatct tcattttatc ttctatcaga tgtccaaaaa gcgcgtccgg   27240
gtggatgatg acttcgaccc cgtctacccc tacgatgcag acaacgcacc gaccgtgccc   27300
ttcatcaacc ccccttcgt ctcttcagat ggattccaag agaagcccct gggggtgttg   27360
tccctgcgac tggccgaccc cgtcaccacc aagaacgggg aaatcaccct caagctggga   27420
gagggggtgg acctcgattc ctcgggaaaa ctcatctcca acacggccac caaggccgcc   27480
gcccctctca gttttttccaa caacaccatt tcccttaaca tggatcaccc cttttacact   27540
aaagatggaa aattatccctt acaagtttct ccaccattaa atatactgag aacaagcatt   27600
ctaaacacac tagctttagg ttttggatca ggtttaggac tccgtggctc tgccttggca   27660
gtacagttag tctctccact tacatttgat actgatggaa acataaagct taccttagac   27720
agaggtttgc atgttacaac aggagatgca attgaaagca cataagctg ggctaaaggt   27780 ttaaaatttg aagatggagc catagcaacc aacattggaa atgggttaga gtttggaagc   27840
agtagtacag aaacaggtgt tgatgatgct tacccaatcc aagttaaact tggatctggc   27900
cttagctttg acagtacagg agccataatg gctggtaaca agaagacga taaactcact   27960 ttgtggacaa cacctgatcc atcaccaaac tgtcaaatac tcgcagaaaa tgatgcaaaa   28020
ctaacacttt gcttgactaa atgtggtagt caaatactgg ccactgtgtc agtcttagtt   28080
gtaggaagtg gaaacctaaa ccccattact ggcaccgtaa gcagtgctca ggtgtttcta   28140
cgttttgatg caaacggtgt tcttttaaca gaacattcta cactaaaaaa atactggggg   28200
tataggcagg gagatagcat agatggcact ccatatacca atgctgtagg attcatgccc   28260
aatttaaaag cttatccaaa gtcacaaagt tctactacta aaaataatat agtagggcaa   28320
gtatacatga atggagatgt tcaaaaccct atgcttctca ctataaccct caatggtact   28380
gatgacagca acagtacata ttcaatgtca ttttcataca cctggactaa tggaagctat   28440
gttggagcaa catttgggc taactcttat accttctcat acatcgccca agaatgaaca   28500
ctgtatccca ccctgcatgc caaccttcc cacccactc tgtggaacaa actctgaaac   28560 acaaataaa ataagttca agtgttttat tgattcaaca gttttacagg attcgagcag   28620 ttattttcc tccacccctcc caggacatgg aatacaccac cctctccccc cgcacagcct   28680
tgaacatctg aatgccattg gtgatggaca tgcttttggt ctccacgttc cacacagttt   28740
cagagcgagc cagtctcggg tcggtcaggg agatgaaacc ctccgggcac tcccgcatct   28800
gcacctcaca gctcaacagc tgaggattgt cctcggtggt cgggatcacg gttatctgga   28860
agaagcagaa gagcggcgt gggaatcata gtccgcgaac gggatcggcc ggtggtgtcg   28920
catcaggccc cgcagcagtc gctgccgccg ccgctccgtc aagctgctgc tcaggggtc   28980 cgggtccagg gactccctca gcatgatgcc cacggccctc agcatcagtc gtctggtgcg   29040
gcgggcgcag cagcgcatgc ggatctcgct caggtcgctg cagtacgtgc aacacagaac   29100
```

```
caccaggttg ttcaacagtc catagttcaa cacgctccag ccgaaactca tcgcgggaag  29160
gatgctaccc acgtggccgt cgtaccagat cctcaggtaa atcaagtggt gcccctcca   29220 gaacacgctg cccacgtaca tgatctcctt gggcatgtgg cggttcacca cctcccggta  29280
ccacatcacc ctctggttga acatgcagcc ccggatgatc ctgcggaacc acagggccag  29340
caccgccccg cccgccatgc agcgaagaga ccccgggtcc cggcaatggc aatggaggac  29400
ccaccgctcg tacccgtgga tcatctggga gctgaacaag tctatgttgg cacagcacag  29460
gcatatgctc atgcatctct tcagcactct caactcctcg ggggtcaaaa ccatatccca  29520
gggcacgggg aactcttgca ggacagcgaa ccccgcagaa cagggcaatc ctcgcacaga  29580
acttacattg tgcatggaca gggtatcgca atcaggcagc accgggtgat cctccaccag  29640
agaagcgcgg gtctcggtct cctcacagcg tggtaagggg gccggccgat acgggtgatg  29700
gcgggacgcg gctgatcgtg ttcgcgaccg tgtcatgatg cagttgcttt cggacatttt  29760
cgtacttgct gtagcagaac ctggtccggg cgctgcacac cgatcgccgg cggcggtctc  29820
ggcgcttgga acgctcggtg ttgaaattgt aaaacagcca ctctctcaga ccgtgcagca  29880
gatctagggc ctcaggagtg atgaagatcc catcatgcct gatggctctg atcacatcga  29940
ccaccgtgga atgggccaga cccagccaga tgatgcaatt ttgttgggtt tcggtgacgg  30000
cgggggaggg aagaacagga agaaccatga ttaacttta atccaaacgg tctcggagta  30060
cttcaaaatg aagatcgcgg agatggcacc tctcgccccc gctgtgttgg tggaaaataa  30120
cagccaggtc aaaggtgata cggttctcga gatgttccac ggtggcttcc agcaaagcct  30180
ccacgcgcac atccagaaac aagacaatag cgaaagcggg agggttctct aattcctcaa  30240
tcatcatgtt acactcctgc accatcccca gataatttc attttccag ccttgaatga    30300 ttcgaactag ttcctgaggt aaatccaagc cagccatgat aaagagctcg cgcagagcgc  30360
cctccaccgg cattcttaag cacaccctca taattccaag atattctgct cctggttcac  30420
ctgcagcaga ttgacaagcg gaatatcaaa atctctgccg cgatccctga gctcctccct  30480
cagcaataac tgtaagtact cttttcatatc ctctccgaaa ttttttagcca taggaccacc  30540 aggaataaga ttagggcaag ccacagtaca gataaaccga agtcctcccc agtgagcatt  30600
gccaaatgca agactgctat aagcatgctg gctagacccg gtgatatctt ccagataact  30660
ggacagaaaa tcgcccaggc aattttttaag aaaatcaaca aaagaaaaat cctccaggtg  30720
gacgtttaga gcctcgggaa caacgatgaa gtaaatgcaa gcggtgcgtt ccagcatggt  30780
tagttagctg atctgtagaa aaaacaaaaa tgaacattaa accatgctag cctggcgaac  30840
aggtgggtaa atcgttctct ccagcaccag gcaggccacg gggtctccgg cgcgacctc    30900 gtaaaaattg tcgctatgat tgaaaaccat cacagagaga cgttcccggt ggccggcgtg  30960
aatgattcga caagatgaat acaccccgg aacattggcg tccgcgagtg aaaaaaagcg   31020
cccgaggaag caataaggca ctacaatgct cagtctcaag tccagcaaag cgatgccatg  31080
cggatgaagc acaaaattct caggtgcgta caaaatgtaa ttactcccct cctgcacagg  31140
cagcaaagcc cccgatccct ccaggtacac atacaaagcc tcagcgtcca tagcttaccg  31200
agcagcagca cacaacaggc gcaagagtca gagaaaggct gagctctaac ctgtccaccc  31260
gctctctgct caatatatag cccagatcta cactgacgta aaggccaaag tctaaaaata  31320
cccgccaaat aatcacacac gcccagcaca cgcccagaaa ccggtgacac actcaaaaaa  31380
atacgcgcac ttcctcaaac gcccaaaact gccgtcattt ccgggttccc acgctacgtc  31440
atcaaaacac gactttcaaa ttccgtcgac cgttaaaaac gtcacccgcc ccgcccctaa  31500
```

-continued

```
cggtcgcccg tctctcagcc aatcagcgcc ccgcatcccc aaattcaaac acctcatttg    31560
catattaacg cgcacaaaaa gtttgagg                                        31588

<210> SEQ ID NO 3
<211> LENGTH: 11447
<212> TYPE: DNA
<213> ORGANISM: Venezuelan equine encephalitis virus

<400> SEQUENCE: 3
atgggcggcg catgagagaa gcccagacca attacctacc caaaatggag aaagttcacg      60
ttgacatcga ggaagacagc ccattcctca gagctttgca gcggagcttc ccgcagtttg     120
aggtagaagc caagcaggtc actgataatg accatgctaa tgccagagcg ttttcgcatc     180
tggcttcaaa actgatcgaa acggaggtgg acccatccga cacgatcctt gacattggaa     240
gtgcgcccgc ccgcagaatg tattctaagc acaagtatca ttgtatctgt ccgatgagat     300
gtgcggaaga tccggacaga ttgtataagt atgcaactaa gctgaagaaa aactgtaagg     360
aaataactga taaggaattg gacaagaaaa tgaaggagct cgccgccgtc atgagcgacc     420
ctgacctgga aactgagact atgtgcctcc acgacgacga gtcgtgtcgc tacgaagggc     480
aagtcgctgt ttaccaggat gtatacgcgg ttgacggacc gacaagtctc tatcaccaag     540
ccataagggg agttagagtc gcctactgga taggctttga caccaccccct tttatgttta     600 agaacttggc tggagcatat ccatcatact ctaccaactg gccgacgaa accgtgttaa       660 cggctcgtaa cataggccta tgcagctctg acgttatgga gcggtcacgt agagggatgt     720
ccattcttag aaagaagtat ttgaaaccat ccaacaatgt tctattctct gttggctcga     780
ccatctacca cgagaagagg gacttactga ggagctggca cctgccgtct gtatttcact     840
tacgtggcaa gcaaaattac acatgtcggt gtgagactat agttagttgc gacgggtacg     900
tcgttaaaag aatagctatc agtccaggcc tgtatgggaa gccttcaggc tatgctgcta     960
cgatgcaccg cgagggattc ttgtgctgca aagtgacaga cacattgaac ggggagaggg    1020 tctctttttcc cgtgtgcacg tatgtgccag ctacattgtg tgaccaaatg actggcatac    1080
tggcaacaga tgtcagtgcg gacgacgcgc aaaaactgct ggttgggctc aaccagcgta    1140
tagtcgtcaa cggtcgcacc cagagaaaca ccaataccat gaaaaattac cttttgcccg    1200
tagtggccca ggcatttgct aggtgggcaa aggaatataa ggaagatcaa gaagatgaaa    1260
ggccactagg actacgagat agacagttag tcatggggtg ttgttgggct tttagaaggc    1320
acaagataac atctatttat aagcgcccgg atacccaaac catcatcaaa gtgaacagcg    1380
atttccactc attcgtgctg cccaggatag gcagtaacac attggagatc gggctgagaa    1440
caagaatcag gaaatgttag aggagcaca aggagccgtc acctctcatt accgccgagg     1500
acgtacaaga agctaagtgc gcagccgatg aggctaagga ggtgcgtgaa gccgaggagt    1560
tgcgcgcagc tctaccacct ttggcagctg atgttgagga gcccactctg gaagccgatg    1620
tcgacttgat gttacaagag gctggggccg gctcagtgga gacacctcgt ggcttgataa    1680
aggttaccag ctacgctggc gaggacaaga tcggctctta cgctgtgctt tctccgcagg    1740
ctgtactcaa gagtgaaaaa ttatcttgca tccacccctct cgctgaacaa gtcatagtga    1800
taacacactc tggccgaaaa gggcgttatg ccgtggaacc ataccatggt aaagtagtgg    1860
tgccagaggg acatgcaata cccgtccagg actttcaagc tctgagtgaa agtgccacca    1920
ttgtgtacaa cgaacgtgag ttcgtaaaca ggtacctgca ccatattgcc acacatggag    1980
```

```
gagcgctgaa cactgatgaa gaatattaca aaactgtcaa gcccagcgag cacgacggcg   2040
aatacctgta cgacatcgac aggaaacagt gcgtcaagaa agaactagtc actgggctag   2100
ggctcacagg cgagctggtg gatcctccct tccatgaatt cgcctacgag agtctgagaa   2160
cacgaccagc cgctccttac caagtaccaa ccatagggt gtatggcgtg ccaggatcag    2220
gcaagtctgg catcattaaa agcgcagtca ccaaaaaaga tctagtggtg agcgccaaga   2280
aagaaaactg tgcagaaatt ataagggacg tcaagaaaat gaaagggctg acgtcaatg    2340 ccagaactgt ggactcagtg ctcttgaatg gatgcaaaca ccccgtagag accctgtata   2400
ttgacgaagc ttttgcttgt catgcaggta ctctcagagc gctcatagcc attataagac   2460
ctaaaaaggc agtgctctgc ggggatccca acagtgcgg ttttttaac atgatgtgcc     2520 tgaaagtgca ttttaaccac gagatttgca cacaagtctt ccacaaaagc atctctcgcc   2580
gttgcactaa atctgtgact tcggtcgtct caaccttgtt ttacgacaaa aaatgagaa    2640 cgacgaatcc gaaagagact aagattgtga ttgacactac cggcagtacc aaacctaagc   2700
aggacgatct cattctcact tgtttcagag ggtgggtgaa gcagttgcaa atagattaca   2760
aaggcaacga aataatgacg cagctgcct ctcaagggct gacccgtaaa ggtgtgtatg    2820
ccgttcggta caaggtgaat gaaaatcctc tgtacgcacc cacctcagaa catgtgaacg   2880
tcctactgac ccgcacggag gaccgcatcg tgtggaaaac actagccggc gacccatgga   2940
taaaaacact gactgccaag taccctggga atttcactgc cacgatagag gagtggcaag   3000
cagagcatga tgccatcatg aggcacatct tggagagacc ggaccctacc gacgtcttcc   3060
agaataaggc aaacgtgtgt tgggccaagg ctttagtgcc ggtgctgaag accgctggca   3120
tagacatgac cactgaacaa tggaacactg tggattattt tgaaacggac aaagctcact   3180
cagcagagat agtattgaac caactatgcg tgaggttctt tggactcgat ctggactccg   3240
gtctattttc tgcacccact gttccgttat ccattaggaa taatcactgg gataactccc   3300
cgtcgcctaa catgtacggg ctgaataaag aagtggtccg tcagctctct cgcaggtacc   3360
cacaactgcc tcgggcagtt gccactggaa gagtctatga catgaacact ggtacactgc   3420
gcaattatga tccgcgcata aacctagtac ctgtaaacag aagactgcct catgctttag   3480
tcctccacca taatgaacac ccacagagtg actttcttc attcgtcagc aaattgaagg    3540
gcagaactgt cctggtggtc ggggaaaagt tgtccgtccc aggcaaaatg gttgactggt   3600
tgtcagaccg gcctgaggct accttcagag ctcggctgga tttaggcatc ccaggtgatg   3660
tgcccaaata tgacataata tttgttaatg tgaggaccc atataaatac catcactatc    3720
agcagtgtga agaccatgcc attaagctta gcatgttgac caagaaagct tgtctgcatc   3780
tgaatcccgg cggaacctgt gtcagcatag gttatggtta cgctgacagg gccagcgaaa   3840
gcatcattgg tgctatagcg cggcagttca gttttcccg ggtatgcaaa ccgaaatcct    3900
cacttgaaga gacggaagtt ctgtttgtat tcattgggta cgatcgcaag gcccgtacgc   3960
acaatcctta caagctttca tcaaccttga ccaacattta tacaggttcc agactccacg   4020
aagccggatg tgcaccctca tatcatgtgg tgcgagggga tattgccacg gccaccgaag   4080
gagtgattat aaatgctgct aacagcaaag gacaacctgg cggaggggtg tgcggagcgc   4140
tgtataagaa attcccggaa agcttcgatt tacagccgat cgaagtagga aaagcgcgac   4200
tggtcaaagg tgcagctaaa catatcattc atgccgtagg accaaacttc aacaaagttt   4260 cggagggttga aggtgacaaa cagttggcag aggcttatga gtccatcgct aagattgtca   4320
acgataacaa ttacaagtca gtagcgattc cactgttgtc caccggcatc ttttccggga   4380
```

```
acaaagatcg actaacccaa tcattgaacc atttgctgac agctttagac accactgatg    4440
cagatgtagc catatactgc agggacaaga aatgggaaat gactctcaag gaagcagtgg    4500
ctaggagaga agcagtggag gagatatgca tatccgacga ctcttcagtg acagaacctg    4560
atgcagagct ggtgagggtg catccgaaga gttctttggc tggaaggaag ggctacagca    4620
caagcgatgg caaaactttc tcatatttgg aagggaccaa gtttcaccag gcggccaagg    4680
atatagcaga aattaatgcc atgtgggccg ttgcaacgga ggccaatgag caggtatgca    4740
tgtatatcct cggagaaagc atgagcagta ttaggtcgaa atgccccgtc gaagagtcgg    4800
aagcctccac accacctagc acgctgcctt gcttgtgcat ccatgccatg actccagaaa    4860
gagtacagcg cctaaaagcc tcacgtccag aacaaattac tgtgtgctca tcctttccat    4920
tgccgaagta tagaatcact ggtgtgcaga agatccaatg ctcccagcct atattgttct    4980
caccgaaagt gcctgcgtat attcatccaa ggaagtatct cgtggaaaca ccaccggtag    5040
acgagactcc ggagccatcg gcagagaacc aatccacaga ggggacacct gaacaaccac    5100
cacttataac cgaggatgag accaggacta gaacgcctga gccgatcatc atcgaagagg    5160
aagaaggaga tagcataagt ttgctgtcag atggcccgac ccaccaggtg ctgcaagtcg    5220
aggcagacat tcacgggccg ccctctgtat ctagctcatc ctggtccatt cctcatgcat    5280
ccgactttga tgtggacagt ttatccatac ttgacccct ggagggagct agcgtgacca    5340
gcggggcaac gtcagccgag actaactctt acttcgcaaa gagtatggag tttctggcgc    5400
gaccggtgcc tgcgcctcga acagtattca ggaaccctcc acatcccgct ccgcgcacaa    5460
gaacaccgtc acttgcaccc agcagggcct gctcgagaac cagcctagtt tccacccccgc    5520
caggcgtgaa tagggtgatc actagagagg agctcgaggc gcttaccccg tcacgcactc    5580
ctagcaggtc ggtctcgaga accagcctgg tctccaaccc gccaggcgta aatagggtga    5640
ttacaagaga ggagtttgag gcgttcgtag cacaacaaca atgacggttt gatgcgggtg    5700
catacatctt ttcctccgac accggtcaag ggcatttaca acaaaaatca gtaaggcaaa    5760
cggtgctatc cgaagtggtg ttggagagga ccgaattgga gatttcgtat gccccgcgcc    5820
tcgaccaaga aaaagaagaa ttactacgca agaaattaca gttaaatccc acacctgcta    5880
acagaagcag ataccagtcc aggaaggtgg agaacatgaa agccataaca gctagacgta    5940
ttctgcaagg cctagggcat tatttgaagg cagaaggaaa agtggagtgc taccgaaccc    6000
tgcatcctgt tcctttgtat tcatctagtg tgaaccgtgc cttttcaagc cccaaggtcg    6060
cagtggaagc ctgtaacgcc atgttgaaag agaactttcc gactgtggct tcttactgta    6120
ttattccaga gtacgatgcc tatttggaca tggttgacgg agcttcatgc tgcttagaca    6180
ctgccagttt ttgccctgca agctgcgca gctttccaaa gaaacactcc tatttggaac    6240
ccacaatacg atcggcagtg ccttcagcga tccagaacac gctccagaac gtcctggcag    6300
ctgccacaaa aagaaattgc aatgtcacgc aaatgagaga attgcccgta ttggattcgg    6360
cggcctttaa tgtggaatgc ttcaagaaat atgcgtgtaa taatgaatat tgggaaacgt    6420
ttaaagaaaa ccccatcagg cttactgaag aaaacgtggt aaattacatt accaaattaa    6480
aaggaccaaa agctgctgct cttttttgcga agacacataa tttgaatatg ttgcaggaca    6540
taccaatgga caggtttgta atggacttaa agagagacgt gaaagtgact ccaggaacaa    6600
aacatactga agaacggccc aaggtacagg tgatccaggc tgccgatccg ctagcaacag    6660
cgtatctgtg cggaatccac cgagagctgg ttaggagatt aaatgcggtc ctgcttccga    6720
```

```
acattcatac actgtttgat atgtcggctg aagactttga cgctattata gccgagcact    6780
tccagcctgg ggattgtgtt ctggaaactg acatcgcgtc gtttgataaa agtgaggacg    6840
acgccatggc tctgaccgcg ttaatgattc tggaagactt aggtgtggac gcagagctgt    6900
tgacgctgat tgaggcggct ttcggcgaaa tttcatcaat acatttgccc actaaaacta    6960
aatttaaatt cggagccatg atgaaatctg gaatgttcct cacactgttt gtgaacacag    7020
tcattaacat tgtaatcgca agcagagtgt tgagagaacg gctaaccgga tcaccatgtg    7080
cagcattcat tggagatgac aatatcgtga aaggagtcaa atcggacaaa ttaatggcag    7140
acaggtgcgc cacctggttg aatatggaag tcaagattat agatgctgtg gtgggcgaga    7200
aagcgcctta tttctgtgga gggtttattt tgtgtgactc cgtgaccggc acagcgtgcc    7260
gtgtggcaga cccctaaaa aggctgttta agcttggcaa acctctggca gcagacgatg    7320
aacatgatga tgacaggaga agggcattgc atgaagagtc aacacgctgg aaccgagtgg    7380
gtattctttc agagctgtgc aaggcagtag aatcaaggta tgaaaccgta ggaacttcca    7440
tcatagttat ggccatgact actctagcta gcagtgttaa atcattcagc tacctgagag    7500
gggcccctat aactctctac ggctaacctg aatggactac gacatagtct agtccgccaa    7560
gatgttcccg ttcagccaa tgtatccgat gcagccaatg ccctatcgca cccgttcgc    7620
ggccccgcgc aggccctggt tccccagaac cgaccctttt ctggcgatgc aggtgcagga    7680
attaacccgc tcgatggcta acctgacgtt caagcaacgc cggacgcgc cacctgaggg    7740
gccatccgct aagaaaccga agaaggaggc ctcgcaaaaa cagaaagggg gaggccaagg    7800
gaagaagaag aagaaccaag ggaagaagaa ggctaagaca gggccgccta atccgaaggc    7860
acagaatgga aacaagaaga agaccaacaa gaaaccaggc aagagacagc gcatggtcat    7920
gaaattggaa tctgacaaga cgttcccaat catgttggaa gggaagataa acggctacgc    7980
ttgtgtggtc ggagggaagt tattcaggcc gatgcatgtg gaaggcaaga tcgacaacga    8040
cgttctggcc gcgcttaaga cgaagaaagc atccaaatac gatcttgagt atgcagatgt    8100
gccacagaac atgcgggccg atacattcaa atacacccat gagaaacccc aaggctatta    8160
cagctggcat catggagcag tccaatatga aaatgggcgt ttcacggtgc cgaaaggagt    8220
tggggccaag ggagacagcg gacgacccat tctggataac cagggacggg tggtcgctat    8280
tgtgctggga ggtgtgaatg aaggatctag gacagcccct tcagtcgtca tgtgaacga    8340
gaagggagtt accgtgaagt atactccgga gaactgcgag caatggtcac tagtgaccac    8400
catgtgtctg ctcgccaatg tgacgttccc atgtgctcaa ccaccaattt gctacgacag    8460
aaaaccagca gagactttgg ccatgctcag cgttaacgtt gacaacccgg ctacgatga    8520
gctgctggaa gcagctgtta agtgcccgg aaggaaaagg agatccaccg aggagctgtt    8580
taaggagtat aagctaacgc gcccttacat ggccagatgc atcagatgtg cagttgggag    8640
ctgccatagt ccaatagcaa tcgaggcagt aaagagcgac gggcacgacg gttatgttag    8700
acttcagact tcctcgcagt atggcctgga ttcctccggc aacttaaagg gcaggaccat    8760
gcggtatgac atgcacggga ccattaaaga gataccacta catcaagtgt cactccatac    8820
atctcgcccg tgtcacattg tggatgggca cggttattc ctgcttgcca ggtgcccggc    8880
agggactcc atcaccatgg aatttaagaa agattccgtc acacactcct gctcggtgcc    8940
gtatgaagtg aaatttaatc ctgtaggcag agaactctat actcatcccc cagaacacgg    9000
agtagagcaa gcgtgccaag tctacgcaca tgatgcacag aacagaggag cttatgtcga    9060
gatgcacctc ccgggctcag aagtggacag cagtttggtt tccttgagcg gcagttcagt    9120
```

```
caccgtgaca cctcctgttg ggactagcgc cctggtggaa tgcgagtgtg gcggcacaaa      9180
gatctccgag accatcaaca agacaaaaca gttcagccag tgcacaaaga aggagcagtg      9240
cagagcatat cggctgcaga acgataagtg ggtgtataat tctgacaaac tgcccaaagc      9300
agcgggagcc accttaaaag gaaaactgca tgtcccattc ttgctggcag acggcaaatg      9360
caccgtgcct ctagcaccag aacctatgat aacctttggt ttcagatcag tgtcactgaa      9420
actgcaccct aagaatccca catatctaac caccgccaa cttgctgatg agcctcacta       9480
cacgcacgag ctcatatctg aaccagctgt taggaatttt accgtcaccg aaaaagggtg      9540
ggagtttgta tggggaaacc acccgccgaa aaggttttgg gcacaggaaa cagcacccgg      9600
aaatccacat gggctaccgc acgaggtgat aactcattat taccacagat accctatgtc      9660
caccatcctg ggtttgtcaa tttgtgccgc cattgcaacc gtttccgttg cagcgtctac      9720
ctggctgttt tgcagatcta gagttgcgtg cctaactcct taccggctaa cacctaacgc      9780
taggatacca ttttgtctgg ctgtgctttg ctgcgcccgc actgcccggg ccgagaccac      9840
ctgggagtcc ttggatcacc tatggaacaa taaccaacag atgttctgga ttcaattgct      9900
gatccctctg gccgccttga tcgtagtgac tcgcctgctc aggtgcgtgt gctgtgtcgt      9960 gccttttta gtcatggccg gcgccgcagg cgccggcgcc tacgagcacg cgaccacgat      10020
gccgagccaa gcgggaatct cgtataacac tatagtcaac agagcaggct acgcaccact     10080
ccctatcagc ataacaccaa caaagatcaa gctgatacct acagtgaact tggagtacgt     10140
cacctgccac tacaaaacag gaatggattc accagccatc aaatgctgcg gatctcagga     10200
atgcactcca acttacaggc ctgatgaaca gtgcaaagtc ttcacagggg tttacccgtt     10260
catgtggggt ggtgcatatt gcttttgcga cactgagaac acccaagtca gcaaggccta     10320
cgtaatgaaa tctgacgact gccttgcgga tcatgctgaa gcatataaag cgcacacagc     10380
ctcagtgcag gcgttcctca acatcacagt gggagaacac tctattgtga ctaccgtgta     10440
tgtgaatgga gaaactcctg tgaatttcaa tgggtcaaa ttaactgcag gtccgctttc      10500
cacagcttgg acaccctttg atcgcaaaat cgtgcagtat gccggggaga tctataatta     10560
tgattttcct gagtatgggg caggacaacc aggagcattt ggagatatac aatccagaac     10620
agtctcaagc tcagatctgt atgccaatac caacctagtg ctgcagagac ccaaagcagg     10680
agcgatccac gtgccataca ctcaggcacc ttcgggtttt gagcaatgga gaaagataa      10740 agctccatca ttgaaattta ccgccccttt cggatgcgaa atatatcaa accccattcg      10800 cgccgaaaac tgtgctgtag ggtcaattcc attagccttt gacattcccg acgccttgtt     10860
caccagggtg tcagaaacac cgacactttc agcggccgaa tgcactctta acgagtgcgt     10920
gtattcttcc gactttggtg ggatcgccac ggtcaagtac tcggccagca gtcaggcaa      10980 gtgcgcagtc catgtgccat cagggactgc taccctaaaa gaagcagcag tcgagctaac     11040
cgagcaaggg tcggcgacta tccatttctc gaccgcaaat atccaccggg agttcaggct     11100
ccaaatatgc acatcatatg ttacgtgcaa aggtgattgt caccccccga aagaccatat     11160
tgtgacacac cctcagtatc acgcccaaac atttacagcc gcggtgtcaa aaaccgcgtg     11220
gacgtggtta acatccctgc tgggaggatc agccgtaatt attataattg cttggtgct      11280 ggctactatt gtggccatgt acgtgctgac caaccagaaa cataattgaa tacagcagca     11340
attggcaagc tgcttacata gaactcgcgg cgattggcat gccgccttaa aatttttatt     11400 ttatttttc ttttcttttc cgaatcggat tttgttttta atatttc                    11447
```

<210> SEQ ID NO 4
<211> LENGTH: 9577
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 4

| | | | | | |
|---|---|---|---|---|---|
| atgggcggcg | catgagagaa | gcccagacca | attacctacc | caaaatggag | aaagttcacg | 60 |
| ttgacatcga | ggaagacagc | ccattcctca | gagctttgca | gcggagcttc | ccgcagtttg | 120 |
| aggtagaagc | caagcaggtc | actgataatg | accatgctaa | tgccagagcg | ttttcgcatc | 180 |
| tggcttcaaa | actgatcgaa | acggaggtgg | acccatccga | cacgatcctt | gacattggaa | 240 |
| gtgcgcccgc | ccgcagaatg | tattctaagc | acaagtatca | ttgtatctgt | ccgatgagat | 300 |
| gtgcggaaga | tccggacaga | ttgtataagt | atgcaactaa | gctgaagaaa | aactgtaagg | 360 |
| aaataactga | taaggaattg | gacaagaaaa | tgaaggagct | cgccgccgtc | atgagcgacc | 420 |
| ctgacctgga | aactgagact | atgtgcctcc | acgacgacga | gtcgtgtcgc | tacgaagggc | 480 |
| aagtcgctgt | ttaccaggat | gtatacgcgc | ttgacggacc | gacaagtctc | tatcaccaag | 540 |
| ccaataaggg | agttagagtc | gcctactgga | taggctttga | caccaccccct | tttatgttta | 600 |
| agaacttggc | tggagcatat | ccatcatact | ctaccaactg | ggccgacgaa | accgtgttaa | 660 |
| cggctcgtaa | cataggccta | tgcagctctg | acgttatgga | gcggtcacgt | agagggatgt | 720 |
| ccattcttag | aaagaagtat | ttgaaaccat | ccaacaatgt | tctattctct | gttggctcga | 780 |
| ccatctacca | cgagaagagg | gacttactga | ggagctggca | cctgccgtct | gtatttcact | 840 |
| tacgtggcaa | gcaaaattac | acatgtcggt | gtgagactat | agttagttgc | gacgggtacg | 900 |
| tcgttaaaag | aatagctatc | agtccaggcc | tgtatgggaa | gccttcaggc | tatgctgcta | 960 |
| cgatgcaccg | cgagggattc | ttgtgctgca | aagtgacaga | cattgaac | ggggagaggg | 1020 |
| tctctttttcc | cgtgtgcacg | tatgtgccag | ctacattgtg | tgaccaaatg | actggcatac | 1080 |
| tggcaacaga | tgtcagtgcg | gacgacgcgc | aaaaactgct | ggttgggctc | aaccagcgta | 1140 |
| tagtcgtcaa | cggtcgcacc | cagagaaaca | ccaataccat | gaaaaattac | cttttgcccg | 1200 |
| tagtggccca | ggcatttgct | aggtgggcaa | aggaatataa | ggaagatcaa | gaagatgaaa | 1260 |
| ggccactagg | actacgagat | agacagttag | tcatggggtg | ttgttgggct | tttagaaggc | 1320 |
| acaagataac | atctatttat | aagcgcccgg | atacccaaac | catcatcaaa | gtgaacagcg | 1380 |
| atttccactc | attcgtgctg | cccaggatag | gcagtaacac | attggagatc | gggctgaaaa | 1440 |
| caagaatcag | gaaaatgtta | gaggagcaca | aggagccgtc | acctctcatt | accgccgagg | 1500 |
| acgtacaaga | agctaagtgc | gcagccgatg | aggctaagga | ggtgcgtgaa | gccgaggagt | 1560 |
| tgcgcgcagc | tctaccacct | ttggcagctg | atgttgagga | gcccactctg | gaagccgatg | 1620 |
| tcgacttgat | gttacaagag | gctggggccg | gctcagtgga | gacacctgt | ggcttgataa | 1680 |
| aggttaccag | ctacgctggc | gaggacaaga | tcggctctta | cgctgtgctt | tctccgcagg | 1740 |
| ctgtactcaa | gagtgaaaaa | ttatcttgca | tccacccctct | cgctgaacaa | gtcatagtga | 1800 |
| taacacactc | tggccgaaaa | gggcgttatg | ccgtggaacc | ataccatggt | aaagtagtgg | 1860 |
| tgccagaggg | acatgcaata | cccgtccagg | actttcaagc | tctgagtgaa | agtgccacca | 1920 |
| ttgtgtacaa | cgaacgtgag | ttcgtaaaca | ggtacctgca | ccatattgcc | acacatggag | 1980 |
| gagcgctgaa | cactgatgaa | gaatattaca | aaactgtcaa | gcccagcgag | cacgacggcg | 2040 |

```
aatacctgta cgacatcgac aggaaacagt gcgtcaagaa agaactagtc actgggctag   2100
ggctcacagg cgagctggtg gatcctccct tccatgaatt cgcctacgag agtctgagaa   2160
cacgaccagc cgctccttac caagtaccaa ccataggggt gtatggcgtg ccaggatcag   2220
gcaagtctgg catcattaaa agcgcagtca ccaaaaaaga tctagtggtg agcgccaaga   2280
aagaaaactg tgcagaaatt ataagggacg tcaagaaaat gaaagggctg gacgtcaatg   2340
ccagaactgt ggactcagtg ctcttgaatg gatgcaaaca ccccgtagag accctgtata   2400
ttgacgaagc ttttgcttgt catgcaggta ctctcagagc gctcatagcc attataagac   2460
ctaaaaaggc agtgctctgc ggggatccca aacagtgcgg tttttttaac atgatgtgcc   2520
tgaaagtgca ttttaaccac gagatttgca cacaagtctt ccacaaaagc atctctcgcc   2580
gttgcactaa atctgtgact tcggtcgtct caaccttgtt ttacgacaaa aaatgagaa   2640 cgacgaatcc gaaagagact aagattgtga ttgacactac cggcagtacc aaacctaagc   2700
aggacgatct cattctcact tgtttcagag ggtgggtgaa gcagttgcaa atagattaca   2760
aaggcaacga ataatgacg gcagctgcct ctcaagggct gacccgtaaa ggtgtgtatg   2820
ccgttcggta caaggtgaat gaaaatcctc tgtacgcacc cacctcagaa catgtgaacg   2880
tcctactgac ccgcacggag gaccgcatcg tgtggaaaac actagccggc gacccatgga   2940
taaaaacact gactgccaag taccctggga atttcactgc cacgatagag gagtggcaag   3000
cagagcatga tgccatcatg aggcacatct ggagagacc ggaccctacc gacgtcttcc   3060
agaataaggc aaacgtgtgt gggccaagg ctttagtgcc ggtgctgaag accgctggca   3120
tagacatgac cactgaacaa tggaacactg tggattattt tgaaacggac aaagctcact   3180
cagcagagat agtattgaac caactatgcg tgaggttctt tggactcgat ctggactccg   3240
gtctattttc tgcacccact gttccgttat ccattaggaa taatcactgg gataactccc   3300
cgtcgcctaa catgtacggg ctgaataaag aagtggtccg tcagctctct cgcaggtacc   3360
cacaactgcc tcgggcagtt gccactggaa gagtctatga catgaacact ggtacactgc   3420
gcaattatga tccgcgcata aacctagtac ctgtaaacag aagactgcct catgctttag   3480
tcctccacca taatgaacac ccacagagtg acttttcttc attcgtcagc aaattgaagg   3540
gcagaactgt cctggtggtc ggggaaaagt tgtccgtccc aggcaaaatg gttgactggt   3600
tgtcagaccg gcctgaggct accttcagag ctcggctgga tttaggcatc ccaggtgatg   3660
tgcccaaata tgacataata tttgttaatg tgaggaccc atataaatac catcactatc   3720
agcagtgtga agaccatgcc attaagctta gcatgttgac caagaaagct tgtctgcatc   3780
tgaatcccgg cggaacctgt gtcagcatag gttatggtta cgctgacagg gccagcgaaa   3840
gcatcattgg tgctatagcg cggcagttca agttttcccg ggtatgcaaa ccgaaatcct   3900
cacttgaaga gacggaagtt ctgtttgtat tcattgggta cgatcgcaag gcccgtacgc   3960
acaatcctta caagctttca tcaaccttga ccaacattta tacaggttcc agactccacg   4020
aagccggatg tgcaccctca tatcatgtgg tgcgagggga tattgccacg ccaccgaag   4080 gagtgattat aaatgctgct aacagcaaag acaacctgg cggaggggtg tgcggagcgc   4140
tgtataagaa attcccggaa agcttcgatt tacagccgat cgaagtagga aaagcgcgac   4200
tggtcaaagg tgcagctaaa catatcattc atgccgtagg accaaacttc aacaaagttt   4260
cggaggttga aggtgacaaa cagttggcag aggcttatga gtccatcgct aagattgtca   4320
acgataacaa ttcaagtca gtagcgattc cactgttgtc caccggcatc ttttccggga   4380
acaaagatcg actaacccaa tcattgaacc atttgctgac agctttagac accactgatg   4440
```

```
cagatgtagc catatactgc agggacaaga aatgggaaat gactctcaag gaagcagtgg    4500
ctaggagaga agcagtggag gagatatgca tatccgacga ctcttcagtg acagaacctg    4560
atgcagagct ggtgagggtg catccgaaga gttctttggc tggaaggaag ggctacagca    4620
caagcgatgg caaaacttc tcatatttgg aagggaccaa gtttcaccag gcggccaagg     4680
atatagcaga aattaatgcc atgtggcccg ttgcaacgga ggccaatgag caggtatgca    4740
tgtatatcct cggagaaagc atgagcagta ttaggtcgaa atgccccgtc gaagagtcgg    4800
aagcctccac accacctagc acgctgcctt gcttgtgcat ccatgccatg actccagaaa    4860
gagtacagcg cctaaaagcc tcacgtccag aacaaattac tgtgtgctca tcctttccat    4920
tgccgaagta tagaatcact ggtgtgcaga agatccaatg ctcccagcct atattgttct    4980
caccgaaagt gcctgcgtat attcatccaa ggaagtatct cgtggaaaca ccaccggtag    5040
acgagactcc ggagccatcg gcagagaacc aatccacaga ggggacacct gaacaaccac    5100
cacttataac cgaggatgag accaggacta gaacgcctga ccgatcatc atcgaagagg     5160 aagaagagga tagcataagt ttgctgtcag atggcccgac ccaccaggtg ctgcaagtcg    5220
aggcagacat tcacgggccg ccctctgtat ctagctcatc ctggtccatt cctcatgcat    5280
ccgactttga tgtggacagt ttatccatac ttgacaccct ggagggagct agcgtgacca    5340
gcggggcaac gtcagccgag actaactctt acttcgcaaa gagtatggag tttctggcgc    5400
gaccggtgcc tgcgcctcga acagtattca ggaaccctcc acatcccgct ccgcgcacaa    5460
gaacaccgtc acttgcaccc agcagggcct gctcgagaac cagcctagtt tccaccccgc    5520
caggcgtgaa tagggtgatc actagagagg agctcgaggc gcttacccc tcacgcactc     5580 ctagcaggtc ggtctcgaga accagcctgg tctccaaccc gccaggcgta aataggggtga   5640 ttacaagaga ggagtttgag gcgttcgtag cacaacaaca atgacggttt gatgcgggtg    5700
catacatctt ttcctccgac accggtcaag ggcatttaca acaaaaatca gtaaggcaaa    5760
cggtgctatc cgaagtggtg ttggagagga ccgaattgga gatttcgtat gccccgcgcc    5820
tcgaccaaga aaaagaagaa ttactacgca agaaattaca gttaaatccc acacctgcta    5880
acagaagcag ataccagtcc aggaaggtgg agaacatgaa agccataaca gctagacgta    5940
ttctgcaagg cctagggcat tatttgaagg cagaaggaaa agtggagtgc taccgaaccc    6000
tgcatcctgt tcctttgtat tcatctagtg tgaaccgtgc cttttcaagc ccaaggtcg    6060 cagtggaagc ctgtaacgcc atgttgaaag agaactttcc gactgtggct tcttactgta    6120
ttattccaga gtacgatgcc tatttggaca tggttgacgg agcttcatgc tgcttagaca    6180
ctgccagttt ttgccctgca aagctgcgca gctttccaaa gaaacactcc tatttggaac    6240
ccacaatacg atcggcagtg ccttcagcga tccagaacac gctccagaac gtcctggcag    6300
ctgccacaaa aagaaattgc aatgtcacgc aaatgagaga attgcccgta ttggattcgg    6360
cggcctttaa tgtggaatgc ttcaagaaat atgcgtgtaa taatgaatat tgggaaacgt    6420
ttaaagaaaa ccccatcagg cttactgaag aaaacgtggt aaattacatt accaaattaa    6480
aaggaccaaa agctgctgct cttttttgcga agacacataa tttgaatatg ttgcaggaca    6540
taccaatgga caggtttgta atggacttaa agagagacgt gaaagtgact ccaggaacaa    6600
aacatactga agaacggccc aaggtacagg tgatccaggc tgccgatccg ctagcaacag    6660
cgtatctgtg cggaatccac cgagagctgg ttaggagatt aaatgcggtc ctgcttccga    6720
acattcatac actgtttgat atgtcggctg aagactttga cgctattata gccgagcact    6780
```

```
tccagcctgg ggattgtgtt ctggaaactg acatcgcgtc gtttgataaa agtgaggacg    6840
acgccatggc tctgaccgcg ttaatgattc tggaagactt aggtgtggac gcagagctgt    6900
tgacgctgat tgaggcggct ttcggcgaaa tttcatcaat acatttgccc actaaaacta    6960
aatttaaatt cggagccatg atgaaatctg aatgttcct cacactgttt gtgaacacag     7020
tcattaacat tgtaatcgca agcagagtgt tgagagaacg gctaaccgga tcaccatgtg    7080
cagcattcat tggagatgac aatatcgtga aaggagtcaa atcggacaaa ttaatggcag    7140
acaggtgcgc cacctggttg aatatggaag tcaagattat agatgctgtg gtgggcgaga    7200
aagcgcctta tttctgtgga gggtttattt tgtgtgactc cgtgaccggc acagcgtgcc    7260
gtgtggcaga cccctaaaa aggctgttta agcttggcaa acctctggca gcagacgatg     7320
aacatgatga tgacaggaga agggcattgc atgaagagtc aacacgctgg aaccgagtgg    7380
gtattctttc agagctgtgc aaggcagtag aatcaaggta tgaaaccgta ggaacttcca    7440
tcatagttat ggccatgact actctagcta gcagtgttaa atcattcagc tacctgagag    7500
gggccctat aactctctac ggctaacctg aatggactac gactctagaa tagtcttaa     7560
ttaagccacc atggcaggca tgtttcaggc gctgagcgaa ggctgcaccc cgtatgatat    7620
taaccagatg ctgaacgtgc tgggcgatca tcaggtctca ggccttgagc agcttgagag    7680
tataatcaac tttgaaaaac tgactgaatg gaccagttct aatgttatgc ctatcctgtc    7740
tcctctgaca aagggcatcc tgggcttcgt gtttaccctg accgtgcctt ctgagagagg    7800
acttagctgc attagcgaag cggatgcgac caccccggaa agcgcgaacc tgggcgaaga    7860
aattctgagc cagctgtatc tttggccaag ggtgacctac cattcccta gttatgctta     7920
ccaccaattt gaaagacgag ccaaatataa aagacacttc cccggctttg ccagagcct     7980
gctgtttggc taccctgtgt acgtgttcgg cgattgcgtg cagggcgatt gggatgcgat    8040
tcgctttcgc tattgcgcgc cgccgggcta tgcgctgctg cgctgcaacg ataccaacta    8100
tagcgctctg ctggctgtgg gggccctaga aggacccagg aatcaggact ggcttggtgt    8160
cccaagacaa cttgtaactc ggatgcaggc tattcagaat gccggcctgt gtaccctggt    8220
ggccatgctg gaagagacaa tcttctggct gcaagcgttt ctgatggcgc tgaccgatag    8280
cggcccgaaa accaacatta ttgtggatag ccagtatgtg atgggcatta gcaaaccgag    8340
cttttcaggaa tttgtggatt gggaaaacgt gagcccggaa ctgaacagca ccgatcagcc    8400
gttttggcaa gccggaatcc tggccagaaa tctggtgcct atggtggcca cagtgcaggg    8460
ccagaacctg aagtaccagg gtcagtcact agtcatctct gcttctatca ttgtcttcaa    8520
cctgctggaa ctggaaggtg attatcgaga tgatggcaac gtgtgggtgc ataccccgct    8580
gagcccgcgc accctgaacg cgtgggtgaa agcggtggaa gaaaaaaaag gtattccagt    8640
tcacctagag ctggccagta tgaccaacat ggagctcatg agcagtattg tgcatcagca    8700
ggtcagaaca tacggccccg tgttcatgtg tctcggcgga ctgcttacaa tggtggctgg    8760
tgctgtgtgg ctgacagtgc gagtgctcga gctgttccgg gccgcgcagc tggccaacga    8820
cgtggtcctc cagatcatgg agctttgtgg tgcagcgttt cgccaggtgt gccataccac    8880
cgtgccgtgg ccgaacgcga gcctgacccc gaaatggaac aacgaaacca cccagcccca    8940
gatcgccaac tgcagcgtgt atgactttt tgtgtggctc cattattatt ctgttcgaga    9000
cacactttgg ccaagggtga cctaccatat gaacaaatat gcgtatcata tgctggaaag    9060
acgagccaaa tataaaagag gaccaggacc tggcgctaaa tttgtggccg cctggacact    9120
gaaagccgct gctggtcctg gacctggcca gtacatcaag gccaacagca gttcatcgg    9180
```

```
catcaccgaa ctcggacccg gaccaggctg atgattcgaa cggccgtatc acgcccaaac    9240
atttacagcc gcggtgtcaa aaaccgcgtg gacgtggtta acatccctgc tgggaggatc    9300
agccgtaatt attataattg gcttggtgct ggctactatt gtggccatgt acgtgctgac    9360
caaccagaaa cataattgaa tacagcagca attggcaagc tgcttacata gaactcgcgg    9420
cgattggcat gccgccttaa aattttattt ttattttttc ttttcttttc cgaatcggat    9480
tttgttttta atatttcaaa aaaaaaaaaa aaaaaaaaaa aaaaaaaaaa aaaaaaaaa     9540 aaaaaaaaaa aaaaaaaaa aaaaaaaaaa aaaaaa                              9577
```

<210> SEQ ID NO 5
<211> LENGTH: 11446
<212> TYPE: DNA
<213> ORGANISM: Venezuelan equine encephalitis virus

<400> SEQUENCE: 5

```
ataggcggcg catgagagaa gcccagacca attacctacc caaaatggag aaagttcacg      60
ttgacatcga ggaagacagc ccattcctca gagctttgca gcggagcttc ccgcagtttg     120
aggtagaagc caagcaggtc actgataatg accatgctaa tgccagagcg ttttcgcatc     180
tggcttcaaa actgatcgaa acggaggtgg acccatccga cacgatcctt gacattggaa     240
gtgcgcccgc ccgcagaatg tattctaagc acaagtatca ttgtatctgt ccgatgagat     300
gtgcggaaga tccggacaga ttgtataagt atgcaactaa gctgaagaaa aactgtaagg     360
aaataactga taaggaattg gacaagaaaa tgaaggagct cgccgccgtc atgagcgacc     420
ctgacctgga aactgagact atgtgcctcc acgacgacga gtcgtgtcgc tacgaagggc     480
aagtcgctgt ttaccaggat gtatacgcgc ttgacggacc gacaagtctc tatcaccaag     540
ccaataaggg agttagagtc gcctactgga taggctttga caccacccct tttatgttta     600
agaacttggc tggagcatat ccatcatact ctaccaactg ggccgacgaa accgtgttaa     660
cggctcgtaa cataggccta tgcagctctg acgttatgga gcggtcacgt agagggatgt     720
ccattcttag aaagaagtat ttgaaaccat ccaacaatgt tctattctct gttggctcga     780
ccatctacca cgagaagagg gacttactga ggagctggca cctgccgtct gtatttcact     840
tacgtggcaa gcaaaattac acatgtcggt gtgagactat agttagttgc gacgggtacg     900
tcgttaaaag aatagctatc agtccaggcc tgtatgggaa gccttcaggc tatgctgcta     960
cgatgcaccg cgagggattc ttgtgctgca aagtgacaga cacattgaac ggggagaggg    1020
tctcttttcc cgtgtgcacg tatgtgccag ctacattgtg tgaccaaatg actggcatac    1080
tggcaacaga tgtcagtgcg gacgacgcgc aaaaactgct ggttgggctc aaccagcgta    1140
tagtcgtcaa cggtcgcacc cagagaaaca ccaataccat gaaaaattac cttttgcccg    1200
tagtggccca ggcatttgct aggtgggcaa aggaatataa ggaagatcaa gaagatgaaa    1260
ggccactagg actacgagat agacagttag tcatggggtt gttgggct tttagaaggc       1320 acaagataac atctatttat aagcgcccgg atacccaaac catcatcaaa gtgaacagcg    1380
atttccactc attcgtgctg cccaggatag gcagtaacac attggagatc gggctgagaa    1440
caagaatcag gaaaatgtta gaggagcaca aggagccgtc acctctcatt accgccgagg    1500
acgtacaaga agctaagtgc gcagccgatg aggctaagga ggtgcgtgaa gccgaggagt    1560
tgcgcgcagc tctaccacct ttggcagctg atgttgagga gcccactctg gaagccgatg    1620
tcgacttgat gttacaagag gctgggccg gtcagtggga gacacctcgt ggcttgataa    1680
```

```
aggttaccag ctacgatggc gaggacaaga tcggctctta cgctgtgctt tctccgcagg   1740
ctgtactcaa gagtgaaaaa ttatcttgca tccaccctct cgctgaacaa gtcatagtga   1800
taacacactc tggccgaaaa gggcgttatg ccgtggaacc ataccatggt aaagtagtgg   1860
tgccagaggg acatgcaata cccgtccagg actttcaagc tctgagtgaa agtgccacca   1920
ttgtgtacaa cgaacgtgag ttcgtaaaca ggtacctgca ccatattgcc acacatggag   1980
gagcgctgaa cactgatgaa gaatattaca aaactgtcaa gcccagcgag cacgacggcg   2040
aatacctgta cgacatcgac aggaaacagt gcgtcaagaa agaactagtc actgggctag   2100
ggctcacagg cgagctggtg gatcctccct tccatgaatt cgcctacgag agtctgagaa   2160
cacgaccagc cgctccttac caagtaccaa ccatagggt gtatggcgtg ccaggatcag   2220
gcaagtctgg catcattaaa agcgcagtca ccaaaaaaga tctagtggtg agcgccaaga   2280
aagaaaactg tgcagaaatt ataagggacg tcaagaaaat gaaagggctg acgtcaatg   2340 ccagaactgt ggactcagtg ctcttgaatg gatgcaaaca ccccgtagag accctgtata   2400
ttgacgaagc ttttgcttgt catgcaggta ctctcagagc gctcatagcc attataagac   2460
ctaaaaaggc agtgctctgc ggggatccca acagtgcgg ttttttttaac atgatgtgcc   2520 tgaaagtgca ttttaaccac gagatttgca cacaagtctt ccacaaaagc atctctcgcc   2580
gttgcactaa atctgtgact tcggtcgtct caaccttgtt ttacgacaaa aaatgagaa   2640 cgacgaatcc gaaagagact aagattgtga ttgacactac cggcagtacc aaacctaagc   2700
aggacgatct cattctcact tgtttcagag ggtgggtgaa gcagttgcaa atagattaca   2760
aaggcaacga ataatgacg gcagctgcct ctcaagggct gacccgtaaa ggtgtgtatg   2820
ccgttcggta caaggtgaat gaaaatcctc tgtacgcacc cacctcagaa catgtgaacg   2880
tcctactgac ccgcacggag gaccgcatcg tgtggaaaac actagccggc gacccatgga   2940
taaaaacact gactgccaag taccctggga atttcactgc cacgatagag gagtggcaag   3000
cagagcatga tgccatcatg aggcacatct ggagagacc ggaccctacc gacgtcttcc   3060
agaataaggc aaacgtgtgt tgggccaagg ctttagtgcc ggtgctgaag accgctggca   3120
tagacatgac cactgaacaa tggaacactg tggattattt tgaaacggac aaagctcact   3180
cagcagagat agtattgaac caactatgcg tgaggttctt tggactcgat ctggactccg   3240 gtctatttc tgcacccact gttccgttat ccattaggaa taatcactgg gataactccc   3300
cgtcgcctaa catgtacggg ctgaataaag aagtggtccg tcagctctct cgcaggtacc   3360
cacaactgcc tcgggcagtt gccactggaa gagtctatga catgaacact ggtacactgc   3420
gcaattatga tccgcgcata aacctagtac ctgtaaacag aagactgcct catgctttag   3480
tcctccacca taatgaacac ccacagagtg acttttcttc attcgtcagc aaattgaagg   3540
gcagaactgt cctggtggtc ggggaaaagt tgtccgtccc aggcaaaatg gttgactggt   3600
tgtcagaccg gcctgaggct accttcagag ctcggctgga tttaggcatc ccaggtgatg   3660
tgcccaaata tgacataata tttgttaatg tgaggacccc atataaatac catcactatc   3720
agcagtgtga agaccatgcc attaagctta gcatgttgac caagaaagct tgtctgcatc   3780
tgaatcccgg cggaacctgt gtcagcatag gttatggtta cgctgacagg gccagcgaaa   3840
gcatcattgg tgctatagcg cggcagttca agttttccc ggtatgcaaa ccgaaatcct   3900
cacttgaaga gacggaagtt ctgtttgtat tcattgggta cgatcgcaag gcccgtacgc   3960
acaatcctta caagctttca tcaaccttga ccaacattta tacaggttcc agactccacg   4020
aagccggatg tgcaccctca tatcatgtgg tgcgagggga tattgccacg gccaccgaag   4080
```

```
gagtgattat aaatgctgct aacagcaaag gacaacctgg cggaggggtg tgcggagcgc    4140
tgtataagaa attcccggaa agcttcgatt tacagccgat cgaagtagga aaagcgcgac    4200
tggtcaaagg tgcagctaaa catatcattc atgccgtagg accaaacttc aacaaagttt    4260
cggaggttga aggtgacaaa cagttggcag aggcttatga gtccatcgct aagattgtca    4320
acgataacaa ttacaagtca gtagcgattc cactgttgtc caccggcatc ttttccggga    4380
acaaagatcg actaacccaa tcattgaacc atttgctgac agctttagac accactgatg    4440
cagatgtagc catatactgc agggacaaga aatgggaaat gactctcaag gaagcagtgg    4500
ctaggagaga agcagtggag gagatatgca tatccgacga ctcttcagtg acagaacctg    4560
atgcagagct ggtgagggtg catccgaaga gttctttggc tggaaggaag ggctacagca    4620
caagcgatgg caaaactttc tcatatttgg aagggaccaa gtttcaccag gcggccaagg    4680
atatagcaga aattaatgcc atgtggcccg ttgcaacgga ggccaatgag caggtatgca    4740
tgtatatcct cggagaaagc atgagcagta ttaggtcgaa atgccccgtc gaagagtcgg    4800
aagcctccac accacctagc acgctgcctt gcttgtgcat ccatgccatg actccagaaa    4860
gagtacagcg cctaaaagcc tcacgtccag aacaaattac tgtgtgctca tcctttccat    4920
tgccgaagta tagaatcact ggtgtgcaga agatccaatg ctcccagcct atattgttct    4980
caccgaaagt gcctgcgtat attcatccaa ggaagtatct cgtggaaaca ccaccggtag    5040
acgagactcc ggagccatcg gcagagaacc aatccacaga ggggacacct gaacaaccac    5100
cacttataac cgaggatgag accaggacta gaacgcctga gccgatcatc atcgaagagg    5160
aagaagagga tagcataagt ttgctgtcag atggcccgac ccaccaggtg ctgcaagtcg    5220
aggcagacat tcacgggccg ccctctgtat ctagctcatc ctggtccatt cctcatgcat    5280
ccgactttga tgtggacagt ttatccatac ttgacaccct ggagggagct agcgtgacca    5340
gcggggcaac gtcagccgag actaactctt acttcgcaaa gagtatggag tttctggcgc    5400
gaccggtgcc tgcgcctcga acagtattca ggaaccctcc acatcccgct ccgcgcacaa    5460
gaacaccgtc acttgcaccc agcagggcct gctcgagaac cagcctagtt tccacccgc     5520 caggcgtgaa tagggtgatc actagagagg agctcgaggc gcttacccg tcacgcactc      5580 ctagcaggtc ggtctcgaga accagcctgg tctccaaccc gccaggcgta aatagggtga    5640
ttacaagaga ggagtttgag gcgttcgtag cacaacaaca atgacggttt gatgcgggtg    5700
catacatctt ttcctccgac accggtcaag ggcatttaca acaaaaatca gtaaggcaaa    5760
cggtgctatc cgaagtggtg ttggagagga ccgaattgga gatttcgtat gccccgcgcc    5820
tcgaccaaga aaaagaagaa ttactacgca agaaattaca gttaaatccc acacctgcta    5880
acagaagcag ataccagtcc aggaaggtgg agaacatgaa agccataaca gctagacgta    5940
ttctgcaagg cctagggcat tatttgaagg cagaaggaaa agtggagtgc taccgaaccc    6000
tgcatcctgt tccttttgtat tcatctagtg tgaaccgtgc cttttcaagc ccaaggtcg     6060 cagtggaagc ctgtaacgcc atgttgaaag agaactttcc gactgtggct tcttactgta    6120
ttattccaga gtacgatgcc tatttggaca tggttgacgg agcttcatgc tgcttagaca    6180
ctgccagttt ttgccctgca aagctgcgca gcttccaaaa gaaacactcc tatttggaac    6240
ccacaatacg atcggcagtg ccttcagcga tccagaacac gctccagaac gtcctggcag    6300
ctgccacaaa aagaaattgc aatgtcacgc aaatgagaga attgcccgta ttggattcgg    6360
cggcctttaa tgtggaatgc ttcaagaaat atgcgtgtaa taatgaatat tgggaaacgt    6420
```

```
ttaaagaaaa ccccatcagg cttactgaag aaaacgtggt aaattacatt accaaattaa      6480
aaggaccaaa agctgctgct cttttttgcga agacacataa tttgaatatg ttgcaggaca     6540
taccaatgga caggtttgta atggacttaa agagagacgt gaaagtgact ccaggaacaa     6600
aacatactga agaacggccc aaggtacagg tgatccaggc tgccgatccg ctagcaacag     6660
cgtatctgtg cggaatccac cgagagctgg ttaggagatt aaatgcggtc ctgcttccga     6720
acattcatac actgtttgat atgtcggctg aagactttga cgctattata gccgagcact     6780
tccagcctgg ggattgtgtt ctggaaactg acatcgcgtc gtttgataaa agtgaggacg     6840
acgccatggc tctgaccgcg ttaatgattc tggaagactt aggtgtggac gcagagctgt     6900
tgacgctgat tgaggcggct ttcggcgaaa tttcatcaat acatttgccc actaaaacta     6960
aatttaaatt cggagccatg atgaaatctg gaatgttcct cacactgttt gtgaacacag     7020
tcattaacat tgtaatcgca agcagagtgt tgagagaacg gctaaccgga tcaccatgtg     7080
cagcattcat tggagatgac aatatcgtga aaggagtcaa atcggacaaa ttaatggcag     7140
acaggtgcgc cacctggttg aatatggaag tcaagattat agatgctgtg gtgggcgaga     7200
aagcgcctta tttctgtgga gggtttattt tgtgtgactc cgtgaccggc acagcgtgcc     7260
gtgtggcaga ccccctaaaa aggctgttta agcttggcaa acctctggca gcagacgatg     7320
aacatgatga tgacaggaga agggcattgc atgaagagtc aacacgctgg aaccgagtgg     7380
gtattctttc agagctgtgc aaggcagtag aatcaaggta tgaaaccgta ggaacttcca    7440
tcatagttat ggccatgact actctagcta gcagtgttaa atcattcagc tacctgagag     7500
gggcccctat aactctctac ggctaacctg aatggactac gacatagtct agtccgccaa     7560
gatgttcccg ttccagccaa tgtatccgat gcagccaatg ccctatcgca acccgttcgc     7620
ggccccgcgc aggccctggt tccccagaac cgaccctttt ctggcgatgc aggtgcagga     7680
attaacccgc tcgatggcta acctgacgtt caagcaacgc cgggacgcgc cacctgaggg     7740
gccatccgct aagaaaccga agaaggaggc ctcgcaaaaa cagaaagggg gaggccaagg     7800
gaagaagaag aagaaccaag ggaagaagaa ggctaagaca gggccgccta atccgaaggc     7860
acagaatgga aacaagaaga gaccaacaa gaaaccaggc aagagacagc gcatggtcat     7920
gaaattggaa tctgacaaga cgttcccaat catgttggaa gggaagataa acggctacgc     7980
ttgtgtggtc ggagggaagt tattcaggcc gatgcatgtg gaaggcaaga tcgacaacga     8040
cgttctggcc gcgcttaaga cgaagaaagc atccaaatac gatcttgagt atgcagatgt     8100
gccacagaac atgcgggccg atacattcaa atacacccat gagaaacccc aaggctatta     8160
cagctggcat catggagcag tccaatatga aaatgggcgt tcacggtgc cgaaaggagt     8220
tgggggccaag ggagacagcg gacgacccat tctggataac cagggacggg tggtcgctat     8280
tgtgctggga ggtgtgaatg aaggatctag gacagcccct tcagtcgtca tgtggaacga     8340
gaagggagtt accgtgaagt atactccgga gaactgcgag caatggtcac tagtgaccac     8400
catgtgtctg ctcgccaatg tgacgttccc atgtgctcaa ccaccaattt gctacgacag     8460
aaaaccagca gagactttgg ccatgctcag cgttaacgtt gacaacccgg gctacgatga     8520
gctgctggaa gcagctgtta agtgcccggg aaggaaaagg agatccaccg aggagctgtt     8580
taatgagtat aagctaacgc gcccttacat ggccagatgc atcagatgtg cagttgggag     8640
ctgccatagt ccaatagcaa tcgaggcagt aaagagcgac gggcacgacg gttatgttag     8700
acttcagact tcctcgcagt atggcctgga ttcctccgc aacttaaagg gcaggaccat     8760
gcggtatgac atgcacggga ccattaaaga gataccacta catcaagtgt cactctatac     8820
```

```
atctcgcccg tgtcacattg tggatgggca cggttatttc ctgcttgcca ggtgcccggc    8880
aggggactcc atcaccatgg aatttaagaa agattccgtc agacactcct gctcggtgcc    8940
gtatgaagtg aaatttaatc ctgtaggcag agaactctat actcatcccc cagaacacgg    9000
agtagagcaa gcgtgccaag tctacgcaca tgatgcacag aacagaggag cttatgtcga    9060
gatgcacctc ccgggctcag aagtggacag cagtttggtt tccttgagcg gcagttcagt    9120
caccgtgaca cctcctgatg ggactagcgc cctggtggaa tgcgagtgtg gcggcacaaa    9180
gatctccgag accatcaaca agacaaaaca gttcagccag tgcacaaaga aggagcagtg    9240
cagagcatat cggctgcaga acgataagtg ggtgtataat tctgacaaac tgcccaaagc    9300
agcgggagcc accttaaaag gaaaactgca tgtcccattc ttgctggcag acggcaaatg    9360
caccgtgcct ctagcaccag aacctatgat aaccttcggt ttcagatcag tgtcactgaa    9420
actgcaccct aagaatccca catatctaat caccccgcca cttgctgatg agcctcacta    9480
cacgcacgag ctcatatctg aaccagctgt taggaatttt accgtcaccg aaaaagggtg    9540
ggagtttgta tgggaaaacc acccgccgaa aaggttttgg gcacaggaaa cagcacccgg    9600
aaatccacat gggctaccgc acgaggtgat aactcattat taccacagat accctatgtc    9660
caccatcctg ggtttgtcaa tttgtgccgc cattgcaacc gtttccgttg cagcgtctac    9720
ctggctgttt tgcagatcta gagttgcgtg cctaactcct taccggctaa cacctaacgc    9780
taggatacca ttttgtctgg ctgtgctttg ctgcgcccgc actgcccggg ccgagaccac    9840
ctgggagtcc ttggatcacc tatgaacaa taaccaacag atgttctgga ttcaattgct    9900
gatccctctg gccgccttga tcgtagtgac tcgcctgctc aggtgcgtgt gctgtgtcgt    9960
gcctttttta gtcatggccg gcgccgcagg cgccggcgcc tacgagcacg cgaccacgat   10020
gccgagccaa gcgggaatct cgtataacac tatagtcaac agagcaggct acgcaccact   10080
ccctatcagc ataacaccaa caaagatcaa gctgatacct acagtgaact tggagtacgt   10140
cacctgccac tacaaaacag gaatggattc accagccatc aaatgctgcg gatctcagga   10200
atgcactcca acttacaggc ctgatgaaca gtgcaaagtc ttcacagggg tttacccgtt   10260
catgtggggt ggtgcatatt gcttttgcga cactgagaac acccaagtca gcaaggccta   10320
cgtaatgaaa tctgacgact gccttgcgga tcatgctgaa gcatataaag cgcacacagc   10380
ctcagtgcag gcgttcctca acatcacagt gggagaacac tctattgtga ctaccgtgta   10440
tgtgaatgga gaaactcctg tgaatttcaa tggggtcaaa ataactgcag gtccgctttc   10500
cacagcttgg acaccctttg atcgcaaaat cgtgcagtat gccggggaga tctataatta   10560
tgatttccct gagtatgggg caggacaacc aggagcattt ggagatatac aatccagaac   10620
agtctcaagc tctgatctgt atgccaatac caacctagtg ctgcagagac caaagcagg   10680 agcgatccac gtgccataca ctcaggcacc ttcgggtttt gagcaatgga gaaagataa   10740 agctccatca ttgaaattta ccgcccctt cggatgcgaa atatatacaa accccattcg   10800
cgccgaaaac tgtgctgtag ggtcaattcc attagccttt gacattcccg acgccttgtt   10860
caccagggtg tcagaaacac cgacactttc agcggccgaa tgcactctta acgagtgcgt   10920
gtattcttcc gactttggtg gatcgccac ggtcaagtac tcggccagca agtcaggcaa   10980
gtgcgcagtc catgtgccat cagggactgc taccctaaaa gaagcagcag tcgagctaac   11040
cgagcaaggg tcggcgacta tccatttctc gaccgcaaat atccacccgg agttcaggct   11100
ccaaatatgc acatcatatg ttacgtgcaa aggtgattgt caccccccga aagaccatat   11160
```

-continued

```
tgtgacacac cctcagtatc acgcccaaac atttacagcc gcggtgtcaa aaaccgcgtg   11220
gacgtggtta acatccctgc tgggaggatc agccgtaatt attataattg gcttggtgct   11280
ggctactatt gtggccatgt acgtgctgac caaccagaaa cataattgaa tacagcagca   11340
attggcaagc tgcttacata gaactcgcgg cgattggcat gccgccttaa aatttttatt   11400 ttattttct tttcttttcc gaatcggatt ttgttttaa tatttc                     11446
```

<210> SEQ ID NO 6
<211> LENGTH: 7895
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 6

```
atgggcggcg catgagagaa gcccagacca attacctacc caaaatggag aaagttcacg     60
ttgacatcga ggaagacagc ccattcctca gagctttgca gcggagcttc ccgcagtttg    120
aggtagaagc caagcaggtc actgataatg accatgctaa tgccagagcg ttttcgcatc    180
tggcttcaaa actgatcgaa acggaggtgg acccatccga cacgatcctt gacattggaa    240
gtgcgcccgc ccgcagaatg tattctaagc acaagtatca ttgtatctgt ccgatgagat    300
gtgcggaaga tccggacaga ttgtataagt atgcaactaa gctgaagaaa actgtaagg    360 aaataactga taaggaattg acaagaaaa tgaaggagct cgccgccgtc atgagcgacc    420
ctgacctgga aactgagact atgtgcctcc acgacgacga gtcgtgtcgc tacgaagggc    480
aagtcgctgt ttaccaggat gtatacgcgg ttgacggacc gacaagtctc tatcaccaag    540
ccaataaggg agttagagtc gcctactgga taggctttga caccacccct tttatgttta    600
agaacttggc tggagcatat ccatcatact ctaccaactg ggccgacgaa accgtgttaa    660
cggctcgtaa cataggccta tgcagctctg acgttatgga gcggtcacgt agagggatgt    720
ccattcttag aaagaagtat ttgaaaccat ccaacaatgt tctattctct gttggctcga    780
ccatctacca cgagaagagg gacttactga ggagctggca cctgccgtct gtatttcact    840
tacgtggcaa gcaaaattac acatgtcggt gtgagactat agttagttgc gacgggtacg    900
tcgttaaaag aatagctatc agtccaggcc tgtatgggaa gccttcaggc tatgctgcta    960
cgatgcaccg cgagggattc ttgtgctgca aagtgacaga cacattgaac ggggagaggg   1020 tctctttttcc cgtgtgcacg tatgtgccag ctacattgtg tgaccaaatg actggcatac   1080
tggcaacaga tgtcagtgcg gacgacgcgc aaaaactgct ggttgggctc aaccagcgta   1140
tagtcgtcaa cggtcgcacc cagagaaaca ccaataccat gaaaaattac cttttgcccg   1200
tagtggccca ggcatttgct aggtgggcaa aggaatataa ggaagatcaa gaagatgaaa   1260
ggccactagg actacgagat agacagttag tcatggggtg ttgttgggct tttagaaggc   1320
acaagataac atctatttat aagcgcccgg atacccaaac catcatcaaa gtgaacagcg   1380
atttccactc attcgtgctg cccaggatag gcagtaacac attggagatc gggctgagaa   1440
caagaatcag gaaaatgtta gaggagcaca aggagccgtc acctctcatt accgccgagg   1500
acgtacaaga agctaagtgc gcagccgatg aggctaagga ggtgcgtgaa gccgaggagt   1560
tgcgcgcagc tctaccacct ttggcagctg atgttgagga gcccactctg gaagccgatg   1620
tcgacttgat gttacaagag gctggggccg gctcagtgga gacacctgt ggcttgataa    1680 aggttaccag ctacgctggc gaggacaaga tcggctctta cgctgtgctt tctccgcagg   1740
```

```
ctgtactcaa gagtgaaaaa ttatcttgca tccaccctct cgctgaacaa gtcatagtga    1800
taacacactc tggccgaaaa gggcgttatg ccgtggaacc ataccatggt aaagtagtgg    1860
tgccagaggg acatgcaata cccgtccagg actttcaagc tctgagtgaa agtgccacca    1920
ttgtgtacaa cgaacgtgag ttcgtaaaca ggtacctgca ccatattgcc acacatggag    1980
gagcgctgaa cactgatgaa gaatattaca aaactgtcaa gcccagcgag cacgacggcg    2040
aatacctgta cgacatcgac aggaaacagt gcgtcaagaa agaactagtc actgggctag    2100
ggctcacagg cgagctggtg gatcctccct tccatgaatt cgcctacgag agtctgagaa    2160
cacgaccagc cgctccttac caagtaccaa ccatagggt gtatggcgtg ccaggatcag     2220
gcaagtctgg catcattaaa agcgcagtca ccaaaaaaga tctagtggtg agcgccaaga    2280
aagaaaactg tgcagaaatt ataagggacg tcaagaaaat gaaagggctg acgtcaatg     2340 ccagaactgt ggactcagtg ctcttgaatg gatgcaaaca ccccgtagag accctgtata    2400
ttgacgaagc ttttgcttgt catgcaggta ctctcagagc gctcatagcc attataagac    2460
ctaaaaaggc agtgctctgc ggggatccca acagtgcgg ttttttttaac atgatgtgcc     2520 tgaaagtgca tttaaccac gagatttgca cacaagtctt ccacaaaagc atctctcgcc     2580
gttgcactaa atctgtgact tcggtcgtct caaccttgtt ttacgacaaa aaatgagaa     2640 cgacgaatcc gaaagagact aagattgtga ttgacactac cggcagtacc aaacctaagc    2700
aggacgatct cattctcact tgtttcagag ggtgggtgaa gcagttgcaa atagattaca    2760
aaggcaacga ataatgacg gcagctgcct ctcaagggct gacccgtaaa ggtgtgtatg     2820
ccgttcggta caaggtgaat gaaaatcctc tgtacgcacc cacctcagaa catgtgaacg    2880
tcctactgac ccgcacggag gaccgcatcg tgtggaaaac actagccggc gacccatgga    2940
taaaaacact gactgccaag taccctggga atttcactgc cacgatagag gagtggcaag    3000
cagagcatga tgccatcatg aggcacatct ggagagacc ggaccctacc gacgtcttcc     3060
agaataaggc aaacgtgtgt tgggccaagg ctttagtgcc ggtgctgaag accgctggca    3120
tagacatgac cactgaacaa tggaacactg tggattattt tgaaacggac aaagctcact    3180
cagcagagat agtattgaac caactatgcg tgaggttctt tggactcgat ctggactccg    3240 gtctatttc tgcacccact gttccgttat ccattaggaa taatcactgg gataactccc     3300
cgtcgcctaa catgtacggg ctgaataaag aagtggtccg tcagctctct cgcaggtacc    3360
cacaactgcc tcgggcagtt gccactggaa gagtctatga catgaacact ggtacactgc    3420
gcaattatga tccgcgcata aacctagtac ctgtaaacag aagactgcct catgctttag    3480
tcctccacca taatgaacac ccacagagtg acttttcttc attcgtcagc aaattgaagg    3540
gcagaactgt cctggtggtc ggggaaaagt tgtccgtccc aggcaaaatg gttgactggt    3600
tgtcagaccg gcctgaggct accttcagag ctcggctgga tttaggcatc ccaggtgatg    3660
tgcccaaata tgacataata tttgttaatg tgaggaccc atataaatac catcactatc     3720
agcagtgtga agaccatgcc attaagctta gcatgttgac caagaaagct tgtctgcatc    3780
tgaatcccgg cggaacctgt gtcagcatag gttatggtta cgctgacagg gccagcgaaa    3840
gcatcattgg tgctatagcg cggcagttca agttttcccg ggtatgcaaa ccgaaatcct    3900
cacttgaaga gacggaagtt ctgtttgtat tcattgggta cgatcgcaag gcccgtacgc    3960
acaatcctta caagctttca tcaaccttga ccaacatta tacaggttcc agactccacg    4020
aagccggatg tgcacccctca tatcatgtgg tgcgagggga tattgccacg ccaccgaag    4080 gagtgattat aaatgctgct aacagcaaag acaacctgg cggagggtg tgcggagcgc      4140
```

```
tgtataagaa attcccggaa agcttcgatt tacagccgat cgaagtagga aaagcgcgac    4200
tggtcaaagg tgcagctaaa catatcattc atgccgtagg accaaacttc aacaaagttt    4260
cggaggttga aggtgacaaa cagttggcag aggcttatga gtccatcgct aagattgtca    4320
acgataacaa ttacaagtca gtagcgattc cactgttgtc caccggcatc ttttccggga    4380
acaaagatcg actaacccaa tcattgaacc atttgctgac agctttagac accactgatg    4440
cagatgtagc catatactgc agggacaaga aatgggaaat gactctcaag gaagcagtgg    4500
ctaggagaga agcagtggag gagatatgca tatccgacga ctcttcagtg acagaacctg    4560
atgcagagct ggtgagggtg catccgaaga gttctttggc tggaaggaag ggctacagca    4620
caagcgatgg caaaactttc tcatatttgg aagggaccaa gtttcaccag gcggccaagg    4680
atatagcaga aattaatgcc atgtggcccg ttgcaacgga ggccaatgag caggtatgca    4740
tgtatatcct cggagaaagc atgagcagta ttaggtcgaa atgccccgtc gaagagtcgg    4800
aagcctccac accacctagc acgctgcctt gcttgtgcat ccatgccatg actccagaaa    4860
gagtacagcg cctaaaagcc tcacgtccag aacaaattac tgtgtgctca tcctttccat    4920
tgccgaagta tagaatcact ggtgtgcaga agatccaatg ctcccagcct atattgttct    4980
caccgaaagt gcctgcgtat attcatccaa ggaagtatct cgtggaaaca ccaccggtag    5040
acgagactcc ggagccatcg gcagagaacc aatccacaga ggggacacct gaacaaccac    5100
cacttataac cgaggatgag accaggacta gaacgcctga gccgatcatc atcgaagagg    5160
aagaaggaga tagcataagt ttgctgtcag atggcccgac ccaccaggtg ctgcaagtcg    5220
aggcagacat tcacgggccg ccctctgtat ctagctcatc ctggtccatt cctcatgcat    5280
ccgactttga tgtggacagt ttatccatac ttgacaccct ggagggagct agcgtgacca    5340 gcgggcaac gtcagccgag actaactctt acttcgcaaa gagtatggag tttctggcgc    5400
gaccggtgcc tgcgcctcga acagtattca ggaaccctcc acatcccgct ccgcgcacaa    5460
gaacaccgtc acttgcaccc agcagggcct gctcgagaac cagcctagtt tccacccgc    5520 caggcgtgaa tagggtgatc actagagagg agctcgaggc gcttacccg tcacgcactc    5580 ctagcaggtc ggtctcgaga accagcctgg tctccaaccc gccaggcgta aatagggtga    5640
ttacaagaga ggagtttgag gcgttcgtag cacaacaaca atgacggttt gatgcgggtg    5700
catacatctt ttcctccgac accggtcaag ggcatttaca acaaaaatca gtaaggcaaa    5760
cggtgctatc cgaagtggtg ttggagagga ccgaattgga gatttcgtat gccccgcgcc    5820
tcgaccaaga aaaagaagaa ttactacgca agaaattaca gttaaatccc acacctgcta    5880
acagaagcag ataccagtcc aggaaggtgg agaacatgaa agccataaca gctagacgta    5940
ttctgcaagg cctagggcat tatttgaagg cagaaggaaa agtggagtgc taccgaaccc    6000
tgcatcctgt tcctttgtat tcatctagtg tgaaccgtgc cttttcaagc cccaaggtcg    6060
cagtggaagc ctgtaacgcc atgttgaaag agaactttcc gactgtggct tcttactgta    6120
ttattccaga gtacgatgcc tatttggaca tggttgacgg agcttcatgc tgcttagaca    6180
ctgccagttt ttgccctgca aagctgcgca gctttccaaa gaaacactcc tatttggaac    6240
ccacaatacg atcggcagtg ccttcagcga tccagaacac gctccagaac gtcctggcag    6300
ctgccacaaa aagaaattgc aatgtcacgc aaatgagaga attgcccgta ttggattcgg    6360
cggcctttaa tgtggaatgc ttcaagaaat atgcgtgtaa taatgaatat tgggaaacgt    6420
ttaaagaaaa cccccatcagg cttactgaag aaaacgtggt aaattacatt accaaattaa    6480
```

| | |
|---|---|
| aaggaccaaa agctgctgct cttttttgcga agacacataa tttgaatatg ttgcaggaca | 6540 |
| taccaatgga caggtttgta atggacttaa agagagacgt gaaagtgact ccaggaacaa | 6600 |
| aacatactga agaacggccc aaggtacagg tgatccaggc tgccgatccg ctagcaacag | 6660 |
| cgtatctgtg cggaatccac cgagagctgg ttaggagatt aaatgcggtc ctgcttccga | 6720 |
| acattcatac actgtttgat atgtcggctg aagactttga cgctattata gccgagcact | 6780 |
| tccagcctgg ggattgtgtt ctggaaactg acatcgcgtc gtttgataaa agtgaggacg | 6840 |
| acgccatggc tctgaccgcg ttaatgattc tggaagactt aggtgtggac gcagagctgt | 6900 |
| tgacgctgat tgaggcggct ttcggcgaaa tttcatcaat acatttgccc actaaaacta | 6960 |
| aatttaaatt cggagccatg atgaaatctg gaatgttcct cacactgttt gtgaacacag | 7020 |
| tcattaacat tgtaatcgca agcagagtgt tgagagaacg gctaaccgga tcaccatgtg | 7080 |
| cagcattcat tggagatgac aatatcgtga aaggagtcaa atcggacaaa ttaatggcag | 7140 |
| acaggtgcgc cacctggttg aatatggaag tcaagattat agatgctgtg gtgggcgaga | 7200 |
| aagcgcctta tttctgtgga gggtttattt tgtgtgactc cgtgaccggc acagcgtgcc | 7260 |
| gtgtggcaga cccctaaaa aggctgttta agcttggcaa acctctggca gcagacgatg | 7320 |
| aacatgatga tgacaggaga agggcattgc atgaagagtc aacacgctgg aaccgagtgg | 7380 |
| gtattctttc agagctgtgc aaggcagtag aatcaaggta tgaaaccgta ggaacttcca | 7440 |
| tcatagttat ggccatgact actctagcta gcagtgttaa atcattcagc tacctgagag | 7500 |
| gggcccctat aactctctac ggctaacctg aatggactac gacgtatcac gcccaaacat | 7560 |
| ttacagccgc ggtgtcaaaa accgcgtgga cgtggttaac atccctgctg ggaggatcag | 7620 |
| ccgtaattat tataattggc ttggtgctgg ctactattgt ggccatgtac gtgctgacca | 7680 |
| accagaaaca taattgaata cagcagcaat tggcaagctg cttacataga actcgcggcg | 7740 |
| attggcatgc cgccttaaaa ttttttatttt atttttttctt ttcttttccg aatcggattt | 7800 |
| tgtttttaat atttcaaaaa aaaaaaaaaa aaaaaaaaaa aaaaaaaaaa aaaaaaaaaa | 7860 |
| aaaaaaaaaa aaaaaaaaaa aaaaaaaaaa aaaaa | 7895 |

<210> SEQ ID NO 7
<211> LENGTH: 7894
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 7

| | |
|---|---|
| ataggcggcg catgagagaa gcccagacca attacctacc caaaatggag aaagttcacg | 60 |
| ttgacatcga ggaagacagc ccattcctca gagctttgca gcggagcttc ccgcagtttg | 120 |
| aggtagaagc caagcaggtc actgataatg accatgctaa tgccagagcg ttttcgcatc | 180 |
| tggcttcaaa actgatcgaa acggaggtgg acccatccga cacgatcctt gacattggaa | 240 |
| gtgcgcccgc ccgcagaatg tattctaagc acaagtatca ttgtatctgt ccgatgagat | 300 |
| gtgcggaaga tccggacaga ttgtataagt atgcaactaa gctgaagaaa aactgtaagg | 360 |
| aaataactga taaggaattg gacaagaaaa tgaaggagct cgccgccgtc atgagcgacc | 420 |
| ctgacctgga aactgagact atgtgcctcc acgacgacga gtcgtgtcgc tacgaagggc | 480 |
| aagtcgctgt ttaccaggat gtatacgcgg ttgacggacc gacaagtctc tatcaccaag | 540 |
| ccaataaggg agttagagtc gcctactgga taggctttga caccaccccct tttatgttta | 600 |

-continued

```
agaacttggc tggagcatat ccatcatact ctaccaactg ggccgacgaa accgtgttaa    660
cggctcgtaa cataggccta tgcagctctg acgttatgga gcggtcacgt agagggatgt    720
ccattcttag aaagaagtat ttgaaaccat ccaacaatgt tctattctct gttggctcga    780
ccatctacca cgagaagagg gacttactga ggagctggca cctgccgtct gtatttcact    840
tacgtggcaa gcaaaattac acatgtcggt gtgagactat agttagttgc gacgggtacg    900
tcgttaaaag aatagctatc agtccaggcc tgtatgggaa gccttcaggc tatgctgcta    960
cgatgcaccg cgagggattc ttgtgctgca aagtgacaga cacattgaac ggggagaggg   1020
tctcttttcc cgtgtgcacg tatgtgccag ctacattgtg tgaccaaatg actggcatac   1080
tggcaacaga tgtcagtgcg gacgacgcgc aaaaactgct ggttgggctc aaccagcgta   1140
tagtcgtcaa cggtcgcacc cagagaaaca ccaataccat gaaaaattac cttttgcccg   1200
tagtggccca ggcatttgct aggtgggcaa aggaatataa ggaagatcaa gaagatgaaa   1260
ggccactagg actacgagat agacagttag tcatggggtg ttgttgggct tttagaaggc   1320
acaagataac atctatttat aagcgcccgg atacccaaac catcatcaaa gtgaacagcg   1380
atttccactc attcgtgctg cccaggatag gcagtaacac attggagatc gggctgagaa   1440
caagaatcag gaaaatgtta gaggagcaca aggagccgtc acctctcatt accgccgagg   1500
acgtacaaga agctaagtgc gcagccgatg aggctaagga ggtgcgtgaa gccgaggagt   1560
tgcgcgcagc tctaccacct ttggcagctg atgttgagga gcccactctg gaagccgatg   1620
tcgacttgat gttacaagag gctggggccg gctcagtgga gacacctcgt ggcttgataa   1680
aggttaccag ctacgatggc gaggacaaga tcggctctta cgctgtgctt tctccgcagg   1740
ctgtactcaa gagtgaaaaa ttatcttgca tccaccctct cgctgaacaa gtcatagtga   1800
taacacactc tggccgaaaa gggcgttatg ccgtggaacc ataccatggt aaagtagtgg   1860
tgccagaggg acatgcaata cccgtccagg actttcaagc tctgagtgaa agtgccacca   1920
ttgtgtacaa cgaacgtgag ttcgtaaaca ggtacctgca ccatattgcc acacatggag   1980
gagcgctgaa cactgatgaa gaatattaca aaactgtcaa gcccagcgag cacgacggcg   2040
aatacctgta cgacatcgac aggaaacagt gcgtcaagaa agaactagtc actgggctag   2100
ggctcacagg cgagctggtg gatcctccct tccatgaatt cgcctacgag agtctgagaa   2160
cacgaccagc cgctccttac caagtaccaa ccataggggt gtatggcgtg ccaggatcag   2220
gcaagtctgg catcattaaa agcgcagtca ccaaaaaaga tctagtggtg agcgccaaga   2280 agaaaactg tgcagaaatt ataagggacg tcaagaaaat gaaagggctg acgtcaatg    2340 ccagaactgt ggactcagtg ctcttgaatg gatgcaaaca ccccgtagag accctgtata   2400
ttgacgaagc ttttgcttgt catgcaggta ctctcagagc gctcatagcc attataagac   2460
ctaaaaaggc agtgctctgc ggggatccca acagtgcgg tttttttaac atgatgtgcc    2520
tgaaagtgca ttttaaccac gagatttgca cacaagtctt ccacaaaagc atctctcgcc   2580
gttgcactaa atctgtgact tcggtcgtct caaccttgtt ttacgacaaa aaatgagaa    2640 cgacgaatcc gaaagagact aagattgtga ttgacactac cggcagtacc aaacctaagc   2700
aggacgatct cattctcact tgtttcagag ggtgggtgaa gcagttgcaa atagattaca   2760
aaggcaacga aataatgacg gcagctgcct ctcaagggct gacccgtaaa ggtgtgtatg   2820
ccgttcggta caaggtgaat gaaaatcctc tgtacgcacc cacctcagaa catgtgaacg   2880
tcctactgac ccgcacggag gaccgcatcg tgtggaaaac actagccggc gacccatgga   2940
taaaaacact gactgccaag taccctggga atttcactgc cacgatagag gagtggcaag   3000
```

```
cagagcatga tgccatcatg aggcacatct tggagagacc ggaccctacc gacgtcttcc    3060
agaataaggc aaacgtgtgt tgggccaagg ctttagtgcc ggtgctgaag accgctggca    3120
tagacatgac cactgaacaa tggaacactg tggattattt tgaaacggac aaagctcact    3180
cagcagagat agtattgaac caactatgcg tgaggttctt tggactcgat ctggactccg    3240
gtctattttc tgcacccact gttccgttat ccattaggaa taatcactgg gataactccc    3300
cgtcgcctaa catgtacggg ctgaataaag aagtggtccg tcagctctct cgcaggtacc    3360
cacaactgcc tcgggcagtt gccactggaa gagtctatga catgaacact ggtacactgc    3420
gcaattatga tccgcgcata aacctagtac ctgtaaacag aagactgcct catgctttag    3480
tcctccacca taatgaacac ccacagagtg acttttcttc attcgtcagc aaattgaagg    3540
gcagaactgt cctggtggtc ggggaaaagt tgtccgtccc aggcaaaatg gttgactggt    3600
tgtcagaccg gcctgaggct accttcagag ctcggctgga tttaggcatc ccaggtgatg    3660
tgcccaaata tgacataata tttgttaatg tgaggacccc atataaatac catcactatc    3720
agcagtgtga agaccatgcc attaagctta gcatgttgac caagaaagct tgtctgcatc    3780
tgaatcccgg cggaacctgt gtcagcatag gttatggtta cgctgacagg gccagcgaaa    3840
gcatcattgg tgctatagcg cggcagttca agttttcccg ggtatgcaaa ccgaaatcct    3900
cacttgaaga gacggaagtt ctgtttgtat tcattgggta cgatcgcaag gcccgtacgc    3960
acaatcctta caagctttca tcaaccttga ccaacattta tacaggttcc agactccacg    4020
aagccggatg tgcaccctca tatcatgtgg tgcgagggga tattgccacg gccaccgaag    4080
gagtgattat aaatgctgct aacagcaaag gacaacctgg cggaggggtg tgcggagcgc    4140
tgtataagaa attcccggaa agcttcgatt tacagccgat cgaagtagga aaagcgcgac    4200
tggtcaaagg tgcagctaaa catatcattc atgccgtagg accaaacttc aacaaagttt    4260
cggaggttga aggtgacaaa cagttggcag aggcttatga gtccatcgct aagattgtca    4320
acgataacaa ttacaagtca gtagcgattc cactgttgtc caccggcatc ttttccggga    4380
acaaagatcg actaacccaa tcattgaacc atttgctgac agctttagac accactgatg    4440
cagatgtagc catatactgc agggacaaga aatgggaaat gactctcaag gaagcagtgg    4500
ctaggagaga agcagtggag gagatatgca tatccgacga ctcttcagtg acagaacctg    4560
atgcagagct ggtgagggtg catccgaaga gttctttggc tggaaggaag ggctacagca    4620
caagcgatgg caaaacttct tcatatttgg aagggaccaa gtttcaccag gcggccaagg    4680
atatagcaga aattaatgcc atgtggcccg ttgcaacgga ggccaatgag caggtatgca    4740
tgtatatcct cggagaaagc atgagcagta ttaggtcgaa atgccccgtc aagagtcgg    4800 aagcctccac accacctagc acgctgcctt gcttgtgcat ccatgccatg actccagaaa    4860
gagtacagcg cctaaaagcc tcacgtccag aacaaattac tgtgtgctca tcctttccat    4920
tgccgaagta tagaatcact ggtgtgcaga agatccaatg ctcccagcct atattgttct    4980
caccgaaagt gcctgcgtat attcatccaa ggaagtatct cgtggaaaca ccaccggtag    5040
acgagactcc ggagccatcg gcagagaacc aatccacaga ggggacacct gaacaaccac    5100
cacttataac cgaggatgag accaggacta gaacgcctga gccgatcatc atcgaagagg    5160
aagaagagga tagcataagt ttgctgtcag atggcccgac ccaccaggtg ctgcaagtcg    5220
aggcagacat tcacgggccg ccctctgtat ctagctcatc ctggtccatt cctcatgcat    5280
ccgactttga tgtggacagt ttatccatac ttgacaccct ggagggagct agcgtgacca    5340
```

```
gcggggcaac gtcagccgag actaactctt acttcgcaaa gagtatggag tttctggcgc    5400
gaccggtgcc tgcgcctcga acagtattca ggaaccctcc acatcccgct ccgcgcacaa    5460
gaacaccgtc acttgcaccc agcagggcct gctcgagaac cagcctagtt tccaccccgc    5520
caggcgtgaa tagggtgatc actagagagg agctcgaggc gcttaccccg tcacgcactc    5580
ctagcaggtc ggtctcgaga accagcctgg tctccaaccc gccaggcgta aatagggtga    5640
ttacaagaga ggagtttgag gcgttcgtag cacaacaaca atgacggttt gatgcgggtg    5700
catacatctt ttcctccgac accggtcaag ggcatttaca acaaaaatca gtaaggcaaa    5760
cggtgctatc cgaagtggtg ttggagagga ccgaattgga gatttcgtat gccccgcgcc    5820
tcgaccaaga aaagaagaa ttactacgca agaaattaca gttaaatccc acacctgcta    5880
acagaagcag ataccagtcc aggaaggtgg agaacatgaa agccataaca gctagacgta    5940
ttctgcaagg cctagggcat tatttgaagg cagaaggaaa agtggagtgc taccgaaccc    6000
tgcatcctgt tcctttgtat tcatctagtg tgaaccgtgc cttttcaagc cccaaggtcg    6060
cagtggaagc ctgtaacgcc atgttgaaag agaacttttcc gactgtggct tcttactgta    6120
ttattccaga gtacgatgcc tatttggaca tggttgacgg agcttcatgc tgcttagaca    6180
ctgccagttt ttgccctgca aagctgcgca gcttttccaaa gaaacactcc tatttggaac    6240
ccacaatacg atcggcagtg ccttcagcga tccagaacac gctccagaac gtcctggcag    6300
ctgccacaaa aagaaattgc aatgtcacgc aaatgagaga attgcccgta ttggattcgg    6360
cggcctttaa tgtggaatgc ttcaagaaat atgcgtgtaa taatgaatat tgggaaacgt    6420
ttaaagaaaa cccatcagg cttactgaag aaaacgtggt aaattacatt accaaattaa    6480
aaggaccaaa agctgctgct ctttttgcga agacacataa tttgaatatg ttgcaggaca    6540
taccaatgga caggttttgta atggacttaa agagagacgt gaaagtgact ccaggaacaa    6600
aacatactga agaacggccc aaggtacagg tgatccaggc tgccgatccg ctagcaacag    6660
cgtatctgtg cggaatccac cgagagctgg ttaggagatt aaatgcggtc ctgcttccga    6720
acattcatac actgtttgat atgtcggctg aagactttga cgctattata gccgagcact    6780
tccagcctgg ggattgtgtt ctggaaactg acatcgcgtc gtttgataaa agtgaggacg    6840
acgccatggc tctgaccgcg ttaatgattc tggaagactt aggtgtggac gcagagctgt    6900
tgacgctgat tgaggcggct ttcggcgaaa tttcatcaat acatttgccc actaaaacta    6960
aattttaaatt cggagccatg atgaaatctg gaatgttcct cacactgttt gtgaacacag    7020
tcattaacat tgtaatcgca agcagagtgt tgagagaacg gctaaccgga tcaccatgtg    7080
cagcattcat tggagatgac aatatcgtga aaggagtcaa atcggacaaa ttaatggcag    7140
acaggtgcgc cacctggttg aatatggaag tcaagattat agatgctgtg gtgggcgaga    7200
aagcgcctta tttctgtgga gggttttattt tgtgtgactc cgtgaccggc acagcgtgcc    7260
gtgtggcaga cccctaaaa aggctgttta agcttggcaa acctctggca gcagacgatg    7320
aacatgatga tgacaggaga agggcattgc atgaagagtc aacacgctgg aaccgagtgg    7380
gtattctttc agagctgtgc aaggcagtag aatcaaggta tgaaaccgta ggaacttcca    7440
tcatagttat ggccatgact actctagcta gcagtgttaa atcattcagc tacctgagag    7500
gggcccctat aactctctac ggctaacctg aatggactac gacgtatcac gcccaaacat    7560
ttacagccgc ggtgtcaaaa accgcgtgga cgtggttaac atccctgctg ggaggatcag    7620
ccgtaattat tataattggc ttggtgctgg ctactattgt ggccatgtac gtgctgacca    7680
accagaaaca taattgaata cagcagcaat tggcaagctg cttacataga actcgcggcg    7740
```

```
attggcatgc cgccttaaaa tttttatttt attttttcttt tcttttccga atcggatttt    7800
gtttttaata tttcaaaaaa aaaaaaaaaa aaaaaaaaaa aaaaaaaaaa aaaaaaaaaa    7860
aaaaaaaaaa aaaaaaaaaa aaaaaaaaaa aaaa                                 7894
```

<210> SEQ ID NO 8
<211> LENGTH: 7928
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 8

```
taatacgact cactatagga tgggcggcgc atgagagaag cccagaccaa ttacctaccc      60
aaaatggaga agttcacgt tgacatcgag aagacagcc cattcctcag agctttgcag      120
cggagcttcc cgcagtttga ggtagaagcc aagcaggtca ctgataatga ccatgctaat     180
gccagagcgt tttcgcatct ggcttcaaaa ctgatcgaaa cggaggtgga cccatccgac     240
acgatccttg acattggaag tgcgcccgcc cgcagaatgt attctaagca caagtatcat     300
tgtatctgtc cgatgagatg tgcggaagat ccggacagat tgtataagta tgcaactaag     360
ctgaagaaaa actgtaagga aataactgat aaggaattgg acaagaaaat gaaggagctc     420
gccgccgtca tgagcgaccc tgacctggaa actgagacta tgtgcctcca cgacgacgag     480
tcgtgtcgct acgaagggca agtcgctgtt taccaggatg tatacgcggt tgacggaccg     540
acaagtctct atcaccaagc caataaggga gttagagtcg cctactggat aggctttgac     600
accacccctt ttatgtttaa gaacttggct ggagcatatc catcatactc taccaactgg     660
gccgacgaaa ccgtgttaac ggctcgtaac ataggcctat gcagctctga cgttatggag     720
cggtcacgta gagggatgtc cattcttaga aagaagtatt tgaaaccatc caacaatgtt     780
ctattctctg ttggctcgac catctaccac gagaagaggg acttactgag gagctggcac     840
ctgccgtctg tatttcactt acgtggcaag caaaattaca catgtcggtg tgagactata     900
gttagttgcg acgggtacgt cgttaaaaga atagctatca gtccaggcct gtatgggaag     960
ccttcaggct atgctgctac gatgcaccgc gagggattct tgtgctgcaa agtgacagac    1020
acattgaacg gggagagggt ctcttttccc gtgtgcacgt atgtgccagc tacattgtgt    1080
gaccaaatga ctggcatact ggcaacagat gtcagtgcgg acgacgcgca aaaactgctg    1140
gttgggctca accagcgtat agtcgtcaac ggtcgcaccc agagaaacac caataccatg    1200
aaaaattacc ttttgcccgt agtggcccag gcatttgcta ggtgggcaaa ggaatataag    1260
gaagatcaag aagatgaaag gccactagga ctacgagata gacagttagt catggggtgt    1320
tgttgggctt ttagaaggca aagataaca tctatttata agcgcccgga tacccaaacc    1380
atcatcaaag tgaacagcga tttccactca ttcgtgctgc ccaggatagg cagtaacaca    1440
ttggagatcg ggctgagaac aagaatcagg aaaatgttag aggagcacaa ggagccgtca    1500
cctctcatta ccgccgagga cgtacaagaa gctaagtgcg cagccgatga ggctaaggag    1560
gtgcgtgaag ccgaggagtt gcgcgcagct ctaccacctt tggcagctga tgttgaggag    1620
cccactctgg aagccgatgt cgacttgatg ttacaagagg ctgggccgg ctcagtggag    1680 acacctcgtg gcttgataaa ggttaccagc tacgctggcg aggacaagat cggctcttac    1740
gctgtgcttt ctccgcaggc tgtactcaag agtgaaaaat tatcttgcat ccaccctctc    1800
gctgaacaag tcatagtgat aacacactct ggccgaaaag ggcgttatgc cgtggaacca    1860
```

```
taccatggta aagtagtggt gccagaggga catgcaatac ccgtccagga ctttcaagct    1920
ctgagtgaaa gtgccaccat tgtgtacaac gaacgtgagt tcgtaaacag gtacctgcac    1980
catattgcca cacatggagg agcgctgaac actgatgaag aatattacaa aactgtcaag    2040
cccagcgagc acgacggcga atacctgtac gacatcgaca ggaaacagtg cgtcaagaaa    2100
gaactagtca ctgggctagg gctcacaggc gagctggtgg atcctcccttt ccatgaattc    2160 gcctacgaga gtctgagaac acgaccagcc gctccttacc aagtaccaac cataggggtg    2220
tatggcgtgc caggatcagg caagtctggc atcattaaaa gcgcagtcac caaaaaagat    2280
ctagtggtga gcgccaagaa agaaaactgt gcagaaatta aagggacgt caagaaaatg    2340 aaagggctgg acgtcaatgc cagaactgtg gactcagtgc tcttgaatgg atgcaaacac    2400
cccgtagaga ccctgtatat tgacgaagct tttgcttgtc atgcaggtac tctcagagcg    2460
ctcatagcca ttataagacc taaaaaggca gtgctctgcg gggatcccaa acagtgcggt    2520 tttttttaaca tgatgtgcct gaaagtgcat tttaaccacg agatttgcac acaagtcttc    2580
cacaaaagca tctctcgccg ttgcactaaa tctgtgactt cggtcgtctc aaccttgttt    2640
tacgacaaaa aaatgagaac gacgaatccg aaagagacta agattgtgat tgacactacc    2700
ggcagtacca aacctaagca ggacgatctc attctcactt gtttcagagg gtgggtgaag    2760
cagttgcaaa tagattacaa aggcaacgaa ataatgacgg cagctgcctc tcaagggctg    2820
acccgtaaag gtgtgtatgc cgttcggtac aaggtgaatg aaaatcctct gtacgcaccc    2880
acctcagaac atgtgaacgt cctactgacc cgcacggagg accgcatcgt gtggaaaaca    2940
ctagccggcg acccatggat aaaaacactg actgccaagt accctgggaa tttcactgcc    3000
acgatagagt agtggcaagc agagcatgat gccatcatga ggcacatctt ggagagaccg    3060
gaccctaccg acgtcttcca gaataaggca aacgtgtgtt gggccaaggc tttagtgccg    3120
gtgctgaaga ccgctggcat agacatgacc actgaacaat ggaacactgt ggattatttt    3180
gaaacggaca aagctcactc agcagagata gtattgaacc aactatgcgt gaggttcttt    3240
ggactcgatc tggactccgg tctatttttct gcacccactg ttccgttatc cattaggaat    3300
aatcactggg ataactcccc gtcgcctaac atgtacgggc tgaataaaga agtggtccgt    3360
cagctctctc gcaggtaccc acaactgcct cgggcagttg ccactggaag agtctatgac    3420
atgaacactg tacactgcg caattatgat ccgcgcataa acctagtacc tgtaaacaga    3480
agactgcctc atgctttagt cctccaccat aatgaacacc cacagagtga cttttcttca    3540
ttcgtcagca aattgaaggg cagaactgtc ctggtggtcg gggaaaagtt gtccgtccca    3600
ggcaaaatgg ttgactggtt gtcagaccgg cctgaggcta ccttcagagc tcggctggat    3660
ttaggcatcc caggtgatgt gcccaaatat gacataatat tgttaatgt gaggacccca    3720 tataaatacc atcactatca gcagtgtgaa gaccatgcca ttaagcttag catgttgacc    3780
aagaaagctt gtctgcatct gaatcccggc ggaacctgtg tcagcatagg ttatggttac    3840
gctgacaggg ccagcgaaag catcattggt gctatagcgc ggcagttcaa gttttcccgg    3900
gtatgcaaac cgaaatcctc acttgaagag acggaagttc tgtttgtatt cattgggtac    3960
gatcgcaagg cccgtacgca caatccttac aagctttcat caaccttgac caacatttat    4020
acaggttcca gactccacga agccggatgt gcaccctcat atcatgtggt gcgaggggat    4080
attgccacgg ccaccgaagg agtgattata aatgctgcta acagcaaagg caacctggc    4140 ggaggggtgt gcggagcgct gtataagaaa ttcccggaaa gcttcgattt acagccgatc    4200
```

```
gaagtaggaa aagcgcgact ggtcaaaggt gcagctaaac atatcattca tgccgtagga    4260
ccaaacttca acaaagtttc ggaggttgaa ggtgacaaac agttggcaga ggcttatgag    4320
tccatcgcta agattgtcaa cgataacaat tacaagtcag tagcgattcc actgttgtcc    4380
accggcatct tttccgggaa caaagatcga ctaacccaat cattgaacca tttgctgaca    4440
gctttagaca ccactgatgc agatgtagcc atatactgca gggacaagaa atgggaaatg    4500
actctcaagg aagcagtggc taggagagaa gcagtggagg agatatgcat atccgacgac    4560
tcttcagtga cagaacctga tgcagagctg gtgagggtgc atccgaagag ttctttggct    4620
ggaaggaagg gctacagcac aagcgatggc aaaactttct catatttgga agggaccaag    4680
tttcaccagg cggccaagga tatagcagaa attaatgcca tgtggcccgt tgcaacggag    4740
gccaatgagc aggtatgcat gtatatcctc ggagaaagca tgagcagtat taggtcgaaa    4800
tgccccgtcg aagagtcgga agcctccaca ccacctagca cgctgccttg cttgtgcatc    4860
catgccatga ctccagaaag agtacagcgc ctaaaagcct cacgtccaga acaaattact    4920
gtgtgctcat cctttccatt gccgaagtat agaatcactg gtgtgcagaa gatccaatgc    4980
tcccagccta tattgttctc accgaaagtg cctgcgtata ttcatccaag gaagtatctc    5040
gtggaaacac caccggtaga cgagactccg gagccatcgg cagagaacca atccacagag    5100
gggacacctg aacaaccacc acttataacc gaggatgaga ccaggactag aacgcctgag    5160
ccgatcatca tcgaagagga agaagaggat agcataagtt tgctgtcaga tggcccgacc    5220
caccaggtgc tgcaagtcga ggcagacatt cacgggccgc cctctgtatc tagctcatcc    5280
tggtccattc ctcatgcatc cgactttgat gtggacagtt tatccatact tgacaccctg    5340
gagggagcta gcgtgaccag cggggcaacg tcagccgaga ctaactctta cttcgcaaag    5400
agtatggagt ttctggcgcg accggtgcct gcgcctcgaa cagtattcag gaaccctcca    5460
catcccgctc cgcgcacaag aacaccgtca cttgcaccca gcagggcctg ctcgagaacc    5520
agcctagttt ccaccccgcc aggcgtgaat agggtgatca ctagagagga gctcgaggcg    5580
cttaccccgt cacgcactcc tagcaggtcg gtctcgagaa ccagcctggt ctccaacccg    5640
ccaggcgtaa ataggggtgat tacaagagag gagtttgagg cgttcgtagc acaacaacaa    5700
tgacggtttg atgcgggtgc atacatcttt tcctccgaca ccggtcaagg gcatttacaa    5760
caaaaatcag taaggcaaac ggtgctatcc gaagtggtgt tggagaggac cgaattggag    5820
atttcgtatg ccccgcgcct cgaccaagaa aaagaagaat tactacgcaa gaaattacag    5880
ttaaatccca cacctgctaa cagaagcaga taccagtcca ggaaggtgga gaacatgaaa    5940
gccataacag ctagacgtat tctgcaaggc ctagggcatt atttgaaggc agaaggaaaa    6000
gtggagtgct accgaaccct gcatcctgtt cctttgtatt catctagtgt gaaccgtgcc    6060
ttttcaagcc ccaaggtcgc agtggaagcc tgtaacgcca tgttgaaaga aactttccg    6120 actgtggctt cttactgtat tattccagag tacgatgcct atttggacat ggttgacgga    6180
gcttcatgct gcttagacac tgccagtttt tgccctgcaa agctgcgcag ctttccaaag    6240
aaacactcct atttggaacc cacaatacga tcggcagtgc cttcagcgat ccagaacacg    6300
ctccagaacg tcctgcagc tgccacaaaa agaaattgca atgtcacgca aatgagagaa    6360
ttgcccgtat tggattcggc ggcctttaat gtggaatgct tcaagaaata tgcgtgtaat    6420
aatgaatatt gggaaacgtt taaagaaaac cccatcaggc ttactgaaga aaacgtggta    6480
aattacatta ccaaattaaa aggaccaaaa gctgctgctc ttttttgcgaa gacacataat    6540 ttgaatatgt tgcaggacat accaatggac aggtttgtaa tggacttaaa gagagacgtg    6600
```

```
aaagtgactc caggaacaaa acatactgaa gaacggccca aggtacaggt gatccaggct    6660
gccgatccgc tagcaacagc gtatctgtgc ggaatccacc gagagctggt taggagatta    6720
aatgcggtcc tgcttccgaa cattcataca ctgtttgata tgtcggctga agactttgac    6780
gctattatag ccgagcactt ccagcctggg gattgtgttc tggaaactga catcgcgtcg    6840
tttgataaaa gtgaggacga cgccatggct ctgaccgcgt taatgattct ggaagactta    6900
ggtgtggacg cagagctgtt gacgctgatt gaggcggctt cggcgaaat ttcatcaata    6960 catttgccca ctaaaactaa atttaaattc ggagccatga tgaaatctgg aatgttcctc    7020
acactgtttg tgaacacagt cattaacatt gtaatcgcaa gcagagtgtt gagagaacgg    7080
ctaaccggat caccatgtgc agcattcatt ggagatgaca atatcgtgaa aggagtcaaa    7140
tcggacaaat aatggcagca caggtgcgcc acctggttga atatgaagt caagattata    7200 gatgctgtgg tgggcgagaa agcgccttat ttctgtggag ggtttatttt gtgtgactcc    7260
gtgaccggca cagcgtgccg tgtggcagac cccctaaaaa ggctgtttaa gcttggcaaa    7320
cctctggcag cagacgatga acatgatgat gacaggagaa gggcattgca tgaagagtca    7380
acacgctgga accagtgggg tattctttca gagctgtgca aggcagtaga atcaaggtat    7440
gaaaccgtag gaacttccat catagttatg gccatgacta ctctagctag cagtgttaaa    7500
tcattcagct acctgagagg ggcccctata actctctacg gctaacctga atggactacg    7560
acgtatcacg cccaaacatt tacagccgcg gtgtcaaaaa ccgcgtggac gtggttaaca    7620
tccctgctgg gaggatcagc cgtaattatt ataattggct tggtgctggc tactattgtg    7680
gccatgtacg tgctgaccaa ccagaaacat aattgaatac agcagcaatt ggcaagctgc    7740
ttacatagaa ctcgcggcga ttggcatgcc gccttaaaat ttttatttta ttttttcttt    7800
tcttttccga atcggatttt gttttttaata tttcaaaaaa aaaaaaaaaa aaaaaaaaa    7860 aaaaaaaaaa aaaaaaaaaa aaaaaaaaaa aaaaaaaaaa aaaaaaaaaa aaaatacgta    7920
gtttaaac                                                            7928
```

<210> SEQ ID NO 9
<211> LENGTH: 7927
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 9

```
taatacgact cactataggg taggcggcgc atgagagaag cccagaccaa ttacctaccc      60
aaaatggaga agttcacgt tgacatcgag gaagacagcc cattcctcag agctttgcag     120
cggagcttcc cgcagtttga ggtagaagcc aagcaggtca ctgataatga ccatgctaat     180
gccagagcgt tttcgcatct ggcttcaaaa ctgatcgaaa cggaggtgga cccatccgac     240
acgatccttg acattggaag tgcgcccgcc cgcagaatgt attctaagca caagtatcat     300
tgtatctgtc cgatgagatg tgcggaagat ccggacagat tgtataagta tgcaactaag     360
ctgaagaaaa actgtaagga aataactgat aaggaattgg acaagaaat gaaggagctc     420 gccgccgtca tgagcgaccc tgacctggaa actgagacta tgtgcctcca cgacgacgag     480
tcgtgtcgct acgaagggca agtcgctgtt taccaggatg tatacgcggt tgacggaccg     540
acaagtctct atcaccaagc caataaggga gttagagtcg cctactggat aggctttgac     600
accacccctt ttatgttaaa gaacttggct ggagcatatc catcatactc taccaactgg     660
```

-continued

```
gccgacgaaa ccgtgttaac ggctcgtaac ataggcctat gcagctctga cgttatggag    720
cggtcacgta gagggatgtc cattcttaga aagaagtatt tgaaaccatc caacaatgtt    780
ctattctctg ttggctcgac catctaccac gagaagaggg acttactgag gagctggcac    840
ctgccgtctg tatttcactt acgtggcaag caaaattaca catgtcggtg tgagactata    900
gttagttgcg acgggtacgt cgttaaaaga atagctatca gtccaggcct gtatgggaag    960
ccttcaggct atgctgctac gatgcaccgc gagggattct tgtgctgcaa agtgacagac   1020
acattgaacg gggagagggt ctctttttccc gtgtgcacgt atgtgccagc tacattgtgt   1080
gaccaaatga ctggcatact ggcaacagat gtcagtgcgg acgacgcgca aaaactgctg   1140
gttgggctca accagcgtat agtcgtcaac ggtcgcaccc agagaaacac caataccatg   1200
aaaaattacc ttttgcccgt agtggcccag gcatttgcta ggtgggcaaa ggaatataag   1260
gaagatcaag aagatgaaag gccactagga ctacgagata gacagttagt catggggtgt   1320
tgttgggctt ttagaaggca caagataaca tctatttata agcgcccgga tacccaaacc   1380
atcatcaaag tgaacagcga tttccactca ttcgtgctgc ccaggatagg cagtaacaca   1440
ttggagatcg ggctgagaac aagaatcagg aaaatgttag aggagcacaa ggagccgtca   1500
cctctcatta ccgccgagga cgtacaagaa gctaagtgcg cagccgatga ggctaaggag   1560
gtgcgtgaag ccgaggagtt gcgcgcagct ctaccaccct tggcagctga tgttgaggag   1620
cccactctgg aagccgatgt cgacttgatg ttacaagagg ctggggccgg ctcagtggag   1680
acacctcgtg gcttgataaa ggttaccagc tacgatggcg aggacaagat cggctcttac   1740
gctgtgcttt ctccgcaggc tgtactcaag agtgaaaaat tatcttgcat ccaccctctc   1800
gctgaacaag tcatagtgat aacacactct ggccgaaaag ggcgttatgc cgtggaacca   1860
taccatggta aagtagtggt gccagaggga catgcaatac ccgtccagga ctttcaagct   1920
ctgagtgaaa gtgccaccat tgtgtacaac gaacgtgagt tcgtaaacag gtacctgcac   1980
catattgcca cacatggagg agcgctgaac actgatgaag aatattacaa aactgtcaag   2040
cccagcgagc acgacggcga atacctgtac gacatcgaca ggaaacagtg cgtcaagaaa   2100
gaactagtca ctgggctagg gctcacaggc gagctggtgg atcctcccct ccatgaattc   2160
gcctacgaga gtctgagaac acgaccagcc gctccttacc aagtaccaac catagggggtg   2220
tatggcgtgc caggatcagg caagtctggc atcattaaaa gcgcagtcac caaaaaagat   2280
ctagtggtga gcgccaagaa agaaaactgt gcagaaatta taagggacgt caagaaaatg   2340
aaagggctgg acgtcaatgc cagaactgtg gactcagtgc tcttgaatgg atgcaaacac   2400
cccgtagaga ccctgtatat tgacgaagct tttgcttgtc atgcaggtac tctcagagcg   2460
ctcatagcca ttataagacc taaaaaggca gtgctctgcg gggatcccaa acagtgcggt   2520
ttttttaaca tgatgtgcct gaaagtgcat tttaaccacg agatttgcac acaagtcttc   2580
cacaaaagca tctctcgccg ttgcactaaa tctgtgactt cggtcgtctc aaccttgttt   2640
tacgacaaaa aaatgagaac gacgaatccg aaagagacta agattgtgat tgacactacc   2700
ggcagtacca aacctaagca ggacgatctc attctcactt gtttcagagg gtgggtgaag   2760
cagttgcaaa tagattacaa aggcaacgaa ataatgacga cagctgcctc tcaagggctg   2820
acccgtaaag gtgtgtatgc cgttcggtac aaggtgaatg aaaatcctct gtacgcaccc   2880
acctcagaac atgtgaacgt cctactgacc cgcacggagg accgcatcgt gtggaaaaca   2940
ctagccggcg acccatggat aaaaacactg actgccaagt accctgggaa tttcactgcc   3000
```

```
acgatagagg agtggcaagc agagcatgat gccatcatga ggcacatctt ggagagaccg    3060
gaccctaccg acgtcttcca gaataaggca aacgtgtgtt gggccaaggc tttagtgccg    3120
gtgctgaaga ccgctggcat agacatgacc actgaacaat ggaacactgt ggattatttt    3180
gaaacggaca aagctcactc agcagagata gtattgaacc aactatgcgt gaggttcttt    3240
ggactcgatc tggactccgg tctatttct gcacccactg ttccgttatc cattaggaat     3300
aatcactggg ataactcccc gtcgcctaac atgtacgggc tgaataaaga agtggtccgt    3360
cagctctctc gcaggtaccc acaactgcct cgggcagttg ccactggaag agtctatgac    3420
atgaacactg gtacactgcg caattatgat ccgcgcataa acctagtacc tgtaaacaga    3480
agactgcctc atgctttagt cctccaccat aatgaacacc cacagagtga cttttcttca    3540
ttcgtcagca aattgaaggg cagaactgtc ctggtggtcg gggaaaagtt gtccgtccca    3600
ggcaaaatgg ttgactggtt gtcagaccgg cctgaggcta ccttcagagc tcggctggat    3660
ttaggcatcc caggtgatgt gcccaaatat gacataatat ttgttaatgt gaggacccca    3720
tataaatacc atcactatca gcagtgtgaa gaccatgcca ttaagcttag catgttgacc    3780
aagaaagctt gtctgcatct gaatcccggc ggaacctgtg tcagcatagg ttatggttac    3840
gctgacaggg ccagcgaaag catcattggt gctatagcgc ggcagttcaa gttttcccgg    3900
gtatgcaaac cgaaatcctc acttgaagag acggaagttc tgtttgtatt cattgggtac    3960
gatcgcaagg cccgtacgca caatcctac aagctttcat caaccttgac caacatttat     4020
acaggttcca gactccacga agccggatgt gcaccctcat atcatgtggt gcgaggggat    4080
attgccacgg ccaccgaagg agtgattata aatgctgcta acagcaaagg acaacctggc    4140 ggagggtgt gcggagcgct gtataagaaa ttcccggaaa gcttcgattt acagccgatc      4200
gaagtaggaa aagcgcgact ggtcaaaggt gcagctaaac atatcattca tgccgtagga    4260
ccaaacttca acaaagtttc ggaggttgaa ggtgacaaac agttggcaga ggcttatgag    4320
tccatcgcta agattgtcaa cgataacaat tacaagtcag tagcgattcc actgttgtcc    4380
accggcatct tttccgggaa caaagatcga ctaacccaat cattgaacca tttgctgaca    4440
gctttagaca ccactgatgc agatgtagcc atatactgca gggacaagaa atgggaaatg    4500
actctcaagg aagcagtggc taggagagaa gcagtggagg agatatgcat atccgacgac    4560
tcttcagtga cagaacctga tgcagagctg gtgagggtgc atccgaagag ttctttggct    4620
ggaaggaagg gctacagcac aagcgatggc aaaactttct catatttgga agggaccaag    4680
tttcaccagg cggccaagga tatagcagaa attaatgcca tgtggcccgt tgcaacggag    4740
gccaatgagc aggtatgcat gtatatcctc ggagaaagca tgagcagtat taggtcgaaa    4800
tgccccgtcg aagagtcgga agcctccaca ccacctagca cgctgccttg cttgtgcatc    4860
catgccatga ctccagaaag agtacagcgc ctaaaagcct cacgtccaga acaaattact    4920
gtgtgctcat cctttccatt gccgaagtat agaatcactg gtgtgcagaa gatccaatgc    4980
tcccagccta tattgttctc accgaaagtg cctgcgtata ttcatccaag gaagtatctc    5040
gtggaaacac caccggtaga cgagactccg gagccatcgg cagagaacca atccacagag    5100
gggacacctg aacaaccacc acttataacc gaggatgaga ccaggactag aacgcctgag    5160
ccgatcatca tcgaagagga agaagaggat agcataagtt tgctgtcaga tggcccgacc    5220
caccaggtgc tgcaagtcga ggcagacatt cacgggccgc cctctgtatc tagctcatcc    5280
tggtccattc ctcatgcatc cgactttgat gtggacagtt atccatact tgacacccctg    5340 gagggagcta gcgtgaccag cggggcaacg tcagccgaga ctaactctta cttcgcaaag    5400
```

```
agtatggagt tctggcgcg accggtgcct gcgcctcgaa cagtattcag gaaccctcca    5460
catcccgctc cgcgcacaag aacaccgtca cttgcaccca gcagggcctg ctcgagaacc    5520
agcctagttt ccaccccgcc aggcgtgaat agggtgatca ctagagagga gctcgaggcg    5580
cttaccccgt cacgcactcc tagcaggtcg gtctcgagaa ccagcctggt ctccaacccg    5640
ccaggcgtaa ataggtgat tacaagagag gagtttgagg cgttcgtagc acaacaacaa     5700
tgacggtttg atgcgggtgc atacatcttt tcctccgaca ccggtcaagg gcatttacaa    5760
caaaaatcag taaggcaaac ggtgctatcc gaagtggtgt tggagaggac cgaattggag    5820
atttcgtatg ccccgcgcct cgaccaagaa aaagaagaat tactacgcaa gaaattcag    5880
ttaaatccca cacctgctaa cagaagcaga taccagtcca ggaaggtgga gaacatgaaa    5940
gccataacag ctagacgtat tctgcaaggc ctagggcatt atttgaaggc agaaggaaaa    6000
gtggagtgct accgaaccct gcatcctgtt cctttgtatt catctagtgt gaaccgtgcc    6060
ttttcaagcc ccaaggtcgc agtggaagcc tgtaacgcca tgttgaaaga gaactttccg    6120
actgtggctt cttactgtat tattccagag tacgatgcct atttggacat ggttgacgga    6180
gcttcatgct gcttagacac tgccagtttt tgccctgcaa agctgcgcag cttttccaaag   6240
aaacactcct atttggaacc cacaatacga tcggcagtgc cttcagcgat ccagaacacg    6300
ctccagaacg tcctgcagc tgccacaaaa agaaattgca atgtcacgca atgagagaa     6360
ttgcccgtat tggattcggc ggcctttaat gtggaatgct tcaagaaata tgcgtgtaat    6420
aatgaatatt gggaaacgtt taagaaaac cccatcaggc ttactgaaga aaacgtggta     6480
aattacatta ccaaattaaa aggaccaaaa gctgctgctc ttttgcgaa gacacataat     6540
ttgaatatgt tgcaggacat accaatggac aggtttgtaa tggacttaaa gagagacgtg    6600
aaagtgactc caggaacaaa acatactgaa gaacggccca aggtacaggt gatccaggct    6660
gccgatccgc tagcaacagc gtatctgtgc ggaatccacc gagagctggt taggagatta    6720
aatgcggtcc tgcttccgaa cattcataca ctgtttgata tgtcggctga agactttgac    6780
gctattatag ccgagcactt ccagcctggg gattgtgttc tggaaactga catcgcgtcg    6840
tttgataaaa gtgaggacga cgccatggct ctgaccgcgt taatgattct ggaagactta    6900
ggtgtggacg cagagctgtt gacgctgatt gaggcggctt tcggcgaaat ttcatcaata    6960
catttgccca ctaaaactaa atttaaattc ggagccatga tgaaatctgg aatgttcctc    7020
acactgtttg tgaacacagt cattaacatt gtaatcgcaa gcagagtgtt gagagaacgg    7080
ctaaccggat caccatgtgc agcattcatt ggagatgaca atatcgtgaa aggagtcaaa    7140
tcggacaaat taatggcaga caggtgcgcc acctggttga atatggaagt caagattata    7200
gatgctgtgg tgggcgagaa agcgccttat ttctgtggag gtttatttt gtgtgactcc     7260
gtgaccggca cagcgtgccg tgtggcagac ccctaaaaa ggctgtttaa gcttggcaaa     7320
cctctggcag cagacgatga acatgatgat gacaggagaa gggcattgca tgaagagtca    7380
acacgctgga accgagtggg tattctttca gagctgtgca aggcagtaga atcaaggtat    7440
gaaaccgtag gaacttccat catagttatg gccatgacta ctctagctag cagtgttaaa    7500
tcattcagct acctgagagg ggcccctata actctctacg gctaacctga atggactacg    7560
acgtatcacg cccaaacatt tacagccgcg gtgtcaaaaa ccgcgtggac gtggttaaca    7620
tccctgctgg gaggatcagc cgtaattatt ataattggct tggtgctggc tactattgtg    7680
gccatgtacg tgctgaccaa ccagaaacat aattgaatac agcagcaatt ggcaagctgc    7740
```

```
ttacatagaa ctcgcggcga ttggcatgcc gccttaaaat tttattttta tttttctttt    7800
cttttccgaa tcggattttg ttttaatat ttcaaaaaaa aaaaaaaaa aaaaaaaaa       7860 aaaaaaaaaa aaaaaaaaaa aaaaaaaaaa aaaaaaaaaa aaaaaaaaaa aaatacgtag    7920
tttaaac                                                              7927

<210> SEQ ID NO 10
<211> LENGTH: 36519
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 10
ccatcttcaa taatatacct caaactttt gtgcgcgtta atatgcaaat gaggcgtttg      60
aatttgggga ggaagggcgg tgattggtcg agggatgagc gaccgttagg ggcggggcga   120
gtgacgtttt gatgacgtgg ttgcgaggag gagccagttt gcaagttctc gtgggaaaag   180
tgacgtcaaa cgaggtgtgg tttgaacacg gaaatactca attttcccgc gctctctgac   240
aggaaatgag gtgtttctgg gcggatgcaa gtgaaaacgg gccattttcg cgcgaaaact   300
gaatgaggaa gtgaaaatct gagtaatttc gcgtttatgg cagggaggag tatttgccga   360
gggccgagta gactttgacc gattacgtgg gggtttcgat taccgtgttt ttcacctaaa   420
tttccgcgta cggtgtcaaa gtccggtgtt tttacgtagg tgtcagctga tcgccagggt   480
atttaaacct gcgctctcca gtcaagaggc cactcttgag tgccagcgag aagagttttc   540
tcctccgcgc cgcgagtcag atctacactt tgaaagatga ggcacctgag agacctgccc   600
gatgagaaaa tcatcatcgc ttccgggaac gagattctgg aactggtggt aaatgccatg   660
atgggcgacg accctccgga gcccccacc ccatttgaga caccttcgct gcacgatttg    720
tatgatctgg aggtggatgt gcccgaggac gatcccaatg aggaggcggt aaatgatttt    780
tttagcgatg ccgcgctgct agctgccgag gaggcttcga gctctagctc agacagcgac   840
tcttcactgc atacccctag acccggcaga ggtgagaaaa agatccccga gcttaaaggg   900
gaagagatgg acttgcgctg ctatgaggaa tgcttgcccc cgagcgatga tgaggacgag   960
caggcgatcc agaacgcagc gagccaggga gtgcaagccg ccagcgagag ctttgcgctg  1020
gactgcccgc ctctgcccgg acacggctgt aagtcttgtg aatttcatcg catgaatact  1080
ggagataaag ctgtgttgtg tgcactttgc tatatgagag cttacaacca ttgtgtttac  1140
agtaagtgtg attaagttga actttagagg gaggcagaga gcagggtgac tgggcgatga  1200
ctggtttatt tatgtatata tgttctttat ataggtcccg tctctgacgc agatgatgag  1260 accccacta caaagtccac ttcgtcaccc ccagaaattg gcacatctcc acctgagaat   1320
attgttagac cagttcctgt tagagccact gggaggagag cagctgtgga atgtttggat  1380
gacttgctac agggtggggt tgaacctttg gacttgtgta cccggaaacg ccccaggcac  1440
taagtgccac acatgtgtgt ttacttgagg tgatgtcagt atttataggg tgtggagtgc  1500
aataaaaaat gtgttgactt taagtgcgtg gtttatgact caggggtggg gactgtgagt  1560
atataagcag gtgcagacct gtgtggttag ctcagagcgg catggagatt tggacggtct  1620
tggaagactt tcacaagact agacagctgc tagagaacgc ctcgaacgga gtctcttacc  1680
tgtggagatt ctgcttcggt ggcgacctag ctaggctagt ctacagggcc aaacaggatt  1740
atagtgaaca atttgaggtt attttgagag agtgttctgg tcttttgac gctcttaact  1800
```

```
tgggccatca gtctcacttt aaccagagga tttcgagagc ccttgatttt actactcctg    1860
gcagaaccac tgcagcagta gccttttttg cttttattct tgacaaatgg agtcaagaaa    1920
cccatttcag cagggattac cagctggatt tcttagcagt agctttgtgg agaacatgga    1980
agtgccagcg cctgaatgca atctccggct acttgccggt acagccgcta gacactctga    2040
ggatcctgaa tctccaggag agtcccaggg cacgccaacg tcgccagcag cagcagcagg    2100
aggaggatca agaagagaac ccgagagccg gcctggaccc tccggcggag gaggaggagt    2160
agctgacctg tttcctgaac tgcgccgggt gctgactagg tcttcgagtg gtcgggagag    2220
ggggattaag cggagagggc atgatgagac taatcacaga actgaactga ctgtgggtct    2280
gatgagtcgc aagcgcccag aaacagtgtg gtggcatgag gtgcagtcga ctggcacaga    2340
tgaggtgtcg gtgatgcatg agaggttttc tctagaacaa gtcaagactt gttggttaga    2400
gcctgaggat gattgggagg tagccatcag gaattatgcc aagctggctc tgaggccaga    2460
caagaagtac aagattacta agctgataaa tatcagaaat gcctgctaca tctcagggaa    2520
tggggctgaa gtggagatct gtctccagga aagggtggct ttcagatgct gcatgatgaa    2580
tatgtacccg ggagtggtgg gcatggatgg ggttaccttt atgaacatga ggttcagggg    2640
agatgggtat aatggcacgg tctttatggc caataccaag ctgacagtcc atggctgctc    2700
cttctttggg tttaataaca cctgcatcga ggcctggggt caggtcggtg tgaggggctg    2760
cagttttca gccaactgga tggggtcgt gggcaggacc aagagtatgc tgtccgtgaa    2820
gaaatgcttg tttgagaggt gccacctggg ggtgatgagc gagggcgaag ccagaatccg    2880
ccactgcgcc tctaccgaga cgggctgctt tgtgctgtgc aagggcaatg ctaagatcaa    2940
gcataatatg atctgtggag cctcggacga gcgcggctac cagatgctga cctgcgccgg    3000
cgggaacagc catatgctgg ccaccgtaca tgtggcttcc catgctcgca gccctggcc    3060
cgagttcgag cacaatgtca tgaccaggtg caatatgcat ctggggtccc gccgaggcat    3120
gttcatgccc taccagtgca acctgaatta tgtgaaggtg ctgctggagc ccgatgccat    3180
gtccagagtg agcctgacgg gggtgtttga catgaatgtg gaggtgtgga agattctgag    3240
atatgatgaa ccaagaccaa ggtgccgagc ctgcgagtgc ggagggaagc atgccaggtt    3300
ccagcccgtg tgtgtggatg tgacggagga cctgcgaccc gatcatttgg tgttgccctg    3360
caccgggacg gagttcggtt ccagcgggga agaatctgac tagagtgagt agtgttctgg    3420
ggcgggggag gacctgcatg agggccagaa taactgaaat ctgtgctttt ctgtgtgttg    3480
cagcagcatg agcggaagcg gctccttga gggaggggta ttcagccctt atctgacggg    3540
gcgtctcccc tcctgggcgg gagtgcgtca gaatgtgatg ggatccacgg tggacggccg    3600
gcccgtgcag cccgcgaact cttcaaccct gacctatgca accctgagct cttcgtcgtt    3660
ggacgcagct gccgccgcag ctgctgcatc tgccgccagc gccgtgcgcg aatggccat    3720
gggcgccggc tactacggca ctctggtggc caactcgagt tccaccaata atcccgccag    3780
cctgaacgag gagaagctgt tgctgctgat ggcccagctc gaggccttga cccagcgcct    3840
gggcgagctg acccagcagg tggctcagct gcaggagcag acgcgggccg cggttgccac    3900
ggtgaaatcc aaataaaaaa tgaatcaata aataaacgga gacggttgtt gattttaaca    3960
cagagtctga atctttatt gattttcgc gcgcggtagg ccctggacca ccggtctcga    4020
tcattgagca cccggtggat cttttccagg acccggtaga ggtgggcttg gatgttgagg    4080
tacatgggca tgagcccgtc ccggggtgg aggtagctcc attgcagggc ctcgtgctcg    4140
ggggtggtgt tgtaaatcac ccagtcatag caggggcgca gggcatggtg ttgcacaata    4200
```

| | |
|---|---|
| tctttgagga ggagactgat ggccacgggc agcccttngg tgtaggtgtt tacaaatctg | 4260 |
| ttgagctggg agggatgcat gcggggggag atgaggtgca tcttggcctg gatcttgaga | 4320 |
| ttggcgatgt taccgcccag atcccgcctg gggttcatgt tgtgcaggac caccagcacg | 4380 |
| gtgtatccgg tgcacttggg gaatttatca tgcaacttgg aagggaaggc gtgaaagaat | 4440 |
| ttggcgacgc ctttgtgccc gcccaggttt tccatgcact catccatgat gatggcgatg | 4500 |
| ggcccgtggg cggcggcctg ggcaaagacg tttcgggggt cggacacatc atagttgtgg | 4560 |
| tcctgggtga ggtcatcata ggccatttta atgaatttgg ggcggagggt gccggactgg | 4620 |
| gggacaaagg taccctcgat cccgggggcg tagttcccct cacagatctg catctcccag | 4680 |
| gctttgagct cggaggggg gatcatgtcc acctgcgggg cgataaagaa cacggtttcc | 4740 |
| ggggcggggg agatgagctg gccgaaagc aagttccgga gcagctggga cttgccgcag | 4800 |
| ccggtggggc cgtagatgac cccgatgacc ggctgcaggt ggtagttgag ggagagacag | 4860 |
| ctgccgtcct cccggaggag ggggccacc tcgttcatca tctcgcgcac gtgcatgttc | 4920 |
| tcgcgcacca gttccgccag gaggcgctct cccccaggg ataggagctc ctggagcgag | 4980 |
| gcgaagtttt tcagcggctt gagtccgtcg gccatgggca ttttggagag ggtttgttgc | 5040 |
| aagagttcca ggcggtccca gagctcggtg atgtgctcta cggcatctcg atccagcaga | 5100 |
| cctcctcgtt tcgcgggttg ggacggctgc gggagtaggg caccagacga tgggcgtcca | 5160 |
| gcgcagccag ggtccggtcc ttccagggtc gcagcgtccg cgtcagggtg gtctccgtca | 5220 |
| cggtgaaggg gtgcgcgccg ggctgggcgc ttgcgagggt gcgcttcagg ctcatccggc | 5280 |
| tggtcgaaaa ccgctcccga tcggcgccct gcgcgtcggc caggtagcaa ttgaccatga | 5340 |
| gttcgtagtt gagcgcctcg gccgcgtggc ctttggcgcg gagcttacct ttggaagtct | 5400 |
| gcccgcaggc gggacagagg agggacttga gggcgtagag cttggggggcg aggaagacgg | 5460 |
| actcgggggc gtaggcgtcc gcgccgcagt gggcgcagac ggtctcgcac tccacgagcc | 5520 |
| aggtgaggtc gggctggtcg gggtcaaaaa ccagtttccc gccgttcttt ttgatgcgtt | 5580 |
| tcttaccttt ggtctccatg agctcgtgtc cccgctgggt gacaaagagg ctgtccgtgt | 5640 |
| ccccgtagac cgactttatg ggccggtcct cgagcggtgt gccgcggtcc tcctcgtaga | 5700 |
| ggaaccccgc ccactccgag acgaaagccc gggtccaggc cagcacgaag gaggccacgt | 5760 |
| gggacgggta gcgtcgttg tccaccagcg ggtccacctt ttccagggta tgcaaacaca | 5820 |
| tgtccccctc gtccacatcc aggaaggtga ttggcttgta agtgtaggcc acgtgaccgg | 5880 |
| gggtcccggc cggggggta taaagggtg cgggtccctg ctcgtcctca ctgtcttccg | 5940 |
| gatcgctgtc caggagcgcc agctgttggg gtaggtattc cctctcgaag gcgggcatga | 6000 |
| cctcggcact caggttgtca gtttctagaa acgaggagga tttgatattg acggtgccgg | 6060 |
| cggagatgcc tttcaagagc ccctcgtcca tctggtcaga aaagacgatc tttttgttgt | 6120 |
| cgagcttggt ggcgaaggag ccgtagaggg cgttggagag gagcttggcg atggagcgca | 6180 |
| tggtctggtt ttttccttg tcggcgcgct ccttggcggc gatgttgagc tgcacgtact | 6240 |
| cgcgcgccac gcacttccat tcggggaaga cggtggtcag ctcgtcgggc acgattctga | 6300 |
| cctgccagcc ccgattatgc agggtgatga ggtccacact ggtggccacc tcgccgcgca | 6360 |
| ggggctcatt agtccagcag aggcgtccgc ccttgcgcga gcagaagggg ggcaggggggt | 6420 |
| ccagcatgac ctcgtcgggg gggtcggcat cgatggtgaa gatgccgggc aggaggtcgg | 6480 |
| ggtcaaagta gctgatggaa gtggccagat cgtccagggc agcttgccat tcgcgcacgg | 6540 |

```
ccagcgcgcg ctcgtaggga ctgaggggcg tgccccaggg catgggatgg gtaagcgcgg   6600
aggcgtacat gccgcagatg tcgtagacgt agagggctc ctcgaggatg ccgatgtagg    6660
tggggtagca gcgcccccg cggatgctgg cgcgcacgta gtcatacagc tcgtgcgagg    6720
gggcgaggag ccccgggccc aggttggtgc gactgggctt ttcggcgcgg tagacgatct   6780
ggcggaaaat ggcatgcgag ttggaggaga tggtgggcct ttggaagatg ttgaagtggg   6840
cgtggggcag tccgaccgag tcgcggatga agtgggcgta ggagtcttgc agcttggcga   6900
cgagctcggc ggtgactagg acgtccagag cgcagtagtc gagggtctcc tggatgatgt   6960
catacttgag ctgtcccttt tgtttccaca gctcgcggtt gagaaggaac tcttcgcggt   7020
ccttccagta ctcttcgagg gggaacccgt cctgatctgc acggtaagag cctagcatgt   7080
agaactggtt gacggccttg taggcgcagc agcccttctc cacggggagg gcgtaggcct   7140
gggcggcctt gcgcagggag gtgtgcgtga gggcgaaagt gtccctgacc atgaccttga   7200
ggaactggtg cttgaagtcg atatcgtcgc agccccctg ctcccagagc tggaagtccg    7260
tgcgcttctt gtaggcgggg ttgggcaaag cgaaagtaac atcgttgaag aggatcttgc   7320
ccgcgcgggg cataaagttg cgagtgatgc ggaaaggttg gggcacctcg gcccggttgt   7380
tgatgacctg ggcggcgagc acgatctcgt cgaagccgtt gatgttgtgg cccacgatgt   7440
agagttccac gaatcgcgga cggcccttga cgtggggcag tttcttgagc tcctcgtagg   7500
tgagctcgtc ggggtcgctg agcccgtgct gctcgagcgc ccagtcggcg agatgggggt   7560
tggcgcggag gaaggaagtc cagagatcca cggccagggc ggtttgcaga cggtcccggt   7620
actgacggaa ctgctgcccg acggccattt tttcggggt gacgcagtag aaggtgcggg    7680
ggtccccgtg ccagcgatcc catttgagct ggagggcgag atcgagggcg agctcgacga   7740
gccggtcgtc cccggagagt ttcatgacca gcatgaaggg gacgagctgc ttgccgaagg   7800
accccatcca ggtgtaggtt ccacatcgt aggtgaggaa gagcctttcg gtgcgaggat    7860
gcgagccgat ggggaagaac tggatctcct gccaccaatt ggaggaatgg ctgttgatgt   7920
gatggaagta gaaatgccga cggcgcgccg aacactcgtg cttgtgttta tacaagcggc   7980
cacagtgctc gcaacgctgc acgggatgca cgtgctgcac gagctgtacc tgagttcctt   8040
tgacgaggaa tttcagtggg aagtggagtc gtggcgcctg catctcgtgc tgtactacgt   8100
cgtggtggtc ggcctggccc tcttctgcct cgatggtggt catgctgacg agcccgcgcg   8160
ggaggcaggt ccagacctcg gcgcgagcgg gtcggagagc gaggacgagg gcgcgcaggc   8220
cggagctgtc cagggtcctg agacgctgcg gagtcaggtc agtgggcagc ggcggcgcgc   8280
ggttgacttg caggagtttt tccagggcgc gcggaggtc cagatggtac ttgatctcca    8340
ccgcgccatt ggtggcgacg tcgatggctt gcagggtccc gtgccctgg ggtgtgacca    8400 ccgtcccccg tttcttcttg ggcggctggg gcgacggggg cggtgcctct tccatggtta   8460
gaagcggcgg cgaggacgcg cgccgggcgg cagggcggc tcgggcccg gaggcagggg     8520 cggcaggggc acgtcggcgc cgcgcgcggg taggttctgg tactgcgccc ggagaagact   8580
ggcgtgagcg acgacgcgac ggttgacgtc ctggatctga cgcctctggg tgaaggccac   8640
gggacccgtg agtttgaacc tgaaagagag ttcgacagaa tcaatctcgg tatcgttgac   8700
ggcggcctgc cgcaggatct cttgcacgtc gcccgagttg tcctggtagg cgatctcggt   8760
catgaactgc tcgatctcct cctcttgaag gtctccgcgg ccggcgcgct ccacggtggc   8820
cgcgaggtcg ttggagatgc ggcccatgag ctgcgagaag gcgttcatgc ccgcctcgtt   8880
ccagacgcgg ctgtagacca cgacgccctc gggatcgcgg gcgcgcatga ccacctgggc   8940
```

```
gaggttgagc tccacgtggc gcgtgaagac cgcgtagttg cagaggcgct ggtagaggta    9000
gttgagcgtg gtggcgatgt gctcggtgac gaagaaatac atgatccagc ggcggagcgg    9060
catctcgctg acgtcgccca gcgcctccaa acgttccatg gcctcgtaaa agtccacggc    9120
gaagttgaaa aactgggagt tgcgcgccga gacggtcaac tcctcctcca gaagacggat    9180
gagctcggcg atggtggcgc gcacctcgcg ctcgaaggcc cccgggagtt cctccacttc    9240
ctcttcttcc tcctccacta acatctcttc tacttcctcc tcaggcggca gtggtggcgg    9300
gggaggggc ctgcgtcgcc ggcggcgcac gggcagacgg tcgatgaagc gctcgatggt    9360
ctcgccgcgc cggcgtcgca tggtctcggt gacggcgcgc ccgtcctcgc ggggccgcag    9420
cgtgaagacg ccgccgcgca tctccaggtg gccgggggg tccccgttgg gcagggagag    9480
ggcgctgaca atgcatctta tcaattgccc cgtagggact ccgcgcaagg acctgagcgt    9540
ctcgagatcc acgggatctg aaaaccgctg aacgaaggct tcgagccagt cgcagtcgca    9600
aggtaggctg agcacggttt cttctggcgg gtcatgttgg ttgggagcgg ggcgggcgat    9660
gctgctggtg atgaagttga ataggcggt tctgagacgg cggatggtgg cgaggagcac    9720
caggtctttg ggcccggctt gctggatgcg cagacggtcg gccatgcccc aggcgtggtc    9780
ctgacacctg gccaggtcct tgtagtagtc ctgcatgagc cgctccacgg gcacctcctc    9840
ctcgcccgcg cggccgtgca tgcgcgtgag cccgaagccg cgctggggct ggacgagcgc    9900
caggtcggcg acgacgcgct cggcgaggat ggcttgctgg atctgggtga gggtggtctg    9960
gaagtcatca aagtcgacga agcggtggta ggctccggtg ttgatggtgt aggagcagtt   10020
ggccatgacg gaccagttga cggtctggtg gcccggacgc acgagctcgt ggtacttgag   10080
gcgcgagtag gcgcgcgtgt cgaagatgta gtcgttgcag gtgcgcacca ggtactggta   10140
gccgatgagg aagtgcggcg gcggctggcg gtagagcggc catcgctcgg tggcggggc   10200
gccgggcgcg aggtcctcga gcatggtgcg gtggtagccg tagatgtacc tggacatcca   10260
ggtgatgccg gcggcggtgg tggaggcgcg cgggaactcg cggacgcggt tccagatgtt   10320
gcgcagcggc aggaagtagt tcatggtggg cacggtctgg cccgtgaggc gcgcgcagtc   10380
gtggatgctc tatacgggca aaaacgaaag cggtcagcgg ctcgactccg tggcctggag   10440
gctaagcgaa cgggttgggc tgcgcgtgta ccccggttcg aatctcgaat caggctggag   10500
ccgcagctaa cgtggtattg gcactcccgt ctcgacccaa gcctgcacca accctccagg   10560
atacggaggc gggtcgtttt gcaactttt tttggaggcc ggatgagact agtaagcgcg   10620
gaaagcggcc gaccgcgatg gctcgctgcc gtagtctgga gaagaatcgc cagggttgcg   10680
ttgcggtgtg ccccggttcg aggccggccg gattccgcgg ctaacgaggg cgtggctgcc   10740
ccgtcgtttc caagaccca tagccagccg acttctccag ttacggagcg agccctctt   10800
ttgttttgtt tgtttttgcc agatgcatcc cgtactgcgg cagatgcgcc cccaccaccc   10860
tccaccgcaa caacagcccc ctccacagcc ggcgcttctg ccccgccc agcagcaact   10920
tccagccacg accgccgcgg ccgccgtgag cggggctgga cagagttatg atcaccagct   10980
ggccttggaa gagggcgagg ggctggcgcg cctgggggcg tcgtcgccgg agcggcaccc   11040
gcgcgtgcag atgaaaggg acgctcgcga ggcctacgtg cccaagcaga acctgttcag   11100
agacaggagc ggcgaggagc ccgaggagat gcgcgcggcc cggttccacg cggggcggga   11160
gctgcggcgc ggcctggacc gaaagagggt gctgagggac gaggatttcg aggcggacga   11220
gctgacgggg atcagccccg cgcgcgcgca cgtggccgcg gccaacctgg tcacggcgta   11280
```

| | |
|---|---|
| cgagcagacc gtgaaggagg agagcaactt ccaaaaatcc ttcaacaacc acgtgcgcac | 11340 |
| cctgatcgcg cgcgaggagg tgaccctggg cctgatgcac ctgtgggacc tgctggaggc | 11400 |
| catcgtgcag aaccccacca gcaagccgct gacggcgcag ctgttcctgg tggtgcagca | 11460 |
| tagtcgggac aacgaagcgt tcagggaggc gctgctgaat atcaccgagc ccagggccg | 11520 |
| ctggctcctg gacctggtga acattctgca gagcatcgtg gtgcaggagc gcggctgcc | 11580 |
| gctgtccgag aagctggcgg ccatcaactt ctcggtgctg agtttgggca agtactacgc | 11640 |
| taggaagatc tacaagaccc cgtacgtgcc catagacaag gaggtgaaga tcgacgggtt | 11700 |
| ttacatgcgc atgaccctga aagtgctgac cctgagcgac gatctgggg tgtaccgcaa | 11760 |
| cgacaggatg caccgtgcgg tgagcgccag caggcggcgc gagctgagcg accaggagct | 11820 |
| gatgcatagt ctgcagcggg ccctgaccgg ggccgggacc gagggggaga gctactttga | 11880 |
| catgggcgcg gacctgcact ggcagcccag ccgccgggcc ttggaggcgg cggcaggacc | 11940 |
| ctacgtagaa gaggtggacg atgaggtgga cgaggagggc gagtacctgg aagactgatg | 12000 |
| gcgcgaccgt attttgcta gatgcaacaa caacagccac ctcctgatcc cgcgatgcgg | 12060 |
| gcggcgctgc agagccagcc gtccggcatt aactcctcgg acgattggac ccaggccatg | 12120 |
| caacgcatca tggcgctgac gacccgcaac cccgaagcct ttagacagca gccccaggcc | 12180 |
| aaccggctct cggccatcct ggaggccgtg gtgccctcgc gctccaaccc cacgcacgag | 12240 |
| aaggtcctgg ccatcgtgaa cgcgctggtg gagaacaagg ccatccgcgg cgacgaggcc | 12300 |
| ggcctggtgt acaacgcgct gctggagcgc gtggcccgct acaacagcac caacgtgcag | 12360 |
| accaacctgg accgcatggt gaccgacgtg cgcgaggccg tgcccagcg cgagcggttc | 12420 |
| caccgcgagt ccaacctggg atccatggtg gcgctgaacg ccttcctcag cacccagccc | 12480 |
| gccaacgtgc cccggggcca ggaggactac accaacttca tcagcgccct gcgcctgatg | 12540 |
| gtgaccgagg tgccccagag cgaggtgtac cagtccgggc cggactactt cttccagacc | 12600 |
| agtcgccagg gcttgcagac cgtgaacctg agccaggctt tcaagaactt gcagggcctg | 12660 |
| tggggcgtgc aggccccggt cggggaccgc gcgacggtgt cgagcctgct gacgccgaac | 12720 |
| tcgcgcctgc tgctgctgct ggtggcccc ttcacggaca gcggcagcat caaccgcaac | 12780 |
| tcgtacctgg gctacctgat taacctgtac cgcgaggcca tcggccaggc gcacgtggac | 12840 |
| gagcagacct accaggagat cacccacgtg agccgcgccc tgggccagga cgacccgggc | 12900 |
| aacctggaag ccacccctgaa cttttttgctg accaaccggt cgcagaagat cccgccccag | 12960 |
| tacgcgctca gcaccgagga ggagcgcatc ctgcgttacg tgcagcagag cgtgggcctg | 13020 |
| ttcctgatgc aggagggggc caccccccagc gccgcgctcg acatgaccgc gcgcaacatg | 13080 |
| gagcccagca tgtacgccag caaccgcccg ttcatcaata aactgatgga ctacttgcat | 13140 |
| cgggcggccg ccatgaactc tgactatttc accaacgcca tcctgaatcc ccactggctc | 13200 |
| ccgccgccgg ggttctacac gggcgagtac gacatgcccg accccaatga cgggttcctg | 13260 |
| tgggacgatg tggacagcag cgtgttctcc ccccgaccgg gtgctaacga gcgccccttg | 13320 |
| tggaagaagg aaggcagcga ccgacgcccg tcctcggcgc tgtccggccg cgagggtgct | 13380 |
| gccgcggcgg tgcccgaggc cgccagtcct ttcccgagct tgcccttctc gctgaacagt | 13440 |
| atccgcagca gcgagctggg caggatcacg cgcccgcgct tgctgggcga agaggagtac | 13500 |
| ttgaatgact cgctgttgag acccgagcgg gagaagaact tccccaataa cgggatagaa | 13560 |
| agcctggtgg acaagatgag ccgctggaag acgtatgcgc aggagcacag ggacgatccc | 13620 |
| cggggcgtcgc agggggccac gagccggggc agcgccgccc gtaaacgccg gtggcacgac | 13680 |

```
aggcagcggg gacagatgtg ggacgatgag gactccgccg acgacagcag cgtgttggac    13740
ttgggtggga gtggtaaccc gttcgctcac ctgcgccccc gtatcgggcg catgatgtaa    13800
gagaaaccga aaataaatga tactcaccaa ggccatggcg accagcgtgc gttcgtttct    13860
tctctgttgt tgttgtatct agtatgatga ggcgtgcgta cccggagggt cctcctccct    13920
cgtacgagag cgtgatgcag caggcgatgg cggcggcggc gatgcagccc ccgctggagg    13980
ctccttacgt gccccgcgg tacctggcgc tacggaggg gcggaacagc attcgttact      14040
cggagctggc acccttgtac gataccaccc ggttgtacct ggtggacaac aagtcggcgg    14100
acatcgcctc gctgaactac cagaacgacc acagcaactt cctgaccacc gtggtgcaga    14160
acaatgactt cacccccacg gaggccagca cccagaccat caactttgac gagcgctcgc    14220
ggtggggcgg ccagctgaaa accatcatgc acaccaacat gcccaacgtg aacgagttca    14280
tgtacagcaa caagttcaag gcgcgggtga tggtctcccg caagaccccc aatggggtga    14340
cagtgacaga ggattatgat ggtagtcagg atgagctgaa gtatgaatgg gtggaatttg    14400
agctgcccga aggcaacttc tcggtgacca tgaccatcga cctgatgaac aacgccatca    14460
tcgacaatta cttggcggtg gggcggcaga acggggtgct ggagagcgac atcgcgtga    14520 agttcgacac taggaacttc aggctgggct gggaccccgt gaccgagctg gtcatgcccg    14580
gggtgtacac caacgaggct ttccatcccg atattgtctt gctgcccggc tgcggggtgg    14640
acttcaccga gagccgcctc agcaacctgc tgggcattcg caagaggcag cccttccagg    14700
aaggcttcca gatcatgtac gaggatctgg aggggggcaa catccccgcg ctcctggatg    14760
tcgacgccta tgagaaaagc aaggaggatg cagcagctga agcaactgca gccgtagcta    14820
ccgcctctac cgaggtcagg ggcgataatt ttgcaagcgc cgcagcagtg gcagcggccg    14880
aggcggctga aaccgaaagt aagatagtca ttcagccggt ggagaaggat agcaagaaca    14940
ggagctacaa cgtactaccg gacaagataa acaccgccta ccgcagctgg tacctagcct    15000
acaactatgg cgaccccgag aagggcgtgc gctcctggac gctgctcacc acctcggacg    15060
tcacctgcgg cgtggagcaa gtctactggt cgctgcccga catgatgcaa gacccggtca    15120
ccttccgctc cacgcgtcaa gttagcaact acccggtggt gggcgccgag ctcctgcccg    15180
tctactccaa gagcttcttc aacgagcagg ccgtctactc gcagcagctg cgcgccttca    15240
cctcgcttac gcacgtcttc aaccgcttcc ccgagaacca gatcctcgtc cgcccgccc    15300 cgcccaccat taccaccgtc agtgaaaacg ttcctgctct cacagatcac gggaccctgc    15360
cgctgcgcag cagtatccgg ggagtccagc gcgtgaccgt tactgacgcc agacgccgca    15420
cctgccccta cgtctacaag gccctgggca tagtcgcgcc gcgcgtcctc tcgagccgca    15480
ccttctaaat gtccattctc atctcgccca gtaataacac cggttgggc ctgcgcgcgc     15540 ccagcaagat gtacggaggc gctcgccaac gctccacgca caccccgtg cgcgtgcgcg     15600 ggcacttccg cgctccctgg ggcgccctca agggccgcgt gcggtcgcgc accaccgtcg    15660
acgacgtgat cgaccaggtg gtggccgacg cgcgcaacta caccccgcc gccgcgcccg     15720 tctccaccgt ggacgccgtc atcgacagcg tggtggccga cgcgcgccgg tacgcccgcg    15780
ccaagagccg gcgcggcgc atcgcccggc ggcaccggag caccccgcc atgcgcgcgg      15840 cgcgagcctt gctgcgcagg gccaggcgca cgggacgcag ggccatgctc agggcggcca    15900
gacgcgcggc ttcaggcgcc agcgccggca ggacccggag acgcgcggcc acggcggcgg    15960
cagcggccat cgccagcatg tcccgcccgc ggcgagggaa cgtgtactgg gtgcgcgacg    16020
```

```
ccgccaccgg tgtgcgcgtg cccgtgcgca cccgccccc  tcgcacttga agatgttcac   16080
ttcgcgatgt tgatgtgtcc cagcggcgag gaggatgtcc aagcgcaaat tcaaggaaga   16140
gatgctccag gtcatcgcgc ctgagatcta cggccctgcg gtggtgaagg aggaaagaaa   16200
gccccgcaaa atcaagcggg tcaaaaagga caaaaaggaa gaagaaagtg atgtggacgg   16260
attggtggag tttgtgcgcg agttcgcccc ccggcggcgc gtgcagtggc gcgggcggaa   16320
ggtgcaaccg gtgctgagac ccggcaccac cgtggtcttc acgcccggcg agcgctccgg   16380
caccgcttcc aagcgctcct acgacgaggt gtacggggat gatgatattc tggagcaggc   16440
ggccgagcgc ctgggcgagt ttgcttacgg caagcgcagc cgttccgcac cgaaggaaga   16500
ggcggtgtcc atcccgctgg accacggcaa ccccacgccg agcctcaagc ccgtgacctt   16560
gcagcaggtg ctgccgaccg cggcgccgcg ccggggttc  aagcgcgagg gcgaggatct   16620
gtaccccacc atgcagctga tggtgcccaa cgccagaaag ctggaagacg tgctggagac   16680
catgaaggtg gacccggacg tgcagcccga ggtcaaggtg cggcccatca agcaggtggc   16740
cccgggcctg ggcgtgcaga ccgtggacat caagattccc acggagccca tggaaacgca   16800
gaccgagccc atgatcaagc ccagcaccag caccatggag gtgcagacgg atccctggat   16860
gccatcggct cctagtcgaa gaccccggcg caagtacggc gcggccagcc tgctgatgcc   16920
caactacgcg ctgcatcctt ccatcatccc cacgccgggc taccgcggca cgcgcttcta   16980
ccgcggtcat accagcagcc gccgccgcaa gaccaccact cgccgccgcc gtcgccgcac   17040
cgccgctgca accaccctg  ccgccctggt gcggagagtg taccgccgcg gccgcgcacc   17100
tctgacccctg ccgcgcgcgc gctaccaccc gagcatcgcc atttaaactt tcgcctgctt   17160
tgcagatcaa tggccctcac atgccgcctt cgcgttccca ttacgggcta ccgaggaaga   17220
aaaccgcgcc gtagaaggct ggcggggaac gggatgcgtc gccaccacca ccggcggcgg   17280
cgcgccatca gcaagcggtt gggggaggc  ttcctgcccg cgctgatccc catcatcgcc   17340
gcggcgatcg gggcgatccc cggcattgct tccgtggcgg tgcaggcctc tcagcgccac   17400
tgagacacac ttggaaacat cttgtaataa accaatggac tctgacgctc ctggtcctgt   17460
gatgtgtttt cgtagacaga tggaagacat caattttcg  tccctggctc cgcgacacgg   17520
cacgcggccg ttcatgggca cctggagcga catcggcacc agccaactga acggggcgc   17580
cttcaattgg agcagtctct ggagcgggct taagaatttc gggtccacgc ttaaaaccta   17640
tggcagcaag gcgtggaaca gcaccacagg gcaggcgctg agggataagc tgaaagagca   17700
gaacttccag cagaaggtgg tcgatgggct cgcctcgggc atcaacgggg tggtggacct   17760
ggccaaccag gccgtgcagc ggcagatcaa cagccgcctg gacccggtgc cgcccgccgg   17820
ctccgtggag atgccgcagg tggaggagga gctgcctccc ctggacaagc ggggcgagaa   17880
gcgacccgc  cccgatgcgg aggagacgct gctgacgcac acgacgagc  cgcccccgta   17940
cgaggaggcg gtgaaactgg gtctgcccac cacgcggccc atcgcgcccc tggccaccgg   18000
ggtgctgaaa cccgaaaagc ccgcgaccct ggacttgcct cctccccagc cttcccgccc   18060
ctctacagtg gctaagcccc tgccgccggt ggccgtggcc cgcgcgcgac ccgggggcac   18120
cgcccgccct catgcgaact ggcagagcac tctgaacagc atcgtgggtc tgggagtgca   18180
gagtgtgaag cgccgccgct gctattaaac ctaccgtagc gcttaacttg cttgtctgtg   18240
tgtgtatgta ttatgtcgcc gccgccgctg tccaccagaa ggaggagtga agaggcgcgt   18300
cgccgagttg caagatggcc accccatcga tgctgcccca gtgggcgtac atgcacatcg   18360
ccggacagga cgcttcggag tacctgagtc cgggtctggt gcagtttgcc cgcgccacag   18420
```

```
acacctactt cagtctgggg aacaagttta ggaacccca c ggtggcgccc acgcacgatg   18480
tgaccaccga ccgcagccag cggctgacgc tgcgcttcgt gcccgtggac cgcgaggaca   18540
acacctactc gtacaaagtg cgctacacgc tggccgtggg cgacaaccgc gtgctggaca   18600
tggccagcac ctactttgac atccgcggcg tgctggatcg gggccctagc ttcaaaccct   18660
actccggcac cgcctacaac agtctggccc ccaagggagc acccaacact tgtcagtgga   18720
catataaagc cgatggtgaa actgccacag aaaaaaccta tacatatgga aatgcacccg   18780
tgcagggcat taacatcaca aaagatggta ttcaacttgg aactgacacc gatgatcagc   18840
caatctacgc agataaaacc tatcagcctg aacctcaagt gggtgatgct gaatggcatg   18900
acatcactgg tactgatgaa agtatggag gcagagctct taagcctgat accaaaatga   18960
agccttgtta tggttctttt gccaagccta ctaataaaga aggaggtcag gcaaatgtga   19020
aaacaggaac aggcactact aaagaatatg acatagacat ggctttcttt gacaacagaa   19080
gtgcggctgc tgctggccta gctccagaaa ttgttttgta tactgaaaat gtggatttgg   19140
aaactccaga tacccatatt gtatacaaag caggcacaga tgacagcagc tcttctatta   19200
atttgggtca gcaagccatg cccaacagac ctaactacat tggtttcaga gacaacttta   19260
tcgggctcat gtactacaac agcactggca atatgggggt gctggccggt caggcttctc   19320
agctgaatgc tgtggttgac ttgcaagaca gaaacaccga gctgtcctac cagctcttgc   19380
ttgactctct gggtgacaga accggtatt tcagtatgtg gaatcaggcg gtggacagct   19440
atgatcctga tgtgcgcatt attgaaaatc atggtgtgga ggatgaactt cccaactatt   19500
gtttccctct ggatgctgtt ggcagaacag atacttatca gggaattaag gctaatggaa   19560
ctgatcaaac cacatggacc aaagatgaca gtgtcaatga tgctaatgag ataggcaagg   19620
gtaatccatt cgccatggaa atcaacatcc aagccaacct gtggaggaac ttcctctacg   19680
ccaacgtggc cctgtacctg cccgactctt acaagtacac gccggccaat gttaccctgc   19740
ccaccaacac caacacctac gattacatga acggccgggt ggtggcgccc tcgctggtgg   19800
actcctacat caacatcggg gcgcgctggt cgctggatcc catggacaac gtgaacccct   19860
tcaaccacca ccgcaatgcg gggctgcgct accgctccat gctcctgggc aacgggcgct   19920
acgtgccctt ccacatccag gtgcccccaga aattttttcgc catcaagagc ctcctgctcc   19980
tgcccgggtc ctacacctac gagtggaact tccgcaagga cgtcaacatg atcctgcaga   20040
gctccctcgg caacgacctg cgcacggacg gggcctccat ctccttcacc agcatcaacc   20100
tctacgccac cttcttcccc atggcgcaca cacggcctc cacgctcgag gccatgctgc   20160
gcaacgacac caacgaccag tccttcaacg actacctctc ggcggccaac atgctctacc   20220
ccatcccggc caacgccacc aacgtgccca tctccatccc ctcgcgcaac tgggccgcct   20280
tccgcggctg gtccttcacg cgtctcaaga ccaaggagac gccctcgctg ggctccgggt   20340
tcgaccccta cttcgtctac tcgggctcca tccctacct cgacggcacc ttctacctca   20400
accacacctt caagaaggtc tccatcaccc tcgactcctc cgtcagctgg cccggcaacg   20460
accggctcct gacgcccaac gagttcgaaa tcaagcgcac cgtcgacggc gagggctaca   20520
acgtggccca gtgcaacatg accaaggact ggttcctggt ccagatgctg ccccactaca   20580
acatcggcta ccagggcttc tacgtgcccg agggctacaa ggaccgcatg tactccttct   20640
tccgcaactt ccagcccatg agccgccagg tggtggacga ggtcaactac aaggactacc   20700
aggccgtcac cctggcctac cagcacaaca actcgggctt cgtcggctac ctcgcgccca   20760
```

```
ccatgcgcca gggccagccc taccccgcca actaccccta cccgctcatc ggcaagagcg    20820
ccgtcaccag cgtcacccag aaaaagttcc tctgcgacag ggtcatgtgg cgcatcccct    20880
tctccagcaa cttcatgtcc atgggcgcgc tcaccgacct cggccagaac atgctctatg    20940
ccaactccgc ccacgcgcta gacatgaatt tcgaagtcga ccccatggat gagtccaccc    21000
ttctctatgt tgtcttcgaa gtcttcgacg tcgtccgagt gcaccagccc caccgcggcg    21060
tcatcgaggc cgtctacctg cgcacccccct tctcggccgg taacgccacc acctaagctc    21120
ttgcttcttg caagccatgg ccgcgggctc cggcgagcag gagctcaggg ccatcatccg    21180
cgacctgggc tgcgggccct acttcctggg caccttcgat aagcgcttcc cgggattcat    21240
ggccccgcac aagctggcct cgccatcgt caacacggcc ggccgcgaga ccggggggcga    21300 gcactggctg gccttcgcct ggaacccgcg ctcgaacacc tgctacctct tcgaccccct    21360
cgggttctcg gacgagcgcc tcaagcagat ctaccagttc gagtacgagg gcctgctgcg    21420
ccgcagcgcc ctggccaccg aggaccgctg cgtcaccctg aaaagtcca cccagaccgt    21480 gcagggtccg cgctcggccg cctgcgggct cttctgctgc atgttcctgc acgccttcgt    21540
gcactggccc gaccgcccca tggacaagaa ccccaccatg aacttgctga cggggggtgcc    21600 caacggcatg ctccagtcgc cccaggtgga acccacccctg cgccgcaacc aggaggcgct    21660
ctaccgcttc ctcaactccc actccgccta ctttcgctcc caccgcgcgc gcatcgagaa    21720
ggccaccgcc ttcgaccgca tgaatcaaga catgtaaacc gtgtgtgtat gttaaatgtc    21780
tttaataaac agcactttca tgttacacat gcatctgaga tgatttattt agaaatcgaa    21840
agggttctgc cgggtctcgg catggcccgc gggcagggac acgttgcgga actggtactt    21900
ggccagccac ttgaactcgg ggatcagcag tttgggcagc ggggtgtcgg ggaaggagtc    21960
ggtccacagc ttccgcgtca gttgcagggc gcccagcagg tcgggcgcgg agatcttgaa    22020
atcgcagttg ggacccgcgt tctgcgcgcg ggagttgcgg tacacggggt tgcagcactg    22080
gaacaccatc agggccgggt gcttcacgct cgccagcacc gtcgcgtcgg tgatgctctc    22140
cacgtcgagg tcctcggcgt tggccatccc gaagggggtc atcttgcagg tctgccttcc    22200
catggtgggc acgcacccgg gcttgtggtt gcaatcgcag tgcaggggga tcagcatcat    22260
ctgggcctgg tcggcgttca tccccgggta catggccttc atgaaagcct ccaattgcct    22320
gaacgcctgc tgggccttgg ctccctcggt gaagaagacc ccgcaggact tgctagagaa    22380
ctggttggtg gcgcacccgg cgtcgtgcac gcagcagcgc gcgtcgttgt tggccagctg    22440
caccacgctg cgccccagc ggttctgggt gatcttggcc cggtcggggt tctccttcag    22500
cgcgcgctgc ccgttctcgc tcgccacatc catctcgatc atgtgctcct tctggatcat    22560
ggtggtcccg tgcaggcacc gcagcttgcc ctcggcctcg gtgcacccgt gcagccacag    22620
cgcgcacccg gtgcactccc agttcttgtg ggcgatctgg gaatgcgcgt gcacgaagcc    22680
ctgcaggaag cggcccatca tggtggtcag ggtcttgttg ctagtgaagg tcagcggaat    22740
gccgcggtgc tcctcgttga tgtacaggtg gcagatgcgg cggtacacct cgccctgctc    22800
gggcatcagc tggaagttgg ctttcaggtc ggtctccacg cggtagcggt ccatcagcat    22860
agtcatgatt tccatacccct ctcccaggc cgagacgatg gcaggctca tagggttctt    22920 caccatcatc ttagcgctag cagccgcggc caggggtcg ctctcgtcca gggtctcaaa    22980
gctccgcttg ccgtccttct cggtgatccg caccgggggg tagctgaagc ccacggccgc    23040
cagctcctcc tcggcctgtc tttcgtcctc gctgtcctgg ctgacgtcct gcaggaccac    23100
atgcttggtc ttgcggggtt tcttcttggg cggcagcggc ggcggagatg ttggagatgg    23160
```

```
cgaggggag   cgcgagttct   cgctcaccac   tactatctct   tcctcttctt   ggtccgaggc   23220
cacgcggcgg   taggtatgtc   tcttcggggg   cagaggcgga   ggcgacgggc   tctcgccgcc   23280
gcgacttggc   ggatggctgg   cagagcccct   tccgcgttcg   ggggtgcgct   cccggcggcg   23340
ctctgactga   cttcctccgc   ggccggccat   tgtgttctcc   tagggaggaa   caacaagcat   23400
ggagactcag   ccatcgccaa   cctcgccatc   tgccccacc    gccgacgaga   agcagcagca   23460
gcagaatgaa   agcttaaccg   ccccgccgcc   cagccccgcc   acctccgacg   cggccgtccc   23520
agacatgcaa   gagatggagg   aatccatcga   gattgacctg   ggctatgtga   cgcccgcgga   23580
gcacgaggag   gagctggcag   tgcgcttttc   acaagaagag   atacaccaag   aacagccaga   23640
gcaggaagca   gagaatgagc   agagtcaggc   tgggctcgag   catgacggcg   actacctcca   23700
cctgagcggg   gggaggacg    cgctcatcaa   gcatctggcc   cggcaggcca   ccatcgtcaa   23760
ggatgcgctg   ctcgaccgca   ccgaggtgcc   cctcagcgtg   gaggagctca   gccgcgccta   23820
cgagttgaac   ctcttctcgc   cgcgcgtgcc   cccaagcgc    cagcccaatg   gcacctgcga   23880
gcccaacccg   cgcctcaact   tctacccggt   cttcgcggtg   cccgaggccc   tggccaccta   23940
ccacatcttt   ttcaagaacc   aaaagatccc   cgtctcctgc   cgcgccaacc   gcacccgcgc   24000
cgacgccctt   ttcaacctgg   gtcccggcgc   ccgcctacct   gatatcgcct   ccttggaaga   24060
ggttcccaag   atcttcgagg   gtctgggcag   cgacgagact   cgggccgcga   acgtctgca   24120
aggagaagga   ggagagcatg   agcaccacag   cgccctggtc   gagttggaag   gcgacaacgc   24180
gcggctggcg   gtgctcaaac   gcacggtcga   gctgacccat   ttcgcctacc   cggctctgaa   24240
cctgccccc    aaagtcatga   gcgcggtcat   ggaccaggtg   ctcatcaagc   gcgcgtcgcc   24300
catctccgag   gacgagggca   tgcaagactc   cgaggagggc   aagcccgtgg   tcagcgacga   24360
gcagctggcc   cggtggctgg   gtcctaatgc   tagtccccag   agtttggaag   agcggcgcaa   24420
actcatgatg   gccgtggtcc   tggtgaccgt   ggagctggag   tgcctgcgcc   gcttcttcgc   24480
cgacgcggag   accctgcgca   aggtcgagga   gaacctgcac   tacctcttca   ggcacgggtt   24540
cgtgcgccag   gcctgcaaga   tctccaacgt   ggagctgacc   aacctggtct   cctacatggg   24600
catcttgcac   gagaaccgcc   tggggcagaa   cgtgctgcac   accaccctgc   gcggggaggc   24660
ccggcgcgac   tacatccgcg   actgcgtcta   cctctacctc   tgccacacct   ggcagacggg   24720
catgggcgtg   tggcagcagt   gtctggagga   gcagaacctg   aaagagctct   gcaagctcct   24780
gcagaagaac   ctcaagggtc   tgtggaccgg   gttcgacgag   cgcaccaccg   cctcggacct   24840
ggccgacctc   attttccccg   agcgcctcag   gctgacgctg   cgcaacgcc   tgcccgactt   24900
tatgagccaa   agcatgttgc   aaaactttcg   ctctttcatc   ctcgaacgct   ccggaatcct   24960
gcccgccacc   tgctccgcgc   tgccctcgga   cttcgtgccg   ctgaccttcc   gcgagtgccc   25020
cccgccgctg   tggagccact   gctacctgct   gcgcctggcc   aactacctgg   cctaccactc   25080
ggacgtgatc   gaggacgtca   gcggcgaggg   cctgctcgag   tgccactgcc   gctgcaacct   25140
ctgcacgccg   caccgctccc   tggcctgcaa   ccccagctg    ctgagcgaga   cccagatcat   25200
cggcaccttc   gagttgcaag   ggcccagcga   aggcgagggt   tcagccgcca   aggggggtct   25260
gaaactcacc   ccggggctgt   ggacctcggc   ctacttgcgc   aagttcgtgc   cgaggacta   25320
ccatcccttc   gagatcaggt   tctacgagga   ccaatcccat   ccgcccaagg   ccgagctgtc   25380
ggcctgcgtc   atcacccagg   gggcgatcct   ggcccaattg   caagccatcc   agaaatcccg   25440
ccaagaattc   ttgctgaaaa   agggccgcgg   ggtctaccct   gaccccagga   ccggtgagga   25500
```

```
gctcaacccc ggcttccccc aggatgcccc gaggaaacaa gaagctgaaa gtggagctgc  25560
cgcccgtgga ggatttggag gaagactggg agaacagcag tcaggcagag gaggaggaga  25620
tggaggaaga ctgggacagc actcaggcag aggaggacag cctgcaagac agtctggagg  25680
aagacgagga ggaggcagag gaggaggtgg aagaagcagc cgccgccaga ccgtcgtcct  25740
cggcggggga gaaagcaagc agcacggata ccatctccgc tccgggtcgg ggtcccgctc  25800
gaccacacag tagatgggac gagaccggac gattcccgaa ccccaccacc cagaccggta  25860
agaaggagcg gcagggatac aagtcctggc gggggcacaa aaacgccatc gtctcctgct  25920
tgcaggcctg cgggggcaac atctccttca cccggcgcta cctgctcttc caccgcgggg  25980
tgaactttcc ccgcaacatc ttgcattact accgtcacct ccacagcccc tactacttcc  26040
aagaagaggc agcagcagca gaaaaagacc agcagaaaac cagcagctag aaaatccaca  26100
gcggcggcag caggtggact gaggatcgcg gcgaacgagc cggcgcaaac ccgggagctg  26160
aggaaccgga tctttcccac cctctatgcc atcttccagc agagtcgggg gcaggagcag  26220
gaactgaaag tcaagaaccg ttctctgcgc tcgctcaccc gcagttgtct gtatcacaag  26280
agcgaagacc aacttcagcg cactctcgag gacgccgagg ctctcttcaa caagtactgc  26340
gcgctcactc ttaaagagta gcccgcgccc gcccagtcgc agaaaaggc gggaattacg  26400 tcacctgtgc ccttcgccct agccgcctcc acccatcatc atgagcaaag agattcccac  26460
gccttacatg tggagctacc agccccagat gggcctggcc gccggtgccg cccaggacta  26520
ctccacccgc atgaattggc tcagcgccgg gcccgcgatg atctcacggg tgaatgacat  26580
ccgcgcccac cgaaaccaga tactcctaga acagtcagcg ctcaccgcca cgccccgcaa  26640
tcacctcaat ccgcgtaatt ggcccgccgc cctggtgtac caggaaattc cccagcccac  26700
gaccgtacta cttccgcgag acgcccaggc cgaagtccag ctgactaact caggtgtcca  26760
gctggcgggc ggcgccaccc tgtgtcgtca ccgccccgct cagggtataa agcggctggt  26820
gatccggggc agaggcacac agctcaacga cgaggtggtg agctcttcgc tgggtctgcg  26880
acctgacgga gtcttccaac tcgccggatc ggggagatct tccttcacgc ctcgtcaggc  26940
cgtcctgact ttggagagtt cgtcctcgca gccccgctcg ggtggcatcg gcactctcca  27000
gttcgtggag gagttcactc cctcggtcta cttcaacccc ttctccggct cccccggcca  27060
ctacccggac gagttcatcc cgaacttcga cgccatcagc gagtcggtgg acggctacga  27120
ttgaatgtcc catggtggcg cagctgacct agctcggctt cgacacctgg accactgccg  27180
ccgcttccgc tgcttcgctc gggatctcgc cgagtttgcc tactttgagc tgcccgagga  27240
gcaccctcag ggcccggccc acggagtgcg gatcgtcgtc aagggggcc tcgactccca  27300 cctgcttcgg atcttcagcc agcgtccgat cctggtcgag cgcgagcaag acagaccct  27360 tctgactctg tactgcatct gcaaccaccc cggcctgcat gaaagtcttt gttgtctgct  27420
gtgtactgag tataataaaa gctgagatca gcgactactc cggacttccg tgtgttcctg  27480
aatccatcaa ccagtctttg ttcttcaccg ggaacgagac cgagctccag ctccagtgta  27540
agccccacaa gaagtacctc acctggctgt tccagggctc cccgatcgcc gttgtcaacc  27600
actgcgacaa cgacggagtc ctgctgagcg ccctgccaa ccttactttt tccacccgca  27660
gaagcaagct ccagctcttc caacccttcc tccccgggac ctatcagtgc gtctcgggac  27720
cctgccatca caccttccac ctgatcccga ataccacagc gtcgctcccc gctactaaca  27780
accaaactaa cctccaccaa cgccaccgtc gcgacctttc tgaatctaat actaccccc  27840 acaccggagg tgagctccga ggtcaaccaa cctctgggat ttactacggc ccctgggagg  27900
```

```
tggtttgggtt aatagcgcta ggcctagttg cgggtgggct tttggttctc tgctacctat   27960
acctcccttg ctgttcgtac ttagtggtgc tgtgttgctg gtttaagaaa tggggaagat   28020
caccctagtg agctgcggtg cgctggtggc ggtgttgctt tcgattgtgg gactgggcgg   28080
tgcggctgta gtgaaggaga aggccgatcc ctgcttgcat ttcaatccca acaaatgcca   28140
gctgagtttt cagcccgatg gcaatcggtg cgcggtactg atcaagtgcg gatgggaatg   28200
cgagaacgtg agaatcgagt acaataacaa gactcggaac aatactctcg cgtccgtgtg   28260
gcagcccggg gaccccgagt ggtacaccgt ctctgtcccc ggtgctgacg gctcccgcg    28320 caccgtgaat aatactttca tttttgcgca catgtgcgac acggtcatgt ggatgagcaa   28380
gcagtacgat atgtggcccc ccacgaagga gaacatcgtg gtcttctcca tcgcttacag   28440
cctgtgcacg gcgctaatca ccgctatcgt gtgcctgagc attcacatgc tcatcgctat   28500
tcgccccaga aataatgccg aaaaagaaaa acagccataa cgttttttt cacaccttt    28560 tcagaccatg gcctctgtta aattttgct tttatttgcc agtctcattg ccgtcattca   28620
tggaatgagt aatgagaaaa ttactattta cactggcact aatcacacat tgaaaggtcc   28680
agaaaaagcc acagaagttt catggtattg ttattttaat gaatcagatg tatctactga   28740
actctgtgga aacaataaca aaaaaaatga gagcattact ctcatcaagt ttcaatgtgg   28800
atctgactta accctaatta acatcactag agactatgta ggtatgtatt atggaactac   28860
agcaggcatt tcggacatgg aattttatca gtttctgtg tctgaaccca ccacgcctag   28920
aatgaccaca accacaaaaa ctacacctgt taccactatg cagctcacta ccaataacat   28980
ttttgccatg cgtcaaatgg tcaacaatag cactcaaccc accccaccca gtgaggaaat   29040
tcccaaatcc atgattggca ttattgttgc tgtagtggtg tgcatgttga tcatcgcctt   29100
gtgcatggtg tactatgcct tctgctacag aaagcacaga ctgaacgaca agctggaaca   29160
cttactaagt gttgaatttt aattttttag aaccatgaag atcctaggcc ttttaatttt   29220
ttctatcatt acctctgctc tatgcaattc tgacaatgag gacgttactg tcgttgtcgg   29280
atcaaattat acactgaaag gtccagcgaa gggtatgctt tcgtggtatt gctattttgg   29340
atctgacact acagaaactg aattatgcaa tcttaagaat ggcaaaattc aaaattctaa   29400
aattaacaat tatatatgca atggtactga tctgatactc ctcaatatca cgaaatcata   29460
tgctggcagt tacacctgcc ctggagatga tgctgacagt atgatttttt acaaagtaac   29520
tgttgttgat cccactactc cacctccacc caccacaact actcacacca cacacacaga   29580
tcaaaccgca gcagaggagg cagcaaagtt agccttgcag gtccaagaca gttcatttgt   29640
tggcattacc cctacacctg atcagcggtg tccggggctg ctagtcagcg gcattgtcgg   29700
tgtgctttcg ggattagcag tcataatcat ctgcatgttc atttttgctt gctgctatag   29760
aaggctttac cgacaaaaat cagacccact gctgaacctc tatgtttaat tttttccaga   29820
gtcatgaagg cagttagcgc tctagttttt tgttctttga ttggcattgt tttttgcaat   29880
cctattccta aagttagctt tattaaagat gtgaatgtta ctgaggggg caatgtgaca    29940 ctggtaggtg tagagggtgc tgaaaacacc acctggacaa aataccacct caatgggtgg   30000
aaagatattt gcaattggag tgtattagtt tatacatgtg agggagttaa tcttaccatt   30060
gtcaatgcca cctcagctca aatggtaga attcaaggac aaagtgtcag tgtatctaat   30120
gggtatttta cccaacatac ttttatctat gacgttaaag tcataccact gcctacgcct   30180
agcccaccta gcactaccac acagacaacc cacactacac agacaaccac atacagtaca   30240
```

```
ttaaatcagc ctaccaccac tacagcagca gaggttgcca gctcgtctgg ggtccgagtg    30300 gcattttga tgttggcccc atctagcagt cccactgcta gtaccaatga gcagactact    30360
gaatttttgt ccactgtcga gagccacacc acagctacct ccagtgcctt ctctagcacc    30420
gccaatctct cctcgctttc tctacacca atcagtcccg ctactactcc tagccccgct    30480
cctcttccca ctcccctgaa gcaaacagac ggcggcatgc aatggcagat caccctgctc    30540
attgtgatcg ggttggtcat cctggccgtg ttgctctact acatcttctg ccgccgcatt    30600
cccaacgcgc accgcaagcc ggtctacaag cccatcattg tcgggcagcc ggagccgctt    30660
caggtggaag ggggtctaag gaatcttctc ttctctttta cagtatggtg attgaactat    30720
gattcctaga caattcttga tcactattct tatctgcctc ctccaagtct gtgccaccct    30780
cgctctggtg gccaacgcca gtccagactg tattgggccc ttcgcctcct acgtgctctt    30840
tgccttcacc acctgcatct gctgctgtag catagtctgc ctgcttatca ccttcttcca    30900
gttcattgac tggatctttg tgcgcatcgc ctacctgcgc caccaccccc agtaccgcga    30960
ccagcgagtg gcgcggctgc tcaggctcct ctgataagca tgcgggctct gctacttctc    31020
gcgcttctgc tgttagtgct ccccccgtcc gtcgacccc ggtccccac ccagtccccc    31080 gaggaggtcc gcaaatgcaa attccaagaa ccctggaaat tcctcaaatg ctaccgccaa    31140
aaatcagaca tgcatcccag ctggatcatg atcattggga tcgtgaacat tctggcctgc    31200
accctcatct cctttgtgat ttaccccttgc tttgactttg gttggaactc gccagaggcg    31260
ctctatctcc cgcctgaacc tgacacacca ccacagcaac ctcaggcaca cgcactacca    31320
ccactacagc ctaggccaca atacatgccc atattagact atgaggccga gccacagcga    31380
cccatgctcc ccgctattag ttacttcaat ctaaccggcg gagatgactg acccactggc    31440
caacaacaac gtcaacgacc ttctcctgga catggacggc cgcgcctcgg agcagcgact    31500
cgcccaactt cgcattcgcc agcagcagga gagagccgtc aaggagctgc aggatgcggt    31560
ggccatccac cagtgcaaga gaggcatctt ctgcctggtg aaacaggcca agatcctcca    31620
cgaggtcact ccaaacgacc atcgcctctc ctacgagctc ctgcagcagc gccagaagtt    31680
cacctgcctg gtcggagtca accccatcgt catcacccag cagtctggcg ataccaaggg    31740
gtgcatccac tgctcctgcg actccccga ctgcgtccac actctgatca agaccctctg    31800
cggcctccgc gacctcctcc ccatgaacta atcaccccct tatccagtga aataaagatc    31860
atattgatga tgatttttaca gaaataaaaa ataatcattt gatttgaaat aaagatacaa    31920
tcatattgat gatttgagtt taacaaaaaa ataaagaatc acttacttga aatctgatac    31980
caggtctctg tccatgtttt ctgccaacac cacttcactc ccctcttccc agctctggta    32040
ctgcaggccc cggcgggctg caaacttcct ccacacgctg aaggggatgt caaattcctc    32100
ctgtccctca atcttcattt tatcttctat cagatgtcca aaaagcgcgt ccgggtggat    32160
gatgacttcg accccgtcta cccctacgat gcagacaacg caccgaccgt gcccttcatc    32220 aacccccct tcgtctcttc agatggattc caagagaagc cctgggggt gttgtccctg    32280 cgactggccg accccgtcac caccaagaac ggggaaatca ccctcaagct gggagagggg    32340
gtggacctcg attcctcggg aaaactcatc tccaacacgg ccaccaaggc cgccgcccct    32400
ctcagttttt ccaacaacac catttccctt aacatggatc accccttta cactaaagat    32460 ggaaaattat ccttacaagt ttctccacca ttaaatatac tgagaacaag cattctaaac    32520
acactagctt taggttttgg atcaggttta ggactccgtg ctctgccttt ggcagtacag    32580
ttagtctctc cacttacatt tgatactgat ggaaacataa agcttacctt agacagaggt    32640
```

```
ttgcatgtta caacaggaga tgcaattgaa agcaacataa gctgggctaa aggtttaaaa    32700
tttgaagatg gagccatagc aaccaacatt ggaaatgggt tagagtttgg aagcagtagt    32760
acagaaacag gtgttgatga tgcttaccca atccaagtta aacttggatc tggccttagc    32820
tttgacagta caggagccat aatggctggt aacaaagaag acgataaact cactttgtgg    32880
acaacacctg atccatcacc aaactgtcaa atactcgcag aaaatgatgc aaaactaaca    32940
ctttgcttga ctaaatgtgg tagtcaaata ctggccactg tgtcagtctt agttgtagga    33000
agtggaaacc taaaccccat tactggcacc gtaagcagtg ctcaggtgtt tctacgtttt    33060
gatgcaaacg gtgttctttt aacagaacat tctacactaa aaaatactg ggggtatagg    33120 cagggagata gcatagatgg cactccatat accaatgctg taggattcat gcccaattta    33180
aaagcttatc caaagtcaca aagttctact actaaaaata atatagtagg gcaagtatac    33240
atgaatggag atgtttcaaa acctatgctt ctcactataa ccctcaatgg tactgatgac    33300
agcaacagta catattcaat gtcattttca tacacctgga ctaatggaag ctatgttgga    33360
gcaacatttg gggctaactc ttataccttc tcatacatcg cccaagaatg aacactgtat    33420
cccaccctgc atgccaaccc ttcccacccc actctgtgga acaaactctg aaacacaaaa    33480
taaaataaag ttcaagtgtt ttattgattc aacagtttta caggattcga gcagttattt    33540
ttcctccacc ctcccaggac atggaataca ccaccctctc cccccgcaca gccttgaaca    33600
tctgaatgcc attggtgatg gacatgcttt tggtctccac gttccacaca gtttcagagc    33660
gagccagtct cgggtcggtc agggagatga aaccctccgg gcactcccgc atctgcacct    33720
cacagctcaa cagctgagga ttgtcctcgg tggtcgggat cacggttatc tggaagaagc    33780
agaagagcgg cggtgggaat catagtccgc gaacgggatc ggccggtggt gtcgcatcag    33840
gccccgcagc agtcgctgcc gccgccgctc cgtcaagctg ctgctcaggg ggtccgggtc    33900
cagggactcc ctcagcatga tgcccacggc cctcagcatc agtcgtctgg tgcggcgggc    33960
gcagcagcgc atgcggatct cgctcaggtc gctgcagtac gtgcaacaca gaaccaccag    34020
gttgttcaac agtccatagt tcaacacgct ccagccgaaa ctcatcgcgg gaaggatgct    34080
acccacgtgg ccgtcgtacc agatcctcag gtaaatcaag tggtgccccc tccagaacac    34140
gctgcccacg tacatgatct ccttgggcat gtggcggttc accacctccc ggtaccacat    34200
caccctctgg ttgaacatgc agcccggat gatcctgcgg aaccacaggg ccagcaccgc    34260
cccgcccgcc atgcagcgaa gagaccccgg gtcccggcaa tggcaatgga ggacccaccg    34320
ctcgtacccg tggatcatct gggagctgaa caagtctatg ttggcacagc acaggcatat    34380
gctcatgcat ctcttcagca ctctcaactc ctcggggtc aaaaccatat cccagggcac    34440
ggggaactct tgcaggacag cgaacccgc agaacagggc aatcctcgca cagaacttac    34500
attgtgcatg gacagggtat cgcaatcagg cagcaccggg tgatcctcca ccagagaagc    34560
gcgggtctcg gtctcctcac agcgtggtaa gggggccggc cgatacgggt gatgcggga    34620 cgcggctgat cgtgttcgcg accgtgtcat gatgcagttg ctttcggaca ttttcgtact    34680
tgctgtagca gaacctggtc cgggcgctgc acaccgatcg ccggcggcgg tctcggcgct    34740
tggaacgctc ggtgttgaaa ttgtaaaaca gccactctct cagaccgtgc agcagatcta    34800
gggcctcagg agtgatgaag atcccatcat gcctgatggc tctgatcaca tcgaccaccg    34860
tggaatgggc cagacccagc cagatgatgc aattttgttg ggtttcggtg acggcggggg    34920
agggaagaac aggaagaacc atgattaact tttaatccaa acggtctcgg agtacttcaa    34980
```

```
aatgaagatc gcggagatgg cacctctcgc ccccgctgtg ttggtggaaa ataacagcca    35040
ggtcaaaggt gatacggttc tcgagatgtt ccacggtggc ttccagcaaa gcctccacgc    35100
gcacatccag aaacaagaca atagcgaaag cgggagggtt ctctaattcc tcaatcatca    35160
tgttacactc ctgcaccatc cccagataat tttcattttt ccagccttga atgattcgaa    35220
ctagttcctg aggtaaatcc aagccagcca tgataaagag ctcgcgcaga gcgccctcca    35280
ccggcattct taagcacacc ctcataattc aagatattc tgctcctggt tcacctgcag     35340
cagattgaca agcggaatat caaaatctct gccgcgatcc ctgagctcct ccctcagcaa    35400
taactgtaag tactctttca tatcctctcc gaaattttta gccataggac caccaggaat    35460
aagattaggg caagccacag tacagataaa ccgaagtcct ccccagtgag cattgccaaa    35520
tgcaagactg ctataagcat gctggctaga cccggtgata tcttccagat aactggacag    35580
aaaatcgccc aggcaatttt taagaaaatc aacaaaagaa aaatcctcca ggtggacgtt    35640
tagagcctcg ggaacaacga tgaagtaaat gcaagcggtg cgttccagca tggttagtta    35700
gctgatctgt agaaaaaaca aaaatgaaca ttaaaccatg ctagcctggc gaacaggtgg    35760
gtaaatcgtt ctctccagca ccaggcaggc cacggggtct ccggcgcgac cctcgtaaaa    35820
attgtcgcta tgattgaaaa ccatcacaga gagacgttcc cggtggccgg cgtgaatgat    35880
tcgacaagat gaatacaccc ccggaacatt ggcgtccgcg agtgaaaaaa agcgcccgag    35940
gaagcaataa ggcactacaa tgctcagtct caagtccagc aaagcgatgc catgcggatg    36000
aagcacaaaa ttctcaggtg cgtacaaaat gtaattactc ccctcctgca caggcagcaa    36060
agcccccgat ccctccaggt acacatacaa agcctcagcg tccatagctt accgagcagc    36120
agcacacaac aggcgcaaga gtcagagaaa ggctgagctc taacctgtcc acccgctctc    36180
tgctcaatat atagcccaga tctacactga cgtaaaggcc aaagtctaaa ataccccgcc    36240
aaataatcac acacgcccag cacacgccca gaaaccggtg acacactcaa aaaaatacgc    36300
gcacttcctc aaacgcccaa aactgccgtc atttccgggt tcccacgcta cgtcatcaaa    36360
acacgacttt caaattccgt cgaccgttaa aaacgtcacc cgccccgccc ctaacggtcg    36420
cccgtctctc agccaatcag cgccccgcat ccccaaattc aaacacctca tttgcatatt    36480
aacgcgcaca aaaagtttga ggtatattat tgatgatgg                          36519
```

<210> SEQ ID NO 11
<211> LENGTH: 31867
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 11

```
ccatcttcaa taatatacct caaacttttt gtgcgcgtta atatgcaaat gaggcgtttg      60
aatttgggga ggaagggcgg tgattggtcg agggatgagc gaccgttagg ggcggggcga     120
gtgacgtttt gatgacgtgg ttgcgaggag gagccagttt gcaagttctc gtgggaaaag    180
tgacgtcaaa cgaggtgtgg tttgaacacg gaaatactca attttcccgc gctctctgac    240
aggaaatgag gtgtttctgg gcggatgcaa gtgaaacgg gccattttcg cgcgaaaact     300
gaatgaggaa gtgaaaatct gagtaatttc gcgtttatgg cagggaggag tatttgccga    360
gggccgagta gactttgacc gattacgtgg gggtttcgat taccgtgttt ttcacctaaa    420
tttccgcgta cggtgtcaaa gtccggtgtt tttacgtagg tgtcagctga tcgccagggt    480
```

```
atttaaacct gcgctctcca gtcaagaggc cactcttgag tgccagcgag aagagttttc    540
tcctccgcgc cgcgagtcag atctacactt tgaaagtagg gataacaggg taatgacatt    600
gattattgac tagttgttaa tagtaatcaa ttacggggtc attagttcat agcccatata    660
tggagttccg cgttacataa cttacggtaa atggcccgcc tggctgaccg cccaacgacc    720
cccgcccatt gacgtcaata atgacgtatg ttcccatagt aacgccaata gggactttcc    780
attgacgtca atgggtggag tatttacggt aaactgccca cttggcagta catcaagtgt    840
atcatatgcc aagtccgccc cctattgacg tcaatgacgg taaatggccc gcctggcatt    900
atgcccagta catgacctta cgggactttc ctacttggca gtacatctac gtattagtca    960
tcgctattac catggtgatg cggttttggc agtacaccaa tgggcgtgga tagcggtttg   1020
actcacgggg atttccaagt ctccacccca ttgacgtcaa tgggagtttg ttttggcacc   1080
aaaatcaacg ggactttcca aatgtcgta ataaccccgc cccgttgacg caaatgggcg   1140
gtaggcgtgt acggtgggag gtctatataa gcagagctcg tttagtgaac cgtcagatcg   1200
cctggaacgc atccacgct gttttgacct ccatagaaga cagcgatcgc gccaccatgg   1260
tgagcaaggg cgaggagctg ttcaccgggg tggtgcccat cctggtcgag ctggacggcg   1320
acgtaaacgg ccacaagttc agcgtgtccg gcgagggcga gggcgatgcc acctacggca   1380
agctgaccct gaagttcatc tgcaccaccg gcaagctgcc cgtgccctgg cccaccctcg   1440
tgaccaccct gacctacggc gtgcagtgct tcagccgcta ccccgaccac atgaagcagc   1500
acgacttctt caagtccgcc atgcccgaag gctacgtcca ggagcgcacc atcttcttca   1560
aggacgacgg caactacaag acccgcgccg aggtgaagtt cgagggcgac accctggtga   1620
accgcatcga gctgaagggc atcgacttca aggaggacgg caacatcctg gggcacaagc   1680
tggagtacaa ctacaacagc cacaacgtct atatcatggc cgacaagcag aagaacggca   1740
tcaaggtgaa cttcaagatc cgccacaaca tcgaggacgg cagcgtgcag ctcgccgacc   1800
actaccagca gaacaccccc atcggcgacg gccccgtgct gctgcccgac aaccactacc   1860
tgagcaccca gtccgccctg agcaaagacc ccaacgagaa gcgcgatcac atggtcctgc   1920
tggagttcgt gaccgccgcc gggatcactc tcggcatgga cgagctttac aagtagtgag   1980
tttaaactcc catttaaatg tgagggttaa tgcttcgagc agacatgata agatacattg   2040
atgagtttgg acaaaccaca actagaatgc agtgaaaaaa atgctttatt tgtgaaattt   2100
gtgatgctat tgctttattt gtaaccatta taagctgcaa taaacaagtt aacaacaaca   2160
attgcattca ttttatgttt caggttcagg gggagatgtg ggaggttttt taaagcaagt   2220
aaaacctcta caaatgtggt aaaataacta taacggtcct aaggtagcga gtgagtagtg   2280
ttctggggcg ggggaggacc tgcatgaggg ccagaataac tgaaatctgt gcttttctgt   2340
gtgttgcagc agcatgagcg gaagcggctc cttgaggga ggggtattca gcccttatct   2400
gacggggcgt ctcccctcct gggcgggagt gcgtcagaat gtgatgggat ccacggtgga   2460
cggccggccc gtgcagcccg cgaactcttc aaccctgacc tatgcaaccc tgagctcttc   2520
gtcgttggac gcagctgccg ccgcagctgc tgcatctgcc gccagcgccg tgcgcggaat   2580
ggccatgggc gccggctact acggcactct ggtggccaac tcgagttcca ccaataatcc   2640
cgccagcctg aacgaggaga agctgttgct gctgatggcc cagctcgagg ccttgaccca   2700
gcgcctgggc gagctgaccc agcaggtggc tcagctgcag gagcagacgc gggccgcggt   2760
tgccacggtg aaatccaaat aaaaaatgaa tcaataaata aacggagacg ttgttgatt   2820
ttaacacaga gtctgaatct ttatttgatt tttcgcgcgc ggtaggccct ggaccaccgg   2880
```

```
tctcgatcat tgagcacccg gtggatcttt tccaggaccc ggtagaggtg ggcttggatg    2940
ttgaggtaca tgggcatgag cccgtcccgg gggtggaggt agctccattg cagggcctcg    3000
tgctcggggg tggtgttgta aatcacccag tcatagcagg ggcgcagggc atggtgttgc    3060
acaatatctt tgaggaggag actgatggcc acgggcagcc cttttggtgta ggtgtttaca    3120
aatctgttga gctgggaggg atgcatgcgg ggggagatga ggtgcatctt ggcctggatc    3180
ttgagattgg cgatgttacc gcccagatcc cgcctggggt tcatgttgtg caggaccacc    3240
agcacggtgt atccggtgca cttggggaat ttatcatgca acttggaagg gaaggcgtga    3300
aagaatttgg cgacgccttt gtgcccgccc aggttttcca tgcactcatc catgatgatg    3360
gcgatgggcc cgtgggcggc ggcctgggca agacgtttc ggggtcgga cacatcatag     3420
ttgtggtcct gggtgaggtc atcataggcc atttttaatga atttggggcg gagggtgccg    3480
gactggggga caaaggtacc ctcgatcccg ggggcgtagt tcccctcaca gatctgcatc    3540
tcccaggctt tgagctcgga gggggggatc atgtccacct gcggggcgat aaagaacacg    3600
gtttccgggg cggggagat gagctggggcc gaaagcaagt tccggagcag ctgggacttg     3660
ccgcagccgg tggggccgta gatgaccccg atgaccggct gcaggtggta gttgagggag    3720
agacagctgc cgtcctcccg gaggagggg gccacctcgt tcatcatctc gcgcacgtgc     3780
atgttctcgc gcaccagttc cgccaggagg cgctctcccc ccagggatag gagctcctgg    3840
agcgaggcga agtttttcag cggcttgagt ccgtcggcca tgggcatttt ggagagggtt    3900
tgttgcaaga gttccaggcg gtcccagagc tcggtgatgt gctctacggc atctcgatcc    3960
agcagacctc ctcgtttcgc gggttgggac ggctgcggga gtagggcacc agacgatggg    4020
cgtccagcgc agccagggtc cggtccttcc agggtcgcag cgtccgcgtc agggtggtct    4080
ccgtcacggt gaagggtgc gcgccgggct gggcgcttgc gaggtgcgc ttcaggctca      4140
tccggctggt cgaaaaccgc tcccgatcgg cgccctgcgc gtcggccagg tagcaattga    4200
ccatgagttc gtagttgagc gcctcggccg cgtggccttt ggcgcggagc ttaccttttgg   4260
aagtctgccc gcaggcggga cagaggaggg acttgagggc gtagagcttg ggggcgagga    4320
agacggactc gggggcgtag gcgtccgcgc gcagtgggc gcagacggtc tcgcactcca     4380
cgagccaggt gaggtcgggc tggtcggggt caaaaaccag tttcccgccg ttcttttttga   4440
tgcgtttctt acctttggtc tccatgagct cgtgtccccg ctgggtgaca aagaggctgt    4500
ccgtgtcccc gtagaccgac tttatgggcc ggtcctcgag cggtgtgccg cggtcctcct    4560
cgtagaggaa ccccgcccac tccgagacga aagcccgggt ccaggccagc acgaaggagg    4620
ccacgtggga cgggtagcgg tcgttgtcca ccagcgggtc cacctttttcc agggtatgca   4680
aacacatgtc cccctcgtcc acatccagga aggtgattgg cttgtaagtg taggccacgt    4740
gaccgggggt cccggccggg ggggtataaa agggtgcggg tccctgctcg tcctcactgt    4800
cttccggatc gctgtccagg agcgccagct gttggggtag gtattccctc tcgaaggcgg    4860
gcatgacctc ggcactcagg ttgtcagttt ctagaaacga ggaggatttg atattgacgg    4920
tgccggcgga gatgcctttc aagagcccct cgtccatctg gtcagaaaag acgatctttt    4980
tgttgtcgag cttggtggcg aaggagccgt agagggcgtt ggagaggagc ttggcgatgg    5040
agcgcatggt ctggtttttt tccttgtcgg cgcgctcctt ggcggcgatg ttgagctgca    5100
cgtactcgcg cgccacgcac ttccattcgg ggaagacggt ggtcagctcg tcgggcacga    5160
ttctgacctg ccagccccga ttatgcaggg tgatgaggtc cacactggtg gccacctcgc    5220
```

```
cgcgcagggg ctcattagtc cagcagaggc gtccgccctt gcgcgagcag aagggggggca    5280 gggggtccag catgacctcg tcggggggt cggcatcgat ggtgaagatg ccgggcagga      5340
ggtcggggtc aaagtagctg atggaagtgg ccagatcgtc cagggcagct tgccattcgc    5400
gcacggccag cgcgctctcg tagggactga ggggcgtgcc ccaggcatg ggatgggtaa     5460 gcgcggaggc gtacatgccg cagatgtcgt agacgtagag gggctcctcg aggatgccga    5520
tgtaggtggg gtagcagcgc ccccccgcgga tgctggcgcg cacgtagtca tacagctcgt   5580 gcgaggggc gaggagcccc gggcccaggt tggtgcgact gggcttttcg gcgcggtaga     5640
cgatctggcg gaaaatggca tgcgagttgg aggagatggt gggcctttgg aagatgttga    5700
agtgggcgtg gggcagtccg accgagtcgc ggatgaagtg ggcgtaggag tcttgcagct    5760
tggcgacgag ctcggcggtg actaggacgt ccagagcgca gtagtcgagg gtctcctgga    5820
tgatgtcata cttgagctgt cccttttgtt tccacagctc gcggttgaga aggaactctt    5880
cgcggtcctt ccagtactct tcagggggga acccgtcctg atctgcacgg taagagccta    5940
gcatgtagaa ctggttgacg gccttgtagg cgcagcagcc cttctccacg ggagggcgt     6000 aggcctgggc ggccttgcgc agggaggtgt gcgtgagggc gaaagtgtcc ctgaccatga    6060
ccttgaggaa ctggtgcttg aagtcgatat cgtcgcagcc cccctgctcc cagagctgga    6120
agtccgtgcg cttcttgtag gcggggttgg gcaaagcgaa agtaacatcg ttgaaggaga    6180
tcttgcccgc gcggggcata aagttgcgag tgatgcggaa aggttggggc acctcggccc    6240
ggttgttgat gacctgggcg gcgagcacga tctcgtcgaa gccgttgatg ttgtggccca    6300
cgatgtagag ttccacgaat cgcggacggc ccttgacgtg gggcagtttc ttgagctcct    6360
cgtaggtgag ctcgtcgggg tcgctgagcc cgtgctgctc gagcgcccag tcggcgagat    6420 ggggggttggc gcggaggaag gaagtccaga gatccacggc cagggcggtt tgcagacggt    6480
cccggtactg acggaactgc tgcccgacgg ccattttttc ggggtgacg cagtagaagg     6540 tgcgggggtc cccgtgccag cgatcccatt tgagctggag ggcgagatcg agggcgagct    6600
cgacgagccg gtcgtccccg gagagtttca tgaccagcat gaagggggacg agctgcttgc    6660 cgaaggaccc catccaggtg taggtttcca catcgtaggt gaggaagagc ctttcggtgc    6720
gaggatgcga gccgatgggg aagaactgga tctcctgcca ccaattggag gaatggctgt    6780
tgatgtgatg gaagtagaaa tgccgacggc gcgccgaaca ctcgtgcttg tgtttataca    6840
agcggccaca gtgctcgcaa cgctgcacgg gatgcacgtg ctgcacgagc tgtacctgag    6900 ttccttgac gaggaatttc agtgggaagt ggagtcgtgg cgcctgcatc tcgtgctgta     6960
ctacgtcgtg gtggtcggcc tggccctctt ctgcctcgat ggtggtcatg ctgacgagcc    7020
cgcgcgggag gcaggtccag acctcggcgc gagcgggtcg gagagcgagg acagggcgc     7080 gcaggccgga gctgtccagg gtcctgagac gctgcggagt caggtcagtg ggcagcggcg    7140
gcgcgcggtt gacttgcagg agttttccca gggcgcgcgg gaggtccaga tggtacttga    7200
tctccaccgc gccattggtg gcgacgtcga tggcttgcag gtcccgtgc ccctgggtg      7260 tgaccaccgt cccccgttc ttcttgggcg gctggggcga cggggcggt gcctcttcca      7320 tggttagaag cggcggcgag gacgcgcgcc gggcggcagg ggcggctcgg ggcccggagg    7380
caggggcggc aggggcacgt cggcgccgcg cgcgggtagg ttctggtact gcgcccggag    7440
aagactggcg tgagcgacga cgcgacggtt gacgtcctgg atctgacgcc tctgggtgaa    7500
ggccacggga cccgtgagtt tgaacctgaa agagagttcg acagaatcaa tctcggtatc    7560
gttgacggcg gcctgccgca ggatctcttg cacgtcgccc gagttgtcct ggtaggcgat    7620
```

-continued

```
ctcggtcatg aactgctcga tctcctcctc ttgaaggtct ccgcggccgg cgcgctccac   7680
ggtggccgcg aggtcgttgg agatgcggcc catgagctgc gagaaggcgt tcatgcccgc   7740
ctcgttccag acgcggctgt agaccacgac gccctcggga tcgcgggcgc gcatgaccac   7800
ctgggcgagg ttgagctcca cgtggcgcgt gaagaccgcg tagttgcaga ggcgctggta   7860
gaggtagttg agcgtggtgg cgatgtgctc ggtgacgaag aaatacatga tccagcggcg   7920
gagcggcatc tcgctgacgt cgcccagcgc ctccaaacgt tccatggcct cgtaaaagtc   7980
cacggcgaag ttgaaaaact gggagttgcg cgccgagacg gtcaactcct cctccagaag   8040
acggatgagc tcggcgatgg tggcgcgcac ctcgcgctcg aaggcccccg ggagttcctc   8100
cacttcctct tcttcctcct ccactaacat ctcttctact tcctcctcag gcggcagtgg   8160
tggcggggga gggggcctgc gtcgccggcg gcgcacgggc agacggtcga tgaagcgctc   8220
gatggtctcg ccgcgccggc gtcgcatggt ctcggtgacg gcgcgcccgt cctcgcgggg   8280
ccgcagcgtg aagacgccgc gcgcatctc caggtggccg ggggggtccc cgttgggcag   8340
ggagagggcg ctgacgatgc atcttatcaa ttgccccgta gggactccgc gcaaggacct   8400
gagcgtctcg agatccacgg gatctgaaaa ccgctgaacg aaggcttcga gccagtcgca   8460
gtcgcaaggt aggctgagca cggtttcttc tggcgggtca tgttggttgg gagcggggcg   8520
ggcgatgctg ctggtgatga agttgaaata ggcggttctg agacggcgga tggtggcgag   8580
gagcaccagg tctttgggcc cggcttgctg gatgcgcaga cggtcggcca tgccccaggc   8640
gtggtcctga cacctggcca ggtccttgta gtagtcctgc atgagccgct ccacgggcac   8700
ctcctcctcg cccgcgcggc cgtgcatgcg cgtgagcccg aagccgcgct ggggctggac   8760
gagcgccagg tcggcgacga cgcgctcggc gaggatggct tgctggatct gggtgagggt   8820
ggtctggaag tcatcaaagt cgacgaagcg gtggtaggct ccggtgttga tggtgtagga   8880
gcagttggcc atgacggacc agttgacggt ctggtggccc ggacgcacga gctcgtggta   8940
cttgaggcgc gagtaggcgc gcgtgtcgaa gatgtagtcg ttgcaggtgc gcaccaggta   9000
ctggtagccg atgaggaagt gcggcggcgg ctggcggtag agcggccatc gctcggtggc   9060
gggggcgccg ggcgcgaggt cctcgagcat ggtgcggtag tagccgtaga tgtacctgga   9120
catccaggtg atgccggcgg cggtggtgga ggcgcgcggg aactcgcgga cgcggttcca   9180
gatgttgcgc agcggcagga agtagttcat ggtgggcacg tctggcccg tgaggcgcgc   9240
gcagtcgtgg atgctctata cgggcaaaaa cgaaagcggt cagcggctcg actccgtggc   9300
ctggaggcta agcgaacggg ttgggctgcg cgtgtaccc ggttcgaatc tcgaatcagg    9360
ctggagccgc agctaacgtg gtattggcac tcccgtctcg acccaagcct gcaccaaccc   9420
tccaggatac ggaggcgggt cgttttgcaa cttttttttg gaggccggat gagactagta   9480
agcgcggaaa gcggccgacc gcgatggctc gctgccgtag tctggagaag aatcgccagg   9540
gttgcgttgc ggtgtgcccc ggttcgaggc cggccggatt ccgcggctaa cgagggcgtg   9600
gctgccccgt cgtttccaag acccccatagc cagccgactt ctccagttac ggagcgagcc   9660
cctcttttgt tttgtttgtt tttgccagat gcatcccgta ctgcggcaga tgcgccccca   9720
ccaccctcca ccgcaacaac agcccctcc acagccggcg cttctgcccc cgccccagca   9780
gcaacttcca gccacgaccg ccgcggccgc cgtgagcggg gctggacaga gttatgatca   9840
ccagctggcc ttgaagagg gcgaggggct ggcgcgcctg ggggcgtcgt cgccggagcg   9900
gcacccgcgc gtgcagatga aagggacgc tcgcgaggcc tacgtgccca agcagaacct   9960
```

```
gttcagagac aggagcggcg aggagcccga ggagatgcgc gcggcccggt tccacgcggg   10020
gcgggagctg cggcgcggcc tggaccgaaa gagggtgctg agggacgagg atttcgaggc   10080
ggacgagctg acgggatca gccccgcgcg cgcgcacgtg gccgcggcca acctggtcac    10140
ggcgtacgag cagaccgtga aggagggagag caacttccaa aaatccttca acaaccacgt  10200
gcgcaccctg atcgcgcgcg aggaggtgac cctgggcctg atgcacctgt gggacctgct   10260
ggaggccatc gtgcagaacc ccaccagcaa gccgctgacg cgcagctgt tcctggtggt    10320 gcagcatagt cgggacaacg aagcgttcag ggaggcgctg ctgaatatca ccgagcccga   10380
gggccgctgg ctcctggacc tggtgaacat tctgcagagc atcgtggtgc aggagcgcgg   10440
gctgccgctg tccgagaagc tggcggccat caacttctcg gtgctgagtt tgggcaagta   10500
ctacgctagg aagatctaca agaccccgta cgtgcccata gacaaggagg tgaagatcga   10560
cgggttttac atgcgcatga ccctgaaagt gctgaccctg agcgacgatc tgggggtgta   10620
ccgcaacgac aggatgcacc gtgcggtgag cgccagcagg cggcgcgagc tgagcgacca   10680
ggagctgatg catagtctgc agcgggccct gaccgggggcc gggaccgagg gggagagcta   10740
ctttgacatg ggcgcggacc tgcactggca gcccagccgc cgggccttgg aggcggcggc   10800
aggaccctac gtagaagagg tggacgatga ggtggacgag gagggcgagt acctggaaga   10860
ctgatggcgc gaccgtattt ttgctagatg caacaacaac agccacctcc tgatcccgcg   10920
atgcgggcgg cgctgcagag ccagccgtcc ggcattaact cctcggacga ttggacccag   10980
gccatgcaac gcatcatggc gctgacgacc cgcaaccccg aagcctttag acagcagccc   11040
caggccaacc ggctctcggc catcctggag gccgtggtgc cctcgcgctc caaccccacg   11100
cacgagaagg tcctggccat cgtgaacgcg ctggtggaga caaggccat ccgcggcgac    11160 gaggccggcc tggtgtacaa cgcgctgctg gagcgcgtgg cccgctacaa cagcaccaac   11220
gtgcagacca acctggaccg catggtgacc gacgtgcgcg aggccgtggc ccagcgcgag   11280
cggttccacc gcgagtccaa cctgggatcc atggtggcgc tgaacgcctt cctcagcacc   11340
cagcccgcca acgtgccccg gggccaggag gactacacca acttcatcag cgccctgcgc   11400
ctgatggtga ccgaggtgcc ccagagcgag gtgtaccagt ccgggccgga ctacttcttc   11460
cagaccagtc gccagggctt gcagaccgtg aacctgagcc aggctttcaa gaacttgcag   11520
ggcctgtggg gcgtgcaggc cccggtcggg gaccgcgcga cggtgtcgag cctgctgacg   11580
ccgaactcgc gcctgctgct gctgctggtg gccccctgca cggacagcgg cagcatcaac   11640
cgcaactcgt acctgggcta cctgattaac ctgtaccgcg aggccatcgg ccaggcgcac   11700
gtggacgagc agacctacca ggagatcacc cacgtgagcc gcgccctggg ccaggacgac   11760
ccgggcaacc tggaagccac cctgaacttt ttgctgacca accggtcgca gaagatcccg   11820
ccccagtacg cgctcagcac cgaggaggag cgcatcctgc gttacgtgca gcagagcgtg   11880
ggcctgttcc tgatgcagga gggggccacc cccagcgccg cgctcgacat gaccgcgcgc   11940
aacatggagc ccagcatgta cgccagcaac cgcccgttca tcaataaact gatggactac   12000
ttgcatcggg cggccgccat gaactctgac tatttcacca acgccatcct gaatccccac   12060
tggctcccgc cgccggggtt ctacacgggc gagtacgaca tgcccgaccc caatgacggg   12120
ttcctgtggg acgatgtgga cagcagcgtg ttctcccccc gaccgggtgc taacgagcgc   12180
cccttgtgga agaaggaagg cagcgaccga cgcccgtcct cggcgctgtc cggccgcgag   12240
ggtgctgccg cggcggtgcc cgaggccgcc agtccttttcc cgagcttgcc cttctcgctg   12300
aacagtatcc gcagcagcga gctgggcagg atcacgcgcc cgcgcttgct gggcgaagag   12360
```

```
gagtacttga atgactcgct gttgagaccc gagcgggaga agaacttccc caataacggg    12420
atagaaagcc tggtggacaa gatgagccgc tggaagacgt atgcgcagga gcacagggac    12480
gatccccggg cgtcgcaggg ggccacgagc cggggcagcg ccgcccgtaa acgccggtgg    12540
cacgacaggc agcggggaca gatgtgggac gatgaggact ccgccgacga cagcagcgtg    12600
ttggacttgg gtgggagtgg taacccgttc gctcacctgc gccccgtat cgggcgcatg    12660 atgtaagaga aaccgaaaat aaatgatact caccaaggcc atggcgacca gcgtgcgttc    12720
gtttcttctc tgttgttgtt gtatctagta tgatgaggcg tgcgtacccg agggtcctc    12780 ctccctcgta cgagagcgtg atgcagcagg cgatggcggc ggcggcgatg cagccccgc    12840 tggaggctcc ttacgtgccc ccgcggtacc tggcgcctac ggaggggcgg aacagcattc    12900
gttactcgga gctggcaccc ttgtacgata ccacccggtt gtacctggtg gacaacaagt    12960
cggcggacat cgcctcgctg aactaccaga acgaccacag caacttcctg accaccgtgg    13020
tgcagaacaa tgacttcacc cccacggagg ccagcaccca gaccatcaac tttgacgagc    13080
gctcgcggtg gggcggccag ctgaaaacca tcatgcacac caacatgccc aacgtgaacg    13140
agttcatgta cagcaacaag ttcaaggcgc gggtgatggt ctcccgcaag accccccaatg   13200 gggtgacagt gacagaggat tatgatggta gtcaggatga gctgaagtat gaatgggtgg    13260
aatttgagct gcccgaaggc aacttctcgg tgaccatgac catcgacctg atgaacaacg    13320
ccatcatcga caattacttg gcggtggggc ggcagaacgg ggtgctggag agcgacatcg    13380
gcgtgaagtt cgacactagg aacttcaggc tgggctggga ccccgtgacc gagctggtca    13440
tgcccggggt gtacaccaac gaggctttcc atcccgatat tgtcttgctg cccggctgcg    13500
gggtggactt caccgagagc cgcctcagca acctgctggg cattcgcaag aggcagccct    13560
tccaggaagg cttccagatc atgtacgagg atctggaggg gggcaacatc cccgcgctcc    13620
tggatgtcga cgcctatgag aaaagcaagg aggatgcagc agctgaagca actgcagccg    13680
tagctaccgc ctctaccgag gtcaggggcg ataatttgc aagcgccgca gcagtggcag    13740
cggccgaggc ggctgaaacc gaaagtaaga tagtcattca gccggtggag aaggatagca    13800
agaacaggag ctacaacgta ctaccggaca agataaacac cgcctaccgc agctggtacc    13860
tagcctacaa ctatgcgac cccgagaagg gcgtgcgctc ctggacgctg ctcaccacct    13920
cggacgtcac ctgcggcgtg gagcaagtct actggtcgct gcccgacatg atgcaagacc    13980
cggtcacctt ccgctccacg cgtcaagtta gcaactaccc ggtggtgggc gccgagctcc    14040
tgcccgtcta ctccaagagc ttcttcaacg agcaggccgt ctactcgcag cagctgcgcg    14100
ccttcacctc gcttacgcac gtcttcaacc gcttccccga gaaccagatc ctcgtccgcc    14160
cgcccgcgcc caccattacc accgtcagtg aaaacgttcc tgctctcaca gatcacggga    14220
ccctgccgct gcgcagcagt atccggggag tccagcgcgt gaccgttact gacgccagac    14280
gccgcacctg cccctacgtc tacaaggccc tgggcatagt cgcgccgcgc gtcctctcga    14340
gccgcacctt ctaaatgtcc attctcatct cgcccagtaa taacaccggt tggggcctgc    14400
gcgcgcccag caagatgtac ggaggcgctc gccaacgctc cacgcaacac cccgtgcgcg    14460
tgcgcgggca cttccgcgct ccctgggggcg ccctcaaggg ccgcgtgcgg tcgcgcacca    14520
ccgtcgacga cgtgatcgac caggtggtgg ccgacgcgcg caactacacc cccgccgccg    14580
cgcccgtctc caccgtggac gccgtcatcg acagcgtggt ggccgacgcg cgccggtacg    14640
cccgcgccaa gagccggcgg cggcgcatcg cccggcggca ccggagcacc cccgccatgc    14700
```

```
gcgcggcgcg agccttgctg cgcagggcca ggcgcacggg acgcagggcc atgctcaggg      14760
cggccagacg cgcggcttca ggcgccagcg ccggcaggac ccggagacgc gcggccacgg      14820
cggcggcagc ggccatcgcc agcatgtccc gcccgcggcg agggaacgtg tactgggtgc      14880
gcgacgccgc caccggtgtg cgcgtgcccg tgcgcacccg ccccctcgc acttgaagat       14940 gttcacttcg cgatgttgat gtgtcccagc ggcgaggagg atgtccaagc gcaaattcaa      15000
ggaagagatg ctccaggtca tcgcgcctga gatctacggc cctgcggtgg tgaaggagga      15060
aagaaagccc cgcaaaatca agcgggtcaa aaaggacaaa aaggaagaag aaagtgatgt      15120
ggacggattg gtggagtttg tgcgcgagtt cgccccccgg cggcgcgtgc agtggcgcgg      15180
gcggaaggtg caaccggtgc tgagacccgg caccaccgtg gtcttcacgc ccggcgagcg      15240
ctccggcacc gcttccaagc gctcctacga cgaggtgtac ggggatgatg atattctgga      15300
gcaggcggcc gagcgcctgg gcgagtttgc ttacggcaag cgcagccgtt ccgcaccgaa      15360
ggaagaggcg gtgtccatcc cgctggacca cggcaacccc acgccgagcc tcaagcccgt      15420
gaccttgcag caggtgctgc cgaccgcggc gccgcgccgg gggttcaagc gcgagggcga      15480
ggatctgtac cccaccatgc agctgatggt gcccaagcgc cagaagctgg aagacgtgct      15540
ggagaccatg aaggtggacc cggacgtgca gcccgaggtc aaggtgcggc ccatcaagca      15600
ggtggccccg ggcctgggcg tgcagaccgt ggacatcaag attcccacgg agcccatgga      15660
aacgcagacc gagcccatga tcaagcccag caccagcacc atggaggtgc agacggatcc      15720
ctggatgcca tcggctccta gtcgaagacc ccggcgcaag tacggcgcgg ccagcctgct      15780
gatgcccaac tacgcgctgc atccttccat catcccacg ccgggctacc gcggcacgcg       15840
cttctaccgc ggtcatacca gcagccgccg ccgcaagacc accactcgcc gccgccgtcg      15900
ccgcaccgcc gctgcaacca cccctgccgc cctggtgcgg agagtgtacc gccgcggccg      15960
cgcacctctg accctgccgc gcgcgcgcta ccacccgagc atcgccattt aaactttcgc      16020
ctgctttgca gatcaatggc cctcacatgc cgccttcgcg ttcccattac gggctaccga      16080
ggaagaaaac cgcgccgtag aaggctggcg gggaacggga tgcgtcgcca ccaccaccgg      16140
cggcggcgcg ccatcagcaa gcggttgggg ggaggcttcc tgcccgcgct gatccccatc      16200
atcgccgcgg cgatcggggc gatccccggc attgcttccg tggcggtgca ggcctctcag      16260
cgccactgag acacacttgg aaacatcttg taataaacca atggactctg acgtcctgg       16320 tcctgtgatg tgttttcgta gacagatgga agacatcaat ttttcgtccc tggctccgcg      16380
acacggcacg cggccgttca tgggcacctg gagcgacatc ggcaccagcc aactgaacgg      16440
gggcgccttc aattggagca gtctctggag cgggcttaag aatttcgggt ccacgcttaa      16500
aacctatggc agcaaggcgt ggaacagcac cacagggcag cgcgctgaggg ataagctgaa     16560 agagcagaac ttccagcaga aggtggtcga tgggctcgcc tcgggcatca acgggtggt      16620 ggacctggcc aaccaggccg tgcagcggca gatcaacagc cgcctggacc cggtgccgcc      16680
cgccggctcc gtggagatgc cgcaggtgga ggaggagctg cctcccctgg acaagcgggg      16740
cgagaagcga ccccgccccg atgcggagga cgctgctg acgcacacgg acgagccgcc       16800
cccgtacgag gaggcggtga aactgggtct gcccaccacg cggcccatcg cgccctggc      16860 caccggggtg ctgaaacccg aaaagcccgc gaccctggac ttgcctcctc cccagccttc      16920
ccgcccctct acagtggcta agccctgcc gccggtggcc gtggcccgcg cgcgacccgg      16980
gggcaccgcc cgccctcatg cgaactggca gagcactctg aacagcatcg tgggtctggg      17040
agtgcagagt gtgaagcgcc gccgctgcta ttaaacctac cgtagcgctt aacttgcttg      17100
```

```
tctgtgtgtg tatgtattat gtcgccgccg ccgctgtcca ccagaaggag gagtgaagag   17160
gcgcgtcgcc gagttgcaag atggccaccc catcgatgct gccccagtgg gcgtacatgc   17220
acatcgccgg acaggacgct tcggagtacc tgagtccggg tctggtgcag tttgcccgcg   17280
ccacagacac ctacttcagt ctggggaaca agtttaggaa ccccacggtg gcgcccacgc   17340
acgatgtgac caccgaccgc agccagcggc tgacgctgcg cttcgtgccc gtggaccgcg   17400 aggacaaacac ctactcgtac aaagtgcgct acacgctggc cgtgggcgac aaccgcgtgc   17460
tggacatggc cagcacctac tttgacatcc gcggcgtgct ggatcggggc cctagcttca   17520
aaccctactc cggcaccgcc tacaacagtc tggcccccaa gggagcaccc aacacttgtc   17580
agtggacata taaagccgat ggtgaaactg ccacagaaaa aacctataca tatggaaatg   17640
cacccgtgca gggcattaac atcacaaaag atggtattca acttggaact gacaccgatg   17700
atcagccaat ctacgcagat aaaacctatc agcctgaacc tcaagtgggt gatgctgaat   17760
ggcatgacat cactggtact gatgaaaagt atggaggcag agctcttaag cctgatacca   17820
aaatgaagcc ttgttatggt tcttttgcca agcctactaa taaagaagga ggtcaggcaa   17880 atgtgaaaaac aggaacaggc actactaaag aatatgacat agacatggct ttctttgaca   17940
acagaagtgc ggctgctgct ggcctagctc cagaaattgt tttgtatact gaaaatgtgg   18000
atttggaaac tccagatacc catattgtat acaaagcagg cacagatgac agcagctctt   18060
ctattaattt gggtcagcaa gccatgccca acagacctaa ctacattggt ttcagagaca   18120
actttatcgg gctcatgtac tacaacagca ctggcaatat gggggtgctg gccggtcagg   18180
cttctcagct gaatgctgtg gttgacttgc aagacagaaa caccgagctg tcctaccagc   18240
tcttgcttga ctctctgggt gacagaaccc ggtatttcag tatgtggaat caggcggtgg   18300
acagctatga tcctgatgtg cgcattattg aaaatcatgg tgtggaggat gaacttccca   18360
actattgttt ccctctggat gctgttggca gaacagatac ttatcaggga attaaggcta   18420
atggaactga tcaaaccaca tggaccaaag atgacagtgt caatgatgct aatgagatag   18480
gcaagggtaa tccattcgcc atggaaatca acatccaagc caacctgtgg aggaacttcc   18540
tctacgccaa cgtggccctg tacctgcccg actcttacaa gtacacgccg gccaatgtta   18600
ccctgcccac caacaccaac acctacgatt acatgaacgg ccgggtggtg gcgccctcgc   18660
tggtggactc ctacatcaac atcggggcgc gctggtcgct ggatcccatg gacaacgtga   18720
accccttcaa ccaccaccgc aatgcggggc tgcgctaccg ctccatgctc ctgggcaacg   18780
ggcgctacgt gccccttccac atccaggtgc cccagaaatt tttcgccatc aagagcctcc   18840
tgctcctgcc cgggtcctac acctacgagt ggaacttccg caaggacgtc aacatgatcc   18900
tgcagagctc cctcggcaac gacctgcgca cggacgggc ctccatctcc ttcaccagca   18960
tcaacctcta cgccaccttc ttccccatgg cgcacaacac ggcctccacg ctcgaggcca   19020
tgctgcgcaa cgacaccaac gaccagtcct tcaacgacta cctctcggcg ccaacatgc   19080 tctaccccat cccggccaac gccaccaacg tgcccatctc catccctcg cgcaactggg   19140 ccgccttccg cggctggtcc ttcacgcgtc tcaagaccaa ggagacgccc tcgctgggct   19200
ccgggttcga cccctacttc gtctactcgg gctccatccc ctacctcgac ggcaccttct   19260
acctcaacca cacccttcaag aaggtctcca tcaccttcga ctcctccgtc agctggcccg   19320
gcaacgaccg gctcctgacg cccaacgagt tcgaaatcaa gcgcaccgtc gacggcgagg   19380
gctacaacgt ggcccagtgc aacatgacca aggactggtt cctggtccag atgctggccc   19440
```

```
actacaacat cggctaccag ggcttctacg tgcccgaggg ctacaaggac cgcatgtact   19500
ccttcttccg caacttccag cccatgagcc gccaggtggt ggacgaggtc aactacaagg   19560
actaccaggc cgtcaccctg gcctaccagc acaacaactc gggcttcgtc ggctacctcg   19620
cgcccaccat gcgccagggc cagccctacc ccgccaacta cccctacccg ctcatcggca   19680
agagcgccgt caccagcgtc acccagaaaa agttcctctg cgacagggtc atgtggcgca   19740
tccccttctc cagcaacttc atgtccatgg gcgcgctcac cgacctcggc cagaacatgc   19800
tctatgccaa ctccgcccac gcgctagaca tgaatttcga agtcgacccc atggatgagt   19860
ccacccttct ctatgttgtc ttcgaagtct tcgacgtcgt ccgagtgcac cagccccacc   19920
gcggcgtcat cgaggccgtc tacctgcgca cccccttctc ggccggtaac gccaccacct   19980
aagctcttgc ttcttgcaag ccatggccgc gggctccggc gagcaggagc tcagggccat   20040
catccgcgac ctgggctgcg ggccctactt cctgggcacc ttcgataagc gcttcccggg   20100
attcatggcc ccgcacaagc tggcctgcgc catcgtcaac acggccggcc gcgagaccgg   20160
gggcgagcac tggctggcct tcgcctggaa cccgcgctcg aacacctgct acctcttcga   20220 cccccttcggg ttctcggacg agcgcctcaa gcagatctac cagttcgagt acgagggcct   20280
gctgcgccgc agcgccctgg ccaccgagga ccgctgcgtc accctggaaa agtccaccca   20340
gaccgtgcag ggtccgcgct cggccgcctg cgggctcttc tgctgcatgt tcctgcacgc   20400
cttcgtgcac tggcccgacc gccccatgga caagaacccc accatgaact tgctgacggg   20460
ggtgcccaac ggcatgctcc agtcgcccca ggtggaaccc accctgcgcc gcaaccagga   20520
ggcgctctac cgcttcctca actcccactc cgcctacttt cgctcccacc gcgcgcgcat   20580
cgagaaggcc accgccttcg accgcatgaa tcaagacatg taaaccgtgt gtgtatgtta   20640
aatgtcttta ataaacagca ctttcatgtt acacatgcat ctgagatgat ttatttagaa   20700
atcgaaaggg ttctgccggg tctcggcatg gccgcgggc agggacacgt tgcggaactg   20760
gtacttggcc agccacttga actcggggat cagcagtttg ggcagcgggg tgtcggggaa   20820
ggagtcggtc cacagcttcc gcgtcagttg cagggcgccc agcaggtcgg gcgcggagat   20880
cttgaaatcg cagttgggac ccgcgttctg cgcgcgggag ttgcggtaca cggggttgca   20940
gcactggaac accatcaggg ccgggtgctt cacgctcgcc agcaccgtcg cgtcggtgat   21000
gctctccacg tcgaggtcct cggcgttggc catcccgaag gggtcatctt gcaggtctg   21060 ccttcccatg gtgggcacgc acccgggctt gtggttgcaa tcgcagtgca ggggatcag   21120 catcatctgg gcctggtcgg cgttcatccc cgggtacatg gccttcatga aagcctccaa   21180
ttgcctgaac gcctgctggg ccttggctcc ctcggtgaag aagacccccgc aggacttgct   21240 agagaactgg ttggtggcgc acccggcgtc gtgcacgcag cagcgcgcgt cgttgttggc   21300
cagctgcacc acgctgcgcc cccagcggtt ctgggtgatc ttggcccggt cggggttctc   21360
cttcagcgcg cgctgcccgt tctcgctcgc cacatccatc tcgatcatgt gctccttctg   21420
gatcatggtg gtcccgtgca ggcaccgcag cttgccctcg gcctcggtgc acccgtgcag   21480
ccacagcgcg cacccggtgc actcccagtt cttgtgggcg atctgggaat gcgcgtgcac   21540
gaagccctgc aggaagcggc ccatcatggt ggtcaggtc ttgttgctag tgaaggtcag   21600
cggaatgccg cggtgctcct cgttgatgta caggtggcag atgcggcggt acacctcgcc   21660
ctgctcgggc atcagctgga agttggcttt caggtcggtc tccacgcggt agcggtccat   21720
cagcatagtc atgatttcca tacccttctc ccaggccgag acgatgggca ggctcatagg   21780
gttcttcacc atcatcttag cgctagcagc cgcggccagg gggtcgctct cgtccagggt   21840
```

```
ctcaaagctc cgcttgccgt ccttctcggt gatccgcacc gggggtagc tgaagcccac    21900
ggccgccagc tcctcctcgg cctgtctttc gtcctcgctg tcctggctga cgtcctgcag   21960
gaccacatgc ttggtcttgc ggggtttctt cttgggcggc agcggcggcg gagatgttgg   22020
agatggcgag ggggagcgcg agttctcgct caccactact atctcttcct cttcttggtc   22080
cgaggccacg cggcggtagg tatgtctctt cggggggcaga ggcggaggcg acgggctctc   22140
gccgccgcga cttggcggat ggctggcaga gcccccttccg cgttcggggg tgcgctcccg   22200
gcggcgctct gactgacttc ctccgcggcc ggccattgtg ttctcctagg gaggaacaac   22260
aagcatggag actcagccat cgccaacctc gccatctgcc cccaccgccg acgagaagca   22320
gcagcagcag aatgaaagct taaccgcccc gccgcccagc cccgccacct ccgacgcggc   22380
cgtcccagac atgcaagaga tggaggaatc catcgagatt gacctgggct atgtgacgcc   22440
cgcggagcac gaggaggagc tggcagtgcg cttttcacaa gaagagatac accaagaaca   22500
gccagagcag gaagcagaga atgagcagag tcaggctggg ctcgagcatg acggcgacta   22560
cctccacctg agcggggggg aggacgcgct catcaagcat ctggcccggc aggccaccat   22620
cgtcaaggat gcgctgctcg accgcaccga ggtgcccctc agcgtggagg agctcagccg   22680
cgcctacgag ttgaacctct tctcgccgcg cgtgcccccc aagcgccagc ccaatggcac   22740
ctgcgagccc aacccgcgcc tcaacttcta cccggtcttc gcggtgcccg aggcctggc    22800
cacctaccac atcttttttca agaaccaaaa gatccccgtc tcctgccgcg ccaaccgcac   22860
ccgcgccgac gcccttttca acctgggtcc cggcgcccgc ctacctgata tcgcctcctt   22920
ggaagaggtt cccaagatct cgagggtct gggcagcgac gagactcggg ccgcgaacgc   22980
tctgcaagga gaaggaggag agcatgagca ccacagcgcc ctggtcgagt tggaaggcga   23040
caacgcgcgg ctggcggtgc tcaaacgcac ggtcgagctg acccatttcg cctacccggc   23100
tctgaacctg cccccccaaag tcatgagcgc ggtcatggac caggtgctca tcaagcgcgc   23160
gtcgcccatc tccgaggacg agggcatgca agactccgag gagggcaagc ccgtggtcag   23220
cgacgagcag ctggcccggt ggctgggtcc taatgctagt ccccagagtt tggaagagcg   23280
gcgcaaactc atgatggccg tggtcctggt gaccgtggag ctggagtgcc tgcgccgctt   23340
cttcgccgac gcggagaccc tgcgcaaggt cgaggagaac ctgcactacc tcttcaggca   23400
cgggttcgtg cgccaggcct gcaagatctc caacgtggag ctgaccaacc tggtctccta   23460
catgggcatc ttgcacgaga accgcctggg gcagaacgtg ctgcacacca ccctgcgcgg   23520
ggaggcccgc cgcgactaca tccgcgactg cgtctacctc tacctctgcc acacctggca   23580
gacgggcatg ggcgtgtggc agcagtgtct ggaggagcag aacctgaaag agctctgcaa   23640
gctcctgcag aagaacctca agggtctgtg gaccgggttc gacgagcgca ccaccgcctc   23700
ggacctggcc gacctcattt tccccgagcg cctcaggctg acgctgcgca acggcctgcc   23760
cgactttatg agccaaagca tgttgcaaaa ctttcgctct ttcatcctcg aacgctccgg   23820
aatcctgccc gccacctgct ccgcgctgcc ctcggacttc gtgccgctga ccttccgcga   23880
gtgcccccccg ccgctgtgga gccactgcta cctgctgcgc ctggccaact acctggccta   23940
ccactcggac gtgatcgagg acgtcagcgg cgagggcctg ctcgagtgcc actgccgctg   24000
caacctctgc acgccgcacc gctccctggc ctgcaacccc cagctgctga gcgagaccca   24060
gatcatcggc accttcgagt tgcaagggcc cagcgaaggc gagggttcag ccgccaaggg   24120
gggtctgaaa ctcacccccgg ggctgtggac ctcggcctac ttgcgcaagt tcgtgcccga   24180
```

```
ggactaccat cccttcgaga tcaggttcta cgaggaccaa tcccatccgc ccaaggccga   24240
gctgtcggcc tgcgtcatca cccagggggc gatcctggcc caattgcaag ccatccagaa   24300
atcccgccaa gaattcttgc tgaaaaaggg ccgcggggtc tacctcgacc cccagaccgg   24360
tgaggagctc aacccgggct cccccagga tgccccgagg aaacaagaag ctgaaagtgg    24420
agctgccgcc cgtggaggat tggaggaag actgggagaa cagcagtcag gcagaggagg    24480
aggagatgga ggaagactgg gacagcactc aggcagagga ggacagcctg caagacagtc   24540
tggaggaaga cgaggaggag gcagaggagg aggtggaaga agcagccgcc gccagaccgt   24600
cgtcctcggc gggggagaaa gcaagcagca cggataccat ctccgctccg ggtcggggtc   24660
ccgctcgacc acacagtaga tgggacgaga ccggacgatt cccgaacccc accacccaga   24720
ccggtaagaa ggagcggcag ggatacaagt cctggcgggg gcacaaaaac gccatcgtct   24780
cctgcttgca ggcctgcggg ggcaacatct ccttcacccg gcgctacctg ctcttccacc   24840
gcggggtgaa cttcccccgc aacatcttgc attactaccg tcacctccac agcccctact   24900
acttccaaga agaggcagca gcagcagaaa aagaccagca gaaaaccagc agctagaaaa   24960
tccacagcgg cggcagcagg tggactgagg atcgcggcga acgagccggc gcaaacccgg   25020
gagctgagga accggatctt tcccaccctc tatgccatct tccagcagag tcgggggcag   25080
gagcaggaac tgaaagtcaa gaaccgttct ctgcgctcgc tcacccgcag ttgtctgtat   25140
cacaagagcg aagaccaact tcagcgcact ctcgaggacg ccgaggctct cttcaacaag   25200
tactgcgcgc tcactcttaa agagtagccc gcgcccgccc agtcgcagaa aaaggcggga   25260
attacgtcac ctgtgcccctt cgccctagcc gcctccaccc atcatcatga gcaaagagat   25320
tcccacgcct tacatgtgga gctaccagcc ccagatgggc ctggccgccg gtgccgccca   25380
ggactactcc acccgcatga attggctcag cgccgggccc gcgatgatct cacgggtgaa   25440
tgacatccgc gcccaccgaa accagatact cctagaacag tcagcgctca ccgccacgcc   25500
ccgcaatcac ctcaatccgc gtaattggcc cgccgccctg gtgtaccagg aaattcccca   25560
gcccacgacc gtactacttc cgcgagacgc ccaggccgaa gtccagctga ctaactcagg   25620
tgtccagctg gcgggcggcg ccaccctgtg tcgtcaccgc cccgctcagg gtataaagcg   25680
gctggtgatc cggggcagag gcacacagct caacgacgag gtggtgagct cttcgctggg   25740
tctgcgacct gacggagtct tccaactcgc cggatcgggg agatcttcct tcacgcctcg   25800
tcaggccgtc ctgactttgg agagttcgtc ctcgcagccc cgctcgggtg gcatcggcac   25860
tctccagttc gtggaggagt tcactccctc ggtctacttc aacccttct ccggctcccc    25920 cggccactac ccggacgagt tcatcccgaa cttcgacgcc atcagcgagt cggtggacgg   25980
ctacgattga atgtcccatg gtggcgcagc tgacctagct cggcttcgac acctggacca   26040
ctgccgccgc ttccgctgct tcgctcggga tctcgccgag tttgcctact ttgagctgcc   26100
cgaggagcac cctcagggcc cggcccacgg agtgcggatc gtcgtcgaag ggggcctcga   26160
ctcccacctg cttcggatct tcagccagcg tccgatcctg gtcgagcgcg agcaaggaca   26220 gaccccttctg actctgtact gcatctgcaa ccacccccggc ctgcatgaaa gtctttgttg   26280
tctgctgtgt actgagtata ataaaagctg agatacagcga ctactccgga cttccgtgtg   26340
ttcctgaatc catcaaccag tctttgttct tcaccgggaa cgagaccgag ctccagctcc   26400
agtgtaagcc ccacaagaag tacctcacct ggctgttcca gggctcccg atcgccgttg    26460 tcaaccactg cgacaacgac ggagtcctgc tgagcggccc tgccaacctt acttttttcca   26520 cccgcagaag caagctccag ctcttccaac ccttcctccc cgggacctat cagtgcgtct   26580
```

```
cgggaccctg ccatcacacc ttccacctga tcccgaatac cacagcgtcg ctccccgcta   26640
ctaacaacca aactaacctc caccaacgcc accgtcgcga cggccacaat acatgcccat   26700
attagactat gaggccgagc cacagcgacc catgctcccc gctattagtt acttcaatct   26760
aaccggcgga gatgactgac ccactggcca acaacaacgt caacgacctt ctcctggaca   26820
tggacggccg cgcctcggag cagcgactcg cccaacttcg cattcgccag cagcaggaga   26880
gagccgtcaa ggagctgcag gatgcggtgg ccatccacca gtgcaagaga ggcatcttct   26940
gcctggtgaa acaggccaag atctcctacg aggtcactcc aaacgaccat cgcctctcct   27000
acgagctcct gcagcagcgc cagaagttca cctgcctggt cggagtcaac cccatcgtca   27060
tcacccagca gtctggcgat accaaggggt gcatccactg ctcctgcgac tcccccgact   27120
gcgtccacac tctgatcaag accctctgcg gcctccgcga cctcctcccc atgaactaat   27180
caccccctta tccagtgaaa taaagatcat attgatgatg attttacaga aataaaaaat   27240
aatcatttga tttgaaataa agatacaatc atattgatga tttgagttta acaaaaaaat   27300
aaagaatcac ttacttgaaa tctgatacca ggtctctgtc catgttttct gccaacacca   27360
cttcactccc ctcttcccag ctctggtact gcaggcccg gcgggctgca aacttcctcc   27420
acacgctgaa ggggatgtca aattcctcct gtccctcaat cttcatttta tcttctatca   27480
gatgtccaaa aagcgcgtcc gggtggatga tgacttcgac cccgtctacc cctacgatgc   27540
agacaacgca ccgaccgtgc ccttcatcaa ccccccttc gtctcttcag atggattcca   27600
agagaagccc ctgggggtgt tgtccctgcg actggccgac cccgtcacca ccaagaacgg   27660
ggaaatcacc ctcaagctgg gagaggggt ggacctcgat tcctcgggaa aactcatctc   27720
caacacggcc accaaggccg ccgcccctct cagttttcc aacaacacca tttcccttaa   27780
catggatcac cccttttaca ctaaagatgg aaaattatcc ttacaagttt ctccaccatt   27840
aaatatactg agaacaagca ttctaaacac actagcttta ggttttggat caggtttagg   27900
actccgtggc tctgccttgg cagtacagtt agtctctcca cttacatttg atactgatgg   27960
aaacataaag cttaccttag acagaggttt gcatgttaca acaggagatg caattgaaag   28020
caacataagc tgggctaaag gtttaaaatt tgaagatgga gccatagcaa ccaacattgg   28080
aaatgggtta gagtttggaa gcagtagtac agaaacaggt gttgatgatg cttacccaat   28140
ccaagttaaa cttggatctg gccttagctt tgacagtaca ggagccataa tggctggtaa   28200
caaagaagac gataaactca ctttgtggac aacacctgat ccatcaccaa actgtcaaat   28260
actcgcagaa aatgatgcaa aactaacact ttgcttgact aaatgtggta gtcaaatact   28320
ggccactgtg tcagtcttag ttgtaggaag tggaaaccta accccatta ctggcaccgt   28380 aagcagtgct caggtgtttc tacgttttga tgcaaacggt gttcttttaa cagaacattc   28440
tacactaaaa aaatactggg ggtataggca gggagatagc atagatggca ctccatatac   28500
caatgctgta ggattcatgc ccaatttaaa agcttatcca aagtcacaaa gttctactac   28560
taaaaataat atagtagggc aagtatacat gaatggagat gtttcaaaac ctatgcttct   28620
cactataacc ctcaatggta ctgatgacag caacagtaca tattcaatgt cattttcata   28680
cacctggact aatggaagct atgttggagc aacatttggg gctaactctt ataccttctc   28740
atacatcgcc caagaatgaa cactgtatcc caccctgcat gccaacccctt cccacccac    28800 tctgtggaac aaactctgaa acacaaaata aaataaagtt caagtgtttt attgattcaa   28860
cagttttaca ggattcgagc agttattttt cctccaccct cccaggacat ggaatacacc   28920
```

-continued

```
accctctccc cccgcacagc cttgaacatc tgaatgccat tggtgatgga catgcttttg    28980
gtctccacgt tccacacagt ttcagagcga gccagtctcg ggtcggtcag ggagatgaaa    29040
ccctccgggc actcccgcat ctgcacctca cagctcaaca gctgaggatt gtcctcggtg    29100
gtcgggatca cggttatctg gaagaagcag aagagcggcg gtgggaatca tagtccgcga    29160
acgggatcgg ccggtggtgt cgcatcaggc cccgcagcag tcgctgccgc cgccgctccg    29220
tcaagctgct gctcaggggg tccgggtcca gggactccct cagcatgatg cccacggccc    29280
tcagcatcag tcgtctggtg cggcgggcgc agcagcgcat gcggatctcg ctcaggtcgc    29340
tgcagtacgt gcaacacaga accaccaggt tgttcaacag tccatagttc aacacgctcc    29400
agccgaaact catcgcggga aggatgctac ccacgtggcc gtcgtaccag atcctcaggt    29460
aaatcaagtg gtgcccctc cagaacacg tgcccacgta catgatctcc ttgggcatgt    29520
ggcggttcac cacctcccgg taccacatca ccctctggtt gaacatgcag ccccggatga    29580
tcctgcggaa ccacagggcc agcaccgccc gcccgccat gcagcgaaga daccccgggt    29640
cccggcaatg gcaatggagg acccaccgct cgtacccgtg gatcatctgg gagctgaaca    29700
agtctatgtt ggcacagcac aggcatatgc tcatgcatct cttcagcact ctcaactcct    29760
cgggggtcaa aaccatatcc cagggcacgg ggaactcttg caggacagcg aaccccgcag    29820
aacagggcaa tcctcgcaca gaacttacat tgtgcatgga cagggtatcg caatcaggca    29880
gcaccgggtg atcctccacc agagaagcgc gggtctcggt ctcctcacag cgtggtaagg    29940
gggccggccg atacgggtga tggcgggacg cggctgatcg tgttcgcgac cgtgtcatga    30000
tgcagttgct ttcggacatt ttcgtacttg ctgtagcaga acctggtccg ggcgctgcac    30060
accgatcgcc ggcggcggtc tcggcgcttg gaacgctcgg tgttgaaatt gtaaaacagc    30120
cactctctca gaccgtgcag cagatctagg gcctcaggag tgatgaagat cccatcatgc    30180
ctgatggctc tgatcacatc gaccaccgtg gaatgggcca gacccagcca gatgatgcaa    30240
ttttgttggg tttcggtgac ggcggggag ggaagaacag gaagaaccat gattaacttt    30300
taatccaaac ggtctcggag tacttcaaaa tgaagatcgc ggagatggca cctctcgccc    30360
ccgctgtgtt ggtggaaaat aacagccagg tcaaaggtga tacggttctc gagatgttcc    30420
acggtggctt ccagcaaagc ctccacgcgc acatccagaa acaagacaat agcgaaagcg    30480
ggagggttct ctaattcctc aatcatcatg ttacactcct gcaccatccc cagataattt    30540
tcatttttcc agccttgaat gattcgaact agttcgtgag gtaaatccaa gccagccatg    30600
ataaagagct cgcgcagagc gccctccacc ggcattctta agcacaccct cataattcca    30660
agatattctg ctcctggttc acctgcagca gattgacaag cggaatatca aaatctctgc    30720
cgcgatccct gagctcctcc ctcagcaata actgtaagta ctctttcata tcctctccga    30780
aattttttagc cataggacca ccaggaataa gattagggca agccacagta cagataaacc    30840
gaagtcctcc ccagtgagca ttgccaaatg caagactgct ataagcatgc tggctagacc    30900
cggtgatatc ttccagataa ctggacagaa aatcgcccag gcaattttta agaaaatcaa    30960
caaaagaaaa atcctccagg tggacgttta gagcctcggg aacaacgatg aagtaaatgc    31020
aagcggtgcg ttccagcatg gttagttagc tgatctgtag aaaaaacaaa aatgaacatt    31080
aaaccatgct agcctggcga acaggtgggt aaatcgttct ctccagcacc aggcaggcca    31140
cggggtctcc ggcgcgaccc tcgtaaaaat tgtcgctatg attgaaaacc atcacagaga    31200
gacgttcccg gtggccggcg tgaatgattc gacaagatga atacaccccc ggaacattgg    31260
cgtccgcgag tgaaaaaaag cgcccgagga agcaataagg cactacaatg ctcagtctca    31320
```

```
agtccagcaa agcgatgcca tgcggatgaa gcacaaaatt ctcaggtgcg tacaaaatgt   31380
aattactccc ctcctgcaca ggcagcaaag cccccgatcc ctccaggtac acatacaaag   31440
cctcagcgtc catagcttac cgagcagcag cacacaacag gcgcaagagt cagagaaagg   31500
ctgagctcta acctgtccac ccgctctctg ctcaatatat agcccagatc tacactgacg   31560
taaaggccaa agtctaaaaa tacccgccaa ataatcacac acgcccagca cacgcccaga   31620
aaccggtgac acactcaaaa aaatacgcgc acttcctcaa acgcccaaaa ctgccgtcat   31680
ttccgggttc ccacgctacg tcatcaaaac acgactttca aattccgtcg accgttaaaa   31740
acgtcacccg ccccgcccct aacggtcgcc cgtctctcag ccaatcagcg ccccgcatcc   31800
ccaaattcaa acacctcatt tgcatattaa cgcgcacaaa aagtttgagg tatattattg   31860
atgatgg                                                           31867
```

<210> SEQ ID NO 12
<211> LENGTH: 32788
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 12

```
ccatcttcaa taatatacct caaactttt gtgcgcgtta atatgcaaat gaggcgtttg    60
aatttgggga ggaagggcgg tgattggtcg agggatgagc gaccgttagg ggcggggcga   120
gtgacgtttt gatgacgtgg ttgcgaggag gagccagttt gcaagttctc gtgggaaaag   180
tgacgtcaaa cgaggtgtgg tttgaacacg gaaatactca atttccccgc gctctctgac   240
aggaaatgag gtgtttctgg gcggatgcaa gtgaaaacgg gccattttcg cgcgaaaact   300
gaatgaggaa gtgaaaatct gagtaatttc gcgtttatgg cagggaggag tatttgccga   360
gggccgagta gactttgacc gattacgtgg gggtttcgat taccgtgttt ttcacctaaa   420
tttccgcgta cggtgtcaaa gtccggtgtt tttacgtagg tgtcagctga tcgccagggt   480
atttaaacct gcgctctcca gtcaagaggc cactcttgag tgccagcgag aagagttttc   540
tcctccgcgc cgcgagtcag atctacactt tgaaagtagg gataacaggg taatgacatt   600
gattattgac tagttgttaa tagtaatcaa ttacggggtc attagttcat agcccatata   660
tggagttccg cgttacataa cttacggtaa atggcccgcc tggctgaccg cccaacgacc   720
cccgcccatt gacgtcaata atgacgtatg ttcccatagt aacgccaata gggactttcc   780
attgacgtca atgggtggag tatttacggt aaactgccca cttggcagta catcaagtgt   840
atcatatgcc aagtccgccc cctattgacg tcaatgacgg taaatggccc gcctggcatt   900
atgcccagta catgacctta cgggactttc ctacttggca gtacatctac gtattagtca   960
tcgctattac catggtgatg cggttttggc agtacaccaa tgggcgtgga tagcggtttg  1020
actcacgggg atttccaagt ctccacccca ttgacgtcaa tgggagtttg ttttggcacc  1080
aaaatcaacg ggactttcca aaatgtcgta ataaccccgc ccgttgacg caaatgggcg  1140 gtaggcgtgt acggtgggag gtctatataa gcagagctcg tttagtgaac cgtcagatcg  1200
cctggaacgc catccacgct gttttgacct ccatagaaga cagcgatcgc gccaccatgg  1260 cgggatgtt ccaggcactg tccgaaggct gcacaccta tgatattaac cagatgctga  1320
atgtcctggg agaccaccag gtctctgcc tggagcagct ggagagcatc atcaacttcg  1380
agaagctgac cgagtggaca agctccaatg tgatgcctat cctgtcccca ctgaccaagg  1440
```

```
gcatcctggg cttcgtgttt accctgacag tgccttctga gcggggcctg tcttgcatca   1500
gcgaggcaga cgcaaccaca ccagagtccg ccaatctggg cgaggagatc ctgtctcagc   1560
tgtacctgtg gccccgggtg acatatcact ccccttctta cgcctatcac cagttcgagc   1620
ggagagccaa gtacaagaga cacttcccag gctttggcca gtctctgctg ttcggctacc   1680
ccgtgtacgt gttcggcgat gcgtgcagg gcgactggga tgccatccgg tttagatact   1740
gcgcaccacc tggatatgca ctgctgaggt gtaacgacac caattattcc gccctgctgg   1800
cagtgggcgc cctggagggc cctcgcaatc aggattggct gggcgtgcca aggcagctgg   1860
tgacacgcat gcaggccatc cagaacgcag gcctgtgcac cctggtggca atgctggagg   1920
agacaatctt ctggctgcag gcctttctga tggccctgac cgacagcggc cccaagacaa   1980
acatcatcgt ggattcccag tacgtgatgg gcatctccaa gccttctttc caggagtttg   2040
tggactggga gaacgtgagc ccagagctga attccaccga tcagccattc tggcaggcag   2100
gaatcctgga aggaacctg gtgcctatgg tggccacagt gcagggccag aatctgaagt   2160
accagggcca gagcctggtc atcagcgcct ccatcatcgt gtttaacctg ctggagctgg   2220
agggcgacta tcgggacgat ggcaacgtgt gggtgcacac cccactgagc cccagaacac   2280
tgaacgcctg ggtgaaggcc gtggaggaga agaagggcat cccagtgcac ctggagctgg   2340
cctccatgac caatatggag ctgatgtcta gcatcgtgca ccagcaggtg aggacatacg   2400
gacccgtgtt catgtgcctg ggaggcctgc tgaccatggt ggcaggagcc gtgtggctga   2460
cagtgcgggt gctggagctg ttcagagccg cccagctggc caacgatgtg gtgctgcaga   2520
tcatggagct gtgcggagca gcctttcgcc aggtgtgcca caccacagtg ccatggccca   2580
atgcctccct gaccccccaag tggaacaatg agacaacaca gcctcagatc gccaactgta   2640
gcgtgtacga cttcttcgtg tggctgcact actatagcgt gagggatacc ctgtggcccc   2700
gcgtgacata cccacatgaat aagtacgcct atcacatgct ggagaggcgc gccaagtata   2760
agagaggccc tggcccaggc gcaaagtttg tggcagcatg gaccctgaag gccgccgccg   2820
gccccggccc cggccagtat atcaaggcta acagtaagtt cattggaatc acagagctgg   2880
gacccggacc tggataatga gtttaaactc ccatttaaat gtgagggtta atgcttcgag   2940
cagacatgat aagatacatt gatgagtttg gacaaaccac aactagaatg cagtgaaaaa   3000
aatgctttat ttgtgaaatt tgtgatgcta ttgctttatt tgtaaccatt ataagctgca   3060
ataaacaagt taacaacaac aattgcattc attttatgtt tcaggttcag ggggagatgt   3120
gggaggtttt ttaaagcaag taaaacctct acaaatgtgg taaataact ataacggtcc   3180 taaggtagcg agtgagtagt gttctggggc gggaggac ctgcatgagg gccagaataa   3240
ctgaaatctg tgcttttctg tgtgttgcag cagcatgagc ggaagcggct cctttgaggg   3300
aggggtattc agcccttatc tgacggggcg tctcccctcc tgggcgggag tgcgtcagaa   3360
tgtgatggga tccacggtgg acggccggcc cgtgcagccc gcgaactctt caaccctgac   3420
ctatgcaacc ctgagctctt cgtcgttgga cgcagctgcc gccgcagctg ctgcatctgc   3480
cgccagcgcc gtgcgcggaa tggccatggg cgccggctac tacggcactc tggtggccaa   3540
ctcgagttcc accaataatc ccgccagcct gaacgaggag aagctgttgc tgctgatggc   3600
ccagctcgag gccttgaccc agcgcctggg cgagctgacc cagcaggtgg ctcagctgca   3660
ggagcagacg cgggccgcgg ttgccacggt gaaatccaaa taaaaaatga atcaataaat   3720
aaacggagac ggttgttgat tttaacacag agtctgaatc tttatttgat ttttcgcgcg   3780
```

```
cggtaggccc tggaccaccg gtctcgatca ttgagcaccc ggtggatctt ttccaggacc    3840
cggtagaggt gggcttggat gttgaggtac atgggcatga gcccgtcccg ggggtggagg    3900
tagctccatt gcagggcctc gtgctcgggg gtggtgttgt aaatcaccca gtcatagcag    3960
gggcgcaggg catggtgttg cacaatatct ttgaggagga gactgatggc cacgggcagc    4020
cctttggtgt aggtgtttac aaatctgttg agctgggagg gatgcatgcg ggggagatg     4080 aggtgcatct tggcctggat cttgagattg gcgatgttac cgcccagatc ccgcctgggg    4140
ttcatgttgt gcaggaccac cagcacggtg tatccggtgc acttgggaa tttatcatgc     4200 aacttggaag ggaaggcgtg aaagaatttg gcgacgcctt tgtgcccgcc caggttttcc    4260
atgcactcat ccatgatgat ggcgatgggc ccgtgggcgg cggcctgggc aaagacgttt    4320
cgggggtcgg acacatcata gttgtggtcc tgggtgaggt catcataggc cattttaatg    4380
aatttggggc ggagggtgcc ggactggggg acaaaggtac cctcgatccc ggggcgtag    4440 ttcccctcac agatctgcat ctcccaggct ttgagctcgg agggggggat catgtccacc    4500
tgcggggcga taagaacac ggtttccggg gcggggagga tgagctgggc cgaaagcaag     4560
ttccggagca gctgggactt gccgcagccg gtggggccgt agatgacccc gatgaccggc    4620
tgcaggtggt agttgaggga gagacagctg ccgtcctccc ggaggagggg gccacctcg     4680 ttcatcatct cgcgcacgtg catgttctcg cgcaccagtt ccgccaggag gcgctctccc    4740
cccagggata ggagctcctg gagcgaggcg aagtttttca gcggcttgag tccgtcggcc    4800
atgggcattt tggagagggt tgttgcaag agttccaggc ggtcccagag ctcggtgatg     4860
tgctctacgg catctcgatc cagcagacct cctcgtttcg cggttggga cggctgcggg     4920 agtagggcac cagacgatgg gcgtccagcg cagccagggt ccgtccttc cagggtcgca     4980 gcgtccgcgt caggtggtc tccgtcacgg tgaaggggtg cgcgccgggc tgggcgcttg     5040
cgagggtgcg cttcaggctc atccggctgg tcgaaaaccg ctcccgatcg gcgccctgcg    5100
cgtcggccag gtagcaattg accatgagtt cgtagttgag cgcctcggcc gcgtggcctt    5160
tggcgcggag cttacctttg gaagtctgcc cgcaggcggg acagaggagg gacttgaggg    5220
cgtagagctt gggggcgagg aagacggact cggggcgta ggcgtccgcg ccgcagtggg     5280
cgcagacggt ctcgcactcc acgagccagg tgaggtcggg ctggtcgggg tcaaaaacca    5340
gtttcccgcc gttcttttg atgcgtttct tacctttggt ctccatgagc tcgtgtcccc     5400
gctgggtgac aaagaggctg tccgtgtccc cgtagaccga ctttatgggc cggtcctcga    5460
gcggtgtgcc gcggtcctcc tcgtagagga accccgccca ctccgagacg aaagcccggg    5520
tccaggccag cacgaaggag gccacgtggg acgggtagcg gtcgttgtcc accagcgggt    5580 ccacctttc cagggtatgc aaacacatgt ccccctcgtc cacatccagg aaggtgattg      5640
gcttgtaagt gtaggccacg tgaccggggg tcccggccgg gggggtataa aagggtgcgg    5700
gtccctgctc gtcctcactg tcttccggat cgctgtccag gagcgccagc tgttggggta    5760
ggtattccct ctcgaaggcg ggcatgacct cggcactcag gttgtcagtt tctagaaacg    5820
aggaggattt gatattgacg gtgccggcgg agatgccttt caagagcccc tcgtccatct    5880
ggtcagaaaa gacgatcttt ttgttgtcga gcttggtggc gaaggagccg tagagggcgt    5940
tggagaggag cttggcgatg gagcgcatgg tctggttttt ttccttgtcg gcgcgctcct    6000
tggcggcgat gttgagctgc acgtactcgc gcgccacgca cttccattcg gggaagacgg    6060
tggtcagctc gtcgggcacg attctgacct gccagcccg attatgcagg gtgatgaggt      6120
ccacactggt ggccacctcg ccgcgcaggg gctcattagt ccagcagagg cgtccgccct    6180
```

-continued

```
tgcgcgagca gaagggggc aggggtcca gcatgacctc gtcgggggg tcggcatcga    6240
tggtgaagat gccgggcagg aggtcggggt caaagtagct gatggaagtg ccagatcgt    6300
ccagggcagc ttgccattcg cgcacggcca gcgcgctctc gtagggactg aggggcgtgc   6360
cccagggcat gggatgggta agcgcggagg cgtacatgcc gcagatgtcg tagacgtaga   6420
ggggctcctc gaggatgccg atgtaggtgg ggtagcagcg ccccccgcgg atgctggcgc   6480
gcacgtagtc atacagctcg tgcgaggggg cgaggagccc cgggcccagg ttggtgcgac   6540
tgggcttttc ggcgcggtag acgatctggc ggaaaatggc atgcgagttg gaggagatgg   6600
tgggcctttg gaagatgttg aagtgggcgt ggggcagtcc gaccgagtcg cggatgaagt   6660
gggcgtagga gtcttgcagc ttggcgacga gctcggcggt gactaggacg tccagagcgc   6720
agtagtcgag ggtctcctgg atgatgtcat acttgagctg tccctttgt ttccacagct    6780
cgcggttgag aaggaactct tcgcggtcct tccagtactc ttcgagggg aacccgtcct    6840
gatctgcacg gtaagagcct agcatgtaga actggttgac ggccttgtag gcgcagcagc   6900
ccttctccac ggggagggcg taggcctggg cggccttgcg cagggaggtg tgcgtgaggg   6960
cgaaagtgtc cctgaccatg accttgagga actggtgctt gaagtcgata tcgtcgcagc   7020
cccctgctc ccagagctgg aagtccgtgc gcttcttgta ggcggggttg gcaaagcga    7080
aagtaacatc gttgaagagg atcttgcccg cgcggggcat aaagttgcga gtgatgcgga   7140
aaggttgggg cacctcggcc cggttgttga tgacctgggc ggcgagcacg atctcgtcga   7200
agccgttgat gttgtggccc acgatgtaga gttccacgaa tcgcgacgg cccttgacgt    7260
ggggcagttt cttgagctcc tcgtaggtga gctcgtcggg gtcgctgagc ccgtgctgct   7320
cgagcgccca gtcggcgaga tgggggttgg cgcggaggaa ggaagtccag agatccacgg   7380
ccagggcggt ttgcagacgg tcccggtact gacggaactg ctgcccgacg gccatttttt   7440
cgggggtgac gcagtagaag gtgcgggggt cccgtgcca gcgatcccat ttgagctgga    7500
gggcgagatc gagggcgagc tcgacgagcc ggtcgtcccc ggagagtttc atgaccagca   7560
tgaaggggac gagctgcttg ccgaaggacc ccatccaggt gtaggtttcc acatcgtagg   7620
tgaggaagag cctttcggtg cgaggatgcg agccgatggg gaagaactgg atctcctgcc   7680
accaattgga ggaatggctg ttgatgtgat ggaagtagaa atgccgacgg cgcgccgaac   7740
actcgtgctt gtgtttatac aagcggccac agtgctcgca acgctgcacg ggatgcacgt   7800
gctgcacgag ctgtacctga gttcctttga cgaggaattt cagtgggaag tggagtcgtg   7860
gcgcctgcat ctcgtgctgt actacgtcgt ggtggtcggc ctggccctct tctgcctcga   7920
tggtggtcat gctgacgagc ccgcgcggga ggcaggtcca gacctcggcg cgagcgggtc   7980
ggagagcgag gacgagggcg cgcaggccgg agctgtccag ggtcctgaga cgctgcggag   8040
tcaggtcagt gggcagcggc ggcgcgcggt tgacttgcag gagttttttcc agggcgcgcg   8100
ggaggtccag atggtacttg atctccaccg cgccattggt ggcgacgtcg atggcttgca   8160
gggtcccgtg cccctggggt gtgaccaccg tcccccgttt cttcttgggc ggctggggcg   8220
acggggggcgg tgcctcttcc atggttagaa gcggcggcga ggacgcgcgc cgggcggcag   8280
gggcggctcg ggcccggag gcaggggcgg caggggcacg tcggcgccgc gcgcgggtag    8340
gttctggtac tgcgcccgga gaagactggc gtgagcgacg acgcgacggt tgacgtcctg   8400
gatctgacgc ctctgggtga aggccacggg acccgtgagt ttgaacctga aagagagttc   8460
gacagaatca atctcggtat cgttgacggc ggcctgccgc aggatctctt gcacgtcgcc   8520
```

```
cgagttgtcc tggtaggcga tctcggtcat gaactgctcg atctcctcct cttgaaggtc    8580
tccgcggccg gcgcgctcca cggtggccgc gaggtcgttg gagatgcggc ccatgagctg    8640
cgagaaggcg ttcatgcccg cctcgttcca gacgcggctg tagaccacga cgccctcggg    8700
atcgcgggcg cgcatgacca cctgggcgag gttgagctcc acgtggcgcg tgaagaccgc    8760
gtagttgcag aggcgctggt agaggtagtt gagcgtggtg gcgatgtgct cggtgacgaa    8820
gaaatacatg atccagcggc ggagcggcat ctcgctgacg tcgcccagcg cctccaaacg    8880
ttccatggcc tcgtaaaagt ccacggcgaa gttgaaaaac tgggagttgc gcgccgagac    8940
ggtcaactcc tcctccagaa gacggatgag ctcggcgatg gtggcgcgca cctcgcgctc    9000
gaaggccccc gggagttcct ccacttcctc ttcttcctcc tccactaaca tctcttctac    9060
ttcctcctca gcggcagtg gtggcggggg aggggcctg cgtcgccggc ggcgcacggg      9120
cagacggtcg atgaagcgct cgatggtctc gccgcgccgg cgtcgcatgg tctcggtgac    9180
ggcgcgcccg tcctcgcggg gccgcagcgt gaagacgccg ccgcgcatct ccaggtggcc    9240
gggggggtcc ccgttgggca gggagagggc gctgacgatg catcttatca attgccccgt    9300
agggactccg cgcaaggacc tgagcgtctc gagatccacg ggatctgaaa accgctgaac    9360
gaaggcttcg agccagtcgc agtcgcaagg taggctgagc acggtttctt ctggcgggtc    9420
atgttggttg ggagcggggc gggcgatgct gctggtgatg aagttgaaat aggcggttct    9480
gagacgcgcg atggtggcga ggagcaccag gtctttgggc ccggcttgct ggatgcgcag    9540
acggtcggcc atgccccagg cgtggtcctg acacctggcc aggtccttgt agtagtcctg    9600
catgagccgc tccacgggca cctcctcctc gcccgcgcgg ccgtgcatgc gcgtgagccc    9660
gaagccgcgc tggggctgga cgagcgccag gtcggcgacg acgcgctcgg cgaggatggc    9720
ttgctggatc tgggtgaggg tggtctggaa gtcatcaaag tcgacgaagc ggtggtaggc    9780
tccggtgttg atggtgtagg agcagttggc catgacggac cagttgacgg tctggtggcc    9840
cggacgcacg agctcgtggt acttgaggcg cgagtaggcg cgcgtgtcga agatgtagtc    9900
gttgcaggtg cgcaccaggt actggtagcc gatgaggaag tgcggcggcg gctggcggta    9960
gagcggccat cgctcggtgg cggggcgccc gggcgcgagg tcctcgagca tggtgcggtg   10020
gtagccgtag atgtacctgg acatccaggt gatgccggcg gcggtggtgg aggcgcgcgg   10080
gaactcgcgg acgcggttcc agatgttgcg cagcggcagg aagtagttca tggtgggcac   10140
ggtctggccc gtgaggcgcg cgcagtcgtg gatgctctat acgggcaaaa acgaaagcgg   10200
tcagcggctc gactccgtgg cctggaggct aagcgaacgg gttgggctgc gcgtgtaccc   10260
cggttcgaat ctcgaatcag gctggagccg cagctaacgt ggtattggca ctcccgtctc   10320
gacccaagcc tgcaccaacc ctccaggata cggaggcggg tcgttttgca acttttttt    10380
ggaggccgga tgagactagt aagcgcggaa agcggccgac cgcgatggct cgctgccgta   10440
gtctggagaa gaatcgccag ggttgcgttg cggtgtgccc cggttcgagg ccggccggat   10500
tccgcggcta acgagggcgt ggctgccccg tcgtttccaa gacccccatag ccagccgact   10560
tctccagtta cggagcgagc ccctcttttg ttttgtttgt ttttgccaga tgcatcccgt   10620
actgcggcag atgcgccccc accacccctcc accgcaacaa cagccccctc cacagccggc   10680
gcttctgccc ccgcccagc agcaacttcc agccacgacc gccgcggccg ccgtgagcgg    10740
ggctggacag agttatgatc accagctggc cttggaagag ggcgaggggc tggcgcgcct   10800
gggggcgtcg tcgccggagc ggcacccgcg cgtgcagatg aaaagggacg ctcgcgaggc   10860
ctacgtgccc aagcagaacc tgttcagaga caggagcggc gaggagcccg aggagatgcg   10920
```

```
cgcggcccgg ttccacgcgg ggcgggagct gcggcgcggc ctggaccgaa agagggtgct   10980
gagggacgag gatttcgagg cggacgagct gacgggatc agccccgcgc gcgcgcacgt    11040
ggccgcggcc aacctggtca cggcgtacga gcagaccgtg aaggaggaga gcaacttcca   11100
aaaatccttc aacaaccacg tgcgcaccct gatcgcgcgc gaggaggtga ccctgggcct   11160
gatgcacctg tgggacctgc tggaggccat cgtgcagaac cccaccagca agccgctgac   11220
ggcgcagctg ttcctggtgg tgcagcatag tcgggacaac gaagcgttca gggaggcgct   11280
gctgaatatc accgagcccg agggccgctg gctcctggac ctggtgaaca ttctgcagag   11340
catcgtggtg caggagcgcg ggctgccgct gtccgagaag ctggcggcca tcaacttctc   11400
ggtgctgagt ttgggcaagt actacgctag gaagatctac aagaccccgt acgtgcccat   11460
agacaaggag gtgaagatcg acgggtttta catgcgcatg accctgaaag tgctgaccct   11520
gagcgacgat ctgggggtgt accgcaacga caggatgcac cgtgcggtga gcgccagcag   11580
gcggcgcgag ctgagcgacc aggagctgat gcatagtctg cagcgggccc tgaccggggc   11640
cgggaccgag ggggagagct actttgacat gggcgcggac ctgcactggc agcccagccg   11700
ccgggccttg gaggcggcgg caggacccta cgtagaagag gtggacgatg aggtggacga   11760
ggagggcgag tacctggaag actgatggcg cgaccgtatt tttgctagat gcaacaacaa   11820
cagccacctc ctgatcccgc gatgcgggcg cgctgcaga gccagccgtc cggcattaac    11880
tcctcggacg attggaccca ggccatgcaa cgcatcatgg cgctgacgac ccgcaacccc   11940
gaagccttta gacagcagcc ccaggccaac cggctctcgg ccatcctgga ggccgtggtg   12000
ccctcgcgct ccaaccccac gcacgagaag gtcctggcca tcgtgaacgc gctggtggag   12060
aacaaggcca tccgcggcga cgaggccggc ctggtgtaca acgcgctgct ggagcgcgtg   12120
gcccgctaca acagcaccaa cgtgcagacc aacctggacc gcatggtgac cgacgtgcgc   12180
gaggccgtgg cccagcgcga gcggttccac cgcgagtcca acctgggatc catggtggcg   12240
ctgaacgcct tcctcagcac ccagcccgcc aacgtgcccc ggggccagga ggactacacc   12300
aacttcatca gcgccctgcg cctgatggtg accgaggtgc cccagagcga ggtgtaccag   12360
tccgggccgg actacttctt ccagaccagt cgccagggct gcagaccgt gaacctgagc     12420 caggctttca agaacttgca gggcctgtgg ggcgtgcagg ccccggtcgg ggaccgcgcg   12480
acggtgtcga gcctgctgac gccgaactcg cgcctgctgc tgctgctggt ggcccccttc   12540
acggacagcg gcagcatcaa ccgcaactcg tacctgggct acctgattaa cctgtaccgc   12600
gaggccatcg gccaggcgca cgtggacgag cagacctacc aggagatcac ccacgtgagc   12660
cgcgccctgg gccaggacga cccgggcaac ctggaagcca ccctgaactt tttgctgacc   12720
aaccggtcgc agaagatccc gccccagtac gcgctcagca ccgaggagga gcgcatcctg   12780
cgttacgtgc agcagagcgt gggcctgttc ctgatgcagg aggggccac ccccagcgcc    12840 gcgctcgaca tgaccgcgcg caacatggag cccagcatgt acgccagcaa ccgcccgttc   12900
atcaataaac tgatggacta cttgcatcgg gcggccgcca tgaactctga ctatttcacc   12960
aacgccatcc tgaatcccca ctggctcccg ccgccggggt tctacacggg cgagtacgac   13020
atgcccgacc ccaatgacgg gttcctgtgg gacgatgtgg acagcagcgt gttctccccc   13080
cgaccgggtg ctaacgagcg ccccttgtgg aagaaggaag gcagcgaccg acgcccgtcc   13140
tcggcgctgt ccgccgcga gggtgctgcc gcggcggtgc ccgaggccgc cagtccttc     13200 ccgagcttgc ccttctcgct gaacagtatc cgcagcagcg agctgggcag gatcacgcgc   13260
```

```
ccgcgcttgc tgggcgaaga ggagtacttg aatgactcgc tgttgagacc cgagcgggag   13320
aagaacttcc ccaataacgg gatagaaagc ctggtggaca agatgagccg ctggaagacg   13380
tatgcgcagg agcacaggga cgatccccgg gcgtcgcagg gggccacgag ccggggcagc   13440
gccgcccgta aacgcggtg gcacgacagg cagcggggac agatgtggga cgatgaggac    13500
tccgccgacg acagcagcgt gttggacttg ggtgggagtg gtaacccgtt cgctcacctg   13560
cgcccccgta tcgggcgcat gatgtaagag aaaccgaaaa taaatgatac tcaccaaggc   13620 catgcgacc agcgtgcgtt cgtttcttct ctgttgttgt tgtatctagt atgatgaggc    13680
gtgcgtaccc ggagggtcct cctccctcgt acgagagcgt gatgcagcag gcgatggcgg   13740
cggcggcgat gcagcccccg ctggaggctc cttacgtgcc cccgcggtac ctggcgccta   13800 cggagggggcg aacagcatt cgttactcgg agctggcacc cttgtacgat accacccggt    13860
tgtacctggt ggacaacaag tcggcggaca tcgcctcgct gaactaccag aacgaccaca   13920
gcaacttcct gaccaccgtg gtgcagaaca atgacttcac ccccacgag gccagcaccc    13980 agaccatcaa ctttgacgag cgctcgcggt ggggcggcca gctgaaaacc atcatgcaca   14040
ccaacatgcc caacgtgaac gagttcatgt acagcaacaa gttcaaggcg cgggtgatgg   14100
tctcccgcaa gacccccaat ggggtgacag tgacagagga ttatgatggt agtcaggatg   14160
agctgaagta tgaatgggtg gaatttgagc tgcccgaagg caacttctcg gtgaccatga   14220
ccatcgacct gatgaacaac gccatcatcg acaattactt ggcggtgggg cggcagaacg   14280
gggtgctgga gagcgacatc ggcgtgaagt tcgacactag gaacttcagg ctgggctggg   14340
accccgtgac cgagctggtc atgcccgggg tgtacaccaa cgaggctttc catcccgata   14400
ttgtcttgct gcccggctgc ggggtggact tcaccgagag ccgcctcagc aacctgctgg   14460
gcattcgcaa gaggcagccc ttccaggaag gcttccagat catgtacgag gatctggagg   14520
ggggcaacat ccccgcgctc ctggatgtcg acgcctatga gaaaagcaag gaggatgcag   14580
cagctgaagc aactgcagcc gtagctaccg cctctaccga ggtcagggc gataatttg     14640 caagcgccgc agcagtggca gcggccgagg cggctgaaac cgaaagtaag atagtcattc   14700
agccggtgga gaaggatagc aagaacagga gctacaacgt actaccggac aagataaaca   14760
ccgcctaccg cagctggtac ctagcctaca actatggcga ccccgagaag ggcgtgcgct   14820
cctggacgct gctcaccacc tcggacgtca cctgcgcgt ggagcaagtc tactggtcgc    14880
tgcccgacat gatgcaagac ccggtcacct tccgctccac gcgtcaagtt agcaactacc   14940
cggtggtggg cgccgagctc ctgcccgtct actccaagag cttcttcaac gagcaggcc    15000 tctactcgca gcagctgcgc gccttcacct cgcttacgca cgtcttcaac cgcttccccg   15060
agaaccagat cctcgtccgc ccgcccgcgc ccaccattac caccgtcagt gaaaacgttc   15120
ctgctctcac agatcacggg accctgccgc tgcgcagcag tatccggga gtccagcgcg    15180 tgaccgttac tgacgccaga cgccgcacct gcccctacgt ctacaaggcc ctgggcatag   15240
tcgcgccgcg cgtcctctcg agccgcacct tctaaatgtc cattctcatc tcgcccagta   15300
ataacaccgg ttggggcctg cgcgcgccca gcaagatgta cggaggcgct cgccaacgct   15360
ccacgcaaca ccccgtgcgc gtgcgcgggc acttccgcgc tccctggggc gccctcaagg   15420
gccgcgtgcg gtcgcgcacc accgtcgacg acgtgatcga ccaggtggtg gccgacgcgc   15480
gcaactacac ccccgccgcc gcgccgtct ccaccgtgga cgccgtcatc gacagcgtgg    15540
tggccgacgg gcgccggtac gcccgcgcca agagccggcg gcggcgcatc gcccggcggc   15600
accggagcac ccccgccatg cgcgcggcgc gagccttgct gcgcagggcc aggcgcacgg   15660
```

```
gacgcagggc catgctcagg gcggccagac gcgcggcttc aggcgccagc gccggcagga   15720
cccggagacg cgcggccacg gcggcggcag cggccatcgc cagcatgtcc cgcccgcggc   15780
gagggaacgt gtactgggtg cgcgacgccg ccaccggtgt gcgcgtgccc gtgcgcaccc   15840
gcccccctcg cacttgaaga tgttcacttc gcgatgttga tgtgtcccag cggcgaggag   15900
gatgtccaag cgcaaattca aggaagagat gctccaggtc atcgcgcctg agatctacgg   15960
ccctgcggtg gtgaaggagg aaagaaagcc ccgcaaaatc aagcgggtca aaaggacaa    16020
aaaggaagaa gaaagtgatg tggacggatt ggtggagttt gtgcgcgagt tcgccccccg   16080
gcggcgcgtg cagtggcgcg gcggaaggt gcaaccggtg ctgagacccg gcaccaccgt    16140
ggtcttcacg cccggcgagc gctccggcac cgcttccaag cgctcctacg acgaggtgta   16200
cggggatgat gatattctgg agcaggcggc cgagcgcctg ggcgagtttg cttacggcaa   16260
gcgcagccgt tccgcaccga aggaagaggc ggtgtccatc ccgctggacc acggcaaccc   16320
cacgccgagc ctcaagcccg tgaccttgca gcaggtgctg ccgaccgcgg cgccgcgccg   16380
ggggttcaag cgcgagggcg aggatctgta ccccaccatg cagctgatgg tgcccaagcg   16440
ccagaagctg gaagacgtgc tggagaccat gaaggtggac ccggacgtgc agcccgaggt   16500
caaggtgcgg cccatcaagc aggtggcccc gggcctgggc gtgcagaccg tggacatcaa   16560
gattcccacg gagcccatgg aaacgcagac cgagcccatg atcaagccca gcaccagcac   16620
catggaggtg cagacggatc cctggatgcc atcggctcct agtcgaagac cccggcgcaa   16680
gtacggcgcg ccagcctgc tgatgcccaa ctacgcgctg catccttcca tcatccccac    16740
gccgggctac cgcggcacgc gcttctaccg cggtcatacc agcagccgcc gccgcaagac   16800
caccactcgc cgccgccgtc gccgcaccgc cgctgcaacc accctgccg ccctggtgcg    16860
gagagtgtac cgccgcggcc gcgcacctct gaccctgccg cgcgcgcgct accacccgag   16920
catcgccatt taaactttcg cctgctttgc agatcaatgg ccctcacatg ccgccttcgc   16980
gttcccatta cgggctaccg aggaagaaaa ccgcgccgta aaggctggc ggggaacggg    17040
atgcgtcgcc accaccaccg gcggcggcgc gccatcagca agcggttggg gggaggcttc   17100
ctgcccgcgc tgatccccat catcgccgcg gcgatcgggg cgatccccgg cattgcttcc   17160
gtggcggtgc aggcctctca gcgccactga gacacacttg gaaacatctt gtaataaacc   17220
aatggactct gacgctcctg gtcctgtgat gtgttttcgt agacagatgg aagacatcaa   17280
tttttcgtcc ctggctccgc gacacggcac gcggccgttc atgggcacct ggagcgacat   17340
cggcaccagc caactgaacg ggggcgcctt caattggagc agtctctgga gcgggcttaa   17400
gaatttcggg tccacgctta aaacctatgg cagcaaggcg tggaacagca ccacagggca   17460
ggcgctgagg gataagctga agagcagaa cttccagcag aagtggtcg atgggctcgc     17520
ctcgggcatc aacggggtgg tggacctggc caaccaggcc gtgcagcggc agatcaacag   17580
ccgcctggac ccggtgccgc ccgccggctc cgtggagatg ccgcaggtgg aggaggagct   17640
gcctcccctg gacaagcggg gcgagaagcg accccgcccc gatgcggagg agacgctgct   17700
gacgcacacg gacgagccgc ccccgtacga ggaggcggtg aaactgggtc tgcccaccac   17760
gcggcccatc gcgcccctgg ccaccggggt gctgaaaccc gaaaagcccg cgaccctgga   17820
cttgcctcct ccccagcctt cccgcccctc tacagtggct aagcccctgc cgccggtggc   17880
cgtggcccgc gcgcgacccg ggggcaccgc ccgcccctcat gcgaactggc agagcactct   17940
gaacagcatc gtgggtctgg gagtgcagag tgtgaagcgc cgccgctgct attaaaccta   18000
```

```
ccgtagcgct taacttgctt gtctgtgtgt gtatgtatta tgtcgccgcc gccgctgtcc    18060
accagaagga ggagtgaaga ggcgcgtcgc cgagttgcaa gatggccacc ccatcgatgc    18120
tgccccagtg ggcgtacatg cacatcgccg gacaggacgc ttcggagtac ctgagtccgg    18180
gtctggtgca gtttgcccgc gccacagaca cctacttcag tctggggaac aagtttagga    18240
accccacggt ggcgcccacg cacgatgtga ccaccgaccg cagccagcgg ctgacgctgc    18300
gcttcgtgcc cgtggaccgc gaggacaaca cctactcgta caaagtgcgc tacacgctgg    18360
ccgtgggcga caaccgcgtg ctggacatgg ccagcaccta ctttgacatc cgcggcgtgc    18420
tggatcgggg ccctagcttc aaaccctact ccggcaccgc ctacaacagt ctggccccca    18480
agggagcacc caacacttgt cagtggacat ataaagccga tggtgaaact gccacagaaa    18540
aaacctatac atatggaaat gcacccgtgc agggcattaa catcacaaaa gatggtattc    18600
aacttggaac tgacaccgat gatcagccaa tctacgcaga taaaacctat cagcctgaac    18660
ctcaagtggg tgatgctgaa tgcatgaca tcactggtac tgatgaaaag tatggaggca    18720
gagctcttaa gcctgatacc aaaatgaagc cttgttatgg ttcttttgcc aagcctacta    18780
ataaagaagg aggtcaggca aatgtgaaaa caggaacagg cactactaaa gaatatgaca    18840
tagacatggc tttctttgac aacagaagtg cggctgctgc tggcctagct ccagaaattg    18900
ttttgtatac tgaaaatgtg gatttggaaa ctccagatac ccatattgta tacaaagcag    18960
gcacagatga cagcagctct tctattaatt gggtcagca agccatgccc aacagaccta    19020
actacattgg tttcagagac aactttatcg ggctcatgta ctacaacagc actggcaata    19080
tgggggtgct ggccggtcag gcttctcagc tgaatgctgt ggttgacttg caagacagaa    19140
acaccgagct gtcctaccag ctcttgcttg actctctggg tgacagaacc cggtatttca    19200
gtatgtggaa tcaggcggtg gacagctatg atcctgatgt gcgcattatt gaaaatcatg    19260
gtgtggagga tgaacttccc aactattgtt tccctctgga tgctgttggc agaacagata    19320
cttatcaggg aattaaggct aatgaactg atcaaaccac atggaccaaa gatgacagtg    19380
tcaatgatgc taatgagata ggcaagggta atccattcgc catggaaatc aacatccaag    19440
ccaacctgtg gaggaacttc ctctacgcca acgtggccct gtacctgccc gactcttaca    19500
agtacacgcc ggccaatgtt accctgccca ccaacaccaa cacctacgat tacatgaacg    19560
gccgggtggt ggcgccctcg ctggtggact cctacatcaa catcggggcg cgctggtcgc    19620
tggatccccat ggacaacgtg aaccccttca ccaccaccg caatgcgggg ctgcgctacc    19680
gctccatgct cctgggcaac gggcgctacg tgcccttcca catccaggtg ccccagaaat    19740
ttttcgccat caagagcctc ctgctcctgc ccgggtccta cacctacgag tggaacttcc    19800
gcaaggacgt caacatgatc ctgcagagct ccctcggcaa cgacctgcgc acggacgggg    19860
cctccatctc cttcaccagc atcaacctct acgccacctt cttccccatg gcgcacaaca    19920
cggcctccac gctcgaggcc atgctgcgca acgacaccaa cgaccagtcc ttcaacgact    19980
acctctcggc ggccaacatg ctctacccca tcccggccaa cgccaccaac gtgcccatct    20040
ccatcccctc gcgcaactgg gccgccttcc gcggctggtc cttcacgcgt ctcaagacca    20100
aggagacgcc ctcgctgggc tccggggttcg acccctactt cgtctactcg ggctccatcc    20160
cctacctcga cggcacctc tacctcaacc acaccttcaa gaaggtctcc atcaccttcg    20220
actcctccgt cagctggccc ggcaacgacc ggctcctgac gcccaacgag ttcgaaatca    20280
agcgcaccgt cgacggcgag ggctacaacg tggcccagtg caacatgacc aaggactggt    20340
tcctggtcca gatgctggcc cactacaaca tcggctacca gggcttctac gtgcccgagg    20400
```

```
gctacaagga ccgcatgtac tccttcttcc gcaacttcca gcccatgagc cgccaggtgg   20460
tggacgaggt caactacaag gactaccagg ccgtcaccct ggcctaccag cacaacaact   20520
cgggcttcgt cggctacctc gcgcccacca tgcgccaggg ccagccctac cccgccaact   20580 accccctaccc gctcatcggc aagagcgccg tcaccagcgt cacccagaaa aagttcctct   20640
gcgacagggt catgtggcgc atccccttct ccagcaactt catgtccatg ggcgcgctca   20700
ccgacctcgg ccagaacatg ctctatgcca actccgccca cgcgctagac atgaatttcg   20760
aagtcgaccc catggatgag tccacccttc tctatgttgt cttcgaagtc ttcgacgtcg   20820
tccgagtgca ccagccccac cgcggcgtca tcgaggcgct ctacctgcgc acccccttct   20880
cggccggtaa cgccaccacc taagctcttg cttcttgcaa gccatggccg cgggctccgg   20940
cgagcaggag ctcagggcca tcatccgcga cctgggctgc gggccctact tcctgggcac   21000
cttcgataag cgcttcccgg gattcatggc cccgcacaag ctggcctgcg ccatcgtcaa   21060 cacgccggc cgcgagaccg ggggcgagca ctggctggcc ttcgcctgga cccgcgctc   21120 gaacacctgc tacctcttcg acccccttcgg gttctcggac gagcgcctca gcagatcta   21180 ccagttcgag tacgagggcc tgctgcgcgcc cagcgccctg gccaccgagg accgctgcgt   21240
caccctggaa aagtccaccc agaccgtgca gggtccgcgc tcggccgcct gcgggctctt   21300
ctgctgcatg ttcctgcacg ccttcgtgca ctggcccgac cgcccatgg acaagaaccc   21360 caccatgaac ttgctgacgg gggtgcccaa cggcatgctc cagtcgcccc aggtggaacc   21420
caccctgcgc cgcaaccagg aggcgctcta ccgcttcctc aactcccact ccgcctactt   21480
tcgctcccac cgcgcgcgca tcgagaaggc caccgccttc gaccgcatga atcaagacat   21540
gtaaaccgtg tgtgtatgtt aaatgtcttt aatagaaacagc actttcatgt tacacatgca   21600
tctgagatga tttattaga aatcgaaagg gttctgccgg gtctcggcat ggcccgcggg   21660
cagggacacg ttgcggaact ggtacttggc cagccacttg aactcgggga tcagcagttt   21720
gggcagcggg gtgtcgggga aggagtcggt ccacagcttc cgcgtcagtt gcagggcgcc   21780
cagcaggtcg ggcgcggaga tcttgaaatc gcagttggga cccgcgttct gcgcgcggga   21840
gttgcggtac acggggttgc agcactggaa caccatcagg gccgggtgct tcacgctcgc   21900
cagcaccgtc gcgtcggtga tgctctccac gtcgaggtcc tcggcgttgg ccatcccgaa   21960
gggggtcatc ttgcaggtct gccttccat ggtgggcacg cacccgggct tgtggttgca   22020
atcgcagtgc aggggatca gcatcatctg ggcctggtcg gcgttcatcc ccgggtacat   22080
ggccttcatg aaagcctcca attgcctgaa cgcctgctgg gccttggctc cctcggtgaa   22140
gaagaccccg caggacttgc tagagaactg gttggtggcg caccccggcgt cgtgcacgca   22200 gcagcgcgcg tcgttgttgg ccagctgcac cacgctgcgc cccagcggt ctgggtgat   22260 cttggcccgg tcggggttct ccttcagcgc gcgctgcccg ttctcgctcg ccacatccat   22320
ctcgatcatg tgctccttct ggatcatggt ggtcccgtgc aggcaccgca gcttgccctc   22380
ggcctcggtg cacccgtgca gccacagcgc gcacccggtg cactcccagt tcttgtgggc   22440
gatctgggaa tgcgcgtgca cgaagccctg caggaagcgg cccatcatgg tggtcagggt   22500
cttgttgcta gtgaaggtca gcggaatgcc gcggtgctcc tcgttgatgt acaggtggca   22560
gatgcggcgg tacacctcgc cctgctcggg catcagctgg aagttggctt tcaggtcggt   22620
ctccacgcgc tagcggtcca tcagcatagt catgatttcc ataccttcct cccaggccga   22680
gacgatgggc aggctcatag ggttcttcac catcatctta gcgctagcag ccgcggccag   22740
```

```
gggggtcgctc tcgtccaggg tctcaaagct ccgcttgccg tccttctcgg tgatccgcac   22800
cggggggtag ctgaagccca cggccgccag ctcctcctcg gcctgtcttt cgtcctcgct   22860
gtcctggctg acgtcctgca ggaccacatg cttggtcttg cggggtttct tcttgggcgg   22920
cagcggcggc ggagatgttg gagatggcga ggggagcgc gagttctcgc tcaccactac    22980
tatctcttcc tcttcttggt ccgaggccac gcggcggtag gtatgtctct tcggggggcag  23040 aggcggaggc gacgggctct cgccgccgcg acttggcgga tggctggcag agccccttcc   23100
gcgttcgggg gtgcgctccc ggcggcgctc tgactgactt cctccgcggc cggccattgt   23160
gttctcctag ggaggaacaa caagcatgga gactcagcca tcgccaacct cgccatctgc   23220
ccccaccgcc gacgagaagc agcagcagca gaatgaaagc ttaaccgccc cgccgcccag   23280
ccccgccacc tccgacgcgg ccgtcccaga catgcaagag atggaggaat ccatcgagat   23340
tgacctgggc tatgtgacgc ccgcggagca cgaggaggag ctggcagtgc gcttttcaca   23400
agaagagata caccaagaac agccagagca ggaagcagag aatgagcaga gtcaggctgg   23460
gctcgagcat gacggcgact acctccacct gagcgggggg gaggacgcgc tcatcaagca   23520
tctggcccgg caggccacca tcgtcaagga tgcgctgctc gaccgcaccg aggtgcccct   23580
cagcgtggag gagctcagcc gcgcctacga gttgaacctc ttctcgccgc gcgtgccccc   23640
caagcgccag cccaatggca cctgcgagcc caacccgcgc ctcaacttct acccggtctt   23700
cgcggtgccc gaggccctgg ccacctacca catcttttc aagaaccaaa agatccccgt   23760
ctcctgccgc gccaaccgca cccgcgccga cgccttttc aacctgggtc ccggcgcccg   23820
cctacctgat atcgcctcct tggaagaggt tcccaagatc ttcgagggtc tgggcagcga   23880
cgagactcgg gccgcgaacg ctctgcaagg agaaggagga gagcatgagc accacagcgc   23940
cctggtcgag ttggaaggcg acaacgcgcg gctggcggtg ctcaaacgca cggtcgagct   24000
gacccatttc gcctacccgg ctctgaacct gcccccaaa gtcatgagcg cggtcatgga   24060
ccaggtgctc atcaagcgcg cgtcgcccat tccgaggac gagggcatgc aagactccga   24120
ggagggcaag cccgtggtca gcgacgagca gctggcccgg tggctgggtc ctaatgctag   24180
tccccagagt ttggaagagc ggcgcaaaact catgatggcc gtggtcctgg tgaccgtgga   24240
gctggagtgc ctgcgccgct tcttcgccga cgcggagacc ctgcgcaagg tcgaggagaa   24300
cctgcactac ctcttcaggc acgggttcgt gcgccaggcc tgcaagatct ccaacgtgga   24360
gctgaccaac ctggtctcct acatgggcat cttgcacgag aaccgcctgg ggcagaacgt   24420
gctgcacacc accctgcgcg gggaggcccg gcgcgactac atccgcgact gcgtctacct   24480
ctacctctgc cacacctggc agacgggcat gggcgtgtgg cagcagtgtc tggaggagca   24540
gaacctgaaa gagctctgca agctcctgca gaagaacctc aagggtctgt ggaccgggtt   24600
cgacgagcgc accaccgcct cggacctggc cgacctcatt ttccccgagc gcctcaggct   24660
gacgctgcgc aacggcctgc ccgactttat gagccaaagc atgttgcaaa actttcgctc   24720
tttcatcctc gaacgctccg gaatcctgcc cgccacctgc tccgcgctgc cctcggactt   24780
cgtgccgctg accttccgcg agtgcccccc gccgctgtgg agccactgct acctgctgcg   24840
cctggccaac tacctggcct accactcgga cgtgatcgag gacgtcagcg gcgagggcct   24900
gctcgagtgc cactgccgct gcaacctctg cacgccgcac cgctccctgg cctgcaaccc   24960
ccagctgctg agcgagaccc agatcatcgg caccttcgag ttgcaagggc ccagcgaagg   25020 cgaggggttca gccgccaagg ggggtctgaa actcacccccg gggctgtgga cctcggccta   25080
cttgcgcaag ttcgtgcccg aggactacca tcccttcgag atcaggttct acgaggacca   25140
```

```
atcccatccg cccaaggccg agctgtcggc ctgcgtcatc acccaggggg cgatcctggc   25200
ccaattgcaa gccatccaga atcccgcca agaattcttg ctgaaaaagg ccgcggggt    25260 ctacctcgac ccccagaccg gtgaggagct caaccccggc ttcccccagg atgccccgag   25320
gaaacaagaa gctgaaagtg gagctgccgc ccgtggagga tttggaggaa gactgggaga   25380
acagcagtca ggcagaggag gaggagatgg aggaagactg gacagcact caggcagagg    25440 aggacagcct gcaagacagt ctggaggaag acgaggagga ggcagaggag gaggtggaag   25500
aagcagccgc cgccagaccg tcgtcctcgg cgggggagaa agcaagcagc acggatacca   25560
tctccgctcc gggtcggggt cccgctcgac cacacagtag atgggacgag accggacgat   25620
tcccgaaccc caccacccag accggtaaga aggagcggca gggatacaag tcctggcggg   25680
ggcacaaaaa cgccatcgtc tcctgcttgc aggcctgcgg gggcaacatc tccttcaccc   25740
ggcgctacct gctcttccac cgcggggtga actttccccg caacatcttg cattactacc   25800
gtcacctcca cagcccctac tacttccaag aagaggcagc agcagcagaa aaagaccagc   25860
agaaaaccag cagctagaaa atccacagcg gcggcagcag gtggactgag gatcgcggcg   25920
aacgagccgc cgcaaacccg ggagctgagg aaccggatct ttcccaccct ctatgccatc   25980
ttccagcaga gtcgggggca ggagcaggaa ctgaaagtca agaaccgttc tctgcgctcg   26040
ctcacccgca gttgtctgta tcacaagagc gaagaccaac ttcagcgcac tctcgaggac   26100
gccgaggctc tcttcaacaa gtactgcgcg ctcactctta aagagtagcc cgcgcccgcc   26160
cagtcgcaga aaaaggcggg aattacgtca cctgtgccct tcgccctagc cgcctccacc   26220
catcatcatg agcaaagaga ttcccacgcc ttacatgtgg agctaccagc cccagatggg   26280
cctggccgcc ggtgccgccc aggactactc caccgcatg aattggctca cgcgccgggcc   26340 cgcgatgatc tcacgggtga atgacatccg cgcccaccga aaccagatac tcctagaaca   26400
gtcagcgctc accgccacgc cccgcaatca cctcaatccg cgtaattggc ccgccgccct   26460
ggtgtaccag gaaattcccc agcccacgac cgtactactt ccgcgagacg cccaggccga   26520
agtccagctg actaactcag gtgtccagct ggcgggcggc gccaccctgt gtcgtcaccg   26580
ccccgctcag ggtataaagc ggctggtgat ccggggcaga ggcacacagc tcaacgacga   26640
ggtggtgagc tcttcgctgg gtctgcgacc tgacggagtc ttccaactcg ccggatcggg   26700
gagatcttcc ttcacgcctc gtcaggccgt cctgactttg gagagttcgt cctcgcagcc   26760
ccgctcgggt ggcatcggca ctctccagtt cgtggaggag ttcactccct cggtctactt   26820
caaccccttc tccggctccc ccggccacta cccggacgag ttcatcccga acttcgacgc   26880
catcagcgag tcggtggacg gctacgattg aatgtcccat ggtggcgcag ctgacctagc   26940
tcggcttcga cacctggacc actgccgccg cttccgctgc ttcgctcggg atctcgccga   27000
gtttgcctac tttgagctgc ccgaggagca ccctcagggc ccgcccacg gagtgcggat    27060 cgtcgtcgaa gggggcctcg actcccacct gcttcggatc ttcagccagc gtccgatcct   27120
ggtcgagcgc gagcaaggac agaccttct gactctgtac tgcatctgca accacccgg    27180 cctgcatgaa agtctttgtt gtctgctgtg tactgagtat aataaaagct gagatcagcg   27240
actactccgg acttccgtgt gttcctgaat ccatcaacca gtctttgttc ttcaccggga   27300
acgagaccga gctccagctc cagtgtaagc cccacaagaa gtacctcacc tggctgttcc   27360
agggctcccc gatcgccgtt gtcaaccact gcgacaacga cggagtcctg ctgagcggcc   27420
ctgccaacct tactttttcc acccgcagaa gcaagctcca gctcttccaa cccttcctcc   27480
```

```
ccgggaccta tcagtgcgtc tcgggaccct gccatcacac cttccacctg atcccgaata   27540
ccacagcgtc gctccccgct actaacaacc aaactaacct ccaccaacgc caccgtcgcg   27600
acggccacaa tacatgccca tattagacta tgaggccgag ccacagcgac ccatgctccc   27660
cgctattagt tacttcaatc taaccggcgg agatgactga cccactggcc aacaacaacg   27720
tcaacgacct tctcctggac atggacggcc gcgcctcgga gcagcgactc gcccaacttc   27780
gcattcgcca gcagcaggag agagccgtca aggagctgca ggatgcggtg ccatccacc    27840 agtgcaagag aggcatcttc tgcctggtga acaggccaa gatctcctac gaggtcactc    27900
caaacgacca tcgcctctcc tacgagctcc tgcagcagcg ccagaagttc acctgcctgg   27960
tcggagtcaa ccccatcgtc atcacccagc agtctggcga taccaagggg tgcatccact   28020
gctcctgcga ctcccccgac tgcgtccaca ctctgatcaa gaccctctgc ggcctccgcg   28080
acctcctccc catgaactaa tcaccccctt atccagtgaa ataaagatca tattgatgat   28140
gattttacag aaataaaaaa taatcatttg atttgaaata agatacaat catattgatg    28200 atttgagttt aacaaaaaaa taagaatca cttacttgaa atctgatacc aggtctctgt    28260
ccatgttttc tgccaacacc acttcactcc cctcttccca gctctggtac tgcaggcccc   28320
ggcgggctgc aaacttcctc cacacgctga aggggatgtc aaattcctcc tgtccctcaa   28380
tcttcatttt atcttctatc agatgtccaa aaagcgcgtc cgggtggatg atgacttcga   28440
ccccgtctac ccctacgatg cagacaacgc accgaccgtg cccttcatca accccccctt   28500
cgtctcttca gatggattcc aagagaagcc cctgggggtg ttgtccctgc gactggccga   28560
ccccgtcacc accaagaacg gggaaatcac cctcaagctg ggagagggg tggacctcga     28620 ttcctcggga aaactcatct ccaacacggc caccaaggcc gccgcccctc tcagttttc    28680 caacaacacc atttccctta acatggatca ccccttttac actaaagatg gaaaattatc   28740
cttacaagtt tctccaccat taaatatact gagaacaagc attctaaaca cactagcttt    28800
aggttttgga tcaggtttag gactccgtgg ctctgccttg gcagtacagt tagtctctcc    28860
acttacattt gatactgatg gaaacataaa gcttaccta gacagaggtt tgcatgttac   28920
aacaggagat gcaattgaaa gcaacataag ctgggctaaa ggtttaaaat ttgaagatgg   28980
agccatagca accaacattg gaaatgggtt agagttgga agcagtagta cagaaacagg    29040
tgttgatgat gcttacccaa tccaagttaa acttggatct ggccttagct ttgacagtac   29100
aggagccata atggctggta acaaagaaga cgataaactc actttgtgga caacacctga   29160
tccatcacca aactgtcaaa tactcgcaga aaatgatgca aaactaacac tttgcttgac   29220
taaatgtggt agtcaaatac tggccactgt gtcagtctta gttgtaggaa gtggaaacct   29280 aaacccatt actggcaccg taagcagtgc tcaggtgttt ctacgttttg atgcaaacgg   29340 tgttcttta acagaacatt ctacactaaa aaatactgg gggtataggc agggagatag   29400
catagatggc actccatata ccaatgctgt aggattcatg cccaatttaa agcttatcc    29460 aaagtcacaa agttctacta ctaaaaataa tatagtaggg caagtataca tgaatggaga   29520
tgtttcaaaa cctatgcttc tcactataac cctcaatggt actgatgaca gcaacagtac   29580
atattcaatg tcattttcat acaccttgac taatggaagc tatgttggag caacatttgg   29640
ggctaactct tataccttct catacatcgc ccaagaatga acactgtatc ccaccctgca   29700
tgccaaccct tcccacccca ctctgtggaa caaactctga acacaaaat aaaataaagt    29760 tcaagtgttt tattgattca acagttttac aggattcgag cagttatttt tcctccaccc   29820
tcccaggaca tggaatacac caccctctcc ccccgcacag ccttgaacat ctgaatgcca   29880
```

```
ttggtgatgg acatgctttt ggtctccacg ttccacacag tttcagagcg agccagtctc    29940
gggtcggtca gggagatgaa accctccggg cactcccgca tctgcacctc acagctcaac    30000
agctgaggat tgtcctcggt ggtcgggatc acggttatct ggaagaagca gaagagcggc    30060
ggtgggaatc atagtccgcg aacgggatcg gccggtggtg tcgcatcagg ccccgcagca    30120
gtcgctgccg ccgccgctcc gtcaagctgc tgctcagggg gtccgggtcc agggactccc    30180
tcagcatgat gcccacggcc ctcagcatca gtcgtctggt gcggcgggcg cagcagcgca    30240
tgcggatctc gctcaggtcg ctgcagtacg tgcaacacag aaccaccagg ttgttcaaca    30300
gtccatagtt caacacgctc cagccgaaac tcatcgcggg aaggatgcta cccacgtggc    30360
cgtcgtacca gatcctcagg taaatcaagt ggtgcccct ccagaacacg ctgcccacgt     30420
acatgatctc cttgggcatg tggcggttca ccacctcccg gtaccacatc accctctggt    30480
tgaacatgca gccccggatg atcctgcgga accacagggc cagcaccgcc ccgcccgcca    30540
tgcagcgaag agaccccggg tcccggcaat ggcaatggag gacccaccgc tcgtacccgt    30600
ggatcatctg ggagctgaac aagtctatgt tggcacagca caggcatatg ctcatgcatc    30660
tcttcagcac tctcaactcc tcggggtca aaaccatatc ccaggcacg gggaactctt      30720
gcaggacagc gaaccccgca gaacagggca atcctcgcac agaacttaca ttgtgcatgg    30780
acagggtatc gcaatcaggc agcaccgggt gatcctccac cagagaagcg cgggtctcgg    30840
tctcctcaca gcgtggtaag ggggccggcc gatacgggtg atggcgggac gcggctgatc    30900
gtgttcgcga ccgtgtcatg atgcagttgc tttcggacat tttcgtactt gctgtagcag    30960
aacctggtcc gggcgctgca caccgatcgc cggcggcggt ctcggcgctt ggaacgctcg    31020
gtgttgaaat tgtaaaacag ccactctctc agaccgtgca gcagatctag ggcctcagga    31080
gtgatgaaga tcccatcatg cctgatggct ctgatcacat cgaccaccgt ggaatgggcc    31140
agacccagcc agatgatgca attttgttgg gtttcggtga cggcggggga gggaagaaca    31200
ggaagaacca tgattaactt ttaatccaaa cggtctcgga gtacttcaaa atgaagatcg    31260
cggagatggc acctctcgcc cccgctgtgt tggtggaaaa taacagccag gtcaaaggtg    31320
atacggttct cgagatgttc cacggtggct tccagcaaag cctccacgcg cacatccaga    31380
aacaagacaa tagcgaaagc gggagggttc tctaattcct caatcatcat gttacactcc    31440
tgcaccatcc ccagataatt ttcatttttc cagccttgaa tgattcgaac tagttcgtga    31500
ggtaaatcca agccagccat gataaagagc tcgcgcagag cgccctccac cggcattctt    31560
aagcacaccc tcataattcc aagatattct gctcctggtt cacctgcagc agattgacaa    31620
gcggaatatc aaaatctctg ccgcgatccc tgagctcctc cctcagcaat aactgtaagt    31680
actctttcat atcctctccg aaattttag ccataggacc accaggaata agattagggc     31740
aagccacagt acagataaac cgaagtcctc cccagtgagc attgccaaat gcaagactgc    31800
tataagcatg ctggctagac ccggtgatat cttccagata actggacaga aaatcgccca    31860
ggcaattttt aagaaaatca acaaaagaaa aatcctccag gtggacgttt agagcctcgg    31920
gaacaacgat gaagtaaatg caagcggtgc gttccagcat ggttagttag ctgatctgta    31980
gaaaaaacaa aaatgaacat taaaccatgc tagcctggcg aacaggtggg taaatcgttc    32040
tctccagcac caggcaggcc acggggtctc cggcgcgacc ctcgtaaaaa ttgtcgctat    32100
gattgaaaac catcacagag agacgttccc ggtggccggc gtgaatgatt cgacaagatg    32160
aatacacccc cggaacattg gcgtccgcga gtgaaaaaaa gcgcccgagg aagcaataag    32220
```

| | |
|---|---|
| gcactacaat gctcagtctc aagtccagca aagcgatgcc atgcggatga agcacaaaat | 32280 |
| tctcaggtgc gtacaaaatg taattactcc cctcctgcac aggcagcaaa gcccccgatc | 32340 |
| cctccaggta cacatacaaa gcctcagcgt ccatagctta ccgagcagca gcacacaaca | 32400 |
| ggcgcaagag tcagagaaag gctgagctct aacctgtcca cccgctctct gctcaatata | 32460 |
| tagcccagat ctacactgac gtaaaggcca aagtctaaaa atacccgcca aataatcaca | 32520 |
| cacgcccagc acacgcccag aaaccggtga cacactcaaa aaaatacgcg cacttcctca | 32580 |
| aacgcccaaa actgccgtca tttccgggtt cccacgctac gtcatcaaaa cacgactttc | 32640 |
| aaattccgtc gaccgttaaa aacgtcaccc gccccgcccc taacggtcgc ccgtctctca | 32700 |
| gccaatcagc gccccgcatc cccaaattca aacacctcat ttgcatatta acgcgcacaa | 32760 |
| aaagtttgag gtatattatt gatgatgg | 32788 |

<210> SEQ ID NO 13
<211> LENGTH: 30684
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 13

| | |
|---|---|
| ccatcttcaa taatatacct caaacttttt gtgcgcgtta atatgcaaat gaggcgtttg | 60 |
| aatttgggga ggaagggcgg tgattggtcg agggatgagc gaccgttagg ggcggggcga | 120 |
| gtgacgtttt gatgacgtgg ttgcgaggag gagccagttt gcaagttctc gtgggaaaag | 180 |
| tgacgtcaaa cgaggtgtgg tttgaacacg gaaatactca attttcccgc gctctctgac | 240 |
| aggaaatgag gtgtttctgg gcggatgcaa gtgaaaacgg gccatttttcg cgcgaaaact | 300 |
| gaatgaggaa gtgaaaatct gagtaatttc gcgtttatgg cagggaggag tatttgccga | 360 |
| gggccgagta gactttgacc gattacgtgg gggtttcgat taccgtgttt ttcacctaaa | 420 |
| tttccgcgta cggtgtcaaa gtccggtgtt tttacgtagg tgtcagctga tcgccagggt | 480 |
| atttaaacct gcgctctcca gtcaagaggc cactcttgag tgccagcgag aagagttttc | 540 |
| tcctccgcgc cgcgagtcag atctacactt tgaaagtagg gataacaggg taatgacatt | 600 |
| gattattgac tagttgttaa tagtaatcaa ttacggggtc attagttcat agcccatata | 660 |
| tggagttccg cgttacataa cttacggtaa atggcccgcc tggctgaccg cccaacgacc | 720 |
| cccgcccatt gacgtcaata atgacgtatg ttcccatagt aacgccaata gggactttcc | 780 |
| attgacgtca atgggtggag tatttacggt aaactgccca cttggcagta catcaagtgt | 840 |
| atcatatgcc aagtccgccc cctattgacg tcaatgacgg taaatggccc gcctggcatt | 900 |
| atgcccagta catgacctta cgggactttc ctacttggca gtacatctac gtattagtca | 960 |
| tcgctattac catggtgatg cggttttggc agtacaccaa tgggcgtgga tagcggtttg | 1020 |
| actcacgggg atttccaagt ctccaccccca ttgacgtcaa tgggagtttg ttttggcacc | 1080 |
| aaaatcaacg ggactttcca aaatgtcgta ataaccccgc cccgttgacg caaatgggcg | 1140 |
| gtaggcgtgt acggtgggag gtctatataa gcagagctcg tttagtgaac cgtcagatcg | 1200 |
| cctggaacgc catccacgct gttttgacct ccatagaaga cagcgatcgc gccaccatgg | 1260 |
| tgagcaaggg cgaggagctg ttcaccgggg tggtgcccat cctggtcgag ctggacggcg | 1320 |
| acgtaaacgg ccacaagttc agcgtgtccg gcgagggcga gggcgatgcc acctacggca | 1380 |
| agctgaccct gaagttcatc tgcaccaccg gcaagctgcc cgtgccctgg cccaccctcg | 1440 |

```
tgaccaccct gacctacggc gtgcagtgct tcagccgcta ccccgaccac atgaagcagc   1500
acgacttctt caagtccgcc atgcccgaag gctacgtcca ggagcgcacc atcttcttca   1560
aggacgacgg caactacaag acccgcgccg aggtgaagtt cgagggcgac accctggtga   1620
accgcatcga gctgaagggc atcgacttca aggaggacgg caacatcctg ggcacaagc    1680 tggagtacaa ctacaacagc cacaacgtct atatcatggc cgacaagcag aagaacggca   1740
tcaaggtgaa cttcaagatc cgccacaaca tcgaggacgg cagcgtgcag ctcgccgacc   1800
actaccagca gaacaccccc atcggcgacg gccccgtgct gctgcccgac aaccactacc   1860
tgagcaccca gtccgccctg agcaaagacc ccaacgagaa gcgcgatcac atggtcctgc   1920
tggagttcgt gaccgccgcc gggatcactc tcggcatgga cgagctttac aagtagtgag   1980
tttaaactcc catttaaatg tgagggttaa tgcttcgagc agacatgata agatacattg   2040
atgagtttgg acaaaccaca actagaatgc agtgaaaaaa atgctttatt tgtgaaattt   2100
gtgatgctat tgctttattt gtaaccatta taagctgcaa taaacaagtt aacaacaaca   2160
attgcattca ttttatgttt caggttcagg gggagatgtg gaggtttttt taaagcaagt   2220
aaaacctcta caaatgtggt aaaataacta taacggtcct aaggtagcga gtgagtagtg   2280
ttctggggcg ggggaggacc tgcatgaggg ccagaataac tgaaatctgt gcttttctgt   2340
gtgttgcagc agcatgagcg gaagcggctc ctttgaggga ggggtattca gcccttatct   2400
gacggggcgt ctcccctcct gggcgggagt gcgtcagaat gtgatgggat ccacggtgga   2460
cggccggccc gtgcagcccg cgaactcttc aaccctgacc tatgcaaccc tgagctcttc   2520
gtcgttggac gcagctgccg ccgcagctgc tgcatctgcc gccagcgccg tgcgcggaat   2580
ggccatgggc gccggctact acggcactct ggtggccaac tcgagttcca ccaataatcc   2640
cgccagcctg aacgaggaga agctgttgct gctgatggcc cagctcgagg ccttgaccca   2700
gcgcctgggc gagctgaccc agcaggtggc tcagctgcag gagcagacgc gggccgcggt   2760
tgccacggtg aaatccaaat aaaaaatgaa tcaataaata aacggagacg ttgttgatt    2820 ttaacacaga gtctgaatct ttatttgatt tttcgcgcgc ggtaggccct ggaccaccgg   2880
tctcgatcat tgagcacccg gtggatcttt ccaggaccc ggtagaggtg ggcttggatg    2940
ttgaggtaca tgggcatgag cccgtccggg gggtggaggt agctccattg cagggcctcg   3000
tgctcggggg tggtgttgta aatcacccag tcatagcagg ggcgcagggc atggtgttgc   3060
acaatatctt tgaggaggag actgatggcc acgggcagcc ctttggtgta ggtgtttaca   3120
aatctgttga gctgggaggg atgcatgcgg ggggagatga ggtgcatctt ggcctggatc   3180
ttgagattgg cgatgttacc gcccagatcc cgcctgggt tcatgttgtg caggaccacc    3240 agcacgtgt atccggtgca cttgggaat ttatcatgca acttggaagg gaaggcgtga     3300
aagaatttgg cgacgccttt gtgcccgccc aggttttcca tgcactcatc catgatgatg   3360
gcgatgggcc cgtgggcggc ggcctgggca agacgtttc gggggtcgga cacatcatag    3420
ttgtggtcct gggtgaggtc atcataggcc attttaatga atttgggcg gagggtgccg    3480 gactggggga caaaggtacc ctcgatcccg ggggcgtagt tccctcaca gatctgcatc    3540 tcccaggctt tgagctcgga gggggggatc atgtccacct gcgggcgat aaagaacacg    3600 gtttccgggg cgggggagat gagctgggcc gaaagcaagt tccggagcag ctgggacttg   3660
ccgcagccgg tgggccgta gatgaccccg atgaccggct gcaggtggta gttgagggag    3720
agacagctgc cgtcctcccg gaggaggggg gccacctcgt tcatcatctc gcgcacgtgc   3780
atgttctcgc gcaccagttc cgccaggagg cgctctcccc ccagggatag gagctcctgg   3840
```

```
agcgaggcga agttttttcag cggcttgagt ccgtcggcca tgggcatttt ggagagggtt   3900
tgttgcaaga gttccaggcg gtcccagagc tcggtgatgt gctctacggc atctcgatcc   3960
agcagacctc ctcgtttcgc gggttgggac ggctgcggga gtagggcacc agacgatggg   4020
cgtccagcgc agccagggtc cggtccttcc agggtcgcag cgtccgcgtc agggtggtct   4080
ccgtcacggt gaaggggtgc gcgccgggct gggcgcttgc gagggtgcgc ttcaggctca   4140
tccggctggt cgaaaaccgc tcccgatcgg cgccctgcgc gtcggccagg tagcaattga   4200
ccatgagttc gtagttgagc gcctcggccg cgtggccttt ggcgcggagc ttacctttgg   4260
aagtctgccc gcaggcggga cagaggaggg acttgagggc gtagagcttg ggggcgagga   4320
agacggactc gggggcgtag gcgtccgcgc cgcagtgggc gcagacggtc tcgcactcca   4380
cgagccaggt gaggtcgggc tggtcggggt caaaaaccag tttcccgccg ttcttttga    4440 tgcgtttctt acctttggtc tccatgagct cgtgtccccg ctgggtgaca agaggctgt    4500 ccgtgtcccc gtagaccgac tttatgggcc ggtcctcgag cggtgtgccg cggtcctcct   4560
cgtagaggaa ccccgcccac tccgagacga aagcccgggt ccaggccagc acgaaggagg   4620
ccacgtggga cgggtagcgg tcgttgtcca ccagcgggtc cacctttcc agggtatgca    4680 aacacatgtc cccctcgtcc acatccagga aggtgattgg cttgtaagtg taggccacgt   4740
gaccgggggt cccggccggg ggggtataaa agggtgcggg tccctgctcg tcctcactgt   4800
cttccggatc gctgtccagg agcgccagct gttggggtag gtattccctc tcgaaggcgg   4860
gcatgacctc ggcactcagg ttgtcagttt ctagaaacga ggaggatttg atattgacgg   4920
tgccggcgga gatgcctttc aagagcccct cgtccatctg gtcagaaaag acgatctttt   4980
tgttgtcgag cttggtggcg aaggagccgt agagggcgtt ggagaggagc ttggcgatgg   5040
agcgcatggt ctggttttttt ccttgtcgg cgcgctcctt ggcggcgatg ttgagctgca   5100
cgtactcgcg cgccacgcac ttccattcgg ggaagacggt ggtcagctcg tcggcacga    5160 ttctgacctg ccagccccga ttatgcaggg tgatgaggtc cacactggtg gccacctcgc   5220
cgcgcagggg ctcattagtc cagcagaggc gtccgccctt gcgcgagcag aaggggggca   5280
gggggtccag catgacctcg tcgggggggt cggcatcgat ggtgaagatg ccgggcagga   5340
ggtcggggtc aaagtagctg atggaagtgg ccagatcgtc cagggcagct tgccattcgc   5400
gcacggccag cgcgcgctcg tagggactga ggggcgtgcc ccaggcatg ggatgggtaa    5460 gcgcggaggc gtacatgccg cagatgtcgt agacgtagag gggctcctcg aggatgccga   5520
tgtaggtggg gtagcagcgc ccccgcgga tgctggcgcg cacgtagtca tacagctcgt    5580
gcgagggggc gaggagcccc gggcccaggt tggtgcgact gggcttttcg gcgcggtaga   5640
cgatctggcg gaaaatggca tgcgagttgg aggagatggt gggcctttgg aagatgttga   5700
agtgggcgtg gggcagtccg accgagtcgc ggatgaagtg ggcgtaggag tcttgcagct   5760
tggcgacgag ctcggcggtg actaggacgt ccagagcgca gtagtcgagg gtctcctgga   5820
tgatgtcata cttgagctgt ccctttttgtt tccacagctc gcggttgaga aggaactctt   5880
cgcggtcctt ccagtactct tcgaggggga acccgtcctg atctgcacgg taagagccta   5940
gcatgtgaaa ctggttgacg gccttgtagg cgcagcagcc cttctccacg ggagggcgt    6000 aggcctgggc ggccttgcgc agggaggtgt gcgtgagggc gaaagtgtcc ctgaccatga   6060
ccttgaggaa ctggtgcttg aagtcgatat cgtcgcagcc ccctgctcc cagagctgga    6120 agtccgtgcg cttcttgtag gcggggttgg gcaaagcgaa agtaacatcg ttgaagagga   6180
```

```
tcttgcccgc gcggggcata aagttgcgag tgatgcggaa aggttggggc acctcggccc    6240
ggttgttgat gacctgggcg gcgagcacga tctcgtcgaa gccgttgatg ttgtggccca    6300
cgatgtagag ttccacgaat cgcggacggc ccttgacgtg gggcagtttc ttgagctcct    6360
cgtaggtgag ctcgtcgggg tcgctgagcc cgtgctgctc gagcgcccag tcggcgagat    6420
gggggttggc gcggaggaag gaagtccaga gatccacggc cagggcggtt tgcagacggt    6480
cccggtactg acggaactgc tgcccgacgg ccatttttc gggggtgacg cagtagaagg    6540
tgcgggggtc cccgtgccag cgatcccatt tgagctggag ggcgagatcg agggcgagct    6600
cgacgagccg gtcgtccccg gagagtttca tgaccagcat gaaggggacg agctgcttgc    6660
cgaaggaccc catccaggtg taggtttcca catcgtaggt gaggaagagc ctttcggtgc    6720
gaggatgcga gccgatgggg aagaactgga tctcctgcca ccaattggag gaatggctgt    6780
tgatgtgatg gaagtagaaa tgccgacggc gcgccgaaca ctcgtgcttg tgtttataca    6840
agcggccaca gtgctcgcaa cgctgcacgg gatgcacgtg ctgcacgagc tgtacctgag    6900
ttcctttgac gaggaatttc agtgggaagt ggagtcgtgg cgcctgcatc tcgtgctgta    6960
ctacgtcgtg gtggtcggcc tggccctctt ctgcctcgat ggtggtcatg ctgacgagcc    7020
cgcgcgggag gcaggtccag acctcggcgc gagcgggtcg gagagcgagg acgagggcgc    7080
gcaggccgga gctgtccagg gtcctgagac gctgcggagt caggtcagtg ggcagcggcg    7140
gcgcgcggtt gacttgcagg agttttttcca gggcgcgcgg gaggtccaga tggtacttga    7200
tctccaccgc gccattggtg gcgacgtcga tggcttgcag ggtcccgtgc ccctggggtg    7260
tgaccaccgt ccccgtttc ttcttgggcg gctggggcga cggggcggt gcctcttcca    7320 tggttagaag cggcggcgag gacgcgcgcc gggcggcagg ggcggctcgg ggcccggagg    7380
caggggcgga aggggcacgt cggcgccgcg cgcgggtagg ttctggtact gcgcccggag    7440
aagactggcg tgagcgacga cgcgacggtt gacgtcctgg atctgacgcc tctgggtgaa    7500
ggccacggga cccgtgagtt tgaacctgaa agagagttcg acagaatcaa tctcggtatc    7560
gttgacggcg gcctgccgca ggatctcttg cacgtcgccc gagttgtcct ggtaggcgat    7620
ctcggtcatg aactgctcga tctcctcctc ttgaaggtct ccgcggccgg cgcgctccac    7680
ggtggccgcg aggtcgttgg agatgcggcc catgagctgc gagaaggcgt tcatgcccgc    7740
ctcgttccag acgcggctgt agaccacgac gccctcggga tcgcgggcgc gcatgaccac    7800
ctgggcgagg ttgagctcca cgtggcgcgt gaagaccgcg tagttgcaga ggcgctggta    7860
gaggtagttg agcgtggtgg cgatgtgctc ggtgacgaag aaatacatga tccagcggcg    7920
gagcggcatc tcgctgacgt cgcccagcgc ctccaaacgt tccatggcct cgtaaaagtc    7980
cacggcgaag ttgaaaaact gggagttgcg cgccgagacg gtcaactcct cctccagaag    8040
acggatgagc tcggcgatgg tggcgcgcac ctcgcgctcg aaggcccccg ggagttcctc    8100
cacttcctct tcttcctcct ccactaacat ctcttctact tcctcctcag gcggcagtgg    8160
tggcggggga gggggcctgc gtcgccggcg gcgcacgggc agacggtcga tgaagcgctc    8220
gatggtctcg ccgcgccggc gtcgcatggt ctcggtgacg gcgcgcccgt cctcgcgggg    8280
ccgcagcgtg aagacgccgc cgcgcatctc caggtggccg gggggtccc cgttgggcag    8340 ggagagggcg ctgacgatgc atcttatcaa ttgccccgta gggactccgc gcaaggacct    8400
gagcgtctcg agatccacgg gatctgaaaa ccgctgaacg aaggcttcga gccagtcgca    8460
gtcgcaaggt aggctgagca cggtttcttc tggcgggtca tgttggttgg gagcggggcg    8520
ggcgatgctg ctggtgatga agttgaaata ggcggttctg agacggcgga tggtggcgag    8580
```

-continued

```
gagcaccagg tctttgggcc cggcttgctg gatgcgcaga cggtcggcca tgccccaggc     8640
gtggtcctga cacctggcca ggtccttgta gtagtcctgc atgagccgct ccacgggcac     8700
ctcctcctcg cccgcgcggc cgtgcatgcg cgtgagcccg aagccgcgct ggggctggac     8760
gagcgccagg tcggcgacga cgcgctcggc gaggatggct tgctggatct gggtgagggt     8820
ggtctggaag tcatcaaagt cgacgaagcg gtggtaggct ccggtgttga tggtgtagga     8880
gcagttggcc atgacggacc agttgacggt ctggtggccc ggacgcacga gctcgtggta     8940
cttgaggcgc gagtaggcgc gcgtgtcgaa gatgtagtcg ttgcaggtgc gcaccaggta     9000
ctggtagccg atgaggaagt gcggcggcgg ctggcggtag agcggccatc gctcggtggc     9060
gggggcgccg ggcgcgaggt cctcgagcat ggtgcggtgg tagccgtaga tgtacctgga     9120
catccaggtg atgccggcgg cggtggtgga ggcgcgcggg aactcgcgga cgcggttcca     9180
gatgttgcgc agcggcagga agtagttcat ggtgggcacg gtctggcccg tgaggcgcgc     9240
gcagtcgtgg atgctctata cgggcaaaaa cgaaagcggt cagcggctcg actccgtggc     9300
ctggaggcta agcgaacggg ttgggctgcg cgtgtacccc ggttcgaatc tcgaatcagg     9360
ctggagccgc agctaacgtg gtattggcac tcccgtctcg acccaagcct gcaccaaccc     9420
tccaggatac ggaggcgggt cgttttgcaa cttttttttg gaggccggat gagactagta     9480
agcgcggaaa gcggccgacc gcgatggctc gctgccgtag tctggagaag aatcgccagg     9540
gttgcgttgc ggtgtgcccc ggttcgaggc cggccggatt ccgcggctaa cgagggcgtg     9600
gctgccccgt cgtttccaag acccatagc cagccgactt ctccagttac ggagcgagcc     9660
cctcttttgt tttgtttgtt tttgccagat gcatcccgta ctgcggcaga tgcgccccca     9720
ccaccctcca ccgcaacaac agccccctcc acagccggcg cttctgcccc cgccccagca     9780
gcaacttcca gccacgaccg ccgcggccgc cgtgagcggg gctggacaga gttatgatca     9840
ccagctggcc ttggaagagg gcgaggggct ggcgcgcctg ggggcgtcgt cgccggagcg     9900
gcacccgcgc gtgcagatga aaagggacgc tcgcgaggcc tacgtgccca agcagaacct     9960
gttcagagac aggagcggcg aggagcccga ggagatgcgc gcggcccggt tccacgcggg     10020
gcgggagctg cggcgcggcc tggaccgaaa gagggtgctg agggacgagg atttcgaggc     10080
ggacgagctg acggggatca gccccgcgcg cgcgcacgtg gccgcggcca acctggtcac     10140
ggcgtacgag cagaccgtga aggaggagag caacttccaa aaatccttca acaaccacgt     10200
gcgcaccctg atcgcgcgcg aggaggtgac cctgggcctg atgcacctgt gggacctgct     10260
ggaggccatc gtgcagaacc ccaccagcaa gccgctgacg cgcagctgt tcctggtggt     10320 gcagcatagt cgggacaacg aagcgttcag ggaggcgctg ctgaatatca ccgagcccga     10380
gggccgctgg ctcctggacc tggtgaacat tctgcagagc atcgtggtgc aggagcgcgg     10440
gctgccgctg tccgagaagc tggcggccat caacttctcg gtgctgagtt gggcaagta     10500 ctacgctagg aagatctaca agaccccgta cgtgcccata gacaaggagg tgaagatcga     10560
cgggttttac atgcgcatga ccctgaaagt gctgaccctg agcgacgatc tgggggtgta     10620
ccgcaacgac aggatgcacc gtgcggtgag cgccagcagg cggcgcgagc tgagcgacca     10680
ggagctgatg catagtctgc agcgggccct gaccggggcc gggaccgagg gggagagcta     10740
ctttgacatg ggcgcggacc tgcactggca gcccagccgc cgggccttgg aggcggcggc     10800
aggaccctac gtagaagagg tggacgatga ggtggacgag gagggcgagt acctggaaga     10860
ctgatggcgc gaccgtattt ttgctagatg caacaacaac agccacctcc tgatcccgcg     10920
```

```
atgcgggcgg cgctgcagag ccagccgtcc ggcattaact cctcggacga ttggacccag    10980
gccatgcaac gcatcatggc gctgacgacc cgcaaccccg aagcctttag acagcagccc    11040
caggccaacc ggctctcggc catcctggag gccgtggtgc cctcgcgctc caaccccacg    11100
cacgagaagg tcctggccat cgtgaacgcg ctggtggaga acaaggccat ccgcggcgac    11160
gaggccggcc tggtgtacaa cgcgctgctg agcgcgtggc cccgctacaa cagcaccaac    11220
gtgcagacca acctggaccg catggtgacc gacgtgcgcg aggccgtggc ccagcgcgag    11280
cggttccacc gcgagtccaa cctgggatcc atggtggcgc tgaacgcctt cctcagcacc    11340
cagcccgcca acgtgccccg gggccaggag gactacacca acttcatcag cgccctgcgc    11400
ctgatggtga ccgaggtgcc ccagagcgag gtgtaccagt ccggccggga ctacttcttc    11460
cagaccagtc gccagggctt gcagaccgtg aacctgagcc aggctttcaa gaacttgcag    11520
ggcctgtggg gcgtgcaggc cccggtcggg gaccgcgcga cggtgtcgag cctgctgacg    11580
ccgaactcgc gcctgctgct gctgctggtg gcccccttca cggacagcgg cagcatcaac    11640
cgcaactcgt acctgggcta cctgattaac ctgtaccgcg aggccatcgg ccaggcgcac    11700
gtggacgagc agacctacca ggagatcacc cacgtgagcc gcgccctggg ccaggacgac    11760
ccgggcaacc tggaagccac cctgaacttt ttgctgacca ccggtcgcg aagatcccg    11820 ccccagtacg cgctcagcac cgaggaggag cgcatcctgc gttacgtgca gcagagcgtg    11880
ggcctgttcc tgatgcagga ggggccacc cccagcgccg cgctcgacat gaccgcgcgc    11940
aacatggagc ccagcatgta cgccagcaac cgcccgttca tcaataaact gatggactac    12000
ttgcatcggg cggccgccat gaactctgac tatttcacca acgccatcct gaatccccac    12060
tggctcccgc cgccggggtt ctacacgggc gagtacgaca tgcccgaccc caatgacggg    12120
ttcctgtggg acgatgtgga cagcagcgtg ttctcccccc gaccgggtgc taacgagcgc    12180
cccttgtgga agaaggaagg cagcgaccga cgcccgtcct cggcgctgtc cggccgcgag    12240
ggtgctgccg cggcggtgcc cgaggccgcc agtcctttcc cgagcttgcc cttctcgctg    12300
aacagtatcc gcagcagcga gctgggcagg atcacgcgcc cgcgcttgct gggcgaagag    12360
gagtacttga tgactcgct gttgagaccc gagcgggaga agaacttccc caataacggg    12420
atagaaagcc tggtggacaa gatgagccgc tggaagacgt atgcgcagga gcacagggac    12480
gatccccggg cgtcgcaggg ggccacgagc cggggcagcg ccgcccgtaa cgccggtgg    12540 cacgacaggc agcggggaca gatgtgggac gatgaggact ccgccgacga cagcagcgtg    12600
ttggacttgg gtgggagtgg taacccgttc gctcacctgc gccccgtat cgggcgcatg    12660 atgtaagaga aaccgaaaat aaatgatact caccaaggcc atggcgacca gcgtgcgttc    12720
gtttcttctc tgttgttgtt gtatctagta tgatgaggcg tgcgtacccg gagggtcctc    12780
ctccctcgta cgagagcgtg atgcagcagg cgatggcggc ggcggcgatg cagccccgc    12840 tggaggctcc ttacgtgccc ccgcggtacc tggcgcctac tggagggggcgg aacagcattc    12900 gttactcgga gctggcaccc ttgtacgata ccacccggtt gtacctggtg acaacaagt    12960 cggcggacat cgcctcgctg aactaccaga cgaccacag caacttcctg accaccgtgg    13020
tgcagaacaa tgacttcacc cccacggagg ccagcaccca gaccatcaac tttgacgagc    13080
gctcgcggtg gggcggccag ctgaaaacca tcatgcacac caacatgccc aacgtgaacg    13140
agttcatgta cagcaacaag ttcaaggcgc gggtgatggt ctcccgcaag accccaatg    13200 gggtgacagt gacagaggat tatgatggta gtcaggatga gctgaagtat gaatgggtgg    13260
aatttgagct gcccgaaggc aacttctcgg tgaccatgac catcgacctg atgaacaacg    13320
```

```
ccatcatcga caattacttg gcggtggggc ggcagaacgg ggtgctggag agcgacatcg   13380
gcgtgaagtt cgacactagg aacttcaggc tgggctggga ccccgtgacc gagctggtca   13440
tgcccggggt gtacaccaac gaggctttcc atcccgatat tgtcttgctg cccggctgcg   13500
gggtggactt caccgagagc cgcctcagca acctgctggg cattcgcaag aggcagccct   13560
tccaggaagg cttccagatc atgtacgagg atctggaggg gggcaacatc cccgcgctcc   13620
tggatgtcga cgcctatgag aaaagcaagg aggatgcagc agctgaagca actgcagccg   13680
tagctaccgc ctctaccgag gtcaggggcg ataattttgc aagcgccgca gcagtggcag   13740
cggccgaggc ggctgaaacc gaaagtaaga tagtcattca gccggtggag aaggatagca   13800
agaacaggag ctacaacgta ctaccggaca agataaacac cgcctaccgc agctggtacc   13860
tagcctacaa ctatggcgac cccgagaagg gcgtgcgctc ctggacgctg ctcaccacct   13920
cggacgtcac ctgcggcgtg gagcaagtct actggtcgct gcccgacatg atgcaagacc   13980
cggtcacctt ccgctccacg cgtcaagtta gcaactaccc ggtggtgggc gccgagctcc   14040
tgcccgtcta ctccaagagc ttcttcaacg agcaggccgt ctactcgcag cagctgcgcg   14100 ccttcaccctc gcttacgcac gtcttcaacc gcttccccga gaaccagatc ctcgtccgcc   14160
cgcccgcgcc caccattacc accgtcagtg aaaacgttcc tgctctcaca gatcacggga   14220
ccctgccgct gcgcagcagt atccggggag tccagcgcgt gaccgttact gacgccagac   14280
gccgcacctg cccctacgtc tacaaggccc tgggcatagt cgcgccgcgc gtcctctcga   14340
gccgcacctt ctaaatgtcc attctcatct cgcccagtaa taacaccggt tggggcctgc   14400
gcgcgcccag caagatgtac ggaggcgctc gccaacgctc cacgcaacac cccgtgcgcg   14460
tgcgcgggca cttccgcgct ccctgggggcg ccctcaaggg ccgcgtgcgg tcgcgcacca   14520
ccgtcgacga cgtgatcgac caggtggtgg ccgacgcgcg caactacacc cccgccgccg   14580
cgcccgtctc caccgtggac gccgtcatcg acagcgtggt ggccgacgcg cgccggtacg   14640
cccgcgccaa gagccggcgg cggcgcatcg cccgcggca ccggagcacc cccgccatgc   14700
gcgcggcgcg agccttgctg cgcagggcca ggcgcacggg acgcagggcc atgtcaggg   14760 cggccagacg cgcggcttca ggcgccacgc ccggcaggac ccggagacgc gcggccacgg   14820
cggcggcagc ggccatcgcc agcatgtccc gcccgcggcg agggaacgtg tactgggtgc   14880
gcgacgccgc caccggtgtg cgcgtgcccg tgcgcacccg ccccccctcgc acttgaagat   14940 gttcacttcg cgatgttgat gtgtcccagc ggcgaggagg atgtccaagc gcaaattcaa   15000
ggaagagatg ctccaggtca tcgcgcctga gatctacggc cctgcggtgg tgaaggagga   15060
aagaaagccc cgcaaaatca agcgggtcaa aaaggacaaa aaggaagaag aaagtgatgt   15120
ggacggattg gtggagtttg tgcgcgagtt cgccccccgg cggcgcgtgc agtggcgcg   15180 gcggaaggtg caaccggtgc tgagacccgg caccaccgtg gtcttcacgc ccggcgagcg   15240
ctccggcacc gcttccaagc gctcctacga cgaggtgtac ggggatgatg atattctgga   15300
gcaggcggcc gagcgcctgg gcgagtttgc ttacggcaag cgcagccgtt ccgcaccgaa   15360
ggaagaggcg gtgtccatcc cgctggacca cggcaacccc acgccgagcc tcaagcccgt   15420
gaccttgcag caggtgctgc cgaccgcggc gccgcgccgg gggttcaagc gcagggcga   15480 ggatctgtac cccaccatgc agctgatggt gcccaagcgc agaagctgg aagacgtgct   15540 ggagaccatg aaggtggacc cggacgtgca gcccgaggtc aaggtgcggc ccatcaagca   15600
ggtggccccg ggcctgggcg tgcagaccgt ggacatcaag attcccacgg agcccatgga   15660
```

```
aacgcagacc gagcccatga tcaagcccag caccagcacc atggaggtgc agacggatcc   15720
ctggatgcca tcggctccta gtcgaagacc ccggcgcaag tacggcgcgg ccagcctgct   15780
gatgcccaac tacgcgctgc atccttccat catccccacg ccgggctacc gcggcacgcg   15840
cttctaccgc ggtcatacca gcagccgccg ccgcaagacc accactcgcc gccgccgtcg   15900
ccgcaccgcc gctgcaacca cccctgccgc cctggtgcgg agagtgtacc gccgcggccg   15960
cgcacctctg accctgccgc gcgcgcgcta ccacccgagc atcgccattt aaactttcgc   16020
ctgctttgca gatcaatggc cctcacatgc cgccttcgcg ttcccattac gggctaccga   16080
ggaagaaaac cgcgccgtag aaggctggcg gggaacggga tgcgtcgcca ccaccaccgg   16140
cggcggcgcg ccatcagcaa gcggttgggg ggaggcttcc tgcccgcgct gatccccatc   16200
atcgccgcgg cgatcggggc gatccccggc attgcttccg tggcggtgca ggcctctcag   16260
cgccactgag acacacttgg aaacatcttg taataaacca atggactctg acgctcctgg   16320
tcctgtgatg tgttttcgta gacagatgga agacatcaat ttttcgtccc tggctccgcg   16380
acacggcacg cggccgttca tgggcacctg gagcgacatc ggcaccagcc aactgaacgg   16440
gggcgccttc aattggagca gtctctggag cgggcttaag aatttcgggt ccacgcttaa   16500
aacctatggc agcaaggcgt ggaacagcac cacagggcag cgcgctgagg gataagctgaa  16560 agagcagaac ttccagcaga aggtggtcga tgggctcgcc tcgggcatca acggggtggt   16620
ggacctggcc aaccaggccg tgcagcggca gatcaacagc cgcctggacc cggtgccgcc   16680
cgccggctcc gtggagatgc cgcaggtgga ggaggagctg cctcccctgg acaagcgggg   16740
cgagaagcga ccccgccccg atgcggagga gacgctgctg acgcacacgg acgagccgcc   16800
cccgtacgag gaggcggtga actgggtct gcccaccacg cggcccatcg cgcccctggc   16860
caccggggtg ctgaaacccg aaaagcccgc gaccctggac ttgcctcctc cccagccttc   16920 ccgccctct acagtggcta agccctgcc gccggtggcc gtggcccgcg cgcgacccgg   16980
gggcaccgcc cgcccctcatg cgaactggca gagcactctg aacagcatcg tgggtctggg   17040
agtgcagagt gtgaagcgcc gccgctgcta ttaaacctac cgtagcgctt aacttgcttg   17100
tctgtgtgtg tatgtattat gtcgccgccg ccgctgtcca ccagaaggag gagtgaagag   17160
gcgcgtcgcc gagttgcaag atggccaccc catcgatgct gccccagtgg gcgtacatgc   17220
acatcgccgg acaggacgct tcggagtacc tgagtccggg tctggtgcag tttgcccgcg   17280
ccacagacac ctacttcagt ctggggaaca agtttaggaa ccccacggtg gcgcccacgc   17340
acgatgtgac caccgaccgc agccagcggc tgacgctgcg cttcgtgccc gtggaccgcg   17400
aggacaacac ctactcgtac aaagtgcgct acacgctggc cgtgggcgac aaccgcgtgc   17460
tggacatggc cagcacctac tttgacatcc gcggcgtgct ggatcggggc cctagcttca   17520
aaccctactc cggcaccgcc tacaacagtc tggcccccaa gggagcaccc aacacttgtc   17580
agtggacata taaagccgat ggtgaaactg ccacagaaaa aacctataca tatgaaatg    17640 cacccgtgca gggcattaac atcacaaaag atggtattca acttggaact gacaccgatg   17700
atcagccaat ctacgcagat aaaacctatc agcctgaacc tcaagtgggt gatgctgaat   17760
ggcatgacat cactggtact gatgaaaagt atggaggcag agctcttaag cctgatacca   17820
aaatgaagcc ttgttatggt tctttttgcca agcctactaa taaagaagga ggtcaggcaa   17880
atgtgaaaac aggaacaggc actactaaag aatatgacat agacatggct ttctttgaca   17940
acagaagtgc ggctgctgct ggcctagctc cagaaattgt tttgtatact gaaaatgtgg   18000
atttggaaac tccagatacc catattgtat acaaagcagg cacagatgac agcagctctt   18060
```

```
ctattaattt gggtcagcaa gccatgccca acagacctaa ctacattggt ttcagagaca    18120
actttatcgg gctcatgtac tacaacagca ctggcaatat gggggtgctg gccggtcagg    18180
cttctcagct gaatgctgtg gttgacttgc aagacagaaa caccgagctg tcctaccagc    18240
tcttgcttga ctctctgggt gacagaaccc ggtatttcag tatgtggaat caggcggtgg    18300
acagctatga tcctgatgtg cgcattattg aaaatcatgg tgtggaggat gaacttccca    18360
actattgttt ccctctggat gctgttggca gaacagatac ttatcaggga attaaggcta    18420
atggaactga tcaaaccaca tggaccaaag atgacagtgt caatgatgct aatgagatag    18480
gcaagggtaa tccattcgcc atggaaatca acatccaagc caacctgtgg aggaacttcc    18540
tctacgccaa cgtggccctg tacctgcccg actcttacaa gtacacgccg gccaatgtta    18600
ccctgcccac caacaccaac acctacgatt acatgaacgg ccgggtggtg cgcccctcgc    18660
tggtggactc ctacatcaac atcggggcgc gctggtcgct ggatcccatg gacaacgtga    18720
accccttcaa ccaccaccgc aatgcggggc tgcgctaccg ctccatgctc ctgggcaacg    18780
gcgctacgt gcccttccac atccaggtgc cccagaaatt tttcgccatc aagagcctcc    18840
tgctcctgcc cggtcctac acctacgagt ggaacttccg caaggacgtc aacatgatcc    18900
tgcagagctc cctcggcaac gacctgcgca cggacggggc ctccatctcc ttcaccagca    18960
tcaacctcta cgccaccttc ttccccatgg cgcacaacac ggcctccacg ctcgaggcca    19020
tgctgcgcaa cgacaccaac gaccagtcct tcaacgacta cctctcggcg ccaacatgc     19080
tctaccccat cccggccaac gccaccaacg tgcccatctc catccctcg cgcaactggg     19140
ccgccttccg cggctggtcc ttcacgcgtc tcaagaccaa ggagacgccc tcgctgggct    19200
ccgggttcga cccctacttc gtctactcgg gctccatccc ctacctcgac ggcacccttct   19260
acctcaacca caccttcaag aaggtctcca tcaccttcga ctcctccgtc agctggcccg    19320
gcaacgaccg gctcctgacg cccaacgagt tcgaaatcaa cgcgaccgtc gacggcgagg    19380
gctacaacgt ggcccagtgc aacatgacca aggactggtt cctggtccag atgctggccc    19440
actacaaacat cggctaccag ggcttctacg tgcccgaggg ctacaaggac cgcatgtact   19500
ccttcttccg caacttccag cccatgagcc gccaggtggt ggacgaggtc aactacaagg    19560
actaccaggc cgtcaccctg gcctaccagc acaacaactc gggcttcgtc ggctacctcg    19620
cgcccaccat cgccagggc cagccctacc ccgccaacta cccctacccg ctcatcggca    19680
agagcgccgt caccagcgtc acccagaaaa agttcctctg cgacagggtc atgtggcgca    19740
tcccccttctc cagcaacttc atgtccatgg gcgcgctcac cgacctcggc cagaacatgc    19800
tctatgccaa ctccgcccac gcgctagaca tgaattcga agtcgacccc atggatgagt    19860
ccacccttct ctatgttgtc ttcgaagtct tcgacgtcgt ccgagtgcac cagccccacc    19920
gcggcgtcat cgaggccgtc tacctgcgca cccccttctc ggccggtaac gccaccacct    19980
aagctcttgc ttcttgcaag ccatggccgc gggctccggc gagcaggagc tcagggccat    20040
catccgcgac ctgggctgcg ggccctactt cctgggcacc ttcgataagc gcttcccggg    20100
attcatggcc ccgcacaagc tggcctgcgc catcgtcaac acggccggcc gcgagaccgg    20160
gggcgagcac tggctggcct tcgctggaa cccgcgctcg aacacctgct acctcttcga    20220
ccccttcggg ttctcggacg agcgcctcaa gcagatctac cagttcgagt acgagggcct    20280
gctgcgccgc agcgccctgg ccaccgagga ccgctgcgtc accctggaaa agtccaccca    20340
gaccgtgcag ggtccgcgct cggccgcctg cgggctcttc tgctgcatgt tcctgcacgc    20400
```

-continued

```
cttcgtgcac tggcccgacc gccccatgga caagaacccc accatgaact tgctgacggg    20460
ggtgcccaac ggcatgctcc agtcgcccca ggtggaaccc accctgcgcc gcaaccagga    20520
ggcgctctac cgcttcctca actcccactc cgcctacttt cgctcccacc gcgcgcgcat    20580
cgagaaggcc accgccttcg accgcatgaa tcaagacatg taaaccgtgt gtgtatgtta    20640
aatgtctttta ataaacagca ctttcatgtt acacatgcat ctgagatgat ttatttagaa    20700
atcgaaaggg ttctgccggg tctcggcatg gcccgcgggc agggacacgt tgcggaactg    20760
gtacttggcc agccacttga actcggggat cagcagtttg ggcagcgggg tgtcggggaa    20820
ggagtcggtc cacagcttcc gcgtcagttg cagggcgccc agcaggtcgg gcgcggagat    20880
cttgaaatcg cagttgggac ccgcgttctg cgcgcgggag ttgcggtaca cggggttgca    20940
gcactggaac accatcaggg ccgggtgctt cacgctcgcc agcaccgtcg cgtcggtgat    21000
gctctccacg tcgaggtcct cggcgttggc catcccgaag ggggtcatct tgcaggtctg    21060
ccttcccatg gtgggcacgc acccgggctt gtggttgcaa tcgcagtgca gggggatcag    21120
catcatctgg gcctggtcgg cgttcatccc cgggtacatg gccttcatga aagcctccaa    21180
ttgcctgaac gcctgctggg ccttggctcc ctcggtgaag aagacccggc aggacttgct    21240
agagaactgg ttggtggcgc acccggcgtc gtgcacgcag cagcgcgcgt cgttgttggc    21300
cagctgcacc acgctgcgcc cccagcggtt ctgggtgatc ttggcccggt cggggttctc    21360
cttcagcgcg cgctgcccgt tctcgctcgc cacatccatc tcgatcatgt gctccttctg    21420
gatcatggtg gtcccgtgca ggcaccgcag cttgccctcg gcctcggtga cccgtgcag    21480
ccacagcgcg cacccggtgc actcccagtt cttgtgggcg atctgggaat gcgcgtgcac    21540
gaagccctgc aggaagcggc ccatcatggt ggtcagggtc ttgttgctag tgaaggtcag    21600
cggaatgccg cggtgctcct cgttgatgta caggtggcag atgcggcggt acacctcgcc    21660
ctgctcgggc atcagctgga agttggcttt caggtcggtc tccacgcggt agcggtccat    21720
cagcatagtc atgatttcca taccttctc ccaggccgag acgatgggca ggctcatagg    21780
gttcttcacc atcatcttag cgctagcagc cgcggccagg gggtcgctct cgtccagggt    21840
ctcaaagctc cgcttgccgt ccttctcggt gatccgcacc gggggggtagc tgaagcccac    21900
ggccgccagc tcctcctcgg cctgtctttc gtcctcgctg tcctggctga cgtcctgcag    21960
gaccacatgc ttggtcttgc ggggtttctt cttgggcggc agcggcggcg gagatgttgg    22020
agatggcgag ggggagcgcg agttctcgct caccactact atctcttcct cttcttggtc    22080
cgaggccacg cggcggtagg tatgtctctt cggggggcaga ggcggaggcg acgggctctc    22140
gccgccgcga cttggcggat ggctggcaga gcccctccg cgttcggggg tgcgctcccg    22200
gcggcgctct gactgacttc ctccgcggcc ggccattgtg ttctcctagg gaggaacaac    22260
aagcatggag actcagccat cgccaacctc gccatctgcc cccaccgccg acgagaagca    22320
gcagcagcag aatgaaagct taaccgcccc gccgcccagc cccgccacct ccgacgcggc    22380
cgtcccagac atgcaagaga tggaggaatc catcgagatt gacctgggct atgtgacgcc    22440
cgcggagcac gaggaggagc tggcagtgcg ctttttcacaa gaagagatac accaagaaca    22500
gccagagcag gaagcagaga atgagcagag tcaggctggg ctcgagcatg acggcgacta    22560
cctccacctg agcggggggg aggacgcgct catcaagcat ctggcccggc aggccaccat    22620
cgtcaaggat gcgctgctcg accgcaccga ggtgcccctc agcgtggagg agctcagccg    22680
cgcctacgag ttgaacctct tctcgccgcg cgtgcccccc aagcgccagc caatggcac    22740
ctgcgagccc aacccgcgcc tcaacttcta cccggtcttc gcggtgcccg aggccctggc    22800
```

```
cacctaccac atcttttca agaaccaaaa gatcccgtc tcctgccgcg ccaaccgcac    22860
ccgcgccgac gcccttttca acctgggtcc cggcgcccgc ctacctgata tcgcctcctt    22920
ggaagaggtt cccaagatct tcgagggtct gggcagcgac gagactcggg ccgcgaacgc    22980
tctgcaagga gaaggaggag agcatgagca ccacagcgcc ctggtcgagt tggaaggcga    23040
caacgcgcgg ctggcggtgc tcaaacgcac ggtcgagctg acccatttcg cctacccggc    23100
tctgaacctg ccccccaaag tcatgagcgc ggtcatggac caggtgctca tcaagcgcgc    23160
gtcgcccatc tccgaggacg agggcatgca agactccgag gagggcaagc ccgtggtcag    23220
cgacgagcag ctgccccggt ggctgggtcc taatgctagt ccccagagtt tggaagagcg    23280
gcgcaaactc atgatggccg tggtcctggt gaccgtggag ctggagtgcc tgcgccgctt    23340
cttcgccgac gcggagaccc tgcgcaaggt cgaggagaac ctgcactacc tcttcaggca    23400
cgggttcgtg cgccaggcct gcaagatctc caacgtggag ctgaccaacc tggtctccta    23460
catgggcatc ttgcacgaga accgcctggg gcagaacgtg ctgcacacca ccctgcgcgg    23520
ggaggcccgg cgcgactaca tccgcgactg cgtctacctc tacctctgcc acacctggca    23580
gacgggcatg ggcgtgtggc agcagtgtct ggaggagcag aacctgaaag agctctgcaa    23640
gctcctgcag aagaacctca agggtctgtg gaccgggttc gacgagcgca ccaccgcctc    23700
ggacctggcc gacctcattt tccccgagcg cctcaggctg acgctgcgca acggcctgcc    23760
cgactttatg agccaaagca tgttgcaaaa ctttcgctct ttcatcctcg aacgctccgg    23820
aatcctgccc gccacctgct ccgcgctgcc ctcggacttc gtgccgctga ccttccgcga    23880
gtgccccccg ccgctgtgga gccactgcta cctgctgcgc ctggccaact acctggccta    23940
ccactcggac gtgatcgagg acgtcagcgg cgagggcctg ctcgagtgcc actgccgctg    24000
caacctctgc acgccgcacc gctccctggc ctgcaacccc cagctgctga gcgagaccca    24060
gatcatcggc accttcgagt tgcaaggggcc cagcgaaggc gagggttcag ccgccaaggg    24120
gggtctgaaa ctcaccccgg ggctgtggac ctcggcctac ttgcgcaagt tcgtgcccga    24180
ggactaccat cccttcgaga tcaggttcta cgaggaccaa tcccatccgc ccaaggccga    24240
gctgtcggcc tgcgtcatca cccagggggc gatcctggcc caattgcaag ccatccagaa    24300
atcccgccaa gaattcttgc tgaaaaaggg ccgcggggtc tacctcgacc cccagaccgg    24360
tgaggagctc aaccccggct tccccccagga tgccccgagg aaacaagaag ctgaaagtgg    24420
agctgccgcc cgtggaggat ttggaggaag actgggagaa cagcagtcag gcagaggagg    24480
aggagatgga ggaagactgg gacagcactc aggcagagga ggacagcctg caagacagtc    24540
tggaggaaga cgaggaggag gcagaggagg aggtggaaga agcagccgcc gccagaccgt    24600
cgtcctcggc gggggagaaa gcaagcagca cggataccat ctccgctccg ggtcggggtc    24660
ccgctcgacc acacagtaga tgggacgaga ccggacgatt cccgaacccc accacccaga    24720
ccggtaagaa ggagcggcag ggatacaagt cctggcgggg gcacaaaaac gccatcgtct    24780
cctgcttgca ggcctgcggg ggcaacatct ccttcacccg gcgctacctg ctcttccacc    24840
gcggggtgaa cttccccgc aacatcttgc attactaccg tcacctccac agcccctact    24900
acttccaaga agaggcagca gcagcagaaa aagaccagca gaaaaccagc agctagaaaa    24960
tccacagcgg cggcagcagg tggactgagg atcgcggcga acgagccggc gcaaacccgg    25020
gagctgagga accggatctt tcccaccctc tatgccatct tccagcagag tcgggggcag    25080
gagcaggaac tgaaagtcaa gaaccgttct ctgcgctcgc tcacccgcag ttgtctgtat    25140
```

```
cacaagagcg aagaccaact tcagcgcact ctcgaggacg ccgaggctct cttcaacaag   25200
tactgcgcgc tcactcttaa agagtagccc gcgcccgccc agtcgcagaa aaaggcggga   25260
attacgtcac ctgtgcccett cgccctagcc gcctccaccc atcatcatga gcaaagagat   25320
tcccacgcct tacatgtgga gctaccagcc ccagatgggc ctggccgccg gtgccgccca   25380
ggactactcc acccgcatga attggctcag cgccgggccc gcgatgatct cacgggtgaa   25440
tgacatccgc gcccaccgaa accagatact cctagaacag tcagcgctca ccgccacgcc   25500
ccgcaatcac ctcaatccgc gtaattggcc cgccgccctg gtgtaccagg aaattcccca   25560
gcccacgacc gtactacttc cgcgagacgc ccaggccgaa gtccagctga ctaactcagg   25620
tgtccagctg gcgggcggcg ccaccctgtg tcgtcaccgc cccgctcagg gtataaagcg   25680
gctggtgatc cggggcagag gcacacagct caacgacgag gtggtgagct cttcgctggg   25740
tctgcgacct gacggagtct tccaactcgc cggatcgggg agatcttcct tcacgcctcg   25800
tcaggccgtc ctgactttgg agagttcgtc ctcgcagccc cgctcgggtg catcggcac   25860 tctccagttc gtggaggagt tcactccctc ggtctacttc aaccccttct ccggctcccc   25920
cggccactac ccggacgagt tcatcccgaa cttcgacgcc atcagcgagt cggtggacgg   25980
ctacgattga aactaatcac cccettatcc agtgaaataa agatcatatt gatgatgatt   26040
ttacagaaat aaaaaataat catttgattt gaaataaaga tacaatcata ttgatgatttt   26100 gagtttaaca aaaaaataaa gaatcactta cttgaaatct gataccaggt ctctgtccat   26160
gttttctgcc aacaccactt cactcccctc ttcccagctc tggtactgca ggccccggcg   26220
ggctgcaaac ttcctccaca cgctgaaggg gatgtcaaat tcctcctgtc cctcaatctt   26280
cattttatct tctatcagat gtccaaaaag cgcgtccggg tggatgatga cttcgacccc   26340
gtctacccct acgatgcaga caacgcaccg accgtgccct tcatcaaccc ccccttcgtc   26400
tcttcagatg gattccaaga gaagcccctg ggggtgttgt ccctgcgact ggccgacccc   26460
gtcaccacca agaacgggga aatcaccctc aagctgggag aggggggtgga cctcgattcc   26520 tcgggaaaac tcatctccaa cacggccacc aaggccgccg cccctctcag ttttttccaac   26580 aacaccattt cccttaacat ggatcacccc ttttacacta aagatggaaa attatccetta   26640 caagtttctc caccattaaa tatactgaga acaagcattc taaacacact agctttaggt   26700
tttggatcag gtttaggact ccgtggctct gccttggcag tacagttagt ctctccactt   26760
acatttgata ctgatggaaa cataaagctt accttagaca gaggtttgca tgttacaaca   26820
ggagatgcaa ttgaaagcaa cataagctgg gctaaaggtt taaaatttga agatggagcc   26880
atagcaacca acattggaaa tgggttagag tttggaagca gtagtacaga aacaggtgtt   26940
gatgatgctt acccaatcca agttaaactt ggatctggcc ttagctttga cagtacagga   27000
gccataatgg ctggtaacaa agaagacgat aaactcactt tgtggacaac acctgatcca   27060
tcaccaaact gtcaaatact cgcagaaaat gatgcaaaac taacactttg cttgactaaa   27120
tgtggtagtc aaatactggc cactgtgtca gtcttagttg taggaagtgg aaacctaaac   27180
cccattactg gcaccgtaag cagtgctcag gtgtttctac gttttgatgc aaacggtgtt   27240
cttttaacag aacattctac actaaaaaaa tactgggggt ataggcaggg agatagcata   27300
gatggcactc catataccaa tgctgtagga ttcatgccca atttaaaagc ttatccaaag   27360
tcacaaagtt ctactactaa aaataatata gtagggcaag tatacatgaa tggagatgtt   27420
tcaaaaccta tgcttctcac tataaccctc aatggtactg atgacagcaa cagtacatat   27480
tcaatgtcat tttcatacac ctggactaat ggaagctatg ttggagcaac atttgggct   27540
```

-continued

```
aactcttata ccttctcata catcgcccaa gaatgaacac tgtatcccac cctgcatgcc  27600
aaccctcccc accccactct gtggaacaaa ctctgaaaca caaataaaa taaagttcaa  27660 gtgttttatt gattcaacag ttttacagga ttcgagcagt tattttcct ccaccctccc  27720 aggacatgga atacaccacc ctctccccc gcacagcctt gaacatctga atgccattgg  27780
tgatggacat gcttttggtc tccacgttcc acacagtttc agagcgagcc agtctcgggt  27840
cggtcaggga gatgaaaccc tccgggcact cccgcatctg cacctcacag ctcaacagct  27900
gaggattgtc ctcggtggtc gggatcacgg ttatctggaa gaagcagaag agcggcggtg  27960
ggaatcatag tccgcgaacg ggatcggccg gtggtgtcgc atcaggcccc gcagcagtcg  28020
ctgccgccgc cgctccgtca agctgctgct caggggtcc gggtccaggg actccctcag  28080
catgatgccc acggccctca gcatcagtcg tctggtgcgg cgggcgcagc agcgcatgcg  28140
gatctcgctc aggtcgctgc agtacgtgca acacagaacc accaggttgt tcaacagtcc  28200
atagttcaac acgctccagc cgaaactcat cgcgggaagg atgctaccca cgtggccgtc  28260
gtaccagatc ctcaggtaaa tcaagtggtg ccccctccag aacacgctgc ccacgtacat  28320
gatctccttg ggcatgtggc ggttcaccac ctcccggtac cacatcaccc tctggttgaa  28380
catgcagccc cggatgatcc tgcggaacca cagggccagc accgccccgc ccgccatgca  28440
gcgaagagac cccgggtccc ggcaatggca atggaggacc caccgctcgt acccgtggat  28500
catctgggag ctgaacaagt ctatgttggc acagcacagg catatgctca tgcatctctt  28560
cagcactctc aactcctcgg gggtcaaaac catatcccag ggcacgggga actcttgcag  28620
gacagcgaac cccgcagaac agggcaatcc tcgcacagaa cttacattgt gcatggacag  28680
ggtatcgcaa tcaggcagca ccgggtgatc ctccaccaga gaagcgcggg tctcggtctc  28740
ctcacagcgt ggtaaggggg ccggccgata cgggtgatgg cgggacgcgg ctgatcgtgt  28800
tcgcgaccgt gtcatgatgc agttgctttc ggacattttc gtacttgctg tagcagaacc  28860
tggtccgggc gctgcacacc gatcgccggc ggcggtctcg gcgcttggaa cgctcggtgt  28920
tgaaattgta aaacagccac tctctcagac cgtgcagcag atctagggcc tcaggagtga  28980
tgaagatccc atcatgcctg atggctctga tcacatcgac caccgtggaa tgggccagac  29040
ccagccagat gatgcaattt tgttgggttt cggtgacggc gggggaggga agaacaggaa  29100
gaaccatgat taacttttaa tccaaacggt ctcggagtac ttcaaaatga agatcgcgga  29160
gatggcacct ctcgcccccg ctgtgttggt ggaaaataac agccaggtca aggtgatac  29220 ggttctcgag atgttccacg gtggcttcca gcaaagcctc cacgcgcaca tccagaaaca  29280
agacaatagc gaaagcggga gggttctcta attcctcaat catcatgtta cactcctgca  29340
ccatccccag ataattttca ttttccagc cttgaatgat tcgaactagt tcctgaggta  29400
aatccaagcc agccatgata aagagctcgc gcagagcgcc ctccaccggc attcttaagc  29460
acaccctcat aattccaaga tattctgctc ctggttcacc tgcagcagat tgacaagcgg  29520
aatatcaaaa tctctgccgc gatccctgag ctcctccctc agcaataact gtaagtactc  29580
tttcatatcc tctccgaaat ttttagccat aggaccacca ggaataagat tagggcaagc  29640
cacagtacag ataaaccgaa gtcctcccca gtgagcattg ccaaatgcaa gactgctata  29700
agcatgctgg ctagacccgg tgatatcttc cagataactg gacagaaaat cgcccaggca  29760 attttttaaga aaatcaacaa aagaaaaatc ctccaggtgg acgtttagag cctcgggaac  29820
aacgatgaag taaatgcaag cggtgcgttc cagcatggtt agttagctga tctgtagaaa  29880
```

| | |
|---|---:|
| aaacaaaaat gaacattaaa ccatgctagc ctggcgaaca ggtgggtaaa tcgttctctc | 29940 |
| cagcaccagg caggccacgg ggtctccggc gcgaccctcg taaaaattgt cgctatgatt | 30000 |
| gaaaaccatc acagagagac gttcccggtg gccggcgtga atgattcgac aagatgaata | 30060 |
| cacccccgga acattggcgt ccgcgagtga aaaaaagcgc ccgaggaagc aataaggcac | 30120 |
| tacaatgctc agtctcaagt ccagcaaagc gatgccatgc ggatgaagca caaaattctc | 30180 |
| aggtgcgtac aaaatgtaat tactcccctc ctgcacaggc agcaaagccc ccgatccctc | 30240 |
| caggtacaca tacaaagcct cagcgtccat agcttaccga gcagcagcac acaacaggcg | 30300 |
| caagagtcag agaaaggctg agctctaacc tgtccacccg ctctctgctc aatatatagc | 30360 |
| ccagatctac actgacgtaa aggccaaagt ctaaaaatac ccgccaaata atcacacacg | 30420 |
| cccagcacac gcccagaaac cggtgacaca ctcaaaaaaa tacgcgcact tcctcaaacg | 30480 |
| cccaaaactg ccgtcatttc cgggttccca cgctacgtca tcaaaacacg actttcaaat | 30540 |
| tccgtcgacc gttaaaaacg tcacccgccc cgcccctaac ggtcgcccgt ctctcagcca | 30600 |
| atcagcgccc cgcatcccca aattcaaaca cctcatttgc atattaacgc gcacaaaaag | 30660 |
| tttgaggtat attattgatg atgg | 30684 |

<210> SEQ ID NO 14
<211> LENGTH: 8602
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 14

| | |
|---|---:|
| atgggcggcg catgagagaa gcccagacca attacctacc caaaatggag aaagttcacg | 60 |
| ttgacatcga ggaagacagc ccattcctca gagctttgca gcggagcttc ccgcagtttg | 120 |
| aggtagaagc caagcaggtc actgataatg accatgctaa tgccagagcg ttttcgcatc | 180 |
| tggcttcaaa actgatcgaa acggaggtgg acccatccga cacgatcctt gacattggaa | 240 |
| gtgcgcccgc ccgcagaatg tattctaagc acaagtatca ttgtatctgt ccgatgagat | 300 |
| gtgcggaaga tccggacaga ttgtataagt atgcaactaa gctgaagaaa aactgtaagg | 360 |
| aaataactga taaggaattg acaagaaaaa tgaaggagct cgccgccgtc atgagcgacc | 420 |
| ctgacctgga aactgagact atgtgcctcc acgacgacga gtcgtgtcgc tacgaagggc | 480 |
| aagtcgctgt ttaccaggat gtatacgcgg ttgacggacc gacaagtctc tatcaccaag | 540 |
| ccaataaggg agttagagtc gcctactgga taggctttga caccacccct tttatgtttt a | 600 |
| agaacttggc tggagcatat ccatcatact ctaccaactg ggccgacgaa accgtgttaa | 660 |
| cggctcgtaa cataggccta tgcagctctg acgttatgga gcggtcacgt agagggatgt | 720 |
| ccattcttag aaagaagtat ttgaaaccat ccaacaatgt tctattctct gttggctcga | 780 |
| ccatctacca cgagaagagg gacttactga ggagctggca cctgccgtct gtatttcact | 840 |
| tacgtggcaa gcaaaattac acatgtcggt gtgagactat agttagttgc gacgggtacg | 900 |
| tcgttaaaag aatagctatc agtccaggcc tgtatgggaa gccttcaggc tatgctgcta | 960 |
| cgatgcaccg cgagggattc ttgtgctgca aagtgacaga cacattgaac ggggagaggg | 1020 |
| tctctttcc cgtgtgcacg tatgtgccag ctacattgtg tgaccaaatg actggcatac | 1080 |
| tggcaacaga tgtcagtgcg gacgacgcgc aaaaactgct ggttgggctc aaccagcgta | 1140 |
| tagtcgtcaa cggtcgcacc cagagaaaca ccaataccat gaaaaattac cttttgcccg | 1200 |

```
tagtggccca ggcatttgct aggtgggcaa aggaatataa ggaagatcaa gaagatgaaa      1260
ggccactagg actacgagat agacagttag tcatggggtg ttgttgggct tttagaaggc      1320
acaagataac atctatttat aagcgcccgg atacccaaac catcatcaaa gtgaacagcg      1380
atttccactc attcgtgctg cccaggatag gcagtaacac attggagatc gggctgagaa      1440
caagaatcag gaaaatgtta gaggagcaca aggagccgtc acctctcatt accgccgagg      1500
acgtacaaga agctaagtgc gcagccgatg aggctaagga ggtgcgtgaa gccgaggagt      1560
tgcgcgcagc tctaccacct ttggcagctg atgttgagga gcccactctg gaagccgatg      1620
tcgacttgat gttacaagag gctggggccg gctcagtgga gacacctcgt ggcttgataa      1680
aggttaccag ctacgctggc gaggacaaga tcggctctta cgctgtgctt tctccgcagg      1740
ctgtactcaa gagtgaaaaa ttatcttgca tccaccctct cgctgaacaa gtcatagtga      1800
taacacactc tggccgaaaa gggcgttatg ccgtggaacc ataccatggt aaagtagtgg      1860
tgccagaggg acatgcaata cccgtccagg actttcaagc tctgagtgaa agtgccacca      1920
ttgtgtacaa cgaacgtgag ttcgtaaaca ggtacctgca ccatattgcc acacatggag      1980
gagcgctgaa cactgatgaa gaatattaca aaactgtcaa gcccagcgag cacgacggcg      2040
aatacctgta cgacatcgac aggaaacagt gcgtcaagaa agaactagtc actgggctag      2100
ggctcacagg cgagctggtg gatcctccct tccatgaatt cgcctacgag agtctgagaa      2160
cacgaccagc cgctccttac caagtaccaa ccataggggt gtatggcgtg ccaggatcag      2220
gcaagtctgg catcattaaa agcgcagtca ccaaaaaaga tctagtggtg agcgccaaga      2280
aagaaaactg tgcagaaatt ataagggacg tcaagaaaat gaaagggctg gacgtcaatg      2340
ccagaactgt ggactcagtg ctcttgaatg gatgcaaaca ccccgtagag accctgtata      2400
ttgacgaagc ttttgcttgt catgcaggta ctctcagagc gctcatagcc attataagac      2460
ctaaaaaggc agtgctctgc ggggatccca acagtgcgg ttttttaac atgatgtgcc      2520 tgaaagtgca ttttaaccac gagatttgca cacaagtctt ccacaaaagc atctctcgcc      2580
gttgcactaa atctgtgact tcggtcgtct caaccttgtt ttacgacaaa aaaatgagaa      2640
cgacgaatcc gaaagagact aagattgtga ttgacactac cggcagtacc aaacctaagc      2700
aggacgatct cattctcact tgtttcagag ggtgggtgaa gcagttgcaa atagattaca      2760
aaggcaacga aataatgacg gcagctgcct ctcaagggct gacccgtaaa ggtgtgtatg      2820
ccgttcggta caaggtgaat gaaaatcctc tgtacgcacc cacctcagaa catgtgaacg      2880
tcctactgac ccgcacggag gaccgcatcg tgtggaaaac actagccggc gacccatgga      2940
taaaaacact gactgccaag tacctgggaa atttcactgc cacgatagag gagtggcaag      3000
cagagcatga tgccatcatg aggcacatct tggagagacc ggaccctacc gacgtcttcc      3060
agaataaggc aaacgtgtgt tgggccaagg ctttagtgcc ggtgctgaag accgctggca      3120
tagacatgac cactgaacaa tggaacactg tggattattt tgaaacggac aaagctcact      3180
cagcagagat agtattgaac caactatgcg tgaggttctt tggactcgat ctggactccg      3240 gtctatttc tgcacccact gttccgttat ccattaggaa taatcactgg gataactccc      3300
cgtcgcctaa catgtacggg ctgaataaag aagtggtccg tcagctctct cgcaggtacc      3360
cacaactgcc tcgggcagtt gccactggaa gagtctatga catgaacact ggtacactgc      3420
gcaattatga tccgcgcata aacctagtac ctgtaaacag aagactgcct catgctttag      3480
tcctccacca taatgaacac ccacagagtg acttttcttc attcgtcagc aaattgaagg      3540
gcagaactgt cctggtggtc ggggaaaagt tgtccgtccc aggcaaaatg gttgactggt      3600
```

```
tgtcagaccg gcctgaggct accttcagag ctcggctgga tttaggcatc ccaggtgatg   3660
tgcccaaata tgacataata tttgttaatg tgaggacccc atataaatac catcactatc   3720
agcagtgtga agaccatgcc attaagctta gcatgttgac caagaaagct tgtctgcatc   3780
tgaatcccgg cggaacctgt gtcagcatag gttatggtta cgctgacagg gccagcgaaa   3840
gcatcattgg tgctatagcg cggcagttca agttttcccg ggtatgcaaa ccgaaatcct   3900
cacttgaaga gacggaagtt ctgtttgtat tcattgggta cgatcgcaag gcccgtacgc   3960
acaatcctta caagctttca tcaaccttga ccaacattta tacaggttcc agactccacg   4020
aagccggatg tgcaccctca tatcatgtgg tgcgagggga tattgccacg gccaccgaag   4080
gagtgattat aaatgctgct aacagcaaag gacaacctgg cggagggtg tgcggagcgc    4140 tgtataagaa attcccggaa agcttcgatt tacagccgat cgaagtagga aaagcgcgac   4200
tggtcaaagg tgcagctaaa catatcattc atgccgtagg accaaacttc aacaaagttt   4260
cggaggttga aggtgacaaa cagttggcag aggcttatga gtccatcgct aagattgtca   4320
acgataacaa ttacaagtca gtagcgattc cactgttgtc caccggcatc ttttccggga   4380
acaaagatcg actaacccaa tcattgaacc atttgctgac agctttagac accactgatg   4440
cagatgtagc catatactgc agggacaaga aatgggaaat gactctcaag gaagcagtgg   4500
ctaggagaga agcagtggag gagatatgca tatccgacga ctcttcagtg acagaacctg   4560
atgcagagct ggtgagggtg catccgaaga gttctttggc tggaaggaag ggctacagca   4620
caagcgatgg caaaactttc tcatatttgg aagggaccaa gtttcaccag gcggccaagg   4680
atatagcaga aattaatgcc atgtggcccg ttgcaacgga ggccaatgag caggtatgca   4740
tgtatatcct cggagaaagc atgagcagta ttaggtcgaa atgccccgtc gaagagtcgg   4800
aagcctccac accacctagc acgctgcctt gcttgtgcat ccatgccatg actccagaaa   4860
gagtacagcg cctaaaagcc tcacgtccag aacaaattac tgtgtgctca tccttccat    4920 tgccgaagta tagaatcact ggtgtgcaga agatccaatg ctcccagcct atattgttct   4980
caccgaaagt gcctgcgtat attcatccaa ggaagtatct cgtggaaaca ccaccggtag   5040
acgagactcc ggagccatcg gcagagaacc aatccacaga ggggacacct gaacaaccac   5100
cacttataac cgaggatgag accaggacta gaacgcctga gccgatcatc atcgaagagg   5160
aagaagagga tagcataagt ttgctgtcag atggcccgac ccaccaggtg ctgcaagtcg   5220
aggcagacat tcacgggccg ccctctgtat ctagctcatc ctggtccatt cctcatgcat   5280
ccgactttga tgtggacagt ttatccatac ttgacaccct ggaggagct agcgtgacca    5340 gcggggcaac gtcagccgag actaactctt acttcgcaaa gagtatggag tttctggcgc   5400
gaccggtgcc tgcgcctcga acagtattca ggaaccctcc acatcccgct ccgcgcacaa   5460
gaacaccgtc acttgcaccc agcagggcct gctcgagaac cagcctagtt tccaccccgc   5520
caggcgtgaa tagggtgatc actagagagg agctcgaggc gcttacccg tcacgcactc    5580 ctagcaggtc ggtctcgaga accagcctgg tctccaaccc gccaggcgta aatagggtga   5640
ttacaagaga ggagtttgag gcgttcgtag cacaacaaca atgacggttt gatgcgggtg   5700
catacatctt ttcctccgac accggtcaag ggcatttaca acaaaaatca gtaaggcaaa   5760
cggtgctatc cgaagtggtg ttggagagga ccgaattgga gatttcgtat gccccgcgcc   5820
tcgaccaaga aaaagaagaa ttactacgca agaaattaca gttaaatccc acacctgcta   5880
acagaagcag ataccagtcc aggaaggtgg agaacatgaa agccataaca gctagacgta   5940
```

```
ttctgcaagg cctagggcat tatttgaagg cagaaggaaa agtggagtgc taccgaaccc    6000
tgcatcctgt tcctttgtat tcatctagtg tgaaccgtgc cttttcaagc cccaaggtcg    6060
cagtggaagc ctgtaacgcc atgttgaaag agaactttcc gactgtggct tcttactgta    6120
ttattccaga gtacgatgcc tatttggaca tggttgacgg agcttcatgc tgcttagaca    6180
ctgccagttt ttgccctgca agctgcgca gctttccaaa gaaacactcc tatttggaac    6240
ccacaatacg atcggcagtg ccttcagcga tccagaacac gctccagaac gtcctggcag    6300
ctgccacaaa aagaaattgc aatgtcacgc aaatgagaga attgcccgta ttggattcgg    6360
cggcctttaa tgtggaatgc ttcaagaaat atgcgtgtaa taatgaatat tgggaaacgt    6420
ttaaagaaaa ccccatcagg cttactgaag aaaacgtggt aaattacatt accaaattaa    6480
aaggaccaaa agctgctgct cttttttgcga agacacataa tttgaatatg ttgcaggaca    6540
taccaatgga caggtttgta atggacttaa agagagacgt gaaagtgact ccaggaacaa    6600
aacatactga agaacggccc aaggtacagg tgatccaggc tgccgatccg ctagcaacag    6660
cgtatctgtg cggaatccac cgagagctgg ttaggagatt aaatgcggtc ctgcttccga    6720
acattcatac actgtttgat atgtcggctg aagactttga cgctattata gccgagcact    6780
tccagcctgg ggattgtgtt ctggaaactg acatcgcgtc gtttgataaa agtgaggacg    6840
acgccatggc tctgaccgcg ttaatgattc tggaagactt aggtgtggac gcagagctgt    6900
tgacgctgat tgaggcggct ttcggcgaaa tttcatcaat acatttgccc actaaaacta    6960
aatttaaatt cggagccatg atgaaatctg gaatgttcct cacactgttt gtgaacacag    7020
tcattaacat tgtaatcgca agcagagtgt tgagagaacg gctaaccgga tcaccatgtg    7080
cagcattcat tggagatgac aatatcgtga aaggagtcaa atcggacaaa ttaatggcag    7140
acaggtgcgc cacctggttg aatatggaag tcaagattat agatgctgtg gtgggcgaga    7200
aagcgcctta tttctgtgga gggttttattt tgtgtgactc cgtgaccggc acagcgtgcc    7260
gtgtggcaga cccctaaaaa aggctgttta agcttggcaa acctctggca gcagacgatg    7320
aacatgatga tgacaggaga agggcattgc atgaagagtc aacacgctgg aaccgagtgg    7380
gtattctttc agagctgtgc aaggcagtag aatcaaggta tgaaaccgta ggaacttcca    7440
tcatagttat ggccatgact actctagcta gcagtgttaa atcattcagc tacctgagag    7500
gggcccctat aactctctac ggctaacctg aatggactac gactctagaa tagtctttaa    7560
ttaaagtccg ccatatgagg ccaccatgca gatcttcgtg aagaccctga ccggcaagac    7620
catcacccta gaggtggagc ccagtgacac catcgagaac gtgaaggcca agatccagga    7680
taaagagggc atcccccctg accagcagag gctgatcttt gccggcaagc agctggaaga    7740
tggccgcacc ctctctgatt acaacatcca gaaggagtca accctgcacc tggtccttcg    7800
cctgagaggt ggcgctgctt acagtataat caactttgaa aaactggctg cttacggcat    7860
cctgggcttt gtgtttacac tggctgccta cctgctgttt ggctatcctg tgtacgtggc    7920
cgcttatgga ctgtgtaccc tggtggccat gctggctgct tacaatctgg tgcctatggt    7980
ggccacagtg gccgcctatt gtcttggcgg actgctgaca atggtggcag cctacagccc    8040
gagctatgcg tatcatcagt ttgcagccta cggcccagga ccaggcgcta aatttgtggc    8100
tgcctggaca ctgaaagccg ccgctggacc aggtcctgga cagtacatca aggccaacag    8160
caagttcatc ggcatcaccg aactcggccc aggaccaggc tatccctacg atgtgcctga    8220
ttacgcctga tagtgatgat tcgaacggcc gtatcacgcc caaacattta cagccgcggt    8280
gtcaaaaacc gcgtggacgt ggttaacatc cctgctggga ggatcagccg taattattat    8340
```

```
aattggcttg gtgctggcta ctattgtggc catgtacgtg ctgaccaacc agaaacataa    8400
ttgaatacag cagcaattgg caagctgctt acatagaact cgcggcgatt ggcatgccgc    8460
cttaaaattt ttattttatt ttttcttttc ttttccgaat cggattttgt ttttaatatt    8520
tcaaaaaaaa aaaaaaaaaa aaaaaaaaaa aaaaaaaaaa aaaaaaaaaa aaaaaaaaaa    8580
aaaaaaaaaa aaaaaaaaaa aa                                             8602
```

<210> SEQ ID NO 15
<211> LENGTH: 9595
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 15

```
atgggcggcg catgagagaa gcccagacca attacctacc caaaatggag aaagttcacg      60
ttgacatcga ggaagacagc ccattcctca gagctttgca gcggagcttc ccgcagtttg     120
aggtagaagc caagcaggtc actgataatg accatgctaa tgccagagcg ttttcgcatc     180
tggcttcaaa actgatcgaa acggaggtgg acccatccga cacgatcctt gacattggaa     240
gtgcgcccgc ccgcagaatg tattctaagc acaagtatca ttgtatctgt ccgatgagat     300
gtgcggaaga tccggacaga ttgtataagt atgcaactaa gctgaagaaa aactgtaagg     360
aaataactga taaggaattg gacaagaaaa tgaaggagct cgccgccgtc atgagcgacc     420
ctgacctgga aactgagact atgtgcctcc acgacgacga gtcgtgtcgc tacgaagggc     480
aagtcgctgt ttaccaggat gtatacgcgg ttgacggacc gacaagtctc tatcaccaag     540
ccaataaggg agttagagtc gcctactgga taggctttga caccacccct tttatgttta     600
agaacttggc tggagcatat ccatcatact ctaccaactg ggccgacgaa accgtgttaa     660
cggctcgtaa cataggccta tgcagctctg acgttatgga gcggtcacgt agagggatgt     720
ccattcttag aaagaagtat ttgaaaccat ccaacaatgt tctattctct gttggctcga     780
ccatctacca cgagaagagg gacttactga ggagctggca cctgccgtct gtatttcact     840
tacgtggcaa gcaaaattac acatgtcggt gtgagactat agttagttgc gacgggtacg     900
tcgttaaaag aatagctatc agtccaggcc tgtatgggaa gccttcaggc tatgctgcta     960
cgatgcaccg cgagggattc ttgtgctgca aagtgacaga cacattgaac ggggagaggg    1020 tctctttttcc cgtgtgcacg tatgtgccag ctacattgtg tgaccaaatg actggcatac    1080
tggcaacaga tgtcagtgcg gacgacgcgc aaaaactgct ggttgggctc aaccagcgta    1140
tagtcgtcaa cggtcgcacc cagagaaaca ccaataccat gaaaaattac cttttgcccg    1200
tagtggccca ggcatttgct aggtgggcaa aggaatataa ggaagatcaa gaagatgaaa    1260
ggccactagg actacgagat agacagttag tcatggggtg ttgttgggct tttagaaggc    1320
acaagataac atctatttat aagcgcccgg atacccaaac catcatcaaa gtgaacagcg    1380
atttccactc attcgtgctg cccaggatag gcagtaacac attggagatc gggctgagaa    1440
caagaatcag gaaaatgtta gaggagcaca aggagccgtc acctctcatt accgccgagg    1500
acgtacaaga agctaagtgc gcagccgatg aggctaagga ggtgcgtgaa gccgaggagt    1560
tgcgcgcagc tctaccacct ttggcagctg atgttgagga gcccactctg gaagccgatg    1620
tcgacttgat gttacaagag gctggggccg gctcagtgga gacacctgt ggcttgataa      1680 aggttaccag ctacgctggc gaggacaaga tcggctctta cgctgtgctt tctccgcagg    1740
```

```
ctgtactcaa gagtgaaaaa ttatcttgca tccaccctct cgctgaacaa gtcatagtga   1800
taacacactc tggccgaaaa gggcgttatg ccgtggaacc ataccatggt aaagtagtgg   1860
tgccagaggg acatgcaata cccgtccagg actttcaagc tctgagtgaa agtgccacca   1920
ttgtgtacaa cgaacgtgag ttcgtaaaca ggtacctgca ccatattgcc acacatggag   1980
gagcgctgaa cactgatgaa gaatattaca aaactgtcaa gcccagcgag cacgacggcg   2040
aatacctgta cgacatcgac aggaaacagt gcgtcaagaa agaactagtc actgggctag   2100
ggctcacagg cgagctggtg gatcctccct tccatgaatt cgcctacgag agtctgagaa   2160
cacgaccagc cgctccttac caagtaccaa ccataggggt gtatggcgtg ccaggatcag   2220
gcaagtctgg catcattaaa agcgcagtca ccaaaaaaga tctagtggtg agcgccaaga   2280
aagaaaactg tgcagaaatt ataagggacg tcaagaaaat gaaagggctg acgtcaatg    2340
ccagaactgt ggactcagtg ctcttgaatg gatgcaaaca ccccgtagag accctgtata   2400
ttgacgaagc ttttgcttgt catgcaggta ctctcagagc gctcatagcc attataagac   2460
ctaaaaaggc agtgctctgc ggggatccca acagtgcgg tttttttaac atgatgtgcc    2520
tgaaagtgca ttttaaccac gagatttgca cacaagtctt ccacaaaagc atctctcgcc   2580
gttgcactaa atctgtgact tcggtcgtct caaccttgtt ttacgacaaa aaaatgagaa   2640
cgacgaatcc gaaagagact aagattgtga ttgacactac cggcagtacc aaacctaagc   2700
aggacgatct cattctcact tgtttcagag ggtgggtgaa gcagttgcaa atagattaca   2760
aaggcaacga aataatgacg gcagctgcct ctcaagggct gacccgtaaa ggtgtgtatg   2820
ccgttcggta caaggtgaat gaaaatcctc tgtacgcacc cacctcagaa catgtgaacg   2880
tcctactgac ccgcacggag gaccgcatcg tgtggaaaac actagccggc gacccatgga   2940
taaaaacact gactgccaag taccctggga atttcactgc cacgatagag gagtggcaag   3000
cagagcatga tgccatcatg aggcacatct tggagagacc ggaccctacc gacgtcttcc   3060
agaataaggc aaacgtgtgt tgggccaagg ctttagtgcc ggtgctgaag accgctggca   3120
tagacatgac cactgaacaa tggaacactg tggattattt tgaaacggac aaagctcact   3180
cagcagagat agtattgaac caactatgcg tgaggttctt tggactcgat ctggactccg   3240
gtctattttc tgcacccact gttccgttat ccattaggaa taatcactgg gataactccc   3300
cgtcgcctaa catgtacggg ctgaataaag aagtggtccg tcagctctct cgcaggtacc   3360
cacaactgcc tcgggcagtt gccactggaa gagtctatga catgaacact ggtacactgc   3420
gcaattatga tccgcgcata aacctagtac ctgtaaacag aagactgcct catgctttag   3480
tcctccacca taatgaacac ccacagagtg acttttcttc attcgtcagc aaattgaagg   3540
gcagaactgt cctggtggtc gggaaaagt gtccgtccc aggcaaaatg gttgactggt    3600
tgtcagaccg gcctgaggct accttcagag ctcggctgga tttaggcatc ccaggtgatg   3660
tgcccaaata tgacataata tttgttaatg tgaggaccc atataaatac catcactatc    3720
agcagtgtga agaccatgcc attaagctta gcatgttgac caagaaagct tgtctgcatc   3780
tgaatcccgg cggaacctgt gtcagcatag gttatggtta cgctgacagg gccagcgaaa   3840
gcatcattgg tgctatagcg cggcagttca agttttcccg ggtatgcaaa ccgaaatcct   3900
cacttgaaga gacggaagtt ctgtttgtat tcattgggta cgatcgcaag gcccgtacgc   3960
acaatcctta caagctttca tcaaccttga ccaacattta tacaggttcc agactccacg   4020
aagccggatg tgcaccctca tatcatgtgg tgcgagggga tattgccacg gccaccgaag   4080
```

-continued

```
gagtgattat aaatgctgct aacagcaaag gacaacctgg cggaggggtg tgcggagcgc    4140
tgtataagaa attcccggaa agcttcgatt tacagccgat cgaagtagga aaagcgcgac    4200
tggtcaaagg tgcagctaaa catatcattc atgccgtagg accaaacttc aacaaagttt    4260
cggaggttga aggtgacaaa cagttggcag aggcttatga gtccatcgct aagattgtca    4320
acgataacaa ttacaagtca gtagcgattc cactgttgtc caccggcatc ttttccggga    4380
acaaagatcg actaacccaa tcattgaacc atttgctgac agctttagac accactgatg    4440
cagatgtagc catatactgc agggacaaga aatgggaaat gactctcaag gaagcagtgg    4500
ctaggagaga agcagtggag gagatatgca tatccgacga ctcttcagtg acagaacctg    4560
atgcagagct ggtgagggtg catccgaaga gttctttggc tggaaggaag ggctacagca    4620
caagcgatgg caaaactttc tcatatttgg aagggaccaa gtttcaccag gcggccaagg    4680
atatagcaga aattaatgcc atgtggcccg ttgcaacgga ggccaatgag caggtatgca    4740
tgtatatcct cggagaaagc atgagcagta ttaggtcgaa atgccccgtc gaagagtcgg    4800
aagcctccac accacctagc acgctgcctt gcttgtgcat ccatgccatg actccagaaa    4860
gagtacagcg cctaaaagcc tcacgtccag aacaaattac tgtgtgctca tcctttccat    4920
tgccgaagta tagaatcact ggtgtgcaga agatccaatg ctcccagcct atattgttct    4980
caccgaaagt gcctgcgtat attcatccaa ggaagtatct cgtggaaaca ccaccggtag    5040
acgagactcc ggagccatcg gcagagaacc aatccacaga ggggacacct gaacaaccac    5100
cacttataac cgaggatgag accaggacta gaacgcctga gccgatcatc atcgaagagg    5160
aagaaggaga tagcataagt ttgctgtcag atggcccgac ccaccaggtg ctgcaagtcg    5220
aggcagacat tcacgggccg ccctctgtat ctagctcatc ctggtccatt cctcatgcat    5280
ccgactttga tgtggacagt ttatccatac ttgacaccct ggaggagct agcgtgacca    5340
gcggggcaac gtcagccgag actaactctt acttcgcaaa gagtatggag tttctggcgc    5400
gaccggtgcc tgcgcctcga acagtattca ggaaccctcc acatcccgct ccgcgcacaa    5460
gaacaccgtc acttgcaccc agcagggcct gctcgagaac cagcctagtt tccaccccgc    5520
caggcgtgaa tagggtgatc actagagagg agctcgaggc gcttacccg tcacgcactc    5580
ctagcaggtc ggtctcgaga accagcctgg tctccaaccc gccaggcgta aatagggtga    5640
ttacaagaga ggagtttgag gcgttcgtag cacaacaaca atgacggttt gatgcgggtg    5700
catacatctt ttcctccgac accggtcaag ggcatttaca acaaaaatca gtaaggcaaa    5760
cggtgctatc cgaagtggtg ttggagagga ccgaattgga gatttcgtat gccccgcgcc    5820
tcgaccaaga aaaagaagaa ttactacgca agaaattaca gttaaatccc acacctgcta    5880
acagaagcag ataccagtcc aggaaggtgg agaacatgaa agccataaca gctagacgta    5940
ttctgcaagg cctagggcat tatttgaagg cagaaggaaa agtggagtgc taccgaaccc    6000
tgcatcctgt tccttttgtat tcatctagtg tgaaccgtgc cttttcaagc cccaaggtcg    6060
cagtggaagc ctgtaacgcc atgttgaaag agaactttcc gactgtggct tcttactgta    6120
ttattccaga gtacgatgcc tatttggaca tggttgacgg agcttcatgc tgcttagaca    6180
ctgccagttt ttgccctgca aagctgcgca gctttccaaa gaaacactcc tatttggaac    6240
ccacaatacg atcggcagtg ccttcagcga tccagaacac gctccagaac gtcctggcag    6300
ctgccacaaa aagaaattgc aatgtcacgc aaatgagaga attgcccgta ttggattcgg    6360
cggcctttaa tgtggaatgc ttcaagaaat atgcgtgtaa taatgaatat tgggaaacgt    6420
ttaaagaaaa ccccatcagg cttactgaag aaaacgtggt aaattacatt accaaattaa    6480
```

```
aaggaccaaa agctgctgct cttttttgcga agacacataa tttgaatatg ttgcaggaca      6540
taccaatgga caggtttgta atggacttaa agagagacgt gaaagtgact ccaggaacaa      6600
aacatactga agaacggccc aaggtacagg tgatccaggc tgccgatccg ctagcaacag      6660
cgtatctgtg cggaatccac cgagagctgg ttaggagatt aaatgcggtc ctgcttccga      6720
acattcatac actgtttgat atgtcggctg aagactttga cgctattata gccgagcact      6780
tccagcctgg ggattgtgtt ctggaaactg acatcgcgtc gtttgataaa agtgaggacg      6840
acgccatggc tctgaccgcg ttaatgattc tggaagactt aggtgtggac gcagagctgt      6900
tgacgctgat tgaggcggct ttcggcgaaa tttcatcaat acatttgccc actaaaacta      6960
aatttaaatt cggagccatg atgaaatctg gaatgttcct cacactgttt gtgaacacag      7020
tcattaacat tgtaatcgca agcagagtgt tgagagaacg gctaaccgga tcaccatgtg      7080
cagcattcat tggagatgac aatatcgtga aaggagtcaa atcggacaaa ttaatggcag      7140
acaggtgcgc cacctggttg aatatggaag tcaagattat agatgctgtg gtgggcgaga      7200
aagcgcctta tttctgtgga gggtttattt tgtgtgactc cgtgaccggc acagcgtgcc      7260
gtgtggcaga ccccctaaaa aggctgttta agcttggcaa acctctggca gcagacgatg      7320
aacatgatga tgacaggaga agggcattgc atgaagagtc aacacgctgg aaccgagtgg      7380
gtattctttc agagctgtgc aaggcagtag aatcaaggta tgaaccgta ggaacttcca      7440
tcatagttat ggccatgact actctagcta gcagtgttaa atcattcagc tacctgagag      7500
gggcccctat aactctctac ggctaacctg aatggactac gactctagaa tagtctttaa      7560
ttaaagtccg ccatatgaga tggaagatgc caaaaacatt aagaagggcc cagcgccatt      7620
ctacccactc gaagacggga ccgccggcga gcagctgcac aaagccatga agcgctacgc      7680
cctggtgccc ggcaccatcg cctttaccga cgcacatatc gaggtggaca ttacctacgc      7740
cgagtacttc gagatgagcg ttcggctggc agaagctatg aagcgctatg gctgaatac      7800
aaaccatcgg atcgtggtgt gcagcgagaa tagcttgcag ttcttcatgc ccgtgttggg      7860
tgccctgttc atcggtgtgg ctgtggcccc agctaacgac atctacaacg agcgcgagct      7920
gctgaacagc atgggcatca gccagcccac cgtcgtattc gtgagcaaga aagggctgca      7980
aaagatcctc aacgtgcaaa agaagctacc gatcatacaa aagatcatca tcatggatag      8040
caagaccgac taccagggct tccaaagcat gtacaccttc gtgacttccc atttgccacc      8100
cggcttcaac gagtacgact tcgtgcccga gagcttcgac cgggacaaaa ccatcgccct      8160
gatcatgaac agtagtggca gtaccggatt gcccaagggc gtagccctac cgcaccgcac      8220
cgcttgtgtc cgattcagtc atgcccgcga ccccatcttc ggcaaccaga tcatccccga      8280
caccgctatc ctcagcgtgg tgccatttca ccacggcttc ggcatgttca ccacgctggg      8340
ctacttgatc tgcggctttc gggtcgtgct catgtaccgc ttcgaggagg agctattctt      8400
gcgcagcttg caagactata agattcaatc tgccctgctg gtgcccacac tatttagctt      8460
cttcgctaag agcactctca tcgacaagta cgacctaagc aacttgcacg agatcgccag      8520
cggcggggcg ccgctcagca aggaggtagg tgaggccgtg gccaaacgct tccacctacc      8580
aggcatccgc cagggctacg gcctgacaga aacaaccagc gccattctga tcaccccga      8640
aggggacgac aagcctggcg cagtaggcaa ggtggtgccc ttcttcgagg ctaaggtggt      8700
ggacttggac accggtaaga cactgggtgt gaaccagcgc ggcgagctgt gcgtccgtgg      8760
ccccatgatc atgagcggct acgttaacaa ccccgaggct acaaacgctc tcatcgacaa      8820
```

-continued

```
ggacggctgg ctgcacagcg gcgacatcgc ctactgggac gaggacgagc acttcttcat   8880
cgtggaccgg ctgaagagcc tgatcaaata caagggctac caggtagccc cagccgaact   8940
ggagagcatc ctgctgcaac accccaacat cttcgacgcc ggggtcgccg gcctgcccga   9000
cgacgatgcc ggcgagctgc cgccgcagt cgtcgtgctg aaacacggta aaaccatgac    9060
cgagaaggag atcgtggact atgtggccag ccaggttaca accgccaaga agctgcgcgg   9120
tggtgttgtg ttcgtggacg aggtgcctaa aggactgacc ggcaagttgg acgcccgcaa   9180
gatccgcgag attctcatta aggccaagaa gggcggcaag atcgccgtgt aattcgaacg   9240
gccgtatcac gcccaaacat ttacagccgc ggtgtcaaaa accgcgtgga cgtggttaac   9300
atccctgctg ggaggatcag ccgtaattat tataattggc ttggtgctgg ctactattgt   9360
ggccatgtac gtgctgacca accagaaaca taattgaata cagcagcaat tggcaagctg   9420
cttacataga actcgcggcg attggcatgc cgccttaaaa ttttttatttt atttttcctt   9480 ttcttttccg aatcggattt tgtttttaat atttcaaaaa aaaaaaaaa aaaaaaaaa    9540 aaaaaaaaaa aaaaaaaaaa aaaaaaaaaa aaaaaaaaaa aaaaaaaaaa aaaaa       9595
```

<210> SEQ ID NO 16
<211> LENGTH: 139
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

Pro Ser Ser Leu Ser Ala Ser Val Gly Asp Arg Val Thr Ile Thr Cys
1               5                   10                  15

Arg Ala Ser Gln Ser Ile Asn Ser Tyr Leu Asp Trp Tyr Gln Gln Lys
                20                  25                  30

Pro Gly Lys Ala Pro Lys Leu Leu Ile Tyr Ala Ala Ser Ser Leu Gln
            35                  40                  45

Ser Gly Val Pro Ser Arg Phe Ser Gly Ser Gly Ser Gly Thr Asp Phe
        50                  55                  60

Thr Leu Thr Ile Ser Ser Leu Gln Pro Glu Asp Phe Ala Thr Tyr Tyr
65                  70                  75                  80

Cys Gln Gln Tyr Tyr Ser Thr Pro Phe Thr Phe Gly Pro Gly Thr Lys
                85                  90                  95

Val Glu Ile Lys Arg Thr Val Ala Ala Pro Ser Val Phe Ile Phe Pro
            100                 105                 110

Pro Ser Asp Glu Gln Leu Lys Ser Gly Thr Ala Ser Val Val Cys Leu
        115                 120                 125

Leu Asn Asn Phe Tyr Pro Arg Glu Ala Lys Val
    130                 135

<210> SEQ ID NO 17
<211> LENGTH: 167
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

Gly Val Val Gln Pro Gly Arg Ser Leu Arg Leu Ser Cys Ala Ala Ser
1               5                   10                  15

Gly Phe Thr Phe Ser Ser Tyr Gly Met His Trp Val Arg Gln Ala Pro

```
                  20                  25                  30

Gly Lys Gly Leu Glu Trp Val Ala Val Ile Trp Tyr Asp Gly Ser Asn
            35                  40                  45

Lys Tyr Tyr Ala Asp Ser Val Lys Gly Arg Phe Thr Ile Ser Arg Asp
 50                  55                  60

Asn Ser Lys Asn Thr Leu Tyr Leu Gln Met Asn Ser Leu Arg Ala Glu
 65                  70                  75                  80

Asp Thr Ala Val Tyr Tyr Cys Ala Arg Asp Pro Arg Gly Ala Thr Leu
                85                  90                  95

Tyr Tyr Tyr Tyr Tyr Gly Met Asp Val Trp Gly Gln Gly Thr Thr Val
            100                 105                 110

Thr Val Ser Ser Ala Ser Thr Lys Gly Pro Ser Val Phe Pro Leu Ala
        115                 120                 125

Pro Cys Ser Arg Ser Thr Ser Glu Ser Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His
                165
```

<210> SEQ ID NO 18
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

```
Gly Phe Thr Phe Ser Ser Tyr Gly Met His
  1               5                  10
```

<210> SEQ ID NO 19
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

```
Val Ile Trp Tyr Asp Gly Ser Asn Lys Tyr Tyr Ala Asp Ser Val
  1               5                  10                  15
```

<210> SEQ ID NO 20
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

```
Asp Pro Arg Gly Ala Thr Leu Tyr Tyr Tyr Tyr Gly Met Asp Val
  1               5                  10                  15
```

<210> SEQ ID NO 21
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 21

Arg Ala Ser Gln Ser Ile Asn Ser Tyr Leu Asp
1               5                   10

<210> SEQ ID NO 22
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Ala Ala Ser Ser Leu Gln Ser
1               5

<210> SEQ ID NO 23
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Gln Gln Tyr Tyr Ser Thr Pro Phe Thr
1               5

<210> SEQ ID NO 24
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 24

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Arg Val Ser Ser Ser
            20                  25                  30

Tyr Leu Ala Trp Tyr Gln Gln Lys Pro Gly Gln Ala Pro Arg Leu Leu
        35                  40                  45

Ile Tyr Asp Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Leu Pro
                85                  90                  95

Trp Thr Phe Gly Gln Gly Thr Lys Val Glu Ile Lys
            100                 105

<210> SEQ ID NO 25
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 25

Glu Val Gln Leu Val Glu Ser Gly Gly Gly Leu Val Gln Pro Gly Gly
1               5                   10                  15
```

```
Ser Leu Arg Leu Ser Cys Ala Ala Ser Gly Phe Thr Phe Ser Arg Tyr
            20                  25                  30

Trp Met Ser Trp Val Arg Gln Ala Pro Gly Lys Gly Leu Glu Trp Val
        35                  40                  45

Ala Asn Ile Lys Gln Asp Gly Ser Glu Lys Tyr Tyr Val Asp Ser Val
 50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                85                  90                  95

Ala Arg Glu Gly Gly Trp Phe Gly Glu Leu Ala Phe Asp Tyr Trp Gly
            100                 105                 110

Gln Gly Thr Leu Val Thr Val Ser Ser
        115                 120

<210> SEQ ID NO 26
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Arg Tyr Trp Met Ser
1               5

<210> SEQ ID NO 27
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Asn Ile Lys Gln Asp Gly Ser Glu Lys Tyr Tyr Val Asp Ser Val Lys
1               5                   10                  15

Gly

<210> SEQ ID NO 28
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Glu Gly Gly Trp Phe Gly Glu Leu Ala Phe Asp Tyr
1               5                   10

<210> SEQ ID NO 29
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Arg Ala Ser Gln Arg Val Ser Ser Ser Tyr Leu Ala
1               5                   10
```

-continued

<210> SEQ ID NO 30
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Asp Ala Ser Ser Arg Ala Thr
1               5

<210> SEQ ID NO 31
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Gln Gln Tyr Gly Ser Leu Pro Trp Thr
1               5

<210> SEQ ID NO 32
<211> LENGTH: 2019
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 32
gcccgggcat ttaaatgcga tcgcatcgat tacgactcta gaatagtcta gtccgcaggc      60
caccatgcag atcttcgtga agaccctgac cggcaagacc atcaccctag aggtggagcc     120
cagtgacacc atcgagaacg tgaaggccaa gatccaggat aaagagggca tccccccctga    180
ccagcagagg ctgatctttg ccggcaagca gctggaagat ggccgcaccc tctctgatta    240
caacatccag aaggagtcaa ccctgcacct ggtccttcgc ctgagaggtg ccatgtttca    300
ggcgctgagc gaaggctgca ccccgtatga tattaaccag atgctgaacg tgctgggcga    360
tcatcaggtc tcaggccttg agcagcttga gagtataatc aactttgaaa aactgactga    420
atggaccagt tctaatgtta tgcctatcct gtctcctctg acaaagggca tcctgggctt    480
cgtgtttacc ctgaccgtgc cttctgagag gaggacttagc tgcattagcg aagcggatgc    540
gaccaccccg gaaagcgcga acctgggcga agaaattctg agccagctgt atctttggcc    600
aagggtgacc taccattccc ctagttatgc ttaccaccaa tttgaaagac gagccaaata    660
taaaagacac ttccccggct tggccagag cctgctgttt ggctaccctg tgtacgtgtt    720
cggcgattgc gtgcagggcg attgggatgc gattcgcttt cgctattgcg cgccgccggg    780
ctatgcgctg ctgcgctgca acgataccaa ctatagcgct ctgctggctg tggggcccct    840
agaaggaccc aggaatcagg actggcttgg tgtcccaaga caacttgtaa ctcggatgca    900
ggctattcag aatgccggcc tgtgtaccct ggtggccatg ctggaagaga caatcttctg    960
gctgcaagcg tttctgatgg cgctgaccga tagcggcccg aaaaccaaca ttattgtgga   1020
tagccagtat gtgatgggca ttagcaaacc gagctttcag gaatttgtgg attgggaaaa   1080
cgtgagcccg gaactgaaca gcaccgatca gccgttttgg caagccggaa tcctggccag   1140
aaatctggtg cctatggtgg ccacagtgca gggccagaac ctgaagtacc agggtcagtc   1200

```
actagtcatc tctgcttcta tcattgtctt caacctgctg gaactggaag gtgattatcg   1260
agatgatggc aacgtgtggg tgcataccccc gctgagcccg cgcaccctga acgcgtgggt   1320
gaaagcggtg gaagaaaaaa aaggtattcc agttcaccta gagctggcca gtatgaccaa   1380
catggagctc atgagcagta ttgtgcatca gcaggtcaga acatacggcc ccgtgttcat   1440
gtgtctcggc ggactgctta caatggtggc tggtgctgtg tggctgacag tgcgagtgct   1500
cgagctgttc cgggccgcgc agctggccaa cgacgtggtc ctccagatca tggagctttg   1560
tggtgcagcg tttcgccagg tgtgccatac caccgtgccg tggccgaacg cgagcctgac   1620
cccgaaatgg aacaacgaaa ccacccagcc ccagatcgcc aactgcagcg tgtatgactt   1680
ttttgtgtgg ctccattatt attctgttcg agacacactt tggccaaggg tgacctacca   1740
tatgaacaaa tatgcgtatc atatgctgga agacgagcc aaatataaaa gaggaccagg   1800
acctggcgct aaatttgtgg ccgcctggac actgaaagcc gctgctggtc ctggacctgg   1860
ccagtacatc aaggccaaca gcaagttcat cggcatcacc gaactcggac ccggaccagg   1920
ctgatgattt cgaaatttaa ataagcttgc ggccgctagg gataacaggg taattatcac   1980
gcccaaacat ttacagccgc ggtgtcaaaa accgcgtgg                          2019
```

<210> SEQ ID NO 33
<211> LENGTH: 619
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 33

Met Gln Ile Phe Val Lys Thr Leu Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Phe Ala Gly Lys
        35                  40                  45

Gln Leu Glu Asp Gly Arg Thr Leu Ser Asp Tyr Asn Ile Gln Lys Glu
    50                  55                  60

Ser Thr Leu His Leu Val Leu Arg Leu Arg Gly Ala Met Phe Gln Ala
65                  70                  75                  80

Leu Ser Glu Gly Cys Thr Pro Tyr Asp Ile Asn Gln Met Leu Asn Val
                85                  90                  95

Leu Gly Asp His Gln Val Ser Gly Leu Glu Gln Leu Glu Ser Ile Ile
            100                 105                 110

Asn Phe Glu Lys Leu Thr Glu Trp Thr Ser Ser Asn Val Met Pro Ile
        115                 120                 125

Leu Ser Pro Leu Thr Lys Gly Ile Leu Gly Phe Val Phe Thr Leu Thr
    130                 135                 140

Val Pro Ser Glu Arg Gly Leu Ser Cys Ile Ser Glu Ala Asp Ala Thr
145                 150                 155                 160

Thr Pro Glu Ser Ala Asn Leu Gly Glu Glu Ile Leu Ser Gln Leu Tyr
                165                 170                 175

Leu Trp Pro Arg Val Thr Tyr His Ser Pro Ser Tyr Ala Tyr His Gln
            180                 185                 190

Phe Glu Arg Arg Ala Lys Tyr Lys Arg His Phe Pro Gly Phe Gly Gln
        195                 200                 205

```
Ser Leu Leu Phe Gly Tyr Pro Val Tyr Val Phe Gly Asp Cys Val Gln
    210                 215                 220

Gly Asp Trp Asp Ala Ile Arg Phe Arg Tyr Cys Ala Pro Pro Gly Tyr
225                 230                 235                 240

Ala Leu Leu Arg Cys Asn Asp Thr Asn Tyr Ser Ala Leu Leu Ala Val
                245                 250                 255

Gly Ala Leu Glu Gly Pro Arg Asn Gln Asp Trp Leu Gly Val Pro Arg
            260                 265                 270

Gln Leu Val Thr Arg Met Gln Ala Ile Gln Asn Ala Gly Leu Cys Thr
        275                 280                 285

Leu Val Ala Met Leu Glu Glu Thr Ile Phe Trp Leu Gln Ala Phe Leu
    290                 295                 300

Met Ala Leu Thr Asp Ser Gly Pro Lys Thr Asn Ile Ile Val Asp Ser
305                 310                 315                 320

Gln Tyr Val Met Gly Ile Ser Lys Pro Ser Phe Gln Glu Phe Val Asp
                325                 330                 335

Trp Glu Asn Val Ser Pro Glu Leu Asn Ser Thr Asp Gln Pro Phe Trp
            340                 345                 350

Gln Ala Gly Ile Leu Ala Arg Asn Leu Val Pro Met Val Ala Thr Val
        355                 360                 365

Gln Gly Gln Asn Leu Lys Tyr Gln Gly Gln Ser Leu Val Ile Ser Ala
    370                 375                 380

Ser Ile Ile Val Phe Asn Leu Leu Glu Leu Glu Gly Asp Tyr Arg Asp
385                 390                 395                 400

Asp Gly Asn Val Trp Val His Thr Pro Leu Ser Pro Arg Thr Leu Asn
                405                 410                 415

Ala Trp Val Lys Ala Val Glu Glu Lys Lys Gly Ile Pro Val His Leu
            420                 425                 430

Glu Leu Ala Ser Met Thr Asn Met Glu Leu Met Ser Ser Ile Val His
        435                 440                 445

Gln Gln Val Arg Thr Tyr Gly Pro Val Phe Met Cys Leu Gly Gly Leu
    450                 455                 460

Leu Thr Met Val Ala Gly Ala Val Trp Leu Thr Val Arg Val Leu Glu
465                 470                 475                 480

Leu Phe Arg Ala Ala Gln Leu Ala Asn Asp Val Val Leu Gln Ile Met
                485                 490                 495

Glu Leu Cys Gly Ala Ala Phe Arg Gln Val Cys His Thr Thr Val Pro
            500                 505                 510

Trp Pro Asn Ala Ser Leu Thr Pro Lys Trp Asn Asn Glu Thr Thr Gln
        515                 520                 525

Pro Gln Ile Ala Asn Cys Ser Val Tyr Asp Phe Phe Val Trp Leu His
    530                 535                 540

Tyr Tyr Ser Val Arg Asp Thr Leu Trp Pro Arg Val Thr Tyr His Met
545                 550                 555                 560

Asn Lys Tyr Ala Tyr His Met Leu Glu Arg Arg Ala Lys Tyr Lys Arg
                565                 570                 575

Gly Pro Gly Pro Gly Ala Lys Phe Val Ala Ala Trp Thr Leu Lys Ala
            580                 585                 590

Ala Ala Gly Pro Gly Pro Gly Gln Tyr Ile Lys Ala Asn Ser Lys Phe
        595                 600                 605

Ile Gly Ile Thr Glu Leu Gly Pro Gly Pro Gly
    610                 615
```

<210> SEQ ID NO 34
<211> LENGTH: 1638
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 34

```
atggccggga tgttccaggc actgtccgaa ggctgcacac cctatgatat taaccagatg      60
ctgaatgtcc tgggagacca ccaggtctct ggcctggagc agctggagag catcatcaac     120
ttcgagaagc tgaccgagtg acaagctcc aatgtgatgc ctatcctgtc cccactgacc      180
aagggcatcc tgggcttcgt gtttaccctg acagtgcctt ctgagcgggg cctgtcttgc     240
atcagcgagg cagacgcaac cacaccagag tccgccaatc tgggcgagga gatcctgtct     300
cagctgtacc tgtggccccg ggtgacatat cactccccctt cttacgccta tcaccagttc    360
gagcggagag ccaagtacaa gagacacttc ccaggctttg ccagtctct gctgttcggc      420
taccccgtgt acgtgttcgg cgattgcgtg cagggcgact gggatgccat ccggtttaga     480
tactgcgcac cacctggata tgcactgctg aggtgtaacg acaccaatta ttccgccctg     540
ctggcagtgg gcgccctgga gggccctcgc aatcaggatt ggctgggcgt gccaaggcag     600
ctggtgacac gcatgcaggc catccagaac gcaggcctgt gcaccctggt ggcaatgctg     660
gaggagacaa tcttctggct gcaggccttt ctgatggccc tgaccgacag cggccccaag     720
acaaacatca tcgtggattc ccagtacgtg atgggcatct ccaagccttc tttccaggag     780
tttgtggact gggagaacgt gagcccagag ctgaattcca ccgatcagcc attctggcag     840
gcaggaatcc tggcaaggaa cctggtgcct atggtggcca cagtgcaggg ccagaatctg     900
aagtaccagg ccagagcct ggtcatcagc gcctccatca tcgtgtttaa cctgctggag      960
ctggagggcg actatcggga cgatggcaac gtgtgggtgc acacccccact gagccccaga    1020
acactgaacg cctgggtgaa ggccgtggag gagaagaagg gcatcccagt gcacctggag    1080
ctggcctcca tgaccaatat ggagctgatg tctagcatcg tgcaccagca ggtgaggaca    1140
tacgacccg tgttcatgtg cctgggaggc ctgctgacca tggtggcagg agccgtgtgg    1200
ctgacagtgc gggtgctgga gctgttcaga gccgcccagc tggccaacga tgtggtgctg    1260
cagatcatgg agctgtgcgg agcagccttt cgccaggtgt gccacaccac agtgccatgg    1320
cccaatgcct ccctgacccc caagtggaac aatgagacaa cacagcctca gatcgccaac    1380
tgtagcgtgt acgacttctt cgtgtggctg cactactata gcgtgaggga tacccctgtgg 1440
ccccgcgtga cataccacat gaataagtac gcctatcaca tgctggagag gcgcgccaag    1500
tataagagag gccctggccc aggcgcaaag tttgtggcag catggacct gaaggccgcc     1560
gccggccccg gccccggcca gtatatcaag gctaacagta agttcattgg aatcacagag    1620
ctgggacccg gacctgga                                                  1638
```

<210> SEQ ID NO 35
<211> LENGTH: 546
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 35

```
Met Ala Gly Met Phe Gln Ala Leu Ser Glu Gly Cys Thr Pro Tyr Asp
1               5                   10                  15
```

```
Ile Asn Gln Met Leu Asn Val Leu Gly Asp His Gln Val Ser Gly Leu
            20                  25                  30

Glu Gln Leu Glu Ser Ile Ile Asn Phe Glu Lys Leu Thr Glu Trp Thr
            35                  40                  45

Ser Ser Asn Val Met Pro Ile Leu Ser Pro Leu Thr Lys Gly Ile Leu
 50                  55                  60

Gly Phe Val Phe Thr Leu Thr Val Pro Ser Glu Arg Gly Leu Ser Cys
 65                  70                  75                  80

Ile Ser Glu Ala Asp Ala Thr Thr Pro Glu Ser Ala Asn Leu Gly Glu
            85                  90                  95

Glu Ile Leu Ser Gln Leu Tyr Leu Trp Pro Arg Val Thr Tyr His Ser
            100                 105                 110

Pro Ser Tyr Ala Tyr His Gln Phe Glu Arg Arg Ala Lys Tyr Lys Arg
            115                 120                 125

His Phe Pro Gly Phe Gly Gln Ser Leu Leu Phe Gly Tyr Pro Val Tyr
 130                 135                 140

Val Phe Gly Asp Cys Val Gln Gly Asp Trp Asp Ala Ile Arg Phe Arg
 145                 150                 155                 160

Tyr Cys Ala Pro Pro Gly Tyr Ala Leu Leu Arg Cys Asn Asp Thr Asn
            165                 170                 175

Tyr Ser Ala Leu Leu Ala Val Gly Ala Leu Glu Gly Pro Arg Asn Gln
            180                 185                 190

Asp Trp Leu Gly Val Pro Arg Gln Leu Val Thr Arg Met Gln Ala Ile
            195                 200                 205

Gln Asn Ala Gly Leu Cys Thr Leu Val Ala Met Leu Glu Glu Thr Ile
            210                 215                 220

Phe Trp Leu Gln Ala Phe Leu Met Ala Leu Thr Asp Ser Gly Pro Lys
 225                 230                 235                 240

Thr Asn Ile Ile Val Asp Ser Gln Tyr Val Met Gly Ile Ser Lys Pro
            245                 250                 255

Ser Phe Gln Glu Phe Val Asp Trp Glu Asn Val Ser Pro Glu Leu Asn
            260                 265                 270

Ser Thr Asp Gln Pro Phe Trp Gln Ala Gly Ile Leu Ala Arg Asn Leu
            275                 280                 285

Val Pro Met Val Ala Thr Val Gln Gly Gln Asn Leu Lys Tyr Gln Gly
 290                 295                 300

Gln Ser Leu Val Ile Ser Ala Ser Ile Ile Val Phe Asn Leu Leu Glu
 305                 310                 315                 320

Leu Glu Gly Asp Tyr Arg Asp Asp Gly Asn Val Trp Val His Thr Pro
            325                 330                 335

Leu Ser Pro Arg Thr Leu Asn Ala Trp Val Lys Ala Val Glu Glu Lys
            340                 345                 350

Lys Gly Ile Pro Val His Leu Glu Leu Ala Ser Met Thr Asn Met Glu
            355                 360                 365

Leu Met Ser Ser Ile Val His Gln Gln Val Arg Thr Tyr Gly Pro Val
            370                 375                 380

Phe Met Cys Leu Gly Gly Leu Leu Thr Met Val Ala Gly Ala Val Trp
 385                 390                 395                 400

Leu Thr Val Arg Val Leu Glu Leu Phe Arg Ala Ala Gln Leu Ala Asn
            405                 410                 415

Asp Val Val Leu Gln Ile Met Glu Leu Cys Gly Ala Ala Phe Arg Gln
            420                 425                 430
```

```
Val Cys His Thr Thr Val Pro Trp Pro Asn Ala Ser Leu Thr Pro Lys
        435                 440                 445

Trp Asn Asn Glu Thr Thr Gln Pro Gln Ile Ala Asn Cys Ser Val Tyr
    450                 455                 460

Asp Phe Phe Val Trp Leu His Tyr Tyr Ser Val Arg Asp Thr Leu Trp
465                 470                 475                 480

Pro Arg Val Thr Tyr His Met Asn Lys Tyr Ala Tyr His Met Leu Glu
                485                 490                 495

Arg Arg Ala Lys Tyr Lys Arg Gly Pro Gly Pro Gly Ala Lys Phe Val
                500                 505                 510

Ala Ala Trp Thr Leu Lys Ala Ala Ala Gly Pro Gly Pro Gly Gln Tyr
            515                 520                 525

Ile Lys Ala Asn Ser Lys Phe Ile Gly Ile Thr Glu Leu Gly Pro Gly
        530                 535                 540

Pro Gly
545

<210> SEQ ID NO 36
<211> LENGTH: 2019
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 36
gcccgggcat ttaaatgcga tcgcatcgat tacgactcta gaatagtcta gtccgcaggc     60
caccatgcag atcttcgtga agaccctgac cggcaagacc atcaccctag aggtggagcc    120
cagtgacacc atcgagaacg tgaaggccaa gatccaggat aaagagggca tccccctga    180 ccagcagagg ctgatctttg ccggcaagca gctggaagat ggccgcaccc tctctgatta    240
caacatccag aaggagtcaa ccctgcacct ggtccttcgc ctgagaggtg ccatgtttca    300
ggcgctgagc gaaggctgca ccccgtatga tattaaccag atgctgaacg tgctgggcga    360
tcatcagttt aagcacatca agcctttga ccggacattt gctaacaacc caggtcccat    420
ggttgtgttt gccacacctg gcctatcct gtctcctctg acaaagggca tcctgggctt    480
cgtgtttacc ctgaccgtgc cttctgagag aggacttagc tgcattagcg aagcggatgc    540
gaccaccccg gaaagcgcga acctgggcga agaaattctg agccagctgt atctttggcc    600
aagggtgacc taccattccc ctagttatgc ttaccaccaa tttgaaagac gagccaaata    660
taaaagacac ttccccggct ttggccagag cctgctgttt ggctaccctg tgtacgtgtt    720
cggcgattgc gtgcagggcg attgggatgc gattcgcttt cgctattgcg cgccgccggg    780
ctatgcgctg ctgcgctgca cgataccaa ctatagcgct ctgctggctg tgggggccct    840
agaaggaccc aggaatcagg actggcttgg tgtcccaaga caacttgtaa ctcggatgca    900
ggctattcag aatgccggcc tgtgtaccct ggtggccatg ctggaagaga caatcttctg    960
gctgcaagcg tttctgatgg cgctgaccga tagcggcccg aaaaccaaca ttattgtgga   1020
tagccagtat gtgatgggca ttagcaaacc gagctttcag gaatttgtgg attgggaaaa   1080
cgtgagcccg gaactgaaca gcaccgatca gccgttttgg caagccggaa tcctggccag   1140
aaatctggtg cctatggtgg ccacagtgca gggccagaac ctgaagtacc agggtcagtc   1200
actagtcatc tctgcttcta tcattgtctt caacctgctg gaactggaag gtgattatcg   1260
agatgatggc aacgtgtggg tgcataccc gctgagcccg cgcaccctga acgcgtgggt   1320
```

-continued

```
gaaagcggtg aagaaaaaa aaggtattcc agttcaccta gagctggcca gtatgaccaa    1380
catggagctc atgagcagta ttgtgcatca gcaggtcaga acatacggcc ccgtgttcat    1440
gtgtctcggc ggactgctta caatggtggc tggtgctgtg tggctgacag tgcgagtgct    1500
cgagctgttc cgggccgcgc agctggccaa cgacgtggtc ctccagatca tggagctttg    1560
tggtgcagcg tttcgccagg tgtgccatac caccgtgccg tggccgaacg cgagcctgac    1620
cccgaaatgg aacaacgaaa ccacccagcc ccagatcgcc aactgcagcg tgtatgactt    1680
ttttgtgtgg ctccattatt attctgttcg agacacactt tggccaaggg tgacctacca    1740
tatgaacaaa tatgcgtatc atatgctgga agacgagcc aaatataaaa gaggaccagg    1800
acctggcgct aaatttgtgg ccgcctggac actgaaagcc gctgctggtc ctggacctgg    1860
ccagtacatc aaggccaaca gcaagttcat cggcatcacc gaactcggac ccggaccagg    1920
ctgatgattt cgaaatttaa ataagcttgc ggccgctagg ataacaggg taattatcac    1980
gcccaaacat ttacagccgc ggtgtcaaaa accgcgtgg                           2019
```

<210> SEQ ID NO 37
<211> LENGTH: 619
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 37

```
Met Gln Ile Phe Val Lys Thr Leu Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Phe Ala Gly Lys
        35                  40                  45

Gln Leu Glu Asp Gly Arg Thr Leu Ser Asp Tyr Asn Ile Gln Lys Glu
    50                  55                  60

Ser Thr Leu His Leu Val Leu Arg Leu Arg Gly Ala Met Phe Gln Ala
65                  70                  75                  80

Leu Ser Glu Gly Cys Thr Pro Tyr Asp Ile Asn Gln Met Leu Asn Val
                85                  90                  95

Leu Gly Asp His Gln Phe Lys His Ile Lys Ala Phe Arg Thr Phe
            100                 105                 110

Ala Asn Asn Pro Gly Pro Met Val Val Phe Ala Thr Pro Gly Pro Ile
        115                 120                 125

Leu Ser Pro Leu Thr Lys Gly Ile Leu Gly Phe Val Phe Thr Leu Thr
    130                 135                 140

Val Pro Ser Glu Arg Gly Leu Ser Cys Ile Ser Glu Ala Asp Ala Thr
145                 150                 155                 160

Thr Pro Glu Ser Ala Asn Leu Gly Glu Glu Ile Leu Ser Gln Leu Tyr
                165                 170                 175

Leu Trp Pro Arg Val Thr Tyr His Ser Pro Ser Tyr Ala Tyr His Gln
            180                 185                 190

Phe Glu Arg Arg Ala Lys Tyr Lys Arg His Phe Pro Gly Phe Gly Gln
        195                 200                 205

Ser Leu Leu Phe Gly Tyr Pro Val Tyr Val Phe Gly Asp Cys Val Gln
    210                 215                 220

Gly Asp Trp Asp Ala Ile Arg Phe Arg Tyr Cys Ala Pro Pro Gly Tyr
225                 230                 235                 240
```

Ala Leu Leu Arg Cys Asn Asp Thr Asn Tyr Ser Ala Leu Leu Ala Val
             245                 250                 255

Gly Ala Leu Glu Gly Pro Arg Asn Gln Asp Trp Leu Gly Val Pro Arg
            260                 265                 270

Gln Leu Val Thr Arg Met Gln Ala Ile Gln Asn Ala Gly Leu Cys Thr
        275                 280                 285

Leu Val Ala Met Leu Glu Glu Thr Ile Phe Trp Leu Gln Ala Phe Leu
    290                 295                 300

Met Ala Leu Thr Asp Ser Gly Pro Lys Thr Asn Ile Ile Val Asp Ser
305                 310                 315                 320

Gln Tyr Val Met Gly Ile Ser Lys Pro Ser Phe Gln Glu Phe Val Asp
                325                 330                 335

Trp Glu Asn Val Ser Pro Glu Leu Asn Ser Thr Asp Gln Pro Phe Trp
            340                 345                 350

Gln Ala Gly Ile Leu Ala Arg Asn Leu Val Pro Met Val Ala Thr Val
        355                 360                 365

Gln Gly Gln Asn Leu Lys Tyr Gln Gly Gln Ser Leu Val Ile Ser Ala
    370                 375                 380

Ser Ile Ile Val Phe Asn Leu Leu Glu Leu Glu Gly Asp Tyr Arg Asp
385                 390                 395                 400

Asp Gly Asn Val Trp Val His Thr Pro Leu Ser Pro Arg Thr Leu Asn
                405                 410                 415

Ala Trp Val Lys Ala Val Glu Glu Lys Lys Gly Ile Pro Val His Leu
            420                 425                 430

Glu Leu Ala Ser Met Thr Asn Met Glu Leu Met Ser Ser Ile Val His
        435                 440                 445

Gln Gln Val Arg Thr Tyr Gly Pro Val Phe Met Cys Leu Gly Gly Leu
    450                 455                 460

Leu Thr Met Val Ala Gly Ala Val Trp Leu Thr Val Arg Val Leu Glu
465                 470                 475                 480

Leu Phe Arg Ala Ala Gln Leu Ala Asn Asp Val Val Leu Gln Ile Met
                485                 490                 495

Glu Leu Cys Gly Ala Ala Phe Arg Gln Val Cys His Thr Thr Val Pro
            500                 505                 510

Trp Pro Asn Ala Ser Leu Thr Pro Lys Trp Asn Asn Glu Thr Thr Gln
        515                 520                 525

Pro Gln Ile Ala Asn Cys Ser Val Tyr Asp Phe Phe Val Trp Leu His
    530                 535                 540

Tyr Tyr Ser Val Arg Asp Thr Leu Trp Pro Arg Val Thr Tyr His Met
545                 550                 555                 560

Asn Lys Tyr Ala Tyr His Met Leu Glu Arg Arg Ala Lys Tyr Lys Arg
                565                 570                 575

Gly Pro Gly Pro Gly Ala Lys Phe Val Ala Ala Trp Thr Leu Lys Ala
            580                 585                 590

Ala Ala Gly Pro Gly Pro Gly Gln Tyr Ile Lys Ala Asn Ser Lys Phe
        595                 600                 605

Ile Gly Ile Thr Glu Leu Gly Pro Gly Pro Gly
    610                 615

<210> SEQ ID NO 38
<211> LENGTH: 228
<212> TYPE: DNA
<213> ORGANISM: Artificial Sequence
<220> FEATURE:

<223> OTHER INFORMATION: Description of Artificial Sequence: Synthetic
      polynucleotide

<400> SEQUENCE: 38

```
atgcagatct tcgtgaagac cctgaccggc aagaccatca ccctagaggt ggagcccagt    60
gacaccatcg agaacgtgaa ggccaagatc caggataaag agggcatccc ccctgaccag   120
cagaggctga tctttgccgg caagcagctg aagatggcc gcaccctctc tgattacaac    180
atccagaagg agtcaaccct gcacctggtc cttcgcctga gaggtggc                228
```

<210> SEQ ID NO 39
<211> LENGTH: 228
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 39

```
atgcagatct tcgtgaagac cctgaccggc aagaccatca ccctagaggt ggagcccagt    60
gacaccatcg agaacgtgaa ggccaagatc caggataaag agggcatccc ccctgaccag   120
cagaggctga tctttgccgg caagcagctg aagatggcc gcaccctctc tgattacaac    180
atccagaagg agtcaaccct gcacctggtc cttcgcctga gaggtgcc                228
```

<210> SEQ ID NO 40
<211> LENGTH: 78
<212> TYPE: DNA
<213> ORGANISM: Homo sapiens

<400> SEQUENCE: 40

```
atggccgtca tggcgcccg aaccctcgtc ctgctactct cggggggctct ggccctgacc    60
cagacctggg cgggctct                                                  78
```

<210> SEQ ID NO 41
<211> LENGTH: 201
<212> TYPE: DNA
<213> ORGANISM: Homo sapiens

<400> SEQUENCE: 41

```
ccgtcttccc agcccaccat ccccatcgtg ggcatcattg ctggcctggt tctctttgga    60
gctgtgatca ctggagctgt ggtcgctgct gtgatgtgga ggaggaagag ctcagataga   120
aaaggaggga gctactctca ggctgcaagc agtgacagtg cccagggctc tgatgtgtct   180
ctcacagctt gtaaagtgtg a                                             201
```

<210> SEQ ID NO 42
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 42

```
atggagaccg atacactgct gctgtgggtg ctgctcctgt gggtgccagg aagcacaggc    60
```

<210> SEQ ID NO 43
<211> LENGTH: 3178
<212> TYPE: DNA
<213> ORGANISM: Homo sapiens

```
<400> SEQUENCE: 43
ggcaccgatt cggggcctgc ccggacttcg ccgcacgctg cagaacctcg cccagcgccc      60
accatgcccc ggcagctcag cgcggcggcc gcgctcttcg cgtccctggc cgtaattttg     120
cacgatggca gtcaaatgag agcaaaagca tttccagaaa ccagagatta ttctcaacct     180
actgcagcag caacagtaca ggacataaaa aaacctgtcc agcaaccagc taagcaagca     240
cctcaccaaa ctttagcagc aagattcatg gatggtcata tcacctttca aacagcggcc     300
acagtaaaaa ttccaacaac taccccagca actacaaaaa acactgcaac caccagccca     360
attacctaca ccctggtcac aacccaggcc acacccaaca actcacacac agctcctcca     420
gttactgaag ttacagtcgg ccctagctta gccccttatt cactgccacc caccatcacc     480
ccaccagctc atacagctgg aaccagttca tcaaccgtca gccacacaac tgggaacacc     540
actcaaccca gtaaccagac cacccttcca gcaactttat cgatagcact gcacaaaagc     600
acaaccggtc agaagcctga tcaacccacc catgccccag gaacaacggc agctgcccac     660
aataccaccc gcacagctgc acctgcctcc acggttcctg gcccacccct tgcacctcag     720
ccatcgtcag tcaagactgg aatttatcag gttctaaacg gaagcagact ctgtataaaa     780
gcagagatgg ggatacagct gattgttcaa gacaaggagt cggttttttc acctcggaga     840
tacttcaaca tcgaccccaa cgcaacgcaa gcctctggga actgtggcac ccgaaaatcc     900
aaccttctgt tgaattttca gggcggattt gtgaatctca catttaccaa ggatgaagaa     960
tcatattata tcagtgaagt gggagcctat ttgaccgtct cagatccaga gacagtttac    1020
caaggaatca acatgcggt ggtgatgttc cagacagcag tcgggcattc cttcaagtgc    1080
gtgagtgaac agagcctcca gttgtcagcc cacctgcagg tgaaaacaac cgatgtccaa    1140
cttcaagcct ttgattttga agatgaccac tttggaaatg tggatgagtg ctcgtctgac    1200
tacacaattg tgcttcctgt gattgggggcc atcgtggttg gtctctgcct tatgggtatg    1260
ggtgtctata aaatccgcct aaggtgtcaa tcatctggat accagagaat ctaattgttg    1320
cccgggggga atgaaaataa tggaattag agaactcttt catcccttcc aggatggatg    1380
ttgggaaatt ccctcagagt gtgggtcctt caaacaatgt aaaccaccat cttctattca    1440
aatgaagtga gtcatgtgtg atttaagttc aggcagcaca tcaatttcta aatactttt    1500
gtttatttta tgaaagatat agtgagctgt ttattttcta gtttcctta gaatatttta    1560
gccactcaaa gtcaacattt gagatatgtt gaattaacat aatatatgta aagtagaata    1620
agccttcaaa ttataaacca agggtcaatt gtaactaata ctactgtgtg tgcattgaag    1680
attttatttt accttgatc ttaacaaagc ctttgctttg ttatcaaatg gactttcagt    1740
gcttttacta tctgtgtttt atggtttcat gtaacataca tattcctggt gtagcactta    1800
actccttttc cactttaaat ttgtttttgt ttttgagac ggagtttcac tcttgtcacc    1860
caggctggag tacagtggca cgatctcggc ttatggcaac ctccgcctcc cgggttcaag    1920
tgattctcct gcttcagctt cccgagtagc tgggattaca ggcacacact accacgcctg    1980
gctaattttt gtattttat tatagacggg tttcaccatg ttggccagac tggtcttgaa    2040
ctcttgacct caggtgatcc acccacctca gcctcccaaa gtgctgggat tacaggcatg    2100
agccattgcg cccggcctta aatgtttttt ttaatcatca aaaagaacaa catatctcag    2160
gttgtctaag tgtttttatg taaaccaac aaaaagaaca aatcagctta tattttttat    2220
cttgatgact cctgctccag aattgctaga ctaagaatta ggtggctaca gatggtagaa    2280
ctaaacaata agcaagagac aataataatg gcccttaatt attaacaaag tgccagagtc    2340
```

```
taggctaagc actttatcta tatctcattt cattctcaca acttataagt gaatgagtaa    2400
actgagactt aagggaactg aatcacttaa atgtcacctg gctaactgat ggcagagcca    2460
gagcttgaat tcatgttggt ctgacatcaa ggtctttggt cttctcccta caccaagtta    2520
cctacaagaa caatgacacc acactctgcc tgaaggctca cacctcatac cagcatacgc    2580
tcaccttaca gggaaatggg tttatccagg atcatgagac attagggtag atgaaaggag    2640
agctttgcag ataacaaaat agcctatcct taataaatcc tccactctct ggaaggagac    2700
tgagggcttt tgtaaaacat tagtcagttg ctcatttttta tgggattgct tagctgggct    2760
gtaaagatga aggcatcaaa taaactcaaa gtattttttaa atttttttga taatagagaa    2820
acttcgctaa ccaactgttc tttcttgagt gtatagcccc atcttgtggt aacttgctgc    2880
ttctgcactt catatccata tttcctattg ttcactttat tctgtagagc agcctgccaa    2940
gaattttatt tctgctgttt tttttgctgc taaagaaagg aactaagtca ggatgttaac    3000
agaaaagtcc ataaaccct agaattctta gtcaaggaat aattcaagtc agcctagaga    3060
ccatgttgac tttcctcatg tgtttcctta tgactcagta agttggcaag gtcctgactt    3120
tagtcttaat aaaacattga attgtagtaa aggttttttgc aataaaaact tactttgg     3178

<210> SEQ ID NO 44
<211> LENGTH: 1858
<212> TYPE: DNA
<213> ORGANISM: Mus sp.

<400> SEQUENCE: 44
attccggagg tgaaaaacaa tggcacaacg tgtataatgg ccagcttctc tgcctccttt      60
ctgaccacct acgagactgc gaatggttct cagatcgtga acatttccct gccagcctct     120
gcagaagtac tgaaaaatgg cagttcttgt ggtaaagaaa atgtttctga ccccagcctc     180
acaattactt ttggaagagg atatttactg acactcaact tcacaaaaaa tacaacacgt     240
tacagtgtcc agcatatgta ttttacatat aacttgtcag atacagaaca ttttcccaat     300
gccatcagca aagagatcta caccatggat tccacaactg acatcaaggc agacatcaac     360
aaagcatacc ggtgtgtcag tgatatccgg gtctacatga agaatgtgac cgttgtgctc     420
cgggatgcca ctatccaggc ctacctgtcg agtggcaact tcagcaagga agagacacac     480
tgcacacagg atggaccttc cccaaccact gggccaccca gccccctcacc accacttgtg    540 cccacaaacc ccactgtatc caagtacaat gttactggta acaacggaac ctgcctgctg    600
gcctctatgg cactgcaact gaatatcacc tacctgaaaa aggacaacaa gacggtgacc    660
agagcgttca acatcagccc aaatgacaca tctagtggga gttgcggtat caacttggtg    720
accctgaaag tggagaacaa gaacagagcc ctggaattgc agtttgggat gaatgccagc    780
tctagcctgt tttcttgca aggagtgcgc ttgaatatga ctcttcctga tgccctagtg    840
cccacattca gcatctccaa ccattcactg aaagctcttc aggccactgt gggaaactca    900
tacaagtgca acactgagga acacatcttt gtcagcaaga tgctctccct caatgtcttc    960
agtgtgcagg tccaggcttt caaggtggac agtgacaggt ttgggtctgt ggaagagtgt   1020
gttcaggatg gtaacaacat gttgatcccc attgctgtgg gcggtgccct ggcagggctg   1080
atcctcatcg tcctcattgc ctacctcatt ggcaggaaga ggagtcacgc cggctatcag   1140
accatctagc ctggtgggca ggtgcaccag agatgcacag gggcctgttc tcacatcccc   1200
aagcttagat aggtgtggaa gggaggcaca ctttctggca aactgtttta aaatctgctt   1260
```

| tatcaaatgt gaagttcatc ttgcaacatt tactatgcac aaaggaataa ctattgaaat | 1320 |
| gacggtgtta attttgctaa ctgggttaaa tattgatgag aaggctccac tgatttgact | 1380 |
| tttaagactt ggtgtttggt tcttcattct tttactcaga tttaagccta tcaaagggat | 1440 |
| actctggtcc agaccttggc ctggcaaggg tggctgatgg ttaggctgca cacacttaag | 1500 |
| aagcaacggg agcagggaag gcttgcacac aggcacgcac agggtcaacc tctggacact | 1560 |
| tggcttgggc tacctggcct tggggggggct gaactctggc atctggctgg gtacacaccc | 1620 |
| ccccaatttc tgtgctctgc cacccgtgag ctgccacttt cctaaataga aaatggcatt | 1680 |
| attttttattt acttttttgt aaagtgattt ccagtcttgt gttggcgttc agggtggccc | 1740 |
| tgtctctgca ctgtgtacaa taatagattc acactgctga cgtgtcttgc agcgtaggtg | 1800 |
| ggttgtacac tgggcatcag ctcacgtaat gcattgcctg taacgatgct aataaaaa | 1858 |

<210> SEQ ID NO 45
<211> LENGTH: 2339
<212> TYPE: DNA
<213> ORGANISM: Homo sapiens

<400> SEQUENCE: 45

| ggcccaaccg ccgcccgcgc ccccgctctc cgcaccgtac ccggccgcct cgcgccatgg | 60 |
| cggcccccgg cagcgcccgg cgaccccctgc tgctgctact gctgttgctg ctgctcggcc | 120 |
| tcatgcattg tgcgtcagca gcaatgttta tggtgaaaaa tggcaacggg accgcgtgca | 180 |
| taatggccaa cttctctgct gccttctcag tgaactacga caccaagagt ggccctaaga | 240 |
| acatgacctt tgacctgcca tcagatgcca cagtggtgct caaccgcagc tcctgtggaa | 300 |
| aagagaacac ttctgacccc agtctcgtga ttgcttttgg aagaggacat acactcactc | 360 |
| tcaatttcac gagaaatgca acacgttaca gcgtccagct catgagtttt gtttataact | 420 |
| tgtcagacac acaccttttc cccaatgcga gctccaaaga aatcaagact gtggaatcta | 480 |
| taactgacat cagggcagat atagataaaa aatacagatg tgttagtggc acccaggtcc | 540 |
| acatgaacaa cgtgaccgta acgctccatg atgccaccat ccaggcgtac ctttccaaca | 600 |
| gcagcttcag caggggagag acacgctgtg aacaagacag gccttcccca accacagcgc | 660 |
| cccctgcgcc acccagcccc tcgccctcac ccgtgcccaa gagcccctct gtggacaagt | 720 |
| acaacgtgag cggcaccaac gggacctgcc tgctggccag catggggctg cagctgaacc | 780 |
| tcacctatga gaggaaggac aacacgacgg tgacaaggct tctcaacatc aaccccaaca | 840 |
| agacctcggc cagcgggagc tgcggcgccc acctggtgac tctggagctg cacagcgagg | 900 |
| gcaccaccgt cctgctcttc cagttcggga tgaatgcaag ttctagccgg ttttttcctac | 960 |
| aaggaatcca gttgaataca attcttcctg acgccagaga ccctgccttt aaagctgcca | 1020 |
| acggctccct gcgagcgctg caggccacag tcggcaattc ctacaagtgc aacgcggagg | 1080 |
| agcacgtccg tgtcacgaag gcgttttcag tcaatatatt caaagtgtgg gtccaggctt | 1140 |
| tcaaggtgga aggtggccag tttggctctg tggaggagtg tctgctggac agaaacagca | 1200 |
| tgctgatccc catcgctgtg ggtggtgccc tggcggggct ggtcctcatc gtcctcatcg | 1260 |
| cctacctcgt cggcaggaag aggagtcacg caggctacca gactatctag cctggtgcac | 1320 |
| gcaggcacag cagctgcagg ggcctctgtt cctttctctg ggcttagggt cctgtcgaag | 1380 |
| gggaggcaca cttctctgca aacgtttctc aaatctgctt catccaatgt gaagttcatc | 1440 |
| ttgcagcatt tactatgcac aacagagtaa ctatcgaaat gacggtgtta attttgctaa | 1500 |
| ctgggttaaa tattttgcta actggttaaa cattaatatt taccaaagta ggattttgag | 1560 |

```
ggtgggggtg ctctctctga gggggtgggg gtgccgctgt ctctgagggg tgggggtgcc   1620
gctgtctctg aggggtgggg gtgccgctct ctctgagggg gtgggggtgc cgctttctct   1680 gaggggtgg  gggtgccgct ctctctgagg gggtgggggt gctgctctct ccgaggggtg   1740
gaatgccgct gtctctgagg ggtgggggtg ccgctctaaa ttggctccat atcatttgag   1800
tttagggttc tggtgtttgg tttcttcatt ctttactgca ctcagattta agccttacaa   1860
agggaaagcc tctggccgtc acacgtagga cgcatgaagg tcactcgtgg tgaggctgac   1920
atgctcacac attacaacag tagagaggga aaatcctaag acagaggaac tccagagatg   1980
agtgtctgga gcgcttcagt tcagctttaa aggccaggac gggccacacg tggctggcgg   2040
cctcgttcca gtggcggcac gtccttgggc gtctctaatg tctgcagctc aagggctggc   2100
acttttttaa atataaaaat gggtgttatt tttatttttt tttgtaaagt gattttggt    2160 cttctgttga cattcggggt gatcctgttc tgcgctgtgt acaatgtgag atcggtgcgt   2220
tctcctgatg ttttgccgtg gcttgggat tgtacacggg accagctcac gtaatgcatt    2280
gcctgtaaca atgtaataaa agcctctttt cttttaaaaa aaaaaaaaaa aaaaaaaa     2339
```

<210> SEQ ID NO 46
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 46
cagtacatca aggccaacag caagttcatc ggcatcaccg aactc             45

<210> SEQ ID NO 47
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Gln Tyr Ile Lys Ala Asn Ser Lys Phe Ile Gly Ile Thr Glu Leu
1               5                   10                  15

<210> SEQ ID NO 48
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 48
gctaaatttg tggctgcctg gacactgaaa gccgccgct                 39

<210> SEQ ID NO 49
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Ala Lys Phe Val Ala Ala Trp Thr Leu Lys Ala Ala Ala

<210> SEQ ID NO 50
<211> LENGTH: 593
<212> TYPE: DNA
<213> ORGANISM: Woodchuck hepatitis virus

<400> SEQUENCE: 50

```
aatcaacctc tggattacaa aatttgtgaa agattgactg gtattcttaa ctatgttgct    60
ccttttacgc tatgtggata cgctgcttta atgcctttgt atcatgctat tgcttcccgt   120
atggctttca ttttctcctc cttgtataaa tcctggttgc tgtctcttta tgaggagttg   180
tggcccgttg tcaggcaacg tggcgtggtg tgcactgtgt ttgctgacgc aacccccact   240
ggttggggca ttgccaccac ctgtcagctc ctttccggga cttttcgcttt ccccctccct  300
attgccacgg cggaactcat cgccgcctgc cttgcccgct gctggacagg ggctcggctg   360
ttgggcactg acaattccgt ggtgttgtcg gggaagctga cgtcctttcc atggctgctc   420
gcctgtgttg ccacctggat tctgcgcggg acgtccttct gctacgtccc ttcggccctc   480
aatccagcgg accttccttc ccgcggcctg ctgccggctc tgcggcctct tccgcgtctt   540
cgccttcgcc ctcagacgag tcggatctcc ctttgggccg cctccccgcc tgt           593
```

<210> SEQ ID NO 51
<211> LENGTH: 589
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 51

```
tctccccccc cccctctcc ctccccccc cctaacgtta ctggccgaag ccgcttggaa     60
taaggccggt gtgcgtttgt ctatatgtta ttttccacca tattgccgtc ttttggcaat   120
gtgagggccc ggaaacctgg ccctgtcttc ttgacgagca ttcctagggg tctttcccct   180
ctcgccaaag gaatgcaagg tctgttgaat gtcgtgaagg aagcagttcc tctggaagct   240
tcttgaagac aaacaacgtc tgtagcgacc ttttgcaggc agcggaaccc cccacctggc   300
gacaggtgcc tctgcggcca aaagccacgt gtataagata cacctgcaaa ggcggcacaa   360
ccccagtgcc acgttgtgag ttggatagtt gtggaaagag tcaaatggct ctcctcaagc   420
gtattcaaca aggggctgaa ggatgcccag aaggtacccc attgtatggg atctgatctg   480
gggcctcggt gcacatgctt tacatgtgtt tagtcgaggt taaaaaaacg tctaggcccc   540
ccgaaccacg gggacgtggt tttcctttga aaaacacgat gataatatg               589
```

<210> SEQ ID NO 52
<211> LENGTH: 720
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 52

```
atggtgagca agggcgagga gctgttcacc ggggtggtgc ccatcctggt cgagctggac    60
ggcgacgtaa acggccacaa gttcagcgtg tccggcgagg gcgagggcga tgccacctac   120
ggcaagctga ccctgaagtt catctgcacc accggcaagc tgcccgtgcc ctggcccacc   180
ctcgtgacca ccctgaccta cggcgtgcag tgcttcagcc gctaccccga ccacatgaag   240
```

```
cagcacgact tcttcaagtc cgccatgccc gaaggctacg tccaggagcg caccatcttc    300
ttcaaggacg acggcaacta caagacccgc gccgaggtga agttcgaggg cgacaccctg    360
gtgaaccgca tcgagctgaa gggcatcgac ttcaaggagg acggcaacat cctggggcac    420
aagctggagt acaactacaa cagccacaac gtctatatca tggccgacaa gcagaagaac    480
ggcatcaagg tgaacttcaa gatccgccac aacatcgagg acggcagcgt gcagctcgcc    540
gaccactacc agcagaacac ccccatcggc gacggccccg tgctgctgcc cgacaaccac    600
tacctgagca cccagtccgc cctgagcaaa gaccccaacg agaagcgcga tcacatggtc    660
ctgctggagt tcgtgaccgc cgccgggatc actctcggca tggacgagct gtacaagtag    720

<210> SEQ ID NO 53
<211> LENGTH: 1563
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 53
atgctgctgc tgctgctgct gctgggcctg aggctacagc tctccctggg catcatccca     60
gttgaggagg agaacccgga cttctggaac cgcgaggcag ccgaggccct gggtgccgcc    120
aagaagctgc agcctgcaca gacagccgcc aagaacctca tcatcttcct gggcgatggg    180
atgggggtgt ctacggtgac agctgccagg atcctaaaag gcagaagaa ggacaaactg    240 gggcctgaga taccctggc catggaccgc ttcccatatg tggctctgtc caagacatac    300
aatgtagaca acatgtgcc agacagtgga gccacagcca cggcctacct gtgcggggtc    360
aagggcaact tccagaccat tggcttgagt gcagccgccc gctttaacca gtgcaacacg    420
acacgcggca acgaggtcat ctccgtgatg aatcgggcca agaaagcagg gaagtcagtg    480
ggagtggtaa ccaccacacg agtgcagcac gcctcgccag ccggcaccta cgcccacacg    540
gtgaaccgca actggtactc ggacgccgac gtgcctgcct cggcccgcca ggaggggtgc    600
caggacatcg ctacgcagct catctccaac atggacattg acgtgatcct aggtggaggc    660
cgaaagtaca tgtttcgcat gggaacccca gaccctgagt acccagatga ctacagccaa    720
ggtgggacca ggctggacgg gaagaatctg gtgcaggaat ggctggcgaa cgccagggt    780 gcccggtatg tgtggaaccg cactgagctc atgcaggctt ccctggaccc gtctgtgacc    840
catctcatgg gtctctttga gcctggagac atgaaatacg agatccaccg agactccaca    900
ctggacccct ccctgatgga gatgacagag gctgccctgc gcctgctgag caggaacccc    960
cgcggcttct tcctcttcgt ggaggtggt cgcatcgacc atggtcatca tgaaagcagg   1020
gcttaccggg cactgactga gacgatcatg ttcgacgacg ccattgagag gcgggccag    1080 ctcaccagcg aggaggacac gctgagcctc gtcactgccg accactccca cgtcttctcc   1140
ttcggaggct acccctgcg agggagctcc atcttcgggc tggcccctgg caaggcccgg   1200
gacaggaagg cctacacggt cctcctatac ggaaacggtc caggctatgt gctcaaggac    1260 ggcgccggc cggatgttac cgagagcgag agcgggagcc ccgagtatcg gcagcagtca   1320
gcagtgcccc tggacgaaga gacccacgca ggcgaggacg tggcggtgtt cgcgcgcggc    1380
ccgcaggcgc acctggttca cggcgtgcag gagcagacct tcatagcgca cgtcatggcc    1440
ttcgccgcct gcctggagcc ctacaccgcc tgcgacctgg cgccccgc cggcaccacc    1500 gacgccgcgc acccggggtta ctctagagtc ggggcggccg gccgcttcga gcagacatga   1560
```

```
taa                                                              1563

<210> SEQ ID NO 54
<211> LENGTH: 1653
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 54
atggaagatg ccaaaaacat taagaagggc ccagcgccat tctacccact cgaagacggg      60
accgccggcg agcagctgca caaagccatg aagcgctacg ccctggtgcc cggcaccatc     120
gcctttaccg acgcacatat cgaggtggac attacctacg ccgagtactt cgagatgagc     180
gttcggctgg cagaagctat gaagcgctat gggctgaata caaaccatcg gatcgtggtg     240
tgcagcgaga atagcttgca gttcttcatg cccgtgttgg gtgccctgtt catcggtgtg     300
gctgtggccc cagctaacga catctacaac gagcgcgagc tgctgaacag catgggcatc     360
agccagccca ccgtcgtatt cgtgagcaag aaagggctgc aaaagatcct caacgtgcaa     420
aagaagctac cgatcataca aaagatcatc atcatggata gcaagaccga ctaccagggc     480
ttccaaagca tgtacacctt cgtgacttcc catttgccac ccggcttcaa cgagtacgac     540
ttcgtgcccg agagcttcga ccgggacaaa accatcgccc tgatcatgaa cagtagtggc     600
agtaccggat tgcccaaggg cgtagcccta ccgcaccgca ccgcttgtgt ccgattcagt     660
catgcccgcg accccatctt cggcaaccag atcatccccg acaccgctat cctcagcgtg     720
gtgccatttc accacggctt cggcatgttc accacgctgg gctacttgat ctgcggcttt     780
cgggtcgtgc tcatgtaccg cttcgaggag gagctattct tgcgcagctt gcaagactat     840
aagattcaat ctgccctgct ggtgcccaca ctatttagct tcttcgctaa gagcactctc     900
atcgacaagt acgacctaag caacttgcac gagatcgcca gcggcgggc gccgctcagc     960
aaggaggtag gtgaggccgt ggccaaacgc ttccacctac caggcatccg ccagggctac    1020
ggcctgacag aaacaaccag cgccattctg atcacccccg aaggggacga caagcctggc    1080
gcagtaggca aggtggtgcc cttcttcgag gctaaggtgg tggacttgga caccggtaag    1140
acactgggtg tgaaccagcg cggcgagctg tgcgtccgtg gccccatgat catgagcggc    1200
tacgttaaca cccccgaggc tacaaacgct ctcatcgaca aggacggctg gctgcacagc    1260
ggcgacatcg cctactggga cgaggacgag cacttcttca tcgtggaccg gctgaagagc    1320
ctgatcaaat acaagggcta ccaggtagcc ccagccgaac tggagagcat cctgctgcaa    1380
cacccccaaca tcttcgacgc cggggtcgcc ggcctgcccg acgacgatgc cggcgagctg    1440
cccgccgcag tcgtcgtgct ggaacacggt aaaaccatga ccgagaagga gatcgtggac    1500
tatgtggcca gccaggttac aaccgccaag aagctgcgcg gtggtgttgt gttcgtggac    1560
gaggtgccta aggactgac cggcaagttg acgcccgca agatccgcga gattctcatt    1620
aaggccaaga agggcggcaa gatcgccgtg taa                                 1653

<210> SEQ ID NO 55
<211> LENGTH: 66
<212> TYPE: DNA
<213> ORGANISM: Foot-and-mouth disease virus

<400> SEQUENCE: 55
gtaaagcaaa cactgaactt tgaccttctc aagttggctg agacgttga gtccaatcct      60
``` gggccc                                                                66

<210> SEQ ID NO 56
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Gly Pro Gly Pro Gly
1               5

<210> SEQ ID NO 57
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Ser Ile Ile Asn Phe Glu Lys Leu
1               5

<210> SEQ ID NO 58
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Ser Pro Ser Tyr Ala Tyr His Gln Phe
1               5

<210> SEQ ID NO 59
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

Tyr Val Tyr Val Ala Asp Val Ala Ala Lys
1               5                   10

<210> SEQ ID NO 60
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

Tyr Glu Met Phe Asn Asp Lys Ser
1               5

<210> SEQ ID NO 61
<211> LENGTH: 17
<212> TYPE: PRT
<213> ORGANISM: Artificial Sequence
<220> FEATURE:

```
<223> OTHER INFORMATION: Description of Artificial Sequence: Synthetic
      peptide

<400> SEQUENCE: 61

Tyr Glu Met Phe Asn Asp Lys Ser Gln Arg Ala Pro Asp Asp Lys Met
1               5                   10                  15
Phe

<210> SEQ ID NO 62
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

Tyr Glu Met Phe Asn Asp Lys Ser Phe
1               5

<210> SEQ ID NO 63
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Pyrrolysine
<220> FEATURE:
<221> NAME/KEY: MOD_RES
<222> LOCATION: (11)..(11)
<223> OTHER INFORMATION: Ile or Leu

<400> SEQUENCE: 63

His Arg Xaa Glu Ile Phe Ser His Asp Phe Xaa
1               5                   10

<210> SEQ ID NO 64
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Ile or Leu
<220> FEATURE:
<221> NAME/KEY: MOD_RES
<222> LOCATION: (5)..(5)
<223> OTHER INFORMATION: Ile or Leu
<220> FEATURE:
<221> NAME/KEY: MOD_RES
<222> LOCATION: (7)..(7)
<223> OTHER INFORMATION: Pyrrolysine

<400> SEQUENCE: 64

Phe Xaa Ile Glu Xaa Phe Xaa Glu Ser Ser
1               5                   10

<210> SEQ ID NO 65
<211> LENGTH: 10
<212> TYPE: PRT
<213> ORGANISM: Artificial Sequence
<220> FEATURE:
<223> OTHER INFORMATION: Description of Artificial Sequence: Synthetic
```

-continued

```
        peptide
<220> FEATURE:
<221> NAME/KEY: MOD_RES
<222> LOCATION: (4)..(4)
<223> OTHER INFORMATION: Pyrrolysine

<400> SEQUENCE: 65

Asn Glu Ile Xaa Arg Glu Ile Arg Glu Ile
1               5                  10

<210> SEQ ID NO 66
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Ile or Leu
<220> FEATURE:
<221> NAME/KEY: MOD_RES
<222> LOCATION: (11)..(11)
<223> OTHER INFORMATION: Ile or Leu
<220> FEATURE:
<221> NAME/KEY: MOD_RES
<222> LOCATION: (15)..(15)
<223> OTHER INFORMATION: Selenocysteine

<400> SEQUENCE: 66

Xaa Phe Lys Ser Ile Phe Glu Met Met Ser Xaa Asp Ser Ser Xaa
1               5                  10                  15

<210> SEQ ID NO 67
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (11)..(11)
<223> OTHER INFORMATION: Pyrrolysine

<400> SEQUENCE: 67

Lys Asn Phe Leu Glu Asn Phe Ile Glu Ser Xaa Phe Ile
1               5                  10

<210> SEQ ID NO 68
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Ile or Leu
<220> FEATURE:
<221> NAME/KEY: MOD_RES
<222> LOCATION: (11)..(11)
<223> OTHER INFORMATION: Ile or Leu
<220> FEATURE:
<221> NAME/KEY: MOD_RES
<222> LOCATION: (15)..(15)
<223> OTHER INFORMATION: Selenocysteine
<220> FEATURE:
<221> NAME/KEY: MOD_RES
<222> LOCATION: (21)..(21)
<223> OTHER INFORMATION: Ile or Leu
```

```
<220> FEATURE:
<221> NAME/KEY: MOD_RES
<222> LOCATION: (27)..(27)
<223> OTHER INFORMATION: Ile or Leu

<400> SEQUENCE: 68

Xaa Phe Lys Ser Ile Phe Glu Met Met Ser Xaa Asp Ser Ser Xaa Ile
1               5                   10                  15

Phe Leu Lys Ser Xaa Phe Ile Glu Ile Phe Xaa
            20                  25

<210> SEQ ID NO 69
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Pyrrolysine
<220> FEATURE:
<221> NAME/KEY: MOD_RES
<222> LOCATION: (14)..(14)
<223> OTHER INFORMATION: Ile or Leu

<400> SEQUENCE: 69

Phe Xaa Glu Ile Phe Asn Asp Lys Ser Leu Asp Lys Phe Xaa Ile
1               5                   10                  15

<210> SEQ ID NO 70
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Pyrrolysine

<400> SEQUENCE: 70

Gln Cys Glu Ile Xaa Trp Ala Arg Glu
1               5

<210> SEQ ID NO 71
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Selenocysteine

<400> SEQUENCE: 71

Phe Ile Glu Xaa His Phe Trp Ile
1               5

<210> SEQ ID NO 72
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
```

```
<220> FEATURE:
<221> NAME/KEY: MOD_RES
<222> LOCATION: (7)..(7)
<223> OTHER INFORMATION: Ile or Leu
<220> FEATURE:
<221> NAME/KEY: MOD_RES
<222> LOCATION: (10)..(10)
<223> OTHER INFORMATION: Selenocysteine
<220> FEATURE:
<221> NAME/KEY: MOD_RES
<222> LOCATION: (11)..(11)
<223> OTHER INFORMATION: Ile or Leu

<400> SEQUENCE: 72

Phe Glu Trp Arg His Arg Xaa Thr Arg Xaa Xaa Arg
1               5                   10

<210> SEQ ID NO 73
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Ile or Leu
<220> FEATURE:
<221> NAME/KEY: MOD_RES
<222> LOCATION: (5)..(5)
<223> OTHER INFORMATION: Pyrrolysine
<220> FEATURE:
<221> NAME/KEY: MOD_RES
<222> LOCATION: (8)..(8)
<223> OTHER INFORMATION: Ile or Leu

<400> SEQUENCE: 73

Gln Ile Glu Xaa Xaa Glu Ile Xaa Glu
1               5

<210> SEQ ID NO 74
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Ile or Leu
<220> FEATURE:
<221> NAME/KEY: MOD_RES
<222> LOCATION: (9)..(9)
<223> OTHER INFORMATION: Pyrrolysine
<220> FEATURE:
<221> NAME/KEY: MOD_RES
<222> LOCATION: (11)..(11)
<223> OTHER INFORMATION: Ile or Leu

<400> SEQUENCE: 74

Phe Xaa Glu Leu Phe Ile Ser Asx Xaa Ser Xaa Phe Ile Glu
1               5                   10

<210> SEQ ID NO 75
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
```

-continued

```
<221> NAME/KEY: MOD_RES
<222> LOCATION: (5)..(5)
<223> OTHER INFORMATION: Pyrrolysine
<220> FEATURE:
<221> NAME/KEY: MOD_RES
<222> LOCATION: (16)..(16)
<223> OTHER INFORMATION: Ile or Leu

<400> SEQUENCE: 75

Gln Cys Glu Ile Xaa Trp Ala Arg Glu Phe Leu Lys Glu Ile Gly Xaa
1               5                   10                  15

<210> SEQ ID NO 76
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Pyrrolysine
<220> FEATURE:
<221> NAME/KEY: MOD_RES
<222> LOCATION: (9)..(9)
<223> OTHER INFORMATION: Ile or Leu

<400> SEQUENCE: 76

Ile Glu Phe Arg Xaa Glu Ile Phe Xaa Glu Phe
1               5                   10

<210> SEQ ID NO 77
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Pyrrolysine
<220> FEATURE:
<221> NAME/KEY: MOD_RES
<222> LOCATION: (9)..(9)
<223> OTHER INFORMATION: Ile or Leu

<400> SEQUENCE: 77

Ile Glu Phe Arg Xaa Glu Ile Phe Xaa
1               5

<210> SEQ ID NO 78
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Pyrrolysine
<220> FEATURE:
<221> NAME/KEY: MOD_RES
<222> LOCATION: (8)..(8)
<223> OTHER INFORMATION: Ile or Leu

<400> SEQUENCE: 78

Glu Phe Arg Xaa Glu Ile Phe Xaa Glu
1               5
```

```
<210> SEQ ID NO 79
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Pyrrolysine
<220> FEATURE:
<221> NAME/KEY: MOD_RES
<222> LOCATION: (7)..(7)
<223> OTHER INFORMATION: Ile or Leu

<400> SEQUENCE: 79

Phe Arg Xaa Glu Ile Phe Xaa Glu Phe
1               5

<210> SEQ ID NO 80
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 80

Ser Ile Asn Phe Glu Lys Leu
1               5

<210> SEQ ID NO 81
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 81

Leu Leu Leu Leu Leu Val Val Val Val
1               5

<210> SEQ ID NO 82
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 82

Glu Lys Leu Ala Ala Tyr Leu Leu Leu
1               5

<210> SEQ ID NO 83
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 83

Lys Leu Ala Ala Tyr Leu Leu Leu Leu Leu
1               5                   10
```

```
<210> SEQ ID NO 84
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 84

Phe Glu Lys Leu Ala Ala Tyr Leu
1               5

<210> SEQ ID NO 85
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 85

Ala Ala Tyr Leu Leu Leu Leu Leu
1               5

<210> SEQ ID NO 86
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 86

Tyr Leu Leu Leu Leu Leu Val Val Val
1               5

<210> SEQ ID NO 87
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 87

Val Val Val Val Ala Ala Tyr Ser Ile Asn
1               5                   10

<210> SEQ ID NO 88
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 88

Val Val Val Val Ala Ala Tyr
1               5

<210> SEQ ID NO 89
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 89
```

Ala Tyr Ser Ile Asn Phe Glu Lys
1               5

<210> SEQ ID NO 90
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 90

Tyr Asn Tyr Ser Tyr Trp Ile Ser Ile Phe Ala His Thr Met Trp Tyr
1               5                   10                  15

Asn Ile Trp His Val Gln Trp Asn Lys
            20                  25

<210> SEQ ID NO 91
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 91

Ile Glu Ala Leu Pro Tyr Val Phe Leu Gln Asp Gln Phe Glu Leu Arg
1               5                   10                  15

Leu Leu Lys Gly Glu Gln Gly Asn Asn
            20                  25

<210> SEQ ID NO 92
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 92

Asp Ser Glu Glu Thr Asn Thr Asn Tyr Leu His Tyr Cys His Phe His
1               5                   10                  15

Trp Thr Trp Ala Gln Gln Thr Thr Val
            20                  25

<210> SEQ ID NO 93
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 93

Gly Met Leu Ser Gln Tyr Glu Leu Lys Asp Cys Ser Leu Gly Phe Ser
1               5                   10                  15

Trp Asn Asp Pro Ala Lys Tyr Leu Arg
            20                  25

<210> SEQ ID NO 94
<211> LENGTH: 25
<212> TYPE: PRT
<213> ORGANISM: Artificial Sequence
<220> FEATURE:
<223> OTHER INFORMATION: Description of Artificial Sequence: Synthetic peptide

<400> SEQUENCE: 94

Val Arg Ile Asp Lys Phe Leu Met Tyr Val Trp Tyr Ser Ala Pro Phe
1               5                   10                  15

Ser Ala Tyr Pro Leu Tyr Gln Asp Ala
            20                  25

<210> SEQ ID NO 95
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 95

Cys Val His Ile Tyr Asn Asn Tyr Pro Arg Met Leu Gly Ile Pro Phe
1               5                   10                  15

Ser Val Met Val Ser Gly Phe Ala Met
            20                  25

<210> SEQ ID NO 96
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 96

Phe Thr Phe Lys Gly Asn Ile Trp Ile Glu Met Ala Gly Gln Phe Glu
1               5                   10                  15

Arg Thr Trp Asn Tyr Pro Leu Ser Leu
            20                  25

<210> SEQ ID NO 97
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 97

Ala Asn Asp Asp Thr Pro Asp Phe Arg Lys Cys Tyr Ile Glu Asp His
1               5                   10                  15

Ser Phe Arg Phe Ser Gln Thr Met Asn
            20                  25

<210> SEQ ID NO 98
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 98

Ala Ala Gln Tyr Ile Ala Cys Met Val Asn Arg Gln Met Thr Ile Val
1               5                   10                  15

Tyr His Leu Thr Arg Trp Gly Met Lys
            20                  25

```
<210> SEQ ID NO 99
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 99

Lys Tyr Leu Lys Glu Phe Thr Gln Leu Leu Thr Phe Val Asp Cys Tyr
1               5                   10                  15

Met Trp Ile Thr Phe Cys Gly Pro Asp
            20                  25

<210> SEQ ID NO 100
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 100

Ala Met His Tyr Arg Thr Asp Ile His Gly Tyr Trp Ile Glu Tyr Arg
1               5                   10                  15

Gln Val Asp Asn Gln Met Trp Asn Thr
            20                  25

<210> SEQ ID NO 101
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 101

Thr His Val Asn Glu His Gln Leu Glu Ala Val Tyr Arg Phe His Gln
1               5                   10                  15

Val His Cys Arg Phe Pro Tyr Glu Asn
            20                  25

<210> SEQ ID NO 102
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 102

Gln Thr Phe Ser Glu Cys Leu Phe Phe His Cys Leu Lys Val Trp Asn
1               5                   10                  15

Asn Val Lys Tyr Ala Lys Ser Leu Lys
            20                  25

<210> SEQ ID NO 103
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 103

Ser Phe Ser Ser Trp His Tyr Lys Glu Ser His Ile Ala Leu Leu Met
```

```
                1               5                  10                 15
Ser Pro Lys Lys Asn His Asn Asn Thr
            20                  25

<210> SEQ ID NO 104
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 104

Ile Leu Asp Gly Ile Met Ser Arg Trp Glu Lys Val Cys Thr Arg Gln
1               5                   10                  15

Thr Arg Tyr Ser Tyr Cys Gln Cys Ala
            20                  25

<210> SEQ ID NO 105
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 105

Tyr Arg Ala Ala Gln Met Ser Lys Trp Pro Asn Lys Tyr Phe Asp Phe
1               5                   10                  15

Pro Glu Phe Met Ala Tyr Met Pro Ile
            20                  25

<210> SEQ ID NO 106
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 106

Pro Arg Pro Gly Met Pro Cys Gln His His Asn Thr His Gly Leu Asn
1               5                   10                  15

Asp Arg Gln Ala Phe Asp Asp Phe Val
            20                  25

<210> SEQ ID NO 107
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 107

His Asn Ile Ile Ser Asp Glu Thr Glu Val Trp Glu Gln Ala Pro His
1               5                   10                  15

Ile Thr Trp Val Tyr Met Trp Cys Arg
            20                  25

<210> SEQ ID NO 108
<211> LENGTH: 25
<212> TYPE: PRT
<213> ORGANISM: Artificial Sequence
<220> FEATURE:
```

```
<223> OTHER INFORMATION: Description of Artificial Sequence: Synthetic
      peptide

<400> SEQUENCE: 108

Ala Tyr Ser Trp Pro Val Val Pro Met Lys Trp Ile Pro Tyr Arg Ala
1               5                   10                  15

Leu Cys Ala Asn His Pro Pro Gly Thr
            20                  25

<210> SEQ ID NO 109
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 109

His Val Met Pro His Val Ala Met Asn Ile Cys Asn Trp Tyr Glu Phe
1               5                   10                  15

Leu Tyr Arg Ile Ser His Ile Gly Arg
            20                  25

<210> SEQ ID NO 110
<211> LENGTH: 484
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 110

Thr His Val Asn Glu His Gln Leu Glu Ala Val Tyr Arg Phe His Gln
1               5                   10                  15

Val His Cys Arg Phe Pro Tyr Glu Asn Ala Met His Tyr Gln Met Trp
            20                  25                  30

Asn Thr Tyr Arg Ala Ala Gln Met Ser Lys Trp Pro Asn Lys Tyr Phe
        35                  40                  45

Asp Phe Pro Glu Phe Met Ala Tyr Met Pro Ile Cys Val His Ile Tyr
    50                  55                  60

Asn Asn Tyr Pro Arg Met Leu Gly Ile Pro Phe Ser Val Met Val Ser
65                  70                  75                  80

Gly Phe Ala Met Ala Tyr Ser Trp Pro Val Val Pro Met Lys Trp Ile
                85                  90                  95

Pro Tyr Arg Ala Leu Cys Ala Asn His Pro Pro Gly Thr Ala Asn Asp
            100                 105                 110

Asp Thr Pro Asp Phe Arg Lys Cys Tyr Ile Glu Asp His Ser Phe Arg
        115                 120                 125

Phe Ser Gln Thr Met Asn Ile Glu Ala Leu Pro Tyr Val Phe Leu Gln
    130                 135                 140

Asp Gln Phe Glu Leu Arg Leu Lys Gly Glu Gln Gly Asn Asn Asp
145                 150                 155                 160

Ser Glu Glu Thr Asn Thr Asn Tyr Leu His Tyr Cys His Phe His Trp
                165                 170                 175

Thr Trp Ala Gln Gln Thr Val Ile Leu Asp Gly Ile Met Ser Arg
            180                 185                 190

Trp Glu Lys Val Cys Thr Arg Gln Thr Arg Tyr Ser Tyr Cys Gln Cys
        195                 200                 205

Ala Phe Thr Phe Lys Gly Asn Ile Trp Ile Glu Met Ala Gly Gln Phe
```

```
                210                 215                 220
Glu Arg Thr Trp Asn Tyr Pro Leu Ser Leu Ser Phe Ser Ser Trp His
225                 230                 235                 240

Tyr Lys Glu Ser His Ile Ala Leu Leu Met Ser Pro Lys Lys Asn His
                245                 250                 255

Asn Asn Thr Gln Thr Phe Ser Glu Cys Leu Phe Phe His Cys Leu Lys
            260                 265                 270

Val Trp Asn Asn Val Lys Tyr Ala Lys Ser Leu Lys His Val Met Pro
        275                 280                 285

His Val Ala Met Asn Ile Cys Asn Trp Tyr Glu Phe Leu Tyr Arg Ile
    290                 295                 300

Ser His Ile Gly Arg His Asn Ile Ile Ser Asp Glu Thr Glu Val Trp
305                 310                 315                 320

Glu Gln Ala Pro His Ile Thr Trp Val Tyr Met Trp Cys Arg Val Arg
                325                 330                 335

Ile Asp Lys Phe Leu Met Tyr Val Trp Tyr Ser Ala Pro Phe Ser Ala
            340                 345                 350

Tyr Pro Leu Tyr Gln Asp Ala Lys Tyr Leu Lys Glu Phe Thr Gln Leu
        355                 360                 365

Leu Thr Phe Val Asp Cys Tyr Met Trp Ile Thr Phe Cys Gly Pro Asp
    370                 375                 380

Ala Ala Gln Tyr Ile Ala Cys Met Val Asn Arg Gln Met Thr Ile Val
385                 390                 395                 400

Tyr His Leu Thr Arg Trp Gly Met Lys Tyr Asn Tyr Ser Tyr Trp Ile
                405                 410                 415

Ser Ile Phe Ala His Thr Met Trp Tyr Asn Ile Trp His Val Gln Trp
            420                 425                 430

Asn Lys Gly Met Leu Ser Gln Tyr Glu Leu Lys Asp Cys Ser Leu Gly
        435                 440                 445

Phe Ser Trp Asn Asp Pro Ala Lys Tyr Leu Arg Pro Arg Pro Gly Met
    450                 455                 460

Pro Cys Gln His His Asn Thr His Gly Leu Asn Asp Arg Gln Ala Phe
465                 470                 475                 480

Asp Asp Phe Val

<210> SEQ ID NO 111
<211> LENGTH: 484
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 111

Ile Glu Ala Leu Pro Tyr Val Phe Leu Gln Asp Gln Phe Glu Leu Arg
1               5                   10                  15

Leu Leu Lys Gly Glu Gln Gly Asn Asn Ile Leu Asp Gly Ile Met Ser
            20                  25                  30

Arg Trp Glu Lys Val Cys Thr Arg Gln Thr Arg Tyr Ser Tyr Cys Gln
        35                  40                  45

Cys Ala His Val Met Pro His Val Ala Met Asn Ile Cys Asn Trp Tyr
    50                  55                  60

Glu Phe Leu Tyr Arg Ile Ser His Ile Gly Arg Thr His Val Asn Glu
65                  70                  75                  80

His Gln Leu Glu Ala Val Tyr Arg Phe His Gln Val His Cys Arg Phe
```

```
                    85                  90                  95
Pro Tyr Glu Asn Phe Thr Phe Lys Gly Asn Ile Trp Ile Glu Met Ala
                100                 105                 110

Gly Gln Phe Glu Arg Thr Trp Asn Tyr Pro Leu Ser Leu Ala Met His
                115                 120                 125

Tyr Gln Met Trp Asn Thr Ser Phe Ser Ser Trp His Tyr Lys Glu Ser
                130                 135                 140

His Ile Ala Leu Leu Met Ser Pro Lys Asn His Asn Asn Thr Val
145                 150                 155                 160

Arg Ile Asp Lys Phe Leu Met Tyr Val Trp Tyr Ser Ala Pro Phe Ser
                165                 170                 175

Ala Tyr Pro Leu Tyr Gln Asp Ala Gln Thr Phe Ser Glu Cys Leu Phe
                180                 185                 190

Phe His Cys Leu Lys Val Trp Asn Asn Val Lys Tyr Ala Lys Ser Leu
                195                 200                 205

Lys Tyr Arg Ala Ala Gln Met Ser Lys Trp Pro Asn Lys Tyr Phe Asp
                210                 215                 220

Phe Pro Glu Phe Met Ala Tyr Met Pro Ile Ala Tyr Ser Trp Pro Val
225                 230                 235                 240

Val Pro Met Lys Trp Ile Pro Tyr Arg Ala Leu Cys Ala Asn His Pro
                245                 250                 255

Pro Gly Thr Cys Val His Ile Tyr Asn Asn Tyr Pro Arg Met Leu Gly
                260                 265                 270

Ile Pro Phe Ser Val Met Val Ser Gly Phe Ala Met His Asn Ile Ile
                275                 280                 285

Ser Asp Glu Thr Glu Val Trp Glu Gln Ala Pro His Ile Thr Trp Val
                290                 295                 300

Tyr Met Trp Cys Arg Ala Ala Gln Tyr Ile Ala Cys Met Val Asn Arg
305                 310                 315                 320

Gln Met Thr Ile Val Tyr His Leu Thr Arg Trp Gly Met Lys Tyr Asn
                325                 330                 335

Tyr Ser Tyr Trp Ile Ser Ile Phe Ala His Thr Met Trp Tyr Asn Ile
                340                 345                 350

Trp His Val Gln Trp Asn Lys Gly Met Leu Ser Gln Tyr Glu Leu Lys
                355                 360                 365

Asp Cys Ser Leu Gly Phe Ser Trp Asn Asp Pro Ala Lys Tyr Leu Arg
                370                 375                 380

Lys Tyr Leu Lys Glu Phe Thr Gln Leu Leu Thr Phe Val Asp Cys Tyr
385                 390                 395                 400

Met Trp Ile Thr Phe Cys Gly Pro Asp Ala Asn Asp Asp Thr Pro Asp
                405                 410                 415

Phe Arg Lys Cys Tyr Ile Glu Asp His Ser Phe Arg Phe Ser Gln Thr
                420                 425                 430

Met Asn Asp Ser Glu Glu Thr Asn Thr Asn Tyr Leu His Tyr Cys His
                435                 440                 445

Phe His Trp Thr Trp Ala Gln Gln Thr Thr Val Pro Arg Pro Gly Met
                450                 455                 460

Pro Cys Gln His His Asn Thr His Gly Leu Asn Asp Arg Gln Ala Phe
465                 470                 475                 480

Asp Asp Phe Val

<210> SEQ ID NO 112
<211> LENGTH: 25
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 112

Ser Ser Thr Pro Tyr Leu Tyr Tyr Gly Thr Ser Ser Val Ser Tyr Gln
1               5                   10                  15

Phe Pro Met Val Pro Gly Gly Asp Arg
            20                  25

<210> SEQ ID NO 113
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 113

Glu Met Ala Gly Lys Ile Asp Leu Leu Arg Asp Ser Tyr Ile Phe Gln
1               5                   10                  15

Leu Phe Trp Arg Glu Ala Ala Glu Pro
            20                  25

<210> SEQ ID NO 114
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 114

Ala Leu Lys Gln Arg Thr Trp Gln Ala Leu Ala His Lys Tyr Asn Ser
1               5                   10                  15

Gln Pro Ser Val Ser Leu Arg Asp Phe
            20                  25

<210> SEQ ID NO 115
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 115

Val Ser Ser His Ser Ser Gln Ala Thr Lys Asp Ser Ala Val Gly Leu
1               5                   10                  15

Lys Tyr Ser Ala Ser Thr Pro Val Arg
            20                  25

<210> SEQ ID NO 116
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 116

Lys Glu Ala Ile Asp Ala Trp Ala Pro Tyr Leu Pro Glu Tyr Ile Asp
1               5                   10                  15
```

His Val Ile Ser Pro Gly Val Thr Ser
            20                  25

<210> SEQ ID NO 117
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 117

Ser Pro Val Ile Thr Ala Pro Pro Ser Ser Pro Val Phe Asp Thr Ser
1               5                   10                  15

Asp Ile Arg Lys Glu Pro Met Asn Ile
            20                  25

<210> SEQ ID NO 118
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 118

Pro Ala Glu Val Ala Glu Gln Tyr Ser Glu Lys Leu Val Tyr Met Pro
1               5                   10                  15

His Thr Phe Phe Ile Gly Asp His Ala
            20                  25

<210> SEQ ID NO 119
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 119

Met Ala Asp Leu Asp Lys Leu Asn Ile His Ser Ile Ile Gln Arg Leu
1               5                   10                  15

Leu Glu Val Arg Gly Ser
            20

<210> SEQ ID NO 120
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 120

Ala Ala Ala Tyr Asn Glu Lys Ser Gly Arg Ile Thr Leu Leu Ser Leu
1               5                   10                  15

Leu Phe Gln Lys Val Phe Ala Gln Ile
            20                  25

<210> SEQ ID NO 121
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 121

Lys Ile Glu Glu Val Arg Asp Ala Met Glu Asn Glu Ile Arg Thr Gln
1               5                   10                  15

Leu Arg Arg Gln Ala Ala Ala His Thr
            20                  25

<210> SEQ ID NO 122
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 122

Asp Arg Gly His Tyr Val Leu Cys Asp Phe Gly Ser Thr Thr Asn Lys
1               5                   10                  15

Phe Gln Asn Pro Gln Thr Glu Gly Val
            20                  25

<210> SEQ ID NO 123
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 123

Gln Val Asp Asn Arg Lys Ala Glu Ala Glu Glu Ala Ile Lys Arg Leu
1               5                   10                  15

Ser Tyr Ile Ser Gln Lys Val Ser Asp
            20                  25

<210> SEQ ID NO 124
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 124

Cys Leu Ser Asp Ala Gly Val Arg Lys Met Thr Ala Ala Val Arg Val
1               5                   10                  15

Met Lys Arg Gly Leu Glu Asn Leu Thr
            20                  25

<210> SEQ ID NO 125
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 125

Leu Pro Pro Arg Ser Leu Pro Ser Asp Pro Phe Ser Gln Val Pro Ala
1               5                   10                  15

Ser Pro Gln Ser Gln Ser Ser Ser Gln
            20                  25

<210> SEQ ID NO 126
```

```
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 126

Glu Leu Val Leu Glu Asp Leu Gln Asp Gly Asp Val Lys Met Gly Gly
1               5                   10                  15

Ser Phe Arg Gly Ala Phe Ser Asn Ser
            20                  25

<210> SEQ ID NO 127
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 127

Val Thr Met Asp Gly Val Arg Glu Glu Asp Leu Ala Ser Phe Ser Leu
1               5                   10                  15

Arg Lys Arg Trp Glu Ser Glu Pro His
            20                  25

<210> SEQ ID NO 128
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 128

Ile Val Gly Val Met Phe Phe Glu Arg Ala Phe Asp Glu Gly Ala Asp
1               5                   10                  15

Ala Ile Tyr Asp His Ile Asn Glu Gly
            20                  25

<210> SEQ ID NO 129
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 129

Thr Val Thr Pro Thr Pro Thr Pro Thr Gly Thr Gln Ser Pro Thr Pro
1               5                   10                  15

Thr Pro Ile Thr Thr Thr Thr Thr Val
            20                  25

<210> SEQ ID NO 130
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 130

Gln Glu Glu Met Pro Pro Arg Pro Cys Gly Gly His Thr Ser Ser Ser
1               5                   10                  15
```

-continued

Leu Pro Lys Ser His Leu Glu Pro Ser
            20                  25

<210> SEQ ID NO 131
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 131

Pro Asn Ile Gln Ala Val Leu Leu Pro Lys Lys Thr Asp Ser His His
1               5                   10                  15

Lys Ala Lys Gly Lys
            20

<210> SEQ ID NO 132
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 132

Asn Leu Val Pro Met Val Ala Thr Val
1               5

<210> SEQ ID NO 133
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 133

Cys Leu Gly Gly Leu Leu Thr Met Val
1               5

<210> SEQ ID NO 134
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 134

Gly Ile Leu Gly Phe Val Phe Thr Leu
1               5

<210> SEQ ID NO 135
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 135

Leu Leu Phe Gly Tyr Pro Val Tyr Val
1               5

<210> SEQ ID NO 136

```
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 136

Gly Leu Cys Thr Leu Val Ala Met Leu
1               5

<210> SEQ ID NO 137
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 137

Trp Leu Ser Leu Leu Val Pro Phe Val
1               5

<210> SEQ ID NO 138
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 138

Phe Leu Leu Thr Arg Ile Cys Thr
1               5

<210> SEQ ID NO 139
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 139

Trp Gln Ala Gly Ile Leu Ala Arg
1               5

<210> SEQ ID NO 140
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 140

Gln Gly Gln Asn Leu Lys Tyr Gln
1               5

<210> SEQ ID NO 141
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 141
```

```
Trp Gln Ala Gly Ile Leu Ala Arg Asn Leu Val Pro Met Val Ala Thr
1               5                   10                  15

Val Gln Gly Gln Asn Leu Lys Tyr Gln
            20                  25

<210> SEQ ID NO 142
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 142
gtggtgtgca gcgagaatag                                              20

<210> SEQ ID NO 143
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 143
cgctcgttgt agatgtcgtt ag                                           22

<210> SEQ ID NO 144
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 144
ttcatgcccg tgttg                                                   15

<210> SEQ ID NO 145
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 145
gtttttgatc cagacccaga tg                                           22

<210> SEQ ID NO 146
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 146
gcccattatt cagagcgagt a                                            21

<210> SEQ ID NO 147
<211> LENGTH: 14
<212> TYPE: DNA
<213> ORGANISM: Artificial Sequence
<220> FEATURE:
<223> OTHER INFORMATION: Description of Artificial Sequence: Synthetic
      probe
```

```
<400> SEQUENCE: 147
tcaccaggat ccac                                                       14

<210> SEQ ID NO 148
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 148
ccttgcacat gccggag                                                    17

<210> SEQ ID NO 149
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 149
acagagcctc gcctttg                                                    17

<210> SEQ ID NO 150
<211> LENGTH: 12
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 150
gtgagctggc gg                                                         12

<210> SEQ ID NO 151
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 151
ctgaaagctc ggtttgctaa tg                                              22

<210> SEQ ID NO 152
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 152
ccatgctgga agagacaatc t                                               21

<210> SEQ ID NO 153
<211> LENGTH: 15
<212> TYPE: DNA
<213> ORGANISM: Artificial Sequence
<220> FEATURE:
<223> OTHER INFORMATION: Description of Artificial Sequence: Synthetic
      probe
```

```
<400> SEQUENCE: 153
tggcgctgac cgata                                                     15

<210> SEQ ID NO 154
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 154
tatgcctatc ctgtctcctc tg                                             22

<210> SEQ ID NO 155
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 155
gctaatgcag ctaagtcctc tc                                             22

<210> SEQ ID NO 156
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 156
tgaccgtgcc ttctg                                                     15

<210> SEQ ID NO 157
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 157

Tyr Glu Met Phe Asn Asp Lys Ser Phe Gln Arg Ala Pro Asp Asp Lys
1               5                   10                  15

Met Phe

<210> SEQ ID NO 158
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Selenocysteine
<220> FEATURE:
<221> NAME/KEY: MOD_RES
<222> LOCATION: (7)..(8)
<223> OTHER INFORMATION: Pyrrolysine

<400> SEQUENCE: 158

Phe Glu Gly Arg Lys Xaa Xaa Xaa Ile
```

```
<210> SEQ ID NO 159
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Ile or Leu
<220> FEATURE:
<221> NAME/KEY: MOD_RES
<222> LOCATION: (5)..(5)
<223> OTHER INFORMATION: Pyrrolysine
<220> FEATURE:
<221> NAME/KEY: MOD_RES
<222> LOCATION: (7)..(7)
<223> OTHER INFORMATION: Ile or Leu
<220> FEATURE:
<221> NAME/KEY: MOD_RES
<222> LOCATION: (8)..(8)
<223> OTHER INFORMATION: Pyrrolysine
<220> FEATURE:
<221> NAME/KEY: MOD_RES
<222> LOCATION: (10)..(10)
<223> OTHER INFORMATION: Ile or Leu
<220> FEATURE:
<221> NAME/KEY: MOD_RES
<222> LOCATION: (14)..(14)
<223> OTHER INFORMATION: Pyrrolysine

<400> SEQUENCE: 159

Pro Xaa Phe Ile Xaa Glu Xaa Xaa Ile Xaa Gly Glu Ile Xaa
1               5                   10

<210> SEQ ID NO 160
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 160

Ala Lys Phe Val Ala Ala Trp Thr Leu Lys Ala Ala Ala
1               5                   10

<210> SEQ ID NO 161
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 161

Gln Tyr Ile Lys Ala Asn Ser Lys Phe Ile Gly Ile Thr Glu
1               5                   10

<210> SEQ ID NO 162
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 162
```

```
Asp Leu Met Gly Tyr Ile Pro Ala Val
1               5

<210> SEQ ID NO 163
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 163

Phe Leu Pro Ser Asp Phe Phe Pro Ser Val
1               5                   10

<210> SEQ ID NO 164
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 164

Phe Leu Leu Thr Arg Ile Leu Thr Ile
1               5

<210> SEQ ID NO 165
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 165

Phe Leu Leu Ser Leu Gly Ile His Leu
1               5

<210> SEQ ID NO 166
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 166

Ile Leu Lys Glu Pro Val His Gly Val
1               5

<210> SEQ ID NO 167
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 167

Tyr Met Leu Asp Leu Gln Pro Glu Thr Thr
1               5                   10

<210> SEQ ID NO 168
<211> LENGTH: 9
<212> TYPE: PRT
<213> ORGANISM: Artificial Sequence
<220> FEATURE:
```

```
<223> OTHER INFORMATION: Description of Artificial Sequence: Synthetic
      peptide

<400> SEQUENCE: 168

Cys Ile Asn Gly Val Cys Trp Thr Val
1               5

<210> SEQ ID NO 169
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 169

Tyr Leu Leu Pro Arg Arg Gly Pro Arg Leu
1               5                   10

<210> SEQ ID NO 170
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 170

Phe Leu Tyr Ala Leu Ala Leu Leu Leu
1               5

<210> SEQ ID NO 171
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 171

Ala Ala Gly Ile Gly Ile Leu Thr Val
1               5

<210> SEQ ID NO 172
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 172

Ser Leu Leu Met Trp Ile Thr Gln Val
1               5

<210> SEQ ID NO 173
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 173

Lys Leu Gly Gly Ala Leu Gln Ala Lys
1               5
```

-continued

```
<210> SEQ ID NO 174
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 174

Arg Leu Arg Ala Glu Ala Gln Val Lys
1               5

<210> SEQ ID NO 175
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 175

Glu Glu Asn Leu Leu Asp Phe Val Arg Phe
1               5                   10

<210> SEQ ID NO 176
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 176

Glu Glu Tyr Leu Gln Ala Phe Thr Tyr
1               5

<210> SEQ ID NO 177
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 177

Cys Thr Pro Tyr Asp Ile Asn Gln Met
1               5

<210> SEQ ID NO 178
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 178

Thr Thr Pro Glu Ser Ala Asn Leu
1               5

<210> SEQ ID NO 179
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 179
```

```
Cys Ala Pro Pro Gly Tyr Ala Leu Leu
1               5

<210> SEQ ID NO 180
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 180

Ser Gly Pro Lys Thr Asn Ile Ile Val
1               5

<210> SEQ ID NO 181
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 181

Leu Ser Pro Arg Thr Leu Asn Ala Trp
1               5

<210> SEQ ID NO 182
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 182

Thr Val Pro Trp Pro Asn Ala Ser Leu
1               5

<210> SEQ ID NO 183
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 183

Glu Gly Pro Arg Asn Gln Asp Trp Leu
1               5

<210> SEQ ID NO 184
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 184

Asp Trp Glu Asn Val Ser Pro Glu Leu
1               5

<210> SEQ ID NO 185
<211> LENGTH: 8
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 185

Ser Ile Ile Val Phe Asn Leu Leu
1               5

<210> SEQ ID NO 186
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 186

Ala Ser Met Thr Asn Met Glu Leu Met
1               5

<210> SEQ ID NO 187
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 187

Ala Gln Leu Ala Asn Asp Val Val Leu
1               5

<210> SEQ ID NO 188
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 188

Ser Val Tyr Asp Phe Phe Val Trp Leu
1               5

<210> SEQ ID NO 189
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 189

Met Asn Lys Tyr Ala Tyr His Met Leu
1               5

<210> SEQ ID NO 190
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 190

Gln Tyr Ile Lys Ala Asn Ser Lys Phe Ile Gly Ile Thr Glu Leu
1               5                   10                  15
```

```
<210> SEQ ID NO 191
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 191

Ser Ile Asn Phe Glu Lys Leu Ala Ala Tyr Leu Leu Leu Leu Leu Val
1               5                   10                  15

Val Val Val

<210> SEQ ID NO 192
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 192

Leu Leu Leu Leu Leu Val Val Val Val Ala Ala Tyr Ser Ile Asn Phe
1               5                   10                  15

Glu Lys Leu

<210> SEQ ID NO 193
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 193

Ser Pro Ser Tyr Val Tyr His Gln Phe
1               5
```

What is claimed is:

1. A composition for delivery of an antigen expression system, comprising:
   the antigen expression system,
   wherein the antigen expression system comprises one or more vectors,
   the one or more vectors comprising:
   (a) an RNA alphavirus backbone, wherein the RNA alphavirus backbone comprises:
     (i) at least one promoter nucleotide sequence, and
     (ii) at least one polyadenylation (poly(A)) sequence; and
   (b) an antigen cassette, wherein the antigen cassette comprises:
     (I) at least two antigen-encoding nucleic acid sequences, each comprising:
       (A) an epitope encoding nucleic acid sequence, and
       (B) a native 5' linker sequence that encodes a native N-terminal amino acid sequence of the epitope, and wherein the 5' linker sequence encodes a peptide that is between 2-20 amino acids in length, and
       (C) a native 3' linker sequence that encodes a native C-terminal amino acid sequence of the epitope, and wherein the 3' linker sequence encodes a peptide that is between 2-20 amino acids in length,
   wherein each of the at least two antigen-encoding nucleic acid sequences is linked directly to one another.

2. A method of treating a subject with cancer, the method comprising administering to the subject an immunotherapy comprising the antigen expression system of claim 1.

3. The composition of claim 1, wherein at least one of the epitope encoding nucleic acid sequences comprises an MHC class I epitope encoding nucleic acid sequence.

4. The composition of claim 1, wherein at least one of the epitope encoding nucleic acid sequences comprises an alteration that makes the encoded peptide sequence distinct from a corresponding peptide sequence encoded by a wild-type nucleic acid sequence, optionally wherein the alteration is selected from the group consisting of: a point mutation, a frameshift mutation, a non-frameshift mutation, a deletion mutation, an insertion mutation, a splice variant, a genomic rearrangement, a proteasome-generated spliced antigen, and combinations thereof.

5. The composition of claim 4, wherein at least one of the encoded epitopes comprising the alteration has (1) increased binding affinity to its corresponding MHC allele relative to the translated, corresponding wild-type nucleic acid sequence, (2) has increased binding stability to its corresponding MHC allele relative to the translated, corresponding wild-type nucleic acid sequence, and/or (3) has an increased likelihood of presentation on its corresponding MHC allele relative to the translated, corresponding wild-type nucleic acid sequence.

6. The composition of claim 1, wherein an ordered sequence of each element of the antigen cassette is described in the formula, from 5' to 3', comprising:

$$P_a\text{-}(L5_b\text{-}N_c\text{-}L3_d)_X\text{-}(G5_e\text{-}U_f)_Y\text{-}G3_g$$

wherein P comprises a second promoter nucleotide sequence, where a=0 or 1,
N comprises one of the epitope encoding nucleic acid sequences, where c=1,
L5 comprises the native 5' linker sequence, where b=1,
L3 comprises the native 3' linker sequence, where d=1,
G5 comprises at least one nucleic acid sequence encoding a GPGPG amino acid linker sequence (SEQ ID NO:56), where e=0 or 1,
G3 comprises at least one second nucleic acid sequence encoding a GPGPG amino acid linker sequence (SEQ ID NO:56), where g=0 or 1,
U comprises at least one MHC class II antigen-encoding nucleic acid sequence, where f=1,
X=2 to 400, and
Y=0, 1, or 2; optionally
  (i) wherein for each X the corresponding N is distinct; and/or
  (ii) wherein for each Y the corresponding U is distinct.

7. The composition of claim 6, wherein
a=0, b=1, d=1, e=1, g=1, h=1, X≥2, Y≥0,
the at least one promoter nucleotide sequence is a single 26S promoter nucleotide sequence provided by the RNA alphavirus backbone,
the at least one polyadenylation poly(A) sequence is a poly(A) sequence of at least 80 consecutive A nucleotides provided by the RNA alphavirus backbone,
the epitope comprises an MHC class I epitope, wherein the MHC class I epitope encoded by each N is 7-15 amino acids in length,
U is each of a PADRE class II sequence and a Tetanus toxoid MHC class II sequence, the RNA alphavirus backbone is the sequence set forth in SEQ ID NO:6, and
each of the MHC class I antigen-encoding nucleic acid sequences encodes a polypeptide that is between 13 and 25 amino acids in length.

8. The composition of claim 1, wherein at least one of the epitopes encoded by at least one of the antigen-encoding nucleic acid sequences is capable of being presented by an MHC allele on a cell surface, optionally wherein the cell is a tumor cell optionally selected from the group consisting of: lung cancer, melanoma, breast cancer, ovarian cancer, prostate cancer, kidney cancer, gastric cancer, colon cancer, testicular cancer, head and neck cancer, pancreatic cancer, bladder cancer, brain cancer, B-cell lymphoma, acute myelogenous leukemia, adult acute lymphoblastic leukemia, chronic myelogenous leukemia, chronic lymphocytic leukemia, T cell lymphocytic leukemia, non-small cell lung cancer, and small cell lung cancer.

9. The composition of claim 1, wherein the at least two antigen-encoding nucleic acid sequence comprises at least 2-10, 11-20, 15-20, 11-100, 11-200, 11-300, 11-400, 11, 12, 13, 14, 15, 16, 17, 18, 19, 20, 2, 3, 4, 5, 6, 7, 8, 9, 10 nucleic acid sequences, or up to 400 nucleic acid sequences, optionally wherein at least two of the antigen-encoding nucleic acid sequences encode epitopes that are capable of being presented by an MHC allele on a cell surface.

10. A pharmaceutical composition comprising the composition of claim 1 and a pharmaceutically acceptable carrier, optionally wherein the composition further comprises (1) an adjuvant, and/or (2) an immune modulator, optionally wherein the immune modulator is an anti-CTLA4 antibody or an antigen-binding fragment thereof, an anti-PD-1 antibody or an antigen-binding fragment thereof, an anti-PD-L1 antibody or an antigen-binding fragment thereof, an anti-4-1BB antibody or an antigen-binding fragment thereof, or an anti-OX-40 antibody or an antigen-binding fragment thereof.

11. An isolated nucleotide sequence or set of isolated nucleotide sequences comprising the antigen cassette of claim 1 and one or more elements obtained from the sequence of SEQ ID NO:3 or SEQ ID NO:5, optionally wherein the one or more elements are selected from the group consisting of the sequences necessary for nonstructural protein-mediated amplification, the 26S promoter nucleotide sequence, the poly(A) sequence, and the nsP1-4 genes of the sequence set forth in SEQ ID NO:3 or SEQ ID NO:5, optionally wherein the sequence or set of isolated nucleotide sequences comprises the antigen cassette of claim 1 inserted at position 7544 of the sequence set forth in SEQ ID NO:6 or SEQ ID NO:7 or inserted at position 7563 of SEQ ID NO:8 or SEQ ID NO:9, and optionally wherein the nucleotide sequence is cDNA, and optionally wherein the sequence or set of isolated nucleotide sequences comprises a T7 or SP6 RNA polymerase promoter nucleotide sequence 5' of the one or more elements obtained from the sequence of SEQ ID NO:3 or SEQ ID NO:5 and/or one or more restriction sites 3' of the poly(A) sequence.

12. A kit comprising the composition of claim 1 and instructions for use.

13. A method for inducing an immune response in a subject, the method comprising administering to the subject an antigen expression system, comprising:
the antigen expression system,
wherein the antigen expression system comprises one or more vectors,
the one or more vectors comprising:
(a) an RNA alphavirus backbone, wherein the RNA alphavirus backbone comprises:
  (i) at least one promoter nucleotide sequence, and
  (ii) at least one polyadenylation (poly(A)) sequence; and
(b) an antigen cassette, wherein the antigen cassette comprises:
  (I) at least two antigen-encoding nucleic acid sequences, each comprising:
    (A) an epitope encoding nucleic acid sequence, and
    (B) a native 5' linker sequence that encodes a native N-terminal amino acid sequence of the epitope, and wherein the 5' linker sequence encodes a peptide that is between 2-20 amino acids in length, and
    (C) a native 3' linker sequence that encodes a native C-terminal amino acid sequence of the epitope, and wherein the 3' linker sequence encodes a peptide that is between 2-20 amino acids in length,
  wherein each of the at least two antigen-encoding nucleic acid sequences is linked directly to one another.

14. A method of manufacturing the one or more vectors of claim 1, the method comprising:
(a) obtaining a linearized DNA sequence comprising the RNA alphavirus backbone and the antigen cassette;
(b) in vitro transcribing the linearized DNA sequence by addition of the linearized DNA sequence to an in vitro transcription reaction containing all the necessary components to transcribe the linearized DNA sequence into RNA, optionally further comprising in vitro addition of the m7g cap to the resulting RNA; and (c) isolating the one or more vectors from the in vitro transcription reaction.

15. A method of manufacturing the composition of claim 1 for delivery of the antigen expression system, the method comprising:
(a) providing components for a nanoparticulate delivery vehicle;
(b) providing the antigen expression system; and
(c) providing conditions sufficient for the nanoparticulate delivery vehicle and the antigen expression system to produce the composition for delivery of the antigen expression system, optionally wherein the conditions are provided by microfluidic mixing.

16. A composition for delivery of an antigen expression system, comprising:
the antigen expression system,
wherein the antigen expression system comprises one or more vectors,
the one or more vectors comprising:
(a) an RNA alphavirus backbone, wherein the RNA alphavirus backbone comprises the sequence set forth in SEQ ID NO:6; and
(b) an antigen cassette, wherein the antigen cassette comprises:
(I) at least one antigen-encoding nucleic acid sequence, comprising:
(A) an epitope encoding nucleic acid sequence, and
(B) optionally, a 5' linker sequence, and
(C) optionally, a 3' linker sequence.

17. The composition of claim 16, wherein the antigen cassette is inserted at position 7544 of the sequence set forth in SEQ ID NO: 6.

18. A method of treating a subject with cancer, the method comprising administering to the subject an immunotherapy comprising the antigen expression system of claim 17.

19. A composition for delivery of an antigen expression system, comprising:
the antigen expression system,
wherein the antigen expression system comprises one or more vectors,
the one or more vectors comprising:
(a) an RNA alphavirus backbone, wherein the RNA alphavirus backbone comprises:
(i) at least one promoter nucleotide sequence, and
(ii) at least one polyadenylation (poly(A)) sequence; and
(b) an antigen cassette, wherein the antigen cassette comprises:
(I) at least two antigen-encoding nucleic acid sequence, each comprising:
(A) an epitope encoding nucleic acid sequence, and
(B) optionally, a 5' linker sequence, and
(C) optionally, a 3' linker sequence;
wherein the antigen cassette comprises junctional epitope sequences encoded by adjacent antigen-encoding nucleic acid sequences in the antigen cassette, wherein at least one or each junctional epitope sequence has an affinity of greater than 500 nM for MEW, and optionally wherein at least one or each junctional epitope sequence is non-self.

20. A method of treating a subject with cancer, the method comprising administering to the subject an immunotherapy comprising the antigen expression system of claim 19.

21. The composition of claim 16, wherein at least one of the epitope encoding nucleic acid sequences comprises an MHC class I epitope encoding nucleic acid sequence.

22. The composition of claim 16, wherein at least one of the epitope encoding nucleic acid sequences comprises an alteration that makes the encoded peptide sequence distinct from a corresponding peptide sequence encoded by a wild-type nucleic acid sequence, optionally wherein the alteration is selected from the group consisting of: a point mutation, a frameshift mutation, a non-frameshift mutation, a deletion mutation, an insertion mutation, a splice variant, a genomic rearrangement, a proteasome-generated spliced antigen, and combinations thereof.

23. The composition of claim 22, wherein at least one of the encoded epitopes comprising the alteration has (1) increased binding affinity to its corresponding MHC allele relative to the translated, corresponding wild-type nucleic acid sequence, (2) has increased binding stability to its corresponding MHC allele relative to the translated, corresponding wild-type nucleic acid sequence, and/or (3) has an increased likelihood of presentation on its corresponding MHC allele relative to the translated, corresponding wild-type nucleic acid sequence.

24. The composition of claim 16, wherein an ordered sequence of each element of the antigen cassette is described in the formula, from 5' to 3', comprising:

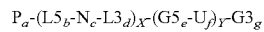

wherein P comprises a second promoter nucleotide sequence, where a=0 or 1,
N comprises one of the epitope encoding nucleic acid sequences, where c=1,
L5 comprises the (optional?) 5' linker sequence, where b=0 or 1,
L3 comprises the native 3' linker sequence, where d=0 or 1,
G5 comprises at least one nucleic acid sequence encoding a GPGPG amino acid linker sequence (SEQ ID NO:56), where e=0 or 1,
G3 comprises at least one second nucleic acid sequence encoding a GPGPG amino acid linker sequence (SEQ ID NO:56), where g=0 or 1,
U comprises at least one MHC class II antigen-encoding nucleic acid sequence, where f=1,
X=2 to 400, and
Y=0, 1, or 2; optionally
(i) wherein for each X the corresponding N is distinct; and/or
(ii) wherein for each Y the corresponding U is distinct.

25. The composition of claim 24, wherein
a=0, b=1, d=1, e=1, g=1, h=1, X≥2, Y≥0,
the at least one promoter nucleotide sequence is a single 26S promoter nucleotide sequence provided by the RNA alphavirus backbone,
the at least one polyadenylation poly(A) sequence is a poly(A) sequence of at least 80 consecutive A nucleotides provided by the RNA alphavirus backbone,
the epitope comprises an MHC class I epitope, wherein the MHC class I epitope encoded by each N is 7-15 amino acids in length,
U is each of a PADRE class II sequence and a Tetanus toxoid MHC class II sequence, and
each of the MHC class I antigen-encoding nucleic acid sequences encodes a polypeptide that is between 13 and 25 amino acids in length.

26. The composition of claim 16, wherein at least one of the epitopes encoded by at least one of the antigen-encoding nucleic acid sequences is capable of being presented by an MHC allele on a cell surface, optionally wherein the cell is a tumor cell optionally selected from the group consisting of: lung cancer, melanoma, breast cancer, ovarian cancer, prostate cancer, kidney cancer, gastric cancer, colon cancer, testicular cancer, head and neck cancer, pancreatic cancer, bladder cancer, brain cancer, B-cell lymphoma, acute myelogenous leukemia, adult acute lymphoblastic leukemia, chronic myelogenous leukemia, chronic lymphocytic leukemia, T cell lymphocytic leukemia, non-small cell lung cancer, and small cell lung cancer.

27. The composition of claim 16, wherein the at least two antigen-encoding nucleic acid sequence comprises at least 2-10, 11-20, 15-20, 11-100, 11-200, 11-300, 11-400, 11, 12, 13, 14, 15, 16, 17, 18, 19, 20, 2, 3, 4, 5, 6, 7, 8, 9, 10 nucleic acid sequences, or up to 400 nucleic acid sequences, optionally wherein at least two of the antigen-encoding nucleic acid sequences encode epitopes that are capable of being presented by an MHC allele on a cell surface.

28. A pharmaceutical composition comprising the composition of claim 16 and a pharmaceutically acceptable carrier, optionally wherein the composition further comprises (1) an adjuvant, and/or (2) an immune modulator, optionally wherein the immune modulator is an anti-CTLA4 antibody or an antigen-binding fragment thereof, an anti-PD-1 antibody or an antigen-binding fragment thereof, an anti-PD-L1 antibody or an antigen-binding fragment thereof, an anti-4-1BB antibody or an antigen-binding fragment thereof, or an anti-OX-40 antibody or an antigen-binding fragment thereof.

29. A kit comprising the composition of claim 16 and instructions for use.

30. A method for inducing an immune response in a subject, the method comprising administering to the subject the antigen expression system of claim 16.

31. A method of manufacturing the one or more vectors of claim 16, the method comprising:
    (a) obtaining a linearized DNA sequence comprising the RNA alphavirus backbone and the antigen cassette;
    (b) in vitro transcribing the linearized DNA sequence by addition of the linearized DNA sequence to an in vitro transcription reaction containing all the necessary components to transcribe the linearized DNA sequence into RNA, optionally further comprising in vitro addition of the m7g cap to the resulting RNA; and
    (c) isolating the one or more vectors from the in vitro transcription reaction.

32. A method of manufacturing the composition of claim 16 for delivery of the antigen expression system, the method comprising:
    (a) providing components for a nanoparticulate delivery vehicle;
    (b) providing the antigen expression system; and
    (c) providing conditions sufficient for the nanoparticulate delivery vehicle and the antigen expression system to produce the composition for delivery of the antigen expression system, optionally wherein the conditions are provided by microfluidic mixing.

33. The composition of claim 19, wherein at least one of the epitope encoding nucleic acid sequences comprises an MHC class I epitope encoding nucleic acid sequence.

34. The composition of claim 19, wherein at least one of the epitope encoding nucleic acid sequences comprises an alteration that makes the encoded peptide sequence distinct from a corresponding peptide sequence encoded by a wild-type nucleic acid sequence, optionally wherein the alteration is selected from the group consisting of: a point mutation, a frameshift mutation, a non-frameshift mutation, a deletion mutation, an insertion mutation, a splice variant, a genomic rearrangement, a proteasome-generated spliced antigen, and combinations thereof.

35. The composition of claim 34, wherein at least one of the encoded epitopes comprising the alteration has (1) increased binding affinity to its corresponding MHC allele relative to the translated, corresponding wild-type nucleic acid sequence, (2) has increased binding stability to its corresponding MHC allele relative to the translated, corresponding wild-type nucleic acid sequence, and/or (3) has an increased likelihood of presentation on its corresponding MHC allele relative to the translated, corresponding wild-type nucleic acid sequence.

36. The composition of claim 19, wherein an ordered sequence of each element of the antigen cassette is described in the formula, from 5' to 3', comprising:

$$P_a\text{-}(L5_b\text{-}N_c\text{-}L3_d)_X\text{-}(G5_e\text{-}U_f)_Y\text{-}G3_g$$

wherein P comprises a second promoter nucleotide sequence, where a=0 or 1,
N comprises one of the epitope encoding nucleic acid sequences, where c=1,
L5 comprises the native 5' linker sequence, where b=1,
L3 comprises the native 3' linker sequence, where d=1,
G5 comprises at least one nucleic acid sequence encoding a GPGPG amino acid linker sequence (SEQ ID NO:56), where e=0 or 1,
G3 comprises at least one second nucleic acid sequence encoding a GPGPG amino acid linker sequence (SEQ ID NO:56), where g=0 or 1,
U comprises at least one MHC class II antigen-encoding nucleic acid sequence, where f=1,
X=2 to 400, and
Y=0, 1, or 2; optionally (i) wherein for each X the corresponding N is distinct; and/or (ii) wherein for each Y the corresponding U is distinct.

37. The composition of claim 36, wherein
a=0, b=1, d=1, e=1, g=1, h=1, X>2, Y>0, the at least one promoter nucleotide sequence is a single 26S promoter nucleotide sequence provided by the RNA alphavirus backbone,
the at least one polyadenylation poly(A) sequence is a poly(A) sequence of at least 80 consecutive A nucleotides provided by the RNA alphavirus backbone, the epitope comprises an MHC class I epitope, wherein the MHC class I epitope encoded by each N is 7-15 amino acids in length,
U is each of a PADRE class II sequence and a Tetanus toxoid MHC class II sequence,
the RNA alphavirus backbone is the sequence set forth in SEQ ID NO:6, and
each of the MHC class I antigen-encoding nucleic acid sequences encodes a polypeptide that is between 13 and 25 amino acids in length.

38. The composition of claim 19, wherein at least one of the epitopes encoded by at least one of the antigen-encoding nucleic acid sequences is capable of being presented by an MHC allele on a cell surface, optionally wherein the cell is a tumor cell optionally selected from the group consisting of: lung cancer, melanoma, breast cancer, ovarian cancer, prostate cancer, kidney cancer, gastric cancer, colon cancer, testicular cancer, head and neck cancer, pancreatic cancer, bladder cancer, brain cancer, B-cell lymphoma, acute myelogenous leukemia, adult acute lymphoblastic leukemia, chronic myelogenous leukemia, chronic lymphocytic leukemia, T cell lymphocytic leukemia, non-small cell lung cancer, and small cell lung cancer.

39. The composition of claim 19, wherein the at least two antigen-encoding nucleic acid sequence comprises at least 2-10, 11-20, 15-20, 11-100, 11-200, 11-300, 11-400, 11, 12, 13, 14, 15, 16, 17, 18, 19, 20, 2, 3, 4, 5, 6, 7, 8, 9, 10 nucleic acid sequences, or up to 400 nucleic acid sequences, optionally wherein at least two of the antigen-encoding nucleic acid sequences encode epitopes that are capable of being presented by an MHC allele on a cell surface.

40. A pharmaceutical composition comprising the composition of claim 19 and a pharmaceutically acceptable carrier, optionally wherein the composition further comprises (1) an adjuvant, and/or (2) an immune modulator, optionally wherein the immune modulator is an anti-CTLA4 antibody or an antigen-binding fragment thereof, an anti-PD-1 antibody or an antigen-binding fragment thereof, an anti-PD-L1 antibody or an antigen-binding fragment thereof, an anti-4-1BB antibody or an antigen-binding fragment thereof, or an anti-OX-40 antibody or an antigen-binding fragment thereof.

41. An isolated nucleotide sequence or set of isolated nucleotide sequences comprising the antigen cassette of claim 19 and one or more elements obtained from the sequence of SEQ ID NO:3 or SEQ ID NO:5, optionally wherein the one or more elements are selected from the group consisting of the sequences necessary for nonstructural protein-mediated amplification, the 26S promoter nucleotide sequence, the poly(A) sequence, and the nsP1-4 genes of the sequence set forth in SEQ ID NO:3 or SEQ ID NO:5, optionally wherein the sequence or set of isolated nucleotide sequences comprises the antigen cassette of claim 1 inserted at position 7544 of the sequence set forth in SEQ ID NO:6 or SEQ ID NO:7 or inserted at position 7563 of SEQ ID NO:8 or SEQ ID NO:9, and optionally wherein the nucleotide sequence is cDNA, and optionally wherein the sequence or set of isolated nucleotide sequences comprises a T7 or SP6 RNA polymerase promoter nucleotide sequence 5' of the one or more elements obtained from the sequence of SEQ ID NO:3 or SEQ ID NO:5 and/or one or more restriction sites 3' of the poly(A) sequence.

42. A kit comprising the composition of claim 19 and instructions for use.

43. A method for inducing an immune response in a subject, the method comprising administering to the subject the antigen expression system of claim 19.

44. A method of manufacturing the one or more vectors of claim 19, the method comprising:
  (a) obtaining a linearized DNA sequence comprising the RNA alphavirus backbone and the antigen cassette;
  (b) in vitro transcribing the linearized DNA sequence by addition of the linearized DNA sequence to an in vitro transcription reaction containing all the necessary components to transcribe the linearized DNA sequence into RNA, optionally further comprising in vitro addition of the m7g cap to the resulting RNA; and
  (c) isolating the one or more vectors from the in vitro transcription reaction.

45. A method of manufacturing the composition of claim 19 for delivery of the antigen expression system, the method comprising:
  (a) providing components for a nanoparticulate delivery vehicle;
  (b) providing the antigen expression system; and
  (c) providing conditions sufficient for the nanoparticulate delivery vehicle and the antigen expression system to produce the composition for delivery of the antigen expression system, optionally wherein the conditions are provided by microfluidic mixing.

46. The composition of claim 19, wherein at least one junctional epitope sequence is non-self.

47. The composition of claim 19, wherein each junctional epitope sequence is non-self.

48. The composition of claim 1, wherein the antigen cassette comprises junctional epitope sequences encoded by adjacent antigen-encoding nucleic acid sequences in the antigen cassette, wherein at least one or each junctional epitope sequence has an affinity of greater than 500 nM for MHC, and optionally wherein at least one or each junctional epitope sequence is non-self.

49. The composition of claim 16, wherein the antigen cassette comprises junctional epitope sequences encoded by adjacent antigen-encoding nucleic acid sequences in the antigen cassette, wherein at least one or each junctional epitope sequence has an affinity of greater than 500 nM for MHC, and optionally wherein at least one or each junctional epitope sequence is non-self.

50. The composition of claim 13, wherein at least one of the epitope encoding nucleic acid sequences comprises an MHC class I epitope encoding nucleic acid sequence.

51. The composition of claim 13, wherein at least one of the epitope encoding nucleic acid sequences comprises an alteration that makes the encoded peptide sequence distinct from a corresponding peptide sequence encoded by a wild-type nucleic acid sequence, optionally wherein the alteration is selected from the group consisting of: a point mutation, a frameshift mutation, a non-frameshift mutation, a deletion mutation, an insertion mutation, a splice variant, a genomic rearrangement, a proteasome-generated spliced antigen, and combinations thereof.

52. The composition of claim 51, wherein at least one of the encoded epitopes comprising the alteration has (1) increased binding affinity to its corresponding MHC allele relative to the translated, corresponding wild-type nucleic acid sequence, (2) has increased binding stability to its corresponding MHC allele relative to the translated, corresponding wild-type nucleic acid sequence, and/or (3) has an increased likelihood of presentation on its corresponding MHC allele relative to the translated, corresponding wild-type nucleic acid sequence.

53. The composition of claim 13, wherein an ordered sequence of each element of the antigen cassette is described in the formula, from 5' to 3', comprising:

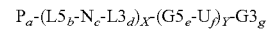

wherein P comprises a second promoter nucleotide sequence, where a=0 or 1,
  N comprises one of the epitope encoding nucleic acid sequences, where c=1,
  L5 comprises the native 5' linker sequence, where b=1,
  L3 comprises the native 3' linker sequence, where d=1,
  G5 comprises at least one nucleic acid sequence encoding a GPGPG amino acid linker sequence (SEQ ID NO:56), where e=0 or 1,
  G3 comprises at least one second nucleic acid sequence encoding a GPGPG amino acid linker sequence (SEQ ID NO:56), where g=0 or 1,
  U comprises at least one MHC class II antigen-encoding nucleic acid sequence, where f=1,
  X=2 to 400, and
  Y=0, 1, or 2; optionally
    (i) wherein for each X the corresponding N is distinct; and/or
    (ii) wherein for each Y the corresponding U is distinct.

54. The composition of claim 53, wherein
a=0, b=1, d=1, e=1, g=1, h=1, X≥2, Y≥0,
the at least one promoter nucleotide sequence is a single 26S promoter nucleotide sequence provided by the RNA alphavirus backbone,
the at least one polyadenylation poly(A) sequence is a poly(A) sequence of at least 80 consecutive A nucleotides provided by the RNA alphavirus backbone,
the epitope comprises an MHC class I epitope, wherein the MHC class I epitope encoded by each N is 7-15 amino acids in length,
U is each of a PADRE class II sequence and a Tetanus toxoid MHC class II sequence,
the RNA alphavirus backbone is the sequence set forth in SEQ ID NO:6, and
each of the MHC class I antigen-encoding nucleic acid sequences encodes a polypeptide that is between 13 and 25 amino acids in length.

55. The composition of claim 13, wherein at least one of the epitopes encoded by at least one of the antigen-encoding nucleic acid sequences is capable of being presented by an MHC allele on a cell surface, optionally wherein the cell is a tumor cell optionally selected from the group consisting of: lung cancer, melanoma, breast cancer, ovarian cancer, prostate cancer, kidney cancer, gastric cancer, colon cancer, testicular cancer, head and neck cancer, pancreatic cancer, bladder cancer, brain cancer, B-cell lymphoma, acute myelogenous leukemia, adult acute lymphoblastic leukemia, chronic myelogenous leukemia, chronic lymphocytic leukemia, T cell lymphocytic leukemia, non-small cell lung cancer, and small cell lung cancer.

56. The composition of claim 13, wherein the at least two antigen-encoding nucleic acid sequence comprises at least 2-10, 11-20, 15-20, 11-100, 11-200, 11-300, 11-400, 11, 12, 13, 14, 15, 16, 17, 18, 19, 20, 2, 3, 4, 5, 6, 7, 8, 9, 10 nucleic acid sequences, or up to 400 nucleic acid sequences, optionally wherein at least two of the antigen-encoding nucleic acid sequences encode epitopes that are capable of being presented by an MHC allele on a cell surface.

57. The composition of claim 13, wherein the antigen cassette comprises junctional epitope sequences encoded by adjacent antigen-encoding nucleic acid sequences in the antigen cassette, wherein at least one or each junctional epitope sequence has an affinity of greater than 500 nM for MHC, and optionally wherein at least one or each junctional epitope sequence is non-self.

* * * * *

UNITED STATES PATENT AND TRADEMARK OFFICE
CERTIFICATE OF CORRECTION

| | | |
|---|---|---|
| PATENT NO. | : 11,510,973 B2 | |
| APPLICATION NO. | : 17/693029 | |
| DATED | : November 29, 2022 | |
| INVENTOR(S) | : Wade Blair et al. | |

It is certified that error appears in the above-identified patent and that said Letters Patent is hereby corrected as shown below:

On the Title Page

In Column 1, item (62), in Related U.S. Application Data, Line 3, delete "2018." and insert -- 2018, now patent number 11,504,421 --, therefor.

In the Claims

In Column 691, Claim 19, Line 59, delete "MEW," and insert -- MHC, --, therefor.

In Column 692, Claim 24, Line 30, delete "the (optional?) 5' linker sequence," and insert -- the 5' linker sequence, --, therefor.

In Column 694, Claim 37, Line 38, delete "X>2," and insert -- $X \geq 2$, --, therefor.

In Column 694, Claim 37, Line 38, delete "Y>0," and insert -- $Y \geq 0$, --, therefor.

In Column 696, Claim 50, Line 20, delete "composition of" and insert -- method of --, therefor.

In Column 696, Claim 51, Line 23, delete "composition of" and insert -- method of --, therefor.

In Column 696, Claim 52, Line 33, delete "composition of" and insert -- method of --, therefor.

In Column 696, Claim 53, Line 43, delete "composition of" and insert -- method of --, therefor.

In Column 697, Claim 54, Line 1, delete "composition of" and insert -- method of --, therefor.

In Column 697, Claim 55, Line 19, delete "composition of" and insert -- method of --, therefor.

Signed and Sealed this
Seventh Day of March, 2023

Katherine Kelly Vidal
*Director of the United States Patent and Trademark Office*

CERTIFICATE OF CORRECTION (continued)
U.S. Pat. No. 11,510,973 B2

In Column 698, Claim 56, Line 8, delete "composition of" and insert -- method of --, therefor.

In Column 698, Claim 57, Line 16, delete "composition of" and insert -- method of --, therefor.